US011629134B2

(12) United States Patent
Sherer et al.

(10) Patent No.: US 11,629,134 B2
(45) Date of Patent: Apr. 18, 2023

(54) TLR7/8 ANTAGONISTS AND USES THEREOF

(71) Applicant: Merck Patent GmbH, Darmstadt (DE)

(72) Inventors: Brian A. Sherer, Nashua, NH (US);
Nadia Brugger, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 17/128,021

(22) Filed: Dec. 19, 2020

(65) Prior Publication Data

US 2021/0115013 A1   Apr. 22, 2021

Related U.S. Application Data

(63) Continuation of application No. 15/929,348, filed on Apr. 28, 2020, now Pat. No. 10,947,213, which is a continuation of application No. 16/696,503, filed on Nov. 26, 2019, now Pat. No. 10,696,649, which is a continuation of application No. 16/507,870, filed on Jul. 10, 2019, now Pat. No. 10,544,122, which is a continuation of application No. 15/381,406, filed on Dec. 16, 2016, now Pat. No. 10,399,957.

(60) Provisional application No. 62/353,603, filed on Jun. 23, 2016, provisional application No. 62/268,765, filed on Dec. 17, 2015.

(51) Int. Cl.

| | |
|---|---|
| *C07D 471/04* | (2006.01) |
| *C07D 401/04* | (2006.01) |
| *C07D 241/42* | (2006.01) |
| *C07D 405/14* | (2006.01) |
| *C07D 413/14* | (2006.01) |
| *C07D 417/04* | (2006.01) |
| *A61K 31/496* | (2006.01) |
| *A61K 31/519* | (2006.01) |
| *A61K 31/5377* | (2006.01) |
| *A61K 31/541* | (2006.01) |
| *C07D 401/14* | (2006.01) |
| *C07D 413/04* | (2006.01) |
| *C07D 487/04* | (2006.01) |

(52) U.S. Cl.
CPC .......... *C07D 401/04* (2013.01); *A61K 31/496* (2013.01); *A61K 31/519* (2013.01); *A61K 31/5377* (2013.01); *A61K 31/541* (2013.01); *C07D 241/42* (2013.01); *C07D 401/14* (2013.01); *C07D 405/14* (2013.01); *C07D 413/04* (2013.01); *C07D 413/14* (2013.01); *C07D 417/04* (2013.01); *C07D 471/04* (2013.01); *C07D 487/04* (2013.01)

(58) Field of Classification Search
CPC .................................................. C07D 471/04
See application file for complete search history.

(56) References Cited

U.S. PATENT DOCUMENTS

| | | | |
|---|---|---|---|
| 4,933,447 A | 6/1990 | Koono et al. | |
| 7,268,232 B2 | 9/2007 | Schlienger et al. | |
| 7,649,001 B2 | 1/2010 | Shiraishi et al. | |
| 8,530,650 B2 | 9/2013 | Schiemann et al. | |
| 8,729,088 B2 | 5/2014 | Carson et al. | |
| 8,735,424 B2 * | 5/2014 | Burger ................ | C07D 417/14 544/125 |
| 9,938,282 B2 | 4/2018 | Janagani et al. | |
| 9,938,292 B2 | 4/2018 | Wu et al. | |
| 10,399,957 B2 | 9/2019 | Sherer et al. | |
| 10,544,122 B2 | 1/2020 | Sherer et al. | |
| 10,696,649 B2 | 6/2020 | Sherer et al. | |
| 10,793,553 B2 | 10/2020 | Sherer et al. | |
| 10,836,750 B1 | 11/2020 | Sherer et al. | |
| 10,947,213 B1 | 3/2021 | Sherer et al. | |
| 10,947,214 B2 | 3/2021 | Sherer et al. | |
| 2007/0225308 A1 | 9/2007 | Nakasato et al. | |
| 2008/0081817 A1 | 4/2008 | Takamuro et al. | |
| 2008/0125463 A1 | 5/2008 | Braeuer et al. | |
| 2009/0042857 A1 | 2/2009 | Yamaoka et al. | |
| 2010/0210598 A1 | 8/2010 | Carson et al. | |
| 2011/0237583 A1 | 9/2011 | Schiemann et al. | |
| 2017/0001976 A1 | 1/2017 | Krainc et al. | |
| 2017/0174653 A1 | 6/2017 | Sherer et al. | |
| 2017/0174703 A1 | 6/2017 | Wu et al. | |
| 2018/0037570 A1 | 2/2018 | Sherer et al. | |
| 2019/0023687 A1 | 1/2019 | Sherer et al. | |
| 2019/0330183 A1 | 10/2019 | Sherer et al. | |
| 2020/0095222 A1 | 3/2020 | Sherer et al. | |
| 2020/0316051 A1 | 10/2020 | Sherer et al. | |
| 2020/0369648 A1 | 11/2020 | Sherer et al. | |
| 2021/0002255 A1 | 1/2021 | Sherer et al. | |
| 2021/0002256 A1 | 1/2021 | Sherer et al. | |
| 2021/0300940 A1 * | 9/2021 | Sherer ................ | C07D 409/14 |

FOREIGN PATENT DOCUMENTS

| | | |
|---|---|---|
| CH | 578535 | 8/1976 |
| CN | 102216299 | 10/2011 |
| CN | 104557913 | 4/2015 |

(Continued)

OTHER PUBLICATIONS

Paudler et al., Journal of Heterocyclic Chemistry (1965), 2(4), pp. 393-398. (Year: 1965).*
Schwoch et al., Helvetica Chimica Acta (1994), 77(8), pp. 2175-2190. (Year: 1994).*
Sacre et al., The Journal of Immunology, 2008, 181, pp. 8002-8009. (Year: 2008).*
PubChem CID 4184, National Center for Biotechnology Information. "PubChem Compound Summary for CID 4184, Mianserin" PubChem, https://pubchem.ncbi.nlm.nih.gov/compound/Mianserin. Accessed Dec. 14, 2021, create date Mar. 25, 2005. (Year: 2005).*
Chemical Abstracts Registry No. 1714797-28-0, indexed in the Registry file on STN CAS Online on May 28, 2015. (Year: 2015).*

(Continued)

*Primary Examiner* — Laura L Stockton
(74) *Attorney, Agent, or Firm* — Grüneberg and Myers PLLC

(57) ABSTRACT

Compounds of Formula 1 and pharmaceutically acceptable compositions thereof are useful as TLR7/8 antagonists.

14 Claims, No Drawings

(56) References Cited

FOREIGN PATENT DOCUMENTS

| CN | 104945377 | 9/2015 |
|---|---|---|
| DE | 8 12 911 | 9/1951 |
| EA | 019768 | 6/2014 |
| EP | 0 308 897 | 3/1989 |
| EP | 1 726 584 | 11/2006 |
| WO | 01/25227 | 4/2001 |
| WO | 03/042208 | 5/2003 |
| WO | 2003/076427 | 9/2003 |
| WO | 03/105850 | 12/2003 |
| WO | 2004/016576 | 2/2004 |
| WO | 2004/043929 | 5/2004 |
| WO | 2004/046124 | 6/2004 |
| WO | 2005/040136 | 5/2005 |
| WO | 2005/087749 | 9/2005 |
| WO | 2005/115361 | 12/2005 |
| WO | 2006/009245 | 1/2006 |
| WO | 2006/124676 | 11/2006 |
| WO | 2006/125621 | 11/2006 |
| WO | 2007/072143 | 6/2007 |
| WO | 2007/092391 | 8/2007 |
| WO | 2007/097289 | 8/2007 |
| WO | 2008/028691 | 3/2008 |
| WO | 2008/037681 | 4/2008 |
| WO | 2008/126034 | 10/2008 |
| WO | 2008/148468 | 11/2008 |
| WO | 2009/140200 | 11/2009 |
| WO | 2010/003133 | 1/2010 |
| WO | 2010/026121 | 3/2010 |
| WO | 2010/063352 | 6/2010 |
| WO | 2010/093436 | 8/2010 |
| WO | 2010/097410 | 9/2010 |
| WO | 2011/009015 | 1/2011 |
| WO | 2012/110603 | 8/2012 |
| WO | 2013/060881 | 5/2013 |
| WO | 2014/086453 | 6/2014 |
| WO | 2014/210255 | 12/2014 |
| WO | 2015/027222 | 2/2015 |
| WO | 2015/057655 | 4/2015 |
| WO | 2015/057659 | 4/2015 |
| WO | 2015/088045 | 6/2015 |
| WO | 2015/092592 | 6/2015 |
| WO | 2015/144001 | 10/2015 |
| WO | 2015/162075 | 10/2015 |
| WO | 2015/198045 | 12/2015 |
| WO | 2016/071293 | 5/2016 |
| WO | 2016/073770 | 5/2016 |
| WO | 2016/087593 | 6/2016 |
| WO | 2016/096686 | 6/2016 |
| WO | 2017/004405 | 1/2017 |
| WO | 2017/031427 | 2/2017 |
| WO | 2017/106607 | 6/2017 |
| WO | 2018/031434 | 2/2018 |
| WO | 2019/125849 | 6/2019 |
| WO | 2020/025517 | 2/2020 |

OTHER PUBLICATIONS

Chemical Abstracts Registry No. 1778748-60-9, indexed in the Registry file on STN CAS Online on Jun. 12, 2015. (Year: 2015).*
Chemical Abstracts Registry No. 1787843-24-6, indexed in the Registry file on STN CAS Online on Jun. 24, 2015. (Year: 2015).*
Chemical Abstracts Registry No. 1214573-72-4, indexed in the Registry file on STN CAS Online on Mar. 25, 2010. (Year: 2010).*
U.S. Office Action dated Dec. 8, 2021 in U.S. Appl. No. 16/946,347, 13 pages.
U.S. Appl. No. 16/946,347, filed Jun. 17, 2020, 2020/0316051, Sherer et al.
Chinese Office Action dated Oct. 12, 2020 in Chinese Application No. 201680081793.1, with English translation, 7 pages.
International Search Report dated Apr. 17, 2019 in PCT/US2018/065112, 4 pages.
Written Opinion dated Apr. 17, 2019 in PCT/US2108/065112, 7 pages.
Babu et al., Monatshefte fuer Chemie, 2008, 139(2), pp. 179-181.
Barrat and Coffman, Immunol Rev, 223:271-283 (2008).
Berge et al., Pharmaceutical Salts, J. Pharma Sciences, 66(1): 1-19 (1977).
Cacchi et al., SYNLETT, 1997, (12)L 1400-1402.
Chemical Abstracts Registry No. 81962-71-2, indexed in the Registry file on STN CAS Online Nov. 16, 1984.
Chemical Abstracts Registry No. 1016829-71-2, indexed in the Registry file on STN CAS Online Apr. 24, 2008.
Chemical Abstracts Registry No. 1020252-84-9, indexed in the Registry file on STN CAS Online May 11, 2008.
Chemical Abstracts Registry No. 1227293-53-9, indexed in the Registry file on STN CAS Online Jun. 9, 2010. (Year: 2010).
Chemical Abstracts Registry No. 1271680-71-7, indexed in the Registry file on STN CAS Online Mar. 29, 2011.
Chemical Abstracts Registry No. 1367747-37-2, indexed in the Registry file on STN CAS Online Apr. 13, 2012. (Year: 2012).
Childers et al., Journal of Medicinal Chemistry, 2010, 53(10), pp. 4066-4084. (Year: 2010).
Coleman, Jr., et al., Journal of Neuroinflammation; 2017, 14:22, pp. 1-15.
Enevold et al., J Rheumatol, 37:905-10 (2010).
Fekete et al., Central European Journal of Chemistry, 2008, 6(1), pp. 33-37.
Ferrarini et al., European Journal of Medicinal Chemistry, 1999, 34(6): 505-513.
Foster A.B., Advances in Drug Research, 14: 1-39 (1985).
Gillette et al., Biochemistry, 33(10): 2927-2937 (1994).
Hanzlik et al., J. Org. Chem., 155: 3992-3997 (1990).
Helley et al., Neuroscience; 2015, 310:686-698.
Iddon et al., Synthesis, 1988, 11, pp. 871-876. (Year: 1988).
International Search Report dated Apr. 26, 2017 in PCT/US2016/067112.
Jarman et al., Carcinogenesis, 16(4): 683-688 (1995).
Kumari et al., Indian Journal of Chemistry Section B, 1992, 318(2): 92-97.
Lehmann et al., Nature Neuroscience; 2012, 15(6):827-35.
Leopoldo et al., Journal of Medicinal Chemistry, 2006, 49(1): 358-365.
Liu et al., Experimental Neurology; 2015, 269:202-212.
Magro-Checa et al., Drugs; 76:459-83.
Nasielski-Hinkens et al., Journal of Heterocyclic Chemistry, 1980, 17(5), pp. 873-876. (Year: 1980).
Office Action dated Apr. 1, 2020 in Russian Federation Patent Application No. 2018123698 with English translation, 10 pages.
Okide et al., Biological & Pharmaceutical Bulletin (2000), 23(2), pp. 257-258. (Year: 2000).
Park et al., Neuron: 2014, 82:47-54.
Patani et al., Chemical Reviews; 1996, 96(8):3147-3176.
PubChem CID 12657162, National Center for Biotechnology Information. PubChem Database. CID=12657162, https://pubchem.ncbi.nlm.nih.gov/compound/12657162 (accessed on Jul. 14, 2020), create date Feb. 8, 2007. (Year: 2007).
PubChem CID 12657163, National Center for Biotechnology Information. PubChem Database. CID=12657163, https://pubchem.ncbi.nlm.nih.gov/compound/12657163 (accessed on Jul. 13, 2020), create date Feb. 8, 2007. (Year: 2007).
PubChem CID 80005677, National Center for Biotechnology Information. PubChem Compound Database; CID=80005677, https://pubchem.ncbi.nlm.nih.gov/compound/80005677 (accessed Dec. 1, 2017), create date Oct. 19, 2014.
PubChem CID 83067212, National Center for Biotechnology Information. PubChem Compound Database; CID=83067212, https://pubchem.ncbi.nlm.nih.gov/compound/83067212 (accessed Dec. 1, 2017), create date Oct. 20, 2014.
PubChem CID 90476953—National Center for Biotechnology Information. PubChem Compound Database; CID=90476953, https://pubchem.ncbi.nlm.nih.gov/compound/90476953 (accessed Jan. 10, 2019), Create Date Feb. 16, 2015. (Year: 2015).
Reider et al., J. Org. Chem., 52(15): 3326-3334 (1987).
Search Report dated Mar. 30, 2020 in Russian Federation Patent Application No. 2018123698 with English translation, 4 pages.
Schön et al., Oncogene, 2008, 27, pp. 190-199. (Year: 2008).

(56) References Cited

OTHER PUBLICATIONS

Varala et al., SYNLETT, 2004, (10): 1747-1750.
Wang et al., Organic Letters, 2003, 5(6), pp. 897-900.
Zhou et al., Bioorganic & Medicinal Chemistry, 2008, 16(14): 6707-6723.
Andaloussi et al., "A novel series of histamine $H_4$ receptor antagonists based on the pyrido[3,2-d]pyrimidine scaffold: Comparison of hERG binding and target residence time with PF-3893787", Bioorganic & Medicinal Chemistry Letters, vol. 23, 2013, pp. 2663-2670.
Antonchick et al., "Direct Selective Oxidative Cross-Coupling of Simple Alkanes with Heteroarenes", Angew. Chem. Int. Ed., vol. 52, 2013, pp. 3267-3271.
V. G. Belikov, "Farmacevtičeskaâ himiâ" (English title: "*Pharmaceutical chemistry*"), textbook, 2007, Moscow, "MEDpress-inform", pp. 27-29. (with English translation).
Bromidge et al., "5-{2-[4-(2-Methyl-5-quinolinyl)-1-piperazinyl]ethyl}-2(1H)-quinolinones and 3,4-dihydro-2(1H)-quinolinones: Dual-acting 5-$HT_1$ receptor antagonists and serotonin reuptake inhibitors. Part 3", Bioorganic & Medicinal Chemistry Letters, vol. 20, 2010, pp. 7092-7096.
Colak et al. "RNA and Imidazoquinolines Are Sensed by Distinct TLR7/8 Ectodomain Sites Resulting in Functionally Disparate Signaling Events", The Journal of Immunology, vol. 192, 2014, pp. 5963-5973.
Database Registry, Chemical Abstracts Service, Columbus, Ohio, 2004, accession 775541-12-3, 3 pages.
Duffy et al., "Toll-like receptors in the pathogenesis of autoimmune diseases: recent and emerging translational developments", ImmunoTargets and Therapy, vol. 5, 2016, pp. 69-80.
Elderfield et al., "The von braun cyanogen bromide reaction. II. application to n-arylpyrrolidines", Journal of Organic Chemistry, vol. 17, No. 3, 1951, pp. 431-441.
Jadwiga Solducho, "Synthesis of Some Pyrido[2,3-d]pyrimidine and Pyrido[3,2-d]pyrimidine Derivatives", Archiv Der Pharmazie, vol. 323, 1990, pp. 513-515.
Knunanc Soviet,"Chemical encyclopedic dictionary", 1983, pp. 130-131.
Kuwano et al., "Catalytic asymmetric hydrogenation of quinoline carbocycles: unusual chemoselectivity in the hydrogenation of quinolines", Chemical Communications, vol. 51, No. 35, 2015, pp. 7558-7561.
Malagu et al., "The discovery and optimisation of pyrido[2,3-d]pyrimidine-2,4-diamines as potent and selective inhibitors of mTOR kinase", Bioorganic & Medicinal Chemistgy Letters, vol. 19, 2009, pp. 5950-5953.
Manninen et al., "Synthesis and characterization of tris-(5-amino-8-hydroxyquinoline) aluminum complexes and their use as anode buffer layers in inverted organic solar cells", Journal of Mater. Chem., vol. 22, 2012, pp. 22971-22982.
Monga et al., "Ring-substituted quinolines. Part 2: Synthesis and antimycobacterial activities of ring-substituted quinolinecarbohydrazide and ring-substituted quinolinecarboxamide analogues", Bioorganic & Medicinal Chemistry, vol. 12, 2004, pp. 6465-6472.
Nayyar et al.,"3D-QSAR study of ring-substituted quinoline class of anti-tuberculosis agents", Bioorganic & Medicinal Chemistry, vol. 14, 2006, pp. 847-856.

Pawar et al., "Inhibition of Toll-Like Receptor-7 (TLR-7) or TLR-7 plus TLR-9 Attenuates Glomerulonephritis and Lung Injury in Experimental Lupus" JASN Journal of the American Society of Nephrology, vol. 18, No. 6, Jun. 2007, pp. 1721-1731.
Rahul et al., "Bacterial DNA Gyrase is not the Target of Quinoline-Based Anti-Tuberculosis Compounds", International research journal of pharmacy, vol. 4, Issue 1, 2013, pp. 284-292.
Shcheblyakov et al.,"Toll-Like Receptors (TLRS): The Role in Tumor Progression", Acta Naturae, vol. 2, No. 3 (6), 2010, pp. 21-29.
Surivet et al., "Structure-guided design, synthesis and biological evaluation of novel DNA ligase inhibitors with in vitro and in vivo anti-staphylococcal activity", Bioorganic & Medicinal Chemistry Letters, vol. 21, Issue 21, 2012, pp. 6705-6711.
Vaitilingam et al.,"Synthesis and antimycobacterial activities of ring-substituted quinolinecarboxylic acid/ester analogues. Part 1", Bioorganic & Medicinal Chemistry, vol. 12, 2004, pp. 4179-4188.
V. V. Alekseyev, "Optical isomerism and drugs pharmacological activity", Sorovskij Educative Journal, 1989, pp. 49-55.
"Fundamentals of New Drug Design and Development", edited by Jiasen Zhao and Guosheng Shi, Nov. 2015, pp. 139-142, with English machine translation.
Zhou et al., "A highly selective $Cd^{2+}$ sensor of naphthyridine: fluorescent enhancement and red-shift by the synergistic action of forming binuclear complex", Tetrahedron Letters, vol. 49, Issue 21, 2008, pp. 3380-3384.
International Search Report dated Apr. 17, 2019 in PCT/US2018/065112, 4 pp.
Office Action dated Jul. 17, 2020 in U.S. Appl. No. 15/929,348, 27 pp.
Written Opinion dated Apr. 17, 2019 in PCT/US2018/065112, 7 pp.
Russian Office Action dated Oct. 22, 2021 in Russian Application No. 2020123151, with English translation, 8 pp.
International Search Report dated Oct. 2, 2019 in PCT/EP2019/070312, 7 pp.
Written Opinion dated Oct. 2, 2019 in PCT/EP2019/070312, 11 pp.
U.S. Office Action dated May 9, 2022 in U.S. Appl. No.16/948,432, 41 pp.
U.S. Office Action dated Apr. 11, 2022 in U.S. Appl. No.17/128,021, 30 pp.
U.S. Appl. No. 16/948,432, filed Sep. 18, 2020, Sherer et al.
U.S. Appl. No. 16/948,467, filed Sep. 21, 2020, Sherer et al.
U.S. Appl. No. 17/250,489, filed Jan. 27, 2021, Sherer et al.
Kovalenko V. N. Al'tertnativnye metody v dokliničeskom izučenii toksičnosti lekarstevnnyh sredstv [Alternative Methods in Preclinical Drug Toxicity Studies], Modern Issues of Toxicology, 2002, No. 4, pp. 14-18.
Pokrovskij V. I. Malaâ medicinskaâ enciklopediâ [Small medical encyclopedia], Medicina, 1996, vol. 5, pp. 90-96.
Russian Office Action dated May 26, 2022, in Russian Application No. 2021130563, with partial English translation, 64 pages.
U.S. Office Action dated Sep. 15, 2022, in U.S. Appl. No. 16/946,347, 6 pages.
U.S. Office Action dated Sep. 19, 2022, in U.S. Appl. No. 16/948,467, 9 pages.

\* cited by examiner

TLR7/8 ANTAGONISTS AND USES THEREOF

CROSS-REFERENCE TO RELATED APPLICATIONS

This application is a continuation of U.S. application Ser. No. 15/929,348, filed on Apr. 28, 2020, which is a continuation of U.S. application Ser. No. 16/696,503, filed on Nov. 26, 2019, now U.S. Pat. No. 10,696,649, which is a continuation of U.S. application Ser. No. 16/507,870, filed on Jul. 10, 2019, now U.S. Pat. No. 10,544,122, which is a continuation of U.S. application Ser. No. 15/381,406 filed on Dec. 16, 2016, now U.S. Pat. No. 10,399,957, which claims the benefit of U.S. Provisional application No. 62/268,765, filed on Dec. 17, 2015, and U.S. Provisional application No. 62/353,603, filed on Jun. 23, 2016. The contents of the aforementioned applications are hereby incorporated by, reference in their entireties.

TECHNICAL FIELD OF THE INVENTION

The present invention provides for compounds of Formula (I) as toll-like receptor 7/8 (TLR7/8) antagonists and their use in the treatment of immune disorders, and other diseases related to TLR7/8 overexpression.

BACKGROUND OF THE INVENTION

Toll-like receptors (TLR) currently comprising a gene family of 10 receptors with different specificities are part of the cellular pathogen pattern recognition system, which has evolved for defense against a variety of infections (bacteria, virus, fungi). Activation of TLRs leads to cytokine responses, e.g. with release of interferons and activation of specified immune cells. The functional expression of selected TLRs in tissues is highly different. Part of the receptors are located at the cell surface such as TLR4 (stimulated by *E. coli* lipopolysaccharide LPS), e.g. on epithelial cells, or TLR3, 7, 8 and 9 located at endosomal membranes in specified immune cells. The latter are all activated by nucleic acids, but recognize various types of them. For instance, TLR9 is activated by single stranded DNA containing CpG subsequences, TLR7 and 8 are activated by single stranded RNA, and TLR3 is activated by double-stranded RNA.

TLRs have been implicated in various autoimmune and inflammatory diseases, with the clearest example being the role played by TLR7 in the pathogenesis of systemic lupus erythematosus (Banat and Coffman, Immunol Rev, 223:271-283, 2008). Additionally, a TLR8 polymorphism has been associated with rheumatoid arthritis (Enevold et al., J Rheumatol, 37:905-10, 2010). Although various TLR7, TLR8 and TLR9 inhibitors have been described, additional TLR inhibitors are desirable. In particular, polynucleotides having inhibitory motifs for one or more of TLR7, TLR8 and TLR9 are needed to precisely inhibit an immune response in a subject (e.g., patient having an autoimmune disease or an inflammatory disorder).

For several years strong efforts are ongoing worldwide trying to exploit the strong immune activation induced by TLR7, 8 or 9 agonists for the treatment of cancer. Cancer immunotherapy, however, experienced a long history of failures. In recent years, though, the knowledge on cancer immune surveillance and the function of subsets of immune cells thereby was improved drastically. TLR7 or TLR9 agonists are in clinical development for cancer mono- or combination therapies, or as vaccine adjuvant. The TLR agonist approach for cancer immunotherapy is different from earlier efforts using, e.g. cytokines, interferons or monovalent vaccinations. TLR agonist mediated immune activation is pleiotropic via specified immune cells (primarily dendritic cells and B-cells, subsequently other cells), which generates an innate and adaptive immune response. Moreover, not only one interferon is induced, but rather the many different isoform's altogether, and not only type I (alpha, beta), but also (indirectly) type II (gamma, NK cells).

SUMMARY OF THE INVENTION

In one aspect, the invention provides compounds of Formula (I):

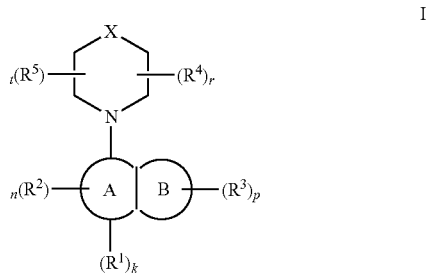

I and pharmaceutically acceptable derivatives, solvates, salts, hydrates and stereoisomers thereof.

In another aspect, the invention provides compounds of Formula (I) which are dual antagonists of TLR7 and TLR8. In another aspect, the invention provides compounds of Formula (I) which are suitable for the treatment and/or prevention of disorders related to TLR7/8. In another aspect, the invention provides compounds which are able to modulate, especially inhibit the activity or function of TLR7/8 in disease states in mammals, especially in humans.

According to another aspect of the invention are provided methods for the treatment and/or prevention of auto-immune disorders.

According to another aspect, the present invention provides compounds of Formula (I) which are selective for TLR7 or TLR8.

According to another aspect, the present invention provides compounds of Formula (I) which are selective for TLR7 and TLR8.

DETAILED DESCRIPTION OF CERTAIN EMBODIMENTS

1. General Description of Compounds of the Invention

In certain aspects, the present invention provides for antagonists of TLR7/8. In some embodiments, such compounds include those of the formulae described herein, or a pharmaceutically acceptable salt thereof, wherein each variable is as defined and described herein.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Exemplary aliphatic groups are linear or branched, substituted or unsubstituted $C_1$-$C_8$ alkyl, $C_2$-$C_8$ alkenyl, $C_2$-$C_8$ alkynyl groups and hybrids thereof such as (cycloalkyl)alkyl, (cycloalkenyl) alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, or phosphorus (including, any oxidized form of nitrogen, sulfur, or phosphorus; the quaternized form of any basic nitrogen or; a substitutable nitrogen of a heterocyclic ring, for example N (as in 3,4-dihydro-2H-pyrrolyl), NH (as in pyrrolidinyl) or NW' (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $(CH_2)_n$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system. Exemplary aryl groups are phenyl, biphenyl, naphthyl, anthracyl and the like, which optionally includes one or more substituents. Also included within the scope of the term "aryl", as it is used herein, is a group in which an aromatic ring is fused to one or more nonaromatic rings, such as indanyl, phthalimidyl, naphthimidyl, phenanthridinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group is optionally mono or bicyclic. The term "heteroaryl" is used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 5 to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen is N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group is optionally mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure (e.g.,

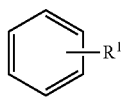

refers to at least

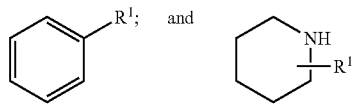

refers to at least

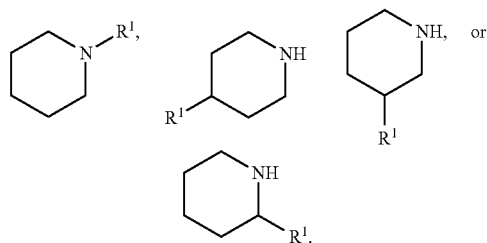

Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently deuterium; halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which are optionally substituted with $R^\circ$; $-(CH_2)_{0-4}O(CH_2)_{0-1}Ph$ which is optionally substituted with $R^\circ$; $-CH=CHPh$, which is optionally substituted with $R^\circ$; $-(CH_2)_{0-4}O(CH_2)_{0-1}$-pyridyl which is optionally substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R^\circ$; $-OC(O)(CH_2)_{0-4}SR^\circ$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ is optionally substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on $R^\circ$ (or the ring formed by taking two independent occurrences of $R^\circ$ together with their intervening atoms), are independently deuterium, halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

In certain embodiments, the terms "optionally substituted", "optionally substituted alkyl," "optionally substituted "optionally substituted alkenyl," "optionally substituted alkynyl", "optionally substituted carbocyclic," "optionally substituted aryl", "optionally substituted heteroaryl," "optionally substituted heterocyclic," and any other optionally substituted group as used herein, refer to groups that are substituted or unsubstituted by independent replacement of one, two, or three or more of the hydrogen atoms thereon with typical substituents including, but not limited to:

—F, —Cl, —Br, —I, deuterium,

—OH, protected hydroxy, alkoxy, oxo, thiooxo,

—NO$_2$, —CN, CF$_3$, N$_3$,

—NH$_2$, protected amino, —NH alkyl, —NH alkenyl, —NH alkynyl, —NH cycloalkyl, —NH-aryl, —NH-heteroaryl, —NH-heterocyclic, -dialkylamino, -diarylamino, -diheteroarylamino, —O— alkyl, —O— alkenyl, —O— alkynyl, —O— cycloalkyl, —O-aryl, —O-heteroaryl, —O-heterocyclic, —C(O)— alkyl, —C(O)— alkenyl, —C(O)— alkynyl, —C(O)— carbocyclyl, —C(O)-aryl, —C(O)— heteroaryl, —C(O)-heterocyclyl, —CONH$_2$, —CONH— alkyl, —CONH— alkenyl, —CONH— alkynyl, —CONH-carbocyclyl, —CONH-aryl, —CONH-heteroaryl, —CONH-heterocyclyl, —OCO$_2$— alkyl, —OCO$_2$— alkenyl, —OCO$_2$— alkynyl, —OCO$_2$— carbocyclyl, —OCO$_2$-aryl, —OCO$_2$— heteroaryl, —OCO$_2$-heterocyclyl, —OCONH$_2$, —OCONH— alkyl, —OCONH— alkenyl, —OCONH— alkynyl, —OCONH— carbocyclyl, —OCONH— aryl, —OCONH— heteroaryl, —OCONH— heterocyclyl, —NHC(O)— alkyl, —NHC(O)— alkenyl, —NHC(O)— alkynyl, —NHC(O)— carbocyclyl, —NHC(O)-aryl, —NHC(O)-heteroaryl, —NHC(O)-heterocyclyl, —NHCO$_2$— alkyl, —NHCO$_2$— alkenyl, —NHCO$_2$— alkynyl, —NHCO$_2$— carbocyclyl, —NHCO$_2$— aryl, —NHCO$_2$— heteroaryl, —NHCO$_2$— heterocyclyl, —NHC(O)NH$_2$, —NHC(O)NH— alkyl, —NHC(O)NH— alkenyl, —NHC(O)NH— alkenyl, —NHC(O)NH— carbocyclyl, —NHC(O)NH-aryl, —NHC(O)NH-heteroaryl, —NHC(O)NH— heterocyclyl, NHC(S)NH$_2$, —NHC(S)NH— alkyl, —NHC(S)NH— alkenyl, —NHC(S)NH— alkynyl, —NHC(S)NH— carbocyclyl, —NHC(S)NH-aryl, —NHC(S)NH-heteroaryl, —NHC(S)NH-heterocyclyl, —NHC(NH)NH$_2$, —NHC(NH)NH— alkyl, —NHC(NH)NH— alkenyl, —NHC(NH)NH— alkenyl, —NHC(NH)NH— carbocyclyl, —NHC(NH)NH-aryl, —NHC(NH)NH-heteroaryl, —NHC(NH)NH— heterocyclyl, —NHC(NH)— alkyl, —NHC(NH)— alkenyl, —NHC(NH)— alkenyl, —NHC(NH)— carbocyclyl, —NHC(NH)-aryl, —NHC(NH)-heteroaryl, —NHC(NH)-heterocyclyl, —C(NH)NH— alkyl, —C(NH)NH— alkenyl, —C(NH)NH— alkynyl, —C(NH)NH— carbocyclyl, —C(NH)NH-aryl, —C(NH)NH-heteroaryl, —C(NH)NH-heterocyclyl, —S(O)— alkyl, —S(O)— alkenyl, —S(O)— alkynyl, —S(O)— carbocyclyl, —S(O)-aryl, —S(O)-heteroaryl, —S(O)-heterocyclyl, —SO$_2$NH$_2$, —SO$_2$NH— alkyl, —SO$_2$NH— alkenyl, —SO$_2$NH— alkynyl, —SO$_2$NH— carbocyclyl, —SO$_2$NH— aryl, —SO$_2$NH— heteroaryl, —SO$_2$NH— heterocyclyl, —NHSO$_2$— alkyl, —NHSO$_2$— alkenyl, —NHSO$_2$— alkynyl, —NHSO$_2$— carbocyclyl, —NHSO$_2$-aryl, —NHSO$_2$-heteroaryl, —NHSO$_2$-heterocyclyl,

—CH$_2$NH$_2$, —CH$_2$SO$_2$CH$_3$,

-mono-, di-, or tri-alkyl silyl,

-alkyl, -alkenyl, -alkynyl, -aryl, -arylalkyl, -heteroaryl, -heteroarylalkyl, -heterocycloalkyl, -cycloalkyl, -carbocyclic, -heterocyclic, polyalkoxyalkyl, polyalkoxy, -methoxymethoxy, -methoxyethoxy, —SH, —S— alkyl, —S— alkenyl, —S— alkynyl, —S— carbocyclyl, —S-aryl, —S-heteroaryl, —S-heterocyclyl, or methylthiomethyl.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. In some embodiments, the group comprises one or more deuterium atoms.

There is furthermore intended that a compound of the formula I includes isotope-labeled forms thereof. An isotope-labeled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labeled compound of the formula I can be used in a number of beneficial ways. For example, an isotope-labeled compound of the formula I into which, for example, a radioisotope, such as $^{3}H$ or $^{14}C$, has been incorporated, is suitable for medicament and/or substrate tissue distribution assays. These radioisotopes, i.e. tritium ($^{3}H$) and carbon-14 ($^{14}C$), are particularly preferred owing to simple preparation and excellent detectability. Incorporation of heavier isotopes, for example deuterium ($^{2}H$), into a compound of the formula I has therapeutic advantages owing to the higher metabolic stability of this isotope-labeled compound. Higher metabolic stability translates directly into an increased in vivo half-life or lower dosages, which under most circumstances would represent a preferred embodiment of the present invention. An isotope-labeled compound of the formula I can usually be prepared by carrying out the procedures disclosed in the synthesis schemes and the related description, in the example part and in the preparation part in the present text, replacing a non-isotope-labeled reactant by a readily available isotope-labeled reactant.

Deuterium ($^{2}H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a com-pound of the formula I that is susceptible to oxidation, the profile of this compound in vivo can be drastically modified and result in improved pharmacokinetic properties.

When discovering and developing therapeutic agents, the person skilled in the art is able to optimize pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favorable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favorable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

As used herein, the term "modulator" is defined as a compound that binds to and/or inhibits the target with measurable affinity. In certain embodiments, a modulator has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in TLR7/8 activity between a sample comprising a compound of the present invention, or composition thereof, and TLR7/8, and an equivalent sample comprising TLR7/8, in the absence of said compound, or composition thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

3. Description of Exemplary Compounds

According to one aspect, the present invention provides a compound of formula I,

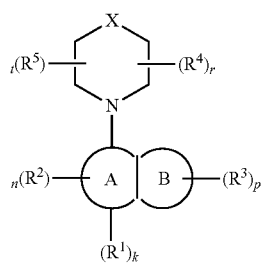

or a pharmaceutically acceptable salt thereof, wherein:
Ring A is aryl or heteroaryl having 1-4 heteroatoms independently selected from nitrogen, oxygen, or sulfur; each of which is optionally substituted;
Ring B is aryl or heteroaryl having 1-4 heteroatoms independently selected from nitrogen, oxygen, or sulfur; each of which is optionally substituted;
$R^1$ is absent, —H, —$CHF_2$, —$CF_3$, —OMe, or —CN;
each $R^2$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each $R^3$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
X is C($R^4$)$_2$, O, $NR^4$, S, S($R^4$), or S($R^4$)$_2$.
each $R^4$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$,
or —N(R)$_2$;
each $R^5$ is independently —H, —R, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted; or
two R groups on the same atom are taken together with the atom to which they are attached to form a $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
k is 0 or 1;
n is 0, 1, or 2;
p is 0, 1, or 2;
r is 0, 1, or 2; and
t is 0, 1, or 2.

In certain embodiments, when

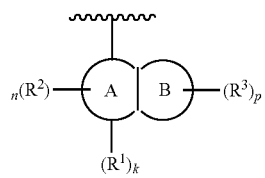

is

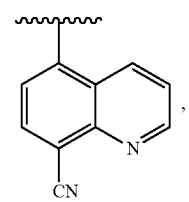 [SMILES: *c1ccc(C#N)c2ncccc12]

and X is $CH_2$; then $R^4$ is not H, methyl, or hydroxyl.

In certain embodiments, when

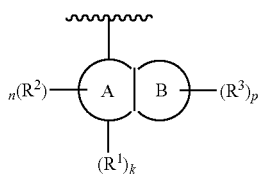

is

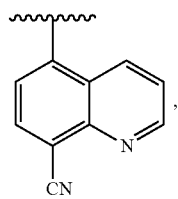 [SMILES: *c1ccc(C#N)c2ncccc12]

and X is O, then $R^4$ is not —C(O)N(R)$_2$.

In certain embodiments, $R^1$ is absent.
In certain embodiments, $R^1$ is, —H.
In certain embodiments, $R^1$ is —CHF$_2$.
In certain embodiments, $R^1$ is —CF$_3$.
In certain embodiments, $R^1$ is —OMe.
In certain embodiments, $R^1$ is —CN.

In certain embodiments, Ring A is C$_6$ aryl or a 6 membered monocyclic heteroaryl having 1-4 heteroatoms independently selected from nitrogen, oxygen, or sulfur; each of which is optionally substituted.

In certain embodiments, Ring A is phenyl, pyridyl, pyrimidinyl, pyrazinyl, pyridazinyl, or triazinyl; each of which is optionally substituted.

In certain embodiments, Ring A is phenyl, pyridyl, or pyrimidinyl; each of which is optionally substituted.

In certain embodiments, Ring A is

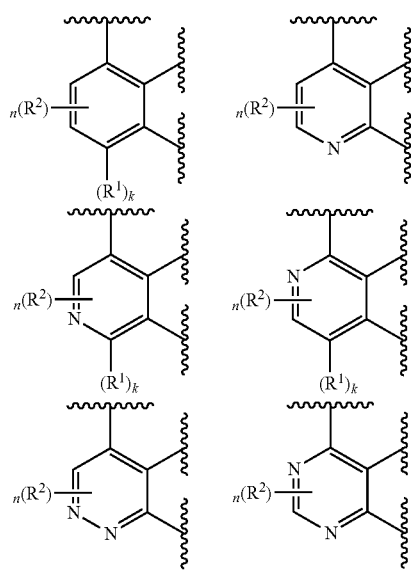

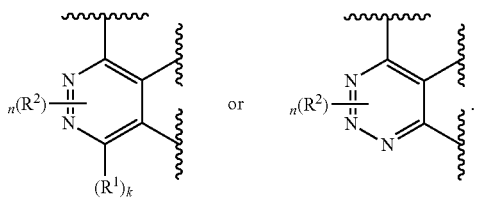

In certain embodiments, Ring A is

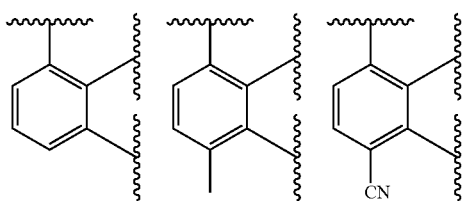

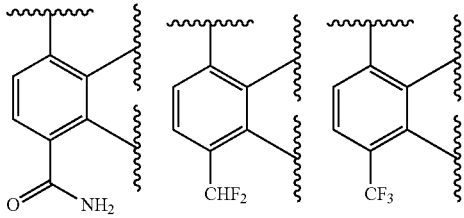

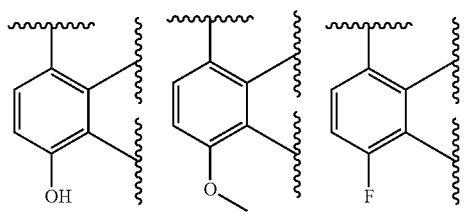

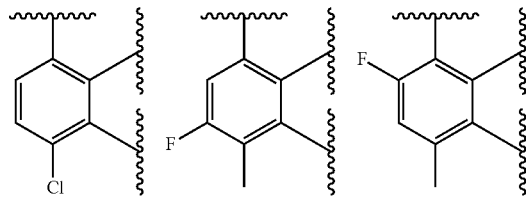

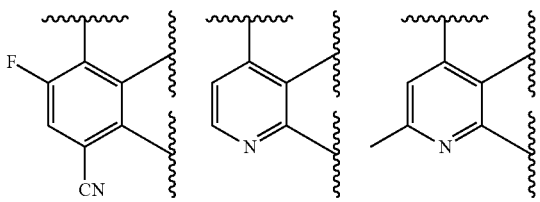

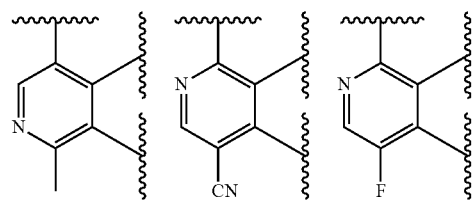

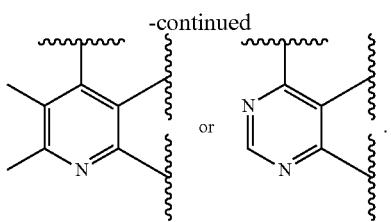

In certain embodiments, Ring B is $C_6$ aryl or a 5-6 membered monocyclic heteroaryl having 1-4 heteroatoms independently selected from nitrogen, oxygen, or sulfur; each of which is optionally substituted.

In certain embodiments, Ring B is phenyl, pyridyl, pyrimidinyl, pyrazinyl, pyridazinyl, triazinyl, pyrrole, imidazole, isoxazole, oxazole, or thiazole; each of which is optionally substituted.

In certain embodiments, Ring B is

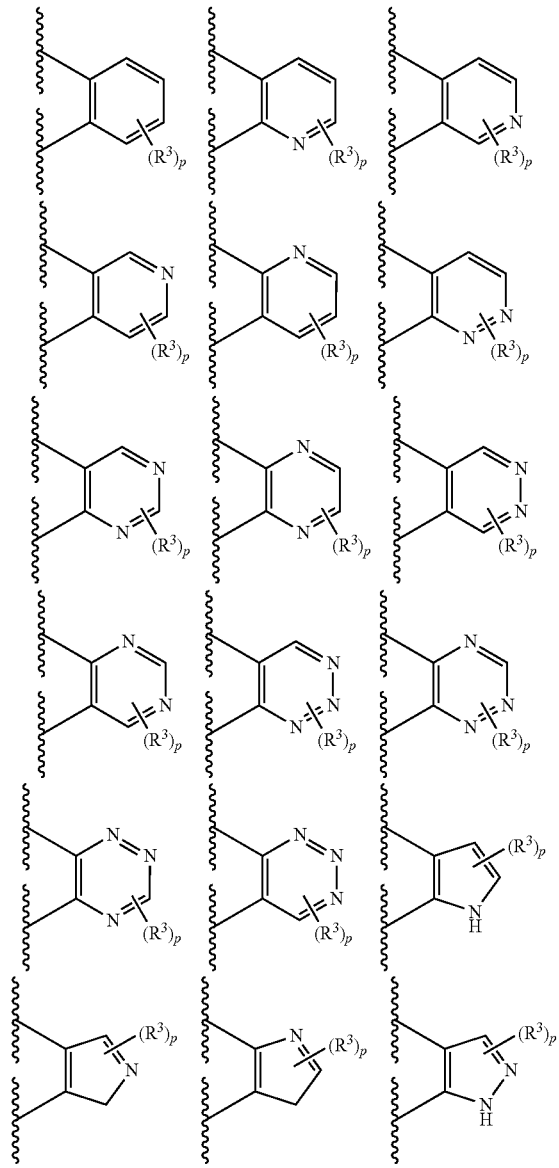

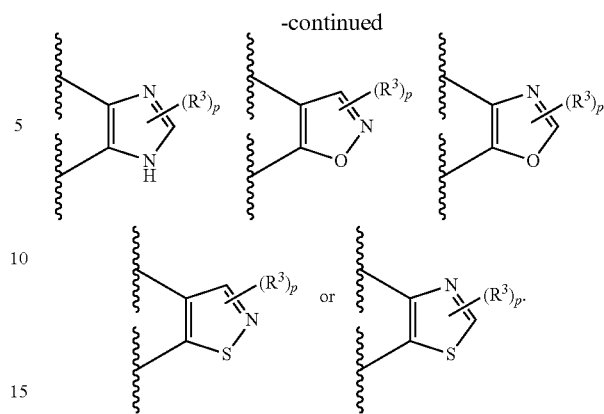

In certain embodiments, Ring B is

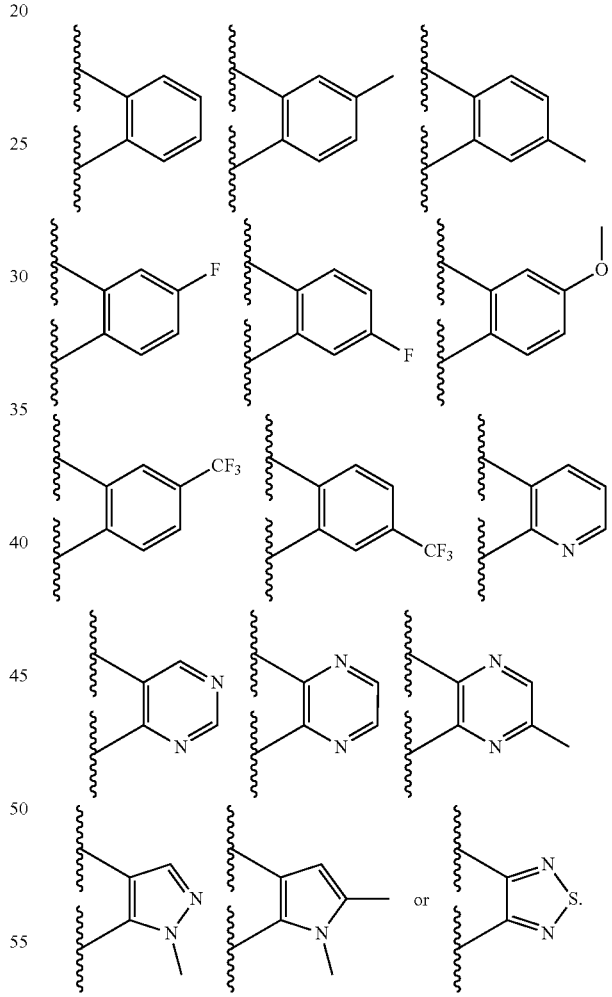

In certain embodiments, each $R^2$ is independently —H.

In certain embodiments, each $R^2$ is independently $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^2$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^2$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^2$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^3$ is independently —H.

In certain embodiments, each $R^3$ is independently $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^3$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^3$ is independently methyl.

In certain embodiments, each $R^3$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-h]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrroly, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^3$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, X is $C(R^4)_2$ or O.

In certain embodiments, X is $C(R^4)_2$. In certain embodiments, X is CH$_2$.

In certain embodiments, X is O.

In certain embodiments, each $R^4$ is independently —H.

In certain embodiments, each $R^4$ is independently $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each $R^4$ is independently methyl, ethyl, ethyl, propyl, i-propyl, butyl, s-butyl, t-butyl, straight or branched pentyl, or straight or branched hexyl; each of which is optionally substituted.

In certain embodiments, each $R^4$ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrroly, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each $R^4$ is independently halogen, -haloalkyl, —OR, —SR, —CN, —NO$_2$, —SO$_2$R, —SOR, —C(O)R, —CO$_2$R, —C(O)N(R)$_2$, —NRC(O)R, —NRC(O)N(R)$_2$, —NRSO$_2$R, or —N(R)$_2$.

In certain embodiments, each $R^4$ is independently —H, $C_{1-6}$ aliphatic, —OR, —C(O)R, —CO$_2$R, —C(O)N(R)$_2$, —NRC(O)R, —NRC(O)N(R)$_2$, —NRSO$_2$R, or —N(R)$_2$; each of which is optionally substituted.

In certain embodiments, each $R^4$ is independently —H, $C_{1-6}$ aliphatic, —C(O)N(R)$_2$, —NRC(O)R, or —N(R)$_2$; each of which is optionally substituted.

In certain embodiments, each $R^4$ is independently

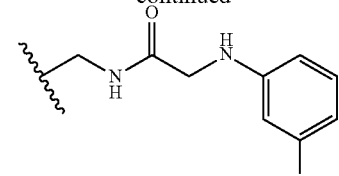
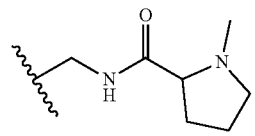
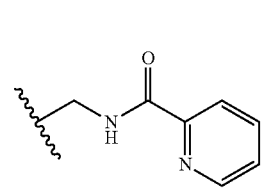
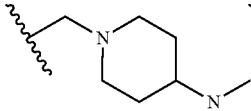
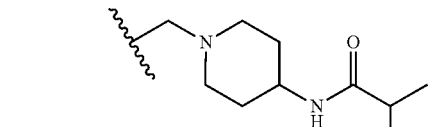
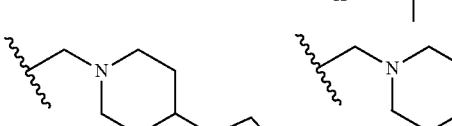
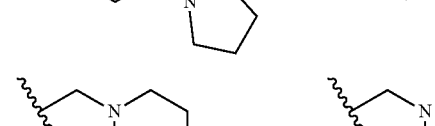
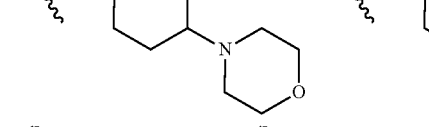
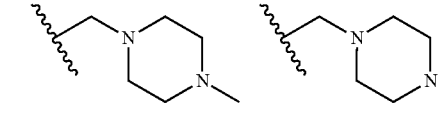
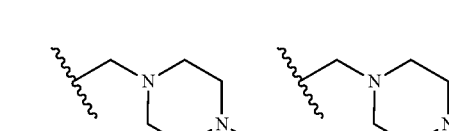
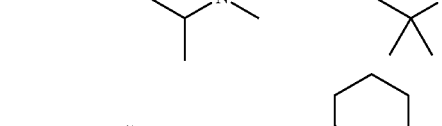
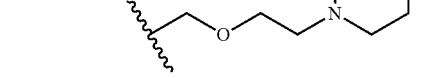
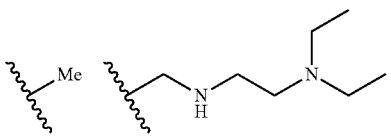
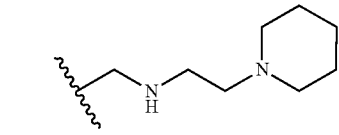
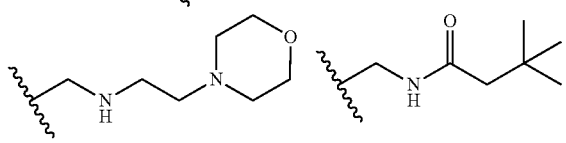
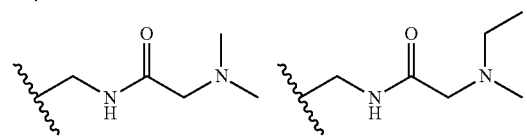
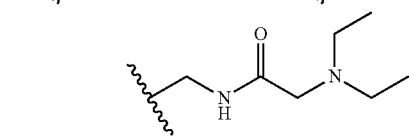
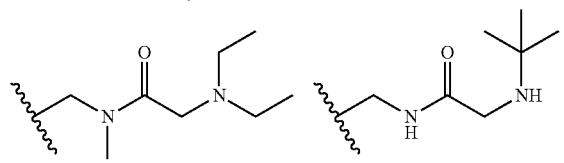
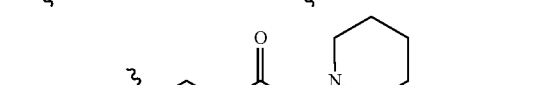
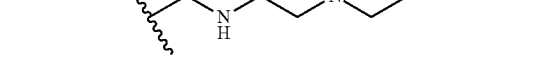

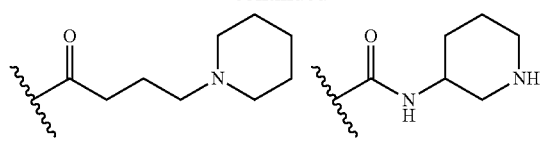
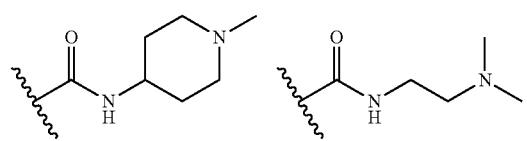
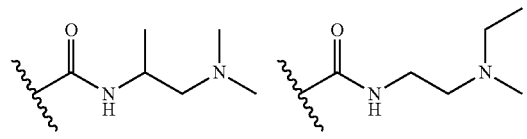
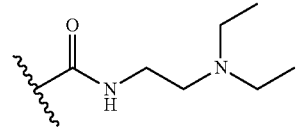
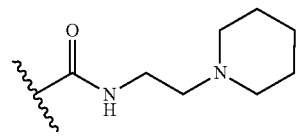
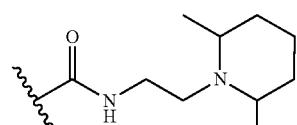
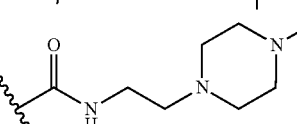
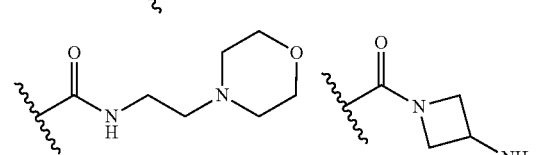
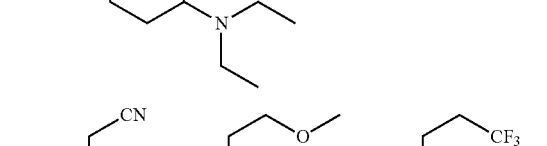
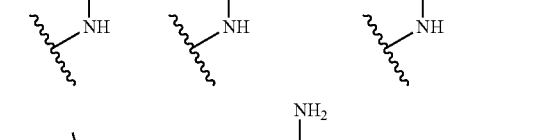
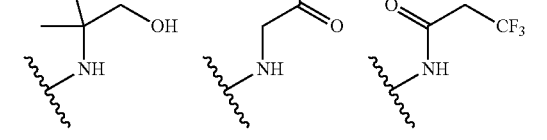
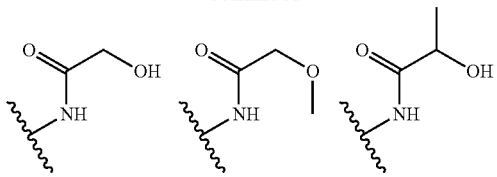
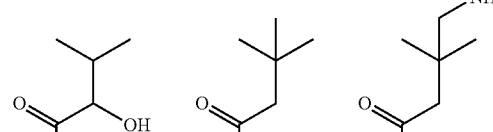
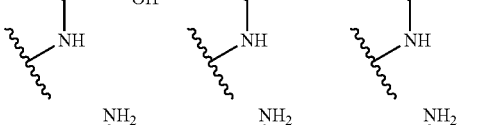
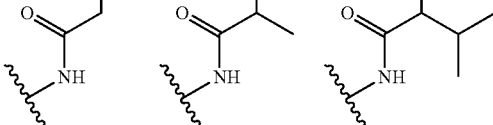
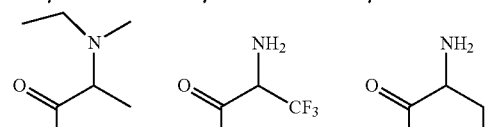
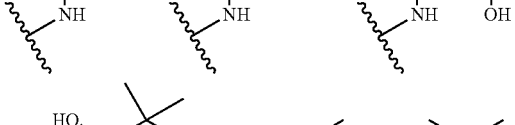
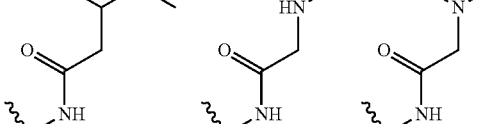
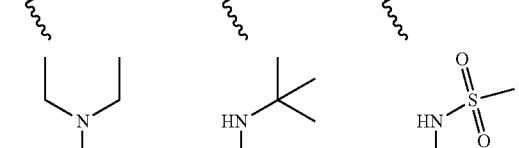
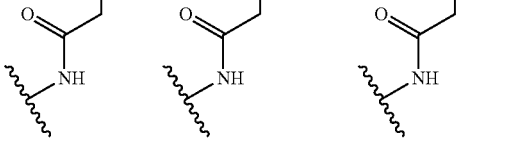
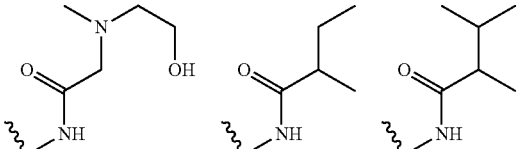
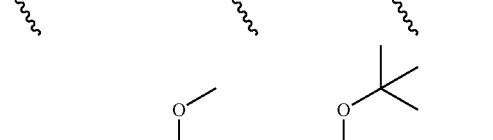
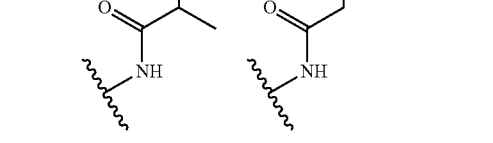

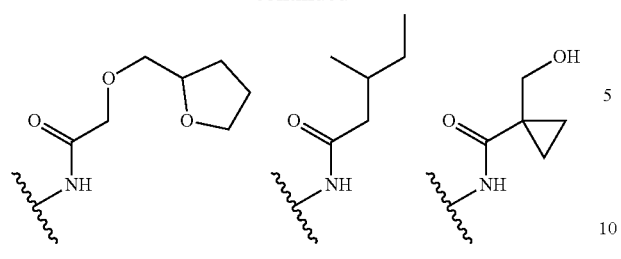
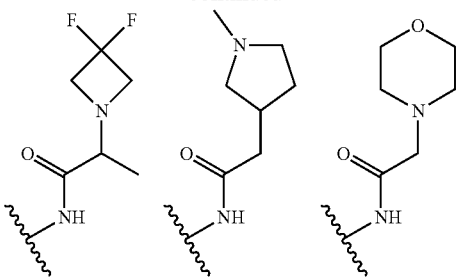
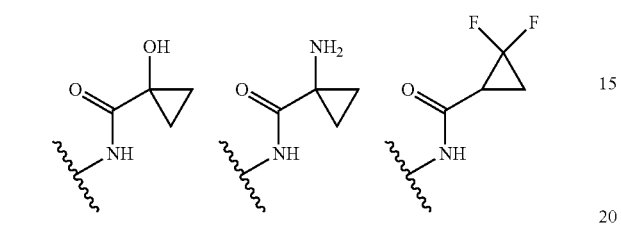
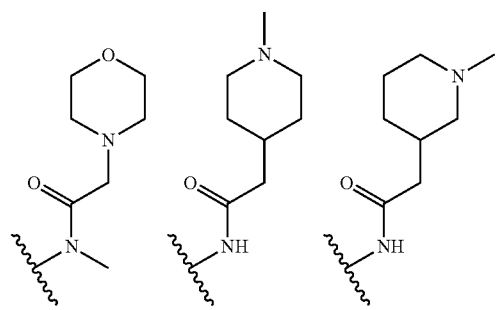
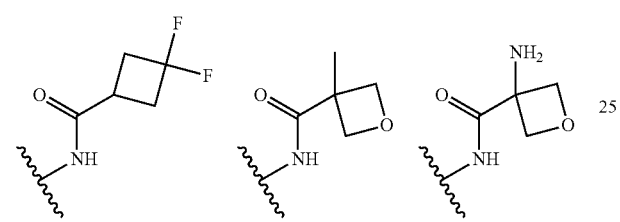
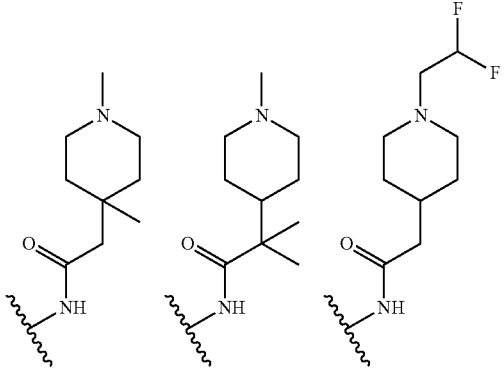
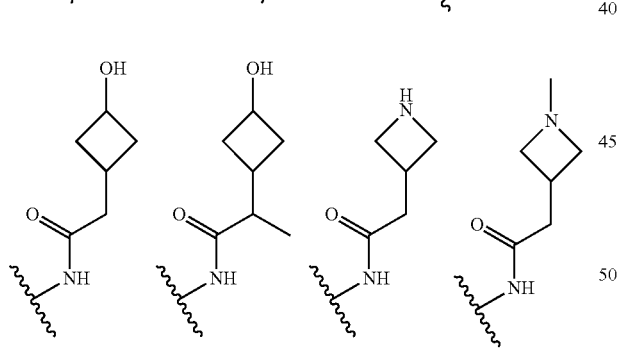
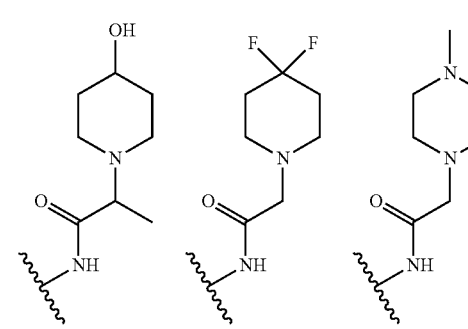
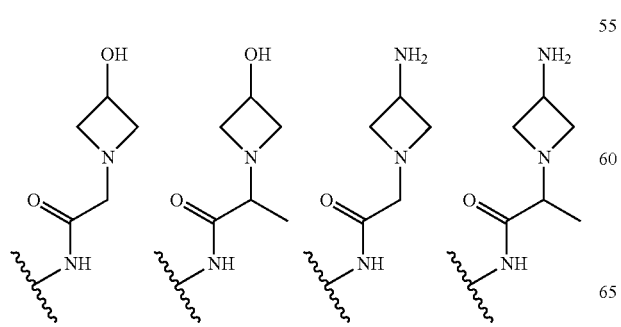

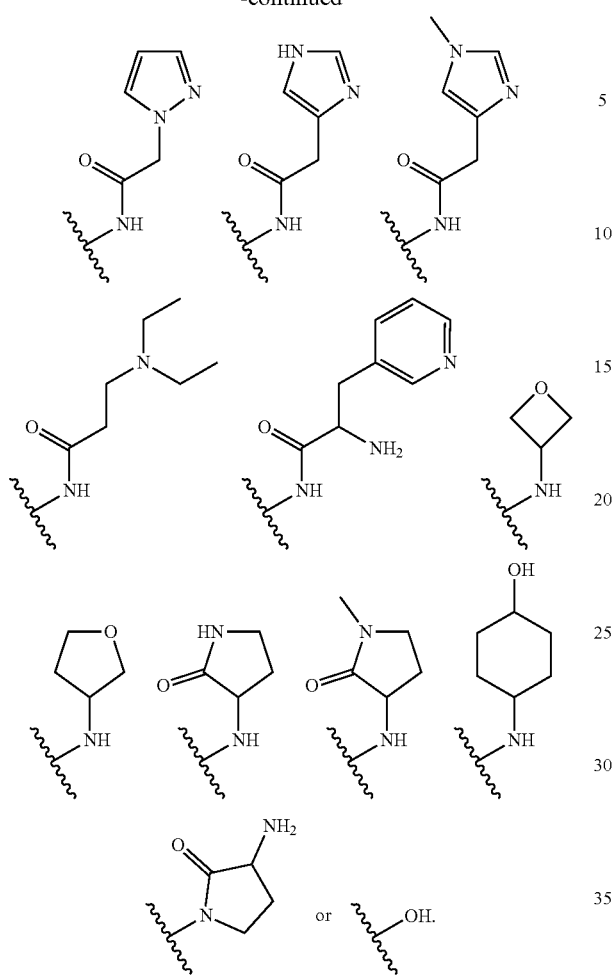
In certain embodiments, each $R^4$ is independently
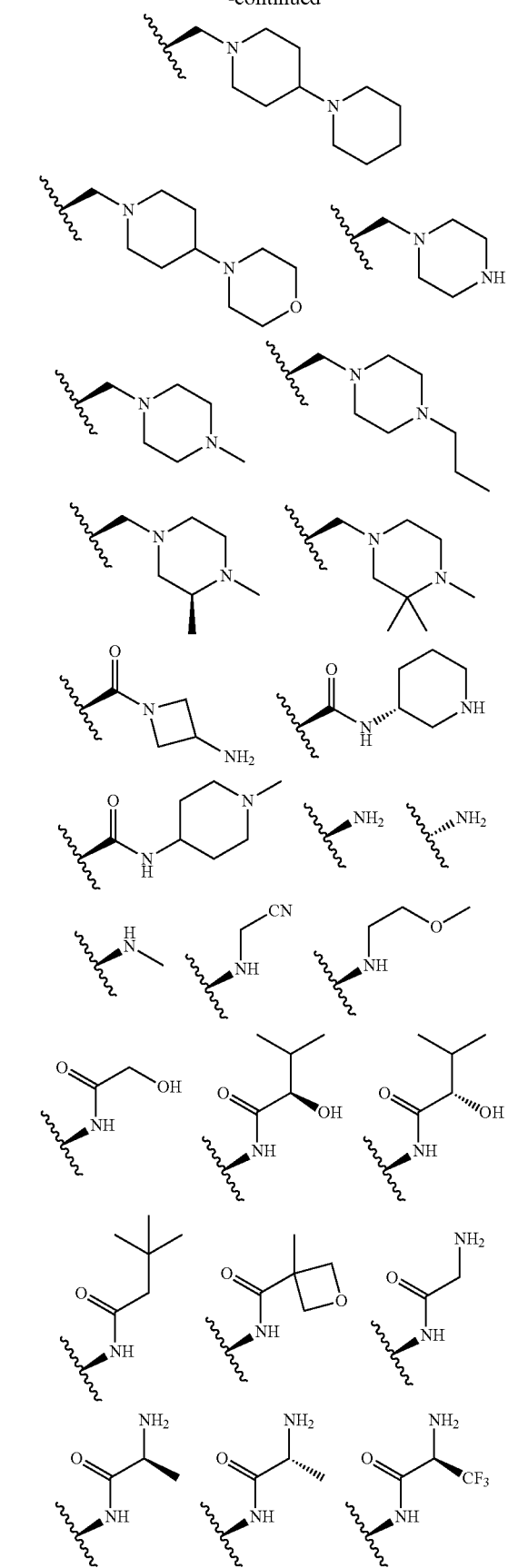

-continued

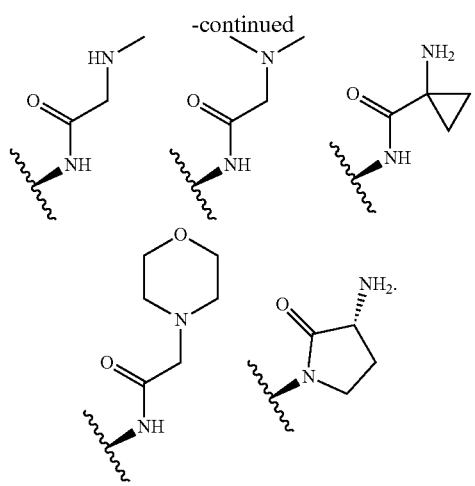

In certain embodiments, each R⁵ is independently —H.

In certain embodiments, each R⁵ is independently C₁₋₆ aliphatic, C₃₋₁₀ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted.

In certain embodiments, each R⁵ is independently methyl, ethyl, ethyl, propyl, i-propyl, butyl, s-butyl, t-butyl, straight or branched pentyl, or straight or branched hexyl; each of which is optionally substituted.

In certain embodiments, each R⁵ is independently phenyl, naphthyl, cyclopropyl, cyclobutyl, cyclopentyl, cyclohexyl, cycloheptyl, adamantyl, cyclooctyl, [3.3.0]bicyclooctanyl, [4.3.0]bicyclononanyl, [4.4.0]bicyclodecanyl, [2.2.2]bicyclooctanyl, fluorenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is optionally substituted.

In certain embodiments, each R⁵ is independently halogen, -haloalkyl, —OR, —SR, —CN, —NO₂, —SO₂R, —SOR, —C(O)R, —CO₂R, —C(O)N(R)₂, —NRC(O)R, —NRC(O)N(R)₂, —NRSO₂R, or —N(R)₂.

In certain embodiments, each R⁵ is independently methyl, cyclopropyl, —F, or —CF₃.

In certain embodiments, each R⁵ is independently

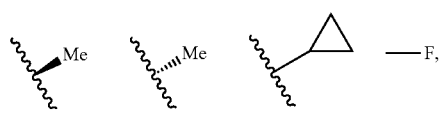

or —CF₃.

In certain embodiments, each of X, Ring A, Ring B, R¹, R², R³, R⁴, R⁵, k, m, n, p, r, and t, is as defined above and described in embodiments, classes and subclasses above and herein, singly or in combination.

In certain embodiments, the present invention provides a compound of formula I-a,

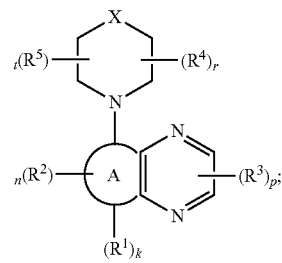

I-a or a pharmaceutically acceptable salt thereof, wherein each of X, Ring A, R¹, R², R³, R⁴, R⁵, k, n, p, r, and t, is as defined above and described in embodiments, classes and subclasses above and herein, singly or in combination.

In certain embodiments, the present invention provides a compound of formula I-b,

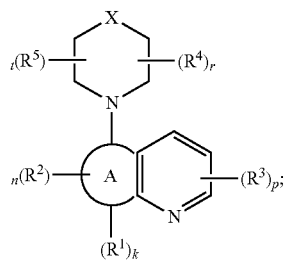

I-b or a pharmaceutically acceptable salt thereof, wherein each of X, Ring A, R¹, R², R³, R⁴, R⁵, k, n, p, r, and t, is as defined above and described in embodiments, classes and subclasses above and herein, singly or in combination.

In certain embodiments, the present invention provides a compound of formula I-c,

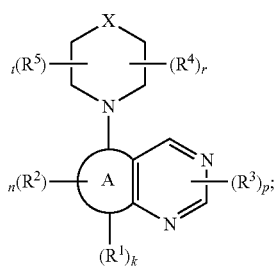

I-c or a pharmaceutically acceptable salt thereof, wherein each of X, Ring A, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-d,

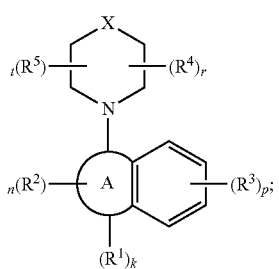

I-d or a pharmaceutically acceptable salt thereof, wherein each of X, Ring A, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-e,

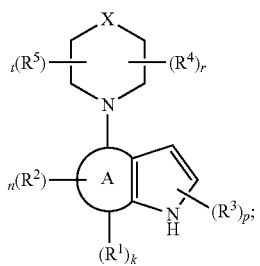

I-e or a pharmaceutically acceptable salt thereof, wherein each of X, Ring A, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-f,

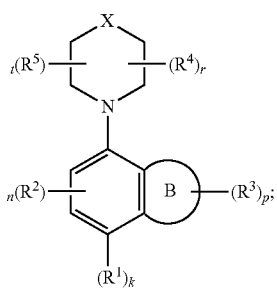

I-f or a pharmaceutically acceptable salt thereof, wherein each of X, Ring B, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-g,

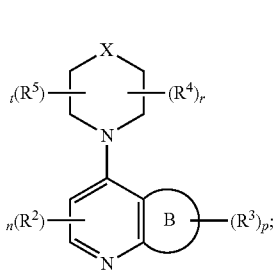

I-g or a pharmaceutically acceptable salt thereof, wherein each of X, Ring B, $R^2$, $R^3$, $R^4$, $R^5$, n, p, r, and t, is as defined above and described in embodiments, classes and subclasses above and herein, singly or in combination.

In certain embodiments, the present invention provides a compound of formula I-h,

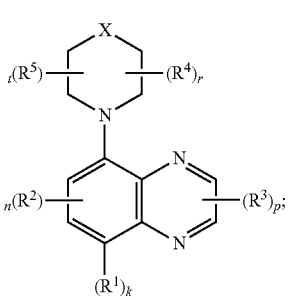

I-h or a pharmaceutically acceptable salt thereof, wherein each of X, $R^1$, $R^2$, $R^3$, $R^4$, $R^5$, k, n, p, r, and t, is as defined above and described in embodiments, classes and subclasses above and herein, singly or in combination.

In certain embodiments, the present invention provides a compound of formula I-j,

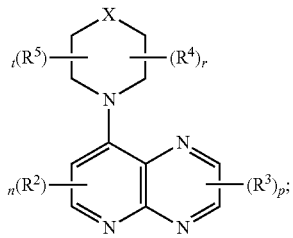

I-j or a pharmaceutically acceptable salt thereof, wherein each of X, R$^2$, R$^3$, R$^4$, R$^5$, n, p, r, and t, is as defined above and described in embodiments, classes and subclasses above and herein, singly or in combination.

In certain embodiments, the present invention provides a compound of formula I-m,

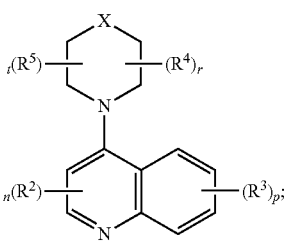

I-m or a pharmaceutically acceptable salt thereof, wherein each of X, R$^2$, R$^3$, R$^4$, R$^5$, n, p, r, and t, is as defined above and described in embodiments, classes and subclasses above and herein, singly or in combination.

In certain embodiments, the present invention provides a compound of formula I-n,

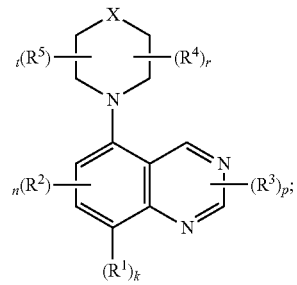

I-n or a pharmaceutically acceptable salt thereof, wherein each of X, R$^1$, R$^2$, R$^3$, R$^4$, R$^5$, k, n, p, r, and t, is as defined above and described in embodiments, classes and subclasses above and herein, singly or in combination.

In certain embodiments, the present invention provides a compound of formula I-p,

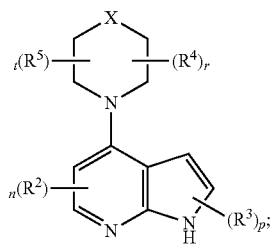

I-p or a pharmaceutically acceptable salt thereof, wherein each of X, R$^2$, R$^3$, R$^4$, R$^5$, n, p, r, and t, is as defined above and described in embodiments, classes and subclasses above and herein, singly or in combination.

In certain embodiments, the invention provides a compound selected from Table 1:

TABLE 1

| Compound Number | Example Number | Chemical Structure |
|---|---|---|
| 1 | 1 | 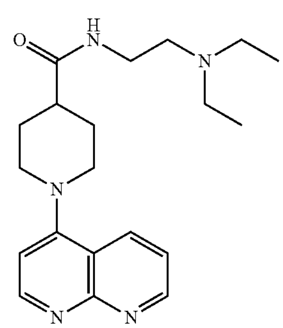 [SMILES: CCN(CC)CCNC(=O)C1CCN(c2ccnc3ncccc23)CC1] |

TABLE 1-continued
| Compound Number | Example Number | Chemical Structure |
|---|---|---|
| 2 | 1 | 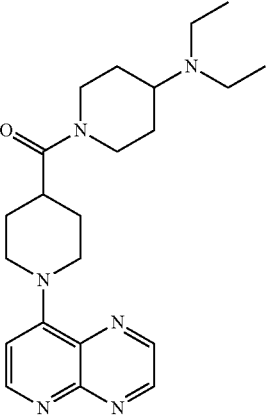 [SMILES: CCN(CC)C1CCN(C(=O)C2CCN(c3ccnc4nccnc34)CC2)CC1] |
| 3 | 2 | 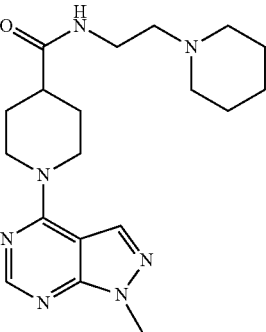 [SMILES: Cn1ncc2c(N3CCC(C(=O)NCCN4CCCCC4)CC3)ncnc21] |
| 4 | 3 | 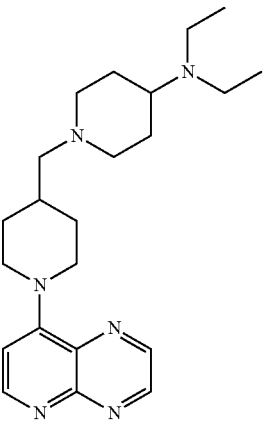 [SMILES: CCN(CC)C1CCN(CC2CCN(c3ccnc4nccnc34)CC2)CC1] |

TABLE 1-continued
| Compound Number | Example Number | Chemical Structure |
|---|---|---|
| 5 | 4 | 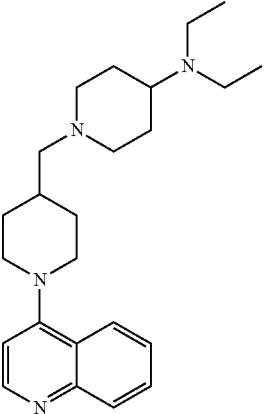 [SMILES: CCN(CC)C1CCN(CC2CCN(c3ccnc4ccccc34)CC2)CC1] |
| 6 | 5 | 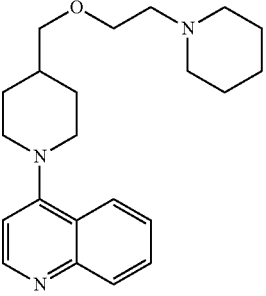 [SMILES: c1ccc2c(N3CCC(COCCN4CCCCC4)CC3)ccnc2c1] |
| 7 | 6 | 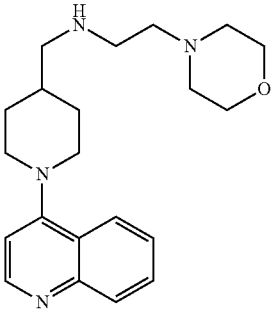 [SMILES: c1ccc2c(N3CCC(CNCCN4CCOCC4)CC3)ccnc2c1] |
| 8 | 7 | 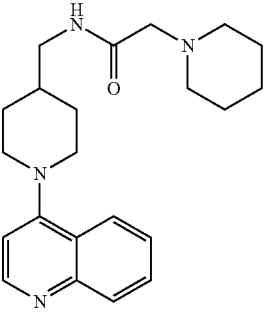 [SMILES: O=C(CN1CCCCC1)NCC1CCN(c2ccnc3ccccc23)CC1] |

TABLE 1-continued

| Compound Number | Example Number | Chemical Structure |
|---|---|---|
| 9 | 8 | 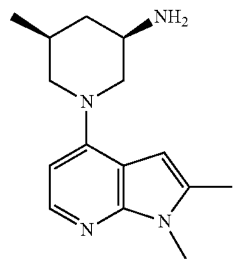 |
| 10 | 9 | 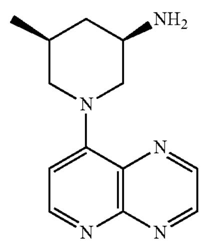 [SMILES: C[C@H]1C[C@@H](N)CN(c2ccnc3nccnc23)C1] |
| 11 | 9 | 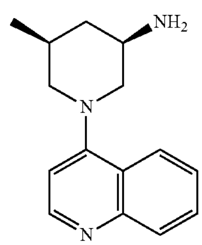 [SMILES: C[C@H]1C[C@@H](N)CN(c2ccnc3ccccc23)C1] |
| 12 | 9 | 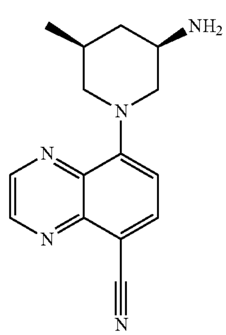 [SMILES: C[C@H]1C[C@@H](N)CN(c2ccc(C#N)c3nccnc23)C1] |
| 13 | 10 | 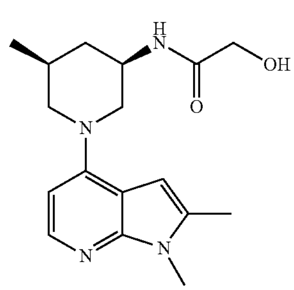 [SMILES: Cc1cc2c(N3C[C@@H](C)C[C@@H](NC(=O)CO)C3)ccnc2n1C] |

TABLE 1-continued
| Compound Number | Example Number | Chemical Structure |
|---|---|---|
| 14 | 10 | 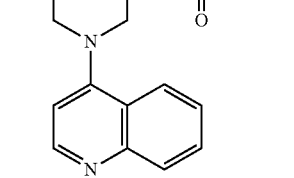 |
| 15 | 10 | 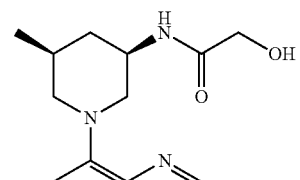 |
| 16 | 11 | 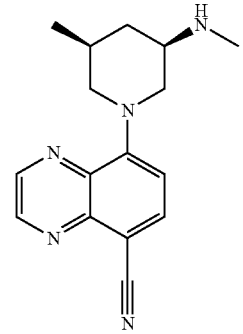 [SMILES: CN[C@@H]1C[C@H](C)CN(c2ccc(C#N)c3nccnc23)C1] |
| 17 | 11 | 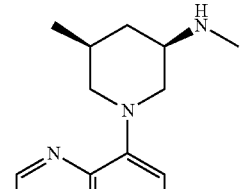 |
| 18 | 12 | 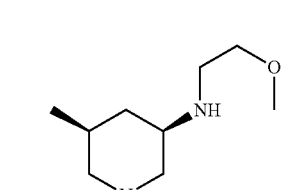 |

TABLE 1-continued
| Compound Number | Example Number | Chemical Structure |
|---|---|---|
| 19 | 12 | 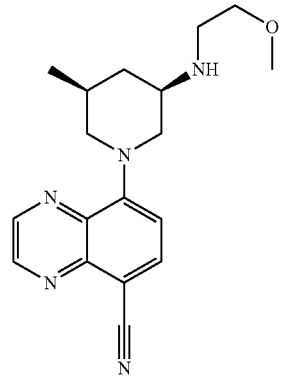 [SMILES: COCCN[C@@H]1C[C@H](C)CN(c2ccc(C#N)c3nccnc23)C1] |
| 20 | 10 | 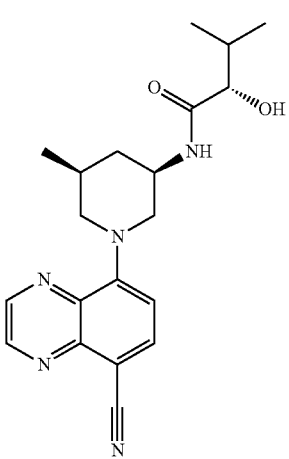 [SMILES: CC(C)[C@H](O)C(=O)N[C@@H]1C[C@H](C)CN(c2ccc(C#N)c3nccnc23)C1] |
| 21 | 10 | 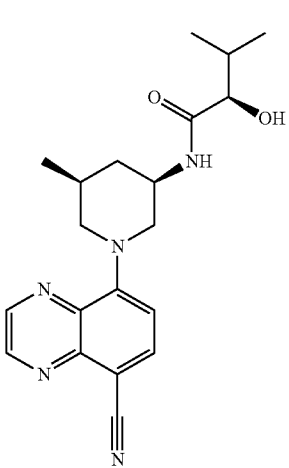 [SMILES: CC(C)[C@@H](O)C(=O)N[C@@H]1C[C@H](C)CN(c2ccc(C#N)c3nccnc23)C1] |

TABLE 1-continued
| Compound Number | Example Number | Chemical Structure |
|---|---|---|
| 22 | 10 | 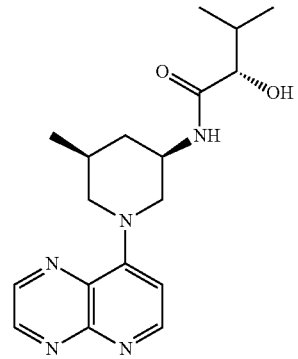 [SMILES: CC(C)[C@H](O)C(=O)N[C@@H]1C[C@H](C)CN(c2ccnc3nccnc23)C1] |
| 23 | 10 | 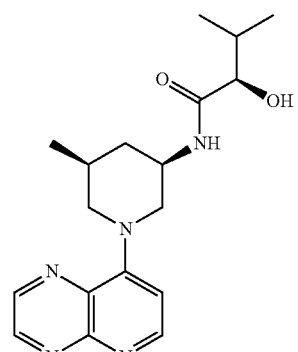 |
| 24 | 13 | 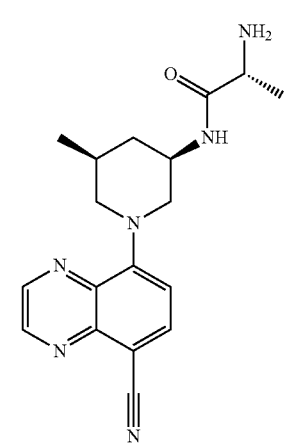 [SMILES: C[C@H]1C[C@@H](NC(=O)[C@@H](C)N)CN(c2ccc(C#N)c3nccnc23)C1] |
| 25 | 13 | 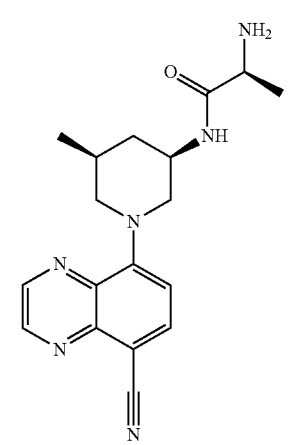 [SMILES: C[C@H]1C[C@@H](NC(=O)[C@H](C)N)CN(c2ccc(C#N)c3nccnc23)C1] |

TABLE 1-continued
| Compound Number | Example Number | Chemical Structure |
|---|---|---|
| 26 | 13 | 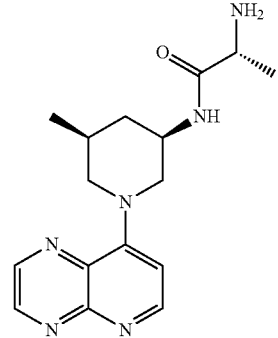 [SMILES: C[C@H]1C[C@@H](NC(=O)[C@@H](C)N)CN(c2ccnc3nccnc23)C1] |
| 27 | 13 | 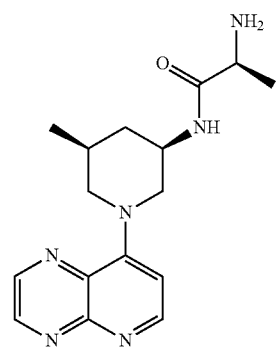 [SMILES: C[C@H]1C[C@@H](NC(=O)[C@H](C)N)CN(c2ccnc3nccnc23)C1] |
| 28 | 13 | 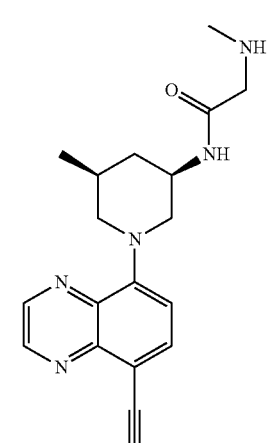 |
| 29 | 13 | 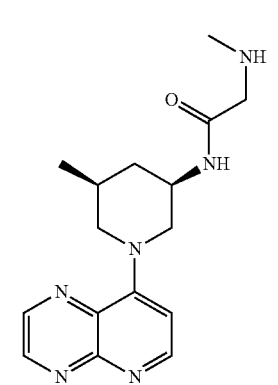 [SMILES: CNCC(=O)N[C@@H]1C[C@H](C)CN(c2ccnc3nccnc23)C1] |

TABLE 1-continued
| Compound Number | Example Number | Chemical Structure |
|---|---|---|
| 30 | 13 | 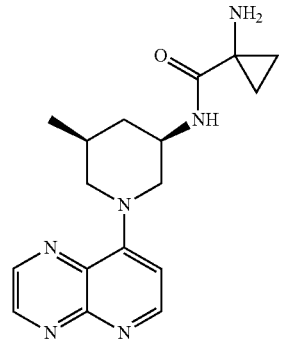 [SMILES: C[C@H]1C[C@@H](NC(=O)C2(N)CC2)CN(c2ccnc3nccnc23)C1] |
| 31 | 13 | 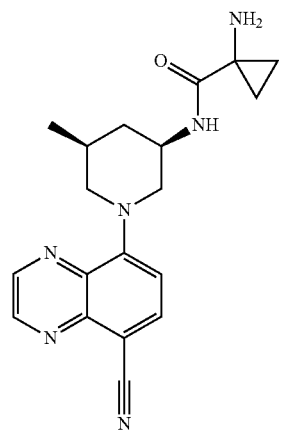 [SMILES: C[C@H]1C[C@@H](NC(=O)C2(N)CC2)CN(c2ccc(C#N)c3nccnc23)C1] |
| 32 | 10 | 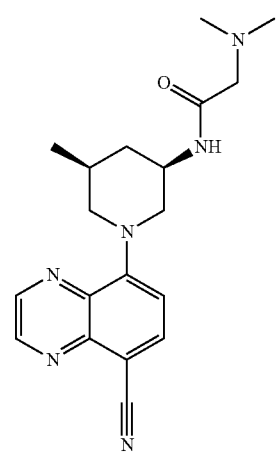 [SMILES: C[C@H]1C[C@@H](NC(=O)CN(C)C)CN(c2ccc(C#N)c3nccnc23)C1] |
| 33 | 10 | 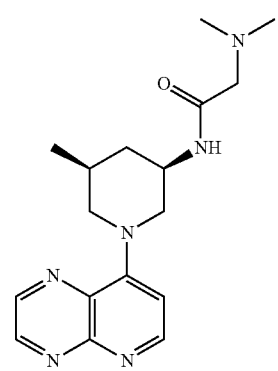 [SMILES: C[C@H]1C[C@@H](NC(=O)CN(C)C)CN(c2ccnc3nccnc23)C1] |

TABLE 1-continued
| Compound Number | Example Number | Chemical Structure |
|---|---|---|
| 34 | 13 | 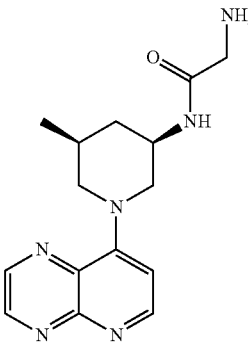 |
| 35 | 13 | 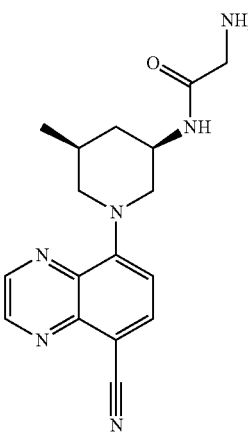 |
| 36 | 10 | 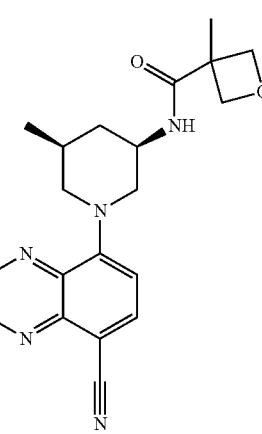 |
| 37 | 10 | 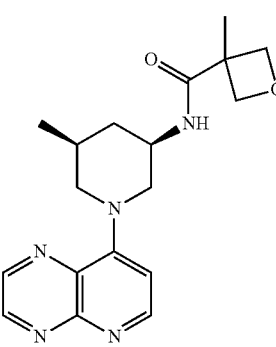 |

TABLE 1-continued
| Compound Number | Example Number | Chemical Structure |
|---|---|---|
| 38 | 12 | 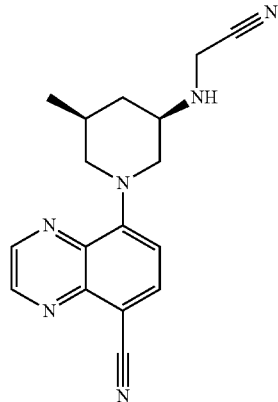 [SMILES: C[C@H]1C[C@@H](NCC#N)CN(c2ccc(C#N)c3nccnc23)C1] |
| 39 | 12 | 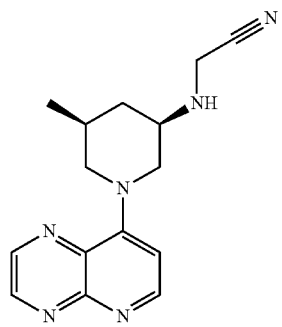 [SMILES: C[C@H]1C[C@@H](NCC#N)CN(c2ccnc3nccnc23)C1] |
| 40 | 10 | 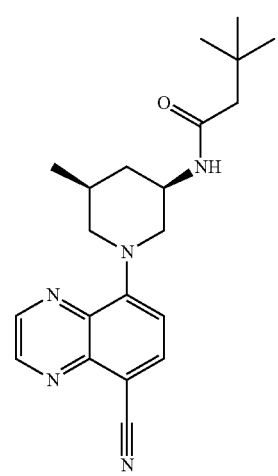 [SMILES: C[C@H]1C[C@@H](NC(=O)CC(C)(C)C)CN(c2ccc(C#N)c3nccnc23)C1] |
| 41 | 10 | 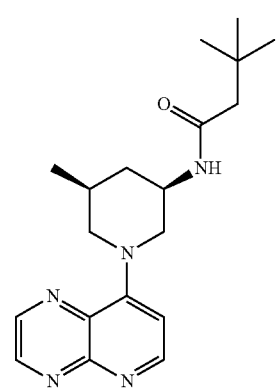 [SMILES: C[C@H]1C[C@@H](NC(=O)CC(C)(C)C)CN(c2ccnc3nccnc23)C1] |

TABLE 1-continued

| Compound Number | Example Number | Chemical Structure |
|---|---|---|
| 42 | 14 | 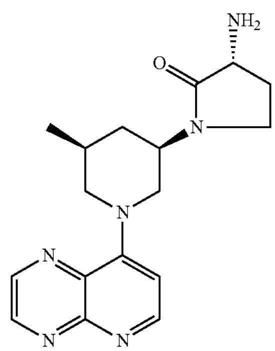 [SMILES: C[C@H]1C[C@@H](N2CC[C@@H](N)C2=O)CN(c2ccnc3nccnc23)C1] |
| 43 | 15 | 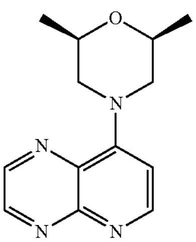 [SMILES: C[C@@H]1CN(c2ccnc3nccnc23)C[C@H](C)O1] |
| 44 | 16 | 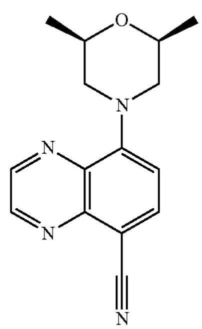 [SMILES: C[C@@H]1CN(c2ccc(C#N)c3nccnc23)C[C@H](C)O1] |
| 45 | 16 | 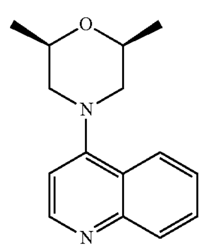 [SMILES: C[C@@H]1CN(c2ccnc3ccccc23)C[C@H](C)O1] |
| 46 | 17 | 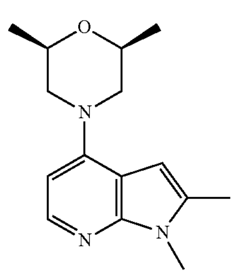 |

TABLE 1-continued

| Compound Number | Example Number | Chemical Structure |
|---|---|---|
| 47 | 18 | 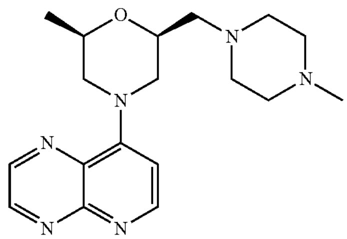 [SMILES: C[C@@H]1CN(c2ccnc3nccnc23)C[C@H](CN2CCN(C)CC2)O1] |
| 48 | 19 | 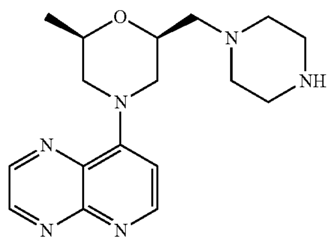 [SMILES: C[C@@H]1CN(c2ccnc3nccnc23)C[C@H](CN2CCNCC2)O1] |
| 49 | 20 | 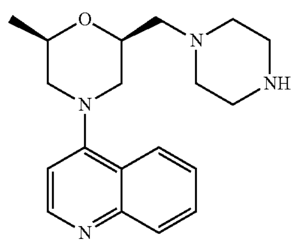 [SMILES: C[C@@H]1CN(c2ccnc3ccccc23)C[C@H](CN2CCNCC2)O1] |
| 50 | 21 | 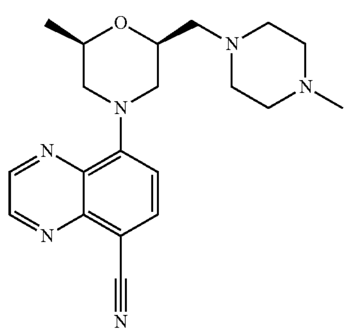 [SMILES: C[C@@H]1CN(c2ccc(C#N)c3nccnc23)C[C@H](CN2CCN(C)CC2)O1] |
| 51 | 22 | 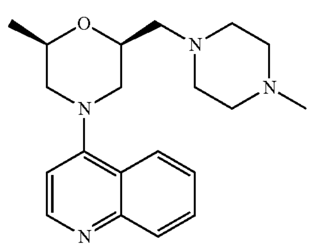 |
| 52 | 22 | 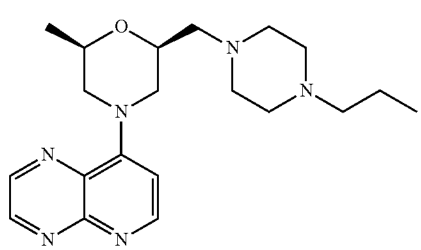 [SMILES: CCCN1CCN(C[C@H]2CN(c3ccnc4nccnc34)C[C@@H](C)O2)CC1] |

TABLE 1-continued

| Compound Number | Example Number | Chemical Structure |
|---|---|---|
| 53 | 22 | 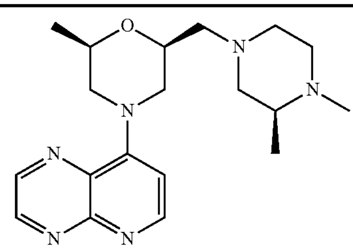 |
| 54 | 22 | 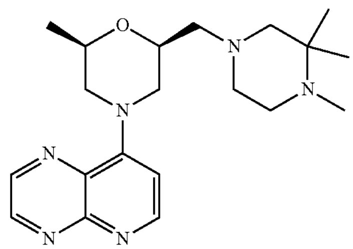 [SMILES: C[C@@H]1CN(c2ccnc3nccnc23)C[C@H](CN2CCN(C)C(C)(C)C2)O1] |
| 55 | 22 | 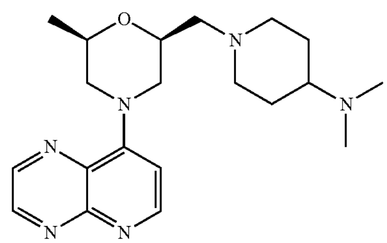 [SMILES: C[C@@H]1CN(c2ccnc3nccnc23)C[C@H](CN2CCC(N(C)C)CC2)O1] |
| 56 | 22 | 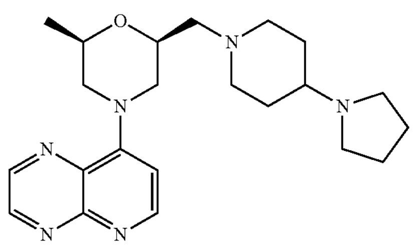 [SMILES: C[C@@H]1CN(c2ccnc3nccnc23)C[C@H](CN2CCC(N3CCCC3)CC2)O1] |
| 57 | 22 | 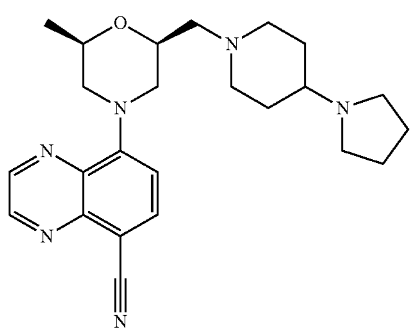 [SMILES: C[C@@H]1CN(c2ccc(C#N)c3nccnc23)C[C@H](CN2CCC(N3CCCC3)CC2)O1] |
| 58 | 22 | 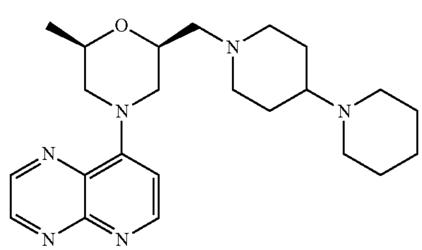 [SMILES: C[C@@H]1CN(c2ccnc3nccnc23)C[C@H](CN2CCC(N3CCCCC3)CC2)O1] |

TABLE 1-continued
| Compound Number | Example Number | Chemical Structure |
|---|---|---|
| 59 | 22 | 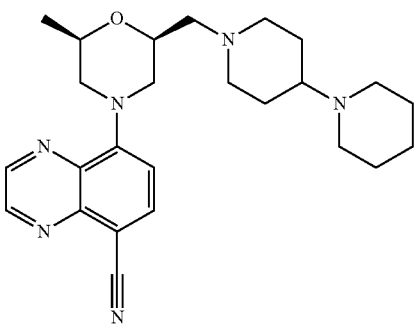 [SMILES: C[C@@H]1CN(c2ccc(C#N)c3nccnc23)C[C@H](CN2CCC(N3CCCCC3)CC2)O1] |
| 60 | 22 | 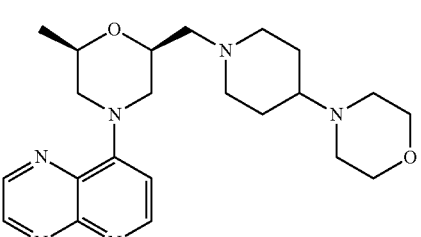 |
| 61 | 23 | 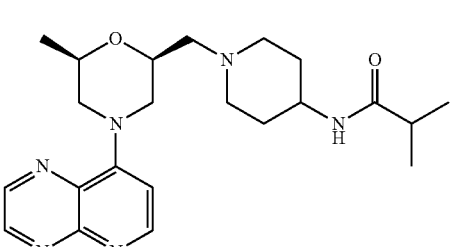 |
| 62 | 24 | 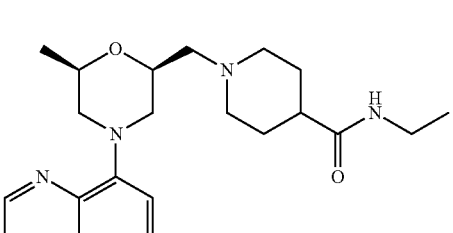 |
| 63 | 25 | 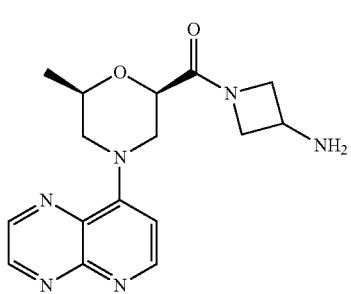 [SMILES: C[C@@H]1CN(c2ccnc3nccnc23)C[C@H](C(=O)N2CC(N)C2)O1] |

TABLE 1-continued
| Compound Number | Example Number | Chemical Structure |
|---|---|---|
| 64 | 25 | 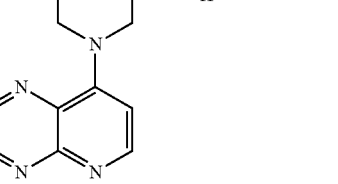 |
| 65 | 25 | 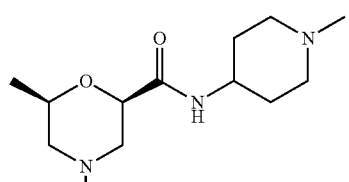 |
| 66 | 26 | 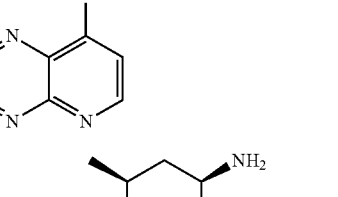 |
| 67 | 27 | 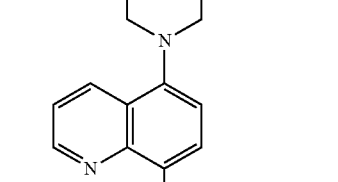 |
| 68 | 28 | 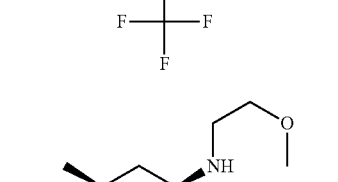 |

TABLE 1-continued
| Compound Number | Example Number | Chemical Structure |
|---|---|---|
| 69 | 29 | 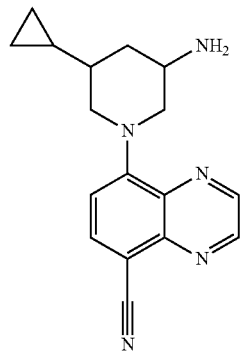<br>cis Isomer 1 |
| 70 | 29 | 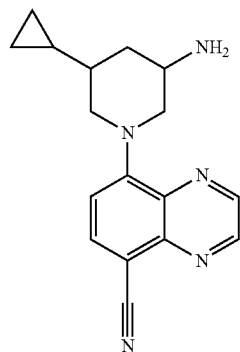<br>cis Isomer 2 |
| 71 | 30 | 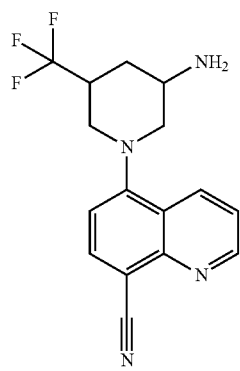<br>Cis racemic |

TABLE 1-continued
| Compound Number | Example Number | Chemical Structure |
|---|---|---|
| 72 | 31 | 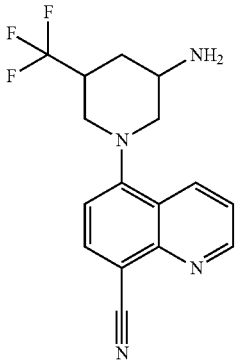<br>cis Isomer 1 |
| 73 | 31 | 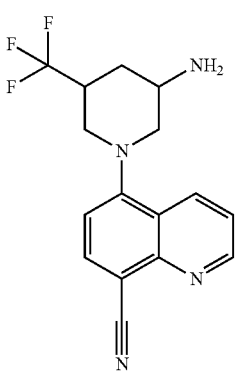<br>cis Isomer 2 |
| 74 | 32 | 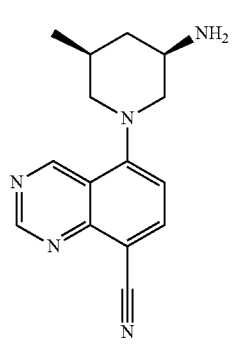 [SMILES: C[C@H]1C[C@@H](N)CN(c2ccc(C#N)c3ncncc23)C1] |
| 75 | 33 | 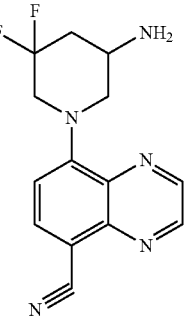<br>Isomer 1 |

TABLE 1-continued

| Compound Number | Example Number | Chemical Structure |
|---|---|---|
| 76 | 33 | Isomer 2 |
| 77 | 34 | 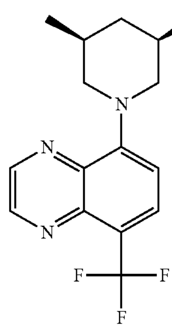 |
| 78 | 35 | 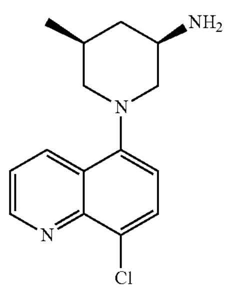 [SMILES: C[C@H]1C[C@@H](N)CN(c2ccc(Cl)c3ncccc23)C1] |
| 79 | 36 | 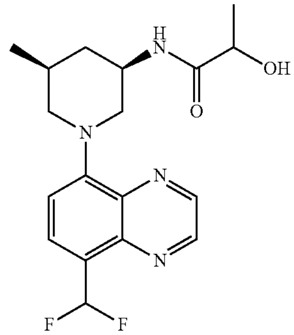 [SMILES: CC(O)C(=O)N[C@@H]1C[C@H](C)CN(c2ccc(C(F)F)c3nccnc23)C1] |
| 80 | 37 | 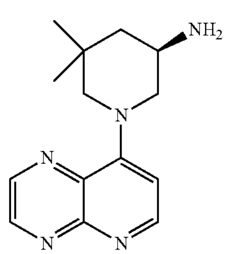 [SMILES: CC1(C)C[C@@H](N)CN(c2ccnc3nccnc23)C1] |

TABLE 1-continued

| Compound Number | Example Number | Chemical Structure |
|---|---|---|
| 81 | 38 | 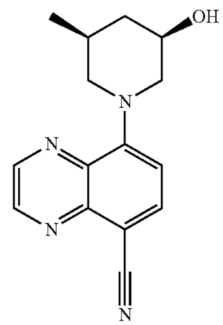 [SMILES: C[C@H]1C[C@@H](O)CN(c2ccc(C#N)c3nccnc23)C1] |
| 82 | 39 | cis Isomer 1 |
| 83 | 39 | cis Isomer 2 |
| 84 | 39 | cis racemic |

TABLE 1-continued
| Compound Number | Example Number | Chemical Structure |
|---|---|---|
| 85 | 40 | 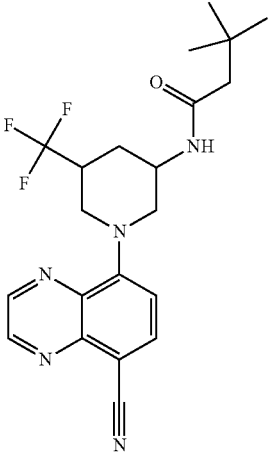<br>cis racemic |
| 86 | 40 | 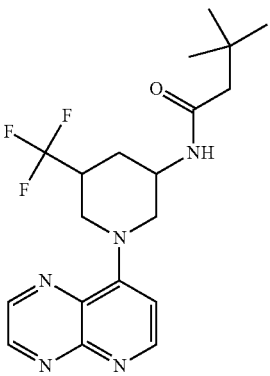<br>cis racemic |
| 87 | 41 | 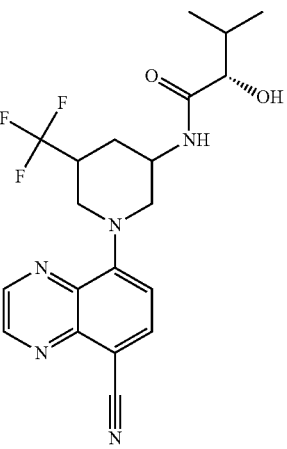<br>cis Isomer 1 |

TABLE 1-continued
| Compound Number | Example Number | Chemical Structure |
|---|---|---|
| 88 | 41 | 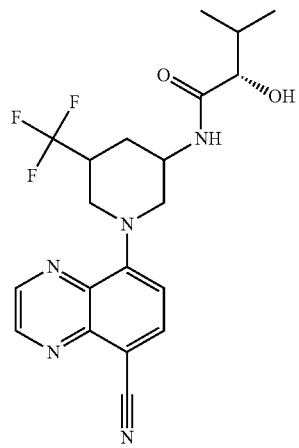<br>cis Isomer 2 |
| 89 | 41 | 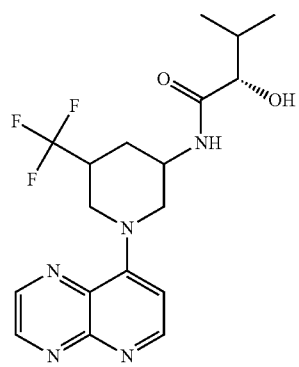<br>Isomer 1 |
| 90 | 41 | 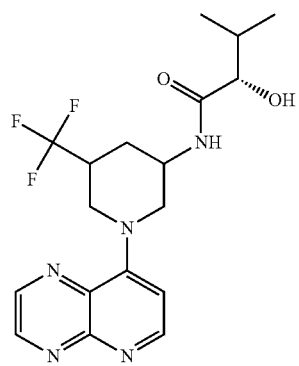<br>cis Isomer 2 |

TABLE 1-continued
| Compound Number | Example Number | Chemical Structure |
|---|---|---|
| 91 | 42 | 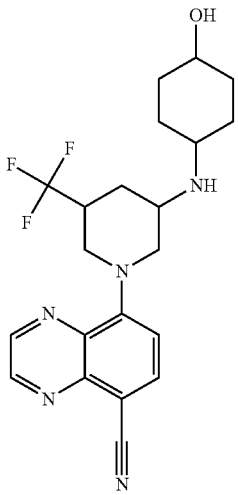<br>Isomer 1 |
| 92 | 42 | 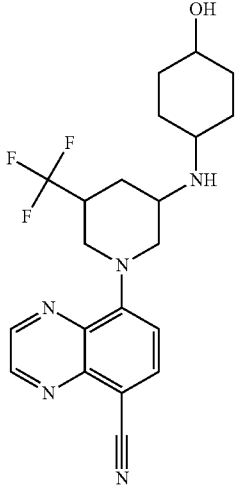<br>Isomer 2 |
| 93 | 42 | 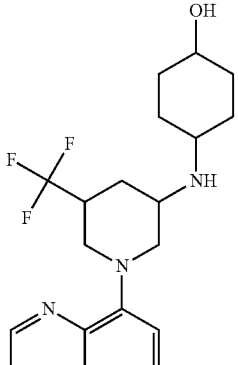<br>Isomer 1 |

TABLE 1-continued
| Compound Number | Example Number | Chemical Structure |
|---|---|---|
| 94 | 42 | 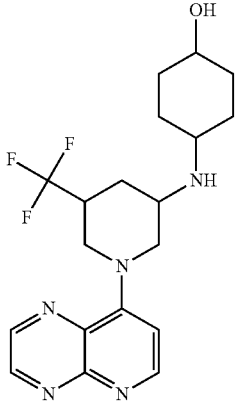<br>Isomer 2 |
| 95 | 42 | 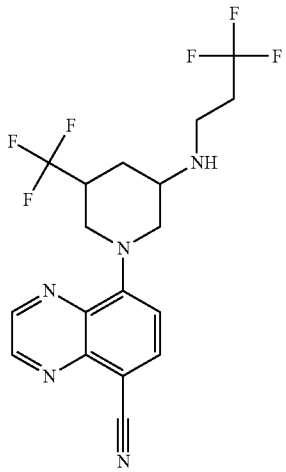<br>cis racemic |
| 96 | 42 | 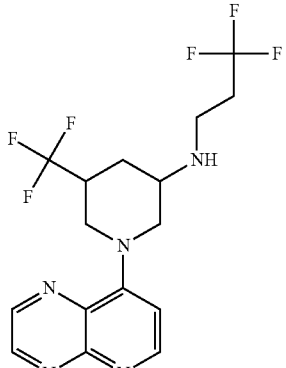<br>cis racemic |

TABLE 1-continued
| Compound Number | Example Number | Chemical Structure |
|---|---|---|
| 97 | 10 | 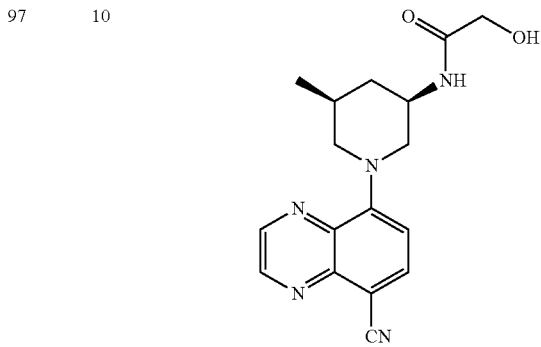 |
| 98 | 43 | 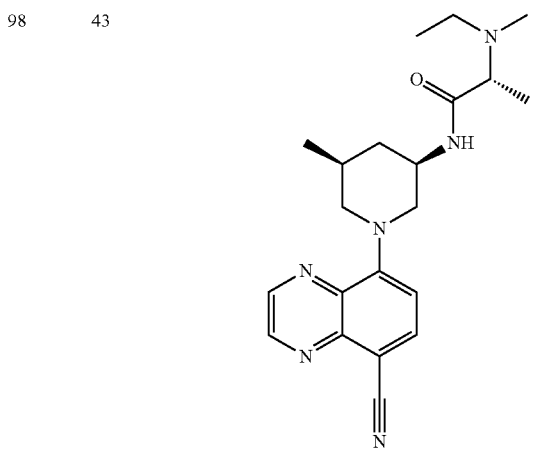 |
| 99 | 43 | 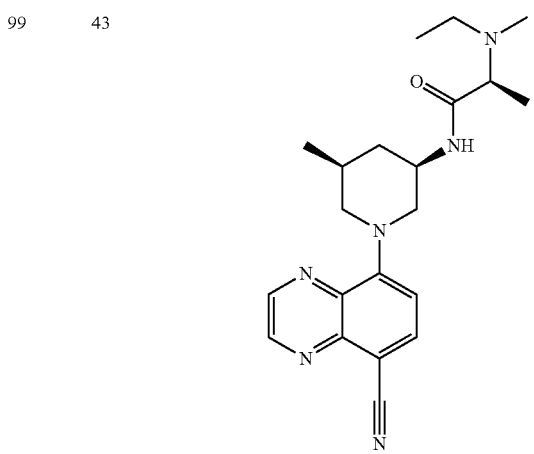 |

TABLE 1-continued
| Compound Number | Example Number | Chemical Structure |
|---|---|---|
| 100 | 43 | 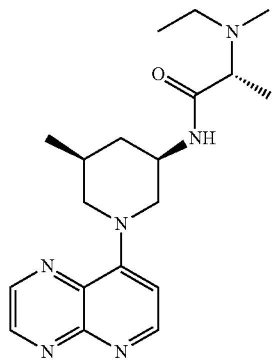 [SMILES: CCN(C)[C@H](C)C(=O)N[C@@H]1C[C@H](C)CN(c2ccnc3nccnc23)C1] |
| 101 | 43 | 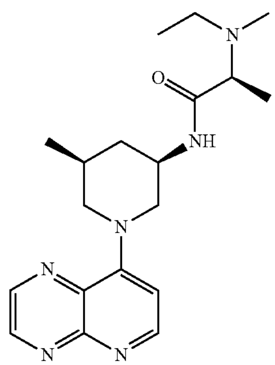 [SMILES: CCN(C)[C@@H](C)C(=O)N[C@@H]1C[C@H](C)CN(c2ccnc3nccnc23)C1] |
| 102 | 13 | 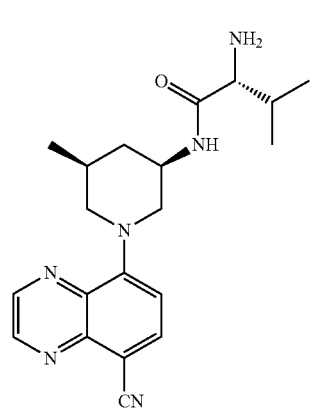 [SMILES: CC(C)[C@@H](N)C(=O)N[C@@H]1C[C@H](C)CN(c2ccc(C#N)c3nccnc23)C1] |
| 103 | 13 | 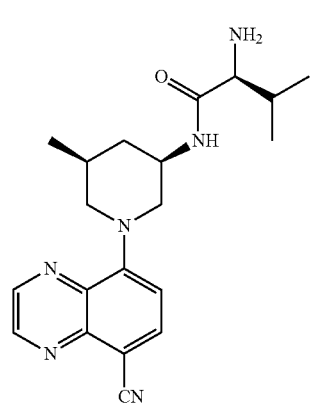 [SMILES: CC(C)[C@H](N)C(=O)N[C@@H]1C[C@H](C)CN(c2ccc(C#N)c3nccnc23)C1] |

TABLE 1-continued
| Compound Number | Example Number | Chemical Structure |
|---|---|---|
| 104 | 13 | 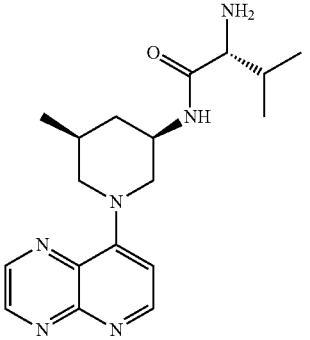 [SMILES: CC(C)[C@@H](N)C(=O)N[C@@H]1C[C@H](C)CN(c2ccnc3nccnc23)C1] |
| 105 | 13 | 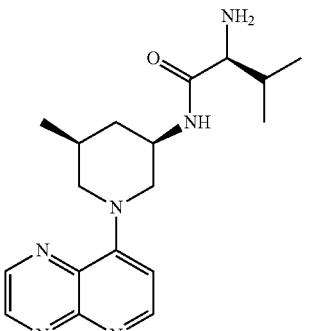 |
| 106 | 13 | 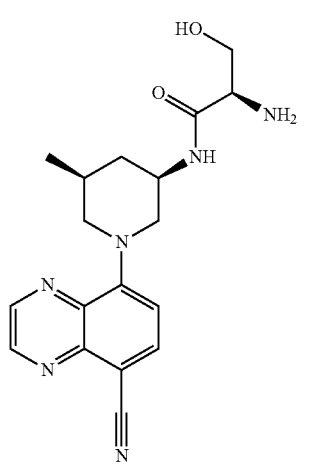 [SMILES: C[C@H]1C[C@@H](NC(=O)[C@H](N)CO)CN(c2ccc(C#N)c3nccnc23)C1] |
| 107 | 13 | 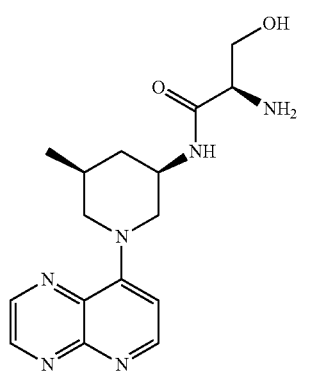 [SMILES: C[C@H]1C[C@@H](NC(=O)[C@H](N)CO)CN(c2ccnc3nccnc23)C1] |

TABLE 1-continued
| Compound Number | Example Number | Chemical Structure |
|---|---|---|
| 108 | 10 | 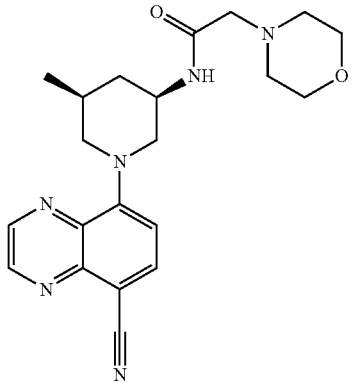 [SMILES: C[C@H]1C[C@@H](NC(=O)CN2CCOCC2)CN(c2ccc(C#N)c3nccnc23)C1] |
| 109 | 10 | 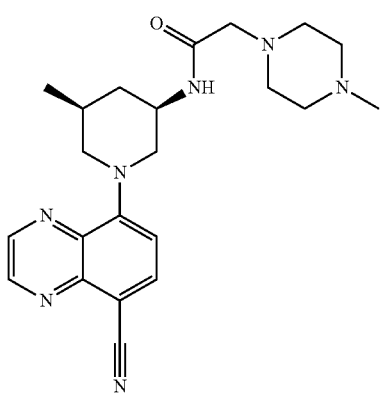 [SMILES: C[C@H]1C[C@@H](NC(=O)CN2CCN(C)CC2)CN(c2ccc(C#N)c3nccnc23)C1] |
| 110 | 10 | 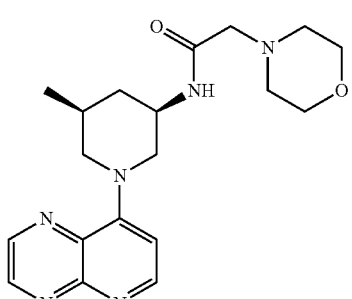 |
| 111 | 10 | 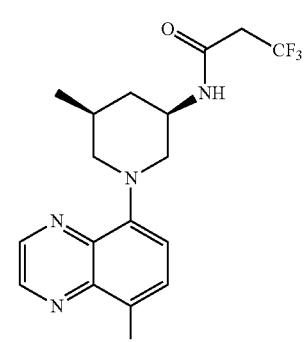 |

TABLE 1-continued
| Compound Number | Example Number | Chemical Structure |
|---|---|---|
| 112 | 44 | 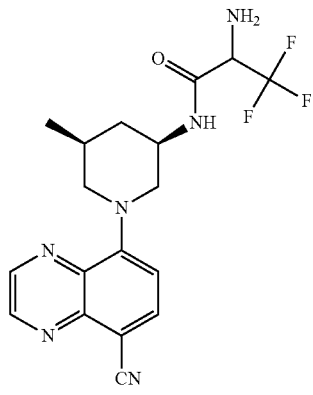<br>Isomer 1 |
| 113 | 44 | 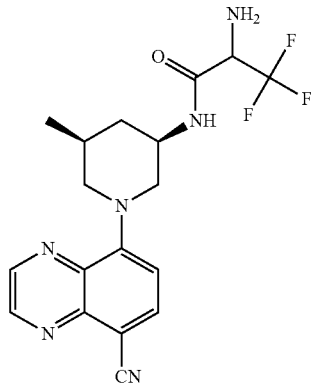<br>Isomer 2 |
| 114 | 44 | 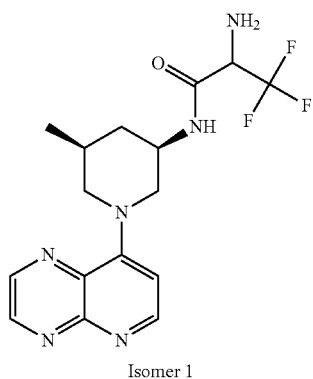 [SMILES: C[C@H]1C[C@@H](NC(=O)C(N)C(F)(F)F)CN(c2ccnc3nccnc23)C1]<br>Isomer 1 |

TABLE 1-continued
| Compound Number | Example Number | Chemical Structure |
|---|---|---|
| 115 | 44 | 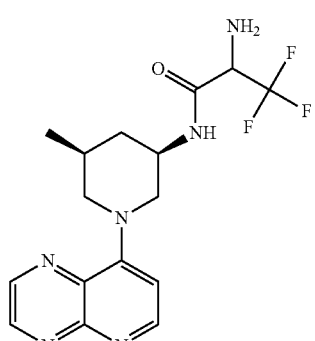<br>Isomer 2 |
| 116 | 13 | 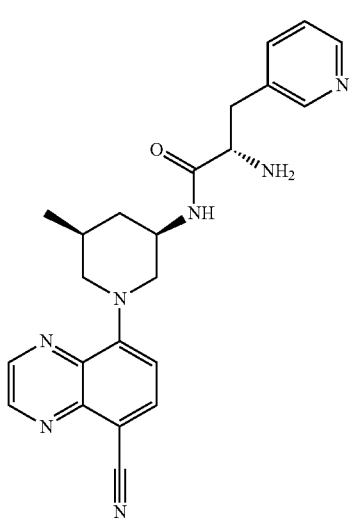 [SMILES: C[C@H]1C[C@@H](NC(=O)[C@@H](N)Cc2cccnc2)CN(c2ccc(C#N)c3nccnc23)C1] |
| 117 | 13 | 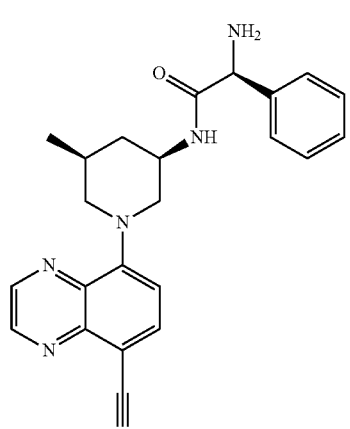 |

TABLE 1-continued

| Compound Number | Example Number | Chemical Structure |
|---|---|---|
| 118 | 13 | 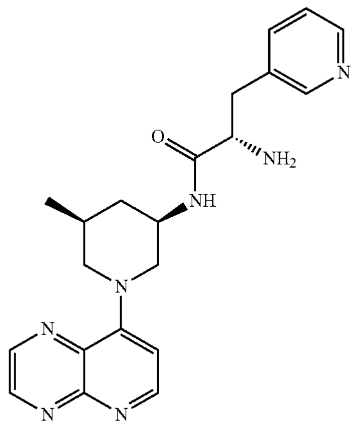 [SMILES: C[C@H]1C[C@@H](NC(=O)[C@@H](N)Cc2cccnc2)CN(c2ccnc3nccnc23)C1] |
| 119 | 13 | 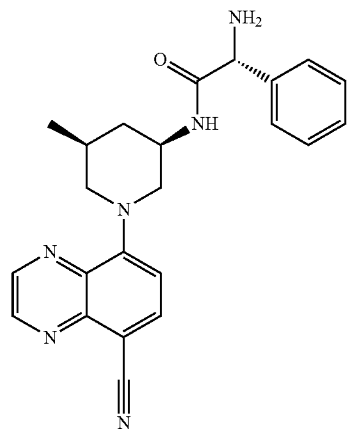 [SMILES: C[C@H]1C[C@@H](NC(=O)[C@H](N)c2ccccc2)CN(c2ccc(C#N)c3nccnc23)C1] |
| 120 | 10 | 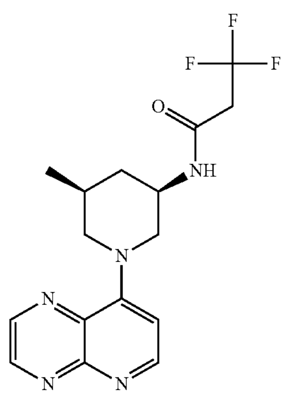 [SMILES: C[C@H]1C[C@@H](NC(=O)CC(F)(F)F)CN(c2ccnc3nccnc23)C1] |
| 121 | 12 | 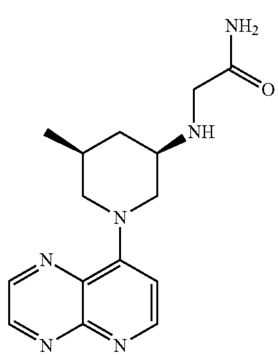 [SMILES: C[C@H]1C[C@@H](NCC(N)=O)CN(c2ccnc3nccnc23)C1] |

TABLE 1-continued
| Compound Number | Example Number | Chemical Structure |
|---|---|---|
| 122 | 12 | 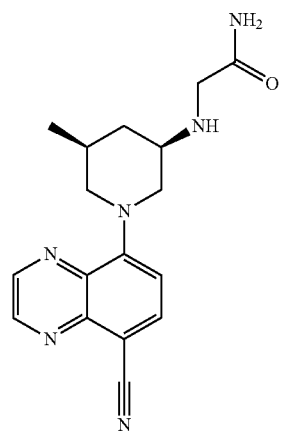 [SMILES: C[C@H]1C[C@@H](NCC(N)=O)CN(c2ccc(C#N)c3nccnc23)C1] |
| 123 | 45 | 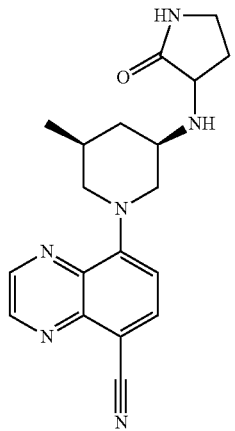 [SMILES: C[C@H]1C[C@@H](NC2CCNC2=O)CN(c2ccc(C#N)c3nccnc23)C1] |
| 124 | 46 | 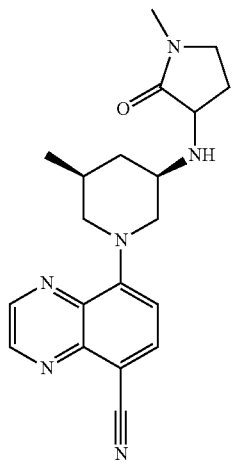<br>Isomer 1 |

TABLE 1-continued
| Compound Number | Example Number | Chemical Structure |
|---|---|---|
| 125 | 46 | 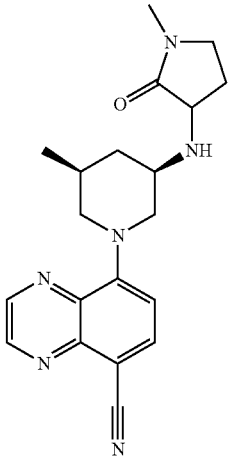<br>Isomer 2 |
| 126 | 12 | 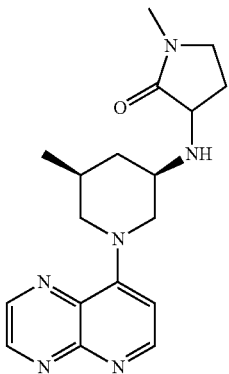 [SMILES: C[C@H]1C[C@@H](NC2CCN(C)C2=O)CN(c2ccnc3nccnc23)C1] |
| 127 | 45 | 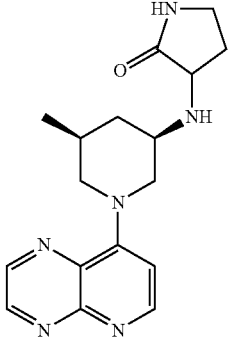 [SMILES: C[C@H]1C[C@@H](NC2CCNC2=O)CN(c2ccnc3nccnc23)C1] |
| 128 | 13 | 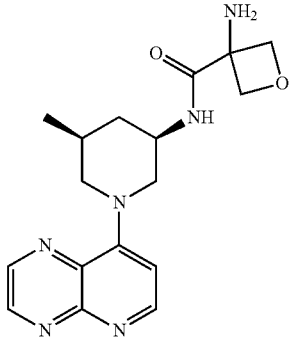 [SMILES: C[C@H]1C[C@@H](NC(=O)C2(N)COC2)CN(c2ccnc3nccnc23)C1] |

TABLE 1-continued
| Compound Number | Example Number | Chemical Structure |
|---|---|---|
| 129 | 13 | 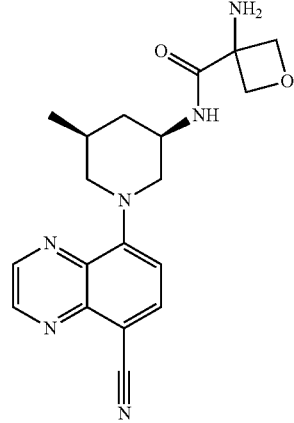 [SMILES: C[C@H]1C[C@@H](NC(=O)C2(N)COC2)CN(c2ccc(C#N)c3nccnc23)C1] |
| 130 | 10 | 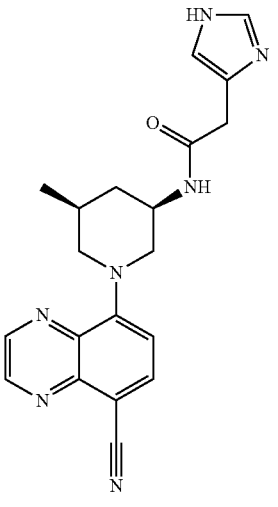 [SMILES: C[C@H]1C[C@@H](NC(=O)Cc2c[nH]cn2)CN(c2ccc(C#N)c3nccnc23)C1] |
| 131 | 10 | 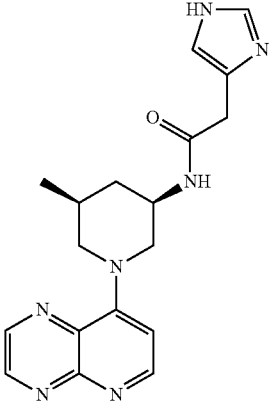 [SMILES: C[C@H]1C[C@@H](NC(=O)Cc2c[nH]cn2)CN(c2ccnc3nccnc23)C1] |

TABLE 1-continued
| Compound Number | Example Number | Chemical Structure |
|---|---|---|
| 132 | 10 | 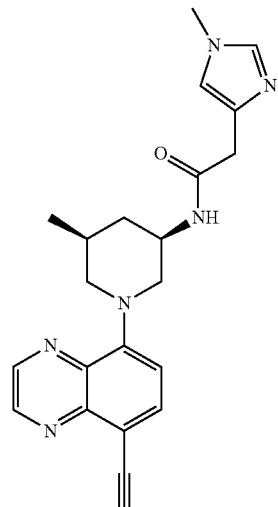 |
| 133 | 10 | 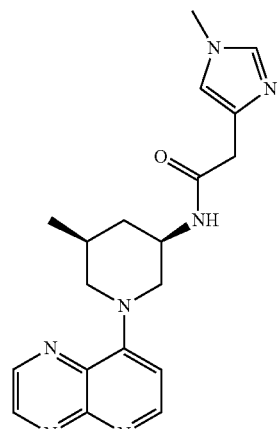 |
| 134 | 10 | 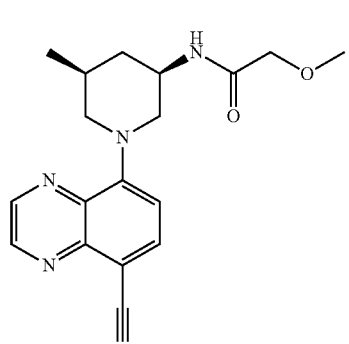 |

TABLE 1-continued
| Compound Number | Example Number | Chemical Structure |
|---|---|---|
| 135 | 42 | 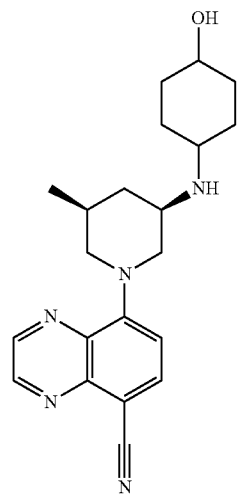<br>Isomer 1 |
| 136 | 42 | 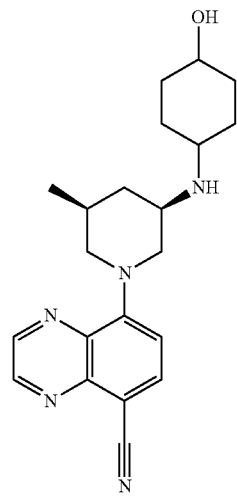<br>Isomer 2 |
| 137 | 42 | 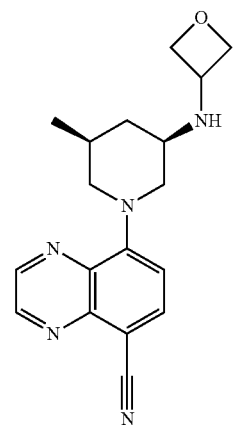 [SMILES: C[C@H]1C[C@@H](NC2COC2)CN(c2ccc(C#N)c3nccnc23)C1] |

TABLE 1-continued
| Compound Number | Example Number | Chemical Structure |
|---|---|---|
| 138 | 42 | 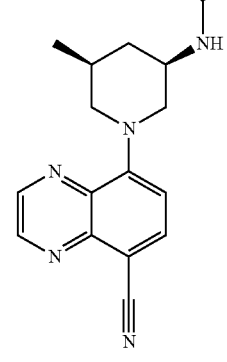 |
| 139 | 42 | 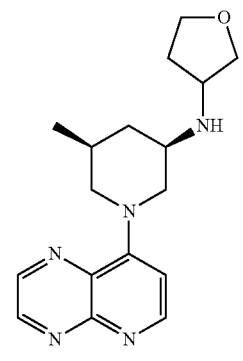 [SMILES: C[C@H]1C[C@@H](NC2CCOC2)CN(c2ccnc3nccnc23)C1] |
| 140 | 10 | 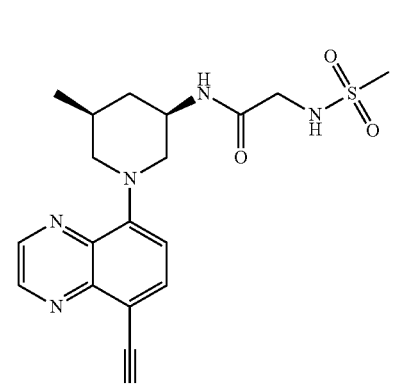 |
| 141 | 10 | 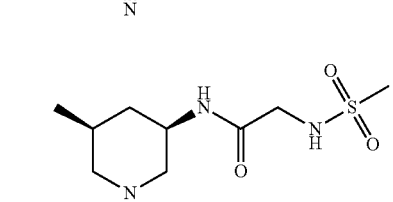 |

TABLE 1-continued

| Compound Number | Example Number | Chemical Structure |
|---|---|---|
| 142 | 10 | 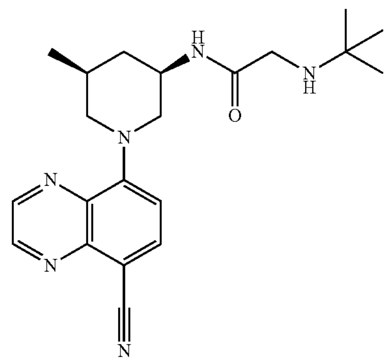 [SMILES: C[C@H]1C[C@@H](NC(=O)CNC(C)(C)C)CN(c2ccc(C#N)c3nccnc23)C1] |
| 143 | 10 | 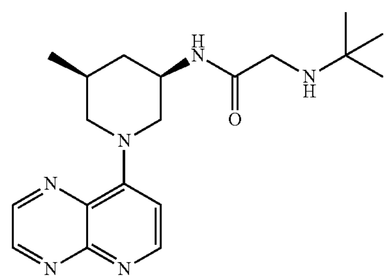 [SMILES: C[C@H]1C[C@@H](NC(=O)CNC(C)(C)C)CN(c2ccnc3nccnc23)C1] |
| 144 | 10 | 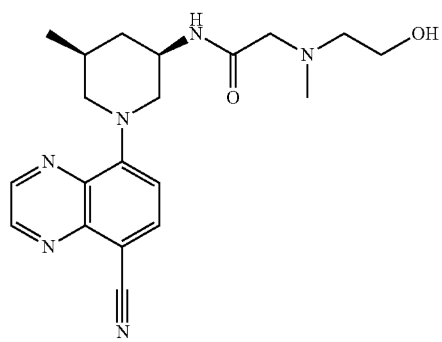 [SMILES: C[C@H]1C[C@@H](NC(=O)CN(C)CCO)CN(c2ccc(C#N)c3nccnc23)C1] |
| 145 | 10 | 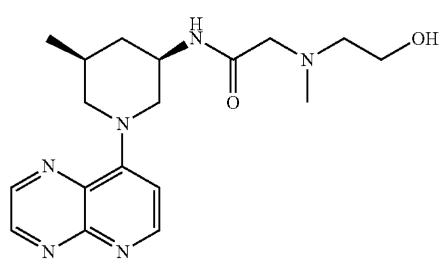 [SMILES: C[C@H]1C[C@@H](NC(=O)CN(C)CCO)CN(c2ccnc3nccnc23)C1] |

TABLE 1-continued
| Compound Number | Example Number | Chemical Structure |
|---|---|---|
| 146 | 41 | 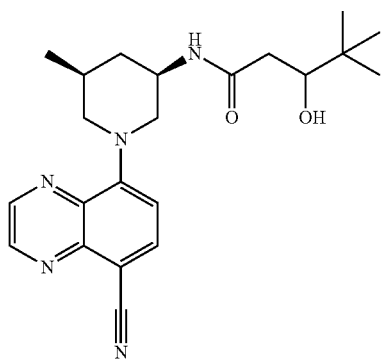<br>Isomer 1 |
| 147 | 41 | 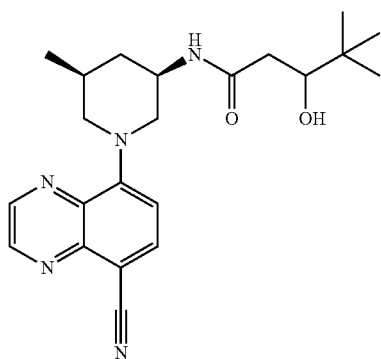<br>Isomer 2 |
| 148 | 41 | 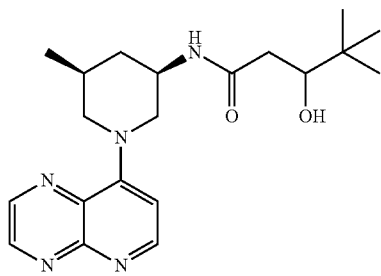<br>Isomer 1 |
| 149 | 41 | 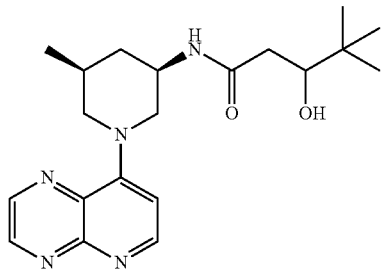<br>Isomer 2 |

TABLE 1-continued
| Compound Number | Example Number | Chemical Structure |
|---|---|---|
| 150 | 41 | 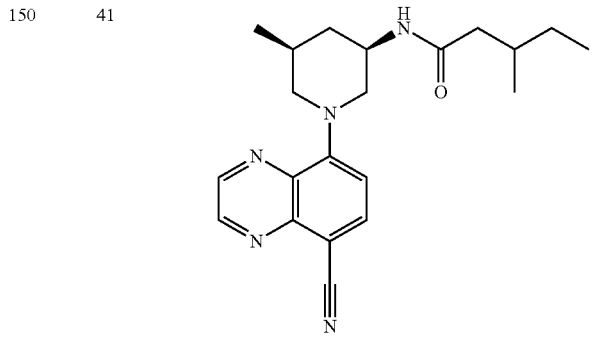<br>Isomer 1 |
| 151 | 41 | 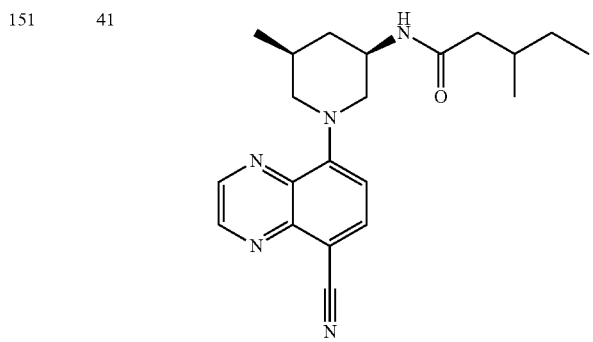<br>Isomer 2 |
| 152 | 41 | 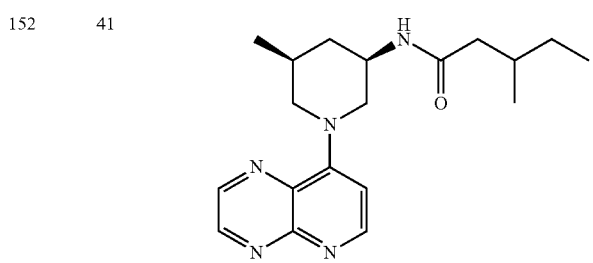<br>Isomer 1 |
| 153 | 41 | 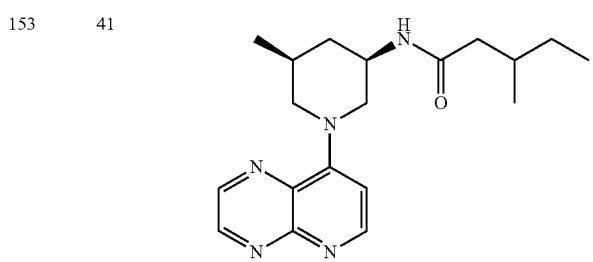<br>Isomer 2 |

TABLE 1-continued
| Compound Number | Example Number | Chemical Structure |
|---|---|---|
| 154 | 41 | 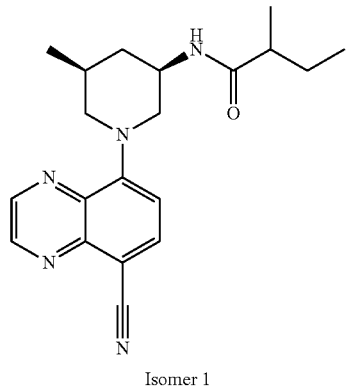 [SMILES: CCC(C)C(=O)N[C@@H]1C[C@H](C)CN(c2ccc(C#N)c3nccnc23)C1]<br>Isomer 1 |
| 155 | 41 | 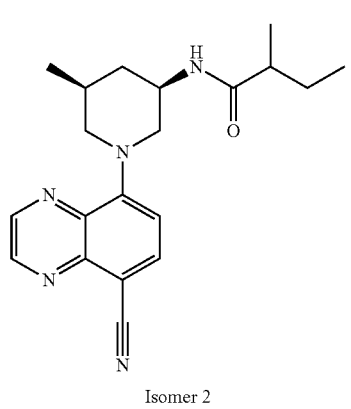 [SMILES: CCC(C)C(=O)N[C@@H]1C[C@H](C)CN(c2ccc(C#N)c3nccnc23)C1]<br>Isomer 2 |
| 156 | 41 | 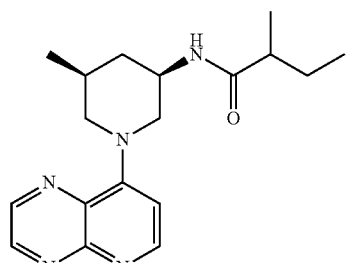<br>Isomer 1 |
| 157 | 41 | 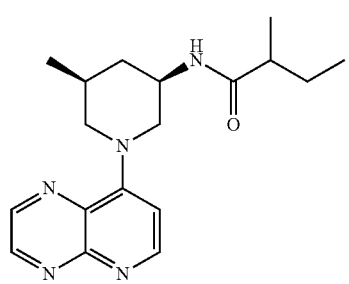<br>Isomer 2 |

TABLE 1-continued
| Compound Number | Example Number | Chemical Structure |
|---|---|---|
| 158 | 41 | 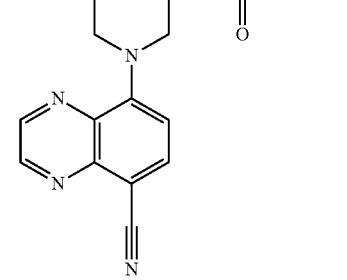<br>Isomer 1 |
| 159 | 41 | 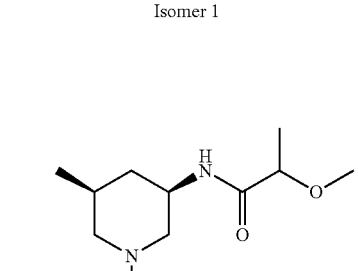<br>Isomer 2 |
| 160 | 41 | <br>Isomer 1 |
| 161 | 41 | <br>Isomer 2 |

TABLE 1-continued
| Compound Number | Example Number | Chemical Structure |
|---|---|---|
| 162 | 47 | 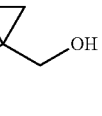 |
| 163 | 10 | 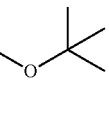 |
| 164 | 10 | 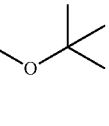 |
| 165 | 10 | 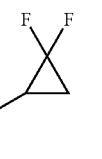 |

TABLE 1-continued

| Compound Number | Example Number | Chemical Structure |
|---|---|---|
| 166 | 10 | 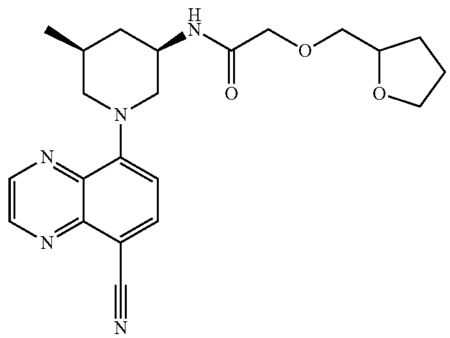 [SMILES: C[C@H]1C[C@@H](NC(=O)COCC2CCCO2)CN(c2ccc(C#N)c3nccnc23)C1] |
| 167 | 10 | 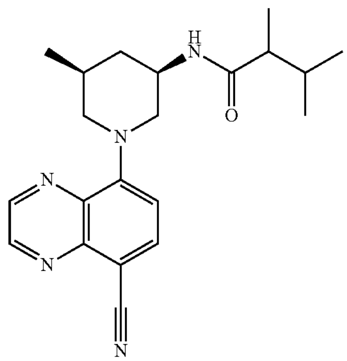 [SMILES: CC(C)C(C)C(=O)N[C@@H]1C[C@H](C)CN(c2ccc(C#N)c3nccnc23)C1] |
| 168 | 10 | 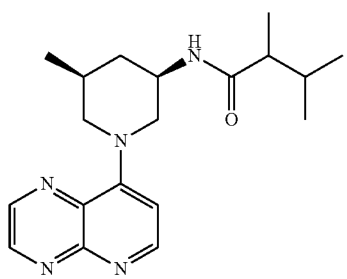 [SMILES: CC(C)C(C)C(=O)N[C@@H]1C[C@H](C)CN(c2ccnc3nccnc23)C1] |
| 169 | 10 | 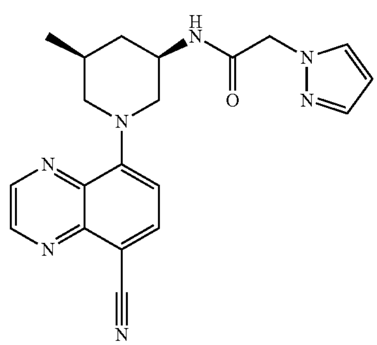 [SMILES: C[C@H]1C[C@@H](NC(=O)Cn2cccn2)CN(c2ccc(C#N)c3nccnc23)C1] |
| 170 | 10 | 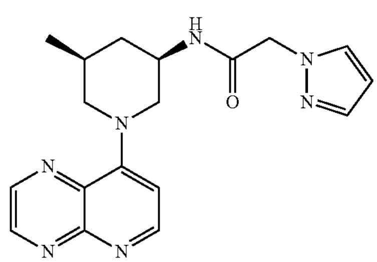 [SMILES: C[C@H]1C[C@@H](NC(=O)Cn2cccn2)CN(c2ccnc3nccnc23)C1] |

TABLE 1-continued
| Compound Number | Example Number | Chemical Structure |
|---|---|---|
| 171 | 10 | 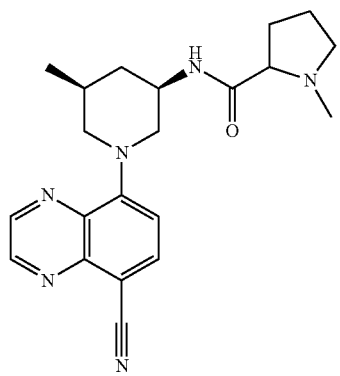 [SMILES: C[C@H]1C[C@@H](NC(=O)C2CCCN2C)CN(c2ccc(C#N)c3nccnc23)C1] |
| 172 | 10 | 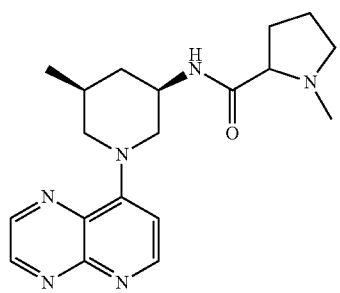 [SMILES: C[C@H]1C[C@@H](NC(=O)C2CCCN2C)CN(c2ccnc3nccnc23)C1] |
| 173 | 41 | 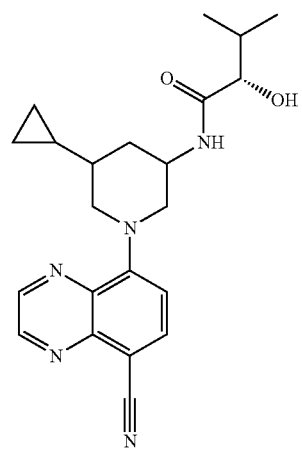<br>cis Isomer 1 |

TABLE 1-continued
| Compound Number | Example Number | Chemical Structure |
|---|---|---|
| 174 | 41 | 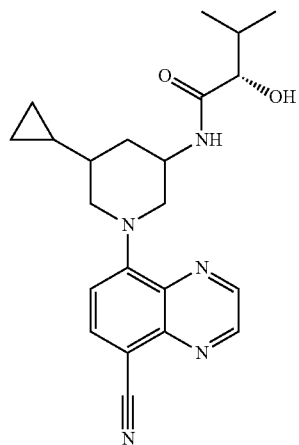<br>cis Isomer 2 |
| 175 | 10 | 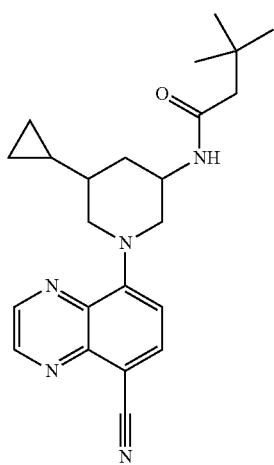<br>cis racemic |
| 176 | 12 | 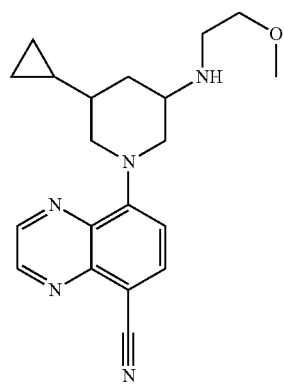<br>cis racemic |

TABLE 1-continued
| Compound Number | Example Number | Chemical Structure |
|---|---|---|
| 177 | 48 | 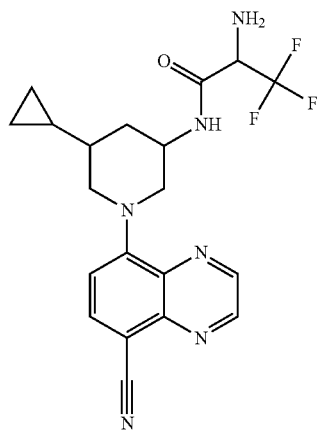<br>cis Isomer 1 |
| 178 | 48 | 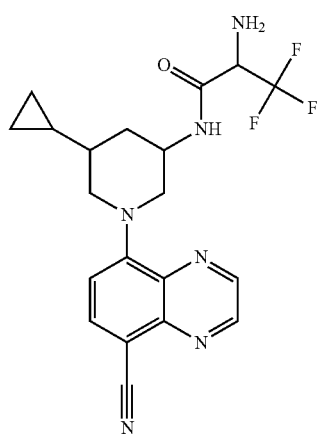<br>cis Isomer 2 |
| 179 | 10 | 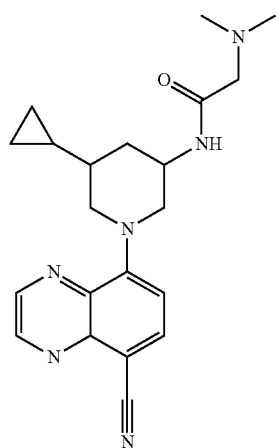<br>cis racemic |

TABLE 1-continued

| Compound Number | Example Number | Chemical Structure |
|---|---|---|
| 180 | 49 | 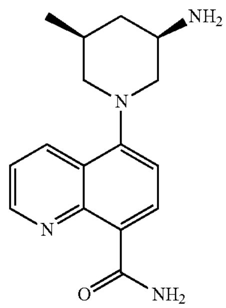 [SMILES: C[C@H]1C[C@@H](N)CN(c2ccc(C(N)=O)c3ncccc23)C1] |
| 181 | 50 | 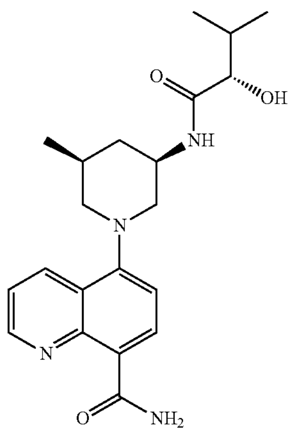 [SMILES: CC(C)[C@H](O)C(=O)N[C@@H]1C[C@H](C)CN(c2ccc(C(N)=O)c3ncccc23)C1] |
| 182 | 50 | 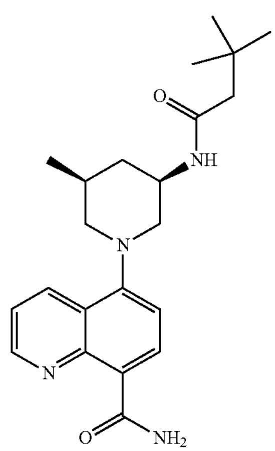 [SMILES: C[C@H]1C[C@@H](NC(=O)CC(C)(C)C)CN(c2ccc(C(N)=O)c3ncccc23)C1] |
| 183 | 51 | 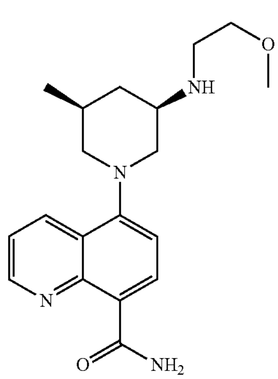 [SMILES: COCCN[C@@H]1C[C@H](C)CN(c2ccc(C(N)=O)c3ncccc23)C1] |

TABLE 1-continued
| Compound Number | Example Number | Chemical Structure |
|---|---|---|
| 184 | 52 | 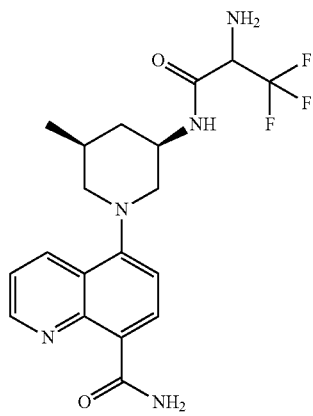<br>Isomer 1 |
| 185 | 52 | 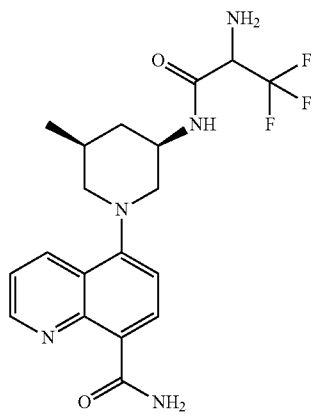<br>Isomer 2 |
| 186 | 42 | 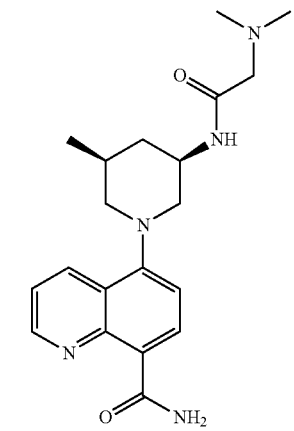 [SMILES: C[C@H]1C[C@@H](NC(=O)CN(C)C)CN(c2ccc(C(N)=O)c3ncccc23)C1] |

TABLE 1-continued

| Compound Number | Example Number | Chemical Structure |
|---|---|---|
| 187 | 53 | 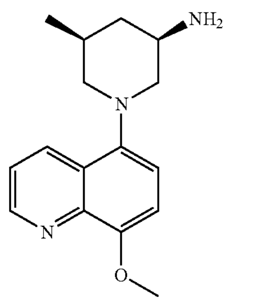 [SMILES: COc1ccc(N2C[C@@H](C)C[C@@H](N)C2)c2cccnc12] |
| 188 | 54 | 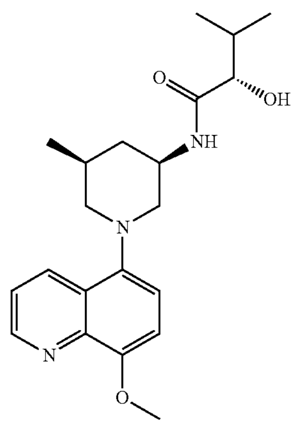 [SMILES: COc1ccc(N2C[C@@H](C)C[C@@H](NC(=O)[C@@H](O)C(C)C)C2)c2cccnc12] |
| 189 | 54 | 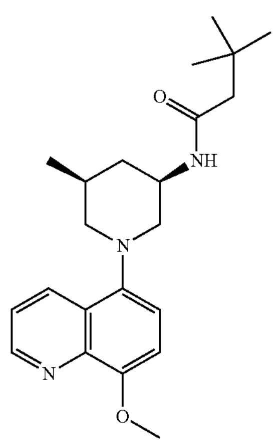 [SMILES: COc1ccc(N2C[C@@H](C)C[C@@H](NC(=O)CC(C)(C)C)C2)c2cccnc12] |
| 190 | 55 | 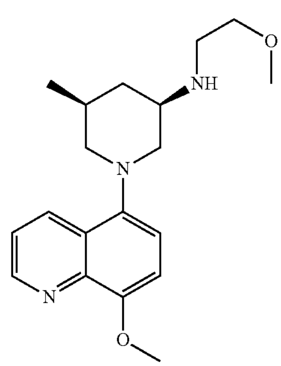 [SMILES: COCCN[C@@H]1C[C@H](C)CN(c2ccc(OC)c3ncccc23)C1] |

TABLE 1-continued
| Compound Number | Example Number | Chemical Structure |
|---|---|---|
| 191 | 56 | 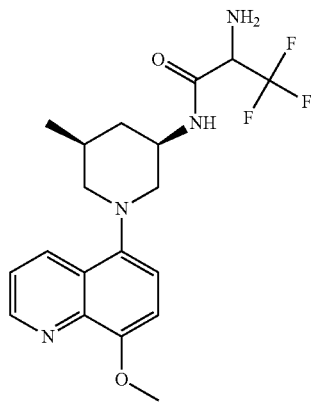<br>Isomer 1 |
| 192 | 56 | 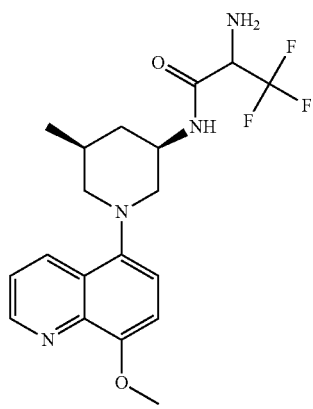<br>Isomer 2 |
| 193 | 54 | 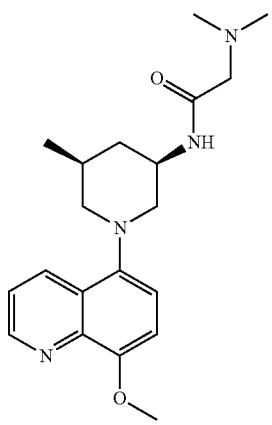 [SMILES: COc1ccc(N2C[C@@H](C)C[C@@H](NC(=O)CN(C)C)C2)c2cccnc12] |

TABLE 1-continued
| Compound Number | Example Number | Chemical Structure |
|---|---|---|
| 194 | 57 | 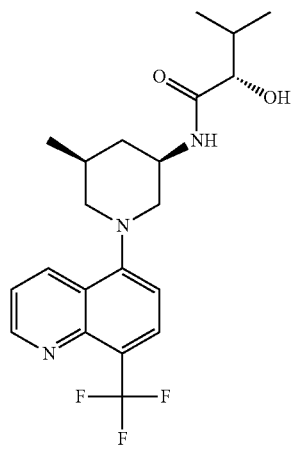 [SMILES: CC(C)[C@H](O)C(=O)N[C@@H]1C[C@H](C)CN(c2ccc(C(F)(F)F)c3ncccc23)C1] |
| 195 | 57 | 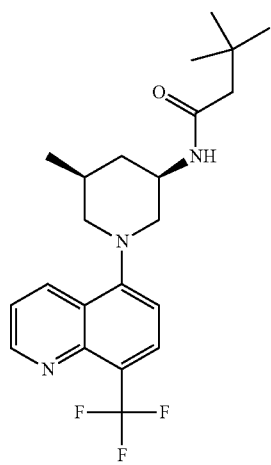 [SMILES: C[C@H]1C[C@@H](NC(=O)CC(C)(C)C)CN(c2ccc(C(F)(F)F)c3ncccc23)C1] |
| 196 | 58 | 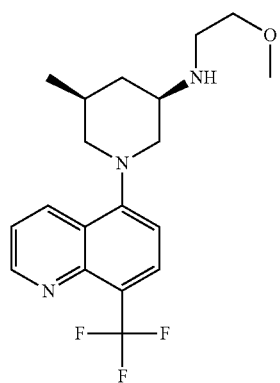 [SMILES: COCCN[C@@H]1C[C@H](C)CN(c2ccc(C(F)(F)F)c3ncccc23)C1] |

TABLE 1-continued
| Compound Number | Example Number | Chemical Structure |
|---|---|---|
| 197 | 59 | 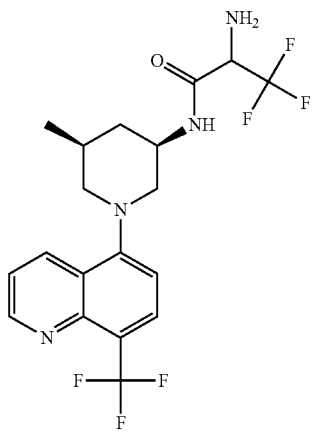<br>Isomer 1 |
| 198 | 59 | 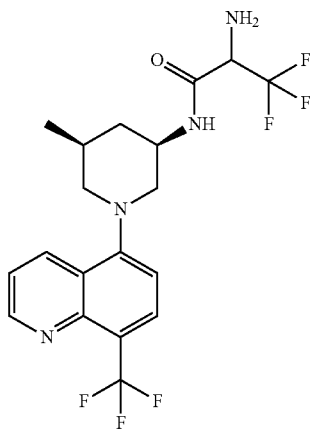<br>Isomer 2 |
| 199 | 57 | 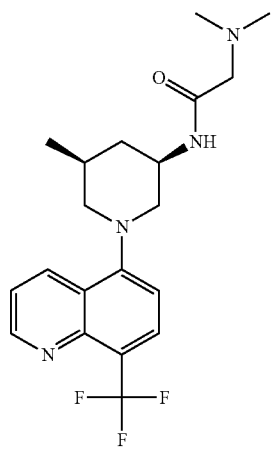 [SMILES: C[C@H]1C[C@@H](NC(=O)CN(C)C)CN(c2ccc(C(F)(F)F)c3ncccc23)C1] |

TABLE 1-continued

| Compound Number | Example Number | Chemical Structure |
|---|---|---|
| 200 | 60 | 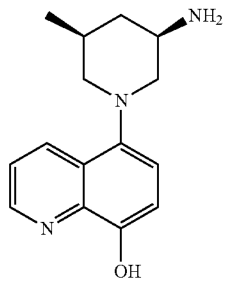 [SMILES: C[C@H]1C[C@@H](N)CN(c2ccc(O)c3ncccc23)C1] |
| 201 | 27 | 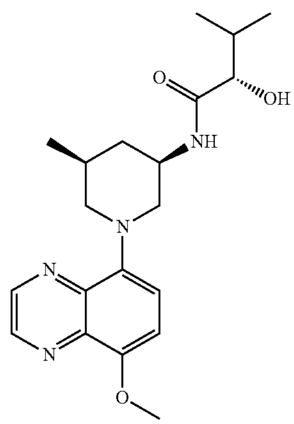 [SMILES: COc1ccc(N2C[C@@H](C)C[C@@H](NC(=O)[C@@H](O)C(C)C)C2)c2nccnc12] |
| 202 | 27 | 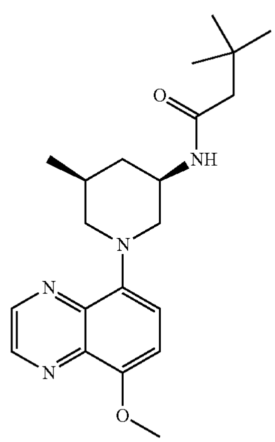 [SMILES: COc1ccc(N2C[C@@H](C)C[C@@H](NC(=O)CC(C)(C)C)C2)c2nccnc12] |
| 203 | 27 | 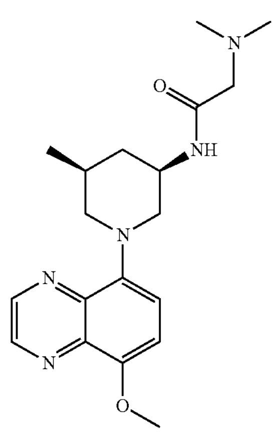 [SMILES: COc1ccc(N2C[C@@H](C)C[C@@H](NC(=O)CN(C)C)C2)c2nccnc12] |

TABLE 1-continued
| Compound Number | Example Number | Chemical Structure |
|---|---|---|
| 204 | 61 | 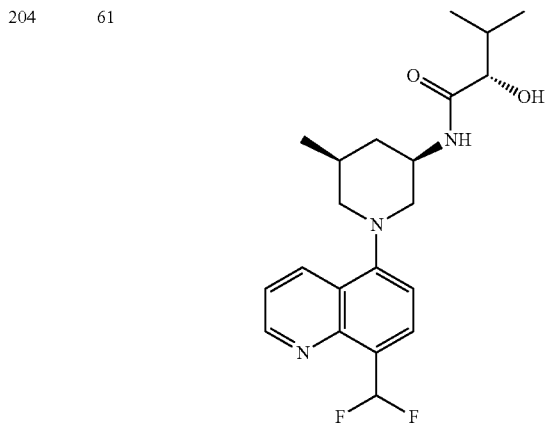 |
| 205 | 61 | 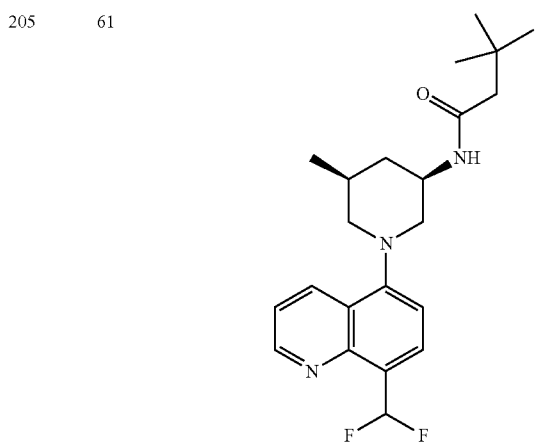 |
| 206 | 62 | 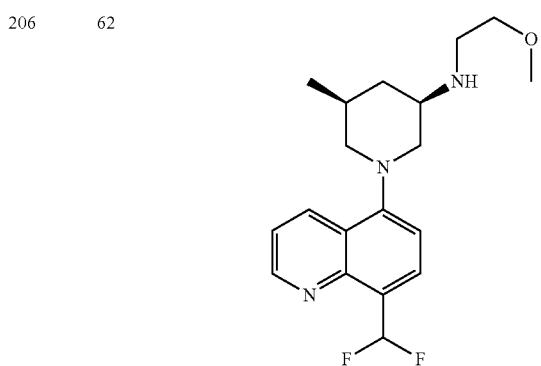 |

TABLE 1-continued
| Compound Number | Example Number | Chemical Structure |
|---|---|---|
| 207 | 63 | 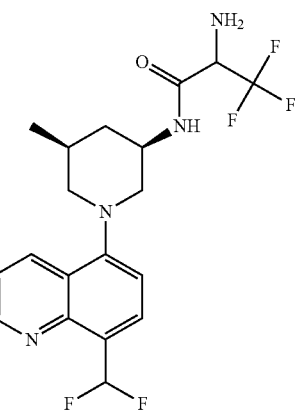<br>Isomer 1 |
| 208 | 63 | 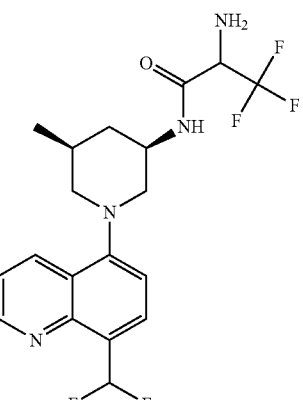<br>Isomer 2 |
| 209 | 61 | 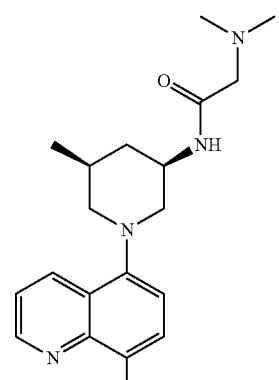 |

TABLE 1-continued

| Compound Number | Example Number | Chemical Structure |
|---|---|---|
| 210 | 64 | 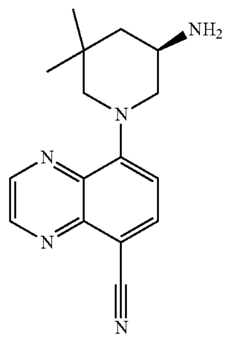 [SMILES: CC1(C)C[C@@H](N)CN(c2ccc(C#N)c3nccnc23)C1] |
| 211 | 65 | Isomer 1 |
| 212 | 65 | Isomer 2 |

TABLE 1-continued
| Compound Number | Example Number | Chemical Structure |
|---|---|---|
| 213 | 66 | 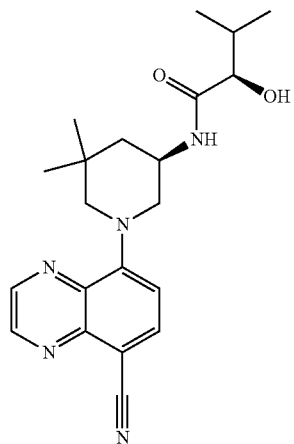 [SMILES: CC(C)[C@@H](O)C(=O)N[C@H]1CN(c2ccc(C#N)c3nccnc23)CC(C)(C)C1] |
| 214 | 66 | 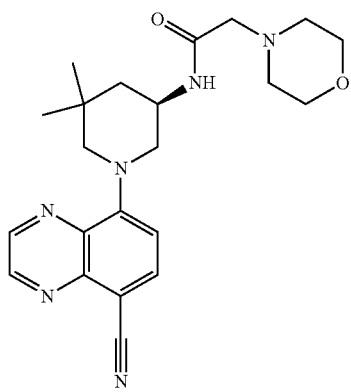 [SMILES: CC1(C)C[C@@H](NC(=O)CN2CCOCC2)CN(c2ccc(C#N)c3nccnc23)C1] |
| 215 | 66 | 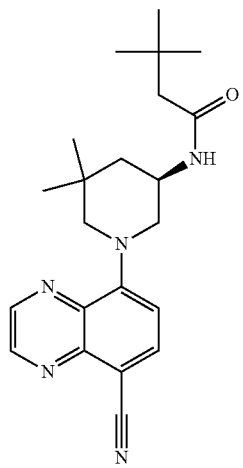 [SMILES: CC(C)(C)CC(=O)N[C@H]1CN(c2ccc(C#N)c3nccnc23)CC(C)(C)C1] |

TABLE 1-continued
| Compound Number | Example Number | Chemical Structure |
|---|---|---|
| 216 | 67 | 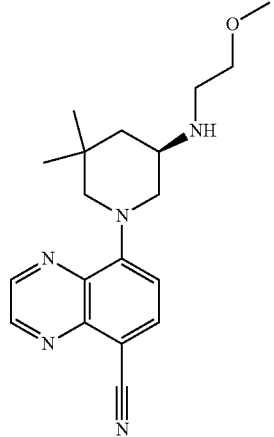 [SMILES: COCCN[C@H]1CN(c2ccc(C#N)c3nccnc23)CC(C)(C)C1] |
| 217 | 66 | 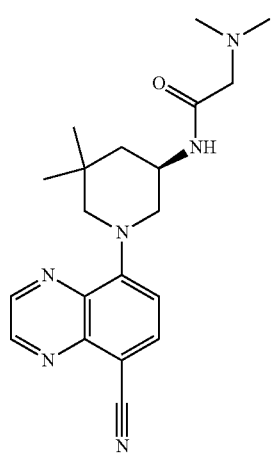 [SMILES: CN(C)CC(=O)N[C@H]1CN(c2ccc(C#N)c3nccnc23)CC(C)(C)C1] |
| 218 | 66 | 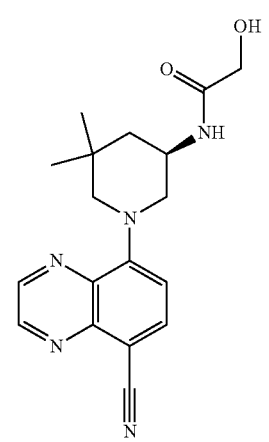 [SMILES: CC1(C)C[C@@H](NC(=O)CO)CN(c2ccc(C#N)c3nccnc23)C1] |

TABLE 1-continued
| Compound Number | Example Number | Chemical Structure |
|---|---|---|
| 219 | 67 | 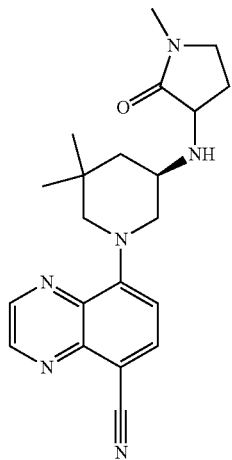 [SMILES: CN1CCC(N[C@H]2CN(c3ccc(C#N)c4nccnc34)CC(C)(C)C2)C1=O] |
| 220 | 66 | 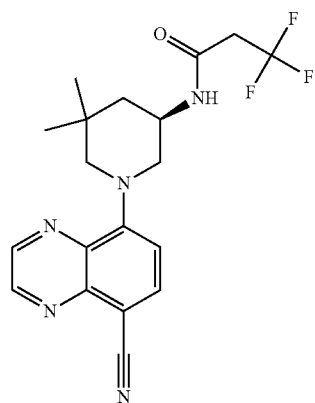 [SMILES: CC1(C)C[C@@H](NC(=O)CC(F)(F)F)CN(c2ccc(C#N)c3nccnc23)C1] |
| 221 | 68 | 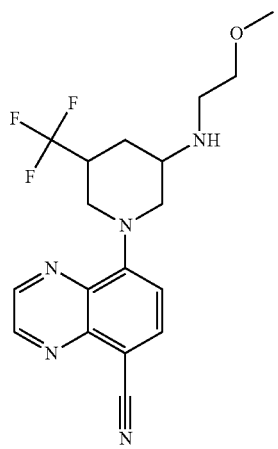 [SMILES: COCCNC1CC(C(F)(F)F)CN(c2ccc(C#N)c3nccnc23)C1] |

TABLE 1-continued
| Compound Number | Example Number | Chemical Structure |
|---|---|---|
| 222 | 40 | 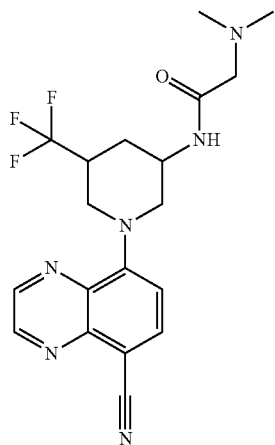 [SMILES: CN(C)CC(=O)NC1CC(C(F)(F)F)CN(c2ccc(C#N)c3nccnc23)C1] |
| 223 | 40 | 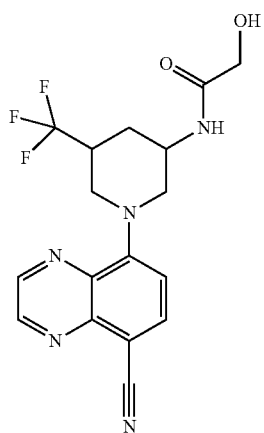 [SMILES: N#Cc1ccc(N2CC(NC(=O)CO)CC(C(F)(F)F)C2)c2nccnc12] |
| 224 | 69 | 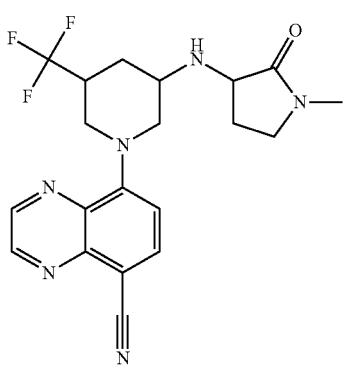<br>Isomer 1 |

TABLE 1-continued
| Compound Number | Example Number | Chemical Structure |
|---|---|---|
| 225 | 69 | 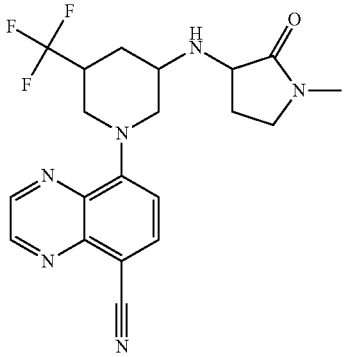<br>Isomer 2 |
| 226 | 69 | 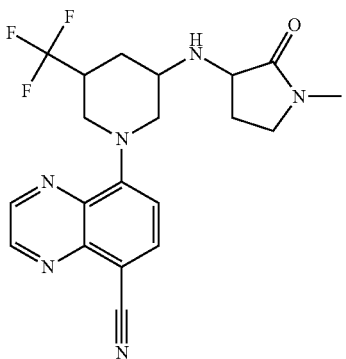<br>Isomer 3 |
| 227 | 69 | 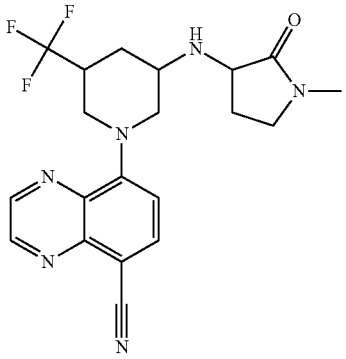<br>Isomer 4 |
| 228 | 40 | 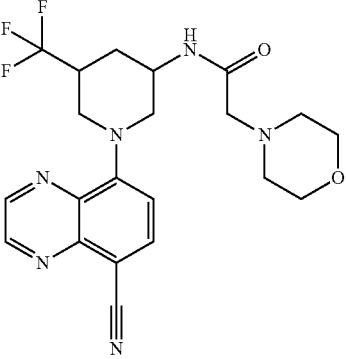 [SMILES: N#Cc1ccc(N2CC(NC(=O)CN3CCOCC3)CC(C(F)(F)F)C2)c2nccnc12] |

TABLE 1-continued
| Compound Number | Example Number | Chemical Structure |
|---|---|---|
| 229 | 40 | 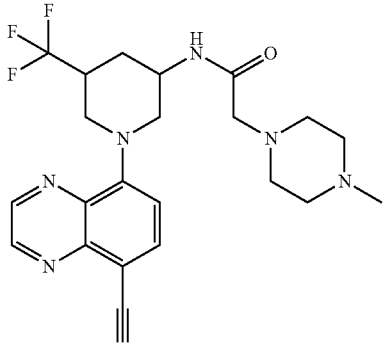 |
| 230 | 10 | 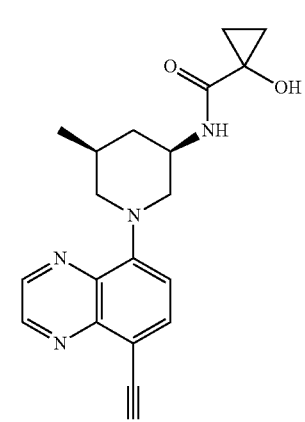 |
| 231 | 70 | 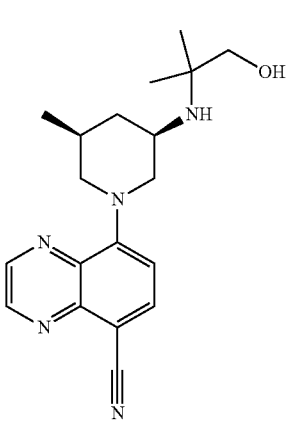 [SMILES: C[C@H]1C[C@@H](NC(C)(C)CO)CN(c2ccc(C#N)c3nccnc23)C1] |
| 232 | 10 | 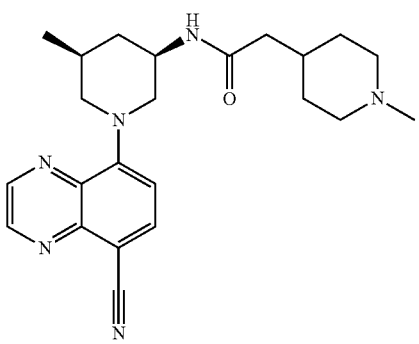 [SMILES: C[C@H]1C[C@@H](NC(=O)CC2CCN(C)CC2)CN(c2ccc(C#N)c3nccnc23)C1] |

TABLE 1-continued

| Compound Number | Example Number | Chemical Structure |
|---|---|---|
| 233 | 10 | 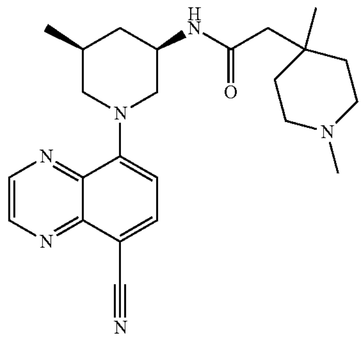 [SMILES: C[C@H]1C[C@@H](NC(=O)CC2(C)CCN(C)CC2)CN(c2ccc(C#N)c3nccnc23)C1] |
| 234 | 10 | 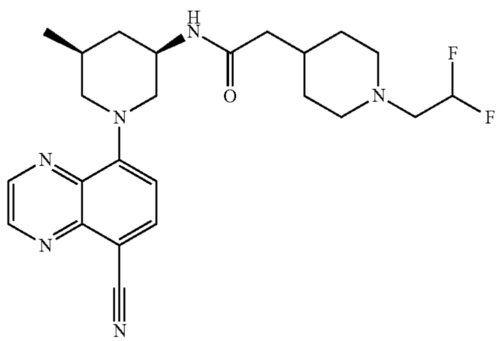 [SMILES: C[C@H]1C[C@@H](NC(=O)CC2CCN(CC(F)F)CC2)CN(c2ccc(C#N)c3nccnc23)C1] |
| 235 | 10 | 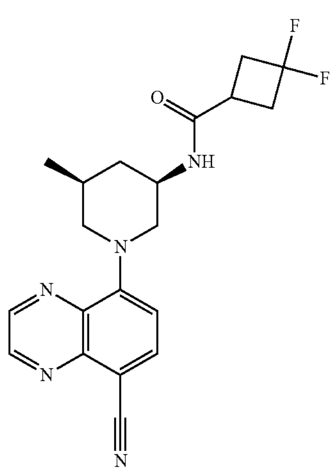 [SMILES: C[C@H]1C[C@@H](NC(=O)C2CC(F)(F)C2)CN(c2ccc(C#N)c3nccnc23)C1] |

TABLE 1-continued
| Compound Number | Example Number | Chemical Structure |
|---|---|---|
| 236 | 10 | 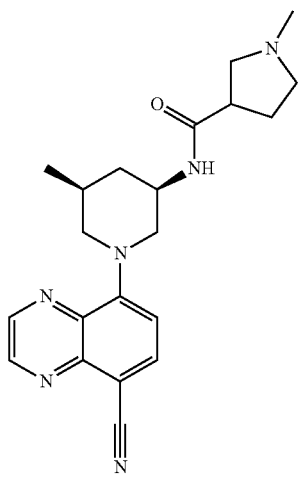 [SMILES: C[C@H]1C[C@@H](NC(=O)C2CCN(C)C2)CN(c2ccc(C#N)c3nccnc23)C1] |
| 237 | 69 | 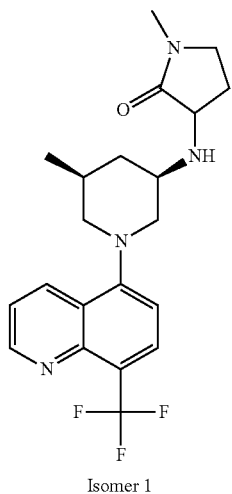 [SMILES: C[C@H]1C[C@@H](NC2CCN(C)C2=O)CN(c2ccc(C(F)(F)F)c3ncccc23)C1]<br>Isomer 1 |
| 238 | 69 | 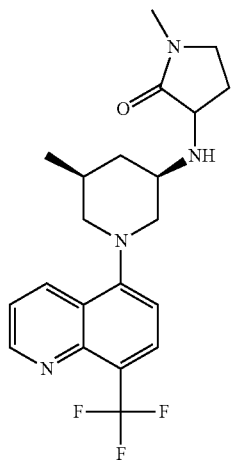<br>Isomer 2 |

TABLE 1-continued
| Compound Number | Example Number | Chemical Structure |
|---|---|---|
| 239 | 57 | 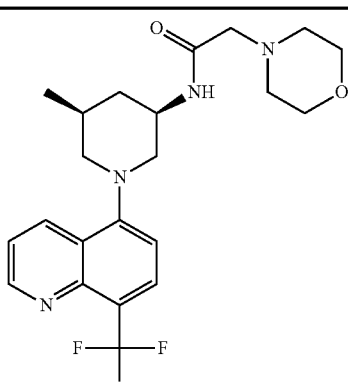 |
| 240 | 57 | 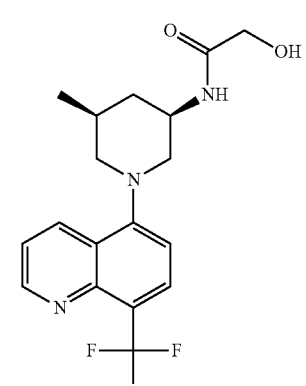 |
| 241 | 57 | 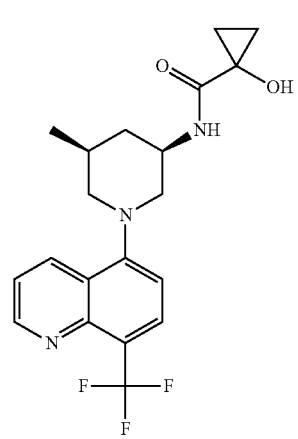 [SMILES: C[C@H]1C[C@@H](NC(=O)C2(O)CC2)CN(c2ccc(C(F)(F)F)c3ncccc23)C1] |
| 242 | 70 | 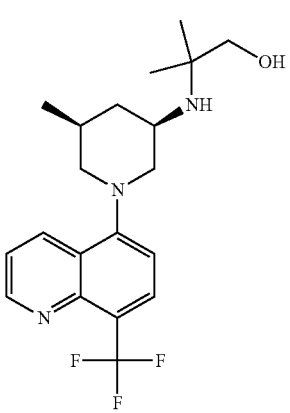 [SMILES: C[C@H]1C[C@@H](NC(C)(C)CO)CN(c2ccc(C(F)(F)F)c3ncccc23)C1] |

TABLE 1-continued
| Compound Number | Example Number | Chemical Structure |
|---|---|---|
| 243 | 57 | 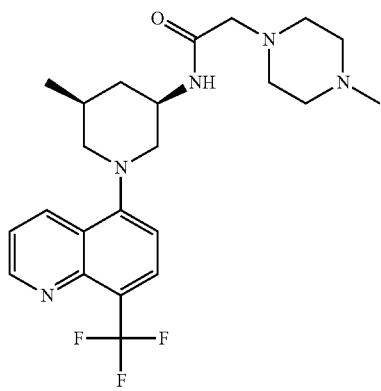 [SMILES: C[C@H]1C[C@@H](NC(=O)CN2CCN(C)CC2)CN(c2ccc(C(F)(F)F)c3ncccc23)C1] |
| 244 | 57 | 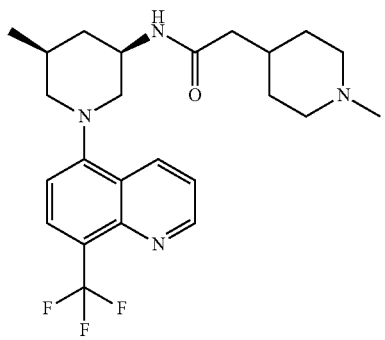 |
| 245 | 57 | 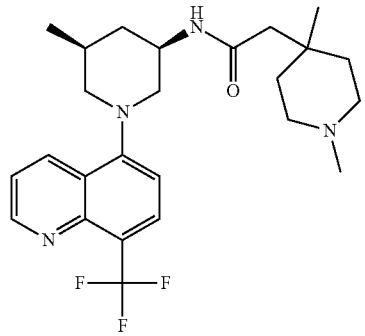 [SMILES: C[C@H]1C[C@@H](NC(=O)CC2(C)CCN(C)CC2)CN(c2ccc(C(F)(F)F)c3ncccc23)C1] |
| 246 | 57 | 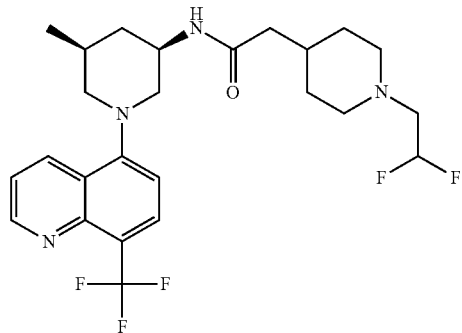 [SMILES: C[C@H]1C[C@@H](NC(=O)CC2CCN(CC(F)F)CC2)CN(c2ccc(C(F)(F)F)c3ncccc23)C1] |

TABLE 1-continued
| Compound Number | Example Number | Chemical Structure |
|---|---|---|
| 247 | 57 | 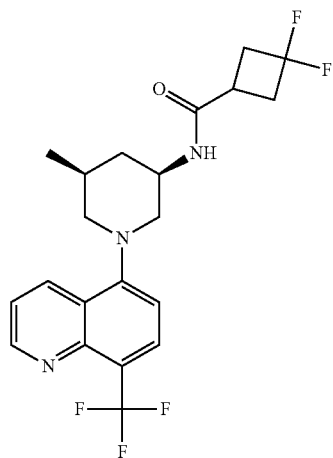 [SMILES: C[C@H]1C[C@@H](NC(=O)C2CC(F)(F)C2)CN(c2ccc(C(F)(F)F)c3ncccc23)C1] |
| 248 | 57 | 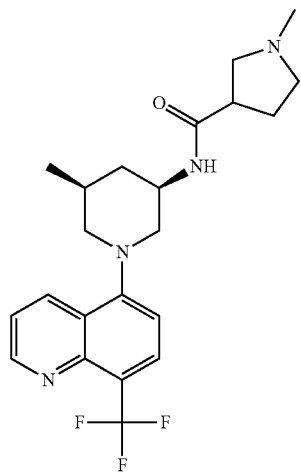 [SMILES: C[C@H]1C[C@@H](NC(=O)C2CCN(C)C2)CN(c2ccc(C(F)(F)F)c3ncccc23)C1] |
| 249 | 71 | 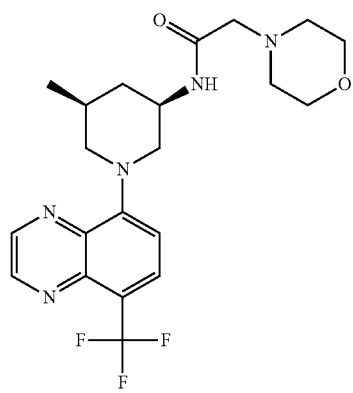 [SMILES: C[C@H]1C[C@@H](NC(=O)CN2CCOCC2)CN(c2ccc(C(F)(F)F)c3nccnc23)C1] |

TABLE 1-continued
| Compound Number | Example Number | Chemical Structure |
|---|---|---|
| 250 | 71 | 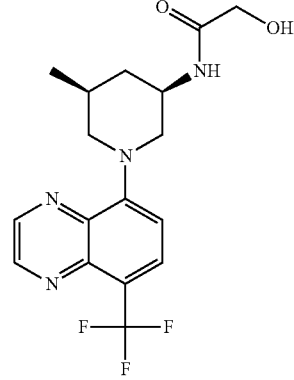 [SMILES: C[C@H]1C[C@@H](NC(=O)CO)CN(c2ccc(C(F)(F)F)c3nccnc23)C1] |
| 251 | 71 | 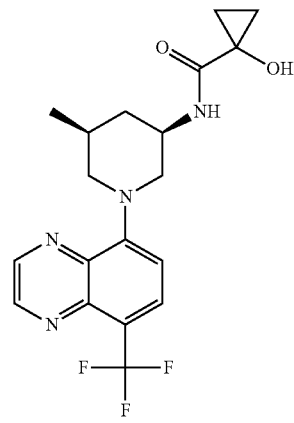 [SMILES: C[C@H]1C[C@@H](NC(=O)C2(O)CC2)CN(c2ccc(C(F)(F)F)c3nccnc23)C1] |
| 252 | 70 | 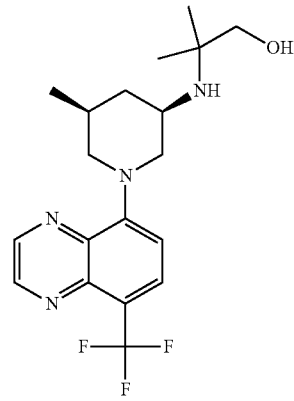 [SMILES: C[C@H]1C[C@@H](NC(C)(C)CO)CN(c2ccc(C(F)(F)F)c3nccnc23)C1] |
| 253 | 71 | 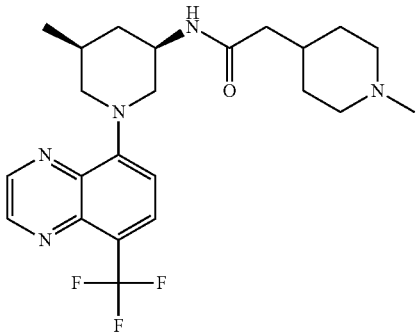 [SMILES: C[C@H]1C[C@@H](NC(=O)CC2CCN(C)CC2)CN(c2ccc(C(F)(F)F)c3nccnc23)C1] |

TABLE 1-continued
| Compound Number | Example Number | Chemical Structure |
|---|---|---|
| 254 | 71 | 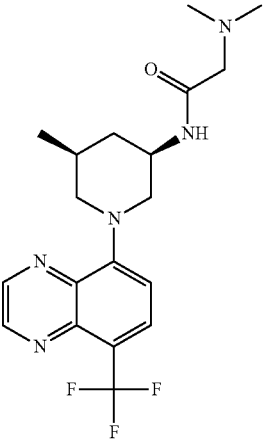 [SMILES: C[C@H]1C[C@@H](NC(=O)CN(C)C)CN(c2ccc(C(F)(F)F)c3nccnc23)C1] |
| 255 | 71 | 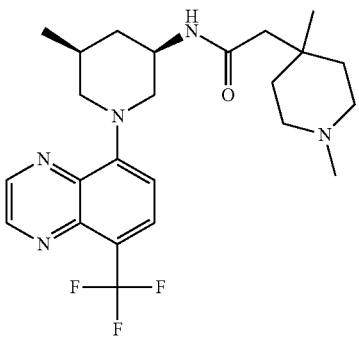 [SMILES: C[C@H]1C[C@@H](NC(=O)CC2(C)CCN(C)CC2)CN(c2ccc(C(F)(F)F)c3nccnc23)C1] |
| 256 | 71 | 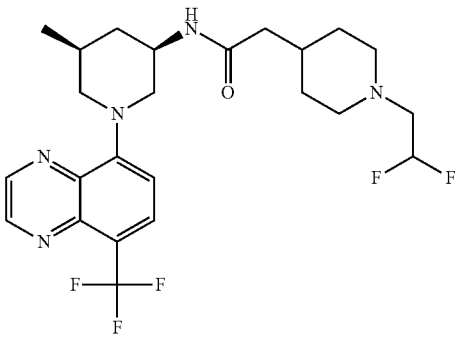 [SMILES: C[C@H]1C[C@@H](NC(=O)CC2CCN(CC(F)F)CC2)CN(c2ccc(C(F)(F)F)c3nccnc23)C1] |
| 257 | 71 | 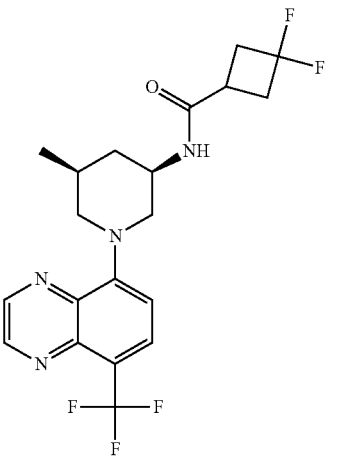 [SMILES: C[C@H]1C[C@@H](NC(=O)C2CC(F)(F)C2)CN(c2ccc(C(F)(F)F)c3nccnc23)C1] |

TABLE 1-continued
| Compound Number | Example Number | Chemical Structure |
|---|---|---|
| 258 | 71 | 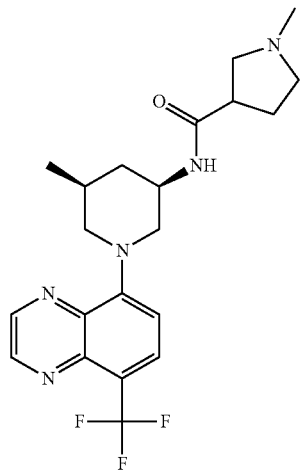 [SMILES: C[C@H]1C[C@@H](NC(=O)C2CCN(C)C2)CN(c2ccc(C(F)(F)F)c3nccnc23)C1] |
| 259 | 71 | 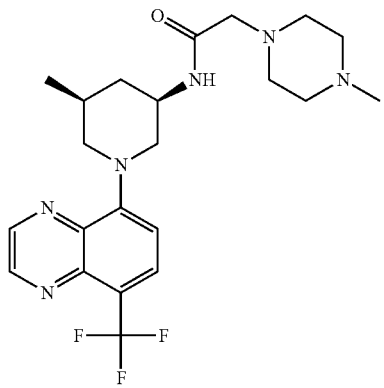 |
| 260 | 72 | 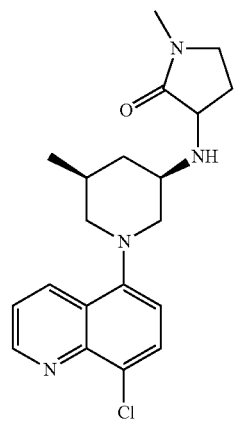<br>Isomer 1 |

TABLE 1-continued
| Compound Number | Example Number | Chemical Structure |
|---|---|---|
| 261 | 72 | 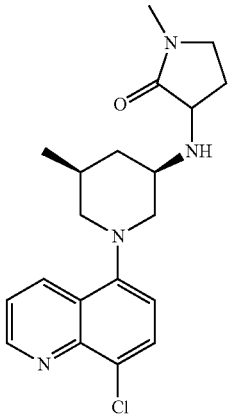 Isomer |
| 262 | 73 | 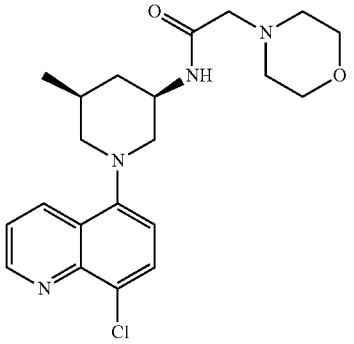 [SMILES: C[C@H]1C[C@@H](NC(=O)CN2CCOCC2)CN(c2ccc(Cl)c3ncccc23)C1] |
| 263 | 73 | 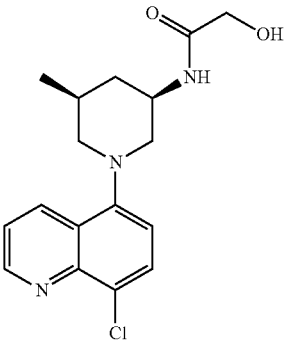 [SMILES: C[C@H]1C[C@@H](NC(=O)CO)CN(c2ccc(Cl)c3ncccc23)C1] |
| 264 | 73 | 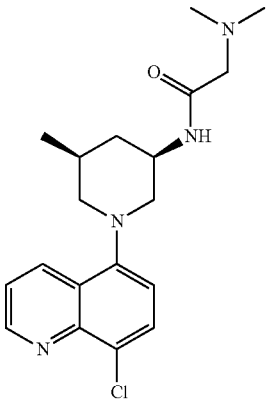 [SMILES: C[C@H]1C[C@@H](NC(=O)CN(C)C)CN(c2ccc(Cl)c3ncccc23)C1] |

TABLE 1-continued

| Compound Number | Example Number | Chemical Structure |
|---|---|---|
| 265 | 10 | 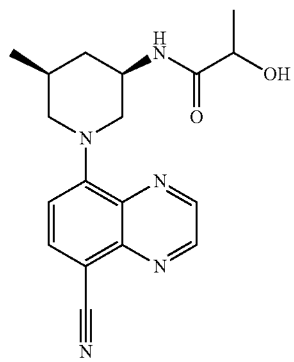 [SMILES: CC(O)C(=O)N[C@@H]1C[C@H](C)CN(c2ccc(C#N)c3nccnc23)C1] |
| 266 | 10 | 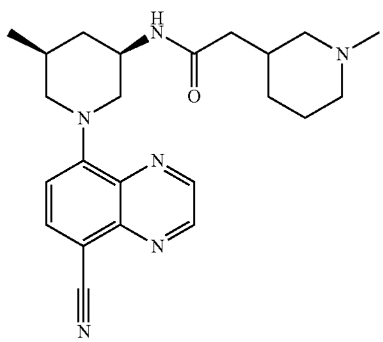 |
| 267 | 74 | 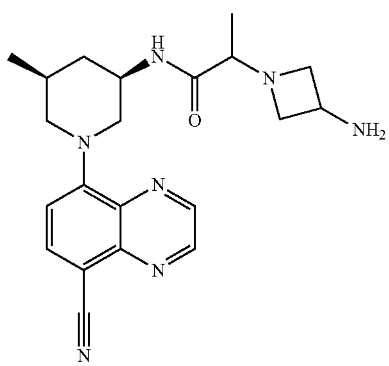 [SMILES: CC(C(=O)N[C@@H]1C[C@H](C)CN(c2ccc(C#N)c3nccnc23)C1)N1CC(N)C1] |
| 268 | 13 | 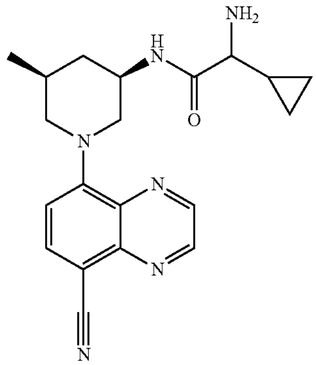 [SMILES: C[C@H]1C[C@@H](NC(=O)C(N)C2CC2)CN(c2ccc(C#N)c3nccnc23)C1] |

TABLE 1-continued

| Compound Number | Example Number | Chemical Structure |
| --- | --- | --- |
| 269 | 10 | 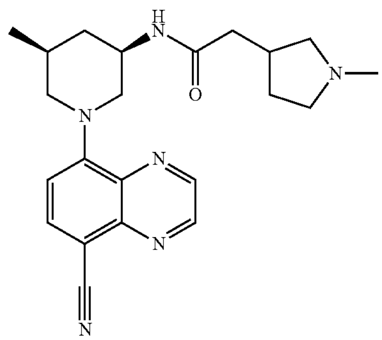 |
| 270 | 75 | 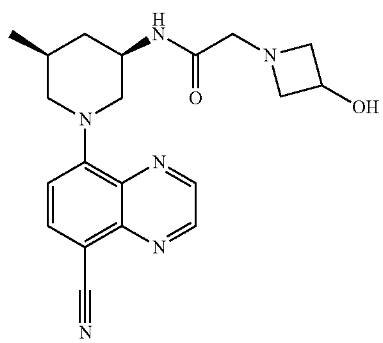 [SMILES: C[C@H]1C[C@@H](NC(=O)CN2CC(O)C2)CN(c2ccc(C#N)c3nccnc23)C1] |
| 271 | 75 | 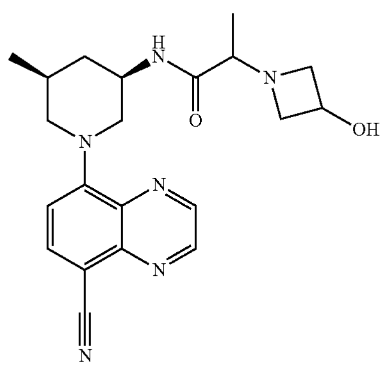 [SMILES: CC(C(=O)N[C@@H]1C[C@H](C)CN(c2ccc(C#N)c3nccnc23)C1)N1CC(O)C1] |
| 272 | 76 | 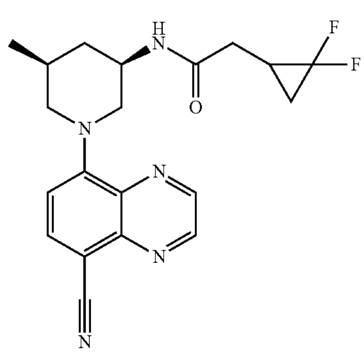 [SMILES: C[C@H]1C[C@@H](NC(=O)CC2CC2(F)F)CN(c2ccc(C#N)c3nccnc23)C1] |

TABLE 1-continued
| Compound Number | Example Number | Chemical Structure |
|---|---|---|
| 273 | 75 | 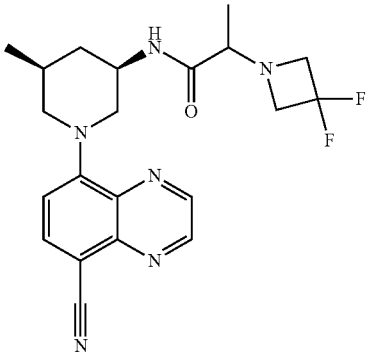 [SMILES: CC(C(=O)N[C@@H]1C[C@H](C)CN(c2ccc(C#N)c3nccnc23)C1)N1CC(F)(F)C1] |
| 274 | 77 | 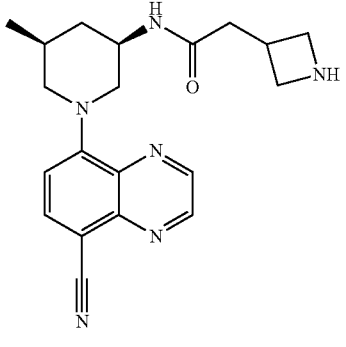 [SMILES: C[C@H]1C[C@@H](NC(=O)CC2CNC2)CN(c2ccc(C#N)c3nccnc23)C1] |
| 275 | 75 | 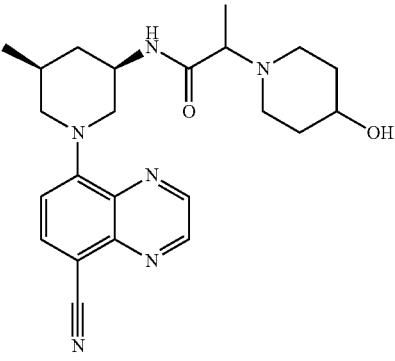 [SMILES: CC(C(=O)N[C@@H]1C[C@H](C)CN(c2ccc(C#N)c3nccnc23)C1)N1CCC(O)CC1] |
| 276 | 78 | 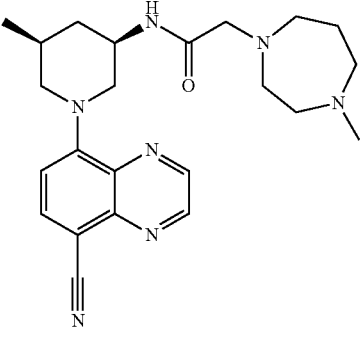 |

TABLE 1-continued
| Compound Number | Example Number | Chemical Structure |
|---|---|---|
| 277 | 13 | 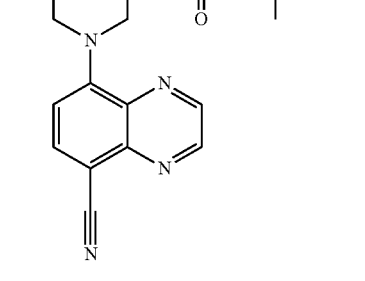 |
| 278 | 57 | 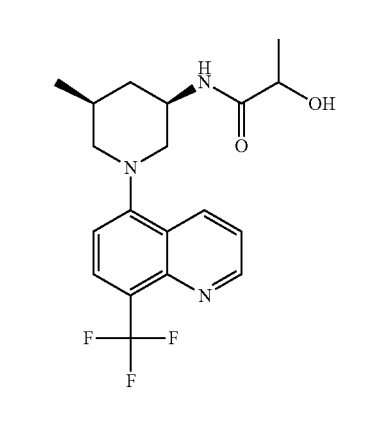 [SMILES: CC(O)C(=O)N[C@@H]1C[C@H](C)CN(c2ccc(C(F)(F)F)c3ncccc23)C1] |
| 279 | 57 | 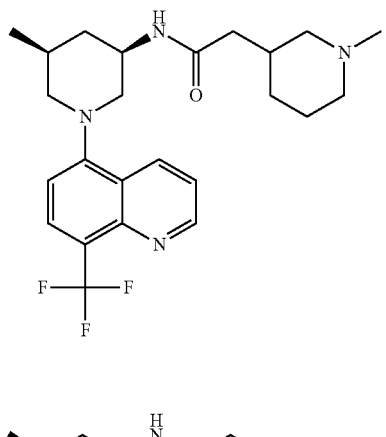 |
| 280 | 79 | 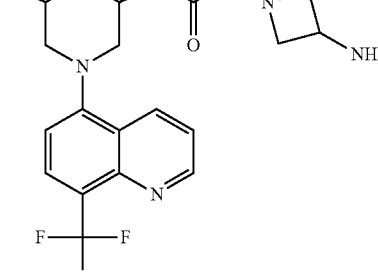 |

TABLE 1-continued
| Compound Number | Example Number | Chemical Structure |
|---|---|---|
| 281 | 80 | 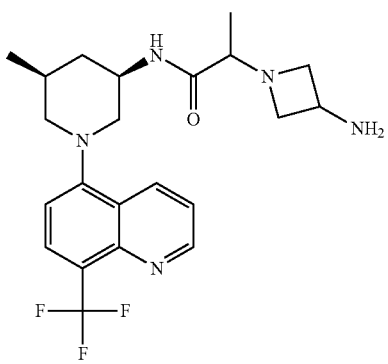 [SMILES: CC(C(=O)N[C@@H]1C[C@H](C)CN(c2ccc(C(F)(F)F)c3ncccc23)C1)N1CC(N)C1] |
| 282 | 80 | 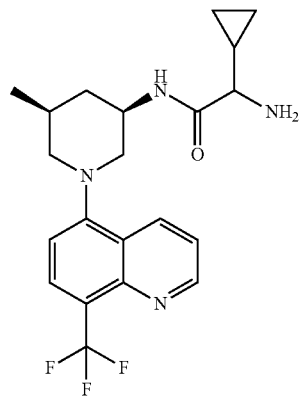 [SMILES: C[C@H]1C[C@@H](NC(=O)C(N)C2CC2)CN(c2ccc(C(F)(F)F)c3ncccc23)C1] |
| 283 | 57 | 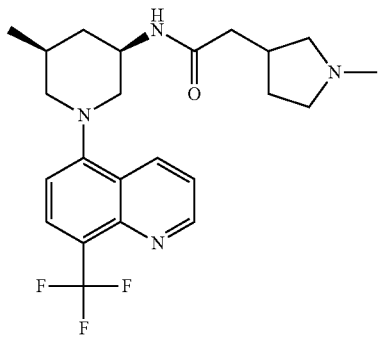 |
| 284 | 75 | 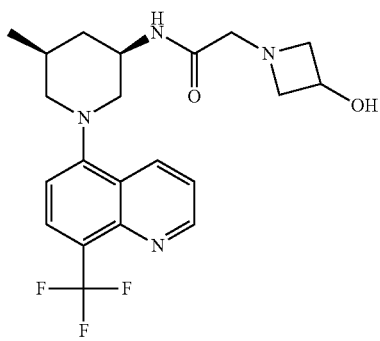 [SMILES: C[C@H]1C[C@@H](NC(=O)CN2CC(O)C2)CN(c2ccc(C(F)(F)F)c3ncccc23)C1] |

TABLE 1-continued
| Compound Number | Example Number | Chemical Structure |
|---|---|---|
| 285 | 75 | 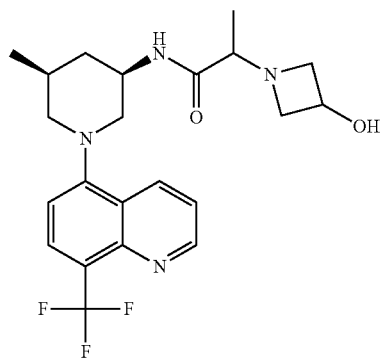 [SMILES: CC(C(=O)N[C@@H]1C[C@H](C)CN(c2ccc(C(F)(F)F)c3ncccc23)C1)N1CC(O)C1] |
| 286 | 76 | 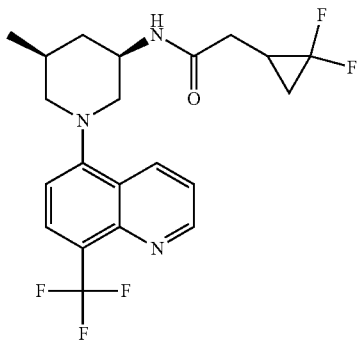 [SMILES: C[C@H]1C[C@@H](NC(=O)CC2CC2(F)F)CN(c2ccc(C(F)(F)F)c3ncccc23)C1] |
| 287 | 57 | 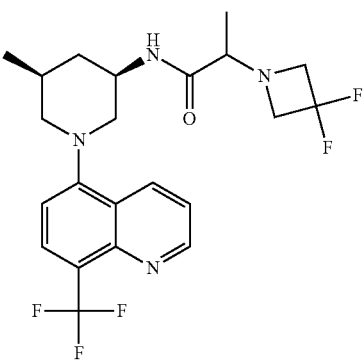 [SMILES: CC(C(=O)N[C@@H]1C[C@H](C)CN(c2ccc(C(F)(F)F)c3ncccc23)C1)N1CC(F)(F)C1] |
| 288 | 80 | 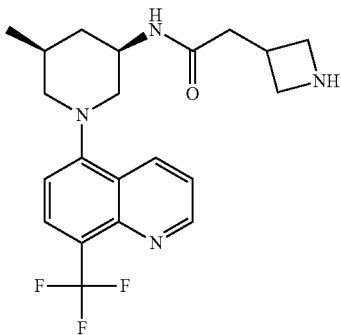 [SMILES: C[C@H]1C[C@@H](NC(=O)CC2CNC2)CN(c2ccc(C(F)(F)F)c3ncccc23)C1] |

TABLE 1-continued

| Compound Number | Example Number | Chemical Structure |
|---|---|---|
| 289 | 57 | 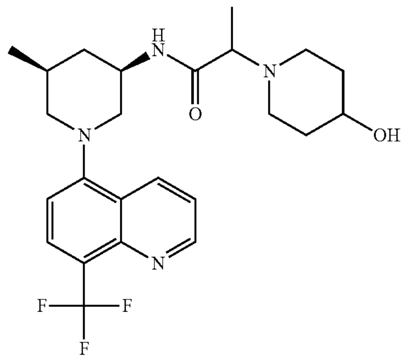 [SMILES: CC(C(=O)N[C@@H]1C[C@H](C)CN(c2ccc(C(F)(F)F)c3ncccc23)C1)N1CCC(O)CC1] |
| 290 | 78 | 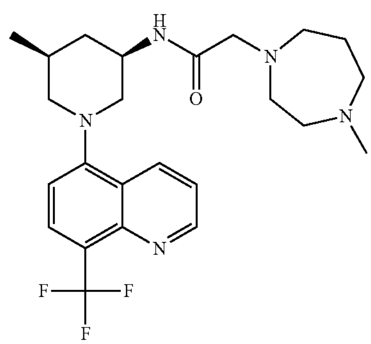 |
| 291 | 80 | 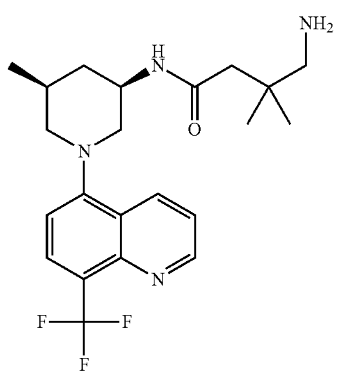 [SMILES: C[C@H]1C[C@@H](NC(=O)CC(C)(C)CN)CN(c2ccc(C(F)(F)F)c3ncccc23)C1] |
| 292 | 71 | 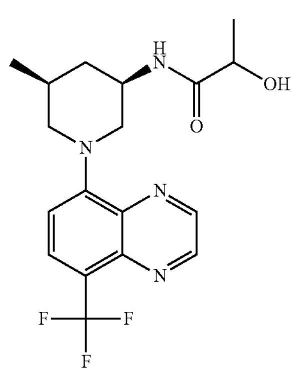 [SMILES: CC(O)C(=O)N[C@@H]1C[C@H](C)CN(c2ccc(C(F)(F)F)c3nccnc23)C1] |

TABLE 1-continued
| Compound Number | Example Number | Chemical Structure |
|---|---|---|
| 293 | 71 | 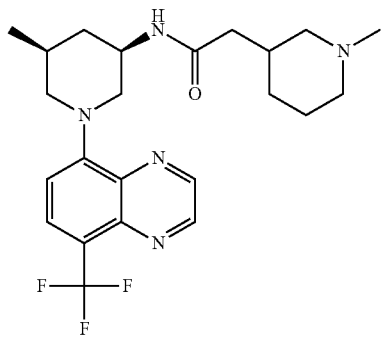 |
| 294 | 81 | 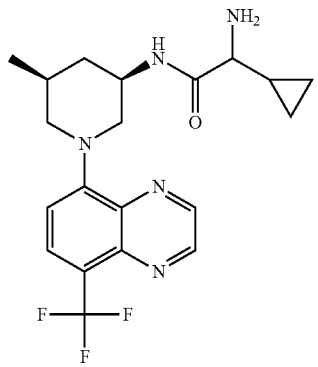 [SMILES: C[C@H]1C[C@@H](NC(=O)C(N)C2CC2)CN(c2ccc(C(F)(F)F)c3nccnc23)C1] |
| 295 | 71 | 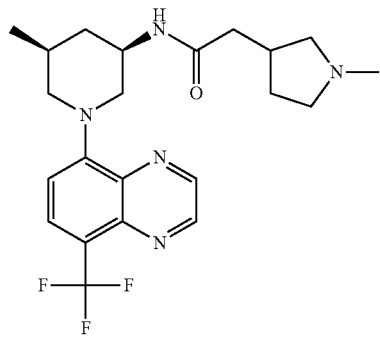 |
| 296 | 75 | 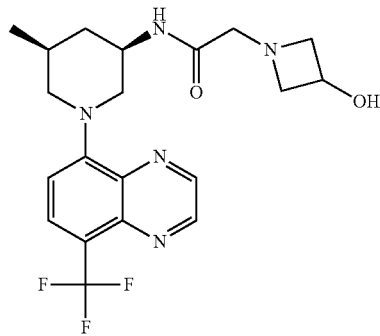 [SMILES: C[C@H]1C[C@@H](NC(=O)CN2CC(O)C2)CN(c2ccc(C(F)(F)F)c3nccnc23)C1] |

TABLE 1-continued
| Compound Number | Example Number | Chemical Structure |
|---|---|---|
| 297 | 75 | 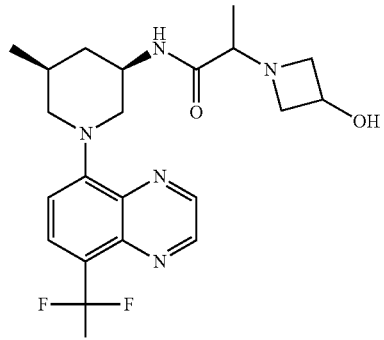 |
| 298 | 76 | 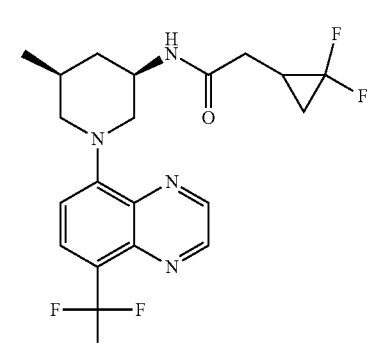 |
| 299 | 71 | 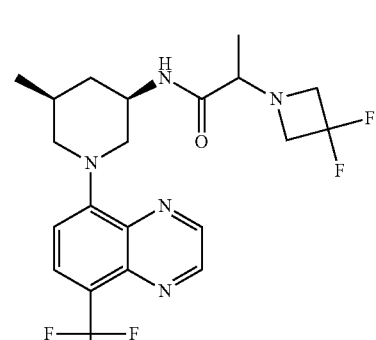 |
| 300 | 81 | 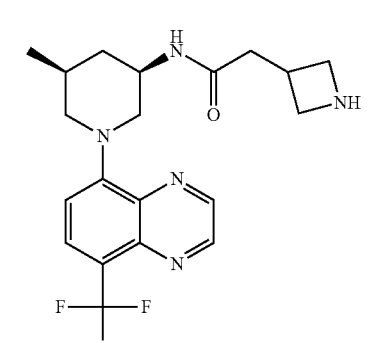 |

TABLE 1-continued
| Compound Number | Example Number | Chemical Structure |
|---|---|---|
| 301 | 81 | 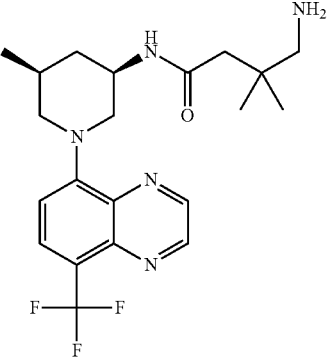 [SMILES: C[C@H]1C[C@@H](NC(=O)CC(C)(C)CN)CN(c2ccc(C(F)(F)F)c3nccnc23)C1] |
| 302 | 61 | 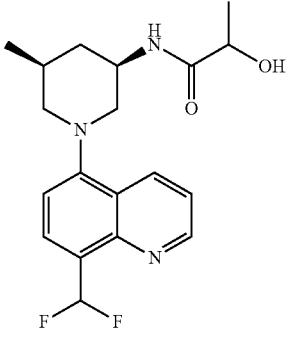 |
| 303 | 61 | 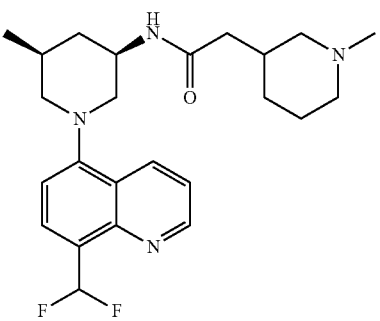 |
| 304 | 82 | 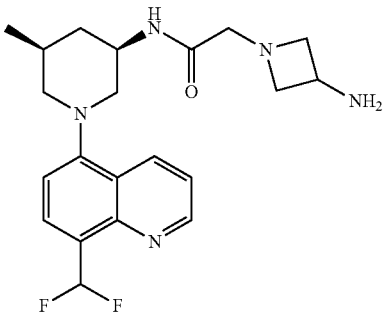 [SMILES: C[C@H]1C[C@@H](NC(=O)CN2CC(N)C2)CN(c2ccc(C(F)F)c3ncccc23)C1] |

TABLE 1-continued
| Compound Number | Example Number | Chemical Structure |
|---|---|---|
| 305 | 83 | 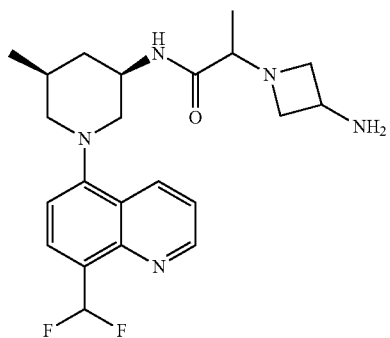 [SMILES: CC(C(=O)N[C@@H]1C[C@H](C)CN(c2ccc(C(F)F)c3ncccc23)C1)N1CC(N)C1] |
| 306 | 83 | 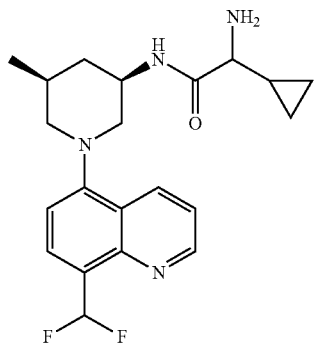 [SMILES: C[C@H]1C[C@@H](NC(=O)C(N)C2CC2)CN(c2ccc(C(F)F)c3ncccc23)C1] |
| 307 | 61 | 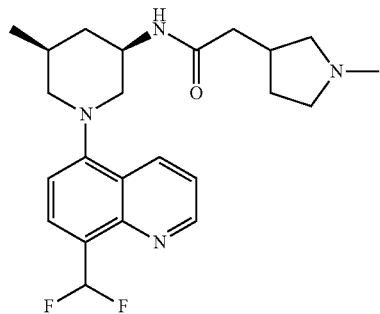 |
| 308 | 75 | 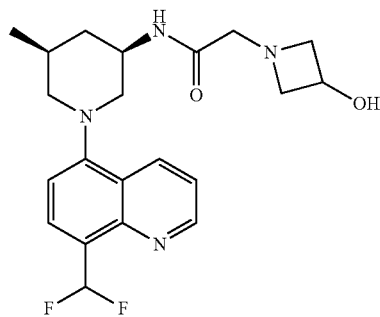 |

TABLE 1-continued
| Compound Number | Example Number | Chemical Structure |
|---|---|---|
| 309 | 75 | 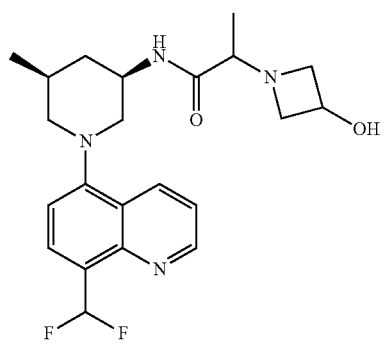 [SMILES: CC(C(=O)N[C@@H]1C[C@H](C)CN(c2ccc(C(F)F)c3ncccc23)C1)N1CC(O)C1] |
| 310 | 76 | 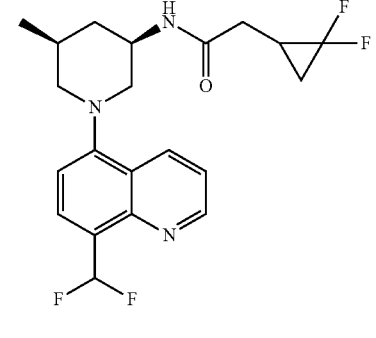 [SMILES: C[C@H]1C[C@@H](NC(=O)CC2CC2(F)F)CN(c2ccc(C(F)F)c3ncccc23)C1] |
| 311 | 61 | 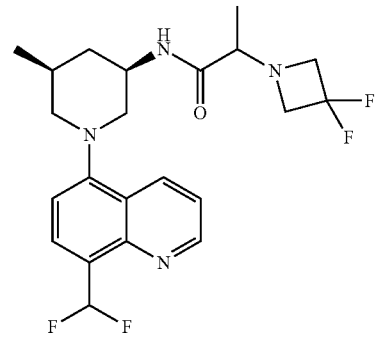 [SMILES: CC(C(=O)N[C@@H]1C[C@H](C)CN(c2ccc(C(F)F)c3ncccc23)C1)N1CC(F)(F)C1] |
| 312 | 83 | 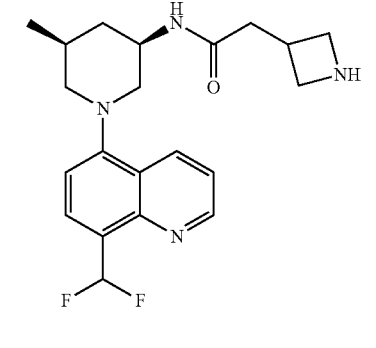 [SMILES: C[C@H]1C[C@@H](NC(=O)CC2CNC2)CN(c2ccc(C(F)F)c3ncccc23)C1] |

TABLE 1-continued
| Compound Number | Example Number | Chemical Structure |
|---|---|---|
| 313 | 61 | 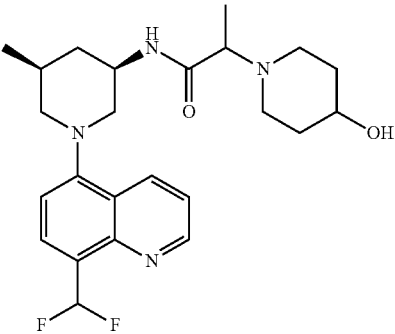 [SMILES: CC(C(=O)N[C@@H]1C[C@H](C)CN(c2ccc(C(F)F)c3ncccc23)C1)N1CCC(O)CC1] |
| 314 | 78 | 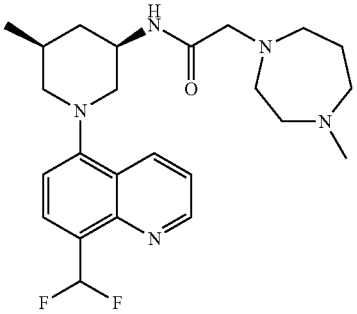 [SMILES: C[C@H]1C[C@@H](NC(=O)CN2CCCN(C)CC2)CN(c2ccc(C(F)F)c3ncccc23)C1] |
| 315 | 83 | 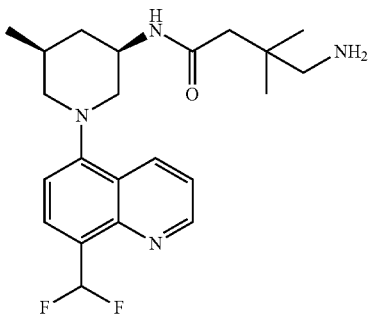 |
| 316 | 61 | 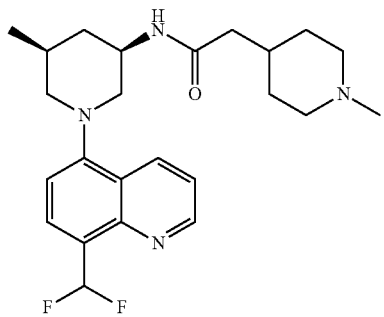 |

TABLE 1-continued
| Compound Number | Example Number | Chemical Structure |
|---|---|---|
| 317 | 61 | 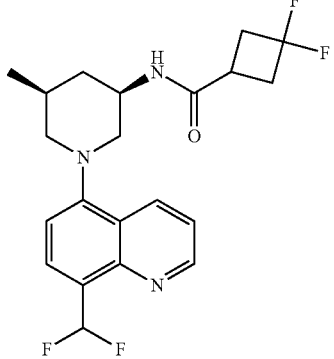 |
| 318 | 61 | 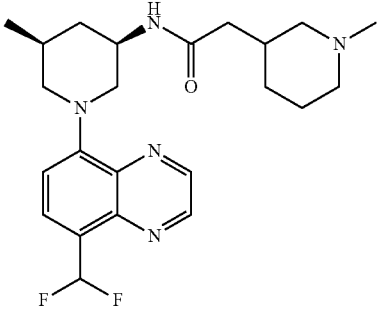 |
| 319 | 61 | 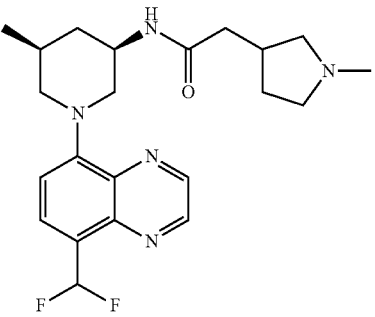 |
| 320 | 75 | 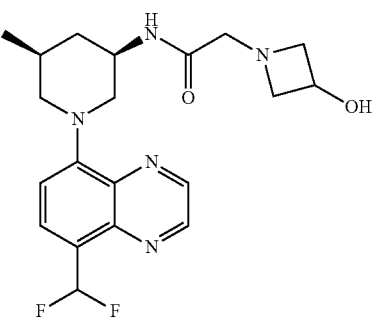 [SMILES: C[C@H]1C[C@@H](NC(=O)CN2CC(O)C2)CN(c2ccc(C(F)F)c3nccnc23)C1] |

TABLE 1-continued
| Compound Number | Example Number | Chemical Structure |
|---|---|---|
| 321 | 75 | 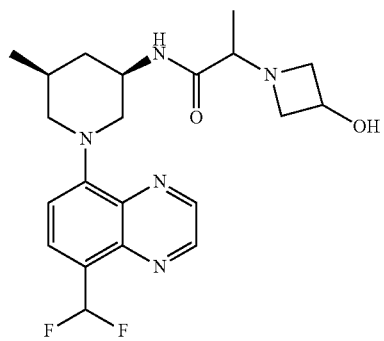 |
| 322 | 76 | 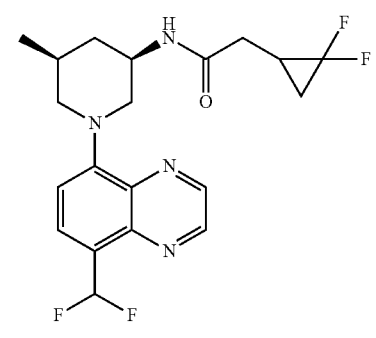 [SMILES: C[C@H]1C[C@@H](NC(=O)CC2CC2(F)F)CN(c2ccc(C(F)F)c3nccnc23)C1] |
| 323 | 61 | 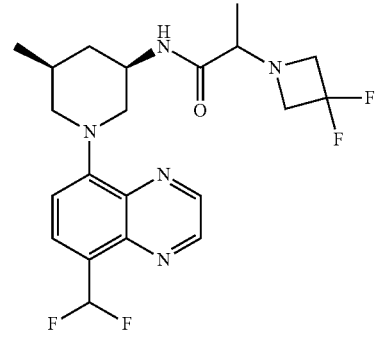 [SMILES: CC(C(=O)N[C@@H]1C[C@H](C)CN(c2ccc(C(F)F)c3nccnc23)C1)N1CC(F)(F)C1] |
| 324 | 83 | 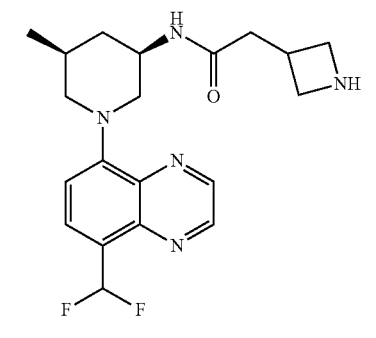 [SMILES: C[C@H]1C[C@@H](NC(=O)CC2CNC2)CN(c2ccc(C(F)F)c3nccnc23)C1] |

TABLE 1-continued
| Compound Number | Example Number | Chemical Structure |
|---|---|---|
| 325 | 61 | 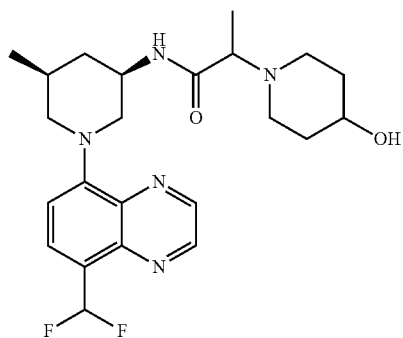 [SMILES: CC(C(=O)N[C@@H]1C[C@H](C)CN(c2ccc(C(F)F)c3nccnc23)C1)N1CCC(O)CC1] |
| 326 | 78 | 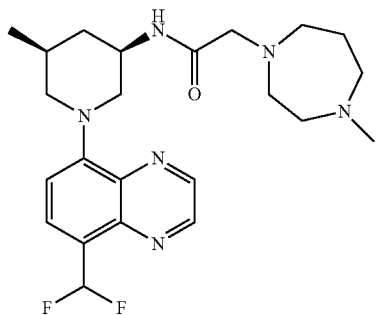 |
| 327 | 83 | 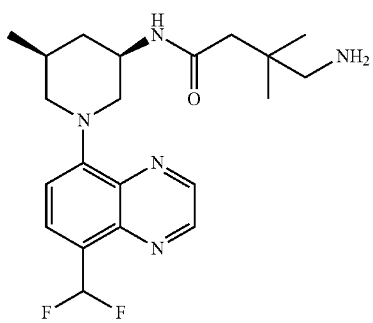 [SMILES: C[C@H]1C[C@@H](NC(=O)CC(C)(C)CN)CN(c2ccc(C(F)F)c3nccnc23)C1] |
| 328 | 61 | 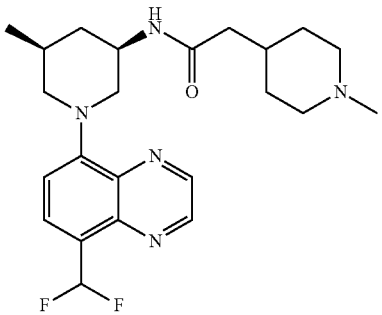 |

TABLE 1-continued
| Compound Number | Example Number | Chemical Structure |
|---|---|---|
| 329 | 61 | 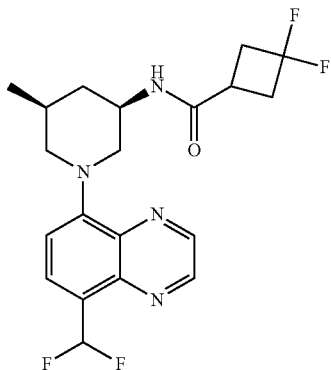 [SMILES: C[C@H]1C[C@@H](NC(=O)C2CC(F)(F)C2)CN(c2ccc(C(F)F)c3nccnc23)C1] |
| 330 | 84 | 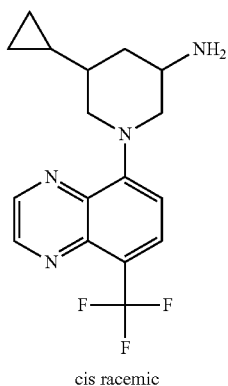 [SMILES: NC1CC(C2CC2)CN(c2ccc(C(F)(F)F)c3nccnc23)C1]<br>cis racemic |
| 331 | 84 | 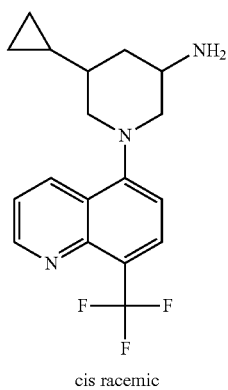 [SMILES: NC1CC(C2CC2)CN(c2ccc(C(F)(F)F)c3ncccc23)C1]<br>cis racemic |
| 332 | 85 | 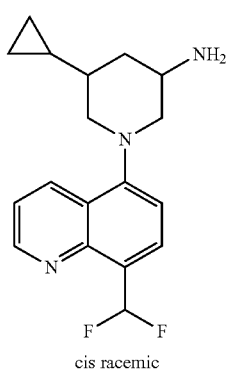 [SMILES: NC1CC(C2CC2)CN(c2ccc(C(F)F)c3ncccc23)C1]<br>cis racemic |

TABLE 1-continued
| Compound Number | Example Number | Chemical Structure |
|---|---|---|
| 333 | 84 | 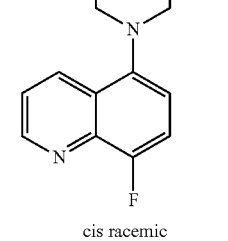<br>cis racemic |
| 334 | 84 | 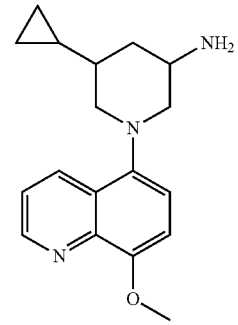<br>cis racemic |
| 335 | 86 | 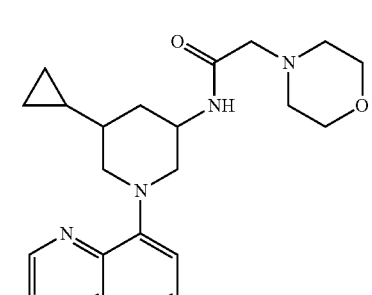<br>cis racemic |
| 336 | 86 | 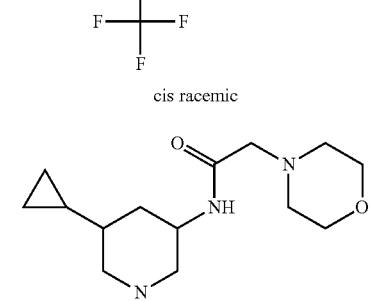<br>cis racemic |

TABLE 1-continued
| Compound Number | Example Number | Chemical Structure |
|---|---|---|
| 337 | 87 | 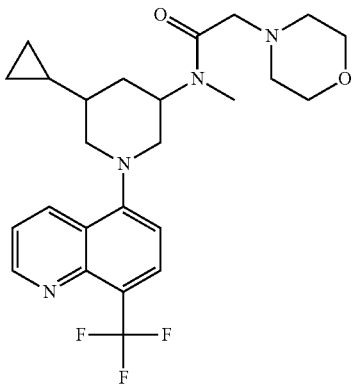<br>cis racemic |
| 338 | 86 | 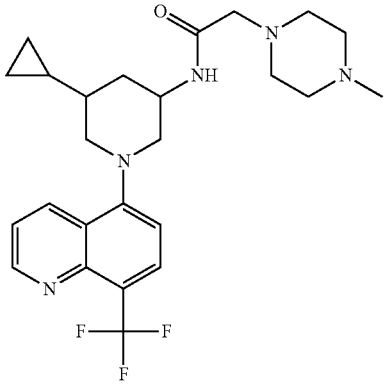<br>cis racemic |
| 339 | 88 | 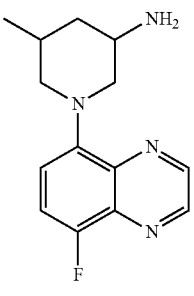<br>cis Isomer 1 |
| 340 | 88 | 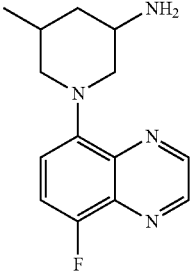<br>cis Isomer 2 |

TABLE 1-continued
| Compound Number | Example Number | Chemical Structure |
|---|---|---|
| 341 | 89 | 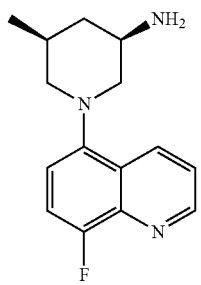 [SMILES: C[C@H]1C[C@@H](N)CN(c2ccc(F)c3ncccc23)C1] |
| 342 | 90 | 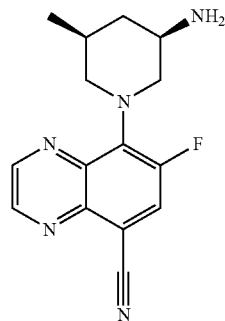 [SMILES: C[C@H]1C[C@@H](N)CN(c2c(F)cc(C#N)c3nccnc23)C1] |
| 343 | 91 | 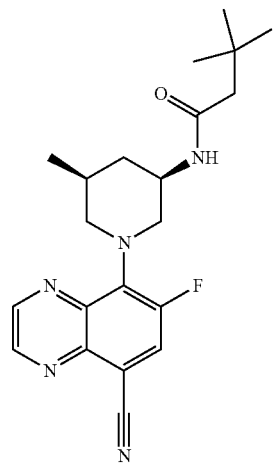 [SMILES: C[C@H]1C[C@@H](NC(=O)CC(C)(C)C)CN(c2c(F)cc(C#N)c3nccnc23)C1] |
| 344 | 95 | 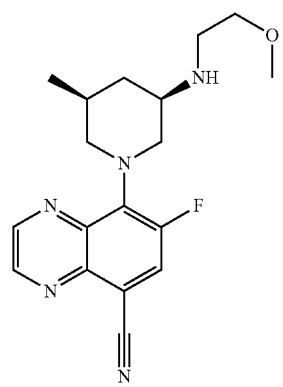 [SMILES: COCCN[C@@H]1C[C@H](C)CN(c2c(F)cc(C#N)c3nccnc23)C1] |

TABLE 1-continued
| Compound Number | Example Number | Chemical Structure |
|---|---|---|
| 345 | 93 | 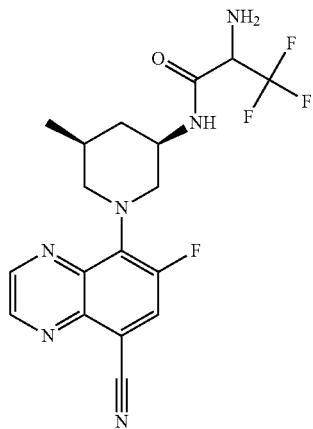<br>Isomer 1 |
| 346 | 93 | 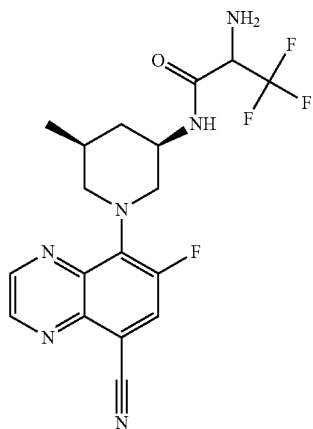<br>Isomer 2 |
| 347 | 94 | 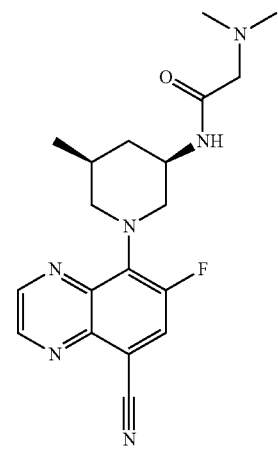 [SMILES: C[C@H]1C[C@@H](NC(=O)CN(C)C)CN(c2c(F)cc(C#N)c3nccnc23)C1] |

TABLE 1-continued
| Compound Number | Example Number | Chemical Structure |
|---|---|---|
| 348 | 95 | 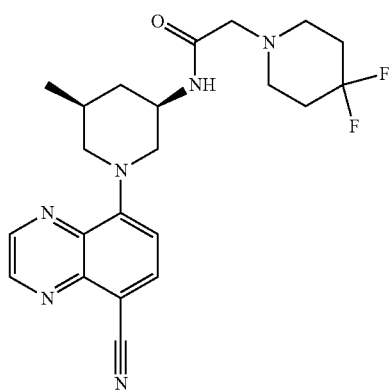 [SMILES: C[C@H]1C[C@@H](NC(=O)CN2CCC(F)(F)CC2)CN(c2ccc(C#N)c3nccnc23)C1] |
| 349 | 96 | 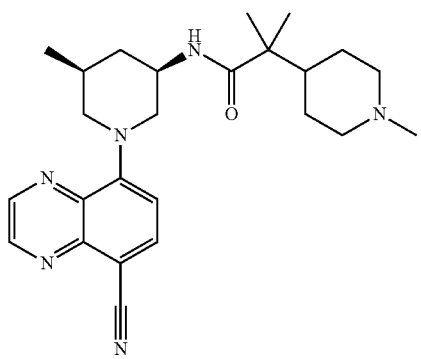 [SMILES: C[C@H]1C[C@@H](NC(=O)C(C)(C)C2CCN(C)CC2)CN(c2ccc(C#N)c3nccnc23)C1] |
| 350 | 95 | 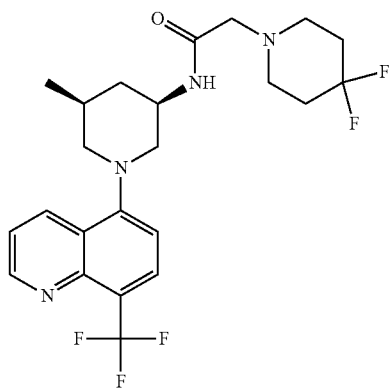 [SMILES: C[C@H]1C[C@@H](NC(=O)CN2CCC(F)(F)CC2)CN(c2ccc(C(F)(F)F)c3ncccc23)C1] |
| 351 | 96 | 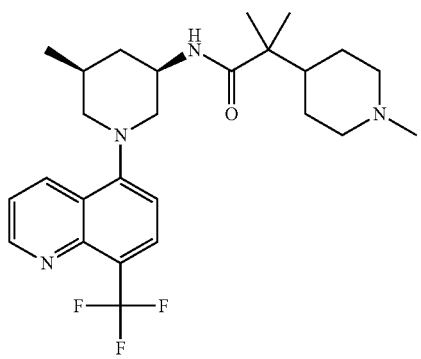 [SMILES: C[C@H]1C[C@@H](NC(=O)C(C)(C)C2CCN(C)CC2)CN(c2ccc(C(F)(F)F)c3ncccc23)C1] |

TABLE 1-continued
| Compound Number | Example Number | Chemical Structure |
|---|---|---|
| 352 | 97 | 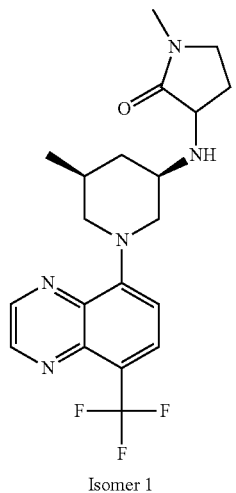 [SMILES: C[C@H]1C[C@@H](NC2CCN(C)C2=O)CN(c2ccc(C(F)(F)F)c3nccnc23)C1]<br>Isomer 1 |
| 353 | 98 | 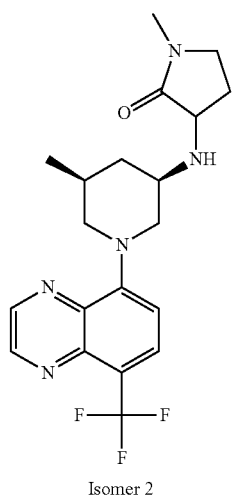 [SMILES: C[C@H]1C[C@@H](NC2CCN(C)C2=O)CN(c2ccc(C(F)(F)F)c3nccnc23)C1]<br>Isomer 2 |
| 354 | 95 | 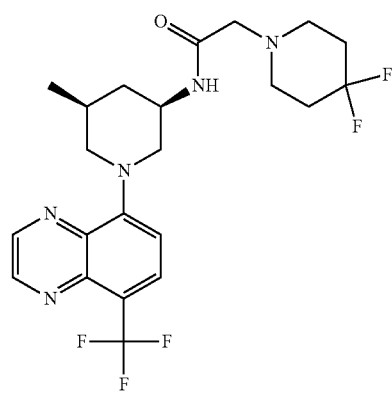 [SMILES: C[C@H]1C[C@@H](NC(=O)CN2CCC(F)(F)CC2)CN(c2ccc(C(F)(F)F)c3nccnc23)C1] |

TABLE 1-continued

| Compound Number | Example Number | Chemical Structure |
|---|---|---|
| 355 | 96 | 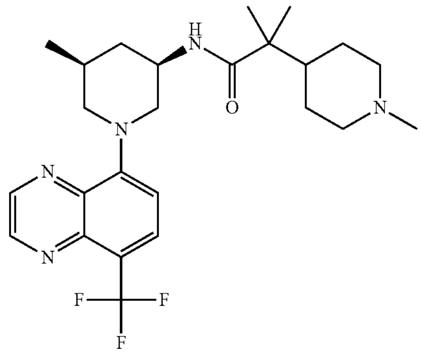 [SMILES: C[C@H]1C[C@@H](NC(=O)C(C)(C)C2CCN(C)CC2)CN(c2ccc(C(F)(F)F)c3nccnc23)C1] |
| 356 | 98 | 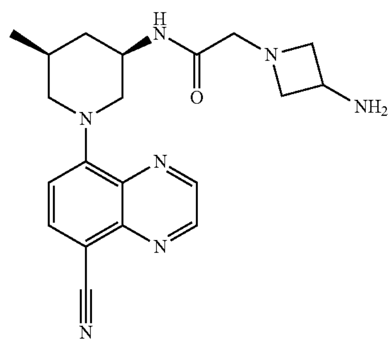 [SMILES: C[C@H]1C[C@@H](NC(=O)CN2CC(N)C2)CN(c2ccc(C#N)c3nccnc23)C1] |
| 357 | 99 | Isomer 1 |
| 358 | 99 | Isomer 2 |

TABLE 1-continued
| Compound Number | Example Number | Chemical Structure |
|---|---|---|
| 359 | 100 | 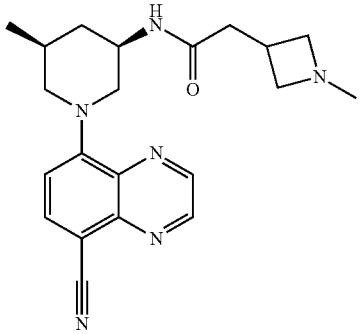 |
| 360 | 100 | 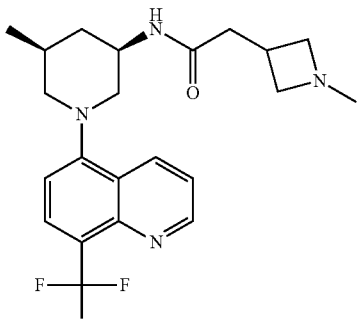 |
| 361 | 82 | 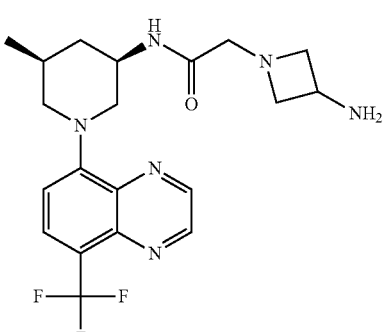 |
| 362 | 78 | 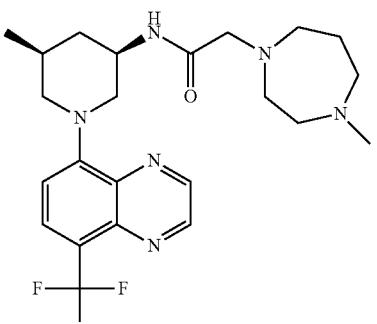 |

TABLE 1-continued
| Compound Number | Example Number | Chemical Structure |
|---|---|---|
| 363 | 100 | 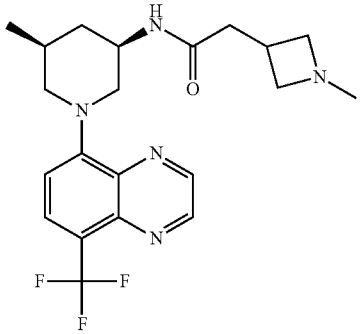 |
| 364 | 100 | 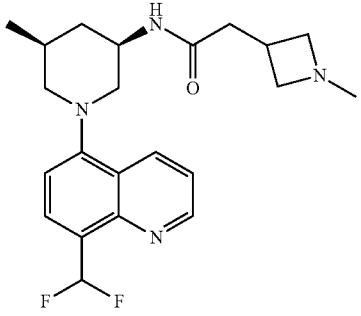 |
| 365 | 82 | 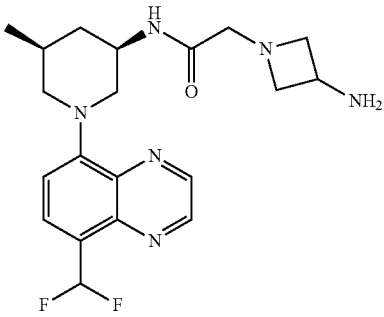 |
| 366 | 101 | 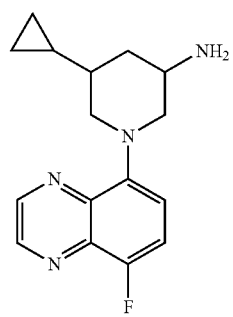  cis racemic |

TABLE 1-continued
| Compound Number | Example Number | Chemical Structure |
|---|---|---|
| 367 | 102 | 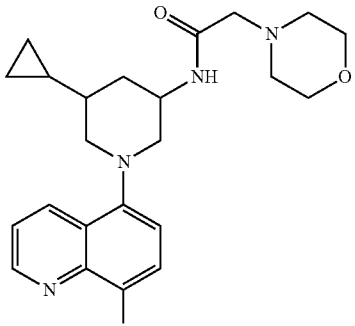<br>cis racemic |
| 368 | 103 | 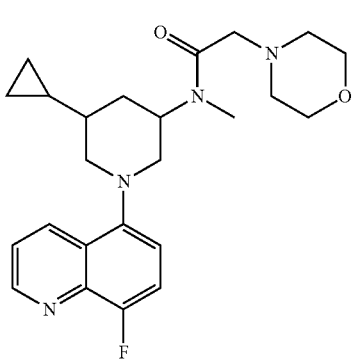<br>cis racemic |
| 369 | 104 | 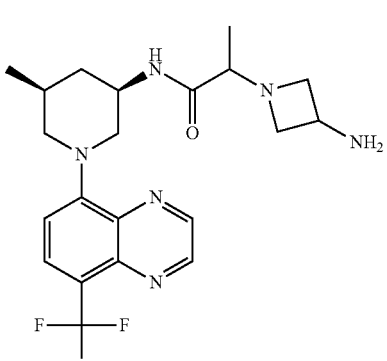<br>Isomer 1 |
| 370 | 104 | 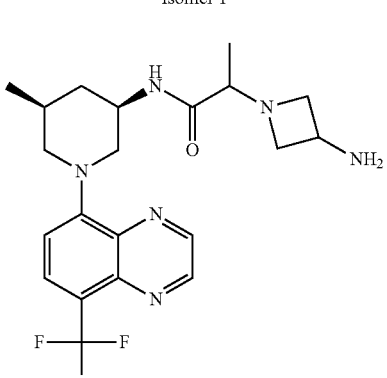<br>Isomer 2 |

TABLE 1-continued
| Compound Number | Example Number | Chemical Structure |
|---|---|---|
| 371 | 104 | 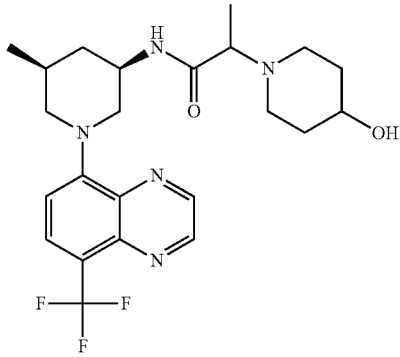<br>Isomer 1 |
| 372 | 104 | 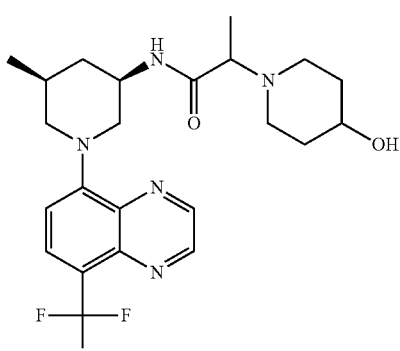<br>Isomer 2 |
| 373 | 105 | 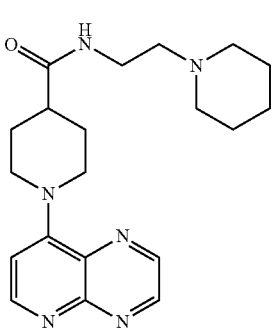 [SMILES: O=C(NCCN1CCCCC1)C1CCN(c2ccnc3nccnc23)CC1] |
| 374 | 106 | 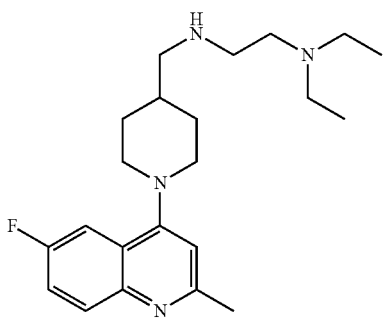 [SMILES: CCN(CC)CCNCC1CCN(c2cc(C)nc3ccc(F)cc23)CC1] |

TABLE 1-continued
| Compound Number | Example Number | Chemical Structure |
|---|---|---|
| 375 | 106 | 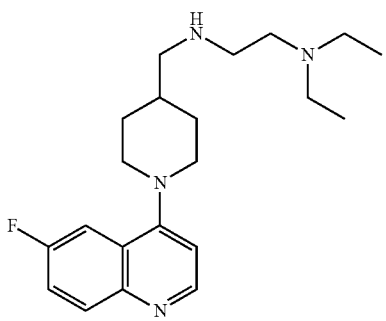 [SMILES: CCN(CC)CCNCC1CCN(c2ccnc3ccc(F)cc23)CC1] |
| 376 | 106 | 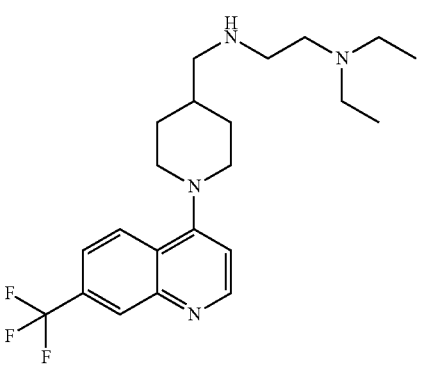 [SMILES: CCN(CC)CCNCC1CCN(c2ccnc3cc(C(F)(F)F)ccc23)CC1] |
| 377 | 106 | 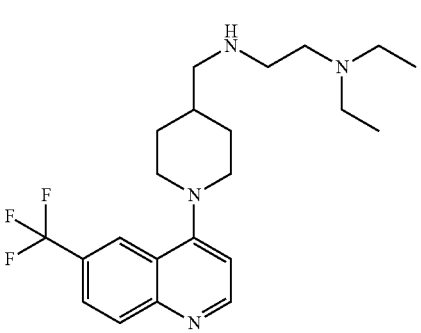 [SMILES: CCN(CC)CCNCC1CCN(c2ccnc3ccc(C(F)(F)F)cc23)CC1] |
| 378 | 106 | 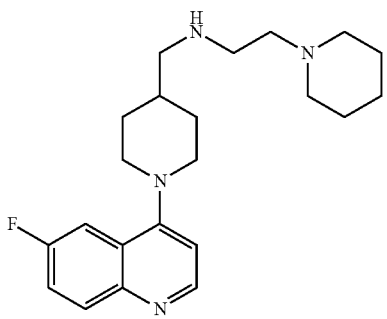 [SMILES: Fc1ccc2nccc(N3CCC(CNCCN4CCCCC4)CC3)c2c1] |

TABLE 1-continued
| Compound Number | Example Number | Chemical Structure |
|---|---|---|
| 379 | 105 | 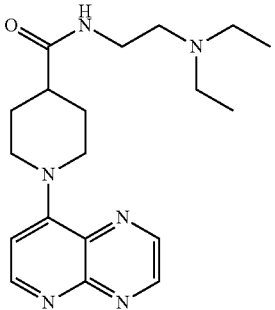 [SMILES: CCN(CC)CCNC(=O)C1CCN(c2ccnc3nccnc23)CC1] |
| 380 | 105 | 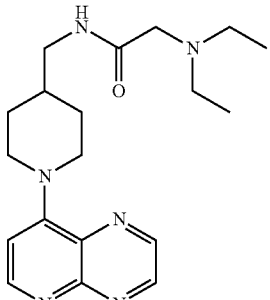 |
| 381 | 106 | 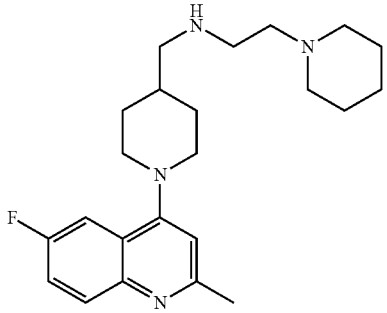 [SMILES: Cc1cc(N2CCC(CNCCN3CCCCC3)CC2)c2cc(F)ccc2n1] |
| 382 | 106 | 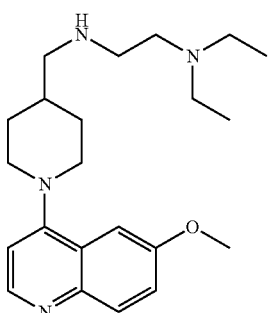 |
| 383 | 106 | 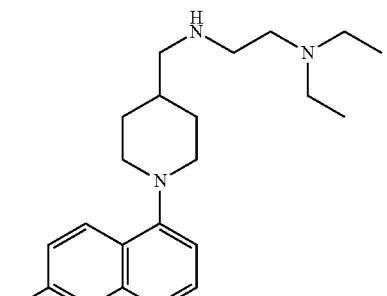 |

TABLE 1-continued
| Compound Number | Example Number | Chemical Structure |
|---|---|---|
| 384 | 106 | 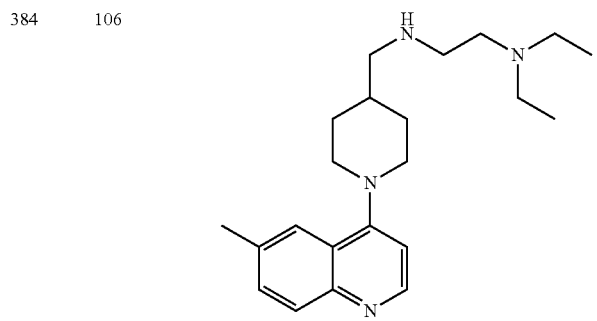 |
| 385 | 106 | 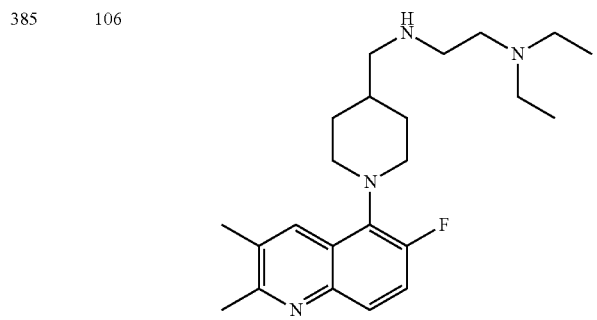 |
| 386 | 106 | 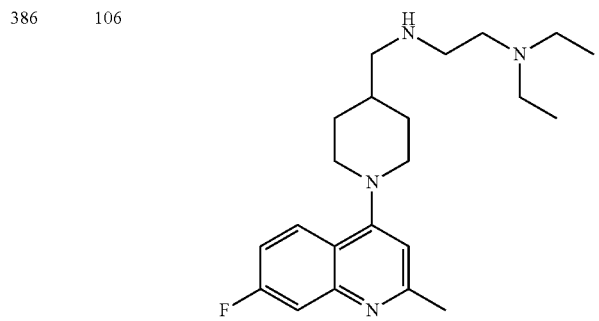 |
| 387 | 106 | 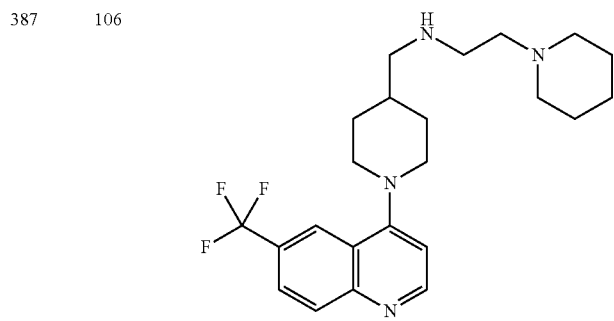 |

TABLE 1-continued

| Compound Number | Example Number | Chemical Structure |
|---|---|---|
| 388 | 7 | 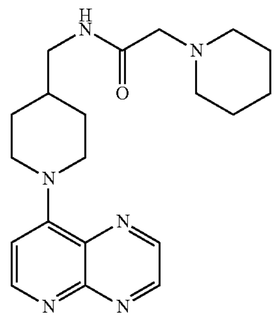 [SMILES: O=C(CN1CCCCC1)NCC1CCN(c2ccnc3nccnc23)CC1] |
| 389 | 106 | 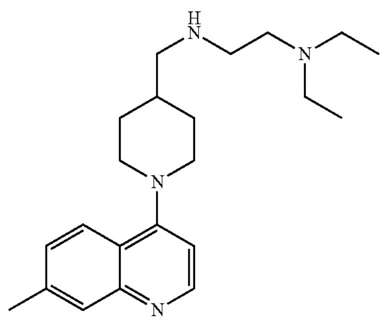 [SMILES: CCN(CC)CCNCC1CCN(c2ccnc3cc(C)ccc23)CC1] |
| 390 | 7 | 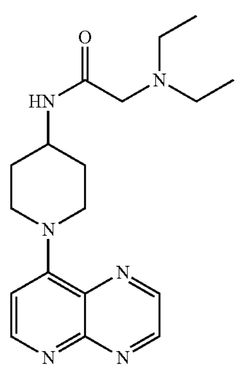 [SMILES: CCN(CC)CC(=O)NC1CCN(c2ccnc3nccnc23)CC1] |
| 391 | 7 | 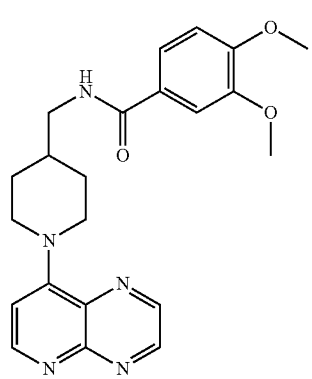 [SMILES: COc1ccc(C(=O)NCC2CCN(c3ccnc4nccnc34)CC2)cc1OC] |

TABLE 1-continued
| Compound Number | Example Number | Chemical Structure |
|---|---|---|
| 392 | 7 | 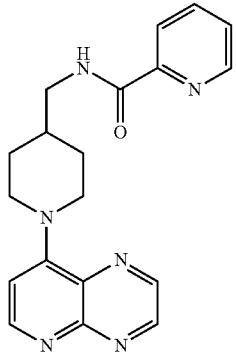 [SMILES: O=C(NCC1CCN(c2ccnc3nccnc23)CC1)c1ccccn1] |
| 393 | 107 | 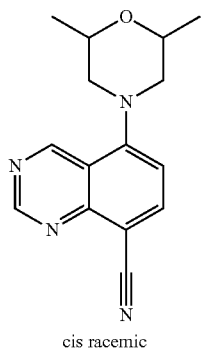 [SMILES: CC1CN(c2ccc(C#N)c3ncncc23)CC(C)O1]<br>cis racemic |
| 394 | 7 | 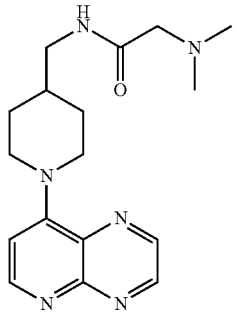 [SMILES: CN(C)CC(=O)NCC1CCN(c2ccnc3nccnc23)CC1] |
| 395 | 108 | 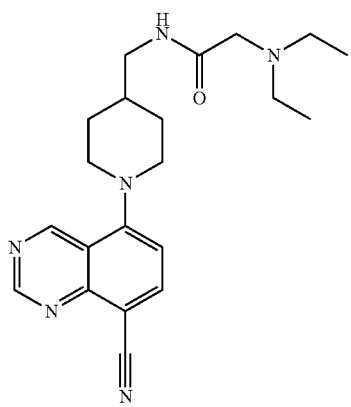 [SMILES: CCN(CC)CC(=O)NCC1CCN(c2ccc(C#N)c3ncncc23)CC1] |

TABLE 1-continued
| Compound Number | Example Number | Chemical Structure |
|---|---|---|
| 396 | 7 | 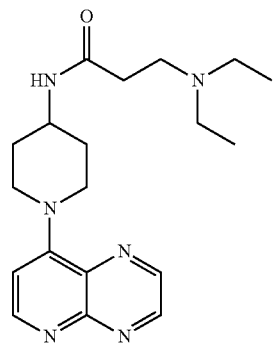 [SMILES: CCN(CC)CCC(=O)NC1CCN(c2ccnc3nccnc23)CC1] |
| 397 | 108 | 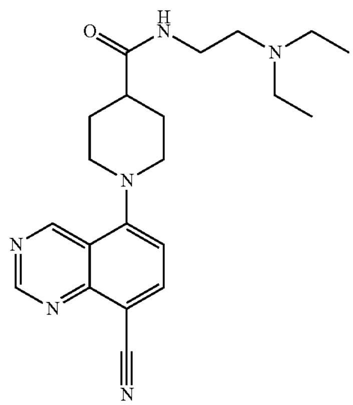 [SMILES: CCN(CC)CCNC(=O)C1CCN(c2ccc(C#N)c3ncncc23)CC1] |
| 398 | 108 | 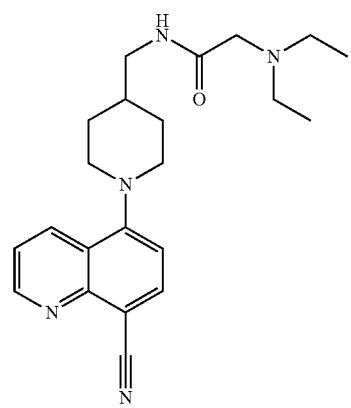 [SMILES: CCN(CC)CC(=O)NCC1CCN(c2ccc(C#N)c3ncccc23)CC1] |
| 399 | 7 | 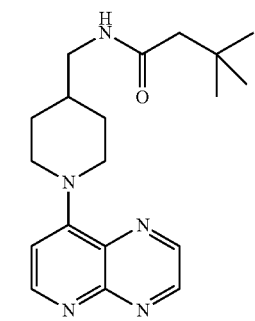 [SMILES: CC(C)(C)CC(=O)NCC1CCN(c2ccnc3nccnc23)CC1] |

TABLE 1-continued
| Compound Number | Example Number | Chemical Structure |
|---|---|---|
| 400 | 7 | 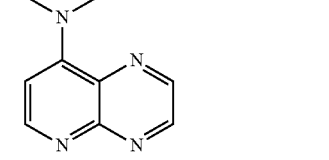 |
| 401 | 106 | 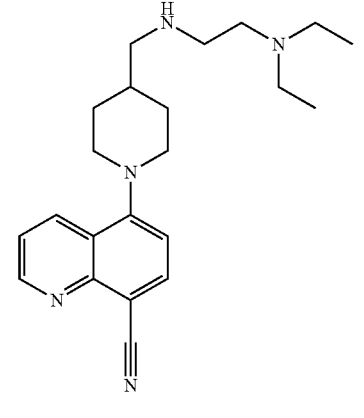 [SMILES: CCN(CC)CCNCC1CCN(c2ccc(C#N)c3ncccc23)CC1] |
| 402 | 7 | 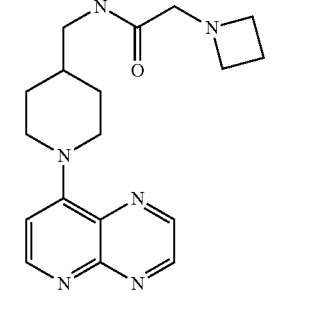 |
| 403 | 108 | 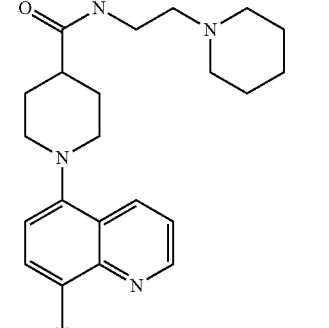 |

TABLE 1-continued
| Compound Number | Example Number | Chemical Structure |
|---|---|---|
| 404 | 109 | 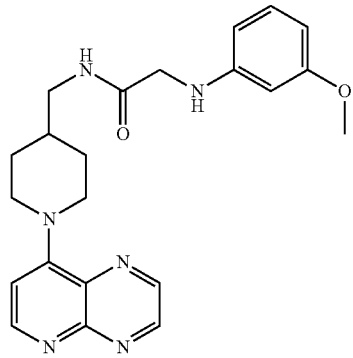 [SMILES: COc1cccc(NCC(=O)NCC2CCN(c3ccnc4nccnc34)CC2)c1] |
| 405 | 7 | 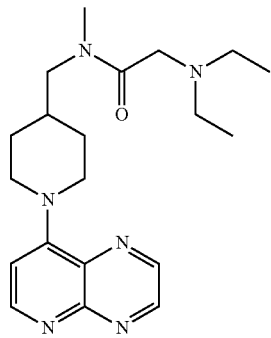 [SMILES: CCN(CC)CC(=O)N(C)CC1CCN(c2ccnc3nccnc23)CC1] |
| 406 | 109 | 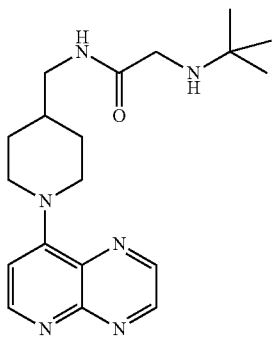 [SMILES: CC(C)(C)NCC(=O)NCC1CCN(c2ccnc3nccnc23)CC1] |
| 407 | 108 | 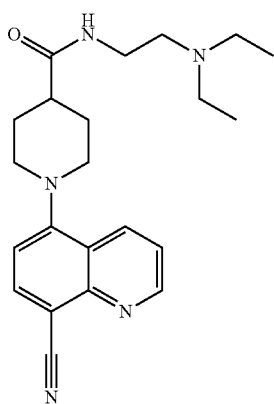 [SMILES: CCN(CC)CCNC(=O)C1CCN(c2ccc(C#N)c3ncccc23)CC1] |

TABLE 1-continued
| Compound Number | Example Number | Chemical Structure |
|---|---|---|
| 408 | 7 | 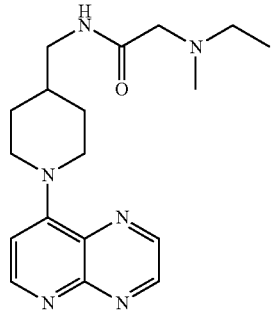 [SMILES: CCN(C)CC(=O)NCC1CCN(c2ccnc3nccnc23)CC1] |
| 409 | 7 | 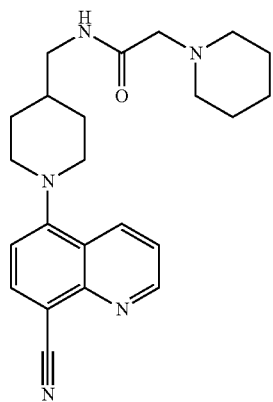 [SMILES: N#Cc1ccc(N2CCC(CNC(=O)CN3CCCCC3)CC2)c2cccnc12] |
| 410 | 7 | 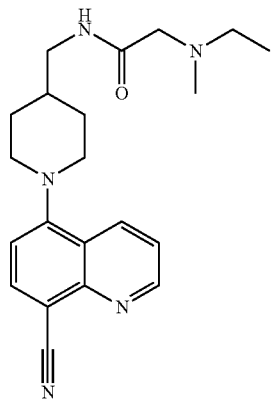 [SMILES: CCN(C)CC(=O)NCC1CCN(c2ccc(C#N)c3ncccc23)CC1] |
| 411 | 7 | 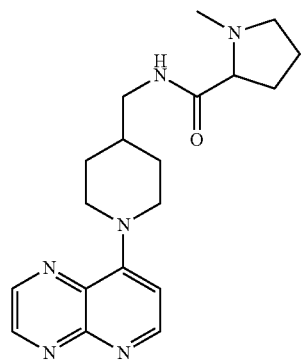 [SMILES: CN1CCCC1C(=O)NCC1CCN(c2ccnc3nccnc23)CC1] |

TABLE 1-continued
| Compound Number | Example Number | Chemical Structure |
|---|---|---|
| 412 | 7 | 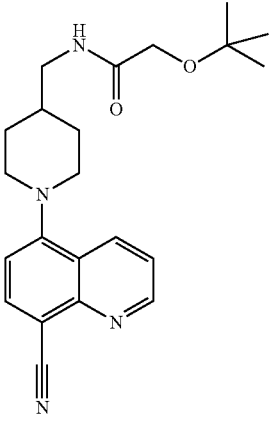 [SMILES: CC(C)(C)OCC(=O)NCC1CCN(c2ccc(C#N)c3ncccc23)CC1] |
| 413 | 109 | 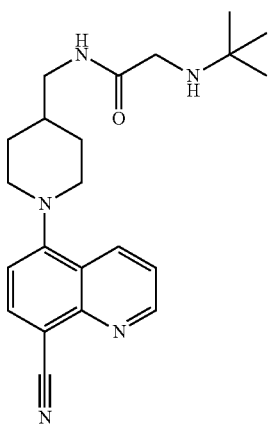 [SMILES: CC(C)(C)NCC(=O)NCC1CCN(c2ccc(C#N)c3ncccc23)CC1] |
| 414 | 1 | 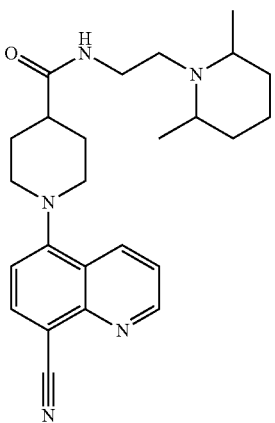 [SMILES: CC1CCCC(C)N1CCNC(=O)C1CCN(c2ccc(C#N)c3ncccc23)CC1] |

TABLE 1-continued
| Compound Number | Example Number | Chemical Structure |
|---|---|---|
| 415 | 1 | 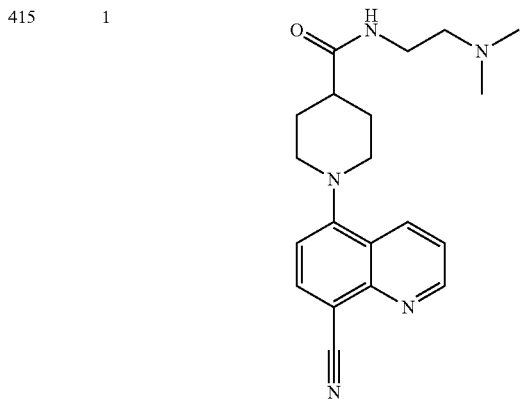 |
| 416 | 1 | 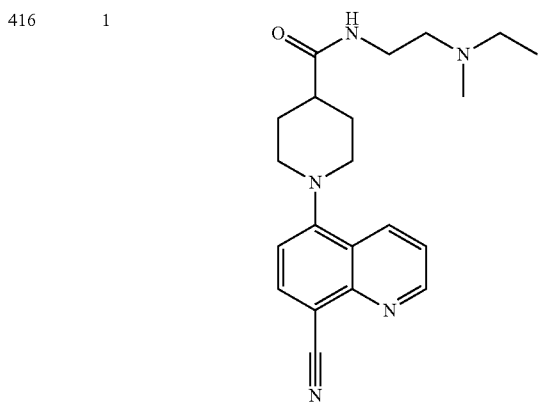 |
| 417 | 7 | 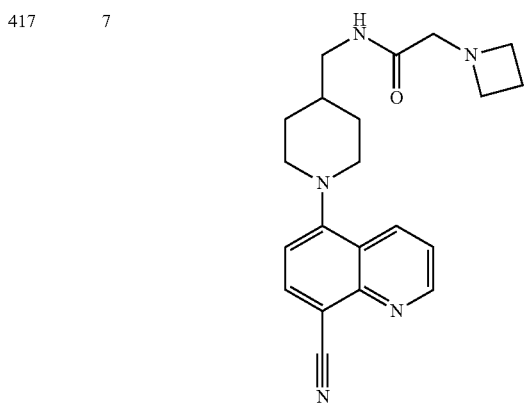 |

TABLE 1-continued
| Compound Number | Example Number | Chemical Structure |
|---|---|---|
| 418 | 7 | 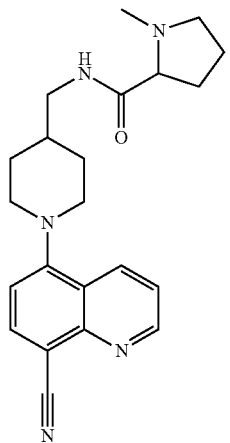 [SMILES: CN1CCCC1C(=O)NCC1CCN(c2ccc(C#N)c3ncccc23)CC1] |
| 419 | 1 | 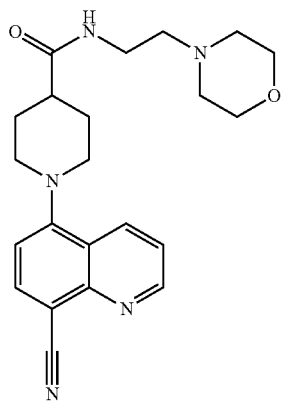 [SMILES: N#Cc1ccc(N2CCC(C(=O)NCCN3CCOCC3)CC2)c2cccnc12] |
| 420 | 1 | 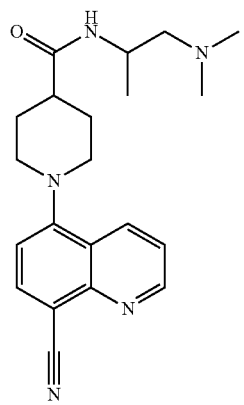 [SMILES: CC(CN(C)C)NC(=O)C1CCN(c2ccc(C#N)c3ncccc23)CC1] |

TABLE 1-continued
| Compound Number | Example Number | Chemical Structure |
|---|---|---|
| 421 | 1 | 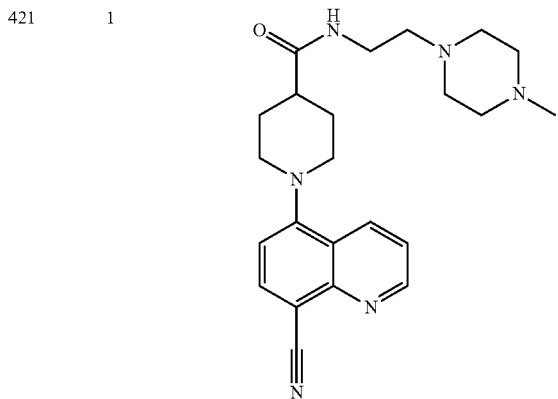 |
| 422 | 1 | 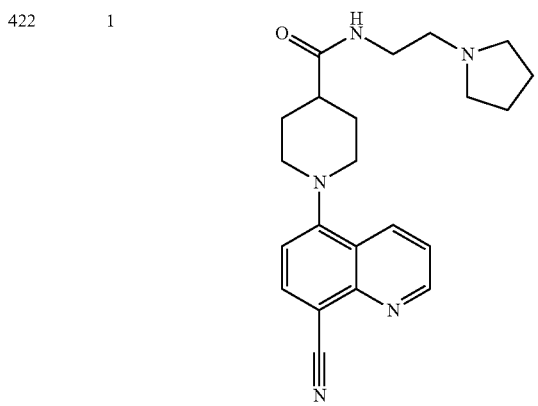 |
| 423 | 30 | 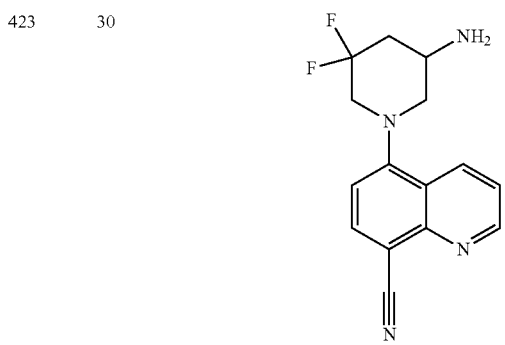 |
| 424 | 40 | 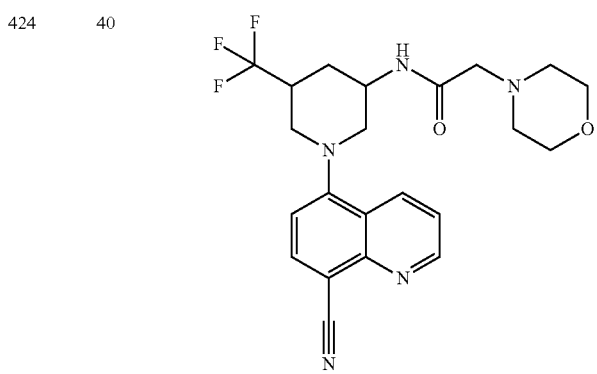<br>cis racemic |

TABLE 1-continued
| Compound Number | Example Number | Chemical Structure |
|---|---|---|
| 425 | 110 | 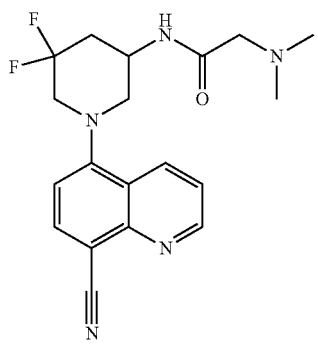 [SMILES: CN(C)CC(=O)NC1CN(c2ccc(C#N)c3ncccc23)CC(F)(F)C1] |
| 426 | 40 | 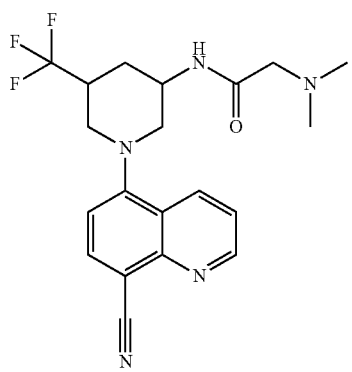<br>cis racemic |
| 427 | 1 | 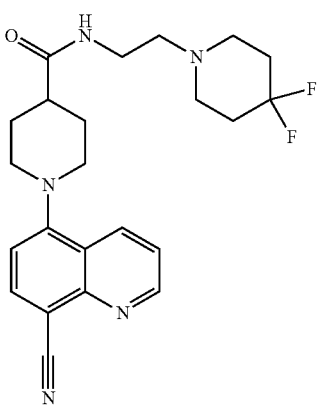 [SMILES: N#Cc1ccc(N2CCC(C(=O)NCCN3CCC(F)(F)CC3)CC2)c2cccnc12] |
| 428 | 40 | 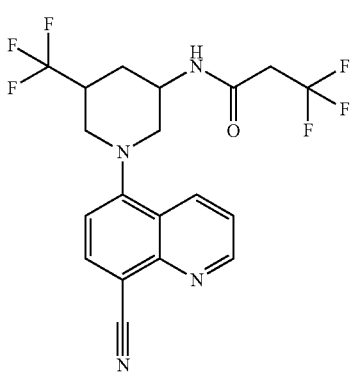<br>cis racemic |

TABLE 1-continued
| Compound Number | Example Number | Chemical Structure |
|---|---|---|
| 429 | 41 | 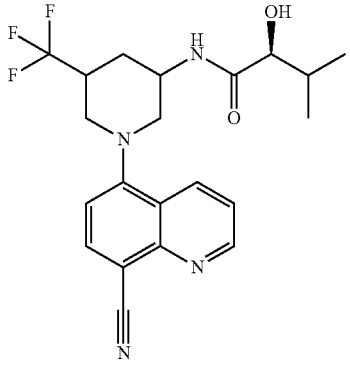<br>cis Isomer 1 |
| 430 | 41 | 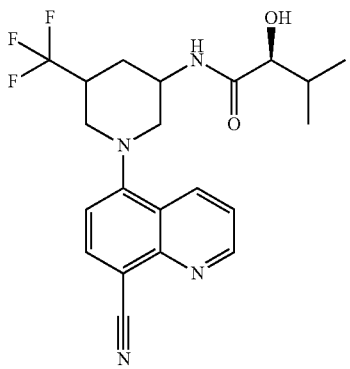<br>cis Isomer 2 |
| 431 | 40 | 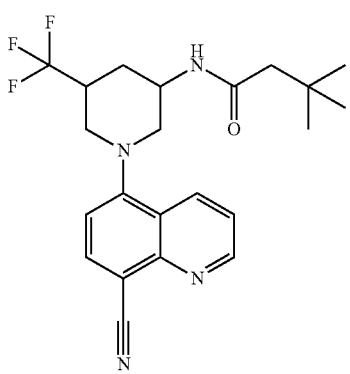<br>cis racemic |

TABLE 1-continued
| Compound Number | Example Number | Chemical Structure |
|---|---|---|
| 432 | 105 | 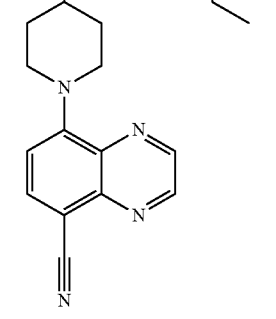 |
| 433 | 1 | 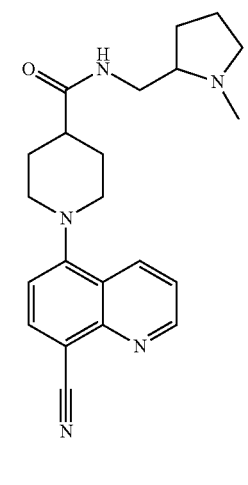 [SMILES: CN1CCCC1CNC(=O)C1CCN(c2ccc(C#N)c3ncccc23)CC1] |
| 434 | 1 | 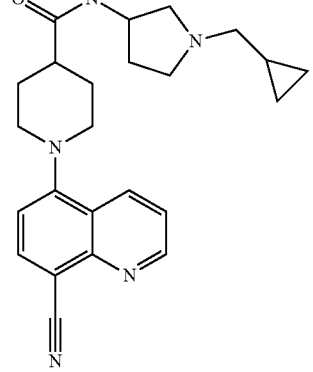 |

TABLE 1-continued
| Compound Number | Example Number | Chemical Structure |
|---|---|---|
| 435 | 1 | 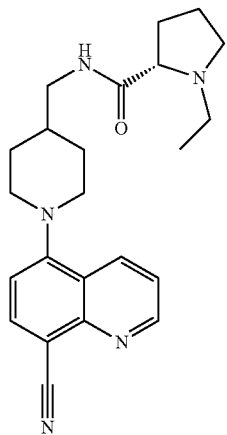 [SMILES: CCN1CCC[C@H]1C(=O)NCC1CCN(c2ccc(C#N)c3ncccc23)CC1] |
| 436 | 111 | 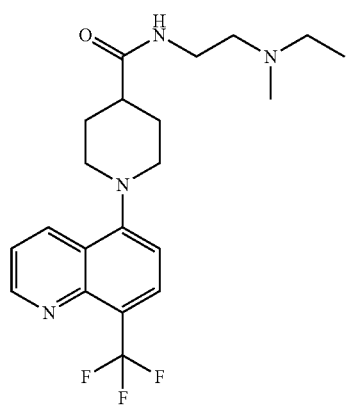 [SMILES: CCN(C)CCNC(=O)C1CCN(c2ccc(C(F)(F)F)c3ncccc23)CC1] |
| 437 | 41 | 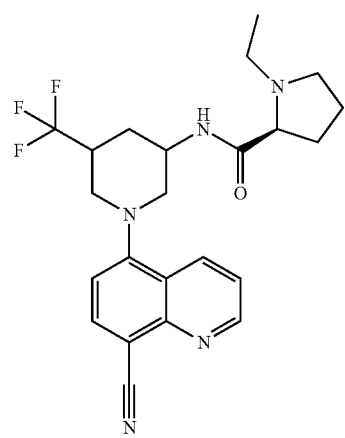<br>cis Isomer 1 |

TABLE 1-continued
| Compound Number | Example Number | Chemical Structure |
|---|---|---|
| 438 | 41 | 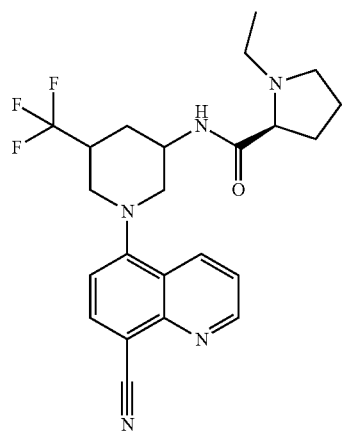<br>cis Isomer 2 |
| 439 | 1 | 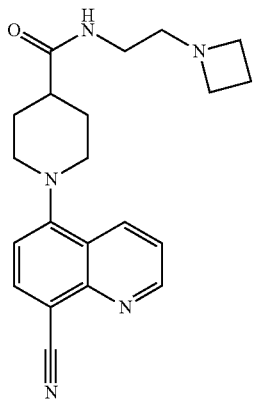 [SMILES: N#Cc1ccc(N2CCC(C(=O)NCCN3CCC3)CC2)c2cccnc12] |
| 440 | 1 | 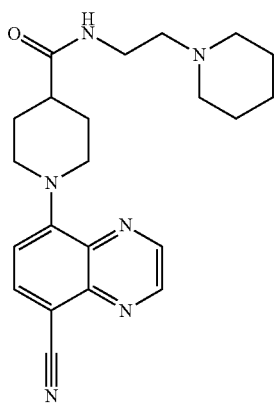 [SMILES: N#Cc1ccc(N2CCC(C(=O)NCCN3CCCCC3)CC2)c2nccnc12] |

TABLE 1-continued
| Compound Number | Example Number | Chemical Structure |
|---|---|---|
| 441 | 111 | 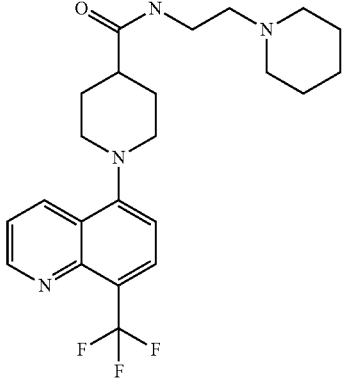 |
| 442 | 111 | 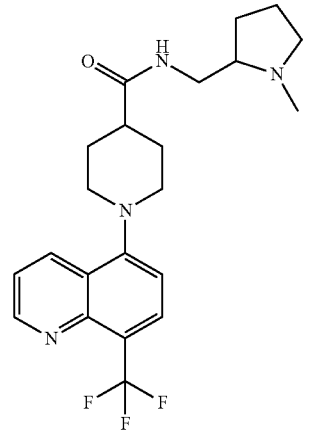 [SMILES: CN1CCCC1CNC(=O)C1CCN(c2ccc(C(F)(F)F)c3ncccc23)CC1] |
| 443 | 112 | 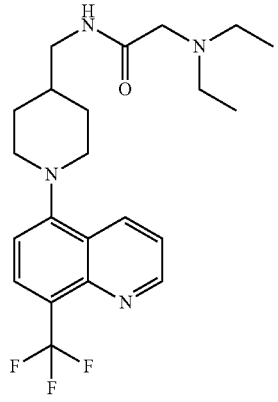 |

TABLE 1-continued
| Compound Number | Example Number | Chemical Structure |
|---|---|---|
| 444 | 113 | 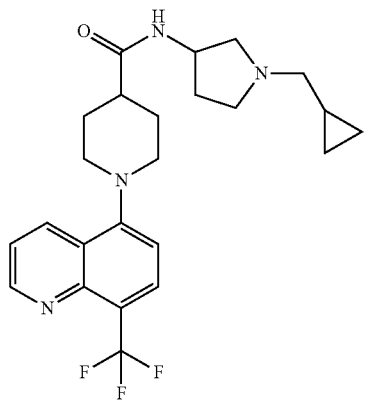 Isomer 1 |
| 445 | 113 | 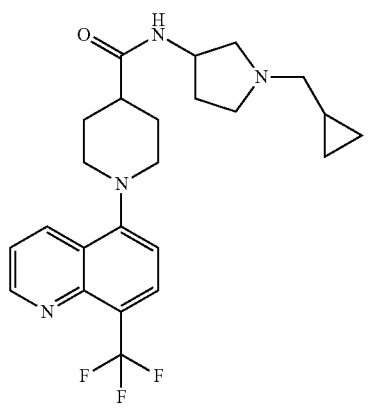 Isomer 2 |
| 446 | 111 | 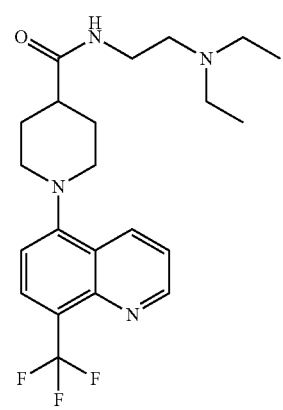 [SMILES: CCN(CC)CCNC(=O)C1CCN(c2ccc(C(F)(F)F)c3ncccc23)CC1] |

TABLE 1-continued

| Compound Number | Example Number | Chemical Structure |
|---|---|---|
| 447 | 114 | 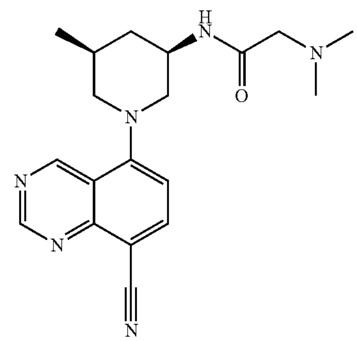 [SMILES: C[C@H]1C[C@@H](NC(=O)CN(C)C)CN(c2ccc(C#N)c3ncncc23)C1] |
| 448 | 112 | 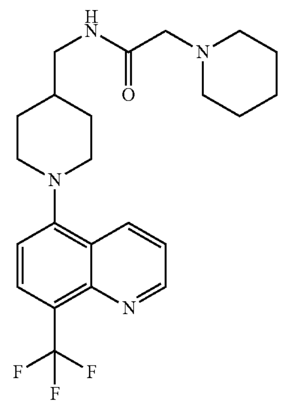 [SMILES: O=C(CN1CCCCC1)NCC1CCN(c2ccc(C(F)(F)F)c3ncccc23)CC1] |
| 449 | 115 | Isomer 1 |
| 450 | 115 | Isomer 2 |

TABLE 1-continued
| Compound Number | Example Number | Chemical Structure |
|---|---|---|
| 451 | 116 | 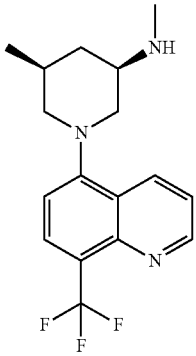 [SMILES: CN[C@@H]1C[C@H](C)CN(c2ccc(C(F)(F)F)c3ncccc23)C1] |
| 452 | 117 | 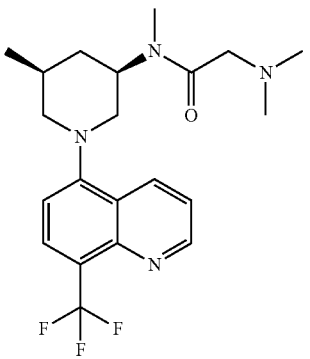 |
| 453 | 118 | 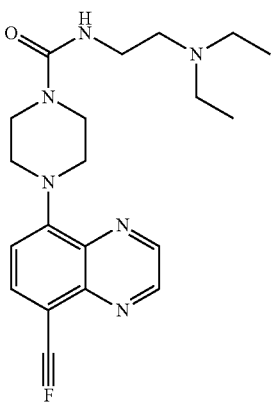 |
| 454 | 1 | 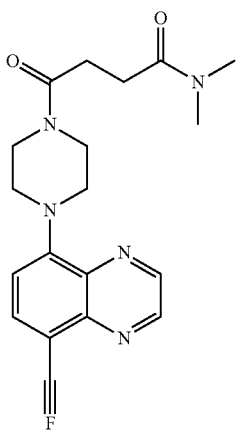 |

TABLE 1-continued

| Compound Number | Example Number | Chemical Structure |
|---|---|---|
| 455 | 107 | 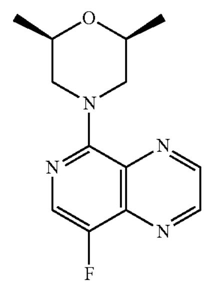 [SMILES: C[C@@H]1CN(c2ncc(F)c3nccnc23)C[C@H](C)O1] |
| 456 | 1 | 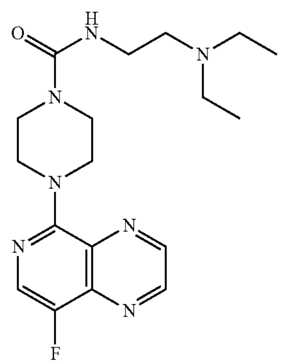 [SMILES: CCN(CC)CCNC(=O)N1CCN(c2ncc(F)c3nccnc23)CC1] |
| 457 | 32 | 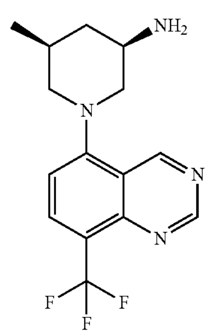 [SMILES: C[C@H]1C[C@@H](N)CN(c2ccc(C(F)(F)F)c3ncncc23)C1] |
| 458 | 119 | 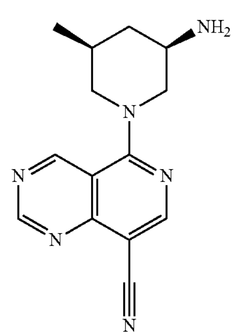 [SMILES: C[C@H]1C[C@@H](N)CN(c2ncc(C#N)c3ncncc23)C1] |
| 459 | 32 | 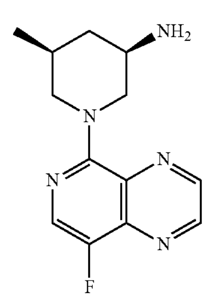 [SMILES: C[C@H]1C[C@@H](N)CN(c2ncc(F)c3nccnc23)C1] |

TABLE 1-continued
| Compound Number | Example Number | Chemical Structure |
|---|---|---|
| 460 | 114 | 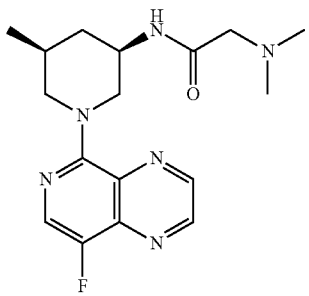 |
| 461 | 119 | 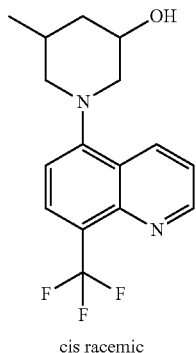 [SMILES: CC1CC(O)CN(c2ccc(C(F)(F)F)c3ncccc23)C1]<br>cis racemic |
| 462 | 89 | 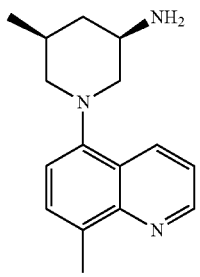 [SMILES: Cc1ccc(N2C[C@@H](C)C[C@@H](N)C2)c2cccnc12] |
| 463 | 118 | 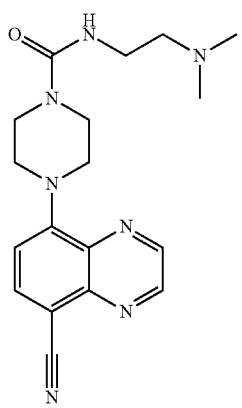 [SMILES: CN(C)CCNC(=O)N1CCN(c2ccc(C#N)c3nccnc23)CC1] |

TABLE 1-continued

| Compound Number | Example Number | Chemical Structure |
|---|---|---|
| 464 | 120 | 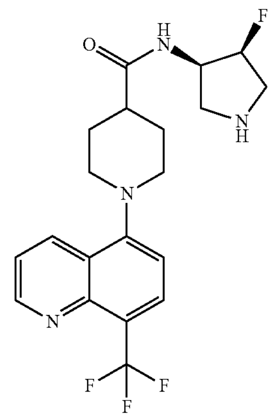 [SMILES: O=C(N[C@@H]1CNC[C@@H]1F)C1CCN(c2ccc(C(F)(F)F)c3ncccc23)CC1] |
| 465 | 121 | 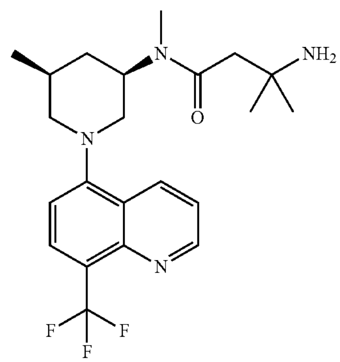 [SMILES: C[C@H]1C[C@@H](N(C)C(=O)CC(C)(C)N)CN(c2ccc(C(F)(F)F)c3ncccc23)C1] |
| 466 | 114 | 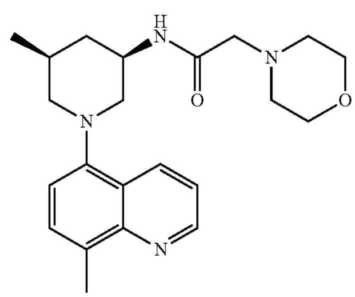 [SMILES: Cc1ccc(N2C[C@@H](C)C[C@@H](NC(=O)CN3CCOCC3)C2)c2cccnc12] |
| 467 | 22 | 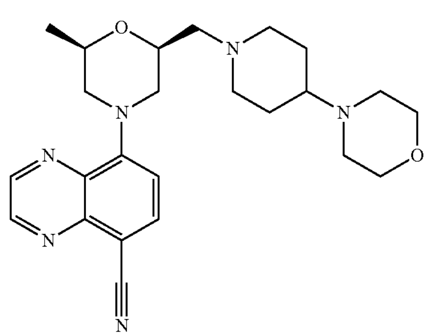 [SMILES: C[C@@H]1CN(c2ccc(C#N)c3nccnc23)C[C@H](CN2CCC(N3CCOCC3)CC2)O1] |

TABLE 1-continued
| Compound Number | Example Number | Chemical Structure |
|---|---|---|
| 468 | 25 | 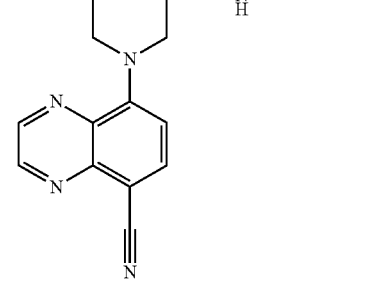 |
| 469 | 114 | 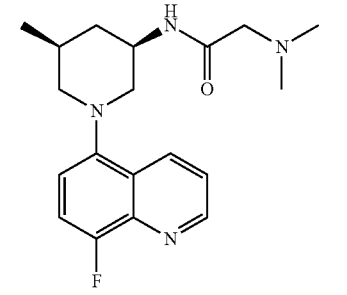 |
| 470 | 114 | 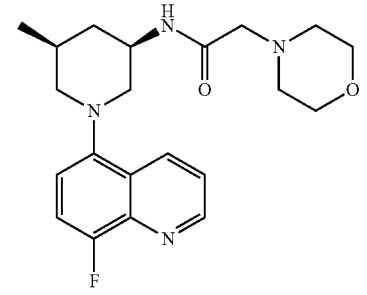 [SMILES: C[C@H]1C[C@@H](NC(=O)CN2CCOCC2)CN(c2ccc(F)c3ncccc23)C1] |
| 471 | 114 | 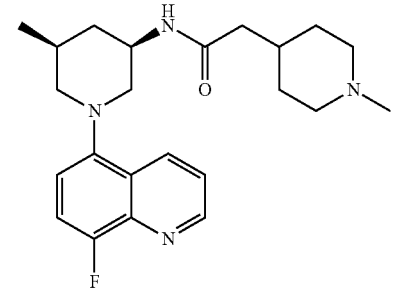 |

TABLE 1-continued
| Compound Number | Example Number | Chemical Structure |
|---|---|---|
| 472 | 57 | 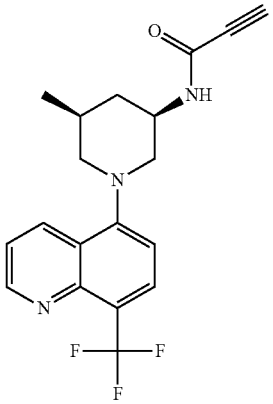 [SMILES: C#CC(=O)N[C@@H]1C[C@H](C)CN(c2ccc(C(F)(F)F)c3ncccc23)C1] |
| 473 | 57 | 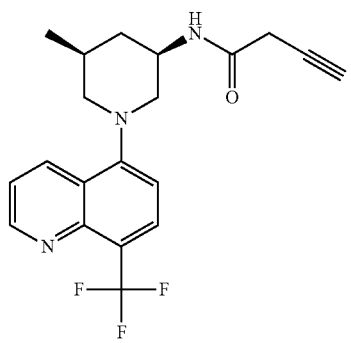 [SMILES: C#CCC(=O)N[C@@H]1C[C@H](C)CN(c2ccc(C(F)(F)F)c3ncccc23)C1] |
| 474 | 57 | 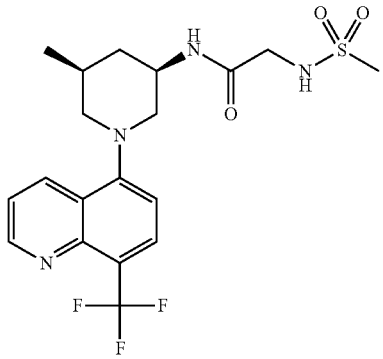 [SMILES: C[C@H]1C[C@@H](NC(=O)CNS(C)(=O)=O)CN(c2ccc(C(F)(F)F)c3ncccc23)C1] |
| 475 | 57 | 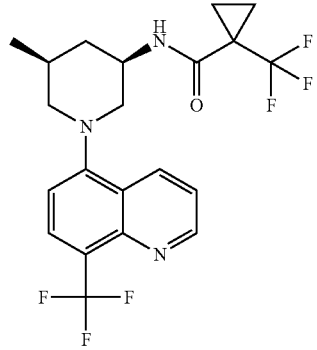 [SMILES: C[C@H]1C[C@@H](NC(=O)C2(C(F)(F)F)CC2)CN(c2ccc(C(F)(F)F)c3ncccc23)C1] |

TABLE 1-continued
| Compound Number | Example Number | Chemical Structure |
|---|---|---|
| 476 | 80 | 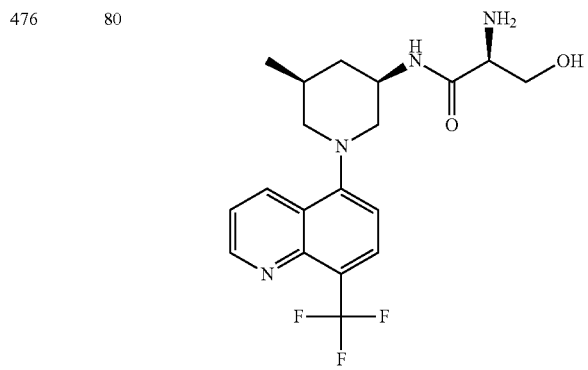 |
| 477 | 121 | 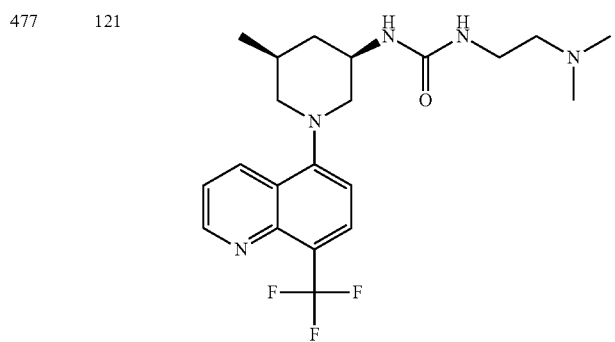 |
| 478 | 122 | 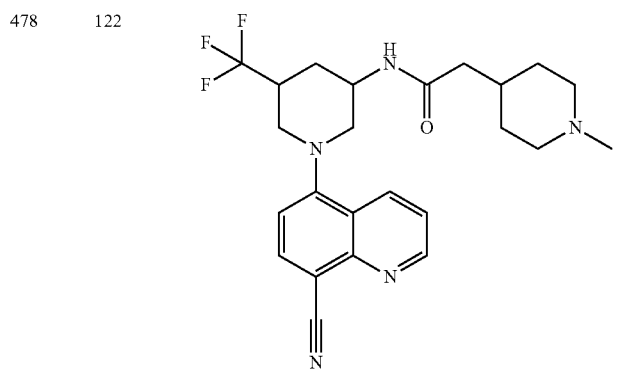
cis racemic |
| 479 | 123 | 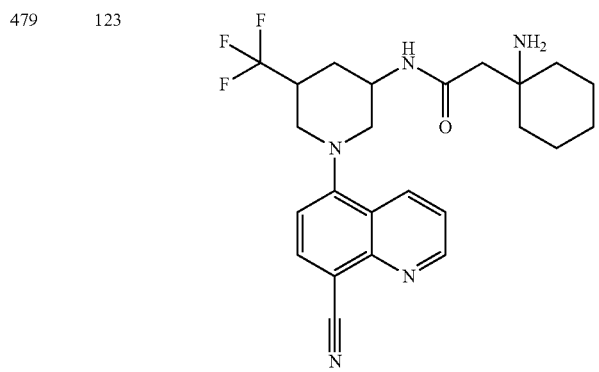
cis racemic |

TABLE 1-continued
| Compound Number | Example Number | Chemical Structure |
|---|---|---|
| 480 | 124 | 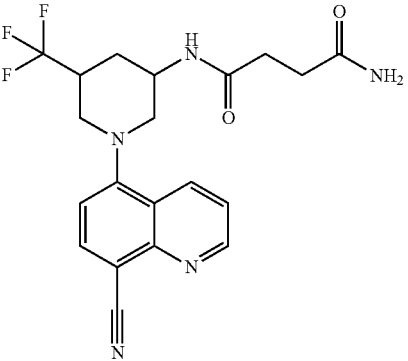<br>cis racemic |
| 481 | 122 | 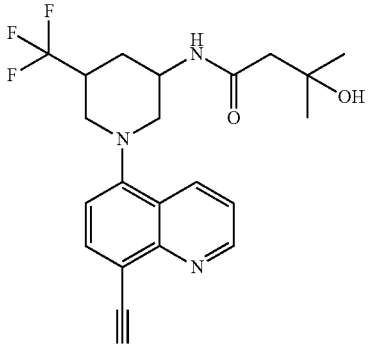<br>cis racemic |
| 482 | 124 | 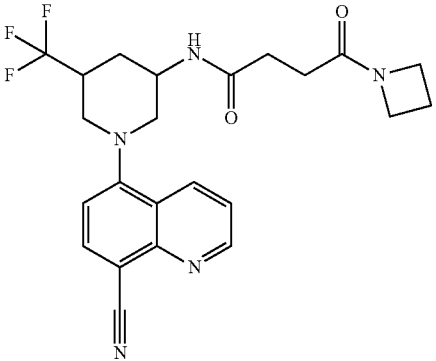<br>cis racemic |
| 483 | 123 | 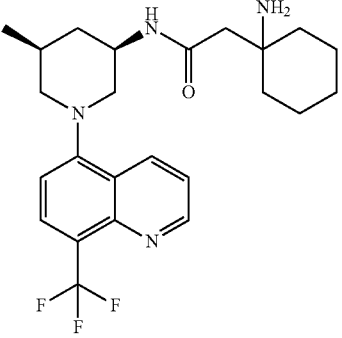 [SMILES: C[C@H]1C[C@@H](NC(=O)CC2(N)CCCCC2)CN(c2ccc(C(F)(F)F)c3ncccc23)C1] |

TABLE 1-continued
| Compound Number | Example Number | Chemical Structure |
|---|---|---|
| 484 | 122 | 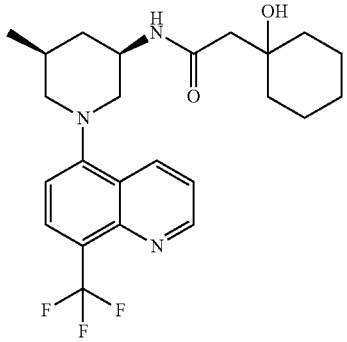 [SMILES: C[C@H]1C[C@@H](NC(=O)CC2(O)CCCCC2)CN(c2ccc(C(F)(F)F)c3ncccc23)C1] |
| 485 | 122 | 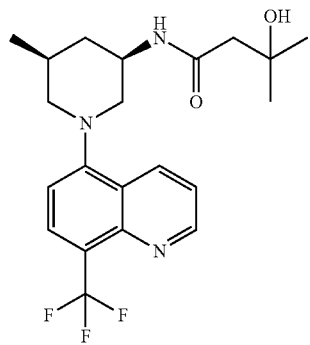 [SMILES: C[C@H]1C[C@@H](NC(=O)CC(C)(C)O)CN(c2ccc(C(F)(F)F)c3ncccc23)C1] |
| 486 | 123 | 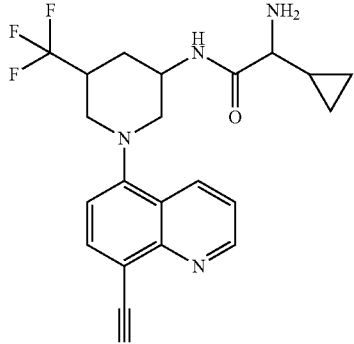<br>racemic Isomer 1 |
| 487 | 123 | 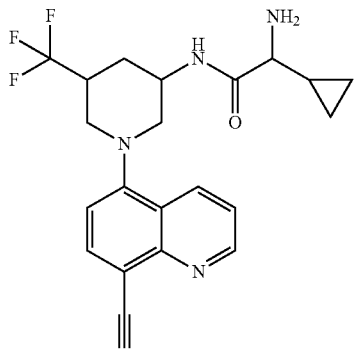<br>racemic isomer 2 |

TABLE 1-continued

| Compound Number | Example Number | Chemical Structure |
|---|---|---|
| 488 | 125 | 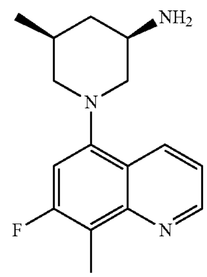 [SMILES: Cc1c(F)cc(N2C[C@@H](C)C[C@@H](N)C2)c2cccnc12] |
| 489 | 125 | 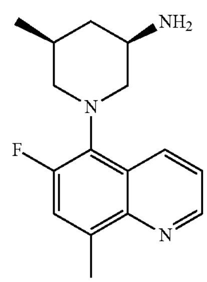 [SMILES: Cc1cc(F)c(N2C[C@@H](C)C[C@@H](N)C2)c2cccnc12] |
| 490 | 122 | cis racemic |
| 491 | 122 | cis racemic |

TABLE 1-continued
| Compound Number | Example Number | Chemical Structure |
|---|---|---|
| 492 | 124 | 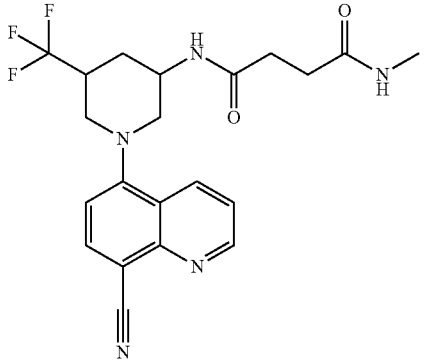<br>cis racemic |
| 493 | 123 | 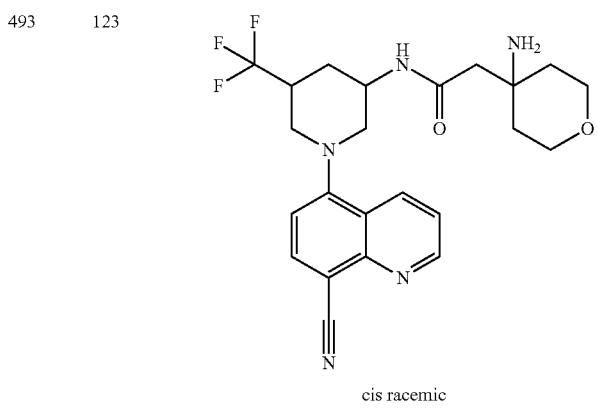<br>cis racemic |
| 494 | 126 | 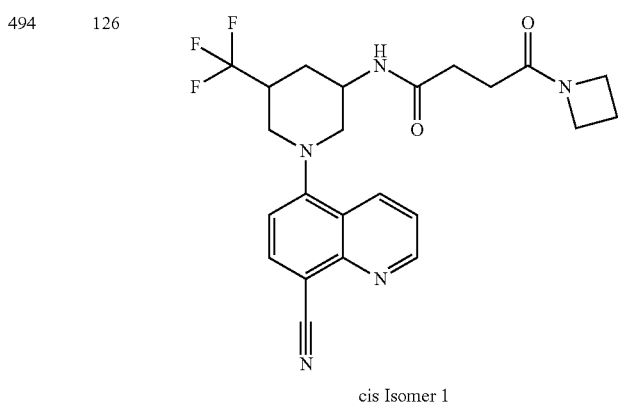<br>cis Isomer 1 |

TABLE 1-continued
| Compound Number | Example Number | Chemical Structure |
|---|---|---|
| 495 | 126 | 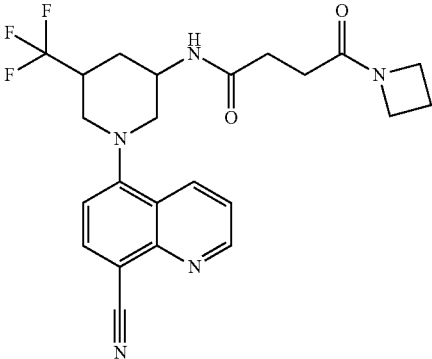<br>cis Isomer 2 |
| 496 | 122 | 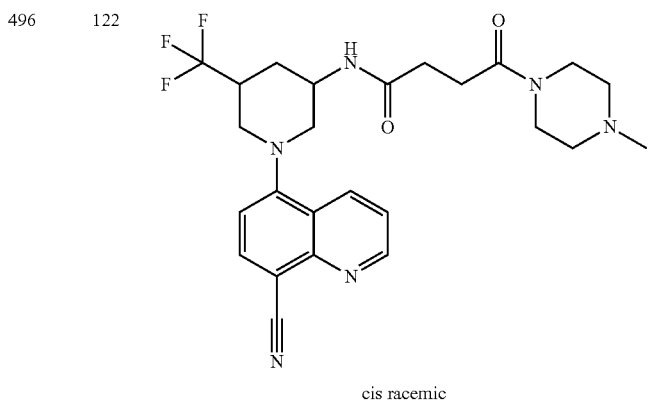<br>cis racemic |
| 497 | 126 | 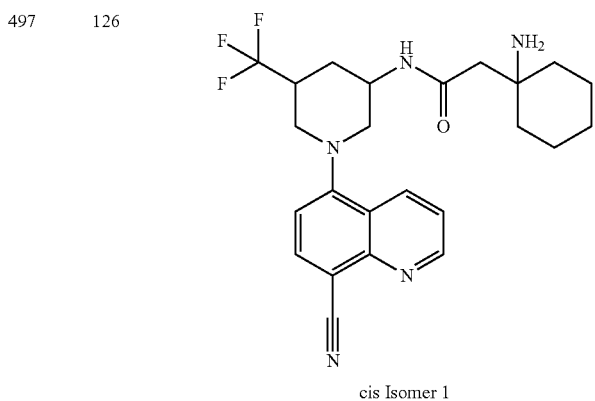<br>cis Isomer 1 |

TABLE 1-continued
| Compound Number | Example Number | Chemical Structure |
|---|---|---|
| 498 | 126 | 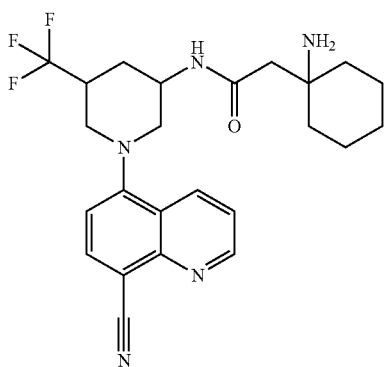 cis Isomer 2 |
| 499 | 127 | 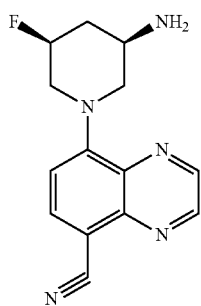 [SMILES: N#Cc1ccc(N2C[C@H](N)C[C@H](F)C2)c2nccnc12] |
| 500 | 127 | 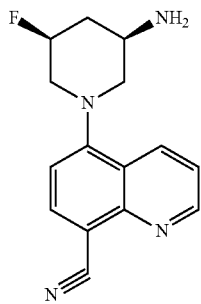 [SMILES: N#Cc1ccc(N2C[C@H](N)C[C@H](F)C2)c2cccnc12] |
| 501 | 127 | 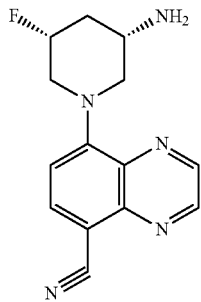 [SMILES: N#Cc1ccc(N2C[C@@H](N)C[C@@H](F)C2)c2nccnc12] |

TABLE 1-continued
| Compound Number | Example Number | Chemical Structure |
|---|---|---|
| 502 | 128 | 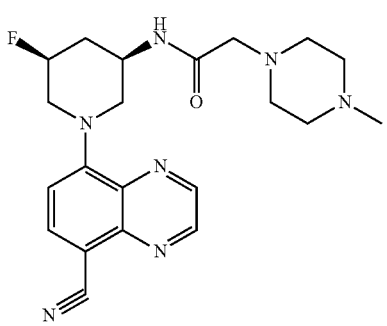 [SMILES: CN1CCN(CC(=O)N[C@@H]2C[C@H](F)CN(c3ccc(C#N)c4nccnc34)C2)CC1] |
| 503 | 129 | 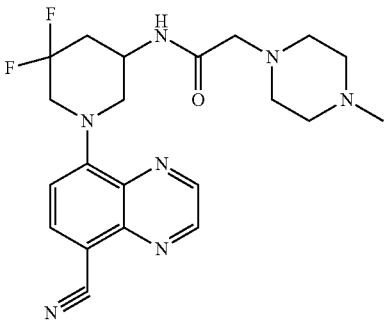 [SMILES: CN1CCN(CC(=O)NC2CN(c3ccc(C#N)c4nccnc34)CC(F)(F)C2)CC1] |
| 504 | 129 | 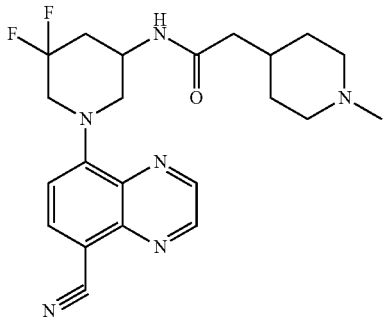 [SMILES: CN1CCC(CC(=O)NC2CN(c3ccc(C#N)c4nccnc34)CC(F)(F)C2)CC1] |
| 505 | 130 | 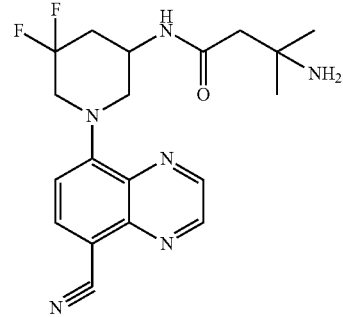 [SMILES: CC(C)(N)CC(=O)NC1CN(c2ccc(C#N)c3nccnc23)CC(F)(F)C1] |

TABLE 1-continued
| Compound Number | Example Number | Chemical Structure |
|---|---|---|
| 506 | 129 | 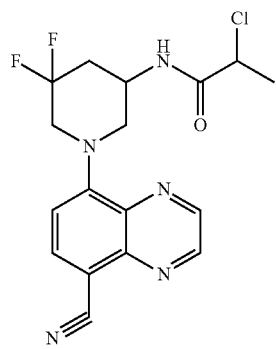 [SMILES: CC(Cl)C(=O)NC1CN(c2ccc(C#N)c3nccnc23)CC(F)(F)C1] |
| 507 | 131 | 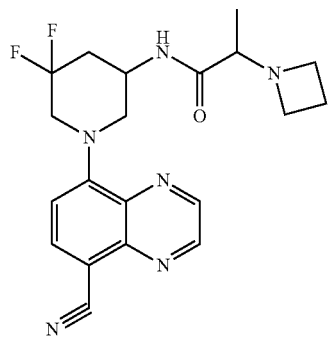 racemic Isomer 1 |
| 508 | 131 | 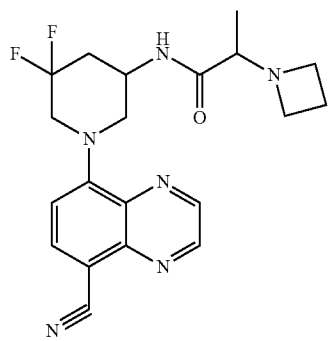 racemic Isomer 2 |
| 509 | 131 | 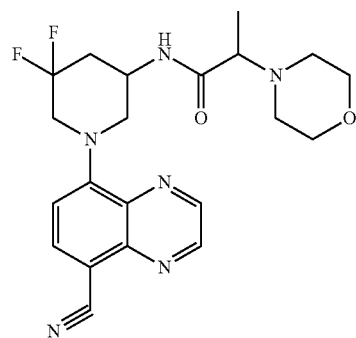 [SMILES: CC(C(=O)NC1CN(c2ccc(C#N)c3nccnc23)CC(F)(F)C1)N1CCOCC1] |

TABLE 1-continued
| Compound Number | Example Number | Chemical Structure |
|---|---|---|
| 510 | 30 | 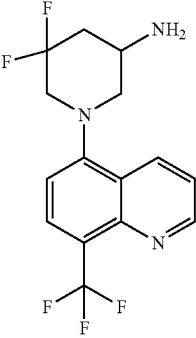 [SMILES: NC1CN(c2ccc(C(F)(F)F)c3ncccc23)CC(F)(F)C1] |
| 511 | 40 | 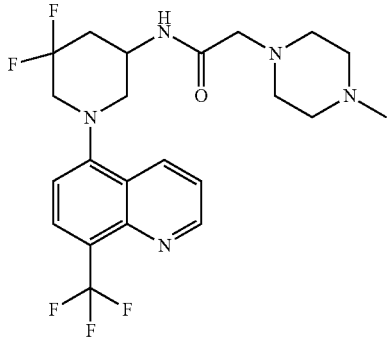 [SMILES: CN1CCN(CC(=O)NC2CN(c3ccc(C(F)(F)F)c4ncccc34)CC(F)(F)C2)CC1] |
| 512 | 40 | 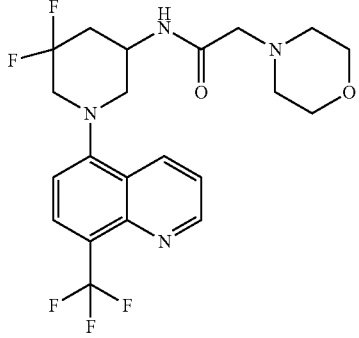 [SMILES: O=C(CN1CCOCC1)NC1CN(c2ccc(C(F)(F)F)c3ncccc23)CC(F)(F)C1] |
| 513 | 40 | 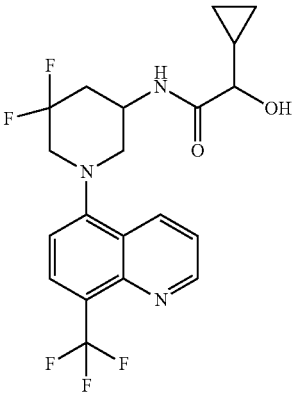 [SMILES: O=C(NC1CN(c2ccc(C(F)(F)F)c3ncccc23)CC(F)(F)C1)C(O)C1CC1] |

TABLE 1-continued
| Compound Number | Example Number | Chemical Structure |
|---|---|---|
| 514 | 80 | 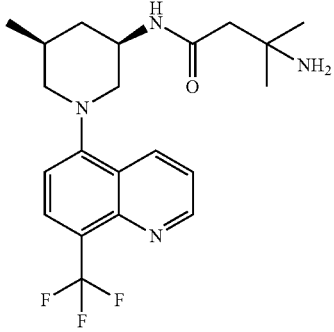 [SMILES: C[C@H]1C[C@@H](NC(=O)CC(C)(C)N)CN(c2ccc(C(F)(F)F)c3ncccc23)C1] |
| 515 | 57 | 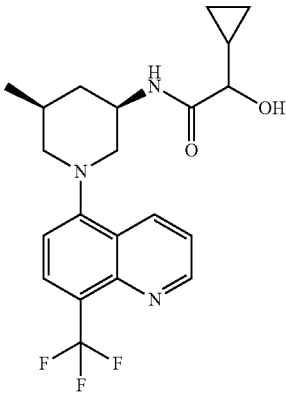 [SMILES: C[C@H]1C[C@@H](NC(=O)C(O)C2CC2)CN(c2ccc(C(F)(F)F)c3ncccc23)C1] |
| 516 | 57 | 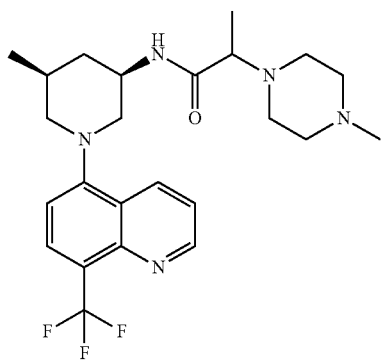 |
| 517 | 57 | 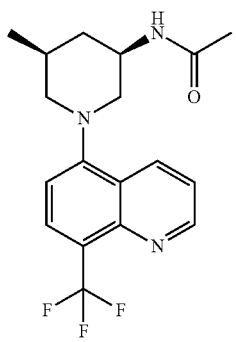 [SMILES: CC(=O)N[C@@H]1C[C@H](C)CN(c2ccc(C(F)(F)F)c3ncccc23)C1] |

TABLE 1-continued
| Compound Number | Example Number | Chemical Structure |
|---|---|---|
| 518 | 132 | 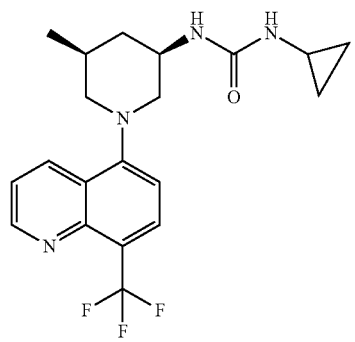 [SMILES: C[C@H]1C[C@@H](NC(=O)NC2CC2)CN(c2ccc(C(F)(F)F)c3ncccc23)C1] |
| 519 | 57 | 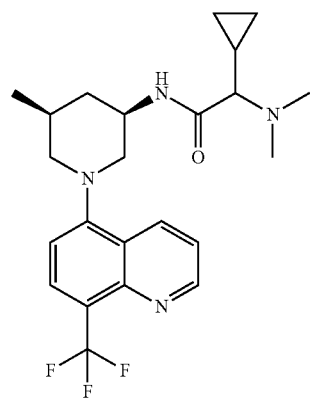 |
| 520 | 126 | 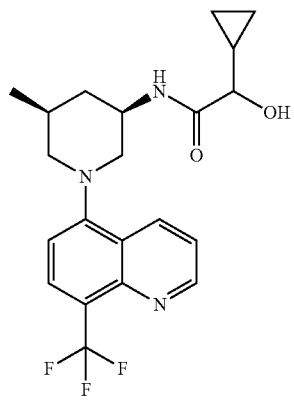
Isomer 1 |

TABLE 1-continued
| Compound Number | Example Number | Chemical Structure |
|---|---|---|
| 521 | 126 | 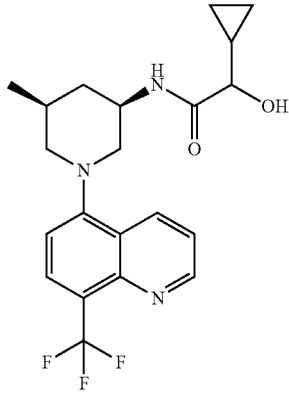<br>Isomer 2 |
| 522 | 126 | 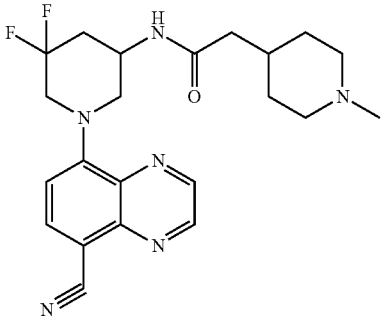<br>Isomer 1 |
| 523 | 126 | 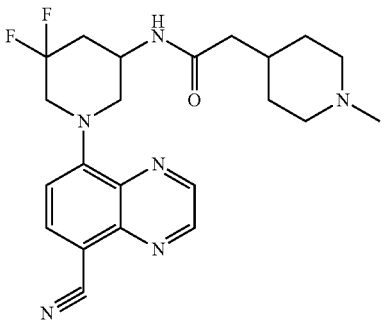<br>Isomer 2 |
| 524 | 30 | 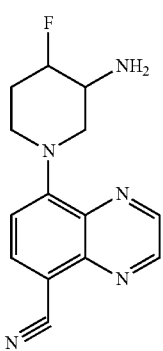 [SMILES: N#Cc1ccc(N2CCC(F)C(N)C2)c2nccnc12] |

TABLE 1-continued
| Compound Number | Example Number | Chemical Structure |
|---|---|---|
| 525 | 133 | 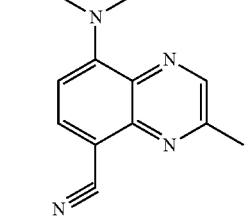 |
| 526 | 57 | 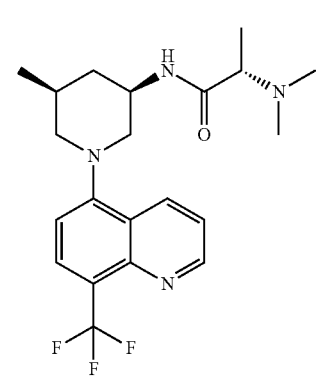 |
| 527 | 126 | 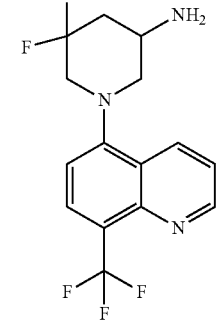<br>Isomer 1 |
| 528 | 126 | 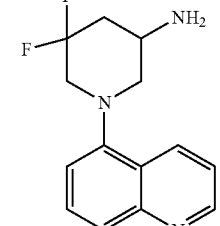<br>Isomer 2 |

TABLE 1-continued
| Compound Number | Example Number | Chemical Structure |
|---|---|---|
| 529 | 134 | 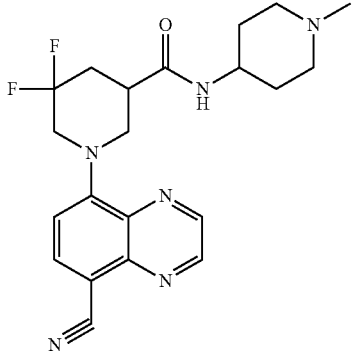 [SMILES: CN1CCC(NC(=O)C2CN(c3ccc(C#N)c4nccnc34)CC(F)(F)C2)CC1] |
| 530 | 134 | 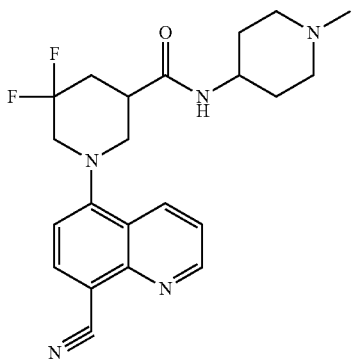 [SMILES: CN1CCC(NC(=O)C2CN(c3ccc(C#N)c4ncccc34)CC(F)(F)C2)CC1] |
| 531 | 134 | 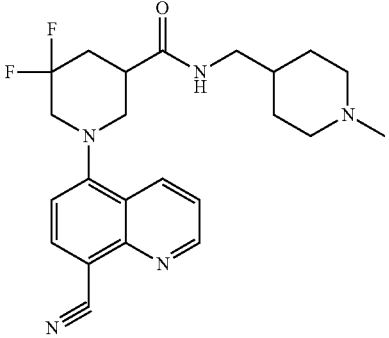 [SMILES: CN1CCC(CNC(=O)C2CN(c3ccc(C#N)c4ncccc34)CC(F)(F)C2)CC1] |
| 532 | 134 | 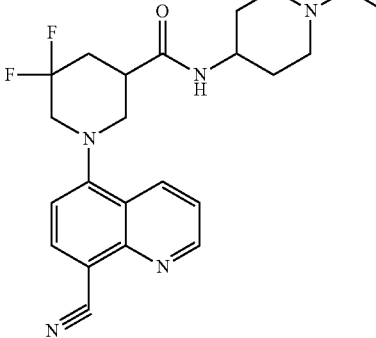 |

TABLE 1-continued
| Compound Number | Example Number | Chemical Structure |
|---|---|---|
| 533 | 135 | 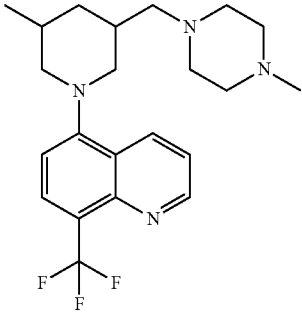<br>Isomer 1 |
| 534 | 135 | 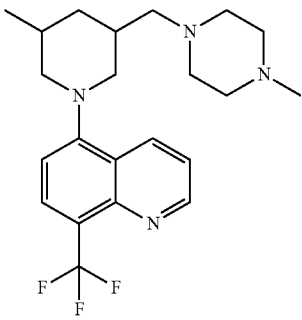<br>Isomer 2 |
| 535 | 135 | 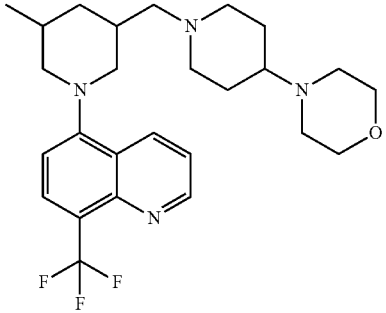<br>Isomer 1 |
| 536 | 135 | 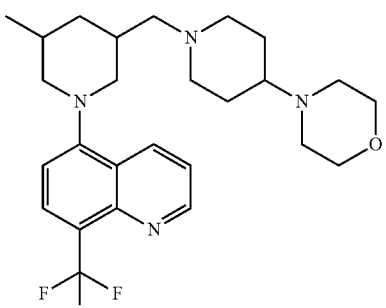<br>Isomer 2 |

TABLE 1-continued
| Compound Number | Example Number | Chemical Structure |
|---|---|---|
| 537 | 134 | 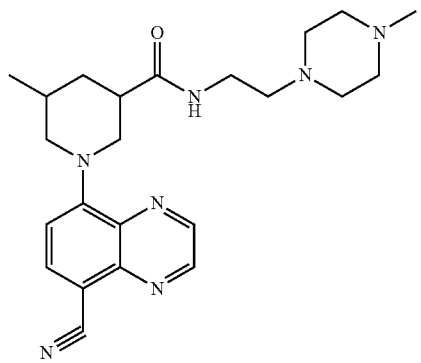<br>Isomer 1 |
| 538 | 134 | 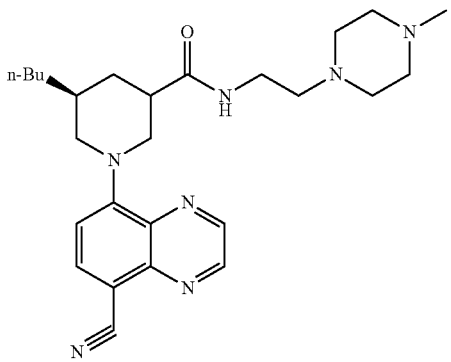<br>Isomer 2 |
| 539 | 134 | 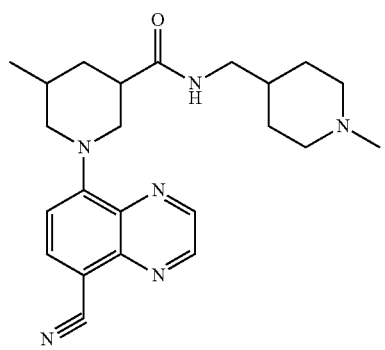 |
| 540 | 134 | 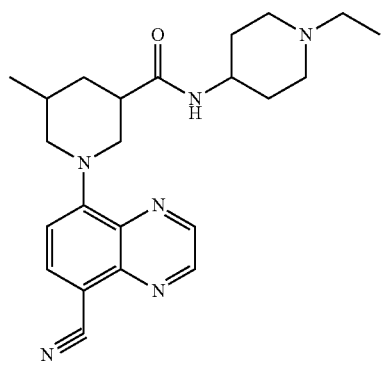 [SMILES: CCN1CCC(NC(=O)C2CC(C)CN(c3ccc(C#N)c4nccnc34)C2)CC1] |

TABLE 1-continued
| Compound Number | Example Number | Chemical Structure |
|---|---|---|
| 541 | 134 | 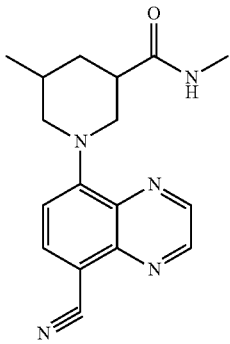<br>Isomer 1 |
| 542 | 134 | 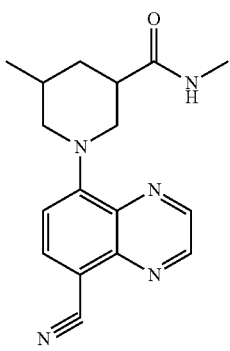<br>Isomer 2 |
| 543 | 134 | 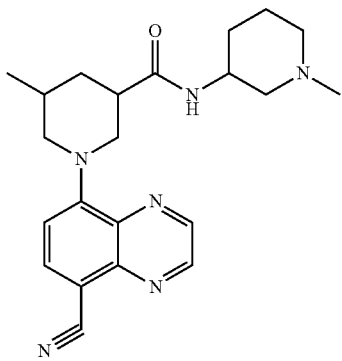<br>Isomer 1 |
| 544 | 134 | 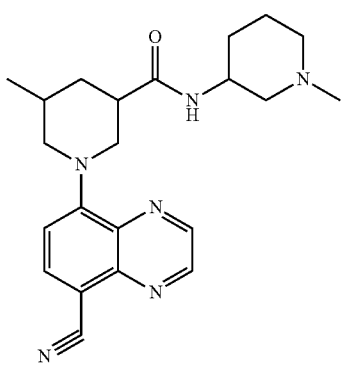<br>Isomer 2 |

TABLE 1-continued
| Compound Number | Example Number | Chemical Structure |
|---|---|---|
| 545 | 136 | 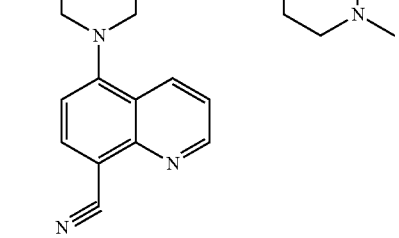 Isomer 1 |
| 546 | 136 | 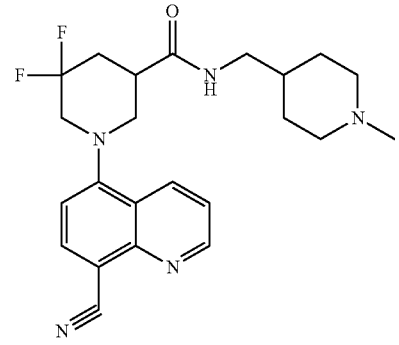 Isomer 2 |
| 547 | 134 | 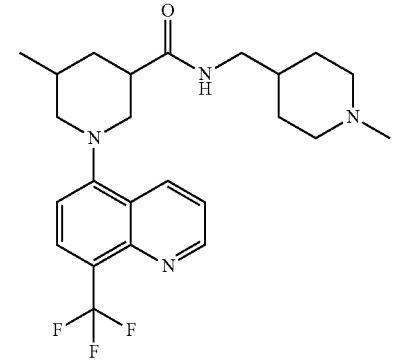 Isomer 1 |
| 548 | 134 | 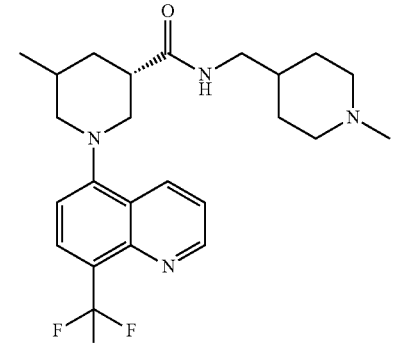 Isomer 2 |

TABLE 1-continued
| Compound Number | Example Number | Chemical Structure |
|---|---|---|
| 549 | 134 | 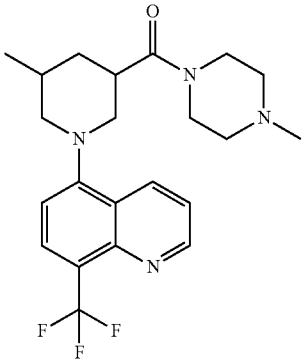 |
| 550 | 57 | 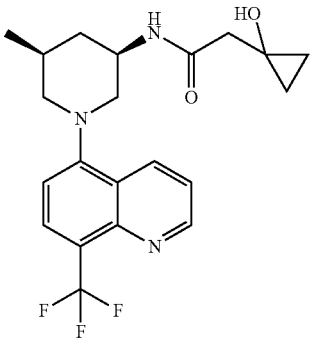 [SMILES: C[C@H]1C[C@@H](NC(=O)CC2(O)CC2)CN(c2ccc(C(F)(F)F)c3ncccc23)C1] |
| 551 | 57 | 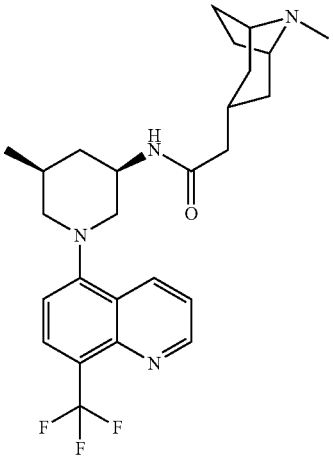 |
| 552 | 137 | 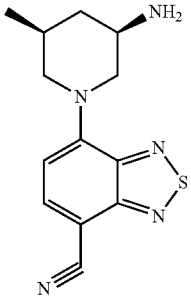 [SMILES: C[C@H]1C[C@@H](N)CN(c2ccc(C#N)c3nsnc23)C1] |

TABLE 1-continued

| Compound Number | Example Number | Chemical Structure |
|---|---|---|
| 553 | 30 | 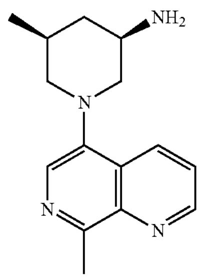 [SMILES: Cc1ncc(N2C[C@@H](C)C[C@@H](N)C2)c2cccnc12] |
| 554 | 122 | 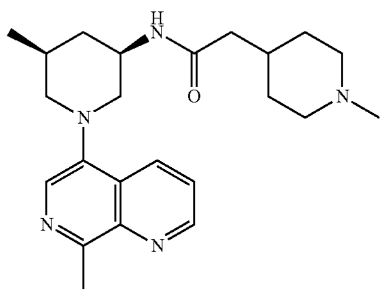 |
| 555 | 122 | 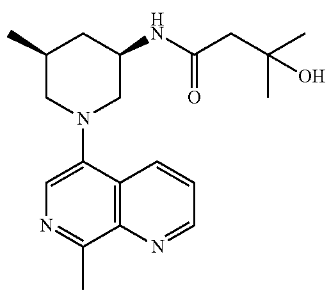 [SMILES: Cc1ncc(N2C[C@@H](C)C[C@@H](NC(=O)CC(C)(C)O)C2)c2cccnc12] |
| 556 | 122 | 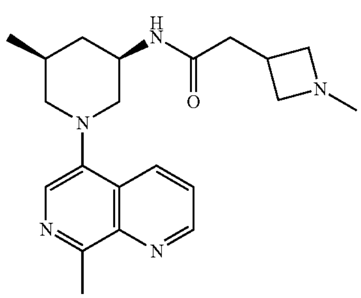 |
| 557 | 122 | 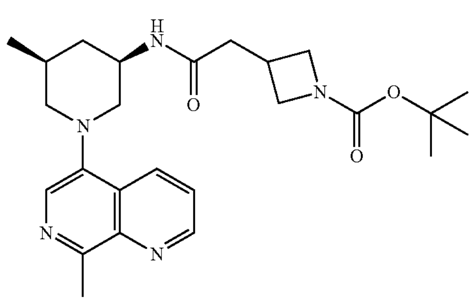 [SMILES: Cc1ncc(N2C[C@@H](C)C[C@@H](NC(=O)CC3CN(C(=O)OC(C)(C)C)C3)C2)c2cccnc12] |

TABLE 1-continued
| Compound Number | Example Number | Chemical Structure |
|---|---|---|
| 558 | 122 | 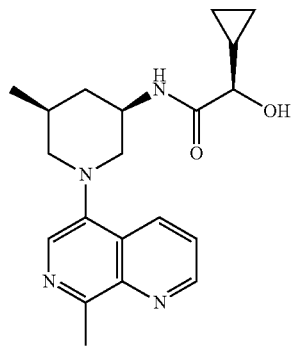 [SMILES: Cc1ncc(N2C[C@@H](C)C[C@@H](NC(=O)[C@H](O)C3CC3)C2)c2cccnc12] |
| 559 | 122 | 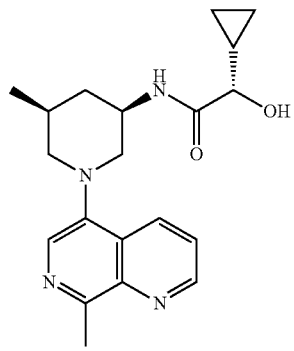 [SMILES: Cc1ncc(N2C[C@@H](C)C[C@@H](NC(=O)[C@@H](O)C3CC3)C2)c2cccnc12] |
| 560 | 122 | 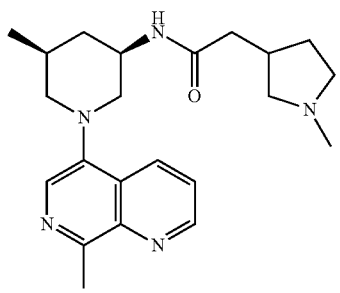 [SMILES: Cc1ncc(N2C[C@@H](C)C[C@@H](NC(=O)CC3CCN(C)C3)C2)c2cccnc12] |
| 561 | 123 | 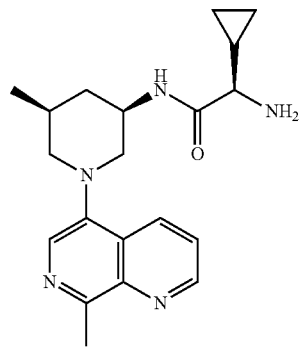 [SMILES: Cc1ncc(N2C[C@@H](C)C[C@@H](NC(=O)[C@H](N)C3CC3)C2)c2cccnc12] |

TABLE 1-continued
| Compound Number | Example Number | Chemical Structure |
|---|---|---|
| 562 | 123 | 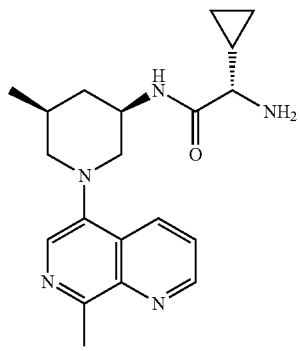 [SMILES: Cc1ncc(N2C[C@@H](C)C[C@@H](NC(=O)[C@@H](N)C3CC3)C2)c2cccnc12] |
| 563 | 123 | 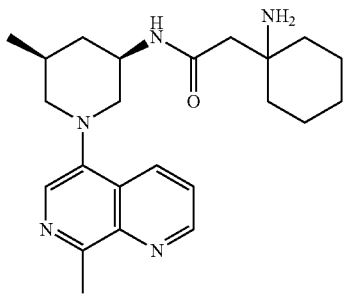 [SMILES: Cc1ncc(N2C[C@@H](C)C[C@@H](NC(=O)CC3(N)CCCCC3)C2)c2cccnc12] |
| 564 | 124 | 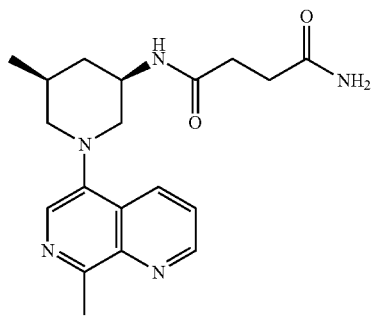 [SMILES: Cc1ncc(N2C[C@@H](C)C[C@@H](NC(=O)CCC(N)=O)C2)c2cccnc12] |
| 565 | 124 | 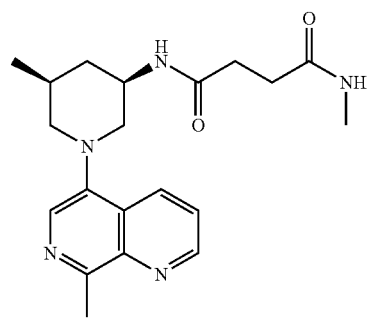 |

TABLE 1-continued

| Compound Number | Example Number | Chemical Structure |
|---|---|---|
| 566 | 124 | 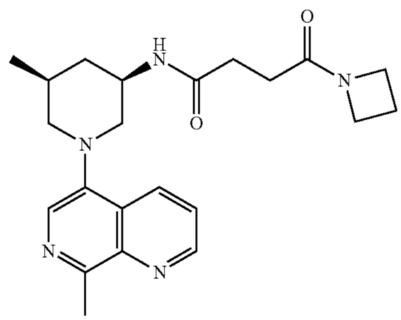 [SMILES: Cc1ncc(N2C[C@@H](C)C[C@@H](NC(=O)CCC(=O)N3CCC3)C2)c2cccnc12] |
| 567 | 138 | 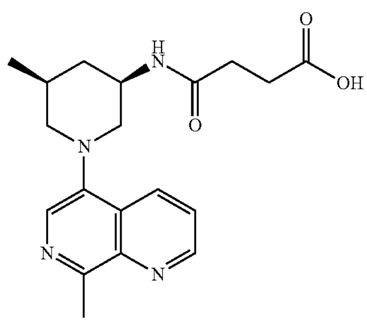 [SMILES: Cc1ncc(N2C[C@@H](C)C[C@@H](NC(=O)CCC(=O)O)C2)c2cccnc12] |
| 568 | 139 | 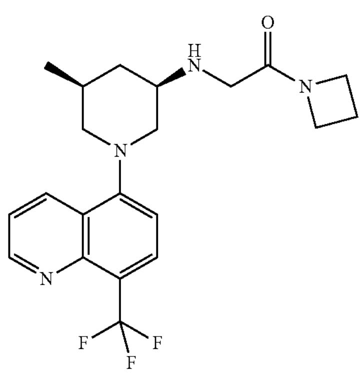 [SMILES: C[C@H]1C[C@@H](NCC(=O)N2CCC2)CN(c2ccc(C(F)(F)F)c3ncccc23)C1] |
| 569 | 139 | 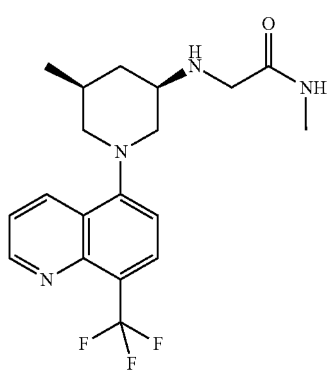 [SMILES: CNC(=O)CN[C@@H]1C[C@H](C)CN(c2ccc(C(F)(F)F)c3ncccc23)C1] |

TABLE 1-continued
| Compound Number | Example Number | Chemical Structure |
|---|---|---|
| 570 | 139 | 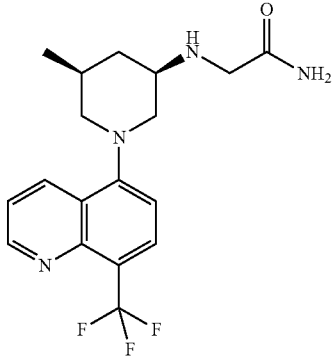 [SMILES: C[C@H]1C[C@@H](NCC(N)=O)CN(c2ccc(C(F)(F)F)c3ncccc23)C1] |
| 571 | 140 | 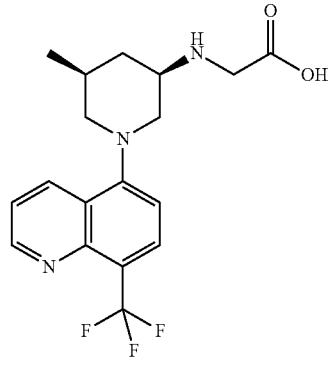 [SMILES: C[C@H]1C[C@@H](NCC(=O)O)CN(c2ccc(C(F)(F)F)c3ncccc23)C1] |
| 572 | 57 | 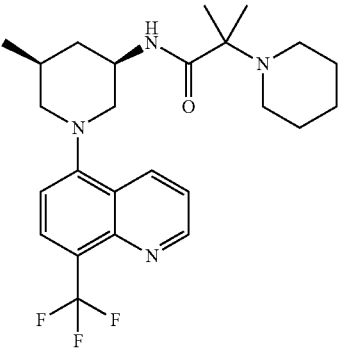 [SMILES: C[C@H]1C[C@@H](NC(=O)C(C)(C)N2CCCCC2)CN(c2ccc(C(F)(F)F)c3ncccc23)C1] |
| 573 | 57 | 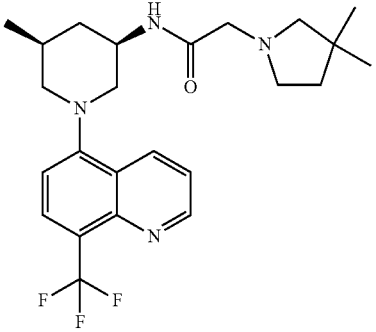 |

TABLE 1-continued
| Compound Number | Example Number | Chemical Structure |
|---|---|---|
| 574 | 57 | 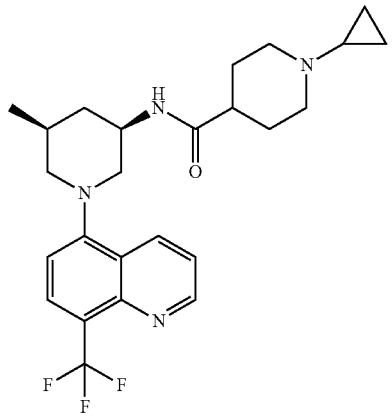 [SMILES: C[C@H]1C[C@@H](NC(=O)C2CCN(C3CC3)CC2)CN(c2ccc(C(F)(F)F)c3ncccc23)C1] |
| 575 | 57 | 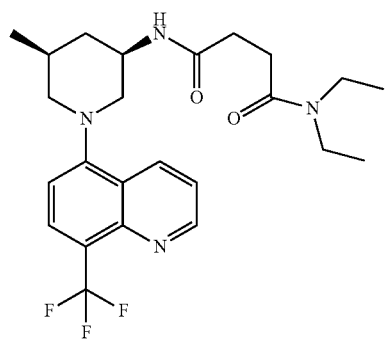 [SMILES: CCN(CC)C(=O)CCC(=O)N[C@@H]1C[C@H](C)CN(c2ccc(C(F)(F)F)c3ncccc23)C1] |
| 576 | 40 | 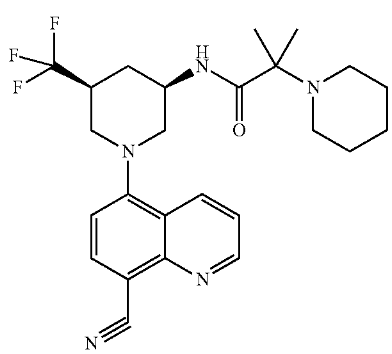 [SMILES: CC(C)(C(=O)N[C@@H]1C[C@H](C(F)(F)F)CN(c2ccc(C#N)c3ncccc23)C1)N1CCCCC1] |
| 577 | 40 | 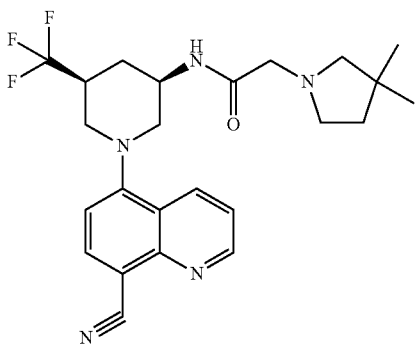 [SMILES: CC1(C)CCN(CC(=O)N[C@@H]2C[C@H](C(F)(F)F)CN(c3ccc(C#N)c4ncccc34)C2)C1] |

TABLE 1-continued
| Compound Number | Example Number | Chemical Structure |
|---|---|---|
| 578 | 40 | 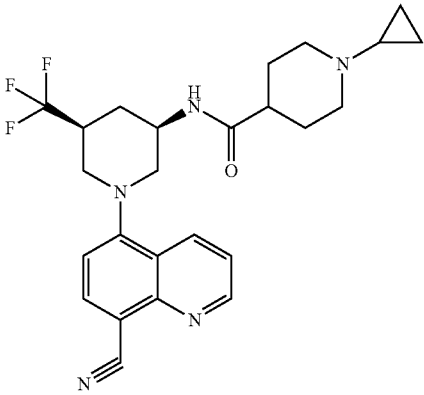 [SMILES: N#Cc1ccc(N2C[C@H](NC(=O)C3CCN(C4CC4)CC3)C[C@H](C(F)(F)F)C2)c2cccnc12] |
| 579 | 40 | 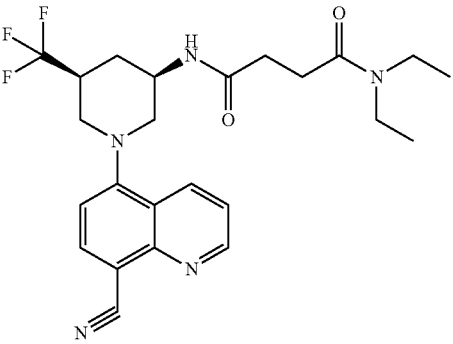 [SMILES: CCN(CC)C(=O)CCC(=O)N[C@@H]1C[C@H](C(F)(F)F)CN(c2ccc(C#N)c3ncccc23)C1] |
| 580 | 141 | 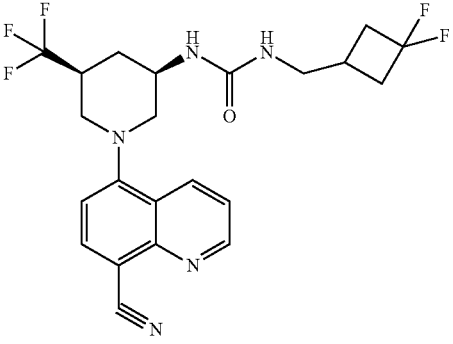 [SMILES: N#Cc1ccc(N2C[C@H](NC(=O)NCC3CC(F)(F)C3)C[C@H](C(F)(F)F)C2)c2cccnc12] |
| 581 | 141 | 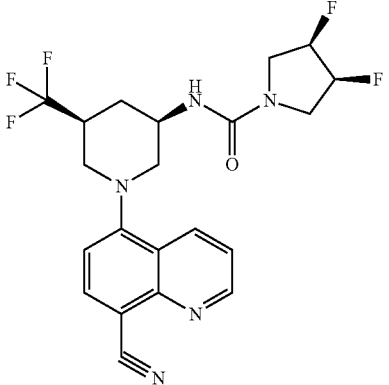 [SMILES: N#Cc1ccc(N2C[C@H](NC(=O)N3C[C@@H](F)[C@@H](F)C3)C[C@H](C(F)(F)F)C2)c2cccnc12] |

TABLE 1-continued

| Compound Number | Example Number | Chemical Structure |
|---|---|---|
| 582 | 141 | 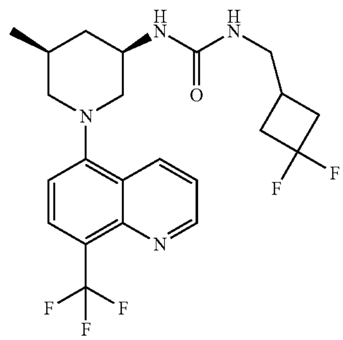 [SMILES: C[C@H]1C[C@@H](NC(=O)NCC2CC(F)(F)C2)CN(c2ccc(C(F)(F)F)c3ncccc23)C1] |
| 583 | 141 | 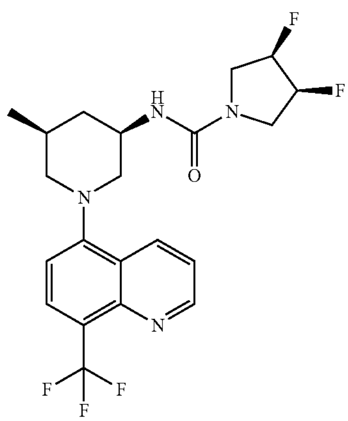 [SMILES: C[C@H]1C[C@@H](NC(=O)N2C[C@@H](F)[C@@H](F)C2)CN(c2ccc(C(F)(F)F)c3ncccc23)C1] |
| 584 | 40 | 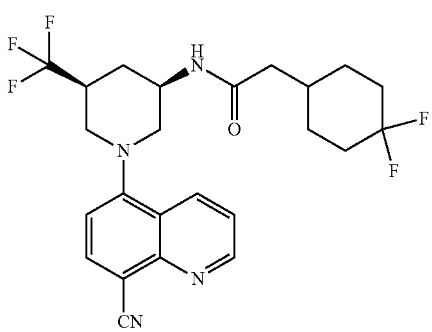 [SMILES: N#Cc1ccc(N2C[C@H](NC(=O)CC3CCC(F)(F)CC3)C[C@H](C(F)(F)F)C2)c2cccnc12] |
| 585 | 40 | 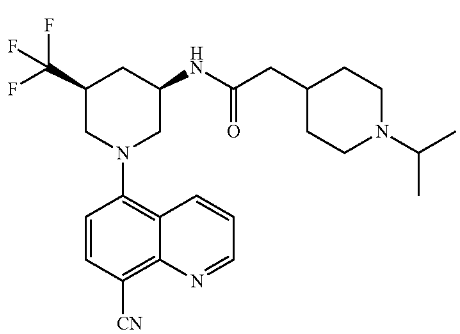 [SMILES: CC(C)N1CCC(CC(=O)N[C@@H]2C[C@H](C(F)(F)F)CN(c3ccc(C#N)c4ncccc34)C2)CC1] |

TABLE 1-continued
| Compound Number | Example Number | Chemical Structure |
|---|---|---|
| 586 | 89 | 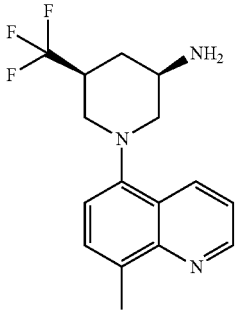 [SMILES: Cc1ccc(N2C[C@H](N)C[C@H](C(F)(F)F)C2)c2cccnc12] |
| 587 | 94 | 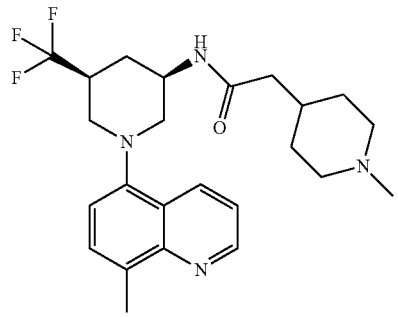 [SMILES: Cc1ccc(N2C[C@H](NC(=O)CC3CCN(C)CC3)C[C@H](C(F)(F)F)C2)c2cccnc12] |
| 588 | 94 | 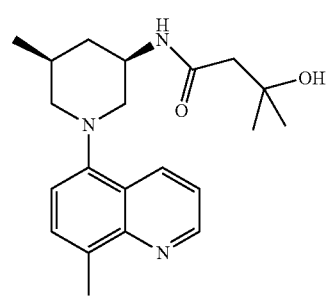 [SMILES: Cc1ccc(N2C[C@@H](C)C[C@@H](NC(=O)CC(C)(C)O)C2)c2cccnc12] |
| 589 | 94 | 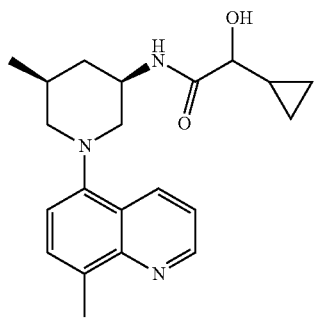 [SMILES: Cc1ccc(N2C[C@@H](C)C[C@@H](NC(=O)C(O)C3CC3)C2)c2cccnc12] |
| 590 | 94 | 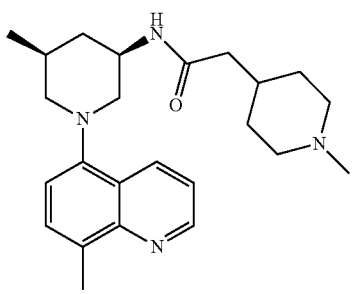 |

TABLE 1-continued

| Compound Number | Example Number | Chemical Structure |
|---|---|---|
| 591 | 94 | 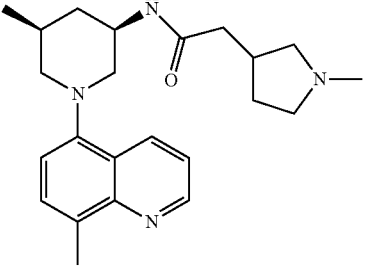 |

In some embodiments, the present invention provides a compound selected from those depicted above, or a pharmaceutically acceptable salt thereof.

Various structural depictions may show a heteroatom without an attached group, radical, charge, or counterion. Those of ordinary skill in the art are aware that such depictions are meant to indicate that the heteroatom is attached to hydrogen (e.g.,

is understood to be

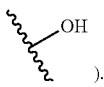).

In certain embodiments, the compounds of the invention were synthesized in accordance with the schemes provided in the Examples below.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit TLR7/8, or a mutant thereof, in a biological sample or in a patient. In certain embodiments, the amount of compound in compositions of this invention is such that is effective to measurably inhibit TLR7/8, or a mutant thereof, in a biological sample or in a patient. In certain embodiments, a composition of this invention is formulated for administration to a patient in need of such composition.

The term "patient" or "subject", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The present invention furthermore relates to a method for treating a subject suffering from a TLR7/8 related disorder, comprising administering to said subject an effective amount of a compound of formula I and related formulae.

The compounds of the present invention are useful as anticancer agents for cancers that are responsive to TLR7 activation. In certain embodiments, the cancers include, but are not limited to cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

In certain embodiments, the compounds of the invention are used to treat cancers of the skin or kidney. Sensitivity of a given cancer to activation of TLR7 can be assessed by, but not limited to measurement of a decrease in primary or metastatic tumor load (minor, partial or complete regression), alterations in the hemogram, altered hormone or cytokine concentrations in the blood, inhibition of further increase of tumor load, stabilization of the disease in the patient, assessment of biomarkers or surrogate markers relevant for the disease, prolonged overall survival of a patient, prolonged time to disease progression of a patient, prolonged progression-free survival of a patient, prolonged disease-free survival of a patient, improved quality of life of a patient, or modulation of the co-morbidity of the disease (for example, but not limited to pain, cachexia, mobilization, hopitalization, altered hemogram, weight loss, wound healing, fever).

The compounds according to the present invention may further be useful as immune response modifiers that can modulate the immune response in a number of different ways, rendering them useful in the treatment of a variety of disorders.

Provided herein are methods of inhibiting an immune response in an individual comprising administering to the individual an effective amount of an inhibitor of TLR7 and/or TLR8 (e.g., TLR inhibitor), using the compounds as described herein. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some variations, the TLR inhibitor inhibits a TLR7-dependent, a TLR8-dependent, and another TLR-dependent immune response. Unless otherwise noted, the term TLR inhibitor refers to any one of the TLR inhibitors disclosed herein. In some preferred embodiments, the individual is a human patient.

Methods of immunoregulation are provided by the present disclosure and include those that suppress and/or inhibit an immune response, including, but not limited to, an immune response. The present disclosure also provides methods for ameliorating symptoms associated with unwanted immune activation, including, but not limited to, symptoms associated with autoimmunity. Immune suppression and/or inhibition according to the methods described herein may be practiced on individuals including those suffering from a disorder associated with an unwanted activation of an immune response. The present disclosure also provides methods for inhibiting a TLR7 and/or TLR8 induced response (e.g., in vitro or in vivo). In some variations, the cell is contacted with the TLR inhibitor in an amount effective to inhibit a response from the cell that contributes to an immune response.

Inhibition of TLR7 and/or TLR8 are useful for treating and/or preventing a variety of diseases or disorders that are responsive to cytokines. Conditions for which TLR7 and/or TLR8 inhibitors may be used as treatments include, but are not limited to autoimmune diseases and inflammatory disorders. Provided herein are methods of treating or preventing a disease or disorder in an individual comprising administering to the individual an effective amount of an inhibitor of TLR7 and/or TLR8. Further, provided are methods for ameliorating symptoms associated with a disease or disorder comprising administering an effective amount of an inhibitor of TLR7 and/or TLR8 to an individual having the disease or disorder. Methods are also provided herein for preventing or delaying development of a disease or a disorder, comprising administering an effective amount of an inhibitor of one or more of TLR7 and/or TLR8 to an individual having the disease or the disorder. In certain embodiments, the inhibitor is a compound as described herein.

Provided herein are methods of inhibiting an immune response in an individual, the method comprising administering to the individual at least one TLR inhibitor as disclosed herein in an amount effective to inhibit the immune response in the individual. In some variations, the immune response is associated with an autoimmune disease. In further aspects, wherein inhibiting the immune response ameliorates one or more symptoms of the autoimmune disease. In still further aspects, wherein inhibiting the immune response treats the autoimmune disease. In yet further aspects, wherein inhibiting the immune response prevents or delays development of the autoimmune disease. In some variations, the TLR inhibitor inhibits a TLR7-dependent immune response. In some variations, the TLR inhibitor inhibits a TLR8-dependent immune response. In some variations, the TLR inhibitor inhibits a TLR7-dependent and a TLR8-dependent immune response. In some aspects, at least one TLR inhibitor is administered in an amount effective to inhibit an immune response in the individual.

Provided herein are also methods of treating or preventing an autoimmune disease in an individual, comprising administering to the individual an effective amount of a TLR7 and/or TLR8 inhibitor. In some aspects, the autoimmune disease is characterized by joint pain, antinuclear antibody positivity, malar rash, or discoid rash. In some aspects, the autoimmune disease is associated with the skin, muscle tissue, and/or connective tissue. In some embodiments, the autoimmune disease is not evidenced in the individual by skin, muscle tissue, and/or connective tissue symptoms. In some embodiments, the autoimmune disease is systemic. Autoimmune diseases include, without limitation, rheumatoid arthritis (RA), autoimmune pancreatitis (AIP), systemic lupus erythematosus (SLE), type I diabetes mellitus, multiple sclerosis (MS), antiphospholipid syndrome (APS), sclerosing cholangitis, systemic onset arthritis, irritable bowel disease (IBD), scleroderma, Sjogren's disease, vitiligo, polymyositis, pemphigus vulgaris, pemphigus foliaceus, inflammatory bowel disease including Crohn's disease and ulcerative colitis, autoimmune hepatitis, hypopituitarism, graft-versus-host disease (GvHD), autoimmune skin diseases, uveitis, pernicious anemia, and hypoparathyroidism. Autoimmune diseases may also include, without limitation, polyangiitis overlap syndrome, Kawasaki's disease, sarcoidosis, glomerulonephritis, and cryopathies.

In some aspects, the autoimmune disease is selected from the group consisting of arthritis, pancreatitis, mixed connective tissue disease (MCTD), lupus, antiphospholipid syndrome (APS), systemic onset arthritis, and irritable bowel syndrome.

In other aspects, the autoimmune disease is selected from the group consisting of systemic lupus erythematosus (SLE), rheumatoid arthritis, autoimmune skin disease, and multiple sclerosis.

In other aspects, the autoimmune disease is selected from the group consisting of pancreatitis, glomerulonephritis, pyelitis, sclerosing cholangitis, and type I diabetes. In some aspects, the autoimmune disease is rheumatoid arthritis. In some aspects, the autoimmune disease is autoimmune pancreatitis (AIP). In some aspects, the autoimmune disease is glomerulonephritis. In some aspects, the autoimmune disease is pyelitis. In some aspects, the autoimmune disease is sclerosing cholangitis. In some aspects the autoimmune disorder is psoriasis. In some aspects, the autoimmune disease is a rheumatoid disease or disorder. In some aspects, the rheumatoid disease or disorder is rheumatoid arthritis. In some aspects, the disease is diabetes and/or diabetic-related disease or disorder. In some aspects, wherein the autoimmune disease is associated with RNA-containing immune complexes. In some aspects, the autoimmune disease is Sjogren's disease.

Provided herein are methods of inhibiting an immune response in an individual, the method comprising administering to the individual at least one TLR inhibitor as disclosed herein in an amount effective to inhibit the immune response in the individual. In some variations, the immune response is associated with an inflammatory disorder. As used herein, the term "inflammatory disorder" encompasses autoimmune diseases, as well as inflammatory conditions without a known autoimmune component (e.g., artherosclerosis, asthma, etc.). In further aspects, inhibiting the immune response ameliorates one or more symptoms of the inflammatory disorder. In still further aspects, inhibiting the immune response treats the inflammatory disorder. In yet further aspects, inhibiting the immune response prevents or delays development of the inflammatory disorder. In some aspects, the inflammatory disorder is selected from the group consisting of non-rheumatoid arthritis, kidney fibrosis, and liver fibrosis. In some aspects, the inflammatory disorder is an interface dermatitis. In some further aspects, the interface dermatitis is selected from the group consisting of lichen planus, lichenoid eruption, lichen planus-like keratosis, lichen striatus, keratosis lichenoides chronica, erythema multiforme, fixed drug eruption, pityriasis lichenoides, phototoxic dermatitis, radiation dermatitis, viral exanthems, dermatomyositis, secondary syphilis, lichen sclerosus et atrophicus, mycosis fungoides, bullous pemphigoid, lichen aureus, porokeratosis, acrodermatitis chronicus atrophicans, and regressing melanoma. In some aspects, the inflammatory condition is a skin disorder such as atopic dermatitis (eczema). In some aspects, the inflammatory disorder is a sterile inflammatory condition such as drug-induced liver and/or pancreas inflammation. In some further aspects, the inflammatory disease is an inflammatory liver disorder. In some other further aspects, the inflammatory disease is an inflammatory pancreatic disorder.

Provided herein are methods of inhibiting an immune response in an individual, the method comprising administering to the individual at least one TLR inhibitor as disclosed herein in an amount effective to inhibit the immune response in the individual. In some variations, the immune response is associated with chronic pathogen stimulation. In some variations, the immune response is associated with infection by HIV. In further aspects, wherein inhibiting the immune response ameliorates one or more symptoms of the viral disease or disorder resulting from infection by HIV. In still further aspects, wherein inhibiting the immune response treats the viral disease or disorder resulting from infection by HIV. In yet further aspects, wherein inhibiting the immune response prevents or delays development of the viral disease or disorder resulting from infection by HIV. Other variations provided herein relate to immunoinhibitory therapy of individuals having been exposed to or infected with HIV. Administration of a TLR inhibitor to an individual having been exposed to or infected with HIV results in suppression of HIV induced cytokine production. In some aspects, at least one TLR inhibitor is administered in an amount effective to suppress HIV induced cytokine production in an individual exposed to or infected with a HIV.

Provided herein are methods for inhibiting a TLR7 and/or TLR8-dependent immune response in an individual, the method comprising administering to the individual a TLR inhibitor in an amount effective to inhibit the immune response in the individual. In some variations, the immune response is associated with an autoimmune disease. In some aspects, the autoimmune disease is rheumatoid arthritis. In some aspects, the TLR inhibitor is effective in suppressing one or more symptoms of rheumatoid arthritis. In some aspects, the autoimmune disease is multiple sclerosis. In some aspects, the TLR inhibitor is effective in suppressing one or more symptoms of multiple sclerosis. In some aspects, the autoimmune disease is lupus. In some aspects, the TLR inhibitor is effective in suppressing one or more symptoms of lupus. In some aspects, the autoimmune disease is pancreatitis. In some aspects, the TLR inhibitor is effective in suppressing one or more symptoms of pancreatitis. In some aspects, the autoimmune disease is diabetes. In some aspects, the TLR inhibitor is effective in suppressing one or more symptoms of diabetes. In some aspects, the disease is Sjogren's disease. In some aspects, the TLR inhibitor is effective in suppressing one or more symptoms of Sjogren's disease. In some variations, the immune response is associated with an inflammatory disorder. In some aspects, the TLR inhibitor is effective in suppressing one or more symptoms of an inflammatory disorder. In some variations, the immune response is associated with chronic pathogen stimulation. In some aspects, the TLR inhibitor is effective in suppressing one or more symptoms of chronic pathogen stimulation. In some variations, the immune response is associated with viral disease resulting from infection with HIV. In some aspects, the TLR inhibitor is effective in suppressing one or more symptoms of viral disease resulting from infection with HIV. In any variation, the TLR inhibitor is a polynucleotide comprising an inhibitory motif for one or more of TLR7, TLR8, and TLR9.

In some embodiments of any of the methods involving administration of a TLR inhibitor to an individual (e.g., methods of inhibiting an immune response, treating or preventing an autoimmune disease or inflammatory disorder, etc.) the TLR inhibitor has a therapeutically acceptable safety profile. The TLR inhibitor may for example, have a therapeutically acceptable histological profile including an acceptably low, if any, toxicity of the liver, kidney, pancreas, or other organs. On occasion, polynucleotides have been associated with toxicity to certain organs such as the liver, kidney and pancreas. In some embodiments, the TLR inhibitor has a safety profile that is unexpected and advantageous. In some embodiments, a safety profile includes evaluation of toxicity, histological profile, and/or necrosis (e.g., liver, kidneys and/or heart). In some embodiments, the TLR inhibitor has a therapeutically acceptable level of toxicity. In some embodiments, the TLR inhibitor has a reduced level of toxicity as compared to another TLR inhibitor. In some embodiments, the TLR inhibitor induces a therapeutically acceptable reduction in body weight as compared to the initial body weight of a treated individual. In some embodiments, the TLR inhibitor induces less than 5%, 7.5%, 10%, 12.5, or 15% reduction in total body weight. In some embodiments, the TLR inhibitor has a therapeutically acceptable histology profile. In some embodiments, the TLR inhibitor has a better (e.g., lower severity score) histology profile, for example, as compared to a reference TLR inhibitor. In some embodiments, the TLR inhibitor has a better (e.g., lower severity score) histology profile upon evaluation of the liver, kidneys and/or heart, for example. In some embodiments, the TLR inhibitor has a therapeutically acceptable necrosis score. In some embodiments, the TLR inhibitor has reduced necrosis and/or better (e.g., lower) necrosis score, for example, as compared to a reference TLR inhibitor. In some embodiments, the TLR inhibitor has reduced renal and/or hepatocellular necrosis and/or a better renal and/or hepatocellular necrosis score, for example, as compared to a reference TLR inhibitor.

Accordingly, the invention provides a method of activating TLR7 in an animal, especially a mammal, preferably a human comprising administering an effective amount of a compound of Formula I to the animal. As with all compositions for inhibition of an immune response, the effective amounts and method of administration of the particular TLR inhibitor formulation can vary based on the individual, what condition is to be treated and other factors evident to one skilled in the art. An effective amount of a compound will vary according to factors known in the art but is expected to be a dose of about 0.1 to 10 mg/kg, 0.5 to 10 mg/kg, 1 to 10 mg/kg, 0.1 to 20 mg/kg, 0.1 to 20 mg/kg, or 1 to 20 mg/kg.

The invention also provides a method of treating a viral infection in an animal comprising administering an effective amount of a compound of Formula I to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose as indicated above with respect to the activation of TLR7, or a dose of about 100 ng/kg to about 50 mg/kg, preferably about 10 g/kg to about 5 mg/kg.

In various embodiments, compounds of formula (I), and related formulae exhibit a IC50 for the binding to TLR7/8 of less than about 5 µM, preferably less than about 1 µM and even more preferably less than about 0.100 µM.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to inhibit TLR7/8 activity, usually between about one hour and one week. In-vitro treatment can be carried out using cultivated cells from a biopsy sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing TLR7/8-dependent signal transduction pathways in animals and/or cell culture models or in the clinical diseases mentioned in this application.

Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of TLR7/8 activity if expedient.

The invention also relates to the use of compounds according to formula (I) and/or physiologically acceptable salts thereof for the prophylactic or therapeutic treatment and/or monitoring of diseases that are caused, mediated and/or propagated by TLR7/8 activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by TLR7/8 activity. In certain embodiments, the invention provides the use of a compound according to formula I or physiologically acceptable salts thereof, for the production of a medicament for the prophylactic or therapeutic treatment of a TLR7/8-mediated disorder.

Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to boost the response and eradicate the pathogens and/or symptoms of the disease completely. Either the identical compound or different compounds can be applied. The methods of the invention can also be used to reduce the likelihood of developing a disorder or even prevent the initiation of disorders associated with TLR7/8 activity in advance or to treat the arising and continuing symptoms.

In the meaning of the invention, prophylactic treatment is advisable if the subject possesses any preconditions for the aforementioned physiological or pathological conditions, such as a familial disposition, a genetic defect, or a previously incurred disease.

The invention furthermore relates to a medicament comprising at least one compound according to the invention and/or pharmaceutically usable derivatives, salts, solvates and stereoisomers thereof, including mixtures thereof in all ratios. In certain embodiments, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with TLR7/8 activity, in such a way that a pathogenic modification of their overall condition or of the condition of particular regions of the organism could establish at least temporarily.

In various embodiments, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially.

The TLR inhibitors of the present disclosure can be administered in combination with one or more additional therapeutic agents. As described herein, the TLR inhibitors can be combined with a physiologically acceptable carrier. The methods described herein may be practiced in combination with other therapies that make up the standard of care for the disorder, such as administration of anti-inflammatory agents.

In some embodiments, a TLR inhibitor as described herein is administered in combination with a corticosteroid. In some embodiments, the corticosteroid is a glucocorticosteroid. In some embodiments, the corticosteroid is a mineralocorticoid. Corticosteroids include, but are not limited to, corticosterone and derivatives, prodrugs, isomers and analogs thereof, cortisone and derivatives, prodrugs, isomers and analogs thereof (i.e., Cortone), aldosterone and derivatives, prodrugs, isomers and analogs thereof, dexamethasone and derivatives, prodrugs, isomers and analogs thereof (i.e., Decadron), prednisone and derivatives, prodrugs, isomers and analogs thereof (i.e., Prelone), fludrocortisones and derivatives, prodrugs, isomers and analogs thereof, hydrocortisone and derivatives, prodrugs, isomers and analogs thereof (i.e., cortisol or Cortef), hydroxycortisone and derivatives, prodrugs, isomers and analogs thereof, betamethasone and derivatives, prodrugs, isomers and analogs thereof (i.e., Celestone), budesonide and derivatives, prodrugs, isomers and analogs thereof (i.e., Entocort EC), methylprednisolone and derivatives, prodrugs, isomers and analogs thereof (i.e., Medrol), prednisolone and derivatives, prodrugs, isomers and analogs thereof (i.e., Deltasone, Crtan, Meticorten, Orasone, or Sterapred), triamcinolone and derivatives, prodrugs, isomers and analogs thereof (i.e., Kenacort or Kenalog), and the like. In some embodiments, the corticosteroid is fludrocortisone or a derivative, prodrug, isomer or analog thereof. In some embodiments, the corticosteroid is fludrocortisone. In some embodiments, the corticosteroid is hydroxycortisone or a derivative, prodrug, isomer or analog thereof. In some embodiments, the corticosteroid is hydroxycortisone.

In some embodiments, the corticosteroid is administered between about any of 0.001 mg to 1 mg, 0.5 mg to 1 mg, 1 mg to 2 mg, 2 mg to 20 mg, 20 mg to 40 mg, 40 to 80 mg, 80 to 120 mg, 120 mg to 200 mg, 200 mg to 500 mg, or 500 mg to 1000 mg per day. In some embodiments, the corticosteroid is administered between about any of 0.1 mg/kg to 0.5 mg/kg, 0.5 mg/kg to 1 mg/kg, 1 mg/kg to 2 mg/kg, 2 mg/kg to 5 mg/kg, 5 mg/kg to 10 mg/kg, 10 mg/kg to 15 mg/kg, 15 mg/kg to 20 mg/kg, 20 mg/kg to 25 mg/kg, 25 mg/kg to 35 mg/kg, or 35 mg/kg to 50 mg/kg per day.

In some embodiments, the TLR inhibitor used in combination therapy, given in amounts of the TLR inhibitor delivered, may be, for example, from about any of 0.1 to 10 mg/kg, 0.5 to 10 mg/kg, 1 to 10 mg/kg, 0.1 to 20 mg/kg, 0.1 to 20 mg/kg, or 1 to 20 mg/kg.

In some embodiments, the TLR inhibitor is administered simultaneously with one or more additional therapeutic agents including, but not limited to, a corticosteroid (simultaneous administration). In some embodiments, the TLR inhibitor is administered sequentially with an additional therapeutic agent including, but not limited to, a corticosteroid (sequential administration). In some embodiments, sequential administration includes administering the TLR inhibitor or additional therapeutic agent followed within about any of one minutes, five minutes, 30 minutes, one hour, five hours, 24 hours, 48 hours, or a week. In some embodiments, the TLR inhibitor is administered by the same route of administration as the additional therapeutic agent. In some embodiments, the TLR inhibitor is administered by a different route of administration than the additional therapeutic agent. In some embodiments, the additional therapeutic agent is administered parentally (e.g., central venous line, intra-arterial, intravenous, intramuscular, intraperitoneal, intradermal, or subcutaneous injection), orally, gastrointestinally, topically, naso-pharyngeal and pulmonary (e.g. inhalation or intranasally). In some embodiments, the additional therapeutic agent is a corticosteroid.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula I, conventional surgery or radiotherapy or medicinal therapy. Such medicinal therapy, e.g. a chemotherapy or a targeted therapy, may include one or more, but preferably one, of the following anti-tumor agents:

Alkylating agents: such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds: such as carboplatin, cisplatin, eptaplatin, miriplatine hydrate, oxaliplatin, lobaplatin, nedaplatin, picoplatin, satraplatin; lobaplatin, nedaplatin, picoplatin, satraplatin;

DNA altering agents: such as amrubicin, bisantrene, decitabine, mitoxantrone, procarbazine, trabectedin, clofarabine; amsacrine, brostallicin, pixantrone, laromustine[1,3];

Topoisomerase Inhibitors: such as etoposide, irinotecan, razoxane, sobuzoxane, teniposide, topotecan; amonafide, belotecan, elliptinium acetate, voreloxin;

Microtubule modifiers: such as cabazitaxel, docetaxel, cribulin, ixabepilone, paclitaxel, vinblastine, vincristine, vinorelbine, vindesine, vinflunine; fosbretabulin, tesetaxel;

Antimetabolites: such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer antibiotics: such as bleomycin, dactinomycin, doxorubicin, epirubicin, idarubicin, levamisole, miltefosine, mitomycin C, romidepsin, streptozocin, valrubicin, zinostatin, zorubicin, daunorubicin, plicamycin; aclarubicin, peplomycin, pirarubicin;

Hormones/Antagonists: such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol; acolbifene, danazol, deslorelin, epitiostanol, orteronel, enzalutamide[1,3];

Aromatase inhibitors: such as aminoglutethimide, anastrozole, exemestane, fadrozole, letrozole, testolactone; formestane;

Small molecule kinase inhibitors: such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib; afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-6474;

Photosensitizers: such as methoxsalen[3]; porfimer sodium, talaporfin, temoporfin;

Antibodies: such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines: such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates: such as denilcukin diftitox, ibritumomab tiuxetan, iobnguanc I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[1,3];

Vaccines: such as sipuleucel[3]; vitespen[3], emepepimut-S[3], oncoVAX[4], rindopepimut[3], troVax[4], MGN-1601[4], MGN-1703[4]; and Miscellaneous: alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4].

([1]Prop. INN (Proposed International Nonproprietary Name); [2]Rec. INN (Recommended International Nonproprietary Names); [3]USAN (United States Adopted Name); [4]no INN).

In some embodiments, the combination of a TLR inhibitor with one or more additional therapeutic agents reduces the effective amount (including, but not limited to, dosage volume, dosage concentration, and/or total drug dose administered) of the TLR inhibitor and/or the one or more additional therapeutic agents administered to achieve the same result as compared to the effective amount administered when the TLR inhibitor or the additional therapeutic agent is administered alone. In some embodiments, the combination of a TLR inhibitor with a corticosteroid reduces the effective amount of corticosteroid administered as compared to the corticosteroid administered alone. In some embodiments, the combination of a TLR inhibitor with the additional therapeutic agents reduces the frequency of administrations of the therapeutic agent compared to administration of the additional therapeutic agent alone. In some embodiments, the combination of a TLR inhibitor with the additional therapeutic agent reduces the total duration of treatment compared to administration of the additional therapeutic agent alone. In some embodiments, the combination of a TLR inhibitor with the additional therapeutic agent reduces the side effects associated with administration of the additional therapeutic agent alone. In some embodiments, the additional therapeutic agent is a corticosteroid. In some embodiments, the corticosteroid is fludrocortisone or a derivative, prodrug, isomer or analog thereof. In some embodiments, the corticosteroid is fludrocortisone. In some embodiments, the combination of an effective amount of the TLR inhibitor with the additional therapeutic agent is more efficacious compared to an effective amount of the TLR inhibitor or the additional therapeutic agent alone.

TLR inhibitors also may be useful as a vaccine adjuvant for use in conjunction with any material that modulates either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; recombinant proteins; glycoproteins; peptides; and the like. In some aspects, the combination therapy including but not limited to the combination of a TLR inhibitor and a vaccine is used in the treatment of an autoimmune disease or an inflammatory disorder. In some aspects, the combination therapy including but not limited to the combination of a TLR inhibitor and a vaccine is used in the treatment of an infectious disease.

In some embodiments, the combination therapy including but not limited to the combination of a TLR inhibitor and a corticosteroid is used in the treatment of an autoimmune disease or an inflammatory disorder. In some embodiments, the autoimmune disease is selected from but not limited to rheumatoid arthritis, systemic lupus erythematosus, autoimmune skin disease, multiple sclerosis, pancreatitis, glomerulonephritis, pyelitis, Sclerosing cholangitis, and type I diabetes. In some embodiments, the autoimmune disease is Sjogren's disease.

Also provided herein are kits comprising a TLR inhibitor as provided herein, and instructions for use in the methods of inhibiting a TLR7- and/or TLR8-dependent immune response.

The kits may comprise one or more containers comprising a TLR inhibitor (or a formulation comprising a TLR inhibitor) as described herein, and a set of instructions, generally written instructions although electronic storage media (e.g., magnetic diskette or optical disk) containing instructions are also acceptable, relating to the use and dosage of the TLR inhibitor or formulation for the intended treatment (e.g., suppression of a response to a TLR7 and/or TLR8 agonists, suppression of a TLR7 and/or TLR8-dependent immune response, ameliorating one or more symptoms of an autoimmune disease, ameliorating a symptom of chronic inflammatory disease, decreasing cytokine production in response to a virus, and/or treating and/or preventing one or more symptoms of a disease or disorder mediated by TLR7 and/or TLR8). The instructions included with the kit generally include information as to dosage, dosing schedule, and route of administration for the intended treatment. The containers for the TLR inhibitor (or formulations comprising a TLR inhibitor) may be unit doses, bulk packages (e.g., multi-dose packages) or sub-unit doses. The kits may further comprise a container comprising an adjuvant.

In another aspect, the invention provides for a kit consisting of separate packs of an effective amount of a compound according to the invention and/or pharmaceutically acceptable salts, derivatives, solvates and stereoisomers thereof, including mixtures thereof in all ratios, and optionally, an effective amount of a further active ingredient. The kit comprises suitable containers, such as boxes, individual bottles, bags or ampoules. The kit may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further active ingredient in dissolved or lyophilized form.

As used herein, the terms "treatment," "treat," and "treating" refer to reversing, alleviating, delaying the onset of, or inhibiting the progress of a disease or disorder, or one or more symptoms thereof, as described herein. In some embodiments, treatment is administered after one or more symptoms have developed. In other embodiments, treatment is administered in the absence of symptoms. For example, treatment is administered to a susceptible individual prior to the onset of symptoms (e.g., in light of a history of symptoms and/or in light of genetic or other susceptibility factors). Treatment is also continued after symptoms have resolved, for example to prevent or delay their recurrence.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoncally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 100 mg/kg and preferably from about 1 mg/kg to about 50 mg/kg, of subject body weight per day, one or more times a day, to obtain the desired therapeutic effect.

In certain embodiments, a therapeutically effective amount of a compound of the formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

In certain embodiments, the pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, c) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprises buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting TLR7/8 activity in a biological sample comprising the step of contacting said biological sample with a compound of this invention, or a composition comprising said compound.

According to another embodiment, the invention relates to a method of inhibiting TLR7/8, or a mutant thereof, activity in a biological sample in a positive manner, comprising the step of contacting said biological sample with a compound of this invention, or a composition comprising said compound.

The compounds of the invention are useful in-vitro as unique tools for understanding the biological role of TLR7/8, including the evaluation of the many factors thought to influence, and be influenced by, the production of TLR7/8 and the interaction of TLR7/8. The present compounds are also useful in the development of other compounds that interact with TLR7/8 since the present compounds provide important structure-activity relationship (SAR) information that facilitate that development. Compounds of the present invention that bind to TLR7/8 can be used as reagents for detecting TLR7/8 in living cells, fixed cells, in biological fluids, in tissue homogenates, in purified, natural biological materials, etc. For example, by labeling such compounds, one can identify cells expressing TLR7/8. In addition, based on their ability to bind TLR7/8, compounds of the present invention can be used in in-situ staining, FACS (fluorescence-activated cell sorting), sodium dodecyl sulfate polyacrylamide gel electrophoresis (SDS-PAGE), ELISA (enzyme-linked immunoadsorptive assay), etc., enzyme purification, or in purifying cells expressing TLR7/8 inside permeabilized cells. The compounds of the invention can also be utilized as commercial research reagents for various medical research and diagnostic uses. Such uses can include but are not limited to: use as a calibration standard for quantifying the activities of candidate TLR7/8 inhibitors in a variety of functional assays; use as blocking reagents in random compound screening, i.e. in looking for new families of TLR7/8 ligands, the compounds can be used to block recovery of the disclosed TLR7/8 compounds; use in the co-crystallization with TLR7/8, i.e. the compounds of the present invention will allow formation of crystals of the compound bound to TLR7/8, enabling the determination of enzyme/compound structure by x-ray crystallography; other research and diagnostic applications, wherein TLR7/8 is preferably activated or such activation is conveniently calibrated against a known quantity of an TLR7/8 inhibitor, etc.; use in assays as probes for determining the expression of TLR7/8 in cells; and developing assays for detecting compounds which bind to the same site as the TLR7/8 binding ligands.

The compounds of the invention can be applied either themselves and/or in combination with physical measurements for diagnostics of treatment effectiveness. Pharmaceutical compositions containing said compounds and the use of said compounds to treat TLR7/8-mediated conditions is a promising, novel approach for a broad spectrum of therapies causing a direct and immediate improvement in the state of health, whether in human or in animal. The orally bioavailable and active new chemical entities of the invention improve convenience for patients and compliance for physicians.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Modulation of TLR7/8, or a mutant thereof, activity in a biological sample is useful for a variety of purposes that are known to one of skill in the art. Examples of such purposes include, but are not limited to, blood transfusion, organ transplantation, biological specimen storage, and biological assays.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

The symbols and conventions used in the following descriptions of processes, schemes, and examples are consistent with those used in the contemporary scientific literature, for example, the Journal of the American Chemical Society or the Journal of Biological Chemistry.

Unless otherwise indicated, all temperatures are expressed in ° C. (degrees Centigrade).

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR, or on Bruker Mercury Plus 300 NMR Spectrometer equipped with a Bruker 300 BBFO probe at 300 MHz for proton NMR, or on Bruker Avance III 400 NMR Spectrometer equipped with a Bruker PABBO BB-1H/D Z GRD probe at 400 MHz for proton NMR. Most deuterated solvents contained typically 0.03% to 0.05% v/v tetramethylsilane, which was used as the reference signal (set at d 0.00 for both $^1$H and $^{13}$C). In cases where the deuterated solvents did not contain tetramethylsilane, the residual non-deuterated solvent peaks were used as a reference signal, as per published guidelines (*J. Org. Chem., Vol.* 62, No. 21, 1997).

LC-MS analyses were performed one either one of the two following instruments:

SHIMADZU LC-MS machine consisting of an UFLC 20-AD system and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

Agilent 1200 Series mass spectrometers from Agilent Technologies, using either Atmospheric Chemical Ionization (APCI) or Electrospray Ionization (ESI). Diode Array detector was scanned from 200-400 nm. The mass spectrometer was scanned between m/z 90-900 with a scan time of 0.6 s. Column: XBridge C8, 3.5 μm, 4.6×50 mm; Solvent A: water+0.1% TFA; Solvent B: ACN+0.1% TFA; Flow: 2 ml/min; Gradient: 0 min: 5% B, 8 min: 100% B, 8.1 min: 100% B, 8.5 min: 5% B, 10 min 5% B or a LC/MS Waters ZMD (ESI).

HPLC data were either obtained from the SHIMAZU LC-MS machine or using Agilent 1100 series HPLC from Agilent technologies using a column (XBridge C8, 3.5 μm, 4.6×50 mm) and two mobile phases (mobile phase A: water+0.1% TFA; mobile phase B: ACN+0.1% TFA). The flow rate was 2 ml/min. The gradient method was: 0 min: 5% B; 8 min: 100% B; 8.1 min: 100% B; 8.5 min: 5% B; 10 min 5% B, unless otherwise indicated.

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Intermediate 1: 8-chloropyrido[2,3-b]pyrazine

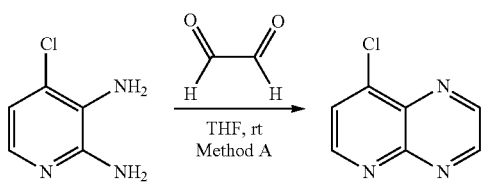

Method A

8-Chloropyrido[2,3-b]pyrazine: To a solution of 4-chloropyridine-2,3-diamine (1.90 g, 13.20 mmol) in THF (100 mL) was added oxaldehyde (1.00 g, 17.20 mmol) at room temperature. The resulting solution was then stirred for 6 h at room temperature. When the reaction was done, the reaction mixture was concentrated under reduced pressure and the residue was purified by flash chromatography eluting with EtOAc in petroleum ether (0% to 50% gradient) to yield 8-chloropyrido[2,3-b]pyrazine as yellow solid (2.10 g, 91%). MS: n/z=166.1 [M+H]+.

Intermediate 2: 4-chloro-1,2-diethyl-1H-pyrrolo[2,3-b]pyridine

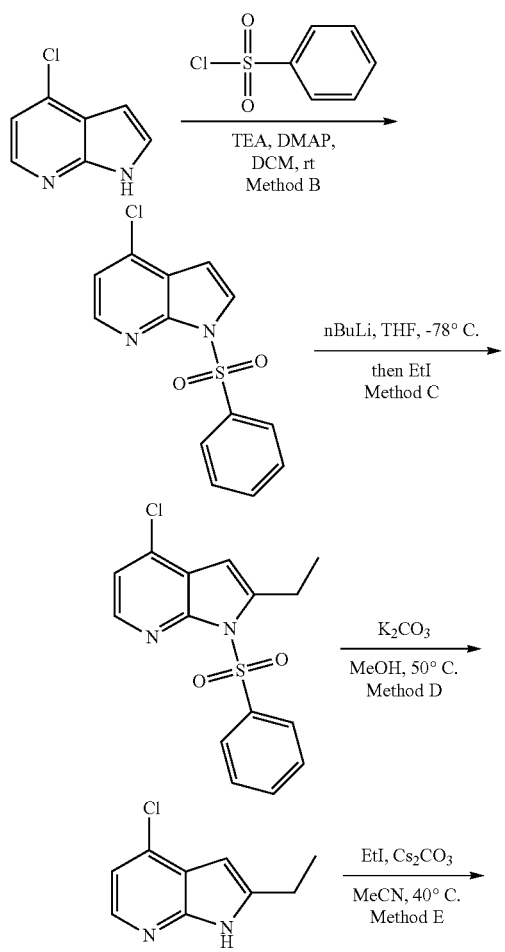

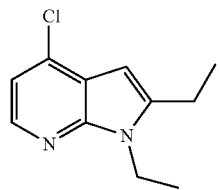

Method B

4-Chloro-1-(phenylsulfonyl)-1H-pyrrolo[2,3-b]pyridine: To a solution of 4-chloro-1H-pyrrolo[2,3-b]pyridine (2.85 g, 18.68 mmol) in DCM (100 mL) were added benzenesulfonyl chloride (4.95 g, 28.02 mmol), 4-dimethylaminopyridine (228 mg, 1.87 mmol) and triethylamine (5.67 g, 56.04 mmol) at room temperature. The resulting solution was then stirred for 3 h at room temperature. When the reaction was done, the reaction mixture was concentrated under reduced pressure and the residue was purified by flash chromatography eluting with EtOAc in petroleum ether (0% to 50% gradient) to yield 1-(benzenesulfonyl)-4-chloro-1H-pyrrolo[2,3-b]pyridine as white solid (4.98 g, 91%). MS: m/z=292.9 [M+H]+.

Method C

4-Chloro-2-ethyl-1-(phenylsulfonyl)-H-pyrrolo[2,3-b]:
At −78° C., to a solution of 1-(benzenesulfonyl)-4-chloro-1H-pyrrolo[2,3-b]pyridine (1.86 g, 6.40 mmol) in THF (35 mL) was added n-BuLi solution (2.5 M in THF, 5 mL, 12.80 mmol) dropwise over 5 min period. The resulting solution was stirred for 1 h at −78° C., and then was added by iodoethane (2.20 g, 14.10 mmol) slowly. Then the reaction mixture was slowly warmed up from −78° C. to 0° C. over 3 h period while stirring. When the reaction was done, it was quenched by the addition of sat. NH4Cl solution (20 mL) and the resulting mixture was extracted with ethyl acetate (60 mL×3). The organic phases were combined, washed with brine and dried over Na2SO4. The solvent was removed under reduced pressure and the residue was purified by flash chromatography eluting with EtOAc in petroleum ether (0% to 5% gradient) to yield 1-(benzenesulfonyl)-4-chloro-2-ethyl-1H-pyrrolo[2,3-b]pyridine as white solid (591 mg, 29%). MS: m/z=320.8 [M+H]+.

Method D

4-Chloro-2-ethyl-1H-pyrrolo[2,3-b]pyridine: To a solution of 1-(benzenesulfonyl)-4-chloro-2-ethyl-1H-pyrrolo[2,3-b]pyridine (575 mg, 1.80 mmol) in MeOH (20 mL) was added potassium carbonate (592 mg, 4.30 mmol) at room temperature. The resulting mixture was then stirred for 3.5 h at 50° C. After cooling to room temperature, the reaction mixture was concentrated under reduced pressure and the residue was diluted with DCM (50 mL). The insoluble solids in the mixture were filtered out and the filtrate was concentrated under reduced pressure to yield 4-chloro-2-ethyl-1H-pyrrolo[2,3-b]pyridine as yellow solid (443 mg, crude). MS: i/z=180.9 [M+H]+.

Method E

4-Chloro-1,2-diethyl-1H-pyrrolo[2,3-b]pyridine: To a solution of 4-chloro-2-ethyl-1H-pyrrolo[2,3-b]pyridine (443 mg, crude) in acetonitrile (23 mL) were added Cs2CO3 (1.40 g, 4.30 mmol) and iodoethane (676 mg, 4.30 mmol) at room temperature. The resulting mixture was then stirred for 3.5 h at 40° C. When the reaction was done, the reaction mixture was concentrated under reduced pressure and the residue was diluted with DCM (30 mL). The insoluble solids in the mixture were filtered out and the filtrate was concentrated under reduced pressure to yield 4-chloro-1,2-diethyl-1H- pyrrolo[2,3-b]pyridine as yellow oil (333 mg, 89% for 2 steps). MS: m/z=209.0 [M+H]$^+$.

Intermediate 3: 4-chloro-1,2-dimethyl-1H-pyrrolo[2,3-b]pyridine

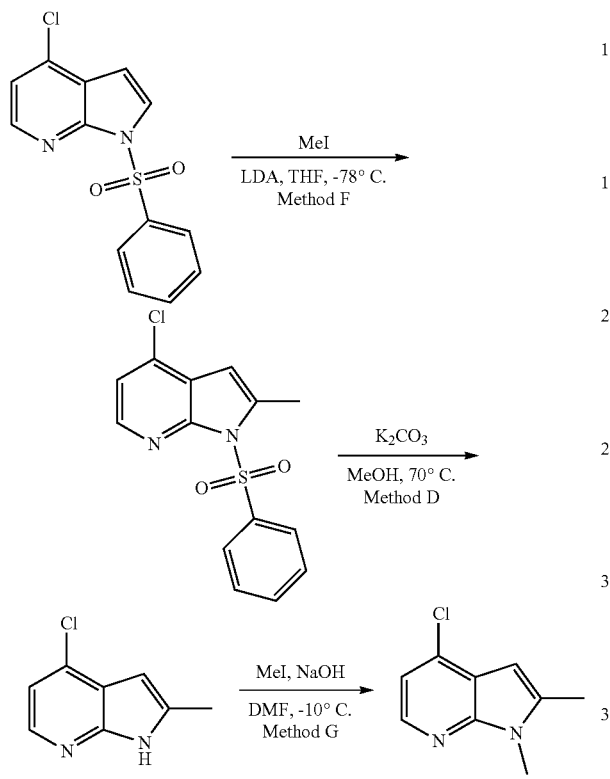

Method F

4-Chloro-2-methyl-1-(phenylsulfonyl)-1H-pyrrolo[2,3-b]: At −78° C., to a solution of 1-(benzenesulfonyl)-4-chloro-1H-pyrrolo[2,3-b]pyridine (2.00 g, 6.85 mmol) in tetrahydrofuran (30 mL) was added LDA solution (2 M in THF, 3.4 mL, 6.85 mmol) dropwise. The resulting solution was stirred for 1 h at −78° C., and then was added by iodomethane (0.97 g, 6.85 mmol) slowly. The resulting mixture was then stirred for 5 h at −78° C. When the reaction was done, it was quenched by H$_2$O (30 mL) and the resulting mixture was extracted with ethyl acetate (50 mL×3). The organic phases were combined, washed with brine and dried over Na$_2$SO$_4$. The solvent was removed under reduced pressure to yield 1-(benzenesulfonyl)-4-chloro-2-methyl-1H-pyrrolo[2,3-b]pyridine as brown oil (2.50 g, crude).

4-Chloro-2-methyl-1H-pyrrolo[2,3-b]pyridine: 4-chloro-2-methyl-1H-pyrrolo[2,3-b]pyridine was prepared from 4-chloro-2-methyl-1-(phenylsulfonyl)-1H-pyrrolo[2,3-b]pyridine using Method D. The crude product was purified by flash chromatography eluting with MeOH in DCM (0% to 10% gradient) to yield 4-chloro-2-methyl-1H-pyrrolo[2,3-b]pyridine as yellow solid (900 mg, 79% for 2 steps). MS: m/z=166.9 [M+H]$^+$.

Method G

4-Chloro-1,2-dimethyl-1H-pyrrolo[2,3-b]pyridine: At −10° C., to a solution of 4-chloro-2-methyl-1H-pyrrolo[2,3-b]pyridine (338 mg, 2.03 mmol) in N,N-dimethylformamide (10 mL) was added sodium hydroxide (240 mg, 6.00 mmol). Then Iodomethane (284 mg, 2.00 mmol) was added and the resulting mixture was stirred for 4 h at −10° C. When the reaction was done, the reaction mixture was diluted by DCM (100 mL) and the resulting mixture was washed with water (30 mL×3). The organic phase was washed with brine and dried over Na$_2$SO$_4$. The solvent was removed under reduced pressure and the residue was purified by flash chromatography eluting with EtOAc in petroleum ether (0% to 10% gradient) to yield 4-chloro-1,2-dimethyl-1H-pyrrolo[2,3-b]pyridine as yellow solid (300 mg, 82%). MS: m/z=181.0 [M+H]$^+$.

Intermediate 4: tert-butyl (3R,5S)-5-methylpiperidin-3-ylcarbamate

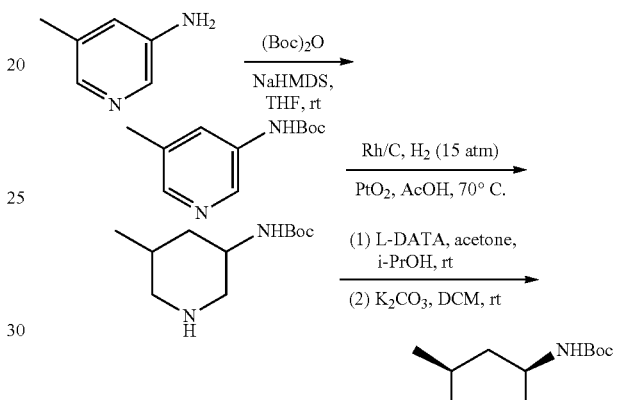

tert-Butyl 5-methylpyridin-3-ylcarbamate: At room temperature, to a solution of 5-methylpyridin-3-amine (9.50 g, 88.0 mmol) in tetrahydrofuran (150 mL) was added NaHMDS solution (2 M in THF, 110 mL, 220.0 mmol) dropwise over 10 min period. The resulting solution was stirred for 1 h at room temperature. Then Boc$_2$O (21.14 g, 92.4 mmol) was added. The reaction mixture was stirred for additional 2 h at room temperature. When the reaction was done, it was quenched by the addition of sat. NH$_4$Cl solution (100 mL). The resulting mixture was extracted with ethyl acetate (150 mL×3) and the organic phases were combined, washed with brine and dried over Na$_2$SO$_4$. The solvent was removed under reduced pressure and the residue was purified by flash chromatography eluting with EtOAc in petroleum ether (0% to 35% gradient) to yield tert-butyl N-(5-methylpyridin-3-yl)carbamate as yellow solid (15.18 g, 83%). MS: m/z=209.2 [M+H]$^+$. $^1$H NMR (300 MHz, DMSO-d$_6$, ppm) δ 9.49 (s, 1H), 8.38 (d, J=2.4 Hz, 1H), 8.05-7.97 (m, 1H), 7.73 (s, 1H), 2.24 (s, 3H), 1.47 (s, 9H).

tert-Butyl 5-methylpiperidin-3-ylcarbamate: In a 500 mL pressure tank reactor, tert-butyl N-(5-methylpyridin-3-yl) carbamate (14.22 g, 68.43 mmol), PtO$_2$ (2.50 g, 11.01 mmol) and Rh/C (5%, 2.50 g, 1.21 mmol) were mixed in AcOH (250 mL) at room temperature. The mixture was hydrogenated at 70° C. under 15 atm of hydrogen pressure for 24 h. When the reaction was done, the reaction mixture was cooled to room temperature. The insoluble solids in the reaction mixture were filtrated out and the filtrate was concentrated under reduced pressure. The residue was diluted with DCM (100 mL) and the pH value of the mixture was adjusted to 12 with sodium hydroxide solution (20%).

The resulting mixture was extracted with DCM (100 mL×3) and the organic phases were combined, washed with brine and dried over Na₂SO₄. The solvent was removed under reduced pressure to yield tert-butyl N-(5-methylpiperidin-3-yl)carbamate as light brown solid (14.19, 97%). MS: n/z=215.2 [M+H]⁺.

tert-Butyl (3R,5S)-5-methylpiperidin-3-ylcarbamate: To a solution of tert-butyl N-(5-methylpiperidin-3-yl)carbamate (11.70 g, 54.60 mmol) in acetone (200 mL) was added a solution of (2R,3R)-2,3-bis[(4-methoxyphenyl)carbonyloxy]butanedioic acid (28.95 g, 69.19 mmol) in isopropanol (13 mL) at room temperature. The resulting mixture was stirred for 24 h at room temperature and precipitation happened. When the reaction was done, the precipitates were collected by filtration to yield a white solid, which was added to a solution of potassium carbonate (29.06 g, 210.27 mmol) in water (15 mL) in portions at 0° C. The resulting mixture was then mixed with dichloromethane (100 mL) at 0° C. and was stirred for 2.5 h at room temperature. Then the mixture was extracted with dichloromethane (100 mL×3). The organic phases were combined, washed with brine and dried over Na₂SO₄. The solvent was removed under reduced pressure to yield tert-butyl N-[(3R,5S)-5-methylpiperidin-3-yl]carbamate as white solid (2.93 g, 25%). MS: m/z=215.2 [M+H]⁺.

Intermediate 5: 8-chloroquinoxaline-5-carbonitrile

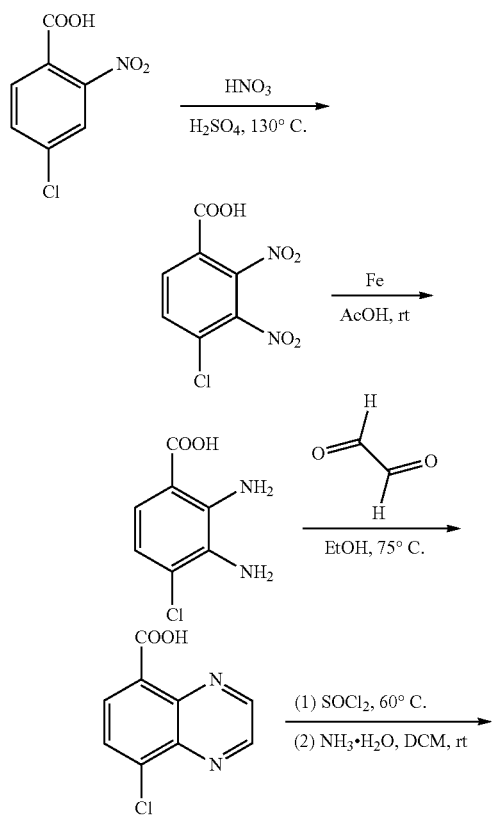

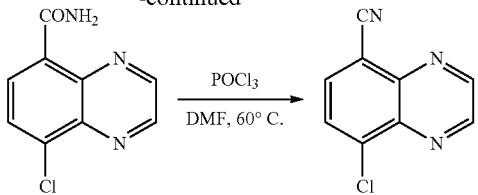

4-Chloro-2,3-dinitrobenzoic acid: At room temperature, HNO₃ (14.4 mol/L, 16 mL, 0.23 mol) was added to a solution of 4-chloro-2-nitrobenzoic acid (19.00 g, 94.52 mmol) in H₂SO₄ (80 mL) dropwise over 30 min period. The resulting solution was then stirred for 1 h at 130° C. After cooling to room temperature, the reaction mixture was poured into the ice water (300 mL). The pH value of the resulting mixture was adjusted to 7 with sodium hydroxide solution (6M). The mixture was then concentrated under reduced pressure and the insoluble solids from the remaining mixture were filtered out. The pH value of filtrate was then adjusted to 3 with hydrochloric acid solution (6 M) and precipitation happened. The precipitates were collected by filtration and dried in oven under vacuum to yield 4-chloro-2,3-dinitrobenzoic acid as light yellow solid (4.8 g, crude). MS: m/z=247.0 [M+H]⁺.

2,3-Diamino-4-chlorobenzoic acid: To a solution of 4-chloro-2,3-dinitrobenzoic acid (4.80 g, crude) in AcOH (80 mL) was added iron powder (1000 mg, 3.58 mmol) at room temperature. The resulting mixture was stirred for 2 h at room temperature. The insoluble solids in the reaction mixture were filtered out and the filtrate was concentrated under reduced pressure to yield 2,3-diamino-4-chlorobenzoic acid as black oil (3.12 g, crude). MS: m/z=186.9 [M+H]⁺.

8-Chloroquinoxaline-5-carboxylic acid: To a solution of 2,3-diamino-4-chlorobenzoic acid (3.12 g, crude) in ethanol (40 mL) was added a solution of oxaldehyde in H₂O (40%, 14.4 mol/L, 20 mL, 0.29 mol) at room temperature. The resulting solution was stirred for 2 h at 75° C. After cooling to room temperature, the reaction mixture was diluted with H₂O (50 mL) and the resulting mixture was extracted with ethyl acetate (100 mL×3). The organic phases were combined, washed with brine and dried over Na₂SO₄. The solvent was removed under reduced pressure to yield 8-chloroquinoxaline-5-carboxylic acid as yellow oil (1.70 g, crude). MS: n/z=208.9 [M+H]⁺.

8-Chloroquinoxaline-5-carboxylic acid): 8-chloroquinoxaline-5-carboxylic acid (1.70 g, crude) was added to thionyl chloride (30 mL, 0.39 mol) at room temperature. The resulting solution was stirred for 2 h at 60° C. After the reaction was done, the reaction mixture was concentrated under reduced pressure and the residue was diluted with DCM (30 mL). The resulting solution was cooled to 0° C. and was added by NH₄OH solution (28%, 14.8 mol/L, 20 mL, 0.30 mol) dropwise over 5 min period. The resulting mixture was then stirred for 1 h at room temperature. When the reaction was done, the reaction mixture was diluted with 20 mL H₂O and was extracted with ethyl acetate (50 mL×3). The organic phases were combined, washed with brine and dried over Na₂SO₄. The solvent was removed under reduced pressure and the residue was purified by flash chromatography eluting with EtOAc in petroleum ether (0% to 50% gradient) to yield 8-chloroquinoxaline-5-carboxamide as yellow oil (1.20 g, 6% for 4 steps). MS: n/z=208.1 [M+H]⁺.

8-chloroquinoxaline-5-carbonitrile: To a solution of 8-chloroquinoxaline-5-carboxamide (0.78 g, 3.77 mmol) in N,N-dimethylfornamide (10 mL) was added POCl₃ (4.00 g, 22.88 mmol) at room temperature. The resulting solution was stirred for 2 h at 60° C. After cooling to room temperature, the reaction mixture was quenched by water (30 mL) and extracted with ethyl acetate (50 mL×3). The organic phases were combined, washed with brine and dried over Na₂SO₄. The solvent was removed under reduced pressure and the residue was purified by flash chromatography eluting with EtOAc in petroleum ether (0% to 2% gradient) to yield 8-chloroquinoxaline-5-carbonitrile as off-white solid (555 mg, 78%). MS: m/z=189.9 [M+H]⁺. ¹H NMR (300 MHz, DMSO-d₆, ppm) δ 9.24 (s, 2H), 8.48 (d, J=8.1 Hz, 1H), 8.23 (d, J=8.1 Hz, 1H).

Intermediate 6: 8-bromoquinoxaline-5-carbonitrile

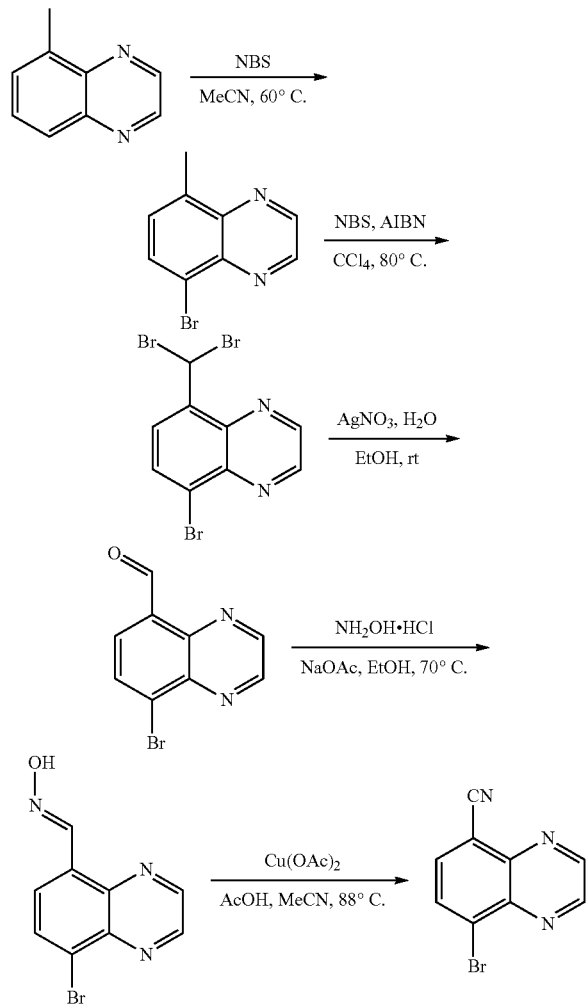

5-Bromo-8-methylquinoxaline: To a solution of 5-methylquinoxaline (9.50 g, 65.97 mmol) in CH₃CN (80 mL) was added 1-bromopyrrolidine-2,5-dione (27.00 g, 151.74 mmol) at room temperature. The resulting solution was stirred for 16 h at 60° C. After cooling to room temperature, the reaction mixture was concentrated under reduced pressure and the residue was diluted with ethyl acetate (500 mL). The insoluble solids in the mixture were filtered out and the filtrate was washed with brine and dried over Na₂SO₄. The solvent was removed under reduced pressure to yield 5-bromo-8-methylquinoxaline as brown solid (6.00 g, 41%). MS: m/z=222.9 [M+H]⁺.

5-Bromo-8-(dibromomethyl)quinoxaline: To a solution of 5-bromo-8-methylquinoxaline (6.00 g, 27.02 mmol) in CCl₄ (200 mL) was added NBS (19.23 g, 108.08 mmol) and AIBN (0.71 g, 4.32 mmol) at room temperature. The resulting solution was then stirred for 16 h at 80° C. After cooling to room temperature, the reaction mixture was concentrated under reduced pressure and the residue was diluted with ethyl acetate (500 mL). The insoluble solids in the mixture were filtered out, and then the filtrate was washed with brine and dried over Na₂SO₄. The solvent was removed under reduced pressure and the residue was purified by flash chromatography eluting with EtOAc in petroleum ether (0% to 5% gradient) to yield 5-bromo-8-(dibromomethyl)quinoxaline as light yellow solid (7.15 g, 70%). MS: m/z=378.7 [M+H]⁺.

8-Bromoquinoxaline-5-carbaldehyde: To a solution of 5-bromo-8-(dibromomethyl)quinoxaline (13.50 g, 35.71 mmol) in ethanol (290 mL) was added a solution of AgNO₃ (24.27 g, 142.86 mmol) in water (90 mL) dropwise at room temperature. The resulting mixture was then stirred for 1 h at room temperature. When the reaction was done, the reaction mixture was diluted with CH₃CN (300 mL) and precipitation happened. The precipitates were filtered out and the filtrate was concentrated under reduced pressure to yield 8-bromoquinoxaline-5-carbaldehyde as yellow solid (10.00 g, crude). MS: m/z=236.8 [M+H]⁺.

(E)-8-Bromoquinoxaline-5-carbaldehyde oxime: To a solution of 8-bromoquinoxaline-5-carbaldehyde (10 g, crude) in ethanol (100 mL) was added NaOAc (6.34 g, 73.42 mmol) and NH₂OH.HCl (3.12 g, 42.65 mmol) at room temperature. The resulting mixture was stirred for 3 h at 70° C. When the reaction was done, the insoluble solids in the reaction mixture were filtered out at 70° C., and then the filtrate was cooled to 0° C. and precipitation happened. The precipitates were collected by filtration and dried in oven to yield (E)-N-[(8-bromoquinoxalin-5-yl)methylidene]hydroxylamine as yellow solid (2.96 g, 33% for 2 steps). MS: m/z=253.9 [M+H]⁺.

8-Bromoquinoxaline-5-carbonitrile: To a solution of (E)-N-[(8-bromoquinoxalin-5-yl)methylidene]hydroxylamine (3.47 g, 13.82 mmol) in acetonitrile (20 mL) was added Cu(OAc)₂ (577 mg, 3.18 mmol) and acetic acid (1.24 g, 20.73 mmol) at room temperature. The resulting mixture was stirred for 15 h at 88° C. After cooling to room temperature, the reaction mixture was diluted with acetonitrile (10 mL). The insoluble solids in the mixture were filtered out and the filtrate was concentrated under reduced pressure. The residue was purified by flash chromatography eluting with EtOAc in petroleum ether (0% to 15% gradient) to yield 8-bromoquinoxaline-5-carbonitrile as yellow solid (1.22 g, 38%). MS: m/z=235.8 [M+H]⁺.

Intermediate 7: 5-Bromoquinazoline-8-carbonitrile

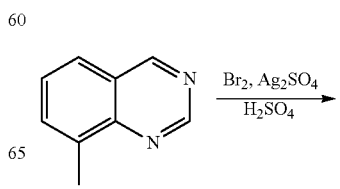

-continued

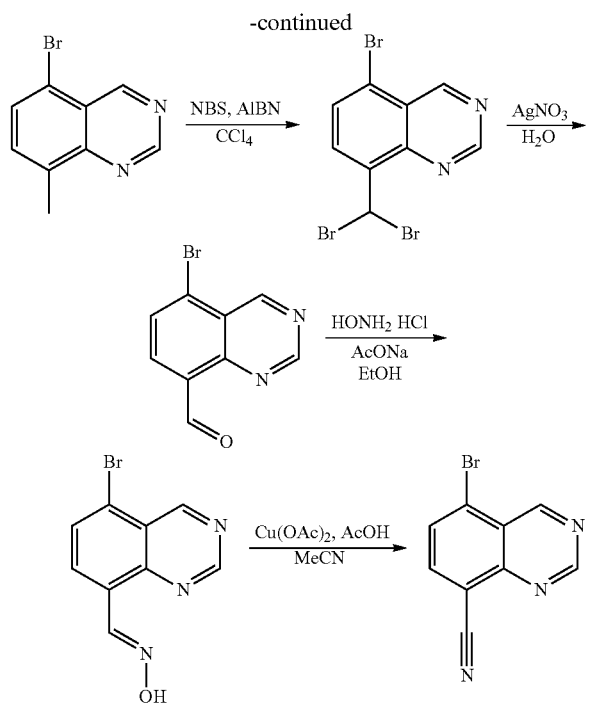

8-Methyl-3H-quinazolin-4-one: 2-Amino-3-methylbenzoic acid (125 g, 0.820 mol), formamidine acetate (257 g, 2.46 mol) and formamide (32.5 mL, 0.8200 mol) were mixed in a 2 L R.B fitted with Mechanical stirrer. The reaction mixture was heated at 180° C. for 3 h. The reaction completion was monitored by LCMS. After completion, the reaction mixture was cooled to RT and diluted with 2N NaOH solution (300 mL). After stirring at the same temperature for 15 min, the reaction mixture neutralized with 1.5N HCl solution. The solid precipitated was filtered off, washed with ice cold water and dried under vacuum to yield 8-methyl-3H-quinazolin-4-one (125 g, 94%) as an off white solid. $^1$H NMR (400 MHz, DMSO-d$_6$, ppm) δ 12.2 (bs, 1H), 8.1 (s, 1H), 8.0 (d, J=7.8 Hz, 1H), 7.7 (d, J=7.2 Hz, 1H), 7.4 (t, J=7.6 Hz, 1H), 2.5 (s, 3H); LC/MS(ESI) 161 (M+H).

4-Chloro-8-methylquinazoline: Phosphorous oxychloride (800 mL) was taken in a 2 L round bottom flask under nitrogen. To this was added 8-Methylquinazolin-4(3H)-one (125 g) in portions. The reaction mixture refluxed at 120° C. for 12 h. Reaction completion was monitored by TLC and LCMS. After completion, the reaction mixture was cooled to RT and evaporated to dryness under reduced pressure. The resulted residue was dissolved in DCM (500 mL) and quenched slowly into an ice cold solution of saturated K$_2$CO$_3$ with constant stirring. Then the organic layer was separated and washed with brine solution, dried over sodium sulfate and concentrated under vacuum to afford 4-chloro-8-methylquinazoline (120 g, 86%) as yellow solid. This was taken for next step without further purification. MS: m/z=179/181 [M+H]$^+$.

8-Methylquinazoline: To a stirred solution of 4-Chloro-8-methylquinazoline (120 g, 0.674 mol) in DCM (700 mL) under nitrogen was added p-toluenesulfonylhydrazide (175.7 g, 0.943 mol) in portions. The reaction mixture was heated at 45° C. for 12 h. The reaction completion was monitored by LCMS and TLC. After completion, the reaction mixture was cooled to RT, the solvent evaporated to dryness, the resulted residue dissolved in EtOH (500 mL), added 5N NaOH solution (500 mL) and refluxed for 6 h. The reaction completion was monitored by LCMS. After completion, the reaction mixture was cooled to RT and extracted with MTBE (3×600 mL). The combined organic layers were washed with a brine solution, dried over sodium sulfate and concentrated under vacuum. The resulted residue was purified by chromatography using neutralised silica gel (60-120 mesh) and eluted with pet ether/ethyl acetate to yield 8-methylquinazoline (60 g, 61%) as a low melting yellow solid. $^1$H NMR (400 MHz, DMSO-d$_6$, ppm) δ 9.54 (s, 1H), 9.31 (s, 1H), 7.96 (dd, J=8.8, 8.1 Hz, 1H), 7.87-7.84 (m, 1H), 7.64 (d, J=15.2 Hz, 1H), 2.67 (s, 3H).

5-Bromo-8-methylquinazoline: To a stirred solution of silver sulfate (151.5 g, 0.486 mol) in concentrated sulfuric acid (700 mL), was added 8-methylquinazoline (50 g, 0.347 mol) in portions at 0° C. Bromine (21.3 mL, 0.382 mol) was added dropwise and the reaction mixture was stirred at RT for 16 h. The reaction was monitored by LCMS at regular intervals. At the end of 16 h, LCMS showed 40% starting material, 7% of isomer, 10% dibromocompound and 40% of product. The reaction mixture was quenched with ice, filtered and basified with an ammonium hydroxide solution. The aqueous layer was extracted with MTBE (4×500 mL), washed with water and a brine solution. The organic layer was dried over sodium sulfate and concentrated under vacuum. The crude was purified by column chromatography using neutralized silica gel (60-120 mesh) and eluted with pet ether/ethyl acetate to yield 5-bromo-8-methylquinazoline (16 g, 20%) as white solid. $^1$H NMR (400 MHz, DMSO-d$_6$, ppm) δ 9.59 (s, 1H), 9.39 (s, 1H), 7.92 (d, J=7.72 Hz, 1H), 7.76 (d, J=7.72 Hz, 1H), 2.62 (s, 3H); MS: m/z=223/225 [M+H]$^+$.

5-Bromo-8-dibromomethylquinazoline: To a stirred solution of 5-bromo-8-methylquinazoline (53 g, 0.237 mol) in CCl$_4$ (800 mL) under nitrogen, was added N-bromosuccinimide (94.1 g, 0.522 mol) followed by AIBN (7.8 g, 0.048 mol) at RT. The reaction mixture was heated at 90° C. for 12 h. After completion, the reaction mixture was cooled to RT, filtered off and washed with CCl$_4$. The filtrate was concentrated and recrystallized to yield 5-bromo-8-dibromomethylquinazoline (61 g, 67%) as yellow solid. $^1$H NMR (400 MHz, DMSO-d$_6$, ppm) δ 9.73 (s, 1H), 9.53 (s, 1H), 8.44 (d, J=8.04 Hz, 1H), 8.21 (d, J=8.04 Hz, 1H), 8.02 (s, 1H).

5-Bromoquinazoline-8-carbaldehyde: To a stirred solution of 5-bromo-8-dibromomethylquinazoline (110 g, crude mixture) in acetone (1 L) and water (200 mL), was added silver nitrate (110 g) in portions at 0° C. The reaction mixture was stirred at RT for 2 h. The reaction completion was confirmed by TLC. The reaction mixture was filtered off and the filtrate was washed with a 10% NaHCO$_3$ solution and extracted with ethyl acetate (3×500 mL). The combined organic layer was washed with water and brine. The solvent was dried over sodium sulfate and concentrated under vacuum to afford 5-bromoquinazoline-8-carbaldehyde. This was taken for next step without further purification. $^1$H NMR (400 MHz, DMSO-d$_6$, ppm) δ 11.14 (s, 1H), 9.80 (s, 1H), 9.58 (s, 1H), 8.29 (d, J=12.3 Hz, 2H); MS: m/z=237/239 [M+H]$^+$.

5-Bromoquinazoline-8-carbonitrile: To a stirred solution of 5-bromoquinazoline-8-carbaldehyde (25 g, 0.105 mol) in DMF (125 mL), was added hydroxylamine (7.3 g 0.105 mol) and triethylamine (89 mL, 0.633 mol) and T3P (100 mL, 0.158 mol). The reaction mixture was heated to 100° C. for 3 h. The reaction was monitored by $^1$HNMR. After completion, the reaction mixture cooled to RT and quenched with ice. The reaction mixture was filtered off and the filtrate was basified with sodium bicarbonate and extracted with ethyl acetate (3×200 mL). The combined organic layer was washed with water and brine, dried over sodium sulfate and concentrated under vacuum to yield 5-bromoquinazoline-8-carbonitrile (8 g, 32%) as a yellow solid. $^1$H NMR (400 MHz, DMSO-d$_6$, ppm) δ 9.80 (s, 1H), 9.58 (s, 1H), 8.55 (d, J=7.9 Hz, 2H), 8.27 (d, J=7.8 Hz, 2H); MS: m/z=232/234 [M+H]$^+$.

Intermediate 8: 5-Bromo-quinoline-8-carbonitrile

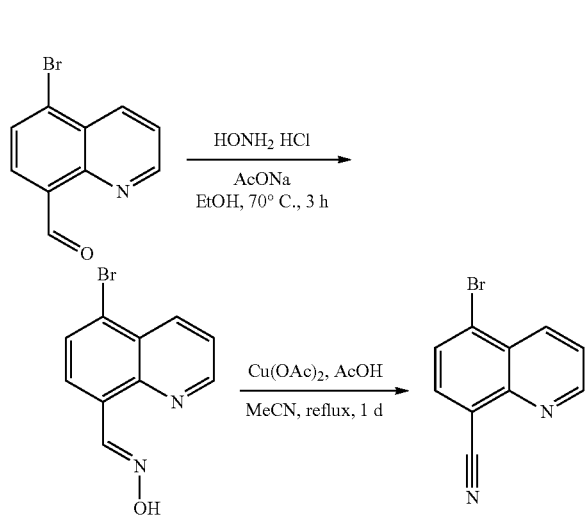

5-Bromo-quinoline-8-carbaldehyde oxime: Sodium acetate (1.9 g; 23.3 mmol), 5-bromoquinoline-8-carbaldehyde (5.0 g; 21.2 mmol) and hydroxylamine hydrochloride (1.6 g; 23.3 mmol) were added to absolute ethanol (50 mL). The beige suspension was heated at 70° C. for 3 h and the reaction mixture was allowed to cool down to room temperature. After water (25 mL) was added, the beige suspension was concentrated under reduced pressure to ~30 mL. Water (25 mL), tert-butylmethyl ether (12 mL) and heptane (12 mL) were added to the beige slurry, the mixture was stirred for 5 min and concentrated under reduced pressure to ~30 mL. Water (25 mL) was added to the beige slurry, the mixture was cooled to 0° C. and an aqueous solution 1N of sodium hydroxide (2 mL) was added. The beige suspension was stirred at 0° C. for 10 min and filtered. The solid was washed with water and dried under vacuo to give 5-bromo-quinoline-8-carbaldehyde oxime (5.20 g; 94%) as a beige solid. $^1$H NMR (400 MHz, DMSO-d$_6$) δ 11.61 (s, 1H), 9.16 (s, 1H), 9.03 (dd, J=4.2, 1.7 Hz, 1H), 8.54 (dd, J=8.6, 1.6 Hz, 1H), 8.08 (d, J=8.0 Hz, 1H), 8.00 (d, J=7.9 Hz, 1H), 7.75 (dd, J=8.6, 4.2 Hz, 1H); MS: m/z=251 [M+H]$^+$.

5-Bromo-quinoline-8-carbonitrile: To a mixture of 5-bromo-quinoline-8-carbaldehyde oxime (5.1 g; 20.3 mmol) and copper(ii) acetate monohydrate (81.1 mg; 0.41 mmol) in anhydrous acetonitrile (40 mL) was added acetic acid (1.4 mL; 24.4 mmol) and the reaction mixture was heated to reflux for 1 day. The brown solution was cooled down and water (40 mL) was added. The beige suspension was concentrated under reduced pressure and water (30 mL) was added to the beige slurry. The mixture was cooled to 0° C. and an aqueous solution 1N of sodium hydroxide (25 mL) was added. The beige suspension was stirred at 0° C. for 10 min and filtered. The brown solid was purified by recrystallization in chloroform and hexanes to afford 5-Bromo-quinoline-8-carbonitrile (1.22 g; 26%) as a cream solid. $^1$H NMR (400 MHz, CDCl$_3$) δ 9.13 (dd, J=4.3, 1.6 Hz, 1H), 8.61 (dd, J=8.6, 1.6 Hz, 1H), 7.98 (d, J=7.8 Hz, 1H), 7.92 (d, J=7.8 Hz, 1H), 7.66 (dd, J=8.6, 4.2 Hz, 1H); MS: m/z=234 [M+H]$^+$.

Intermediate 9: 5-Bromo-8-trifluoromethyl-quinazoline

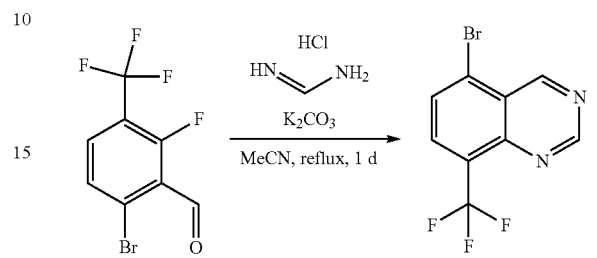

5-Bromo-8-trifluoromethyl-quinazoline: A solution of 6-bromo-2-fluoro-3-(trifluoromethyl)benzaldehyde (1.0 g; 3.69 mmol) and formamidine hydrochloride (594 mg; 7.38 mmol) in anhydrous acetonitrile (30 mL) was added potassium carbonate (1.8 g; 12.9 mmol) and molecular sieves 4 Å (650 mg). The reaction mixture was heated at reflux overnight. The resulting suspension was cooled down, filtered on celite, the solids were washed with acetonitrile and the filtrate was concentrated under reduced pressure. The residue was purified by chromatography on a PuriFlash column (40 g 15 μm), eluting with hexane and ethyl acetate to afford 5-Bromo-8-trifluoromethyl-quinazoline (222 mg, 22%) as a light yellow solid. MS: n/z=277 [M+H]$^+$. $^1$H NMR (400 MHz, DMSO-d, ppm) δ 9.81 (s, 1H), 9.56 (s, 1H), 8.35 (d, J=8.0 Hz, 1H), 8.24 (d, J=8.0 Hz, 1H).

Intermediate 10: 5-bromo-8-methyl-[1,7]naphthyridine

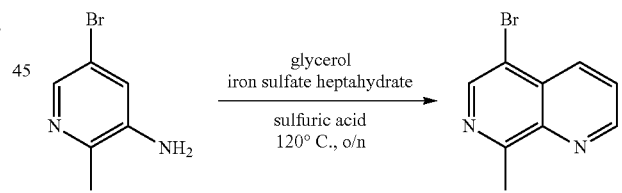

5-bromo-8-methyl-[1,7]naphthyridine: To a mixture of 5-bromo-2-methyl-pyridin-3-ylamine (3.00 g; 16.0 mmo), glycerol (4.7 mL; 64.1 mmol), iron(II) sulfate heptahydrate (892 mg; 3.2 mmol) was added sulfuric acid (5.6 mL; 96.2 mmol) dropwise. The resulting mixture was heated at 120° C. overnight. The reaction mixture was treated with ice, a solution 2N of sodium hydroxide, ethyl acetate and dichloromethane. After filteration to remove the dark brown solid solids, the organic layer was separated and washed with brine, dried and concentrated. The crude was purified by chromatography on silica gel, eluting with ethyla acetate and hexanes, to afford 5-bromo-8-methyl-[1,7]naphthyridine (470 mg, 13%). MS: n/z=224 [M+H]$^+$. $^1$H NMR (400 MHz, DMSO-d$_6$) 9.14 (dd, J=4.2, 1.6 Hz, 1H), 8.72 (s, 1H), 8.50 (dd, J=8.6, 1.6 Hz, 1H), 7.96 (dd, J=8.5, 4.1 Hz, 1H), 2.95 (s, 3H).

375

Example 1: Synthesis of Compound 1 (N-(2-(diethylamino)ethyl)-1-(1,8-naphthyridin-4-yl)piperidine-4-carboxamide)

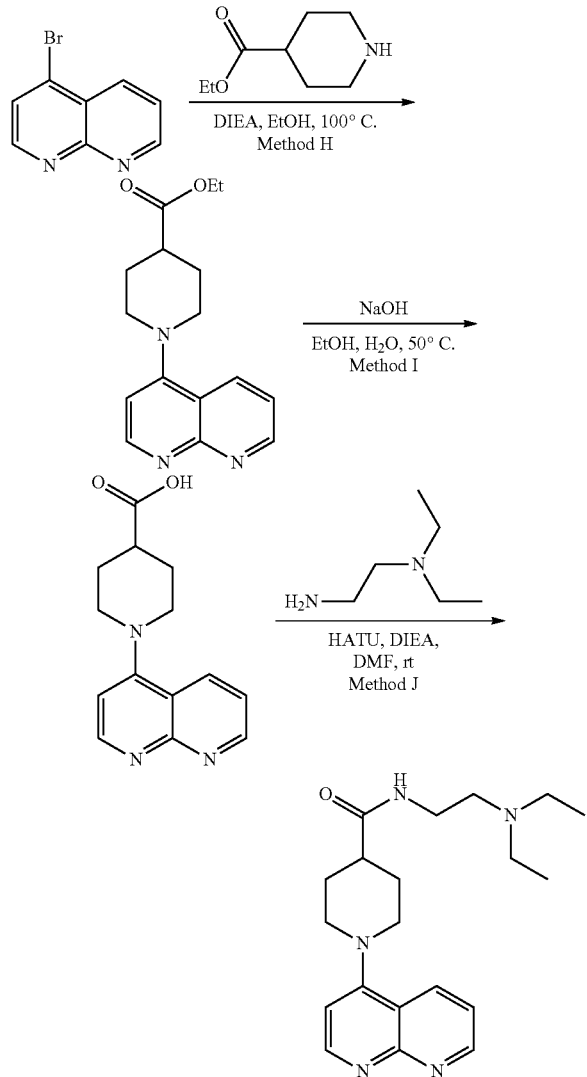

Method H

Ethyl 1-(1,8-naphthyridin-4-yl)piperidine-4-carboxylate: In a 25 mL reaction tube, ethyl piperidine-4-carboxylate (157 mg, 1.00 mmol) and DIEA (153 mg, 1.18 mmol) were added to a solution of 4-bromo-1,8-naphthyridine (190 mg, 0.91 mmol) in ethanol (10 mL) at room temperature. The tube was sealed and the reaction mixture was heated to 100° C. and stirred for 16 h. After cooling to room temperature, the reaction mixture was diluted with water (20 mL) and the resulting mixture was extracted with DCM (50 mL×3). The organic phases were combined, washed with brine and dried over $Na_2SO_4$. The solvent was removed under reduced pressure to yield 1-(1,8-naphthyridin-4-yl)piperidine-4-carboxylate as yellow solid (211 mg, 81%).

(Note: In Method H, the solvent may also be acetonitrile, dmso or NMP instead of EtOH and the reaction temperature may range from 95° C. to 130° C.)

376

Method I 1-(1,8-Naphthyridin-4-yl)piperidine-4-carboxylic acid: To a solution of ethyl 1-(1,8-naphthyridin-4-yl)piperidine-4-carboxylate (210 mg, 0.74 mmol) in ethanol (9 mL) were added sodium hydroxide (147 mg, 3.67 mmol) and water (3 mL) at room temperature. The resulting mixture was stirred for 3 h at 50° C. After cooling to room temperature, the reaction mixture was diluted with water (10 mL). The pH value of resulting mixture was adjusted to 5 with HCl solution (3M). The mixture was extracted with DCM (50 mL×3), and the organic phases were combined, washed with brine and dried over $Na_2SO_4$. The solvent was removed under reduced pressure to yield 1-(1,8-naphthyridin-4-yl)piperidine-4-carboxylic acid as a yellow solid (170 mg, 90%).

(Note: In Method I, sodium hydroxide may also be replaced by lithium hydroxide, the solvent may also be methanol or a mixture of methanol and THF instead of ethanol and the reaction temperature may range from room temperature to 50° C.)

Method J

N-(2-(diethylamino)ethyl)-1-(1,8-naphthyridin-4-yl)piperidine-4-carboxamide. To a solution of 1-(1,8-naphthyridin-4-yl)piperidin-4-carboxylic acid (114 mg, 0.44 mmol) in N,N-dimethylformamide (5 mL) were added (2-aminoethyl) diethylamine (103 mg, 0.89 mmol), DIEA (286 mg, 2.21 mmol) and HATU (177 mg, 0.46 mmol) at room temperature. The resulting solution was stirred for 16 h at room temperature. When the reaction was done, it was quenched by the addition of water (10 mL). The resulting mixture was extracted with DCM (50 mL×3), and the organic phases were combined, washed with brine and dried over $Na_2SO_4$. The solvent was removed under reduced pressure and the residue was purified by prep-HPLC under the following conditions: Column, XBridge BEH130 Prep C18 OBD column, 19×150 mm 5 um 13 nm; Mobile phase, acetonitrile in water (with 10 mmol/L $NH_4HCO_3$), 10% to 50% gradient in 10 min; Detector, UV 254 nm. N-[2-(diethylamino)ethyl]-1-(1,8-naphthyridin-4-yl)piperidine-4-carboxamide as a yellow syrup (29 mg, 17%).

Compound 1: HPLC: 94.5% purity, RT=0.80 min. MS: m/z=356.2 [M+H]$^+$. $^1$H NMR (300 MHz, CDCl$_3$, ppm) δ 9.06 (dd, J=4.2, 2.0 Hz, 1H), 8.92 (d, J=5.0 Hz, 1H), 8.38 (dd, J=8.4, 2.0 Hz, 1H), 7.43 (dd, J=8.4, 4.2 Hz, 1H), 6.90 (d, J=5.1 Hz, 1H), 6.64 (s, 1H), 3.72-3.60 (m, 2H), 3.54-3.35 (m, 2H), 3.01-2.86 (m, 2H), 2.66 (d, J=8.1 Hz, 6H), 2.50-2.30 (m, 1H), 2.21-2.00 (m, 4H), 1.20-1.00 (m, 6H).

The following compounds were synthesized in an analogous manner:

Compound 2 ((4-(diethylamino)piperidin-1-yl)(1-(pyrido[2,3-b]pyrazin-8-yl)piperidin-4-yl)methanone): From 8-chloropyrido[2,3-b]pyrazine, ethyl piperidine-4-carboxylate and N,N-diethylpiperidin-4-amine. HPLC: 96.5% purity, RT=1.18 min. MS: m/z=397.1 [M+H]$^+$. $^1$H NMR (400 MHz, DMSO-d$_6$, ppm) δ 8.97 (d, J=1.7 Hz, 1H), 8.81 (d, J=1.7 Hz, 1H), 8.69 (d, J=5.4 Hz, 1H), 7.04 (d, J=5.5 Hz, 1H), 4.42 (d, J=12.3 Hz, 3H), 4.05 (d, J=13.6 Hz, 1H), 3.25-3.10 (m, 2H), 3.06-2.93 (m, 2H), 2.74-2.65 (m, 1H), 2.55-2.45 (m, 5H), 1.85-1.60 (m, 6H), 1.40-1.10 (m, 2H), 1.00-0.90 (m, 6H).

Compound 414 (1-(8-Cyano-quinolin-5-yl)-piperidine-4-carboxylic acid [2-(2,6-dimethyl-piperidin-1-yl)-ethyl]-amide): From 5-bromo-quinoline-8-carbonitrile, ethyl piperidine-4-carboxylate and 2-(3,5-Dimethyl-piperidin-1-yl)-ethylamine. HPLC: 95.7% purity, RT=2.60 min. MS: m/z=420 [M+H]$^+$. $^1$H NMR (400 MHz, Chloroform-d, ppm) δ 9.05 (dd, J=4.2, 1.7 Hz, 1H), 8.45 (dd, J=8.5, 1.7 Hz, 1H), 8.01 (d, J=8.0 Hz, 1H), 7.49 (dd, J=8.5, 4.2 Hz, 1H), 7.05 (d, J=8.0 Hz, 1H), 6.23 (s, 1H), 3.53 (dt, J=12.9, 3.0 Hz, 2H), 3.39 (q, J=5.6 Hz, 2H), 2.90 (td, J=11.9, 2.8 Hz, 2H), 2.79 (d, J=10.2 Hz, 2H), 2.48 (t, J=6.0 Hz, 2H), 2.35 (tt, J=11.1, 4.2 Hz, 1H), 2.13 (qd, J=12.2, 11.2, 3.8 Hz, 2H), 2.04 (dd, J=13.2, 3.7 Hz, 2H), 1.81-1.56 (m, 3H), 1.51 (t, J=10.8 Hz, 2H), 0.87 (d, J=6.5 Hz, 6H), 0.56 (q, J=11.8 Hz, 1H).

Compound 415 (1-(8-Cyano-quinolin-5-yl)-piperidine-4-carboxylic acid (2-dimethylamino-ethyl)-amide): From 5-bromo-quinoline-8-carbonitrile, ethyl piperidine-4-carboxylate and (2-aminoethyl)dimethylamine. HPLC: 97.8% purity, RT=1.84 min. MS: m/z=352 [M+H]$^+$. $^1$H NMR (400 MHz, Chloroform-d, ppm) δ 9.05 (dd, J=4.2, 1.7 Hz, 1H), 8.45 (dd, J=8.5, 1.7 Hz, 1H), 8.01 (d, J=7.9 Hz, 1H), 7.49 (dd, J=8.5, 4.2 Hz, 1H), 7.05 (d, J=8.0 Hz, 1H), 6.17 (s, 1H), 3.53 (dt, J=12.0, 2.8 Hz, 2H), 3.37 (q, J=6.1, 4.9 Hz, 2H), 2.89 (td, J=12.0, 2.7 Hz, 2H), 2.49-2.40 (m, 2H), 2.36 (tt, J=11.2, 4.1 Hz, 1H), 2.25 (s, 6H), 2.14 (qd, J=12.3, 11.4, 3.8 Hz, 2H), 2.08-1.98 (m, 2H).

Compound 416 (1-(8-Cyano-quinolin-5-yl)-piperidine-4-carboxylic acid [2-(ethyl-methyl-amino)-ethyl]-amide): From 5-bromo-quinoline-8-carbonitrile, ethyl piperidine-4-carboxylate and (2-aminoethyl)(ethyl)methylamine. HPLC: >99% purity, RT=1.94 min. MS: m/z=366 [M+H]$^+$. $^1$H NMR (400 MHz, Chloroform-d, ppm) δ 9.05 (dd, J=4.2, 1.7 Hz, 1H), 8.45 (dd, J=8.5, 1.7 Hz, 1H), 8.01 (d, J=8.0 Hz, 1H), 7.49 (dd, J=8.5, 4.2 Hz, 1H), 7.05 (d, J=8.0 Hz, 1H), 6.20 (s, 1H), 3.53 (dt, J=12.0, 2.7 Hz, 2H), 3.37 (q, J=5.3 Hz, 2H), 2.89 (td, J=11.9, 2.7 Hz, 2H), 2.55-2.41 (m, 4H), 2.35 (tt, J=11.2, 4.2 Hz, 1H), 2.23 (s, 3H), 2.13 (qd, J=12.2, 11.3, 3.8 Hz, 2H), 2.08-1.99 (m, 2H), 1.07 (t, J=7.1 Hz, 3H).

Compound 419 (1-(8-Cyano-quinolin-5-yl)-piperidine-4-carboxylic acid (2-morpholin-4-yl-ethyl)-amide): From 5-bromo-quinoline-8-carbonitrile, ethyl piperidine-4-carboxylate and 4-(2-aminoethyl)morpholine. HPLC: >99% purity, RT=1.92 min. MS: m/z=394 [M+H]$^+$. $^1$H NMR (400 MHz, Chloroform-d, ppm) δ 9.06 (dd, J=4.2, 1.7 Hz, 1H), 8.45 (dd, J=8.6, 1.7 Hz, 1H), 8.02 (d, J=8.0 Hz, 1H), 7.49 (dd, J=8.5, 4.2 Hz, 1H), 7.06 (d, J=8.0 Hz, 1H), 6.08 (s, 1H), 3.73 (t, J=4.7 Hz, 4H), 3.54 (d, J=12.2 Hz, 2H), 3.41 (q, J=5.6 Hz, 2H), 2.91 (td, J=11.9, 2.7 Hz, 2H), 2.53 (t, J=6.0 Hz, 2H), 2.48 (t, J=4.7 Hz, 4H), 2.36 (tt, J=11.2, 4.2 Hz, 1H), 2.14 (qd, J=12.2, 11.4, 3.8 Hz, 2H), 2.08-1.98 (m, 2H).

Compound 420 (1-(8-Cyano-quinolin-5-yl)-piperidine-4-carboxylic acid (2-dimethylamino-1-methyl-ethyl)-amide): From 5-bromo-quinoline-8-carbonitrile, ethyl piperidine-4-carboxylate and 1-dimethylamino-2-propylamine. HPLC: >99% purity, RT=2.06 min. MS: n/z=366 [M+H]$^+$. $^1$H NMR (400 MHz, Chloroform-d, ppm) δ 9.06 (dd, J=4.2, 1.7 Hz, 1H), 8.46 (dd, J=8.5, 1.7 Hz, 1H), 8.02 (d, J=8.0 Hz, 1H), 7.50 (dd, J=8.5, 4.2 Hz, 1H), 7.06 (d, J=8.0 Hz, 1H), 5.96 (s, 1H), 3.96 (dq, J=9.5, 5.9 Hz, 1H), 3.54 (d, J=12.2 Hz, 2H), 2.90 (td, J=11.9, 2.8 Hz, 2H), 2.44-2.29 (m, 2H), 2.25 (s, 6H), 2.23-2.08 (m, 3H), 2.09-1.99 (m, 2H), 1.23 (d, J=6.4 Hz, 3H).

Compound 421 (1-(8-Cyano-quinolin-5-yl)-piperidine-4-carboxylic acid [2-(4-methyl-piperazin-1-yl)-ethyl]-amide): From 5-bromo-quinoline-8-carbonitrile, ethyl piperidine-4-carboxylate and 2-(4-methyl-piperazin-1-yl)-ethylamine. HPLC: 89.1% purity, RT=1.83 min. MS: m/z=407 [M+H]$^+$. $^1$H NMR (400 MHz, Chloroform-d, ppm) δ 9.06 (dd, J=4.2, 1.7 Hz, 1H), 8.45 (dd, J=8.6, 1.7 Hz, 1H), 8.02 (d, J=8.0 Hz, 1H), 7.49 (dd, J=8.6, 4.2 Hz, 1H), 7.06 (d, J=7.9 Hz, 1H), 6.16 (s, 1H), 3.54 (d, J=12.3 Hz, 2H), 3.40 (q, J=5.5 Hz, 2H), 2.91 (td, J=11.9, 2.7 Hz, 2H), 2.54 (t, J=6.0 Hz, 4H), 2.47 (s, 4H), 2.36 (ddd, J=11.3, 7.0, 4.2 Hz, 1H), 2.31 (s, 3H), 2.13 (qd, J=12.1, 11.3, 3.8 Hz, 2H), 2.07-2.01 (m, 2H).

Compound 422 (1-(8-Cyano-quinolin-5-yl)-piperidine-4-carboxylic acid (2-pyrrolidin-1-yl-ethyl)-amide): From 5-bromo-quinoline-8-carbonitrile, ethyl piperidine-4-carboxylate and n-(2-aminoethyl)pyrrolidine. HPLC: >99% purity, RT=2.05 min. MS: m/z=378 [M+H]$^+$. $^1$H NMR (400 MHz, Chloroform-d, ppm) δ 9.05 (dd, J=4.2, 1.7 Hz, 1H), 8.45 (dd, J=8.5, 1.8 Hz, 1H), 8.01 (d, J=8.0 Hz, 1H), 7.49 (dd, J=8.5, 4.2 Hz, 1H), 7.05 (d, J=8.0 Hz, 1H), 6.19 (s, 1H), 3.53 (dt, J=12.1, 2.8 Hz, 2H), 3.40 (q, J=5.4 Hz, 2H), 2.89 (td, J=12.0, 2.6 Hz, 2H), 2.67-2.59 (m, 2H), 2.58-2.45 (m, 4H), 2.36 (tt, J=11.3, 4.1 Hz, 1H), 2.14 (qd, J=12.3, 11.5, 3.9 Hz, 2H), 2.03 (dd, J=12.8, 3.1 Hz, 2H), 1.87-1.74 (m, 4H).

Compound 427 (1-(8-Cyano-quinolin-5-yl)-piperidine-4-carboxylic acid [2-(4,4-difluoro-piperidin-1-yl)-ethyl]-amide): From 5-bromo-quinoline-8-carbonitrile, ethyl piperidine-4-carboxylate and 2-(4,4-difluoropiperidin-1-yl) ethylamine. HPLC: >99% purity, RT=2.23 min. MS: m/z=428 [M+H]$^+$. $^1$H NMR (400 MHz, Chloroform-d, ppm) δ 9.05 (dd, J=4.2, 1.7 Hz, 1H), 8.44 (dd, J=8.6, 1.7 Hz, 1H), 8.01 (d, J=8.0 Hz, 1H), 7.49 (dd, J=8.5, 4.2 Hz, 1H), 7.05 (d, J=8.0 Hz, 1H), 6.07-5.96 (m, 1H), 3.54 (ddt, J=11.9, 4.1, 2.0 Hz, 2H), 3.41 (q, J=5.6 Hz, 2H), 2.90 (td, J=12.0, 2.6 Hz, 2H), 2.67-2.48 (m, 6H), 2.35 (tt, J=11.2, 4.1 Hz, 1H), 2.14 (qd, J=12.3, 11.4, 3.8 Hz, 2H), 2.07-1.91 (m, 6H).

Compound 433 (1-(8-Cyano-quinolin-5-yl)-piperidine-4-carboxylic acid (1-methyl-pyrrolidin-2-ylmethyl)-amide): From 5-bromo-quinoline-8-carbonitrile, ethyl piperidine-4-carboxylate and (1-methylpyrrolidin-2-yl)methanamine. HPLC: 98.9% purity, RT=2.01 min. MS: m/z=378 [M+H]$^+$. $^1$H NMR (400 MHz, Chloroform-d, ppm) δ 9.06 (dd, J=4.2, 1.7 Hz, 1H), 8.45 (dd, J=8.6, 1.7 Hz, 1H), 8.01 (d, J=8.0 Hz, 1H), 7.49 (dd, J=8.5, 4.2 Hz, 1H), 7.05 (d, J=8.0 Hz, 1H), 6.10 (s, 1H), 3.65 (ddd, J=13.8, 7.8, 2.5 Hz, 1H), 3.59-3.48 (m, 2H), 3.13 (ddd, J=13.7, 4.2, 2.3 Hz, 1H), 3.07 (t, J=7.8 Hz, 1H), 2.90 (tt, J=12.1, 3.6 Hz, 2H), 2.42-2.35 (m, 1H), 2.33 (s, 3H), 2.25 (q, J=8.9 Hz, 1H), 2.21-2.08 (m, 2H), 2.04 (dd, J=13.4, 3.8 Hz, 2H), 1.97-1.83 (m, 1H), 1.81-1.66 (m, 2H), 1.65-1.50 (m, 2H).

Compound 434 (1-(8-Cyano-quinolin-5-yl)-piperidine-4-carboxylic acid (1-cyclopropylmethyl-pyrrolidin-3-yl)-amide): From 5-bromo-quinoline-8-carbonitrile, ethyl piperidine-4-carboxylate and 1-(cyclopropylmethyl)pyrrolidin-3-amine. HPLC: 96.6% purity, RT=2.18 min. MS: m/z=404 [M+H]$^+$. $^1$H NMR (400 MHz, Chloroform-d, ppm) δ 9.05 (dd, J=4.2, 1.7 Hz, 1H), 8.44 (dd, J=8.6, 1.7 Hz, 1H), 8.01 (d, J=8.0 Hz, 1H), 7.49 (dd, J=8.6, 4.2 Hz, 1H), 7.05 (d, J=8.0 Hz, 1H), 6.08 (s, 1H), 4.51 (tddd, J=8.4, 6.3, 3.7, 2.3 Hz, 1H), 3.53 (dt, J=11.9, 2.6 Hz, 2H), 3.05 (td, J=8.8, 3.4 Hz, 1H), 2.88 (td, J=11.9, 2.7 Hz, 2H), 2.80 (dd, J=10.1, 2.6 Hz, 1H), 2.54 (dd, J=10.1, 6.4 Hz, 1H), 2.43-2.20 (m, 5H), 2.12 (qd, J=12.0, 11.5, 3.8 Hz, 2H), 2.06-1.97 (m, 2H), 1.65 (dtt, J=11.5, 7.4, 3.2 Hz, 1H), 0.94-0.85 (m, 1H), 0.53 (ddd, J=8.0, 5.5, 4.2 Hz, 2H), 0.19-0.07 (m, 2H).

Compound 435 ((S)-1-Ethyl-pyrrolidine-2-carboxylic acid [1-(8-cyano-quinolin-5-yl)-piperidin-4-ylmethyl]-amide): From 5-bromo-quinoline-8-carbonitrile, ethyl piperidine-4-carboxylate and 1-ethyl-1-proline. HPLC: >99% purity, RT=2.21 min. MS: m/z=392 [M+H]$^+$. $^1$H NMR (400 MHz, Chloroform-d, ppm) δ 9.05 (dd, J=4.2, 1.7 Hz, 1H), 8.41 (dd, J=8.5, 1.7 Hz, 1H), 8.01 (d, J=8.0 Hz, 1H), 7.66 (s, 1H), 7.47 (dd, J=8.6, 4.2 Hz, 1H), 7.04 (d, J=8.0 Hz, 1H), 3.50 (d, J=12.0 Hz, 2H), 3.38-3.23 (m, 2H), 3.19 (td, J=6.9, 3.4 Hz, 1H), 3.08 (dd, J=10.3, 4.4 Hz, 1H), 2.86 (tt, J=11.9, 2.9 Hz, 2H), 2.68 (dq, J=12.1, 7.3 Hz, 1H), 2.52 (dq, J=12.1, 7.1 Hz, 1H), 2.34 (ddd, J=10.5, 9.1, 6.2 Hz, 1H), 2.19 (dtd, J=12.8, 10.2, 7.8 Hz, 1H), 1.98-1.67 (m, 6H), 1.62 (qd, J=12.2, 4.2 Hz, 2H), 1.10 (t, J=7.2 Hz, 3H).

Compound 439 (1-(8-Cyano-quinolin-5-yl)-piperidine-4-carboxylic acid (2-azetidin-1-yl-ethyl)-amide): From 5-bromo-quinoline-8-carbonitrile, ethyl piperidine-4-carboxylate and 2-(azetidin-1-yl)ethan-1-amine. HPLC: >99% purity, RT=1.89 min. MS: m/z=364 [M+H]$^+$. $^1$H NMR (400 MHz, Chloroform-d, ppm) δ 9.05 (dd, J=4.2, 1.7 Hz, 1H), 8.45 (dd, J=8.5, 1.7 Hz, 1H), 8.01 (d, J=7.9 Hz, 1H), 7.49 (dd, J=8.6, 4.2 Hz, 1H), 7.05 (d, J=8.0 Hz, 1H), 6.09 (s, 1H), 3.53 (dt, J=12.3, 2.6 Hz, 2H), 3.31-3.15 (m, 6H), 2.88 (td, J=11.9, 2.7 Hz, 2H), 2.55 (dd, J=6.3, 5.3 Hz, 2H), 2.34 (tt, J=11.2, 4.1 Hz, 1H), 2.22-1.98 (m, 6H).

Compound 440 (1-(8-Cyano-quinoxalin-5-yl)-piperidine-4-carboxylic acid (2-piperidin-1-yl-ethyl)-amide): Form 8-Bromo-quinoxaline-5-carbonitrile, ethyl piperidine-4-carboxylate and 1-(2-aminoethyl)piperidine. HPLC: >99% purity, RT=1.96 min. MS: m/z=393 [M+H]$^+$. $^1$H NMR (400 MHz, Chloroform-d, ppm) δ 8.95 (d, J=1.8 Hz, 1H), 8.83 (d, J=1.8 Hz, 1H), 8.00 (d, J=8.3 Hz, 1H), 7.07 (d, J=8.3 Hz, 1H), 6.25 (s, 1H), 4.23 (dt, J=12.4, 2.8 Hz, 1H), 3.35 (td, J=6.0, 4.8 Hz, 2H), 3.12 (ddd, J=12.4, 10.2, 3.9 Hz, 2H), 2.50-2.30 (m, 7H), 2.16-1.99 (m, 3H), 1.58 (p, J=5.5 Hz, 4H), 1.46 (q, J=6.1 Hz, 2H).

Compound 454 (4-[4-(8-Cyano-quinoxalin-5-yl)-piperazin-1-yl]-N,N-dimethyl-4-oxo-butyramide): From 8-Bromo-quinoxaline-5-carbonitrile, 1-boc-piperazine and N,N-dimethylsuccinamic acid. HPLC: >99% purity, RT=2.13 min. MS: m/z=367 [M+H]$^+$. $^1$H NMR (400 MHz, Chloroform-d, ppm) δ 8.98 (d, J=1.8 Hz, 1H), 8.85 (d, J=1.8 Hz, 1H), 8.03 (d, J=8.2 Hz, 1H), 7.05 (d, J=8.3 Hz, 1H), 3.93 (t, J=5.2 Hz, 2H), 3.87 (t, J=5.1 Hz, 2H), 3.69 (t, J=5.1 Hz, 2H), 3.58 (t, J=5.2 Hz, 2H), 3.08 (s, 3H), 2.96 (s, 3H), 2.83-2.66 (m, 4H).

Compound 456 (1-(8-Fluoro-pyrido[3,4-b]pyrazin-5-yl)-piperidine-4-carboxylic acid (2-diethylamino-ethyl)-amide): From 5-chloro-8-fluoropyrido[3,4-b]pyrazine, ethyl piperidine-4-carboxylate and N,N-diethylethylenediamine. HPLC: >99% purity, RT=1.38 min. MS: m/z=376 [M+H]$^+$. $^1$H NMR (400 MHz, Chloroform-d, ppm) δ 8.95 (d, J=1.8 Hz, 1H), 8.80 (d, J=1.8 Hz, 1H), 8.22 (d, J=1.3 Hz, 1H), 6.23 (s, 1H), 4.83-4.72 (m, 2H), 3.36-3.26 (m, 2H), 3.20-3.07 (m, 2H), 2.59-2.48 (m, 6H), 2.48-2.37 (m, 1H), 2.04-1.89 (m, 4H), 1.02 (t, J=7.1 Hz, 6H).

Example 2: Synthesis of Compound 3 (1-(1-methyl-H-pyrazolo[3,4-d]pyrimidin-4-yl)-N-(2-(piperidin-1-yl)ethyl)piperidine-4-carboxamide)

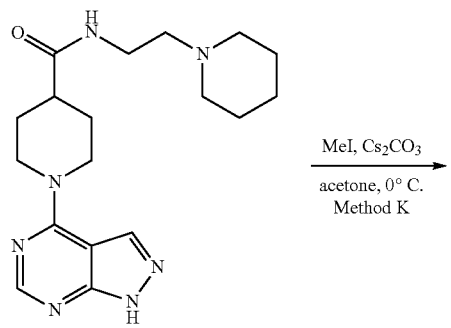

MeI, Cs$_2$CO$_3$
acetone, 0° C.
Method K

-continued

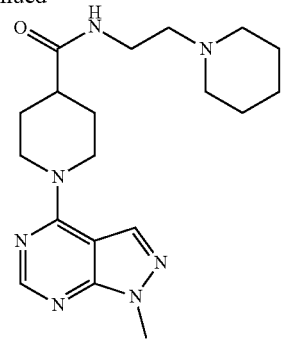

Method K 1-(1-Methyl-1H-pyrazolo[3,4-d]pyrimidin-4-yl)-N-(2-(piperidin-1-yl)ethyl)piperidine-4-carboxamide. At 0° C., to a solution of N-[2-(piperidin-1-yl)ethyl]-1-[1H-pyrazolo[3,4-d]pyrimidin-4-yl]piperidine-4-carboxamide (67 mg, 0.19 mmol) in acetone (5 mL) was added MeI (53 mg, 0.37 mmol) and Cs$_2$CO$_3$ (100 mg, 0.31 mmol). The resulting solution was stirred for 1.5 h at 0° C. When the reaction was done, it was quenched by the addition of water (10 mL). The resulting mixture was extracted with DCM (30 mL×3) and the organic phases were combined, washed with brine and dried over Na$_2$SO$_4$. The solvent was removed under reduced pressure and the residue was purified by prep-HPLC under the following conditions: Column, XBridge C18 OBD Prep Column, 5 um, 19 mm×250 mm; Mobile phase, acetonitrile in water (with 10 mmol/L NH$_4$HCO$_3$), 10% to 23% gradient in 10 min; Detector, UV 254. 1-[1-methyl-1H-pyrazolo[3,4-d]pyrimidin-4-yl]-N-[2-(piperidin-1-yl)ethyl]piperidine-4-carboxamide as a off-white solid (7 mg, 10%).

Compound 3: HPLC: 99.1% purity, RT=0.81 min. MS: m/z=372.2 [M+H]$^+$. $^1$H NMR (300 MHz, CDCl$_3$, ppm) δ 8.38 (s, 1H), 7.95 (s, 1H), 6.44 (s, 1H), 4.76 (d, J=13.2 Hz, 2H), 4.04 (s, 3H), 3.42-3.23 (m, 4H), 2.60-2.30 (m, 7H), 2.10-1.40 (m, 10H).

Example 3: Synthesis of Compound 4 (N,N-diethyl-1-((1-(pyrido[2,3-b]pyrazin-8-yl)piperidin-4-yl)methyl)piperidin-4-amine)

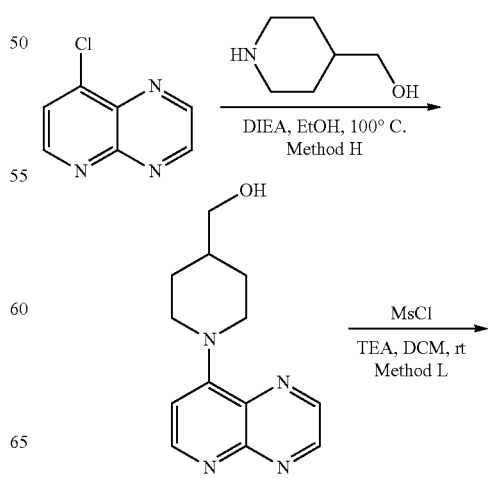

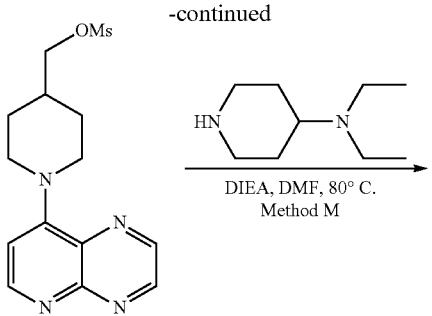
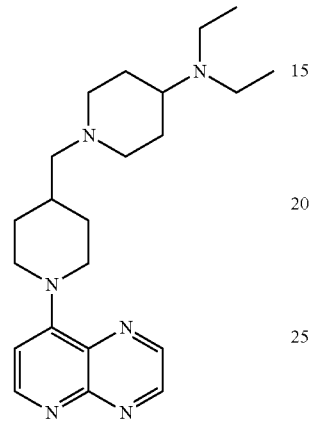

(1-(Pyrido[2,3-b]pyrazin-8-yl)piperidin-4-yl)methanol: (1-(pyrido[2,3-b]pyrazin-8-yl)piperidin-4-yl)methanol was prepared from 8-chloropyrido[2,3-b]pyrazine and piperidin-4-ylmethanol using Method H. (1-[pyrido[2,3-b]pyrazin-8-yl]piperidin-4-yl)methanol was obtained as yellow solid (275 mg, 89%).

Method L (1-(Pyrido[2,3-b]pyrazin-8-yl)piperidin-4-yl)methyl methanesulfonate: To a solution of (1-[pyrido[2,3-b]pyrazin-8-yl]piperidin-4-yl)methanol (250 mg, 1.02 mmol) and triethylamine (155 mg, 1.53 mmol) in dichloromethane (15 mL) was added methyl sulfonyl chloride (152 mg, 1.33 mmol) in several batches at room temperature. The resulting solution was stirred for 2 h at room temperature. When the reaction was done, it was quenched by the addition of water (20 mL). The resulting mixture was extracted with dichloromethane (40 mL×3), and the organic phases were combined, washed with brine and dried over Na$_2$SO$_4$. The solvent was removed under reduced pressure to yield (1-[pyrido[2,3-b]pyrazin-8-yl]piperidin-4-yl)methyl methanesulfonate as brown solid (300 mg, 91%). MS: m/z=323.1 [M+H]$^+$.

Method M

N,N-diethyl-1-((1-(pyrido[2,3-b]pyrazin-8-yl)piperidin-4-yl)methyl)piperidin-4-amine: To a solution of (1-[pyrido[2,3-b]pyrazin-8-yl]piperidin-4-yl)methyl methanesulfonate (170 mg, 0.53 mmol) in N,N-dimethylformamide (5 mL) were added N,N-diethylpiperidin-4-amine (330 mg, 2.11 mmol) and DIEA (136 mg, 1.05 mmol, 2.00 equiv) at room temperature. The resulting solution was stirred for 8 h at 80° C. After cooling to room temperature, the reaction mixture was quenched by water (10 mL) and was extracted with DCM (50 mL×3). The organic phases were combined, washed with brine and dried over Na$_2$SO$_4$. The solvent was removed under reduced pressure and the residue was purified by prep-HPLC under the following conditions: Column, XBridge BEH130 Prep C18 OBD Column, 19×150 mm 5 um 13 nm; Mobile phase, acetonitrile in water (with 10 mmol/L NH$_4$HCO$_3$), 10% to 23% gradient in 18 min; Detector, UV 254 nm. N,N-diethyl-1-[(1-[pyrido[2,3-b]pyrazin-8-yl]piperidin-4-yl)methyl]piperidin-4-amine was obtained as brown solid (47 mg, 23%).

(Note: The reaction temperature in Method M may range from 80° C. to 130° C.)

Compound 4: HPLC: 97.6% purity, RT=0.73 min. MS: m/z=383.2 [M+H]$^+$. $^1$H NMR (400 MHz, DMSO-d$_6$, ppm) δ 8.96 (d, J=1.7 Hz, 1H), 8.80 (d, J=1.7 Hz, 1H), 8.67 (d, J=5.4 Hz, 1H), 7.02 (d, J=5.5 Hz, 1H), 4.39 (d, J=12.5 Hz, 2H), 3.11-3.00 (m, 2H), 2.85 (d, J=11.1 Hz, 2H), 2.49-2.31 (m, 5H), 2.13 (d, J=6.7 Hz, 2H), 1.88-1.76 (m, 5H), 1.61 (d, J=12.0 Hz, 2H), 1.45-1.21 (m, 4H), 0.95-0.85 (m, 6H).

Example 4: Synthesis of Compound 5 (N,N-diethyl-1-((1-(quinolin-4-yl)piperidin-4-yl)methyl)piperidin-4-amine)

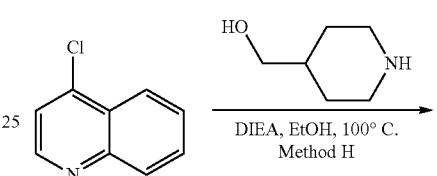
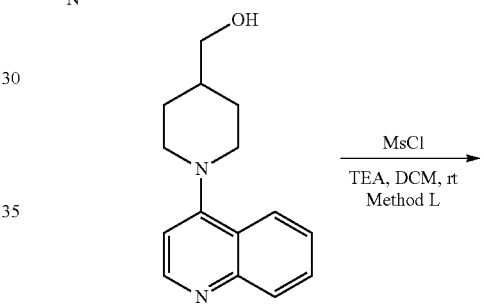
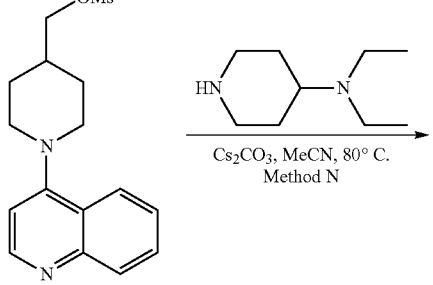
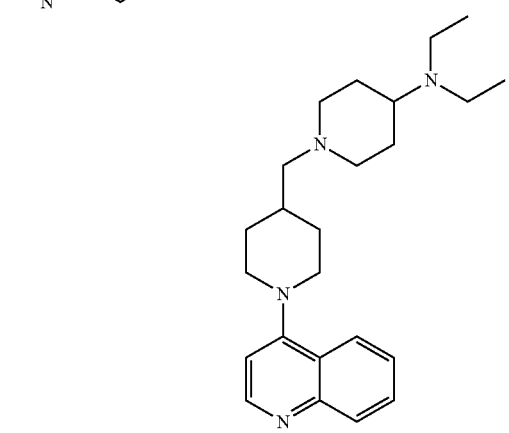

(1-(Quinolin-4-yl)piperidin-4-yl)methyl methanesulfonate: (1-(quinolin-4-yl)piperidin-4-yl)methyl methanesulfonate was prepared from 4-chloroquinoline, piperidin-4-ylmethanol, and methanesulfonyl chloride using Method H and L. [1-(quinolin-4-yl)piperidin-4-yl]methyl methanesulfonate was obtained as yellow solid (550 mg, crude). MS: m/z=321.0 [M+H]$^+$.

Method N

N,N-diethyl-1-((1-(quinolin-4-yl)piperidin-4-yl)methyl)piperidin-4-amine. To a solution of [1-(quinolin-4-yl)piperidin-4-yl]methyl methanesulfonate (450 mg, crude) in acetonitrile (8 mL) was added N,N-diethylpiperidin-4-amine (209 mg, 1.34 mmol) and $Cs_2CO_3$ (651 mg, 2.00 mmol) at room temperature. The resulting mixture was stirred overnight at 80° C. After cooling to room temperature, the reaction mixture was quenched by water (10 mL) and was extracted with DCM (40 mL×3). The organic phases were combined, washed with brine and dried over $Na_2SO_4$. The solvent was removed under reduced pressure and the residue was purified by prep-HPLC under the following conditions: Column, XBridge C18 OBD Prep Column, 5 um, 19 mm×250 mm; Mobile phase, acetonitrile in water (with 10 mmol/L $NH_4HCO_3$), 15% to 60% gradient in 8 min; Detector, UV 254 nm. N,N-diethyl-1-[[1-(quinolin-4-yl)piperidin-4-yl]methyl]piperidin-4-amine was obtained as light yellow solid (40 mg, 15% for 3 steps).

(Note: In Method N, the solvent may also be DMF instead of acetonitrile and the reaction temperature may range from 60° C. to 130° C.)

Compound 5: HPLC: 99.7% purity, RT=0.53 min. MS: m/z=381.3 [M+H]$^+$. $^1$H NMR (300 MHz, CDCl$_3$, ppm) δ 8.70 (d, J=5.0 Hz, 1H), 8.08-7.94 (m, 2H), 7.70-7.55 (m, 1H), 7.50-7.40 (m, 1H), 6.82 (d, J=5.0 Hz, 1H), 3.62 (d, J=12.0 Hz, 2H), 2.97 (d, J=11.5 Hz, 2H), 2.81 (dd, J=12.8, 10.6 Hz, 2H), 2.78-2.48 (m, 5H), 2.27 (d, J=7.0 Hz, 2H), 2.00-1.40 (m, 11H), 1.20-1.00 (m, 6H).

Example 5: Synthesis of Compound 6 (4-(4-((2-(piperidin-1-yl)ethoxy)methyl)piperidin-1-yl)quinolone)

Method O 4-(4-((2-(Piperidin-1-yl)ethoxy)methyl)piperidin-1-yl): To a solution of [1-(quinolin-4-yl)piperidin-4-yl]methanol (190 mg, 0.78 mmol) in N,N-dimethylformamide (20 mL) was added sodium hydride (59 mg, 2.48 mmol) at room temperature. The resulting suspension was stirred for 30 min at room temperature, and then was added by the 1-(2-chloroethyl)piperidine hydrochloride (304 mg, 1.65 mmol). The reaction mixture was stirred for additional 20 h at room temperature. When the reaction was done, it was quenched by the addition of water (10 mL). The resulting mixture was extracted with DCM (50 mL×3) and the organic phases were combined, washed with brine and dried over $Na_2SO_4$. The solvent was removed under reduced pressure and the residue was purified by prep-HPLC under the following conditions: Column: XBridge C18 OBD Prep Column, 5 um, 19 mm×250 mm; Mobile phase, acetonitrile in water (with 10 mmol/L $NH_4HCO_3$), 41% to 50% gradient in 9 min; Detector, UV 254 nm. 4-(4-[[2-(piperidin-1-yl)ethoxy]methyl]piperidin-1-yl)quinoline as a off-white solid (35 mg, 13%).

Compound 6: HPLC: 98.9% purity, RT=1.17 min. MS: m/z=354.2 [M+H]$^+$. $^1$H NMR (300 MHz, CDCl$_3$, ppm) δ 8.70 (d, J=5.0 Hz, 1H), 8.06-7.96 (m, 2H), 7.70-7.60 (m, 1H), 7.50-7.40 (m, 1H), 6.83 (d, J=5.0 Hz, 1H), 3.69-3.56 (m, 4H), 3.41 (d, J=6.0 Hz, 2H), 2.90-2.75 (m, 2H), 2.70-2.30 (m, 6H), 2.00-1.35 (m, 11H).

Example 6: Synthesis of Compound 7 (2-morpholino-N-((1-(quinolin-4-yl)piperidin-4-yl)methyl)ethanamine)

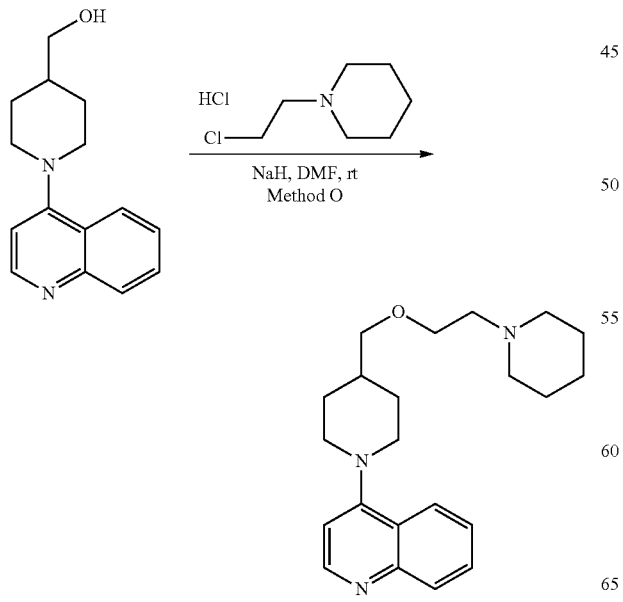

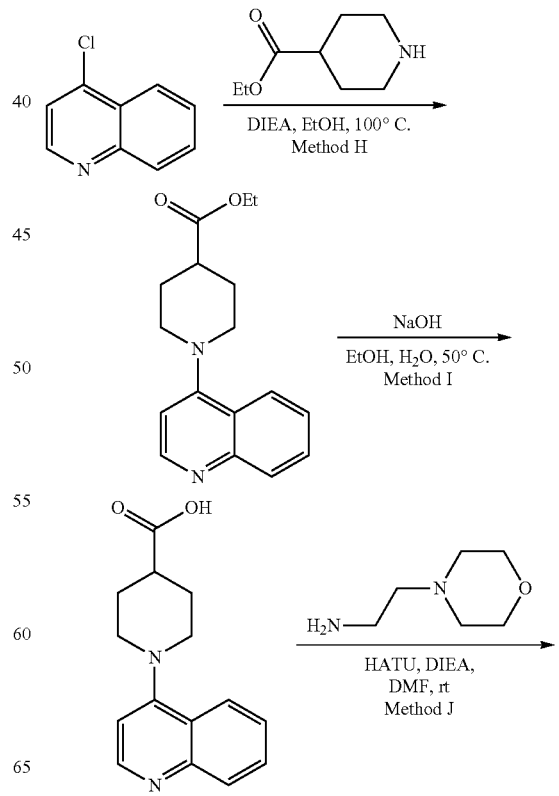

-continued

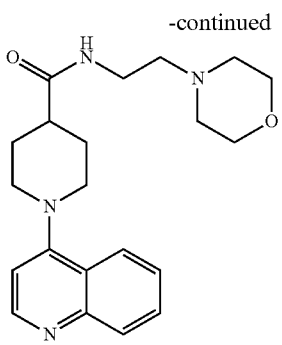

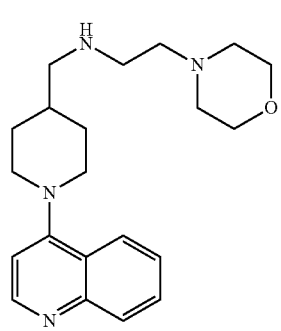

N-(2-Morpholinoethyl)-1-(quinolin-4-yl)piperidine-4-carboxamide: N-(2-morpholinoethyl)-1-(quinolin-4-yl)piperidine-4-carboxamide was prepared from 4-chloroquinoline, ethyl piperidine-4-carboxylat, and 2-morpholinoethanamine using Method H, I, and J. N-[2-(morpholin-4-yl)ethyl]-1-(quinolin-4-yl)piperidine-4-carboxamide was obtained as yellow oil (374 mg, crude). MS: m/z=369.1 [M+H]$^+$.

Method P

2-Morpholino-N-((1-(quinolin-4-yl)piperidin-4-yl)methyl)ethanamine: To a solution of N-[2-(morpholin-4-yl)ethyl]-1-(quinolin-4-yl)piperidine-4-carboxamide (374 mg, crude) in tetrahydrofuran (5 mL) was added BH$_3$-THF (10 mL, 1M, 1.00 mmol) at room temperature. The resulting solution was then stirred for 6 h at 65° C. After cooling to room temperature, the reaction mixture was quenched by MeOH (2 mL) and was extracted with DCM (50 mL×3). The organic phases were combined, washed with brine and dried over Na$_2$SO$_4$. The solvent was removed under reduced pressure and the residue was purified by flash chromatography eluting with MeOH in DCM (0% to 25% gradient) to yield of 2-morpholino-N-((1-(quinolin-4-yl)piperidin-4-yl)methyl)ethanamine as light yellow solid (50 mg, 10% for 4 steps).

Compound 7: HPLC: 98.9% purity, RT=0.82 min. MS: m/z=355.2 [M+H]$^+$. $^1$H NMR (300 MHz, CD$_3$OD, ppm) δ 8.58 (d, J=5.2 Hz, 1H), 8.04 (dd, J=8.5, 1.5 Hz, 1H), 7.91 (dd, J=8.4, 1.3 Hz, 1H), 7.75-7.65 (m, 1H), 7.57-7.47 (m, 1H), 6.99 (d, J=5.2 Hz, 1H), 3.80-3.60 (m, 6H), 3.21-2.80 (m, 6H), 2.70-2.40 (m, 2H), 2.06-1.91 (m, 3H), 1.77-1.50 (m, 2H), 1.34-1.19 (m, 2H).

Example 7: Synthesis of Compound 8 (2-morpholino-N-((1-(quinolin-4-yl)piperidin-4-yl)methyl)ethanamine)

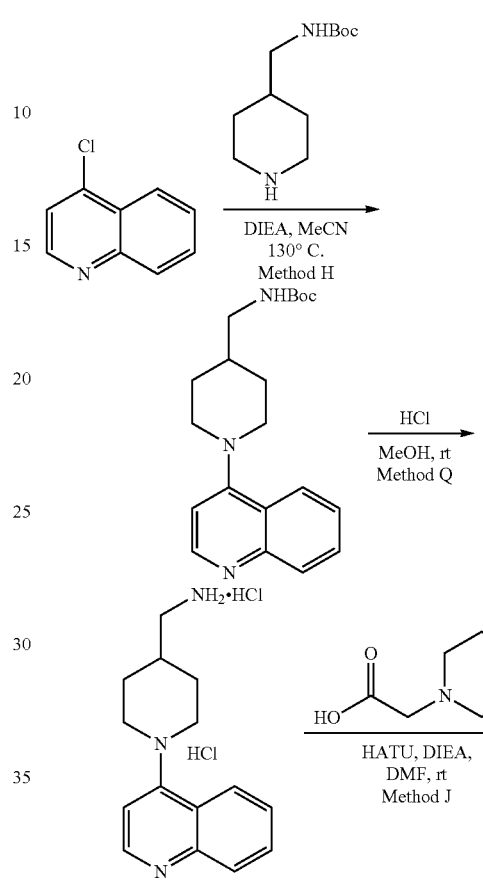

tert-Butyl (1-(quinolin-4-yl)piperidin-4-yl)methylcarbamate: tert-butyl (1-(quinolin-4-yl)piperidin-4-yl)methylcarbamate was prepared from 4-chloroquinoline and tert-butyl piperidin-4-ylmethylcarbamate using Method H. The crude product was purified by flash chromatography eluting with MeOH in DCM (0% to 15% gradient) to yield tert-butyl N-[[1-(quinolin-4-yl)piperidin-4-yl]methyl]carbamate as light yellow solid (600 mg, 94%). MS: n/z=342.1 [M+H]$^+$.

Method Q (1-(Quinolin-4-yl)piperidin-4-yl)methanamine: To a solution of tert-butyl N-[[1-(quinolin-4-yl)piperidin-4-yl]methyl]carbamate (557 mg, 1.63 mmol) in MeOH (10 mL), was added conc. HCl solution (12 M, 1.5 mL) at room temperature. The resulting solution was stirred for 24 h at room temperature. When the reaction was done, the reaction mixture was concentrated under reduced pressure to yield [1-(quinolin-4-yl)piperidin-4-yl]methanamine dihydrochloride as yellow solid (380 mg, 84%). MS: m/z=242.1 [M+H]⁺.

(Note: In Method Q, the solvent may also be 1:1 mixture of dioxane/MeOH or dioxane instead of MeOH)

2-(Piperidin-1-yl)-N-((1-(quinolin-4-yl)piperidin-4-yl)methyl)acetamide: 2-(piperidin-1-yl)-N-((1-(quinolin-4-yl)piperidin-4-yl)methyl)acetamide was prepared from (1-(quinolin-4-yl)piperidin-4-yl)methanamine hydrochloride and 2-(piperidin-1-yl)acetic acid using Method J. The crude product was purified by prep-HPLC under the following conditions: Column, XBridge C18 OBD Prep Column, 5 um, 19 mm×250 mm; Mobile phase, acetonitrile in water (with 10 mmol/L $NH_4HCO_3$), 40% to 55% gradient in 10 min; Detector, UV 254 nm. 2-(piperidin-1-yl)-N-[[1-(quinolin-4-yl)piperidin-4-yl]methyl]acetamide was obtained as light yellow solid (152 mg, 72%).

Compound 8: HPLC: 98.1% purity, RT=1.46 min. MS: m/z=367.2 [M+H]⁺. ¹H NMR (300 MHz, DMSO-$d_6$, ppm) δ 8.66 (d, J=4.9 Hz, 1H), 8.01-7.90 (m, 2H), 7.83-7.62 (m, 2H), 7.58-7.48 (m, 1H), 6.96 (d, J=5.0 Hz, 1H), 3.54 (d, J=12.1 Hz, 2H), 3.19-3.09 (m, 2H), 2.91 (s, 2H), 2.86-2.70 (m, 2H), 2.50-2.30 (m, 4H), 1.85-1.62 (m, 3H), 1.62-1.31 (m, 8H).

The following compounds were synthesized in an analogous manner:

Compound 388 (2-Piperidin-1-yl-N-(1-pyrido[2,3-b]pyrazin-8-yl-piperidin-4-ylmethyl)-acetamide): From 8-Chloro-pyrido[2,3-b]pyrazine, 4-(boc-aminomethyl) piperidine and piperidin-1-yl-acetic acid. HPLC: 98.6% purity, RT=1.16 min. MS: m/z=369 [M+H]⁺. ¹H NMR (400 MHz, Chloroform-d, ppm) δ 8.95 (d, J=1.7 Hz, 1H), 8.80 (d, J=5.4 Hz, 1H), 8.72 (d, J=1.7 Hz, 1H), 7.45 (s, 1H), 6.88 (d, J=5.4 Hz, 1H), 4.45 (d, J=12.7 Hz, 2H), 3.28 (t, J=6.3 Hz, 2H), 3.08 (td, J=12.4, 2.3 Hz, 2H), 2.97 (s, 2H), 2.46 (s, 4H), 1.98-1.79 (m, 3H), 1.64-1.52 (m, 6H), 1.46 (dd, J=11.2, 5.5 Hz, 2H).

Compound 390 (2-Diethylamino-N-(1-pyrido[2,3-b]pyrazin-8-yl-piperidin-4-yl)-acetamide): From 8-Chloro-pyrido[2,3-b]pyrazine, 4-n-boc-aminopiperidine and 2-(diethylamino)acetic acid hydrochloride. HPLC: >99% purity, RT=0.92 min. MS: m/z=343 [M+H]⁺. ¹H NMR (400 MHz, Chloroform-d, ppm) δ 8.97 (d, J=1.7 Hz, 1H), 8.82 (d, J=5.3 Hz, 1H), 8.74 (d, J=1.7 Hz, 1H), 7.49 (d, J=8.5 Hz, 1H), 6.90 (d, J=5.4 Hz, 1H), 4.34 (dt, J=13.0, 2.9 Hz, 2H), 4.13 (dddd, J=15.0, 10.7, 8.6, 4.3 Hz, 1H), 3.26 (ddd, J=12.9, 11.4, 2.6 Hz, 2H), 3.04 (s, 2H), 2.56 (q, J=7.1 Hz, 4H), 2.13 (dd, J=13.1, 3.8 Hz, 2H), 1.77 (qd, J=11.5, 3.8 Hz, 2H), 1.03 (t, J=7.1 Hz, 6H).

Compound 391 (3,4-Dimethoxy-N-(1-pyrido[2,3-b]pyrazin-8-yl-piperidin-4-ylmethyl)-benzamide): From 8-Chloro-pyrido[2,3-b]pyrazine, 4-(boc-aminomethyl) piperidine and 3,4-dimethoxybenzoic acid. HPLC: >99% purity, RT=1.90 min. MS: m/z=408 [M+H]⁺. ¹H NMR (400 MHz, Chloroform-d, ppm) δ 8.95 (d, J=1.7 Hz, 1H), 8.80 (d, J=5.4 Hz, 1H), 8.72 (d, J=1.8 Hz, 1H), 7.45 (d, J=2.0 Hz, 1H), 7.27 (dd, J=8.3, 2.1 Hz, 1H), 6.92-6.83 (m, 2H), 6.25 (t, J=6.2 Hz, 1H), 4.45 (d, J=12.4 Hz, 2H), 3.94 (s, 3H), 3.93 (s, 3H), 3.45 (t, J=6.3 Hz, 2H), 3.08 (td, J=12.4, 2.4 Hz, 2H), 2.08-1.97 (m, 1H), 1.96 (d, J=13.7 Hz, 2H), 1.65 (qd, J=12.1, 3.9 Hz, 2H).

Compound 392 (Pyridine-2-carboxylic acid (1-pyrido[2,3-b]pyrazin-8-yl-piperidin-4-ylmethyl)-amide): From 8-Chloro-pyrido[2,3-b]pyrazine, 4-(boc-aminomethyl) piperidine and 2-picolinic acid. HPLC: 98.7% purity, RT=1.19 min. MS: m/z=349 [M+H]⁺. ¹H NMR (400 MHz, Chloroform-d, ppm) δ 8.99 (d, J=1.8 Hz, 1H), 8.74 (d, J=5.3 Hz, 1H), 8.62 (d, J=1.8 Hz, 1H), 8.59 (ddd, J=4.9, 1.8, 1.0 Hz, 1H), 7.80 (td, J=7.7, 1.7 Hz, 1H), 7.62 (dt, J=7.9, 1.1 Hz, 1H), 7.34 (ddd, J=7.6, 4.9, 1.2 Hz, 1H), 6.73 (t, J=6.1 Hz, 1H), 6.58 (d, J=5.4 Hz, 1H), 4.83 (d, J=12.8 Hz, 1H), 4.04 (d, J=13.5 Hz, 1H), 3.33 (td, J=6.5, 2.6 Hz, 2H), 3.09 (td, J=13.5, 2.7 Hz, 1H), 2.84 (td, J=12.9, 2.9 Hz, 1H), 2.07 (ddt, J=11.6, 8.3, 4.3 Hz, 1H), 2.00 (d, J=15.3 Hz, 1H), 1.83 (d, J=13.3 Hz, 1H), 1.47 (pd, J=12.3, 4.2 Hz, 2H).

Compound 394 (2-Dimethylamino-N-(1-pyrido[2,3-b]pyrazin-8-yl-piperidin-4-ylmethyl)-acetamide): From 8-Chloro-pyrido[2,3-b]pyrazine, 4-(boc-aminomethyl) piperidine and N,N-dimethylglycine. HPLC: >99% purity, RT=0.89 min. MS: n/z=329 [M+H]⁺. ¹H NMR (400 MHz, Chloroform-d, ppm) δ 8.95 (d, J=1.7 Hz, 1H), 8.79 (d, J=5.4 Hz, 1H), 8.72 (d, J=1.7 Hz, 1H), 7.32 (s, 1H), 6.87 (d, J=5.4 Hz, 1H), 4.43 (dt, J=12.8, 2.4 Hz, 2H), 3.28 (t, J=6.3 Hz, 2H), 3.06 (td, J=12.4, 2.4 Hz, 2H), 2.97 (s, 2H), 2.30 (s, 6H), 1.97-1.82 (m, 3H), 1.58 (dtd, J=13.3, 11.7, 3.8 Hz, 2H).

Compound 396 (3-Diethylamino-N-(1-pyrido[2,3-b]pyrazin-8-yl-piperidin-4-yl)-propionamide): From 8-Chloro-pyrido[2,3-b]pyrazine, 4-(n-boc-amino)piperidine and 3-(diethylamino)propanoic acid hydrochloride. HPLC: 90.1% purity, RT=1.02 min. MS: m/z=357 [M+H]⁺. ¹H NMR (400 MHz, Chloroform-d, ppm) δ 9.04 (s, 1H), 8.97 (d, J=1.7 Hz, 1H), 8.83 (d, J=5.3 Hz, 1H), 8.75 (d, J=1.7 Hz, 1H), 6.90 (d, J=5.4 Hz, 1H), 4.27 (dt, J=12.7, 3.1 Hz, 2H), 4.17-4.03 (m, 1H), 3.27 (ddd, J=13.0, 11.1, 2.7 Hz, 2H), 2.67 (t, J=5.9 Hz, 2H), 2.57 (q, J=7.1 Hz, 4H), 2.38 (t, J=5.8 Hz, 2H), 2.13 (dd, J=12.8, 3.7 Hz, 2H), 1.73 (qd, J=11.0, 3.8 Hz, 2H), 1.06 (t, J=7.1 Hz, 6H).

Compound 399 (3,3-Dimethyl-N-(1-pyrido[2,3-b]pyrazin-8-yl-piperidin-4-ylmethyl)-butyramide): From 8-Chloro-pyrido[2,3-b]pyrazine, 4-(boc-aminomethyl) piperidine and 3,3-dimethylbutyric acid. HPLC: 98.9% purity, RT=2.00 min. MS: m/z=342 [M+H]⁺. ¹H NMR (400 MHz, Chloroform-d, ppm) δ 8.95 (d, J=1.7 Hz, 1H), 8.80 (d, J=5.4 Hz, 1H), 8.72 (d, J=1.7 Hz, 1H), 6.87 (d, J=5.4 Hz, 1H), 5.51 (s, 1H), 4.43 (dt, J=11.0, 3.3 Hz, 2H), 3.24 (t, J=6.2 Hz, 2H), 3.07 (td, J=12.4, 2.3 Hz, 2H), 2.07 (s, 2H), 1.93-1.79 (m, 3H), 1.56 (qd, J=13.5, 12.9, 3.7 Hz, 3H), 1.05 (s, 9H).

Compound 400 (4-Piperidin-1-yl-1-(4-pyrido[2,3-b]pyrazin-8-yl-piperazin-1-yl)-butan-1-one): From 8-Chloro-pyrido[2,3-b]pyrazine, 1-boc-piperazine and 4-(piperidin-1-yl)butanoic acid hydrochloride. HPLC: >99% purity, RT=1.02 min. MS: n/z=369 [M+H]⁺. ¹H NMR (400 MHz, Chloroform-d, ppm) δ 9.00 (d, J=1.7 Hz, 1H), 8.86 (d, J=5.3 Hz, 1H), 8.76 (d, J=1.7 Hz, 1H), 6.87 (d, J=5.3 Hz, 1H), 3.96-3.79 (m, 5H), 3.83-3.66 (m, 4H), 2.51-2.27 (m, 8H), 1.87 (p, J=7.3 Hz, 2H), 1.57 (p, J=5.6 Hz, 4H), 1.50-1.37 (m, 2H).

Compound 402 (2-Azetidin-1-yl-N-(1-pyrido[2,3-b]pyrazin-8-yl-piperidin-4-ylmethyl)-acetamide): From 8-Chloro-pyrido[2,3-b]pyrazine, 4-(boc-aminomethyl) piperidine and 2-(azetidin-1-yl)acetic acid hydrochloride. HPLC: >99% purity, RT=0.94 min. MS: m/z=341 [M+H]⁺. ¹H NMR (400 MHz, Chloroform-d, ppm) δ 8.95 (d, J=1.7 Hz, 1H), 8.80 (d, J=5.3 Hz, 1H), 8.72 (d, J=1.7 Hz, 1H), 7.19 (s, 1H), 6.87 (d, J=5.4 Hz, 1H), 4.43 (d, J=12.5 Hz, 2H), 3.32 (t, J=7.1 Hz, 4H), 3.26 (t, J=6.3 Hz, 2H), 3.12 (s, 2H), 3.06 (td, J=12.4, 2.3 Hz, 2H), 2.10 (p, J=7.1 Hz, 2H), 1.96-1.78 (m, 3H), 1.58 (qd, J=13.3, 3.7 Hz, 2H).

Compound 405 (2-Diethylamino-N-methyl-N-(1-pyrido[2,3-b]pyrazin-8-yl-piperidin-4-ylmethyl)-acetamide): From 8-Chloro-pyrido[2,3-b]pyrazine, tert-butyl methyl(piperidin-4-ylmethyl)carbamate and 2-(diethylamino)acetic acid hydrochloride. HPLC: >99% purity, RT=1.07 min. MS:

m/z=371 [M+H]⁺. ¹H NMR (400 MHz, Chloroform-d, ppm) δ δ 8.94 (d, J=1.7 Hz, 1H), 8.79 (d, J=5.4 Hz, 1H), 8.72 (d, J=1.7 Hz, 1H), 6.87 (d, J=5.4 Hz, 1H), 4.41 (d, J=12.7 Hz, 2H), 3.34 (d, J=7.3 Hz, 2H), 3.28 (s, 2H), 3.16 (s, 3H), 3.08 (td, J=12.3, 2.6 Hz, 2H), 2.61 (q, J=7.4 Hz, 4H), 2.07 (ddtd, J=14.7, 11.1, 7.6, 4.0 Hz, 1H), 1.84-1.77 (m, 2H), 1.59 (qd, J=13.0, 12.5, 3.9 Hz, 2H), 1.05 (t, J=6.9 Hz, 6H).

Compound 408 (2-(Ethyl-methyl-amino)-N-(1-pyrido[2,3-b]pyrazin-8-yl-piperidin-4-ylmethyl)-acetamide): From 8-Chloro-pyrido[2,3-b]pyrazine, 4-(boc-aminomethyl)piperidine and [ethyl(methyl)amino]acetic acid. HPLC: 98.9% purity, RT=1.35 min. MS: m/z=343 [M+H]⁺. ¹H NMR (400 MHz, Chloroform-d, ppm) δ 8.94 (d, J=1.7 Hz, 1H), 8.79 (d, J=5.3 Hz, 1H), 8.72 (d, J=1.7 Hz, 1H), 7.43 (s, 1H), 6.87 (d, J=5.4 Hz, 1H), 4.44 (dt, J=12.4, 2.4 Hz, 2H), 3.27 (t, J=6.3 Hz, 2H), 3.07 (td, J=12.5, 2.4 Hz, 2H), 3.01 (s, 2H), 2.49 (q, J=7.2 Hz, 2H), 2.28 (s, 3H), 1.96-1.81 (m, 3H), 1.58 (qd, J=13.3, 3.7 Hz, 2H), 1.06 (t, J=7.1 Hz, 3H).

Compound 409 (N-[1-(8-Cyano-quinolin-5-yl)-piperidin-4-ylmethyl]-2-piperidin-1-yl-acetamide): From 5-bromo-quinoline-8-carbonitrile, 4-(boc-aminomethyl)piperidine and piperidin-1-yl-acetic acid. HPLC: 99.0% purity, RT=2.25 min. MS: m/z=392 [M+H]⁺. ¹H NMR (400 MHz, Chloroform-d, ppm) δ 9.05 (dd, J=4.2, 1.7 Hz, 1H), 8.41 (dd, J=8.5, 1.7 Hz, 1H), 8.01 (d, J=8.0 Hz, 1H), 7.47 (dd, J=8.5, 4.2 Hz, 2H), 7.04 (d, J=8.0 Hz, 1H), 3.50 (d, J=12.5 Hz, 2H), 3.33 (t, J=6.5 Hz, 2H), 2.99 (s, 2H), 2.86 (td, J=12.0, 2.3 Hz, 2H), 2.49 (s, 4H), 1.90 (d, J=12.7 Hz, 2H), 1.79 (dtt, J=14.0, 6.8, 3.9 Hz, 1H), 1.71-1.52 (m, 6H), 1.47 (s, 2H).

Compound 410 (N-[1-(8-Cyano-quinolin-5-yl)-piperidin-4-ylmethyl]-2-(ethyl-methyl-amino)-acetamide): From 5-bromo-quinoline-8-carbonitrile, 4-(boc-aminomethyl)piperidine and [ethyl(methyl)amino]acetic acid. HPLC: 95.9% purity, RT=2.09 min. MS: m/z=366 [M+H]⁺. ¹H NMR (400 MHz, Chloroform-d, ppm) δ 9.05 (dd, J=4.2, 1.7 Hz, 1H), 8.41 (dd, J=8.6, 1.7 Hz, 1H), 8.01 (d, J=8.0 Hz, 1H), 7.47 (dd, J=8.5, 4.2 Hz, 2H), 7.04 (d, J=8.0 Hz, 1H), 3.50 (d, J=12.3 Hz, 2H), 3.33 (t, J=6.5 Hz, 2H), 3.04 (s, 2H), 2.86 (td, J=12.0, 2.3 Hz, 2H), 2.52 (q, J=6.7 Hz, 2H), 2.32 (s, 3H), 1.91 (d, J=12.8 Hz, 2H), 1.79 (ddt, J=14.2, 6.9, 3.7 Hz, 1H), 1.62 (qd, J=12.0, 3.8 Hz, 2H), 1.09 (t, J=7.1 Hz, 3H).

Compound 411 (1-Methyl-pyrrolidine-2-carboxylic acid (1-pyrido[2,3-b]pyrazin-8-yl-piperidin-4-ylmethyl)-amide): From 8-Chloro-pyrido[2,3-b]pyrazine, 4-(boc-aminomethyl)piperidine and 1-methylpyrrolidine-2-carboxylic acid. HPLC: 99.7% purity, RT=1.02 min. MS: n/z=355 [M+H]⁺. ¹H NMR (400 MHz, Chloroform-d, ppm) δ 8.95 (d, J=1.7 Hz, 1H), 8.79 (d, J=5.4 Hz, 1H), 8.72 (d, J=1.7 Hz, 1H), 7.49 (s, 1H), 6.87 (d, J=5.4 Hz, 1H), 4.44 (d, J=12.6 Hz, 2H), 3.25 (td, J=6.5, 2.3 Hz, 2H), 3.17-2.99 (m, 3H), 2.91 (dd, J=10.1, 5.3 Hz, 1H), 2.42-2.31 (m, 4H), 2.31-2.17 (m, 1H), 1.99-1.65 (m, 6H), 1.65-1.48 (m, 2H).

Compound 412 (2-tert-Butoxy-N-[1-(8-cyano-quinolin-5-yl)-piperidin-4-ylmethyl]-acetamide): From 5-bromo-quinoline-8-carbonitrile, 4-(boc-aminomethyl)piperidine and tert-butoxy acetic acid. HPLC: >99% purity, RT=3.73 min. MS: m/z=381 [M+H]⁺. ¹H NMR (400 MHz, Chloroform-d, ppm) δ 9.05 (dd, J=4.2, 1.7 Hz, 1H), 8.41 (dd, J=8.5, 1.7 Hz, 1H), 8.01 (d, J=8.0 Hz, 1H), 7.47 (dd, J=8.5, 4.2 Hz, 1H), 7.04 (d, J=8.0 Hz, 1H), 6.81 (s, 1H), 3.92 (s, 2H), 3.50 (d, J=11.9 Hz, 2H), 3.34 (t, J=6.6 Hz, 2H), 2.85 (td, J=12.0, 2.3 Hz, 2H), 1.92 (d, J=13.4 Hz, 2H), 1.80 (dtt, J=14.3, 6.9, 3.8 Hz, 1H), 1.62 (qd, J=12.0, 3.8 Hz, 2H), 1.25 (s, 9H).

Compound 417 (2-Azetidin-1-yl-N-[1-(8-cyano-quinolin-5-yl)-piperidin-4-ylmethyl]-acetamide): From 5-bromo-quinoline-8-carbonitrile, 4-(boc-aminomethyl)piperidine and 2-(azetidin-1-yl)acetic acid hydrochloride. HPLC: >99% purity, RT=2.05 min. MS: m/z=364 [M+H]⁺. ¹H NMR (400 MHz, Chloroform-d, ppm) δ 9.05 (dd, J=4.2, 1.7 Hz, 1H), 8.41 (dd, J=8.5, 1.7 Hz, 1H), 8.01 (d, J=8.0 Hz, 1H), 7.47 (dd, J=8.5, 4.2 Hz, 1H), 7.21 (s, 1H), 7.04 (d, J=8.0 Hz, 1H), 3.50 (d, J=12.1 Hz, 2H), 3.43-3.20 (m, 6H), 3.14 (s, 2H), 2.85 (td, J=12.1, 2.3 Hz, 2H), 2.11 (p, J=7.0 Hz, 2H), 1.91 (d, J=12.9 Hz, 2H), 1.78 (dtt, J=14.3, 7.0, 3.8 Hz, 1H), 1.61 (qd, J=12.0, 3.9 Hz, 2H).

Compound 418 (1-Methyl-pyrrolidine-2-carboxylic acid [1-(8-cyano-quinolin-5-yl)-piperidin-4-ylmethyl]-amide): From 5-bromo-quinoline-8-carbonitrile, 4-(boc-aminomethyl)piperidine and 1-methylpyrrolidine-2-carboxylic acid. HPLC: >99% purity, RT=2.11 min. MS: m/z=378 [M+H]⁺. ¹H NMR (400 MHz, Chloroform-d, ppm) δ 9.04 (dd, J=4.2, 1.7 Hz, 1H), 8.40 (dd, J=8.5, 1.7 Hz, 1H), 8.00 (d, J=8.0 Hz, 1H), 7.58-7.49 (m, 1H), 7.47 (dd, J=8.5, 4.2 Hz, 1H), 7.04 (d, J=8.0 Hz, 1H), 3.50 (dt, J=12.2, 3.2 Hz, 2H), 3.30 (td, J=6.6, 2.0 Hz, 2H), 3.12 (ddd, J=9.0, 6.6, 1.9 Hz, 1H), 2.93 (dd, J=10.2, 5.3 Hz, 1H), 2.85 (tdd, J=12.0, 4.0, 2.3 Hz, 2H), 2.45-2.33 (m, 4H), 2.26 (ddt, J=12.7, 9.8, 8.5 Hz, 1H), 1.96-1.87 (m, 2H), 1.86-1.69 (m, 4H), 1.67-1.53 (m, 2H).

Example 8: Synthesis of Compound 9 ((3R,5S)-1-(1,2-dimethyl-H-pyrrolo[2,3-b]pyridin-4-yl)-5-methylpiperidin-3-amine)

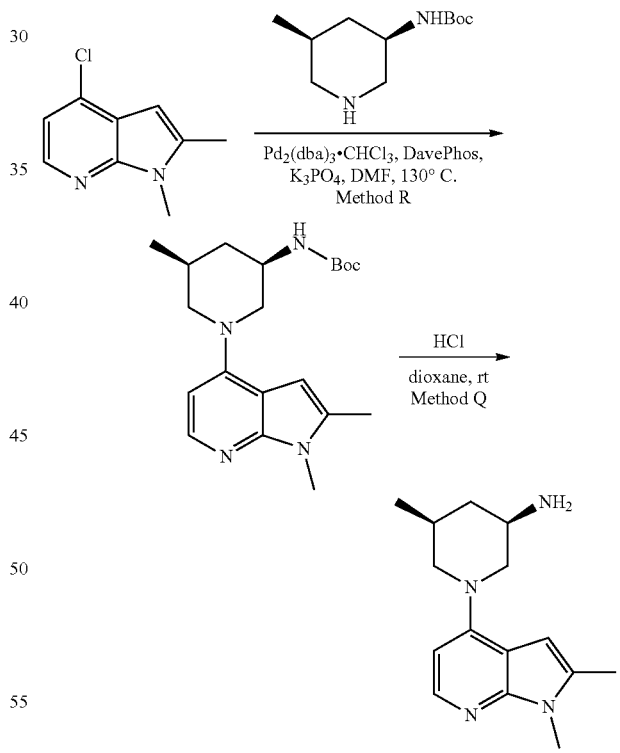

Method R tert-Butyl (3R,5S)-1-(1,2-dimethyl-1H-pyrrolo[2,3-b]pyridin-4-yl)-5-methylpiperidin-3-ylcarbamate: To a solution of 4-chloro-1,2-dimethyl-1H-pyrrolo[2,3-b]pyridine (200 mg, 1.11 mmol) in N,N-dimethylformamide (10 mL) was added tert-butyl N-[(3R,5S)-5-methylpiperidin-3-yl] carbamate (237 mg, 1.11 mmol), Pd₂(dba)₃.CHCl₃ (115 mg, 0.11 mmol), DavePhos (87 mg, 0.22 mmol) and K₃PO₄ (588 mg, 2.77 mmol) at room temperature. The resulting mixture was stirred for 2 h at 130° C. After cooling to room temperature, the reaction mixture was diluted with water (10 mL). The resulting mixture was extracted with ethyl acetate (50 mL×3), and the organic phases were combined, washed with brine and dried over $Na_2SO_4$. The solvent was removed under reduced pressure and the residue was purified by flash chromatography eluting with EtOAc in petroleum ether (0% to 2% gradient) to yield tert-butyl N-[(3R,5S)-1-[1,2-dimethyl-1H-pyrrolo[2,3-b]pyridin-4-yl]-5-methylpiperidin-3-yl]carbamate as yellow solid (150 mg, 38%). MS: n/z=359.1 [M+H]+.

(Note: The catalyst in Method R may be $Pd_2(dppf)C_{1-2}.CHCl_3$) instead of $Pd_2(dba)_3.CHCl_3$ (3R,5S)-1-(1,2-dimethyl-1H-pyrrolo[2,3-b]pyridin-4-yl)-5-methylpiperidin-3-amine: (3R,5S)-1-(1,2-dimethyl-1H-pyrrolo[2,3-b]pyridin-4-yl)-5-methylpiperidin-3-amine was prepared from tert-butyl (3R,5S)-1-(1,2-dimethyl-1H-pyrrolo[2,3-b]pyridin-4-yl)-5-methylpiperidin-3-ylcarbamate using Method Q. The crude product was purified by prep-HPLC under the following conditions: Column, XBridge C18 OBD Prep Column, 5 um, 19 mm×250 mm; Mobile phase, methanol in water (with 10 mmol/L $NH_4HCO_3$), 3% to 65% gradient in 8 min; Detector, UV 254 nm. (3R,5S)-1-[1,2-dimethyl-1H-pyrrolo[2,3-b]pyridin-4-yl]-5-methylpiperidin-3-amine was obtained as off-white solid (30 mg, 26%).

Compound 9: HPLC: 97.8% purity, RT=0.91 min. MS: m/z=259.1 [M+H]+. 1H NMR (400 MHz, CD3OD, ppm) δ 7.91 (d, J=5.7 Hz, 1H), 6.49 (d, J=5.7 Hz, 1H), 6.30 (d, J=1.2 Hz, 1H), 4.22-4.12 (m, 1H), 4.00-3.91 (m, 1H), 3.71 (s, 3H), 3.11-3.00 (m, 1H), 2.63-2.41 (m, 5H), 2.17-2.07 (m, 1H), 2.00-1.80 (m, 1H), 1.10-0.96 (m, 4H).

Example 9: Synthesis of Compound 10 ((3R,5S)-1-(1,2-dimethyl-1H-pyrrolo[2,3-b]pyridin-4-yl)-5-methylpiperidin-3-amine)

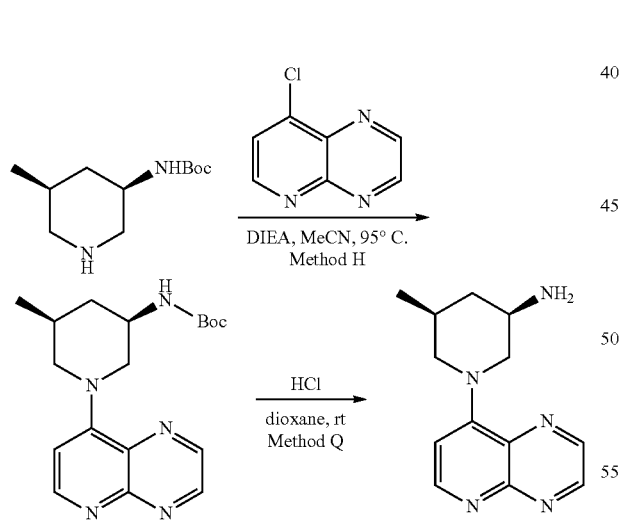

(3R,5S)-5-methyl-1-(pyrido[2,3-b]pyrazin-8-yl)piperidin-3-amine: (3R,5S)-5-methyl-1-(pyrido[2,3-b]pyrazin-8-yl)piperidin-3-amine was prepared from tert-butyl (3R,5S)-5-methylpiperidin-3-ylcarbamate and 8-chloropyrido[2,3-b]pyrazine using Method H and Q. The crude product was purified by prep-HPLC under the following conditions: Column, XBridge C18 OBD Prep Column, 5 um, 19 mm×250 mm; Mobile phase, acetonitrile in water (with 10 mmol/L $NH_4HCO_3$), 3% to 22% gradient in 9 min; Detector, UV 254 nm. (3R,5S)-5-methyl-1-[pyrido[2,3-b]pyrazin-8-yl]piperidin-3-amine was obtained as yellow syrup (20 mg, 10% for 2 steps).

Compound 10: HPLC: 94.1% purity, RT=1.10 min. MS: n/z=244.0 [M+H]+. 1H NMR (400 MHz, CD3OD, ppm) δ 8.93 (d, J=1.8 Hz, 1H), 8.82 (d, J=1.8 Hz, 1H), 8.65 (d, J=5.6 Hz, 1H), 7.06 (d, J=5.7 Hz, 1H), 4.78-4.68 (m, 1H), 4.56-4.46 (m, 1H), 3.12-2.98 (m, 1H), 2.80-2.60 (m, 2H), 2.19-2.08 (m, 1H), 2.08-1.88 (m, 1H), 1.18-0.89 (m, 4H).

The following compounds were synthesized in an analogous manner:

Compound 11 ((3R,5S)-5-methyl-1-(quinolin-4-yl)piperidin-3-amine): From tert-butyl (3R,5S)-5-methylpiperidin-3-ylcarbamate and 4-chloroquinoline. HPLC: 99.9% purity, RT=0.86 min. MS: m/z=242.1 [M+H]+. 1H NMR (400 MHz, CD3OD, ppm) δ 8.64 (d, J=5.2 Hz, 1H), 8.11-8.04 (m, 1H), 8.00-7.93 (m, 1H), 7.78-7.68 (m, 1H), 7.63-7.53 (m, 1H), 7.04 (d, J=5.2 Hz, 1H), 3.83-3.74 (m, 1H), 3.64-3.55 (m, 1H), 3.35-3.20 (m, 1H), 2.60-2.40 (m, 2H), 2.24-2.07 (m, 2H), 1.13-0.99 (m, 4H).

Compound 12 (8-((3R,5S)-3-amino-5-methylpiperidin-1-yl)quinoxaline-5-carbonitrile): From 8-chloroquinoxaline-5-carbonitrile and tert-butyl (3R,5S)-5-methylpiperidin-3-ylcarbamate. HPLC: 98.3% purity, RT=1.20 min. MS: m/z=268.0 [M+H]+. 1H NMR (300 MHz, CDCl3, ppm) δ 8.96 (s, 1H), 8.91 (s, 1H), 8.12 (d, J=8.5 Hz, 1H), 7.24 (d, J=8.5 Hz, 1H), 4.50-4.38 (m, 1H), 4.22-4.08 (m, 1H), 3.34-3.15 (m, 1H), 2.80-2.55 (m, 2H), 2.30-1.95 (m, 2H), 1.20-1.00 (m, 4H).

Example 10: Synthesis of Compound 13 (N-((3R,5S)-1-(1,2-dimethyl-1H-pyrrolo[2,3-b]pyridin-4-yl)-5-methylpiperidin-3-yl)-2-hydroxyacetamide)

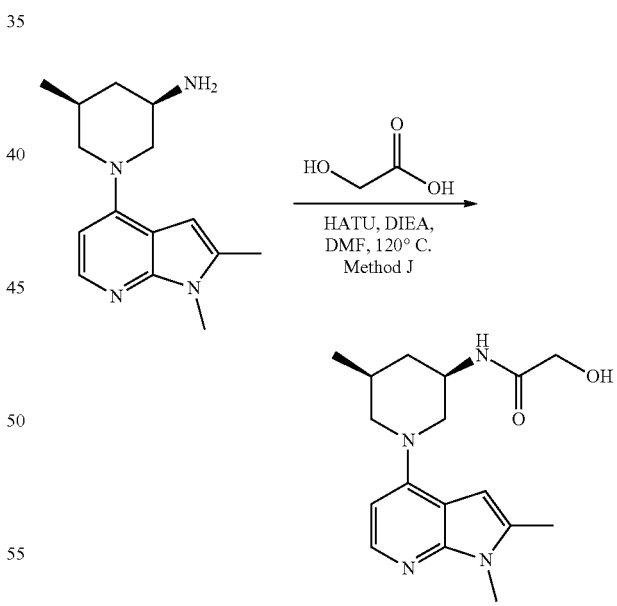

N-((3R,5S)-1-(1,2-dimethyl-1H-pyrrolo[2,3-b]pyridin-4-yl)-5-methylpiperidin-3-yl)-2-hydroxyacetamide: N-((3R,5S)-1-(1,2-dimethyl-1H-pyrrolo[2,3-b]pyridin-4-yl)-5-methylpiperidin-3-yl)-2-hydroxyacetamide was prepared from (3R,5S)-1-(1,2-dimethyl-1H-pyrrolo[2,3-b]pyridin-4-yl)-5-methylpiperidin-3-amine and 2-hydroxyacetic acid using Method J. The crude product was purified by prep-HPLC under the following conditions: Column, XBridge C18 OBD Prep Column, 5 um, 19 mm×150 mm; Mobile phase, acetonitrile in water (with 10 mmol/L NH$_4$HCO$_3$), 3% to 75% gradient in 8 min; Detector, UV 254 nm. N-[(3R,5S)-1-[1,2-dimethyl-1H-pyrrolo[2,3-b]pyridin-4-yl]-5-methylpiperidin-3-yl]-2-hydroxyacetamide was obtained as white solid (30 mg, 17%).

Compound 13: HPLC: 96.9% purity, RT=0.67 min. MS: m/z=317.1 [M+H]$^+$. $^1$H NMR (400 MHz, DMSO-d$_6$, ppm) δ 7.81 (d, J=5.4 Hz, 1H), 7.61 (d, J=7.9 Hz, 1H), 6.35 (d, J=5.5 Hz, 1H), 6.20 (s, 1H), 5.42 (s, 1H), 4.00-3.91 (m, 1H), 3.88-3.74 (m, 4H), 3.57 (s, 3H), 2.51 (d, J=11.5 Hz, 1H), 2.47-2.28 (m, 3H), 1.90-1.60 (m, 2H), 1.28-1.10 (m, 1H), 0.86 (d, J=6.5 Hz, 3H).

The following compounds were synthesized in an analogous manner:

Compound 14 (2-hydroxy-N-((3R,5S)-5-methyl-1-(quinolin-4-yl)piperidin-3-yl)acetamide): From (3R,5S)-5-methyl-1-(quinolin-4-yl)piperidin-3-amine and 2-hydroxyacetic acid. HPLC: 98.3% purity, RT=1.04 min. MS: m/z=300.2 [M+H]$^+$. $^1$H NMR (400 MHz, CD$_3$OD, ppm) δ 8.62 (d, J=5.2 Hz, 1H), 8.15 (dd, J=8.3, 1.4 Hz, 1H), 7.96 (dd, J=8.4, 1.2 Hz, 1H), 7.78-7.68 (m, 1H), 7.64-7.54 (m, 1H), 7.05 (d, J=5.3 Hz, 1H), 4.38-4.26 (m, 1H), 4.01 (s, 2H), 3.90-3.81 (m, 1H), 3.64 (d, J=12.3 Hz, 1H), 2.70-2.50 (m, 2H), 2.19-2.10 (m, 2H), 1.37-1.25 (m, 1H), 1.07 (d, J=6.4 Hz, 3H).

Compound 15 (2-hydroxy-N-((3R,5S)-5-methyl-1-(pyrido[2,3-b]pyrazin-8-yl)piperidin-3-yl)acetamide): From (3R,5S)-5-methyl-1-(pyrido[2,3-b]pyrazin-8-yl)piperidin-3-amine and 2-hydroxyacetic acid. HPLC: 95.3% purity, RT=0.73 min. MS: m/z=302.0 [M+H]$^+$. $^1$H NMR (400 MHz, CD$_3$OD, ppm) δ 8.92 (d, J=1.8 Hz, 1H), 8.80 (d, J=1.7 Hz, 1H), 8.65 (d, J=5.7 Hz, 1H), 7.13 (d, J=5.6 Hz, 1H), 4.72-4.56 (m, 2H), 4.20-4.08 (m, 1H), 3.99 (s, 2H), 3.05-2.95 (m, 1H), 2.83-2.73 (m, 1H), 2.14-1.94 (m, 2H), 1.45-1.25 (m, 1H), 1.02 (d, J=6.6 Hz, 3H).

Compound 20 ((S)—N-((3R,5S)-1-(8-cyanoquinoxalin-5-yl)-5-methylpiperidin-3-yl)-2-hydroxy-3-methylbutanamide): From 8-((3R,5S)-3-amino-5-methylpiperidin-1-yl)quinoxaline-5-carbonitrile and (S)-2-hydroxy-3-methylbutanoic acid. HPLC: 98.4% purity, RT=3.24 min. MS: m/z=368.1 [M+H]$^+$. $^1$H NMR (300 MHz, DMSO-d$_6$, ppm) δ 9.03 (d, J=1.8 Hz, 1H), 8.93 (d, J=1.8 Hz, 1H), 8.20 (d, J=8.4 Hz, 1H), 7.70 (d, J=8.0 Hz, 1H), 7.27 (d, J=8.5 Hz, 1H), 5.32 (d, J=5.7 Hz, 1H), 4.30 (d, J=13.2 Hz, 1H), 4.17 (d, J=11.8 Hz, 1H), 4.05-3.85 (m, 1H), 3.66 (dd, J=5.8, 4.0 Hz, 1H), 2.94-2.84 (m, 1H), 2.73-2.63 (m, 1H), 2.03-1.86 (m, 3H), 1.40-1.20 (m, 1H), 0.95-0.85 (m, 6H), 0.78 (d, J=6.8 Hz, 3H).

Compound 21 (((R)—N-((3R,5S)-1-(8-cyanoquinoxalin-5-yl)-5-methylpiperidin-3-yl)-2-hydroxy-3-methylbutanamide): From 8-((3R,5S)-3-amino-5-methylpiperidin-1-yl)quinoxaline-5-carbonitrile and (R)-2-hydroxy-3-methylbutanoic acid. HPLC: 97.6% purity, RT=1.31 min. MS: m/z=368.3 [M+H]$^+$. $^1$H NMR (300 MHz, DMSO-d$_6$, ppm) δ 9.03 (d, J=1.7 Hz, 1H), 8.94 (d, J=1.7 Hz, 1H), 8.19 (d, J=8.4 Hz, 1H), 7.69 (d, J=8.1 Hz, 1H), 7.26 (d, J=8.5 Hz, 1H), 5.34 (d, J=5.6 Hz, 1H), 4.30-4.15 (m, 2H), 4.05-3.90 (m, 1H), 3.68 (dd, J=5.6, 3.9 Hz, 1H), 2.98-2.88 (m, 1H), 2.75-2.60 (m, 1H), 2.02-1.85 (m, 3H), 1.40-1.20 (m, 1H), 0.96-0.85 (m, 6H), 0.78 (d, J=6.8 Hz, 3H).

Compound 22 ((S)-2-hydroxy-3-methyl-N-((3R,5S)-5-methyl-1-(pyrido[2,3-b]pyrazin-8-yl)piperidin-3-yl)butanamide): From (3R,5S)-5-methyl-1-(pyrido[2,3-b]pyrazin-8-yl)piperidin-3-amine and (S)-2-hydroxy-3-methylbutanoic acid. HPLC: 96.8% purity, RT=1.05 min. MS: m/z=344.0 [M+H]$^+$. $^1$H NMR (400 MHz, CD$_3$OD, ppm) δ 8.95 (d, J=1.8 Hz, 1H), 8.82 (d, J=1.7 Hz, 1H), 8.68 (d, J=5.6 Hz, 1H), 7.17 (d, J=5.7 Hz, 1H), 4.71-4.60 (m, 2H), 4.18-4.08 (m, 1H), 3.87 (s, 1H), 3.05-2.94 (m, 1H), 2.87-2.76 (m, 1H), 2.15-1.95 (m, 3H), 1.50-1.30 (m, 1H), 1.09-0.99 (m, 6H), 0.91 (d, J=6.8 Hz, 3H).

Compound 23 ((R)-2-hydroxy-3-methyl-N-((3R,5S)-5-methyl-1-(pyrido[2,3-b]pyrazin-8-yl)piperidin-3-yl)butanamide): From (3R,5S)-5-methyl-1-(pyrido[2,3-b]pyrazin-8-yl)piperidin-3-amine and (R)-2-hydroxy-3-methylbutanoic acid. HPLC: 96.9% purity, RT=1.02 min. MS: m/z=344.2 [M+H]$^+$. $^1$H NMR (400 MHz, CD$_3$OD, ppm) δ 8.95 (d, J=1.8 Hz, 1H), 8.83 (d, J=1.8 Hz, 1H), 8.68 (d, J=5.6 Hz, 1H), 7.16 (d, J=5.7 Hz, 1H), 4.58-4.72 (m, 2H), 4.20-4.10 (m, 1H), 3.89 (m, 1H), 3.06-2.96 (m, 1H), 2.86-2.75 (m, 1H), 2.15-1.95 (m, 3H), 1.42-1.30 (m, 1H), 1.10-1.00 (m, 6H), 0.90 (d, J=6.8 Hz, 3H).

Compound 32 (N-((3R,5S)-1-(8-cyanoquinoxalin-5-yl)-5-methylpiperidin-3-yl)-2-(dimethylamino)acetamide): From 8-((3R,5S)-3-amino-5-methylpiperidin-1-yl)quinoxaline-5-carbonitrile and 2-(dimethylamino)acetic acid. HPLC: 96.9% purity, RT=1.25 min. MS: m/z=353.2 [M+H]$^+$. $^1$H NMR (300 MHz, DMSO-d, ppm) δ 9.03 (d, J=1.7 Hz, 1H), 8.94 (d, J=1.7 Hz, 1H), 8.19 (d, J=8.4 Hz, 1H), 7.75 (d, J=8.1 Hz, 1H), 7.27 (d, J=8.5 Hz, 1H), 4.33-4.13 (m, 2H), 4.05-3.88 (m, 1H), 2.97-2.79 (m, 3H), 2.72-2.60 (m, 1H), 2.21 (s, 6H), 1.98-1.82 (m, 2H), 1.34-1.20 (m, 1H), 0.92 (d, J=6.2 Hz, 3H).

Compound 33 (2-(dimethylamino)-N-((3R,5S)-5-methyl-1-(pyrido[2,3-b]pyrazin-8-yl)piperidin-3-yl)acetamide): From (3R,5S)-5-methyl-1-(pyrido[2,3-b]pyrazin-8-yl)piperidin-3-amine and 2-(dimethylamino)acetic acid. HPLC: 99.6% purity, RT=1.31 min. MS: m/z=329.0 [M+H]$^+$. $^1$H NMR (400 MHz, CD$_3$OD, ppm) δ 8.94 (d, J=1.7 Hz, 1H), 8.82 (d, J=1.7 Hz, 1H), 8.67 (d, J=5.6 Hz, 1H), 7.16 (d, J=5.6 Hz, 1H), 4.74-4.59 (m, 3H), 4.20-4.04 (m, 1H), 3.10-2.89 (m, 3H), 2.83-2.73 (m, 1H), 2.34 (s, 6H), 2.16-1.93 (m, 2H), 1.40-1.28 (m, 1H), 1.04 (d, J=6.6 Hz, 3H).

Compound 36 (N-((3R,5S)-1-(8-cyanoquinoxalin-5-yl)-5-methylpiperidin-3-yl)-3-methyloxetane-3-carboxamide): From 8-chloroquinoxaline-5-carbonitrile, tert-butyl (3R,5S)-5-methylpiperidin-3-ylcarbamate and 3-methyloxetane-3-carboxylic acid. HPLC: 99.2% purity, RT=1.15 min. MS: m/z=366.0 [M+H]$^+$. $^1$H NMR (300 MHz, CD$_3$OD, ppm) δ 8.89 (d, J=1.7 Hz, 1H), 8.86 (d, J=1.8 Hz, 1H), 8.05 (d, J=8.4 Hz, 1H), 7.25 (d, J=8.4 Hz, 1H), 4.95-4.85 (m, 2H), 4.41-4.02 (m, 5H), 2.80-2.55 (m, 2H), 2.12-1.93 (m, 2H), 1.57 (s, 3H), 1.31-1.12 (m, 1H), 0.98 (d, J=6.4 Hz, 3H).

Compound 37 (3-methyl-N-((3R,5S)-5-methyl-1-(pyrido[2,3-b]pyrazin-8-yl)piperidin-3-yl)oxetane-3-carboxamide): From (3R,5S)-5-methyl-1-(pyrido[2,3-b]pyrazin-8-yl)piperidin-3-amine and 3-methyloxetane-3-carboxylic acid. HPLC: 99.8% purity, RT=0.88 min. MS: m/z=342.2 [M+H]$^+$. $^1$H NMR (400 MHz, CD$_3$OD, ppm) δ 8.92 (d, J=1.7 Hz, 1H), 8.81 (d, J=1.7 Hz, 1H), 8.66 (d, J=5.6 Hz, 1H), 7.16 (d, J=5.6 Hz, 1H), 4.90-4.80 (m, 2H), 4.73-4.61 (m, 2H), 4.39 (d, J=6.1 Hz, 2H), 4.15-4.03 (m, 1H), 2.91-2.71 (m, 2H), 2.12-1.92 (m, 2H), 1.60 (s, 3H), 1.34-1.22 (m, 1H), 1.01 (d, J=6.6 Hz, 3H).

Compound 40 (N-((3R,5S)-1-(8-cyanoquinoxalin-5-yl)-5-methylpiperidin-3-yl)-3,3-dimethylbutanamide): From 8-((3R,5S)-3-amino-5-methylpiperidin-1-yl)quinoxaline-5-carbonitrile and 3,3-dimethylbutanoic acid. HPLC: 95.2% purity, RT=3.11 min. MS: m/z=366.1 [M+H]$^+$. $^1$H NMR (300 MHz, DMSO-d$_6$, ppm) δ 9.02 (d, J=1.7 Hz, 1H), 8.93 (d, J=1.7 Hz, 1H), 8.20 (d, J=8.4 Hz, 1H), 7.79 (d, J=7.4 Hz, 1H), 7.28 (d, J=8.5 Hz, 1H), 4.38-4.19 (m, 2H), 3.99-3.84 (m, 1H), 2.79-2.63 (m, 2H), 2.00-1.80 (s, 4H), 1.24-1.10 (m, 1H), 1.02-0.87 (m, 12H).

Compound 41 (3,3-dimethyl-N-((3R,5S)-5-methyl-1-(pyrido[2,3-b]pyrazin-8-yl)piperidin-3-yl)butanamide): From (3R,5S)-5-methyl-1-(pyrido[2,3-b]pyrazin-8-yl)piperidin-3-amine and 3,3-dimethylbutanoic acid. HPLC: 94.8% purity, RT=0.96 min. MS: m/z=342.2 [M+H]$^+$. $^1$H NMR (300 MHz, DMSO-d$_6$, ppm) δ 9.00 (d, J=1.7 Hz, 1H), 8.83 (d, J=1.7 Hz, 1H), 8.71 (d, J=5.5 Hz, 1H), 7.82 (d, J=7.5 Hz, 1H), 7.16 (d, J=5.6 Hz, 1H), 4.59 (d, J=13.1 Hz, 1H), 4.46 (d, J=12.6 Hz, 1H), 3.94-3.80 (m, 1H), 2.82-2.68 (m, 2H), 2.00-1.85 (m, 4H), 1.31-1.18 (m, 1H), 1.00-0.80 (m, 12H).

Compound 97 (N-[(3R,5S)-1-(8-cyanoquinoxalin-5-yl)-5-methylpiperidin-3-yl]-2-hydroxyacetamide): From 8-((3R,5S)-3-amino-5-methylpiperidin-1-yl)quinoxaline-5-carbonitrile and 2-hydroxyacetic acid. HPLC: 97.5% purity, RT=1.35 min. MS: m/z=326.1 [M+H]$^+$. $^1$H NMR (400 MHz, CD$_3$OD, ppm) δ 9.05-8.83 (m, 2H), 8.10 (d, J=8.4 Hz, 1H), 7.28 (d, J=8.4 Hz, 1H), 4.34 (dd, J=12.0, 4.3 Hz, 1H), 4.29-4.17 (m, 2H), 4.02 (s, 2H), 2.99-2.87 (m, 1H), 2.72 (t, J=11.6 Hz, 1H), 2.16-2.00 (m, 2H), 1.42-1.30 (m, 1H), 1.04 (d, J=6.4 Hz, 3H).

Compound 108 (N-[(3R,5S)-1-(8-cyanoquinoxalin-5-yl)-5-methylpiperidin-3-yl]-2-(morpholin-4-yl)acetamide): From (3R,5S)-5-methyl-1-(pyrido[2,3-b]pyrazin-8-yl)piperidin-3-amine and (R)-2-(tert-butoxycarbonylamino)-3-hydroxypropanoic acid. HPLC: 98.7% purity, RT=1.95 min. MS: m/z=395.1 [M+H]$^+$. $^1$H NMR (400 MHz, CD$_3$OD, ppm) δ 8.95-8.83 (m, 2H), 8.10 (d, J=12.0 Hz, 1H), 7.28 (d, J=12.0 Hz, 1H), 4.37-4.13 (m, 3H), 3.78-3.68 (m, 4H), 3.05 (s, 2H), 2.92-2.78 (m, 1H), 2.75-2.65 (m, 1H), 2.58-2.48 (m, 4H), 2.15-1.95 (m, 2H), 1.38-1.20 (m, 1H), 1.02 (d, J=12.0 Hz, 3H).

Compound 109 (N-[(3R,5S)-1-(8-cyanoquinoxalin-5-yl)-5-methylpiperidin-3-yl]-2-(4-methylpiperazin-1-yl)acetamide): From 8-((3R,5S)-3-amino-5-methylpiperidin-1-yl)quinoxaline-5-carbonitrile and 2-(4-methylpiperazin-1-yl)acetic acid. HPLC: 99.8% purity, RT=1.47 min. MS: m/z=408.2 [M+H]$^+$. $^1$H NMR (400 MHz, CD$_3$OD, ppm) δ 8.99-8.85 m, 2H), 8.10 (d, J=8.4 Hz, 1H), 7.29 (d, J=8.4 Hz, 1H), 4.41-4.12 (m, 3H), 3.14-3.01 (m, 2H), 2.86 (dd, J=11.9, 10.6 Hz, 1H), 2.72 (dd, J=12.6, 10.8 Hz, 1H), 2.60-2.40 (m, 7H), 2.32 (s, 3H), 2.09 (t, J=14.0 Hz, 2H), 1.36-1.24 (m, 1H), 1.04 (d, J=6.4 Hz, 3H).

Compound 110 (N-[(3R,5S)-5-methyl-1-[pyrido[2,3-b]pyrazin-8-yl]piperidin-3-yl]-2-(morpholin-4-yl)acetamide): From (3R,5S)-5-methyl-1-(pyrido[2,3-b]pyrazin-8-yl)piperidin-3-amine and 2-morpholinoacetic acid. HPLC: 96.5% purity, RT=1.31 min. MS: m/z=371.3 [M+H]$^+$. $^1$H NMR (400 MHz, CD$_3$OD, ppm) δ 8.89 (d, J=1.7 Hz, 1H), 8.77 (d, J=1.7 Hz, 1H), 8.63 (d, J=5.6 Hz, 1H), 7.11 (d, J=5.7 Hz, 1H), 4.70-4.55 (m, 2H), 4.08 (t, J=11.4 Hz, 1H), 3.74-3.65 (m, 4H), 3.11-2.84 (m, 3H), 2.75 (dd, J=12.9, 11.1 Hz, 1H), 2.52-2.49 (m, 4H), 2.08-1.94 (m, 2H), 1.40-1.20 (m, 1H), 0.99 (d, J=6.5 Hz, 3H).

Compound 111 (N-[(3R,5S)-1-(8-cyanoquinoxalin-5-yl)-5-methylpiperidin-3-yl]-3,3,3-trifluoropropanamide): From 8-((3R,5S)-3-amino-5-methylpiperidin-1-yl)quinoxaline-5-carbonitrile and 3,3,3-trifluoropropionic acid. HPLC: 91.5% purity, RT=1.38 min. MS: m/z=378.2 [M+H]$^+$. $^1$H NMR (400 MHz, CD$_3$OD, ppm) δ 8.93-8.80 (m, 2H), 8.06 (d, J=8.4 Hz, 1H), 7.24 (d, J=8.4 Hz, 1H), 4.44-4.30 (m, 1H), 4.29-4.03 (m, 2H), 3.14 (q, J=10.7 Hz, 2H), 2.68 (dt, J=23.6, 11.6 Hz, 2H), 2.14-1.93 (m, 2H), 1.21-1.16 (m, 1H), 0.98 (d, J=6.4 Hz, 3H).

Compound 120 (3,3,3-trifluoro-N-[(3R,5S)-5-methyl-1-[pyrido[2,3-b]pyrazin-8-yl]piperidin-3-yl]propanamide): From (3R,5S)-5-methyl-1-(pyrido[2,3-b]pyrazin-8-yl)piperidin-3-amine and 3,3,3-trifluoropropionic acid. HPLC: 95.3% purity, RT=1.07 min. MS: m/z=354.2 [M+H]$^+$. $^1$H NMR (300 MHz, CD$_3$OD, ppm) δ 8.90 (d, J=1.7 Hz, 1H), 8.78 (d, J=1.7 Hz, 1H), 8.63 (d, J=5.6 Hz, 1H), 7.11 (d, J=5.7 Hz, 1H), 4.75-4.56 (m, 2H), 4.15-3.98 (m, 1H), 3.15 (q, J=10.7 Hz, 2H), 2.85-2.65 (m, 2H), 2.15-1.85 (m, 2H), 1.22 (td, J=12.0, 12.0 Hz, 1H), 0.99 (d, J=6.5 Hz, 3H).

Compound 130 (N-[(3R,5S)-1-(8-cyanoquinoxalin-5-yl)-5-methylpiperidin-3-yl]-2-(1H-imidazol-4-yl)acetamide hydrochloride): From 2-(1H-imidazol-4-yl)acetic acid and 8-((3R,5S)-3-amino-5-methylpiperidin-1-yl)quinoxaline-5-carbonitrile. HPLC: 99.0% purity, RT=1.05 min. MS: m/z=367.2 [M+H]$^+$. $^1$H NMR (300 MHz, CD$_3$OD, ppm) δ 8.98-8.85 (m, 3H), 8.11 (d, J=8.4 Hz, 1H), 7.45 (s, 1H), 7.32 (d, J=8.4 Hz, 1H), 4.42 (d, J=13.3 Hz, 1H), 4.30 (d, J=12.7 Hz, 1H), 4.23-4.12 (m, 1H), 3.78 (br s, 2H), 2.85-2.65 (m, 2H), 2.20-1.95 (m, 2H), 1.27 (td, J=11.9, 11.9 Hz, 1H), 1.15-0.95 (m, 3H).

Compound 131 (2-(1H-imidazol-4-yl)-N-[(3R,5S)-5-methyl-1-[pyrido[2,3-b]pyrazin-8-yl]piperidin-3-yl]acetamide): From 2-(1H-imidazol-4-yl)acetic acid and (3R,5S)-5-methyl-1-(pyrido[2,3-b]pyrazin-8-yl)piperidin-3-amine. HPLC: 99.2% purity, RT=0.79 min. MS: m/z=352.2 [M+H]$^+$. $^1$H NMR (400 MHz, CD$_3$OD, ppm) δ 8.91 (d, J=1.7 Hz, 1H), 8.79 (d, J=1.8 Hz, 1H), 8.64 (d, J=5.6 Hz, 1H), 7.62 (d, J=1.2 Hz, 1H), 7.14 (d, J=5.6 Hz, 1H), 6.96 (s, 1H), 4.72-4.63 (m, 2H), 4.12-4.00 (m, 1H), 3.52 (br s, 2H), 2.90-2.70 (m, 2H), 2.15-1.85 (m, 2H), 1.26 (td, J=12.0, 12.0 Hz, 1H), 1.00 (d, J=6.6 Hz, 3H).

Compound 132 (N-[(3R,5S)-1-(8-cyanoquinoxalin-5-yl)-5-methylpiperidin-3-yl]-2-(1-methyl-1H-imidazol-4-yl)acetamide): From 2-(1-methyl-1H-imidazol-4-yl)acetic acid and 8-((3R,5S)-3-amino-5-methylpiperidin-1-yl)quinoxaline-5-carbonitrile. HPLC: 96.2% purity, RT=1.39 min. MS: m/z=390.1 [M+H]$^+$. $^1$H NMR (400 MHz, CD$_3$OD, ppm) δ 8.99-8.82 (m, 2H), 8.09 (d, J=8.4 Hz, 1H), 7.55 (d, J=1.3 Hz, 1H), 7.29 (d, J=8.4 Hz, 1H), 7.01-6.95 (m, 1H), 4.44-4.28 (m, 2H), 4.20-4.08 (m, 1H), 3.71 (s, 3H), 3.48 (br s, 2H), 2.84-2.63 (m, 2H), 2.16-1.95 (m, 2H), 1.33-1.11 (m, 1H), 1.02 (d, J=6.5 Hz, 3H).

Compound 133 (N-[(3R,5S)-5-methyl-1-[pyrido[2,3-b]pyrazin-8-yl]piperidin-3-yl]-2-(1-methyl-1H-imidazol-4-yl)acetamide): From 2-(1-methyl-H-imidazol-4-yl)acetic acid and (3R,5S)-5-methyl-1-(pyrido[2,3-b]pyrazin-8-yl)piperidin-3-amine. HPLC: 95.9% purity, RT=0.84 min. MS: n/z=366.2 [M+H]$^+$. $^1$H NMR (400 MHz, CD$_3$OD, ppm) δ 8.91 (s, 1H), 8.78 (s, 1H), 8.63 (d, J=5.6 Hz, 1H), 7.53 (s, 1H), 7.13 (d, J=5.6 Hz, 1H), 6.96 (s, 1H), 4.77-4.57 (m, 2H), 4.13-3.99 (m, 1H), 3.69 (s, 3H), 3.47 (s, 2H), 2.90-2.70 (m, 2H), 2.15-1.85 (m, 1H), 1.26 (td, J=12.0, 12.0 Hz, 1H), 0.99 (d, J=6.6 Hz, 3H).

Compound 134 (N-[(3R,5S)-1-(8-cyanoquinoxalin-5-yl)-5-methylpiperidin-3-yl]-2-methoxyacetamide): From 2-methoxyacetic acid and 8-((3R,5S)-3-amino-5-methylpiperidin-1-yl)quinoxaline-5-carbonitrile. HPLC: 96.7% purity, RT=1.20 min. MS: m/z=340.2 [M+H]$^+$. $^1$H NMR (300 MHz, CD$_3$OD, ppm) δ 8.99-8.82 (m, 2H), 8.06 (d, J=8.4 Hz, 1H), 7.24 (d, J=8.4 Hz, 1H), 4.35-4.15 (m, 3H), 3.88 (d, J=0.6 Hz, 2H), 3.39 (s, 3H), 2.87 (dd, J=11.8, 10.4 Hz, 1H), 2.67 (dd, J=12.4, 10.6 Hz, 1H), 2.04 (d, J=11.8 Hz, 2H), 1.30 (td, J=12.5, 12.5 Hz, 1H), 0.99 (d, J=6.4 Hz, 3H).

Compound 140 (N-[(3R,5S)-1-(8-cyanoquinoxalin-5-yl)-5-methylpiperidin-3-yl]-2-methanesulfonamidoacetamide): From 2-(methylsulfonamido)acetic acid and 8-((3R,5S)-3-amino-5-methylpiperidin-1-yl)quinoxaline-5-carbonitrile. HPLC: 93.6% purity, RT=2.22 min. MS: m/z=403.2 [M+H]$^+$. $^1$H NMR (400 MHz, CD$_3$OD, ppm) δ 8.95-8.81

(m, 2H), 8.06 (d, J=8.4 Hz, 1H), 7.24 (d, J=8.4 Hz, 1H), 4.38-4.05 (m, 3H), 3.74 (s, 2H), 2.97 (s, 3H), 2.87-2.68 (m, 2H), 2.16-2.00 (m, 2H), 1.26 (td, J=11.8, 11.8 Hz, 1H), 0.99 (d, J=6.4 Hz, 3H).

Compound 141 (2-methanesulfonamido-N-[(3R,5S)-5-methyl-1-[pyrido[2,3-b]pyrazin-8-yl]piperidin-3-yl]acetamide): From 2-(methylsulfonamido)acetic acid and (3R,5S)-5-methyl-1-(pyrido[2,3-b]pyrazin-8-yl)piperidin-3-amine. HPLC: 98.5% purity, RT=0.82 min. MS: m/z=379.2 [M+H]$^+$. $^1$H NMR (300 MHz, CD$_3$OD, ppm) δ 8.89 (d, J=1.8 Hz, 1H), 8.77 (d, J=1.7 Hz, 1H), 8.63 (d, J=5.6 Hz, 1H), 7.11 (d, J=5.7 Hz, 1H), 4.71-4.55 (m, 2H), 4.13-3.99 (m, 1H), 3.74 (s, 2H), 2.97 (s, 3H), 2.95-2.66 (m, 2H), 2.07 (d, J=12.9 Hz, 1H), 2.00-1.90 (m, 1H), 1.27 (td, J=12.0, 12.0 Hz, 1H), 0.99 (d, J=6.5 Hz, 3H).

Compound 142 (2-(tert-butylamino)-N-[(3R,5S)-1-(8-cyanoquinoxalin-5-yl)-5-methylpiperidin-3-yl]acetamide): From 2-(tert-butylamino)acetic acid and 8-((3R,5S)-3-amino-5-methylpiperidin-1-yl)quinoxaline-5-carbonitrile. HPLC: 99.0% purity, RT=1.38 min. MS: m/z=381.2 [M+H]$^+$. $^1$H NMR (400 MHz, CD$_3$OD, ppm) δ 8.95-8.80 (m, 2H), 8.12-8.03 (m, 1H), 7.25 (dd, J=8.3, 6.2 Hz, 1H), 4.44-4.36 (m, 1H), 4.27 (d, J=13.1 Hz, 1H), 4.18-4.14 (m, 1H), 3.25 (m, 2H), 2.80 (t, J=11.3 Hz, 1H), 2.68 (t, J=11.8 Hz, 1H), 2.16-2.02 (m, 2H), 1.32-1.21 (m, 1H), 1.13 (s, 9H), 1.03 (d, J=6.4 Hz, 3H).

Compound 143 (2-(tert-butylamino)-N-[(3R,5S)-5-methyl-1-[pyrido[2,3-b]pyrazin-8-yl]piperidin-3-yl]acetamide): From 2-(tert-butylamino)acetic acid and (3R,5S)-5-methyl-1-(pyrido[2,3-b]pyrazin-8-yl)piperidin-3-amine. HPLC: 97.7% purity, RT=1.04 min. MS: m/z=357.3 [M+H]$^+$. $^1$H NMR (400 MHz, Chloroform-d, ppm) δ 8.94 (d, J=1.7 Hz, 1H), 8.80 (d, J=5.4 Hz, 1H), 8.74 (d, J=1.7 Hz, 1H), 7.05 (d, J=5.5 Hz, 1H), 4.65-4.45 (m, 2H), 4.25-4.11 (m, 1H), 3.25 (s, 2H), 2.86-2.70 (m, 2H), 2.19-2.09 (m, 1H), 2.07-1.93 (m, 1H), 1.25-1.05 (m, 10H), 0.99 (d, J=6.6 Hz, 3H).

Compound 144 (N-[(3R,5S)-1-(8-cyanoquinoxalin-5-yl)-5-methylpiperidin-3-yl]-2-[(2-hydroxyethyl)(methyl)amino]acetamide): From 2-((2-hydroxyethyl)(methyl)amino)acetic acid and 8-((3R,5S)-3-amino-5-methylpiperidin-1-yl)quinoxaline-5-carbonitrile. HPLC: 93.1% purity, RT=1.09 min. MS: m/z=383.2 [M+H]$^+$. $^1$H NMR (300 MHz, DMSO-d$_6$, ppm) δ 8.97 (d, J=1.8 Hz, 1H), 8.89 (d, J=1.8 Hz, 1H), 8.11 (d, J=8.4 Hz, 1H), 7.71 (d, J=6.6 Hz, 1H), 7.23 (d, J=8.4 Hz, 1H), 3.28 (d, J=7.2 Hz, 2H), 3.92-4.02 (m, 1H), 3.50-3.54 (m, 2H), 2.83-3.07 (m, 3H), 2.55-2.72 (m, 3H), 2.025 (s, 3H), 1.89-1.98 (m, 3H), 1.88-2.01 (m, 1H), 1.19-1.31 (m, 2H), 0.93-1.01 (m, 3H).

Compound 145 (2-[(2-hydroxyethyl)(methyl)amino]-N-[(3R,5S)-5-methyl-1-[pyrido[2,3-b]pyrazin-8-yl]piperidin-3-yl]acetamide): From 2-((2-hydroxyethyl)(methyl)amino)acetic acid and (3R,5S)-5-methyl-1-(pyrido[2,3-b]pyrazin-8-yl)piperidin-3-amine. HPLC: 90.7% purity, RT=1.70 min. MS: m/z=359.2 [M+H]$^+$. $^1$H NMR (300 MHz, DMSO-d$_6$, ppm) δ 8.94 (d, J=1.5 Hz, 1H), 8.77 (d, J=1.8 Hz, 1H), 8.69 (d, J=5.4 Hz, 1H), 7.64 (d, J=7.2 Hz, 1H), 7.08 (d, J=5.7 Hz, 1H), 4.43-4.56 (m, 2H), 4.28 (s, 1H), 3.91-3.96 (m, 1H), 3.48 (s, 2H), 2.97-3.03 (m, 1H), 2.83-2.91 (m, 1H), 2.61-2.72 (m, 2H), 2.49-2.52 (m, 2H), 2.24-2.28 (m, 3H), 1.76-2.01 (m, 2H), 1.21-1.33 (m, 1H), 0.94 (d, J=6.3 Hz, 3H).

Compound 163 (2-(tert-butoxy)-N-[(3R,5S)-1-(8-cyanoquinoxalin-5-yl)-5-methylpiperidin-3-yl]acetamide): From 2-tert-butoxyacetic acid and 8-((3R,5S)-3-amino-5-methylpiperidin-1-yl)quinoxaline-5-carbonitrile. HPLC: 99.3% purity, RT=1.54 min. MS: m/z=382.2 [M+H]$^+$. $^1$H NMR (300 MHz, DMSO-d$_6$, ppm) δ 8.97-8.85 (m, 2H), 8.10 (d, J=8.4 Hz, 1H), 7.28 (d, J=8.4 Hz, 1H), 4.38-4.16 (m, 3H), 3.93 (s, 2H), 2.95 (dd, J=11.9, 10.5 Hz, 1H), 2.73 (dd, J=12.5, 10.6 Hz, 1H), 2.18-2.00 (m, 2H), 1.44-1.33 (m, 1H), 1.27 (s, 9H), 1.04 (d, J=6.4 Hz, 3H).

Compound 164 (2-(tert-butoxy)-N-[(3R,5S)-5-methyl-1-[pyrido[2,3-b]pyrazin-8-yl]piperidin-3-yl]acetamide): From 2-tert-butylacetic acid and (3R,5S)-5-methyl-1-(pyrido[2,3-b]pyrazin-8-yl)piperidin-3-amine. HPLC: 97.9% purity, RT=1.23 min. MS: m/z=358.3 [M+H]$^+$. $^1$H NMR (300 MHz, CD$_3$OD, ppm) δ 8.95 (d, J=1.8 Hz, 1H), 8.83 (d, J=1.8 Hz, 1H), 8.68 (d, J=5.6 Hz, 1H), 7.16 (d, J=5.6 Hz, 1H), 4.73-4.58 (m, 2H), 4.17 (tt, J=11.2, 4.2 Hz, 1H), 3.93 (s, 2H), 3.09-2.95 (m, 1H), 2.81 (dd, J=12.8, 11.0 Hz, 1H), 2.15-1.95 (m, 2H), 1.43 (td, J=11.8, 11.8 Hz, 1H), 1.28 (s, 9H), 1.05 (d, J=6.5 Hz, 3H).

Compound 165 (N-[(3R,5S)-1-(8-cyanoquinoxalin-5-yl)-5-methylpiperidin-3-yl]-2,2-difluorocyclopropane-1-carboxamide): From 2,2-difluorocyclopropanecarboxylic acid and 8-((3R,5S)-3-amino-5-methylpiperidin-1-yl)quinoxaline-5-carbonitrile. HPLC: 99.3% purity, RT=1.39 min. MS: n/z=372.2 [M+H]$^+$. $^1$H NMR (400 MHz, CD$_3$OD, ppm) δ 8.94 (d, J=1.8 Hz, 1H), 8.91 (d, J=1.8 Hz, 1H), 8.11 (d, J=8.4 Hz, 1H), 7.30 (dd, J=8.4, 2.4 Hz, 1H), 4.47-4.27 (m, 2H), 4.25-4.09 (m, 1H), 2.84-2.64 (m, 2H), 2.59-2.45 (m, 1H), 2.20-1.95 (m, 3H), 1.81-1.73 (m, 1H), 1.25 (td, J=12.0, 12.0 Hz, 1H), 1.03 (dd, J=6.6, 2.4 Hz, 3H).

Compound 166 (N-[(3R,5S)-1-(8-cyanoquinoxalin-5-yl)-5-methylpiperidin-3-yl]-2-(oxolan-2-ylmethoxy)acetamide): From 2-(oxolan-2-ylmethoxy)acetic acid and 8-((3R,5S)-3-amino-5-methylpiperidin-1-yl)quinoxaline-5-carbonitrile. HPLC: 99.0% purity, RT=2.78 min. MS: m/z=410.2 [M+H]$^+$. $^1$H NMR (400 MHz, CD3OD, ppm) δ 8.94 (d, J=1.8 Hz, 1H), 8.91 (d, J=1.8 Hz, 1H), 8.11 (d, J=8.4 Hz, 1H), 7.29 (d, J=8.4 Hz, 1H), 4.40 (d, J=11.9 Hz, 1H), 4.35-4.00 (m, 5H), 3.98-3.79 (m, 2H), 3.64 (dd, J=10.5, 2.8 Hz, 1H), 3.53-3.43 (m, 1H), 2.87 (t, J=11.3 Hz, 1H), 2.71 (t, J=11.7 Hz, 1H), 2.18-1.89 (m, 5H), 1.72-1.56 (m, 1H), 1.32 (td, J=11.9, 11.9 Hz, 1H), 1.05 (d, J=6.5 Hz, 3H).

Compound 167 (N-[(3R,5S)-1-(8-cyanoquinoxalin-5-yl)-5-methylpiperidin-3-yl]-2,3-dimethylbutanamide): From 2,3-dimethylbutanoic acid and 8-((3R,5S)-3-amino-5-methylpiperidin-1-yl)quinoxaline-5-carbonitrile. HPLC: 98.7% purity, RT=1.52 min. MS: m/z=366.3 [M+H]$^+$. $^1$H NMR (400 MHz, Chloroform-d, ppm) δ 8.96 (d, J=1.4 Hz, 1H), 8.83 (d, J=1.4 Hz, 1H), 8.02 (d, J=8.3 Hz, 1H), 7.42-7.30 (m, 1H), 5.47 (d, J=6.9 Hz, 1H), 4.39-4.19 (m, 3H), 2.94-2.79 (m, 2H), 2.18-1.79 (m, 4H), 1.30-1.16 (m, 1H), 1.14 (d, J=6.4 Hz, 3H), 1.01-0.89 (m, 9H).

Compound 168 (2,3-dimethyl-N-[(3R,5S)-5-methyl-1-[pyrido[2,3-b]pyrazin-8-yl]piperidin-3-yl]butanamide): From 2,3-dimethylbutanoic acid and (3R,5S)-5-methyl-1-(pyrido[2,3-b]pyrazin-8-yl)piperidin-3-amine. HPLC: 98.7% purity, RT=1.21 min. MS: m/z=342.3 [M+H]$^+$. $^1$H NMR (400 MHz, CD$_3$OD, ppm) δ 8.92 (d, J=1.5 Hz, 1H), 8.80 (dd, J=5.8, 1.8 Hz, 1H), 8.65 (dd, J=5.6, 1.1 Hz, 1H), 7.16 (d, J=5.7 Hz, 1H), 4.75-4.60 (m, 2H), 4.11-3.99 (m, 1H), 2.90-2.70 (m, 2H), 2.12-1.88 (m, 3H), 1.83-1.69 (m, 1H), 1.34-1.19 (m, 1H), 1.14-0.82 (m, 12H).

Compound 169 (N-[(3R,5S)-1-(8-cyanoquinoxalin-5-yl)-5-methylpiperidin-3-yl]-2-(1H-pyrazol-1-yl)acetamide): From 2-(1H-pyrazol-1-yl)acetic acid and 8-((3R,5S)-3-amino-5-methylpiperidin-1-yl)quinoxaline-5-carbonitrile. HPLC: 99.4% purity, RT=1.18 min. MS: n/z=376.2 [M+H]$^+$. $^1$H NMR (400 MHz, CD$_3$OD, ppm) δ 8.93 (d, J=1.7 Hz, 1H), 8.89 (d, J=1.7 Hz, 1H), 8.19-8.06 (m, 1H), 7.71 (d, J=1.5 Hz, 1H), 7.56 (d, J=1.5 Hz, 1H), 7.28 (d, J=8.3 Hz, 1H), 6.39-6.33 (m, 1H), 4.42 (d, J=11.7 Hz, 1H), 4.34-4.26

(m, 1H), 4.22-4.11 (m, 1H), 3.37-3.27 (m, 1H), 3.15-2.95 (m, 1H), 2.85-2.65 (m, 2H), 2.22-1.98 (m, 2H), 1.26 (td, J=12.0, 12.0 Hz, 1H), 1.03 (d, J=6.4 Hz, 3H).

Compound 170 (N-[(3R,5S)-5-methyl-1-[pyrido[2,3-b]pyrazin-8-yl]piperidin-3-yl]-2-(1H-pyrazol-1-yl)acetamide): From 2-(1H-pyrazol-1-yl)acetic acid and (3R,5S)-5-methyl-1-(pyrido[2,3-b]pyrazin-8-yl)piperidin-3-amine. HPLC: 98.9% purity, RT=1.73 min. MS: m/z=352.1 [M+H]$^+$. $^1$H NMR (400 MHz, CD$_3$OD, ppm) δ 8.91 (d, J=1.7 Hz, 1H), 8.79 (d, J=1.7 Hz, 1H), 8.64 (d, J=5.6 Hz, 1H), 7.71-7.66 (m, 1H), 7.56-7.51 (m, 1H), 7.13 (d, J=5.6 Hz, 1H), 6.34 (t, J=2.2 Hz, 1H), 4.95-4.80 (m, 2H), 4.75-4.61 (m, 2H), 4.15-3.99 (m, 1H), 2.94-2.82 (m, 1H), 2.81-2.70 (m, 1H), 2.17-2.06 (m, 1H), 2.05-1.95 (m, 1H), 1.28 (td, J=12.0, 12.0 Hz, 1H), 1.01 (d, J=6.6 Hz, 3H).

Compound 171 (N-[(3R,5S)-1-(8-cyanoquinoxalin-5-yl)-5-methylpiperidin-3-yl]-1-methylpyrrolidine-2-carboxamide): From 1-methylpyrrolidine-2-carboxylic acid and 8-((3R,5S)-3-amino-5-methylpiperidin-1-yl)quinoxaline-5-carbonitrile. HPLC: 98.5% purity, RT=1.85 min. MS: m/z=379.1 [M+H]$^+$. $^1$H NMR (300 MHz, CD$_3$OD, ppm) δ 8.89 (d, J=1.7 Hz, 1H), 8.85 (d, J=1.7 Hz, 1H), 8.05 (d, J=8.4 Hz, 1H), 7.24 (d, J=8.4 Hz, 1H), 4.38-4.05 (m, 3H), 3.16-3.03 (m, 1H), 2.91-2.75 (m, 2H), 2.73-2.59 (m, 1H), 2.40-2.26 (m, 4H), 2.21-1.97 (m, 3H), 1.85-1.71 (m, 3H), 1.33-1.19 (m, 1H), 0.99 (d, J=6.3 Hz, 3H).

Compound 172 (Methyl-N-[(3R,5S)-5-methyl-1-[pyrido[2,3-b]pyrazin-8-yl]piperidin-3-yl]pyrrolidine-2-carboxamide): From 1-methylpyrrolidine-2-carboxylic acid and (3R,5S)-5-methyl-1-(pyrido[2,3-b]pyrazin-8-yl)piperidin-3-amine. HPLC: 97.5% purity, RT=2.22 min. MS: m/z=355.2 [M+H]$^+$. $^1$H NMR (300 MHz, CD$_3$OD, ppm) δ 8.88 (d, J=1.8 Hz, 1H), 8.76 (t, J=1.4 Hz, 1H), 8.61 (d, J=5.6 Hz, 1H), 7.08 (dd, J=5.7, 1.3 Hz, 1H), 4.66-4.50 (m, 2H), 4.11-3.97 (m, 1H), 3.16-3.00 (m, 1H), 3.01-2.64 (m, 3H), 2.40-1.66 (m, 10H), 1.29 (td, J=11.8, 11.8 Hz, 1H), 0.97 (d, J=6.5 Hz, 3H).

Compound 175 (cis-N-[1-(8-cyanoquinoxalin-5-yl)-5-cyclopropylpiperidin-3-yl]-3,3-dimethylbutanamide): From 3,3-dimethylbutanoic acid and cis-8-(3-amino-5-cyclopropylpiperidin-1-yl)quinoxaline-5-carbonitrile. HPLC: 95.1% purity, RT=2.95 min. MS: m/z=392.3 [M+H]$^+$. $^1$H NMR (300 MHz, CD$_3$OD, ppm) δ 8.89 (d, J=1.8 Hz, 1H), 8.84 (d, J=1.8 Hz, 1H), 8.05 (d, J=8.4 Hz, 1H), 7.22 (d, J=8.4 Hz, 1H), 4.46-4.26 (m, 2H), 4.11-4.00 (m, 1H), 2.91-2.69 (m, 2H), 2.21-2.09 (m, 1H), 2.06 (s, 2H), 1.40-1.02 (m, 2H), 1.01 (s, 9H), 0.63-0.38 (m, 3H), 0.18 (d, J=3.5 Hz, 2H).

Compound 179 (cis-N-[1-(8-cyanoquinoxalin-5-yl)-5-cyclopropylpiperidin-3-yl]-2-(dimethylamino)acetamide): From 2-(dimethylamino)acetic acid hydrochloride and cis-8-(3-amino-5-cyclopropylpiperidin-1-yl)quinoxaline-5-carbonitrile. HPLC: 97.2% purity, RT=2.42 min. MS: m/z=379.2 [M+H]$^+$. $^1$H NMR (300 MHz, CD$_3$OD, ppm) δ 8.89 (d, J=1.8 Hz, 1H), 8.84 (d, J=1.8 Hz, 1H), 8.05 (d, J=8.4 Hz, 1H), 7.22 (d, J=8.4 Hz, 1H), 4.38-4.20 (m, 2H), 4.16-3.99 (m, 1H), 3.01-2.80 (m, 4H), 2.29 (s, 6H), 2.23-2.06 (m, 1H), 1.44 (q, J=11.8 Hz, 1H), 1.21-1.07 (m, 1H), 0.69-0.38 (m, 3H), 0.27-0.11 (m, 2H).

Compound 230 (N-[(3R,5S)-1-(8-cyanoquinoxalin-5-yl)-5-methylpiperidin-3-yl]-1-hydroxycyclopropane-1-carboxamide): From 1-hydroxycyclopropane-1-carboxylic acid and 8-[(3R,5S)-3-amino-5-methylpiperidin-1-yl]quinoxaline-5-carbonitrile. HPLC: 98.8% purity, RT=3.40 min. MS: m/z=352.1 [M+H]$^+$. $^1$H NMR (300 MHz, CD$_3$OD, ppm) δ 8.94-8.80 (m, 2H), 8.06 (d, J=8.4 Hz, 1H), 7.23 (d, J=8.4 Hz, 1H), 4.35-4.09 (m, 3H), 2.98-2.86 (m, 1H), 2.78-2.62 (m, 1H), 2.15-1.95 (m, 2H), 1.40-1.15 (m, 3H), 1.00-0.89 (m, 5H).

Compound 232 (N-[(3R,5S)-1-(8-cyanoquinoxalin-5-yl)-5-methylpiperidin-3-yl]-2-(1-methylpiperidin-4-yl)acetamide: From 2-(1-methylpiperidin-4-yl)acetic acid and 8-[(3R,5S)-3-amino-5-methylpiperidin-1-yl]quinoxaline-5-carbonitrile. HPLC: 95.5% purity, RT=2.03 min. MS: m/z=407.3 [M+H]$^+$. $^1$H NMR (300 MHz, Chloroform-d, ppm) δ 8.95 (d, J=1.7 Hz, 1H), 8.83 (d, J=1.8 Hz, 1H), 8.00 (d, J=8.3 Hz, 1H), 7.23 (d, J=8.4 Hz, 1H), 5.57 (d, J=7.3 Hz, 1H), 4.38-4.14 (m, 3H), 2.95-2.69 (m, 4H), 2.30 (s, 3H), 2.19-1.93 (m, 6H), 1.89-1.68 (m, 3H), 1.47-1.09 (m, 3H), 0.98 (d, J=6.6 Hz, 3H).

Compound 233 (N-[(3R,5S)-1-(8-cyanoquinoxalin-5-yl)-5-methylpiperidin-3-yl]-2-(1,4-dimethylpiperidin-4-yl)acetamide): From 2-(1,4-dimethylpiperidin-4-yl)acetic acid and 8-((3R,5S)-3-amino-5-methylpiperidin-1-yl)quinoxaline-5-carbonitrile. HPLC: 95.7% purity, RT=2.95 min. MS: m/z=421.2 [M+H]$^+$. $^1$H NMR (300 MHz, CD$_3$OD, ppm) δ 8.99-8.85 (m, 2H), 8.10 (d, J=8.4 Hz, 1H), 7.29 (d, J=8.4 Hz, 1H), 4.38-4.30 (m, 2H), 4.15 (t, J=11.9 Hz, 1H), 2.83-2.55 (m, 4H), 2.46 (s, 2H), 2.33 (s, 3H), 2.22-1.95 (m, 4H), 1.72-1.67 (m, 2H), 1.56-1.48 (m, 2H), 1.21 (td, J=12.1, 12.1 Hz, 1H), 1.08 (s, 3H), 1.01 (d, J=6.3 Hz, 3H).

Compound 234 (N-[(3R,5S)-1-(8-cyanoquinoxalin-5-yl)-5-methylpiperidin-3-yl]-2-[1-(2,2-difluoroethyl)piperidin-4-yl]acetamide): From 2-(1-methylpiperidin-4-yl)acetic acid and 8-[(3R,5S)-3-amino-5-methylpiperidin-1-yl]quinoxaline-5-carbonitrile. HPLC: 93.9% purity, RT=2.45 min. MS: m/z=457.3 [M+H]$^+$. $^1$H NMR (300 MHz, Chloroform-d, ppm) δ 8.92 (d, J=1.7 Hz, 1H), 8.79 (d, J=1.8 Hz, 1H), 7.97 (d, J=8.3 Hz, 1H), 7.20 (d, J=8.4 Hz, 1H), 6.10-5.70 (m, 1H), 5.51 (d, J=7.2 Hz, 1H), 4.35-4.10 (m, 3H), 2.98-2.85 (m, 2H), 2.85-2.62 (m, 4H), 2.28-1.63 (m, 8H), 1.42-1.06 (m, 4H), 0.95 (d, J=6.6 Hz, 3H).

Compound 235 (N-[(3R,5S)-1-(8-cyanoquinoxalin-5-yl)-5-methylpiperidin-3-yl]-3,3-difluorocyclobutane-1-carboxamide): From 3,3-difluorocyclobutane-1-carboxylic acid and 8-[(3R,5S)-3-amino-5-methylpiperidin-1-yl]quinoxaline-5-carbonitrile. HPLC: 93.9% purity, RT=4.03 min. MS: m/z=386.0 [M+H]$^+$. $^1$H NMR (300 MHz, Chloroform-d, ppm) δ 8.94 (d, J=1.7 Hz, 1H), 8.81 (d, J=1.7 Hz, 1H), 7.99 (d, J=8.3 Hz, 1H), 7.23 (d, J=8.4 Hz, 1H), 5.63 (d, J=6.9 Hz, 1H), 4.30-4.22 (m, 3H), 2.96-2.63 (m, 7H), 2.17-1.99 (m, 2H), 1.21 (td, J=11.3, 11.3 Hz, 1H), 0.97 (d, J=6.5 Hz, 3H).

Compound 236 (N-[(3R,5S)-1-(8-cyanoquinoxalin-5-yl)-5-methylpiperidin-3-yl]-1-methylpyrrolidine-3-carboxamide): From 3,3-difluorocyclobutane-1-carboxylic acid and 8-[(3R,5S)-3-amino-5-methylpiperidin-1-yl]quinoxaline-5-carbonitrile. HPLC: 97.5% purity, RT=2.06 min. MS: m/z=379.1 [M+H]$^+$. $^1$H NMR (400 MHz, Chloroform-d, ppm) δ 8.94 (d, J=1.7 Hz, 1H), 8.82 (d, J=1.7 Hz, 1H), 7.99 (d, J=8.4 Hz, 1H), 7.23 (d, J=8.4 Hz, 1H), 6.86 (d, J=7.3 Hz, 1H), 4.33 (dd, J=12.5, 4.6 Hz, 2H), 4.23-4.08 (m, 1H), 2.93-2.86 (m, 3H), 2.83-2.69 (m, 2H), 2.65-2.52 (m, 1H), 2.46-2.40 (m, 4H), 2.28-2.19 (m, 1H), 2.12 (apparent d, J=12.3 Hz, 1H), 2.08-1.93 (m, 2H), 1.35-1.10 (m, 1H), 0.98 (d, J=6.6 Hz, 3H).

Compound 265 (N-[(3R,5S)-1-(8-cyanoquinoxalin-5-yl)-5-methylpiperidin-3-yl]-2-hydroxypropanamide): From 2-hydroxypropanoic acid and 8-((3R,5S)-3-amino-5-methylpiperidin-1-yl)quinoxaline-5-carbonitrile HPLC: 99.3% purity, RT=1.16 min. MS: m/z=340.2 [M+H]$^+$. $^1$H NMR (300 MHz, CD$_3$OD, ppm) δ 8.95-8.81 (m, 2H), 8.06 (d, J=8.4 Hz, 1H), 7.24 (d, J=8.4 Hz, 1H), 4.27-4.22 (m, 2H), 4.12-4.07 (m, 2H), 2.86 (dd, J=12.0, 10.4 Hz, 1H), 2.74-2.60 (m, 1H), 2.07-2.03 (m, 2H), 1.36-1.30 (m, 4H), 0.99 (d, J=6.4 Hz, 3H).

Compound 266: (N-[(3R,5S)-1-(8-cyanoquinoxalin-5-yl)-5-methylpiperidin-3-yl]-2-(1-methylpiperidin-3-yl)acetamide hydrochloride): From 2-(1-methylpiperidin-3-yl)acetic acid and 8-((3R,5S)-3-amino-5-methylpiperidin-1-yl)quinoxaline-5-carbonitrile. HPLC: 96.3% purity, RT=1.19 min. MS: m/z=407.2 [M+H]$^+$. $^1$H NMR (300 MHz, CD$_3$OD, ppm) δ 9.01-8.89 (m, 2H), 8.15 (d, J=8.2 Hz, 1H), 7.57 (dd, J=7.8, 2.9 Hz, 1H), 4.29-4.08 (m, 3H), 3.45 (d, J=12.2 Hz, 2H), 3.07-2.79 (m, 6H), 2.72 (t, J=11.3 Hz, 1H), 2.31-2.03 (m, 5H), 2.04-1.65 (m, 3H), 1.37-1.14 (m, 2H), 1.00 (d, J=6.4 Hz, 3H).

Compound 269 (N-[(3R,5S)-1-(8-cyanoquinoxalin-5-yl)-5-methylpiperidin-3-yl]-2-(1-methylpyrrolidin-3-yl)acetamide): From 2-(tert-butoxycarbonylamino)-2-cyclopropylacetic acid and 8-((3R,5S)-3-amino-5-methylpiperidin-1-yl)quinoxaline-5-carbonitrile. HPLC: 95.1% purity, RT=2.41 min. MS: m/z=393.2 [M+H]$^+$. $^1$H NMR (300 MHz, Chloroform-d, ppm) δ 8.91 (d, J=1.7 Hz, 1H), 8.79 (t, J=1.5 Hz, 1H), 7.96 (d, J=8.4 Hz, 1H), 7.20 (d, J=8.4 Hz, 1H), 6.65 (d, J=7.1 Hz, 1H), 4.36-4.08 (m, 3H), 2.84-2.64 (m, 3H), 2.64-2.24 (m, 9H), 2.19-1.88 (m, 3H), 1.58-1.52 (m, 1H), 1.25-0.90 (m, 4H).

Example 11: Synthesis of Compound 16 (8-((3S,5R)-3-methyl-5-(methylamino)piperidin-1-yl)quinoxaline-5-carbonitrile hydrochloride)

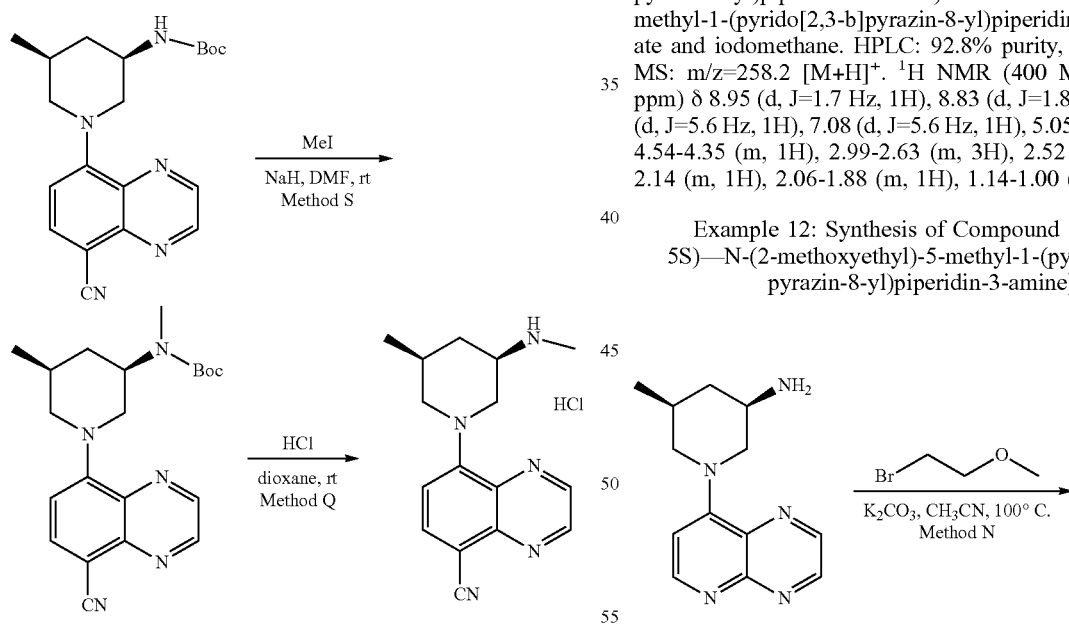

Method S tert-Butyl (3R,5S)-1-(8-cyanoquinoxalin-5-yl)-5-methylpiperidin-3-yl(methyl)carbamate: To a solution of tert-butyl N-[(3R,5S)-1-(8-cyanoquinoxalin-5-yl)-5-methylpiperidin-3-yl]carbamate (152 mg, 0.41 mmol) in N,N-dimethylformamide (10 mL) was added sodium hydride (18 mg, 0.74 mmol, 1.78 equiv) at room temperature. The mixture was stirred for 10 min at room temperature, and then was added by iodomethane (70 mg, 0.49 mmol). The reaction mixture was stirred for 1 h at room temperature. When the reaction was done, it was quenched by the addition of water (10 mL). The resulting mixture was extracted with ethyl acetate (50 mL×3), and the organic phases were combined, washed with brine and dried over Na$_2$SO$_4$. The solvent was removed under reduced pressure to yield tert-butyl N-[(3R,5S)-1-(8-cyanoquinoxalin-5-yl)-5-methylpiperidin-3-yl]-N-methylcarbamate as yellow solid (180 mg, crude).

8-((3S,5R)-3-methyl-5-(methylamino)piperidin-1-yl)quinoxaline-5-carbonitrile hydrochloride: 8-((3S,5R)-3-methyl-5-(methylamino)piperidin-1-yl)quinoxaline-5-carbonitrile hydrochloride was prepared from tert-butyl (3R,5S)-1-(8-cyanoquinoxalin-5-yl)-5-methylpiperidin-3-yl (methyl)carbamate and iodomethane using Method Q. The crude product was purified by prep-HPLC under the following conditions: Column, XBridge C18 OBD Prep Column, 5 um, 19 mm×150 mm; Mobile phase, acetonitrile in water (with 0.02% v/v HCl), 30% to 40% gradient in 10 min; Detector, UV 254 nm. 8-[(3S,5R)-3-methyl-5-(methylamino)piperidin-1-yl]quinoxaline-5-carbonitrile hydrochloride was obtained as yellow solid (36 mg, 26% for 2 steps).

Compound 16: HPLC: 90.3% purity, RT=1.97 min. MS: m/z=282.1 [M+H]$^+$. $^1$H NMR (400 MHz, CD$_3$OD, ppm) δ 8.92 (d, J=2.0 Hz, 1H), 8.88 (d, J=1.6 Hz, 1H), 8.09 (d, J=8.4 Hz, 1H), 7.22 (d, J=8.4 Hz, 1H), 4.63-4.53 (m, 1H), 4.14-4.04 (m, 1H), 3.02-2.90 (m, 1H), 2.70-2.55 (m, 2H), 2.50 (s, 3H), 2.26-2.14 (m, 1H), 2.10-1.90 (m, 1H), 1.10-0.96 (m, 4H).

The following compound was synthesized in an analogous manner:

Compound 17 ((3R,5S)—N,5-dimethyl-1-(pyrido[2,3-b]pyrazin-8-yl)piperidin-3-amine): From tert-butyl (3R,5S)-5-methyl-1-(pyrido[2,3-b]pyrazin-8-yl)piperidin-3-ylcarbamate and iodomethane. HPLC: 92.8% purity, RT=0.71 min. MS: m/z=258.2 [M+H]$^+$. $^1$H NMR (400 MHz, CD$_3$OD, ppm) δ 8.95 (d, J=1.7 Hz, 1H), 8.83 (d, J=1.8 Hz, 1H), 8.67 (d, J=5.6 Hz, 1H), 7.08 (d, J=5.6 Hz, 1H), 5.05-4.95 (m, 1H), 4.54-4.35 (m, 1H), 2.99-2.63 (m, 3H), 2.52 (s, 3H), 2.27-2.14 (m, 1H), 2.06-1.88 (m, 1H), 1.14-1.00 (m, 4H).

Example 12: Synthesis of Compound 18 ((3R,5S)—N-(2-methoxyethyl)-5-methyl-1-(pyrido[2,3-b]pyrazin-8-yl)piperidin-3-amine)

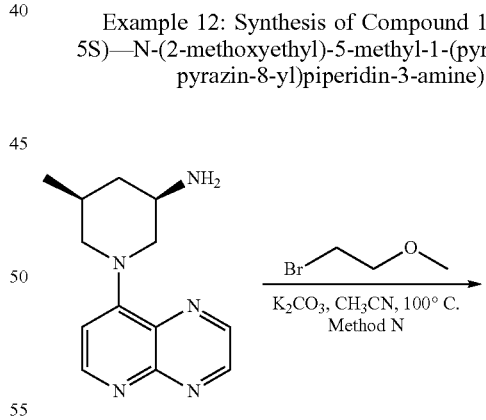

(3R,5S)—N-(2-methoxyethyl)-5-methyl-1-(pyrido[2,3-b]pyrazin-8-yl)piperidin-3-amine: (3R,5S)—N-(2-methoxyethyl)-5-methyl-1-(pyrido[2,3-b]pyrazin-8-yl)piperidin-3-amine was prepared from (3R,5S)-5-methyl-1-(pyrido[2,3-b]pyrazin-8-yl)piperidin-3-amine and 1-bromo-2-methoxyethane using Method N. The crude product was purified by prep-HPLC under the following conditions: Column, XBridge C18 OBD Prep Column, 5 um, 19 mm×150 mm; Mobile phase, MeOH in water (with 10 mmol/L NH$_4$HCO$_3$), 3% to 80% gradient in 8 min; Detector, UV 254 nm. (3R,5S)—N-(2-methoxyethyl)-5-methyl-1-[pyrido[2,3-b]pyrazin-8-yl]piperidin-3-amine as yellow oil (60 mg, 31%).

Compound 18: HPLC: 96.8% purity, RT=1.88 min. MS: m/z=302.2 [M+H]$^+$. $^1$H NMR (400 MHz, CD$_3$OD, ppm) δ 8.94 (d, J=1.8 Hz, 1H), 8.82 (d, J=1.8 Hz, 1H), 8.66 (d, J=5.6 Hz, 1H), 7.08 (d, J=5.7 Hz, 1H), 4.61 (br s, 2H), 4.46 (d, J=12.6 Hz, 1H), 3.60-3.52 (m, 2H), 3.39 (s, 3H), 3.02-2.90 (m, 3H), 2.80-2.68 (m, 2H), 2.25-2.15 (m, 1H), 2.05-1.95 (s, 1H), 1.18-1.02 (m, 3H).

The following compounds were synthesized in an analogous manner:

Compound 19 (8-((3R,5S)-3-(2-methoxyethylamino)-5-methylpiperidin-1-yl)quinoxaline-5-carbonitrile): From 8-((3R,5S)-3-amino-5-methylpiperidin-1-yl)quinoxaline-5-carbonitrile and 1-bromo-2-methoxyethane. HPLC: 97.8% purity, RT=1.22 min. MS: m/z=326.2 [M+H]$^+$. $^1$H NMR (300 MHz, CD$_3$OD, ppm) δ 8.89 (s, 1H), 8.85 (s, 1H), 8.05 (d, J=8.4 Hz, 1H), 7.18 (d, J=8.5 Hz, 1H), 4.59-4.47 (m, 1H), 4.14-4.03 (m, 1H), 3.55-3.45 (m, 2H), 3.34 (s, 3H), 3.06-2.78 (m, 3H), 2.66-2.51 (m, 2H), 2.20-1.85 (m, 2H), 1.10-0.91 (m, 4H).

Compound 38 (8-((3R,5S)-3-(cyanomethylamino)-5-methylpiperidin-1-yl)quinoxaline-5-carbonitrile): From 8-((3R,5S)-3-amino-5-methylpiperidin-1-yl)quinoxaline-5-carbonitrile and 2-chloroacetonitrile. HPLC: 90.7% purity, RT=1.24 min. MS: m/z=307.2 [M+H]$^+$. $^1$H NMR (300 MHz, CD$_3$OD, ppm) δ 8.93-8.86 (m, 2H), 8.05 (d, J=8.4 Hz, 1H), 7.18 (d, J=8.4 Hz, 1H), 4.65-4.52 (m, 1H), 4.05 (dd, J=13.3, 3.4 Hz, 1H), 3.72 (s, 2H), 3.25-3.10 (m, 1H), 2.66-2.50 (m, 2H), 2.20-1.90 (m, 2H), 1.11-0.93 (m, 4H).

Compound 39 (2-((3R,5S)-5-methyl-1-(pyrido[2,3-b]pyrazin-8-yl)piperidin-3-ylamino)acetonitrile hydrochloride): From (3R,5S)-5-methyl-1-(pyrido[2,3-b]pyrazin-8-yl)piperidin-3-amine and 2-chloroacetonitrile. HPLC: 87.2% purity, RT=0.97 min. MS: m/z=283.0 [M+H]$^+$. $^1$H NMR (400 MHz, CD$_3$OD, ppm) δ 9.12-9.02 (m, 2H), 8.55 (d, J=6.6 Hz, 1H), 7.40 (d, J=6.9 Hz, 1H), 5.92-5.72 (m, 1H), 4.60-4.30 (m, 2H), 3.95-3.60 (m, 2H), 3.20-3.10 (m, 1H), 2.48-2.38 (m, 1H), 2.16-2.06 (m, 1H), 1.65-1.52 (m, 1H), 1.16-0.96 (m, 4H).

Compound 121 (2-[[(3R,5S)-5-methyl-1-[pyrido[2,3-b]pyrazin-8-yl]piperidin-3-yl]amino]acetamide): From (3R,5S)-5-methyl-1-(pyrido[2,3-b]pyrazin-8-yl)piperidin-3-amine and 2-chloroacetamide. HPLC: 99.1% purity, RT=0.75 min. MS: m/z=301.2 [M+H]$^+$. $^1$H NMR (400 MHz, CD$_3$OD, ppm) δ 8.93 (d, J=1.8 Hz, 1H), 8.83 (t, J=1.7 Hz, 1H), 8.64 (dd, J=5.8, 1.5 Hz, 1H), 7.09-7.02 (m, 1H), 5.03-4.90 (m, 1H), 4.41 (dd, J=12.8, 4.2 Hz, 1H), 3.49-3.34 (m, 2H), 3.00-2.86 (m, 1H), 2.80-2.64 (m, 2H), 2.26-2.13 (m, 1H), 2.03-1.90 (m, 1H), 1.19-1.01 (m, 4H).

Compound 122 (2-[[(3R,5S)-1-(8-cyanoquinoxalin-5-yl)-5-methylpiperidin-3-yl]amino]acetamide): From 8-((3R,5S)-3-amino-5-methylpiperidin-1-yl)quinoxaline-5-carbonitrile and 2-chloroacetamide. HPLC: 99.5% purity, RT=1.03 min. MS: m/z=325.2 [M+H]$^+$. $^1$H NMR (400 MHz, CD$_3$OD, ppm) δ 8.95-8.85 (m, 2H), 8.06 (d, J=8.4 Hz, 1H), 7.29-7.15 (m, 1H), 4.62-4.48 (m, 1H), 4.12-4.02 (m, 1H), 3.46-3.31 (m, 2H), 2.99 (tt, J=11.0, 4.0 Hz, 1H), 2.72-2.56 (m, 2H), 2.22-1.88 (m, 2H), 0.96 (m, 4H).

Compound 126 (1-methyl-3-[[(3R,5S)-5-methyl-1-[pyrido[2,3-b]pyrazin-8-yl]piperidin-3-yl]amino]pyrrolidin-2-one): From (3R,5S)-5-methyl-1-(pyrido[2,3-b]pyrazin-8-yl)piperidin-3-amine and 3-bromo-1-methylpyrrolidin-2-one. HPLC: 99.0% purity, RT=1.13 min. MS: n/z=341.2 [M+H]$^+$. $^1$H NMR (400 MHz, CD$_3$OD, ppm) δ 8.92 (d, J=1.7 Hz, 1H), 8.80 (d, J=1.8 Hz, 1H), 8.63 (d, J=5.6 Hz, 1H), 7.07 (t, J=5.4 Hz, 1H), 5.08-4.88 (m, 1H), 4.48-4.38 (m, 1H), 3.76-3.62 (m, 1H), 3.48-3.35 (m, 2H), 3.21-3.04 (m, 1H), 2.87 (s, 3H), 2.80-2.65 (m, 2H), 2.56-2.39 (m, 1H), 2.28-2.12 (m, 1H), 2.02-1.76 (m, 2H), 1.18-0.99 (m, 4H).

Compound 176 (cis-8-[3-cyclopropyl-5-[(2-methoxyethyl)amino]piperidin-1-yl]quinoxaline-5-carbonitrile): From 3,3-dimethylbutanoic acid and cis-8-(3-amino-5-cyclopropylpiperidin-1-yl)quinoxaline-5-carbonitrile. HPLC: 99.0% purity, RT=1.42 min. MS: m/z=352.2 [M+H]$^+$. $^1$H NMR (300 MHz, CD$_3$OD, ppm) δ 8.91 (d, J=1.8 Hz, 1H), 8.86 (d, J=1.8 Hz, 1H), 8.07 (d, J=8.4 Hz, 1H), 7.20 (d, J=8.4 Hz, 1H), 4.61-4.45 (m, 1H), 4.30-4.24 (m, 1H), 3.61-3.45 (m, 2H), 3.37 (s, 3H), 3.05-2.75 (m, 4H), 2.74-2.68 (m, 1H), 2.37-2.25 (m, 1H), 1.31-1.03 (m, 2H), 0.71-0.41 (m, 3H), 0.30-0.12 (m, 2H).

Example 13: Synthesis of Compound 24 ((R)-2-amino-N-((3R,5S)-1-(8-cyanoquinoxalin-5-yl)-5-methylpiperidin-3-yl)propanamide)

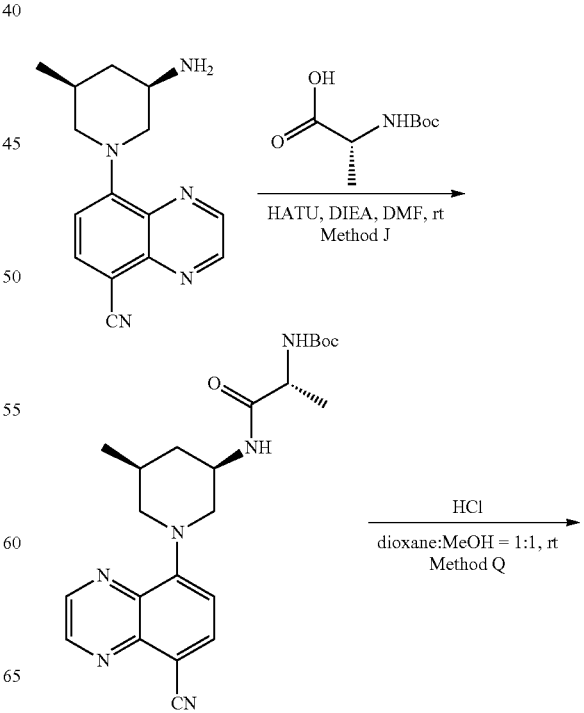

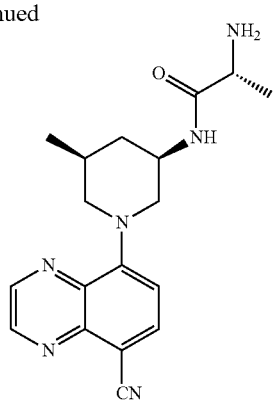

(R)-2-amino-N-((3R,5S)-1-(8-cyanoquinoxalin-5-yl)-5-methylpiperidin-3-yl)propanamide: (R)-2-amino-N-((3R,5S)-1-(8-cyanoquinoxalin-5-yl)-5-methylpiperidin-3-yl)propanamide was prepared from 8-((3R,5S)-3-amino-5-methylpiperidin-1-yl)quinoxaline-5-carbonitrile and (R)-2-(tert-butoxycarbonylamino)propanoic acid using Method J and Q. The crude product was purified by prep-HPLC under the following conditions: Column, XBridge C18 OBD Prep Column, 5 um, 19 mm×250 mm; MeOH in water (with 10 mmol/L NH$_4$HCO$_3$), 30% to 80% gradient in 10 min; Detector, UV 254 nm. (2R)-2-amino-N-[(3R,5S)-1-(8-cyanoquinoxalin-5-yl)-5-methylpiperidin-3-yl]propanamide was obtained as yellow solid (25 mg, 26% for 2 steps).

Compound 24: HPLC: 94.4% purity, RT=1.39 min. MS: m/z=339.1 [M+H]$^+$. $^1$H NMR (300 MHz, CD$_3$OD, ppm) δ 8.94 (d, J=1.8 Hz, 1H), 8.91 (d, J=1.8 Hz, 1H), 8.11 (d, J=8.4 Hz, 1H), 7.30 (d, J=8.4 Hz, 1H), 4.44-4.26 (m, 2H), 4.20-4.03 (m, 1H), 3.50-3.38 (m, 1H), 2.87-2.62 (m, 2H), 2.20-1.99 (m, 2H), 1.35-1.17 (m, 4H), 1.04 (d, J=6.4 Hz, 3H).

The following compounds were synthesized in an analogous manner:

Compound 25 ((S)-2-amino-N-((3R,5S)-1-(8-cyanoquinoxalin-5-yl)-5-methylpiperidin-3-yl)propanamide): From 8-((3R,5S)-3-amino-5-methylpiperidin-1-yl)quinoxaline-5-carbonitrile and (S)-2-(tert-butoxycarbonylamino)propanoic acid. HPLC: 91.3% purity, RT=1.40 min. MS: m/z=339.2 [M+H]$^+$. $^1$H NMR (300 MHz, CD$_3$OD, ppm) δ 8.97 (d, J=1.8 Hz, 1H), 8.92 (d, J=1.8 Hz, 1H), 8.13 (d, J=8.4 Hz, 1H), 7.32 (d, J=8.4 Hz, 1H), 4.44-4.26 (m, 2H), 4.20-4.02 (m, 1H), 3.52-3.38 (m, 1H), 2.89-2.64 (m, 2H), 2.20-2.01 (m, 3H), 1.37-1.22 (m, 4H), 1.05 (d, J=6.4 Hz, 3H).

Compound 26 ((R)-2-amino-N-((3R,5S)-5-methyl-1-(pyrido[2,3-b]pyrazin-8-yl)piperidin-3-yl)propanamide): From (3R,5S)-5-methyl-1-(pyrido[2,3-b]pyrazin-8-yl)piperidin-3-amine and (R)-2-(tert-butoxycarbonylamino)propanoic acid. HPLC: 94.9% purity, RT=0.55 min. MS: m/z=315.1 [M+H]+. $^1$H NMR (300 MHz, DMSO-d$_6$, ppm) δ 8.99 (s, 1H), 8.83 (s, 1H), 8.71 (d, J=4.8 Hz, 1H), 7.81 (d, J=7.6 Hz, 1H), 7.15 (d, J=5.5 Hz, 1H), 4.55 (d, J=13.4 Hz, 1H), 4.39 (m, J=13.4 Hz, 1H), 3.92-3.76 (m, 1H), 3.45-3.35 (m, 1H), 2.90-2.60 (m, 2H), 2.03-1.75 (m, 4H), 1.33-1.08 (m, 4H), 0.92 (d, J=6.5 Hz, 3H).

Compound 27 ((S)-2-amino-N-((3R,5S)-5-methyl-1-(pyrido[2,3-b]pyrazin-8-yl)piperidin-3-yl)propanamide): From (3R,5S)-5-methyl-1-(pyrido[2,3-b]pyrazin-8-yl)piperidin-3-amine and (S)-2-(tert-butoxycarbonylamino)propanoic acid. HPLC: 94.0% purity, RT=0.93 min. MS: m/z=315.2 [M+H]$^+$. $^1$H NMR (300 MHz, CD$_3$OD, ppm) δ 8.90 (d, J=1.7 Hz, 1H), 8.77 (d, J=1.7 Hz, 1H), 8.63 (d, J=5.7 Hz, 1H), 7.12 (d, J=5.6 Hz, 1H), 4.72-4.58 (m, 2H), 4.07-3.93 m, 1H), 3.46-3.34 (m, 1H), 2.90-2.65 (m, 2H), 2.15-1.92 (m, 2H), 1.36-1.15 (m, 4H), 0.99 (d, J=6.5 Hz, 3H).

Compound 28 (N-((3R,5S)-1-(8-cyanoquinoxalin-5-yl)-5-methylpiperidin-3-yl)-2-(methylamino)acetamide hydrochloride): From 8-((3R,5S)-3-amino-5-methylpiperidin-1-yl)quinoxaline-5-carbonitrile and 2-(tert-butoxycarbonyl(methyl)amino)acetic acid. HPLC: 98.3% purity, RT=1.21 min. MS: m/z=339.1 [M+H]$^+$. $^1$H NMR (300 MHz, CD$_3$OD, ppm) δ 8.90 (d, J=1.7 Hz, 1H), 8.84 (d, J=1.7 Hz, 1H), 8.07 (d, J=8.4 Hz, 1H), 7.24 (d, J=8.4 Hz, 1H), 4.40 (d, J=12.2 Hz, 1H), 4.28-4.06 (m, 2H), 3.75 (s, 2H), 2.82-2.57 (m, 5H), 2.16-1.97 (m, 2H), 1.251.13 (m, 1H), 0.99 (d, J=6.5 Hz, 3H).

Compound 29 (N-((3R,5S)-5-methyl-1-(pyrido[2,3-b]pyrazin-8-yl)piperidin-3-yl)-2-(methylamino)acetamide): From (3R,5S)-5-methyl-1-(pyrido[2,3-b]pyrazin-8-yl)piperidin-3-amine and 2-(tert-butoxycarbonyl(methyl)amino)acetic acid. HPLC: 99.6% purity, RT=0.83 min. MS: m/z=315.1 [M+H]$^+$. $^1$H NMR (300 MHz, DMSO-d$_6$, ppm) δ 9.00 (d, J=1.7 Hz, 1H), 8.83 (d, J=1.7 Hz, 1H), 8.72 (d, J=5.4 Hz, 1H), 8.09 (d, J=7.8 Hz, 1H), 7.14 (d, J=5.5 Hz, 1H), 4.58-4.38 (m, 2H), 4.00-3.85 (m, 1H), 3.40-3.30 (m, 2H), 2.88-2.68 (m, 2H), 2.38 (s, 3H), 2.01-1.79 (m, 2H), 1.30-1.16 (m, 1H), 0.93 (d, J=6.4 Hz, 3H).

Compound 30 (1-amino-N-((3R,5S)-5-methyl-1-(pyrido[2,3-b]pyrazin-8-yl)piperidin-3-yl)cyclopropanecarboxamide hydrochloride): From (3R,5S)-5-methyl-1-(pyrido[2,3-b]pyrazin-8-yl)piperidin-3-amine and 1-(tert-butoxycarbonylamino)cyclopropanecarboxylic acid. HPLC: 99.8% purity, RT=0.84 min. MS: m/z=327.1 [M+H]$^+$. $^1$H NMR (300 MHz, CD$_3$OD, ppm) δ 8.99 (d, J=1.8 Hz, 1H), 8.94 (d, J=1.8 Hz, 1H), 8.44 (d, J=7.4 Hz, 1H), 7.34 (d, J=7.5 Hz, 1H), 4.15-4.00 (m, 1H), 3.36-3.13 (m, 2H), 3.13-2.99 (m, 1H), 2.13-1.86 (m, 2H), 1.67-1.27 (m, 6H), 1.06 (d, J=6.4 Hz, 3H).

Compound 31 (1-amino-N-((3R,5S)-1-(8-cyanoquinoxalin-5-yl)-5-methylpiperidin-3-yl)cyclopropanecarboxamide hydrochloride): From 8-((3R,5S)-3-amino-5-methylpiperidin-1-yl)quinoxaline-5-carbonitrile and 1-(tert-butoxycarbonylamino)cyclopropanecarboxylic acid. HPLC: 97.5% purity, RT=1.22 min. MS: m/z=351.1 [M+H]$^+$. $^1$H NMR (300 MHz, CD$_3$OD, ppm) δ 8.90 (d, J=1.7 Hz, 1H), 8.85 (d, J=1.7 Hz, 1H), 8.07 (d, J=8.4 Hz, 1H), 7.27 (d, J=8.4 Hz, 1H), 4.35-4.08 (m, 3H), 2.85-2.60 (m, 2H), 2.08-1.93 (m, 2H), 1.59-1.15 (m, 5H), 0.98 (d, J=6.3 Hz, 3H).

Compound 34 (2-amino-N-((3R,5S)-5-methyl-1-(pyrido[2,3-b]pyrazin-8-yl)piperidin-3-yl)acetamide): From (3R,5S)-5-methyl-1-(pyrido[2,3-b]pyrazin-8-yl)piperidin-3-amine and 2-(tert-butoxycarbonylamino)acetic acid. HPLC: 99.6% purity, RT=0.83 min. MS: m/z=300.9 [M+H]$^+$. $^1$H NMR (300 MHz, DMSO-d$_6$, ppm) δ 8.98 (s, 1H), 8.81 (s, 1H), 8.69 (d, J=5.3 Hz, 1H), 7.82 (d, J=7.6 Hz, 1H), 7.12 (d, J=5.4 Hz, 1H), 4.55-4.46 (m, 1H), 4.46-4.37 (m, 1H), 3.94-3.82 (m, 1H), 3.07 (s, 2H), 2.86-2.76 (m, 1H), 2.74-2.64 (m, 1H), 2.30-2.78 (m, 4H), 1.29-1.15 (m, 1H), 0.91 (d, J=6.4 Hz, 3H).

Compound 35 (2-amino-N-((3R,5S)-1-(8-cyanoquinoxalin-5-yl)-5-methylpiperidin-3-yl)acetamide hydrochloride): From 8-((3R,5S)-3-amino-5-methylpiperidin-1-yl)quinoxaline-5-carbonitrile and 2-(tert-butoxycarbonylamino)acetic acid. HPLC: 96.6% purity, RT=1.19 min. MS: m/z=325.1 [M+H]$^+$. $^1$H NMR (300 MHz, CD$_3$OD, ppm) δ 8.91 (d, J=1.7 Hz, 1H), 8.85 (d, J=1.8 Hz, 1H), 8.07 (d, J=8.4 Hz, 1H), 7.28 (d, J=8.4 Hz, 1H), 4.45-4.33 (m, 1H), 4.27-4.07 (m, 2H), 3.66 (s, 2H), 2.85-2.60 (m, 2H), 2.18-1.95 (m, 2H), 1.27-1.13 (m, 1H), 0.99 (d, J=6.4 Hz, 3H).

Compound 102 ((2R)-2-amino-N-[(3R,5S)-1-(8-cyanoquinoxalin-5-yl)-5-methylpiperidin-3-yl]-3-methylbutanamide): From (3R,5S)-5-methyl-1-(pyrido[2,3-b]pyrazin-8-yl)piperidin-3-amine and (R)-2-(ethyl(methyl)amino) propanoic acid. HPLC: 99.7% purity, RT=1.54 min. MS: m/z=367.2 [M+H]$^+$. $^1$H NMR (400 MHz, CD$_3$OD, ppm) δ 8.99-8.85 (m, 2H), 8.10 (d, J=8.4 Hz, 1H), 7.28 (d, J=8.5 Hz, 1H), 4.46-4.37 (m, 1H), 4.35-4.26 (m, 1H), 4.24-4.12 (m, 1H), 3.08 (d, J=5.9 Hz, 1H), 2.81 (t, J=11.3 Hz, 1H), 2.70 (t, J=11.3 Hz, 1H), 2.17-1.85 (m, 3H), 1.33-1.21 (m, 1H), 1.06-0.93 (m, 9H).

Compound 103 ((2S)-2-amino-N-[(3R,5S)-1-(8-cyanoquinoxalin-5-yl)-5-methylpiperidin-3-yl]-3-methylbutanamide): From (3R,5S)-5-methyl-1-(pyrido[2,3-b]pyrazin-8-yl)piperidin-3-amine and (S)-2-(ethyl(methyl)amino) propanoic acid. HPLC: 97.8% purity, RT=2.07 min. MS: m/z=367.2 [M+H]$^+$. $^1$H NMR (400 MHz, CD$_3$OD, ppm) δ 8.94-8.90 (m, 2H), 8.11 (d, J=8.4 Hz, 1H), 7.29 (d, J=8.4 Hz, 1H), 4.46-4.37 (m, 1H), 4.36-4.27 (m, 1H), 4.17 (dd, J=11.2, 7.1 Hz, 1H), 3.07 (d, J=6.0 Hz, 1H), 2.81 (t, J=11.4 Hz, 1H), 2.69 (t, J=11.8 Hz, 1H), 2.17-2.00 (m, 2H), 1.99-1.89 (m, 1H), 1.32-1.18 (m, 1H), 1.07-0.95 (m, 9H).

Compound 104 ((2R)-2-amino-3-methyl-N-[(3R,5S)-5-methyl-1-[pyrido[2,3-b]pyrazin-8-yl]piperidin-3-yl]butanamide): From (3R,5S)-5-methyl-1-(pyrido[2,3-b]pyrazin-8-yl)piperidin-3-amine and (R)-2-(tert-butoxycarbonylamino)-3-methylbutanoic acid. HPLC: 94.0% purity, RT=0.90 min. MS: m/z=343.1 [M+H]$^+$. $^1$H NMR (300 MHz, CD$_3$OD, ppm) δ 8.89 (s, 1H), 8.75 (s, 1H), 8.62 (d, J=5.6 Hz, 1H), 7.09 (d, J=5.6 Hz, 1H), 4.99-4.59 (m, 2H), 4.26-3.92 (m, 1H), 3.07-2.95 (d, J=11.5 Hz, 1H), 2.85-2.62 (m, 2H), 2.12-1.82 (m, 3H), 1.45-1.20 (m, 1H), 1.13-0.85 (m, 9H).

Compound 105 ((2S)-2-amino-3-methyl-N-[(3R,5S)-5-methyl-1-[pyrido[2,3-b]pyrazin-8-yl]piperidin-3-yl]butanamide): From (3R,5S)-5-methyl-1-(pyrido[2,3-b]pyrazin-8-yl)piperidin-3-amine and (S)-2-(tert-butoxycarbonylamino)-3-methylbutanoic acid. HPLC: 97.6% purity, RT=1.65 min. MS: m/z=343.2 [M+H]$^+$. $^1$H NMR (400 MHz, CD$_3$OD, ppm) δ 8.95 (s, 1H), 8.82 (s, 1H), 8.68 (d, J=5.6 Hz, 1H), 7.17 (d, J=5.7 Hz, 1H), 4.87 (s, 2H), 4.18-4.02 (m, 1H), 3.08 (d, J=6.0 Hz, 1H), 2.95-2.84 (m, 1H), 2.79 (t, J=12.1 Hz, 1H), 2.17-1.85 (m, 3H), 1.30 (d, J=12.0 Hz, 1H), 1.07-0.9 (m, 9H).

Compound 106 ((2R)-2-amino-N-[(3R,5S)-1-(8-cyanoquinoxalin-5-yl)-5-methylpiperidin-3-yl]-3-hydroxypropanamide): From 8-((3R,5S)-3-amino-5-methylpiperidin-1-yl)quinoxaline-5-carbonitrile and (R)-2-(tert-butoxycarbonylamino)-3-hydroxypropanoic acid. HPLC: 92.4% purity, RT=0.93 min. MS: m/z=355.2 [M+H]$^+$. $^1$H NMR (400 MHz, CD$_3$OD, ppm) δ 8.89-9.11 (m, 2H), 8.10 (d, J=12 Hz, 1H), 7.29 (d, J=12 Hz, 1H), 4.39-4.01 (m, 3H), 3.63-3.73 (m, 2H), 3.41-3.2 (m, 1H), 2.84-2.55 (m, 2H), 2.18-1.95 (m, 2H), 1.35-1.20 (m, 1H), 1.02 (d, J=8 Hz, 3H).

Compound 107 ((2R)-2-amino-3-hydroxy-N-[(3R,5S)-5-methyl-1-[pyrido[2,3-b]pyrazin-8-yl]piperidin-3-yl]propanamide): From (3R,5S)-5-methyl-1-(pyrido[2,3-b]pyrazin-8-yl)piperidin-3-amine and (R)-2-(tert-butoxycarbonylamino)-3-hydroxypropanoic acid. HPLC: 95.0% purity, RT=0.96 min. MS: m/z=331.2 [M+H]$^+$. $^1$H NMR (400 MHz, CD$_3$OD, ppm) δ 8.92 (s, 1H), 8.80 (s, 1H), 8.65 (d, J=8.0 Hz, 1H), 7.15 (d, J=8.0 Hz, 1H), 4.75-4.59 (m, 2H), 4.15-4.01 (m, 1H), 3.72-3.62 (m, 2H), 3.40-3.32 (m, 1H), 2.91-2.80 (m, 1H), 2.79-2.69 (m, 1H), 2.11 (d, J=16.0 Hz, 1H), 2.05-1.85 (m, 1H), 1.35-1.23 (m, 1H), 1.01 (d, J=8.0 Hz, 3H).

Compound 116 ((2S)-2-amino-N-[(3R,5S)-1-(8-cyanoquinoxalin-5-yl)-5-methylpiperidin-3-yl]-3-(pyridin-3-yl) propanamide): From 8-((3R,5S)-3-amino-5-methylpiperidin-1-yl)quinoxaline-5-carbonitrile and (S)-2-(tert-butoxycarbonylamino)-3-(pyridin-3-yl)propanoic acid. HPLC: 98.2% purity, RT=6.08 min. MS: m/z=416.2 [M+H]$^+$. $^1$H NMR (300 MHz, CD$_3$OD, ppm) δ 8.95-8.82 (m, 2H), 8.38 (dt, J=3.0, 1.5 Hz, 2H), 8.06 (d, J=8.4 Hz, 1H), 7.70 (dd, J=7.8, 1.9 Hz, 1H), 7.35 (dd, J=7.8, 4.9 Hz, 1H), 7.20 (d, J=8.4 Hz, 1H), 4.33-4.15 (m, 2H), 4.07-3.92 (m, 1H), 3.51 (t, J=6.9 Hz, 1H), 2.93 (d, J=6.9 Hz, 2H), 2.70-2.49 (m, 2H), 1.97 (br s, 1H), 1.82-1.77 (m, 1H), 1.06-0.87 (m, 4H).

Compound 117 ((2S)-2-amino-N-[(3R,5S)-1-(8-cyanoquinoxalin-5-yl)-5-methylpiperidin-3-yl]-2-phenylacetamide): From 8-((3R,5S)-3-amino-5-methylpiperidin-1-yl)quinoxaline-5-carbonitrile and (S)-2-(tert-butoxycarbonylamino)-2-phenylacetic acid. HPLC: 99.9% purity, RT=1.66 min. MS: m/z=401.1 [M+H]$^+$. $^1$H NMR (400 MHz, DMSO-d$_6$, ppm) δ 9.02 (d, J=1.7 Hz, 1H), 8.94 (d, J=1.8 Hz, 1H), 8.25-8.09 (m, 2H), 7.45-7.17 (m, 6H), 4.40-4.20 (m, 3H), 3.91-3.80 (m, 1H), 2.88-2.56 (m, 2H), 1.96-1.82 (m, 2H), 1.28-1.04 (m, 1H), 0.90 (d, J=6.3 Hz, 3H).

Compound 118 ((2S)-2-amino-N-[(3R,5S)-5-methyl-1-[pyrido[2,3-b]pyrazin-8-yl]piperidin-3-yl]-3-(pyridin-3-yl) propanamide): From (3R,5S)-5-methyl-1-(pyrido[2,3-b]pyrazin-8-yl)piperidin-3-amine and (S)-2-(tert-butoxycarbonylamino)-3-(pyridin-3-yl)propanoic acid. HPLC: 98.4% purity, RT=1.79 min. MS: m/z=392.2 [M+H]$^+$. $^1$H NMR (300 MHz, CD$_3$OD, ppm) δ 8.90 (d, J=1.7 Hz, 1H), 8.77 (d, J=1.7 Hz, 1H), 8.63 (d, J=5.7 Hz, 1H), 8.40-8.38 (m, 2H), 7.72-7.68 (m, 1H), 7.36 (dd, J=7.9, 4.9 Hz, 1H), 7.09 (d, J=5.7 Hz, 1H), 4.63-4.54 (m, 2H), 3.99-3.89 (m, 1H), 3.54-3.49 (m, 1H), 2.93 (d, J=6.9 Hz, 2H), 2.80-2.58 (m, 2H), 2.00-1.74 (m, 2H), 1.12-0.85 (m, 4H).

Compound 119 ((2R)-2-amino-N-[(3R,5S)-1-(8-cyanoquinoxalin-5-yl)-5-methylpiperidin-3-yl]-2-phenylacetamide): From 8-((3R,5S)-3-amino-5-methylpiperidin-1-yl)quinoxaline-5-carbonitrile and (R)-2-(tert-butoxycarbonylamino)-2-phenylacetic acid. HPLC: 97.3% purity, RT=1.87 min. MS: m/z=401.2 [M+H]$^+$. $^1$H NMR (300 MHz, CD$_3$OD, ppm) δ 9.02 (d, J=1.8 Hz, 1H), 8.92 (d, J=1.8 Hz, 1H), 8.25-8.12 (dd, J=24.8, 8.0 Hz, 2H), 7.43-7.19 (m, 6H), 4.38-4.15 (m, 3H), 3.96-3.84 (m, 1H), 2.82-2.68 (m, 2H), 1.99-1.80 (m, 2H), 1.27-1.23 (m, 1H), 0.92 (d, J=6.5 Hz, 3H).

Compound 128 (3-amino-N-[(3R,5S)-5-methyl-1-[pyrido[2,3-b]pyrazin-8-yl]piperidin-3-yl]oxetane-3-carboxamide): From (3R,5S)-5-methyl-1-(pyrido[2,3-b]pyrazin-8-yl)piperidin-3-amine and 3-((tert-butoxycarbonyl)amino)oxetane-3-carboxylic acid. HPLC: 97.4% purity, RT=0.79 min. MS: m/z=343.2 [M+H]$^+$. $^1$H NMR (300 MHz, CD$_3$OD, ppm) δ 8.90 (d, J=1.7 Hz, 1H), 8.79 (d, J=1.9 Hz, 1H), 8.63 (d, J=5.7 Hz, 1H), 7.13 (d, J=5.7 Hz, 1H), 4.73-4.55 (m, 2H), 4.20-3.50 (m, 3H), 3.00-2.68 (m, 2H), 2.20-1.85 (m, 3H), 1.70-1.58 (m, 1H), 1.40-1.10 (m, 1H), 1.00 (d, J=6.8 Hz, 3H).

Compound 129 (3-amino-N-[(3R,5S)-1-(8-cyanoquinoxalin-5-yl)-5-methylpiperidin-3-yl]oxetane-3-carboxamide): From 3-(tert-butoxycarbonylamino)oxetane-3-carboxylic acid and 8-((3R,5S)-3-amino-5-methylpiperidin-1-yl)quinoxaline-5-carbonitrile. HPLC: 99.0% purity, RT=1.05 min. MS: m/z=367.2 [M+H]$^+$. $^1$H NMR (400 MHz, CD$_3$OD, ppm) δ 8.97-8.86 (m, 2H), 8.10 (dt, J=8.6, 2.3 Hz, 1H), 7.29 (d, J=8.4 Hz, 1H), 4.39-4.09 (m, 4H), 3.99-3.74 (m, 2H), 2.96-2.80 (m, 1H), 2.79-2.63 (m, 1H), 2.18-1.85 (m, 3H), 1.38-1.21 (m, 1H), 1.04 (dd, J=6.6, 2.0 Hz, 3H).

Compound 268 (2-amino-N-[(3R,5S)-1-(8-cyanoquinoxalin-5-yl)-5-methylpiperidin-3-yl]-2-cyclopropylacetamide): From 2-(tert-butoxycarbonylamino)-2-cyclopropylacetic acid and 8-((3R,5S)-3-amino-5-methylpiperidin-1-yl)quinoxaline-5-carbonitrile. HPLC: 47.7+47.3% purity, RT=2.04+2.17 min. MS: m/z=365.2 [M+H]$^+$. $^1$H NMR (300 MHz, Chloroform-d, ppm) δ 8.93 (d, J=1.7 Hz, 1H), 8.83 (d, J=1.8 Hz, 1H), 7.99 (dd, J=8.4, 2.8 Hz, 1H), 7.21 (d, J=8.2 Hz, 1H), 4.39-4.11 (m, 3H), 3.07-2.65 (m, 3H), 2.20-1.90 (m, 4H), 1.23 (d, J=14.2 Hz, 2H), 1.15-1.01 (m, 1H), 0.96 (d, J=6.6 Hz, 3H), 0.72-0.50 (m, 3H), 0.37 (s, 1H).

Compound 277 (4-amino-N-[(3R,5S)-1-(8-cyanoquinoxalin-5-yl)-5-methylpiperidin-3-yl]-3,3-dimethylbutanamide): From 4-(tert-butoxycarbonylamino)-3,3-dimethylbutanoic acid and 8-((3R,5S)-3-amino-5-methylpiperidin-1-yl)quinoxaline-5-carbonitrile. HPLC: 93.8% purity, RT=2.08 min. MS: m/z=381.1 [M+H]$^+$. $^1$H NMR (400 MHz, CD$_3$OD, ppm) δ 8.94-8.83 (m, 2H), 8.07 (dd, J=8.3, 1.0 Hz, 1H), 7.26 (d, J=8.4 Hz, 1H), 4.42-4.24 (m, 2H), 4.13 (tt, J=10.2, 4.2 Hz, 1H), 2.80-2.60 (m, 4H), 2.23 (s, 2H), 2.13-1.97 (m, 2H), 1.27-1.12 (m, 1H), 1.10-0.92 (m, 10H).

Example 14: Synthesis of Compound 42 ((R)-3-amino-1-((3R,5S)-5-methyl-1-(pyrido[3,2-b]pyrazin-8-yl)piperidin-3-yl)pyrrolidin-2-one)

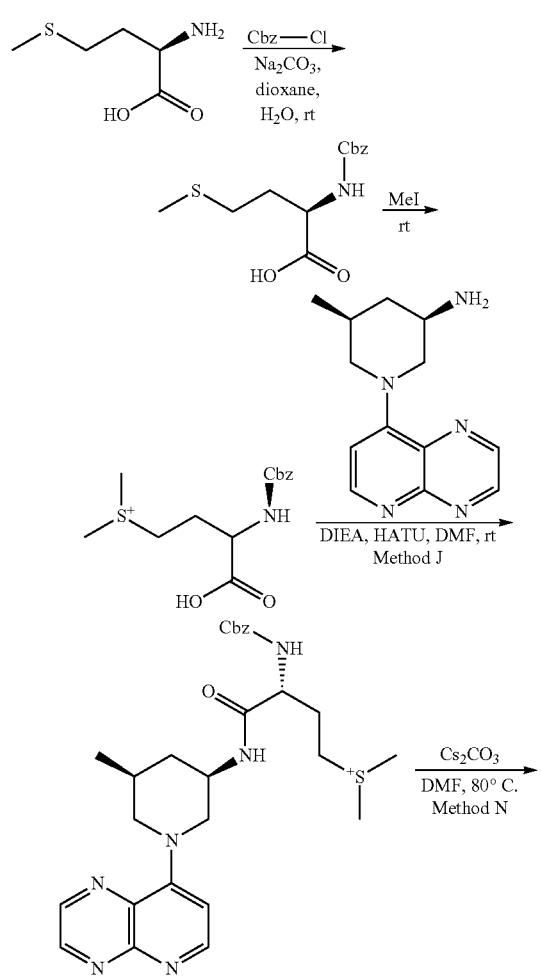

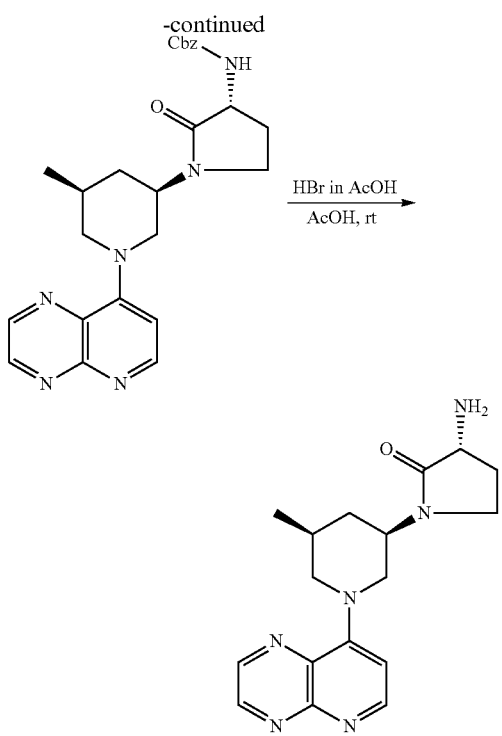

(R)-2-(benzyloxycarbonylamino)-4-(methylthio)butanoic acid: At room temperature (2R)-2-amino-4-(methylsulfanyl) butanoic acid (4.90 g, 32.84 mmol) and sodium carbonate (16.91 g, 159.54 mmol) were dissolved in water (100 mL), to which was added a solution of benzyl chloroformate (5.59 g, 32.74 mmol) in dioxane (50 mL) dropwise over 10 min period. The resulting solution was then stirred for 5 h at room temperature. When the reaction was done, it was quenched by the addition of water (100 mL). The resulting mixture was extracted with ethyl acetate (300 mL×3), and the organic phases were combined, washed with brine and dried over Na$_2$SO$_4$. The solvent was removed under reduced pressure and the residue was purified in a C18 reverse phase column eluting with acetonitrile in water (0% to 50% gradient in 30 min) to yield (2R)-2-[[(benzyloxy)carbonyl]amino]-4-(methylsulfanyl)butanoic acid as yellow oil (3.48 g, 36%).

(3-(Benzyloxycarbonylamino)-3-carboxypropyl)dimethylsulfonium: At room temperature, (2R)-2-[[(benzyloxy)carbonyl]amino]-4-(methylsulfanyl)butanoic acid (3.31 g, 11.67 mmol) was added to CH$_3$I (15 mL, 0.48 mol) slowly. The resulting solution was stirred for 15 h at room temperature. When the reaction was done, the reaction mixture was concentrated under reduced pressure to yield [(3R)-3-[[(benzyloxy)carbonyl]amino]-3-carboxypropyl]dimethylsulfanium as brown oil (3.50 g, crude). The crude was used in the next step directly without further purification.

((R)-3-(benzyloxycarbonylamino)-4-((3R,5S)-5-methyl-1-(pyrido[3,2-b]pyrazin-8-yl)piperidin-3-ylamino)-4-oxobutyl)dimethylsulfonium: ((R)-3-(benzyloxycarbonylamino)-4-((3R,5S)-5-methyl-1-(pyrido[3,2-b]pyrazin-8-yl)piperidin-3-ylamino)-4-oxobutyl)dimethylsulfonium was prepared from (3R,5S)-5-methyl-1-(pyrido[2,3-b]pyrazin-8-yl)piperidin-3-amine and (3-benzyloxycarbonylamino)-3-carboxypropyl)dimethylsulfonium using Method J to yield N-[(1R)-3-(dimethylsulfaniumyl)-1-[[(3R,5S)-5-methyl-1-[pyrido[2,3-b]pyrazin-8-yl]piperidin-3-yl]carbamoyl]propyl] carbamate as brown solid (3.10 g, crude). The crude was used in the next step directly without further purification.

Benzyl (R)-1-((3R,5S)-5-methyl-1-(pyrido[3,2-b]pyrazin-8-yl)piperidin-3-yl)-2-oxopyrrolidin-3-ylcarbamate: benzyl (R)-1-((3R,5S)-5-methyl-1-(pyrido[3,2-b]pyrazin-8-yl)piperidin-3-yl)-2-oxopyrrolidin-3-ylcarbamate was prepared from ((R)-3-(benzyloxycarbonylamino)-4-((3R,5S)-5-methyl-1-(pyrido[3,2-b]pyrazin-8-yl)piperidin-3-ylamino)-4-oxobutyl)dimethylsulfonium using Method N. The crude product was purified in a C18 reverse phase column eluting with acetonitrile in water (0% to 80% gradient in 45 min) to yield benzyl N-[(3R)-1-[(3R,5S)-5-methyl-1-[pyrido[2,3-b]pyrazin-8-yl]piperidin-3-yl]-2-oxopyrrolidin-3-yl]carbamate as yellow solid (270 mg, 5% for 3 steps).

(R)-3-amino-1-((3R,5S)-5-methyl-1-(pyrido[3,2-b]pyrazin-8-yl)piperidin-3-yl)pyrrolidin-2-one: To a solution of benzyl N-[(3R)-1-[(3R,5S)-5-methyl-1-[pyrido[2,3-b]pyrazin-8-yl]piperidin-3-yl]-2-oxopyrrolidin-3-yl]carbamate (125 mg, 0.27 mmol) in acetic acid (2 mL) was added a solution of HBr in AcOH (40%, 7 mol/L, 3 mL, 21 mmol) dropwise at room temperature. The resulting solution was stirred for 2 h at room temperature. When the reaction was done, the reaction mixture was concentrated under vacuum. The crude product was purified by prep-HPLC under the following conditions: Column, XBridge C18 OBD Prep Column, 5 um, 19 mm×150 mm; Mobile phase, MeOH in water (with 10 mmol/L NH$_4$HCO$_3$), 30% to 80% gradient in 10 min; Detector, UV 254 nm. (3R)-3-amino-1-[(3R,5S)-5-methyl-1-[pyrido[2,3-b]pyrazin-8-yl]piperidin-3-yl]pyrrolidin-2-one was obtained as brown solid (30 mg, 32%).

Compound 42: HPLC: 96.0% purity, RT=1.84 min. MS: n/z=327.1 [M+H]$^+$. $^1$H NMR (400 MHz, DMSO-d$_6$, ppm) δ 8.98 (d, J=1.7 Hz, 1H), 8.82 (d, J=1.7 Hz, 1H), 8.70 (d, J=5.3 Hz, 1H), 7.11 (d, J=5.4 Hz, 1H), 4.44 (dd, J=12.8, 3.9 Hz, 1H), 4.28-4.17 (m, 1H), 4.05-3.95 (m, 1H), 3.39-3.10 (m, 4H), 2.75-2.63 (m, 1H), 2.28-1.70 (m, 5H), 1.63-1.38 (m, 2H), 0.92 (d, J=6.5 Hz, 3H).

Example 15: Synthesis of Compound 43 ((2S,6R)-2,6-dimethyl-4-(pyrido[2,3-b]pyrazin-8-yl)morpholine)

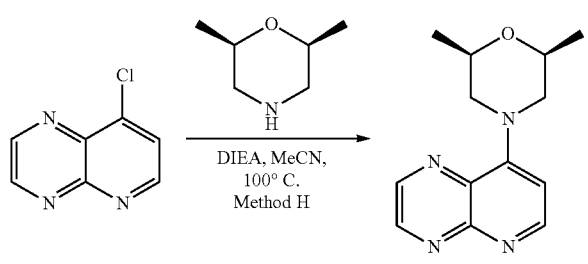

(2S,6R)-2,6-dimethyl-4-(pyrido[2,3-b]pyrazin-8-yl): (2S,6R)-2,6-dimethyl-4-(pyrido[2,3-b]pyrazin-8-yl)morpholine was prepared from 8-chloropyrido[2,3-b]pyrazine and (2R,6S)-2,6-dimethylmorpholine using Method H. The crude product was purified by prep-HPLC under the following conditions: Column, XBridge C18 OBD Prep Column, 5 um, 19 mm×150 mm; Mobile phase, MeOH in water (with 10 mmol/L NH$_4$HCO$_3$), 25% to 75% gradient in 10 min; Detector, UV 254 nm. (2R,6S)-2,6-dimethyl-4-[pyrido[2,3-b]pyrazin-8-yl]morpholine was obtained as yellow solid (30 mg, 21%).

Compound 43: HPLC: 99.0% purity, RT=0.93 min. MS: m/z=245.2 [M+H]$^+$. $^1$H NMR (300 MHz, CD$_3$OD, ppm) δ 8.91 (d, J=1.7 Hz, 1H), 8.78 (d, J=1.7 Hz, 1H), 8.66 (d, J=5.6 Hz, 1H), 7.02 (d, J=5.6 Hz, 1H), 4.52-4.41 (m, 2H), 3.97-3.83 (m, 2H), 2.84-2.68 (m, 2H), 1.22 (d, J=6.3 Hz, 6H).

Example 16: Synthesis of Compound 44 (8-((2R,6S)-2,6-dimethylmorpholino)quinoxaline-5-carbonitrile)

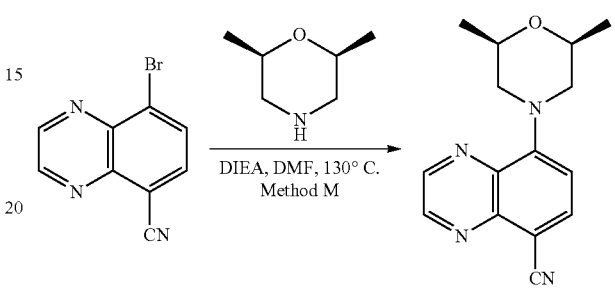

8-((2R,6S)-2,6-dimethylmorpholino)quinoxaline-5-carbonitrile: 8-((2R,6S)-2,6-dimethylmorpholino)quinoxaline-5-carbonitrile was prepared from 8-bromoquinoxaline-5-carbonitrile and (2R,6S)-2,6-dimethylmorpholine using Method M. The crude product was purified by prep-HPLC under the following conditions: Column, XBridge C18 OBD Prep Column, 5 um, 19 mm×250 mm; Mobile phase, MeOH in water (with 10 mmol/L NH$_4$HCO$_3$), 30% to 80% gradient in 10 min; Detector, UV 254 nm. 8-[(2R,6S)-2,6-dimethylmorpholin-4-yl]quinoxaline-5-carbonitrile was obtained as yellow solid (30 mg, 39%).

Compound 44: HPLC: 98.0% purity, RT=1.30 min. MS: m/z=269.2 [M+H]$^+$. $^1$H NMR (400 MHz, DMSO, ppm) δ 9.04 (d, J=1.8 Hz, 1H), 8.95 (d, J=1.8 Hz, 1H), 8.21 (d, J=8.4 Hz, 1H), 7.21 (d, J=8.4 Hz, 1H), 4.19-4.10 (m, 2H), 3.91-3.79 (m, 2H), 2.75-2.61 (m, 2H), 1.14 (d, J=6.2 Hz, 6H).

The following compound was synthesized in an analogous manner:

Compound 45 ((2S,6R)-2,6-dimethyl-4-(quinolin-4-yl)morpholine): From 4-chloroquinoline and (2R,6S)-2,6-dimethylmorpholine. HPLC: 99.9% purity, RT=1.33 min. MS: m/z=243.2 [M+H]$^+$. $^1$H NMR (300 MHz, CD$_3$OD, ppm) δ 8.60 (d, J=5.2 Hz, 1H), 8.06 (dd, J=8.6, 1.5 Hz, 1H), 7.93 (d, J=8.5 Hz, 1H), 7.73-7.63 (m, 1H), 7.57-7.47 (m, 1H), 6.97 (dd, J=5.3, 1.8 Hz, 1H), 4.06-3.94 (m, 2H), 3.47 (d, J=11.7 Hz, 2H), 2.64-2.50 (m, 2H), 1.21 (dd, J=6.3, 1.1 Hz, 6H).

Example 17: Synthesis of Compound 46 ((2S,6R)-4-(1,2-dimethyl-1H-pyrrolo[2,3-b]pyridin-4-yl)-2,6-dimethylmorpholine)

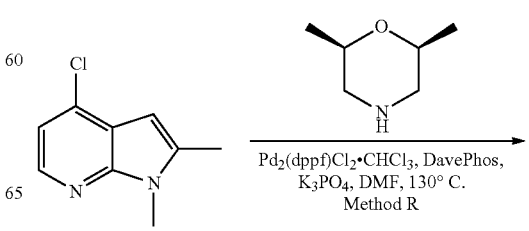

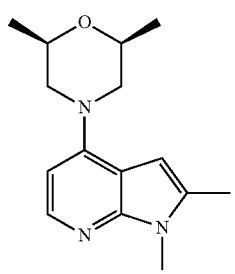

(2S,6R)-4-(1,2-dimethyl-1H-pyrrolo[2,3-b]pyridin-4-yl)-2,6-dimethylmorpholine: (2S,6R)-4-(1,2-dimethyl-1H-pyrrolo[2,3-b]pyridin-4-yl)-2,6-dimethylmorpholine was prepared from 4-chloro-1,2-dimethyl-1H-pyrrolo[2,3-b]pyridine and (2R,6S)-2,6-dimethylmorpholine using Method R. The Column, 5 um, 19 mm×250 mm; Mobile phase, MeOH in water (with 10 mmol/L NH$_4$HCO$_3$), 25% to 70% gradient in 10 min; Detector, UV 254 nm. (2R,6S)-4-[1,2-dimethyl-1H-pyrrolo[2,3-b]pyridin-4-yl]-2,6-dimethylmorpholine was obtained as white solid (32 mg, 12%).

Compound 46: HPLC: 95.0% purity, RT=1.88 min. MS: n/z=260.1 [M+H]$^+$. $^1$H NMR (300 MHz, CD$_3$OD, ppm) δ 7.88 (d, J=5.7 Hz, 1H), 6.44 (d, J=5.7 Hz, 1H), 6.22 (s, 1H), 3.92-3.74 (m, 4H), 3.67 (s, 3H), 2.63-2.48 (m, 2H), 2.40 (s, 3H), 1.21 (d, J=6.2 Hz, 6H).

Example 18: Synthesis of Compound 47 ((2R,6S)-2-methyl-6-((4-methylpiperazin-1-yl)methyl)-4-(pyrido[2,3-b]pyrazin-8-yl)morpholine)

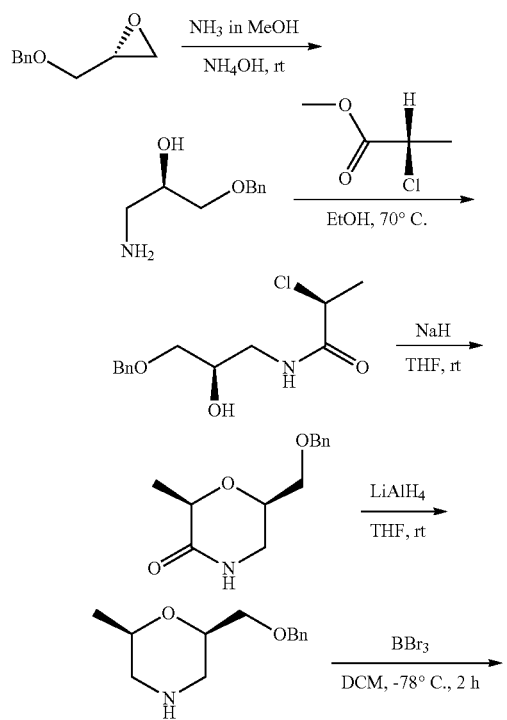

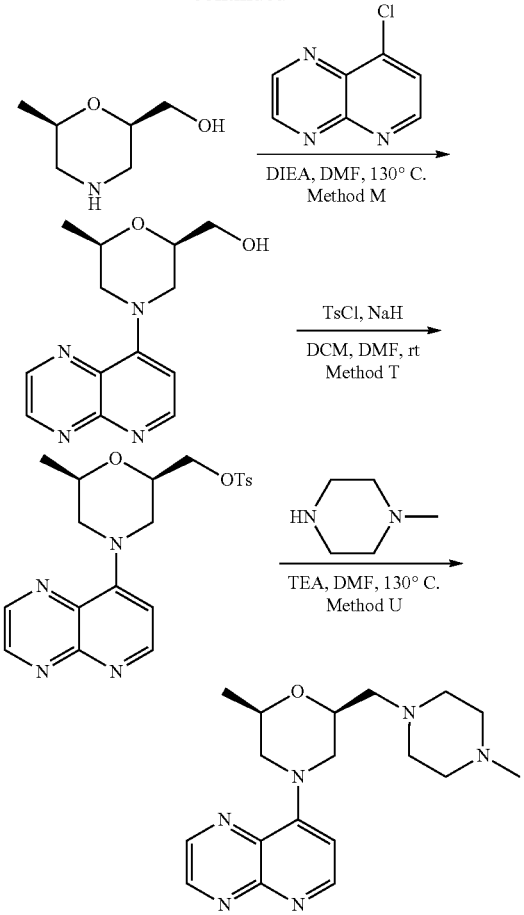

(R)-1-amino-3-(benzyloxy)propan-2-ol: At room temperature, to a solution of (2R)-2-[(benzyloxy)methyl]oxirane (5.22 g, 31.82 mmol) in ethanol (25 mL) was added a solution of NH$_3$ in MeOH (25 mL, 7M, 175 mmol) and NH$_3$.H$_2$O (28%, 14.8 mol/L, 53 mL, 0.78 mol) in sequence. The resulting solution was stirred for 16 h at room temperature. When the reaction was done, the reaction mixture was concentrated under reduced pressure to yield (2R)-1-amino-3-(benzyloxy)propan-2-ol as colorless oil (6.2 g, crude).

(R)-1-amino-3-(benzyloxy)propan-2-ol: To a solution of (2R)-1-amino-3-(benzyloxy)propan-2-ol (6.20 g, crude) in ethanol (50 mL) was added methyl (2S)-2-chloropropanoate (3.33 g, 54.42 mmol) at room temperature. The resulting solution was stirred for 20 h at 70° C. After cooling to room temperature, the reaction mixture was concentrated under reduced pressure and the residue was purified by flash chromatography eluting with EtOAc in petroleum ether (0% to 50% gradient) to yield (2S)—N-[(2R)-3-(benzyloxy)-2-hydroxypropyl]-2-chloropropanamide as light yellow oil (5.65 g, 65% for 2 steps).

(2R,6R)-6-(benzyloxymethyl)-2-methylmorpholin-3-one: To a solution of (2S)—N-[(2R)-3-(benzyloxy)-2-hydroxypropyl]-2-chloropropanamide (4.12 g, 15.18 mmol) in tetrahydrofuran (30 mL) was added sodium hydride (1.02 g, 42.50 mmol) in portions at room temperature. The resulting mixture was stirred for 2 h at room temperature. When the reaction was done, it was quenched by the addition of water (30 mL) slowly. The mixture was extracted with ethyl acetate (100 mL×3), and the organic phases were combined, washed with brine and dried over Na$_2$SO$_4$. The solvent was removed under reduced pressure and the residue was purified by flash chromatography eluting with EtOAc in petroleum ether (0% to 100% gradient) to yield (2R,6R)-6-[(benzyloxy)methyl]-2-methylmorpholin-3-one as light yellow oil (2.68 g, 75%).

(2R,6R)-2-(benzyloxymethyl)-6-methylmorpholine: To a solution of (2R,6R)-6-[(benzyloxy)methyl]-2-methylmorpholin-3-one (5.40 g, 22.93 mmol) in tetrahydrofuran (50 mL) was added LiAlH₄ (2.00 g, 52.56 mmol) in portions at room temperature. The resulting mixture was stirred for 2 h at room temperature. When the reaction was done, it was quenched by the addition of water (40 mL). The resulting mixture was extracted with ethyl acetate (100 mL×3), and the organic phases were combined, washed with brine and dried over Na₂SO₄. The solvent was removed under reduced pressure to yield (2R,6R)-2-[(benzyloxy)methyl]-6-methylmorpholine as light yellow oil (5.40 g, crude).

((2R,6R)-6-methylmorpholin-2-yl)methanol: At −78° C., to a solution of (2R,6R)-2-[(benzyloxy)methyl]-6-methylmorpholine (1.00 g, crude) in dichloromethane (20 mL) was added a solution of BBr₃ in dichloromethane (5 mL, 3 M, 15.00 mmol) dropwise over 10 min period. The resulting solution was then stirred for 3 h at −78° C. When the reaction was done, it was quenched by the addition of NaOH solution (1M, 15 mL) slowly. The resulting mixture was extracted with dichloromethane (60 mL×3), and the organic phases were combined, washed with brine and dried over Na₂SO₄. The solvent was removed under reduced pressure to yield [(2R,6R)-6-methylmorpholin-2-yl]methanol as white solid (500 mg, crude).

((2R,6R)-6-methyl-4-(pyrido[2,3-b]pyrazin-8-yl)morpholin-2-yl)methanol: ((2R,6R)-6-methyl-4-(pyrido[2,3-b]pyrazin-8-yl)morpholin-2-yl)methanol was prepared from ((2R,6R)-6-methylmorpholin-2-yl)methanol and 8-chloropyrido[2,3-b]pyrazine using Method M. The crude product was purified by flash chromatography eluting with EtOAc in petroleum ether (0% to 50% gradient) to yield [(2R,6R)-6-methyl-4-[pyrido[2,3-b]pyrazin-8-yl]morpholin-2-yl]methanol as yellow oil (2.00 g, 28% for 3 steps).

Method T ((2R,6R)-6-methyl-4-(pyrido[2,3-b]pyrazin-8-yl)morpholin-2-yl)methyl 4-methylbenzenesulfonate: At 5° C., to a solution of [(2R,6R)-6-methyl-4-[pyrido[2,3-b]pyrazin-8-yl]morpholin-2-yl]methanol (638 mg, 2.45 mmol) in N,N-dimethylformamide (30 mL) was added sodium hydride (203 mg, 8.45 mmol) in portions. The resulting mixture was stirred for 10 min at 5° C., and then was added by a solution of 4-methylbenzene-1-sulfonyl chloride (926 mg, 4.86 mmol) in dichloromethane (3 mL) dropwise over 5 min period. The reaction mixture was then stirred for 8 h at room temperature. When the reaction was done, it was quenched by the addition of water (50 mL). The mixture was extracted with ethyl acetate (100 mL×3), and the organic phases were combined, washed with brine and dried over Na₂SO₄. The solvent was removed under reduced pressure to yield [(2R,6R)-6-methyl-4-[pyrido[2,3-b]pyrazin-8-yl]morpholin-2-yl]methyl 4-methylbenzene-1-sulfonate as yellow solid (600 mg, crude).

Method U (2R,6S)-2-methyl-6-((4-methylpiperazin-1-yl)methyl)-4-(pyrido[2,3-b]pyrazin-8-yl)morpholine: To a solution of [(2R,6R)-6-methyl-4-[pyrido[2,3-b]pyrazin-8-yl]morpholin-2-yl]methyl 4-methylbenzene-1-sulfonate (60 mg, crude) in N,N-dimethylformamide (5 mL) were added 1-methylpiperazine (21 mg, 0.21 mmol) and TEA (42 mg, 0.41 mmol) at room temperature. The resulting solution was stirred for 10 h at 130° C. After cooling to room temperature, the reaction mixture was diluted with water (10 mL) and was extracted with DCM (30 mL×3). The organic phases were combined, washed with brine and dried over Na₂SO₄. The solvent was removed under reduced pressure and the residue was purified by prep-HPLC under the following conditions: Column, SunFire Prep C18 OBD Column, 19×150 mm 5 um 10 nm; Mobile phase, MeOH in water (with 10 mmol/L NH₄HCO₃), 25% to 75% gradient in 10 min; Detector, UV 254 nm. (2R,6S)-2-methyl-6-[(4-methylpiperazin-1-yl)methyl]-4-[pyrido[2,3-b]pyrazin-8-yl]morpholine was obtained as yellow solid (30 mg, 36% 2 for steps).

Compound 47: HPLC: 94.7% purity, RT=1.41 min. MS: m/z=343.3 [M+H]⁺. ¹H NMR (300 MHz, CD₃OD, ppm) δ 8.92 (d, J=1.7 Hz, 1H), 8.78 (d, J=1.7 Hz, 1H), 8.67 (d, J=5.6 Hz, 1H), 7.04 (d, J=5.6 Hz, 1H), 4.65-4.53 (m, 1H), 4.47-4.37 (m, 1H), 4.10-3.85 (m, 2H), 2.85-2.39 (m, 11H), 2.35-2.25 (m, 4H), 1.23 (d, J=6.2 Hz, 3H).

Example 19: Synthesis of Compound 48 ((2R,6S)-2-methyl-6-(piperazin-1-ylmethyl)-4-(pyrido[2,3-b]pyrazin-8-yl)morpholine)

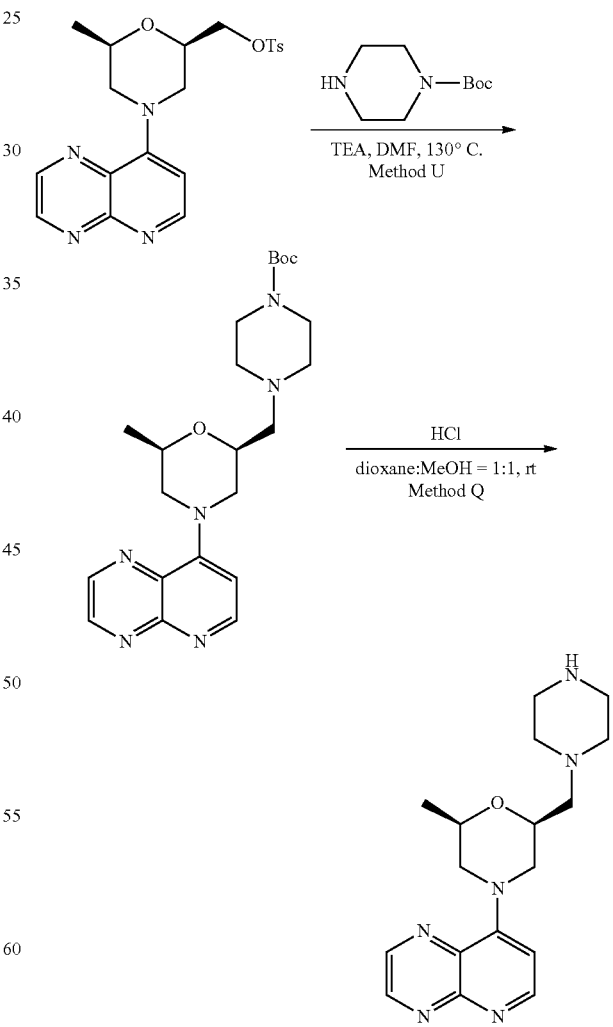

(2R,6S)-2-methyl-6-(piperazin-1-ylmethyl)-4-(pyrido[2,3-b]pyrazin-8-yl)morpholine: (2R,6S)-2-methyl-6-(piperazin-1-ylmethyl)-4-(pyrido[2,3-b]pyrazin-8-yl)morpholine was prepared from ((2R,6R)-6-methyl-4-(pyrido[2,3-b]pyrazin-8-yl)morpholin-2-yl)methyl 4-methylbenzenesulfonate and tert-butyl piperazine-1-carboxylate using Method U and Q. The crude product was purified by prep-HPLC under the following conditions: Column, XBridge C18 OBD Prep Column, 5 um, 19 mm×150 mm; Mobile phase, MeOH in water (with 0.02% v/v HCl), 3% to 8% gradient in 10 min; Detector, UV 254 nm. (2R,6S)-2-methyl-6-(piperazin-1-ylmethyl)-4-[pyrido[2,3-b]pyrazin-8-yl]morpholine was obtained as light brown solid (15 mg, 22% for 2 steps).

Compound 48: HPLC: 99.5% purity, RT=0.92 min. MS: n/z=329.3 [M+H]$^+$. $^1$H NMR (300 MHz, CD$_3$OD, ppm) δ 8.92 (d, J=1.7 Hz, 1H), 8.78 (d, J=1.8 Hz, 1H), 8.67 (d, J=5.6 Hz, 1H), 7.04 (d, J=5.6 Hz, 1H), 4.64-4.52 (m, 1H), 4.47-4.37 (m, 1H), 4.12-3.83 (m, 2H), 2.95-2.40 (m, 12H), 1.23 (d, J=6.2 Hz, 3H).

Example 20: Synthesis of Compound 49 ((2R,6S)-2-methyl-6-(piperazin-1-ylmethyl)-4-(quinolin-5-yl)morpholine)

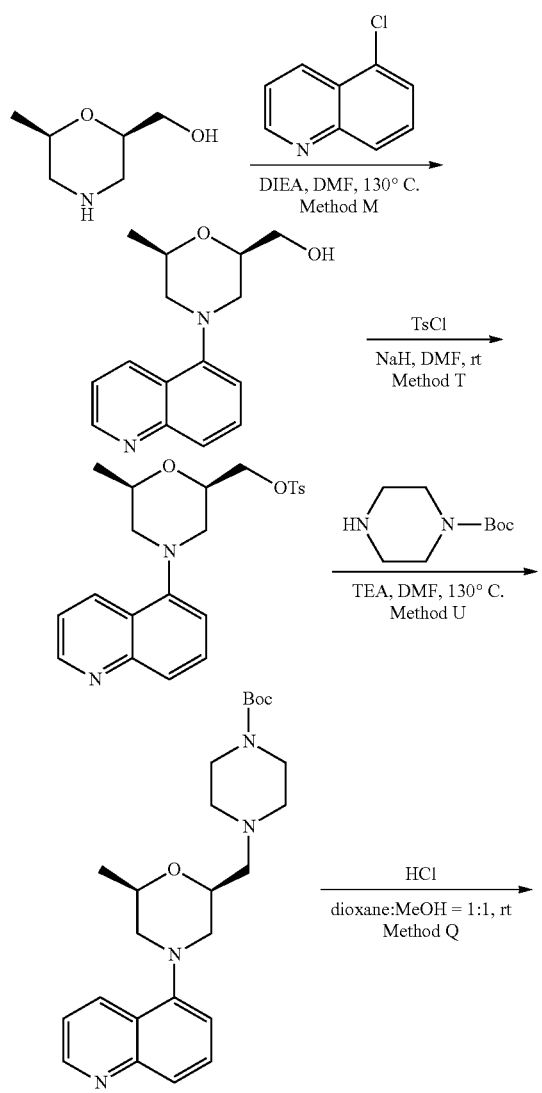

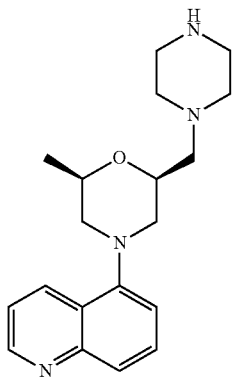

(2R,6S)-2-methyl-6-(piperazin-1-ylmethyl)-4-(quinolin-5-yl)morpholine: (2R,6S)-2-methyl-6-(piperazin-1-ylmethyl)-4-(quinolin-5-yl)morpholine was prepared from ((2R,6R)-6-methylmorpholin-2-yl)methanol, 5-chloroquinoline, 4-methylbenzene-1-sulfonyl chloride, and tert-butyl piperazine-1-carboxylate using Method M, T, U, and Q. The crude product was purified by prep-HPLC under the following conditions: Column, XBridge C18 OBD Prep Column, 5 um, 19 mm×150 mm; Mobile phase, MeOH in water (with 10 mmol/L NH$_4$HCO$_3$), 30% to 80% gradient in 10 min; Detector, UV 254 nm. 4-[(2R,6S)-2-methyl-6-(piperazin-1-ylmethyl)morpholin-4-yl]quinoline was obtained as off-white solid (35 mg, 15% for 4 steps).

Compound 49: HPLC: 95.1% purity, RT=0.53 min. MS: n/z=327.2 [M+H]$^+$. $^1$H NMR (300 MHz, CD$_3$OD, ppm) δ 8.61 (d, J=5.1 Hz, 1H), 8.13-8.03 (m, 1H), 7.98-7.88 (m, 1H), 7.74-7.64 (m, 1H), 7.58-7.48 (m, 1H), 6.99 (d, J=5.2 Hz, 1H), 4.20-3.94 (m, 2H), 3.72-3.32 (m, 2H), 2.92-2.82 (m, 4H), 2.75-2.38 (m, 8H), 1.22 (d, J=6.2 Hz, 3H).

Example 21: Synthesis of Compound 50 (8-((2R,6S)-2-methyl-6-((4-methylpiperazin-1-yl)methyl)morpholino)quinoxaline-5-carbonitrile)

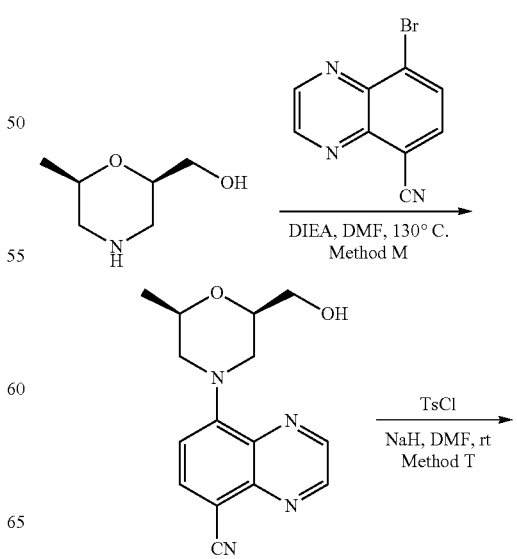

419

-continued

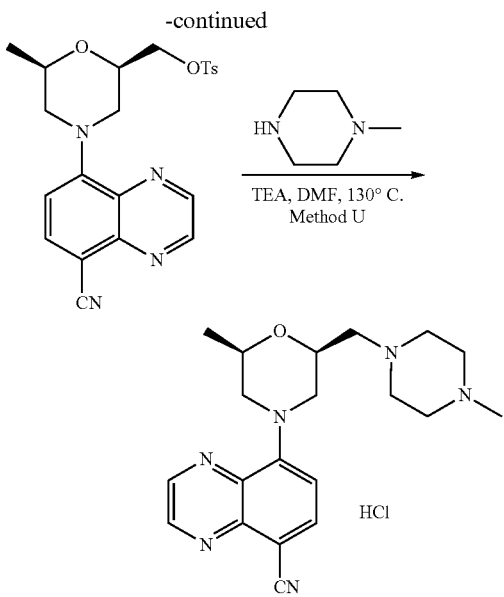

8-((2R,6S)-2-methyl-6-((4-methylpiperazin-1-yl)methyl)morpholino)quinoxaline-5-carbonitrile hydrochloride: 8-((2R,6S)-2-methyl-6-((4-methylpiperazin-1-yl)methyl)morpholino)quinoxaline-5-carbonitrile hydrochloride was prepared from ((2R,6R)-6-methylmorpholin-2-yl)methanol, 8-bromoquinoxaline-5-carbonitrile, 4-methylbenzene-1-sulfonyl chloride and 1-methylpiperazine using Method M, T, and U. The crude product was purified by prep-HPLC under the following conditions: Column, XBridge C18 OBD Prep Column, 5 um, 19 mm×150 mm; Mobile phase, MeOH in water (with 0.02% v/v HCl), 15% to 40% gradient in 10 min; Detector, UV 254 nm. 8-((2R,6S)-2-methyl-6-((4-methylpiperazin-1-yl)methyl)morpholino)quinoxaline-5-carbonitrile hydrochloride was obtained as black solid (50 mg, 20% for 3 steps).

Compound 50: HPLC: 98.5% purity, RT=1.48 min. MS: n/z=367.2 [M+H]$^+$. $^1$H NMR (300 MHz, CD$_3$OD, ppm) δ 8.92 (d, J=1.8 Hz, 1H), 8.85 (d, J=1.8 Hz, 1H), 8.08 (d, J=8.3 Hz, 1H), 7.20 (d, J=8.4 Hz, 1H), 4.57-4.39 (m, 1H), 4.30-4.20 (m, 1H), 4.18-3.40 (m, 12H), 3.02 (s, 3H), 2.90-2.74 (m, 2H), 1.30 (d, J=6.1 Hz, 3H).

Example 22: Synthesis of Compound 51 ((2R,6S)-2-methyl-6-((4-methylpiperazin-1-yl)methyl)-4-(quinolin-5-yl)morpholine)

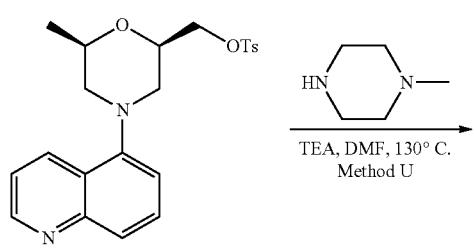

420

-continued (2R,6S)-2-methyl-6-((4-methylpiperazin-1-yl)methyl)-4-(quinolin-5-yl)morpholine: (2R,6S)-2-methyl-6-((4-methylpiperazin-1-yl)methyl)-4-(quinolin-5-yl)morpholine was prepared from ((2R,6R)-6-methyl-4-(quinolin-5-yl)morpholin-2-yl)methyl 4-methylbenzenesulfonate and 1-methylpiperazine using Method U. The crude product was purified by prep-HPLC under the following conditions: Column, XBridge C18 OBD Prep Column, 5 um, 19 mm×150 mm; Mobile phase, MeOH in water (with 10 mmol/L NH$_4$HCO$_3$), 20% to 40% gradient in 8 min; Detector, UV 254 nm. 4-[(2R,6S)-2-methyl-6-[(4-methylpiperazin-1-yl)methyl]morpholin-4-yl]quinoline was obtained as light brown solid (45 mg, 55%).

Compound 51: HPLC: 99.9% purity, RT=1.10 min. MS: m/z=341.3 [M+H]$^+$. $^1$H NMR (300 MHz, CD$_3$OD, ppm) δ 8.61 (d, J=5.1 Hz, 1H), 8.13-8.03 (m, 1H), 8.01-7.88 (m, 1H), 7.77-7.61 (m, 1H), 7.59-7.47 (m, 1H), 6.99 (d, J=5.1 Hz, 1H), 4.19-3.94 (m, 2H), 3.62-3.42 (m, 2H), 2.84 (s, 2H), 2.70-2.36 (m, 10H), 2.26 (s, 3H), 1.22 (d, J=6.2 Hz, 3H).

The following compounds were synthesized in an analogous manner:

Compound 52 ((2R,6S)-2-methyl-6-((4-propylpiperazin-1-yl)methyl)-4-(pyrido[2,3-b]pyrazin-8-yl)morpholine): From ((2R,6R)-6-methyl-4-(pyrido[2,3-b]pyrazin-8-yl)morpholin-2-yl)methyl 4-methylbenzenesulfonate and 1-propylpiperazine. HPLC: 96.3% purity, RT=0.99 min. MS: m/z=371.30 [M+H]$^+$. $^1$H NMR (300 MHz, CD$_3$OD, ppm) δ 8.92 (d, J=1.7 Hz, 1H), 8.77 (d, J=1.7 Hz, 1H), 8.67 (d, J=5.6 Hz, 1H), 7.03 (d, J=5.6 Hz, 1H), 4.64-4.52 (m, 1H), 4.47-4.35 (m, 1H), 4.11-3.83 (m, 2H), 2.88-2.25 (m, 14H), 1.62-1.43 (m, 2H), 1.23 (d, J=6.2 Hz, 3H), 0.90 (t, J=7.4 Hz, 3H).

Compound 53 ((2S,6R)-2-(((S)-3,4-dimethylpiperazin-1-yl)methyl)-6-methyl-4-(pyrido[2,3-b]pyrazin-8-yl)morpholine): From ((2R,6R)-6-methyl-4-(pyrido[2,3-b]pyrazin-8-yl)morpholin-2-yl)methyl 4-methylbenzenesulfonate and (S)-1,2-dimethylpiperazine hydrochloride. HPLC: 97.8% purity, RT=0.86 min. MS: m/z=357.3 [M+H]$^+$. $^1$H NMR (300 MHz, CD$_3$OD, ppm) δ 8.92 (d, J=1.7 Hz, 1H), 8.78 (d, J=1.8 Hz, 1H), 8.67 (d, J=5.5 Hz, 1H), 7.04 (d, J=5.6 Hz, 1H), 4.68-4.52 (m, 1H), 4.49-4.37 (m, 1H), 4.11-3.85 (m, 2H), 2.98 (d, J=15.9 Hz, 1H), 2.89-2.70 (m, 4H), 2.59-2.20 (m, 8H), 2.06-1.92 (m, 1H), 1.23 (d, J=6.3 Hz, 3H), 1.06 (d, J=6.3 Hz, 3H).

Compound 54 ((2R,6S)-2-methyl-4-(pyrido[2,3-b]pyrazin-8-yl)-6-((3,3,4-trimethylpiperazin-1-yl)methyl)morpholine): From ((2R,6R)-6-methyl-4-(pyrido[2,3-b]pyrazin-8-yl)morpholin-2-yl)methyl 4-methylbenzenesulfonate and 1,2,2-trimethylpiperazine. HPLC: 98.2% purity, RT=1.63 min. MS: m/z=371.3 [M+H]$^+$. $^1$H NMR (300 MHz, CD$_3$OD, ppm) δ 8.92 (d, J=1.7 Hz, 1H), 8.77 (d, J=1.8 Hz, 1H), 8.67 (d, J=5.6 Hz, 1H), 7.02 (d, J=5.6 Hz, 1H), 4.81-4.67 (m, 1H), 4.41-4.29 (m, 1H), 4.05-3.82 (m, 2H), 2.89-2.15 (m, 13H), 1.22 (d, J=6.3 Hz, 3H), 1.08 (s, 6H).

Compound 55 (N,N-dimethyl-1-(((2S,6R)-6-methyl-4-(pyrido[2,3-b]pyrazin-8-yl)morpholin-2-yl)methyl)piperidin-4-amine): From ((2R,6R)-6-methyl-4-(pyrido[2,3-b]pyrazin-8-yl)methyl 4-methylbenzenesulfonate and N,N-dimethylpiperidin-4-amine. HPLC: 93.3% purity, RT=0.83 min. MS: m/z=371.3 [M+H]+. 1H NMR (300 MHz, CD3OD, ppm) δ 8.92 (d, J=1.7 Hz, 1H), 8.78 (d, J=1.8 Hz, 1H), 8.67 (d, J=5.6 Hz, 1H), 7.03 (d, J=5.6 Hz, 1H), 4.64-4.52 (m, 1H), 4.48-4.36 (m, 1H), 4.09-3.83 (m, 2H), 3.24-3.08 (m, 1H), 3.02 (d, J=11.2 Hz, 1H), 2.85-2.73 (m, 2H), 2.60-2.39 (m, 2H), 2.35-1.99 (m, 9H), 1.92-1.78 (m, 2H), 1.63-1.49 (m, 2H), 1.23 (d, J=6.2 Hz, 3H).

Compound 56 ((2R,6S)-2-methyl-4-(pyrido[2,3-b]pyrazin-8-yl)-6-((4-(pyrrolidin-1-yl)piperidin-1-yl)methyl)morpholine): From ((2R,6R)-6-methyl-4-(pyrido[2,3-b]pyrazin-8-yl)morpholin-2-yl)methyl 4-methylbenzenesulfonate and 4-(pyrrolidin-1-yl)piperidine. HPLC: 98.8% purity, RT=0.90 min. MS: m/z=397.3 [M+H]+. 1H NMR (300 MHz, CD3OD, ppm) δ 8.92 (d, J=1.7 Hz, 1H), 8.78 (d, J=1.8 Hz, 1H), 8.67 (d, J=5.6 Hz, 1H), 7.03 (d, J=5.6 Hz, 1H), 4.66-4.54 (m, 1H), 4.47-4.35 (m, 1H), 4.09-3.83 (m, 2H), 3.19-3.06 (m, 1H), 3.04-2.91 (m, 1H), 2.87-2.71 (m, 2H), 2.70-2.39 (m, 6H), 2.22-1.86 (m, 5H), 1.88-1.72 (m, 4H), 1.68-1.47 (m, 2H), 1.23 (d, J=6.2 Hz, 3H).

Compound 57 (8-((2R,6S)-2-methyl-6-((4-(pyrrolidin-1-yl)piperidin-1-yl)methyl)morpholino)quinoxaline-5-carbonitrile): From ((2R,6R)-4-(8-cyanoquinoxalin-5-yl)-6-methylmorpholin-2-yl)methyl 4-methylbenzenesulfonate and 4-(pyrrolidin-1-yl)piperidine. HPLC: 97.4% purity, RT=2.24 min. MS: m/z=421.2 [M+H]+. 1H NMR (300 MHz, CD3OD, ppm) δ 8.98 (d, J=1.8 Hz, 1H), 8.84 (s, 1H), 8.03 (d, J=8.3 Hz, 1H), 7.06 (d, J=8.3 Hz, 1H), 4.24 (d, J=12.2 Hz, 1H), 4.13-3.97 (m, 3H), 3.08 (s, 1H), 2.91 (s, 1H), 2.80-2.40 (m, 6H), 2.20-1.40 (m, 13H), 1.27 (d, J=6.2 Hz, 3H).

Compound 58 ((2S,6R)-2-(1,4'-bipiperidin-1'-ylmethyl)-6-methyl-4-(pyrido[2,3-b]pyrazin-8-yl)morpholine): From ((2R,6R)-6-methyl-4-(pyrido[2,3-b]pyrazin-8-yl)morpholin-2-yl)methyl 4-methylbenzenesulfonate and 1,4'-bipiperidine. HPLC: 94.8% purity, RT=1.11 min. MS: m/z=411.3 [M+H]+. 1H NMR (300 MHz, CD3OD, ppm) δ 8.92 (d, J=1.8 Hz, 1H), 8.78 (d, J=1.8 Hz, 1H), 8.67 (d, J=5.5 Hz, 1H), 7.03 (d, J=5.6 Hz, 1H), 4.64-4.50 (m, 1H), 4.49-4.35 (m, 1H), 4.09-3.85 (m, 2H), 3.25-2.97 (m, 2H), 2.86-2.72 (m, 2H), 2.65-2.29 (m, 6H), 2.15-1.80 (m, 4H), 1.69-1.41 (m, 9H), 1.23 (d, J=6.2 Hz, 3H).

Compound 59 (8-((2S,6R)-2-(1,4'-bipiperidin-1'-ylmethyl)-6-methylmorpholino)quinoxaline-5-carbonitrile): From ((2R,6R)-4-(8-cyanoquinoxalin-5-yl)-6-methylmorpholin-2-yl)methyl 4-methylbenzenesulfonate and 1,4'-bipiperidine. HPLC: 98.8% purity, RT=0.72 min. MS: n/z=435.2 [M+H]+. 1H NMR (300 MHz, CD3OD, ppm) δ 8.92 (d, J=1.7 Hz, 1H), 8.85 (d, J=1.8 Hz, 1H), 8.09 (d, J=8.4 Hz, 1H), 7.18 (d, J=8.4 Hz, 1H), 4.28-3.90 (m, 4H), 3.25-3.15 (m, 1H), 3.10-3.00 (m, 1H), 2.80-2.35 (m, 9H), 2.20-1.80 (m, 4H), 1.70-1.40 (m, 8H), 1.22 (d, J=6.2 Hz, 3H).

Compound 60 ((2R,6S)-2-methyl-6-((4-morpholinopiperidin-1-yl)methyl)-4-(pyrido[2,3-b]pyrazin-8-yl)morpholine): From ((2R,6R)-6-methyl-4-(pyrido[2,3-b]pyrazin-8-yl)morpholin-2-yl)methyl 4-methylbenzenesulfonate and 4-(piperidin-4-yl)morpholine. HPLC: 96.3% purity, RT=1.85 min. MS: n/z=413.3 [M+H]+. 1H NMR (300 MHz, CD3OD, ppm) δ 8.92 (d, J=1.7 Hz, 1H), 8.78 (d, J=1.7 Hz, 1H), 8.67 (d, J=5.6 Hz, 1H), 7.03 (d, J=5.6 Hz, 1H), 4.65-4.43 (m, 1H), 4.47-4.35 (m, 1H), 4.10-3.83 (m, 2H), 3.72-3.63 (m, 4H), 3.24-3.10 (m, 1H), 3.09-2.98 (m, 1H), 2.88-2.70 (m, 2H), 2.61-2.41 (m, 6H), 2.27-2.01 (m, 3H), 1.96-1.82 (m, 2H), 1.62-1.44 (m, 2H), 1.23 (d, J=6.2 Hz, 3H).

Compound 467 (8-[(2R,6S)-2-methyl-6-{[4-(morpholin-4-yl)piperidin-1-yl]methyl}morpholin-4-yl]quinoxaline-5-carbonitrile: From [(2R,6R)-4-(8-cyanoquinoxalin-5-yl)-6-methylmorpholin-2-yl]methyl 4-methylbenzyne-1-sulfonate and 4-(piperidin-4-yl)morpholine. HPLC: 99.8% purity, RT=1.46 min. MS: m/z=437.3 [M+H]+. 1H NMR (400 MHz, CD3OD, ppm) δ 8.97 (d, J=1.8 Hz, 1H), 8.90 (d, J=1.8 Hz, 1H), 8.14 (d, J=8.3 Hz, 1H), 7.23 (d, J=8.4 Hz, 1H), 4.28 (dt, J=12.2, 2.3 Hz, 1H), 4.19-4.08 (m, 2H), 4.01 (ddd, J=10.3, 6.4, 2.5 Hz, 1H), 3.76-3.69 (m, 4H), 3.22 (d, J=12.0 Hz, 1H), 3.07 (d, J=11.6 Hz, 1H), 2.75 (ddd, J=12.5, 10.3, 2.7 Hz, 2H), 2.64-2.45 (m, 6H), 2.28-2.07 (m, 3H), 1.93 (d, J=9.9 Hz, 2H), 1.66-1.54 (m, 2H), 1.27 (d, J=6.2 Hz, 3H).

Example 23: Synthesis of Compound 61 (N-(1-(((2S,6R)-6-methyl-4-(pyrido[2,3-b]pyrazin-8-yl)morpholin-2-yl)methyl)piperidin-4-yl)isobutyramide)

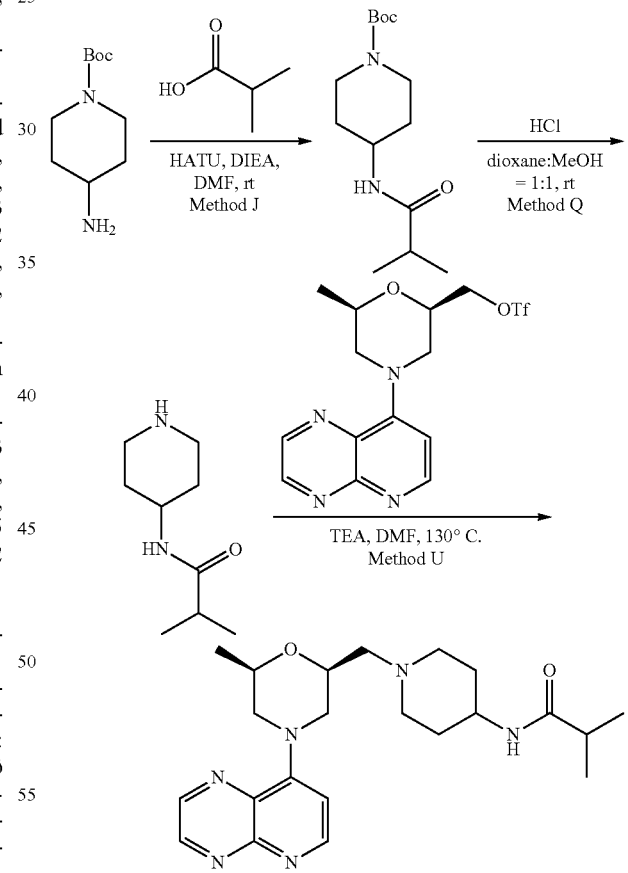

N-(1-(((2S,6R)-6-methyl-4-(pyrido[2,3-b]pyrazin-8-yl)morpholin-2-yl)methyl)piperidin-4-yl)isobutyramide: N-(1-(((2S,6R)-6-methyl-4-(pyrido[2,3-b]pyrazin-8-yl)morpholin-2-yl)methyl)piperidin-4-yl)isobutyramide was prepared from tert-butyl 4-aminopiperidine-1-carboxylate, isobutyric acid, and ((2R,6R)-6-methyl-4-(pyrido[2,3-b]pyrazin-8-yl)morpholin-2-yl)methyl trifluoromethanesulfonate using Method J, Q, and U. The crude product was purified by prep-HPLC under the following conditions: Column, XBridge C18 OBD Prep Column, 5 um, 19 mm×150 mm; Mobile phase, MeOH in water (with 10 mmol/L NH₄HCO₃), 30% to 80% gradient in 8 min; Detector, UV 254 nm. (2R,6S)-2-methyl-6-[[4-(morpholin-4-yl)piperidin-1-yl]methyl]-4-[pyrido[2,3-b]pyrazin-8-yl]morpholine was obtained as yellow solid (15 mg, 1.4%).

Compound 61: HPLC: 96.6% purity, RT=1.21 min. MS: m/z=413.3 [M+H]⁺. ¹H NMR (300 MHz, CD₃OD, ppm) δ 8.92 (d, J=1.7 Hz, 1H), 8.78 (d, J=1.8 Hz, 1H), 8.67 (d, J=5.6 Hz, 1H), 7.04 (d, J=5.6 Hz, 1H), 4.66-4.54 (m, 1H), 4.47-4.35 (m, 1H), 4.10-3.85 (m, 2H), 3.71-3.54 (m, 1H), 3.08 (d, J=12.0 Hz, 1H), 2.96 (d, J=11.9 Hz, 1H), 2.87-2.61 (m, 2H), 2.64-2.12 (m, 5H), 1.83 (d, J=12.4 Hz, 2H), 1.65-1.45 (m, 2H), 1.24 (d, J=6.2 Hz, 3H), 1.07 (d, J=6.9 Hz, 6H).

Example 24: Synthesis of Compound 62 (N-ethyl-1-(((2S,6R)-6-methyl-4-(pyrido[2,3-b]pyrazin-8-yl)morpholin-2-yl)methyl)piperidine-4-carboxamide)

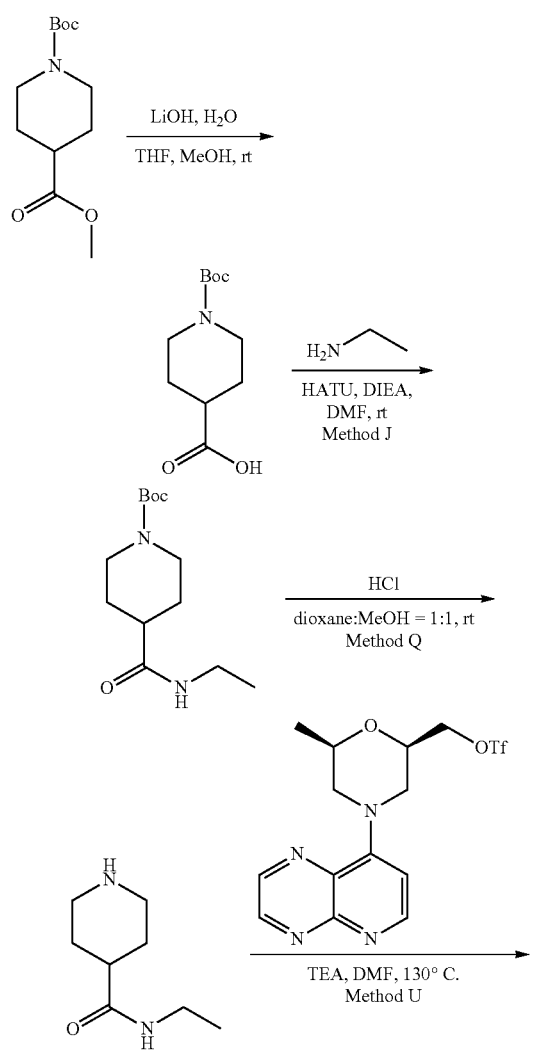

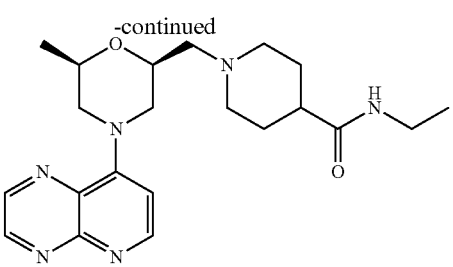

1-(tert-butoxycarbonyl)piperidine-4-carboxylic acid: To a solution of 1-tert-butyl 4-methyl piperidine-1,4-dicarboxylate (1.19 g, 4.87 mmol) in methanol (24 mL) and tetrahydrofuran (24 mL) were added a solution of LiOH (599 mg, 24.99 mmol) in water (8 mL) at room temperature. The resulting mixture was stirred for 15 h at room temperature. When the reaction was done, the pH value of the reaction mixture was adjusted to 2 with hydrogen chloride solution (1 M). The resulting mixture was extracted with ethyl acetate (200 mL×3), and the organic phases were combined, washed with brine and dried over Na₂SO₄. The solvent was removed under reduced pressure to yield 1-[(tert-butoxy)carbonyl]piperidine-4-carboxylic acid as white solid (1.10 g, 84%). MS: m/z=128.0 [M−H]⁺.

N-ethyl-1-(((2S,6R)-6-methyl-4-(pyrido[2,3-b]pyrazin-8-yl)morpholin-2-yl)methyl)piperidine-4-carboxamide: N-ethyl-1-(((2S,6R)-6-methyl-4-(pyrido[2,3-b]pyrazin-8-yl)morpholin-2-yl)methyl)piperidine-4-carboxamide was prepared from 1-(tert-butoxycarbonyl)piperidine-4-carboxylic acid, ethanamine and ((2R,6R)-6-methyl-4-(pyrido[2,3-b]pyrazin-8-yl)morpholin-2-yl)methyl trifluoromethanesulfonate using Method J, Q, and U. The crude product was purified by prep-HPLC under the following conditions: Column, XBridge C18 OBD Prep Column, 5 um, 19 mm×150 mm; Mobile phase, MeOH in water (with 10 mmol/L NH₄HCO₃), 30% to 80% gradient in 10 min; Detector, UV 254 nm. N-ethyl-1-[[(2S,6R)-6-methyl-4-[pyrido[2,3-b]pyrazin-8-yl]morpholin-2-yl]methyl]piperidine-4-carboxamide was obtained as yellow solid (20 mg, 10%).

Compound 62: HPLC: 90.4% purity, RT=1.11 min. MS: n/z=399.3 [M+H]⁺. ¹H NMR (300 MHz, CD₃OD, ppm) δ 8.92 (d, J=1.7 Hz, 1H), 8.78 (d, J=1.7 Hz, 1H), 8.67 (d, J=5.6 Hz, 1H), 7.04 (d, J=5.6 Hz, 1H), 4.66-4.54 (m, 1H), 4.47-4.35 (m, 1H), 4.08-3.83 (m, 2H), 3.23-3.09 (m, 3H), 3.05-2.93 (m, 1H), 2.86-2.72 (m, 2H), 2.60-2.40 (m, 2H), 2.23-2.01 (m, 3H), 1.87-1.68 (m, 4H), 1.23 (d, J=6.2 Hz, 3H), 1.08 (t, J=7.2 Hz, 3H).

Example 25: Synthesis of Compound 63 ((3-aminoazetidin-1-yl)((2R,6R)-6-methyl-4-(pyrido[2,3-b]pyrazin-8-yl)morpholin-2-yl)methanone)

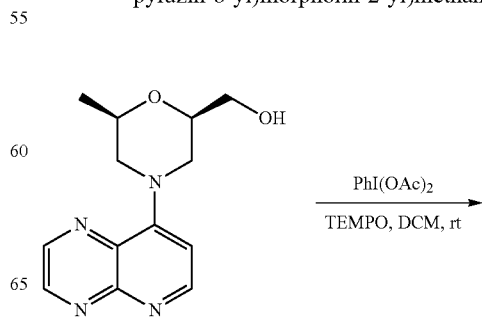

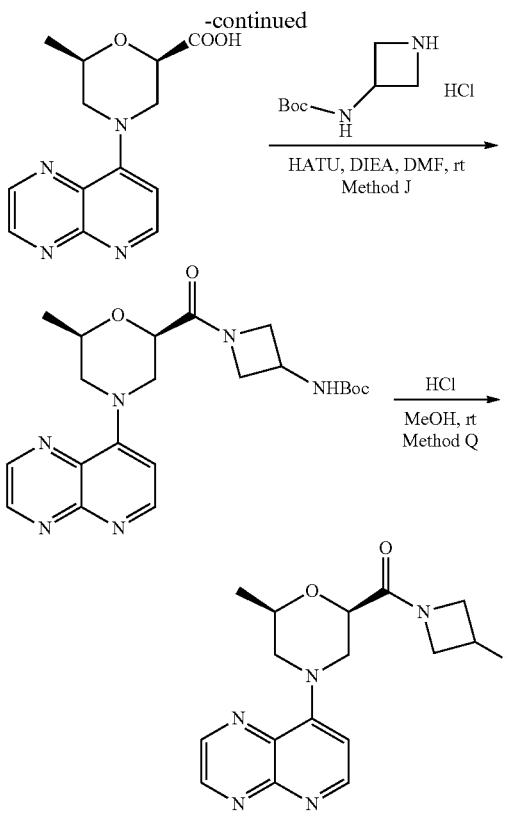

(2R,6R)-6-methyl-4-(pyrido[2,3-b]pyrazin-8-yl)morpholine-2-carboxylic acid: At 10° C., to a solution of [(2R,6R)-6-methyl-4-[pyrido[2,3-b]pyrazin-8-yl]morpholin-2-yl]methanol (90 mg, 0.35 mmol) in dichloromethane (15 mL) were added (acetyloxy)(phenyl)-lambda3-iodanyl acetate (234 mg, 0.73 mmol) and TEMPO (11 mg, 0.07 mmol). The resulting solution was stirred for 30 min at 10° C., and then warmed up to room temperature and stirred for additional 17 h at room temperature. When the reaction was done, it was quenched by sat. Na$_2$S$_2$O$_4$ solution (2.5 mL). The pH value of the mixture was adjusted to 9 with sodium hydroxide solution (1 M). The resulting mixture was washed with water (5 mL×3) and the combined aqueous phases were diluted by BuOH (10 mL). The pH of the aqueous solution was adjusted to 5 by H$_2$SO$_4$ (5 M) and the resulting solution was extracted with BuOH (10 mL×3). The organic phases were combined and concentrated under reduced pressure to yield (2R,6R)-6-methyl-4-[pyrido[2,3-b]pyrazin-8-yl]morpholine-2-carboxylic acid was obtained as yellow solid (76 mg, crude). MS: m/z=275.0 [M−H]$^+$. The crude product was used in next step without further purification.

(3-aminoazetidin-1-yl)((2R,6R)-6-methyl-4-(pyrido[2,3-b]pyrazin-8-yl)morpholin-2-yl)methanone: (3-aminoazetidin-1-yl)((2R,6R)-6-methyl-4-(pyrido[2,3-b]pyrazin-8-yl)morpholin-2-yl)methanone was prepared from (2R,6R)-6-methyl-4-(pyrido[2,3-b]pyrazin-8-yl)morpholine-2-carboxylic acid and tert-butyl azetidin-3-ylcarbamate hydrochloride using Method J and Q. The crude product was purified by prep-HPLC under the following conditions: Column, XBridge C18 OBD Prep Column, 5 um, 19 mm×150 mm; Mobile phase, MeOH in water (with 10 mmol/L NH$_4$HCO$_3$), 30% to 70% gradient in 10 min; Detector, UV 254 nm. 1-[[(2R,6R)-6-methyl-4-[pyrido[2,3-b]pyrazin-8-yl]morpholin-2-yl] carbonyl]azetidin-3-amine was obtained as light yellow solid (15 mg, 6%).

Compound 63: HPLC: 98.5% purity, RT=0.86 min. MS: m/z=329.1 [M+H]$^+$. $^1$H NMR (400 MHz, CD$_3$OD, ppm) δ 8.98 (d, J=1.7 Hz, 1H), 8.86 (dd, J=3.3, 1.8 Hz, 1H), 8.74 (d, J=5.5 Hz, 1H), 7.11 (d, J=5.6 Hz, 1H), 4.88-4.78 (m, 1H), 4.76-4.64 (m, 1H), 4.59-4.07 (m, 4H), 4.06-3.62 (m, 3H), 3.17-3.05 (m, 1H), 2.97-2.81 (m, 1H), 1.32 (d, J=6.0 Hz, 3H).

The following compounds were synthesized in an analogous manner:

Compound 64 ((2R,6R)-6-methyl-N—((R)-piperidin-3-yl)-4-(pyrido[2,3-b]pyrazin-8-yl)morpholine-2-carboxamide): From (2R,6R)-6-methyl-4-(pyrido[2,3-b]pyrazin-8-yl)morpholine-2-carboxylic acid and (R)-tert-butyl 3-aminopiperidine-1-carboxylate. HPLC: 93.0% purity, RT=0.96 min. MS: m/z=357.2 [M+H]$^+$. $^1$H NMR (300 MHz, CD$_3$OD, ppm) δ 8.94 (d, J=1.7 Hz, 1H), 8.83 (d, J=1.7 Hz, 1H), 8.71 (d, J=5.6 Hz, 1H), 7.09 (d, J=5.5 Hz, 1H), 4.91-4.83 (m, 1H), 4.49-4.29 (m, 2H), 4.07-3.95 (m, 2H), 3.11 (d, J=11.5 Hz, 1H), 3.06-2.79 (m, 3H), 2.70-2.52 (m, 2H), 1.9-1.72 (m, 2H), 1.65-1.53 (m, 2H), 1.33 (d, J=6.2 Hz, 3H).

Compound 65 ((2R,6R)-6-methyl-N-(1-methylpiperidin-4-yl)-4-(pyrido[2,3-b]pyrazin-8-yl)morpholine-2-carboxamide): From (2R,6R)-6-methyl-4-(pyrido[2,3-b]pyrazin-8-yl)morpholine-2-carboxylic acid and 1-methylpiperidin-4-amine. HPLC: 95.8% purity, RT=1.00 min. MS: m/z=371.1 [M+H]$^+$. $^1$H NMR (300 MHz, CD$_3$OD, ppm) δ 8.94 (d, J=1.7 Hz, 1H), 8.82 (d, J=1.7 Hz, 1H), 8.71 (d, J=5.6 Hz, 1H), 7.09 (d, J=5.6 Hz, 1H), 4.49-4.27 (m, 2H), 4.06-3.94 (m, 1H), 3.87-3.68 (m, 2H), 3.05-2.83 (m, 4H), 2.32-2.10 (m, 5H), 1.91-1.77 (m, 2H), 1.72-1.56 (s, 2H), 1.33 (d, J=6.2 Hz, 3H).

Compound 468 ((2R,6R)-4-(8-cyanoquinoxalin-5-yl)-6-methyl-N-(1-methylpiperidin-4-yl)morpholine-2-carboxamide): From (2R,6R)-4-(8-cyanoquinoxalin-5-yl)-6-methylmorpholine-2-carboxylic acid and 1-methylpiperidin-4-amine. HPLC: 98.0% purity, RT=1.19 min. MS: m/z=395.2 [M+H]$^+$. $^1$H NMR (400 MHz, CD$_3$OD, ppm) δ 8.96 (dd, J=17.8, 1.7 Hz, 2H), 8.16 (d, J=8.3 Hz, 1H), 7.27 (d, J=8.4 Hz, 1H), 4.96-4.87 (m, 1H), 4.54 (dt, J=12.4, 2.4 Hz, 1H), 4.42 (dd, J=10.7, 2.8 Hz, 1H), 4.21-4.04 (m, 2H), 3.79 (td, J=11.0, 5.6 Hz, 1H), 2.98-2.78 (m, 4H), 2.32 (s, 3H), 2.19 (t, J=12.0 Hz, 2H), 1.95-1.83 (m, 2H), 1.74-1.58 (m, 2H), 1.40-1.25 (m, 3H)

Example 26: Synthesis of Compound 66 ((3R,5S)-5-methyl-1-[8-(trifluoromethyl)quinolin-5-yl]piperidin-3-amine)

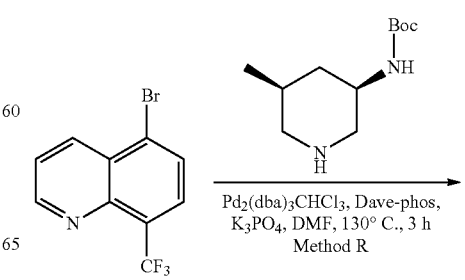

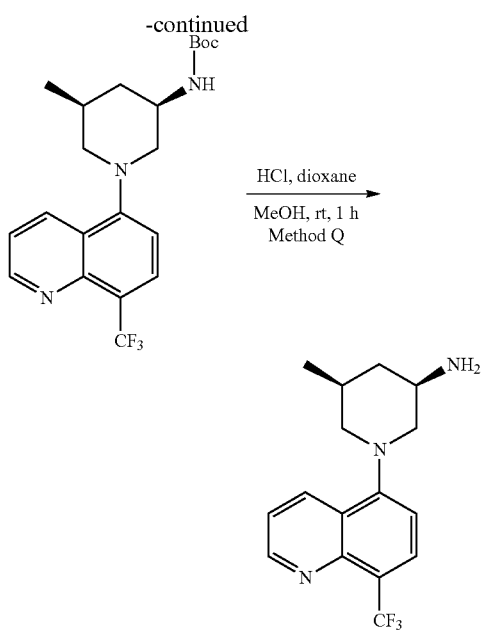

Example 27: Synthesis of Compound 67 ((3R, 5S)-N-(2-methoxyethyl)-1-(8-methoxyquinoxalin-5-yl)-5-methylpiperidin-3-amine)

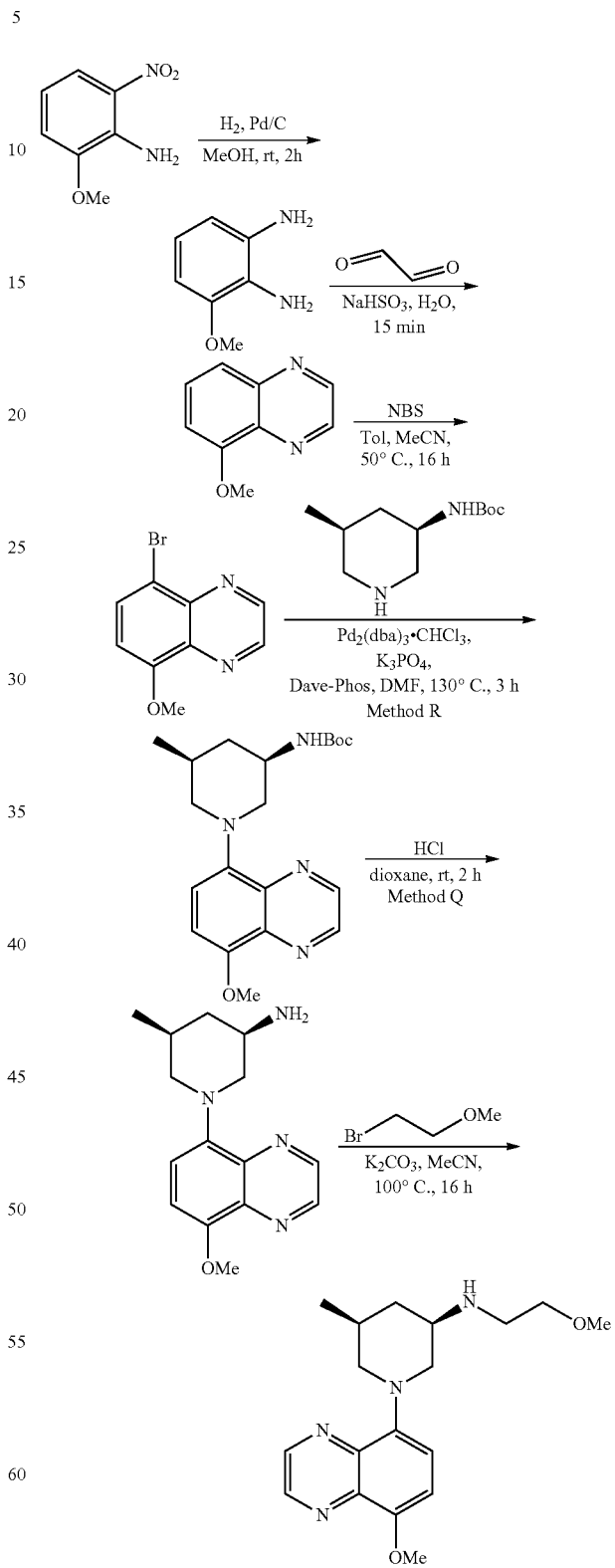

tert-Butyl N-[(3R,5S)-5-methyl-1-[8-(trifluoromethyl)quinolin-5-yl]piperidin-3-yl]carbamate: At room temperature, to a solution of 5-bromo-8-(trifluoromethyl)quinoline (950 mg, 3.44 mmol) in DMF (10 mL) was added tert-butyl N-[(3R,5S)-5-methylpiperidin-3-yl]carbamate (718 mg, 3.35 mol), $K_3PO_4$ (2.19 g, 10.29 mmol), $Pd_2(dba)_3CHCl_3$ (356 mg, 0.34 mmol) and DavePhos (270 mg, 0.69 mmol). The resulting mixture was heated to 130° C. and stirred for 3 h. After cooling to room temperature, the reaction mixture was diluted with water (10 mL). The resulting mixture was extracted with ethyl acetate (20 mL×3). The organic phases were combined, washed with brine and dried over $Na_2SO_4$. The solvent was removed under reduced pressure and the residue was purified by flash chromatography eluting with EtOAc in hexane (0% to 14% gradient) to yield tert-butyl N-[(3R,5S)-5-methyl-1-[8-(trifluoromethyl)quinolin-5-yl]piperidin-3-yl]carbamate as yellow solid (1.10 g, 77%). MS: m/z=410.2 [M+H]$^+$.

(3R,5S)-1-[8-(trifluoromethyl)quinolin-5-yl]-5-methylpiperidin-3-amine: At room temperature, to a solution of tert-butyl N-[(3R,5S)-5-methyl-1-[8-(trifluoromethyl)quinolin-5-yl]piperidin-3-yl]carbamate (787 mg, 1.92 mmol) in methanol (10 mL) was added a solution of hydrogen chloride in 1,4-dioxane (5 mL, 4 M). The resulting solution was stirred for 1 h at room temperature. After the reaction was done, the reaction mixture was concentrated under reduced pressure. The residue was purified by prep-HPLC under the following conditions: column, XBridge BEH130 Prep C18 OBD column, 150 mm, 5 um, 13 nm; mobile phase, acetonitrile in water (with 0.05% $NH_4OH$), 30% to 60% gradient in 10 min; detector, UV 254 nm. (3R,5S)-5-methyl-1-[8-(trifluoromethyl)quinolin-5-yl]piperidin-3-amine was obtained as light yellow solid (500 mg, 83%).

Compound 66: HPLC: 99.7% purity, RT=3.18 min. MS: n/z=310.0 [M+H]$^+$. $^1$H NMR (400 MHz, $CD_3OD$, ppm) δ 8.94 (dd, J=4.4, 1.6 Hz, 1H), 8.67-8.57 (m, 1H), 8.05 (d, J=8.0 Hz, 1H), 7.62 (dd, J=8.6, 4.2 Hz, 1H), 7.24 (d, J=8.1 Hz, 1H), 3.59-3.50 (m, 1H), 3.42-3.33 (m, 1H), 3.27-3.17 (m, 1H), 2.52-2.36 (m, 2H), 2.21-2.07 (m, 2H), 1.08-0.93 (m, 4H).

3-Methoxybenzene-1,2-diamine: At room temperature, to a solution of 2-methoxy-6-nitroaniline (4.75 g, 28.25 mmol)

in methanol (150 mL) was added Pd/C (10%, 500 mg) under nitrogen atmosphere. The reaction flask was vacuumed and flushed with hydrogen. The reaction mixture was hydrogenated for 2 h at room temperature under $H_2$ atmosphere using a hydrogen balloon. When the reaction was done, the reaction mixture was filtered through a Celite pad and the filtrate was concentrated under reduced pressure to yield 3-methoxybenzene-1,2-diamine as dark red oil (3.66 g, 94%). MS: m/z=139.1 [M+H]$^+$.

5-Methoxyquinoxaline: At room temperature, a solution of oxaldehyde in $H_2O$ (40%, 4 mL) was added to a solution of 3-methoxybenzene-1,2-diamine (3.66 g, 26.53 mmol) in water (100.00 mL). Then $NaHSO_3$ (7.59 g, 72.94 mmol) was added slowly. The resulting solution was stirred for 15 min at room temperature. When the reaction was done, the insoluble solids in the reaction mixture were filtered out. The filtrate was extracted with DCM (300 mL×3), and the organic phases were combined, washed with brine and dried over $Na_2SO_4$. The solvent was removed under reduced pressure and the residue was purified by flash chromatography eluting with EtOAc in hexane (0% to 100% gradient) to yield 5-methoxyquinoxaline as dark red oil (3.02 g, 71%). MS: m/z=161.0 [M+H]$^+$.

5-Bromo-8-methoxyquinoxaline: To a solution of 5-methoxyquinoxaline (3.02 g, 18.86 mmol) in toluene (100 mL) and acetonitrile (100 mL) was added NBS (5.04 g, 28.29 mmol) at room temperature. The resulting solution was then stirred for 16 h at 50° C. After cooling to room temperature, the reaction mixture was diluted with water (50 mL). The resulting mixture was extracted with ethyl acetate (100 mL×3). The organic phases were combined, washed with brine and dried over $Na_2SO_4$. The solvent was removed under reduced pressure and the residue was purified by flash chromatography eluting with EtOAc in hexane (0% to 100% gradient) to yield 5-bromo-8-methoxyquinoxaline as yellow solid (4.23 g, 94%). MS: m/z=238.8 [M+H]$^+$.

tert-Butyl N-[(3R,5S)-1-(8-methoxyquinoxalin-5-yl)-5-methylpiperidin-3-yl]carbamate: To a solution of 5-bromo-8-methoxyquinoxaline (1.92 g, 8.04 mmol) in DMF (30 mL) was added tert-butyl N-[(3R,5S)-5-methylpiperidin-3-yl] carbamate (1.52 g, 7.09 mmol), $K_3PO_4$ (5.13 g, 24.17 mmol), $Pd_2(dba)_3CHCl_3$ (760 mg, 0.73 mmol) and Davephos (570 mg, 1.45 mmol) at room temperature. The resulting mixture was then stirred for 3 h at 130° C. After cooling to room temperature, the reaction mixture was diluted with water (100 mL). The resulting mixture was extracted with DCM (100 mL×3). The organic phases were combined, washed with brine and dried over $Na_2SO_4$. The solvent was removed under reduced pressure and the residue was purified by flash chromatography eluting with EtOAc in hexane (0% to 100% gradient) to yield tert-butyl N-[(3R,5S)-1-(8-methoxyquinoxalin-5-yl)-5-methylpiperidin-3-yl]carbamate as dark red oil (1.11 g, 37%). MS: m/z=373.1 [M+H]$^+$.

(3R,5S)-1-(8-methoxyquinoxalin-5-yl)-5-methylpiperidin-3-amine: To a solution of tert-butyl N-[(3R,5S)-1-(8-methoxyquinoxalin-5-yl)-5-methylpiperidin-3-yl]carbamate (429 mg, 1.15 mmol) in dioxane (10 mL) was added a solution of hydrogen chloride in dioxane (4 M, 30 mL) at room temperature. The resulting solution was then stirred for 1 h at room temperature. When the reaction was done, it was quenched by the addition of $H_2O$ (50 mL). Then the pH value of the resulting mixture was adjusted to 8 with sat. sodium bicarbonate solution. The mixture was extracted with DCM (100 mL×3). The organic phases were combined, washed with brine and dried over $Na_2SO_4$. The solvent was removed under reduced pressure to yield (3R,5S)-1-(8-methoxyquinoxalin-5-yl)-5-methylpiperidin-3-amine as dark red oil (180 mg, 57%). MS: m/z=273.1 [M+H]$^+$. $^1$H NMR (400 MHz, DMSO-d, ppm) δ 8.92 (s, 1H), 8.86 (s, 1H), 7.20-7.13 (m, 2H), 3.94 (s, 3H), 3.67 (d, J=10.0 Hz, 1H), 3.59 (dd, J=11.4, 3.1 Hz, 1H), 2.96 (td, J=10.1, 9.0, 5.2 Hz, 1H), 2.20 (dt, J=15.5, 10.8 Hz, 2H), 1.95 (d, J=12.2 Hz, 2H), 0.91 (d, J=6.3 Hz, 3H), 0.79 (q, J=12.0 Hz, 1H).

(3R,5S)—N-(2-methoxyethyl)-1-(8-methoxyquinoxalin-5-yl)-5-methylpiperidin-3-amine: To a solution of (3R,5S)-1-(8-methoxyquinoxalin-5-yl)-5-methylpiperidin-3-amine (90 mg, 0.33 mmol) in acetonitrile (5 mL) was added 1-bromo-2-methoxyethane (45 mg, 0.34 mmol) and potassium carbonate (238 mg, 1.72 mmol) at room temperature. The resulting solution was heated to 100° C. and stirred for 16 h. After cooling to room temperature, the reaction mixture was quenched by the addition of water (50 mL). The resulting mixture was extracted with ethyl acetate (50 mL×3). The organic phases were combined, washed with brine and dried over $Na_2SO_4$. The solvent was removed under reduced pressure and the residue was purified by prep-HPLC under the following conditions: column, XBridge BEH130 Prep C18 OBD column, 150 mm, 5 um, 13 nm; mobile phase, acetonitrile in water (with 0.05% $NH_4OH$), 35% to 65% gradient in 10 min; detector, UV 254 nm. (3R,5S)—N-(2-methoxyethyl)-1-(8-methoxyquinoxalin-5-yl)-5-methylpiperidin-3-amine was obtained as yellow syrup (38 mg, 32%).

Compound 67: HPLC: 92.7% purity, RT=0.99 min. MS: m/z=331.3 [M+H]$^+$. $^1$H NMR (400 MHz, CD$_3$OD, ppm) δ 8.94 (d, J=1.8 Hz, 1H), 8.81 (d, J=1.8 Hz, 1H), 7.32 (d, J=8.5 Hz, 1H), 7.21 (d, J=8.6 Hz, 1H), 4.04 (s, 3H), 3.92-3.84 (m, 1H), 3.60-3.48 (m, 3H), 3.36 (s, 3H), 3.11 (dd, J=13.9, 8.0 Hz, 1H), 2.97-2.81 (m, 2H), 2.41-2.29 (m, 2H), 2.20-2.04 (m, 2H), 1.04-0.87 (m, 4H).

The following compounds were synthesized in an analogous manner:

Compound 201 ((2R)-2-hydroxy-N-[(3R,5S)-1-(8-methoxyquinoxalin-5-yl)-5-methylpiperidin-3-yl]-3-methylbutanamide): From (S)-2-hydroxy-3-methylbutanoic acid and (3R,5S)-1-(8-methoxyquinoxalin-5-yl)-5-methylpiperidin-3-amine. HPLC: 97.9% purity, RT=1.12 min. MS: m/z=373.3 [M+H]$^+$. $^1$H NMR (400 MHz, DMSO-d$_6$, ppm) δ 8.99-8.85 (m, 2H), 7.61 (d, J=8.3 Hz, 1H), 7.22-7.12 (m, 2H), 5.29 (d, J=5.8 Hz, 1H), 4.04 (s, 1H), 3.93 (s, 3H), 3.69-3.55 (m, 3H), 2.62-2.50 (m, 1H), 2.27 (t, J=11.0 Hz, 1H), 2.03-1.85 (m, 3H), 1.23-1.12 (m, 1H), 0.91 and 0.89 (d, J=8.2 Hz, 6H), 0.76 (d, J=6.7 Hz, 3H).

Compound 202 (N-[(3R,5S)-1-(8-methoxyquinoxalin-5-yl)-5-methylpiperidin-3-yl]-3,3-dimethylbutanamide): From 3,3-dimethylbutanoic acid and (3R,5S)-1-(8-methoxyquinoxalin-5-yl)-5-methylpiperidin-3-amine. HPLC: 98.8% purity, RT=1.33 min. MS: m/z=371.3 [M+H]+. $^1$H NMR (400 MHz, Chloroform-d, ppm) δ 8.98-8.82 (m, 2H), 7.70 (d, J=7.8 Hz, 1H), 7.22-7.12 (m, 2H), 4.08-3.90 (m, 4H), 3.70-3.61 (m, 2H), 2.48-2.32 (m, 1H), 2.30-2.28 (m, 1H), 2.02-1.86 (m, 4H), 1.05-0.85 (m, 13H).

Compound 203 (2-(dimethylamino)-N-[(3R,5S)-1-(8-methoxyquinoxalin-5-yl)-5-methylpiperidin-3-yl]acetamide): From 2-(dimethylamino)acetic acid and (3R,5S)-1-(8-methoxyquinoxalin-5-yl)-5-methylpiperidin-3-amine. HPLC: 98.3% purity, RT=1.92 min. MS: m/z=371.3 [M+H]$^+$. $^1$H NMR (400 MHz, CD$_3$OD, ppm) δ 8.84 (d, J=1.8 Hz, 1H), 8.71 (d, J=1.8 Hz, 1H), 7.22 (d, J=8.6 Hz, 1H), 7.10 (d, J=8.5 Hz, 1H), 4.24-4.12 (m, 1H), 3.94 (s, 3H), 3.66 (dd, J=10.9, 4.3 Hz, 1H), 3.56-3.48 (m, 1H), 2.89 (s, 2H), 2.45 (t, J=10.6 Hz, 1H), 2.33-2.15 (m, 7H), 2.09-1.91 (m, 2H), 1.04 (td, J=11.9, 11.9 Hz, 1H), 0.90 (d, J=6.5 Hz, 3H).

Example 28: Synthesis of Compound 68 ((3R,5S)-1-[8-(difluoromethyl)quinolin-5-yl]-5-methylpiperidin-3-amine)

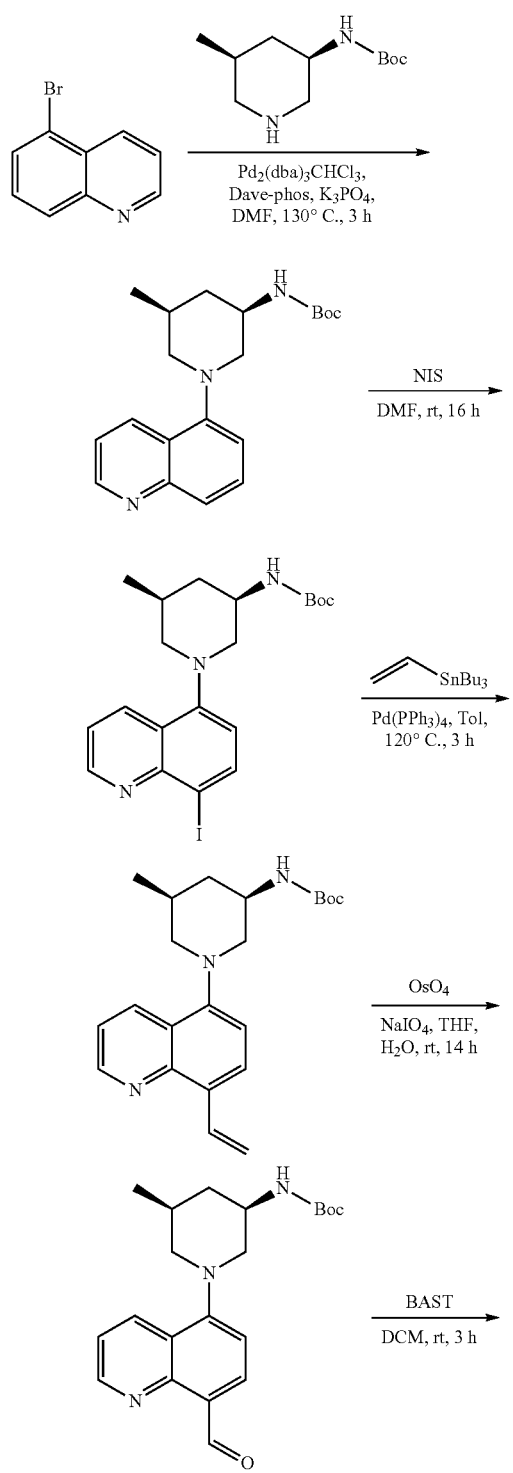

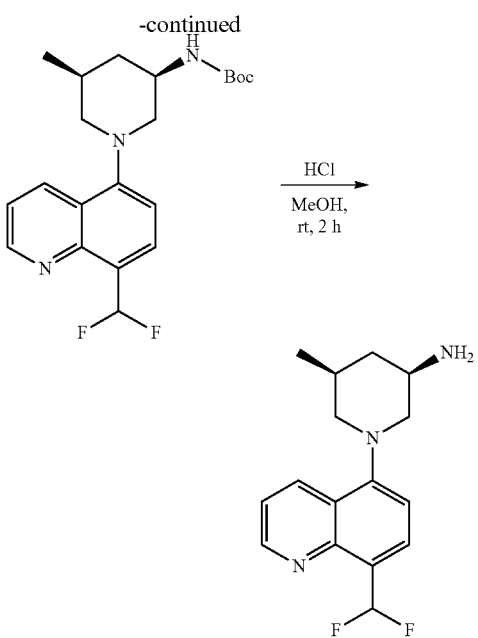

tert-Butyl (3R,5S)-5-methyl-1-(quinolin-5-yl)piperidin-3-ylcarbamate: To a solution of tert-butyl N-[(3R,5S)-5-methylpiperidin-3-yl]carbamate (4.75 g, 22.16 mmol) in DMF (50 mL) was added 5-bromoquinoline (5.07 g, 24.38 mmol), K$_3$PO$_4$ (14.16 g, 66.73 mmol), Davephos (1.75 g, 4.44 mmol) and Pd$_2$(dba)$_3$·CHCl$_3$ (2.30 g, 2.22 mmol) at room temperature. The resulting mixture was then stirred for 3 h at 130° C. After cooling to room temperature, the reaction mixture was diluted with water (50 mL). The resulting mixture was extracted with ethyl acetate (100 mL×3). The organic phases were combined, washed with brine and dried over Na$_2$SO$_4$. The solvent was removed under reduced pressure and the residue was purified by flash chromatography eluting with EtOAc in hexane (0% to 20% gradient) to yield tert-butyl N-[(3R,5S)-5-methyl-1-(quinolin-5-yl)piperidin-3-yl]carbamate as yellow solid (4.00 g, 53%). MS: m/z=342.1 [M+H]$^+$.

tert-Butyl N-[(3R,5S)-1-(8-iodoquinolin-5-yl)-5-methylpiperidin-3-yl]carbamate: To a solution of tert-butyl N-[(3R,5S)-5-methyl-1-(quinolin-5-yl)piperidin-3-yl]carbamate (3.80 g, 11.13 mmol) in DMF (50 mL) was added NIS (2.76 g, 12.25 mmol) at room temperature. The resulting solution was then stirred for 16 h at room temperature. When the reaction was done, it was quenched by the addition of water (30 mL). The resulting mixture was extracted with ethyl acetate (60 mL×3). The organic phases were combined, washed with brine and dried over Na$_2$SO$_4$. The solvent was removed under reduced pressure and the residue was purified by flash chromatography eluting with EtOAc in hexane (0% to 35% gradient) to yield tert-butyl N-[(3R,5S)-1-(8-iodoquinolin-5-yl)-5-methylpiperidin-3-yl]carbamate as yellow solid (4.30 g, 83%). MS: m/z=468.1 [M+H]$^+$.

tert-Butyl N-[(3R,5S)-1-(8-ethenylquinolin-5-yl)-5-methylpiperidin-3-yl]carbamate: To a solution of tert-butyl N-[(3R,5S)-1-(8-iodoquinolin-5-yl)-5-methylpiperidin-3-yl]carbamate (4.09 g, 8.74 mmol) in toluene (50 mL) was added Pd(PPh$_3$)$_4$ (1.01 g, 0.87 mmol) and tributyl(ethenyl) stannane (4.16 g, 13.12 mmol) at room temperature. The reaction mixture was then stirred for 3 h at 120° C. After cooling to room temperature, the reaction mixture was diluted with water (30 mL). The resulting mixture was extracted with ethyl acetate (60 mL×3). The organic phases were combined, washed with brine and dried over Na₂SO₄. The solvent was removed under reduced pressure and the residue was purified by flash chromatography eluting with EtOAc in hexane (0% to 17% gradient) to yield tert-butyl N-[(3R,5S)-1-(8-ethenylquinolin-5-yl)-5-methylpiperidin-3-yl]carbamate as yellow solid (2.20 g, 68%). MS: m/z=368.2 [M+H]⁺.

tert-Butyl N-[(3R,5S)-1-(8-formylquinolin-5-yl)-5-methylpiperidin-3-yl]carbamate: To a solution of tert-butyl N-[(3R,5S)-1-(8-ethenylquinolin-5-yl)-5-methylpiperidin-3-yl]carbamate (2.09 g, 5.69 mmol) in THF (73 mL) was added OsO₄ (145 mg, 0.57 mmol), NaIO₄ (4.86 g, 22.74 mmol), and water (14 mL) at room temperature. The reaction mixture was stirred for 14 h at room temperature. When the reaction was done, it was quenched by the addition of sat. Na₂S₂O₃ solution (20 mL). The resulting mixture was extracted with ethyl acetate (50 mL×3). The organic phases were combined, washed with brine and dried over Na₂SO₄. The solvent was removed under reduced pressure to yield tert-butyl N-[(3R,5S)-1-(8-formylquinolin-5-yl)-5-methylpiperidin-3-yl]carbamate as yellow solid (800 mg, 38%). MS: m/z=370.1 [M+H]⁺.

tert-Butyl N-[(3R,5S)-1-[8-(difluoromethyl)quinolin-5-yl]-5-methylpiperidin-3-yl]carbamate: To a solution of tert-butyl N-[(3R,5S)-1-(8-formylquinolin-5-yl)-5-methylpiperidin-3-yl]carbamate (760 mg, 2.06 mmol) in DCM (10 mL) was added BAST (1.37 g, 6.18 mmol) at room temperature. The resulting solution was stirred for 3 h at room temperature. When the reaction was done, it was quenched by the addition of sat. sodium bicarbonate solution (30 mL). The resulting mixture was extracted with ethyl acetate (30 mL×3). The organic phases were combined, washed with brine and dried over Na₂SO₄. The solvent was removed under reduced pressure and the residue was purified by flash chromatography eluting with EtOAc in hexane (0% to 17% gradient) to yield tert-butyl N-[(3R,5S)-1-[8-(difluoromethyl)quinolin-5-yl]-5-methylpiperidin-3-yl]carbamate as yellow solid (400 mg, 50%). MS: m/z=392.2 [M+H]⁺.

(3R,5S)-1-[8-(difluoromethyl)quinolin-5-yl]-5-methylpiperidin-3-amine: To a solution of tert-butyl N-[(3R,5S)-1-[8-(difluoromethyl)quinolin-5-yl]-5-methylpiperidin-3-yl]carbamate (45 mg, 0.12 mmol) in methanol (5 mL) was added con. HCl solution (12 M, 0.2 mL) at room temperature. The resulting solution was stirred for 2 h at room temperature. When the reaction was done, it was quenched by the addition of water (10 mL). The resulting mixture was extracted with DCM (20 mL×3), and the organic phases were combined, washed with brine and dried over Na₂SO₄. The solvent was removed under reduced pressure and the residue was purified by prep-HPLC under the following conditions: column, XBridge BEH130 Prep C18 OBD column, 150 mm, 5 um, 13 nm; mobile phase, acetonitrile in water (with 0.05% NH₄OH), 45% to 75% gradient in 10 min; detector, UV 254 nm. (3R,5S)-1-[8-(difluoromthyl)quinolin-5-yl]-5-methylpiperidin-3-amine was obtained as yellow oil (20 mg, 57%).

Compound 68: HPLC: 97.3% purity, RT=1.34 min. MS: m/z=292.2 [M+H]⁺. ¹H NMR (300 MHz, CD₃OD, ppm) δ 8.86 (dd, J=4.2, 1.8 Hz, 1H), 8.52 (dd, J=8.6, 1.8 Hz, 1H), 7.96-7.87 (m, 1H), 7.86-7.44 (m, 2H), 7.23 (d, J=7.9 Hz, 1H), 3.52-3.42 (m, 1H), 3.34-3.11 (m, 2H), 2.49-2.29 (m, 2H), 2.19-1.97 (m, 2H), 1.07-0.86 (m, 4H).

Example 29: Synthesis of Compound 69 and compound 70 (8-(3-amino-5-cyclopropylpiperidin-1-yl)quinoxaline-5-carbonitrile)

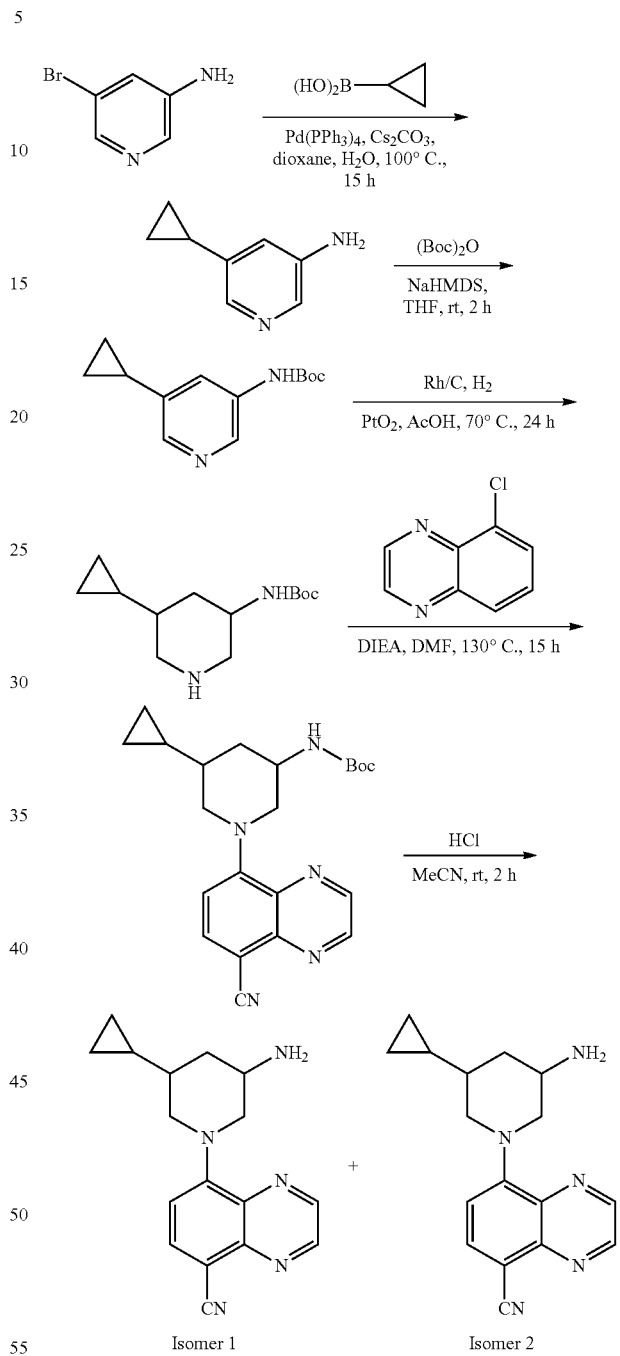

5-Cyclopropylpyridin-3-amine: To a solution of 5-bromopyridin-3-amine (4.75 g, 27.45 mmol) in dioxane (45 mL) was added cyclopropylboronic acid (4.75 g, 55.30 mmol), Cs₂CO₃ (28 g, 85.67 mmol), tetrakis(triphenylphosphane) palladium (1.66 g, 1.44 mmol) and water (5 mL) at room temperature. The resulting mixture was then stirred for 15 h at 100° C. After cooling to room temperature, the reaction mixture was diluted with water (200 mL). The resulting mixture was extracted with ethyl acetate (500 mL×3). The organic phases were combined, washed with brine and dried over Na$_2$SO$_4$. The solvent was removed under reduced pressure and the residue was purified by flash chromatography eluting with EtOAc in hexane (0% to 100% gradient) to yield 5-cyclopropylpyridin-3-amine as light brown oil (2.08 g, 56%). MS: m/z=135.0 [M+H]$^+$.

tert-Butyl N-(5-cyclopropylpyridin-3-yl)carbamate: At 0° C., to a solution of 5-cyclopropylpyridin-3-amine (2.08 g, 15.49 mmol) in tetrahydrofuran (30 mL) was added a solution of NaHMDS (6.84 g, 37.30 mmol) in tetrahydrofuran (20 mL) dropwise over 10 min period. The resulting solution was stirred for 1 h at 0° C., and then was added by a solution of di-tert-butyl dicarbonate (4.85 g, 22.20 mmol) in tetrahydrofuran (25 mL) dropwise. The resulting mixture was stirred for additional 2 h at room temperature. When the reaction was done, it was quenched by the addition of sat. NH$_4$Cl solution (100 mL). The resulting mixture was extracted with ethyl acetate (100 mL×3). The organic phases were combined, washed with brine and dried over Na$_2$SO$_4$. The solvent was removed under reduced pressure and the residue was purified by flash chromatography eluting with MeOH in EtOAc (0% to 80% gradient) to yield tert-butyl N-(5-cyclopropylpyridin-3-yl)carbamate as white solid (2.52 g, 69%). MS: m/z=235.0 [M+H]$^+$.

tert-Butyl 5-cyclopropylpiperidin-3-ylcarbamate: Into a sealed tube were added tert-butyl N-(5-cyclopropylpyridin-3-yl)carbamate (2.52 g, 10.74 mmol), PtO$_2$ (520 mg, 2.29 mmol), Rh/C (520 mg, 5%) and acetic acid (220 mL) at room temperature under nitrogen atmosphere. The reaction tube was vacuumed and flushed with hydrogen. Then the reaction was hydrogenated for 24 h at 70° C. under 15 atm hydrogen atmosphere. After cooling to room temperature, the reaction mixture was filtered through a Celite pad and the filtrate was concentrated under reduced pressure. The residue was diluted with H$_2$O (50 mL) and the pH value of the mixture was adjusted to 9 by NaOH solution (0.5 mol/L). The resulting mixture was extracted with DCM (150 mL×3). The organic phases were combined, washed with brine and dried over Na$_2$SO$_4$. The solvent was removed under reduced pressure to yield tert-butyl N-(5-cyclopropylpiperidin-3-yl)carbamate as white solid (2.47 g, 57%). MS: m/z=241.1 [M+H]$^+$.

tert-Butyl N-[1-(8-cyanoquinoxalin-5-yl)-5-cyclopropylpiperidin-3-yl]carbamate: To a solution of 8-bromoquinoxaline-5-carbonitrile (2.47 g, 10.55 mmol) in N,N-dimethylformamide (25 mL) was added tert-butyl N-(5-cyclopropylpiperidin-3-yl)carbamate (2.10 g, 8.74 mmol) and DIEA (3.14 g, 24.26 mmol) at room temperature. The resulting solution was then stirred for 15 h at 130° C. After cooling to room temperature, the reaction mixture was quenched by the addition of water (80 mL). The resulting mixture was extracted with DCM (150 mL×3). The organic phases were combined, washed with brine and dried over Na$_2$SO$_4$. The solvent was removed under reduced pressure and the residue was purified by flash chromatography eluting with MeOH in DCM (0% to 20% gradient) to yield tert-butyl N-[1-(8-cyanoquinoxalin-5-yl)-5-cyclopropylpiperidin-3-yl]carbamate as yellow solid (2.80 g, 67%). MS: m/z=394.2 [M+H]$^+$.

8-(3-amino-5-cyclopropylpiperidin-1-yl)quinoxaline-5-carbonitrile: To a solution of tert-butyl N-[1-(8-cyanoquinoxalin-5-yl)-5-cyclopropylpiperidin-3-yl]carbamate (850 mg, 2.16 mmol) in methanol (15 mL) was added a solution of hydrogen chloride in dioxane (4 M, 4 mL). The resulting solution was stirred for 1 h at 40° C. When the reaction was done, the reaction mixture was concentrated under reduced pressure and the residue was first purified by prep-HPLC under the following conditions: column, XBridge BEH130 Prep C18 OBD column, 150 mm, 5 um, 13 nm; mobile phase, acetonitrile in water (with 0.05% NH$_4$OH), 30% to 60% gradient in 10 min; detector, UV 254 nm. Then the two enantiomers were obtained by separation on chiral prep-HPLC under the following conditions: column, CHIRAL-PAK AD-3, 0.46×10 cm, 5 um; mobile phase, hexane (0.1% DEA) in EtOH, 60% isocratic in 15 min; detector, UV 254 nm. 8-[(3S,5S)-3-amino-5-cyclopropylpiperidin-1-yl]quinoxaline-5-carbonitrile was obtained as yellow solid (78 mg, 12%).

Isomer 1: HPLC: 99.3% purity, RT=1.44 min. MS: m/z=294.2 [M+H]$^+$. $^1$H NMR (300 MHz, CD$_3$OD, ppm) δ 8.87 (dd, J=15.6, 1.8 Hz, 2H), 8.06 (d, J=8.4 Hz, 1H), 7.18 (d, J=8.4 Hz, 1H), 4.39-4.17 (m, 2H), 3.09-2.97 (m, 1H), 2.81-2.60 (m, 2H), 2.23 (d, J=11.1 Hz, 1H), 1.28-1.06 (m, 2H), 0.65-0.38 (m, 3H), 0.23-0.11 (m, 2H).

Isomer 2: HPLC: 99% purity, MS: m/z=294.2 [M+H]$^+$. $^1$H NMR (300 MHz, CD$_3$OD, ppm) δ 8.87 (dd, J=15.6, 1.8 Hz, 2H), 8.06 (d, J=8.4 Hz, 1H), 7.18 (d, J=8.4 Hz, 1H), 4.39-4.17 (m, 2H), 3.09-2.97 (m, 1H), 2.81-2.60 (m, 2H), 2.23 (d, J=11.1 Hz, 1H), 1.28-1.06 (m, 2H), 0.65-0.38 (m, 3H), 0.23-0.11 (m, 2H).

Example 30: Synthesis of Compound 71 (cis-5-(3-Amino-5-trifluoromethyl-piperidin-1-yl)-quinoline-8-carbonitrile)

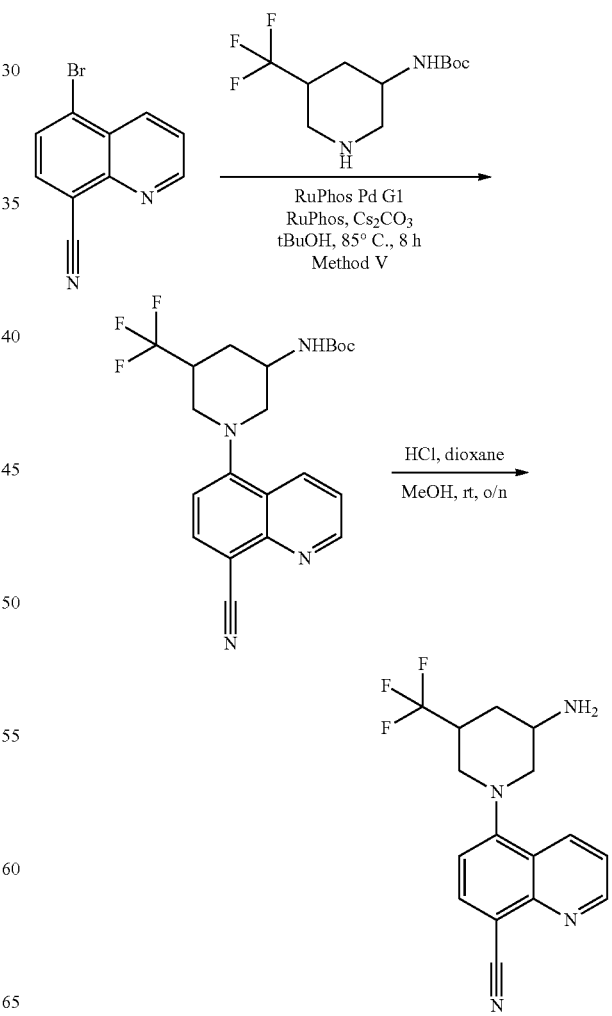

Method V

Cis-[1-(8-cyano-quinolin-5-yl)-5-trifluoromethyl-piperidin-3-yl]-carbamic acid tert-butyl ester: A mixture of 5-bromo-quinoline-8-carbonitrile (500 mg; 2.15 mmol), cis-3-(boc-amino)-5-(trifluormethyl)piperidine (691 mg; 2.57 mmol), chloro(2-dicyclohexylphosphino-2',6'-di-1-propoxy-1,1'-biphenyl)[2-(2-aminoethylphenyl)]palladium (II), methyl-t-butylether adduct (88 mg; 0.11 mmol), 2-dicyclohexylphosphino-2',6'-di-1-propoxy-1,1'-biphenyl (50 mg; 0.11 mmol) and cesium carbonate (1.4 g; 4.3 mmol) in anhydrous tert-butanol (15 mL) was microwaved at 85° C. for 8 h. The reaction mixture was concentrated under reduced pressure and purified by chromatography, eluting with hexanes and ethyl acetate to afford [1-(8-cyano-quinolin-5-yl)-5-trifluoromethyl-piperidin-3-yl]-carbamic acid tert-butyl ester (731 mg; 80%) as a light yellow solid. $^1$H NMR (400 MHz, CDCl$_3$) δ 9.09 (dd, J=4.2, 1.7 Hz, 1H), 8.44 (dd, J=8.6, 1.7 Hz, 1H), 8.04 (d, J=7.9 Hz, 1H), 7.57 (ddd, J=8.3, 6.2, 4.2 Hz, 1H), 7.12 (d, J=8.0 Hz, 1H), 4.50 (s, 1H), 4.06 (s, 1H), 3.75 (dd, J=11.8, 4.6 Hz, 1H), 3.65-3.55 (m, 1H), 2.89 (t, J=11.3 Hz, 1H), 2.79 (dtq, J=15.3, 7.5, 3.8 Hz, 1H), 2.56-2.39 (m, 2H), 1.54-1.33 (m, 10H); MS: m/z=421 [M+H]$^+$.

(Note: In Method V, the palladium complex may also be RuPhos Palladacycle Gen. 3 (Methanesulfonato(2-dicyclohexylphosphino-2',6'-di-1-propoxy-1,1'-biphenyl)(2'-amino-1,1'-biphenyl-2-yl) palladium(II)) instead of RuPhos Palladacycle Gen. 1 (chloro(2-dicyclohexylphosphino-2',6'-di-1-propoxy-1,1'-biphenyl)[2-(2-aminoethylphenyl)]palladium(II)), the solvent may also be THF or dioxane instead of tert-butanol, the base may also be sodium tert-butoxide instead of cesium carbonate and the reaction temperature may range from 85° C. to 100° C.)

Cis-5-(3-Amino-5-trifluoromethyl-piperidin-1-yl)-quinoline-8-carbonitrile: To a solution of [1-(8-cyano-quinolin-5-yl)-5-trifluoromethyl-piperidin-3-yl]-carbamic acid tert-butyl ester (720 mg; 1.71 mmol) in anhydrous methanol (17 mL) was added a solution of hydrochloric acid (12.8 mL; 51.4 mmol) 4M in dioxane and the orange solution was stirred at room temperature overnight. Ether (40 mL) was added to the reaction mixture and the orange solution was stirred at room temperature for 20 min. The orange suspension was filtered, the yellow solid was washed with ether and dried under vacuo to afford 5-(3-amino-5-trifluoromethyl-piperidin-1-yl)-quinoline-8-carbonitrile hydrochloride (571 mg; 94%) as a yellow solid.

Compound 71: $^1$H NMR (400 MHz, D$_2$O) δ 8.94 (dd, J=4.6, 1.7 Hz, 1H), 8.66 (dd, J=8.6, 1.8 Hz, 1H), 8.17 (d, J=8.1 Hz, 1H), 7.77 (dd, J=8.8, 4.5 Hz, 1H), 7.34 (d, J=8.2 Hz, 1H), 4.02-3.87 (m, 1H), 3.82 (dd, J=11.5, 3.6 Hz, 1H), 3.71 (d, J=11.8 Hz, 1H), 3.17 (td, J=8.0, 3.9 Hz, 1H), 3.05 (td, J=11.4, 8.8 Hz, 2H), 2.64 (d, J=12.3 Hz, 1H), 1.81 (q, J=12.2 Hz, 1H); MS: m/z=321 [M+H]$^+$.

The following compounds were synthesized in an analogous manner:

Compound 423 (5-(5-Amino-3,3-difluoro-piperidin-1-yl)-quinoline-8-carbonitrile hydrochloride): From 5-Bromo-quinoline-8-carbonitrile and (5,5-Difluoro-piperidin-3-yl)-carbamic acid tert-butyl ester. HPLC: >99% purity, RT=1.88 min. MS: m/z=289 [M+H]$^+$. $^1$H NMR (400 MHz, Deuterium Oxide, ppm) δ 8.96 (dd, J=4.6, 1.6 Hz, 1H), 8.89 (dd, J=8.7, 1.6 Hz, 1H), 8.22 (d, J=8.0 Hz, 1H), 7.82 (dd, J=8.7, 4.6 Hz, 1H), 7.46 (d, J=8.1 Hz, 1H), 4.17 (s, 1H), 3.81-3.68 (m, 2H), 3.64-3.40 (m, 2H), 2.74 (tdd, J=19.9, 7.8, 5.4 Hz, 1H), 2.67-2.48 (m, 1H).

Compound 510 (5,5-Difluoro-1-(8-trifluoromethyl-quinolin-5-yl)-piperidin-3-ylamine): From 5-Bromo-8-trifluoromethyl-quinoline and (5,5-Difluoro-piperidin-3-yl)-carbamic acid tert-butyl ester. $^1$H NMR (400 MHz, DMSO-d$_6$) δ 9.05 (dd, J=4.2, 1.7 Hz, 1H), 8.58 (dd, J=8.6, 1.8 Hz, 1H), 8.10 (d, J=8.0 Hz, 1H), 7.71 (dd, J=8.6, 4.2 Hz, 1H), 7.30 (d, J=8.0 Hz, 1H), 3.53 (t, J=9.8 Hz, 1H), 3.47-3.36 (m, 1H), 3.30-3.17 (m, 2H), 2.78-2.64 (m, 1H), 2.43 (d, J=11.3 Hz, 1H), 1.95-1.65 (m, 3H). MS: m/z=332 [M+H]$^+$.

Compound 524 (8-(3-Amino-4-fluoro-piperidin-1-yl)-quinoxaline-5-carbonitrile hydrochloride): From 8-Bromo-quinoxaline-5-carbonitrile and 4-Fluoro-piperidin-3-yl)-carbamic acid tert-butyl ester. $^1$H NMR (400 MHz, DMSO-d$_6$) 9.10 (d, J=1.8 Hz, 1H), 9.02 (d, J=1.8 Hz, 1H), 8.60 (s, 3H), 8.29 (d, J=8.3 Hz, 1H), 7.34 (d, J=8.4 Hz, 1H), 5.03 (td, J=9.0, 4.8 Hz, 1H), 4.90 (td, J=8.9, 4.8 Hz, 1H), 4.39 (d, J=12.8 Hz, 1H), 4.10 (d, J=13.2 Hz, 1H), 3.58 (d, J=8.1 Hz, 1H), 3.54-3.37 (m, 1H), 2.32 (ddt, J=13.0, 8.6, 3.7 Hz, 1H), 2.06-1.81 (m, 1H). MS: m/z=272 [M+H]$^+$.

Compound 553 ((3R,5S)-5-methyl-1-(8-methyl-1,7-naphthyridin-5-yl)piperidin-3-amine): From 5-bromo-8-methyl-[1,7]naphthyridine and tert-butyl N-[(3R,5S)-5-methylpiperidin-3-yl]carbamate. MS: n/z=257 [M+H]$^+$. $^1$H NMR (400 MHz, DMSO-d$_6$) δ 9.27 (dd, J=4.1, 1.5 Hz, 1H), 8.64 (dd, J=8.7, 1.7 Hz, 1H), 8.17 (s, 1H), 8.06 (dd, J=8.6, 4.2 Hz, 1H), 3.67 (d, J=11.3 Hz, 1H), 3.61-3.56 (m, 1H), 3.34 (d, J=12.0 Hz, 1H), 3.08 (s, 3H), 2.79 (t, J=11.0 Hz, 1H), 2.58 (d, J=11.4 Hz, 1H), 2.19 (d, J=12.5 Hz, 1H), 2.13-1.98 (m, 1H), 1.22 (q, J=12.0 Hz, 1H), 0.99 (d, J=6.6 Hz, 3H).

Example 31: Separation of compound 72 and compound 73 (5-((3S,5R)-3-Amino-5-trifluoromethyl-piperidin-1-yl)-quinoline-8-carbonitrile and 5-((3R,5S)-3-Amino-5-trifluoromethyl-piperidin-1-yl)-quinoline-8-carbonitrile)

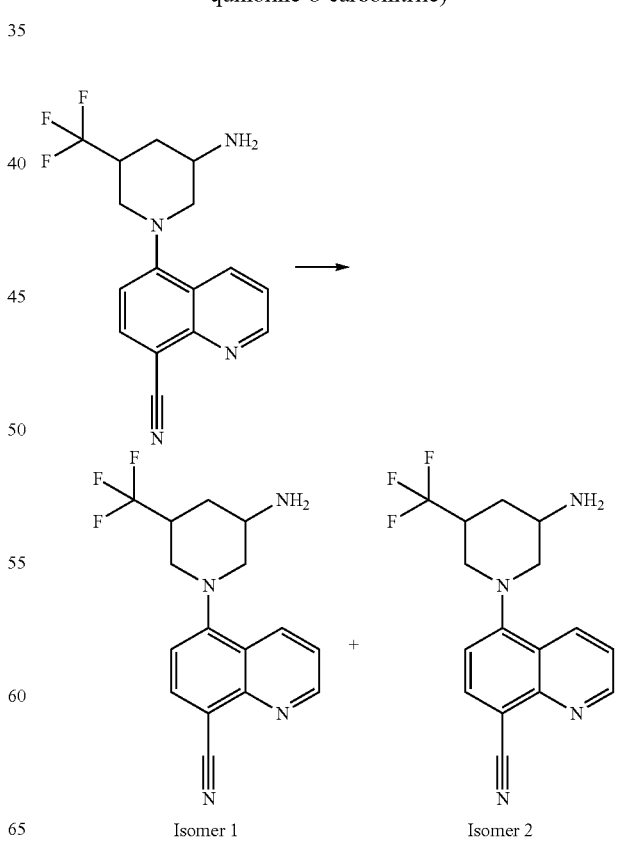

Isomer 1     Isomer 2

The title compounds were isolated via chiral SFC chromatography of compound 71. (Column: 2.1×25.0 cm Chiralpak AD-H from Chiral Technologies (West Chester, Pa.); CO2 Co-solvent (Solvent B): Methanol with 0.2% Ammonium Hydroxide; Isocratic Method: 20% Co-solvent at 80 g/min; System Pressure: 100 bar; Column Temperature: 25° C.).

Isomer 1: $^1$H NMR (400 MHz, Acetone-d6) δ 8.60 (dd, J=4.2, 1.7 Hz, 1H), 8.06 (dd, J=8.6, 1.7 Hz, 1H), 7.78 (d, J=8.0 Hz, 1H), 7.24 (dd, J=8.6, 4.2 Hz, 1H), 6.84 (d, J=8.0 Hz, 1H), 3.07 (dt, J=12.0, 2.3 Hz, 1H), 3.05-2.96 (m, 1H), 2.66 (tt, J=11.2, 4.3 Hz, 1H), 2.57 (ddd, J=15.5, 7.4, 3.4 Hz, 1H), 2.40 (t, J=11.4 Hz, 1H), 2.04-1.97 (m, 1H), 1.78-1.67 (m, 1H), 1.29 (s, 2H), 0.80 (q, J=12.1 Hz, 1H). MS: m/z=321 [M+H]$^+$.

Isomer 2: $^1$H NMR (400 MHz, Acetone-d6) δ 8.63 (dd, J=4.2, 1.7 Hz, 1H), 8.12 (dd, J=8.6, 1.7 Hz, 1H), 7.74 (d, J=8.0 Hz, 1H), 7.12 (dd, J=8.6, 4.2 Hz, 1H), 6.84 (d, J=8.0 Hz, 1H), 3.09 (dt, J=12.0, 2.3 Hz, 1H), 3.11-2.99 (m, 1H), 2.66 (tt, J=11.2, 4.3 Hz, 1H), 2.58 (ddd, J=15.5, 7.4, 3.4 Hz, 1H), 2.47 (t, J=11.4 Hz, 1H), 2.07-1.79 (m, 1H), 1.75-1.67 (m, 1H), 1.23 (s, 2H), 0.84 (q, J=12.1 Hz, 1H). MS: m/z=321 [M+H]$^+$.

Example 32: Synthesis of Compound 74 (5-((3R,5S)-3-Amino-5-methyl-piperidin-1-yl)-quinazoline-8-carbonitrile)

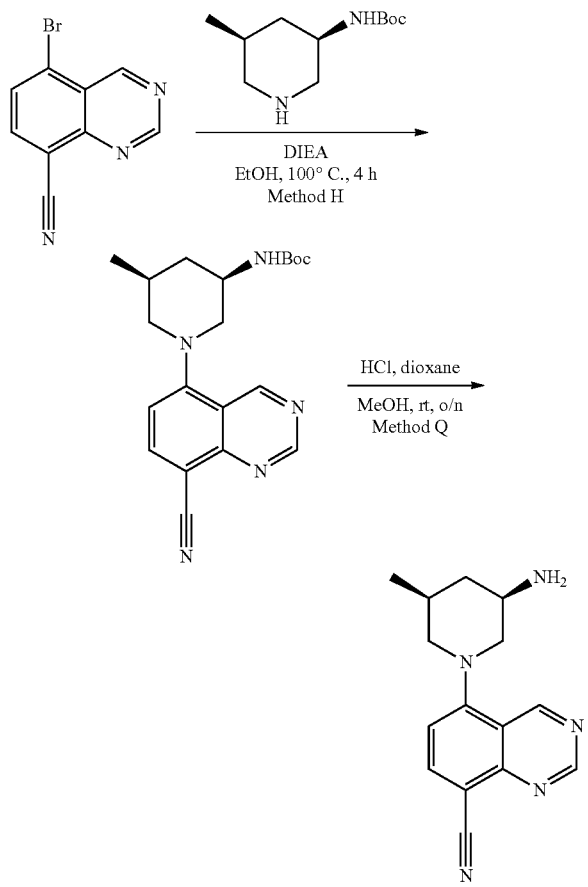

[(3R,5S)-1-(8-Cyano-quinazolin-5-yl)-5-methyl-piperidin-3-yl]-carbamic acid tert-butyl ester: A solution of 5-bromo-quinazoline-8-carbonitrile (200 mg; 0.855 mmol), tert-butyl-N-[(3R,5S)-5-methylpiperidin-3-yl]carbamate (220 mg; 1.03 mmol) and DIPEA (450 µl; 2.6 mmol) in anhydrous ethanol (3 mL) was microwaved at 100° C. for 4 h. The brown solution was concentrated under reduced pressure and purified by chromatography, eluting with hexanes and ethyl acetate to afford [1-(8-cyano-quinazolin-5-yl)-5-methyl-piperidin-3-yl]-carbamic acid tert-butyl ester (270 mg; 86%) as a yellow solid. $^1$H NMR (400 MHz, CDCl$_3$) δ 9.58 (s, 1H), 9.41 (s, 1H), 8.12 (d, J=8.2 Hz, 1H), 7.11 (d, J=8.2 Hz, 1H), 4.46 (s, 1H), 3.93 (d, J=11.0 Hz, 2H), 3.58 (d, J=12.3 Hz, 1H), 2.73-2.56 (m, 2H), 2.28-2.16 (m, 1H), 2.17-2.04 (m, 1H), 1.46 (s, 9H), 1.05 (t, J=11.9 Hz, 1H), 0.99 (d, J=6.6 Hz, 3H); MS: m/z=368 [M+H]$^+$.

5-((3R,5S)-3-Amino-5-methyl-piperidin-1-yl)-quinazoline-8-carbonitrile hydrochloride: To a solution of [(3R,5S)-1-(8-Cyano-quinazolin-5-yl)-5-methyl-piperidin-3-yl]-carbamic acid tert-butyl ester (220 mg; 0.612 mmol) in anhydrous methanol (6 mL) was added a solution of hydrochloric acid (4.6 mL; 18.4 mmol) 4M in dioxane and the orange solution was stirred at room temperature overnight. Methanol (5 mL) was added to the cloudy solution and ether (20 mL) was added. The orange solution was stirred at room temperature for 30 min and the orange suspension was filtered, the light orange solid was washed with ether and dried under vacuum to give 5-(3-amino-5-methyl-1-piperidyl)quinazoline-8-carbonitrile hydrochloride (204 mg; 99%) as an orange solid.

Compound 74: $^1$H NMR (400 MHz, DMSO-d$_6$) δ 9.63 (s, 1H), 9.41 (s, 1H), 8.43 (d, J=8.3 Hz, 1H), 8.32 (s, 3H), 7.29 (d, J=8.3 Hz, 1H), 3.92 (d, J=11.6 Hz, 1H), 3.58 (d, J=11.7 Hz, 2H), 2.94 (t, J=11.5 Hz, 1H), 2.65 (t, J=11.8 Hz, 1H), 2.19 (d, J=12.1 Hz, 1H), 2.14-1.97 (m, 1H), 1.25 (q, J=12.0 Hz, 1H), 0.97 (d, J=6.6 Hz, 3H); MS: m/z=268 [M+H]$^+$.

The following compounds were synthesized in an analogous manner:

Compound 457 (5-((3R,5S)-3-Amino-5-methyl-piperidin-1-yl)-quinazoline-8-carbonitrile hydrochloride): From 5-bromo-quinazoline-8-carbonitrile and tert-butyl N-[(3R,5S)-5-methylpiperidin-3-yl]carbamate. HPLC: >99% purity, RT=4.02 min. MS: m/z=368 [M+H]$^+$. $^1$H NMR (400 MHz, Chloroform-d, ppm) δ 9.58 (s, 1H), 9.41 (s, 1H), 8.12 (d, J=8.2 Hz, 1H), 7.11 (d, J=8.2 Hz, 1H), 4.46 (s, 1H), 3.93 (d, J=11.0 Hz, 2H), 3.58 (d, J=12.3 Hz, 1H), 2.73-2.56 (m, 2H), 2.28-2.16 (m, 1H), 2.17-2.04 (m, 1H), 1.46 (s, 9H), 1.05 (t, J=11.9 Hz, 1H), 0.99 (d, J=6.6 Hz, 3H).

Compound 459 ((3R,5S)-1-(8-Fluoro-pyrido[3,4-b]pyrazin-5-yl)-5-methyl-piperidin-3-ylamine hydrochloride): From 5-chloro-8-fluoropyrido[3,4-b]pyrazine and tert-butyl N-[(3R,5S)-5-methylpiperidin-3-yl]carbamate. HPLC: >99% purity, RT=3.62 min. MS: m/z=362 [M+H]$^+$. $^1$H NMR (400 MHz, Chloroform-d, ppm) δ 8.95 (d, J=1.8 Hz, 1H), 8.82 (d, J=1.8 Hz, 1H), 8.22 (d, J=1.3 Hz, 1H), 4.92 (d, J=12.2 Hz, 1H), 4.64 (ddt, J=12.7, 3.8, 1.8 Hz, 1H), 4.45 (s, 1H), 3.82 (s, 1H), 2.72 (d, J=11.6 Hz, 1H), 2.58 (dd, J=12.7, 11.1 Hz, 1H), 2.18 (d, J=12.5 Hz, 1H), 2.09-1.95 (m, 1H), 1.45 (s, 9H), 1.04 (t, J=11.9 Hz, 1H), 0.99 (d, J=6.6 Hz, 3H).

Example 33: Synthesis of Compound 75 and Compound 76 (8-((S)-5-Amino-3,3-difluoro-piperidin-1-yl)-quinoxaline-5-carbonitrile and 8-((R)-5-Amino-3,3-difluoro-piperidin-1-yl)-quinoxaline-5-carbonitrile)

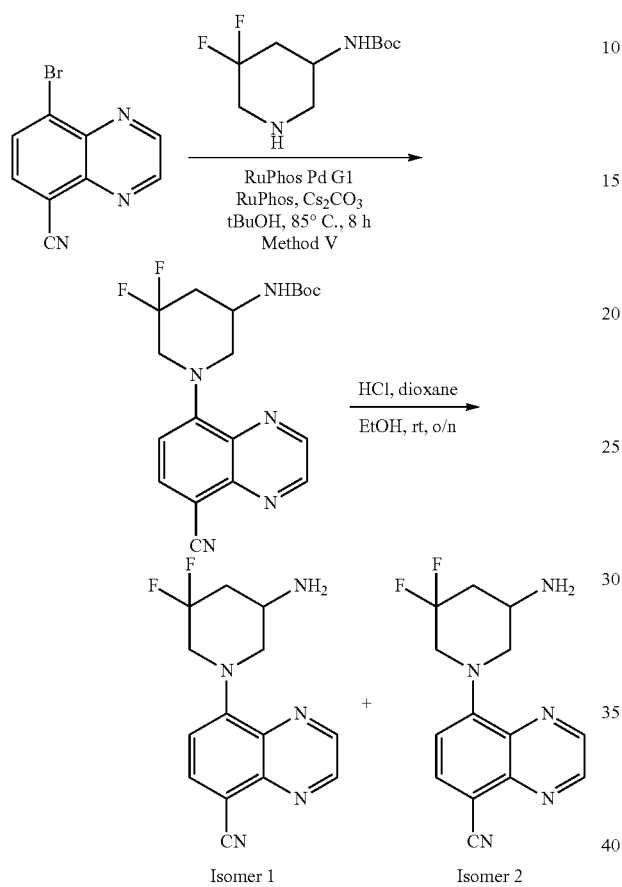

[1-(8-Cyano-qunoxalin-5-yl)-5,5-difluoro-piperidin-3-yl]-carbamic acid tert-butyl ester: The title compound was prepared from 8-Bromo-quinoxaline-5-carbonitrile and (5,5-difluoro-piperidin-3-yl)-carbamic acid tert-butyl ester to afford [1-(8-Cyano-quinoxalin-5-yl)-5,5-difluoro-piperidin-3-yl]-carbamic acid tert-butyl ester (245 mg, 45%) as a yellow solid. MS: m/z=390 [M+H].

8-(5-Amino-3,3-difluoro-piperidin-1-yl)-quinoxaline-5-carbonitrile: To a solution of [1-(8-Cyano-quinoxalin-5-yl)-5,5-difluoro-piperidin-3-yl]-carbamic acid tert-butyl ester (245 mg; 0.63 mmo) in ethanol (3 mL) was added a solution of hydrogen chloride (4.0M in dioxane) (3.1 mL; 12.58 mmol) and the resulting solution was stirred at room temperature overnight. The reaction mixture was concentrated under reduced pressure and the resulting solid was washed the solid with acetonitrile to afford a racemic mixture of 8-(5-Amino-3,3-difluoro-piperidin-1-yl)-quinoxaline-5-carbonitrile hydrochloride (200 mg, 97%) as a yellow solid. The 2 enantiomers were separated by chiral SFC (ASH column, methanol, carbon dioxide, 20 min run) to provide the desired pure chiral compounds.

Isomer 1: MS: m/z=290 [M+H]$^+$. $^1$H NMR (400 MHz, DMSO-d$_6$) δ 9.07 (d, J=1.8 Hz, 1H), 8.98 (d, J=1.8 Hz, 1H), 8.23 (d, J=8.4 Hz, 1H), 7.33 (d, J=8.5 Hz, 1H), 4.71 (s, 1H), 4.15-4.06 (m, 1H), 3.60 (ddd, J=29.7, 13.6, 2.1 Hz, 1H), 3.23 (s, 1H), 2.94 (dd, J=12.7, 10.2 Hz, 1H), 2.38 (s, 1H), 1.94-1.73 (m, 1H), 1.81 (s, 2H).

Isomer 2: MS: m/z=290 [M+H]$^+$. $^1$H NMR (400 MHz, DMSO-d$_6$) δ 9.07 (d, J=1.8 Hz, 1H), 8.98 (d, J=1.8 Hz, 1H), 8.23 (d, J=8.4 Hz, 1H), 7.33 (d, J=8.5 Hz, 1H), 4.71 (s, 1H), 4.15-4.06 (m, 1H), 3.60 (ddd, J=29.7, 13.6, 2.1 Hz, 1H), 3.23 (s, 1H), 2.94 (dd, J=12.7, 10.2 Hz, 1H), 2.38 (s, 1H), 1.94-1.73 (m, 1H), 1.81 (s, 2H).

Example 34: Synthesis of Compound 77 ((3R,5S)-5-methyl-1-[8-(trifluoromethyl)quinoxalin-5-yl]piperidin-3-amine)

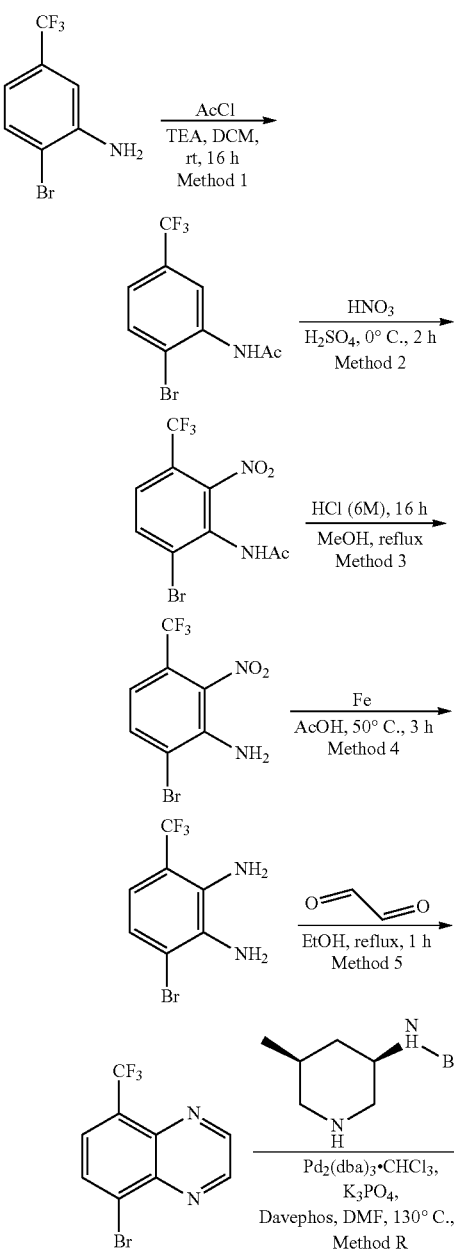

-continued

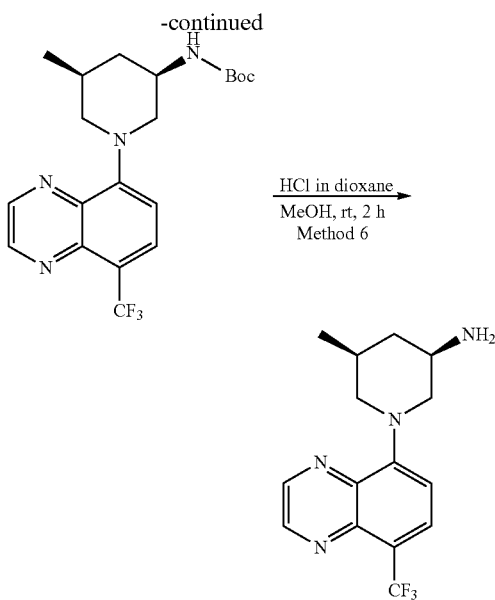

Method 1

N-(2-bromo-5-(trifluoromethyl)phenyl)acetamide: At 0° C., triethylamine (798 mg, 7.89 mmol) was added to a solution of 2-bromo-5-(trifluoromethyl)aniline (950 mg, 3.96 mmol) in DCM (30 mL), to which was added acetyl chloride (18 mg, 7.87 mmol) dropwise. The resulting solution was stirred for 16 h at room temperature. When the reaction was done, it was quenched by the addition of water (100 mL). The resulting mixture was extracted with ethyl acetate (50 mL×3). The organic phases were combined, washed with brine and dried over $Na_2SO_4$. The solvent was removed under reduced pressure to yield N-[2-bromo-5-(trifluoromethyl)phenyl]acetamide as light yellow solid (1.08 g, 98%). MS: m/z=281.9 $[M+H]^+$.

Method 2

N-(6-bromo-2-nitro-3-(trifluoromethyl)phenyl)acetamide: At 0° C., to a solution of $HNO_3$ (7.5 mL, 68%) in sulfuric acid (12.5 mL, 98%) was added N-[2-bromo-5-(trifluoromethyl)phenyl]acetamide (1.08 g, 3.84 mmol) in portions over 20 min period. The resulting solution was stirred for 2 h at 0° C. When the reaction was done, it was quenched by the addition of water (50 mL). The resulting mixture was extracted with ethyl acetate (50 mL×3). The organic phases were combined, washed with brine and dried over $Na_2SO_4$. The solvent was removed under reduced pressure and the residue was purified by reverse phase flash chromatography eluting with acetonitrile in water (with 0.02% HCl), 0% to 80% gradient in 45 min, to yield N-[6-bromo-2-nitro-3-(trifluoromethyl)phenyl]acetamide as yellow solid (445 mg, 32%). MS: m/z=326.9 $[M+H]^+$.

Method 3

6-bromo-2-nitro-3-(trifluoromethyl)benzenamine: To a solution of N-[6-bromo-2-nitro-3-(trifluoromethyl)phenyl]acetamide (240 mg, 0.73 mmol) in methanol (16 mL) was added hydrogen chloride solution (6 M in water, 4 mL, 24 mmol) at room temperature. The resulting solution was heated to reflux and stirred for 16 h. When the reaction was done, the pH value of the reaction mixture was adjusted to 8 with sat. sodium bicarbonate solution. The resulting mixture was extracted with EtOAc (50 mL×3) and the organic phases were combined, washed with brine and dried over $Na_2SO_4$. The solvent was removed under reduced pressure to yield 6-bromo-2-nitro-3-(trifluoromethyl)aniline as brown oil (165 mg, 79%). $^1$H NMR (400 MHz, $CD_3OD$, ppm) δ 7.81 (d, J=8.4 Hz, 1H), 7.00 (d, J=8.3 Hz, 1H).

Method 4

3-bromo-6-(trifluoromethyl)benzene-1,2-diamine: To a solution of 6-bromo-2-nitro-3-(trifluoromethyl)aniline (189 mg, 0.66 mmol) in AcOH (10 mL) was added Fe powder (252 mg, 4.51 mmol) at room temperature. The resulting mixture was then stirred for 3 h at 50° C. After the reaction was done, the reaction mixture was filtrated and the filtrate was concentrated under reduced pressure. The pH value of the residue was adjusted to 8 with sat. sodium bicarbonate solution. The resulting mixture was extracted with ethyl acetate (20 mL×3). The organic phases were combined, washed with brine and dried over $Na_2SO_4$. The solvent was removed under reduced pressure to yield 3-bromo-6-(trifluoromethyl)benzene-1,2-diamine as brown solid (143 mg, 84%). MS: m/z=326.9 $[M+H]^+$.

Method 5

5-bromo-8-(trifluoromethyl)quinoxaline: To a solution of 3-bromo-6-(trifluoromethyl)benzene-1,2-diamine (143 mg, 0.56 mmol) in ethanol (5 mL) was added oxaldehyde (409 mg, 8.18 mmol) at room temperature. The resulting solution was heated to reflux and stirred for 1 h. After the reaction was done, the reaction mixture was concentrated under reduced pressure and the residue was purified by flash chromatography eluting with EtOAc in hexane (1% isotropic) to yield 5-bromo-8-(trifluoromethyl)quinoxaline as yellow solid (150 mg, 95%). MS: m/z=278.9 $[M+H]^+$.

(3R,5S)-5-methyl-1-[8-(trifluoromethyl)quinoxalin-5-yl]piperidin-3-amine: To a solution of 5-bromo-8-(trifluoromethyl)quinoxaline (157 mg, 0.57 mmol) in DMF (5 mL) were added tert-butyl N-[(3R,5S)-5-methylpiperidin-3-yl]carbamate (118 mg, 0.55 mmol), $Pd_2(dba)_3CHCl_3$ (57 mg, 0.06 mmol), $K_3PO_4$ (351 mg, 1.65 mmol), Davephos (43 mg, 0.11 mmol) at room temperature. The resulting mixture was stirred for 3 h at 130° C. After cooling to room temperature, the reaction mixture was quenched by the addition of water (10 mL). The resulting mixture was extracted with ethyl acetate (20 mL×3). The organic phases were combined, washed with brine and dried over $Na_2SO_4$. The solvent was removed under reduced pressure and the residue was purified by flash chromatography eluting with EtOAc in hexane (0% to 16% gradient) to yield tert-butyl N-[(3R,5S)-5-methyl-1-[8-(trifluoromethyl)quinoxalin-5-yl]piperidin-3-yl]carbamate as yellow solid (107 mg, 46%). MS: m/z=411.2 $[M+H]^+$.

Method 6

(3R,5S)-1-[8-(difluoromethyl)quinolin-5-yl]-5-methylpiperidin-3-amine: To a solution of tert-butyl N-[(3R,5S)-5-methyl-1-[8-(trifluoromethyl)quinoxalin-5-yl]piperidin-3-yl]carbamate (107 mg, 0.26 mmol) in methanol (5 mL) was added a solution of HCl in dioxane (5 M, 3.1 mL, 15.63 mmol) at room temperature. The resulting solution was stirred for 1 h at room temperature. When the reaction was done, the pH value of the reaction mixture was adjusted to 7 with sat. sodium bicarbonate solution. The resulting mixture was extracted with ethyl acetate (20 mL×3). The organic phases were combined, washed with brine and dried over $Na_2SO_4$. The solvent was removed under reduced pressure and the residue was purified by prep-HPLC under the following conditions: column, XBridge Shield RP18 OBD column, 150 mm, 5 um, 13 nm; mobile phase, acetonitrile in water (with 10 mmol/L $NH_4HCO_3$), 48% to 68% gradient in 8 min; detector, UV 254 nm. (3R,5S)-5-methyl-1-[8-(trifluoromethyl)quinoxalin-5-yl]piperidin-3-amine was obtained as yellow solid (30 mg, 37%).

Compound 77: HPLC: 99.2% purity, RT=0.88 min. MS: m/z=311.0 [M+H]$^+$. $^1$H NMR (400 MHz, CD$_3$OD, ppm) δ 9.01-8.87 (m, 2H), 8.05 (d, J=8.3 Hz, 1H), 7.26 (d, J=8.3 Hz, 1H), 4.22 (m, 1H), 4.09-3.93 (m, 1H), 3.21 (m, 1H), 2.60-2.44 (m, 2H), 2.26-2.01 (m, 2H), 1.10-0.84 (m, 4H).

Example 35: Synthesis of Compound 78 ((3R,5S)-1-(8-chloroquinolin-5-yl)-5-methylpiperidin-3-amine)

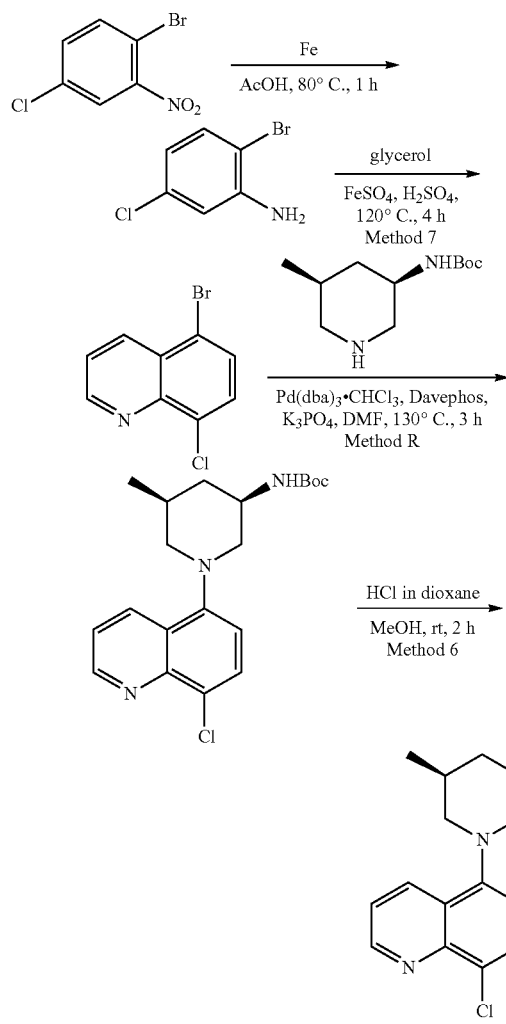

2-bromo-5-chlorobenzenamine: To a solution of 4-bromo-1-chloro-2-nitrobenzene (2.94 g, 12.43 mmol) in AcOH (50 mL) was added Fe powder (5.67 g, 100.52 mmol) at room temperature. The resulting mixture was stirred for 1 h at 80° C. When the reaction was done, the solids in the reaction mixture were filtered out and the filtrate was concentrated under reduced pressure. The pH value of the residue was adjusted to 7-8 with sodium hydroxide solution (2N). The resulting mixture was extracted with ethyl acetate (100 mL×3). The organic phases were combined, washed with brine and dried over Na$_2$SO$_4$. The solvent was removed under reduced pressure to yield 5-bromo-2-chloroaniline as yellow solid (2.06 g, 80%). MS: m/z=207.9 [M+H]$^+$. Method 7

5-bromo-8-chloroquinoline: To a solution of 5-bromo-2-chloroaniline (2.06 g, 9.88 mmol) in propane-1,2,3-triol (4.23 g, 45.90 mmol) was added FeSO$_4$·7H$_2$O (520 mg, 1.87 mmol) and sulfuric acid (3 g, 29.67 mmol) at room temperature. The resulting mixture was stirred for 4 h at 120° C. After cooling to room temperature, the reaction mixture was adjusted to pH 13 using sodium hydroxide solution (2 M). The resulting mixture was extracted with ethyl acetate (50 mL×3). The organic phases were combined, washed with brine and dried over Na$_2$SO$_4$. The solvent was removed under reduced pressure and the residue was purified by flash chromatography eluting with EtOAc in hexane (0% to 94% gradient) to yield 5-bromo-8-chloroquinoline as yellow solid (760 mg, 32%). MS: m/z=243.8 [M+H]$^+$.

(3R,5S)-1-(8-chloroquinolin-5-yl)-5-methylpiperidin-3-amine: (3R,5S)-1-(8-chloroquinolin-5-yl)-5-methylpiperidin-3-amine was prepared from 5-bromo-8-chloroquinoline and tert-butyl (3R,5S)-5-methylpiperidin-3-ylcarbamate using Method R and 6. The crude product was purified by prep-HPLC under the following conditions: column, XBridge C18 OBD Prep Column, 5 um, 19 mm×150 mm; mobile phase, MeOH in water (with 10 mmol/L NH$_4$HCO$_3$), 20% to 50% gradient in 10 min; detector, UV 254 nm. (3R,5S)-1-(8-chloroquinolin-5-yl)-5-methylpiperidin-3-amine was obtained as light yellow solid (25 mg, 35%).

Compound 78: HPLC: 99.6% purity, RT=0.76 min. MS: m/z=276.1 [M+H]$^+$. $^1$H NMR (400 MHz, CD$_3$OD, ppm) δ 8.93 (dd, J=4.3, 1.6 Hz, 1H), 8.66 (dd, J=8.5, 1.7 Hz, 1H), 7.83 (d, J=8.1 Hz, 1H), 7.63 (dd, J=8.5, 4.2 Hz, 1H), 7.21 (d, J=8.1 Hz, 1H), 3.52-3.36 (m, 1H), 3.36-3.19 (m, 2H), 2.48 (t, J=10.7 Hz, 1H), 2.38 (t, J=11.1 Hz, 1H), 2.20-2.08 (m, 2H), 1.06-1.00 (m, 4H).

Example 36: Synthesis of Compound 79 (N-[(3R,5S)-1-[8-(difluoromethyl)quinoxalin-5-yl]-5-methylpiperidin-3-yl]-2-hydroxypropanamide)

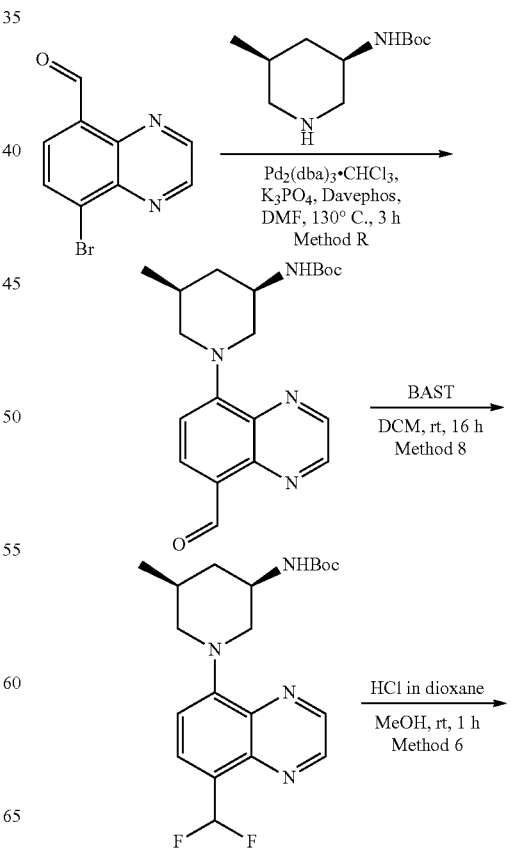

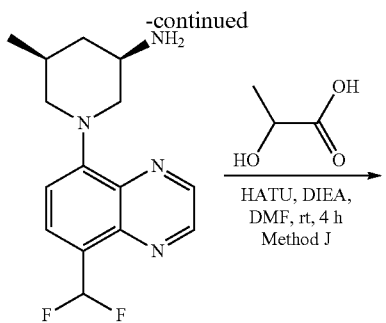

tert-butyl N-[(3R,5S)-1-(8-formylquinoxalin-5-yl)-5-methylpiperidin-3-yl]carbamate: tert-butyl (3R,5S)-1-(8-formylquinoxalin-5-yl)-5-methylpiperidin-3-ylcarbamate was prepared from 8-bromoquinoxaline-5-carbaldehyde and tert-butyl (3R,5S)-5-methylpiperidin-3-ylcarbamate using Method R. The crude product was purified by flash chromatography eluting with EtOAc in hexane (0% to 20% gradient) to yield tert-butyl N-[(3R,5S)-5-methyl-1-[8-(trifluoromethyl)quinolin-5-yl]piperidin-3-yl]carbamate as yellow solid (467 mg, 39%). MS: m/z=371.1 [M+H]+.
Method 8 tert-butyl (3R,5S)-1-(8-(difluoromethyl)quinoxalin-5-yl)-5-methylpiperidin-3-ylcarbamate: To a solution of tert-butyl N-[(3R,5S)-1-(8-formylquinoxalin-5-yl)-5-methylpiperidin-3-yl]carbamate (140 mg, 0.38 mmol) in dichloromethane (5 mL) was added DAST (1.24 g, 7.66 mmol) at room temperature. The resulting solution was stirred for 16 h at room temperature. When the reaction was done, it was quenched by the addition of sodium bicarbonate solution (10%, 30 mL). The resulting mixture was extracted with ethyl acetate (50 mL×3). The organic phases were combined, washed with brine and dried over $Na_2SO_4$. The solvent was removed under reduced pressure and the residue was purified by flash chromatography eluting with EtOAc in hexane (0% to 15% gradient) to yield tert-butyl N-[(3R,5S)-1-[8-(difluoromethyl)quinoxalin-5-yl]-5-methylpiperidin-3-yl]carbamate as light brown solid (49 mg, 33%). MS: m/z=393.2 [M+H]+.

N-[(3R,5S)-1-[8-(difluoromethyl)quinoxalin-5-yl]-5-methylpiperidin-3-yl]-2-hydroxypropanamide: N-[(3R,5S)-1-[8-(difluoromethyl)quinoxalin-5-yl]-5-methylpiperidin-3-yl]-2-hydroxypropanamide was prepared from 2-hydroxypropanoic acid and tert-butyl (3R,5S)-1-(8-(difluoromethyl)quinoxalin-5-yl)-5-methylpiperidin-3-ylcarbamate using Method 6 and J. The crude product was purified by prep-HPLC under the following conditions: column, XBridge C18 OBD Prep Column, 5 um, 19 mm×150 mm; mobile phase, MeOH in water (with 10 mmol/L $NH_4HCO_3$), 30% to 60% gradient in 10 min; detector, UV 254 nm. N-[(3R,5S)-1-[8-(difluoromethyl)quinoxalin-5-yl]-5-methylpiperidin-3-yl]-2-hydroxypropanamide was obtained as yellow solid (21 mg, 18%).

Compound 79: HPLC: 95.6% purity, RT=1.58 min. MS: n/z=365.2 [M+H]+. $^1$H NMR (300 MHz, $CD_3OD$, ppm) δ 8.88-8.80 (m, 2H), 7.94 (d, J=8.2 Hz, 1H), 7.80-7.40 (m, 1H), 7.31 (d, J=8.2 Hz, 1H), 4.26-3.89 (m, 4H), 2.73 (t, J=10.8 Hz, 1H), 2.52 (t, J=11.1 Hz, 1H), 2.15-1.95 (m, 2H), 1.32 (d, J=6.8 Hz, 3H), 1.27-1.16 (m, 1H), 0.99 (d, J=6.4 Hz, 3H).

Example 37: Synthesis of Compound 80 ((R)-5,5-dimethyl-1-(pyrido[2,3-b]pyrazin-8-yl)piperidin-3-amine)

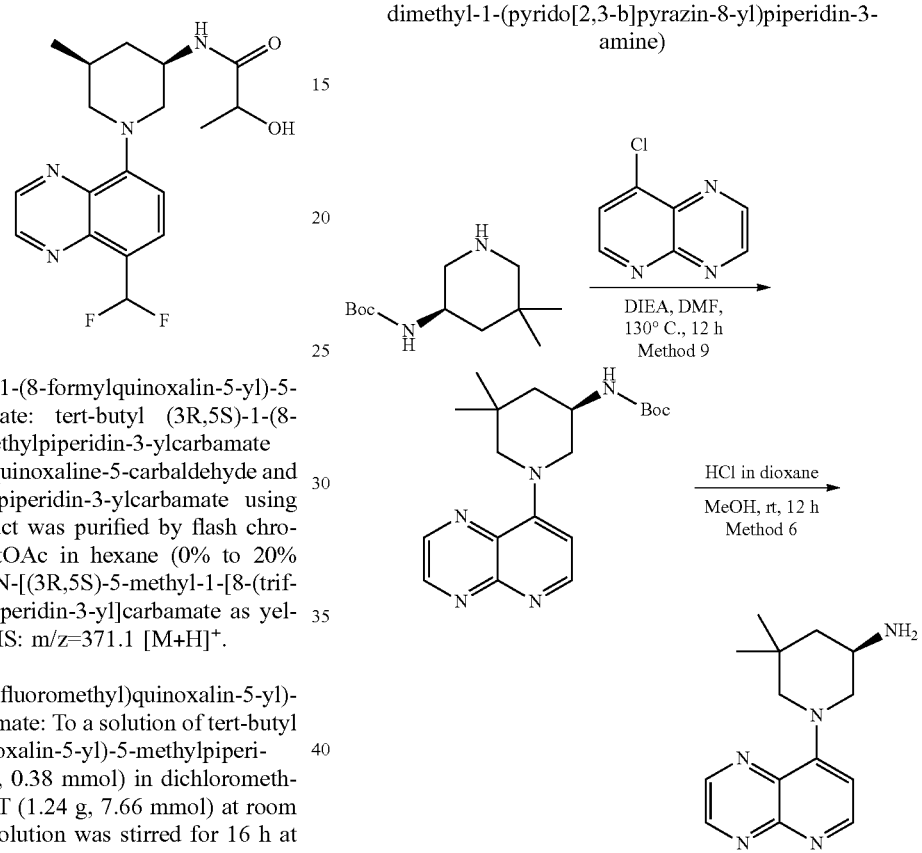

Method 9

(R)-tert-butyl 5,5-dimethyl-1-(pyrido[2,3-b]pyrazin-8-yl)piperidin-3-ylcarbamate: To a solution of tert-butyl N-[(3R)-5,5-dimethylpiperidin-3-yl]carbamate (27 mg, 0.12 mmol) in DMF (2 mL) were added 8-chloropyrido[2,3-b]pyrazine (22 mg, 0.13 mmol) and DIEA (24 mg, 0.19 mmol) at room temperature. The resulting solution was stirred for 12 h at 130° C. After cooling to room temperature, the reaction mixture was quenched by the addition of water (20 mL). The resulting mixture was extracted with ethyl acetate (20 mL×3). The organic phases were combined, washed with brine and dried over $Na_2SO_4$. The solvent was removed under reduced pressure and the residue was purified by flash chromatography eluting with EtOAc in hexane (0% to 50% gradient) to yield tert-butyl N-[(3R)-1-(8-cyanoquinoxalin-5-yl)-5,5-dimethylpiperidin-3-yl]carbamate as yellow solid (40 mg, 98%). MS: m/z=358.2 [M+H]+.

(3R)-5,5-dimethyl-1-[pyrido[2,3-b]pyrazin-8-yl]piperidin-3-amine: To a solution of tert-butyl N-[(3R)-5,5-dimethyl-1-[pyrido[2,3-b]pyrazin-8-yl]piperidin-3-yl]carbamate (39 mg, 0.11 mmol) in methanol (5 mL) was added a solution of HCl in dioxane (4 M, 5 mL, 20 mmol) at room temperature. The resulting solution was stirred for 12 h at room temperature. After the reaction was done, the resulting mixture was concentrated under reduced pressure and the residue was purified by prep-HPLC under the following conditions: column, XBridge BEH130 Prep C18 OBD column, 150 mm, 5 um, 13 nm; mobile phase, acetonitrile in water (with 0.05% NH$_4$OH), 30% to 80% gradient in 10 min; detector, UV 254 nm. (3R)-5,5-dimethyl-1-[pyrido[2,3-b]pyrazin-8-yl]piperidin-3-amine was obtained as yellow oil (12 mg, 44%).

Compound 80: HPLC: 99.2% purity, RT=0.77 min. MS: n/z=258.1 [M+H]$^+$. $^1$H NMR (400 MHz, CD$_3$OD, ppm) δ 8.95 (d, J=1.7 Hz, 1H), 8.83 (d, J=1.7 Hz, 1H), 8.66 (d, J=5.6 Hz, 1H), 7.10 (d, J=5.7 Hz, 1H), 4.72 (dd, J=12.3, 4.1 Hz, 1H), 4.34 (d, J=12.7 Hz, 1H), 3.49-3.36 (m, 1H), 2.93 (d, J=12.6 Hz, 1H), 2.78 (t, J=11.4 Hz, 1H), 1.90 (dd, J=12.7, 3.9 z, 1H), 1.40-1.27 (m, 1H), 1.08 and 1.06 (s, 6H).

Example 38: Synthesis of Compound 81 (8-[(3R,5S)-3-hydroxy-5-methylpiperidin-1-yl]quinoxaline-5-carbonitrile)

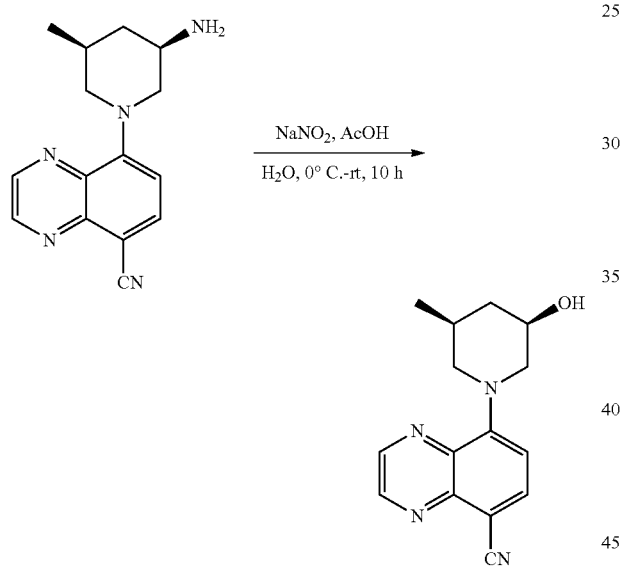

8-[(3R,5S)-3-hydroxy-5-methylpiperidin-1-yl]quinoxaline-5-carbonitrile: At 0° C., to a solution of 8-[(3R,5S)-3-amino-5-methylpiperidin-1-yl]quinoxaline-5-carbonitrile (178 mg, 0.67 mmol) in AcOH (5 mL) was added a solution of NaNO$_2$ (229 mg, 3.33 mmol) in water (1 mL) dropwise. The resulting solution was stirred for 10 h at room temperature. After the reaction was done, the reaction mixture was concentrated under reduced pressure and the residue was purified by prep-HPLC under the following conditions: column, XBridge BEH130 Prep C18 OBD column, 19×150 mm, 5 um, 13 nm; mobile phase, MeOH in water (with 10 mmol/L NH$_4$HCO$_3$), 30% to 80% gradient in 10 min; detector, UV 254 nm. 8-[(3R,5S)-3-hydroxy-5-methylpiperidin-1-yl]quinoxaline-5-carbonitrile was obtained as yellow solid (30 mg, 17%).

Compound 81: HPLC: 99.9% purity, RT=1.13 min. MS: n/z=269.2 [M+H]$^+$. $^1$H NMR (400 MHz, CD$_3$OD, ppm) δ 8.99-8.88 (m, 2H), 8.11 (d, J=8.4 Hz, 1H), 7.27 (d, J=8.4 Hz, 1H), 4.42 (dd, J=11.5, 4.2 Hz, 1H), 4.14-3.92 (m, 2H), 2.73 (dd, J=11.5, 10.3 Hz, 1H), 2.62 (t, J=11.7 Hz, 1H), 2.30-2.12 (m, 1H), 2.11-1.99 (m, 1H), 1.24-1.10 (m, 1H), 1.05 (d, J=6.6 Hz, 3H).

Example 39: Synthesis of Compound 82 and compound 83 (8-[(3R,5S)-3-amino-5-(trifluoromethyl)piperidin-1-yl]quinoxaline-5-carbonitrile and 8-[(3S,5R)-3-amino-5-(trifluoromethyl)piperidin-1-yl]quinoxaline-5-carbonitrile)

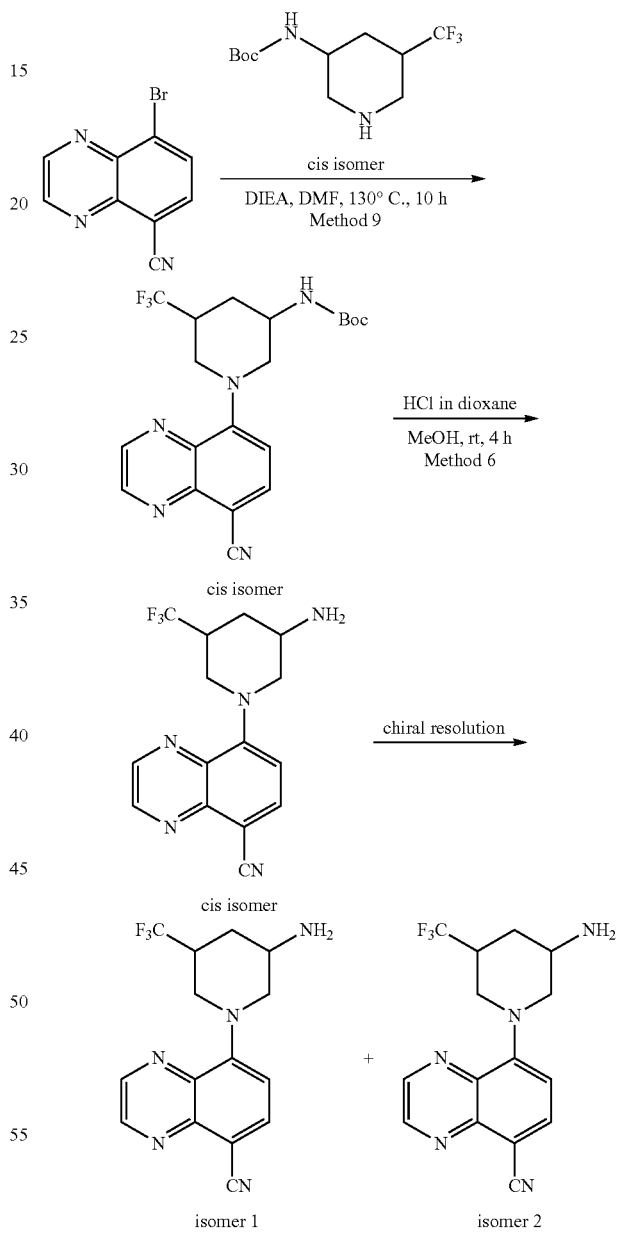

Cis-8-[3-amino-5-(trifluoromethyl)piperidin-1-yl]quinoxaline-5-carbonitrile: cis-8-[3-amino-5-(trifluoromethyl)piperidin-1-yl]quinoxaline-5-carbonitrile was prepared from 8-bromoquinoxaline-5-carbonitrile and tert-butyl cis-5-(trifluoromethyl)piperidin-3-ylcarbamate using Method 9 and 6. Cis-8-[3-amino-5-(trifluoromethyl)piperidin-1-yl]quinoxaline-5-carbonitrile was obtained by purification on prep-HPLC under the following conditions: column, XBridge C18 OBD Prep Column, 5 um, 19 mm×150 mm; mobile phase, MeOH in water (with 10 mmol/L NH₄HCO₃), 20% to 50% gradient in 10 min; detector, UV 254 nm. HPLC: 99.0% purity, RT=1.21 min. MS: m/z=322.1 [M+H]⁺. ¹H NMR (300 MHz, CD₃OD, ppm) δ 8.99-8.85 (m, 2H), 8.15 (d, J=8.3 Hz, 1H), 7.30 (d, J=8.3 Hz, 1H), 4.54 (d, J=10.5 Hz, 1H), 4.28-4.19 (m, 1H), 3.24-3.12 (m, 1H), 3.03-2.84 (m, 2H), 2.75 (t, J=11.2 Hz, 1H), 2.36 (d, J=12.3 Hz, 1H), 1.52-1.38 (m, 1H).

8-[(3R,5S)-3-amino-5-(trifluoromethyl)piperidin-1-yl]quinoxaline-5-carbonitrile and 8-[(3S,5R)-3-amino-5-(trifluoromethyl)piperidin-1-yl]quinoxaline-5-carbonitrile: The two enantiomers of cis-8-[3-amino-5-(trifluoromethyl)piperidin-1-yl]quinoxaline-5-carbonitrile were obtained by separation on chiral prep-HPLC under the following conditions: column, Repaired ADH, 0.46×15 cm, 5um; mobile phase, EtOH in Hexane (0.1% DEA), 30% isocratic in 20 min; detector, UV 254 nm. Two products were separated and obtained.

Isomer 1: (60 mg, 13%, yellow solid) HPLC: 99.3% purity, RT=1.21 min. MS: m/z=322.0 [M+H]⁺. ¹H NMR (300 MHz, CD₃OD, ppm) δ 8.99-8.85 (m, 2H), 8.15 (d, J=8.3 Hz, 1H), 7.30 (d, J=8.3 Hz, 1H), 4.54 (d, J=10.5 Hz, 1H), 4.28-4.19 (m, 1H), 3.24-3.12 (m, 1H), 3.03-2.84 (m, 2H), 2.75 (t, J=11.2 Hz, 1H), 2.36 (d, J=12.3 Hz, 1H), 1.52-1.38 (m, 1H).

Isomer 2: (56 mg, 12%, yellow solid) HPLC: 99.2% purity, RT=1.21 min. MS: m/z=322.0 [M+H]⁺. ¹H NMR (300 MHz, CD₃OD, ppm) δ 8.99-8.85 (m, 2H), 8.15 (d, J=8.3 Hz, 1H), 7.30 (d, J=8.3 Hz, 1H), 4.54 (d, J=10.5 Hz, 1H), 4.28-4.19 (m, 1H), 3.24-3.12 (m, 1H), 3.03-2.84 (m, 2H), 2.75 (t, J=11.2 Hz, 1H), 2.36 (d, J=12.3 Hz, 1H), 1.52-1.38 (m, 1H).

The following compounds were synthesized in an analogous manner:

Compound 84 (cis-8-(3-amino-5-(trifluoromethyl)piperidin-1-yl)quinoxaline-5-carbonitrile): From 8-chloropyrido[2,3-b]pyrazine and tert-butyl cis-5-(trifluoromethyl)piperidin-3-ylcarbamate. HPLC: 99.1% purity, RT=0.88 min. MS: m/z=298.2 [M+H]⁺. ¹H NMR (400 MHz, CD₃OD, ppm) δ 8.96 (d, J=1.7 Hz, 1H), 8.83 (d, J=1.7 Hz, 1H), 8.71 (d, J=5.6 Hz, 1H), 7.12 (d, J=5.5 Hz, 1H), 4.91-4.98 (m, 1H), 4.46-4.55 (m, 1H), 3.21-3.00 (m, 2H), 2.94-2.74 (m, 2H), 2.39-2.29 (m, 1H), 1.59-1.41 (m, 1H).

Example 40: Synthesis of Compound 85 (cis-N-[1-(8-cyanoquinoxalin-5-yl)-5-(trifluoromethyl)piperidin-3-yl]-3,3-dimethylbutanamide)

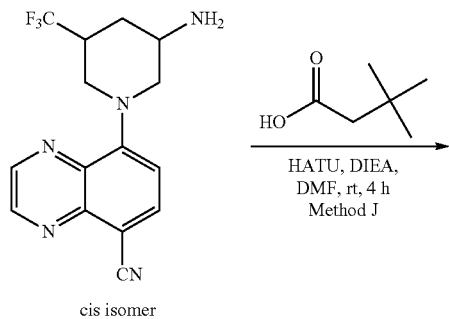

cis isomer

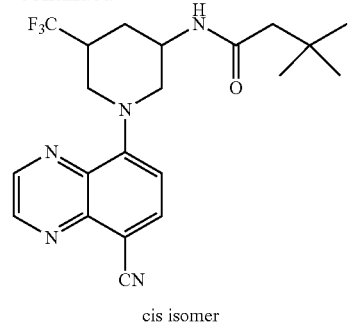

cis isomer

Cis-N-[1-(8-cyanoquinoxalin-5-yl)-5-(trifluoromethyl)piperidin-3-yl]-3,3-dimethylbutanamide: cis-N-[1-(8-cyanoquinoxalin-5-yl)-5-(trifluoromethyl)piperidin-3-yl]-3,3-dimethylbutanamide was prepared from cis-8-[3-amino-5-(trifluoromethyl)piperidin-1-yl]quinoxaline-5-carbonitrile and 3,3-dimethylbutanoic acid using Method J. The crude product was purified by prep-HPLC under the following conditions: column, XBridge C18 OBD Prep Column, 5 um, 19 mm×150 mm; mobile phase, MeOH in water (with 10 mmol/L NH₄HCO₃), 30% to 80% gradient in 10 min; detector, UV 254 nm. Cis-N-[1-(8-cyanoquinoxalin-5-yl)-5-(trifluoromethyl)piperidin-3-yl]-3,3-dimethylbutanamide was obtained as yellow solid (50 mg, 45%).

Compound 85: HPLC: 99.3% purity, RT=2.12 min. MS: m/z=420.2 [M+H]⁺. ¹H NMR (300 MHz, CD₃OD, ppm) δ 8.99-8.85 (m, 2H), 8.10 (d, J=8.3 Hz, 1H), 7.30 (d, J=8.4 Hz, 1H), 4.62 (d, J=11.5 Hz, 1H), 4.27-4.12 (m, 2H), 3.08-2.73 (m, 3H), 2.28 (d, J=12.5 Hz, 1H), 2.07 (s, 2H), 1.59 (d, J=12.2 Hz, 1H), 1.01 (s, 9H).

The following compounds were synthesized in an analogous manner:

Compound 86 (cis-3,3-dimethyl-N-[1-[pyrido[2,3-b]pyrazin-8-yl]-5-(trifluoromethyl)piperidin-3-yl]butanamide): From cis-1-(pyrido[2,3-b]pyrazin-8-yl)-5-(trifluoromethyl)piperidin-3-amine and 3,3-dimethylbutanoic acid. HPLC: 99.4% purity, RT=1.33 min. MS: m/z=396.2 [M+H]⁺. ¹H NMR (400 MHz, CD₃OD, ppm) δ 8.99 (d, J=1.7 Hz, 1H), 8.87 (d, J=1.7 Hz, 1H), 8.76 (d, J=5.5 Hz, 1H), 7.24 (d, J=5.6 Hz, 1H), 5.18-5.10 (m, 1H), 4.60-4.51 (m, 1H), 4.22-4.12 (m, 1H), 3.24-3.13 (m, 1H), 2.99-2.87 (m, 2H), 2.32 (d, J=12.5 Hz, 1H), 2.13 (s, 2H), 1.78-1.62 (m, 1H), 1.07 (s, 9H).

Compound 222 (cis-N-[1-(8-cyanoquinoxalin-5-yl)-5-(trifluoromethyl)piperidin-3-yl]-2-(dimethylamino)acetamide): From 2-(dimethylamino)acetic acid and 8-(cis-3-amino-5-(trifluoromethyl)piperidin-1-yl)quinoxaline-5-carbonitrile. HPLC: 95.1% purity, RT=2.57 min. MS: m/z=407.2 [M+H]⁺. ¹H NMR (300 MHz, CD₃OD, ppm) δ 8.99-8.85 (m, 2H), 8.10 (d, J=8.3 Hz, 1H), 7.30 (d, J=8.3 Hz, 1H), 4.58 (d, J=11.3 Hz, 1H), 4.29-4.12 (m, 2H), 3.10-2.83 (m, 5H), 2.32-2.27 (m, 7H), 1.70 (td, J=12.1, 12.1 Hz, 1H).

Compound 223 (cis-N-[1-(8-cyanoquinoxalin-5-yl)-5-(trifluoromethyl)piperidin-3-yl]-2-hydroxyacetamide): From 2-hydroxyacetic acid and cis-8-(3-amino-5-(trifluoromethyl)piperidin-1-yl)quinoxaline-5-carbonitrile. HPLC: 95.3% purity, RT=1.16 min. MS: m/z=380.1 [M+H]⁺. ¹H NMR (300 MHz, CD₃OD, ppm) δ 8.99-8.85 (m, 2H), 8.14 (d, J=8.4 Hz, 1H), 7.33 (d, J=8.3 Hz, 1H), 4.65-4.54 (m, 1H), 4.36-4.14 (m, 2H), 4.02 (s, 2H), 3.15-2.88 (m, 3H), 2.32 (d, J=12.9 Hz, 1H), 1.78 (td, J=12.1, 12.1 Hz, 1H).

Compound 228 (cis-N-[1-(8-cyanoquinoxalin-5-yl)-5-(trifluoromethyl)piperidin-3-yl]-2-(morpholin-4-yl)acetamide): From 2-(morpholin-4-yl)acetic acid and 8-(cis-3-amino-5-(trifluoromethyl)piperidin-1-yl)quinoxaline-5-carbonitrile. HPLC: 90.3% purity, RT=1.73 min. MS: m/z=449.2 [M+H]$^+$. $^1$H NMR (300 MHz, CD$_3$OD, ppm) δ 8.99-8.85 (m, 2H), 8.09 (d, J=8.3 Hz, 1H), 7.29 (d, J=8.3 Hz, 1H), 4.64-4.53 (m, 1H), 4.31-4.12 (m, 2H), 3.75-3.65 (m, 4H), 3.12-2.84 (m, 5H), 2.56-2.46 (m, 4H), 2.35-2.21 (m, 1H), 1.71 (td, J=12.1, 12.1 Hz, 1H).

Compound 229 (cis-N-[1-(8-cyanoquinoxalin-5-yl)-5-(trifluoromethyl)piperidin-3-yl]-2-(4-methylpiperazin-1-yl)acetamide): From 2-(4-methylpiperazin-1-yl)acetic acid and cis-8-(3-amino-5-(trifluoromethyl)piperidin-1-yl)quinoxaline-5-carbonitrile. HPLC: 99.4% purity, RT=1.26 min. MS: m/z=462.2 [M+H]$^+$. $^1$H NMR (300 MHz, CD$_3$OD, ppm) δ 8.99-8.85 (m, 2H), 8.13 (d, J=8.4 Hz, 1H), 7.33 (d, J=8.4 Hz, 1H), 4.62 (apparent d, J=11.7 Hz, 1H), 4.34-4.16 (m, 2H), 3.17-2.87 (m, 5H), 2.75-2.45 (m, 8H), 2.39-2.27 (m, 4H), 1.73 (td, J=12.1, 12.1 Hz, 1H).

Compound 424 (cis-N-[1-(8-Cyano-quinolin-5-yl)-5-trifluoromethyl-piperidin-3-yl]-2-morpholin-4-yl-acetamide): From cis-5-(3-Amino-5-trifluoromethyl-piperidin-1-yl)-quinoline-8-carbonitrile hydrochloride and 2-morpholino-acetic acid hydrochloride. HPLC: >99% purity, RT=2.66 min. MS: m/z=448 [M+H]$^+$. $^1$H NMR (400 MHz, Chloroform-d, ppm) δ 9.09 (dd, J=4.2, 1.7 Hz, 1H), 8.47 (dd, J=8.6, 1.7 Hz, 1H), 8.04 (d, J=7.9 Hz, 1H), 7.59 (dd, J=8.6, 4.2 Hz, 1H), 7.13 (dd, J=8.1, 4.0 Hz, 2H), 4.41 (dtt, J=12.2, 8.4, 4.3 Hz, 1H), 3.84-3.71 (m, 1H), 3.71 (t, J=4.6 Hz, 4H), 3.63 (ddd, J=11.4, 3.8, 1.9 Hz, 1H), 3.09-2.95 (m, 2H), 2.94 (t, J=11.2 Hz, 1H), 2.84 (dtq, J=15.5, 7.6, 4.1 Hz, 1H), 2.64-2.45 (m, 5H), 2.48-2.35 (m, 1H), 1.54 (q, J=12.2 Hz, 1H).

Compound 426 (cis-N-[1-(8-Cyano-quinolin-5-yl)-5-trifluoromethyl-piperidin-3-yl]-2-dimethylamino-acetamide): From cis-5-(3-Amino-5-trifluoromethyl-piperidin-1-yl)-quinoline-8-carbonitrile hydrochloride and N,N-dimethyl-glycine. HPLC: 98.8% purity, RT=2.61 min. MS: m/z=406 [M+H]$^+$. $^1$H NMR (400 MHz, Chloroform-d, ppm) δ 9.09 (dd, J=4.2, 1.7 Hz, 1H), 8.48 (dd, J=8.6, 1.7 Hz, 1H), 8.04 (d, J=7.9 Hz, 1H), 7.59 (dd, J=8.6, 4.2 Hz, 1H), 7.23 (s, 1H), 7.12 (d, J=7.9 Hz, 1H), 4.41 (dtd, J=15.5, 8.4, 4.2 Hz, 1H), 3.81-3.73 (m, 1H), 3.63 (d, J=11.1 Hz, 1H), 2.97-2.90 (m, 2H), 2.83 (ddp, J=11.4, 7.6, 3.7 Hz, 1H), 2.54 (t, J=11.1 Hz, 1H), 2.44 (d, J=12.2 Hz, 1H), 2.28 (s, 6H), 1.55 (q, J=12.3 Hz, 1H), 1.28-1.24 (m, 1H).

Compound 428 (cis-N-[1-(8-Cyano-quinolin-5-yl)-5-trifluoromethyl-piperidin-3-yl]-3,3,3-trifluoro-propionamide): From cis-5-(3-Amino-5-trifluoromethyl-piperidin-1-yl)-quinoline-8-carbonitrile hydrochloride and 3,3,3-trifluoro-propionic acid. HPLC: >99% purity, RT=4.03 min. MS: m/z=431 [M+H]$^+$. $^1$H NMR (400 MHz, Chloroform-d, ppm) δ 9.06 (dd, J=4.2, 1.7 Hz, 1H), 8.45 (dd, J=8.6, 1.7 Hz, 1H), 8.02 (d, J=7.9 Hz, 1H), 7.59 (dd, J=8.6, 4.2 Hz, 1H), 7.11 (d, J=8.0 Hz, 1H), 5.93 (d, J=7.6 Hz, 1H), 4.42 (dtd, J=15.0, 8.6, 8.1, 4.1 Hz, 1H), 3.79 (ddt, J=11.6, 4.1, 1.7 Hz, 1H), 3.62 (ddt, J=11.3, 3.7, 1.5 Hz, 1H), 3.11 (q, J=10.5 Hz, 2H), 2.93 (t, J=11.2 Hz, 1H), 2.83 (dtq, J=15.4, 7.6, 3.9 Hz, 1H), 2.56 (dd, J=11.6, 10.7 Hz, 1H), 2.47 (dt, J=12.6, 4.0 Hz, 1H), 1.55 (q, J=12.2 Hz, 1H).

Compound 431 (cis-N-[1-(8-Cyano-quinolin-5-yl)-5-trifluoromethyl-piperidin-3-yl]-3,3-dimethyl-butyramide): cis-5-(3-Amino-5-trifluoromethyl-piperidin-1-yl)-quinoline-8-carbonitrile hydrochloride and 3,3-dimethylbutyric acid. HPLC: >99% purity, RT=4.37 min. MS: m/z=419 [M+H]$^+$. $^1$H NMR (400 MHz, Chloroform-d, ppm) δ 9.08 (dd, J=4.2, 1.7 Hz, 1H), 8.48 (dd, J=8.6, 1.7 Hz, 1H), 8.03 (d, J=7.9 Hz, 1H), 7.60 (dd, J=8.6, 4.2 Hz, 1H), 7.11 (d, J=8.0 Hz, 1H), 5.28 (d, J=7.8 Hz, 1H), 4.41 (dddd, J=16.2, 12.4, 8.2, 4.3 Hz, 1H), 3.79 (dq, J=10.0, 2.2 Hz, 1H), 3.66-3.57 (m, 1H), 2.92 (t, J=11.3 Hz, 1H), 2.82 (ddq, J=15.5, 7.9, 3.8 Hz, 1H), 2.53-2.36 (m, 2H), 2.05 (d, J=1.7 Hz, 2H), 1.48 (q, J=12.2 Hz, 1H), 1.03 (s, 9H).

Compound 511 (N-[5,5-Difluoro-1-(8-trifluoromethyl-quinolin-5-yl)-piperidin-3-yl]-2-(4-methyl-piperazin-1-yl)-acetamide): From (4-Methyl-piperazin-1-yl)-acetic acid and 5,5-Difluoro-1-(8-trifluoromethyl-quinolin-5-yl)-piperidin-3-ylamine. $^1$H NMR (400 MHz, DMSO-d6) δ 9.07 (d, J=4.0 Hz, 1H), 8.61 (d, J=8.7 Hz, 1H), 8.13 (d, J=8.2 Hz, 1H), 8.05-7.92 (m, 1H), 7.74 (dd, J=8.3, 3.8 Hz, 1H), 7.37 (d, J=8.0 Hz, 1H), 4.41 (s, 2H), 3.47 (dt, J=33.3, 11.5 Hz, 4H), 3.11 (s, 1H), 2.95 (t, J=3.6 Hz, 2H), 2.43 (s, 4H), 2.29 (s, 4H), 2.12 (d, J=2.8 Hz, 3H). MS: m/z=472 [M+H]$^+$.

Compound 512 (N-[5,5-Difluoro-1-(8-trifluoromethyl-quinolin-5-yl)-piperidin-3-yl]-2-morpholin-4-yl-acetamide): From Morpholin-4-yl-acetic acid and 5,5-Difluoro-1-(8-trifluoromethyl-quinolin-5-yl)-piperidin-3-ylamine. $^1$H NMR (400 MHz, DMSO-d$_6$) δ 9.06 (d, J=3.8 Hz, 1H), 8.59 (d, J=8.6 Hz, 1H), 8.12 (d, J=7.8 Hz, 1H), 8.02 (d, J=8.3 Hz, 1H), 7.75 (dd, J=8.5, 3.9 Hz, 1H), 7.37 (d, J=8.1 Hz, 1H), 4.39 (s, 1H), 3.57 (d, J=5.5 Hz, 4H), 3.43 (d, J=13.6 Hz, 3H), 3.08 (d, J=9.7 Hz, 2H), 2.97 (s, 2H), 2.47-2.37 (m, 4H), 2.28 (d, J=15.5 Hz, 1H). MS: n/z=459 [M+H]$^+$.

Compound 513 (2-Cyclopropyl-N-[5,5-difluoro-1-(8-trifluoromethyl-quinolin-5-yl)-piperidin-3-yl]-2-hydroxy-acetamide): From Cyclopropyl-hydroxyl-acetic acid and 5,5-Difluoro-1-(8-trifluoromethyl-quinolin-5-yl)-piperidin-3-ylamine. $^1$H NMR (400 MHz, DMSO-d6) δ 9.05 (dd, J=4.2, 1.6 Hz, 1H), 8.57 (ddd, J=8.6, 4.7, 1.8 Hz, 1H), 8.12 (dd, J=8.1, 2.0 Hz, 1H), 7.88 (d, J=8.3 Hz, 1H), 7.73 (ddd, J=8.7, 4.2, 3.1 Hz, 1H), 7.35 (dd, J=8.0, 4.6 Hz, 1H), 5.56 (d, J=4.4 Hz, 1H), 4.35 (dd, J=8.8, 4.4 Hz, 1H), 3.65-3.49 (m, 2H), 3.49-3.36 (m, 2H), 3.01 (q, J=9.8, 8.9 Hz, 1H), 2.48-2.16 (m, 2H), 1.12-1.00 (m, 1H), 1.00-0.85 (m, 1H), 0.54-0.19 (m, 4H). MS: m/z=430 [M+H]$^+$.

Compound 576 (N-[(3R,5S)-1-(8-Cyano-quinolin-5-yl)-5-trifluoromethyl-piperidin-3-yl]-2-piperidin-1-yl-isobutyramide): From 5-((3R,5S)-3-Amino-5-trifluoromethyl-piperidin-1-yl)-quinoline-8-carbonitrile hydrochloride and 2-Methyl-2-piperidin-1-yl-propionic acid. HPLC: >99% purity, RT=2.92 min. MS: m/z=474.6 [M+H]$^+$. $^1$H NMR (400 MHz, DMSO-d6, ppm) δ 9.06 (dd, J=4.2, 1.6 Hz, 1H), 8.58 (dd, J=8.6, 1.7 Hz, 1H), 8.26 (d, J=8.0 Hz, 1H), 7.75-7.68 (m, 2H), 7.33 (d, J=8.1 Hz, 1H), 4.23-4.11 (m, 1H), 3.59-3.43 (m, 2H), 3.20 (s, 1H), 2.94 (t, J=11.5 Hz, 1H), 2.75 (t, J=11.1 Hz, 1H), 2.33 (t, J=5.4 Hz, 4H), 2.14-2.06 (m, 1H), 1.76 (q, J=12.2 Hz, 1H), 1.55 (q, J=5.0 Hz, 4H), 1.40 (d, J=6.9 Hz, 2H), 1.06 (d, J=13.1 Hz, 6H).

Compound 577 (N-[(3R,5S)-1-(8-Cyano-quinolin-5-yl)-5-trifluoromethyl-piperidin-3-yl]-2-(3,3-dimethyl-pyrrolidin-1-yl)-acetamide): From 5-((3R,5S)-3-Amino-5-trifluoromethyl-piperidin-1-yl)-quinoline-8-carbonitrile hydrochloride and (3,3-Dimethyl-pyrrolidin-1-yl)-acetic acid. HPLC: >99% purity, RT=2.98 min. MS: m/z=460.5 [M+H]+. 1H NMR (400 MHz, DMSO-d6, ppm) δ 9.06 (dd, J=4.2, 1.6 Hz, 1H), 8.58 (dd, J=8.6, 1.7 Hz, 1H), 8.25 (d, J=8.0 Hz, 1H), 7.77 (d, J=8.0 Hz, 1H), 7.72 (dd, J=8.6, 4.2 Hz, 1H), 7.33 (d, J=8.1 Hz, 1H), 3.62-3.47 (m, 2H), 3.21 (s, 1H), 2.93 (t, J=11.5 Hz, 1H), 2.75 (t, J=11.1 Hz, 1H), 2.66-2.58 (m, 2H), 2.37-2.28 (m, 2H), 2.15 (d, J=12.3 Hz, 1H), 1.71 (q, J=12.3 Hz, 1H), 1.53 (t, J=7.0 Hz, 2H), 1.05 (d, J=1.0 Hz, 6H).

Compound 578 (1-Cyclopropyl-piperidine-4-carboxylic acid [(3R,5S)-1-(8-cyano-quinolin-5-yl)-5-trifluoromethyl-piperidin-3-yl]-amide): From 5-((3R,5S)-3-Amino-5-trifluoromethyl-piperidin-1-yl)-quinoline-8-carbonitrile hydrochloride and 1-Cyclopropyl-piperidine-4-carboxylic acid. HPLC: >99% purity, RT=2.77 min. MS: n/z=472.30 [M+H]+. 1H NMR (400 MHz, DMSO-d6) δ 9.06 (dd, J=4.2, 1.6 Hz, 1H), 8.58 (dd, J=8.6, 1.7 Hz, 1H), 8.25 (d, J=8.0 Hz, 1H), 7.91 (d, J=7.3 Hz, 1H), 7.72 (dd, J=8.6, 4.2 Hz, 1H), 7.32 (d, J=8.1 Hz, 1H), 3.62-3.50 (m, 2H), 3.19 (d, J=11.4 Hz, 1H), 2.93 (td, J=9.6, 7.8, 4.0 Hz, 3H), 2.60 (t, J=11.2 Hz, 1H), 2.23-2.01 (m, 4H), 1.71-1.37 (m, 6H), 0.38 (dt, J=6.5, 3.2 Hz, 2H), 0.30-0.20 (m, 2H).

Compound 579 (N-[(3R,5S)-1-(8-Cyano-quinolin-5-yl)-5-trifluoromethyl-piperidin-3-yl]-N',N'-diethyl-succinamide): From 5-((3R,5S)-3-Amino-5-trifluoromethyl-piperidin-1-yl)-quinoline-8-carbonitrile hydrochloride and N,N-Diethyl-succinamic acid. HPLC: >99% purity, RT=3.82 min. MS: m/z=476.5 [M+H]+. 1H NMR (400 MHz, DMSO-d6, ppm) δ 9.06 (dd, J=4.2, 1.6 Hz, 1H), 8.58 (dd, J=8.6, 1.7 Hz, 1H), 8.26 (d, J=8.0 Hz, 1H), 8.02 (d, J=7.4 Hz, 1H), 7.71 (dd, J=8.6, 4.2 Hz, 1H), 7.32 (d, J=8.1 Hz, 1H), 4.13 (s, 1H), 3.61-3.51 (m, 2H), 3.30 (d, J=7.0 Hz, 2H), 3.27-3.16 (m, 3H), 2.95 (t, J=11.6 Hz, 1H), 2.60 (t, J=11.2 Hz, 1H), 2.42-2.27 (m, 3H), 2.18 (d, J=12.2 Hz, 1H), 1.51 (q, J=12.3 Hz, 1H), 1.11 (t, J=7.1 Hz, 3H), 0.96 (t, J=7.1 Hz, 3H).

Compound 584 (N-[(3R,5S)-1-(8-Cyano-quinolin-5-yl)-5-trifluoromethyl-piperidin-3-yl]-2-(4,4-difluoro-cyclohexyl)-acetamide): From 5-((3R,5S)-3-Amino-5-trifluoromethyl-piperidin-1-yl)-quinoline-8-carbonitrile hydrochloride and (4,4-Difluoro-cyclohexyl)-acetic acid. HPLC: >99% purity, RT=4.39 min. MS: m/z=481.5 [M+H]+. 1H NMR (400 MHz, DMSO-d6, ppm) δ 9.07 (dd, J=4.2, 1.6 Hz, 1H), 8.59 (dd, J=8.6, 1.7 Hz, 1H), 8.26 (d, J=8.0 Hz, 1H), 8.04 (d, J=7.2 Hz, 1H), 7.72 (dd, J=8.6, 4.2 Hz, 1H), 7.33 (d, J=8.1 Hz, 1H), 4.15 (s, 1H), 3.62-3.52 (m, 2H), 3.21 (d, J=11.6 Hz, 1H), 2.95 (t, J=11.6 Hz, 1H), 2.61 (t, J=11.2 Hz, 1H), 2.19 (d, J=12.4 Hz, 1H), 2.07-2.02 (m, 2H), 1.96 (s, 2H), 1.82 (s, 2H), 1.71 (t, J=11.1 Hz, 3H), 1.51 (q, J=12.3 Hz, 1H), 1.19 (dq, J=11.9, 6.1 Hz, 2H).

Compound 585 (N-[(3R,5S)-1-(8-Cyano-quinolin-5-yl)-5-trifluoromethyl-piperidin-3-yl]-2-(1-isopropyl-piperidin-4-yl)-acetamide): From 5-((3R,5S)-3-Amino-5-trifluoromethyl-piperidin-1-yl)-quinoline-8-carbonitrile and (1-Isopropyl-piperidin-4-yl)-acetic acid. HPLC: >99% purity, RT=2.85 min. MS: m/z=488.5 [M+H]+. 1H NMR (400 MHz, DMSO-d6, ppm) δ 9.06 (dd, J=4.2, 1.6 Hz, 1H), 8.58 (dd, J=8.6, 1.7 Hz, 1H), 8.25 (d, J=8.0 Hz, 1H), 7.99 (d, J=7.3 Hz, 1H), 7.72 (dd, J=8.6, 4.2 Hz, 1H), 7.32 (d, J=8.1 Hz, 1H), 4.14 (s, 1H), 3.57 (d, J=8.9 Hz, 2H), 3.19 (s, 1H), 2.94 (t, J=11.6 Hz, 1H), 2.69 (s, 2H), 2.66-2.56 (m, 2H), 2.17 (d, J=12.1 Hz, 1H), 2.08-1.97 (m, 4H), 1.65-1.45 (m, 4H), 1.10 (d, J=12.6 Hz, 2H), 0.93 (d, J=6.4 Hz, 6H).

Example 41: Synthesis of Compound 87 and Compound 88 ((S)—N-((3R,5S)-1-(8-cyanoquinoxalin-5-yl)-5-(trifluoromethyl)piperidin-3-yl)-2-hydroxy-3-methylbutanamide and (S)—N-((3S,5R)-1-(8-cyanoquinoxalin-5-yl)-5-(trifluoromethyl)piperidin-3-yl)-2-hydroxy-3-methylbutanamide)

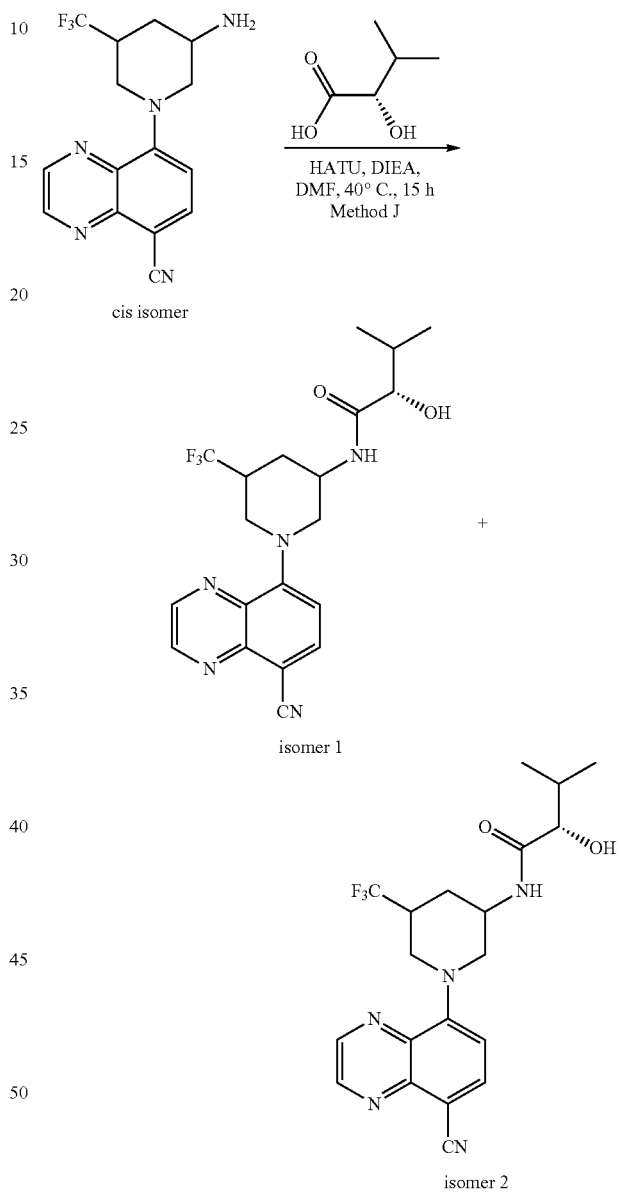

(S)—N-((3R,5S)-1-(8-cyanoquinoxalin-5-yl)-5-(trifluoromethyl)piperidin-3-yl)-2-hydroxy-3-methylbutanamide and (S)—N-((3S,5R)-1-(8-cyanoquinoxalin-5-yl)-5-(trifluoromethyl)piperidin-3-yl)-2-hydroxy-3-methylbutanamide: (S)—N-((3R,5S)-1-(8-cyanoquinoxalin-5-yl)-5-(trifluoromethyl)piperidin-3-yl)-2-hydroxy-3-methylbutanamide and (S)—N-((3S,5R)-1-(8-cyanoquinoxalin-5-yl)-5-(trifluoromethyl)piperidin-3-yl)-2-hydroxy-3-methylbutanamide were prepared from cis-8-(3-amino-5-(trifluoromethyl)piperidin-1-yl)quinoxaline-5-carbonitrile and (S)-2-hydroxy-3-methylbutanoic acid using Method J. The product was first purified by prep-HPLC under the following conditions:

column, XBridge Shield RP18 OBD Column, 19×250 mm 10 um; mobile phase, acetonitrile in water (0.05% NH$_3$H$_2$O), 30% to 40% gradient in 15 min; detector, UV 254 nm. Then the two diastereomeric isomers of (S)—N-((3R,5S)-1-(8-cyanoquinoxalin-5-yl)-5-(trifluoromethyl)piperidin-3-yl)-2-hydroxy-3-methylbutanamide were obtained by separation on chiral prep-HPLC under the following conditions: column, CHIRALPAK AD-3, 0.46×5 cm, 3 um; mobile phase, EtOH (0.1% DEA) in Hexane, 40% isocratic in 20 min; detector, UV 254 nm. Two diastereomeric products were separated and obtained.

Isomer 1: (54 mg, 18%, yellow solid) HPLC: 98.5% purity, RT=2.58 min. MS: m/z=294.2 [M+H]$^+$. $^1$H NMR (300 MHz, CD$_3$OD, ppm) δ 8.93 (d, J=1.8 Hz, 1H), 8.89 (d, J=1.8 Hz, 1H), 8.11 (d, J=8.3 Hz, 1H), 7.29 (d, J=8.3 Hz, 1H), 4.58 (d, J=12.0 Hz, 1H), 4.30-4.09 (m, 2H), 3.83 (d, J=3.7 Hz, 1H), 3.11-2.82 (m, 3H), 2.29-2.25 (m, 1H), 2.09-2.03 (m, 1H), 1.81-1.69 (m, 1H), 0.99 (d, J=6.9 Hz, 3H), 0.85 (d, J=6.8 Hz, 3H).

Isomer 2: (19 mg, 6%, yellow solid) HPLC: 95.7% purity, RT=3.03 min. MS: m/z=422.1 [M+H]$^+$. $^1$H NMR (300 MHz, CD$_3$OD, ppm) δ 8.93 (d, J=1.8 Hz, 1H), 8.89 (d, J=1.8 Hz, 1H), 8.11 (d, J=8.3 Hz, 1H), 7.29 (d, J=8.3 Hz, 1H), 4.58 (d, J=12.0 Hz, 1H), 4.30-4.09 (m, 2H), 3.83 (d, J=3.7 Hz, 1H), 3.11-2.82 (m, 3H), 2.29-2.25 (m, 1H), 2.09-2.03 (m, 1H), 1.81-1.69 (m, 1H), 0.99 (d, J=6.9 Hz, 3H), 0.85 (d, J=6.8 Hz, 3H).

The following compounds were synthesized in an analogous manner:

Compound 89 and compound 90 ((2S)-2-hydroxy-3-methyl-N-[(3R,5S)-1-[pyrido[2,3-b]pyrazin-8-yl]-5-(trifluoromethyl)piperidin-3-yl]butanamide hydrochloride and ((2S)-2-hydroxy-3-methyl-N-[(3S,5R)-1-[pyrido[2,3-b]pyrazin-8-yl]-5-(trifluoromethyl)piperidin-3-yl]butanamide hydrochloride): From cis-1-(pyrido[2,3-b]pyrazin-8-yl)-5-(trifluoromethyl)piperidin-3-amine and (S)-2-hydroxy-3-methylbutanoic acid. Isomer 1: HPLC: 99.6% purity, RT=1.42 min. MS: m/z=398.1 [M+H]$^+$. $^1$H NMR (300 MHz, CD$_3$OD, ppm) δ 9.10-8.95 (m, 2H), 8.63 (d, J=1.5 Hz, 1H), 7.41-7.32 (d, J=5.6 Hz, 1H), 6.12-5.31 (m, 1H), 5.21-4.82 (s, 1H), 4.29-4.19 (m, 1H), 3.75 (d, J=10.5 Hz, 1H), 3.61-3.52 (m, 1H), 3.41-3.27 (m, 1H), 3.06-2.99 (m, 1H), 2.38-2.20 (m, 1H), 2.15-1.88 (m, 2H), 1.16-1.01 (m, 3H), 0.82-0.93 (m, 3H). Isomer 2: HPLC: 95.8% purity, RT=0.89 min. MS: m/z=398.1 [M+H]$^+$. $^1$H NMR (300 MHz, CD$_3$OD, ppm) δ 910-8.95 (m, 2H), 8.63 (d, J=1.5 Hz, 1H), 7.41-7.32 (d, J=5.6 Hz, 1H), 6.12-5.31 (m, 1H), 5.21-4.82 (s, 1H), 4.29-4.19 (m, 1H), 3.75 (d, J=10.5 Hz, 1H), 3.61-3.52 (m, 1H), 3.41-3.27 (m, 1H), 3.06-2.99 (m, 1H), 2.38-2.20 (m, 1H), 2.15-1.88 (m, 2H), 1.16-1.01 (m, 3H), 0.82-0.93 (m, 3H).

Compound 146 and compound 147 ((R)—N-((3R,5S)-1-(8-cyanoquinoxalin-5-yl)-5-methylpiperidin-3-yl)-3-hydroxy-4,4-dimethylpentanamide and (S)—N-((3R,5S)-1-(8-cyanoquinoxalin-5-yl)-5-methylpiperidin-3-yl)-3-hydroxy-4,4-dimethylpentanamide): From 8-((3R,5S)-3-amino-5-methylpiperidin-1-yl)quinoxaline-5-carbonitrile and 3-hydroxy-4,4-dimethylpentanoic acid. Isomer 1: HPLC: 98.0% purity, RT=1.39 min. MS: m/z=396.2 [M+H]$^+$. $^1$H NMR (300 MHz, CD$_3$OD, ppm) δ 8.95-8.82 (m, 2H), 8.09 (d, J=8.4 Hz, 1H), 7.28 (d, J=8.5 Hz, 1H), 4.35 (dd, J=28.2, 11.8 Hz, 2H), 4.22-4.08 (m, 1H), 3.69 (dd, J=10.2, 2.6 Hz, 1H), 2.80-2.60 (m, 2H), 2.40 (dd, J=14.2, 2.6 Hz, 1H), 2.28-2.06 (m, 3H), 1.23 (td, J=12.0, 12.0 Hz, 1H), 1.00 (d, J=6.5 Hz, 3H), 0.92 (s, 9H). Isomer 2: HPLC: 99.3% purity, RT=1.41 min. MS: m/z=396.2 [M+H]$^+$. $^1$H NMR (300 MHz, CD$_3$OD, ppm) δ 8.95-8.82 (m, 2H), 8.09 (d, J=8.4 Hz, 1H), 7.31 (d, J=8.4 Hz, 1H), 4.34 (t, J=11.4 Hz, 2H), 4.13 (d, J=12.1 Hz, 1H), 3.68 (dd, J=10.3, 2.6 Hz, 1H), 2.83-2.63 (m, 2H), 2.40 (dd, J=14.1, 2.6 Hz, 1H), 2.29-2.04 (m, 3H), 1.22 (td, J=12.0, 12.0 Hz, 1H), 1.01 (d, J=6.4 Hz, 3H), 0.92 (s, 9H).

Compound 148 and compound 149 ((R)-3-hydroxy-4,4-dimethyl-N-((3R,5S)-5-methyl-1-(pyrido[2,3-b]pyrazin-8-yl)piperidin-3-yl)pentanamide and (S)-3-hydroxy-4,4-dimethyl-N-((3R,5S)-5-methyl-1-(pyrido[2,3-b]pyrazin-8-yl)piperidin-3-yl)pentanamide): From (3R,5S)-5-methyl-1-(pyrido[2,3-b]pyrazin-8-yl)piperidin-3-amine and 3-hydroxy-4,4-dimethylpentanoic acid. Isomer 1: HPLC: 99.0% purity, RT=1.09 min. MS: n/z=372.3 [M+H]$^+$. $^1$H NMR (300 MHz, CD$_3$OD, ppm) δ 8.89 (d, J=1.8 Hz, 1H), 8.78 (d, J=1.8 Hz, 1H), 8.62 (d, J=5.7 Hz, 1H), 7.13 (d, J=5.7 Hz, 1H), 4.67 (t, J=11.0 Hz, 2H), 4.10-3.98 (m, 1H), 3.66 (dd, J=10.2, 2.6 Hz, 1H), 2.88-2.65 (m, 2H), 2.38 (dd, J=14.2, 2.7 Hz, 1H), 2.26-2.07 (m, 2H), 1.99-1.89 (m, 1H), 1.23 (td, J=12.1, 12.1 Hz, 1H), 0.98 (d, J=6.6 Hz, 3H), 0.89 (s, 9H). Isomer 2: HPLC: 99.3% purity, RT=1.12 min. MS: m/z=372.3 [M+H]$^+$. $^1$H NMR (300 MHz, CD$_3$OD, ppm) δ 8.89 (d, J=1.8 Hz, 1H), 8.78 (d, J=1.8 Hz, 1H), 8.62 (d, J=5.7 Hz, 1H), 7.13 (d, J=5.7 Hz, 1H), 4.67 (t, J=11.0 Hz, 2H), 4.10-3.98 (m, 1H), 3.66 (dd, J=10.2, 2.6 Hz, 1H), 2.88-2.65 (m, 2H), 2.38 (dd, J=14.2, 2.7 Hz, 1H), 2.26-2.07 (m, 2H), 1.99-1.89 (m, 1H), 1.23 (td, J=12.1, 12.1 Hz, 1H), 0.98 (d, J=6.6 Hz, 3H), 0.89 (s, 9H).

Compound 150 and compound 151 ((S)—N-((3R,5S)-1-(8-cyanoquinoxalin-5-yl)-5-methylpiperidin-3-yl)-3-methylpentanamide and (R)—N-((3R,5S)-1-(8-cyanoquinoxalin-5-yl)-5-methylpiperidin-3-yl)-3-methylpentanamide): From 8-((3R,5S)-3-amino-5-methylpiperidin-1-yl)quinoxaline-5-carbonitrile and 3-methylpentanoic acid. Isomer 1: HPLC: 92.2% purity, RT=2.86 min. MS: m/z=366.2 [M+H]$^+$. $^1$H NMR (300 MHz, CD$_3$OD, ppm) δ 8.99-8.85 (m, 2H), 8.11 (d, J=8.4 Hz, 1H), 7.30 (d, J=8.4 Hz, 1H), 4.40 (d, J=11.9 Hz, 1H), 4.32 (d, J=12.5 Hz, 1H), 4.22-4.10 (m, 1H), 2.83-2.63 (m, 2H), 2.23 (dd, J=13.4, 6.1 Hz, 1H), 2.15-1.95 (m, 3H), 1.94-1.84 (m, 1H), 1.47-1.36 (m, 1H), 1.34-1.16 (m, 2H), 1.02 (d, J=6.4 Hz, 3H), 0.95 (d, J=6.9 Hz, 6H). Isomer 2: HPLC: 90.4% purity, RT=1.54 min. MS: m/z=366.2 [M+H]$^+$. $^1$H NMR (300 MHz, CD$_3$D, ppm) δ 8.99-8.85 (m, 2H), 8.11 (d, J=8.4 Hz, 1H), 7.30 (d, J=8.4 Hz, 1H), 4.40 (d, J=11.9 Hz, 1H), 4.32 (d, J=12.5 Hz, 1H), 4.22-4.10 (m, 1H), 2.83-2.63 (m, 2H), 2.23 (dd, J=13.4, 6.1 Hz, 1H), 2.15-1.95 (m, 3H), 1.94-1.84 (m, 1H), 1.47-1.36 (m, 1H), 1.34-1.16 (m, 2H), 1.02 (d, J=6.4 Hz, 3H), 0.95 (d, J=6.9 Hz, 6H).

Compound 152 and compound 153 ((S)-3-methyl-N-((3R,5S)-5-methyl-1-(pyrido[2,3-b]pyrazin-8-yl)piperidin-3-yl)pentanamide and (R)-3-methyl-N-((3R,5S)-5-methyl-1-(pyrido[2,3-b]pyrazin-8-yl)piperidin-3-yl)pentanamide): From (3R,5S)-5-methyl-1-(pyrido[2,3-b]pyrazin-8-yl)piperidin-3-amine and 3-methylpentanoic acid. Isomer 1: HPLC: 97.4% purity, RT=1.23 min. MS: i/z=342.3 [M+H]$^+$. $^1$H NMR (400 MHz, CD$_3$OD, ppm) δ 8.95 (d, J=1.8 Hz, 1H), 8.83 (d, J=1.8 Hz, 1H), 8.68 (d, J=5.6 Hz, 1H), 7.17 (dd, J=5.8, 1.6 Hz, 1H), 4.77-4.65 (m, 2H), 4.16-4.02 (m, 1H), 2.91-2.72 (m, 2H), 2.25 (dd, J=13.4, 6.1 Hz, 1H), 2.16-1.94 (m, 3H), 1.98-1.82 (m, 1H), 1.50-1.19 (m, 3H), 1.11-0.91 (m, 9H). Isomer 2: HPLC: 96.6% purity, RT=1.23 min. MS: m/z=342.3 [M+H]$^+$. $^1$H NMR (400 MHz, CD$_3$OD, ppm) δ 8.95 (d, J=1.8 Hz, 1H), 8.83 (d, J=1.8 Hz, 1H), 8.68 (d, J=5.6 Hz, 1H), 7.17 (dd, J=5.8, 1.6 Hz, 1H), 4.77-4.65 (m, 2H), 4.16-4.02 (m, 1H), 2.91-2.72 (m, 2H), 2.25 (dd, J=13.4, 6.1 Hz, 1H), 2.16-1.94 (m, 3H), 1.98-1.82 (m, 1H), 1.50-1.19 (m, 3H), 1.11-0.91 (m, 9H).

Compound 154 and compound 155 ((R)—N-((3R,5S)-1-(8-cyanoquinoxalin-5-yl)-5-methylpiperidin-3-yl)-2-methylbutanamide and (S)—N-((3R,5S)-1-(8-cyanoquinoxalin-5-yl)-5-methylpiperidin-3-yl)-2-methylbutanamide): From 8-((3R,5S)-3-amino-5-methylpiperidin-1-yl)quinoxaline-5-carbonitrile and 2-methylbutanoic acid. Isomer 1: HPLC: 92.2% purity, RT=2.41 min. MS: m/z=352.2 [M+H]$^+$. $^1$H NMR (400 MHz, CD$_3$OD, ppm) δ 8.95-8.82 (m, 2H), 8.08 (d, J=8.4 Hz, 1H), 7.28 (d, J=8.4 Hz, 1H), 4.40-4.24 (m, 2H), 4.20-4.04 (m, 1H), 2.80-2.60 (m, 2H), 2.29-2.16 (m, 1H), 2.13-1.96 (m, 3H), 1.68-1.32 (m, 2H), 1.35-1.07 (m, 5H), 1.03-0.86 (m, 6H). Isomer 2: HPLC: 95.1% purity, RT=1.42 min. MS: m/z=342.3 [M+H]$^+$. $^1$H NMR (400 MHz, CD$_3$OD, ppm) δ 8.90 (dd, J=13.6, 1.8 Hz, 2H), 8.08 (d, J=8.4 Hz, 1H), 7.28 (d, J=8.4 Hz, 1H), 4.40-4.24 (m, 2H), 4.20-4.04 (m, 1H), 2.80-2.60 (m, 2H), 2.29-2.16 (m, 1H), 2.13-1.96 (m, 3H), 1.68-1.32 (m, 2H), 1.35-1.07 (m, 5H), 1.03-0.86 (m, 6H).

Compound 156 and compound 157 ((R)-2-methyl-N-((3R,5S)-5-methyl-1-(pyrido[2,3-b]pyrazin-8-yl)piperidin-3-yl)butanamide and (S)-2-methyl-N-((3R,5S)-5-methyl-1-(pyrido[2,3-b]pyrazin-8-yl)piperidin-3-yl)butanamide): From (3R,5S)-5-methyl-1-(pyrido[2,3-b]pyrazin-8-yl)piperidin-3-amine and 2-methylbutanoic acid. Isomer 1: HPLC: 96.0% purity, RT=1.11 min. MS: m/z=328.2 [M+H]$^+$. $^1$H NMR (400 MHz, CD$_3$OD, ppm) δ 8.94 (d, J=1.8 Hz, 1H), 8.85 (d, J=1.8 Hz, 1H), 8.62 (d, J=6.0 Hz, 1H), 7.21 (d, J=6.0 Hz, 1H), 4.70-4.50 (m, 2H), 4.13-3.99 (m, 1H), 2.97-2.77 (m, 2H), 2.32-2.15 (m, 1H), 2.14-1.91 (m, 2H), 1.70-1.54 (m, 1H), 1.51-1.36 (m, 1H), 1.37-1.23 (m, 3H), 1.19-1.00 (m, 6H), 0.92 (t, J=7.4 Hz, 3H). Isomer 2: HPLC: 91.8% purity, RT=1.11 min. MS: m/z=328.2 [M+H]$^+$. $^1$H NMR (400 MHz, CD$_3$OD, ppm) δ 8.94 (d, J=1.8 Hz, 1H), 8.85 (d, J=1.8 Hz, 1H), 8.62 (d, J=6.0 Hz, 1H), 7.21 (d, J=6.0 Hz, 1H), 4.70-4.50 (m, 2H), 4.13-3.99 (m, 1H), 2.97-2.77 (m, 2H), 2.32-2.15 (m, 1H), 2.14-1.91 (m, 2H), 1.70-1.54 (m, 1H), 1.51-1.36 (m, 1H), 1.37-1.23 (m, 3H), 1.19-1.00 (m, 6H), 0.92 (t, J=7.4 Hz, 3H).

Compound 158 and compound 159 ((S)—N-((3R,5S)-1-(8-cyanoquinoxalin-5-yl)-5-methylpiperidin-3-yl)-2-methoxypropanamide and (R)—N-((3R,5S)-1-(8-cyanoquinoxalin-5-yl)-5-methylpiperidin-3-yl)-2-methoxypropanamide): From 8-((3R,5S)-3-amino-5-methylpiperidin-1-yl)quinoxaline-5-carbonitrile and 2-methoxypropanoic acid. Isomer 1: HPLC: 99.6% purity, RT=1.27 min. MS: m/z=354.2 [M+H]$^+$. $^1$H NMR (400 MHz, CD$_3$OD, ppm) δ 8.98-8.84 (m, 2H), 8.09 (d, J=8.4 Hz, 1H), 7.28 (d, J=8.4 Hz, 1H), 4.32-4.10 (m, 3H), 3.75 (q, J=6.7 Hz, 1H), 3.37 (s, 3H), 2.89 (dd, J=12.0, 10.4 Hz, 1H), 2.70 (dd, J=12.6, 10.6 Hz, 1H), 2.15-1.99 (m, 2H), 1.41-1.27 (m, 4H), 1.02 (d, J=6.4 Hz, 3H). Isomer 2: HPLC: 96.0% purity, RT=2.60 min. MS: m/z=354.1 [M+H]$^+$. $^1$H NMR (400 MHz, CD$_3$OD, ppm) δ 8.96-8.82 (m, 2H), 8.09 (d, J=8.4 Hz, 1H), 7.28 (d, J=8.4 Hz, 1H), 4.32-4.10 (m, 3H), 3.75 (q, J=6.7 Hz, 1H), 3.37 (s, 3H), 2.89 (dd, J=12.0, 10.4 Hz, 1H), 2.70 (dd, J=12.6, 10.6 Hz, 1H), 2.15-1.99 (m, 2H), 1.41-1.27 (m, 4H), 1.02 (d, J=6.4 Hz, 3H).

Compound 160 and compound 161 ((S)-2-methoxy-N-((3R,5S)-5-methyl-1-(pyrido[2,3-b]pyrazin-8-yl)piperidin-3-yl)propanamide and (R)-2-methoxy-N-((3R,5S)-5-methyl-1-(pyrido[2,3-b]pyrazin-8-yl)piperidin-3-yl)propanamide): From (3R,5S)-5-methyl-1-(pyrido[2,3-b]pyrazin-8-yl)piperidin-3-amine and 2-methoxypropanoic acid. Isomer 1: HPLC: 99.6% purity, RT=1.27 min. MS: m/z=354.2 [M+H]$^+$. $^1$H NMR (400 MHz, CD$_3$OD, ppm) δ 8.92 (d, J=1.8 Hz, 1H), 8.81 (d, J=1.8 Hz, 1H), 8.65 (d, J=5.6 Hz, 1H), 7.14 (d, J=5.6 Hz, 1H), 4.70-4.54 (m, 2H), 4.10 (tt, J=11.1, 4.2 Hz, 1H), 3.75 (q, J=6.7 Hz, 1H), 3.37 (s, 3H), 2.96 (dd, J=12.4, 10.8 Hz, 1H), 2.77 (dd, J=12.9, 11.1 Hz, 1H), 2.13-1.92 (m, 2H), 1.43-1.26 (m, 4H), 1.02 (d, J=6.5 Hz, 3H). Isomer 2: HPLC: 96.0% purity, RT=2.60 min. MS: m/z=354.1 [M+H]$^+$. $^1$H NMR (400 MHz, CD$_3$OD, ppm) δ 8.92 (d, J=1.8 Hz, 1H), 8.81 (d, J=1.8 Hz, 1H), 8.65 (d, J=5.6 Hz, 1H), 7.14 (d, J=5.6 Hz, 1H), 4.70-4.54 (m, 2H), 4.10 (tt, J=11.1, 4.2 Hz, 1H), 3.75 (q, J=6.7 Hz, 1H), 3.37 (s, 3H), 2.96 (dd, J=12.4, 10.8 Hz, 1H), 2.77 (dd, J=12.9, 11.1 Hz, 1H), 2.13-1.92 (m, 2H), 1.43-1.26 (m, 4H), 1.02 (d, J=6.5 Hz, 3H).

Compound 173 and compound 174 ((S)—N-((3R,5R)-1-(8-cyanoquinoxalin-5-yl)-5-cyclopropylpiperidin-3-yl)-2-hydroxy-3-methylbutanamide and (S)—N-((3S,5S)-1-(8-cyanoquinoxalin-5-yl)-5-cyclopropylpiperidin-3-yl)-2-hydroxy-3-methylbutanamide): From cis-8-(3-amino-5-cyclopropylpiperidin-1-yl)quinoxaline-5-carbonitrile and (S)-2-hydroxy-3-methylbutanoic acid. Isomer 1: HPLC: 94.0% purity, RT=2.52 min. MS: m/z=394.3 [M+H]$^+$. $^1$H NMR (300 MHz, CD$_3$OD, ppm) δ 8.89 (d, J=1.8 Hz, 1H), 8.85 (d, J=1.8 Hz, 1H), 8.05 (d, J=8.4 Hz, 1H), 7.22 (d, J=8.4 Hz, 1H), 4.34-4.00 (m, 3H), 3.82 (d, J=3.7 Hz, 1H), 3.03-2.85 (m, 2H), 2.20-1.97 (m, 2H), 1.54 (q, J=11.6 Hz, 1H), 1.22-1.04 (m, 1H), 0.99 (d, J=6.9 Hz, 3H), 0.85 (d, J=6.8 Hz, 3H), 0.72-0.56 (m, 1H), 0.52-0.38 (m, 2H), 0.18 (dd, J=4.8, 2.9 Hz, 2H). Isomer 2: HPLC: 93.8% purity, RT=2.57 min. MS: n/z=394.3 [M+H]$^+$. $^1$H NMR (300 MHz, CD$_3$OD, ppm) δ 8.89 (d, J=1.8 Hz, 1H), 8.85 (d, J=1.8 Hz, 1H), 8.05 (d, J=8.4 Hz, 1H), 7.22 (d, J=8.4 Hz, 1H), 4.34-4.00 (m, 3H), 3.82 (d, J=3.7 Hz, 1H), 3.03-2.85 (m, 2H), 2.20-1.97 (m, 2H), 1.54 (q, J=11.6 Hz, 1H), 1.22-1.04 (m, 1H), 0.99 (d, J=6.9 Hz, 3H), 0.85 (d, J=6.8 Hz, 3H), 0.72-0.56 (m, 1H), 0.52-0.38 (m, 2H), 0.18 (dd, J=4.8, 2.9 Hz, 2H).

Compound 429 and compound 430 ((S)—N-[(3R,5S)-1-(8-Cyano-quinolin-5-yl)-5-trifluoromethyl-piperidin-3-yl]-2-hydroxy-3-methyl-butyramide and (S)—N-[(3S,5R)-1-(8-Cyano-quinolin-5-yl)-5-trifluoromethyl-piperidin-3-yl]-2-hydroxy-3-methyl-butyramide): From cis-5-(3-Amino-5-trifluoromethyl-piperidin-1-yl)-quinoline-8-carbonitrile hydrochloride and (2S)-2-hydroxy-3-methylbutanoic acid. Isomer 1: HPLC: 98.8% purity, RT=3.80 min. MS: m/z=341 [M+H]$^+$. $^1$H NMR (400 MHz, Chloroform-d, ppm) δ 9.08 (dd, J=4.2, 1.7 Hz, 1H), 8.48 (dd, J=8.6, 1.7 Hz, 1H), 8.04 (d, J=8.0 Hz, 1H), 7.59 (dd, J=8.6, 4.2 Hz, 1H), 7.12 (d, J=8.0 Hz, 1H), 6.59 (d, J=8.1 Hz, 1H), 4.41 (dtd, J=16.1, 8.2, 4.2 Hz, 1H), 4.02 (d, J=3.1 Hz, 1H), 3.82-3.73 (m, 1H), 3.68-3.59 (m, 1H), 2.94 (t, J=11.3 Hz, 1H), 2.83 (dtd, J=12.0, 8.0, 4.1 Hz, 1H), 2.54 (t, J=11.2 Hz, 1H), 2.44 (d, J=12.6 Hz, 1H), 2.24 (pd, J=6.9, 3.0 Hz, 1H), 1.54 (q, J=12.3 Hz, 1H), 1.04 (d, J=7.0 Hz, 3H), 0.88 (d, J=6.9 Hz, 3H). Isomer 2: HPLC: >99% purity, RT=3.70 min. MS: m/z=341 [M+H]$^+$. $^1$H NMR (400 MHz, Chloroform-d, ppm) δ 9.09 (dd, J=4.2, 1.7 Hz, 1H), 8.48 (dd, J=8.6, 1.7 Hz, 1H), 8.04 (d, J=7.9 Hz, 1H), 7.60 (dd, J=8.6, 4.2 Hz, 1H), 7.13 (d, J=8.0 Hz, 1H), 6.55 (d, J=8.0 Hz, 1H), 4.40 (dtt, J=16.3, 8.3, 4.2 Hz, 1H), 4.03 (d, J=3.0 Hz, 1H), 3.81-3.72 (m, 1H), 3.68-3.60 (m, 1H), 2.93 (t, J=11.2 Hz, 1H), 2.82 (ddt, J=15.0, 7.5, 3.9 Hz, 1H), 2.54 (t, J=11.1 Hz, 1H), 2.45 (d, J=12.5 Hz, 1H), 2.19 (pd, J=6.9, 3.0 Hz, 1H), 1.56 (q, J=12.2 Hz, 1H), 1.02 (d, J=7.0 Hz, 3H), 0.80 (d, J=6.9 Hz, 3H).

Compound 437 and compound 438 ((S)-1-Ethyl-pyrrolidine-2-carboxylic acid [(3S,5R)-1-(8-cyano-quinolin-5-yl)-5-trifluoromethyl-piperidin-3-yl]-amide and (S)-1-Ethyl-pyrrolidine-2-carboxylic acid [(3R,5S)-1-(8-cyano-quinolin-5-yl)-5-trifluoromethyl-piperidin-3-yl]-amide): From cis-5-(3-Amino-5-trifluoromethyl-piperidin-1-yl)-quinoline-8-carbonitrile hydrochloride and 1-ethyl-1-proline. Isomer 1: HPLC: >99% purity, RT=2.77 min. MS: m/z=446 [M+H]+. 1H NMR (400 MHz, Chloroform-d, ppm) δ 9.09 (dd, J=4.2, 1.7 Hz, 1H), 8.49 (dd, J=8.5, 1.7 Hz, 1H), 8.04 (d, J=7.9 Hz, 1H), 7.60 (dd, J=8.6, 4.2 Hz, 1H), 7.54 (d, J=8.2 Hz, 1H), 7.13 (d, J=7.9 Hz, 1H), 4.34 (dddd, J=16.3, 12.6, 8.4, 4.3 Hz, 1H), 3.77-3.69 (m, 1H), 3.67-3.57 (m, 1H), 3.14 (dd, J=8.7, 6.8 Hz, 1H), 3.05 (dd, J=10.5, 4.3 Hz, 1H), 2.93 (t, J=11.2 Hz, 1H), 2.83 (ddp, J=11.6, 7.8, 3.8 Hz, 1H), 2.71-2.46 (m, 3H), 2.41 (d, J=12.4 Hz, 1H), 2.33 (ddd, J=10.6, 9.2, 6.0 Hz, 1H), 2.14 (dtd, J=13.0, 9.8, 7.5 Hz, 1H), 1.84-1.69 (m, 2H), 1.68-1.57 (m, 1H), 1.54-1.46 (m, 1H), 1.10 (t, J=7.2 Hz, 3H). Isomer 2: HPLC: >99% purity, RT=2.79 min. MS: m/z=446 [M+H]+. 1H NMR (400 MHz, Chloroform-d, ppm) δ 9.09 (dd, J=4.2, 1.7 Hz, 1H), 8.50 (dd, J=8.6, 1.7 Hz, 1H), 8.03 (d, J=7.9 Hz, 1H), 7.60 (dd, J=8.6, 4.2 Hz, 1H), 7.55 (d, J=8.4 Hz, 1H), 7.12 (d, J=8.0 Hz, 1H), 4.42-4.29 (m, 1H), 3.82-3.73 (m, 1H), 3.66-3.58 (m, 1H), 3.17 (t, J=7.6 Hz, 1H), 3.03 (dd, J=10.3, 4.4 Hz, 1H), 2.95 (t, J=11.3 Hz, 1H), 2.82 (ddt, J=15.5, 7.9, 3.8 Hz, 1H), 2.60-2.38 (m, 4H), 2.38-2.29 (m, 1H), 2.18 (dtd, J=13.0, 10.3, 7.8 Hz, 1H), 1.88 (ddd, J=12.6, 8.2, 4.0 Hz, 1H), 1.84-1.76 (m, 1H), 1.71 (dd, J=12.7, 5.9 Hz, 1H), 1.54-1.47 (m, 1H), 1.01 (t, J=7.2 Hz, 3H).

Example 42: Synthesis of Compound 91 and Compound 92 (cis,cis-8-(3-((4-hydroxycyclohexyl)amino)-5-(trifluoromethyl)piperidin-1-yl)quinoxaline-5-carbonitrile and cis,trans-8-(-3-((4-hydroxycyclohexyl)amino)-5-(trifluoromethyl)piperidin-1-yl)quinoxaline-5-carbonitrile)

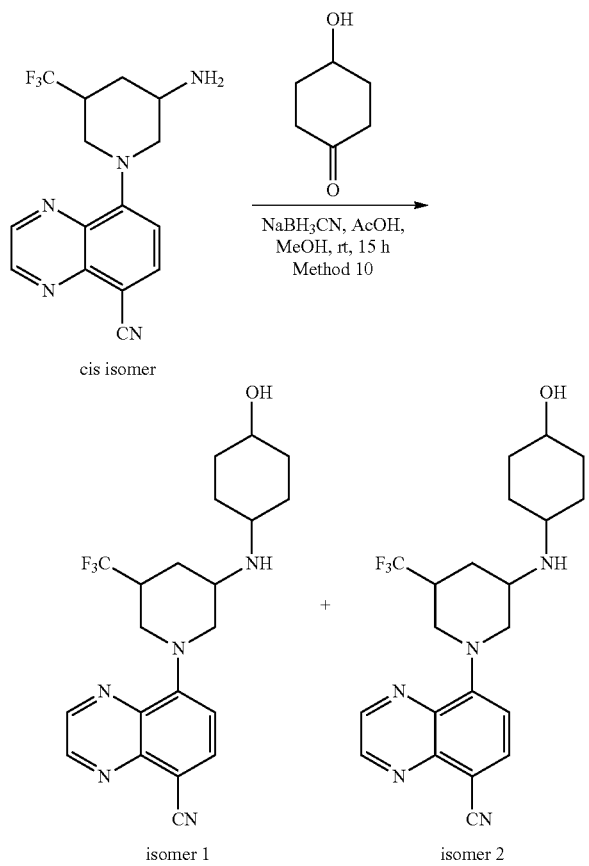

Method 10

Cis,cis-8-(3-((4-hydroxycyclohexyl)amino)-5-(trifluoromethyl)piperidin-1-yl)quinoxaline-5-carbonitrile and cis,trans-8-(3-((4-hydroxycyclohexyl)amino)-5-(trifluoromethyl)piperidin-1-yl)quinoxaline-5-carbonitrile): To a solution of cis-8-[3-amino-5-(trifluoromethyl)piperidin-1-yl]quinoxaline-5-carbonitrile (220 mg, 0.68 mmo) in methanol (5 mL) was added 4-hydroxycyclohexan-1-one (118 mg, 1.03 mmol), NaBH3CN (124 mg, 1.97 mmol), acetic acid (0.5 mL) at room temperature. The resulting solution was stirred for 15 h at room temperature. When the reaction was done, it was quenched by the addition of sat. NH4Cl (10 mL). The resulting mixture was extracted with EtOAc (50 mL×3). The organic phases were combined, washed with brine and dried over Na2SO4. The solvent was removed under reduced pressure, and the cis and trans isomers (each as racemic mixture) were separated by prep-HPLC under the following conditions: column, XBridge Shield RP18 OBD Column, 19×150 mm 10 um; mobile phase, acetonitrile in water (with 0.05% NH3.H2O), 30% to 45% gradient in 11 min; detector, UV 254 nm.

Isomer 1: (25 mg, 23%, yellow solid) HPLC: 99.4% purity, RT=1.25 min. MS: m/z=420.2 [M+H]+. 1H NMR (300 MHz, CD3OD, ppm) δ 8.95-8.84 (m, 2H), 8.10 (d, J=8.3 Hz, 1H), 7.24 (d, J=8.3 Hz, 1H), 4.46-4.28 (m, 2H), 3.59-3.44 (m, 1H), 3.24-3.13 (m, 1H), 3.01-2.93 (m, 1H), 3.01-2.80 (m, 2H), 2.70-2.57 (m, 2H), 2.33 (d, J=12.5 Hz, 1H), 2.13 (dd, J=9.3, 6.1 Hz, 1H), 2.04-1.87 (m, 3H), 1.49-1.08 (m, 5H).

Isomer 2: (19 mg, 18%, yellow solid) HPLC: 97.6% purity, RT=1.87 min. MS: m/z=420.0 [M+H]+. 1H NMR (300 MHz, CD3OD, ppm) δ 8.95-8.84 (m, 2H), 8.10 (d, J=8.3 Hz, 1H), 7.24 (d, J=8.4 Hz, 1H), 4.43-4.33 (m, 2H), 3.87 (br s, 1H), 3.24-3.16 (m, 1H), 3.08-2.58 (m, 4H), 2.35 (apparent d, J=12.4 Hz, 1H), 1.89-1.35 (m, 9H).

The following compounds were synthesized in an analogous manner:

Compound 93 and compound 94 (cis,cis-4-((1-(pyrido[2,3-b]pyrazin-8-yl)-5-(trifluoromethyl)piperidin-3-yl)amino)cyclohexanol and trans,cis-4-((1-(pyrido[2,3-b]pyrazin-8-yl)-5-(trifluoromethyl)piperidin-3-yl)amino)cyclohexanol): From cis-1-(pyrido[2,3-b]pyrazin-8-yl)-5-(trifluoromethyl)piperidin-3-amine and 4-hydroxycyclohexanone. Isomer 1: HPLC: 98.3% purity, RT=0.98 min. MS: m/z=396.2 [M+H]+. 1H NMR (300 MHz, CD3OD, ppm) δ 8.94 (d, J=1.7 Hz, 1H), 8.79 (d, J=1.7 Hz, 1H), 8.69 (d, J=5.5 Hz, 1H), 7.09 (d, J=5.6 Hz, 1H), 4.83-4.63 (m, 2H), 3.59-3.44 (m, 1H), 3.23-3.00 (m, 2H), 2.84 (dd, J=8.1, 3.9 Hz, 1H), 2.75-2.65 (m, 2H), 2.40-2.28 (m, 1H), 2.18-2.05 (m, 1H), 2.03-1.88 (m, 3H), 1.50-1.42 (m, 1H), 1.35-1.15 (m, 4H). Isomer 2: NMR (300 MHz, CD3OD, ppm) δ 8.93 (d, J=1.7 Hz, 1H), 8.79 (d, J=1.7 Hz, 1H), 8.69 (d, J=5.5 Hz, 1H), 7.09 (d, J=5.6 Hz, 1H), 4.78-4.69 (m, 2H), 3.88 (d, J=4.6 Hz, 1H), 3.23-2.99 (m, 2H), 2.94-2.67 (m, 3H), 2.36 (dd, J=12.2, 4.2 Hz, 1H), 1.83-1.73 (m, 3H), 1.71-1.53 (m, 5H), 1.53-1.37 (m, 1H).

Compound 95 (cis-8-[3-(trifluoromethyl)-5-[(3,3,3-trifluoropropyl)amino]piperidin-1-yl]quinoxaline-5-carbonitrile): From cis-8-(3-amino-5-(trifluoromethyl)piperidin-1-yl)quinoxaline-5-carbonitrile and 3,3,3-trifluoropropanal. HPLC: 98.5% purity, RT=2.95 min. MS: m/z=418.1 [M+H]+. 1H NMR (300 MHz, CD3OD, ppm) δ 8.99-8.85 (m, 2H), 8.10 (d, J=8.3 Hz, 1H), 7.25 (d, J=8.4 Hz, 1H), 4.44-4.34 (m, 2H), 3.12-2.80 (m, 5H), 2.73-2.57 (m, 1H), 2.40-2.20 (m, 3H), 1.45-1.33 (m, 1H).

Compound 96 (cis-1-[pyrido[2,3-b]pyrazin-8-yl]-5-(trifluoromethyl)-N-(3,3,3-trifluoropropyl)piperidin-3-amine hydrochloride): From cis-1-(pyrido[2,3-b]pyrazin-8-yl)-5-(trifluoromethyl)piperidin-3-amine and 3,3,3-trifluoropropanal. HPLC: 95.0% purity, RT=1.33 min. MS: m/z=394.1 [M+H]+. 1H NMR (300 MHz, CD3OD, ppm) δ 8.94 (d, J=1.8 Hz, 1H), 8.80 (d, J=1.8 Hz, 1H), 8.70 (d, J=5.6 Hz, 1H), 7.11 (d, J=5.6 Hz, 1H), 4.82-4.68 (m, 2H), 3.12-2.69 (m, 6H), 2.49-2.31 (m, 3H), 1.50-1.38 (m, 1H).

Compound 135 and compound 136 (cis-8-((3R,5S)-3-((4-hydroxycyclohexyl)amino)-5-methylpiperidin-1-yl)quinoxaline-5-carbonitrile and trans-8-((3R,5S)-3-((4-hydroxycyclohexyl)amino)-5-methylpiperidin-1-yl)quinoxaline-5-carbonitrile): From 8-((3R,5S)-3-amino-5-methylpiperidin-1-yl)quinoxaline-5-carbonitrile and 4-hydroxycyclohexanone. Isomer 1: (40 mg, 13%, yellow solid) HPLC: 98.9% purity, RT=1.07 min. MS: m/z=366.2 [M+H]+. 1H NMR (400 MHz, CD3OD, ppm) δ 8.92 (d, J=1.8 Hz, 1H), 8.84 (d, J=1.7 Hz, 1H), 8.07 (d, J=8.4 Hz, 1H), 7.19 (d, J=8.4 Hz, 1H), 4.63 (dd, J=13.4, 3.8 Hz, 1H), 4.04-3.95 (m, 1H), 3.54 (tt, J=10.7, 4.0 Hz, 1H), 3.24-3.11 (m, 1H), 2.74-2.49 (m, 3H), 2.22-2.08 (m, 2H), 2.06-1.89 (m, 4H), 1.41-1.11 (m, 4H), 1.09-0.95 (m, 4H). Isomer 2: HPLC: 93.0% purity, RT=1.12 min. MS: n/z=366.2 [M+H]+. 1H NMR (400 MHz, CD3OD, ppm) δ 8.92 (d, J=1.8 Hz, 1H), 8.84 (d, J=1.8 Hz, 1H), 8.08 (d, J=8.4 Hz, 1H), 7.20 (d, J=8.4 Hz, 1H), 4.69-4.55 (m, 1H), 4.06-3.97 (m, 1H), 3.96-3.86 (m, 1H), 3.30-3.16 (m, 1H), 2.84-2.70 (m, 1H), 2.66-2.52 (m, 2H), 2.19-1.94 (m, 2H), 1.92-1.74 (m, 3H), 1.73-1.51 (m, 5H), 1.12-0.92 (m, 4H).

Compound 137 (8-[(3S,5R)-3-methyl-5-[(oxetan-3-yl)amino]piperidin-1-yl]quinoxaline-5-carbonitrile): From oxetan-3-one and 8-((3R,5S)-3-amino-5-methylpiperidin-1-yl)quinoxaline-5-carbonitrile. HPLC: 95.1% purity, RT=1.12 min. MS: m/z=324.2 [M+H]+. 1H NMR (400 MHz, CD3OD, ppm) δ 8.99-8.85 (m, 2H), 8.05 (d, J=8.3 Hz, 1H), 7.16 (d, J=8.4 Hz, 1H), 4.88-4.76 (m, 2H), 4.59-4.40 (m, 3H), 4.26-4.12 (m, 1H), 4.07-3.98 (m, 1H), 3.04-2.90 (m, 1H), 2.68-2.48 (m, 2H), 2.16-1.91 (m, 2H), 1.14-0.96 (m, 4H).

Compound 138 (8-[(3S,5R)-3-methyl-5-[(oxolan-3-yl)amino]piperidin-1-yl]quinoxaline-5-carbonitrile): From dihydrofuran-3(2H)-one and 8-((3R,5S)-3-amino-5-methylpiperidin-1-yl)quinoxaline-5-carbonitrile. HPLC: 99.6% purity, RT=1.20 min. MS: m/z=338.2 [M+H]+. 1H NMR (400 MHz, CD3OD, ppm) δ 8.95-8.83 (m, 2H), 8.06 (d, J=8.4 Hz, 1H), 7.18 (d, J=8.4 Hz, 1H), 4.68-4.54 (m, 1H), 4.09-3.72 (m, 4H), 3.68-3.48 (m, 2H), 3.14-2.98 (m, 1H), 2.65-2.52 (m, 2H), 2.31-2.11 (m, 2H), 2.08-1.93 (m, 1H), 1.89-1.69 (m, 1H), 1.11-0.95 (m, 4H).

Compound 139 ((3R,5S)-5-methyl-N-(oxolan-3-yl)-1-[pyrido[2,3-b]pyrazin-8-yl]piperidin-3-amine): From dihydrofuran-3(2H)-one and (3R,5S)-5-methyl-1-(pyrido[2,3-b]pyrazin-8-yl)piperidin-3-amine. HPLC: 97.1% purity, RT=0.89 min. MS: m/z=314.2 [M+H]+. 1H NMR (400 MHz, CD3OD, ppm) δ 8.92 (d, J=1.7 Hz, 1H), 8.80 (t, J=1.8 Hz, 1H), 8.63 (d, J=5.6 Hz, 1H), 7.05 (d, J=5.7 Hz, 1H), 5.09-4.99 (m, 1H), 4.43-4.28 (m, 1H), 4.00-3.84 (m, 2H), 3.87-3.49 (m, 3H), 3.06-2.94 (m, 1H), 2.76-2.61 (m, 2H), 2.31-2.13 (m, 2H), 2.03-1.88 (m, 1H), 1.88-1.70 (m, 1H), 1.16-1.00 (m, 4H).

Example 43: Synthesis of Compound 98 ((2R)—N-[(3R,5S)-1-(8-cyanoquinoxalin-5-yl)-5-methylpiperidin-3-yl]-2-[ethyl(methyl)amino]propanamide)

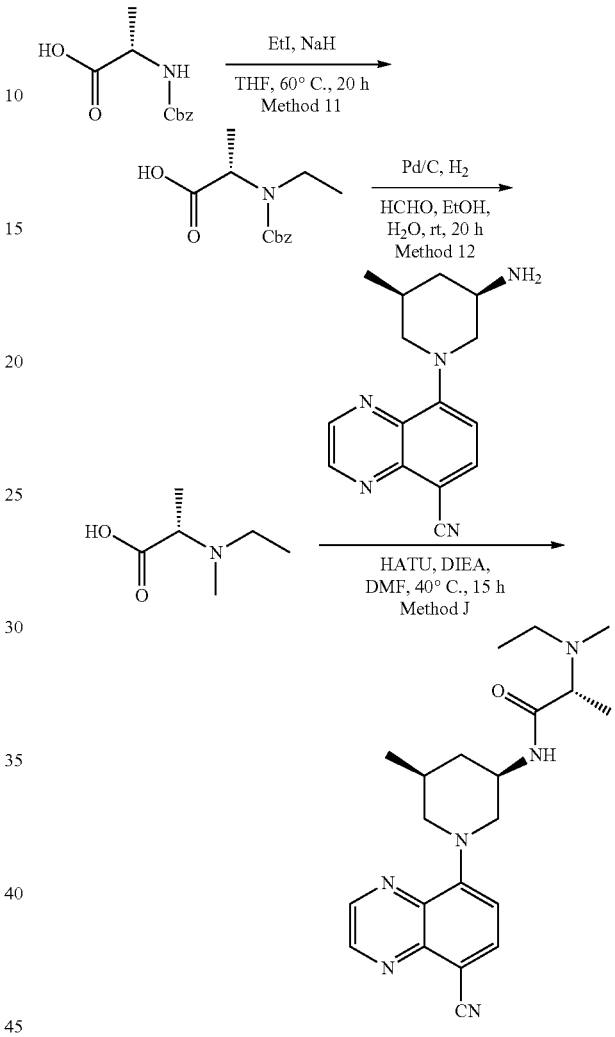

Method 11

(S)-2-((benzyloxycarbonyl)(ethyl)amino)propanoic: At 0° C., sodium hydride (324 mg, 13.50 mmol) was added to a solution of (2R)-2-[[(benzyloxy)carbonyl]amino]propanoic acid (950 mg, 4.26 mmol) in tetrahydrofuran (50 mL). The mixture was stirred for 10 min at 0° C., and then was added by iodoethane (5.32 g, 34.11 mmol). The reaction mixture was heated to 60° C. and stirred for 20 h. When the reaction was done, it was quenched by the addition of water (50 mL). The resulting mixture was extracted with ethyl acetate (60 mL×3). The organic phases were combined, washed with brine and dried over Na2SO4. The solvent was removed under reduced pressure to yield (2R)-2-[[(benzyloxy)carbonyl](ethyl)amino]propanoic acid as light yellow oil (900 mg, 32%). MS: m/z=252.2 [M+H]+.

Method 12

(S)-2-(ethyl(methyl)amino)propanoic acid: Under nitrogen atmosphere, Pd/C (0.1 g, 10%) was added to a solution of (2R)-2-[[(benzyloxy)carbonyl](ethyl)amino]propanoic acid (900 mg, 3.58 mmol, 1.00 equiv) and formalin (0.8 mL, 8.74 mmol, 40%) in ethanol (20 mL) and water (20 mL) at room temperature. The reaction flask was vacuumed and purged with hydrogen. The reaction mixture was stirred and hydrogenated for 20 h at room temperature under a hydrogen balloon. When the reaction was done, the reaction mixture was filtered through a Celite pad and the filtrate was concentrated under reduced pressure to yield (2R)-2-[ethyl (methyl)amino]propanoic acid as white solid (387 mg, 82%). MS: m/z=132.2 [M+H]+.

(R)—N-((3R,5S)-1-(8-cyanoquinoxalin-5-yl)-5-methylpiperidin-3-yl)-2-(ethyl(methyl)amino)propanamide: (R)—N-((3R,5S)-1-(8-cyanoquinoxalin-5-yl)-5-methylpiperidin-3-yl)-2-(ethyl(methyl)amino)propanamide was prepared from 8-((3R,5S)-3-amino-5-methylpiperidin-1-yl)quinoxaline-5-carbonitrile and (S)-2-(ethyl(methyl)amino) propanoic acid using Method J. The crude product was purified by prep-HPLC under the following conditions: column, XBridge C18 OBD Prep Column, 5 um, 19 mm×150 mm; mobile phase, MeOH in water (with 0.05% NH$_3$.H$_2$O), 15% to 45% gradient in 10 min; detector, UV 254 nm. (2R)—N-[(3R,5S)-1-(8-cyanoquinoxalin-5-yl)-5-methylpiperidin-3-yl]-2-[ethyl(methyl)amino]propanamide was obtained as yellow solid (36 mg, 32%).

Compound 98: HPLC: 90.0% purity, RT=1.95 min. MS: n/z=381.2 [M+H]+. $^1$H NMR (400 MHz, CD$_3$OD, ppm) δ 8.89 (d, J=1.7 Hz, 1H), 8.85 (d, J=1.8 Hz, 1H), 8.05 (d, J=8.4 Hz, 1H), 7.24 (d, J=8.4 Hz, 1H), 4.33-4.22 (m, 2H), 4.16-4.05 (m, 1H), 3.20-3.13 (m, 1H), 2.82-2.75 (m, 1H), 2.70-2.62 (m, 1H), 2.55-2.42 (m, 2H), 2.25 (s, 3H), 2.08-1.95 (m, 2H), 1.25-1.16 (m, 4H), 1.08 (t, J=7.0 Hz, 3H), 0.98 (d, J=6.4 Hz, 3H).

The following compounds were synthesized in an analogous manner:

Compound 99 ((2S)—N-[(3R,5S)-1-(8-cyanoquinoxalin-5-yl)-5-methylpiperidin-3-yl]-2-[ethyl(methyl)amino]propanamide): From 8-((3R,5S)-3-amino-5-methylpiperidin-1-yl)quinoxaline-5-carbonitrile and (R)-2-(ethyl(methyl) amino)propanoic acid. HPLC: 97.5% purity, RT=2.81 min. MS: m/z=381.2 [M+H]+. $^1$H NMR (400 MHz, CD$_3$OD, ppm) δ 8.89 (d, J=1.8 Hz, 1H), 8.85 (d, J=1.8 Hz, 1H), 8.06 (d, J=8.4 Hz, 1H), 7.25 (d, J=8.4 Hz, 1H), 4.34-4.23 (m, 2H), 4.13-4.05 (m, 1H), 3.18-3.11 (m, 1H), 2.83-2.75 (m, 1H), 2.71-2.61 (m, 1H), 2.54-2.45 (m, 2H), 2.25 (s, 3H), 2.10-1.96 (m, 2H), 1.29-1.15 (m, 4H), 1.06 (t, J=7.2 Hz, 3H), 0.98 (d, J=6.4 Hz, 3H).

Compound 100 ((2R)-2-[ethyl(methyl)amino]-N-[(3R,5S)-5-methyl-1-[pyrido[2,3-b]pyrazin-8-yl]piperidin-3-yl]propanamide): From (3R,5S)-5-methyl-1-(pyrido[2,3-b]pyrazin-8-yl)piperidin-3-amine and (S)-2-(ethyl(methyl) amino)propanoic acid. HPLC: 95.7% purity, RT=1.11 min. MS: m/z=357.2 [M+H]+. $^1$H NMR (300 MHz, CD$_3$OD, ppm) δ 8.89 (d, J=1.7 Hz, 1H), 8.77 (d, J=1.8 Hz, 1H), 8.63 (d, J=5.6 Hz, 1H), 7.12 (d, J=5.7 Hz, 1H), 4.63 (d, J=13.3 Hz, 2H), 4.12-3.95 (m, 1H), 3.18-3.12 (m, 1H), 2.92-2.84 (m, 1H), 2.79-2.71 (m, 1H), 2.55-2.46 (m, 2H), 2.26 (s, 3H), 2.10-1.92 (m, 2H), 1.34-1.24 (m, 1H), 1.20 (d, J=6.9 Hz, 3H), 1.09-1.04 (m, 3H), 0.99 (d, J=6.5 Hz, 3H).

Compound 101 ((2S)-2-[ethyl(methyl)amino]-N-[(3R,5S)-5-methyl-1-[pyrido[2,3-b]pyrazin-8-yl]piperidin-3-yl]propanamide): From (3R,5S)-5-methyl-1-(pyrido[2,3-b]pyrazin-8-yl)piperidin-3-amine and (R)-2-(ethyl(methyl) amino)propanoic acid. HPLC: 95.7% purity, RT=1.11 min. MS: m/z=357.2 [M+H]+. $^1$H NMR (300 MHz, CD$_3$OD, ppm) δ 8.89 (d, J=1.7 Hz, 1H), 8.77 (d, J=1.8 Hz, 1H), 8.63 (d, J=5.6 Hz, 1H), 7.12 (d, J=5.7 Hz, 1H), 4.63 (d, J=13.3 Hz, 2H), 4.12-3.95 (m, 1H), 3.18-3.12 (m, 1H), 2.92-2.84 (m, 1H), 2.79-2.71 (m, 1H), 2.55-2.46 (m, 2H), 2.26 (s, 3H), 2.10-1.92 (m, 2H), 1.34-1.24 (m, 1H), 1.20 (d, J=6.9 Hz, 3H), 1.09-1.04 (m, 3H), 0.99 (d, J=6.5 Hz, 3H).

Example 44: Synthesis of Compound 112 and compound 113 ((S)-2-amino-N-((3R,5S)-1-(8-cyanoquinoxalin-5-yl)-5-methylpiperidin-3-yl)-3,3,3-trifluoropropanamide hydrochloride and (R)-2-amino-N-((3R,5S)-1-(8-cyanoquinoxalin-5-yl)-5-methylpiperidin-3-yl)-3,3,3-trifluoropropanamide hydrochloride)

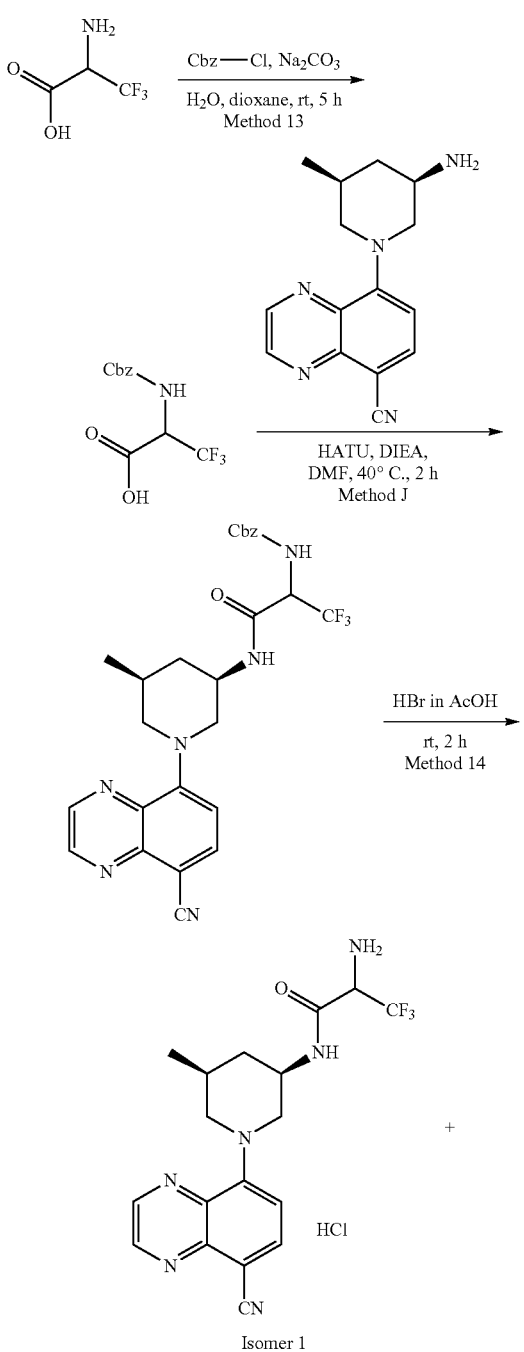

Isomer 1

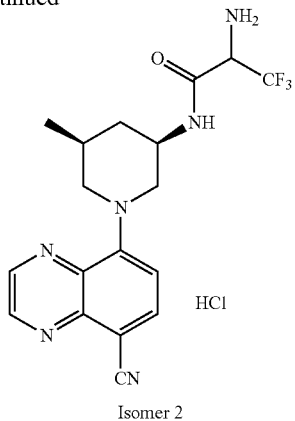

Isomer 2

Method 13

2-(benzyloxycarbonylamino)-3,3,3-trifluoropropanoic acid: At 0° C., to a solution of 2-amino-3,3,3-trifluoropropanoic acid (475 mg, 3.32 mmol) in dioxane (15 mL) and water (15 mL) was added sodium carbonate (1.90 g, 17.93 mmol) and Cbz-Cl (624 mg, 3.65 mmol). The resulting mixture was stirred for 5 h at room temperature. When reaction was done, the pH value of the reaction mixture was adjusted to 2-3 with hydrogen chloride solution (4 M). The resulting mixture was extracted with ethyl acetate (50 mL×3). The organic phases were combined, washed with brine and dried over $Na_2SO_4$. The solvent was removed under reduced pressure and the residue was purified by reverse phase flash chromatography eluting with acetonitrile in water (15% to 35% gradient in 30 min) to yield 2-[[(benzyloxy)carbonyl]amino]-3,3,3-trifluoropropanoic acid as white solid (500 mg, 54%). MS: m/z=276 [M−H]$^+$.

benzyl 3-((3R,5S)-1-(8-cyanoquinoxalin-5-yl)-5-methylpiperidin-3-ylamino)-1,1,1-trifluoro-3-oxopropan-2-ylcarbamate: 3-((3R,5S)-1-(8-cyanoquinoxalin-5-yl)-5-methylpiperidin-3-ylamino)-1,1,1-trifluoro-3-oxopropan-2-ylcarbamate was prepared from 8-((3R,5S)-3-amino-5-methylpiperidin-1-yl)quinoxaline-5-carbonitrile and 2-(benzyloxycarbonylamino)-3,3,3-trifluoropropanoic acid using Method J. The crude product was purified by flash chromatography eluting with EtOAc in hexane (0% to 50% gradient) to yield benzyl N-(1-[[(3R,5S)-1-(8-cyanoquinoxalin-5-yl)-5-methylpiperidin-3-yl]carbamoyl]-2,2,2-trifluoroethyl)carbamate as yellow solid (220 mg, 50%). MS: m/z=527 [M−H]$^+$.

Method 14

(S)-2-amino-N-((3R,5S)-1-(8-cyanoquinoxalin-5-yl)-5-methylpiperidin-3-yl)-3,3,3-trifluoropropanamide hydrochloride and (R)-2-amino-N-((3R,5S)-1-(8-cyanoquinoxalin-5-yl)-5-methylpiperidin-3-yl)-3,3,3-trifluoropropanamide hydrochloride: To a solution of benzyl N-(1-[[(3R,5S)-1-(8-cyanoquinoxalin-5-yl)-5-methylpiperidin-3-yl]carbamoyl]-2,2,2-trifluoroethyl)carbamate (110 mg, 0.21 mmol) in acetic acid (5 mL) was added HBr solution (40% in dioxane, 2 mL). The resulting solution was stirred for 2 h at room temperature. After the reaction was done, the reaction mixture was concentrated under reduced pressure. The residue was purified by prep-HPLC under the following conditions: column, XBridge Prep C18 OBD Column, 5 um, 19 mm×150 mm; mobile phase, MeOH in water (with 0.02% HCl), 10% to 27% gradient in 10 min; detector, UV 254 nm. Two diastereomeric products were separated and obtained.

Isomer 1: (30 mg, 20%, brown solid) HPLC: 99.1% purity, RT=1.01 min. MS: m/z=393.0 [M+H]$^+$. $^1$H NMR (300 MHz, $CD_3OD$, ppm) δ 8.90-8.82 (m, 2H), 8.07 (d, J=8.3 Hz, 1H), 7.25 (d, J=8.4 Hz, 1H), 4.78-4.71 (m, 1H), 4.39-4.15 (m, 3H), 2.85-2.60 (m, 2H), 2.21-2.02 (m, 2H), 1.33-1.21 (m, 1H), 1.00 (d, J=6.5 Hz, 3H).

Isomer 2: (60 mg, 40%, brown solid) HPLC: 99.1% purity, RT=1.05 min. MS: m/z=393.0 [M+H]$^+$. $^1$H NMR (300 MHz, $CD_3OD$, ppm) δ 9.00-8.80 (m, 2H), 8.08 (d, J=8.4 Hz, 1H), 7.26 (d, J=8.4 Hz, 1H), 4.76-4.69 (q, J=7.4 Hz, 1H), 4.49-4.03 (m, 3H), 2.86-2.60 (m, 2H), 2.20-1.96 (m, 2H), 1.33-1.15 (m, 1H), 1.03-0.95 (m, 3H).

The following compounds were synthesized in an analogous manner:

Compound 114 and compound 115 ((S)-2-amino-3,3,3-trifluoro-N-((3R,5S)-5-methyl-1-(quinoxalin-5-yl)piperidin-3-yl)propanamide hydrochloride and (R)-2-amino-3,3,3-trifluoro-N-((3R,5S)-5-methyl-1-(quinoxalin-5-yl)piperidin-3-yl)propanamide hydrochloride): From (3R,5S)-5-methyl-1-(quinoxalin-5-yl)piperidin-3-amine and 2-(benzyloxycarbonylamino)-3,3,3-trifluoropropanoic acid. Isomer 1: HPLC: 93.9% purity, RT=0.97 min. MS: m/z=369.1 [M+H]$^+$. $^1$H NMR (300 MHz, $CD_3OD$, ppm) δ 9.12 (d, J=1.8 Hz, 1H), 8.97 (d, J=1.9 Hz, 1H), 8.61 (d, J=7.3 Hz, 1H), 7.35 (d, J=7.5 Hz, 1H), 5.10-4.90 (m, 3H), 4.11-3.91 (m, 1H), 3.37 (t, J=11.8 Hz, 1H), 3.16 (t, J=12.3 Hz, 1H), 2.12-1.92 (m, 2H), 1.49-1.45 (m, 1H), 1.03 (d, J=6.4 Hz, 3H). Isomer 2: HPLC: 95.8% purity, RT=1.04 min. MS: m/z=369.1 [M+H]$^+$. $^1$H NMR (300 MHz, $CD_3OD$, ppm) δ 9.02 (d, J=2.2 Hz, 1H), 8.68-8.58 (m, 1H), 7.33 (d, J=7.4 Hz, 1H), 5.00-4.84 (m, 3H), 4.10-3.90 (m, 1H), 3.33 (t, J=11.9 Hz, 1H), 3.17 (t, J=12.4 Hz, 1H), 2.10-1.89 (m, 2H), 1.45-1.40 (m, 1H), 1.02 (d, J=6.3 Hz, 3H).

Example 45: Synthesis of Compound 123 (8-[(3S,5R)-3-methyl-5-[(2-oxopyrrolidin-3-yl)amino]piperidin-1-yl]quinoxaline-5-carbonitrile)

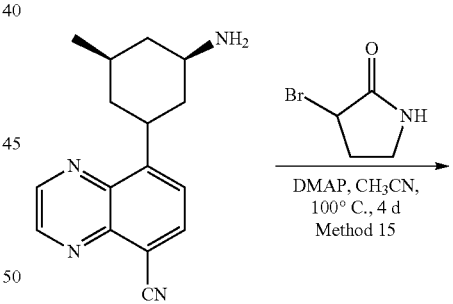

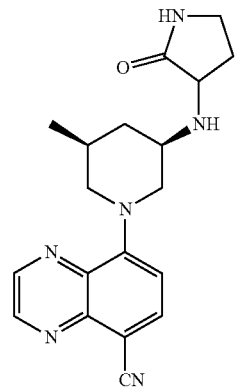

Method 15

8-[(3S,5R)-3-methyl-5-[(2-oxopyrrolidin-3-yl)amino]piperidin-1-yl]quinoxaline-5-carbonitrile: To a solution of 8-[(3R,5S)-3-amino-5-methylpiperidin-1-yl]quinoxaline-5-carbonitrile (50 mg, 0.19 mmol) in acetonitrile (3 mL) was added 3-bromopyrrolidin-2-one (36 mg, 0.22 mmol), 4-dimethylaminopyridine (4 mg, 0.03 mmol) and triethylamine (48 mg, 0.47 mmol) at room temperature. The resulting solution was stirred for 4 days at 100° C. After the reaction was done, the reaction mixture was concentrated under reduced pressure. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 10% to 40% gradient in 10 min; detector, UV 254 nm. 8-[(3S,5R)-3-methyl-5-[(2-oxopyrrolidin-3-yl)amino]piperidin-1-yl]quinoxaline-5-carbonitrile was obtained as yellow solid (15 mg, 23%).

Compound 123: HPLC: 97.9% purity, RT=1.90 min. MS: m/z=351.1 $[M+H]^+$. $^1$H NMR (400 MHz, $CD_3OD$, ppm) δ 8.96-8.87 (m, 2H), 8.08 (dd, J=9.5, 3.7 Hz, 1H), 7.23 (dt, J=8.2, 4.0 Hz, 1H), 4.71-4.52 (m, 1H), 4.12 (dt, J=10.7, 5.1 Hz, 1H), 3.67 (dd, J=10.1, 8.0 Hz, 1H), 3.47-3.12 (m, 3H), 2.73-2.45 (m, 3H), 2.30-2.15 (m, 1H), 2.11-1.86 (m, 2H), 1.16-0.99 (m, 4H).

The following compounds were synthesized in an analogous manner:

Compound 127 (3-[[(3R,5S)-5-methyl-1-[pyrido[2,3-b]pyrazin-8-yl]piperidin-3-yl]amino]pyrrolidin-2-one): From (3R,5S)-5-methyl-1-(pyrido[2,3-b]pyrazin-8-yl)piperidin-3-amine and 3-bromopyrrolidin-2-one. HPLC: 90.8% purity, RT=1.70 min. MS: m/z=327.1 $[M+H]^+$. $^1$H NMR (400 MHz, $CD_3OD$, ppm) δ 8.96 (d, J=1.7 Hz, 1H), 8.83-8.70 (m, 2H), 6.90 (dd, J=5.5, 4.0 Hz, 1H), 4.84-4.65 (m, 1H), 4.30-4.19 (m, 1H), 3.62-3.51 (m, 1H), 3.46-3.28 (m, 2H), 3.12-2.98 (m, 1H), 2.74-2.44 (m, 3H), 2.20 (dd, J=28.8, 12.5 Hz, 1H), 2.07-1.91 (m, 2H), 1.14-0.98 (m, 4H).

Example 46: Synthesis of Compound 124 and compound 125 (8-[(3S,5R)-3-methyl-5-{[(3R)-1-methyl-2-oxopyrrolidin-3-yl]amino}piperidin-1-yl]quinoxaline-5-carbonitrile and 8-[(3S,5R)-3-methyl-5-{[(3S)-1-methyl-2-oxopyrrolidin-3-yl]amino}piperidin-1-yl]quinoxaline-5-carbonitrile)

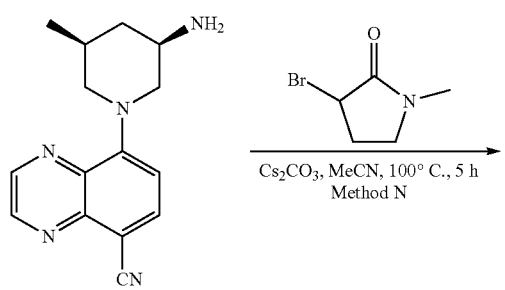

$Cs_2CO_3$, MeCN, 100° C., 5 h
Method N

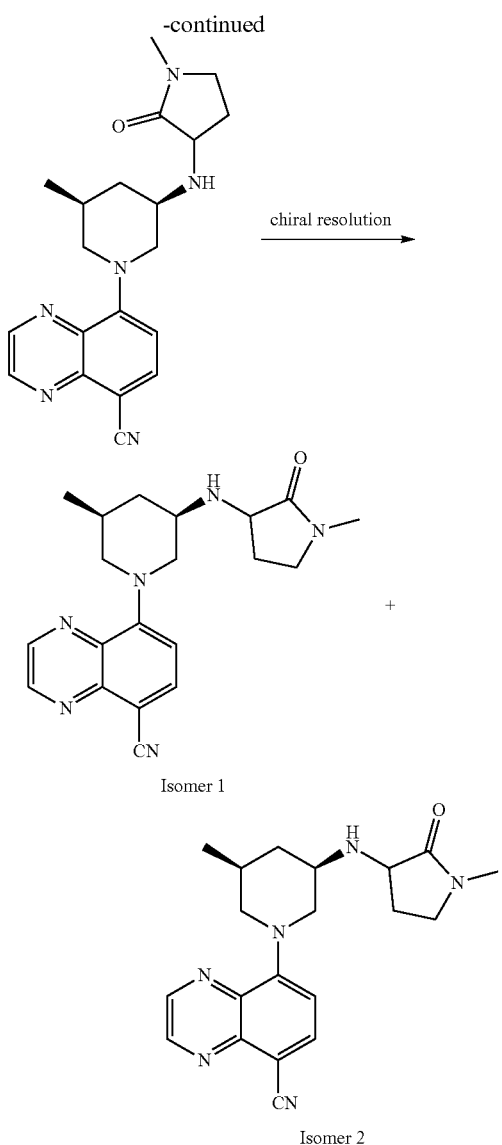

8-[(3S,5R)-3-methyl-5-[(2-oxopyrrolidin-3-yl)amino]piperidin-1-yl]quinoxaline-5-carbonitrile): 8-[(3S,5R)-3-methyl-5-[(2-oxopyrrolidin-3-yl)amino]piperidin-1-yl]quinoxaline-5-carbonitrile was prepared from 8-((3R,5S)-3-amino-5-methylpiperidin-1-yl)quinoxaline-5-carbonitrile and 3-bromo-1-methylpyrrolidin-2-one using Method N. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 10% to 40% gradient in 10 min; detector, UV 254 nm. (19 mg, 28%, yellow solid). HPLC: 94.2% purity, RT=0.63 min. MS: m/z=365.1 $[M+H]^+$. $^1$H NMR (400 MHz, $CD_3OD$, ppm) δ 8.99-8.88 (m, 2H), 8.13 (dd, J=8.4, 3.1 Hz, 1H), 7.27 (dd, J=8.4, 5.0 Hz, 1H), 4.75-4.55 (m, 1H), 4.17-4.04 (m, 1H), 3.93-3.84 (m, 1H), 3.52-3.38 (m, 3H), 2.91 (s, 3H), 2.83-2.57 (m, 3H), 2.36-2.20 (m, 1H), 2.13-1.86 (m, 2H), 1.27-1.04 (m, 4H). Then the 2 isomers of 8-[(3S,5R)-3-methyl-5-[(2-oxopyrrolidin-3-yl)amino]piperidin-1-yl]quinoxaline-5-carbonitrile were obtained by separation on chiral prep-HPLC under the following conditions: column, EnantioPak A1-5, 2.12×25 cm, 5um; mobile phase, EtOH in Hexane, 55% isocratic in 32 min; detector, UV 254/220 nm.

Isomer 1: HPLC: 98.8% purity, RT=1.15 min. MS: m/z=365.2 [M+H]+. 1H NMR (400 MHz, CD3OD, ppm) δ 8.99-8.88 (m, 2H), 8.13 (dd, J=8.4, 3.1 Hz, 1H), 7.27 (dd, J=8.4, 5.0 Hz, 1H), 4.75-4.55 (m, 1H), 4.17-4.04 (m, 1H), 3.93-3.84 (m, 1H), 3.52-3.38 (m, 3H), 2.91 (s, 3H), 2.83-2.57 (m, 3H), 2.36-2.20 (m, 1H), 2.13-1.86 (m, 2H), 1.27-1.04 (m, 4H).

Isomer 2: HPLC: 99.3% purity, RT=1.15 min. MS: m/z=365.2 [M+H]+. 1H NMR (400 MHz, CD3OD, ppm) δ 8.99-8.88 (m, 2H), 8.13 (dd, J=8.4, 3.1 Hz, 1H), 7.27 (dd, J=8.4, 5.0 Hz, 1H), 4.75-4.55 (m, 1H), 4.17-4.04 (m, 1H), 3.93-3.84 (m, 1H), 3.52-3.38 (m, 3H), 2.91 (s, 3H), 2.83-2.57 (m, 3H), 2.36-2.20 (m, 1H), 2.13-1.86 (m, 2H), 1.27-1.04 (m, 4H).

Example 47: Synthesis of Compound 162 (N-[(3R,5S)-1-(8-cyanoquinoxalin-5-yl)-5-methylpiperidin-3-yl]-1-(hydroxymethyl)cyclopropane-1-carboxamide)

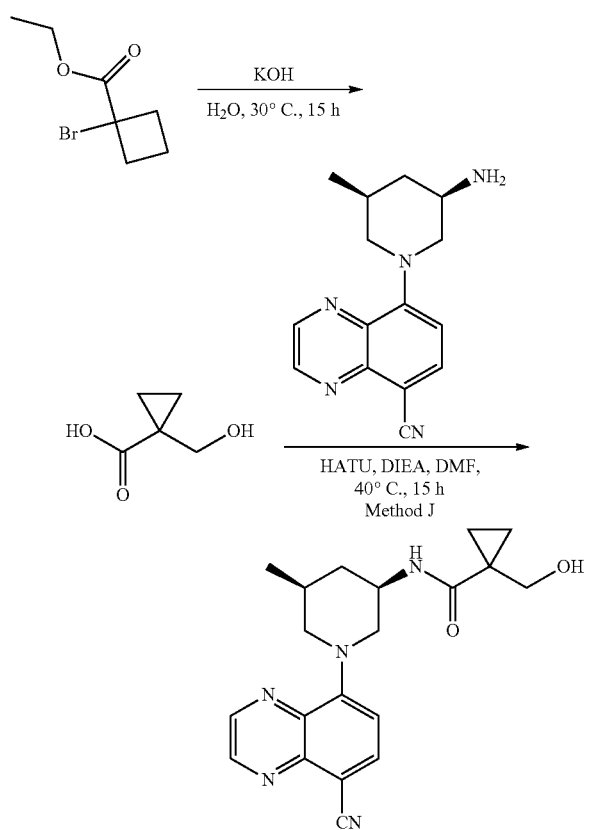

1-(hydroxymethyl)cyclopropanecarboxylic acid: To a solution of ethyl 1-bromocyclobutane-1-carboxylate (475 mg, 2.29 mmol) in water (10 mL) was added KOH (255 mg, 4.55 mmol) at room temperature. The resulting mixture was stirred at 30° C. for 15 h. After the reaction was done, the pH value of the reaction mixture was adjusted to 1 with hydrogen chloride solution (2 M). The resulting mixture was concentrated under reduced pressure and diluted with methanol (15 mL). The insoluble solids were filtered out and the filtrate was concentrated under reduced pressure to yield 1-(hydroxymethyl)cyclopropane-1-carboxylic acid as light yellow solid (189 mg, 71%). MS: m/z=117.2 [M+H]+.

N-[(3R,5S)-1-(8-cyanoquinoxalin-5-yl)-5-methylpiperidin-3-yl]-1-(hydroxymethyl)cyclopropane-1-carboxamide: N-[(3R,5S)-1-(8-cyanoquinoxalin-5-yl)-5-methylpiperidin-3-yl]-1-(hydroxymethyl)cyclopropane-1-carboxamide was prepared from 1-(hydroxymethyl)cyclopropanecarboxylic acid and 8-((3R,5S)-3-amino-5-methylpiperidin-1-yl)quinoxaline-5-carbonitrile using Method J. The crude product was purified by prep-HPLC under the following conditions: column, XBridge Prep C18 OBD Column, 5 um, 19 mm×150 mm; mobile phase, acetonitrile in water (with 0.05% NH3.H2O), 25% to 45% gradient in 10 min; detector, UV 254 nm. N-[(3R,5S)-1-(8-cyanoquinoxalin-5-yl)-5-methylpiperidin-3-yl]-1-(hydroxymethyl)cyclopropane-1-carboxamide was obtained as yellow solid (28 mg, 27%).

Compound 162: HPLC: 94.2% purity, RT=1.17 min. MS: m/z=366.2 [M+H]+. 1H NMR (300 MHz, CD3OD, ppm) δ 8.92-8.82 (m, 2H), 8.05 (d, J=8.4 Hz, 1H), 7.25 (d, J=8.4 Hz, 1H), 4.30 (t, J=13.8 Hz, 2H), 4.11 (d, J=11.5 Hz, 1H), 3.69-3.52 (m, 2H), 2.84-2.64 (m, 2H), 2.12-1.96 (m, 2H), 1.24 (q, J=11.7 Hz, 1H), 1.25-1.11 (m, 2H), 0.98 (d, J=6.5 Hz, 3H), 0.78-0.62 (m, 2H).

Example 48: Synthesis of Compound 177 and compound 178 ((R)-2-amino-N-((3R,5R)-1-(8-cyanoquinoxalin-5-yl)-5-cyclopropylpiperidin-3-yl)-3,3,3-trifluoropropanamide and (R)-2-amino-N-((3S,5S)-1-(8-cyanoquinoxalin-5-yl)-5-cyclopropylpiperidin-3-yl)-3,3,3-trifluoropropanamide)

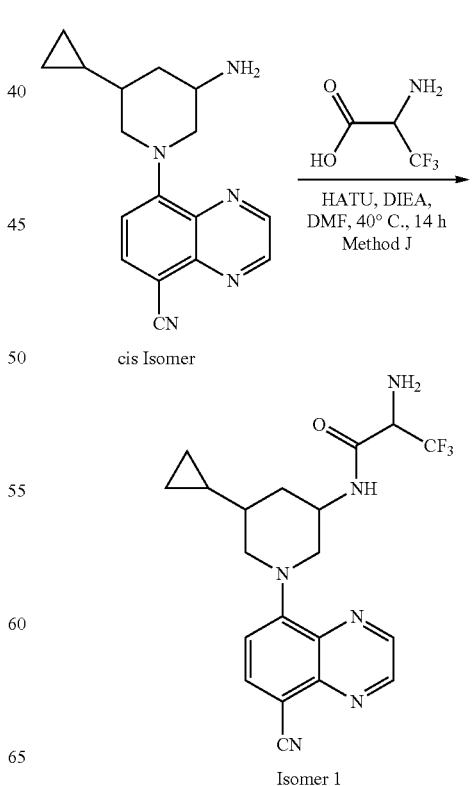

473
-continued

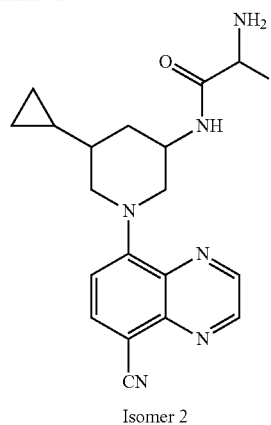

Isomer 2

(R)-2-amino-N-((3R,5R)-1-(8-cyanoquinoxalin-5-yl)-5-cyclopropylpiperidin-3-yl)-3,3,3-trifluoropropanamide and (R)-2-amino-N-((3S,5S)-1-(8-cyanoquinoxalin-5-yl)-5-cyclopropylpiperidin-3-yl)-3,3,3-trifluoropropanamide: cis-(2R)-2-amino-N-[1-(8-cyanoquinoxalin-5-yl)-5-cyclopropylpiperidin-3-yl]-3,3,3-trifluoropropanamide was prepared from cis-8-(3-amino-5-cyclopropylpiperidin-1-yl)quinoxaline-5-carbonitrile and 2-amino-3,3,3-trifluoropropanoic acid using Method J. The two cis diastereoisomers were separated by prep-HPLC under the following conditions: column, XBridge Shield RP18 OBD Column, 19×150 mm 10 um; mobile phase, acetonitrile in water (with 0.05% NH$_3$.H$_2$O), 35% to 65% gradient in 10 min; detector, UV 254 nm.

Isomer 1: (14 mg, 12%, yellow solid) HPLC: 95.0% purity, RT=2.76 min. MS: m/z=419.2 [M+H]$^+$. $^1$H NMR (300 MHz, CD$_3$OD, ppm) δ 8.90 (d, J=1.8 Hz, 1H), 8.86 (d, J=1.8 Hz, 1H), 8.07 (d, J=8.4 Hz, 1H), 7.23 (d, J=8.4 Hz, 1H), 4.41-4.24 (m, 2H), 4.20-4.00 (m, 1H), 3.99-3.85 (m, 1H), 2.95-2.75 (m, 2H), 2.29-2.13 (m, 1H), 1.52-1.05 (m, 2H), 0.70-0.37 (m, 3H), 0.22-0.12 (m, 2H).

Isomer 2: (14 mg, 12%, yellow solid) HPLC: 94.4% purity, RT=3.14 min. MS: m/z=419.2 [M+H]$^+$. $^1$H NMR (300 MHz, CD$_3$OD, ppm) δ 8.90 (d, J=1.8 Hz, 1H), 8.86 (d, J=1.8 Hz, 1H), 8.07 (d, J=8.4 Hz, 1H), 7.23 (d, J=8.4 Hz, 1H), 4.41-4.24 (m, 2H), 4.20-4.00 (m, 1H), 3.99-3.85 (m, 1H), 2.95-2.75 (m, 2H), 2.29-2.13 (m, 1H), 1.52-1.05 (m, 2H), 0.70-0.37 (m, 3H), 0.22-0.12 (m, 2H).

Example 49: Synthesis of Compound 180 (5-[(3R,5S)-3-amino-5-methylpiperidin-1-yl]quinoline-8-carboxamide)

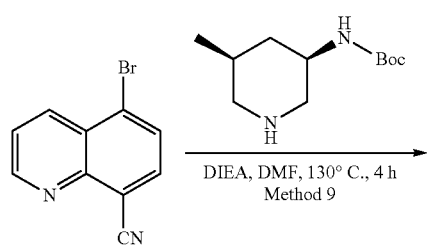

474
-continued

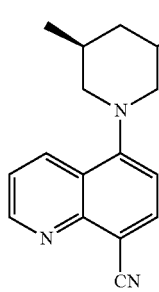

$\xrightarrow{\text{H}_2\text{SO}_4}$
TFA, 40° C., 16 h

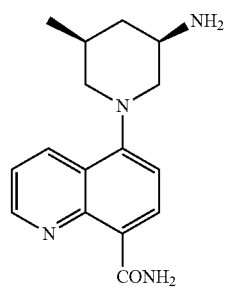

tert-butyl N-[(3R,5S)-1-(8-cyanoquinolin-5-yl)-5-methylpiperidin-3-yl]carbamate: tert-butyl N-[(3R,5S)-1-(8-cyanoquinolin-5-yl)-5-methylpiperidin-3-yl]carbamate was prepared from 5-bromoquinoline-8-carbonitrile and tert-butyl (3R,5S)-5-methylpiperidin-3-ylcarbamate using Method 9. The crude product was purified by flash chromatography eluting with DCM in petroleum ether (0% to 100% gradient) to yield tert-butyl N-[(3R,5S)-1-(8-cyanoquinolin-5-yl)-5-methylpiperidin-3-yl]carbamate as yellow solid (128 mg, 29%). MS: m/z=367.0 [M+H]$^+$.

5-[(3R,5S)-3-amino-5-methylpiperidin-1-yl]quinoline-8-carboxamide: To a solution of tert-butyl N-[(3R,5S)-1-(8-cyanoquinolin-5-yl)-5-methylpiperidin-3-yl]carbamate (128 mg, 0.35 mmol) in trifluoroacetic acid (4 mL) was added sulfuric acid (1 mL) at room temperature. The resulting solution was stirred for 16 h at 40° C. When the reaction was done, it was quenched by the addition of ice water (30 mL) and the pH value of the solution was adjusted to 10-12 with ammonia solution. The resulting solution was extracted with DCM (50 mL×3). The organic phases were combined, washed with brine and dried over Na$_2$SO$_4$. The solvent was removed under reduced pressure and the residue was purified by prep-HPLC under the following conditions: column, XBridge Prep C18 OBD Column, 5 um, 19 mm×150 mm; mobile phase, acetonitrile in water (with 0.05% NH$_3$.H$_2$O), 20% to 50% gradient in 10 min; detector, UV 254 nm. 5-[(3R,5S)-3-amino-5-methylpiperidin-1-yl]quinoline-8-carboxamide was obtained as light yellow solid (79 mg, 80%).

Compound 180: HPLC: 99.0% purity, RT=0.96 min. MS: m/z=285.2 [M+H]$^+$. $^1$H NMR (400 MHz, CD$_3$OD, ppm) δ 8.94 (dd, J=4.3, 1.8 Hz, 1H), 8.65-8.57 (m, 2H), 7.56 (dd, J=8.6, 4.2 Hz, 1H), 7.25 (d, J=8.2 Hz, 1H), 3.60-3.44 (m, 1H), 3.39-3.31 (m, 1H), 3.24-3.12 (m, 1H), 2.55-2.35 (m, 2H), 2.19-2.01 (m, 2H), 1.03-0.89 (m, 4H).

Example 50: Synthesis of Compound 181 (5-[(3R,5S)-3-[(2S)-2-hydroxy-3-methylbutanamido]-5-methylpiperidin-1-yl]quinoline-8-carboxamide)

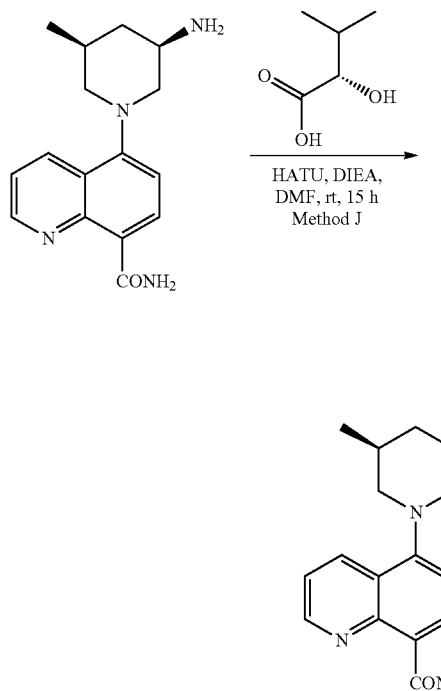

5-[(3R,5S)-3-[(2S)-2-hydroxy-3-methylbutanamido]-5-methylpiperidin-1-yl]quinoline-8-carboxamide: 5-[(3R,5S)-3-[(2S)-2-hydroxy-3-methylbutanamido]-5-methylpiperidin-1-yl]quinoline-8-carboxamide was prepared from (S)-2-hydroxy-3-methylbutanoic acid and 5-((3R,5S)-3-amino-5-methylpiperidin-1-yl)quinoline-8-carboxamide using Method J. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 30% to 60% gradient in 10 min; detector, UV 254 nm. 5-[(3R,5S)-3-[(2S)-2-hydroxy-3-methylbutanamido]-5-methylpiperidin-1-yl]quinoline-8-carboxamide was obtained as yellow solid (35 mg, 52%).

Compound 181: HPLC: 97.4% purity, RT=1.21 min. MS: m/z=385.2 [M+H]$^+$. $^1$H NMR (400 MHz, CD$_3$OD, ppm) δ 8.98-8.92 (m, 1H), 8.73-8.65 (m, 1H), 8.61 (d, J=8.1 Hz, 1H), 7.59 (dd, J=8.6, 4.3 Hz, 1H), 7.30-7.23 (m, 1H), 4.35-4.21 (m, 1H), 3.83 (d, J=3.8 Hz, 1H), 3.61-3.52 (m, 1H), 3.38 (d, J=11.8 Hz, 1H), 2.64-2.44 (m, 2H), 2.23-1.98 (m, 3H), 1.34-1.19 (m, 1H), 1.08-0.92 (m, 6H), 0.81 (d, J=6.8 Hz, 3H).

The following compounds were synthesized in an analogous manner:

Compound 182 (5-[(3R,5S)-3-(3,3-dimethylbutanamido)-5-methylpiperidin-1-yl]quinoline-8-carboxamide): From 3,3-dimethylbutanoic acid and 5-((3R,5S)-3-amino-5-methylpiperidin-1-yl)quinoline-8-carboxamide. HPLC: 99.6% purity, RT=1.45 min. MS: m/z=383.3 [M+H]$^+$. $^1$H NMR (400 MHz, CD$_3$OD, ppm) δ 8.95 (dd, J=4.2, 1.8 Hz, 1H), 8.69 (dd, J=8.6, 1.8 Hz, 1H), 8.61 (d, J=8.2 Hz, 1H), 7.60 (dd, J=8.6, 4.2 Hz, 1H), 7.26 (d, J=8.2 Hz, 1H), 4.29-4.17 (m, 1H), 3.67-3.55 (m, 1H), 3.42-3.32 (m, 1H), 2.55-2.41 (m, 2H), 2.20-2.04 (m, 4H), 1.15 (td, J=12.0, 12.0 Hz, 1H), 1.06-0.93 (m, 12H).

Compound 186 (5-[(3R,5S)-3-[2-(dimethylamino)acetamido]-5-methylpiperidin-1-yl]quinoline-8-carboxamide): From 2-(dimethylamino)acetic acid and 5-((3R,5S)-3-amino-5-methylpiperidin-1-yl)quinoline-8-carboxamide. HPLC: 97.3% purity, RT=1.18 min. MS: m/z=370.3 [M+H]$^+$. $^1$H NMR (400 MHz, CD$_3$OD, ppm) δ 8.95 (dd, J=4.3, 1.8 Hz, 1H), 8.69 (dd, J=8.6, 1.8 Hz, 1H), 8.61 (d, J=8.1 Hz, 1H), 7.59 (dd, J=8.6, 4.2 Hz, 1H), 7.27 (d, J=8.2 Hz, 1H), 4.33-4.20 (m, 1H), 3.61-3.57 (m, 1H), 3.39-3.36 (m, 1H), 2.99 (s, 2H), 2.62-2.42 (m, 2H), 2.29 (s, 6H), 2.16-2.09 (m, 2H), 1.20 (td, J=12.0, 12.0 Hz, 1H), 1.03 (d, J=6.4 Hz, 3H).

Example 51: Synthesis of Compound 183 (5-[(3R,5S)-3-[(2-methoxyethyl)amino]-5-methylpiperidin-1-yl]quinoline-8-carboxamide)

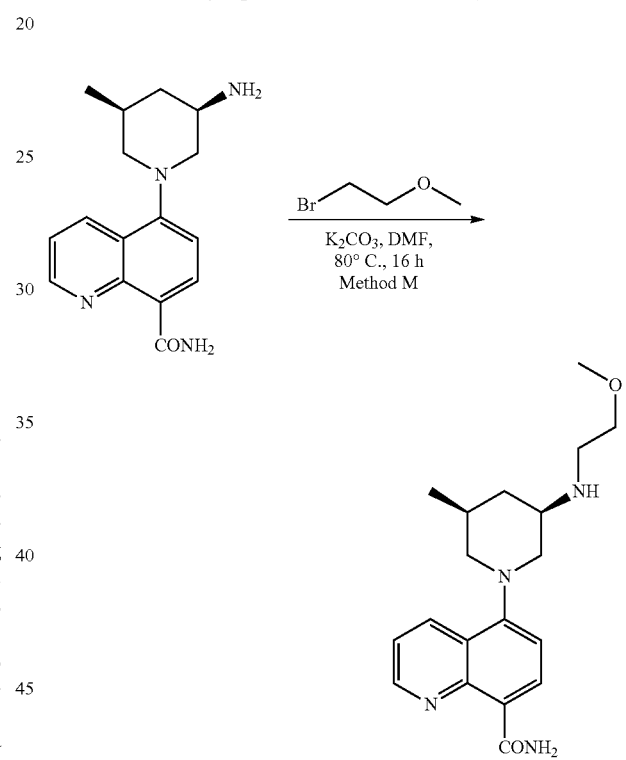

5-[(3R,5S)-3-[(2-methoxyethyl)amino]-5-methylpiperidin-1-yl]quinoline-8-carboxamide: 5-[(3R,5S)-3-[(2-methoxyethyl)amino]-5-methylpiperidin-1-yl]quinoline-8-carboxamide was prepared from 1-bromo-2-methoxyethane and 5-((3R,5S)-3-amino-5-methylpiperidin-1-yl)quinoline-8-carboxamide using Method M. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 35% to 65% gradient in 10 min; detector, UV 254 nm. 5-[(3R,5S)-3-[(2-methoxyethyl)amino]-5-methylpiperidin-1-yl]quinoline-8-carboxamide was obtained as yellow solid (18 mg, 23%).

Compound 183: HPLC: 98.9% purity, RT=1.18 min. MS: m/z=343.2 [M+H]$^+$. $^1$H NMR (400 MHz, CD$_3$OD, ppm) δ 8.95 (dd, J=4.2, 1.8 Hz, 1H), 8.69 (dd, J=8.6, 1.8 Hz, 1H), 8.61 (d, J=8.2 Hz, 1H), 7.60 (dd, J=8.6, 4.2 Hz, 1H), 7.26 (d, J=8.2 Hz, 1H), 3.69-3.60 (m, 1H), 3.56-3.44 (m, 2H), 3.42-3.30 (m, 4H), 3.18-3.06 (m, 1H), 2.97-2.80 (m, 2H), 2.58-2.38 (m, 2H), 2.28-2.05 (m, 2H), 1.06-0.92 (m, 4H).

Example 52: Synthesis of Compound 184 and compound 185 (5-((3R,5S)-3-((R)-2-amino-3,3,3-trifluoropropanamido)-5-methylpiperidin-1-yl)quinoline-8-carboxamide and 5-((3R,5S)-3-((S)-2-amino-3,3,3-trifluoropropanamido)-5-methylpiperidin-1-yl)quinoline-8-carboxamide)

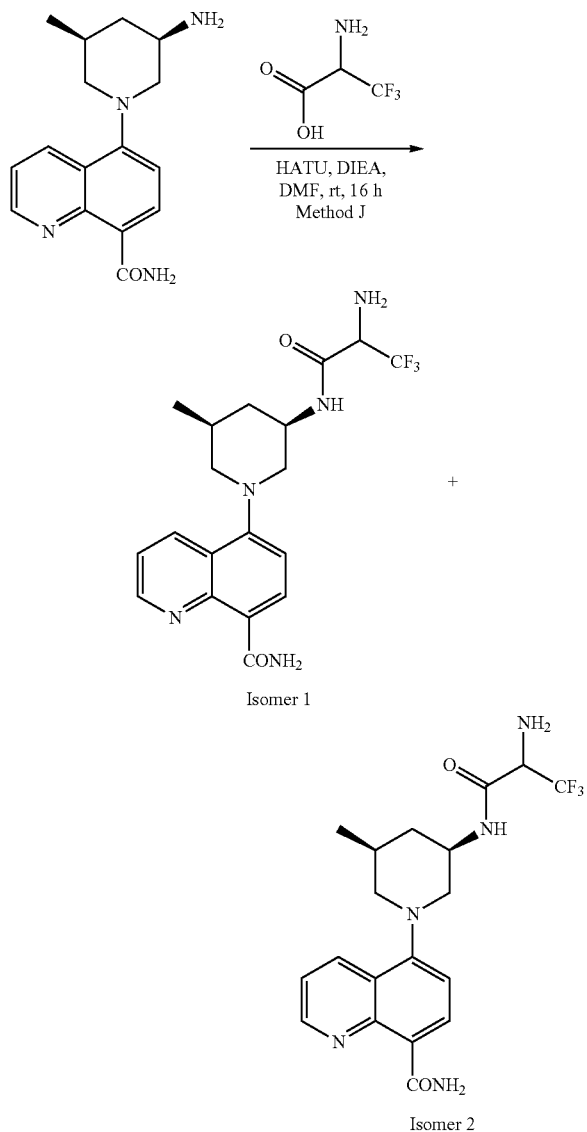

mobile phase, acetonitrile in water (with 0.05% NH$_3$.H$_2$O), 30% to 60% gradient in 10 min; detector, UV 254 nm.

Isomer 1: (16 mg, 12%, off-white solid) HPLC: 98.3% purity, RT=1.18 min. MS: m/z=410.2 [M+H]$^+$. $^1$H NMR (300 MHz, CD$_3$OD, ppm) δ 8.96 (dd, J=4.3, 1.8 Hz, 1H), 8.72-8.58 (m, 2H), 7.60 (dd, J=8.6, 4.2 Hz, 1H), 7.27 (d, J=8.2 Hz, 1H), 4.38-4.22 (m, 1H), 3.91 (q, J=7.7 Hz, 1H), 3.65-3.56 (m, 1H), 3.40 (dd, J=11.9, 2.9 Hz, 1H), 2.60-2.42 (m, 2H), 2.23-2.10 (m, 2H), 1.19 (td, J=12.6, 12.6 Hz, 1H), 1.04 (d, J=6.3 Hz, 3H).

Isomer 2: (16 mg, 12%, yellow solid) HPLC: 96.9% purity, RT=2.35 min. MS: m/z=410.2 [M+H]$^+$. $^1$H NMR (300 MHz, CD$_3$OD, ppm) δ 8.96 (dd, J=4.3, 1.8 Hz, 1H), 8.72-8.58 (m, 2H), 7.60 (dd, J=8.6, 4.2 Hz, 1H), 7.27 (d, J=8.2 Hz, 1H), 4.38-4.22 (m, 1H), 3.91 (q, J=7.7 Hz, 1H), 3.65-3.56 (m, 1H), 3.40 (dd, J=11.9, 2.9 Hz, 1H), 2.60-2.42 (m, 2H), 2.23-2.10 (m, 2H), 1.19 (td, J=12.6, 12.6 Hz, 1H), 1.04 (d, J=6.3 Hz, 3H).

Example 53: Synthesis of Compound 187 ((3R,5S)-1-(8-methoxyquinolin-5-yl)-5-methylpiperidin-3-amine)

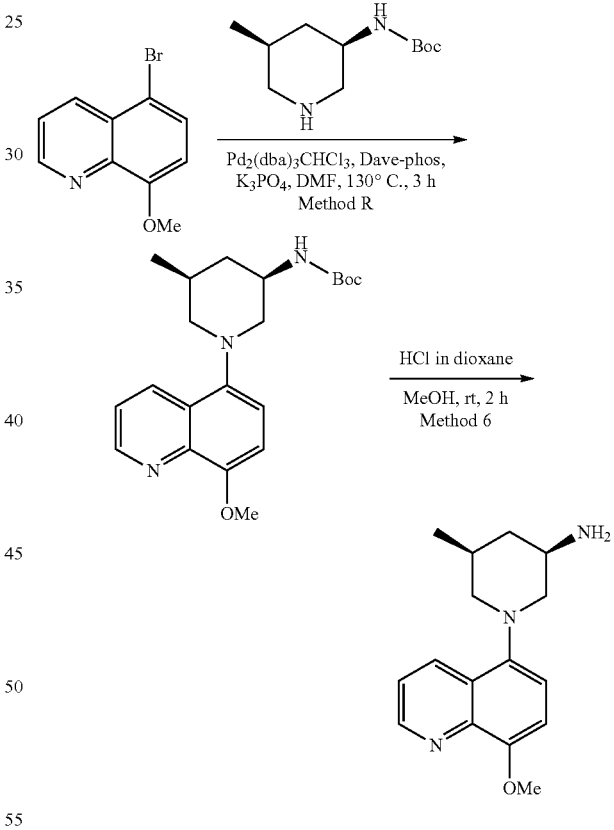

5-((3R,5S)-3-((R)-2-amino-3,3,3-trifluoropropanamido)-5-methylpiperidin-1-yl)quinoline-8-carboxamide and 5-((3R,5S)-3-((S)-2-amino-3,3,3-trifluoropropanamido)-5-methylpiperidin-1-yl)quinoline-8-carboxamide: 5-((3R,5S)-3-(2-amino-3,3,3-trifluoropropanamido)-5-methylpiperidin-1-yl)quinoline-8-carboxamide was prepared from 5-((3R,5S)-3-amino-5-methylpiperidin-1-yl)quinoline-8-carboxamide and 2-amino-3,3,3-trifluoropropanoic acid using Method J. The two diastereoisomers were separated by prep-HPLC under the following conditions: column, XBridge Shield RP18 OBD Column, 19×150 mm 10 um;

(3R,5S)-1-(8-methoxyquinolin-5-yl)-5-methylpiperidin-3-amine: (3R,5S)-1-(8-methoxyquinolin-5-yl)-5-methylpiperidin-3-amine was prepared from 5-bromo-8-methoxyquinoline and tert-butyl (3R,5S)-5-methylpiperidin-3-ylcarbamate using Method R and 6. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), 20% to 50% gradient in 10 min; detector, UV 254 nm. (3R,5S)-1-(8-methoxyquinolin-5-yl)-5-methylpiperidin-3-amine was obtained as yellow solid (27 mg, 13% for 2 steps).

Compound 187: HPLC: 98.8% purity, RT=1.42 min. MS: m/z=272.2 [M+H]⁺. ¹H NMR (400 MHz, CD₃OD, ppm) δ 8.83-8.77 (m, 1H), 8.66-8.59 (m, 1H), 7.58 (dd, J=8.5, 4.3 Hz, 1H), 7.23 (d, J=8.3 Hz, 1H), 7.14 (d, J=8.3 Hz, 1H), 4.04 (s, 3H), 3.40-3.30 (m, 1H), 3.28-3.12 (m, 2H), 2.45 (t, J=10.5 Hz, 1H), 2.33 (t, J=11.0 Hz, 1H), 2.18-2.03 (m, 2H), 1.05-0.91 (m, 4H).

Example 54: Synthesis of Compound 188 ((2S)-2-hydroxy-N-[(3R,5S)-1-(8-methoxyquinolin-5-yl)-5-methylpiperidin-3-yl]-3-methylbutanamide)

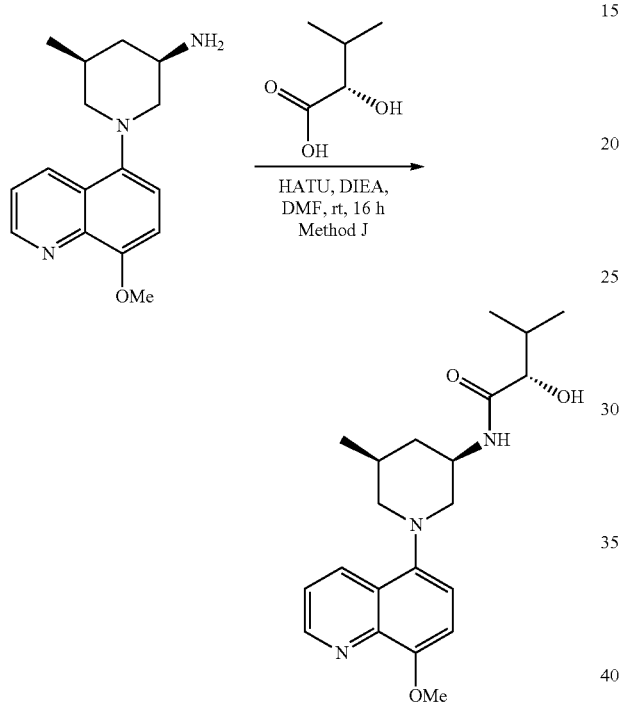

(2S)-2-hydroxy-N-[(3R,5S)-1-(8-methoxyquinolin-5-yl)-5-methylpiperidin-3-yl]-3-methylbutanamide: (2S)-2-hydroxy-N-[(3R,5S)-1-(8-methoxyquinolin-5-yl)-5-methylpiperidin-3-yl]-3-methylbutanamide was prepared from (S)-2-hydroxy-3-methylbutanoic acid and (3R,5S)-1-(8-methoxyquinolin-5-yl)-5-methylpiperidin-3-amine using Method J. The crude product was purified by prep-HPLC under the following conditions: column, XBridge Prep C18 OBD Column, 5 um, 19 mm×150 mm; mobile phase, acetonitrile in water (with 0.05% NH₃.H₂O), 30% to 60% gradient in 10 min; detector, UV 254 nm. (2S)-2-hydroxy-N-[(3R,5S)-1-(8-methoxyquinolin-5-yl)-5-methylpiperidin-3-yl]-3-methylbutanamide was obtained as yellow solid (15 mg, 25%).

Compound 188: HPLC: 93.1% purity, RT=1.24 min. MS: m/z=372.3 [M+H]⁺. ¹H NMR (400 MHz, DMSO-d₆, ppm) δ 8.83 (d, J=4.1 Hz, 1H), 8.46 (d, J=8.6 Hz, 1H), 7.62-7.53 (m, 2H), 7.15-7.05 (m, 2H), 5.30 (d, J=5.7 Hz, 1H), 4.06 (d, J=10.8 Hz, 1H), 3.91 (s, 3H), 3.64 (t, J=4.8 Hz, 1H), 3.16 (d, J=10.0 Hz, 1H), 3.12-3.03 (m, 1H), 2.49-2.41 (m, 1H), 2.27 (t, J=11.0 Hz, 1H), 2.07-1.98 (m, 1H), 1.97-1.87 (m, 2H), 1.18 (td, J=12.7, 12.7 Hz, 1H), 0.89 (dd, J=22.8, 6.7 Hz, 6H), 0.72 (d, J=6.7 Hz, 3H).

The following compounds were synthesized in an analogous manner:

Compound 189 (N-[(3R,5S)-1-(8-methoxyquinolin-5-yl)-5-methylpiperidin-3-yl]-3,3-dimethylbutanamide): From 3,3-dimethylbutanoic acid and (3R,5S)-1-(8-methoxyquinolin-5-yl)-5-methylpiperidin-3-amine. HPLC: 99.1% purity, RT=1.45 min. MS: m/z=370.2 [M+H]⁺. ¹H NMR (400 MHz, Chloroform-d, ppm) δ 8.94 (dd, J=4.2, 1.7 Hz, 1H), 8.57 (dd, J=8.5, 1.7 Hz, 1H), 7.50 (dd, J=8.5, 4.2 Hz, 1H), 7.06 (d, J=8.2 Hz, 1H), 6.95 (d, J=8.3 Hz, 1H), 5.22 (d, J=8.0 Hz, 1H), 4.35-4.33 (m, 1H), 4.07 (s, 3H), 3.55-3.46 (m, 1H), 3.21-3.13 (m, 1H), 2.42-2.28 (m, 2H), 2.22-2.07 (m, 2H), 2.04 (d, J=1.7 Hz, 2H), 1.08-0.92 (m, 13H).

Compound 193 (2-(dimethylamino)-N-[(3R,5S)-1-(8-methoxyquinolin-5-yl)-5-methylpiperidin-3-yl]acetamide): From 2-(dimethylamino)acetic acid and (3R,5S)-1-(8-methoxyquinolin-5-yl)-5-methylpiperidin-3-amine. HPLC: 99.2% purity, RT=1.74 min. MS: m/z=357.1 [M+H]⁺. ¹H NMR (400 MHz, CD₃OD, ppm) δ 8.80 (dd, J=4.3, 1.7 Hz, 1H), 8.67 (dd, J=8.5, 1.7 Hz, 1H), 7.59 (dd, J=8.5, 4.2 Hz, 1H), 7.21 (d, J=8.4 Hz, 1H), 7.13 (d, J=8.3 Hz, 1H), 4.28-4.22 (m, 1H), 4.04 (s, 3H), 3.39-3.32 (m, 1H), 3.22-3.13 (m, 1H), 2.99 (s, 2H), 2.51 (t, J=10.6 Hz, 1H), 2.39 (t, J=11.0 Hz, 1H), 2.30 (s, 6H), 2.19-2.04 (m, 2H), 1.15 (td, J=12.0, 12.0 Hz, 1H), 1.03 (d, J=6.4 Hz, 3H).

Example 55: Synthesis of Compound 190 ((3R,5S)—N-(2-methoxyethyl)-1-(8-methoxyquinolin-5-yl)-5-methylpiperidin-3-amine)

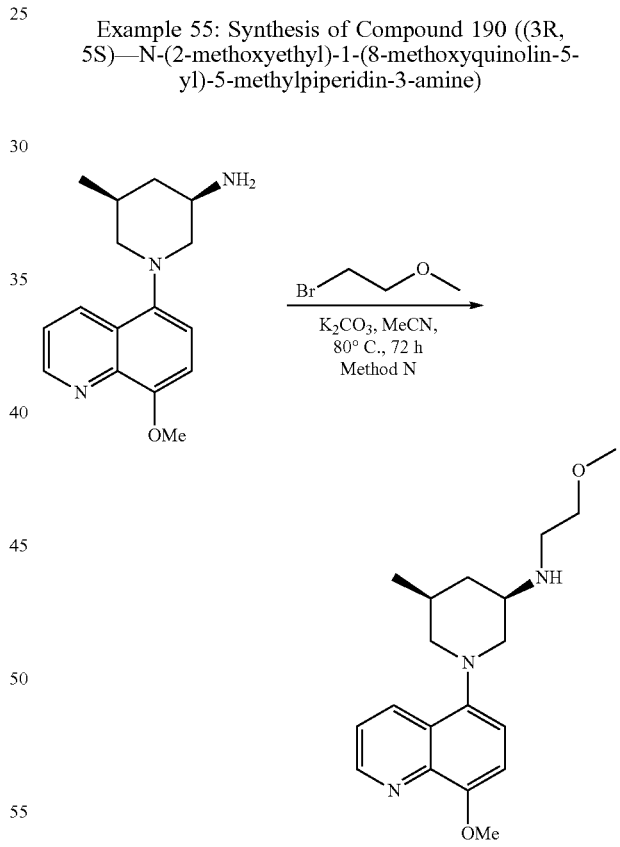

(3R,5S)—N-(2-methoxyethyl)-1-(8-methoxyquinolin-5-yl)-5-methylpiperidin-3-amine: (3R,5S)—N-(2-methoxyethyl)-1-(8-methoxyquinolin-5-yl)-5-methylpiperidin-3-amine was prepared from (S)-2-hydroxy-3-methylbutanoic acid and (3R,5S)-1-(8-methoxyquinolin-5-yl)-5-methylpiperidin-3-amine using Method J. The crude product was purified by prep-HPLC under the following conditions: column, XBridge Prep C18 OBD Column, 5 um, 19 mm×150 mm; mobile phase, acetonitrile in water (with 0.05% NH₃.H₂O), 35% to 65% gradient in 10 min; detector, UV 254 nm. (3R,5S)—N-(2-methoxyethyl)-1-(8-methoxy-quinolin-5-yl)-5-methylpiperidin-3-amine was obtained as yellow solid (24 mg, 35%).

Compound 190: HPLC: 99.2% purity, RT=1.89 min. MS: m/z=330.2 [M+H]$^+$. $^1$H NMR (400 MHz, CD$_3$OD, ppm) δ 8.80 (dd, J=4.2, 1.7 Hz, 1H), 8.61 (dd, J=8.5, 1.7 Hz, 1H), 7.58 (dd, J=8.5, 4.2 Hz, 1H), 7.22 (d, J=8.3 Hz, 1H), 7.13 (d, J=8.3 Hz, 1H), 4.04 (s, 3H), 3.52 (t, J=5.3 Hz, 2H), 3.44-3.30 (m, 4H), 3.20-2.95 (m, 2H), 2.94-2.77 (m, 2H), 2.48-2.28 (m, 2H), 2.23-2.00 (m, 2H), 1.04-0.87 (m, 4H).

Example 56: Synthesis of Compound 191 and compound 192 (5-((3R,5S)-3-((R)-2-amino-3,3,3-trifluoropropanamido)-5-methylpiperidin-1-yl)quinoline-8-carboxamide and 5-((3R,5S)-3-((S)-2-amino-3,3,3-trifluoropropanamido)-5-methylpiperidin-1-yl)quinoline-8-carboxamide)

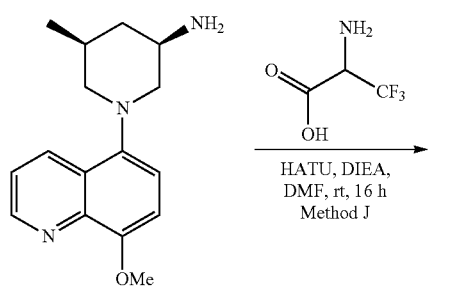

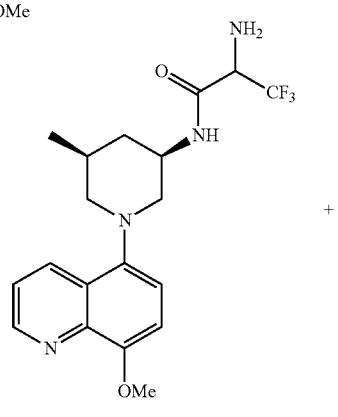

Isomer 1

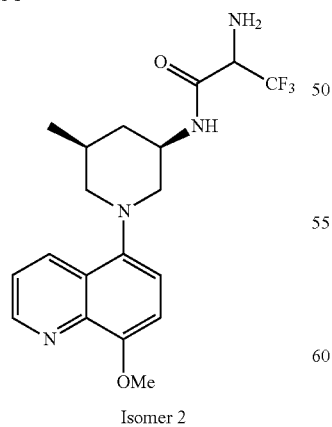

Isomer 2

5-((3R,5S)-3-((R)-2-amino-3,3,3-trifluoropropanamido)-5-methylpiperidin-1-yl)quinoline-8-carboxamide and 5-((3R,5S)-3-((S)-2-amino-3,3,3-trifluoropropanamido)-5-methylpiperidin-1-yl)quinoline-8-carboxamide: 2-amino-3,3,3-trifluoro-N-((3R,5S)-1-(8-methoxyquinolin-5-yl)-5-methylpiperidin-3-yl)propanamide was prepared from (3R,5S)-1-(8-methoxyquinolin-5-yl)-5-methylpiperidin-3-amine and 2-amino-3,3,3-trifluoropropanoic acid using Method J. The two diastereoisomers were separated by prep-HPLC under the following conditions: column, XBridge Shield RP18 OBD Column, 19×150 mm 10 um; mobile phase, acetonitrile in water (with 0.05% NH$_3$.H$_2$O), 35% to 65% gradient in 10 min; detector, UV 254 nm.

Isomer 1: (7 mg, 6%, light yellow solid) HPLC: 97.3% purity, RT=1.94 min. MS: m/z=397.1 [M+H]$^+$. $^1$H NMR (300 MHz, CD$_3$OD, ppm) δ 8.79 (dd, J=4.3, 1.7 Hz, 1H), 8.65 (dd, J=8.5, 1.7 Hz, 1H), 7.58 (dd, J=8.5, 4.2 Hz, 1H), 7.19 (d, J=8.4 Hz, 1H), 7.11 (d, J=8.3 Hz, 1H), 4.25-4.20 (m, 1H), 4.02 (s, 3H), 3.90 (q, J=7.7 Hz, 1H), 3.17 (d, J=11.3 Hz, 1H), 2.50-2.28 (m, 2H), 2.15-2.07 (m, 2H), 1.38-1.24 (m, 1H), 1.12 (td, J=12.7, 12.7 Hz, 1H), 1.01 (d, J=6.4 Hz, 3H).

Isomer 2: (7 mg, 6%, light yellow solid) HPLC: 95.7% purity, RT=2.21 min. MS: m/z=397.1 [M+H]$^+$. $^1$H NMR (300 MHz, CD$_3$OD, ppm) δ 8.79 (dd, J=4.3, 1.7 Hz, 1H), 8.65 (dd, J=8.5, 1.7 Hz, 1H), 7.58 (dd, J=8.5, 4.2 Hz, 1H), 7.19 (d, J=8.4 Hz, 1H), 7.11 (d, J=8.3 Hz, 1H), 4.22 (t, J=11.3 Hz, 1H), 4.02 (s, 3H), 3.90 (q, J=7.7 Hz, 1H), 3.17 (d, J=11.3 Hz, 1H), 2.50-2.28 (m, 2H), 2.15-2.07 (m, 2H), 1.38-1.24 (m, 1H), 1.12 (td, J=12.7, 12.7 Hz, 1H), 1.01 (d, J=6.4 Hz, 3H).

Example 57: Synthesis of Compound 194 ((2S)-2-hydroxy-3-methyl-N-[(3R,5S)-5-methyl-1-[8-(trifluoromethyl)quinolin-5-yl]piperidin-3-yl]butanamide)

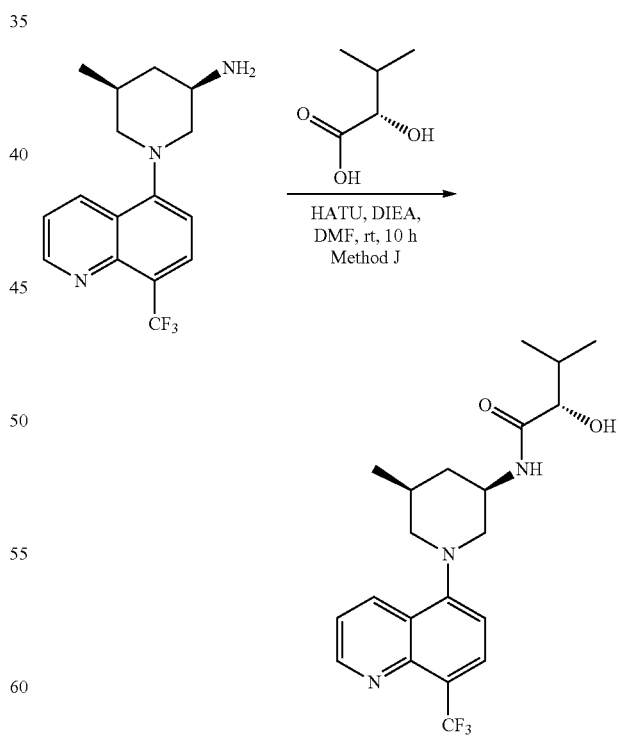

(2S)-2-hydroxy-3-methyl-N-[(3R,5S)-5-methyl-1-[8-(trifluoromethyl)quinolin-5-yl]piperidin-3-yl]butanamide: (2S)-2-hydroxy-3-methyl-N-[(3R,5S)-5-methyl-1-[8-(trifluoromethyl)quinolin-5-yl]piperidin-3-yl]butanamide was prepared from 2-(dimethylamino)acetic acid and (3R,5S)-1-(8-methoxyquinolin-5-yl)-5-methylpiperidin-3-amine using Method J. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 40% to 65% gradient in 10 min; detector, UV 254 nm. (2S)-2-hydroxy-3-methyl-N-[(3R,5S)-5-methyl-1-[8-(trifluoromethyl)quinolin-5-yl]piperidin-3-yl]butanamide was obtained as white solid (19 mg, 16%).

Compound 194: HPLC: 93.9% purity, RT=3.58 min. MS: m/z=410.2 [M+H]$^+$. $^1$H NMR (400 MHz, CD$_3$OD, ppm) δ 8.95 (dd, J=4.0, 1.7 Hz, 1H), 8.67 (dd, J=8.7, 1.7 Hz, 1H), 8.05 (d, J=8.0 Hz, 1H), 7.64 (dd, J=8.6, 4.3 Hz, 1H), 7.24 (d, J=8.0 Hz, 1H), 4.32-4.27 (m, 1H), 3.85 (d, J=3.7 Hz, 1H), 3.69-3.54 (m, 1H), 3.44-3.39 (m, 1H), 2.66-2.46 (m, 2H), 2.25-2.00 (m, 3H), 1.36-1.18 (m, 1H), 1.09-0.81 (m, 9H).

The following compounds were synthesized in an analogous manner:

Compound 195 (3,3-dimethyl-N-[(3R,5S)-5-methyl-1-[8-(trifluoromethyl)quinolin-5-yl]piperidin-3-yl]butanamide): From 2-(dimethylamino)acetic acid and (3R,5S)-1-(8-methoxyquinolin-5-yl)-5-methylpiperidin-3-amine. HPLC: 99.9% purity, RT=2.91 min. MS: m/z=408.3 [M+H]$^+$. $^1$H NMR (400 MHz, CD$_3$OD, ppm) δ 8.94 (dd, J=4.3, 1.5 Hz, 1H), 8.66 (dd, J=8.6, 1.6 Hz, 1H), 8.03 (d, J=8.1 Hz, 1H), 7.63 (dd, J=8.6, 4.2 Hz, 1H), 7.21 (d, J=8.1 Hz, 1H), 4.30-4.20 (m, 1H), 3.61 (dd, J=11.0, 4.2 Hz, 1H), 3.40-3.33 (m, 1H), 2.60-2.40 (m, 2H), 2.21-2.06 (m, 4H), 1.16 (td, J=12.2, 12.2 Hz, 1H), 1.05 (s, 3H), 1.03 (s, 9H).

Compound 199 (2-(dimethylamino)-N-[(3R,5S)-5-methyl-1-[8-(trifluoromethyl)quinolin-5-yl]piperidin-3-yl]acetamide): From 2-(dimethylamino)acetic acid and (3R,5S)-1-(8-methoxyquinolin-5-yl)-5-methylpiperidin-3-amine. HPLC: 96.2% purity, RT=2.68 min. MS: m/z=395.2 [M+H]$^+$. $^1$H NMR (400 MHz, CD$_3$OD, ppm) δ 8.98-8.91 (m, 1H), 8.71-8.63 (m, 1H), 8.04 (d, J=8.0 Hz, 1H), 7.63 (dd, J=8.6, 4.2 Hz, 1H), 7.24 (d, J=8.1 Hz, 1H), 4.32-4.26 (m, 1H), 3.66-3.57 (m, 1H), 3.40 (d, J=12.1 Hz, 1H), 3.00 (s, 2H), 2.65-2.45 (m, 2H), 2.31 (s, 6H), 2.25-2.07 (m, 2H), 1.22 (td, J=12.0, 12.0 Hz, 1H), 1.05 (d, J=6.4 Hz, 3H).

Compound 239 (N-[(3R,5S)-5-methyl-1-[8-(trifluoromethyl)quinolin-5-yl]piperidin-3-yl]-2-(morpholin-4-yl)acetamide): From 2-(morpholin-4-yl)acetic acid and (3R,5S)-5-methyl-1-[8-(trifluoromethyl)quinolin-5-yl]piperidin-3-amine. HPLC: 99.7% purity, RT=1.85 min. MS: m/z=437.2 [M+H]$^+$. $^1$H NMR (300 MHz, CD$_3$OD, ppm) δ 8.89 (dd, J=4.2, 1.7 Hz, 1H), 8.61 (dd, J=8.6, 1.8 Hz, 1H), 7.99 (d, J=8.1 Hz, 1H), 7.58 (dd, J=8.6, 4.2 Hz, 1H), 7.18 (d, J=8.0 Hz, 1H), 4.29-4.19 (m, 1H), 3.73-3.63 (m, 4H), 3.62-3.50 (m, 1H), 3.38-3.30 (m, 1H), 2.99 (s, 2H), 2.60-2.38 (m, 6H), 2.17-2.04 (m, 2H), 1.19 (td, J=12.3, 12.3 Hz, 1H), 1.00 (d, J=6.4 Hz, 3H).

Compound 240 (2-hydroxy-N-[(3R,5S)-5-methyl-1-[8-(trifluoromethyl)quinolin-5-yl]piperidin-3-yl]acetamide): From 2-hydroxyacetic acid and (3R,5S)-5-methyl-1-[8-(trifluoromethyl)quinolin-5-yl]piperidin-3-amine. HPLC: 94.5% purity, RT=3.23 min. MS: m/z=368.1 [M+H]$^+$. $^1$H NMR (400 MHz, CD$_3$OD, ppm) δ 8.92 (dd, J=4.3, 1.7 Hz, 1H), 8.65 (dd, J=8.6, 1.8 Hz, 1H), 8.02 (d, J=8.0 Hz, 1H), 7.61 (dd, J=8.6, 4.2 Hz, 1H), 7.21 (d, J=8.0 Hz, 1H), 4.34-4.26 (m, 1H), 3.98 (s, 2H), 3.60-3.56 (m, 1H), 3.42-3.33 (m, 1H), 2.60 (t, J=11.0 Hz, 1H), 2.48 (t, J=11.2 Hz, 1H), 2.22-2.07 (m, 2H), 1.25 (td, J=11.9, 11.9 Hz, 1H), 1.03 (d, J=6.4 Hz, 3H).

Compound 241 (1-hydroxy-N-[(3R,5S)-5-methyl-1-[8-(trifluoromethyl)quinolin-5-yl]piperidin-3-yl]cyclopropane-1-carboxamide): From 2-(morpholin-4-yl)acetic acid and (3R,5S)-5-methyl-1-[8-(trifluoromethyl)quinolin-5-yl]piperidin-3-amine. HPLC: 95.9% purity, RT=3.12 min. MS: m/z=394.1 [M+H]$^+$. $^1$H NMR (400 MHz, CD$_3$OD, ppm) δ 8.92 (dd, J=4.3, 1.7 Hz, 1H), 8.64 (dd, J=8.6, 1.8 Hz, 1H), 8.02 (d, J=8.0 Hz, 1H), 7.61 (dd, J=8.6, 4.2 Hz, 1H), 7.22 (d, J=8.1 Hz, 1H), 4.33-4.21 (m, 1H), 3.62-3.53 (m, 1H), 3.38 (apparent d, J=11.5 Hz, 1H), 2.63 (t, J=10.9 Hz, 1H), 2.50 (t, J=11.3 Hz, 1H), 2.18-2.11 (m, 2H), 1.30 (td, J=11.9, 11.9 Hz, 1H), 1.25-1.14 (m, 2H), 1.07-0.98 (m, 3H), 0.98-0.90 (m, 2H).

Compound 243 (N-[(3R,5S)-5-methyl-1-[8-(trifluoromethyl)quinolin-5-yl]piperidin-3-yl]-2-(4-methylpiperazin-1-yl)acetamide): From 2-(4-methylpiperazin-1-yl)acetic acid and (3R,5S)-5-methyl-1-[8-(trifluoromethyl)quinolin-5-yl]piperidin-3-amine. HPLC: 98.9% purity, RT=2.66 min. MS: m/z=450.3 [M+H]$^+$. $^1$H NMR (300 MHz, CD$_3$OD, ppm) δ 8.89 (dd, J=4.3, 1.7 Hz, 1H), 8.61 (dd, J=8.6, 1.8 Hz, 1H), 7.99 (d, J=8.1 Hz, 1H), 7.58 (dd, J=8.6, 4.2 Hz, 1H), 7.18 (d, J=8.0 Hz, 1H), 4.29-4.19 (m, 1H), 3.62-3.51 (m, 1H), 3.38-3.30 (m, 1H), 3.04-2.97 (m, 2H), 2.59-2.38 (m, 2H), 2.59-2.38 (m, 1OH), 2.26 (s, 3H), 2.20-2.02 (m, 2H), 1.17 (td, J=12.2, 12.2 Hz, 1H), 1.00 (d, J=6.4 Hz, 3H).

Compound 244 (N-[(3R,5S)-5-methyl-1-[8-(trifluoromethyl)quinolin-5-yl]piperidin-3-yl]-2-(1-methylpiperidin-4-yl)acetamide): From 2-(1-methylpiperidin-4-yl)acetic acid and (3R,5S)-5-methyl-1-[8-(trifluoromethyl)quinolin-5-yl]piperidin-3-amine. HPLC: 99.2% purity, RT=0.99 min. MS: m/z=225.0 [M+H]$^+$. $^1$H NMR (300 MHz, CD$_3$OD, ppm) δ 8.94-8.85 (m, 1H), 8.61 (dt, J=8.6, 2.0 Hz, 1H), 8.03-7.93 (m, 1H), 7.56-7.60 (m, 1H), 7.17 (dd, J=8.0, 2.6 Hz, 1H), 4.23-4.13 (m, 1H), 3.58 (apparent d, J=9.9 Hz, 1H), 3.34 (apparent d, J=11.2 Hz, 1H), 2.92-2.76 (m, 2H), 2.47-2.38 (m, 2H), 2.24 (s, 3H), 2.20-1.90 (m, 6H), 1.80-1.58 (m, 3H), 1.36-1.19 (m, 2H), 1.09 (td, J=12.2, 12.2 Hz, 1H), 0.99 (d, J=6.5, 3H).

Compound 245 (2-(1,4-dimethylpiperidin-4-yl)-N-[(3R,5S)-5-methyl-1-[8-(trifluoromethyl)quinolin-5-yl]piperidin-3-yl]acetamide): From 2-(1,4-dimethylpiperidin-4-yl)acetic acid and (3R,5S)-5-methyl-1-[8-(trifluoromethyl)quinolin-5-yl]piperidin-3-amine. HPLC: 95.9% purity, RT=4.37 min. MS: m/z=463.5 [M+H]$^+$. $^1$H NMR (300 MHz, CD$_3$OD, ppm) δ 8.83 (dd, J=4.2, 1.7 Hz, 1H), 8.55 (dd, J=8.6, 1.8 Hz, 1H), 7.92 (d, J=7.9 Hz, 1H), 7.52 (dd, J=8.6, 4.2 Hz, 1H), 7.11 (d, J=8.0 Hz, 1H), 4.17-4.08 (m, 1H), 3.57-3.46 (m, 1H), 3.28 (apparent d, J=11.6 Hz, 1H), 2.50-2.20 (m, 6H), 2.19 (s, 3H), 2.15-1.95 (m, 4H), 1.65-1.49 (m, 2H), 1.45-1.32 (m, 2H), 1.15-0.89 (m, 7H).

Compound 246 (2-[1-(2,2-difluoroethyl)piperidin-4-yl]-N-[(3R,5S)-5-methyl-1-[8-(trifluoromethyl)quinolin-5-yl]piperidin-3-yl]acetamide): From 2-(1,4-dimethylpiperidin-4-yl)acetic acid and (3R,5S)-5-methyl-1-[8-(trifluoromethyl)quinolin-5-yl]piperidin-3-amine. HPLC: 97.6% purity, RT=3.21 min. MS: m/z=499.3 [M+H]$^+$. $^1$H NMR (300 MHz, CD$_3$OD, ppm) δ 8.89 (dd, J=4.3, 1.7 Hz, 1H), 8.66-8.56 (m, 1H), 7.99 (d, J=8.1 Hz, 1H), 7.58 (dd, J=8.6, 4.2 Hz, 1H), 7.17 (d, J=8.1 Hz, 1H), 5.90 (tt, J=48.6, 4.5 Hz, 1H), 4.27-4.10 (m, 1H), 3.59 (d, J=11.3 Hz, 1H), 3.35 (d, J=11.9 Hz, 1H), 2.98-2.86 (m, 2H), 2.62-2.74 (m, 2H), 2.51-2.36 (m, 2H), 2.24-2.03 (m, 6H), 1.79-1.55 (m, 3H), 1.35-1.21 (m, 2H), 1.11 (td, J=12.4, 12.4 Hz, 1H), 1.03-0.96 (m, 3H).

Compound 247 (3,3-difluoro-N-[(3R,5S)-5-methyl-1-[8-(trifluoromethyl)quinolin-5-yl]piperidin-3-yl]cyclobutane-1-carboxamide): From 2-(1,4-dimethylpiperidin-4-yl)acetic acid and (3R,5S)-5-methyl-1-[8-(trifluoromethyl)quinolin-5-yl]piperidin-3-amine. HPLC: 99.9% purity, RT=1.55 min.

MS: m/z=428.2 [M+H]$^+$. $^1$H NMR (300 MHz, CD$_3$OD, ppm) δ 8.92 (dd, J=4.3, 1.7 Hz, 1H), 8.64 (dd, J=8.6, 1.8 Hz, 1H), 8.02 (d, J=8.1 Hz, 1H), 7.62 (dd, J=8.6, 4.2 Hz, 1H), 7.20 (d, J=8.0 Hz, 1H), 4.17-4.25 (m, 1H), 3.66-3.57 (m, 1H), 3.42-3.34 (m, 1H), 2.91-2.84 (m, 1H), 2.83-2.59 (m, 4H), 2.50-2.43 (m, 2H), 2.19-2.09 (m, 2H), 1.13 (td, J=12.3, 12.3 Hz, 1H), 1.02 (d, J=6.4 Hz, 3H).

Compound 248 (1-methyl-N-[(3R,5S)-5-methyl-1-[8-(trifluoromethyl)quinolin-5-yl]piperidin-3-yl]pyrrolidine-3-carboxamide): From 1-methylpyrrolidine-3-carboxylic acid and (3R,5S)-5-methyl-1-[8-(trifluoromethyl)quinolin-5-yl] piperidin-3-amine using. HPLC: 92.7% purity, RT=1.05 min. MS: m/z=421.3 [M+H]$^+$. $^1$H NMR (300 MHz, Chloroform-d, ppm) δ 9.01 (dd, J=4.2, 1.8 Hz, 1H), 8.56-8.45 (m, 1H), 7.92 (d, J=8.1 Hz, 1H), 7.49 (dd, J=8.6, 4.2 Hz, 1H), 7.03 (d, J=8.0 Hz, 1H), 6.83 (d, J=7.9 Hz, 1H), 4.29-4.16 (m, 1H), 3.64 (apparent d, J=10.9 Hz, 1H), 3.35-3.24 (m, 1H), 2.89-2.82 (m, 3H), 2.52-2.31 (m, 7H), 2.27-1.88 (m, 4H), 1.11-0.92 (m, 4H).

Compound 278 (2-hydroxy-N-[(3R,5S)-5-methyl-1-[8-(trifluoromethyl)quinolin-5-yl]piperidin-3-yl]propanamide): From 2-hydroxypropanoic acid and (3R,5S)-5-methyl-1-(8-(trifluoromethyl)quinolin-5-yl)piperidin-3-amine. HPLC: 96.9% purity, RT=1.26 min. MS: m/z=382.2 [M+H]$^+$. $^1$H NMR (400 MHz, Chloroform-d, ppm) δ 9.02 (dd, J=4.2, 1.7 Hz, 1H), 8.51 (dd, J=8.6, 1.8 Hz, 1H), 7.93 (d, J=8.0 Hz, 1H), 7.51 (dd, J=8.6, 4.2 Hz, 1H), 7.04 (d, J=8.0 Hz, 1H), 6.42 (d, J=8.1 Hz, 1H), 4.35-4.16 (m, 2H), 3.70-3.60 (m, 1H), 3.31 (d, J=11.6 Hz, 1H), 2.52-2.32 (m, 2H), 2.25-2.190 (m, 3H) 1.40 (d, J=6.8 Hz, 3H), 1.14-0.95 (m, 4H).

Compound 279 (N-[(3R,5S)-5-methyl-1-[8-(trifluoromethyl)quinolin-5-yl]piperidin-3-yl]-2-(1-methylpiperidin-3-yl)acetamide): From 2-hydroxypropanoic acid and (3R,5S)-5-methyl-1-(8-(trifluoromethyl)quinolin-5-yl)piperidin-3-amine. HPLC: 97.4% purity, RT=3.49 min. MS: m/z=449.2 [M+H]$^+$. $^1$H NMR (300 MHz, CD$_3$OD, ppm) δ 8.89 (dt, J=4.4, 1.3 Hz, 1H), 8.61 (dt, J=8.7, 2.1 Hz, 1H), 7.98 (d, J=8.2 Hz, 1H), 7.64-7.52 (m, 1H), 7.17 (dd, J=8.2, 2.4 Hz, 1H), 4.27-4.10 (m, 1H), 3.58 (d, J=11.2 Hz, 1H), 3.34 (d, J=11.5 Hz, 1H), 3.10-2.90 (m, 2H), 2.51-2.36 (m, 5H), 2.32-2.17 (m, 1H), 2.08 (d, J=9.7 Hz, 6H), 1.85-1.55 (m, 3H), 1.21-0.95 (m, 5H).

Compound 283 (N-[(3R,5S)-5-methyl-1-[8-(trifluoromethyl)quinolin-5-yl]piperidin-3-yl]-2-(1-methylpyrrolidin-3-yl)acetamide hydrochloride): From 2-(1-methylpyrrolidin-3-yl)acetic acid and (3R,5S)-5-methyl-1-(8-(trifluoromethyl)quinolin-5-yl)piperidin-3-amine. HPLC: 99.7% purity, RT=2.71 min. MS: m/z=435.2 [M+H]$^+$. $^1$H NMR (300 MHz, CD$_3$OD, ppm) δ 9.27 (d, J=8.6 Hz, 1H), 9.12 (d, J=5.2 Hz, 1H), 8.31 (d, J=8.2 Hz, 1H), 8.07 (dd, J=8.6, 5.2 Hz, 1H), 7.52-7.42 (m, 1H), 4.16 (d, J=12.3 Hz, 1H), 3.78-3.38 (m, 4H), 3.29-3.04 (m, 1H), 2.94-2.72 (m, 4H), 2.68-2.59 (m, 3H), 2.45-2.08 (m, 5H), 1.86-1.66 (m, 1H), 1.21 (td, J=12.3, 12.3 Hz, 1H), 1.02 (d, J=6.4 Hz, 3H).

Compound 287 (2-(3,3-difluoroazetidin-1-yl)-N-[(3R,5S)-5-methyl-1-[8-(trifluoromethyl)quinolin-5-yl]piperidin-3-yl]propanamide): From 2-(3,3-difluoroazetidin-1-yl)propanoic acid and (3R,5S)-5-methyl-1-(8-(trifluoromethyl)quinolin-5-yl)piperidin-3-amine. HPLC: 98.4% purity, RT=1.81 min. MS: m/z=457.3 [M+H]$^+$. $^1$H NMR (400 MHz, CD$_3$OD, ppm) δ 8.92 (dd, J=4.3, 1.7 Hz, 1H), 8.63 (dt, J=8.6, 1.6 Hz, 1H), 8.01 (d, J=8.1 Hz, 1H), 7.60 (dd, J=8.6, 4.2 Hz, 1H), 7.21 (dd, J=8.0, 1.9 Hz, 1H), 4.27-4.18 (m, 1H), 3.70-3.61 (m, 4H), 3.56-3.53 (m, 1H), 3.42-3.20 (m, 2H), 3.10-2.99 (m, 1H), 2.61-2.41 (m, 2H), 2.20-2.04 (m, 2H), 1.31-1.14 (m, 4H), 1.03 (d, J=6.5 Hz, 3H).

Compound 289 (2-(4-hydroxypiperidin-1-yl)-N-[(3R,5S)-5-methyl-1-[8-(trifluoromethyl)quinolin-5-yl]piperidin-3-yl]propanamide): From 2-(4-hydroxypiperidin-1-yl)propanoic acid and (3R,5S)-5-methyl-1-(8-(trifluoromethyl) quinolin-5-yl)piperidin-3-amine. HPLC: 99.8% purity, RT=1.75 min. MS: m/z=465.3 [M+H]$^+$. $^1$H NMR (300 MHz, CD$_3$OD, ppm) δ 8.90 (dd, J=4.3, 1.7 Hz, 1H), 8.62 (dt, J=8.6, 1.7 Hz, 1H), 7.99 (d, J=8.0 Hz, 1H), 7.59 (dd, J=8.6, 4.3 Hz, 1H), 7.19 (d, J=8.1 Hz, 1H), 4.24-4.16 (m, 1H), 3.58-3.55 (m, 2H), 3.37-3.32 (m, 1H), 3.07-2.96 (m, 1H), 2.80-2.71 (m, 2H), 2.55-2.42 (m, 2H), 2.34-2.06 (m, 4H), 1.89-1.77 (m, 2H), 1.55-1.50 (m, 2H), 1.23-1.07 (m, 4H), 1.01 (d, J=6.4 Hz, 3H).

Compound 472 (Propynoic acid [(3R,5S)-5-methyl-1-(8-trifluoromethyl-quinolin-5-yl)-piperidin-3-yl]-amide): From (3R,5S)-1-[8-(trifluoromethyl)quinolin-5-yl]-5-methylpiperidin-3-amine and propiolic acid. HPLC: >99% purity, RT=3.97 min. MS: m/z=362.1 [M+H]$^+$. $^1$H NMR (400 MHz, DMSO-d$_6$, ppm) δ 9.01 (dd, J=4.2, 1.8 Hz, 1H), 8.84 (d, J=7.4 Hz, 1H), 8.50 (dd, J=8.6, 1.8 Hz, 1H), 8.05 (d, J=8.0 Hz, 1H), 7.66 (dd, J=8.6, 4.2 Hz, 1H), 7.20 (d, J=8.1 Hz, 1H), 4.15 (d, J=0.8 Hz, 1H), 4.08 (s, 1H), 3.48 (d, J=11.0 Hz, 1H), 2.40 (t, J=11.3 Hz, 1H), 2.00 (d, J=14.0 Hz, 2H), 1.13 (d, J=12.1 Hz, 1H), 0.94 (d, J=6.5 Hz, 3H).

Compound 473 (But-3-ynoic acid [(3R,5S)-5-methyl-1-(8-trifluoromethyl-quinolin-5-yl)-piperidin-3-yl]-amide): From (3R,5S)-1-[8-(trifluoromethyl)quinolin-5-yl]-5-methylpiperidin-3-amine and 3-butynoic acid. HPLC: >99% purity, RT=4.01 min. MS: m/z=376.1 [M+H]$^+$. $^1$H NMR (400 MHz, DMSO-d$_6$, ppm) δ 9.01 (dd, J=4.2, 1.7 Hz, 1H), 8.52 (dd, J=8.6, 1.8 Hz, 1H), 8.04 (d, J=8.1 Hz, 1H), 7.97 (d, J=7.4 Hz, 1H), 7.66 (dd, J=8.6, 4.2 Hz, 1H), 7.20 (d, J=8.0 Hz, 1H), 5.74 (t, J=6.6 Hz, 1H), 5.29 (d, J=6.6 Hz, 2H), 4.08 (s, 1H), 3.54 (d, J=11.2 Hz, 1H), 3.39-3.32 (m, 1H), 2.48-2.36 (m, 2H), 2.15-1.96 (m, 3H), 1.12 (q, J=12.0 Hz, 2H), 0.95 (d, J=6.5 Hz, 3H).

Compound 474 (2-Methanesulfonylamino-N-[(3R,5S)-5-methyl-1-(8-trifluoromethyl-quinolin-5-yl)-piperidin-3-yl]-acetamide): From (3R,5S)-1-[8-(trifluoromethyl)quinolin-5-yl]-5-methylpiperidin-3-amine and N-(methylsulfonyl)glycine. HPLC: >99% purity, RT=3.52 min. MS: m/z=445.1 [M+H]$^+$. $^1$H NMR (400 MHz, DMSO-d$_6$, ppm) δ 9.01 (dd, J=4.2, 1.7 Hz, 1H), 8.53 (dd, J=8.6, 1.8 Hz, 1H), 8.02 (dd, J=24.1, 7.8 Hz, 2H), 7.66 (dd, J=8.6, 4.2 Hz, 1H), 7.30 (s, 1H), 7.20 (d, J=8.0 Hz, 1H), 4.07 (d, J=6.6 Hz, 1H), 3.61 (d, J=4.1 Hz, 2H), 3.50 (d, J=10.2 Hz, 1H), 3.34 (d, J=11.0 Hz, 1H), 2.92 (s, 3H), 2.46-2.37 (m, 1H), 2.04 (dd, J=29.3, 9.1 Hz, 2H), 1.14 (q, J=12.0 Hz, 1H), 0.94 (t, J=7.1 Hz, 3H).

Compound 475 (1-Trifluoromethyl-cyclopropanecarboxylic acid [(3R,5S)-5-methyl-1-(8-trifluoromethyl-quinolin-5-yl)-piperidin-3-yl]-amide): From (3R,5S)-1-[8-(trifluoromethyl)quinolin-5-yl]-5-methylpiperidin-3-amine and 1-(trifluoromethyl)cyclopropane-1-carboxylic acid. HPLC: >99% purity, RT=4.83 min. MS: m/z=446.2 [M+H]$^+$. $^1$H NMR (400 MHz, DMSO-d$_6$, ppm) δ 9.01 (dd, J=4.2, 1.7 Hz, 1H), 8.51 (dd, J=8.6, 1.8 Hz, 1H), 8.05 (d, J=8.1 Hz, 1H), 7.67 (dd, J=8.5, 4.0 Hz, 2H), 7.20 (d, J=8.1 Hz, 1H), 4.08 (s, 1H), 3.46-3.33 (m, 2H), 2.56 (d, J=10.9 Hz, 1H), 2.39 (t, J=11.4 Hz, 1H), 2.15-1.89 (m, 2H), 1.36-1.15 (m, 5H), 0.94 (d, J=6.6 Hz, 3H).

Compound 515 (2-Cyclopropyl-2-hydroxy-N-[(3R,5S)-5-methyl-1-(8-trifluoromethyl-quinolin-5-yl)-piperidin-3-yl]-acetamide): From Cyclopropyl-hydroxyl-acetic acid and (3R,5S)-5-Methyl-1-(8-trifluoromethyl-quinolin-5-yl)-piperidin-3-ylamine hydrochloride. $^1$H NMR (400 MHz, DMSO-d$_6$) δ 9.02 (dt, J=4.1, 1.4 Hz, 1H), 8.54 (dt, J=8.6, 2.1 Hz, 1H), 8.07 (d, J=8.1 Hz, 1H), 7.76-7.62 (m, 1H), 7.60 (d, J=7.7 Hz, 1H), 7.21 (dd, J=8.1, 4.3 Hz, 1H), 5.31 (dd, J=12.5, 5.4 Hz, 2H), 3.57-3.38 (m, 2H), 2.59 (t, J=10.9 Hz, 1H), 2.43 (t, J=11.3 Hz, 1H), 1.98 (d, J=12.6 Hz, 2H), 1.24 (qd, J=12.1, 2.8 Hz, 1H), 1.12-1.01 (m, 1H), 0.96 (dt, J=6.5, 1.5 Hz, 3H), 0.43-0.21 (m, 4H). MS: m/z=408 [M+H]+.

Compound 516 (2-(4-Methyl-piperazin-1-yl)-N-[(3R,5S)-5-methyl-1-(8-trifluoromethyl-quinolin-5-yl)-piperidin-3-yl]-propionamide: From 2-(4-Methyl-piperazin-1-yl)-propionic acid and (3R,5S)-5-Methyl-1-(8-trifluoromethyl-quinolin-5-yl)-piperidin-3-ylamine hydrochloride. $^1$H NMR (400 MHz, DMSO-d$_6$) δ 9.02 (dt, J=4.1, 1.5 Hz, 1H), 8.61-8.44 (m, 1H), 8.06 (dt, J=8.2, 2.7 Hz, 1H), 7.68 (dtd, J=9.2, 5.1, 4.6, 1.9 Hz, 2H), 7.20 (dd, J=12.5, 8.0 Hz, 1H), 4.20 (s, 1H), 3.55-3.39 (m, 1H), 3.34 (d, J=8.1 Hz, 3H), 3.33-3.25 (m, 2H), 3.08-2.90 (m, 1H), 2.44 (dt, J=11.1, 5.5 Hz, 7H), 2.14 (d, J=12.0 Hz, 3H), 2.12 (m, 2H), 1.99 (d, J=12.5 Hz, 2H), 1.18 (qd, J=12.0, 2.5 Hz, 1H), 1.08 (dd, J=6.9, 1.4 Hz, 3H), 0.95 (dd, J=9.9, 6.4 Hz, 3H). MS: m/z=464 [M+H]+.

Compound 517 (N-[(3R,5S)-5-Methyl-1-(8-trifluoromethyl-quinolin-5-yl)-piperidin-3-yl]-acetamide): From Acetic acid and (3R,5S)-5-Methyl-1-(8-trifluoromethyl-quinolin-5-yl)-piperidin-3-ylamine hydrochloride. $^1$H NMR (400 MHz, DMSO-d$_6$) δ 9.01 (dd, J=4.2, 1.7 Hz, 1H), 8.53 (dd, J=8.6, 1.8 Hz, 1H), 8.05 (d, J=8.2 Hz, 1H), 7.90 (d, J=7.4 Hz, 1H), 7.67 (dd, J=8.6, 4.2 Hz, 1H), 7.20 (d, J=8.1 Hz, 1H), 3.52 (d, J=9.2 Hz, 1H), 2.43 (q, J=11.4 Hz, 2H), 2.03 (dd, J=26.1, 12.3 Hz, 2H), 1.82 (s, 3H), 1.08 (q, J=12.1 Hz, 1H), 0.96 (d, J=6.5 Hz, 3H). MS: m/z=352 [M+H]+.

Compound 519 (2-Cyclopropyl-2-dimethylamino-N-[(3R,5S)-5-methyl-1-(8-trifluoromethyl-quinolin-5-yl)-piperidin-3-yl]-acetamide): From Cyclopropyl-dimethylamine-acetic acid hydrochloride and (3R,5S)-5-Methyl-1-(8-trifluoromethyl-quinolin-5-yl)-piperidin-3-ylamine hydrochloride. $^1$H NMR (400 MHz, Methanol-d$_4$) δ 8.95 (dd, J=4.2, 1.7 Hz, 1H), 8.67 (dt, J=8.6, 1.8 Hz, 1H), 8.04 (d, J=8.2 Hz, 1H), 7.63 (dd, J=8.6, 4.2 Hz, 1H), 7.23 (dd, J=8.0, 1.8 Hz, 1H), 4.28 (dddd, J=14.9, 12.0, 5.8, 2.4 Hz, 1H), 3.60 (m, 1H), 3.40 (d, J=11.6 Hz, 1H), 2.53 (dtd, J=25.3, 11.2, 2.9 Hz, 2H), 2.35 (d, J=7.9 Hz, 6H), 2.23-2.04 (m, 2H), 1.86 (dd, J=9.5, 3.3 Hz, 1H), 1.20 (q, J=12.1 Hz, 1H), 1.09-0.89 (m, 4H), 0.82-0.64 (m, 1H), 0.58-0.43 (m, 1H), 0.35 (tdd, J=12.5, 9.3, 4.8 Hz, 2H). MS: m/z=435 [M+H]+.

Compound 526 ((S)-2-Dimethylamino-N-[(3R,5S)-5-methyl-1-(8-trifluoromethyl-quinolin-5-yl)-piperidin-3-yl]-propionamide): From (S)-2-Dimethylamino-propionic acid and (3R,5S)-5-Methyl-1-(8-trifluoromethyl-quinolin-5-yl)-piperidin-3-ylamine hydrochloride. $^1$H NMR (400 MHz, DMSO-d$_6$) 9.02 (dd, J=4.2, 1.7 Hz, 1H), 8.54 (dd, J=8.6, 1.8 Hz, 1H), 8.06 (d, J=8.1 Hz, 1H), 7.79-7.64 (m, 2H), 7.21 (d, J=8.0 Hz, 1H), 4.20-4.15 (m, 2H), 3.47 (d, J=9.3 Hz, 1H), 2.92 (q, J=6.8 Hz, 1H), 2.42 (t, J=11.4 Hz, 1H), 2.15 (s, 6H), 2.13-1.88 (m, 2H), 1.20 (q, J=12.0 Hz, 1H), 1.07 (d, J=6.9 Hz, 3H), 0.95 (d, J=6.6 Hz, 3H). MS: m/z=409 [M+H]+.

Compound 550 (2-(1-Hydroxy-cyclopropyl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine hydrochloride and 2-(1-hydroxycyclopropyl) acetic acid. $^1$H NMR (400 MHz, DMSO-d$_6$) δ 9.02 (dd, J=4.2, 1.7 Hz, 1H), 8.54 (dd, J=8.6, 1.8 Hz, 1H), 8.06 (d, J=8.1 Hz, 1H), 7.74 (d, J=7.4 Hz, 1H), 7.67 (dd, J=8.6, 4.1 Hz, 1H), 7.21 (d, J=8.1 Hz, 1H), 4.06 (s, 1H), 3.54 (d, J=9.1 Hz, 1H), 2.50-2.38 (m, 2H), 2.34 (s, 2H), 2.14-1.93 (m, 2H), 1.12 (q, J=12.0 Hz, 1H), 0.96 (dd, J=6.5, 3.6 Hz, 3H), 0.63-0.53 (m, 2H), 0.53-0.38 (m, 2H). MS: m/z=408 [M+H]+.

Compound 551 (2-(8-Methyl-8-aza-bicyclo[3.2.1]oct-3-yl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine hydrochloride and 2-(8-methyl-8-azabicyclo[3.2.1]octan-3-yl)acetic acid hydrochloride. $^1$H NMR (400 MHz, DMSO-d$_6$) δ 9.01 (dd, J=4.2, 1.7 Hz, 1H), 8.53 (dd, J=8.6, 1.8 Hz, 1H), 8.06 (d, J=8.1 Hz, 1H), 7.92 (d, J=7.3 Hz, 1H), 7.67 (dd, J=8.6, 4.2 Hz, 1H), 7.20 (d, J=8.0 Hz, 1H), 4.15 (m, 1H) 3.51 (d, J=9.9 Hz, 2H), 3.34 (d, J=11.6 Hz, 2H), 3.14 (s, 2H), 2.43 (dt, J=11.3, 5.9 Hz, 1H), 2.23 (d, J=5.7 Hz, 3H), 2.15 (dd, J=15.8, 7.9 Hz, 2H), 2.02 (dd, J=16.8, 10.7 Hz, 4H), 1.68 (d, J=8.2 Hz, 2H), 1.22 (dd, J=13.8, 7.4 Hz, 2H), 1.10 (q, J=12.0 Hz, 1H), 0.95 (d, J=6.5 Hz, 3H). MS: m/z=475 [M+H]+.

Compound 572 (2-(1-Isopropyl-piperidin-4-yl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine hydrochloride and 2-Methyl-2-piperidin-1-yl-propionic acid. HPLC: >99% purity, RT=3.27 min. MS: m/z=463.6 [M+H]+. $^1$H NMR (400 MHz, DMSO-d$_6$, ppm) δ 9.02 (dd, J=4.1, 1.7 Hz, 1H), 8.53 (dd, J=8.6, 1.8 Hz, 1H), 8.06 (d, J=8.1 Hz, 1H), 7.68 (dd, J=8.6, 4.2 Hz, 1H), 7.49 (d, J=8.2 Hz, 1H), 7.21 (d, J=8.0 Hz, 1H), 4.11-3.97 (m, 1H), 3.45 (dd, J=11.6, 3.9 Hz, 1H), 2.56 (t, J=10.9 Hz, 1H), 2.45 (t, J=11.4 Hz, 1H), 2.33 (s, 4H), 2.09 (s, 1H), 1.97 (d, J=12.4 Hz, 1H), 1.54 (s, 4H), 1.41 (d, J=6.9 Hz, 2H), 1.22 (q, J=12.0 Hz, 1H), 1.06 (d, J=9.0 Hz, 6H), 0.96 (d, J=6.6 Hz, 3H).

Compound 573 (2-(3,3-Dimethyl-pyrrolidin-1-yl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine and (3,3-Dimethyl-pyrrolidin-1-yl)-acetic acid. HPLC: >99% purity, RT=3.32 min. MS: m/z=449.5 [M+H]+. $^1$H NMR (400 MHz, DMSO-d6, ppm) δ 9.02 (dd, J=4.2, 1.7 Hz, 1H), 8.53 (dd, J=8.6, 1.8 Hz, 1H), 8.05 (d, J=8.1 Hz, 1H), 7.67 (dd, J=8.6, 4.2 Hz, 1H), 7.57 (d, J=8.0 Hz, 1H), 7.21 (d, J=8.0 Hz, 1H), 4.13-4.06 (m, 1H), 3.50-3.43 (m, 1H), 3.02 (d, J=3.0 Hz, 2H), 2.63 (m, 2H), 2.56 (t, J=10.9 Hz, 1H), 2.43 (t, J=11.4 Hz, 1H), 2.38-2.29 (m, 2H), 2.08 (td, J=10.4, 9.1, 5.4 Hz, 1H), 1.99 (dd, J=12.4, 3.9 Hz, 1H), 1.53 (t, J=7.1 Hz, 2H), 1.21 (q, J=12.0 Hz, 1H), 1.05 (d, J=1.3 Hz, 6H), 0.96 (d, J=6.6 Hz, 3H).

Compound 574 (1-Cyclopropyl-piperidine-4-carboxylic acid [(3R,5S)-5-methyl-1-(8-trifluoromethyl-quinolin-5-yl)-piperidin-3-yl]-amide): From (3R,5S)-5-Methyl-1-(8-trifluoromethyl-quinolin-5-yl)-piperidin-3-ylamine hydrochloride and 1-Cyclopropyl-piperidine-4-carboxylic acid. HPLC: 98% purity, RT=3.12 min. MS: m/z=461.5 [M+H]+. $^1$H NMR (400 MHz, DMSO-d$_6$, ppm) δ 9.01 (dd, J=4.2, 1.7 Hz, 1H), 8.53 (dd, J=8.7, 1.8 Hz, 1H), 8.05 (d, J=8.1 Hz, 1H), 7.76 (d, J=7.4 Hz, 1H), 7.67 (dd, J=8.6, 4.2 Hz, 1H), 7.20 (d, J=8.1 Hz, 1H), 4.02 (s, 0H), 3.48 (d, J=10.9 Hz, 1H), 3.36 (d, J=5.3 Hz, 0H), 2.92 (td, J=7.9, 3.9 Hz, 1H), 2.43 (q, J=11.2 Hz, 1H), 2.08 (ddt, J=11.5, 8.2, 3.7 Hz, 1H), 1.98 (d, J=13.0 Hz, 0H), 1.67-1.40 (m, 2H), 1.10 (q, J=12.1 Hz, 1H), 0.95 (d, J=6.6 Hz, 2H), 0.38 (dt, J=5.2, 2.6 Hz, 1H), 0.27 (q, J=3.1, 2.5 Hz, 1H).

Compound 575 (N,N-Diethyl-N'-[(3R,5S)-5-methyl-1-(8-trifluoromethyl-quinolin-5-yl)-piperidin-3-yl]-succinamide): From (3R,5S)-5-Methyl-1-(8-trifluoromethyl-quinolin-5-yl)-piperidin-3-ylamine hydrochloride and N,N-Diethyl-succinamic acid. HPLC: >99% purity, RT=3.98 min. MS: m/z=465.5 [M+H]+. $^1$H NMR (400 MHz, DMSO-d$_6$, ppm) δ 9.01 (dd, J=4.2, 1.7 Hz, 1H), 8.53 (dd, J=8.6, 1.8 Hz, 1H), 8.06 (d, J=8.1 Hz, 1H), 7.87 (d, J=7.4 Hz, 1H), 7.67

(dd, J=8.6, 4.2 Hz, 1H), 7.20 (d, J=8.0 Hz, 1H), 4.03 (s, 1H), 3.51 (d, J=10.2 Hz, 1H), 3.30 (d, J=6.8 Hz, 2H), 3.28-3.18 (m, 2H), 2.49 (d, J=6.9 Hz, 2H), 2.43 (td, J=11.1, 4.1 Hz, 2H), 2.34 (q, J=7.6, 7.1 Hz, 2H), 2.06 (s, 1H), 1.99 (d, J=13.1 Hz, 1H), 1.15-1.03 (m, 4H), 0.97 (t, J=6.8 Hz, 6H).

Example 58: Synthesis of Compound 196 ((3R,5S)—N-(2-methoxyethyl)-5-methyl-1-[8-(trifluoromethyl)quinolin-5-yl]piperidin-3-amine)

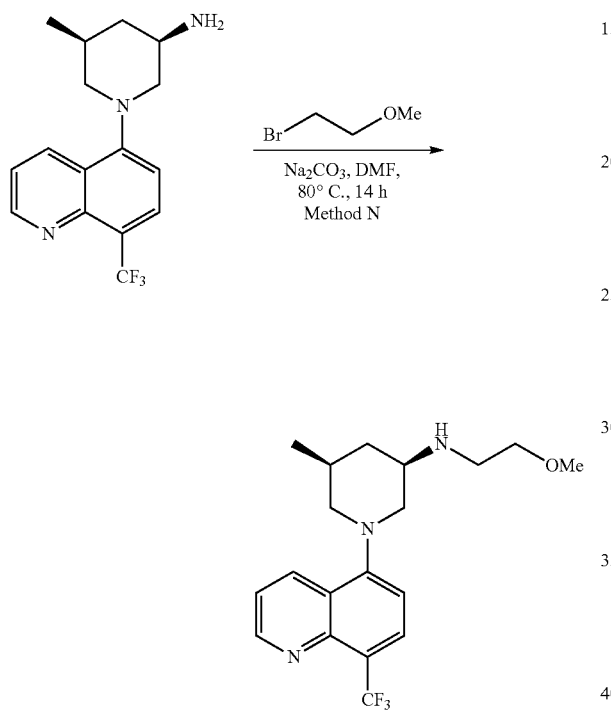

(3R,5S)—N-(2-methoxyethyl)-5-methyl-1-[8-(trifluoromethyl)quinolin-5-yl]piperidin-3-amine: (3R,5S)—N-(2-methoxyethyl)-5-methyl-1-[8-(trifluoromethyl)quinolin-5-yl]piperidin-3-amine was prepared from 2-(dimethylamino) acetic acid and (3R,5S)-1-(8-methoxyquinolin-5-yl)-5-methylpiperidin-3-amine using Method N. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), 30% to 60% gradient in 10 min; detector, UV 254 nm. (3R,5S)—N-(2-methoxyethyl)-5-methyl-1-[8-(trifluoromethyl)quinolin-5-yl]piperidin-3-amine was obtained as yellow oil (14 mg, 15%).

Compound 196: HPLC: 94.9% purity, RT=2.77 min. MS: m/z=368.2 [M+H]$^+$. $^1$H NMR (400 MHz, DMSO-d$_6$, ppm) δ 9.04-8.97 (m, 1H), 8.48 (dd, J=8.7, 1.7 Hz, 1H), 8.05 (d, J=8.0 Hz, 1H), 7.66 (dd, J=8.6, 4.2 Hz, 1H), 7.19 (d, J=8.1 Hz, 1H), 3.57-3.49 (m, 1H), 3.42-3.28 (m, 2H), 3.24 (s, 3H), 2.93 (t, J=10.8 Hz, 1H), 2.82-2.66 (m, 2H), 2.41-2.33 (m, 2H), 2.12-1.94 (m, 2H), 1.59 (br s, 2H), 0.97-0.78 (m, 4H).

Example 59: Synthesis of Compound 197 and compound 198 ((R)-2-amino-3,3,3-trifluoro-N-((3R,5S)-5-methyl-1-(8-(trifluoromethyl)quinolin-5-yl)piperidin-3-yl)propanamide and(S)-2-amino-3,3,3-trifluoro-N-((3R,5S)-5-methyl-1-(8-(trifluoromethyl)quinolin-5-yl)piperidin-3-yl)propanamide)

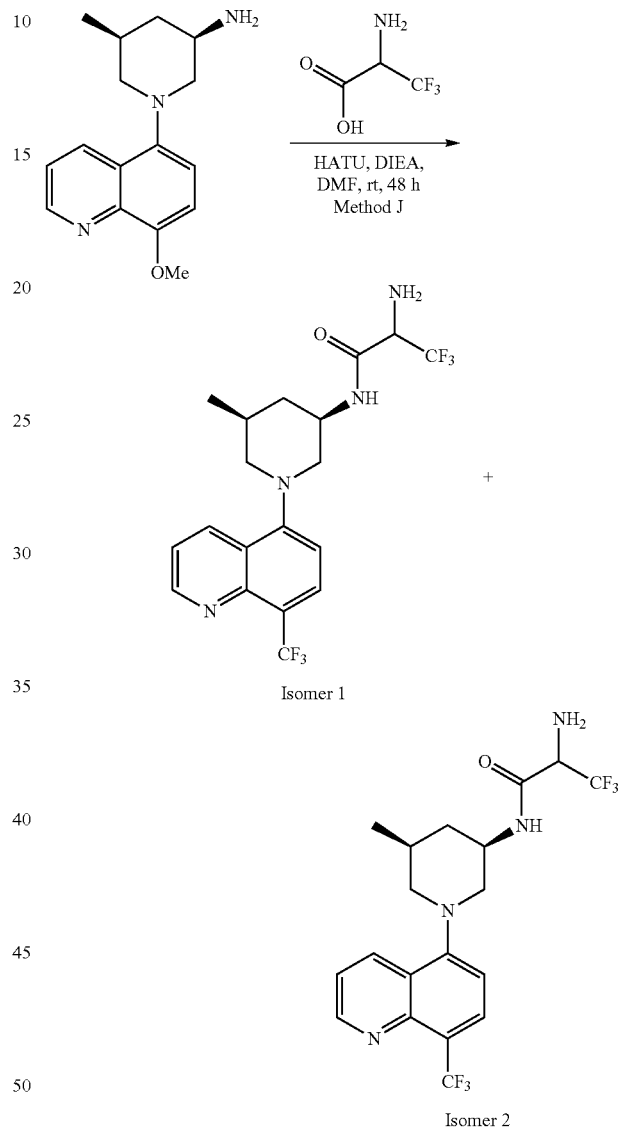

(R)-2-amino-3,3,3-trifluoro-N-((3R,5S)-5-methyl-1-(8-(trifluoromethyl)quinolin-5-yl)piperidin-3-yl)propanamide and (S)-2-amino-3,3,3-trifluoro-N-((3R,5S)-5-methyl-1-(8-(trifluoromethyl)quinolin-5-yl)piperidin-3-yl)propanamide: 2-amino-3,3,3-trifluoro-N-[(3R,5S)-5-methyl-1-[8-(trifluoromethyl)quinolin-5-yl]piperidin-3-yl]propanamide was prepared from (3R,5S)-5-methyl-1-(8-(trifluoromethyl)quinolin-5-yl)piperidin-3-amine and 2-amino-3,3,3-trifluoropropanoic acid using Method J. The two diastereoisomers were separated by prep-HPLC under the following conditions: column, XBridge Prep C18 OBD Column, 19×150 mm 10 um; mobile phase, acetonitrile in water (with 0.05% NH$_3$.H$_2$O), 30% to 60% gradient in 10 min; detector, UV 254 nm.

Isomer 1: (14 mg, 21%, white solid) HPLC: 93.2% purity, RT=2.62 min. MS: m/z=434.9 [M+H]+. 1H NMR (300 MHz, DMSO-d6, ppm) δ 9.02 (dd, J=4.2, 1.7 Hz, 1H), 8.53 (dd, J=8.6, 1.8 Hz, 1H), 8.37 (d, J=7.3 Hz, 1H), 8.06 (d, J=8.1 Hz, 1H), 7.68 (dd, J=8.6, 4.2 Hz, 1H), 7.20 (d, J=8.0 Hz, 1H), 4.09-4.04 (m, 1H), 3.93-3.84 (m, 1H), 3.49 (apparent d, J=11.6 Hz, 1H), 2.51-2.39 (m, 1H), 2.31 (apparent d, J=8.9 Hz, 2H), 2.10-1.90 (m, 2H), 1.15 (td, J=12.0, 12.0 Hz, 1H), 0.96 (d, J=6.5 Hz, 3H).

Isomer 2: (9 mg, 13%, white solid) HPLC: 90.5% purity, RT=2.71 min. MS: m/z=434.9 [M+H]+. 1H NMR (300 MHz, CD3OD, ppm) δ 9.02 (dd, J=4.2, 1.7 Hz, 1H), 8.53 (dd, J=8.6, 1.8 Hz, 1H), 8.37 (d, J=7.3 Hz, 1H), 8.06 (d, J=8.1 Hz, 1H), 7.68 (dd, J=8.6, 4.2 Hz, 1H), 7.20 (d, J=8.0 Hz, 1H), 4.09-4.04 (m, 1H), 3.93-3.84 (m, 1H), 3.49 (apparent d, J=11.6 Hz, 1H), 2.51-2.39 (m, 1H), 2.31 (apparent d, J=8.9 Hz, 2H), 2.10-1.90 (m, 2H), 1.15 (td, J=12.0, 12.0 Hz, 1H), 0.96 (d, J=6.5 Hz, 3H).

Example 60: Synthesis of Compound 200 (5-[(3R,5S)-3-amino-5-methylpiperidin-1-yl]quinolin-8-ol hydrochloride)

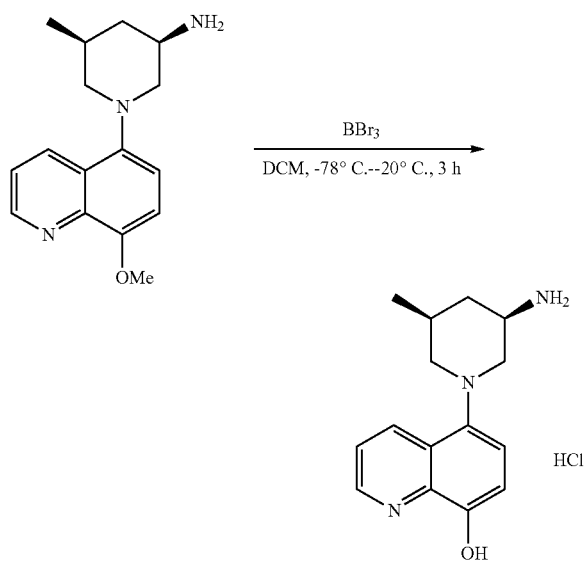

5-[(3R,5S)-3-amino-5-methylpiperidin-1-yl]quinolin-8-ol: At −78° C., to a solution of (3R,5S)-1-(8-methoxyquinolin-5-yl)-5-methylpiperidin-3-amine (95 mg, 0.35 mmol) in DCM (10 mL) was added a solution of BBr3 (553 mg, 2.19 mmol) in DCM (5 mL) dropwise. The resulting solution was stirred for 1 h at −78° C., warmed up to −20° C. and stirred for 2 h at −20° C. When the reaction was done, it was quenched by the addition of water (10 mL). The resulting mixture was extracted with DCM (20 mL×3). The organic phases were combined, washed with brine and dried over Na2SO4. The solvent was removed under reduced pressure and the residue was purified by prep-HPLC under the following conditions: column, Xbridge Shield RP18 OBD, 5 um, 19 mm×150 mm; mobile phase, acetonitrile in water (with 0.05% HCl), 35% to 65% gradient in 10 min; detector, UV 254 nm. 5-[(3R,5S)-3-amino-5-methylpiperidin-1-yl]quinolin-8-ol hydrochloride was obtained as brown solid (24 mg, 21%).

Compound 200: HPLC: 96.6% purity, RT=1.05 min. MS: m/z=258.1 [M+H]+. 1H NMR (400 MHz, CD3OD, ppm) δ 9.38 (dd, J=8.5, 1.5 Hz, 1H), 9.09 (dd, J=5.2, 1.3 Hz, 1H), 8.13 (dd, J=8.6, 5.4 Hz, 1H), 7.57 (d, J=8.4 Hz, 1H), 7.47 (d, J=8.5 Hz, 1H), 3.73-3.67 (m, 1H), 3.53 (dd, J=10.8, 3.9 Hz, 1H), 3.24 (dd, J=11.6, 3.6 Hz, 1H), 2.85 (t, J=10.7 Hz, 1H), 2.51 (t, J=11.2 Hz, 1H), 2.35-2.17 (m, 2H), 1.27 (td, J=11.9, 11.9 Hz, 1H), 1.08 (d, J=6.5 Hz, 3H).

Example 61: Synthesis of Compound 204 ((2S)—N-[(3R,5S)-1-[8-(difluoromethyl)quinolin-5-yl]-5-methylpiperidin-3-yl]-2-hydroxy-3-methylbutanamide)

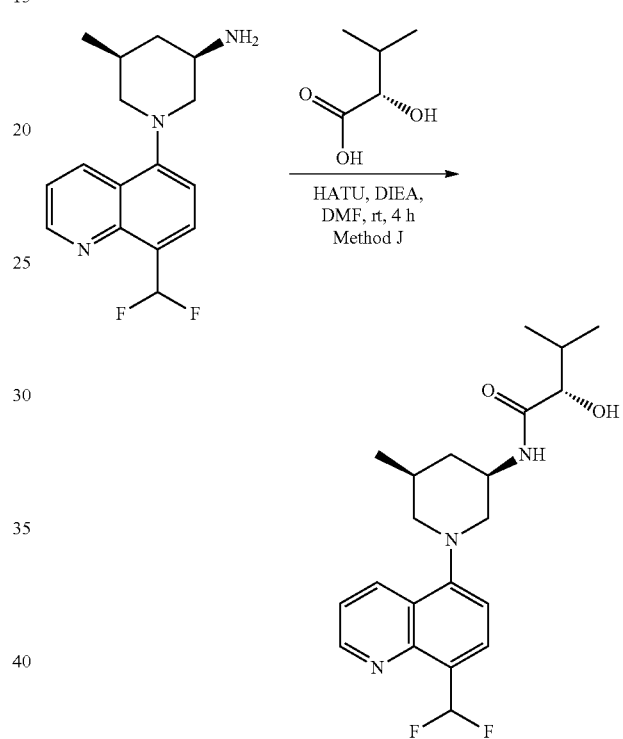

(2S)—N-[(3R,5S)-1-[8-(difluoromethyl)quinolin-5-yl]-5-methylpiperidin-3-yl]-2-hydroxy-3-methylbutanamide: (2S)—N-[(3R,5S)-1-[8-(difluoromethyl)quinolin-5-yl]-5-methylpiperidin-3-yl]-2-hydroxy-3-methylbutanamide was prepared from 2-(dimethylamino)acetic acid and (3R,5S)-1-(8-(difluoromethyl)quinolin-5-yl)-5-methylpiperidin-3-amine using Method J. The crude product was purified by prep-HPLC under the following conditions: column, XBridge Shield RP18 OBD Column, 5 um, 19 mm×150 mm; mobile phase, acetonitrile in water (with 0.05% NH3.H2O), 25% to 50% gradient in 10 min; detector, UV 254 nm. (2S)—N-[(3R,5S)-1-[8-(difluoromethyl)quinolin-5-yl]-5-methylpiperidin-3-yl]-2-hydroxy-3-methylbutanamide was obtained as white solid (17 mg, 27%).

Compound 204: HPLC: 91.5% purity, RT=2.73 min. MS: m/z=392.2 [M+H]+. 1H NMR (400 MHz, CD3OD, ppm) δ 8.91 (dd, J=4.2, 1.7 Hz, 1H), 8.65 (dd, J=8.6, 1.8 Hz, 1H), 7.95 (d, J=7.8 Hz, 1H), 7.88-7.54 (m, 2H), 7.27 (d, J=7.9 Hz, 1H), 4.34-4.24 (m, 1H), 3.85 (d, J=3.8 Hz, 1H), 3.58-3.45 (m, 1H), 3.40-3.28 (m, 1H), 2.59 (t, J=10.8 Hz, 1H), 2.48 (t, J=11.2 Hz, 1H), 2.24-2.00 (m, 4H), 1.38-1.18 (m, 1H), 1.05 (d, J=6.6 Hz, 3H), 1.00 (d, J=6.6 Hz, 3H), 0.84 (d, J=6.8 Hz, 3H).

The following compounds were synthesized in an analogous manner:

Compound 205 (N-[(3R,5S)-1-[8-(difluoromethyl)quinolin-5-yl]-5-methylpiperidin-3-yl]-3,3-dimethylbutanamide): From 3,3-dimethylbutanoic acid and (3R,5S)-1-(8-(difluoromethyl)quinolin-5-yl)-5-methylpiperidin-3-amine. HPLC: 98.9% purity, RT=1.59 min. MS: m/z=390.2 [M+H]$^+$. $^1$H NMR (400 MHz, CD$_3$OD, ppm) δ 8.91 (dd, J=4.2, 1.7 Hz, 1H), 8.64 (dd, J=8.6, 1.8 Hz, 1H), 7.95 (dt, J=7.9, 1.5 Hz, 1H), 7.85-7.65 (m, 2H), 7.26 (d, J=7.9 Hz, 1H), 4.29-4.21 (m, 1H), 3.62-3.53 (m, 1H), 3.39-3.36 (m, 1H), 2.57-2.37 (m, 2H), 2.23-2.06 (m, 4H), 1.15 (td, J=12.1, 12.1 Hz, 1H), 1.05 (s, 3H), 1.03 (s, 9H).

Compound 209 (N-[(3R,5S)-1-[8-(difluoromethyl)quinolin-5-yl]-5-methylpiperidin-3-yl]-2-(dimethylamino)acetamide): From 3,3-dimethylbutanoic acid and (3R,5S)-1-(8-(difluoromethyl)quinolin-5-yl)-5-methylpiperidin-3-amine. HPLC: 95.9% purity, RT=2.58 min. MS: m/z=377.2 [M+H]$^+$. $^1$H NMR (400 MHz, CD$_3$OD, ppm) δ 8.91 (dd, J=4.2, 1.7 Hz, 1H), 8.64 (dd, J=8.6, 1.8 Hz, 1H), 7.95 (dd, J=7.9, 1.3 Hz, 1H), 7.86-7.54 (m, 2H), 7.28 (d, J=7.9 Hz, 1H), 4.33-4.24 (m, 1H), 3.61-3.54 (m, 1H), 3.40-3.28 (m, 1H), 3.10 (s, 2H), 2.60-2.40 (m, 2H), 2.37 (s, 6H), 2.24-2.09 (m, 2H), 1.20 (td, J=12.1, 12.1 Hz, 1H), 1.05 (d, J=6.4 Hz, 3H).

Compound 302 (N-[(3R,5S)-1-[8-(difluoromethyl)quinolin-5-yl]-5-methylpiperidin-3-yl]-2-hydroxypropanamide): From 2-hydroxypropanoic acid and (3R,5S)-1-(8-(difluoromethyl)quinolin-5-yl)-5-methylpiperidin-3-amine. HPLC: 99.0% purity, RT=2.13 min. MS: m/z=364.1 [M+H]$^+$. $^1$H NMR (400 MHz, CD$_3$OD, ppm) δ 8.89 (dd, J=4.2, 1.7 Hz, 1H), 8.62 (dd, J=8.6, 1.7 Hz, 1H), 7.93 (dd, J=7.9, 1.4 Hz, 1H), 7.86-7.50 (m, 2H), 7.26 (d, J=8.0 Hz, 1H), 4.28-4.20 (m, 1H), 4.11 (td, J=6.8, 6.8 Hz, 1H), 3.54-3.49 (m, 1H), 3.38-3.30 (m, 1H), 2.56 (t, J=10.9 Hz, 1H), 2.45 (t, J=11.2 Hz, 1H), 2.21-2.05 (m, 2H), 1.32 (d, J=6.8 Hz, 3H), 1.22 (td, J=12.1, 12.1 Hz, 1H), 1.03 (d, J=6.4 Hz, 3H).

Compound 303 (N-[(3R,5S)-1-[8-(difluoromethyl)quinolin-5-yl]-5-methylpiperidin-3-yl]-2-(1-methylpiperidin-3-yl)acetamide): From 2-(1-methylpiperidin-3-yl)acetic acid and (3R,5S)-1-(8-(difluoromethyl)quinolin-5-yl)-5-methylpiperidin-3-amine. HPLC: 98.8% purity, RT=1.52 min. MS: m/z=431.3 [M+H]$^+$. $^1$H NMR (300 MHz, CD$_3$OD, ppm) δ 8.89 (dd, J=4.2, 1.7 Hz, 1H), 8.62 (dd, J=8.6, 1.8 Hz, 1H), 7.98-7.84 (m, 1H), 7.73-7.46 (m, 2H), 7.25 (d, J=7.8 Hz, 1H), 4.22 (t, J=11.4 Hz, 1H), 3.57 (apparent d, J=11.6 Hz, 1H), 3.40-3.30 (m, 1H), 2.89-2.72 (m, 2H), 2.50-2.41 (m, 2H), 2.25-2.23 (m, 3H), 2.19-1.82 (m, 6H), 1.81-1.48 (m, 4H), 1.22-0.87 (m, 5H).

Compound 307 (N-[(3R,5S)-1-[8-(difluoromethyl)quinolin-5-yl]-5-methylpiperidin-3-yl]-2-(1-methylpyrrolidin-3-yl)acetamide): From 2-(1-methylpyrrolidin-3-yl)acetic acid and (3R,5S)-1-(8-(difluoromethyl)quinolin-5-yl)-5-methylpiperidin-3-amine. HPLC: 96.0% purity, RT=2.82 min. MS: m/z=417.2 [M+H]$^+$. $^1$H NMR (300 MHz, CD$_3$OD, ppm) δ 8.86 (dd, J=4.2, 1.7 Hz, 1H), 8.58 (dd, J=8.6, 1.8 Hz, 1H), 7.96-7.41 (m, 3H), 7.21 (d, J=7.9 Hz, 1H), 4.26-4.09 (m, 1H), 3.59-3.47 (m, 1H), 3.39-3.29 (m, 1H), 2.80-2.73 (m, 1H), 2.67-2.49 (m, 3H), 2.46-2.37 (m, 2H), 2.33-2.30 (m, 3H), 2.28-2.17 (m, 3H), 2.12-1.95 (m, 3H), 1.54-1.40 (m, 1H), 1.25 (d, J=1.4 Hz, 1H), 1.11 (td, J=12.4, 12.4 Hz, 1H), 0.99 (d, J=6.4 Hz, 3H).

Compound 311 (2-(3,3-difluoroazetidin-1-yl)-N-[(3R,5S)-1-[8-(difluoromethyl)quinolin-5-yl]-5-methylpiperidin-3-yl]propanamide): From 2-(3,3-difluoroazetidin-1-yl)propanoic acid and (3R,5S)-1-(8-(difluoromethyl)quinolin-5-yl)-5-methylpiperidin-3-amine. HPLC: 96.8% purity, RT=2.53 min. MS: m/z=439.3 [M+H]$^+$. $^1$H NMR (400 MHz, CD$_3$OD, ppm) b 8.89 (dd, J=4.2, 1.7 Hz, 1H), 8.61 (dt, J=8.6, 1.7 Hz, 1H), 7.93 (dd, J=8.0, 1.5 Hz, 1H), 7.85-7.53 (m, 2H), 7.26 (d, J=7.9, 2.0 Hz, 1H), 4.27-4.18 (m, 1H), 3.75-3.56 (m, 4H), 3.53-3.49 (m, 1H), 3.39-3.20 (m, 1H), 3.10-3.00 (m, 1H), 2.60-2.40 (m, 2H), 2.21-2.04 (m, 2H), 1.31-1.13 (m, 4H), 1.03 (d, J=6.5 Hz, 3H).

Compound 313 (N-[(3R,5S)-1-[8-(difluoromethyl)quinolin-5-yl]-5-methylpiperidin-3-yl]-2-(4-hydroxypiperidin-1-yl)propanamide): From 2-(4-hydroxypiperidin-1-yl)propanoic acid and (3R,5S)-1-(8-(difluoromethyl)quinolin-5-yl)-5-methylpiperidin-3-amine. HPLC: 93.5% purity, RT=1.51 min. MS: m/z=447.3 [M+H]$^+$. $^1$H NMR (300 MHz, CD$_3$OD, ppm) δ 8.86 (dd, J=4.2, 1.6 Hz, 1H), 8.59 (dt, J=8.6, 1.8 Hz, 1H), 7.95-7.44 (m, 3H), 7.23 (d, J=7.9 Hz, 1H), 4.21 (d, J=11.8 Hz, 1H), 3.69-3.50 (m, 2H), 3.40-3.20 (m, 1H), 3.01 (tt, J=3.6, 3.3 Hz, 1H), 2.82-2.68 (m, 2H), 2.56-2.02 (m, 6H), 1.89-1.73 (m, 2H), 1.58-1.45 (m, 2H), 1.23-1.05 (m, 4H), 1.00 (d, J=6.4 Hz, 3H).

Compound 316 (N-[(3R,5S)-1-[8-(difluoromethyl)quinolin-5-yl]-5-methylpiperidin-3-yl]-2-(1-methylpiperidin-4-yl)acetamide): From 2-(1-methylpiperidin-4-yl)acetic acid and (3R,5S)-1-(8-(difluoromethyl)quinolin-5-yl)-5-methylpiperidin-3-amine. HPLC: 98.7% purity, RT=1.02 min. MS: m/z=431.3 [M+H]$^+$. $^1$H NMR (300 MHz, CD$_3$OD, ppm) δ 8.86 (dd, J=4.2, 1.7 Hz, 1H), 8.59 (dd, J=8.6, 1.7 Hz, 1H), 7.94-7.43 (m, 3H), 7.21 (d, J=7.9 Hz, 1H), 4.24-4.13 (m, 1H), 3.60-3.48 (m, 1H), 3.40-3.20 (m, 1H), 2.95-2.91 (m, 2H), 2.46-2.37 (m, 2H), 2.29 (s, 3H), 2.18-2.02 (m, 6H), 1.83-1.60 (m, 3H), 1.37-1.20 (m, 2H), 1.07-1.00 (m, 1H), 0.99 (d, J=6.3 Hz, 3H).

Compound 317 (N-[(3R,5S)-1-[8-(difluoromethyl)quinolin-5-yl]-5-methylpiperidin-3-yl]-3,3-difluorocyclobutane-1-carboxamide: From 3,3-difluorocyclobutane-1-carboxylic acid and (3R,5S)-1-(8-(difluoromethyl)quinolin-5-yl)-5-methylpiperidin-3-amine. HPLC: 98.6% purity, RT=2.25 min. MS: m/z=410.2 [M+H]$^+$. $^1$H NMR (300 MHz, Chloroform-d, ppm) δ 8.93 (dd, J=4.5, 1.8 Hz, 1H), 8.54 (d, J=8.5 Hz, 1H), 7.99-7.43 (m, 3H), 7.12 (d, J=7.9 Hz, 1H), 5.38-5.28 (m, 1H), 4.39-4.23 (m, 1H), 3.68-3.64 (m, 1H), 3.31-3.27 (m, 1H), 2.94-2.62 (m, 5H), 2.49-2.29 (m, 2H), 2.22-2.07 (m, 2H), 1.03-0.95 (m, 4H).

Compound 318 (N-[(3R,5S)-1-[8-(difluoromethyl)quinoxalin-5-yl]-5-methylpiperidin-3-yl]-2-(1-methylpiperidin-3-yl)acetamide): From 2-(1-methylpiperidin-3-yl)acetic acid and (3R,5S)-1-[8-(difluoromethyl)quinoxalin-5-yl]-5-methylpiperidin-3-amine. HPLC: 92.0% purity, RT=2.22 min. MS: m/z=432.3 [M+H]$^+$. $^1$H NMR (300 MHz, Chloroform-d, ppm) δ 9.07-8.87 (m, 2H), 7.94-7.54 (m, 3H), 7.30 (d, J=8.3 Hz, 1H), 4.12-3.85 (m, 3H), 2.69-2.40 (m, 4H), 2.10 (s, 3H), 2.02-1.70 (m, 4H), 1.65-1.35 (m, 3H), 1.16-0.98 (m, 1H), 0.95-0.75 (m, 4H).

Compound 319 (N-[(3R,5S)-1-[8-(difluoromethyl)quinoxalin-5-yl]-5-methylpiperidin-3-yl]-2-(1-methylpyrrolidin-3-yl)acetamide): From 2-(1-methylpyrrolidin-3-yl)acetic acid and (3R,5S)-1-[8-(difluoromethyl)quinoxalin-5-yl]-5-methylpiperidin-3-amine. HPLC: 91.0% purity, RT=6.42 min. MS: m/z=418.3 [M+H]$^+$. $^1$H NMR (300 MHz, CD$_3$OD, ppm) δ 8.95-8.85 (m, 2H), 7.93 (d, J=8.1 Hz, 1H), 7.63 (t, J=55.8 Hz, 1H), 7.30 (d, J=8.2 Hz, 1H), 4.23-3.92 (m, 3H), 3.04-2.89 (m, 1H), 2.85-2.40 (m, 9H), 2.29 (d, J=7.5 Hz, 2H), 2.20-2.00 (m, 3H), 1.63-1.49 (m, 1H), 1.12-1.09 (m, 1H), 0.97 (d, J=6.4 Hz, 3H).

Compound 323 (2-(3,3-difluoroazetidin-1-yl)-N-[(3R,5S)-1-[8-(difluoromethyl)quinoxalin-5-yl]-5-methylpiperidin-3-yl]propanamide): From 2-(3,3-difluoroazetidin-1-yl) propanoic acid and (3R,5S)-1-[8-(difluoromethyl)

quinoxalin-5-yl]-5-methylpiperidin-3-amine. HPLC: 94.2% purity, RT=1.25 min. MS: m/z=440.3 [M+H]⁺. ¹H NMR (400 MHz, CD₃OD, ppm) δ 8.95-8.85 (m, 2H), 7.97 (dd, J=8.2, 1.5 Hz, 1H), 7.63 (t, J=55.9 Hz, 1H), 7.34 (d, J=8.3 Hz, 1H), 4.27-4.13 (m, 1H), 4.09-3.95 (m, 2H), 3.77-3.58 (m, 4H), 3.11-3.01 (m, 1H), 2.75-2.68 (m, 1H), 2.57-2.05 (m, 1H), 2.14-2.03 (m, 2H), 1.31-1.13 (m, 4H), 1.01 (d, J=6.5 Hz, 3H).

Compound 325 (N-[(3R,5S)-1-[8-(difluoromethyl)quinoxalin-5-yl]-5-methylpiperidin-3-yl]-2-(4-hydroxypiperidin-1-yl)propanamide): From 2-(4-hydroxypiperidin-1-yl)propanoic acid and (3R,5S)-1-[8-(difluoromethyl) quinoxalin-5-yl]-5-methylpiperidin-3-amine. HPLC: 90.5% purity, RT=1.50 min. MS: m/z=448.3 [M+H]⁺. ¹H NMR (300 MHz, CD₃OD, ppm) δ 8.97-8.81 (m, 2H), 7.97 (d, J=8.2 Hz, 1H), 7.63 (t, J=55.8 Hz, 1H), 7.34 (d, J=8.0 Hz, 1H), 4.29-3.90 (m, 3H), 3.65-3.62 (m, 1H), 3.17-3.09 (m, 1H), 2.95-2.20 (m, 6H), 2.19-1.79 (m, 4H), 1.70-1.50 (m, 2H), 1.31-1.11 (m, 4H), 1.02 (d, J=6.3 Hz, 3H).

Compound 328 (N-[(3R,5S)-1-[8-(difluoromethyl)quinoxalin-5-yl]-5-methylpiperidin-3-yl]-2-(1-methylpiperidin-4-yl)acetamide): From 2-(1-methylpiperidin-4-yl)acetic acid and (3R,5S)-1-[8-(difluoromethyl)quinoxalin-5-yl]-5-methylpiperidin-3-amine. HPLC: 90.4% purity, RT=1.31 min. MS: m/z=432.3 [M+H]⁺. ¹H NMR (300 MHz, CD₃OD, ppm) δ 8.95-8.81 (m, 2H), 7.97 (d, J=8.3 Hz, 1H), 7.64 (t, J=55.8 Hz, 1H), 7.34 (d, J=8.1 Hz, 1H), 4.29-3.95 (m, 3H), 2.97-2.94 (m, 2H), 2.66-2.46 (m, 2H), 2.35 (s, 3H), 2.24-2.03 (m, 6H), 1.90-1.70 (m, 3H), 1.40-1.36 (m, 2H), 1.14 (td, J=12.2, 12.2 Hz, 1H), 1.01 (dd, J=6.4, 2.3 Hz, 3H).

Compound 329 (N-[(3R,5S)-1-[8-(difluoromethyl)quinoxalin-5-yl]-5-methylpiperidin-3-yl]-3,3-difluorocyclobutane-1-carboxamide): From 3,3-difluorocyclobutane-1-carboxylic acid and (3R,5S)-1-[8-(difluoromethyl)quinoxalin-5-yl]-5-methylpiperidin-3-amine. HPLC: 91.2% purity, RT=2.91 min. MS: m/z=411.2 [M+H]⁺. ¹H NMR (400 MHz, CD₃OD, ppm) δ 8.98-8.85 (m, 2H), 7.99 (dd, J=8.2, 1.5 Hz, 1H), 7.65 (t, J=55.6 Hz, 1H), 7.36 (d, J=8.2 Hz, 1H), 4.28-4.11 (m, 2H), 4.06-3.98 (m, 1H), 2.97-2.46 (m, 7H), 2.15-2.07 (m, 2H), 1.15 (td, J=12.2, 12.2 Hz, 1H), 1.02 (d, J=6.4 Hz, 3H).

Example 62: Synthesis of Compound 206 ((3R,5S)-1-[8-(difluoromethyl)quinolin-5-yl]-N-(2-methoxyethyl)-5-methylpiperidin-3-amine)

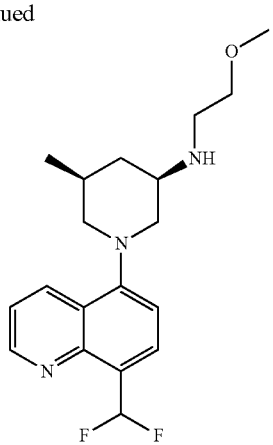

(3R,5S)-1-[8-(difluoromethyl)quinolin-5-yl]-N-(2-methoxyethyl)-5-methylpiperidin-3-amine): (3R,5S)-1-[8-(difluoromethyl)quinolin-5-yl]-N-(2-methoxyethyl)-5-methylpiperidin-3-amine was prepared from 1-bromo-2-methoxyethane and (3R,5S)-1-(8-(difluoromethyl)quinolin-5-yl)-5-methylpiperidin-3-amine using Method N. The crude product was purified by prep-HPLC under the following conditions: column, XBridge Shield RP18 OBD Column, 5 um, 19 mm×150 mm; mobile phase, acetonitrile in water (with 0.05% NH₃.H₂O), 35% to 65% gradient in 8 min; detector, UV 254 nm. (3R,5S)-1-[8-(difluoromethyl) quinolin-5-yl]-N-(2-methoxyethyl)-5-methylpiperidin-3-amine was obtained as yellow solid (11 mg, 24%).

Compound 206: HPLC: 96.4% purity, RT=1.41 min. MS: m/z=350.1 [M+H]⁺. ¹H NMR (300 MHz, CD₃OD, ppm) δ 8.85 (dd, J=4.2, 1.8 Hz, 1H), 8.51 (dd, J=8.6, 1.8 Hz, 1H), 7.95-7.85 (m, 1H), 7.82-7.43 (m, 2H), 7.22 (d, J=7.9 Hz, 1H), 3.61-3.43 (m, 3H), 3.35-3.25 (m, 4H), 3.10-2.98 (m, 1H), 2.93-2.72 (m, 2H), 2.50-2.30 (m, 2H), 2.23-1.96 (m, 2H), 1.02-0.83 (m, 4H).

Example 63: Synthesis of Compound 207 and compound 208 ((R)-2-amino-N-((3R,5S)-1-(8-(difluoromethyl)quinolin-5-yl)-5-methylpiperidin-3-yl)-3,3,3-trifluoropropanamide and(S)-2-amino-N-[(3R,5S)-1-[8-(difluoromethyl)quinolin-5-yl]-5-methylpiperidin-3-yl]-3,3,3-trifluoropropanamide)

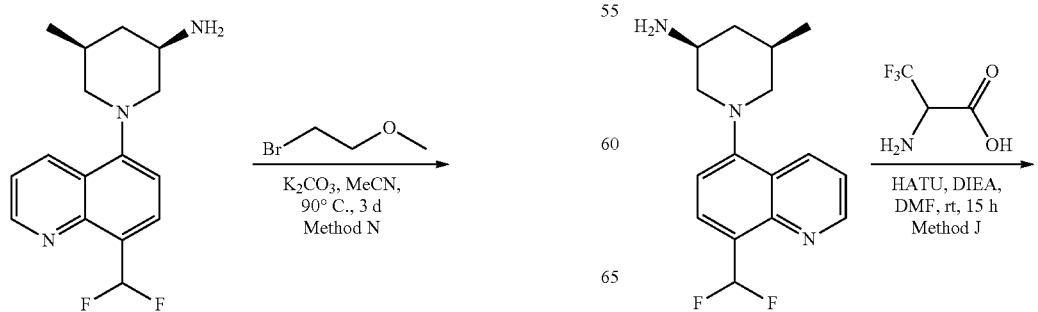

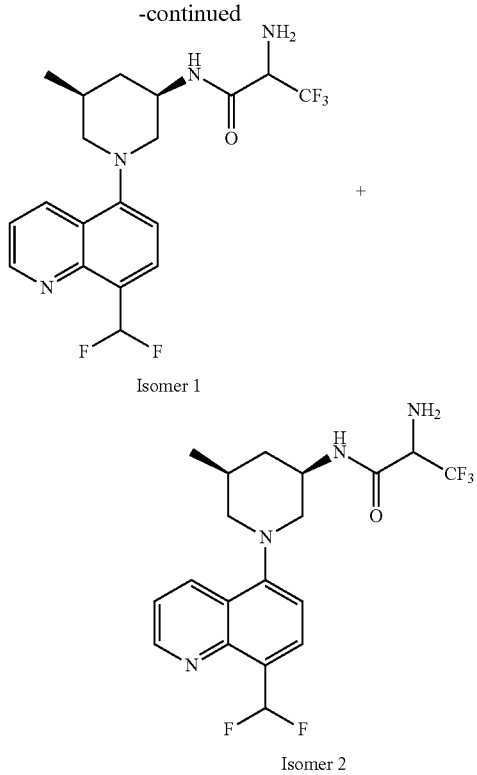

Isomer 1

Isomer 2

(R)-2-amino-N-((3R,5S)-1-(8-(difluoromethyl)quinolin-5-yl)-5-methylpiperidin-3-yl)-3,3,3-trifluoropropanamide and (S)-2-amino-N-[(3R,5S)-1-[8-(difluoromethyl)quinolin-5-yl]-5-methylpiperidin-3-yl]-3,3,3-trifluoropropanamide: 2-amino-N-[(3R,5S)-1-[8-(difluoromethyl)quinolin-5-yl]-5-methylpiperidin-3-yl]-3,3,3-trifluoropropanamide was prepared from (3R,5S)-1-(8-(difluoromethyl)quinolin-5-yl)-5-methylpiperidin-3-amine and 2-amino-3,3,3-trifluoropropanoic acid using Method J. The two diastereoisomers were separated by prep-HPLC under the following conditions: column, XBridge Shield RP18 OBD Column, 19×150 mm 10 um; mobile phase, acetonitrile in water (with 0.05% $NH_3 \cdot H_2O$), 53% to 55% gradient in 12 min; detector, UV 254 nm.

Isomer 1: (11 mg, 16%, white solid) HPLC: 98.5% purity, RT=1.88 min. MS: m/z=417.2 $[M+H]^+$. $^1H$ NMR (300 MHz, DMSO-$d_6$, ppm) δ 8.87 (dd, J=4.2, 1.7 Hz, 1H), 8.58 (dd, J=8.6, 1.8 Hz, 1H), 7.91 (d, J=8.0 Hz, 1H), 7.87-7.44 (m, 2H), 7.22 (d, J=7.9 Hz, 1H), 4.30-4.18 (m, 1H), 3.89 (dt, J=7.7, 7.7 Hz, 1H), 3.58-3.47 (m, 1H), 3.39-3.28 (m, 1H), 2.55-2.35 (m, 2H), 2.3.9-2.08 (m, 2H), 1.29-1.05 (m, 1H), 1.00 (d, J=6.3 Hz, 3H).

Isomer 2: (13 mg, 19%, yellow solid) HPLC: 93.8% purity, RT=3.84 min. MS: m/z=417.1 $[M+H]^+$. $^1H$ NMR (300 MHz, $CD_3OD$, ppm) δ 8.87 (dd, J=4.2, 1.7 Hz, 1H), 8.58 (dd, J=8.6, 1.8 Hz, 1H), 7.91 (d, J=8.0 Hz, 1H), 7.87-7.44 (m, 2H), 7.22 (d, J=7.9 Hz, 1H), 4.30-4.18 (m, 1H), 3.89 (dt, J=7.7, 7.7 Hz, 1H), 3.58-3.47 (m, 1H), 3.39-3.28 (m, 1H), 2.55-2.35 (m, 2H), 2.3.9-2.08 (m, 2H), 1.29-1.05 (m, 1H), 1.00 (d, J=6.3 Hz, 3H).

Example 64: Synthesis of Compound 210 (8-[(5R)-5-amino-3,3-dimethylpiperidin-1-yl]quinoxaline-5-carbonitrile hydrochloride)

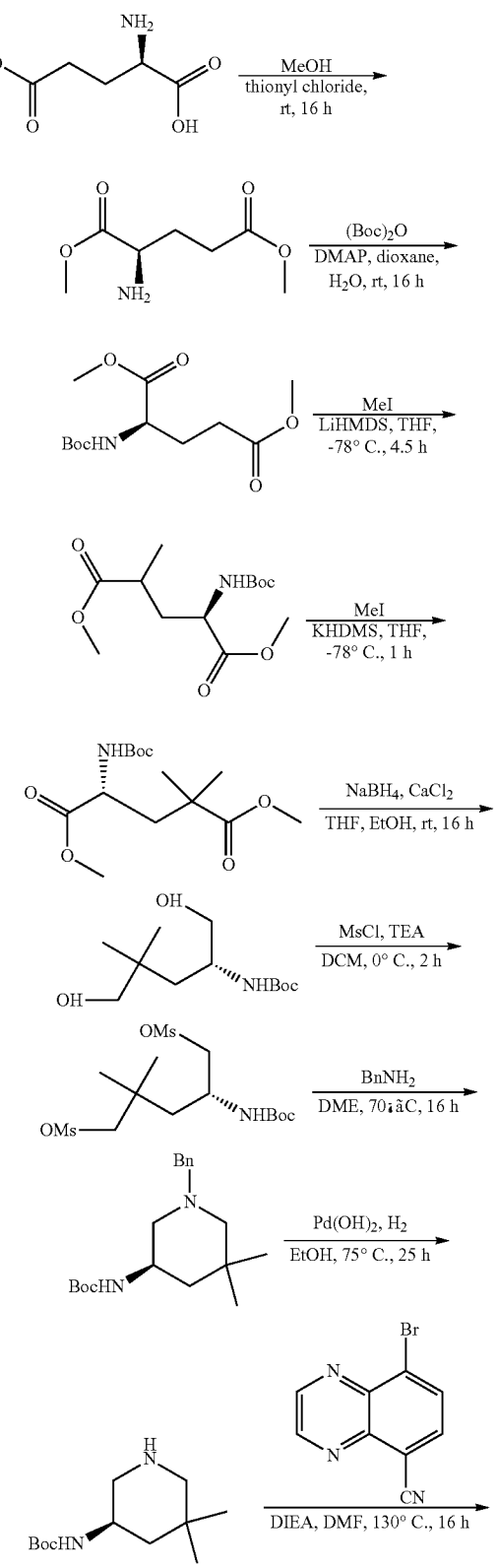

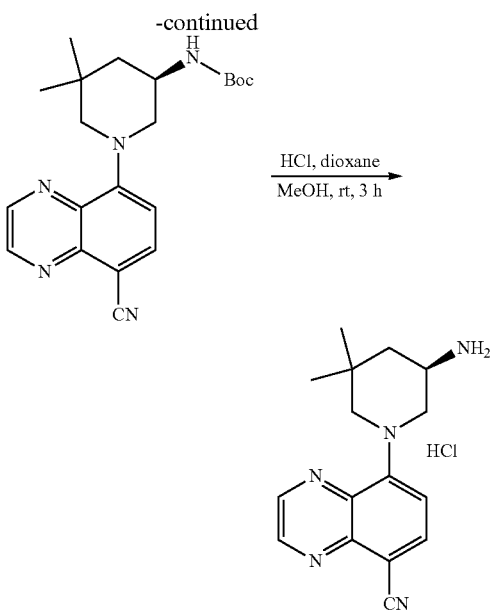

1,5-Dimethyl (2R)-2-aminopentanedioate: At 0° C., to a solution of (2R)-2-aminopentanedioic acid (19.00 g, 129.14 mmol) in methanol (400 mL) was added thionyl chloride (60.95 g, 512.33 mmol) dropwise over 20 min period. The resulting solution was then stirred for 16 h at room temperature. After the reaction was done, the reaction mixture was concentrated under reduced pressure. The residue was diluted with DCM (500 mL), and the pH value of mixture was adjusted to 8 by sat. sodium bicarbonate solution. The resulting mixture was extracted with DCM (300 mL×3). The organic phases were combined, washed with brine and dried over $Na_2SO_4$. The solvent was removed under reduced pressure to yield 1,5-dimethyl (2R)-2-aminopentanedioate as yellow oil (19.80 g, 88%). MS: n/z=176.0 $[M+H]^+$.

1,5-Dimethyl (2R)-2-[[(tert-butoxy)carbonyl]amino]pentanedioate: To a solution of 1,5-dimethyl (2R)-2-aminopentanedioate (19.80 g, 119.30 mmol) in dioxane (200 mL) was added 4-dimethylaminopyridine (291 mg, 2.38 mmol), $(Boc)_2O$ (29.93 g, 137.16 mmol) and water (200 mL) at room temperature. The resulting solution was stirred for 16 h at room temperature. When the reaction was done, it was quenched by the addition of water (100 mL). The resulting mixture was extracted with DCM (200 mL×3). The organic phases were combined, washed with brine and dried over $Na_2SO_4$. The solvent was removed under reduced pressure and the residue was purified by flash chromatography eluting with DCM in hexane (0% to 30% gradient) to yield 1,5-dimethyl (2R)-2-[[(tert-butoxy)carbonyl]amino]pentanedioate as colorless oil (23.75 g, 72%). MS: m/z=276.1 $[M+H]^+$.

1,5-Dimethyl (2R)-2-[[(tert-butoxy)carbonyl]amino]-4-methylpentanedioate: At −78° C., to a solution of 1,5-dimethyl (2R)-2-[[(tert-butoxy)carbonyl]amino]pentanedioate (3.80 g, 13.80 mmol) in THF (40 mL) was added LiHMDS solution (1 M in THF, 29 mL, 28.98 mmol) dropwise over 5 min period. The resulting mixture was stirred at −78° C. for 1 h, and then was added by MeI (3.13 g, 22.13 mmol) slowly. The resulting solution was stirred for another 4.5 h at −78° C. When the reaction was done, it was quenched by the addition of hydrogen chloride solution (1 M, 40 mL). The resulting mixture was extracted with ethyl acetate (100 mL×3). The organic phases were combined, washed with brine and dried over $Na_2SO_4$. The solvent was removed under reduced pressure and the residue was purified by flash chromatography eluting with EtOAc in hexane (0% to 10% gradient) to yield 1,5-dimethyl (2R)-2-[[(tert-butoxy)carbonyl]amino]-4-methylpentanedioate as white solid (3.33 g, 83%). MS: m/z=290.1 $[M+H]^+$.

1,5-Dimethyl (4R)-4-[[(tert-butoxy)carbonyl]amino]-2,2-dimethylpentanedioate: At −78° C., a solution of KHMDS in THF (1 M, 152 mL, 152 mmol) was added to THF (150 mL), to which was added a solution of 1,5-dimethyl (2R)-2-[[(tert-butoxy)carbonyl]amino]-4-methylpentanedioate (3.52 g, 12.66 mmol) in tetrahydrofuran (50 mL) dropwise over 5 min period. The resulting solution was stirred for 0.5 h at −78° C., and then was added by MeI (1079 g, 76 mmol) slowly. The resulting solution was then stirred for another 1 h at −78° C. When the reaction was done, it was quenched by the addition of sat. $NH_4Cl$ solution (100 mL). The resulting mixture was extracted with ethyl acetate (200 mL×3). The organic phases were combined, washed with brine and dried over $Na_2SO_4$. The solvent was removed under reduced pressure and the residue was purified by flash chromatography eluting with EtOAc in hexane (0% to 5% gradient) to yield 1,5-dimethyl (4R)-4-[[(tert-butoxy)carbonyl]amino]-2,2-dimethylpentanedioate as light yellow solid (2.00 g, 52%). MS: m/z=304.1 $[M+H]^+$.

tert-Butyl N-[(2R)-1,5-dihydroxy-4,4-dimethylpentan-2-yl]carbamate: At 0° C., to a solution of 1,5-dimethyl (4R)-4-[[(tert-butoxy)carbonyl]amino]-2,2-dimethylpentanedioate (1.44 g, 4.75 mmol) in EtOH (18 mL) was added THF (18 mL) and $CaCl_2$ (2.19 g, 19.77 mmol). Then $NaBH_4$ (1.56 g, 41.18 mmol) was added in portions over 20 min period at 0° C. The resulting mixture was stirred for 16 h at room temperature. When the reaction was done, it was quenched by the addition of $Na_2CO_3$ solution (10%, 50 mL). The resulting mixture was extracted with ethyl acetate (100 mL×3). The organic phases were combined, washed with brine and dried over $Na_2SO_4$. The solvent was removed under reduced pressure to yield tert-butyl N-[(2R)-1,5-dihydroxy-4,4-dimethylpentan-2-yl]carbamate as colorless oil (1.42 g, crude). MS: m/z=248.1 $[M+H]^+$.

tert-Butyl N-[(2R)-1,5-bis(methanesulfonyloxy)-4,4-dimethylpentan-2-yl]carbamate: At 0° C., to a solution of tert-butyl N-[(2R)-1,5-dihydroxy-4,4-dimethylpentan-2-yl]carbamate (1.42 g, crude) in DCM (50 mL) was added TEA (2.32 g, 22.91 mmol), to which was added MsCl (5.70 g, 49.76 mmol) dropwise over 10 min period. The resulting solution was then stirred for 2 h at 0° C. When the reaction was done, it was quenched by the addition of water (20 mL). The resulting mixture was extracted with ethyl acetate (60 mL×3). The organic phases were combined, washed with brine and dried over $Na_2SO_4$. The solvent was removed under reduced pressure to yield tert-butyl N-[(2R)-1,5-bis(methanesulfonyloxy)-4,4-dimethylpentan-2-yl]carbamate as colorless oil (2.60 g, crude). MS: m/z=426.1 $[M+H]^+$.

tert-Butyl N-[(3R)-1-benzyl-5,5-dimethylpiperidin-3-yl]carbamate: At room temperature, tert-butyl N-[(2R)-1,5-bis(methanesulfonyloxy)-4,4-dimethylpentan-2-yl]carbamate (2.60 g, crude) was added to phenylmethanamine (20 mL). The resulting solution was then stirred for 16 h at 70° C. After cooling to room temperature, the reaction mixture was concentrated under reduced pressure and the residue was purified by flash chromatography eluting with EtOAc in hexane (0% to 3% gradient) to yield tert-butyl N-[(3R)-1-benzyl-5,5-dimethylpiperidin-3-yl]carbamate as colorless oil (740 mg, 49% for 3 steps). MS: m/z=319.2 $[M+H]^+$.

tert-Butyl N-[(3R)-5,5-dimethylpiperidin-3-yl]carbamate: In a 30-mL pressure tank reactor, tert-butyl N-[(3R)-1- benzyl-5,5-dimethylpiperidin-3-yl]carbamate (666 mg, 2.09 mmol) and Pd(OH)$_2$/C (200 mg, 1.42 mmol) were mixed in methanol (5 mL, 123.49 mmol, 291.31 equiv) at room temperature under nitrogen atmosphere. The reactor was vacuumed and flushed with hydrogen. The reaction mixture was then hydrogenated for 25 h at 75° C. under 15 atm hydrogen atmosphere. When the reaction was done, the reaction mixture was filtered through a Celite pad and the filtrate was concentrated under reduced pressure to yield tert-butyl N-[(3R)-5,5-dimethylpiperidin-3-yl]carbamate as colorless oil (560 mg, crude). MS: m/z=229.0 [M+H]$^+$.

tert-Butyl N-[(3R)-1-(8-cyanoquinoxalin-5-yl)-5,5-dimethylpiperidin-3-yl]carbamate: To a solution of tert-butyl N-[(3R)-5,5-dimethylpiperidin-3-yl]carbamate (560 mg, crude) in DMF (5 mL) was added 8-bromoquinoxaline-5-carbonitrile (766 mg, 3.27 mmol) and DIEA (904 mg, 7.00 mmol) at room temperature. The resulting solution was then stirred for 16 h at 130° C. After cooling to room temperature, the reaction mixture was quenched by the addition of water (30 mL). The resulting mixture was extracted with ethyl acetate (50 mL×3). The organic phases were combined, washed with brine and dried over Na$_2$SO$_4$. The solvent was removed under reduced pressure and the residue was purified by flash chromatography eluting with EtOAc in hexane (0% to 14% gradient) to yield tert-butyl N-[(3R)-1-(8-cyanoquinoxalin-5-yl)-5,5-dimethylpiperidin-3-yl]carbamate as yellow solid (477 mg, 60% for 2 steps). MS: m/z=382.0 [M+H]$^+$.

8-[(5R)-5-amino-3,3-dimethylpiperidin-1-yl]quinoxaline-5-carbonitrile hydrochloride: To a solution of tert-butyl N-[(3R)-1-(8-cyanoquinoxalin-5-yl)-5,5-dimethylpiperidin-3-yl]carbamate (439 mg, 1.15 mmol) in MeOH (5 mL) was added a solution of HCl in dioxane (4 M, 5 mL) at room temperature. The resulting solution was stirred for 3 h at room temperature. When the reaction was done, the resulting mixture was concentrated under reduced pressure to yield 8-[(5R)-5-amino-3,3-dimethylpiperidin-1-yl]quinoxaline-5-carbonitrile hydrochloride as yellow solid (450 mg, crude). MS: m/z=282.2 [M+H]$^+$.

Compound 210: MS: m/z=282.1 [M+H]$^+$.

Example 65: Synthesis of Compound 211 and 212 (((R)-2-amino-N—((R)-1-(8-cyanoquinoxalin-5-yl)-5,5-dimethylpiperidin-3-yl)-3,3,3-trifluoropropanamide and (S)-2-amino-N—((R)-1-(8-cyanoquinoxalin-5-yl)-5,5-dimethylpiperidin-3-yl)-3,3,3-trifluoropropanamide)

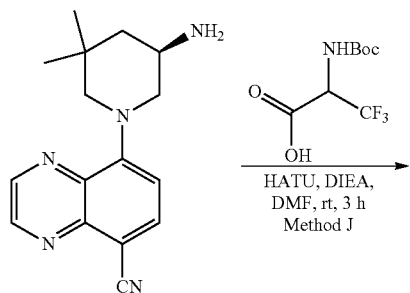

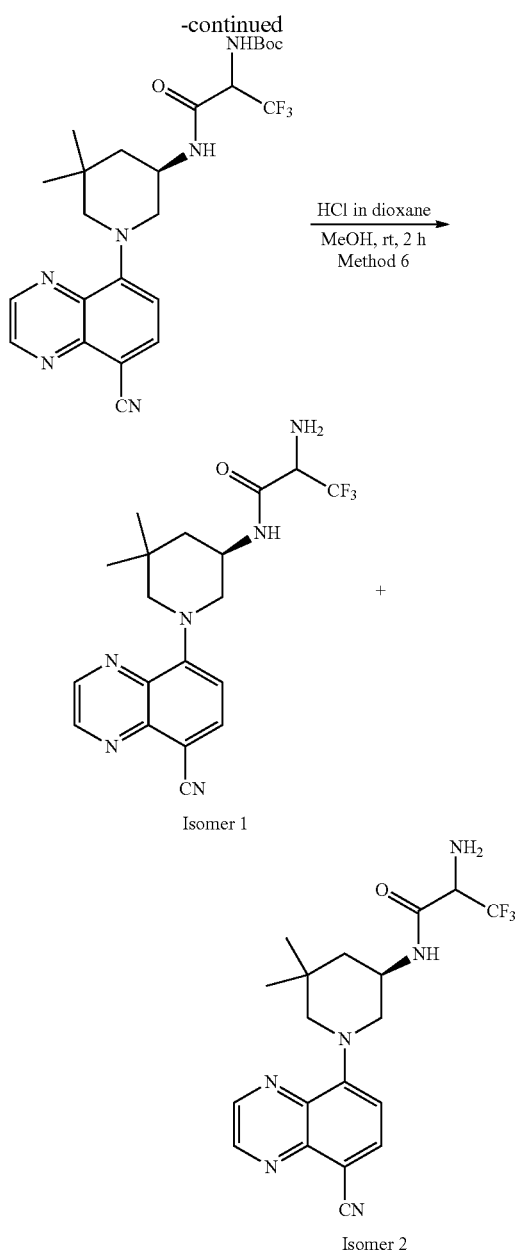

(R)-2-amino-N—((R)-1-(8-cyanoquinoxalin-5-yl)-5,5-dimethylpiperidin-3-yl)-3,3,3-trifluoropropanamide and (S)-2-amino-N—((R)-1-(8-cyanoquinoxalin-5-yl)-5,5-dimethylpiperidin-3-yl)-3,3,3-trifluoropropanamide: 2-amino-N—((R)-1-(8-cyanoquinoxalin-5-yl)-5,5-dimethylpiperidin-3-yl)-3,3,3-trifluoropropanamide was prepared from (R)-8-(5-amino-3,3-dimethylpiperidin-1-yl)quinoxaline-5-carbonitrile and 2-(tert-butoxycarbonylamino)-3,3,3-trifluoropropanoic acid using Method J and 6. The two diastereoisomers were separated by prep-HPLC under the following conditions: column, XBridge Prep C18 OBD Column, 19×150 mm 10 um; mobile phase, acetonitrile in water (with 0.05% NH$_3$.H$_2$O), 40% to 70% gradient in 10 min; detector, UV 254 nm.

Isomer 1: (19 mg, 14% for 2 steps, yellow solid) HPLC: 93.0% purity, RT=2.39 min. MS: m/z=407.2 [M+H]$^+$. $^1$H NMR (400 MHz, CD$_3$OD, ppm) δ 9.01-8.91 (m, 2H), 8.13 (d, J=8.4 Hz, 1H), 7.31 (d, J=8.4 Hz, 1H), 4.50-4.38 (m, 1H), 4.24 (dd, J=12.1, 4.1 Hz, 1H), 4.01-3.90 (m, 2H), 3.00-2.84 (m, 2H), 1.86-1.70 (m, 1H), 1.58-1.48 (m, 1H), 1.12 (s, 3H), 1.08 (m, 3H).

Isomer 2: (17 mg, 12% for 2 steps, yellow solid) HPLC: 93.7% purity, RT=2.46 min. MS: m/z=407.2 [M+H]$^+$. $^1$H NMR (400 MHz, CD$_3$OD, ppm) δ 9.01-8.91 (m, 2H), 8.13 (d, J=8.4 Hz, 1H), 7.31 (d, J=8.4 Hz, 1H), 4.50-4.38 (m, 1H), 4.24 (dd, J=12.1, 4.1 Hz, 1H), 4.01-3.90 (m, 2H), 3.00-2.84 (m, 2H), 1.86-1.70 (m, 1H), 1.58-1.48 (m, 1H), 1.12 (s, 3H), 1.08 (m, 3H).

Example 66: Synthesis of Compound 213 ((2R)—N-[(3R)-1-(8-cyanoquinoxalin-5-yl)-5,5-dimethylpiperidin-3-yl]-2-hydroxy-3-methylbutanamide)

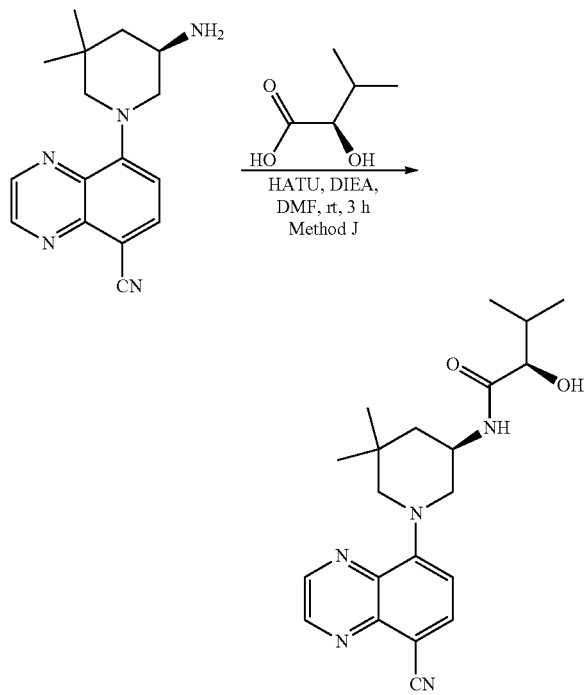

(2R)—N-[(3R)-1-(8-cyanoquinoxalin-5-yl)-5,5-dimethylpiperidin-3-yl]-2-hydroxy-3-methylbutanamide: (2R)—N-[(3R)-1-(8-cyanoquinoxalin-5-yl)-5,5-dimethylpiperidin-3-yl]-2-hydroxy-3-methylbutanamide was prepared from (2R)-2-hydroxy-3-methylbutanoic acid and (R)-8-(5-amino-3,3-dimethylpiperidin-1-yl)quinoxaline-5-carbonitrile using Method J. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), 35% to 65% gradient in 8 min; detector, UV 254 nm. (2R)—N-[(3R)-1-(8-cyanoquinoxalin-5-yl)-5,5-dimethylpiperidin-3-yl]-2-hydroxy-3-methylbutanamide was obtained as yellow solid (18 mg, 33%).

Compound 213: HPLC: 97.2% purity, RT=2.51 min. MS: m/z=382.3 [M+H]$^+$. $^1$H NMR (400 MHz, CD$_3$OD, ppm) δ 8.94 (dd, J=8.7, 1.8 Hz, 2H), 8.11 (d, J=8.3 Hz, 1H), 7.29 (d, J=8.4 Hz, 1H), 4.44-4.33 (m, 1H), 4.01 (dd, J=12.0, 4.0 Hz, 1H), 3.91 (d, J=3.7 Hz, 1H), 3.79 (d, J=12.1 Hz, 1H), 3.22-3.15 (m, 1H), 3.03 (d, J=12.1 Hz, 1H), 2.22-2.10 (m, 1H), 1.82-1.61 (m, 2H), 1.16-1.00 (m, 9H), 0.90 (d, J=6.8 Hz, 3H).

The following compounds were synthesized in an analogous manner:

Compound 214 (N-[(3R)-1-(8-cyanoquinoxalin-5-yl)-5,5-dimethylpiperidin-3-yl]-2-(morpholin-4-yl)acetamide): From 8-[(5R)-5-amino-3,3-dimethylpiperidin-1-yl]quinoxaline-5-carbonitrile hydrochloride and 2-(morpholin-4-yl) acetic acid. HPLC: 97.0% purity, room temperature=1.87 min. MS: m/z=409.3 [M+H]$^+$. $^1$H NMR (400 MHz, CD$_3$OD, ppm) δ 8.92 (d, J=15.0 Hz, 2H), 8.09 (d, J=8.4 Hz, 1H), 7.28 (d, J=6.3 Hz, 1H), 4.49-4.35 (m, 1H), 4.16-4.07 (m, 1H), 3.90 (d, J=12.3 Hz, 1H), 3.77-3.63 (m, 4H), 3.17-2.95 (m, 4H), 2.60-2.52 (m, 4H), 1.83-1.74 (m, 1H), 1.62-1.51 (m, 1H), 1.15-1.05 (m, 6H).

Compound 215(N-[(3R)-1-(8-cyanoquinoxalin-5-yl)-5,5-dimethylpiperidin-3-yl]-3,3-dimethylbutanamide): From 3,3-dimethylbutanoic acid and (R)-8-(5-amino-3,3-dimethylpiperidin-1-yl)quinoxaline-5-carbonitrile. HPLC: 99.2% purity, RT=4.17 min. MS: n/z=380.1 [M+H]$^+$. $^1$H NMR (400 MHz, CD$_3$OD, ppm) δ 8.95-8.85 (m, 2H), 8.10 (d, J=8.4 Hz, 1H), 7.30 (d, J=8.4 Hz, 1H), 4.48-4.36 (m, 1H), 4.36-4.26 (m, 1H), 4.11 (d, J=12.6 Hz, 1H), 2.90 (d, J=12.4 Hz, 1H), 2.80-2.68 (m, 1H), 2.12 (s, 2H), 1.85-1.75 (m, 1H), 1.44 (t, J=12.3 Hz, 1H), 1.13 (s, 3H), 1.04 (s, 9H), 1.02 (s, 3H).

Compound 217 (N-[(3R)-1-(8-cyanoquinoxalin-5-yl)-5,5-dimethylpiperidin-3-yl]-2-(dimethylamino)acetamide): From 2-(dimethylamino)acetic acid and (R)-8-(5-amino-3,3-dimethylpiperidin-1-yl)quinoxaline-5-carbonitrile. HPLC: 97.9% purity, RT=2.95 min. MS: m/z=367.1 [M+H]$^+$. $^1$H NMR (400 MHz, CD$_3$OD, ppm) δ 8.99-8.85 (m, 2H), 8.12-8.04 (m, 1H), 7.31-7.23 (m, 1H), 4.46-4.33 (m, 1H), 4.11 (dd, J=11.6, 4.1 Hz, 1H), 3.91 (d, J=12.2 Hz, 1H), 3.11-2.92 (m, 4H), 2.34 (s, 6H), 1.78 (dd, J=12.9, 4.3 Hz, 1H), 1.58 (dd, J=12.8, 10.5 Hz, 1H), 1.12 (s, 3H), 1.07 (s, 3H).

Compound 218 (N-[(3R)-1-(8-cyanoquinoxalin-5-yl)-5,5-dimethylpiperidin-3-yl]-2-hydroxyacetamide): From 2-hydroxyacetamide and (R)-8-(5-amino-3,3-dimethylpiperidin-1-yl)quinoxaline-5-carbonitrile. HPLC: 99.6% purity, RT=2.18 min. MS: m/z=340.1 [M+H]$^+$. $^1$H NMR (400 MHz, CD$_3$OD, ppm) δ 8.99-8.85 (m, 2H), 8.11 (d, J=8.3 Hz, 1H), 7.29 (d, J=8.4 Hz, 1H), 4.44-4.33 (m, 1H), 4.10-3.92 (m, 3H), 3.78 (d, J=12.1 Hz, 1H), 3.24 (dd, J=12.2, 8.5 Hz, 1H), 3.03 (d, J=12.1 Hz, 1H), 1.81-1.67 (m, 2H), 1.12 and 1.09 (s, 6H).

Compound 220 (N-[(3R)-1-(8-cyanoquinoxalin-5-yl)-5,5-dimethylpiperidin-3-yl]-3,3,3-trifluoropropanamide): From 3,3,3-trifluoropropanoic acid and (R)-8-(5-amino-3,3-dimethylpiperidin-1-yl)quinoxaline-5-carbonitrile. HPLC: 96.0% purity, RT=2.62 min. MS: m/z=392.2 [M+H]$^+$. $^1$H NMR (400 MHz, CD$_3$OD, ppm) δ 8.99-8.85 (m, 2H), 8.11 (dd, J=8.4, 1.5 Hz, 1H), 7.30 (d, J=8.4 Hz, 1H), 4.51-4.30 (m, 2H), 4.13-3.99 (m, 1H), 3.32-3.16 (m, 2H), 2.94 (d, J=12.3 Hz, 1H), 2.82 (t, J=11.9 Hz, 1H), 1.90-1.81 (m, 1H), 1.47 (t, J=12.2 Hz, 1H), 1.15 (s, 3H), 1.08 (s, 3H).

Example 67: Synthesis of Compound 216 (8-[(5R)-5-[(2-methoxyethyl)amino]-3,3-dimethylpiperidin-1-yl]quinoxaline-5-carbonitrile)

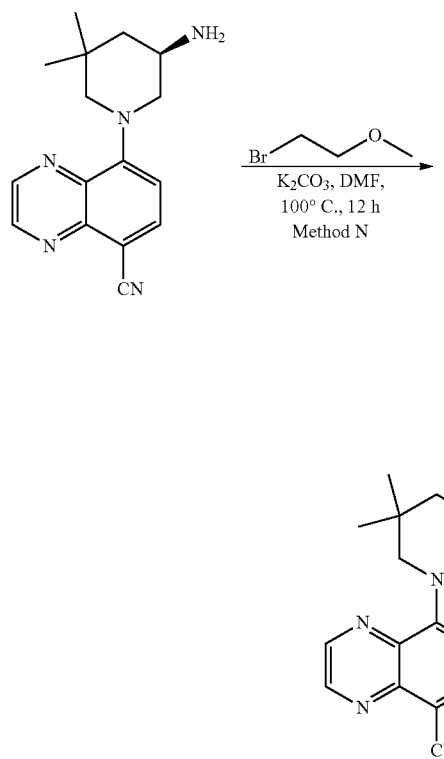

8-[(5R)-5-[(2-methoxyethyl)amino]-3,3-dimethylpiperidin-1-yl]quinoxaline-5-carbonitrile: 8-[(5R)-5-[(2-methoxyethyl)amino]-3,3-dimethylpiperidin-1-yl]quinoxaline-5-carbonitrile was prepared from 3,3-dimethylbutanoic acid and (R)-8-(5-amino-3,3-dimethylpiperidin-1-yl)quinoxaline-5-carbonitrile using Method N. The crude product was purified by prep-HPLC under the following conditions: column, XBridge Prep C18 OBD Column, 5 um, 19 mm×150 mm; mobile phase, acetonitrile in water (with 0.05% $NH_3 \cdot H_2O$), 35% to 65% gradient in 8 min; detector, UV 254 nm. 8-[(5R)-5-[(2-methoxyethyl)amino]-3,3-dimethylpiperidin-1-yl]quinoxaline-5-carbonitrile was obtained as yellow oil (13 mg, 11%).

Compound 216: HPLC: 95.0% purity, RT=2.30 min. MS: m/z=340.2 [M+H]$^+$. $^1$H NMR (400 MHz, $CD_3D$, ppm) δ 8.96-8.86 (m, 2H), 8.09 (d, J=8.4 Hz, 1H), 7.22 (d, J=8.5 Hz, 1H), 4.61-4.52 (m, 1H), 3.93-3.85 (m, 1H), 3.63-3.51 (m, 2H), 3.40 (s, 3H), 3.37-3.30 (m, 1H), 2.98-2.91 (m, 2H), 2.86 (d, J=12.1 Hz, 1H), 2.62 (t, J=11.2 Hz, 1H), 1.96-1.87 (m, 1H), 1.33-1.20 (m, 1H), 1.12 (s, 3H), 1.06 (s, 3H).

The following compounds were synthesized in an analogous manner:

Compound 219 (8-[(5R)-3,3-dimethyl-5-[(1-methyl-2-oxopyrrolidin-3-yl)amino]piperidin-1-yl]quinoxaline-5-carbonitrile): From 2-hydroxyacetamide and (R)-8-(5-amino-3,3-dimethylpiperidin-1-yl)quinoxaline-5-carbonitrile.

HPLC: 96.3% purity, RT=2.46 min. MS: m/z=379.2 [M+H]$^+$. $^1$H NMR (400 MHz, $CD_3OD$, ppm) δ 8.99-8.85 (m, 2H), 8.05 (dd, J=8.3, 0.9 Hz, 1H), 7.20 (dd, J=8.5, 2.1 Hz, 1H), 4.59 (br s, 1H), 3.95-3.81 (m, 1H), 3.70 (t, J=8.7 Hz, 1H), 3.48-3.35 (m, 3H), 2.89-2.80 (m, 4H), 2.67-2.48 (m, 2H), 1.97-1.76 (m, 2H), 1.31-1.18 (m, 1H), 1.11 and 1.06 (s, 6H).

Example 68: Synthesis of Compound 221 (cis-8-[3-[(2-methoxyethyl)amino]-5-(trifluoromethyl)piperidin-1-yl]quinoxaline-5-carbonitrile)

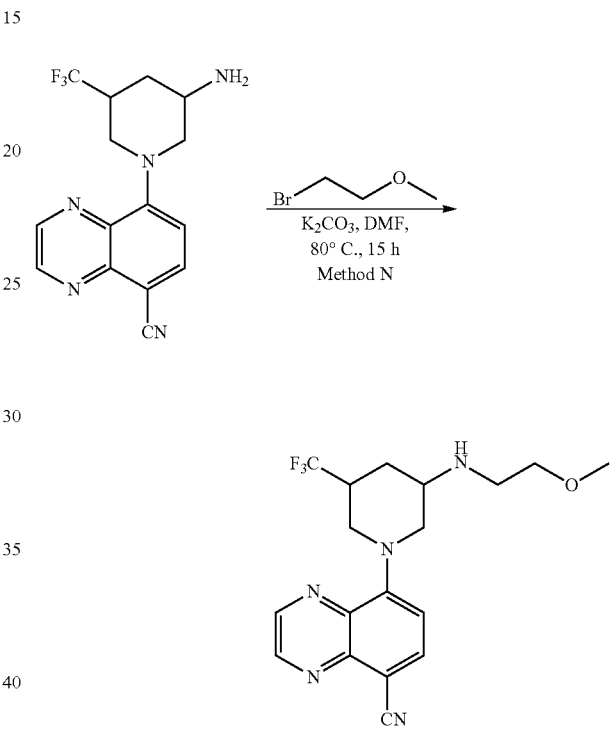

Cis-8-[3-[(2-methoxyethyl)amino]-5-(trifluoromethyl)piperidin-1-yl]quinoxaline-5-carbonitrile: cis-8-[3-[(2-methoxyethyl)amino]-5-(trifluoromethyl)piperidin-1-yl]quinoxaline-5-carbonitrile was prepared from 1-bromo-2-methoxyethane and cis-8-(3-amino-5-(trifluoromethyl)piperidin-1-yl)quinoxaline-5-carbonitrile using Method N. The crude product was purified by prep-HPLC under the following conditions: column, XBridge Prep C18 OBD Column, 5 um, 19 mm×150 mm; mobile phase, acetonitrile in water (with 0.05% $NH_3 \cdot H_2O$), 37% to 57% gradient in 8 min; detector, UV 254 nm. Cis-8-[3-[(2-methoxyethyl)amino]-5-(trifluoromethyl)piperidin-1-yl]quinoxaline-5-carbonitrile was obtained as yellow solid (30 mg, 27%).

Compound 221: HPLC: 99.2% purity, RT=1.37 min. MS: m/z=380.2 [M+H]$^+$. $^1$H NMR (400 MHz, $CD_3OD$, ppm) δ 8.99-8.85 (m, 2H), 8.13 (d, J=8.3 Hz, 1H), 7.28 (d, J=8.4 Hz, 1H), 4.50-4.33 (m, 2H), 3.59-3.47 (m, 2H), 3.36 (s, 3H), 3.13-2.79 (m, 5H), 2.76-2.66 (m, 1H), 2.45-2.37 (m, 1H), 1.43 (td, J=12.1, 12.1 Hz, 1H).

Example 69: Synthesis of Compound 224, Compound 225, Compound 226 and Compound 227 (8-((3R,5S)-3-(((R)-1-methyl-2-oxopyrrolidin-3-yl)amino)-5-(trifluoromethyl)piperidin-1-yl)quinoxaline-5-carbonitrile, 8-((3R,5S)-3-(((S)-1-methyl-2-oxopyrrolidin-3-yl)amino)-5-(trifluoromethyl)piperidin-1-yl)quinoxaline-5-carbonitrile, 8-((3S,5R)-3-(((R)-1-methyl-2-oxopyrrolidin-3-yl)amino)-5-(trifluoromethyl)piperidin-1-yl)quinoxaline-5-carbonitrile and 8-((3S,5R)-3-(((S)-1-methyl-2-oxopyrrolidin-3-yl)amino)-5-(trifluoromethyl)piperidin-1-yl)quinoxaline-5-carbonitrile)

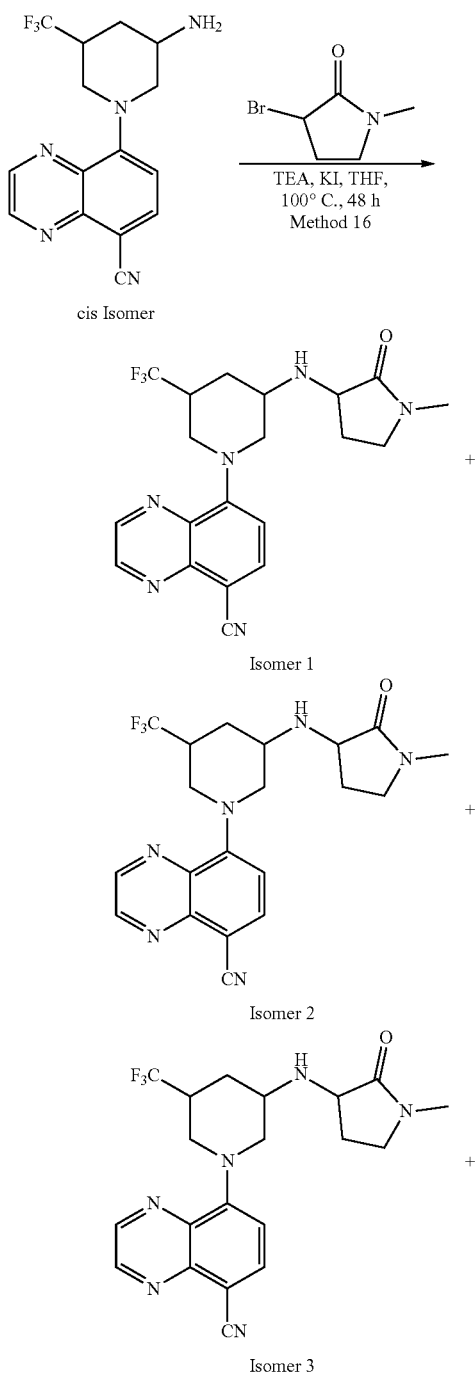

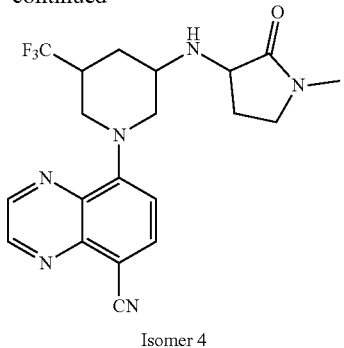

Isomer 4

Method 16

8-((3R,5S)-3-(((R)-1-methyl-2-oxopyrrolidin-3-yl)amino)-5-(trifluoromethyl)piperidin-1-yl)quinoxaline-5-carbonitrile, 8-((3R,5S)-3-(((S)-1-methyl-2-oxopyrrolidin-3-yl)amino)-5-(trifluoromethyl)piperidin-1-yl)quinoxaline-5-carbonitrile, 8-((3S,5R)-3-(((R)-1-methyl-2-oxopyrrolidin-3-yl)amino)-5-(trifluoromethyl)piperidin-1-yl)quinoxaline-5-carbonitrile and 8-((3S,5R)-3-(((S)-1-methyl-2-oxopyrrolidin-3-yl)amino)-5-(trifluoromethyl)piperidin-1-yl)quinoxaline-5-carbonitrile: To a solution of cis-8-[3-amino-5-(trifluoromethyl)piperidin-1-yl]quinoxaline-5-carbonitrile (228 mg, 0.71 mmol) in tetrahydrofuran (2 mL) was added TEA (359.03 mg, 3.55 mmol), KI (353.39 mg, 2.13 mmol), 3-bromo-1-methylpyrrolidin-2-one (377.73 mg, 2.12 mmol) at room temperature. The resulting solution was stirred for 2 days at 100° C. When the reaction was done, it was quenched by the addition of water (15 mL). The resulting mixture was extracted with ethyl acetate (30 mL×3). The organic phases were combined, washed with brine and dried over $Na_2SO_4$. The solvent was removed under reduced pressure and the residue was purified by prep-HPLC under the following conditions: column, XBridge Prep C18 OBD Column, 5 um, 19 mm×150 mm; mobile phase, acetonitrile in water (with 0.05% $NH_3.H_2$), 35% to 65% gradient in 10 min; detector, UV 254 nm. Then the four enantiomers of cis-8-(3-(1-methyl-2-oxopyrrolidin-3-ylamino)-5-(trifluoromethyl)piperidin-1-yl)quinoxaline-5-carbonitrile were obtained by separation on chiral prep-HPLC under the following conditions: column, CHIRAL ADH, 0.46×15 cm, 5 um; mobile phase, EtOH (0.1% DEA) in Hexane, 50% isocratic in 20 min; detector, UV 254 nm. Four products were separated and obtained.

Isomer 1: (25 mg, 8%, yellow solid) HPLC: 98.4% purity, RT=0.90 min. MS: n/z=419.2 [M+H]$^+$. $^1$H NMR (400 MHz, CD$_3$OD, ppm) δ 8.99-8.85 (m, 2H), 8.15 (d, J=8.3 Hz, 1H), 7.31 (d, J=8.4 Hz, 1H), 4.56-4.46 (m, 1H), 4.43-4.33 (m, 1H), 3.71 (t, J=8.7 Hz, 1H), 3.48-3.34 (m, 2H), 3.32-3.25 (m, 1H), 3.09-2.82 (m, 5H), 2.77 (dd, J=11.9, 10.6 Hz, 1H), 2.55-2.39 (m, 2H), 1.93-1.78 (m, 1H), 1.47 (q, J=12.1 Hz, 1H).

Isomer 2: (25 mg, 8%, yellow solid) HPLC: 97.4% purity, RT=1.17 min. MS: m/z=407.2 [M+H]$^+$. $^1$H NMR (400 MHz, Chloroform-d, ppm) δ 8.99 (d, J=1.7 Hz, 1H), 8.85 (d, J=1.8 Hz, 1H), 8.03 (d, J=8.1 Hz, 1H), 7.24 (d, J=8.0 Hz, 1H), 4.56-4.42 (m, 1H), 4.38-4.30 (m, 1H), 4.22-4.06 (m, 1H), 3.82-3.68 (m, 1H), 3.60-3.20 (m, 3H), 3.10-2.40 (m, 8H), 2.15-1.82 (m, 1H), 1.30-1.20 (s, 1H).

Isomer 3: (25 mg, 8%, yellow solid) HPLC: 97.1% purity, RT=0.90 min. MS: m/z=419.2 [M+H]$^+$. $^1$H NMR (400 MHz, CD$_3$OD, ppm) δ 8.99-8.82 (m, 2H), 8.13 (d, J=8.3 Hz, 1H), 7.30 (d, J=8.4 Hz, 1H), 4.49-4.43 (m, 2H), 3.77-3.63 (m 1H), 3.49-3.34 (m, 2H), 3.29-3.01 (m, 1H), 3.07-2.80 (m, 5H), 2.79-2.67 (m, 1H), 2.56-2.36 (m, 2H), 1.93-1.81 (m, 1H), 1.55-1.41 (m, 1H).

Isomer 4: (25 mg, 8%, yellow solid) HPLC: 93.9% purity, RT=0.90 min. MS: m/z=419.2 [M+H]+. 1H NMR (400 MHz, CD3OD, ppm) δ 8.99-8.85 (m, 2H), 8.15 (d, J=8.3 Hz, 1H), 7.31 (d, J=8.4 Hz, 1H), 4.56-4.46 (m, 1H), 4.43-4.33 (m, 1H), 3.71 (t, J=8.7 Hz, 1H), 3.48-3.34 (m, 2H), 3.32-3.25 (m, 1H), 3.09-2.82 (m, 5H), 2.77 (dd, J=11.9, 10.6 Hz, 1H), 2.55-2.39 (m, 2H), 1.93-1.78 (m, 1H), 1.47 (q, J=12.1 Hz, 1H).

The following compounds were synthesized in an analogous manner:

Compound 237 and compound 238 ((R)-1-methyl-3-(((3R,5S)-5-methyl-1-(8-(trifluoromethyl)quinolin-5-yl)piperidin-3-yl)amino)pyrrolidin-2-one and (S)-1-methyl-3-[[(3R,5S)-5-methyl-1-[8-(trifluoromethyl)quinolin-5-yl]piperidin-3-yl]amino]pyrrolidin-2-one): From (3R,5S)-5-methyl-1-[8-(trifluoromethyl)quinolin-5-yl]piperidin-3-amine and 3-bromo-1-methylpyrrolidin-2-one. Isomer 1: 14 mg, 11%, yellow solid) HPLC: 97.0% purity, RT=1.69 min. MS: m/z=407.2 [M+H]+. 1H NMR (400 MHz, CD3OD, ppm) δ 8.92 (dd, J=4.2, 1.7 Hz, 1H), 8.59 (dd, J=8.6, 1.8 Hz, 1H), 8.02 (d, J=8.0 Hz, 1H), 7.60 (dd, J=8.6, 4.2 Hz, 1H), 7.22 (d, J=8.0 Hz, 1H), 3.73-3.59 (m, 2H), 3.43-3.24 (m, 4H), 2.85 (s, 3H), 2.54-2.36 (m, 3H), 2.28-2.18 (m, 1H), 2.15-2.07 (m, 1H), 1.89-1.79 (m, 1H), 1.07-0.92 (m, 4H). Isomer 2: (11 mg, 9%, yellow solid) HPLC: 98.7% purity, RT=1.46 min. MS: m/z=407.2 [M+H]+. 1H NMR (300 MHz, CD3OD, ppm) δ 8.92 (dd, J=4.2, 1.7 Hz, 1H), 8.59 (dd, J=8.6, 1.8 Hz, 1H), 8.02 (d, J=8.0 Hz, 1H), 7.60 (dd, J=8.6, 4.2 Hz, 1H), 7.22 (d, J=8.0 Hz, 1H), 3.73-3.59 (m, 2H), 3.43-3.24 (m, 4H), 2.85 (s, 3H), 2.54-2.36 (m, 3H), 2.28-2.18 (m, 1H), 2.15-2.07 (m, 1H), 1.89-1.79 (m, 1H), 1.07-0.92 (m, 4H).

Example 70: Synthesis of Compound 231 (8-[(3R,5S)-3-[(1-hydroxy-2-methylpropan-2-yl)amino]-5-methylpiperidin-1-yl]quinoxaline-5-carbonitrile)

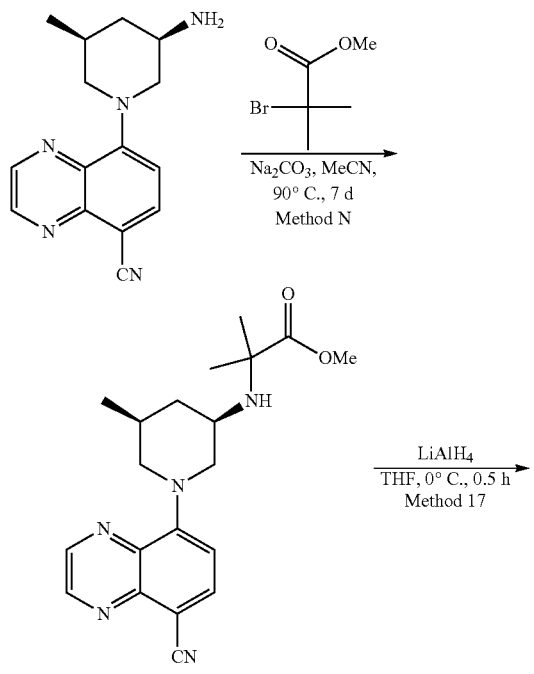

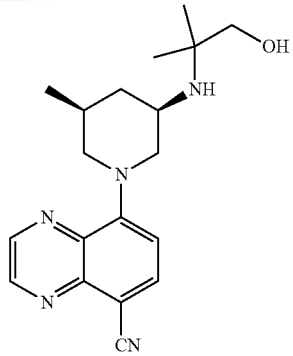

methyl 2-((3R,5S)-1-(8-cyanoquinoxalin-5-yl)-5-methylpiperidin-3-ylamino)-2-methylpropanoate: methyl 2-((3R,5S)-1-(8-cyanoquinoxalin-5-yl)-5-methylpiperidin-3-ylamino)-2-methylpropanoate was prepared from methyl 2-bromo-2-methylpropanoate acid and 8-[(3R,5S)-3-amino-5-methylpiperidin-1-yl]quinoxaline-5-carbonitrile using Method N. The crude product was purified by flash chromatography eluting with MeOHc in DCM (0% to 5% gradient) to yield methyl 2-[[(3R,5S)-1-(8-cyanoquinoxalin-5-yl)-5-methylpiperidin-3-yl]amino]-2-methylpropanoate as yellow solid (190 mg, 61%). MS: m/z=368.2 [M+H]+.

Method 17

8-[(3R,5S)-3-[(1-hydroxy-2-methylpropan-2-yl)amino]-5-methylpiperidin-1-yl]quinoxaline-5-carbonitrile: At 0° C., to a solution of methyl 2-[[(3R)-1-(8-cyanoquinoxalin-5-yl)piperidin-3-yl]amino]-2-methylpropanoate (143 mg, 0.40 mmol) in tetrahydrofuran (5 mL) was added LiAlH4 (14 mg, 0.37 mmol) slowly. The resulting mixture was stirred for 0.5 h at 0° C. When the reaction was done, it was quenched by the addition of water (10 mL). The resulting mixture was extracted with DCM (20 mL×3). The organic phases were combined, washed with brine and dried over Na2SO4. The solvent was removed under reduced pressure and the residue was purified by prep-HPLC under the following conditions: column, XBridge Shield RP18 OBD Column, 5 um, 19 mm×150 mm; mobile phase, acetonitrile in water (with 0.05% NH3.H2O), 32% to 35% gradient in 10 min; detector, UV 254 nm. 8-[(3R,5S)-3-[(1-hydroxy-2-methylpropan-2-yl)amino]-5-methylpiperidin-1-yl]quinoxaline-5-carbonitrile was obtained as yellow solid (15 mg, 11%).

Compound 231: HPLC: 98.9% purity, RT=0.56 min. MS: m/z=340.0 [M+H]+. 1H NMR (400 MHz, CD3OD, ppm) δ 8.94 (d, J=1.7 Hz, 1H), 8.87 (d, J=1.7 Hz, 1H), 8.10 (d, J=8.4 Hz, 1H), 7.21 (d, J=8.4 Hz, 1H), 4.60-4.50 (m, 1H), 3.99-3.90 (m, 1H), 3.48 (d, J=10.8 Hz, 1H), 3.40 (d, J=10.8 Hz, 1H), 3.23-3.11 (m, 1H), 2.64-2.52 (m, 2H), 2.14-1.97 (m, 2H), 1.21-1.01 (m, 10H).

The following compounds were synthesized in an analogous manner:

Compound 242 (2-methyl-2-[[(3R,5S)-5-methyl-1-[8-(trifluoromethyl)quinolin-5-yl]piperidin-3-yl]amino]propan-1-ol): From 2-(morpholin-4-yl)acetic acid and (3R,5S)-5-methyl-1-[8-(trifluoromethyl)quinolin-5-yl]piperidin-3-amine. HPLC: 99.6% purity, RT=1.54 min. MS: m/z=382.2 [M+H]+. 1H NMR (400 MHz, CD3OD, ppm) δ 8.89 (dd, J=4.2, 1.7 Hz, 1H), 8.57 (dd, J=8.6, 1.7 Hz, 1H), 7.99 (d, J=8.0 Hz, 1H), 7.55 (dd, J=8.6, 4.2 Hz, 1H), 7.17 (d, J=8.0 Hz, 1H), 3.50-3.21 (m, 4H), 3.20-3.10 (m, 1H), 2.47-2.32 (m, 2H), 2.17-2.01 (m, 2H), 1.07 (d, J=9.0 Hz, 6H), 0.99-0.95 (m, 4H).

Compound 252 (2-methyl-2-[[(3R,5S)-5-methyl-1-[8-(trifluoromethyl)quinoxalin-5-yl]piperidin-3-yl]amino]propan-1-ol): From 2-(morpholin-4-yl)acetic acid and (3R,5S)-5-methyl-1-(8-(trifluoromethyl)quinoxalin-5-yl)piperidin-3-amine. HPLC: 99.1% purity, RT=1.27 min. MS: m/z=383.1 [M+H]$^+$. $^1$H NMR (300 MHz, DMSO-d$_6$, ppm) δ 9.16-8.86 (m, 2H), 8.05 (d, J=8.5 Hz, 1H), 7.18 (d, J=8.2 Hz, 1H), 4.70-4.47 (m, 1H), 4.23 (d, J=11.8 Hz, 1H), 3.88 (dd, J=11.6, 3.8 Hz, 1H), 3.49-3.10 (m, 5H), 3.09-2.89 (m, 1H), 2.50-2.35 (m, 3H), 2.03-1.87 (m, 2H), 1.15-0.80 (m, 7H).

Example 71: Synthesis of Compound 249 (N-[(3R,5S)-5-methyl-1-[8-(trifluoromethyl)quinoxalin-5-yl]piperidin-3-yl]-2-(morpholin-4-yl)acetamide)

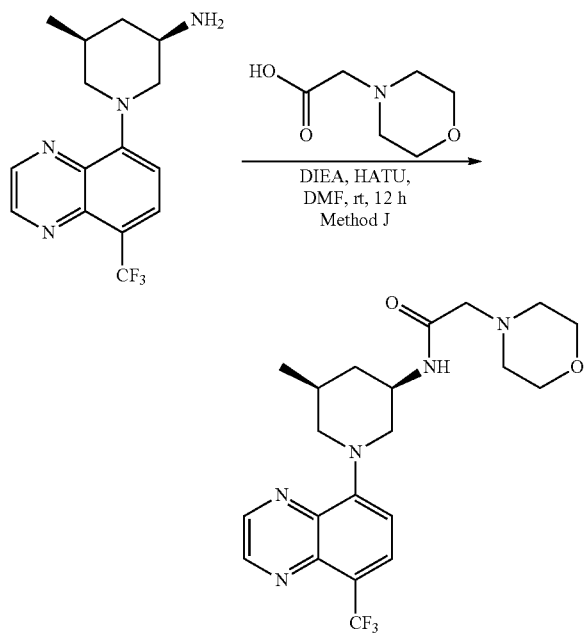

N-[(3R,5S)-5-methyl-1-[8-(trifluoromethyl)quinoxalin-5-yl]piperidin-3-yl]-2-(morpholin-4-yl)acetamide: N-[(3R,5S)-5-methyl-1-[8-(trifluoromethyl)quinoxalin-5-yl]piperidin-3-yl]-2-(morpholin-4-yl)acetamide was prepared from 1-methylpyrrolidine-3-carboxylic acid and (3R,5S)-5-methyl-1-(8-(trifluoromethyl)quinoxalin-5-yl)piperidin-3-amine using Method J. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), 44% to 46% gradient in 8 min; detector, UV 254 nm. N-[(3R,5S)-5-methyl-1-[8-(trifluoromethyl)quinoxalin-5-yl]piperidin-3-yl]-2-(morpholin-4-yl)acetamide was obtained as yellow solid (30 mg, 46%).

Compound 249: HPLC: 99.7% purity, RT=1.40 min. MS: m/z=438.3 [M+H]$^+$. $^1$H NMR (400 MHz, CD$_3$OD, ppm) δ 8.95-8.88 (m, 2H), 8.04 (d, J=8.3 Hz, 1H), 7.29 (d, J=8.3 Hz, 1H), 4.29-4.07 (m, 2H), 4.13-4.05 (m, 1H), 3.74 (apparent t, J=4.6 Hz, 4H), 3.12-2.99 (m, 2H), 2.77 (t, J=10.6 Hz, 1H), 2.65-2.50 (m, 5H), 2.15-2.06 (m, 2H), 1.27 (td, J=12.3, 12.3 Hz, 1H), 1.04 (d, J=6.4 Hz, 3H).

The following compounds were synthesized in an analogous manner:

Compound 250 (2-hydroxy-N-[(3R,5S)-5-methyl-1-[8-(trifluoromethyl)quinoxalin-5-yl]piperidin-3-yl]acetamide): From 2-hydroxyacetic acid and (3R,5S)-5-methyl-1-(8-(trifluoromethyl)quinoxalin-5-yl)piperidin-3-amine. HPLC: 99.0% purity, RT=2.60 min. MS: m/z=369.2 [M+H]$^+$. $^1$H NMR (400 MHz, CD$_3$OD, ppm) δ 8.95-8.88 (m, 2H), 8.05 (d, J=8.3 Hz, 1H), 7.29 (d, J=8.3 Hz, 1H), 4.31-4.23 (m, 1H), 4.18 (dd, J=11.6, 4.3 Hz, 1H), 4.10-4.03 (m, 1H), 3.30-3.20 (m, 2H), 2.84 (dd, J=11.5, 10.4 Hz, 1H), 2.63 (dd, J=12.1, 10.4 Hz, 1H), 2.16-2.10 (m, 2H), 1.33 (td, J=12.1, 12.1 Hz, 1H), 1.05 (d, J=6.4 Hz, 3H).

Compound 251 (1-hydroxy-N-[(3R,5S)-5-methyl-1-[8-(trifluoromethyl)quinoxalin-5-yl]piperidin-3-yl]cyclopropane-1-carboxamide): From 1-hydroxycyclopropanecarboxylic acid and (3R,5S)-5-methyl-1-(8-(trifluoromethyl)quinoxalin-5-yl)piperidin-3-amine. HPLC: 99.8% purity, RT=1.46 min. MS: m/z=395.2 [M+H]$^+$. $^1$H NMR (400 MHz, CD$_3$OD, ppm) δ 8.96-8.85 (q, J=1.7 Hz, 2H), 8.05 (d, J=8.3 Hz, 1H), 7.29 (d, J=8.3 Hz, 1H), 4.28-4.00 (m, 3H), 2.88 (t, J=10.9 Hz, 1H), 2.65 (t, J=12.0 Hz, 1H), 2.18-2.06 (m, 2H), 1.37 (td, J=12.3, 12.3 Hz, 1H), 1.31-1.15 (m, 2H), 1.09-0.96 (m, 5H).

Compound 253 (N-[(3R,5S)-5-methyl-1-[8-(trifluoromethyl)quinoxalin-5-yl]piperidin-3-yl]-2-(1-methylpiperidin-4-yl)acetamide): From 2-(1-methylpiperidin-4-yl)acetic acid and (3R,5S)-5-methyl-1-(8-(trifluoromethyl)quinoxalin-5-yl)piperidin-3-amine. HPLC: 96.5% purity, RT=2.27 min. MS: m/z=450.2 [M+H]$^+$. $^1$H NMR (400 MHz, DMSO-d$_6$, ppm) δ 9.02 (d, J=1.7 Hz, 1H), 8.95 (d, J=1.7 Hz, 1H), 8.06 (d, J=8.4 Hz, 1H), 7.87 (d, J=7.5 Hz, 1H), 7.27 (d, J=8.4 Hz, 1H), 4.21-4.07 (m, 2H), 3.99-3.94 (m, 1H), 2.75-2.50 (m, 4H), 2.12 (s, 3H), 2.03-1.87 (m, 4H), 1.80 (t, J=11.5 Hz, 2H), 1.67-1.50 (m, 3H), 1.23-1.04 (m, 3H), 0.92 (d, J=6.3 Hz, 3H).

Compound 254 (2-(dimethylamino)-N-[(3R,5S)-5-methyl-1-[8-(trifluoromethyl)quinoxalin-5-yl]piperidin-3-yl]acetamide): From 2-(1-methylpiperidin-4-yl)acetic acid and (3R,5S)-5-methyl-1-(8-(trifluoromethyl)quinoxalin-5-yl)piperidin-3-amine. HPLC: 97.4% purity, RT=0.98 min. MS: m/z=396.2 [M+H]$^+$. $^1$H NMR (400 MHz, CD$_3$OD, ppm) δ 8.95-8.88 (m, 2H), 8.04 (d, J=8.3 Hz, 1H), 7.29 (d, J=8.4 Hz, 1H), 4.30-4.16 (m, 2H), 4.11-4.07 (m, 1H), 3.01 (d, J=1.6 Hz, 2H), 2.82-2.71 (m, 1H), 2.60 (dd, J=12.2, 10.6 Hz, 1H), 2.33 (s, 6H), 2.18-2.05 (m, 2H), 1.26 (td, J=12.4, 12.4 Hz, 1H), 1.03 (d, J=6.4 Hz, 3H).

Compound 255 (2-(1,4-dimethylpiperidin-4-yl)-N-[(3R,5S)-5-methyl-1-[8-(trifluoromethyl)quinoxalin-5-yl]piperidin-3-yl]acetamide): From 2-(1-methylpiperidin-4-yl)acetic acid and (3R,5S)-5-methyl-1-(8-(trifluoromethyl)quinoxalin-5-yl)piperidin-3-amine. HPLC: 93.3% purity, RT=5.03 min. MS: m/z=464.5 [M+H]$^+$. $^1$H NMR (300 MHz, CD$_3$OD, ppm) δ 8.95-8.86 (m, 2H), 8.08-7.99 (m, 1H), 7.28 (d, J=8.4 Hz, 1H), 4.28-4.08 (m, 3H), 2.70-2.25 (m, 9H), 2.20-2.04 (m, 4H), 1.80-1.62 (m, 2H), 1.58-1.40 (m, 2H), 1.25-0.90 (m, 7H).

Compound 256 (2-[1-(2,2-difluoroethyl)piperidin-4-yl]-N-[(3R,5S)-5-methyl-1-[8-(trifluoromethyl)quinoxalin-5-yl]piperidin-3-yl]acetamide): From 2-(1-methylpiperidin-4-yl)acetic acid and (3R,5S)-5-methyl-1-(8-(trifluoromethyl)quinoxalin-5-yl)piperidin-3-amine. HPLC: 99.1% purity, RT=2.62 min. MS: m/z=500.3 [M+H]$^+$. $^1$H NMR (400 MHz, CD$_3$OD, ppm) δ 8.95-8.88 (m, 2H), 8.04 (d, J=8.4 Hz, 1H), 7.29 (d, J=8.3 Hz, 1H), 6.15-5.85 (m, 1H), 4.27-4.08 (m, 3H), 3.02-2.94 (m, 2H), 2.82-2.51 (m, 4H), 2.27-2.21 (m, 2H), 2.19-2.05 (m, 4H), 1.85-1.67 (m, 3H), 1.43-1.27 (m, 2H), 1.18 (td, J=12.5, 12.5 Hz, 1H), 1.02 (d, J=6.3 Hz, 3H).

Compound 257 (3,3-difluoro-N-[(3R,5S)-5-methyl-1-[8-(trifluoromethyl)quinoxalin-5-yl]piperidin-3-yl]cyclobutane-1-carboxamide): From 3,3-difluorocyclobutanecarboxylic acid and (3R,5S)-5-methyl-1-(8-(trifluoromethyl)quinoxalin-5-yl)piperidin-3-amine. HPLC: 98.3% purity, RT=1.72 min. MS: n/z=429.2 [M+H]⁺. ¹H NMR (400 MHz, CD₃OD, ppm) δ 8.95-8.89 (m, 2H), 8.05 (d, J=8.3 Hz, 1H), 7.29 (d, J=8.3 Hz, 1H), 4.25-4.10 (m, 3H), 2.97-2.86 (m, 1H), 2.84-2.54 (m, 6H), 2.19-2.03 (m, 2H), 1.17 (td, J=12.3, 12.3 Hz, 1H), 1.02 (d, J=6.3 Hz, 3H).

Compound 258 (1-methyl-N-[(3R,5S)-5-methyl-1-[8-(trifluoromethyl)quinoxalin-5-yl]piperidin-3-yl]pyrrolidine-3-carboxamide): From 3,3-difluorocyclobutanecarboxylic acid and (3R,5S)-5-methyl-1-(8-(trifluoromethyl)quinoxalin-5-yl)piperidin-3-amine. HPLC: 90.4% purity, RT=1.28 min. MS: m/z=422.1 [M+H]⁺. ¹H NMR (400 MHz, CD₃OD, ppm) δ 8.93-8.86 (m, 2H), 8.02 (d, J=8.3 Hz, 1H), 7.27 (d, J=8.3 Hz, 1H), 4.25-4.06 (m, 3H), 3.04-2.89 (m, 2H), 2.82-2.77 (m, 1H), 2.70-2.42 (m, 4H), 2.37 (s, 3H), 2.17-1.96 (m, 4H), 1.16 (td, J=12.4, 12.4 Hz, 1H), 1.00 (d, J=6.4 Hz, 3H).

Compound 259 (N-[(3R,5S)-5-methyl-1-[8-(trifluoromethyl)quinoxalin-5-yl]piperidin-3-yl]-2-(4-methylpiperazin-1-yl)acetamide): From 3,3-difluorocyclobutanecarboxylic acid and (3R,5S)-5-methyl-1-(8-(trifluoromethyl)quinoxalin-5-yl)piperidin-3-amine. HPLC: 97.1% purity, RT=1.38 min. MS: m/z=451.3 [M+H]⁺. ¹H NMR (400 MHz, DMSO-d₆, ppm) δ 9.10-8.95 (m, 2H), 8.07 (d, J=8.3 Hz, 1H), 7.65 (d, J=8.0 Hz, 1H), 7.27 (d, J=8.4 Hz, 1H), 4.17-3.93 (m, 3H), 3.40-3.30 (m, 1H), 3.00-2.85 (m, 2H), 2.78 (t, J=11.1 Hz, 1H), 2.62-2.22 (m, 8H), 2.16 (s, 3H), 1.95 (d, J=11.5 Hz, 2H), 1.26 (td, J=12.3, 12.3 Hz, 1H), 0.94 (d, J=6.3 Hz, 3H).

Compound 292 (2-hydroxy-N-[(3R,5S)-5-methyl-1-[8-(trifluoromethyl)quinoxalin-5-yl]piperidin-3-yl]propanamide): From 2-hydroxypropanoic acid and (3R,5S)-5-methyl-1-(8-(trifluoromethyl)quinoxalin-5-yl)piperidin-3-amine. HPLC: 98.9% purity, RT=2.41 min. MS: m/z=385.2 [M+H]⁺. ¹H NMR (400 MHz, CD₃OD, ppm) δ 8.95-8.86 (m, 2H), 8.05 (d, J=8.3 Hz, 1H), 7.29 (d, J=8.3 Hz, 1H), 4.27-4.05 (m, 4H), 2.83 (t, J=10.8 Hz, 1H), 2.62 (t, J=11.3 Hz, 1H), 2.16-2.06 (m, 2H), 1.41-1.24 (m, 4H), 1.04 (d, J=6.4 Hz, 3H).

Compound 293 (N-[(3R,5S)-5-methyl-1-[8-(trifluoromethyl)quinoxalin-5-yl]piperidin-3-yl]-2-(1-methylpiperidin-3-yl)acetamide): From 2-(1-methylpiperidin-3-yl)acetic acid and (3R,5S)-5-methyl-1-(8-(trifluoromethyl)quinoxalin-5-yl)piperidin-3-amine. HPLC: 99.4% purity, RT=1.03 min. MS: m/z=450.2 [M+H]⁺. ¹H NMR (400 MHz, DMSO-d₆, ppm) δ 9.05-8.95 (m, 2H), 8.06 (d, J=8.4 Hz, 1H), 7.87 (d, J=7.5 Hz, 1H), 7.27 (d, J=8.3 Hz, 1H), 4.25-4.07 (m, 2H), 3.99-3.87 (m, 1H), 2.59-2.40 (m, 4H), 2.10 (s, 3H), 2.02-1.72 (m, 6H), 1.65-1.35 (m, 4H), 1.10 (td, J=12.0, 12.0 Hz, 1H), 0.95-0.78 (m, 4H).

Compound 295 (N-[(3R,5S)-5-methyl-1-[8-(trifluoromethyl)quinoxalin-5-yl]piperidin-3-yl]-2-(1-methylpyrrolidin-3-yl)acetamide): From 2-(1-methylpyrrolidin-3-yl)acetic acid and (3R,5S)-5-methyl-1-(8-(trifluoromethyl)quinoxalin-5-yl)piperidin-3-amine. HPLC: 92.1% purity, RT=4.92 min. MS: m/z=436.1 [M+H]⁺. ¹H NMR (400 MHz, DMSO-d₆, ppm) δ 9.03 (d, J=1.7 Hz, 1H), 8.97 (d, J=1.7 Hz, 1H), 8.07 (d, J=8.4 Hz, 1H), 7.89 (d, J=7.6 Hz, 1H), 7.28 (d, J=8.4 Hz, 1H), 4.22-4.07 (m, 2H), 3.99-3.85 (m, 1H), 2.70-2.30 (m, 9H), 2.18-2.02 (m, 3H), 2.00-1.80 (m, 3H), 1.42-1.29 (m, 1H), 1.20-1.04 (m, 1H), 0.93 (d, J=6.3 Hz, 3H).

Compound 299 (2-(3,3-difluoroazetidin-1-yl)-N-[(3R,5S)-5-methyl-1-[8-(trifluoromethyl)quinoxalin-5-yl]piperidin-3-yl]propanamide): From 2-(3,3-difluoroazetidin-1-yl)propanoic acid and (3R,5S)-5-methyl-1-(8-(trifluoromethyl)quinoxalin-5-yl)piperidin-3-amine. HPLC: 94.2% purity, RT=2.63 min. MS: m/z=458.2 [M+H]⁺. ¹H NMR (400 MHz, CD₃OD, ppm) δ 8.92-8.88 (m, 2H), 8.02 (d, J=8.3 Hz, 1H), 7.27 (d, J=8.3 Hz, 1H), 4.20-4.06 (m, 3H), 3.76-3.59 (m, 4H), 3.14-3.02 (m, 1H), 2.81-2.70 (m, 1H), 2.61-2.55 (m, 1H), 2.14-1.99 (m, 2H), 1.32-1.18 (m, 4H), 1.01 (d, J=6.4 Hz, 3H).

Example 72: Synthesis of Compound 260 and Compound 261 ((R)-3-(((3R,5S)-1-(8-chloroquinolin-5-yl)-5-methylpiperidin-3-yl)amino)-1-methylpyrrolidin-2-one and (S)-3-[[(3R,5S)-1-(8-chloroquinolin-5-yl)-5-methylpiperidin-3-yl]amino]-1-methylpyrrolidin-2-one)

(R)-3-(((3R,5S)-1-(8-chloroquinolin-5-yl)-5-methylpiperidin-3-yl)amino)-1-methylpyrrolidin-2-one and (S)-3-[[(3R,5S)-1-(8-chloroquinolin-5-yl)-5-methylpiperidin-3-yl]amino]-1-methylpyrrolidin-2-one: 3-[[(3R,5S)-1-(8-chloroquinolin-5-yl)-5-methylpiperidin-3-yl]amino]-1-methylpyrrolidin-2-one was prepared from (3R,5S)-1-(8-chloroquinolin-5-yl)-5-methylpiperidin-3-amine and 3-bromo-1-methylpyrrolidin-2-one using Method 16. The crude product was first purified by prep-HPLC under the following conditions: column, XBridge Prep C18 OBD Column, 19×150 mm 10 um; mobile phase, acetonitrile in water (with 0.05% NH₃.H₂O), 20% to 55% gradient in 8 min; detector, UV 254 nm. Then the two diastereoisomers of 3-[[(3R,5S)-1-(8-chloroquinolin-5-yl)-5-methylpiperidin-3-yl]amino]-1-methylpyrrolidin-2-one were obtained by separation on chiral prep-HPLC under the following conditions: column, Chiral PAK ID-3, 0.46×10 cm, 3 um; mobile phase, EtOH in Hexane, 50% isocratic in 12 min; detector, UV 254/220 nm.

Isomer 1: (30 mg, 15%, light yellow solid) HPLC: 99.4% purity, RT=1.26 min. MS: m/z=373.2 [M+H]$^+$. $^1$H NMR (400 MHz, CD$_3$OD, ppm) δ 8.96 (d, J=4.3 Hz, 1H), 8.72-8.65 (m, 1H), 7.86 (d, J=8.1 Hz, 1H), 7.67 (dd, J=8.5, 4.3 Hz, 1H), 7.28 (d, J=8.1 Hz, 1H), 4.09 (t, J=9.1 Hz, 1H), 3.83-3.64 (m, 2H), 3.54-3.40 (m, 2H), 3.40-3.25 (m, 1H), 2.92 (s, 3H), 2.71 (t, J=10.5 Hz, 1H), 2.56 (dt, J=12.7, 6.9 Hz, 1H), 2.46 (t, J=11.3 Hz, 1H), 2.34 (d, J=12.4 Hz, 1H), 2.26-2.14 (m, 1H), 2.13-1.97 (m, 1H), 1.21 (td, J=12.0, 12.0 Hz, 1H), 1.07 (d, J=6.5 Hz, 3H).

Isomer 2: (30 mg, 15%, light yellow solid) HPLC: 99.1% purity, RT=0.98 min. MS: m/z=373.2 [M+H]$^+$. $^1$H NMR (300 MHz, CD$_3$OD, ppm) δ 8.96 (d, J=4.3 Hz, 1H), 8.72-8.65 (m, 1H), 7.86 (d, J=8.1 Hz, 1H), 7.67 (dd, J=8.5, 4.3 Hz, 1H), 7.28 (d, J=8.1 Hz, 1H), 4.09 (t, J=9.1 Hz, 1H), 3.83-3.64 (m, 2H), 3.54-3.40 (m, 2H), 3.40-3.25 (m, 1H), 2.92 (s, 3H), 2.71 (t, J=10.5 Hz, 1H), 2.56 (dt, J=12.7, 6.9 Hz, 1H), 2.46 (t, J=11.3 Hz, 1H), 2.34 (d, J=12.4 Hz, 1H), 2.26-2.14 (m, 1H), 2.13-1.97 (m, 1H), 1.21 (td, J=12.0, 12.0 Hz, 1H), 1.07 (d, J=6.5 Hz, 3H).

Example 73: Synthesis of Compound 262 (N-[(3R,5S)-1-(8-chloroquinolin-5-yl)-5-methylpiperidin-3-yl]-2-(morpholin-4-yl)acetamide)

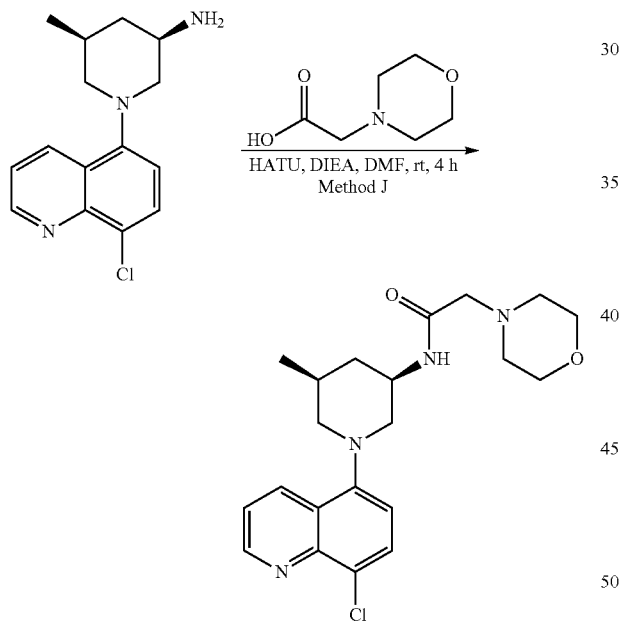

N-[(3R,5S)-1-(8-chloroquinolin-5-yl)-5-methylpiperidin-3-yl]-2-(morpholin-4-yl)acetamide: N-[(3R,5S)-1-(8-chloroquinolin-5-yl)-5-methylpiperidin-3-yl]-2-(morpholin-4-yl)acetamide was prepared from 3,3-difluorocyclobutanecarboxylic acid and (3R,5S)-1-(8-chloroquinolin-5-yl)-5-methylpiperidin-3-aminee using Method J. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), 20% to 39% (hold 39.0% in 7 min) gradient in 10 min; detector, UV 254 nm. N-[(3R,5S)-1-(8-chloroquinolin-5-yl)-5-methylpiperidin-3-yl]-2-(morpholin-4-yl)acetamide was obtained as light yellow solid (30 mg, 30%).

Compound 262: HPLC: 99.8% purity, RT=1.43 min. MS: m/z=403.2 [M+H]$^+$. $^1$H NMR (400 MHz, CD$_3$OD, ppm) δ 8.93 (dd, J=4.2, 1.7 Hz, 1H), 8.71 (dd, J=8.5, 1.7 Hz, 1H), 7.81 (d, J=7.8 Hz, 1H), 7.65 (dd, J=8.5, 4.2 Hz, 1H), 7.20 (d, J=8.2 Hz, 1H), 4.31-4.24 (m, 1H), 3.73 (t, J=4.6 Hz, 4H), 3.54-3.44 (m, 1H), 3.32-3.23 (m, 1H), 3.04 (s, 2H), 2.59-2.40 (m, 6H), 2.23-2.03 (m, 2H), 1.21 (td, J=12.0, 12.0 Hz, 1H), 1.04 (d, J=6.5 Hz, 3H).

The following compounds were synthesized in an analogous manner:

Compound 263 (N-[(3R,5S)-1-(8-chloroquinolin-5-yl)-5-methylpiperidin-3-yl]-2-hydroxyacetamide): From 2-hydroxyacetic acid and (3R,5S)-1-(8-chloroquinolin-5-yl)-5-methylpiperidin-3-amine. HPLC: 99.9% purity, RT=1.25 min. MS: m/z=334.2 [M+H]$^+$. $^1$H NMR (400 MHz, CD$_3$OD, ppm) δ 8.93 (dd, J=4.2, 1.6 Hz, 1H), 8.71 (dd, J=8.5, 1.6 Hz, 1H), 7.81 (d, J=8.1 Hz, 1H), 7.65 (dd, J=8.5, 4.2 Hz, 1H), 7.20 (d, J=8.1 Hz, 1H), 4.35-4.27 (m, 1H), 3.99 (s, 2H), 3.52-3.43 (m, 1H), 3.31-3.25 (m, 1H), 2.58 (t, J=10.8 Hz, 1H), 2.45 (t, J=11.1 Hz, 1H), 2.24-2.07 (m, 2H), 1.24 (td, J=12.0, 12.0 Hz, 1H), 1.04 (d, J=6.5 Hz, 3H).

Compound 264 (N-[(3R,5S)-1-(8-chloroquinolin-5-yl)-5-methylpiperidin-3-yl]-2-(dimethylamino)acetamide): From 2-hydroxyacetic acid and (3R,5S)-1-(8-chloroquinolin-5-yl)-5-methylpiperidin-3-amine. HPLC: 99.4% purity, RT=1.50 min. MS: m/z=361.2 [M+H]$^+$. $^1$H NMR (300 MHz, CD$_3$OD, ppm) δ 8.91 (dd, J=4.3, 1.7 Hz, 1H), 8.74-8.64 (m, 1H), 7.79 (dd, J=8.3, 0.8 Hz, 1H), 7.62 (dd, J=8.5, 4.2 Hz, 1H), 7.23-7.13 (m, 1H), 4.29-4.20 (m, 1H), 3.48-3.43 (m, 1H), 3.27-3.22 (m, 1H), 2.97 (s, 2H), 2.51 (t, J=10.8 Hz, 1H), 2.42 (t, J=11.2 Hz, 1H), 2.28 (s, 6H), 2.17-2.06 (m, 2H), 1.17 (td, J=12.2, 12.2 Hz, 1H), 1.02 (d, J=6.4 Hz, 3H).

Example 74: Synthesis of Compound 267 (2-(3-aminoazetidin-1-yl)-N-[(3R,5S)-1-(8-cyanoquinoxalin-5-yl)-5-methylpiperidin-3-yl]propanamide)

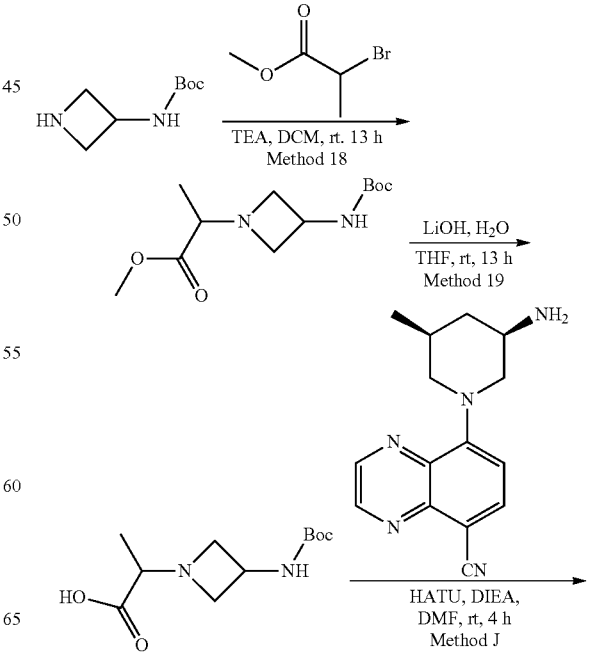

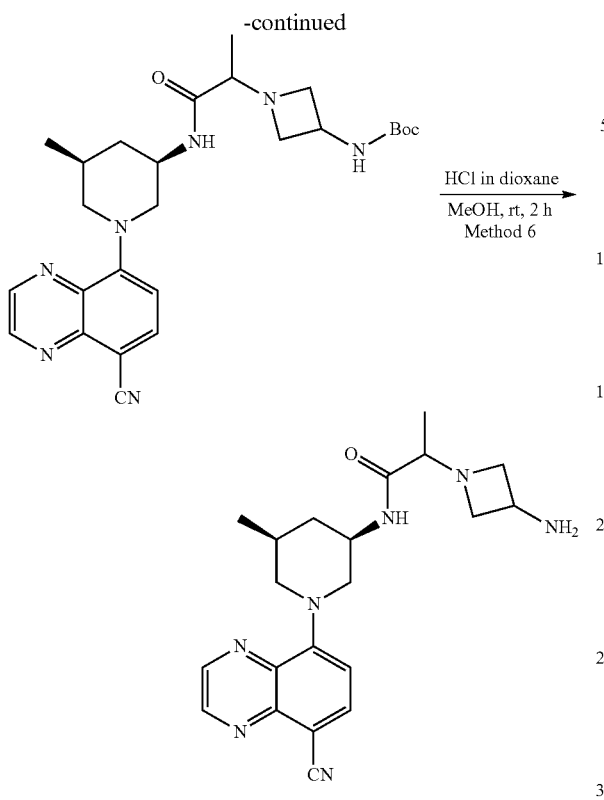

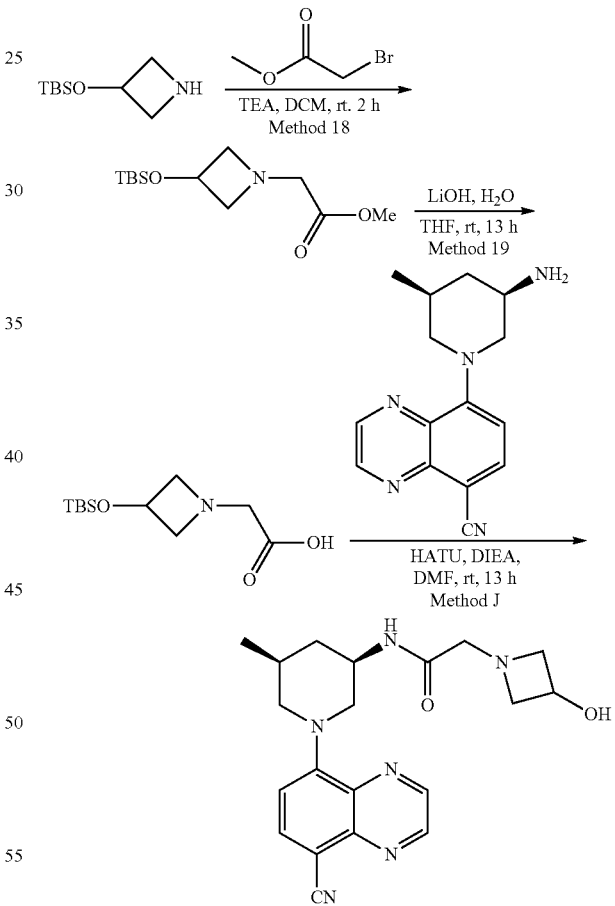

Method 18

Ethyl 2-(3-[[(tert-butoxy)carbonyl]amino]azetidin-1-yl)propanoate: To a solution of tert-butyl N-(azetidin-3-yl)carbamate (475 mg, 2.76 mmol) in DCM (40 m) was added triethylamine (418 mg, 4.14 mmol) and ethyl 2-bromopropanoate (749 mg, 4.14 mmol) at room temperature. The resulting solution was stirred for 13 h at room temperature. When the reaction was done, it was quenched by the addition of water (10 mL). The resulting solution was extracted with ethyl acetate (30 mL×3). The organic phases were combined, washed with brine and dried over $Na_2SO_4$. The solvent was removed under reduced pressure and the residue was purified by flash chromatography eluting with EtOAc in hexane (0% to 50% gradient) to yield ethyl 2-(3-[[(tert-butoxy)carbonyl]amino]azetidin-1-yl)propanoate as yellow oil (330 mg, 44%). MS: m/z=259.3 [M+H]$^+$.

Method 19

Ethyl 2-(3-[[(tert-butoxy)carbonyl]amino]azetidin-1-yl): To a solution of ethyl 2-(3-[[(tert-butoxy)carbonyl]amino]azetidin-1-yl)propanoate (475 mg, 1.74 mmo) in THF (5 mL) was added a solution of LiOH (125 mg) in water (15 mL) at room temperature. The resulting mixture was then stirred for 13 h at room temperature. When the reaction was done, the pH value of the reaction mixture was adjusted to 5 with hydrogen chloride solution (2 M). The resulting mixture was extracted with DCM (50 mL×3). The organic phases were combined, washed with brine and dried over $Na_2SO_4$. The solvent was removed under reduced pressure to yield 2-(3-[[(tert-butoxy)carbonyl]amino]azetidin-1-yl)propanoic acid as a white solid (300 mg, 70%). MS: m/z=245.1 [M+H]$^+$ 2-(3-aminoazetidin-1-yl)-N-[(3R,5S)-1-(8-cyanoquinoxalin-5-yl)-5-methylpiperidin-3-yl]propanamide: 2-(3-aminoazetidin-1-yl)-N-[(3R,5S)-1-(8-cyanoquinoxalin-5-yl)-5-methylpiperidin-3-yl]propanamide was prepared from 2-(3-(tert-butoxycarbonylamino)azetidin-1-yl)propanoic acid and 8-((3R,5S)-3-amino-5-methylpiperidin-1-yl)quinoxaline-5-carbonitrile using Method J and 6. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 24% to 31% gradient in 6 min; detector, UV 254 nm. 2-(3-aminoazetidin-1-yl)-N-[(3R,5S)-1-(8-cyanoquinoxalin-5-yl)-5-methylpiperidin-3-yl]propanamide was obtained as yellow solid (24 mg, 17% for 2 steps).

Compound 267: HPLC: 95.6% purity, RT=1.27 min. MS: m/z=394.3 [M+H]$^+$. $^1$H NMR (300 MHz, $CD_3OD$, ppm) δ 8.95-8.85 (m, 2H), 8.09 (d, J=8.4 Hz, 1H), 7.28 (d, J=8.5 Hz, 1H), 4.35-4.05 (m, 3H), 3.66-3.50 (m, 3H), 2.96-2.65 (m, 5H), 2.07 (d, J=11.9 Hz, 2H), 1.33-1.22 (m, 1H), 1.16 (d, J=6.7 Hz, 3H), 1.02 (d, J=6.3 Hz, 3H).

Example 75: Synthesis of Compound 270 ((3R,5S)-1-(8-cyanoquinoxalin-5-yl)-5-methylpiperidin-3-yl 2-(3-hydroxyazetidin-1-yl)acetate)

(3R,5S)-1-(8-cyanoquinoxalin-5-yl)-5-methylpiperidin-3-yl 2-(3-hydroxyazetidin-1-yl)acetate: (3R,5S)-1-(8-cyanoquinoxalin-5-yl)-5-methylpiperidin-3-yl 2-(3-hydroxyazetidin-1-yl)acetate was prepared from 3-(tert-butyldimethylsilyloxy)azetidine, methyl 2-bromoacetate and 8-((3R,5S)-3-amino-5-methylpiperidin-1-yl)quinoxaline-5-carbonitrile using Method 18, 19, and J. The crude product was purified by prep-HPLC under the following conditions: column, XBridge Shield RP18 OBD Column, 5 um, 19 mm×150 mm; mobile phase, acetonitrile in water (with 0.05% NH$_3$.H$_2$O), 28% to 32% gradient in 7 min; detector, UV 254 nm. (3R,5S)-1-(8-cyanoquinoxalin-5-yl)-5-methylpiperidin-3-yl 2-(3-hydroxyazetidin-1-yl)acetate was obtained as yellow solid (22 mg, 10% for 3 steps).

Compound 270: HPLC: 97.7% purity, RT=2.43 min. MS: m/z=381.2 [M+H]$^+$. $^1$H NMR (400 MHz, CD$_3$OD, ppm) δ 8.95-8.85 (m, 2H), 8.08 (d, J=8.4 Hz, 1H), 7.26 (d, J=8.4 Hz, 1H), 4.42-4.21 (m, 3H), 4.19-4.07 (m, 1H), 3.77-3.68 (m, 2H), 3.18 (d, J=1.1 Hz, 2H), 3.08-2.99 (m, 2H), 2.87-2.76 (m, 1H), 2.72-2.60 (m, 1H), 2.12-1.96 (m, 2H), 1.26 (td, J=12.1, 12.1 Hz, 1H), 1.01 (d, J=6.3 Hz, 3H).

The following compounds were synthesized in an analogous manner:

Compound 271 ((3R,5S)-1-(8-cyanoquinoxalin-5-yl)-5-methylpiperidin-3-yl 2-(3-hydroxyazetidin-1-yl)propanoate): From 3-(tert-butyldimethylsilyloxy)azetidine, ethyl 2-bromopropanoate and 8-((3R,5S)-3-amino-5-methylpiperidin-1-yl)quinoxaline-5-carbonitrile. HPLC: 96.9% purity, RT=1.06 min. MS: m/z=395.2 [M+H]$^+$. $^1$H NMR (400 MHz, CD$_3$OD, ppm) δ 8.95-8.85 (m, 2H), 8.09 (d, J=8.4 Hz, 1H), 7.27 (dd, J=8.4, 1.1 Hz, 1H), 4.39-4.23 (m, 3H), 4.18-4.07 (m, 1H), 3.66-3.60 (m, 2H), 3.01-2.76 (m, 4H), 2.73-2.62 (m, 1H), 2.08-2.03 (m, 1H), 1.36-1.20 (m, 1H), 1.16 (d, J=6.8 Hz, 3H), 1.01 (d, J=6.4 Hz, 3H).

Compound 273 (N-[(3R,5S)-1-(8-cyanoquinoxalin-5-yl)-5-methylpiperidin-3-yl]-2-(3,3-difluoroazetidin-1-yl)propanamide): From 3,3-difluoroazetidine, ethyl 2-bromopropanoate and 8-((3R,5S)-3-amino-5-methylpiperidin-1-yl)quinoxaline-5-carbonitrile. HPLC: 97.0% purity, RT=1.50 min. MS: m/z=415.2 [M+H]$^+$. $^1$H NMR (400 MHz, CD$_3$OD, ppm) δ 8.99-8.85 (m, 2H), 8.09 (d, J=8.4 Hz, 1H), 7.27 (d, J=8.4 Hz, 1H), 4.34-4.21 (m, 2H), 4.20-4.06 (m, 1H), 3.77-3.58 (m, 4H), 3.12-3.02 (m, 1H), 2.90-2.78 (m, 1H), 2.74-2.62 (m, 1H), 2.11-1.98 (m, 2H), 1.37-1.18 (m, 4H), 1.01 (d, J=6.4 Hz, 3H).

Compound 275 (N-[(3R,5S)-1-(8-cyanoquinoxalin-5-yl)-5-methylpiperidin-3-yl]-2-(4-hydroxypiperidin-1-yl)propanamide): From piperidin-4-ol, ethyl 2-bromopropanoate, and 8-((3R,5S)-3-amino-5-methylpiperidin-1-yl)quinoxaline-5-carbonitrile. HPLC: 96.7% purity, RT=1.82 and 1.86 min. MS: m/z=423.2 [M+H]$^+$. $^1$H NMR (300 MHz, CD$_3$OD, ppm) δ 8.99-8.85 (m, 2H), 8.09 (d, J=8.4 Hz, 1H), 7.28 (dd, J=8.4, 1.8 Hz, 1H), 4.39-4.10 (m, 3H), 3.62 (dd, J=9.2, 4.9 Hz, 1H), 3.15-2.98 (m, 1H), 2.90-2.63 (m, 4H), 2.42-2.19 (m, 2H), 2.15-1.80 (m, 4H), 1.56 (d, J=9.7 Hz, 2H), 1.36-1.19 (m, 4H), 1.02 (d, J=6.3 Hz, 3H).

Compound 284 ((3R,5S)-5-methyl-1-[8-(trifluoromethyl)quinolin-5-yl]piperidin-3-yl 2-(3-hydroxyazetidin-1-yl)acetate): From 2-(3-(tert-butyldimethylsilyloxy)azetidin-1-yl) acetic acid. HPLC: 99.9% purity, RT=1.32 min. MS: m/z=423.2 [M+H]$^+$. $^1$H NMR (400 MHz, CD$_3$OD, ppm) δ 8.91 (dd, J=4.2, 1.7 Hz, 1H), 8.63 (dd, J=8.6, 1.8 Hz, 1H), 8.01 (d, J=8.1 Hz, 1H), 7.60 (dd, J=8.6, 4.2 Hz, 1H), 7.21 (d, J=8.1 Hz, 1H), 4.40-4.16 (m, 2H), 3.74-3.65 (m, 2H), 3.61-3.52 (m, 1H), 3.41-3.32 (m, 1H), 3.15 (s, 2H), 3.01 (dd, J=8.2, 6.0 Hz, 2H), 2.60-2.40 (m, 2H), 2.20-2.05 (m, 2H), 1.19 (td, J=12.0, 12.0 Hz, 1H), 1.02 (d, J=6.4 Hz, 3H).

Compound 285 (2-(3-hydroxyazetidin-1-yl)-N-[(3R,5S)-5-methyl-1-[8-(trifluoromethyl)quinolin-5-yl]piperidin-3-yl]propanamide): From 2-(3-(tert-butyldimethylsilyloxy) azetidin-1-yl)propanoic acid and (3R,5S)-5-methyl-1-(8-(trifluoromethyl)quinolin-5-yl)piperidin-3-amine. HPLC: 98.2% purity, RT=3.41 min. MS: m/z=437.2 [M+H]$^+$. $^1$H NMR (400 MHz, CD$_3$OD, ppm) δ 8.94 (dd, J=4.3, 1.7 Hz, 1H), 8.69-8.62 (m, 1H), 8.04 (d, J=8.3 Hz, 1H), 7.63 (dd, J=8.6, 4.2 Hz, 1H), 7.23 (d, J=8.0 Hz, 1H), 4.38-4.31 (m, 1H), 4.25 (dd, J=11.7, 4.7 Hz, 1H), 3.62 (d, J=6.4 Hz, 3H), 3.39 (d, J=12.0 Hz, 1H), 2.95 (dt, J=23.0, 6.3 Hz, 3H), 2.62-2.42 (m, 2H), 2.11-2.16 (m, 2H), 1.28-1.12 (m, 4H), 1.08-1.01 (m, 3H).

Compound 296 (2-(3-hydroxyazetidin-1-yl)-N-[(3R,5S)-5-methyl-1-[8-(trifluoromethyl)quinoxalin-5-yl]piperidin-3-yl]acetamide): From 2-(3-(tert-butyldimethylsilyloxy)azetidin-1-yl)acetic acid and (3R,5S)-5-methyl-1-(8-(trifluoromethyl)quinoxalin-5-yl)piperidin-3-amine. HPLC: 99.1% purity, RT=1.26 min. MS: m/z=424.2 [M+H]$^+$. $^1$H NMR (400 MHz, CD$_3$OD, ppm) δ 8.92-8.85 (m, 2H), 8.02 (d, J=8.4 Hz, 1H), 7.29-7.22 (m, 1H), 4.34 (tt, J=6.1, 6.1 Hz, 1H), 4.21-416 (m, 2H), 4.08-4.05 (m, 1H), 3.71 (dd, J=8.4, 6.2 Hz, 2H), 3.17 (s, 2H), 3.05-3.01 (m, 2H), 2.78-2.67 (m, 1H), 2.57 (t, J=11.4 Hz, 1H), 2.09-2.05 (m, 2H), 1.22 (td, J=12.7, 11.8 Hz, 1H), 1.01 (d, J=6.4 Hz, 3H).

Compound 297 ((3R,5S)-5-methyl-1-[8-(trifluoromethyl)quinoxalin-5-yl]piperidin-3-yl 2-(3-hydroxyazetidin-1-yl)propanoate): From 2-(3-(tert-butyldimethylsilyloxy)azetidin-1-yl)propanoic acid and (3R,5S)-5-methyl-1-(8-(trifluoromethyl)quinoxalin-5-yl)piperidin-3-amine. HPLC: 93.0% purity, RT=3.18 min. MS: m/z=438.2 [M+H]$^+$. $^1$H NMR (400 MHz, CD$_3$OD, ppm) δ 8.95-8.88 (m, 2H), 8.04 (d, J=8.3 Hz, 1H), 7.29 (d, J=8.3 Hz, 1H), 4.38-4.34 (m, 1H), 4.20-4.06 (m, 3H), 3.69-3.60 (m, 2H), 3.00-2.82 (m, 3H), 2.76-2.74 (m, 1H), 2.59 (t, J=11.7 Hz, 1H), 2.18-2.04 (m, 2H), 1.33-1.14 (m, 4H), 1.03 (d, J=6.5 Hz, 3H).

Compound 308 (N-[(3R,5S)-1-[8-(difluoromethyl)quinolin-5-yl]-5-methylpiperidin-3-yl]-2-(3-hydroxyazetidin-1-yl)acetamide): From 2-(3-(tert-butyldimethylsilyloxy)azetidin-1-yl)acetic acid and (3R,5S)-1-(8-(difluoromethyl)quinolin-5-yl)-5-methylpiperidin-3-amine. HPLC: 97.9% purity, RT=2.52 min. MS: n/z=405.2 [M+H]$^+$. $^1$H NMR (400 MHz, CD$_3$OD, ppm) δ 8.89 (dd, J=4.2, 1.7 Hz, 1H), 8.61 (dd, J=8.6, 1.8 Hz, 1H), 7.93 (d, J=8.0 Hz, 1H), 7.83-7.55 (m, 2H), 7.25 (d, J=7.9 Hz, 1H), 4.40-4.30 (m, 1H), 4.27-4.18 (m, 1H), 3.74-3.65 (m, 2H), 3.58-3.49 (m, 1H), 3.35-3.20 (m, 1H), 3.15 (s, 2H), 3.05-2.96 (m, 2H), 2.58-2.38 (m, 2H), 2.18-2.02 (m, 2H), 1.17 (td, J=12.0, 12.0 Hz, 1H), 1.03 (d, J=6.5 Hz, 3H).

Compound 309 (N-[(3R,5S)-1-[8-(difluoromethyl)quinolin-5-yl]-5-methylpiperidin-3-yl]-2-(3-hydroxyazetidin-1-yl)propanamide): From 2-(3-(tert-butyldimethylsilyloxy) azetidin-1-yl)propanoic acid and (3R,5S)-1-(8-(difluoromethyl)quinolin-5-yl)-5-methylpiperidin-3-amine. HPLC: 95.7% purity, RT=2.47 min. MS: m/z=419.2 [M+H]$^+$. $^1$H NMR (400 MHz, CD$_3$OD, ppm) δ 8.89 (dd, J=4.2, 1.7 Hz, 1H), 8.61 (dt, J=8.6, 1.7 Hz, 1H), 7.93 (d, J=8.0 Hz, 1H), 7.85-7.55 (m, 2H), 7.26 (d, J=7.9 Hz, 1H), 4.36-4.28 (m, 1H), 4.26-4.17 (m, 1H), 3.62-3.55 (m, 2H), 3.55-3.48 (m, 1H), 3.39-3.20 (m, 1H), 2.94-2.85 (m, 3H), 2.56-2.41 (m, 2H), 2.20-2.04 (m, 2H), 1.23-1.13 (m, 4H), 1.03 (d, J=6.5 Hz, 3H).

Compound 320 (N-[(3R,5S)-1-[8-(difluoromethyl)quinoxalin-5-yl]-5-methylpiperidin-3-yl]-2-(3-hydroxyazetidin-1-yl)acetamide): From 2-[3-[(tert-butyldimethylsilyl)oxy]azetidin-1-yl]acetic acid and (3R,5S)-1-[8-(difluoromethyl)quinoxalin-5-yl]-5-methylpiperidin-3-amine. HPLC: 91.1% purity, RT=2.97 min. MS: m/z=406.2 [M+H]$^+$. $^1$H NMR (400 MHz, CD$_3$OD, ppm) δ 8.90-8.82 (m, 2H), 7.96 (d, J=8.2 Hz, 1H), 7.63 (t, J=55.6 Hz, 1H), 7.33 (d, J=8.1 Hz, 1H), 4.40-4.30 (m, 1H), 4.25-4.15 (m, 1H), 4.09 (dd, J=11.4, 4.1 Hz, 1H), 3.98 (d, J=12.0 Hz, 1H), 3.74-3.70 (m, 2H), 3.17 (s, 2H), 3.05-3.01 (m, 2H), 2.69 (t, J=11.0 Hz, 1H), 2.53 (t, J=11.4 Hz, 1H), 2.18-2.04 (m, 2H), 1.22-1.18 (m, 1H), 1.01 (d, J=6.4 Hz, 3H).

Compound 321 (N-[(3R,5S)-1-[8-(difluoromethyl)quinoxalin-5-yl]-5-methylpiperidin-3-yl]-2-(3-hydroxyazetidin-1-yl)propanamide): From 2-[3-[(tert-butyldimethylsilyl)oxy]azetidin-1-yl]propanoic acid and (3R,5S)-1-[8-(difluoromethyl)quinoxalin-5-yl]-5-methylpiperidin-3-amine. HPLC: 94.2% purity, RT=1.24 min. MS: m/z=420.3 [M+H]$^+$. $^1$H NMR (400 MHz, CD$_3$OD, ppm) δ 8.91-8.80 (m, 2H), 8.00-7.92 (m, 1H), 7.63 (t, J=55.9 Hz, 1H), 7.33 (d, J=8.2 Hz, 1H), 4.36-4.30 (m, 1H), 4.22-4.16 (m, 1H), 4.11-3.95 (m, 2H), 3.66-3.60 (m, 2H), 3.00-2.85 (m, 3H), 2.72-2.65 (m, 1H), 2.52 (t, J=11.5 Hz, 1H), 2.09 (m, 2H), 1.31-1.13 (m, 4H), 1.01 (d, J=6.4 Hz, 3H).

Example 76: Synthesis of Compound 272 (N-[(3R,5S)-1-(8-cyanoquinoxalin-5-yl)-5-methylpiperidin-3-yl]-2-(2,2-difluorocyclopropyl)acetamide)

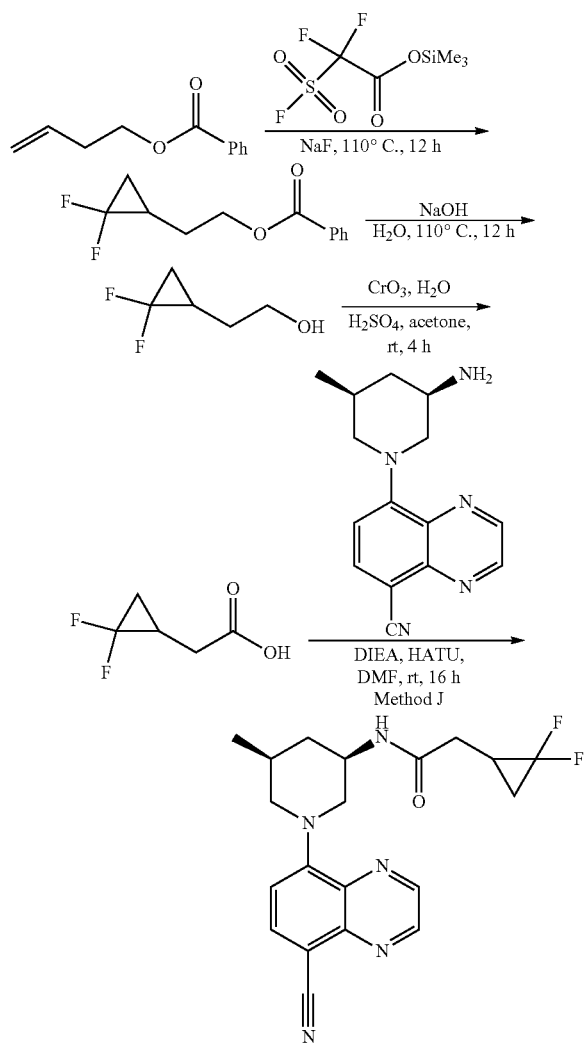

2-(2,2-difluorocyclopropyl)ethyl benzoate: But-3-en-1-yl benzoate (2.85 g, 16.17 mmol) and trimethylsilyl 2,2-difluoro-2-(fluorosulfonyl)acetate (7.98 g, 31.89 mmol) were mixed in neat condition, to which was added NaF (36 mg, 0.86 mmol). The resulting mixture was stirred for 12 h at 110° C. After cooling to room temperature, the reaction was quenched by the addition of water (20 mL). The resulting mixture was extracted with ethyl acetate (80 mL×3). The organic phases were combined, washed with brine and dried over Na$_2$SO$_4$. The solvent was removed under reduced pressure and the residue was purified by flash chromatography eluting with EtOAc in hexane (0% to 6% gradient) to yield 2-(2,2-difluorocyclopropyl)ethyl benzoate as yellow oil (1.84 g, 50%). MS: m/z=227.1 [M+H]$^+$.

2-(2,2-difluorocyclopropyl)ethan-1-ol: To a solution of 2-(2,2-difluorocyclopropyl)ethyl benzoate (900 mg, 3.98 mmol) in water (20 mL) was added sodium hydroxide (1.60 g, 40.00 mmol) at room temperature. The resulting mixture was stirred for 16 h at 100° C. After cooling to room temperature, the reaction mixture was extracted with ethyl acetate (50 mL×3). The organic phases were combined, washed with brine and dried over Na$_2$SO$_4$. The solvent was removed under reduced pressure to yield 2-(2,2-difluorocyclopropyl)ethan-1-ol as a colorless liquid (210 mg, 43%). GCMS: m/z=122 [M]$^+$.

2-(2,2-difluorocyclopropyl)acetic acid: At 0° C., to a solution of CrO$_3$ (5.70 g, 57.00 mmol) in sulfuric acid (8.3 mL) was added water (92 mL). Then a solution of 2-(2,2-difluorocyclopropyl)ethan-1-ol (180 mg, 1.47 mmol) in acetone (30 mL) was added dropwise over 20 min period. The resulting mixture was stirred for 4 h at room temperature. When the reaction was done, the reaction mixture was extracted with ether (50 mL×4). The organic layers were combined, washed with 2 M sodium hydroxide solution (50 mL×4) and the aqueous layers were combined. The pH value of the resulting aqueous solution was adjusted to 1 using sulfuric acid and extracted with ether (50 mL×4). The organic phases were combined, washed with brine and dried over Na$_2$SO$_4$. The solvent was removed under reduced pressure to yield 2-(2,2-difluorocyclopropyl)acetic acid as colorless oil (117 mg, 58%). GCMS: m/z=136 [M]$^+$.

(3R,5S)-1-(8-cyanoquinoxalin-5-yl)-5-methylpiperidin-3-yl-2-(3-hydroxyazetidin-1-yl)propanoate: N-[(3R,5S)-1-(8-cyanoquinoxalin-5-yl)-5-methylpiperidin-3-yl]-2-(2,2-difluorocyclopropyl)acetamide was prepared from 3-(tert-butyldimethylsilyloxy)azetidine, ethyl 2-bromopropanoate, and 8-((3R,5S)-3-amino-5-methylpiperidin-1-yl)quinoxaline-5-carbonitrile using Method J. The crude product was purified by prep-HPLC under the following conditions: column, XBridge Prep C18 OBD Column, 5 um, 19 mm×150 mm; mobile phase, acetonitrile in water (with 0.1% NH$_3$.H$_2$O), 30% to 60% gradient in 7 min; detector, UV 254 nm. N-[(3R,5S)-1-(8-cyanoquinoxalin-5-yl)-5-methylpiperidin-3-yl]-2-(2,2-difluorocyclopropyl)acetamide was obtained as yellow solid (30 mg, 33%).

Compound 272: HPLC: 98.5% purity, RT=1.45 min. MS: m/z=386.2 [M+H]$^+$. $^1$H NMR (400 MHz, CD$_3$OD, ppm) δ 8.99-8.85 (m, 2H), 8.10 (d, J=8.4 Hz, 1H), 7.30 (d, J=8.4 Hz, 1H), 4.45-4.36 (m, 1H), 4.32 (d, J=12.7 Hz, 1H), 4.21-4.09 (m, 1H), 2.82-2.62 (m, 2H), 2.51-2.30 (m, 2H), 2.16-1.83 (m, 3H), 1.62-1.48 (m, 1H), 1.33-1.07 (m, 2H), 1.02 (d, J=6.4 Hz, 3H).

The following compounds were synthesized in an analogous manner:

Compound 286 (2-(2,2-difluorocyclopropyl)-N-[(3R,5S)-5-methyl-1-[8-(trifluoromethyl)quinolin-5-yl]piperidin-3-yl]acetamide): From 2-(2,2-difluorocyclopropyl)acetic acid and (3R,5S)-5-methyl-1-(8-(trifluoromethyl)quinolin-5-yl)piperidin-3-amine. HPLC: 98.0% purity, RT=1.77 min. MS: m/z=428.2 [M+H]$^+$. $^1$H NMR (400 MHz, CD$_3$OD, ppm) δ 8.97-8.91 (m, 1H), 8.74-8.62 (m, 1H), 8.03 (d, J=8.0 Hz, 1H), 7.64 (dd, J=8.6, 4.2 Hz, 1H), 7.22 (d, J=8.0 Hz, 1H), 4.24 (m, 1H), 3.69-3.60 (m, 1H), 3.44-3.35 (m, 1H), 2.56-

2.39 (m, 3H), 2.33 (dd, J=15.4, 7.4 Hz, 1H), 2.24-2.09 (m, 2H), 2.00-1.80 (m, 1H), 1.61-1.45 (m, 1H), 1.23-0.97 (m, 5H).

Compound 298 (2-(2,2-difluorocyclopropyl)-N-[(3R,5S)-5-methyl-1-[8-(trifluoromethyl)quinoxalin-5-yl]piperidin-3-yl]acetamide): From 2-(2,2-difluorocyclopropyl)acetic acid and (3R,5S)-5-methyl-1-(8-(trifluoromethyl)quinoxalin-5-yl)piperidin-3-amine. HPLC: 97.0% purity, RT=1.73 min. MS: m/z=429.2 [M+H]+. 1H NMR (400 MHz, CD3OD, ppm) δ 8.99-0.88 (m, 2H), 8.10 (d, J=8.3 Hz, 1H), 7.35 (d, J=8.4 Hz, 1H), 4.34-4.14 (m, 3H), 2.78-2.28 (m, 4H), 2.22-2.11 (m, 2H), 2.05-1.86 (m, 1H), 1.66-1.52 (m, 1H), 1.31-1.13 (m, 2H), 1.08 (d, J=6.4 Hz, 3H).

Compound 310 (2-(2,2-difluorocyclopropyl)-N-[(3R,5S)-1-[8-(difluoromethyl)quinolin-5-yl]-5-methylpiperidin-3-yl]acetamide): From 2-(2,2-difluorocyclopropyl)acetic acid and (3R,5S)-1-(8-(difluoromethyl)quinolin-5-yl)-5-methylpiperidin-3-amine. HPLC: 99.3% purity, RT=1.46 min. MS: m/z=410.2 [M+H]+. 1H NMR (400 MHz, CD3OD, ppm) δ 8.91 (dd, J=4.1, 1.7 Hz, 1H), 8.67-8.60 (m, 1H), 7.95 (d, J=7.9 Hz, 1H), 7.85-7.54 (m, 2H), 7.26 (d, J=7.9 Hz, 1H), 4.28-4.20 (m, 1H), 3.65-3.56 (m, 1H), 3.40-3.34 (m, 1H), 2.52-2.41 (m, 3H), 2.32 (dd, J=15.6, 7.8 Hz, 1H), 2.24-2.08 (m, 2H), 1.96-1.84 (m, 1H), 1.58-1.49 (m, 1H), 1.22-1.01 (m, 5H).

Compound 322 (2-(2,2-difluorocyclopropyl)-N-[(3R,5S)-1-[8-(difluoromethyl)quinoxalin-5-yl]-5-methylpiperidin-3-yl]acetamide): From 2-(2,2-difluorocyclopropyl)acetic acid and (3R,5S)-1-(8-(difluoromethyl)quinoxalin-5-yl)-5-methylpiperidin-3-amine. HPLC: 96.9% purity, RT=3.24 min. MS: m/z=411.1 [M+H]+. 1H NMR (400 MHz, CD3OD, ppm) δ 8.95-8.85 (m, 2H), 7.96 (d, J=8.2 Hz, 1H), 7.63 (t, J=55.9 Hz, 1H), 7.34 (d, J=8.2 Hz, 1H), 4.27-4.10 (m, 2H), 4.05-3.97 (m, 1H), 2.64-2.58 (m, 1H), 2.55-2.38 (m, 2H), 2.37-2.26 (m, 1H), 2.13-2.06 (m, 2H), 1.95-1.83 (m, 1H), 1.59-1.45 (m, 1H), 1.21-1.04 (m, 2H), 1.00 (d, J=6.3 Hz, 3H).

Example 77: Synthesis of Compound 274 (N-[(3R,5S)-1-(8-cyanoquinoxalin-5-yl)-5-methylpiperidin-3-yl]-2-(3,3-difluoroazetidin-1-yl)propanamide)

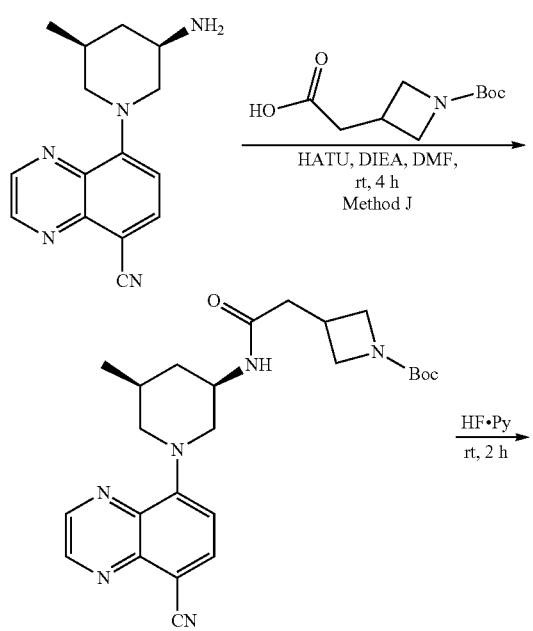

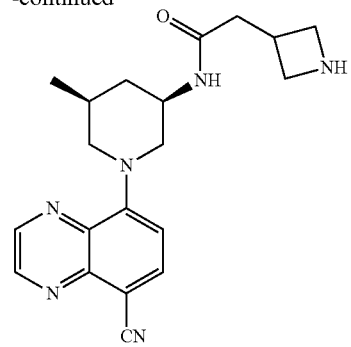

tert-butyl 3-([[[(3R,5S)-1-(8-cyanoquinoxalin-5-yl)-5-methylpiperidin-3-yl]carbamoyl]methyl)azetidine-1-carboxylate: tert-butyl 3-([[[(3R,5S)-1-(8-cyanoquinoxalin-5-yl)-5-methylpiperidin-3-yl]carbamoyl]methyl)azetidine-1-carboxylate was prepared from 2-(1-(tert-butoxycarbonyl)azetidin-3-yl)acetic acid and 8-((3R,5S)-3-amino-5-methylpiperidin-1-yl)quinoxaline-5-carbonitrile using Method J. The crude was purified by flash chromatography eluting with EtOAc in hexane (0% to 50% gradient) to yield tert-butyl 3-([[[(3R,5S)-1-(8-cyanoquinoxalin-5-yl)-5-methylpiperidin-3-yl]carbamoyl]methyl)azetidine-1-carboxylate as yellow solid (90 mg, 15%). MS: m/z=465.3 [M+H]+.

2-(azetidin-3-yl)-N-[(3R,5S)-1-(8-cyanoquinoxalin-5-yl)-5-methylpiperidin-3-yl]acetamide: At 0° C., tert-butyl 3-([[[(3R,5S)-1-(8-cyanoquinoxalin-5-yl)-5-methylpiperidin-3-yl]carbamoyl]methyl)azetidine-1-carboxylate (85 mg, 0.18 mmol) was added by HF-Pyridine solution (7 mL) dropwise. The resulting solution was stirred for another 2 h at room temperature. When the reaction was done, it was quenched by the addition of water (15 mL). The resulting mixture was extracted with DCM (30 mL×3). The organic phases were combined, washed with brine and dried over Na2SO4. The solvent was removed under reduced pressure and the residue was purified by flash chromatography eluting with MeOH in DCM (0% to 10% gradient) to yield 2-(azetidin-3-yl)-N-[(3R,5S)-1-(8-cyanoquinoxalin-5-yl)-5-methylpiperidin-3-yl]acetamide as yellow solid (14 mg 21%).

Compound 274: HPLC: 91.4% purity, RT=2.80 min. MS: n/z=365.1 [M+H]+. 1H NMR (300 MHz, CD3OD, ppm) δ 8.95-8.80 (m, 2H), 8.10-7.98 (m, 1H), 7.22 (d, J=8.4 Hz, 1H), 4.28 (t, J=14.1 Hz, 2H), 4.13-3.85 (m, 3H), 3.65 (t, J=8.4 Hz, 2H), 3.13 (dt, J=15.7, 7.8 Hz, 1H), 2.77-2.42 (m, 4H), 2.12-1.92 (m, 2H), 1.25-0.92 (m, 4H).

Example 78: Synthesis of Compound 276 (N-[(3R,5S)-1-(8-cyanoquinoxalin-5-yl)-5-methylpiperidin-3-yl]-2-(4-methyl-1,4-diazepan-1-yl)acetamide)

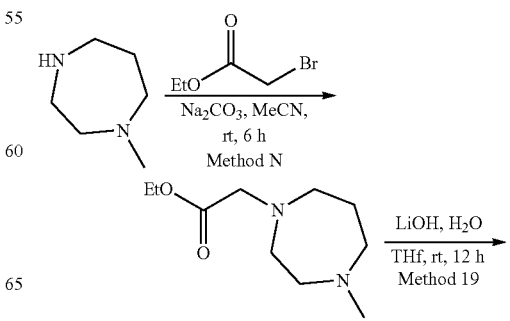

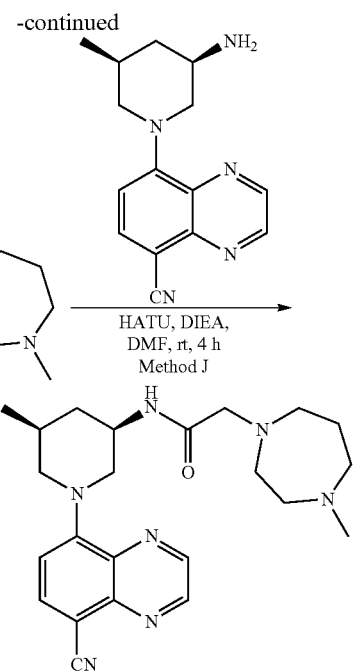

N-[(3R,5S)-1-(8-cyanoquinoxalin-5-yl)-5-methylpiperidin-3-yl]-2-(4-methyl-1,4-diazepan-1-yl)acetamide:

N-[(3R,5S)-1-(8-cyanoquinoxalin-5-yl)-5-methylpiperidin-3-yl]-2-(4-methyl-1,4-diazepan-1-yl)acetamide was prepared from 1-methyl-1,4-diazepane, ethyl 2-bromoacetate, and 8-((3R,5S)-3-amino-5-methylpiperidin-1-yl)quinoxaline-5-carbonitrile using Method N, 19, and J. The crude product was purified by prep-HPLC under the following conditions: column, XBridge Shield RP18 OBD Column, 5 um, 19 mm×150 mm; mobile phase, acetonitrile in water (with 0.05% $NH_3 \cdot H_2O$), 27% to 28% gradient in 10 min; detector, UV 254 nm. N-[(3R,5S)-1-(8-cyanoquinoxalin-5-yl)-5-methylpiperidin-3-yl]-2-(4-methyl-1,4-diazepan-1-yl)acetamide was obtained as yellow solid (12 mg, 5% for 3 steps).

Compound 276: HPLC: 96.6% purity, RT=1.08 min. MS: m/z=422.3 [M+H]$^+$. $^1$H NMR (300 MHz, CD$_3$OD, ppm) δ 8.99-8.85 (m, 2H), 8.06 (d, J=8.4 Hz, 1H), 7.24 (d, J=8.5 Hz, 1H), 4.38-4.12 (m, 3H), 3.15 (s, 2H), 2.90-2.60 (m, 10H), 2.37 (s, 3H), 2.14-1.94 (m, 2H), 1.90-1.74 (m, 2H), 1.29 (d, J=12.4 Hz, 1H), 1.00 (d, J=6.4 Hz, 3H).

The following compounds were synthesized in an analogous manner:

Compound 290 (2-(4-methyl-1,4-diazepan-1-yl)-N-[(3R,5S)-5-methyl-1-[8-(trifluoromethyl)quinolin-5-yl]piperidin-3-yl]acetamide): From 2-(4-methyl-1,4-diazepan-1-yl)acetic acid and (3R,5S)-5-methyl-1-(8-(trifluoromethyl)quinolin-5-yl)piperidin-3-amine. HPLC: 96.5% purity, RT=1.47 min. MS: m/z=464.3 [M+H]$^+$. $^1$H NMR (400 MHz, CD$_3$OD, ppm) δ 8.92 (dd, J=4.2, 1.8 Hz, 1H), 8.65 (dd, J=8.6, 1.8 Hz, 1H), 8.02 (d, J=8.1 Hz, 1H), 7.61 (dd, J=8.6, 4.2 Hz, 1H), 7.22 (d, J=8.0 Hz, 1H), 4.28 (t, J=11.4 Hz, 1H), 3.58 (d, J=11.0 Hz, 1H), 3.38 (d, J=11.7 Hz, 1H), 3.18-3.14 (m, 2H), 2.81-2.30 (m, 13H), 2.23-2.03 (m, 2H), 1.83 (q, J=5.7 Hz, 2H), 1.25 (td, J=11.9, 11.9 Hz, 1H), 1.04 (d, J=6.4 Hz, 3H).

Compound 314 (N-[(3R,5S)-1-[8-(difluoromethyl)quinolin-5-yl]-5-methylpiperidin-3-yl]-2-(4-methyl-1,4-diazepan-1-yl)acetamide): From 2-(4-methyl-1,4-diazepan-1-yl)acetic acid and (3R,5S)-1-(8-(difluoromethyl)quinolin-5-yl)-5-methylpiperidin-3-amine. HPLC: 95.3% purity, RT=2.46 min. MS: m/z=446.2 [M+H]$^+$. $^1$H NMR (400 MHz, CD$_3$OD, ppm) δ 8.91 (dd, J=4.3, 1.8 Hz, 1H), 8.65 (dd, J=8.5, 1.8 Hz, 1H), 8.00-7.54 (m, 3H), 7.29 (d, J=7.9 Hz, 1H), 4.36-4.24 (m, 1H), 3.61-3.52 (m, 1H), 3.44-3.30 (m, 1H), 3.18 (s, 2H), 2.84-2.67 (m, 8H), 2.64-2.44 (m, 2H), 2.41 (s, 3H), 2.27-2.08 (m, 2H), 1.87-1.81 (m, 2H), 1.26 (td, J=12.1, 12.0 Hz, 1H), 1.06 (d, J=6.4 Hz, 3H).

Compound 326 (N-[(3R,5S)-1-[8-(difluoromethyl)quinoxalin-5-yl]-5-methylpiperidin-3-yl]-2-(4-methyl-1,4-diazepan-1-yl)acetamide): From 2-(4-methyl-1,4-diazepan-1-yl)acetic acid and (3R,5S)-1-[8-(difluoromethyl)quinoxalin-5-yl]-5-methylpiperidin-3-amine. HPLC: 87.1% purity, RT=1.29 min. MS: m/z=447.5 [M+H]$^+$. $^1$H NMR (400 MHz, CD$_3$OD, ppm) δ 8.95-8.85 (m, 2H), 7.97 (d, J=8.2 Hz, 1H), 7.63 (t, J=56.0 Hz, 1H), 7.34 (d, J=8.3 Hz, 1H), 4.32-4.18 (m, 1H), 4.13-4.09 (m, 1H), 4.00-3.98 (m, 1H), 3.20-2.95 (m, 2H), 2.83-2.64 (m, 9H), 2.55 (t, J=11.3 Hz, 1H), 2.39 (s, 3H), 2.13-2.07 (m, 2H), 1.90-1.76 (m, 2H), 1.30-1.24 (m, 1H), 1.12-0.99 (m, 3H).

Compound 362 (2-(4-methyl-1,4-diazepan-1-yl)-N-[(3R,5S)-5-methyl-1-[8-(trifluoromethyl)quinoxalin-5-yl]piperidin-3-yl]acetamide): From (3R,5S)-5-methyl-1-[8-(trifluoromethyl)quinoxalin-5-yl]piperidin-3-amine and 2-(4-methyl-1,4-diazepan-1-yl)acetic acid. HPLC: 93.7% purity, RT=2.36 min. MS: m/z=465.1 [M+H]$^+$. $^1$H NMR (300 MHz, CD$_3$OD, ppm) δ 8.95-8.86 (m, 2H), 8.04 (d, J=8.3 Hz, 1H), 7.28 (d, J=8.3 Hz, 1H), 4.23-4.09 (m, 3H), 3.21 (s, 2H), 2.86-2.60 (m, 10H), 2.49 (s, 3H), 2.12-2.08 (m, 2H), 1.89-1.85 (m, 2H), 1.36-1.20 (m, 1H), 1.04 (d, J=6.3 Hz, 3H).

Example 79: Synthesis of Compound 280 (2-(3-aminoazetidin-1-yl)-N-[(3R,5S)-5-methyl-1-[8-(trifluoromethyl)quinolin-5-yl]piperidin-3-yl]acetamide)

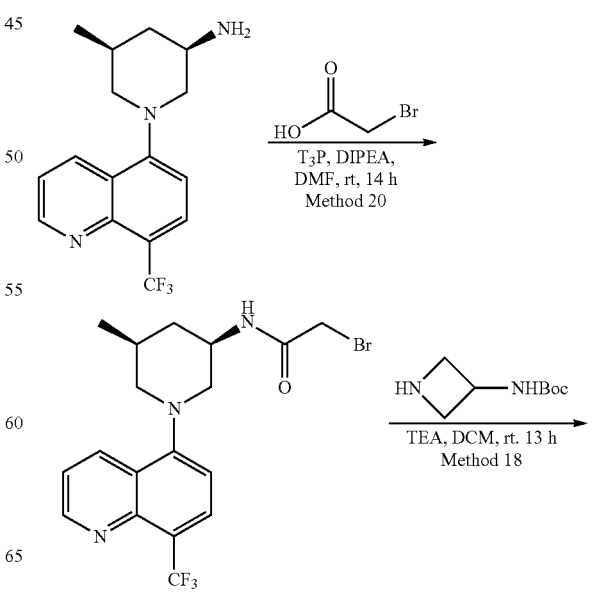

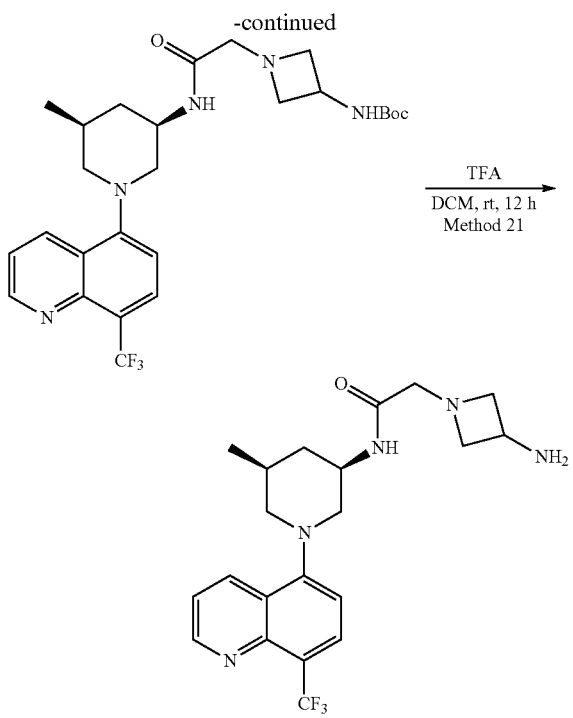

Method 20

2-bromo-N-[(3R,5S)-5-methyl-1-[8-(trifluoromethyl)quinolin-5-yl]piperidin-3-yl]acetamide: To a solution of (3R,5S)-5-methyl-1-[8-(trifluoromethyl)quinolin-5-yl]piperidin-3-amine (266 mg, 0.86 mmol) in N,N-dimethylformamide (10 mL) were added 2-bromoacetic acid (475 mg, 3.42 mmol), T3P (817 mg, 2.57 mmol), DIEA (551 mg, 4.26 mmol) at room temperature. The resulting solution was stirred for 14 h at room temperature. When the reaction was done, it was quenched by the addition of water (10 mL). The resulting mixture was extracted with DCM (50 mL×3). The organic phases were combined, washed with brine and dried over Na$_2$SO$_4$. The solution was removed under reduced pressure to yield 2-bromo-N-[(3R,5S)-5-methyl-1-[8-(trifluoromethyl)quinolin-5-yl]piperidin-3-yl]acetamide as a yellow solid (400 mg, crude).

(Note: In Method 20, the solvent may also be dichloromethane instead of N,N-dimethylformamide)

tert-butyl N-[1-([[(3R,5S)-5-methyl-1-[8-(trifluoromethyl)quinolin-5-yl]piperidin-3-yl]carbamoyl]methyl)azetidin-3-yl]carbamate: tert-butyl N-[1-([[(3R,5S)-5-methyl-1-[8-(trifluoromethyl)quinolin-5-yl]piperidin-3-yl]carbamoyl] methyl)azetidin-3-yl]carbamate was prepared from tert-butyl azetidin-3-ylcarbamate and 2-bromo-N-((3R,5S)-5-methyl-1-(8-(trifluoromethyl)quinolin-5-yl)piperidin-3-yl) acetamide using Method 18. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), 30% to 45% gradient in 8 min; detector, UV 254 nm. tert-butyl N-[1-([[(3R,5S)-5-methyl-1-[8-(trifluoromethyl)quinolin-5-yl]piperidin-3-yl]carbamoyl]methyl)azetidin-3-yl]carbamate was obtained as white solid (38 mg, 26% for 2 steps). MS: m/z=522.3 [M+H]$^+$.

Method 21

2-(3-aminoazetidin-1-yl)-N-[(3R,5S)-5-methyl-1-[8-(trifluoromethyl)quinolin-5-yl]piperidin-3-yl]acetamide: To a solution of tert-butyl N-[1-([[(3R,5S)-5-methyl-1-[8-(trifluoromethyl)quinolin-5-yl]piperidin-3-yl]carbamoyl] methyl)azetidin-3-yl]carbamate (18 mg, 0.03 mmol) in dichloromethane (5 mL) was added trifluoroacetic acid (0.5 mL) at room temperature. The resulting solution was stirred for 12 h at room temperature. After the reaction was done, the reaction mixture was concentrated under reduced pressure. The residue was purified by prep-HPLC under the following conditions: column, XBridge Shield RP18 OBD Column, 5 um, 19 mm×150 mm; mobile phase, acetonitrile in water (with 10 mmol/L NH$_4$HCO$_3$+0.1% NH$_3$.H$_2$O), 30% to 45% gradient in 7 min; detector, UV 254 nm. N-[(3R,5S)-5-methyl-1-[8-(trifluoromethyl)quinolin-5-yl]piperidin-3-yl]-2-(1-methylpiperidin-3-yl)acetamide was obtained as white solid (7 mg, 44%).

Compound 280: HPLC: 92.4% purity, RT=2.48 min. MS: n/z=422.3 [M+H]$^+$. $^1$H NMR (400 MHz, CD$_3$OD, ppm) δ 8.92 (dd, J=4.3, 1.7 Hz, 1H), 8.64 (dd, J=8.6, 1.8 Hz, 1H), 8.02 (d, J=8.1 Hz, 1H), 7.60 (dd, J=8.6, 4.2 Hz, 1H), 7.21 (d, J=8.0 Hz, 1H), 4.30-4.16 (m, 1H), 3.70-3.53 (m, 4H), 3.38 (d, J=11.5 Hz, 1H), 3.14 (s, 2H), 2.98-2.90 (m, 2H), 2.60-2.40 (m, 2H), 2.22-2.08 (m, 2H), 1.20 (td, J=12.0, 12.0 Hz, 1H), 1.03 (d, J=6.5 Hz, 3H).

Example 80: Synthesis of Compound 281 (2-(3-aminoazetidin-1-yl)-N-[(3R,5S)-5-methyl-1-[8-(trifluoromethyl)quinolin-5-yl]piperidin-3-yl]propanamide)

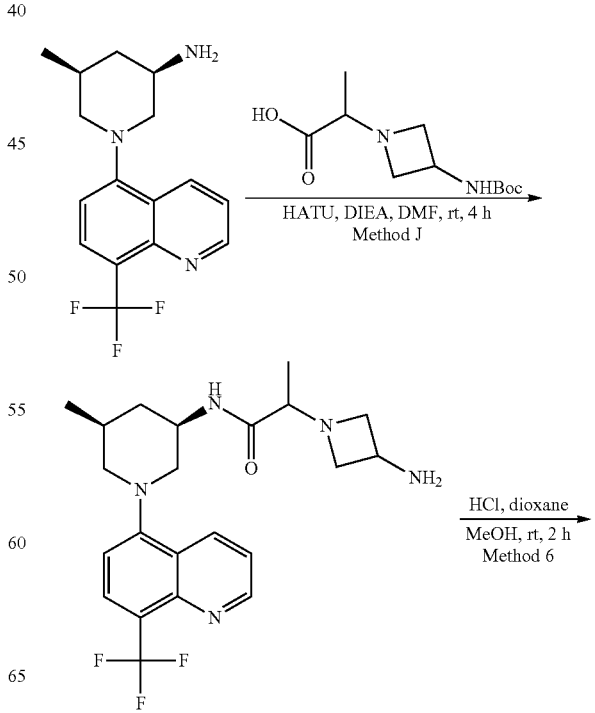

-continued

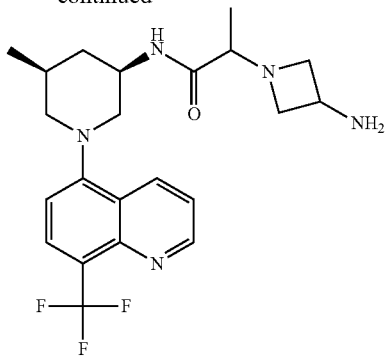

2-(3-aminoazetidin-1-yl)-N-[(3R,5S)-5-methyl-1-[8-(trifluoromethyl)quinolin-5-yl]piperidin-3-yl]propanamide: 2-(3-aminoazetidin-1-yl)-N-[(3R,5S)-5-methyl-1-[8-(trifluoromethyl)quinolin-5-yl]piperidin-3-yl]propanamide was prepared from 2-(3-(tert-butoxycarbonylamino)azetidin-1-yl)propanoic acid and (3R,5S)-5-methyl-1-(8-(trifluoromethyl)quinolin-5-yl)piperidin-3-amine using Method J and 6. The crude product was purified by prep-HPLC under the following conditions: column, XBridge Prep C18 OBD Column, 5 um, 19 mm×150 mm; mobile phase, acetonitrile in water (with 10 mmol/L $NH_4HCO_3$), 30% to 37% gradient in 7 min; detector, UV 254 nm. 2-(3-aminoazetidin-1-yl)-N-[(3R,5S)-5-methyl-1-[8-(trifluoromethyl)quinolin-5-yl]piperidin-3-yl]propanamide was obtained as white solid (17 mg, 17% for 2 steps).

Compound 281: HPLC: 99.2% purity, RT=2.51 min. MS: m/z=436.2 [M+H]$^+$. $^1$H NMR (400 MHz, $CD_3OD$, ppm) δ 8.92 (dd, J=4.2, 1.7 Hz, 1H), 8.63 (dt, J=8.6, 1.8 Hz, 1H), 8.02 (d, J=8.1 Hz, 1H), 7.61 (dd, J=8.6, 4.2 Hz, 1H), 7.21 (d, J=8.0 Hz, 1H), 4.29-4.15 (m, 1H), 3.61-3.47 (m, 4H), 3.41-3.33 (m, 1H), 2.91-2.75 (m, 3H), 2.59-2.41 (m, 2H), 2.21-2.05 (m, 2H), 1.31-1.09 (m, 4H), 1.03 (d, J=6.4 Hz, 3H).

The following compounds were synthesized in an analogous manner:

Compound 282 (2-amino-2-cyclopropyl-N-[(3R,5S)-5-methyl-1-[8-(trifluoromethyl)quinolin-5-yl]piperidin-3-yl]acetamide): From 2-(tert-butoxycarbonylamino)-2-cyclopropylacetic acid and (3R,5S)-5-methyl-1-(8-(trifluoromethyl)quinolin-5-yl)piperidin-3-amine. HPLC: 96.3% purity, RT=1.76 min. MS: n/z=407.3 [M+H]$^+$. $^1$H NMR (300 MHz, $CD_3OD$, ppm) δ 9.19-9.04 (m, 2H), 8.26 (d, J=6.2 Hz, 1H), 7.98-7.95 (m, 1H), 7.42 (t, J=7.8 Hz, 1H), 4.26-4.25 (m, 1H), 3.69 (d, J=11.4 Hz, 1H), 3.48 (d, J=11.3 Hz, 1H), 3.15 (dd, J=9.7, 4.8 Hz, 1H), 2.77-2.53 (m, 2H), 2.25-2.05 (m, 2H), 1.28-1.23 (m, 2H), 1.03 (d, J=6.3 Hz, 3H), 0.84-0.58 (m, 3H), 0.56-0.45 (m, 1H).

Compound 288 (2-(azetidin-3-yl)-N-[(3R,5S)-5-methyl-1-[8-(trifluoromethyl)quinolin-5-yl]piperidin-3-yl]acetamide): From 2-(3,3-difluoroazetidin-1-yl)propanoic acid and (3R,5S)-5-methyl-1-(8-(trifluoromethyl)quinolin-5-yl)piperidin-3-amine. HPLC: 91.7% purity, RT=4.98 min. MS: m/z=407.3 [M+H]$^+$. $^1$H NMR (300 MHz, $CD_3OD$, ppm) δ 8.13-9.00 (m, 2H), 8.23 (d, J=8.2 Hz, 1H), 7.92 (dd, J=8.6, 4.8 Hz, 1H), 7.40 (d, J=8.2 Hz, 1H), 4.28-4.08 (m, 3H), 3.93 (t, J=8.9 Hz, 2H), 3.70 (d, J=11.1 Hz, 1H), 3.48 (d, J=11.7 Hz, 1H), 3.30-3.16 (m, 1H), 2.69-2.52 (m, 4H), 2.25-2.09 (m, 2H), 1.21 (td, J=14.0, 11.9 Hz, 1H), 1.04 (d, J=6.3 Hz, 3H).

Compound 291 (4-amino-3,3-dimethyl-N-[(3R,5S)-5-methyl-1-[8-(trifluoromethyl)quinolin-5-yl]piperidin-3-yl]butanamide): From 4-[[(tert-butoxy)carbonyl]amino]-3,3-dimethylbutanoic acid and (3R,5S)-5-methyl-1-(8-(trifluoromethyl)quinolin-5-yl)piperidin-3-amine. HPLC: 95.1% purity, RT=1.09 min. MS: m/z=423.2 [M+H]$^+$. $^1$H NMR (300 MHz, $CD_3OD$, ppm) δ 8.89 (dd, J=4.3, 1.7 Hz, 1H), 8.61 (dd, J=8.6, 1.8 Hz, 1H), 7.99 (d, J=8.0 Hz, 1H), 7.58 (dd, J=8.6, 4.2 Hz, 1H), 7.17 (d, J=8.0 Hz, 1H), 4.23-4.16 (m, 1H), 3.63-3.52 (m, 1H), 3.35 (apparent d, J=12.0 Hz, 1H), 2.64 (s, 2H), 2.52-2.38 (m, 2H), 2.18 (s, 2H), 2.13-2.04 (m, 2H), 1.29-0.96 (m, 10H).

Compound 476 ((S)-2-Amino-3-hydroxy-N-[(3R,5S)-5-methyl-1-(8-trifluoromethyl-quinolin-5-yl)-piperidin-3-yl]-propionamide): From (3R,5S)-1-[8-(trifluoromethyl)quinolin-5-yl]-5-methylpiperidin-3-amine and (S)-2-tert-Butoxycarbonylamino-3-hydroxy-propionic acid. HPLC: >99% purity, RT=2.69 min. MS: m/z=397.2 [M+H]$^+$. $^1$H NMR (400 MHz, DMSO-$d_6$, ppm) δ 9.01 (dd, J=4.2, 1.7 Hz, 1H), 8.53 (dd, J=8.6, 1.8 Hz, 1H), 8.05 (d, J=8.1 Hz, 1H), 7.81 (d, J=7.7 Hz, 1H), 7.67 (dd, J=8.6, 4.2 Hz, 1H), 7.19 (d, J=8.1 Hz, 1H), 4.67 (t, J=5.6 Hz, 1H), 3.48 (dt, J=10.2, 5.0 Hz, 2H), 3.42-3.33 (m, 2H), 3.17 (dd, J=6.2, 4.9 Hz, 1H), 2.42 (t, J=11.4 Hz, 1H), 2.14-1.93 (m, 2H), 1.78 (s, 2H), 1.16 (q, J=12.1 Hz, 1H), 0.95 (d, J=6.5 Hz, 3H).

Compound 514 (3-Amino-3-methyl-N-[(3R,5S)-5-methyl-1-(8-trifluoromethyl-quinolin-5-yl)-piperidin-3-yl]-butyramide): From (3R,5S)-5-Methyl-1-(8-trifluoromethyl-quinolin-5-yl)-piperidin-3-ylamine hydrochloride and 3-tert-Butoxycarbonylamino-3-methyl-butyric acid. $^1$H NMR (400 MHz, DMSO-$d_6$) δ 9.02 (dd, J=4.2, 1.7 Hz, 1H), 8.54 (dd, J=8.6, 1.8 Hz, 1H), 8.21 (d, J=7.5 Hz, 1H), 8.06 (d, J=8.1 Hz, 1H), 7.68 (dd, J=8.6, 4.2 Hz, 1H), 7.20 (d, J=8.1 Hz, 1H), 3.61-3.46 (m, 1H), 2.47-2.34 (m, 2H), 2.10 (s, 4H), 1.68 (s, 2H), 1.06 (s, 6H), 0.96 (d, J=6.5 Hz, 3H). MS: m/z=409 [M+H]$^+$.

Example 81: Synthesis of Compound 294 (2-amino-2-cyclopropyl-N-[(3R,5S)-5-methyl-1-[8-(trifluoromethyl)quinoxalin-5-yl]piperidin-3-yl]acetamide)

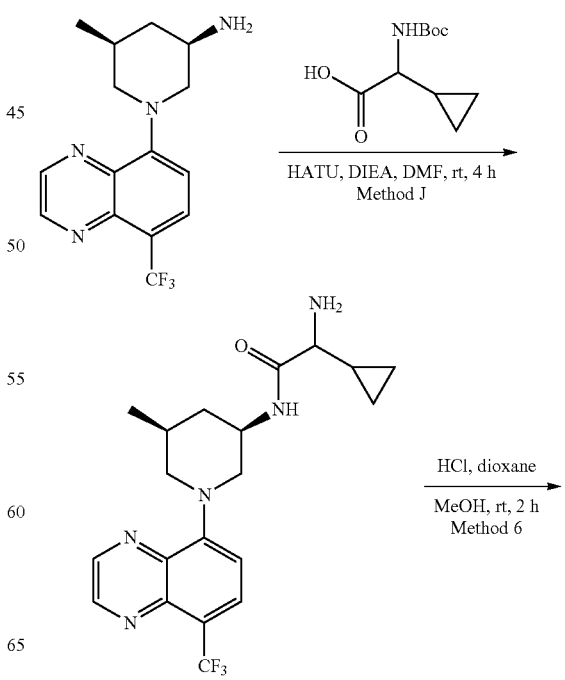

531
-continued

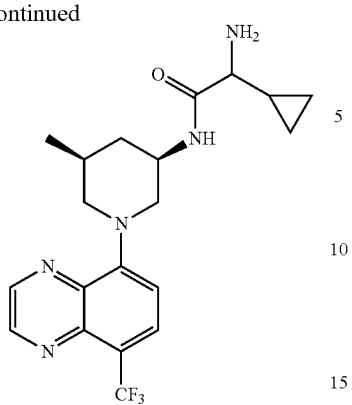

2-amino-2-cyclopropyl-N-[(3R,5S)-5-methyl-1-[8-(trifluoromethyl)quinoxalin-5-yl]piperidin-3-yl]acetamide: 2-amino-2-cyclopropyl-N-[(3R,5S)-5-methyl-1-[8-(trifluoromethyl)quinoxalin-5-yl]piperidin-3-yl]acetamide was prepared from 2-(1-methylpiperidin-3-yl)acetic acid and (3R,5S)-5-methyl-1-(8-(trifluoromethyl)quinoxalin-5-yl)piperidin-3-amine using Method J and 6. The crude product was purified by prep-HPLC under the following conditions: column, XBridge Prep C18 OBD Column, 5 um, 19 mm×150 mm; mobile phase, acetonitrile in water (with 0.05% $NH_3.H_2O$), 30% to 55% gradient in 8 min; detector, UV 254 nm. 2-amino-2-cyclopropyl-N-[(3R,5S)-5-methyl-1-[8-(trifluoromethyl)quinoxalin-5-yl]piperidin-3-yl]acetamide was obtained as yellow solid (30 mg, 38% for 2 steps).

Compound 294: HPLC: 99.3% purity, RT=1.46 min. MS: m/z=408.2 [M+H]$^+$. $^1$H NMR (400 MHz, CD$_3$OD, ppm) δ 8.95-8.88 (m, 2H), 8.05 (d, J=8.3 Hz, 1H), 7.29 (d, J=8.3 Hz, 1H), 4.26-4.20 (m, 2H), 4.11 (dd, J=12.3, 3.3 Hz, 1H), 2.77-2.53 (m, 3H), 2.18-2.05 (m, 2H), 1.31-1.17 (m, 1H), 1.11-0.96 (m, 4H), 0.64-0.44 (m, 3H), 0.40-0.31 (m, 1H).

The following compounds were synthesized in an analogous manner:

Compound 300 (2-(azetidin-3-yl)-N-[(3R,5S)-5-methyl-1-[8-(trifluoromethyl)quinoxalin-5-yl]piperidin-3-yl]acetamide): From 2-(1-(tert-butoxycarbonyl)azetidin-3-yl)acetic acid and (3R,5S)-5-methyl-1-(8-(trifluoromethyl)quinoxalin-5-yl)piperidin-3-amine. HPLC: 91.9% purity, RT=5.29 min. MS: m/z=408.2 [M+H]$^+$. $^1$H NMR (400 MHz, DMSO-d$_6$, ppm) δ 9.02 (d, J=1.8 Hz, 1H), 8.96 (d, J=1.8 Hz, 1H), 8.06 (d, J=8.4 Hz, 1H), 7.95 (s, 1H), 7.27 (d, J=8.4 Hz, 1H), 4.21-4.05 (m, 2H), 4.00-3.84 (m, 1H), 3.63-3.40 (m, 4H), 2.81-2.48 (m, 3H), 2.39 (d, J=7.7 Hz, 2H), 1.99-1.94 (m, 2H), 1.12 (td, J=12.0, 12.0 Hz, 1H), 0.92 (d, J=6.3 Hz, 3H).

Compound 301 (4-amino-3,3-dimethyl-N-[(3R,5S)-5-methyl-1-[8-(trifluoromethyl)quinoxalin-5-yl]piperidin-3-yl]butanamide): From 4-(tert-butoxycarbonylamino)-3,3-dimethylbutanoic acid and (3R,5S)-5-methyl-1-(8-(trifluoromethyl)quinoxalin-5-yl)piperidin-3-amine. HPLC: 92.8% purity, RT=1.06 min. MS: m/z=424.2 [M+H]$^+$. $^1$H NMR (400 MHz, CD$_3$OD, ppm) δ 8.92 (d, J=7.3 Hz, 2H), 8.05 (d, J=8.3 Hz, 1H), 7.29 (d, J=8.3 Hz, 1H), 4.31-4.05 (m, 3H), 2.78-2.46 (m, 4H), 2.19 (s, 2H), 2.13-2.10 (m, 2H), 1.19 (td, J=12.2, 12.2 Hz, 1H), 1.03 (d, J=5.1 Hz, 9H).

Example 82: Synthesis of Compound 304 (2-(3-aminoazetidin-1-yl)-N-[(3R,5S)-1-[8-(difluoromethyl)quinolin-5-yl]-5-methylpiperidin-3-yl]acetamide)

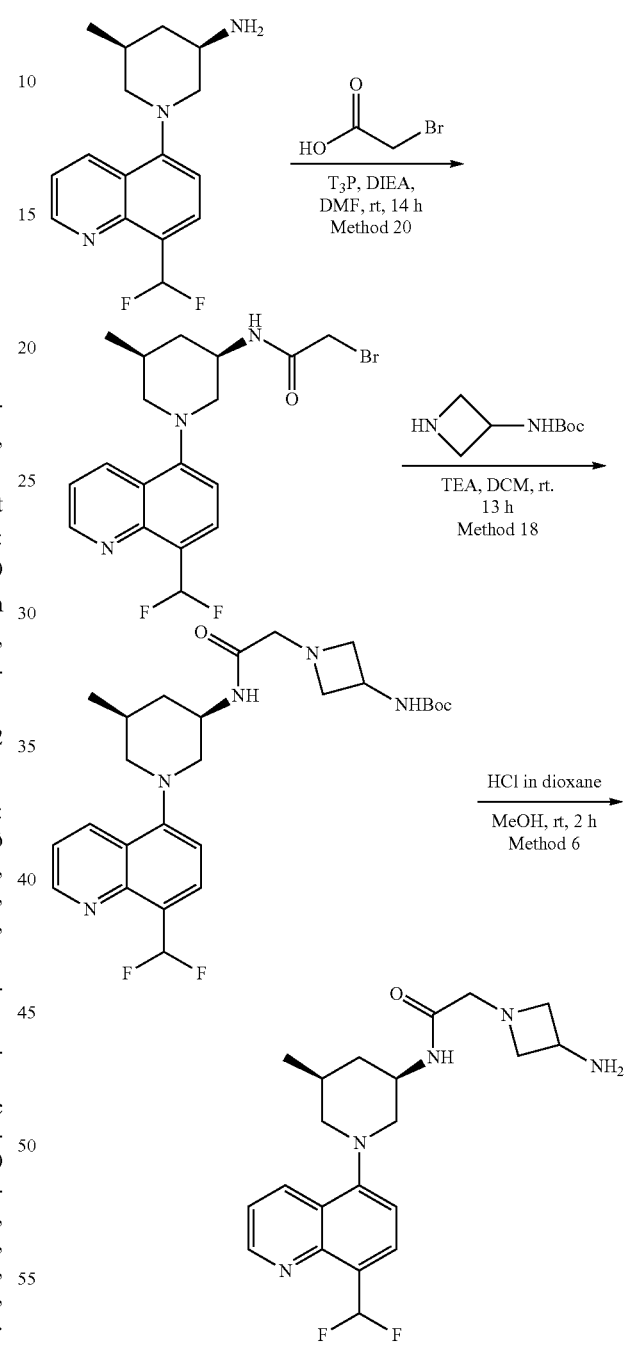

2-(3-aminoazetidin-1-yl)-N-[(3R,5S)-1-[8-(difluoromethyl)quinolin-5-yl]-5-methylpiperidin-3-yl]acetamide: 2-(3-aminoazetidin-1-yl)-N-[(3R,5S)-1-[8-(difluoromethyl)quinolin-5-yl]-5-methylpiperidin-3-yl]acetamide was prepared from 2-bromoacetic acid, tert-butyl azetidin-3-ylcarbamate, and (3R,5S)-1-(8-(difluoromethyl)quinolin-5-yl)-5-methylpiperidin-3-amine using Method 20, 18, and 6. The crude product was purified by prep-HPLC under the following conditions: column, XBridge Prep C18 OBD Column, 5 um, 19 mm×150 mm; mobile phase, acetonitrile in water (with 10 mmol/L NH₄HCO₃), 30% to 60% gradient in 8 min; detector, UV 254 nm. 2-(3-aminoazetidin-1-yl)-N-[(3R,5S)-1-[8-(difluoromethyl)quinolin-5-yl]-5-methylpiperidin-3-yl]acetamide was obtained as white solid (20 mg, 12% for 3 steps).

Compound 304: HPLC: 92.6% purity, RT=2.72 min. MS: n/z=404.2 [M+H]⁺. ¹H NMR (400 MHz, CD₃OD, ppm) δ 8.88 (dd, J=4.3, 1.7 Hz, 1H), 8.66-8.57 (m, 1H), 8.00-7.86 (m, 1H), 7.85-7.51 (m, 2H), 7.25 (d, J=7.9 Hz, 1H), 4.27-4.19 (m, 1H), 3.68-3.61 (m, 2H), 3.62-3.49 (m, 2H), 3.42-3.32 (m, 1H), 3.14 (s, 2H), 2.98-2.90 (m, 2H), 2.58-2.38 (m, 2H), 2.21-2.00 (m, 2H), 1.18 (td, J=12.0, 12.0 Hz, 1H), 1.02 (d, J=6.4 Hz, 3H).

The following compounds were synthesized in an analogous manner:

Compound 361 (2-(3-aminoazetidin-1-yl)-N-((3R,5S)-5-methyl-1-(8-(trifluoromethyl)quinoxalin-5-yl)piperidin-3-yl)acetamide): From (3R,5S)-5-methyl-1-(8-(trifluoromethyl)quinoxalin-5-yl)piperidin-3-amine, 2-bromoacetic acid, and tert-butyl azetidin-3-ylcarbamate. HPLC: 99.1% purity, RT=2.27 min. MS: m/z=423.2 [M+H]⁺. ¹H NMR (400 MHz, DMSO-d₆, ppm) δ 9.02 (d, J=1.7 Hz, 1H), 8.97 (d, J=1.6 Hz, 1H), 8.06 (d, J=8.4 Hz, 1H), 7.62 (d, J=8.0 Hz, 1H), 7.26 (d, J=8.4 Hz, 1H), 4.12-3.92 (m, 3H), 3.5-3.53 (m, 2H), 3.41-3.39 (m, 1H), 3.06-2.90 (m, 2H), 2.84-2.64 (m, 3H), 2.58-2.55 (m, 1H), 1.92-1.88 (m, 2H), 1.26-1.16 (m, 1H), 0.93 (d, J=6.3 Hz, 3H).

Compound 365 (2-(3-aminoazetidin-1-yl)-N-[(3R,5S)-1-[8-(difluoromethyl)quinoxalin-5-yl]-5-methylpiperidin-3-yl]acetamide): From 2-(azetidin-3-yl)-N-[(3R,5S)-1-[8-(difluoromethyl)quinolin-5-yl]-5-methylpiperidin-3-yl] acetamide and polyformaldehyde. HPLC: 87.4% purity, RT=1.21 min. MS: m/z=405.4 [M+H]⁺. ¹H NMR (400 MHz, CD₃OD, ppm) δ 8.92-8.82 (m, 2H), 7.96 (d, J=8.2 Hz, 1H), 7.80-7.51 (m, 1H), 7.33 (d, J=8.1 Hz, 1H), 4.28-4.05 (m, 2H), 4.04-3.94 (m, 1H), 3.82-3.68 (m, 3H), 3.25-3.12 (m, 4H), 2.69-2.64 (m, 1H), 2.53-2.49 (m, 1H), 2.09-2.05 (m, 2H), 1.31-1.12 (m, 1H), 1.01 (d, J=6.4 Hz, 3H).

Example 83: Synthesis of Compound 305 (2-(3-aminoazetidin-1-yl)-N-[(3R,5S)-1-[8-(difluoromethyl)quinolin-5-yl]-5-methylpiperidin-3-yl]propanamide)

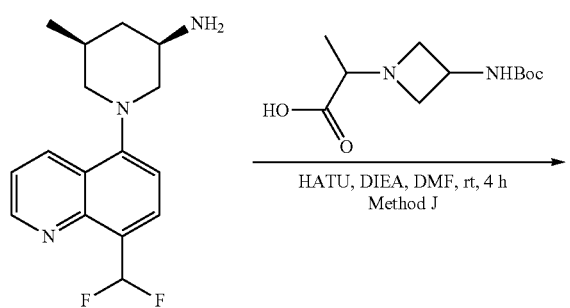

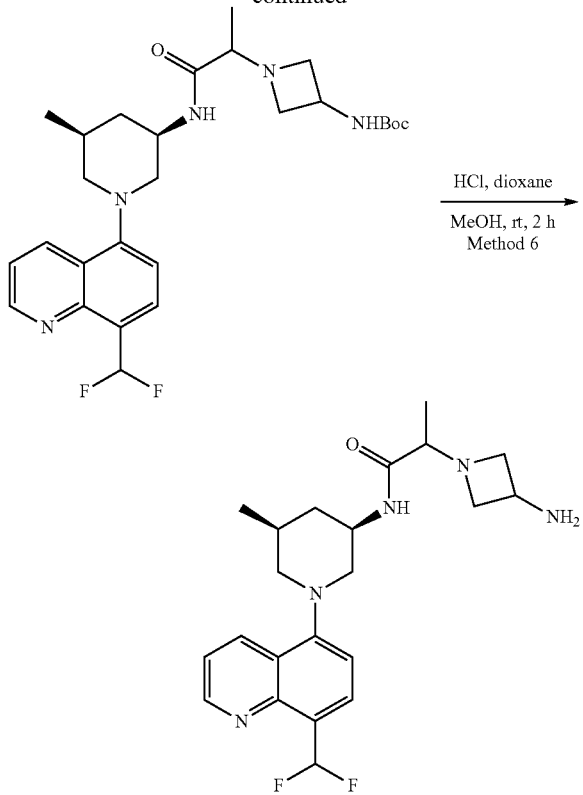

2-(3-aminoazetidin-1-yl)-N-[(3R,5S)-1-[8-(difluoromethyl)quinolin-5-yl]-5-methylpiperidin-3-yl]propanamide: 2-(3-aminoazetidin-1-yl)-N-[(3R,5S)-1-[8-(difluoromethyl)quinolin-5-yl]-5-methylpiperidin-3-yl]propanamide was prepared from 2-(1-(tert-butoxycarbonyl)azetidin-3-yl)acetic acid and (3R,5S)-1-(8-(difluoromethyl)quinolin-5-yl)-5-methylpiperidin-3-amine using Method J and 6. The crude product was purified by prep-HPLC under the following conditions: column, XBridge Prep C18 OBD Column, 5 um, 19 mm×150 mm; mobile phase, acetonitrile in water (with 10 mmol/L NH₄HCO₃), 37% to 39% gradient in 10 min; detector, UV 254 nm. 2-(3-aminoazetidin-1-yl)-N-[(3R,5S)-1-[8-(difluoromethyl)quinolin-5-yl]-5-methylpiperidin-3-yl]propanamide was obtained as white solid (29 mg, 23% for 2 steps).

Compound 305: HPLC: 94.5% purity, RT=1.37 min. MS: m/z=418.3 [M+H]⁺. ¹H NMR (300 MHz, CD₃OD, ppm) δ 8.86 (dd, J=4.2, 1.7 Hz, 1H), 8.58 (d, J=8.6 Hz, 1H), 7.95-7.43 (m, 3H), 7.22 (d, J=7.9 Hz, 1H), 4.26-4.12 (m, 1H), 3.61-3.42 (m, 4H), 3.40-3.20 (m, 1H), 2.91-2.74 (m, 3H), 2.56-2.35 (m, 2H), 2.16-1.96 (m, 2H), 1.25-1.05 (m, 4H), 1.00 (d, J=6.4 Hz, 3H).

The following compounds were synthesized in an analogous manner:

Compound 306 (2-amino-2-cyclopropyl-N-[(3R,5S)-1-[8-(difluoromethyl)quinolin-5-yl]-5-methylpiperidin-3-yl]acetamide): From 2-(tert-butoxycarbonylamino)-2-cyclopropylacetic acid and (3R,5S)-1-(8-(difluoromethyl)quinolin-5-yl)-5-methylpiperidin-3-amine. HPLC: 84.9% purity, RT=2.57+2.60 min. MS: m/z=389.2 [M+H]⁺. ¹H NMR (400 MHz, Chloroform-d, ppm) δ 8.92 (d, J=3.7 Hz, 1H), 8.54-8.50 (m, 1H), 7.99-7.56 (m, 2H), 7.50-7.47 (m, 1H), 7.19-6.98 (m, 2H), 4.34-4.26 (m, 1H), 3.71-3.59 (m, 1H), 3.32-3.28 (m, 1H), 2.85-2.70 (m, 1H), 2.42 (apparent q, J=11.3 Hz, 2H), 2.22-1.75 (m, 4H), 1.13-0.92 (m, 5H), 0.68-0.47 (m, 3H), 0.32-0.23 (m, 1H).

Compound 312 (2-(azetidin-3-yl)-N-[(3R,5S)-1-[8-(difluoromethyl)quinolin-5-yl]-5-methylpiperidin-3-yl]acetamide): From 2-(3,3-difluoroazetidin-1-yl)propanoic acid and (3R,5S)-1-(8-(difluoromethyl)quinolin-5-yl)-5-methylpiperidin-3-amine. HPLC: 96.7% purity, RT=6.65 min. MS: m/z=389.4 [M+H]$^+$. $^1$H NMR (400 MHz, CD$_3$OD, ppm) δ 8.90 (dd, J=4.3, 1.8 Hz, 1H), 8.62 (dd, J=8.7, 1.8 Hz, 1H), 7.94 (d, J=7.9 Hz, 1H), 7.85-7.50 (m, 2H), 7.26 (d, J=7.9 Hz, 1H), 4.22 (d, J=12.4 Hz, 1H), 3.96-3.75 (m, 2H), 3.65-3.45 (m, 3H), 3.24-3.05 (m, 2H), 2.63-2.36 (m, 4H), 2.20-2.08 (m, 2H), 1.22-0.94 (m, 4H).

Compound 315 (4-amino-N-[(3R,5S)-1-[8-(difluoromethyl)quinolin-5-yl]-5-methylpiperidin-3-yl]-3,3-dimethylbutanamide): From 4-[[(tert-butoxy)carbonyl]amino]-3,3-dimethylbutanoic acid and (3R,5S)-1-(8-(difluoromethyl)quinolin-5-yl)-5-methylpiperidin-3-amine. HPLC: 95.7% purity, RT=5.17 min. MS: n/z=405.3 [M+H]$^+$. $^1$H NMR (300 MHz, CD$_3$OD, ppm) δ 8.86 (dd, J=4.2, 1.7 Hz, 1H), 8.59 (dd, J=8.6, 1.7 Hz, 1H), 7.94-7.45 (m, 3H), 7.22 (d, J=7.9 Hz, 1H), 4.28-4.11 (m, 1H), 3.55-3.50 (m, 1H), 3.40-3.20 (m, 1H), 2.56 (s, 2H), 2.53-2.33 (m, 2H), 2.19-2.02 (m, 4H), 1.18-1.07 (m, 1H), 0.98-0.88 (m, 9H).

Compound 324 (2-(azetidin-3-yl)-N-[(3R,5S)-1-[8-(difluoromethyl)quinoxalin-5-yl]-5-methylpiperidin-3-yl]acetamide): From 2-(1-(tert-butoxycarbonyl)azetidin-3-yl)acetic acid and (3R,5S)-1-[8-(difluoromethyl)quinoxalin-5-yl]-5-methylpiperidin-3-amine. HPLC: 95.8% purity, RT=1.15 min. MS: m/z=390.2 [M+H]$^+$. $^1$H NMR (400 MHz, CD$_3$OD, ppm) δ 8.95-8.85 (m, 2H), 7.96 (d, J=8.1 Hz, 1H), 7.63 (t, J=55.9 Hz, 1H), 7.33 (d, J=8.2 Hz, 1H), 4.22-4.01 (m, 2H), 3.94-3.90 (m, 2H), 3.66-3.62 (m, 2H), 3.23-3.09 (m, 1H), 2.65-2.44 (m, 4H), 2.10-2.03 (m, 2H), 1.13 (td, J=12.4, 12.4 Hz, 1H), 1.00 (d, J=6.4 Hz, 3H).

Compound 327 (4-amino-N-[(3R,5S)-1-[8-(difluoromethyl)quinoxalin-5-yl]-5-methylpiperidin-3-yl]-3,3-dimethylbutanamide): From 4-[[(ter-butoxy)carbonyl]amino]-3,3-dimethylbutanoic acid and (3R,5S)-1-[8-(difluoromethyl)quinoxalin-5-yl]-5-methylpiperidin-3-amine. HPLC: 90.8% purity, RT=1.29 min. MS: m/z=406.2 [M+H]$^+$. $^1$H NMR (400 MHz, CD$_3$OD, ppm) δ 8.93-8.82 (m, 2H), 7.96 (d, J=8.1 Hz, 1H), 7.63 (t, J=56.0 Hz, 1H), 7.33 (d, J=8.2 Hz, 1H), 4.23-3.95 (m, 3H), 2.67-2.56 (m, 3H), 2.50 (t, J=11.4 Hz, 1H), 2.19 (s, 2H), 2.11-2.08 (m, 1H), 1.21-1.07 (m, 1H), 1.04-0.94 (m, 9H).

Example 84: Synthesis of Compound 330 (cis-5-cyclopropyl-1-[8-(trifluoromethyl)quinoxalin-5-yl]piperidin-3-amine)

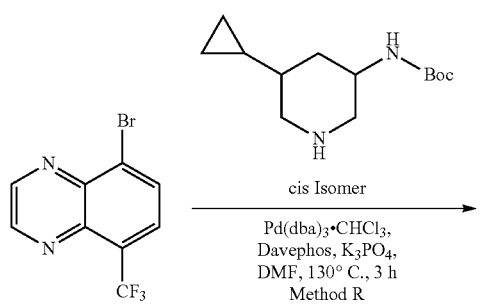

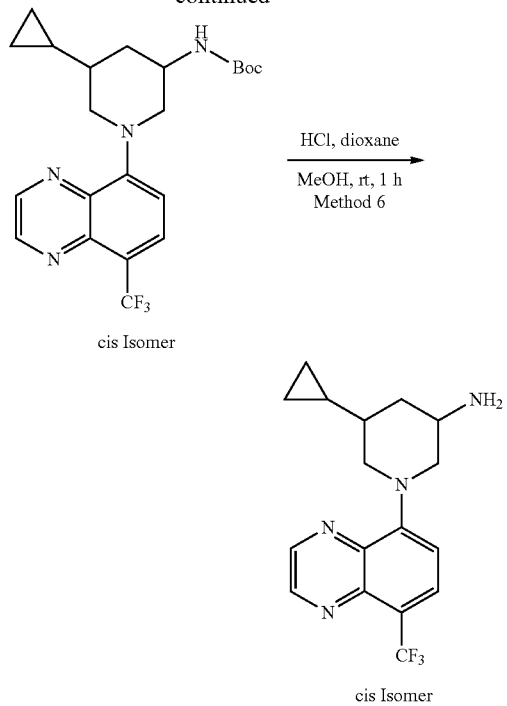

cis-5-cyclopropyl-1-[8-(trifluoromethyl)quinoxalin-5-yl]piperidin-3-amine: cis-5-cyclopropyl-1-[8-(trifluoromethyl)quinoxalin-5-yl]piperidin-3-amine was prepared from 5-bromo-8-(trifluoromethyl)quinoxaline and tert-butyl cis-5-cyclopropylpiperidin-3-ylcarbamate using Method R and 6. The crude product was purified by prep-HPLC under the following conditions: column, XBridge Prep C18 OBD Column, 5 um, 19 mm×150 mm; mobile phase, acetonitrile in water (with 0.05% NH$_3$.H$_2$O), hold at 36% gradient in 10 min; detector, UV 254 nm. cis-5-cyclopropyl-1-[8-(trifluoromethyl)quinoxalin-5-yl]piperidin-3-amine was obtained as yellow solid (20 mg, 6.5% for 2 steps).

Compound 330: HPLC: 96.7% purity, RT=1.62 min. MS: m/z=337.2 [M+H]$^+$. $^1$H NMR (400 MHz, DMSO-d$_6$, ppm) δ 9.01 (d, J=1.8 Hz, 1H), 8.96 (d, J=1.7 Hz, 1H), 8.05 (d, J=8.4 Hz, 1H), 7.28-7.16 (m, 1H), 4.18-4.07 (m, 2H), 2.97-2.81 (m, 1H), 2.77-2.61 (m, 1H), 2.60-2.57 (m, 2H), 2.50-2.20 (m, 1H), 2.10-2.03 (m, 1H), 1.15-0.99 (m, 2H), 0.63-0.51 (m, 1H), 0.48-0.34 (m, 2H), 0.24-0.11 (m, 2H).

The following compounds were synthesized in an analogous manner:

Compound 331 (cis-5-cyclopropyl-1-[8-(trifluoromethyl)quinolin-5-yl]piperidin-3-amine): From 5-bromo-8-(trifluoromethyl)quinoline and tert-butyl cis-5-cyclopropylpiperidin-3-ylcarbamate. HPLC: 93.2% purity, RT=2.71 min. MS: n/z=336.2 [M+H]$^+$. $^1$H NMR (300 MHz, CD$_3$OD, ppm) δ 8.89 (dd, J=4.2, 1.8 Hz, 1H), 8.50 (dd, J=8.7, 1.8 Hz, 1H), 8.01 (d, J=8.1 Hz, 1H), 7.55 (dd, J=8.6, 4.2 Hz, 1H), 7.20 (d, J=8.0 Hz, 1H), 3.55-3.38 (m, 2H), 3.20-3.03 (m, 1H), 2.63-2.44 (m, 2H), 2.25 (d, J=10.9 Hz, 1H), 1.28-1.03 (m, 2H), 0.66-0.34 (m, 3H), 0.28-0.09 (m, 2H).

Compound 333 (cis-5-cyclopropyl-1-(8-fluoroquinolin-5-yl)piperidin-3-amine): From 5-bromo-8-fluoroquinoline and tert-butyl cis-5-cyclopropylpiperidin-3-ylcarbamate. HPLC: 99.3% purity, RT=1.20 min. MS: m/z=286.2 [M+H]$^+$. $^1$H NMR (400 MHz, CD$_3$OD, ppm) δ 8.86 (dd, J=4.2, 1.6 Hz, 1H), 8.58 (dt, J=8.6, 1.6 Hz, 1H), 7.61 (dd, J=8.6, 4.3 Hz, 1H), 7.42 (dd, J=10.7, 8.4 Hz, 1H), 7.22 (dd, J=8.4, 4.2 Hz, 1H), 3.40-3.25 (m, 2H), 3.22-3.08 (m, 1H), 2.62-2.42 (m, 2H), 2.26 (d, J=10.7 Hz, 1H), 1.31-1.07 (m, 2H), 0.67-0.37 (m, 3H), 0.29-0.10 (m, 2H).

Compound 334 (cis-5-cyclopropyl-1-(8-methoxyquinolin-5-yl)piperidin-3-amine): From 5-bromo-8-fluoroquinoline and tert-butyl cis-5-cyclopropylpiperidin-3-ylcarbamate. HPLC: 98.0% purity, RT=1.11 min. MS: m/z=298.2 [M+H]$^+$. $^1$H NMR (400 MHz, CD$_3$OD, ppm) δ 8.80 (dd, J=4.3, 1.7 Hz, 1H), 8.57 (dd, J=8.6, 1.7 Hz, 1H), 7.57 (dd, J=8.5, 4.3 Hz, 1H), 7.25 (d, J=8.3 Hz, 1H), 7.15 (d, J=8.3 Hz, 1H), 4.05 (s, 3H), 3.40-3.10 (m, 3H), 2.60-2.40 (m, 2H), 2.27 (d, J=10.8 Hz, 1H), 1.28-1.07 (m, 2H), 0.71-0.56 (m, 1H), 0.44-0.48 (m, 2H), 0.18-0.23 (m, 2H).

Example 85: Synthesis of Compound 332 (cis-5-cyclopropyl-1-[8-(difluoromethyl)quinolin-5-yl]piperidin-3-amine)

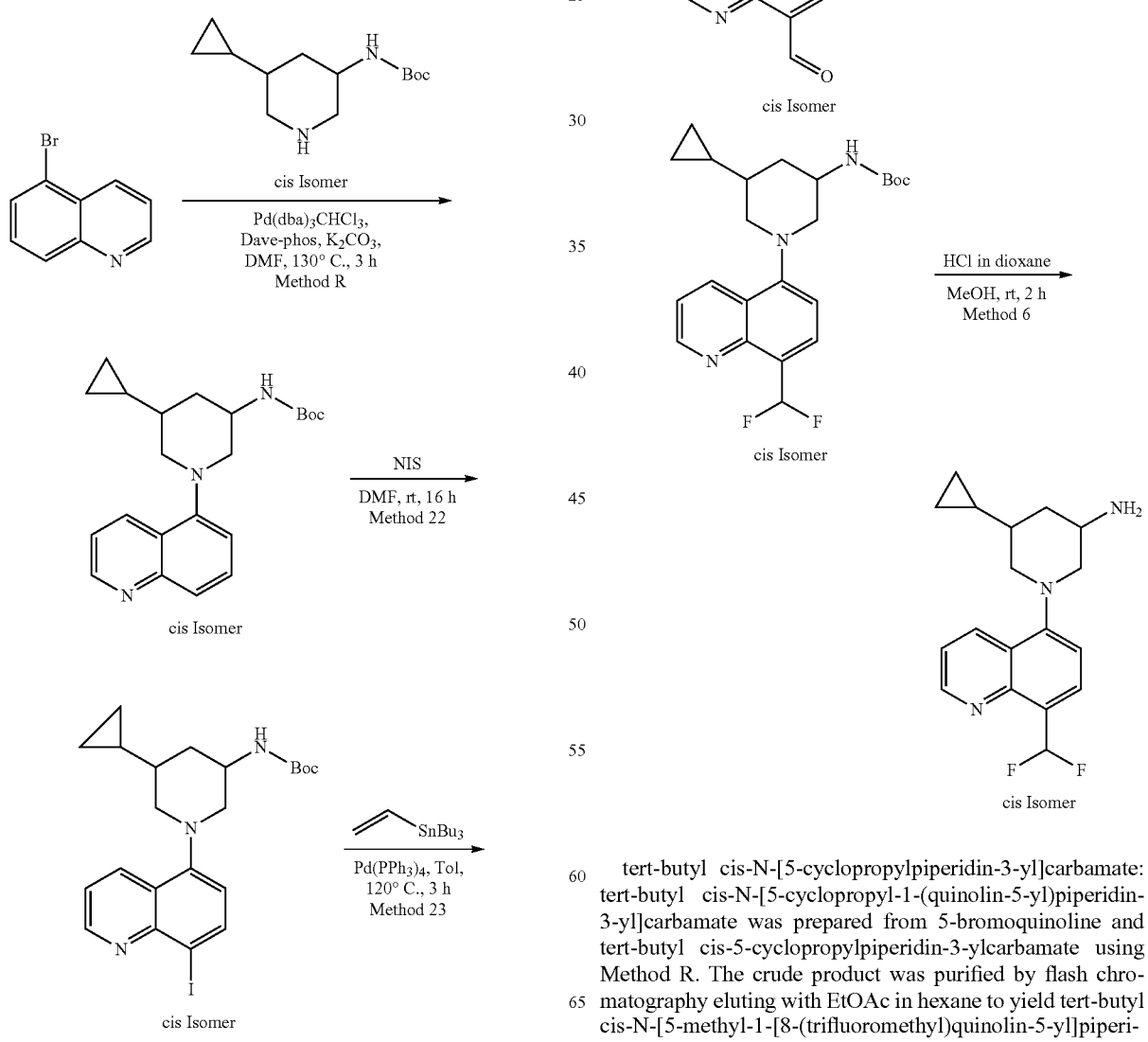

tert-butyl cis-N-[5-cyclopropylpiperidin-3-yl]carbamate: tert-butyl cis-N-[5-cyclopropyl-1-(quinolin-5-yl)piperidin-3-yl]carbamate was prepared from 5-bromoquinoline and tert-butyl cis-5-cyclopropylpiperidin-3-ylcarbamate using Method R. The crude product was purified by flash chromatography eluting with EtOAc in hexane to yield tert-butyl cis-N-[5-methyl-1-[8-(trifluoromethyl)quinolin-5-yl]piperidin-3-yl]carbamate as yellow solid (400 mg, 48%).

Method 22 tert-Butyl cis-N-[5-cyclopropyl-1-(8-iodoquinolin-5-yl)piperidin-3-yl]carbamate: To a solution of tert-butyl cis-N-[5-cyclopropyl-1-(quinolin-5-yl)piperidin-3-yl]carbamate (400 mg, 1.03 mmol) in DMF (10 mL) was added NIS (367 mg, 1.55 mmol) at room temperature. The resulting solution was then stirred for 16 h at room temperature. When the reaction was done, it was quenched by the addition of water (10 mL). The resulting mixture was extracted with ethyl acetate (50 mL×3). The organic phases were combined, washed with brine and dried over $Na_2SO_4$. The solvent was removed under reduced pressure and the residue was purified by flash chromatography eluting with EtOAc in hexane to yield tert-butyl cis-N-[5-cyclopropyl-1-(8-iodoquinolin-5-yl)piperidin-3-yl]carbamate as yellow solid (350 mg, 69%). MS: m/z=494.2 $[M+H]^+$.

Method 23 tert-butyl cis-N-[5-cyclopropyl-1-(8-ethenylquinolin-5-yl)piperidin-3-yl]carbamate: To a solution of cis-N-[5-cyclopropyl-1-(8-iodoquinolin-5-yl)piperidin-3-yl]carbamate (350 mg, 0.67 mmol) in toluene (40 mL) was added $Pd(PPh_3)_4$ (82 mg, 0.07 mmol) and tributyl(ethenyl)stannane (337 mg, 1.01 mmol) at room temperature. The reaction mixture was then stirred for 3 h at 120° C. After cooling to room temperature, the reaction mixture was diluted with water (30 mL). The resulting mixture was extracted with ethyl acetate (60 mL×3). The organic phases were combined, washed with brine and dried over $Na_2SO_4$. The solvent was removed under reduced pressure and the residue was purified by flash chromatography eluting with EtOAc in hexane to yield cis-N-[5-cyclopropyl-1-(8-ethenylquinolin-5-yl)piperidin-3-yl]carbamate as a yellow solid (200 mg, 75%). MS: m/z=394.2 $[M+H]^+$.

Method 24 tert-butyl cis-N-[5-cyclopropyl-1-(8-formylquinolin-5-yl)piperidin-3-yl]carbamate: To a solution of cis-N-[5-cyclopropyl-1-(8-ethenylquinolin-5-yl)piperidin-3-yl]carbamate (200 mg, 0.48 mmol) in THF (10 mL) was added $OsO_4$ (13 mg, 0.05 mmol), $NaIO_4$ (435 mg, 1.93 mmol), and water (2.3 mL) at room temperature. The reaction mixture was stirred for 2 h at room temperature. When the reaction was done, it was quenched by the addition of sat. $Na_2S_2O_3$ solution (10 mL). The resulting mixture was extracted with ethyl acetate (50 mL×3). The organic phases were combined, washed with brine and dried over $Na_2SO_4$. The solvent was removed under reduced pressure. This resulted in tert-butyl cis-N-[5-cyclopropyl-1-(8-formylquinolin-5-yl)piperidin-3-yl]carbamate as a yellow solid (150 mg, 79%). MS: m/z=396.2 $[M+H]^+$.

tert-butyl cis-N-[5-cyclopropyl-1-[8-(difluoromethyl)quinolin-5-yl]piperidin-3-yl]carbamate: To a solution of tert-butyl cis-N-[5-cyclopropyl-1-(8-formylquinolin-5-yl)piperidin-3-yl]carbamate (150 mg, 0.36 mmol) in DCM (8 mL) was added BAST (252 mg, 1.08 mmol) at room temperature. The resulting solution was stirred for 2 h at room temperature. When the reaction was done, it was quenched by the addition of sat. sodium bicarbonate solution (30 mL). The resulting mixture was extracted with ethyl acetate (30 mL×3). The organic phases were combined, washed with brine and dried over $Na_2SO_4$. The solvent was removed under reduced pressure and the residue was purified by flash chromatography eluting with EtOAc in hexane to yield tert-butyl cis-N-[5-cyclopropyl-1-[8-(difluoromethyl)quinolin-5-yl]piperidin-3-yl]carbamate as a yellow solid (80 mg, 53%). MS: m/z=418.2 $[M+H]^+$.

cis-5-cyclopropyl-1-[8-(difluoromethyl)quinolin-5-yl]piperidin-3-amine: cis-5-cyclopropyl-1-[8-(difluoromethyl)quinolin-5-yl]piperidin-3-amine was prepared from tert-butyl cis-N-[5-cyclopropyl-1-[8-(difluoromethyl)quinolin-5-yl]piperidin-3-yl]carbamate using Method 6. The crude product was purified by flash chromatography eluting with MeOH in DCM (0% to 10% gradient). cis-5-cyclopropyl-1-[8-(difluoromethyl)quinolin-5-yl]piperidin-3-amine was obtained as light yellow solid (14 mg, 40%).

Compound 332: HPLC: 99.3% purity, RT=1.29 min. MS: n/z=318.1 $[M+H]^+$. $^1$H NMR (400 MHz, $CD_3OD$, ppm) δ 8.89 (dd, J=4.2, 1.7 Hz, 1H), 8.51 (dd, J=8.6, 1.8 Hz, 1H), 7.95 (d, J=7.8 Hz, 1H), 7.88-7.48 (m, 2H), 7.28 (d, J=7.9 Hz, 1H), 3.67-3.38 (m, 2H), 3.28-3.07 (m, 1H), 2.61 (t, J=10.9 Hz, 1H), 2.52 (t, J=10.8 Hz, 1H), 2.37-2.20 (m, 1H), 1.29-1.10 (m, 2H), 0.47-0.60 (m, 1H), 0.55-0.36 (m, 2H), 0.23-0.18 (m, 2H).

Example 86: Synthesis of Compound 335 cis-(N-5-cyclopropyl-1-[8-(trifluoromethyl)quinoxalin-5-yl]piperidin-3-yl]-2-(morpholin-4-yl)acetamide)

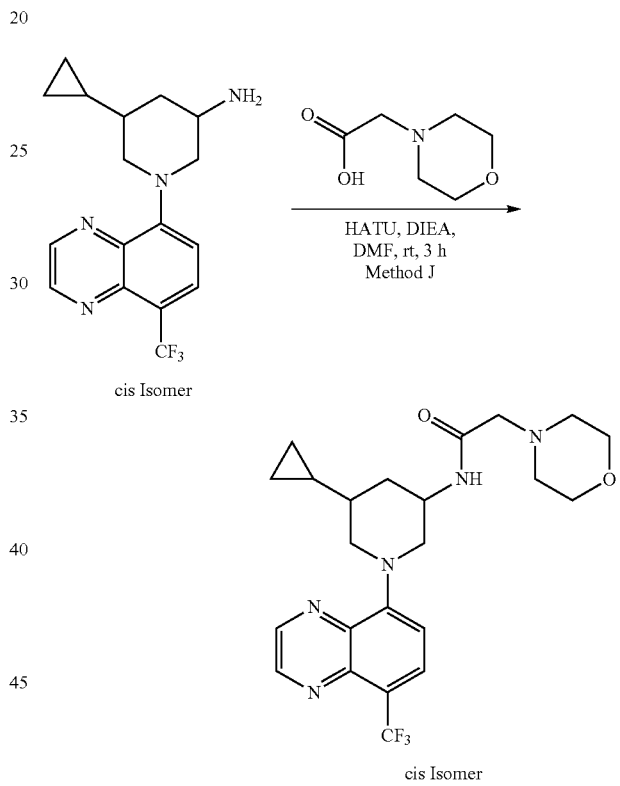

Cis-N-[5-cyclopropyl-1-[8-(trifluoromethyl)quinoxalin-5-yl]piperidin-3-yl]-2-(morpholin-4-yl)acetamide: cis-N-[5-cyclopropyl-1-[8-(trifluoromethyl)quinoxalin-5-yl]piperidin-3-yl]-2-(morpholin-4-yl)acetamide was prepared from 2-(morpholin-4-yl)acetic acid and cis-5-cyclopropyl-1-[8-(trifluoromethyl)quinoxalin-5-yl]piperidin-3-amine using Method J. The crude product was purified by prep-HPLC under the following conditions: column, XBridge Prep C18 OBD Column, 5 um, 19 mm×150 mm; mobile phase, acetonitrile in water (with 0.0.5% $NH_3.H_2O$), 46% to 52% gradient in 8 min; detector, UV 254 nm. Cis-N-[5-cyclopropyl-1-[8-(trifluoromethyl)quinoxalin-5-yl]piperidin-3-yl]-2-(morpholin-4-yl)acetamide was obtained as light yellow solid (11 mg, 13%).

Compound 335: HPLC: 97.2% purity, RT=0.90 min. MS: m/z=464.1 $[M+H]^+$. $^1$H NMR (400 MHz, $CD_3OD$, ppm) δ 8.95-8.85 (m, 2H), 8.05 (d, J=8.3 Hz, 1H), 7.29 (d, J=8.3 Hz, 1H), 4.19-4.11 (m, 3H), 3.88-3.62 (m, 4H), 3.22-2.98 (m, 2H), 2.94-2.74 (m, 2H), 2.69-2.42 (m, 4H), 2.22 (d, J=12.5 Hz, 1H), 1.48 (d, J=11.7 Hz, 1H), 1.40-1.13 (m, 1H), 0.67-0.64 (m, 1H), 0.52-0.49 (m, 2H), 0.24 (dt, J=6.7, 2.6 Hz, 2H).

The following compounds were synthesized in an analogous manner:

Compound 336 (cis-N-[5-cyclopropyl-1-[8-(trifluoromethyl)quinolin-5-yl]piperidin-3-yl]-2-(morpholin-4-yl)acetamide): from 2-(morpholin-4-yl)acetic acid and cis-5-cyclopropyl-1-[8-(trifluoromethyl)quinoxalin-5-yl]piperidin-3-amine. HPLC: 99.3% purity, RT=1.91 min. MS: m/z=463.2 [M+H]$^+$. $^1$H NMR (400 MHz, CD$_3$OD, ppm) δ 8.92 (dd, J=4.3, 1.7 Hz, 1H), 8.60 (dt, J=8.6, 1.6 Hz, 1H), 8.02 (d, J=8.0 Hz, 1H), 7.60 (dd, J=8.6, 4.2 Hz, 1H), 7.26-7.19 (m, 1H), 4.25-4.17 (m, 1H), 3.71 (t, J=4.7 Hz, 4H), 3.62-3.53 (m, 1H), 3.52-3.43 (m, 1H), 3.02 (d, J=1.3 Hz, 2H), 2.70 (t, J=11.3 Hz, 1H), 2.65-2.47 (m, 5H), 2.22 (d, J=12.3 Hz, 1H), 1.41 (q, J=12.0 Hz, 1H), 1.26 (q, J=10.5 Hz, 1H), 0.67-0.60 (m, 1H), 0.51-0.48 (m, 2H), 0.30-0.15 (m, 2H).

Compound 338 (cis-N-[5-cyclopropyl-1-[8-(trifluoromethyl)quinolin-5-yl]piperidin-3-yl]-2-(4-methylpiperazin-1-yl)acetamide): From 2-(4-methylpiperazin-1-yl)acetic acid and cis-5-cyclopropyl-1-[8-(trifluoromethyl)quinolin-5-yl]piperidin-3-amine. HPLC: 96.7% purity, RT=3.28 min. MS: m/z=476.3 [M+H]$^+$. $^1$H NMR (400 MHz, CD$_3$OD, ppm) δ 8.92 (dd, J=4.3, 1.7 Hz, 1H), 8.61 (dd, J=8.6, 1.7 Hz, 1H), 8.03 (d, J=8.0 Hz, 1H), 7.60 (dd, J=8.6, 4.2 Hz, 1H), 7.23 (d, J=8.0 Hz, 1H), 4.27-4.14 (m, 1H), 3.63-3.54 (m, 1H), 3.47 (d, J=11.2 Hz, 1H), 3.04 (d, J=1.6 Hz, 2H), 2.75-2.40 (m, 10H), 2.32-2.20 (m, 4H), 1.40 (q, J=11.9 Hz, 1H), 1.27 (t, J=10.5 Hz, 1H), 0.71-0.58 (m, 1H), 0.55-0.41 (m, 2H), 0.30-0.16 (m, 2H).

Example 87: Synthesis of Compound 337 (cis-N-[5-cyclopropyl-1-[8-(trifluoromethyl)quinolin-5-yl]piperidin-3-yl]-N-methyl-2-(morpholin-4-yl)acetamide)

Cis-N-[5-cyclopropyl-1-[8-(trifluoromethyl)quinolin-5-yl]piperidin-3-yl]-N-methyl-2-(morpholin-4-yl)acetamide: cis-N-[5-cyclopropyl-1-[8-(trifluoromethyl)quinolin-5-yl]piperidin-3-yl]-N-methyl-2-(morpholin-4-yl)acetamide was prepared from MeI and cis-N-(5-cyclopropyl-1-(8-(trifluoromethyl)quinolin-5-yl)piperidin-3-yl)-2-morpholinoacetamide using Method S. The crude product was purified by prep-HPLC under the following conditions: column, XBridge Prep C18 OBD Column, 5 um, 19 mm×150 mm; mobile phase, acetonitrile in water (with 10 mmol/L NH$_4$HCO$_3$ and 0.1% NH$_3$.H$_2$), 52% to 59% gradient in 8 min; detector, UV 254 nm. Cis-N-[5-cyclopropyl-1-[8-(trifluoromethyl)quinolin-5-yl]piperidin-3-yl]-N-methyl-2-(morpholin-4-yl)acetamide was obtained as light yellow solid (20 mg, 23%).

Compound 337: HPLC: 93.0% purity, RT=2.58 min. MS: m/z=477.3 [M+H]$^+$. $^1$H NMR (400 MHz, CD$_3$OD, ppm) δ 8.94-8.90 (m, 1H), 8.61-8.55 (m, 1H), 8.03 (dd, J=10.8, 8.0 Hz, 1H), 7.62-7.57 (m, 1H), 7.27 (dd, J=16.4, 8.1 Hz, 1H), 4.81 (d, J=12.2 Hz, 1H), 3.69 (t, J=4.7 Hz, 2H), 3.52-3.45 (m, 3H), 3.40-3.10 (m, 3H), 3.05 (s, 2H), 2.90-2.80 (m, 2H), 2.70-2.40 (m, 5H), 2.20-2.00 (m, 1H), 1.70 (dt, J=24.3, 12.0 Hz, 1H), 1.42-1.22 (m, 1H), 0.73-0.59 (m, 1H), 0.57-0.38 (m, 2H), 0.33-0.09 (m, 2H).

Example 88: Synthesis of Compound 339 and Compound 340 ((3R,5S)-1-(8-fluoroquinoxalin-5-yl)-5-methylpiperidin-3-amine and (3S,5R)-1-(8-fluoroquinoxalin-5-yl)-5-methylpiperidin-3-amine)

-continued

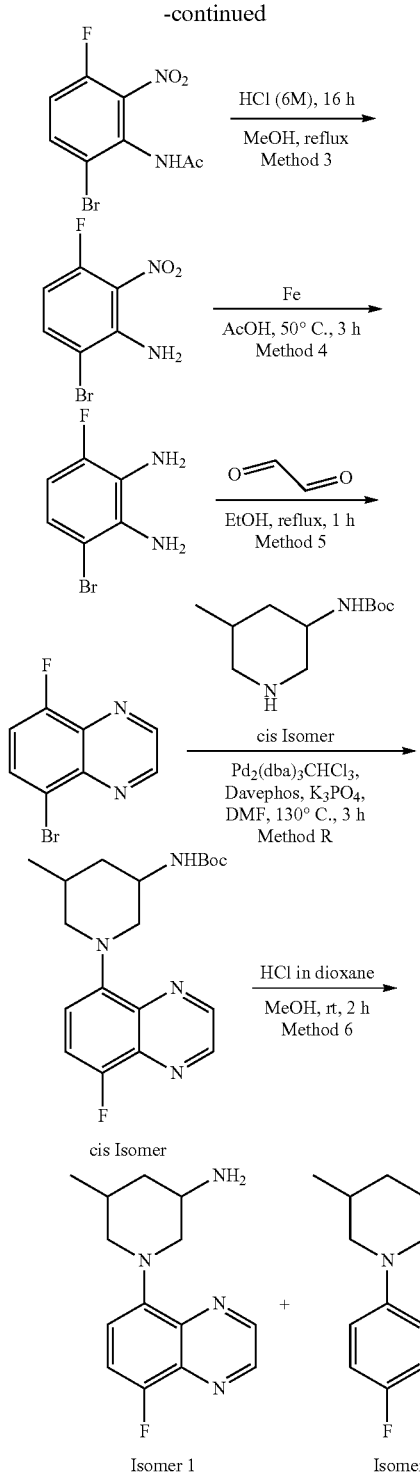

(3R,5S)-1-(8-fluoroquinoxalin-5-yl)-5-methylpiperidin-3-amine and (3S,5R)-1-(8-fluoroquinoxalin-5-yl)-5-methylpiperidin-3-amine: cis-1-(8-fluoroquinoxalin-5-yl)-5-methylpiperidin-3-amine was prepared from 2-bromo-5-fluorobenzenamine, oxalaldehyde, and tert-butyl cis-5-methylpiperidin-3-ylcarbamate using Method 1, 2, 3, 4, 5, R, and 6. The crude product was first purified by prep-HPLC under the following conditions: column, XBridge Shield RP18 OBD Column, 19×150 mm 10 um; mobile phase, acetonitrile in water (with 10 mmol/L $NH_4HCO_3$+0.1% $NH_3.H_2O$), 5% to 47% gradient in 10 min; detector, UV 254 nm. Then the two enantiomeric isomers were obtained by separation on chiral prep-HPLC under the following conditions: column, CHIRALPAK IE, 2×25 cm, 5um; mobile phase, EtOH in Hexane, 30% isocratic in 25 min; detector, UV 254/220 nm.

Isomer 1: (35 mg, 0.13%, yellow solid, for 7 steps) HPLC: 95.2% purity, RT=2.57 min. MS: m/z=261.0 [M+H]$^+$. $^1$H NMR (300 MHz, DMSO-$d_6$, ppm) δ 9.05-8.93 (m, 2H), 7.57 (dd, J=10.2, 8.7 Hz, 1H), 7.15 (dd, J=8.7, 4.9 Hz, 1H), 3.83-3.64 (m, 2H), 3.40-3.20 (m, 2H), 3.03-2.87 (m, 1H), 2.31-2.21 (m, 2H), 1.97-1.87 (m, 2H), 0.98-0.72 (m, 4H).

Isomer 2: (33 mg, 0.12%, yellow solid, for 7 steps) HPLC: 97.3% purity, RT=2.58 min. MS: m/z=261.0 [M+H]$^+$. $^1$H NMR (300 MHz, DMSO-$d_6$, ppm) δ 9.05-8.93 (m, 2H), 7.57 (dd, J=10.2, 8.7 Hz, 1H), 7.15 (dd, J=8.7, 4.9 Hz, 1H), 3.83-3.64 (m, 2H), 3.40-3.20 (m, 2H), 3.03-2.87 (m, 1H), 2.31-2.21 (m, 2H), 1.97-1.87 (m, 2H), 0.98-0.72 (m, 4H).

Example 89: Synthesis of Compound 341 ((3R,5S)-1-(8-fluoroquinolin-5-yl)-5-methylpiperidin-3-amine)

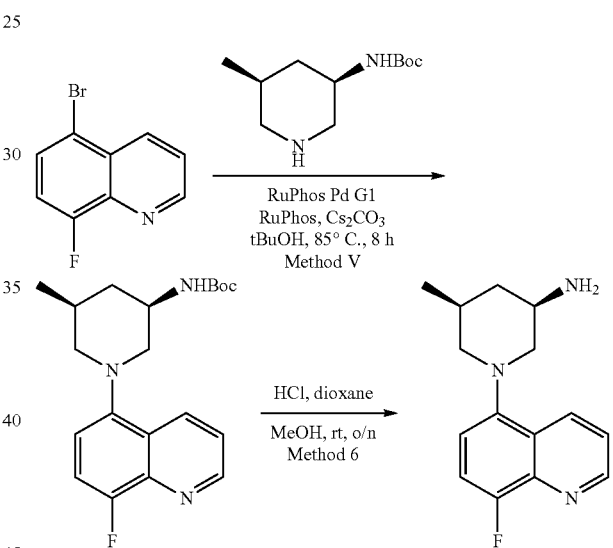

(3R,5S)-1-(8-fluoroquinolin-5-yl)-5-methylpiperidin-3-amine: (3R,5S)-1-(8-fluoroquinolin-5-yl)-5-methylpiperidin-3-amine was obtained in 35% yield over 2 steps from 5-bromo-8-fluoroquinoline and tert-butyl N-[(3R,5S)-5-methylpiperidin-3-yl]carbamate, using Method V and 6.

Compound 341: HPLC: 97.7% purity, RT=1.45 min. MS: m/z=260 [M+H]$^+$. $^1$H NMR (400 MHz, DMSO-$d_6$, ppm) δ 8.97 (dd, J=4.2, 1.6 Hz, 1H), 8.53 (d, J=8.5 Hz, 1H), 8.19 (s, 3H), 7.66 (dd, J=8.6, 4.2 Hz, 1H), 7.52 (dd, J=10.8, 8.3 Hz, 1H), 7.19 (dd, J=8.4, 4.2 Hz, 1H), 3.61-3.39 (m, 2H), 3.16 (d, J=10.0 Hz, 1H), 2.62 (t, J=10.7 Hz, 1H), 2.36 (t, J=11.2 Hz, 1H), 2.16 (d, J=12.3 Hz, 1H), 2.05 (ddd, J=16.8, 8.9, 5.2 Hz, 1H), 1.15 (q, J=11.7 Hz, 1H), 0.96 (d, J=6.6 Hz, 3H).

The following compounds were synthesized in an analogous manner:

Compound 462 ((3R,5S)-5-Methyl-1-(8-methyl-quinolin-5-yl)-piperidin-3-ylamine hydrochloride): From 5-Chloro-8-methyl-quinoline and tert-butyl N-[(3R,5S)-5-methylpiperidin-3-yl]carbamate. HPLC: >99% purity, RT=1.37 min. MS: m/z=256 [M+H]$^+$. $^1$H NMR (400 MHz, Deuterium Oxide, ppm) δ 9.35 (d, J=8.9 Hz, 1H), 9.09 (dt, J=5.4, 1.4

Hz, 1H), 8.08 (ddd, J=8.6, 5.5, 1.1 Hz, 1H), 7.96 (d, J=8.1 Hz, 1H), 7.55 (d, J=7.9 Hz, 1H), 3.89-3.74 (m, 1H), 3.66 (d, J=11.3 Hz, 1H), 3.39 (d, J=11.0 Hz, 1H), 2.98 (t, J=10.8 Hz, 1H), 2.80 (s, 3H), 2.54 (t, J=11.5 Hz, 1H), 2.37 (d, J=12.7 Hz, 1H), 2.33-2.17 (m, 1H), 1.33 (q, J=12.0 Hz, 1H), 1.05 (d, J=6.7 Hz, 3H).

Compound 586 (((3R,5S)-1-(8-Methyl-quinolin-5-yl)-5-trifluoromethyl-piperidin-3-ylamine hydrochloride): From 5-bromo-8-methylquinoline and ((3R,5S)-5-Trifluoromethyl-piperidin-3-yl)-carbamic acid tert-butyl ester. HPLC: >99% purity, RT=1.60 min. MS: m/z=310.30 [M+H]$^+$. $^1$H NMR (400 MHz, Deuterium Oxide, ppm) δ 9.34-9.29 (m, 1H), 9.03 (dd, J=5.5, 1.6 Hz, 1H), 8.04 (ddt, J=8.6, 5.5, 1.4 Hz, 1H), 7.91 (dd, J=7.9, 1.1 Hz, 1H), 7.56 (d, J=7.9 Hz, 1H), 3.82 (td, J=11.3, 5.7 Hz, 1H), 3.71 (s, 1H), 3.63-3.56 (m, 1H), 3.56-3.48 (m, 1H), 3.10 (ddp, J=11.9, 7.7, 3.9 Hz, 1H), 2.97 (dt, J=17.3, 11.2 Hz, 2H), 2.73 (d, J=1.0 Hz, 3H), 2.54 (d, J=12.2 Hz, 1H), 1.71 (q, J=12.2 Hz, 1H).

Example 90: Synthesis of Compound 342 (8-[(3R, 5S)-3-amino-5-methylpiperidin-1-yl]-7-fluoroquinoxaline-5-carbonitrile)

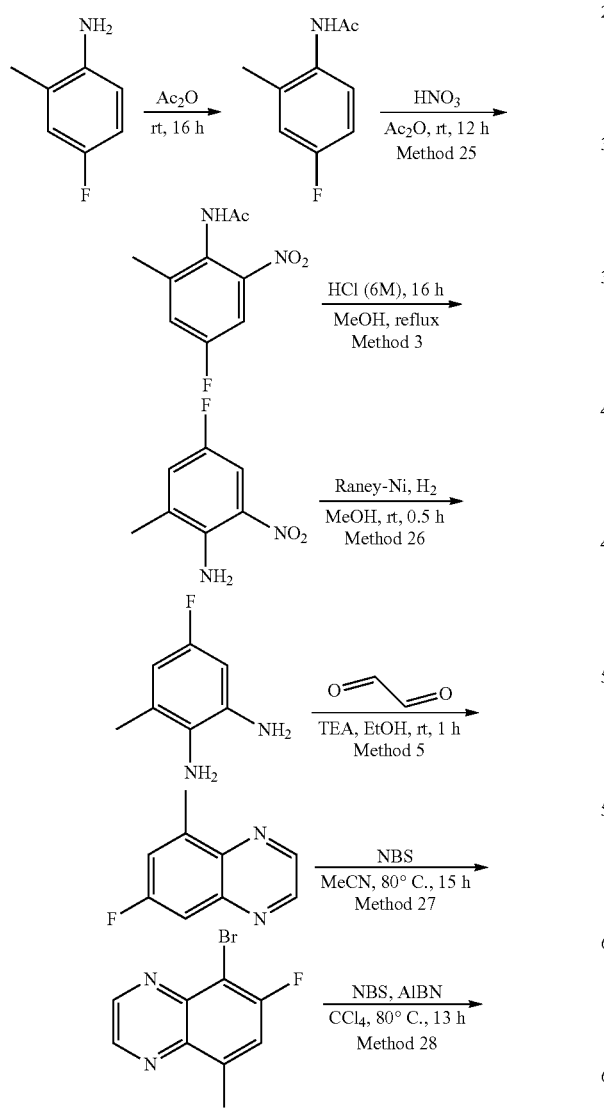

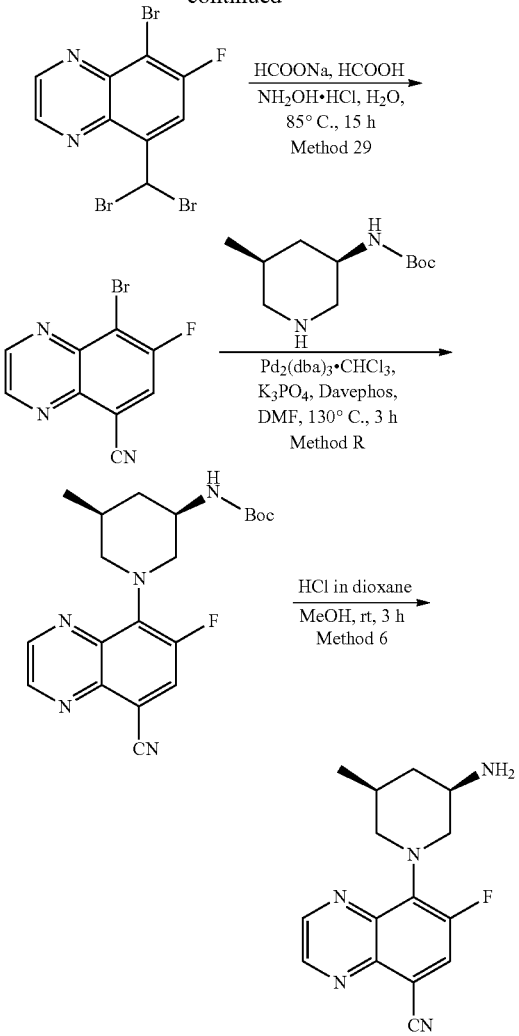

N-(4-fluoro-2-methylphenyl)acetamide: 4-fluoro-2-methylaniline (3.80 g, 30.37 mmol) was added to 100 mL acetyl anhydride at room temperature. The resulting solution was stirred for 3 h at room temperature. When the reaction was done, it was quenched by the addition of water (100 mL) and the resulting mixture was extracted with dichloromethane (300 mL×3). The organic phases were combined, washed with brine and dried over Na$_2$SO$_4$. The solvent was removed under reduced pressure to yield N-(4-fluoro-2-methylphenyl)acetamide as white solid (2.70 g, 50%). MS: m/z=168.2 [M+H]$^+$.

Method 25

N-(4-fluoro-2-methyl-6-nitrophenyl)acetamide: At 0° C., to a solution of N-(4-fluoro-2-methylphenyl)acetamide (2.70 g, 16.15 mmol) in acetic anhydride (60 mL), was added HNO$_3$ (65% in water, 3.2 mL, 46.22 mmol) dropwise over 20 min period. The resulting mixture was then stirred for 15 h at room temperature. After the reaction was done, it was quenched by the addition of ice water (100 mL) and the pH value of the resulting mixture was adjusted to 7-8 with sat. sodium bicarbonate solution. The mixture was extracted with dichloromethane (300 mL×3). The organic phases were combined, washed with brine and dried over Na$_2$SO$_4$. The solvent was removed under reduced pressure and the residue was purified by flash chromatography eluting with EtOAc in hexane (0% to 15% gradient) to yield N-(4-fluoro-2-methyl-6-nitrophenyl)acetamide as brown solid (1.35 g, 39%). MS: m/z=213.1 [M+H]$^+$.

4-fluoro-2-methyl-6-nitroaniline: 4-fluoro-2-methyl-6-nitroaniline was prepared from N-(4-fluoro-2-methyl-6-nitrophenyl)acetamide using Method 3. The crude product was purified by flash chromatography eluting with EtOAc in hexane (0% to 17% gradient) to yield 4-fluoro-2-methyl-6-nitroaniline as yellow solid (730 mg, 64%). MS: m/z=171.1 [M+H]$^+$.

Method 26

5-fluoro-3-methylbenzene-1,2-diamine: To a solution of 4-fluoro-2-methyl-6-nitroaniline (730 mg, 4.29 mmol) in methanol (10 mL) was added Raney Ni (95 mg, 11.09 mmol) at room temperature under nitrogen atmosphere. The reaction flask was vacuumed and purged with hydrogen. The reaction mixture was then stirred for 30 min at room temperature under hydrogen atmosphere with a hydrogen balloon. When the reaction was done, the reaction mixture was filtered through a Celite pad. The filtrate was concentrated under reduced pressure and the residue was purified by flash chromatography eluting with EtOAc in hexane (0% to 35% gradient) to yield 5-fluoro-3-methylbenzene-1,2-diamine as yellow solid (631 mg, 97%). MS: m/z=141.1 [M+H]$^+$.

7-fluoro-5-methylquinoxaline: 7-fluoro-5-methylquinoxaline was prepared from 5-fluoro-3-methylbenzene-1,2-diamine and oxalaldehyde using Method 5. The crude product was purified by flash chromatography eluting with EtOAc in hexane (0% to 25% gradient) to yield 7-fluoro-5-methylquinoxaline as yellow solid (540 mg, 62%). MS: m/z=163.1 [M+H]$^+$.

Method 27

5-bromo-6-fluoro-8-methylquinoxaline: To a solution of 7-fluoro-5-methylquinoxaline (540 mg, 3.33 mmol) in acetonitrile (10 mL) was added NBS (1425 mg, 8.01 mmol) slowly at room temperature. The resulting solution was stirred for 15 h at 80° C. When the reaction was done, it was quenched by the addition of water (20 mL). The resulting mixture was extracted with ethyl acetate (50 mL×3). The organic phases were combined, washed with brine and dried over Na$_2$SO$_4$. The solvent was removed under reduced pressure and the residue was purified by flash chromatography eluting with EtOAc in hexane (0% to 10% gradient) to yield 5-bromo-6-fluoro-8-methylquinoxaline as white solid (495 mg, 62%). MS: m/z=240.8 [M+H]$^+$.

Method 28

5-bromo-6-fluoro-8-methylquinoxaline: At room temperature, to a solution of 5-bromo-6-fluoro-8-methylquinoxaline (440 mg, 1.83 mmol) in CCl$_4$ was added NBS (4275 mg, 24.02 mmol) and AIBN (67 mg, 0.40 mmol) slowly in sequence. The resulting solution was stirred for 15 h at 80° C. When the reaction was done, it was quenched by the addition of water (20 mL). The resulting mixture was extracted with ethyl acetate (60 mL×3). The organic phases were combined, washed with brine and dried over Na$_2$SO$_4$. The solvent was removed under reduced pressure and the residue was purified by flash chromatography eluting with EtOAc in hexane (0% to 15% gradient) to yield 5-bromo-8-(dibromomethyl)-6-fluoroquinoxaline as yellow solid (450 mg, 62%). MS: m/z=400.5 [M+H]$^+$.

Method 29

8-bromo-7-fluoroquinoxaline-5-carbonitrile: To a solution of 5-bromo-8-(dibromomethyl)-6-fluoroquinoxaline (450 mg, 1.13 mmol) in HCOOH (10 mL) was added sodium formate (404 mg, 5.94 mmol), NH$_2$OH.HCl (165 mg, 2.38 mmol), and water (3 mL) at room temperature. The resulting mixture was stirred for 15 h at 85° C. When the reaction was done, it was quenched by the addition of water (50 mL). The resulting mixture was extracted with ethyl acetate (100 mL×3). The organic phases were combined, washed with brine and dried over Na$_2$SO$_4$. The solvent was removed under reduced pressure and the residue was purified by flash chromatography eluting with EtOAc in hexane (0% to 17% gradient) to yield 8-bromo-7-fluoroquinoxaline-5-carbonitrile as white solid (240 mg, 84%). MS: m/z=253.8 [M+H]$^+$.

8-[(3R,5S)-3-amino-5-methylpiperidin-1-yl]-7-fluoroquinoxaline-5-carbonitrile: 8-[(3R,5S)-3-amino-5-methylpiperidin-1-yl]-7-fluoroquinoxaline-5-carbonitrile was prepared from 8-bromo-7-fluoroquinoxaline-5-carbonitrile and tert-butyl (3R,5S)-5-methylpiperidin-3-ylcarbamate using Method R and 6. The crude product was purified by prep-HPLC under the following conditions: column, XBridge Prep C18 OBD Column, 5 um, 19 mm×150 mm; mobile phase, acetonitrile in water (with 10 mmol/L NH$_4$HCO$_3$ and 0.1% NH$_3$.H$_2$O), 5% to 65% gradient in 8 min; detector, UV 254 nm. 8-[(3R,5S)-3-amino-5-methylpiperidin-1-yl]-7-fluoroquinoxaline-5-carbonitrile was obtained as yellow solid (55 mg, 48% for 2 steps).

Compound 342: HPLC: 99.2% purity, RT=1.08 min. MS: n/z=286.3 [M+H]$^+$. $^1$H NMR (400 MHz, Chloroform-d, ppm) δ 8.94 (d, J=1.7 Hz, 1H), 8.88 (d, J=1.7 Hz, 1H), 7.88 (d, J=12.2 Hz, 1H), 4.05 (d, J=12.0 Hz, 1H), 3.76 (d, J=12.6 Hz, 1H), 3.49-3.32 (m, 1H), 3.1-3.04 (m, 1H), 3.02-2.90 (m, 1H), 2.28-1.92 (m, 2H), 1.21-1.16 (m, 1H), 1.00 (d, J=6.6 Hz, 3H).

Example 91: Synthesis of Compound 343 (N-[(3R,5S)-1-(8-cyano-6-fluoroquinoxalin-5-yl)-5-methylpiperidin-3-yl]-3,3-dimethylbutanamide)

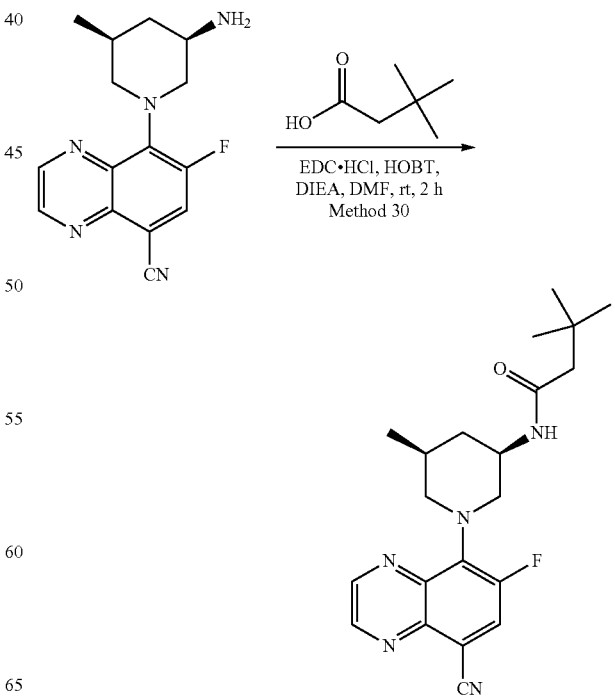

Method 30

N-[(3R,5S)-1-(8-cyano-6-fluoroquinoxalin-5-yl)-5-methylpiperidin-3-yl]-3,3-dimethylbutanamide: To a solution of 8-[(3R,5S)-3-amino-5-methylpiperidin-1-yl]-7-fluoroquinoxaline-5-carbonitrile (50 mg, 0.17 mmol) in DMF (3 mL) was added 3,3-dimethylbutanoic acid (48 mg, 0.42 mmol), HOBT (29 mg, 0.22 mmol), EDCl (51 mg, 0.27 mmol) and DIEA (107 mg, 0.83 mmol) at room temperature. The resulting solution was stirred for 2 h at room temperature. When the reaction was done, it was quenched by the addition of water (5 mL). The resulting mixture was extracted with ethyl acetate (20 mL×3). The organic phases were combined, washed with brine and dried over $Na_2SO_4$. The solvent was removed under reduced pressure and the residue was purified by prep-HPLC under the following conditions: column, XBridge Prep C18 OBD Column, 5 um, 19 mm×150 mm; mobile phase, acetonitrile in water (with 10 mmol/L $NH_4HCO_3$ and 0.1% $NH_3.H_2O$), 45% to 67% gradient in 7 min; detector, UV 254 nm. N-[(3R,5S)-1-(8-cyano-6-fluoroquinoxalin-5-yl)-5-methylpiperidin-3-yl]-3,3-dimethylbutanamide was obtained as yellow solid (35 mg, 52%).

Compound 343: HPLC: 99.5% purity, RT=1.85 min. MS: n/z=384.2 $[M+H]^+$. $^1H$ NMR (300 MHz, DMSO-d, ppm) δ 9.09-8.95 (m, 2H), 8.43 (d, J=12.9 Hz, 1H), 7.73 (d, J=7.7 Hz, 1H), 3.72-3.93 (m, 3H), 3.03-2.96 (m, 1H), 2.87-2.78 (m, 1H), 1.97-1.94 (m, 4H), 1.13-0.89 (m, 13H).

Example 92: Synthesis of Compound 344 (7-fluoro-8-[(3R,5S)-3-[(2-methoxyethyl)amino]-5-methylpiperidin-1-yl]quinoxaline-5-carbonitrile)

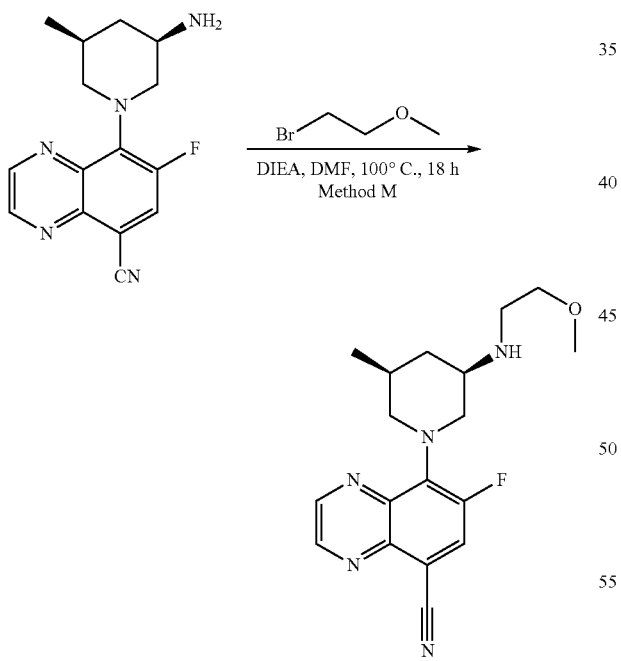

7-fluoro-8-[(3R,5S)-3-[(2-methoxyethyl)amino]-5-methylpiperidin-1-yl]quinoxaline-5-carbonitrile: 7-fluoro-8-[(3R,5S)-3-[(2-methoxyethyl)amino]-5-methylpiperidin-1-yl]quinoxaline-5-carbonitrile was prepared from 8-[(3R,5S)-3-amino-5-methylpiperidin-1-yl]-7-fluoroquinoxaline-5-carbonitrile and 1-bromo-2-methoxyethane using Method M. The crude product was purified by prep-HPLC under the following conditions: column, XBridge Prep C18 OBD Column, 5 um, 19 mm×150 mm; mobile phase, acetonitrile in water (with 10 mmol/L $NH_4HCO_3$ and 0.1% $NH_3.H_2O$), 42% to 43% gradient in 7 min; detector, UV 254 nm. 7-fluoro-8-[(3R,5S)-3-[(2-methoxyethyl)amino]-5-methylpiperidin-1-yl]quinoxaline-5-carbonitrile was obtained as yellow oil (13 mg, 22%).

Compound 344: HPLC: 98.6% purity, RT=1.39 min. MS: m/z=344.3 $[M+H]^+$. $^1H$ NMR (400 MHz, $CD_3OD$, ppm) δ 8.99-8.85 (m, 2H), 8.10 (d, J=12.7 Hz, 1H), 4.16-4.11 (m, 1H), 3.86-3.76 (m, 1H), 3.61-3.49 (m, 2H), 3.38 (s, 3H), 3.14-2.83 (m, 5H), 2.18 (d, J=12.4 Hz, 1H), 2.01-1.88 (m, 1H), 1.13-0.96 (m, 4H).

Example 93: Synthesis of Compound 345 and Compound 346 ((2R)-2-amino-N-[(3R,5S)-1-(8-cyano-6-fluoroquinoxalin-5-yl)-5-methylpiperidin-3-yl]-3,3,3-trifluoropropanamide and (2S)-2-amino-N-[(3R,5S)-1-(8-cyano-6-fluoroquinoxalin-5-yl)-5-methylpiperidin-3-yl]-3,3,3-trifluoropropanamide)

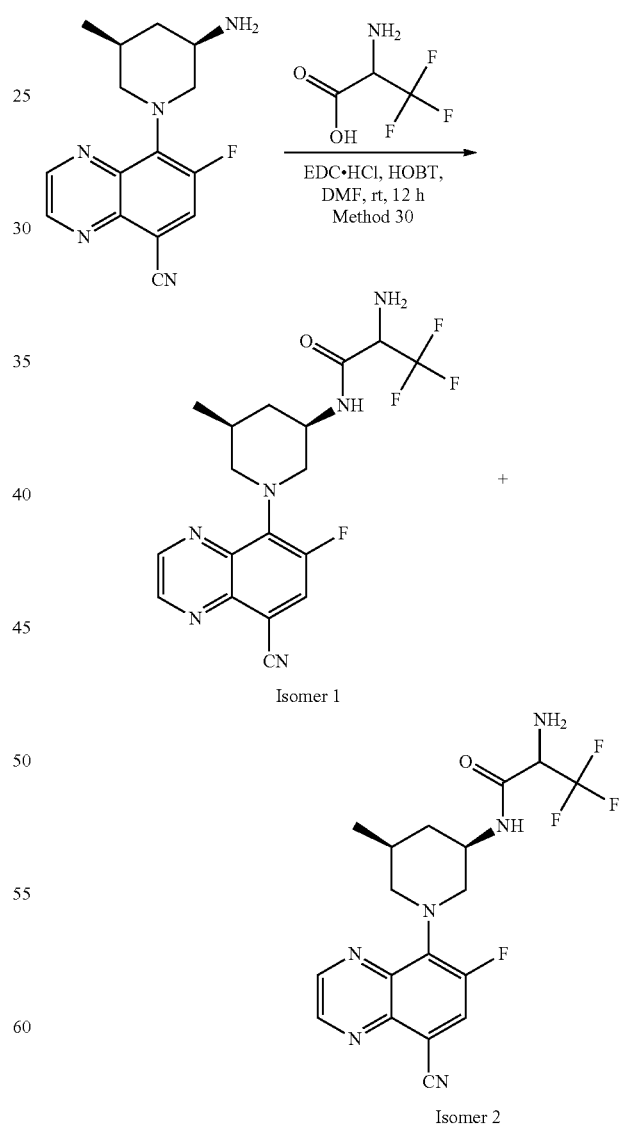

(2R)-2-amino-N-[(3R,5S)-1-(8-cyano-6-fluoroquinoxalin-5-yl)-5-methylpiperidin-3-yl]-3,3,3-trifluoropropanamide and (2S)-2-amino-N-[(3R,5S)-1-(8-cyano-6-fluoroquinoxalin-5-yl)-5-methylpiperidin-3-yl]-3,3,3-trifluoropropanamide: cis-2-amino-N-[(3R,5S)-1-(8-cyano-6-fluoroquinoxalin-5-yl)-5-methylpiperidin-3-yl]-3,3,3-trifluoropropanamide was prepared from 2-amino-3,3,3-trifluoropropanoic acid and 8-((3R,5S)-3-amino-5-methylpiperidin-1-yl)-7-fluoroquinoxaline-5-carbonitrile using Method 30. The crude product was purified by prep-HPLC under the following conditions: column, XBridge Shield RP18 OBD Column, 19×150 mm 10 um; mobile phase, acetonitrile in water (with 10 mmol/L NH$_4$HCO$_3$ and 0.1% NH$_3$.H$_2$O), 40% to 45% gradient in 10 min; detector, UV 254 nm. Two diastereoisomers were separated and obtained.

Isomer 1: (34 mg, 16%, yellow solid) HPLC: 97.1% purity, RT=1.04 min. MS: n/z=411.1 [M+H]$^+$. $^1$H NMR (300 MHz, DMSO-d, ppm) δ 9.05-8.95 (m, 2H), 8.42 (d, J=12.8 Hz, 1H), 8.30 (d, J=7.7 Hz, 1H), 4.10-3.70 (m, 4H), 3.11-2.95 (m, 1H), 2.94-2.78 (m, 1H), 2.38-2.22 (m, 2H), 2.07-1.91 (m, 2H), 1.26-1.10 (m, 1H), 0.92 (d, J=6.2 Hz, 3H).

Isomer 2: (34 mg, 16%, yellow solid) HPLC: 96.4% purity, RT=2.16 min. MS: m/z=411.1 [M+H]$^+$. $^1$H NMR (300 MHz, DMSO-d$_6$, ppm) δ 9.07-8.97 (m, 2H), 8.43 (d, J=12.8 Hz, 1H), 8.32 (d, J=7.8 Hz, 1H), 4.05-3.80 (m, 3H), 3.74 (d, J=12.8 Hz, 1H), 3.12-2.96 (m, 1H), 2.94-2.78 (m, 1H), 2.38-2.20 (m, 2H), 2.06-1.92 (m, 2H), 1.22-1.08 (m, 1H), 0.92 (d, J=6.3 Hz, 3H).

Example 94: Synthesis of Compound 347 (N-[(3R,5S)-1-(8-cyano-6-fluoroquinoxalin-5-yl)-5-methylpiperidin-3-yl]-2-(dimethylamino)acetamide)

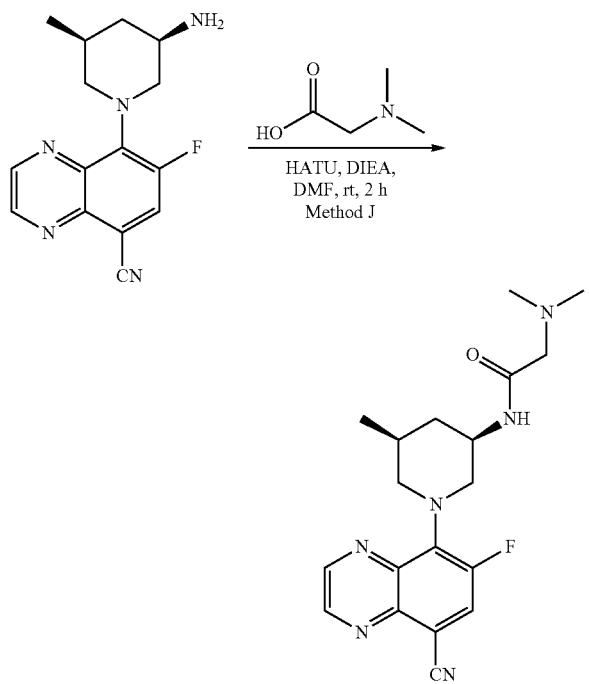

N-[(3R,5S)-1-(8-cyano-6-fluoroquinoxalin-5-yl)-5-methylpiperidin-3-yl]-2-(dimethylamino)acetamide: N-[(3R,5S)-1-(8-cyano-6-fluoroquinoxalin-5-yl)-5-methylpiperidin-3-yl]-2-(dimethylamino)acetamide was prepared from 8-[(3R,5S)-3-amino-5-methylpiperidin-1-yl]-7-fluoroquinoxaline-5-carbonitrile and 2-(dimethylamino)acetic acid using Method J. The crude product was purified by prep-HPLC under the following conditions: column, XBridge Prep C18 OBD Column, 5 um, 19 mm×150 mm; mobile phase, acetonitrile in water (with 10 mmol/L NH$_4$HCO$_3$ and 0.1% NH$_3$.H$_2$), 42% to 43% gradient in 7 min; detector, UV 254 nm. N-[(3R,5S)-1-(8-cyano-6-fluoroquinoxalin-5-yl)-5-methylpiperidin-3-yl]-2-(dimethylamino)acetamide was obtained as yellow solid (23 mg, 37%).

Compound 347: HPLC: 97.5% purity, RT=0.91 min. MS: n/z=371.1 [M+H]$^+$. $^1$H NMR (400 MHz, DMSO-d$_6$, ppm) δ 9.11-8.95 (m, 2H), 8.41 (d, J=12.9 Hz, 1H), 7.69 (d, J=8.4 Hz, 1H), 4.06-3.92 (m, 1H), 3.83-3.67 (m, 2H), 3.20-3.04 (m, 1H), 2.95-2.76 (m, 3H), 2.19 (s, 6H), 2.00-1.84 (m, 2H), 1.32-1.16 (m, 1H), 0.91 (d, J=6.3 Hz, 3H).

The following compounds were synthesized in an analogous manner:

Compound 587 (2-(1-Methyl-piperidin-4-yl)-N-[(3R,5S)-1-(8-methyl-quinolin-5-yl)-5-trifluoromethyl-piperidin-3-yl]-acetamide): From (3R,5S)-1-(8-Methyl-quinolin-5-yl)-5-trifluoromethyl-piperidin-3-ylamine hydrochloride and (1-Methyl-piperidin-4-yl)-acetic acid. HPLC: 99% purity, RT=1.90 min. MS: m/z=449.30 [M+H]$^+$. $^1$H NMR (400 MHz, DMSO-d$_6$, ppm) δ 8.93 (dd, J=4.1, 1.7 Hz, 1H), 8.53 (dd, J=8.5, 1.8 Hz, 1H), 7.95 (d, J=7.5 Hz, 1H), 7.57 (dd, J=8.5, 4.1 Hz, 1H), 7.54 (dd, J=7.6, 1.1 Hz, 1H), 7.19 (d, J=7.6 Hz, 1H), 4.13 (s, 1H), 3.13 (d, J=11.6 Hz, 2H), 2.76 (t, J=11.4 Hz, 2H), 2.69 (dd, J=7.4, 3.6 Hz, 2H), 2.46 (d, J=10.9 Hz, 1H), 2.16 (d, J=12.0 Hz, 1H), 2.12 (s, 3H), 1.99 (d, J=6.9 Hz, 2H), 1.85-1.77 (m, 2H), 1.63-1.49 (m, 3H), 1.44 (q, J=12.2 Hz, 1H), 1.15 (dq, J=9.1, 5.9, 4.7 Hz, 2H).

Compound 588 (3-Hydroxy-3-methyl-N-[(3R,5S)-5-methyl-1-(8-methyl-quinolin-5-yl)-piperidin-3-yl]-butyramide): From (3R,5S)-5-Methyl-1-(8-methyl-quinolin-5-yl)-piperidin-3-ylamine hydrochloride and 3-Hydroxy-3-methyl-butyric acid. HPLC: 98% purity, RT=2.06 min. MS: m/z=356.30 [M+H]$^+$. $^1$H NMR (400 MHz, DMSO-d$_6$, ppm) δ 8.91 (dd, J=4.1, 1.8 Hz, 1H), 8.47 (dd, J=8.5, 1.8 Hz, 1H), 7.85 (d, J=7.7 Hz, 1H), 7.55 (dd, J=8.5, 4.1 Hz, 1H), 7.51 (dd, J=7.6, 1.1 Hz, 1H), 7.08 (d, J=7.6 Hz, 1H), 4.77 (s, 1H), 3.16 (dd, J=10.9, 2.9 Hz, 1H), 2.65 (d, J=0.9 Hz, 3H), 2.38 (t, J=10.7 Hz, 1H), 2.30 (t, J=11.1 Hz, 1H), 2.20 (s, 2H), 2.04 (s, 1H), 1.99 (d, J=13.3 Hz, 1H), 1.13 (d, J=1.2 Hz, 6H), 1.04 (q, J=11.9 Hz, 1H), 0.94 (d, J=6.4 Hz, 3H).

Compound 589 (2-Cyclopropyl-2-hydroxy-N-[(3R,5S)-5-methyl-1-(8-methyl-quinolin-5-yl)-piperidin-3-yl]-acetamide): From (3R,5S)-5-Methyl-1-(8-methyl-quinolin-5-yl)-piperidin-3-ylamine hydrochloride and Cyclopropyl-hydroxy-acetic acid. HPLC: >99% purity, RT=2.09 min. MS: m/z=354.30 [M+H]$^+$. $^1$H NMR (400 MHz, DMSO-d$_6$, ppm) δ 8.91 (ddd, J=4.2, 1.8, 0.8 Hz, 1H), 8.48 (ddd, J=8.5, 2.7, 1.8 Hz, 1H), 7.59-7.48 (m, 2H), 7.08 (dd, J=7.6, 4.1 Hz, 1H), 5.28 (s, 1H), 4.07 (s, 0H), 3.55-3.48 (m, 1H), 3.28 (d, J=11.0 Hz, 1H), 3.16 (d, J=10.0 Hz, 1H), 2.65 (t, J=0.9 Hz, 2H), 2.47 (dd, J=10.7, 2.1 Hz, 1H), 2.31 (t, J=11.1 Hz, 1H), 1.95 (d, J=12.6 Hz, 1H), 1.24-1.10 (m, 1H), 1.11-0.91 (m, 3H), 0.43-0.23 (m, 3H).

Compound 590 (N-[(3R,5S)-5-Methyl-1-(8-methyl-quinolin-5-yl)-piperidin-3-yl]-2-(1-methyl-piperidin-4-yl)-acetamide): From (3R,5S)-5-Methyl-1-(8-methyl-quinolin-5-yl)-piperidin-3-ylamine hydrochloride and (1-Methyl-piperidin-4-yl)-acetic acid. HPLC: >99% purity, RT=1.71 min. MS: m/z=395.40 [M+H]$^+$. $^1$H NMR (400 MHz, DMSO-d$_6$, ppm) δ 8.91 (dd, J=4.1, 1.8 Hz, 1H), 8.47 (dd, J=8.5, 1.8 Hz, 1H), 7.79 (d, J=7.6 Hz, 1H), 7.54 (dd, J=8.5, 4.1 Hz, 1H), 7.51 (dd, J=7.5, 1.1 Hz, 1H), 7.07 (d, J=7.6 Hz, 1H), 3.15 (d, J=10.6 Hz, 2H), 2.68 (d, J=3.3 Hz, 2H), 2.64 (d, J=1.0 Hz, 3H), 2.32 (dt, J=18.2, 10.9 Hz, 2H), 2.10 (s, 3H), 1.97 (d, J=6.8 Hz, 2H), 1.94 (s, 1H), 1.82-1.72 (m, 2H), 1.62-1.48 (m, 3H), 1.13 (dd, J=10.2, 6.1 Hz, 2H), 1.03 (q, J=12.1 Hz, 1H), 0.93 (d, J=6.5 Hz, 3H).

Compound 591 (N-[(3R,5S)-5-Methyl-1-(8-methyl-quinolin-5-yl)-piperidin-3-yl]-2-(1-methyl-pyrrolidin-3-yl)-acetamide): From (3R,5S)-5-Methyl-1-(8-methyl-quinolin-5-yl)-piperidin-3-ylamine hydrochloride and (1-Methyl-pyrrolidin-3-yl)-acetic acid. HPLC: >99% purity, RT=1.65 min. MS: m/z=381.40 [M+H]⁺. ¹H NMR (400 MHz, DMSO-d₆, ppm) δ 8.91 (dd, J=4.1, 1.8 Hz, 1H), 8.47 (dd, J=8.5, 1.8 Hz, 1H), 7.82 (d, J=7.6 Hz, 1H), 7.55 (dd, J=8.5, 4.1 Hz, 1H), 7.51 (dd, J=7.6, 1.2 Hz, 1H), 7.07 (dd, J=7.7, 1.4 Hz, 1H), 4.02 (s, 1H), 3.16 (d, J=11.4 Hz, 2H), 2.64 (d, J=0.9 Hz, 3H), 2.40 (ddd, J=9.1, 6.3, 2.7 Hz, 4H), 2.36-2.25 (m, 3H), 2.20 (d, J=3.6 Hz, 3H), 2.12 (dt, J=7.7, 1.5 Hz, 2H), 2.10-2.04 (m, 2H), 2.03 (s, 1H), 1.96 (d, J=13.2 Hz, 2H), 1.34 (tdd, J=13.0, 7.3, 5.8 Hz, 1H), 1.03 (q, J=12.0 Hz, 1H), 0.93 (d, J=6.5 Hz, 3H).

Example 95: Synthesis of Compound 348 (N-[(3R,5S)-1-(8-cyanoquinoxalin-5-yl)-5-methylpiperidin-3-yl]-2-(4,4-difluoropiperidin-1-yl)acetamide)

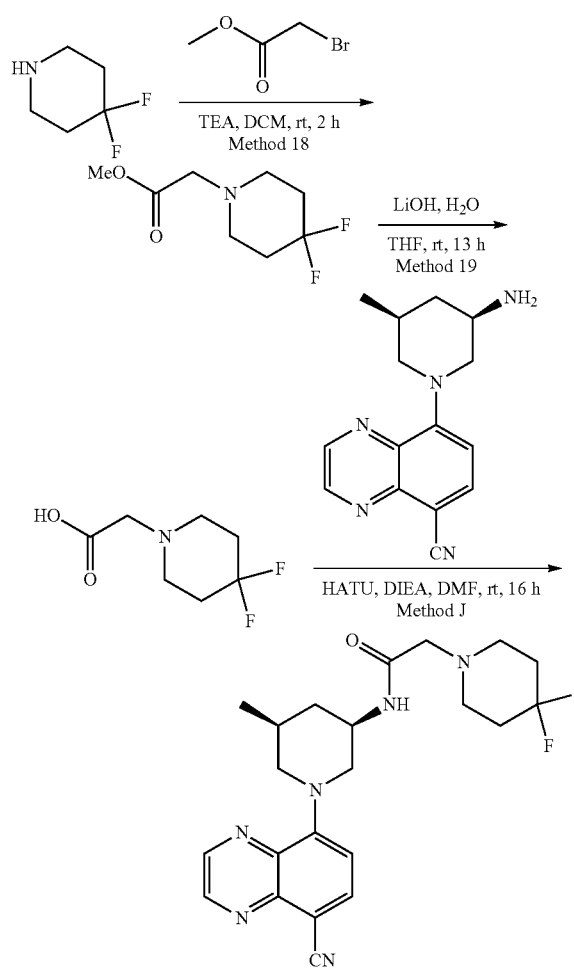

N-[(3R,5S)-1-(8-cyanoquinoxalin-5-yl)-5-methylpiperidin-3-yl]-2-(4,4-difluoropiperidin-1-yl)acetamide: N-[(3R,5S)-1-(8-cyanoquinoxalin-5-yl)-5-methylpiperidin-3-yl]-2-(4,4-difluoropiperidin-1-yl)acetamide was prepared from 8-[(3R,5S)-3-amino-5-methylpiperidin-1-yl]quinoxaline-5-carbonitrile, 4,4-difluoropiperidine, methyl 2-bromoacetate and 2-(dimethylamino)acetic acid using Method 18, 19, and J. The crude product was purified by prep-HPLC under the following conditions: column, XBridge Prep C18 OBD Column, 5 um, 19 mm×150 mm; mobile phase, acetonitrile in water (with 0.05% NH₃.H₂O), 42% to 55% gradient in 7 min; detector, UV 254 nm. N-[(3R,5S)-1-(8-cyanoquinoxalin-5-yl)-5-methylpiperidin-3-yl]-2-(4,4-difluoropiperidin-1-yl)acetamide was obtained as yellow solid (13 mg, 2.7% for 3 steps).

Compound 348: HPLC: 99.4% purity, RT=1.51 min. MS: m/z=429.3 [M+H]⁺. ¹H NMR (400 MHz, Chloroform-d, ppm) δ 8.97 (d, J=1.7 Hz, 1H), 8.86 (d, J=1.7 Hz, 1H), 8.02 (d, J=8.3 Hz, 1H), 7.21 (d, J=8.4 Hz, 1H), 7.18-6.98 (m, 1H), 4.46-4.37 (m, 1H), 4.36-4.21 (m, 2H), 3.14 (s, 2H), 2.85-2.68 (m, 6H), 2.23-2.00 (m, 6H), 1.30-1.14 (m, 1H), 1.03 (d, J=6.6 Hz, 3H).

The following compounds were synthesized in an analogous manner:

Compound 350 (2-(4,4-difluoropiperidin-1-yl)-N-[(3R,5S)-5-methyl-1-[8-(trifluoromethyl)quinolin-5-yl]piperidin-3-yl]acetamide): From (3R,5S)-5-methyl-1-[8-(trifluoromethyl)quinolin-5-yl]piperidin-3-amine and 2-(4,4-difluoropiperidin-1-yl)acetic acid. HPLC: 99.1% purity, RT=2.83 min. MS: m/z=471.2 [M+H]⁺. ¹H NMR (400 MHz, DMSO-d₆, ppm) δ 9.02 (dd, J=4.1, 1.6 Hz, 1H), 8.53 (dd, J=8.6, 1.7 Hz, 1H), 8.07 (d, J=8.1 Hz, 1H), 7.79 (d, J=8.0 Hz, 1H), 7.68 (dd, J=8.6, 4.2 Hz, 1H), 7.22 (d, J=8.1 Hz, 1H), 4.15-4.05 (m, 1H), 3.51-3.30 (m, 2H), 3.02 (s, 2H), 2.57-2.35 (m, 6H), 2.12-1.93 (m, 6H), 1.25-1.21 (m, 1H), 0.96 (d, J=6.5 Hz, 3H).

Compound 354 (2-(4,4-difluoropiperidin-1-yl)-N-[(3R,5S)-5-methyl-1-[8-(trifluoromethyl)quinoxalin-5-yl]piperidin-3-yl]acetamide): From (3R,5S)-5-methyl-1-[8-(trifluoromethyl)quinoxalin-5-yl]piperidin-3-amine and 2-(4,4-difluoropiperidin-1-yl)acetic acid. HPLC: 99.0% purity, RT=2.00 min. MS: m/z=472.2 [M+H]⁺. ¹H NMR (400 MHz, DMSO-d₆, ppm) δ 9.03 (d, J=1.7 Hz, 1H), 8.97 (d, J=1.7 Hz, 1H), 8.07 (d, J=8.4 Hz, 1H), 7.78 (d, J=8.0 Hz, 1H), 7.28 (d, J=8.4 Hz, 1H), 4.19-3.95 (m, 3H), 3.06-2.97 (m, 2H), 2.87-2.81 (m, 1H), 2.58-2.49 (m, 5H), 2.07-1.58 (m, 6H), 1.35-1.20 (m, 1H), 0.94 (d, J=6.3 Hz, 3H).

Example 96: Synthesis of Compound 349 (N-[(3R,5S)-1-(8-cyanoquinoxalin-5-yl)-5-methylpiperidin-3-yl]-2-methyl-2-(1-methylpiperidin-4-yl)propanamide)

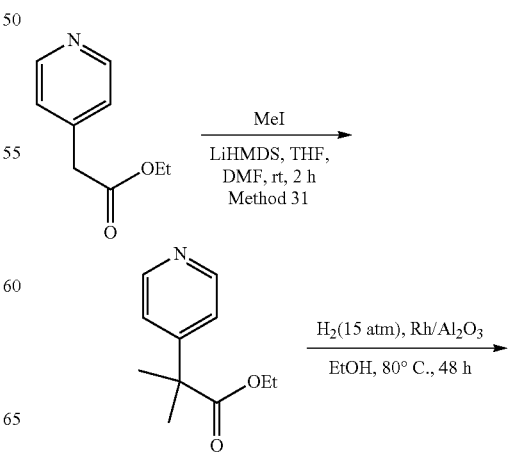

-continued

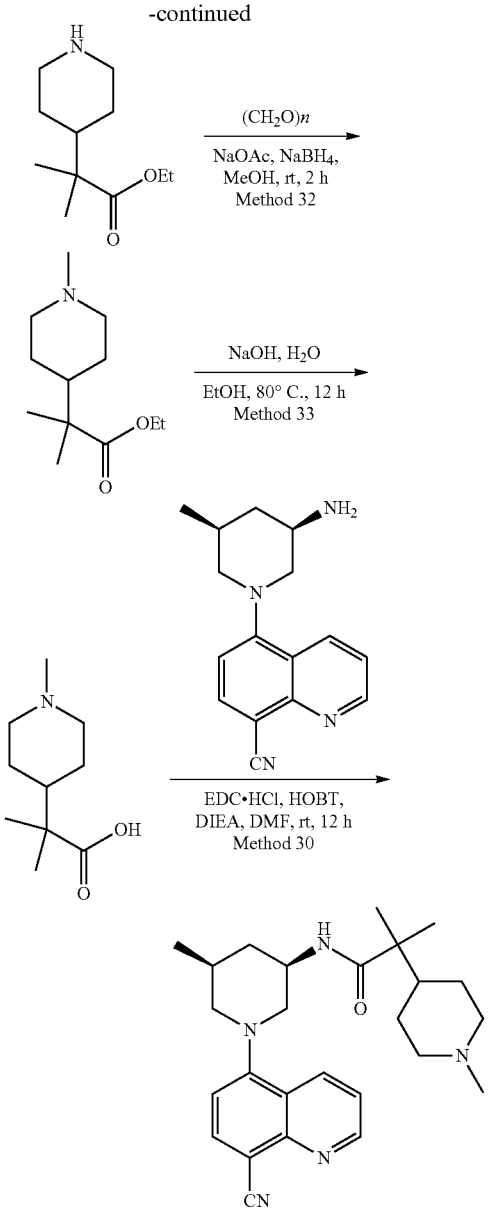

Method 31

Ethyl 2-methyl-2-(pyridin-4-yl)propanoate: To a solution of ethyl 2-(pyridin-4-yl)acetate (1.90 g, 11.50 mmol) in N,N-dimethylformamide (30 mL) was added LiHMDS solution (1 M in THF, 14.4 mL, 14.4 mmol) slowly at 0° C. The resulting solution was stirred at room temperature for 0.5 h, and then was added by CH$_3$I (2.61 g, 18.4 mmol) slowly. The reaction mixture was stirred at room temperature for 1 h. Then the reaction mixture was added by LiHMDS solution (1 M in THF, 14.4 mL, 14.4 mmol) again at 0° C. The resulting mixture was stirred at room temperature for 0.5 h, and then was added by CH$_3$I (2.61 g, 18.4 mmol) slowly. The reaction mixture was stirred at room temperature for additional 2 h. When the reaction was done, it was quenched by the addition of ice water (50 mL). The resulting mixture was extracted with DCM (150 mL×3). The organic phases were combined, washed with brine and dried over Na$_2$SO$_4$. The solvent was removed under reduced pressure and the residue was purified by flash chromatography eluting with EtOAc in hexane (0% to 25% gradient) to yield ethyl 2-methyl-2-(pyridin-4-yl)propanoate as yellow solid (1.20 g, 54%). MS: m/z=194.1 [M+H]$^+$.

Ethyl 2-methyl-2-(piperidin-4-yl)propanoate: To a solution of ethyl 2-methyl-2-(pyridin-4-yl)propanoate (1.14 g, 5.92 mmol) in EtOH (20 mL) was added Rh/Al$_2$O$_3$ (285 mg, 2.77 mmol) in a pressure tank. The resulting mixture was hydrogenated at room temperature under 4 bars of hydrogen for 12 h. When the reaction was done, the reaction mixture was filtered through a Celite pad. The filtrate was concentrated under reduced pressure and the residue was purified by flash chromatography eluting with MeOH in DCM (0% to 50% gradient) to yield ethyl 2-methyl-2-(piperidin-4-yl) propanoate as yellow oil (300 mg, 25%). MS: m/z=200.1 [M+H]$^+$.

Method 32

Ethyl 2-methyl-2-(1-methylpiperidin-4-yl)propanoate: To a solution of ethyl 2-methyl-2-(piperidin-4-yl)propanoate (180 mg, 0.90 mmol) in methanol (10 mL) were added polyformaldehyde (836 mg, 9.28 mmol), NaOAc (1.56 g, 18.99 mmol) at room temperature. The resulting mixture was stirred at room temperature for 2 h, and then was added by NaBH$_4$ (541 mg, 14.31 mmol) at room temperature. The resulting mixture was stirred for another 12 h at room temperature. When the reaction was done, it was quenched by the addition of water (20 mL). The resulting solution was extracted with ethyl acetate (50 mL×3). The organic phases were combined, washed with brine and dried over Na$_2$SO$_4$. The solvent was removed under reduced pressure and the residue was purified by flash chromatography eluting with EtOAc in hexane (0% to 25% gradient) to yield ethyl 2-methyl-2-(1-methylpiperidin-4-yl)propanoate as colorless oil (160 mg, 83%). MS: m/z=214.1 [M+H]$^+$.

Method 33

Ethyl 2-methyl-2-(1-methylpiperidin-4-yl)propanoate: At room temperature, ethyl 2-methyl-2-(1-methylpiperidin-4-yl)propanoate (160 mg, 0.75 mmol) was dissolved in EtOH (4 mL), to which was added a solution of sodium hydroxide (355 mg, 8.86 mmol) in water (2 mL). The resulting mixture was stirred for 12 h at 80° C. After cooling to room temperature, the reaction mixture was concentrated under reduced pressure. The residue was purified by prep-HPLC under the following conditions: column, XBridge BEH130 Prep C18 OBD Column, 5 um, 19 mm×150 mm; mobile phase, acetonitrile in water (with 0.05% TFA), 0% to 15% gradient in 9 min; detector, UV 254 nm. 2-methyl-2-(1-methylpiperidin-4-yl)propanoic acid was obtained as colorless oil (100 mg, 58%). MS: m/z=186.0 [M+H]$^+$.

N-[(3R,5S)-1-(8-cyanoquinoxalin-5-yl)-5-methylpiperidin-3-yl]-2-methyl-2-(1-methylpiperidin-4-yl)propanamide: N-[(3R,5S)-1-(8-cyanoquinoxalin-5-yl)-5-methylpiperidin-3-yl]-2-methyl-2-(1-methylpiperidin-4-yl)propanamide was prepared from 8-[(3R,5S)-3-amino-5-methylpiperidin-1-yl] quinoxaline-5-carbonitrile and 2-methyl-2-(1-methylpiperidin-4-yl)propanoic acid using Method 30. The crude product was purified by prep-HPLC under the following conditions: column, XBridge BEH130 Prep C18 OBD Column, 5 um, 19 mm×150 mm; mobile phase, acetonitrile in water (with 0.05% NH$_3$.H$_2$O), 26% to 45% gradient in 8 min; detector, UV 254 nm. N-[(3R,5S)-1-(8-cyanoquinoxalin-5-yl)-5-methylpiperidin-3-yl]-2-methyl-2-(1-methylpiperidin-4-yl) propanamide was obtained as yellow solid (28 mg, 39%).

Compound 349: HPLC: 99.9% purity, RT=0.67 min. MS: m/z=379.2 [M+H]$^+$. $^1$H NMR (300 MHz, CD$_3$OD, ppm) δ 8.95-8.82 (m, 2H), 8.08 (d, J=8.4 Hz, 1H), 7.29 (d, J=8.4 Hz, 1H), 4.37-4.10 (m, 3H), 3.00-2.78 (m, 3H), 2.72-2.65 (m, 1H), 2.26 (s, 3H), 2.04-1.96 (m, 4H), 1.69-1.25 (m, 6H), 1.13 (s, 6H), 1.00 (d, J=6.3 Hz, 3H).

The following compounds were synthesized in an analogous manner:

Compound 351 (2-methyl-N-[(3R,5S)-5-methyl-1-[8-(trifluoromethyl)quinolin-5-yl]piperidin-3-yl]-2-(1-methylpiperidin-4-yl)propanamide): From 2-methyl-N-[(3R,5S)-5-methyl-1-[8-(trifluoromethyl)quinolin-5-yl]piperidin-3-yl]-2-(1-methylpiperidin-4-yl)propanamide and 2-methyl-2-(1-methylpiperidin-4-yl)propanoic acid. HPLC: 96.3% purity, RT=3.56 min. MS: m/z=477.2 [M+H]+. 1H NMR (300 MHz, DMSO-d6, ppm) δ 9.02 (dd, J=4.1, 1.7 Hz, 1H), 8.54 (dd, J=8.6, 1.7 Hz, 1H), 8.07 (d, J=8.1 Hz, 1H), 7.69 (dd, J=8.6, 4.2 Hz, 1H), 7.32-7.16 (m, 2H), 4.20-4.05 (m, 1H), 3.50-3.30 (m, 2H), 2.84-2.70 (m, 2H), 2.50-2.35 (m, 1H), 2.15-1.85 (m, 5H), 1.80-1.65 (m, 2H), 1.50-1.10 (m, 7H), 1.05-0.90 (m, 9H).

Compound 355 (2-methyl-N-[(3R,5S)-5-methyl-1-[8-(trifluoromethyl)quinoxalin-5-yl]piperidin-3-yl]-2-(1-methylpiperidin-4-yl)propanamide): From (3R,5S)-5-methyl-1-[8-(trifluoromethyl)quinoxalin-5-yl]piperidin-3-amine and 2-methyl-2-(1-methylpiperidin-4-yl)propanoic acid. HPLC: 97.7% purity, RT=2.35 min. MS: m/z=478.3 [M+H]+. 1H NMR (300 MHz, CD3OD, ppm) δ 8.95-8.86 (m, 2H), 8.04 (d, J=8.4 Hz, 1H), 7.30 (d, J=8.3 Hz, 1H), 4.30-4.05 (m, 3H), 3.09 (d, J=11.2 Hz, 2H), 2.90-2.72 (m, 1H), 2.66-2.50 (m, 1H), 2.40 (s, 3H), 2.30-1.96 (m, 4H), 1.75-1.60 (m, 3H), 1.51-1.26 (m, 4H), 1.15 (s, 6H), 1.02 (d, J=6.4 Hz, 3H).

Example 97: Synthesis of Compound 352 and compound 353 ((3S)-1-methyl-3-[[(3R,5S)-5-methyl-1-[8-(trifluoromethyl)quinoxalin-5-yl]piperidin-3-yl]amino]pyrrolidin-2-one and (3R)-1-methyl-3-[[(3R,5S)-5-methyl-1-[8-(trifluoromethyl)quinoxalin-5-yl]piperidin-3-yl]amino]pyrrolidin-2-one)

(3S)-1-methyl-3-[[(3R,5S)-5-methyl-1-[8-(trifluoromethyl)quinoxalin-5-yl]piperidin-3-yl]amino]pyrrolidin-2-one and (3R)-1-methyl-3-[[(3R,5S)-5-methyl-1-[8-(trifluoromethyl)quinoxalin-5-yl]piperidin-3-yl]amino]pyrrolidin-2-one: cis-1-methyl-3-[[(3R,5S)-5-methyl-1-[8-(trifluoromethyl)quinoxalin-5-yl]piperidin-3-yl]amino]pyrrolidin-2-one was prepared from (3R,5S)-5-methyl-1-[8-(trifluoromethyl)quinoxalin-5-yl]piperidin-3-amine and 3-bromo-1-methylpyrrolidin-2-one using Method 16. The crude product was first purified by prep-HPLC under the following conditions: column, XBridge Shield RP18 OBD Column, 19×150 mm 10 um; mobile phase, acetonitrile in water (0.05% NH3.H2O), 36% to 43% gradient in 7 min; detector, UV 254 nm. Then the two diastereomeric isomers were obtained by separation on chiral prep-HPLC under the following conditions: column, Lux 5u Cellulose-4, AXIA Packed, 2.12×25 cm, 5 um; mobile phase, EtOH in Hexane, 50% isocratic in 12 min; detector, UV 254/220 nm.

Isomer 1: (25 mg, 19%, yellow solid) HPLC: 95.4% purity, RT=2.06 min. MS: m/z=430.3 [M+Na]+. 1H NMR (400 MHz, DMSO-d6, ppm) δ 9.08-8.95 (m, 2H), 8.05 (d, J=8.4 Hz, 1H), 7.22 (d, J=8.4 Hz, 1H), 4.29 (d, J=11.5 Hz, 1H), 4.03 (d, J=11.6 Hz, 1H), 3.47-3.21 (m, 4H), 3.05-2.98 (m, 1H), 2.74 (s, 3H), 2.60-2.45 (m, 1H), 2.38-2.22 (m, 1H), 2.18-2.08 (m, 1H), 1.99-1.85 (m, 2H), 1.73-1.58 (m, 1H), 0.95-0.92 (m, 4H).

Isomer 2: (24 mg, 18%, yellow solid) HPLC: 94.7% purity, RT=2.22 min. MS: m/z=430.3 [M+Na]+. 1H NMR (400 MHz, DMSO-d6, ppm) δ 9.08-8.95 (m, 2H), 8.05 (d, J=8.4 Hz, 1H), 7.22 (d, J=8.4 Hz, 1H), 4.29 (d, J=11.5 Hz, 1H), 4.03 (d, J=11.6 Hz, 1H), 3.47-3.21 (m, 5H), 3.05-2.98 (m, 1H), 2.74 (s, 3H), 2.60-2.45 (m, 1H), 2.38-2.22 (m, 1H), 2.10-2.00 (m, 1H), 1.99-1.85 (m, 1H), 1.73-1.58 (m, 1H), 0.95-0.92 (m, 4H).

Example 98: Synthesis of Compound 356 (2-(3-aminoazetidin-1-yl)-N-[(3R,5S)-1-(8-cyanoquinoxalin-5-yl)-5-methylpiperidin-3-yl]acetamide)

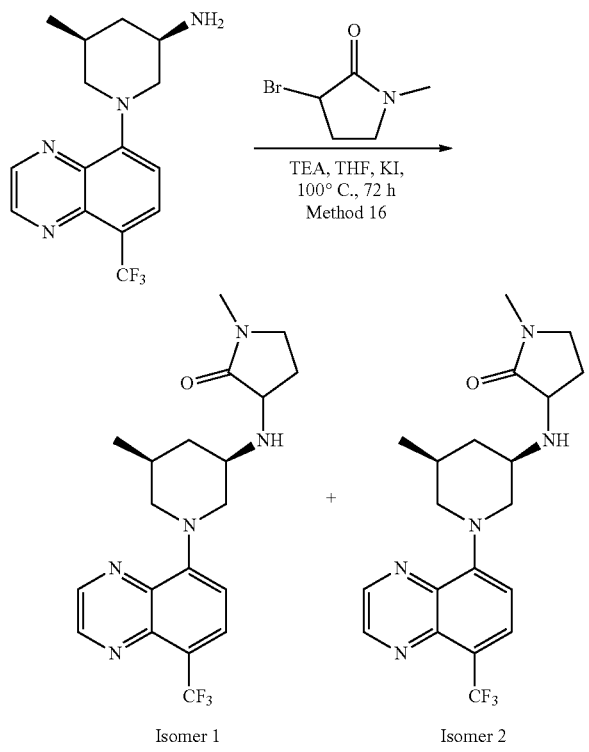

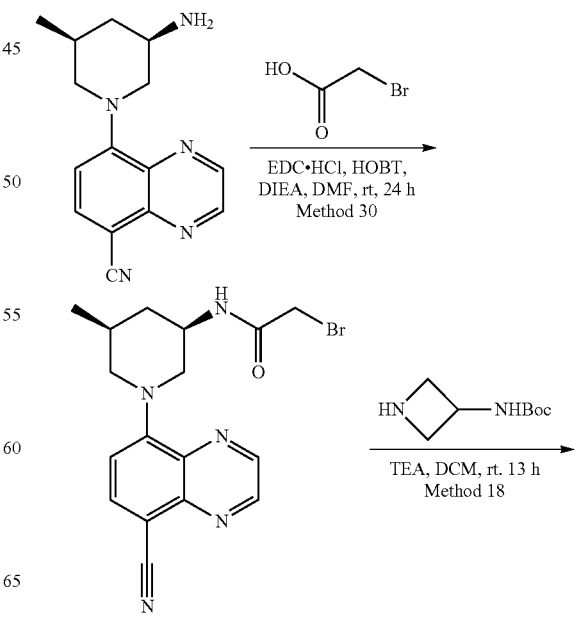

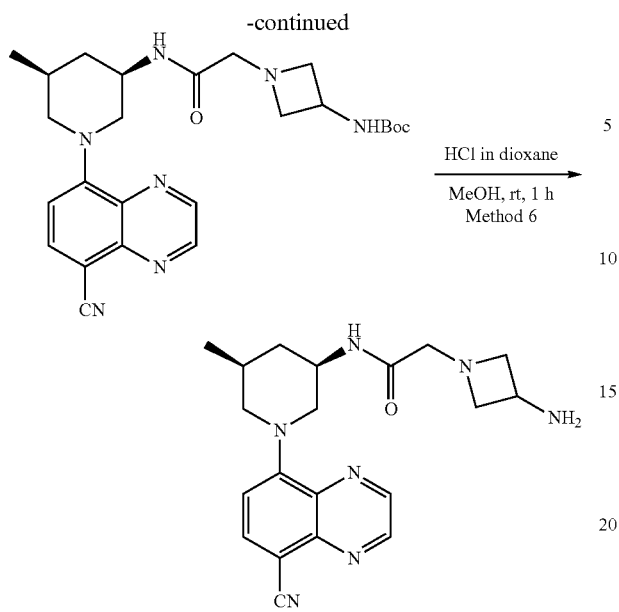

2-(3-aminoazetidin-1-yl)-N-[(3R,5S)-1-(8-cyanoquinoxalin-5-yl)-5-methylpiperidin-3-yl]acetamide: 2-(3-aminoazetidin-1-yl)-N-[(3R,5S)-1-(8-cyanoquinoxalin-5-yl)-5-methylpiperidin-3-yl]acetamide was prepared from 8-((3R,5S)-3-amino-5-methylpiperidin-1-yl)quinoxaline-5-carbonitrile, 2-bromoacetic acid, and tert-butyl azetidin-3-ylcarbamate using Method 30, 18, and 6. The crude product was purified by prep-HPLC under the following conditions: column, XBridge Prep C18 OBD Column, 5 um, 19 mm×150 mm; mobile phase, acetonitrile in water (with 0.05% $NH_3 \cdot H_2O$), 2% to 33% gradient in 10 min; detector, UV 254 nm. 2-(3-aminoazetidin-1-yl)-N-[(3R,5S)-1-(8-cyanoquinoxalin-5-yl)-5-methylpiperidin-3-yl]acetamide was obtained as yellow solid (34 mg, 29%).

Compound 356: HPLC: 97.8% purity, RT=0.96 min. MS: m/z=380.2 [M+H]$^+$. $^1$H NMR (300 MHz, $CD_3OD$, ppm) δ 9.10-8.90 (m, 2H), 8.21 (d, J=8.4 Hz, 1H), 7.66 (d, J=8.1 Hz, 1H), 7.27 (d, J=8.5 Hz, 1H), 4.39-3.85 (m, 3H), 3.70-3.37 (m, 4H), 3.07-2.60 (m, 7H), 1.98-1.82 (m, 2H), 1.33-1.24 (m, 1H), 0.93-0.76 (m, 3H).

Example 99: Synthesis of Compound 357 and 358 (N-((3R,5S)-1-(8-cyanoquinoxalin-5-yl)-5-methylpiperidin-3-yl)-2-((1R,5S,6r)-3-methyl-3-aza-bicyclo[3.1.1]heptan-6-yl)acetamide and N-((3R,5S)-1-(8-cyanoquinoxalin-5-yl)-5-methylpiperidin-3-yl)-2-((1S,5R,6s)-3-methyl-3-aza-bicyclo[3.1.1]heptan-6-yl)acetamide)

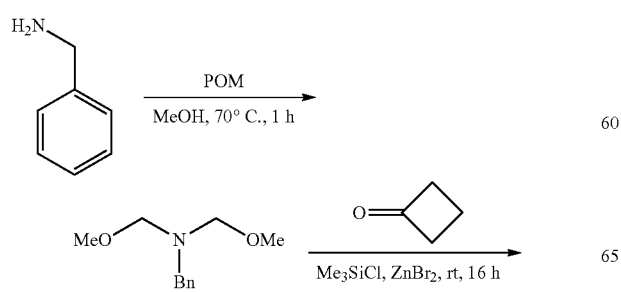

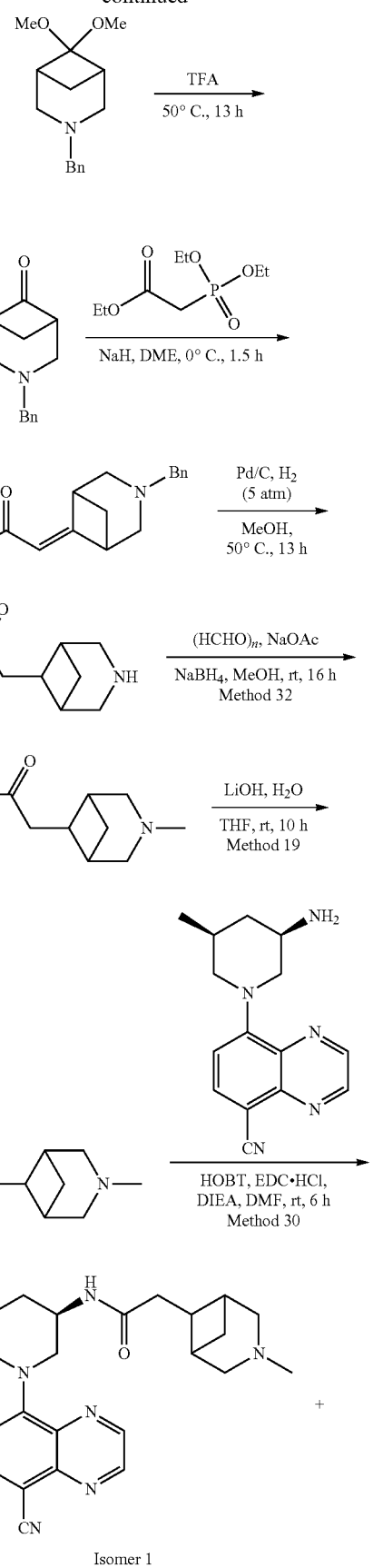

Isomer 1

+

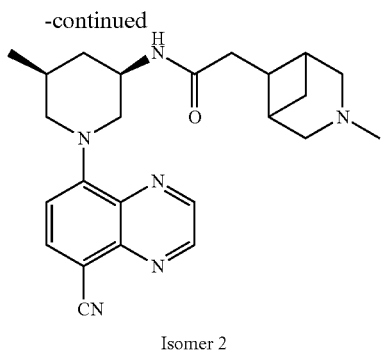

Isomer 2

Benzylbis(methoxymethyl)amine: To a solution of phenylmethanamine (95 g, 886.58 mmol) in MeOH (1 L) was added polyformaldehyde (78.4 g, 870.08 mmol) at room temperature. The resulting solution was then stirred overnight at 70° C. When the reaction was done, it was quenched by the addition of water (mL). The solvent was removed under reduced pressure and the residue was purified by distillation under reduced pressure (10 mm Hg) and the fraction was collected at 70-72° C. to yield benzylbis(methoxymethyl)amine as colorless liquid (104.0 g, 75%).

Benzylbis(methoxymethyl)amine: To a solution of benzylbis(methoxymethyl)amine (16.0 g, 81.94 mmol) in DCM (200 mL) was added cyclobutanone (6.8 g, 96.62 mmo), chlorotrimethylsilane (22.8 g, 210.74 mmol) and $ZnBr_2$ (21.7 g, 96.17 mmol) at room temperature. The resulting mixture was stirred for 16 h at room temperature. After cooling to room temperature, the reaction mixture was quenched by the addition of water (500 mL). The resulting mixture was extracted with ethyl acetate (200 mL×3). The organic phases were combined, washed with brine and dried over $Na_2SO_4$. The solvent was removed under reduced pressure and the residue was purified by flash chromatography eluting with EtOAc in hexane (0% to 90% gradient) to yield 3-benzyl-6,6-dimethoxy-3-azabicyclo[3.1.1]heptan as light yellow oil (6.4 g, 32%). MS: m/z=248.3 $[M+H]^+$.

Benzylbis(methoxymethyl)amine: 3-benzyl-6,6-dimethoxy-3-azabicyclo[3.1.1]heptane (3.6 g, 14.56 mmol) was slowly added to trifluoroacetic acid (100 mL) at room temperature. The resulting solution was then stirred for 13 h at 50° C. After the reaction was done, the reaction mixture was concentrated under reduced pressure and diluted with $H_2O$ (50 mL). The pH value of the resulting mixture was adjusted to 9 with sat. sodium carbonate solution. The mixture was extracted with ethyl acetate (100 mL×3). The organic phases were combined, washed with brine and dried over $Na_2SO_4$. The solvent was removed under reduced pressure and the residue was purified by flash chromatography eluting with EtOAc in hexane (0% to 10% gradient) to yield 3-benzyl-3-azabicyclo[3.1.1]heptan-6-one as brown oil (2.5 g, 84%). MS: m/z=202.0 $[M+H]^+$.

Ethyl 2-[3-benzyl-3-azabicyclo[3.1.1]heptan-6-ylidene]acetate: At 0° C., to a solution of 3-benzyl-3-azabicyclo[3.1.1]heptan-6-one (2.0 g, 9.83 mmol) in ethylene glycol dimethyl ether (100 mL) was added sodium hydride (294 mg, 12.25 mmol) slowly. The resulting mixture was stirred at 0° C. for 10 min, and then was added by ethyl 2-(diethoxyphosphoryl)acetate (3.9 g, 17.29 mmol). The reaction mixture was then stirred for another 1.5 h at 0° C. When the reaction was done, it was quenched by the addition of sat. $NH_4Cl$ solution. The resulting mixture was extracted with ethyl acetate (100 mL×3). The organic phases were combined, washed with brine and dried over $Na_2SO_4$. The solvent was removed under reduced pressure and the residue was purified by flash chromatography eluting with MeOH in DCM (0% to 10% gradient) to yield ethyl 2-[3-benzyl-3-azabicyclo[3.1.1]heptan-6-ylidene]acetate as light yellow oil (1.4 g, 53%). MS: m/z=272.1 $[M+H]^+$.

Ethyl 2-[3-benzyl-3-azabicyclo[3.1.1]heptan-6-ylidene]acetate: To a solution of ethyl 2-[3-benzyl-3-azabicyclo[3.1.1]heptan-6-ylidene]acetate (1.4 g, 5.16 mmol) in MeOH (100 mL) was added Pd/C (10%, 400 mg) at room temperature under nitrogen atmosphere. The reaction flask was vacuumed and purged with hydrogen. The reaction mixture was then hydrogenated at 550° C. for 16 h under hydrogen atmosphere under a hydrogen balloon. After the reaction was done, the reaction mixture was filtered through a Celite pad and the filtrate was concentrated under reduced pressure to yield ethyl 2-[3-azabicyclo[3.1.1]heptan-6-yl]acetate as light yellow oil (800 mg, 85%). MS: m/z=184.2 $[M+H]^+$.

N-((3R,5S)-1-(8-cyanoquinoxalin-5-yl)-5-methylpiperidin-3-yl)-2-((1R,5S,6r)-3-methyl-3-aza-bicyclo[3.1.1]heptan-6-yl)acetamide and N-((3R,5S)-1-(8-cyanoquinoxalin-5-yl)-5-methylpiperidin-3-yl)-2-((1S,5R,6s)-3-methyl-3-aza-bicyclo[3.1.1]heptan-6-yl)acetamide: N-((3R,5S)-1-(8-cyanoquinoxalin-5-yl)-5-methylpiperidin-3-yl)-2-(3-methyl-3-aza-bicyclo[3.1.1]heptan-6-yl)acetamide was prepared from 8-((3R,5S)-3-amino-5-methylpiperidin-1-yl)quinoxaline-5-carbonitrile, ethyl 2-(3-aza-bicyclo[3.1.1]heptan-6-yl)acetate, and polyformaldehyde using Method 32, 19, and 30. The crude product was purified by prep-HPLC under the following conditions: column, XBridge Prep C18 OBD Column, 19×150 mm 10 um; mobile phase, acetonitrile in water (with 10 mmol/L $NH_4HCO_3$ and 0.1% $NH_3.H_2O$), 29% to 33% gradient in 7 min; detector, UV 254 nm. Two diastereoisomers were separated and obtained.

Isomer 1: (5 mg, 4% for 3 steps, light yellow solid) HPLC: 96.9% purity, RT=2.90 min. MS: m/z=419.1 $[M+Na]^+$. $^1$H NMR (400 MHz, $CD_3OD$, ppm) δ 8.99-8.89 (m, 2H), 8.10 (d, J=8.3 Hz, 1H), 7.30 (d, J=8.4 Hz, 1H), 4.43-4.28 (m, 2H), 4.17-4.10 (m, 1H), 3.16-3.07 (m, 2H), 2.85-2.63 (m, 4H), 2.54 (d, J=8.0 Hz, 2H), 2.41 (s, 3H), 2.33-2.31 (m, 1H), 2.18-1.99 (m, 5H), 1.69-1.66 (m, 1H), 1.30-1.14 (m, 1H), 1.02 (d, J=6.5 Hz, 3H).

Isomer 2: (6 mg, 4.4% for 3 steps, light yellow solid) HPLC: 97.7% purity, RT=1.16 min. MS: n/z=419.5 $[M+Na]^+$. $^1$H NMR (400 MHz, $CD_3OD$, ppm) δ 8.99-8.89 (m, 2H), 8.10 (d, J=8.4 Hz, 1H), 7.29 (d, J=8.3 Hz, 1H), 4.38-4.31 (m, 2H), 4.15-4.09 (m, 1H), 3.17-3.04 (m, 2H), 2.92-2.80 (m, 2H), 2.79-2.51 (m, 3H), 2.41 (s, 3H), 2.37-2.30 (m, 4H), 2.11-2.03 (m, 2H), 1.92-1.75 (m, 2H), 1.23-1.15 (m, 1H), 1.02 (d, J=6.4 Hz, 3H).

Example 100: Synthesis of Compound 359 (N-[(3R,5S)-1-(8-cyanoquinoxalin-5-yl)-5-methylpiperidin-3-yl]-2-(1-methylazetidin-3-yl)acetamide)

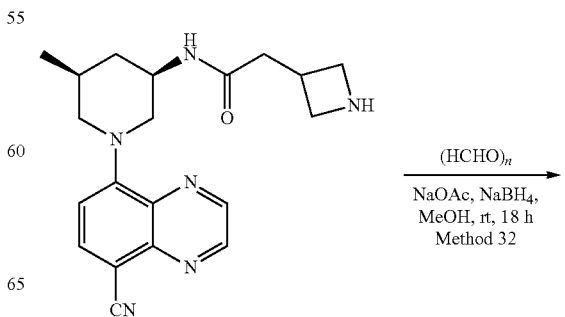

(HCHO)$_n$
→
NaOAc, NaBH$_4$,
MeOH, rt, 18 h
Method 32

-continued

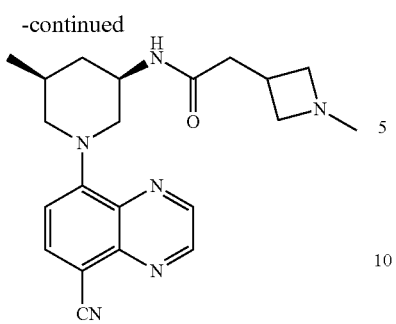

N-[(3R,5S)-1-(8-cyanoquinoxalin-5-yl)-5-methylpiperidin-3-yl]-2-(1-methylazetidin-3-yl)acetamide: N-[(3R,5S)-1-(8-cyanoquinoxalin-5-yl)-5-methylpiperidin-3-yl]-2-(1-methylazetidin-3-yl)acetamide was prepared from 2-(azetidin-3-yl)-N-[(3R,5S)-1-(8-cyanoquinoxalin-5-yl)-5-methylpiperidin-3-yl]acetamide and polyformaldehyde using Method 32. The crude product was purified by prep-HPLC under the following conditions: column, XBridge Prep C18 OBD Column, 5 um, 19 mm×150 mm; mobile phase, acetonitrile in water (with 10 mmol/L NH$_4$HCO$_3$ and 0.1% NH$_3$.H$_2$), 25% to 31% gradient in 7 min; detector, UV 254 nm. N-[(3R,5S)-1-(8-cyanoquinoxalin-5-yl)-5-methylpiperidin-3-yl]-2-(1-methylazetidin-3-yl)acetamide was obtained as yellow solid (5 mg, 12%).

Compound 359: HPLC: 97.2% purity, RT=0.84 min. MS: m/z=379.2 [M+H]$^+$. $^1$H NMR (300 MHz, CD$_3$OD, ppm) δ 8.99-8.88 (m, 2H), 8.07 (d, J=8.4 Hz, 1H), 7.26 (d, J=8.4 Hz, 1H), 4.36-4.31 (m, 2H), 4.12-4.04 (m, 1H), 3.55-3.50 (m, 2H), 3.03-2.98 (m, 2H), 2.90-2.60 (m, 3H), 2.45 (d, J=7.7 Hz, 2H), 2.33 (s, 3H), 2.15-1.94 (m, 2H), 1.26-1.10 (m, 1H), 0.99 (d, J=6.3 Hz, 3H).

The following compounds were synthesized in an analogous manner:

Compound 360 (N-[(3R,5S)-5-methyl-1-[8-(trifluoromethyl)quinolin-5-yl]piperidin-3-yl]-2-(1-methylazetidin-3-yl)acetamide): From 2-(azetidin-3-yl)-N-[(3R,5S)-1-(8-cyanoquinoxalin-5-yl)-5-methylpiperidin-3-yl]acetamide and polyformaldehyde. HPLC: 94.0% purity, RT=2.27 min. MS: m/z=421.1 [M+H]$^+$. $^1$H NMR (300 MHz, DMSO-d$_6$, ppm) δ 9.02 (dd, J=4.2, 1.6 Hz, 1H), 8.52 (dd, J=8.6, 1.8 Hz, 1H), 8.06 (d, J=8.1 Hz, 1H), 7.92 (d, J=7.4 Hz, 1H), 7.68 (dd, J=8.6, 4.2 Hz, 1H), 7.21 (d, J=8.1 Hz, 1H), 4.01-3.99 (m, 1H), 3.48-3.21 (m, 3H), 2.81-2.70 (m, 2H), 2.51-2.28 (m, 4H), 2.16 (s, 3H), 2.09-1.95 (m, 3H), 1.18-0.91 (m, 4H).

Compound 363 (N-[(3R,5S)-5-methyl-1-[8-(trifluoromethyl)quinoxalin-5-yl]piperidin-3-yl]-2-(1-methylazetidin-3-yl)acetamide): From 2-(azetidin-3-yl)-N-[(3R,5S)-5-methyl-1-[8-(trifluoromethyl)quinoxalin-5-yl]piperidin-3-yl]acetamide and polyformaldehyde. HPLC: 93.5% purity, RT=5.81 min. MS: m/z=422.3 [M+H]$^+$. $^1$H NMR (300 MHz, DMSO-d$_6$, ppm) δ 9.08-8.95 (m, 2H), 8.07 (d, J=8.2 Hz, 1H), 7.91 (d, J=7.6 Hz, 1H), 7.28 (d, J=8.5 Hz, 1H), 4.23-4.04 (m, 2H), 3.92-3.81 (m, 1H), 3.43-3.26 (m, 2H), 2.80-2.65 (m, 5H), 2.34-2.31 (m, 2H), 2.16 (s, 3H), 1.95-1.83 (m, 2H), 1.21-1.02 (m, 1H), 0.93 (d, J=6.2 Hz, 3H).

Compound 364 (N-[(3R,5S)-1-[8-(difluoromethyl)quinolin-5-yl]-5-methylpiperidin-3-yl]-2-(1-methylazetidin-3-yl)acetamide): From 2-(azetidin-3-yl)-N-[(3R,5S)-1-[8-(difluoromethyl)quinolin-5-yl]-5-methylpiperidin-3-yl]acetamide and polyformaldehyde. HPLC: 88.7% purity, RT=1.24 min. MS: m/z=403.1 [M+H]$^+$. $^1$H NMR (400 MHz, CD$_3$OD, ppm) δ 8.89 (dd, J=4.2, 1.7 Hz, 1H), 8.60 (dd, J=8.6, 1.8 Hz, 1H), 7.93 (dd, J=7.8, 1.6 Hz, 1H), 7.83-7.55 (m, 2H), 7.24 (d, J=7.9 Hz, 1H), 4.25-4.12 (m, 1H), 3.59-3.43 (m, 3H), 2.98-2.93 (m, 2H), 2.79-2.75 (m, 1H), 2.51-2.36 (m, 4H), 2.30 (s, 3H), 2.13-2.07 (m, 2H), 1.19-0.97 (m, 5H).

Example 101: Synthesis of Compound 366 (cis-5-cyclopropyl-1-(8-fluoroquinoxalin-5-yl)piperidin-3-amine)

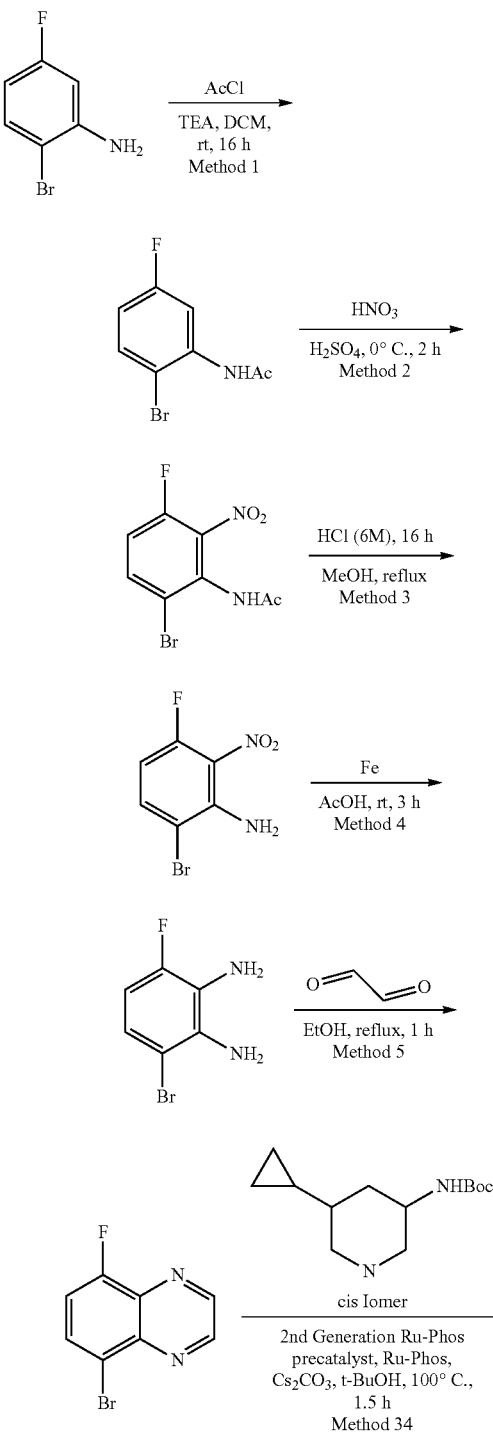

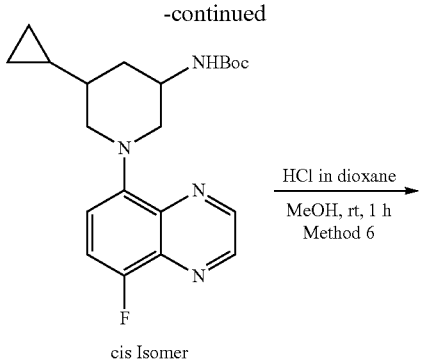

cis Isomer

HCl in dioxane
MeOH, rt, 1 h
Method 6

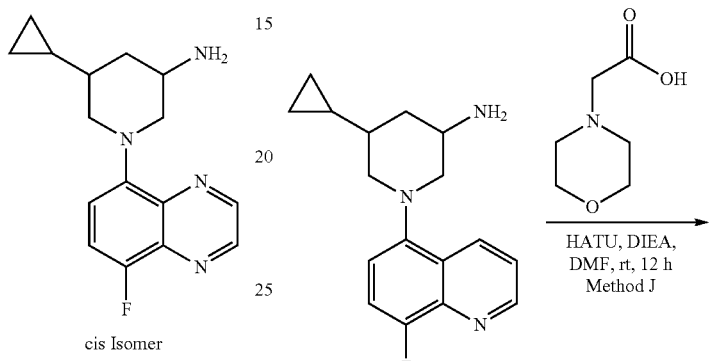

cis Isomer 5-bromo-8-fluoroquinoxaline: 5-bromo-8-fluoroquinoxaline was prepared from 2-bromo-5-fluorobenzenamine, acetyl chloride, and oxalaldehyde using Method 1 to 5. The crude product was purified by flash chromatography eluting with EtOAc in hexane (0% to 10% gradient) to yield 5-bromo-8-fluoroquinoxaline as white solid (637 mg, 71%, for 5 steps). MS: m/z=226.8 [M+H]$^+$.

Method 34 tert-butyl cis-N-[5-cyclopropyl-1-(8-fluoroquinoxalin-5-yl)piperidin-3-yl]carbamate: To a solution of 5-bromo-8-fluoroquinoxaline (66 mg, 0.29 mmol) in tert-Butanol (10 mL) was added tert-butyl N-(5-cyclopropylpiperidin-3-yl) carbamate (62 mg, 0.26 mmol), RuPhos (29 mg, 0.06 mmol), Cs$_2$CO$_3$ (151.6 mg, 0.44 mmol) and 2nd Generation RuPhos precatalyst (23 mg, 0.03 mmol) at room temperature. The resulting mixture was stirred for 3 h at 100° C. After cooling to room temperature, the reaction mixture was quenched by the addition of water (20 mL). The resulting mixture was extracted with ethyl acetate (20 mL×3). The organic phases were combined, washed with brine and dried over Na$_2$SO$_4$. The solvent was removed under reduced pressure and the residue was applied onto C18 gel column and purified by reverse phase flash chromatography eluting with acetonitrile in water (with 10 mmol/L NH$_4$HCO$_3$) (0% to 60% gradient in 30 min) to yield tert-butyl N-[5-cyclopropyl-1-(8-fluoroquinoxalin-5-yl)piperidin-3-yl]carbamate as yellow solid (32 mg, 29%). MS: m/z=387.2 [M+H]$^+$.

cis-5-cyclopropyl-1-(8-fluoroquinoxalin-5-yl)piperidin-3-amine: cis-5-cyclopropyl-1-(8-fluoroquinoxalin-5-yl)piperidin-3-amine was prepared from tert-butyl N-[5-cyclopropyl-1-(8-fluoroquinoxalin-5-yl)piperidin-3-yl]carbamate using Method 6. The crude product was purified by prep-HPLC under the following conditions: column, XBridge Prep C18 OBD Column, 5 um, 19 mm×150 mm; mobile phase, acetonitrile in water (with 10 mmol/L NH$_4$HCO$_3$ and 0.1% NH$_3$.H$_2$O), 35% to 65% gradient in 7 min; detector, UV 254 nm. cis-5-cyclopropyl-1-(8-fluoroquinoxalin-5-yl)piperidin-3-amine was obtained as yellow solid (7 mg, 29%).

Compound 366: HPLC: 99.0% purity, RT=1.78 min. MS: m/z=278.1 [M+H]$^+$. $^1$H NMR (300 MHz, DMSO-d$_6$, ppm) δ 9.02-8.92 (m, 2H), 7.57 (dd, J=10.2, 8.6 Hz, 1H), 7.16 (dd, J=8.7, 4.9 Hz, 1H), 3.86-3.72 (m, 2H), 2.93-2.88 (m, 1H), 2.50-2.40 (m, 2H), 2.33-2.29 (m, 1H), 2.15-1.90 (m, 2H), 1.02-1.1 (m, 2H), 0.65-0.32 (m, 3H), 0.16-0.14 (m, 2H).

Example 102: Synthesis of Compound 367 (cis-N-[5-cyclopropyl-1-(8-fluoroquinolin-5-yl)piperidin-3-yl]-2-(morpholin-4-yl)acetamide)

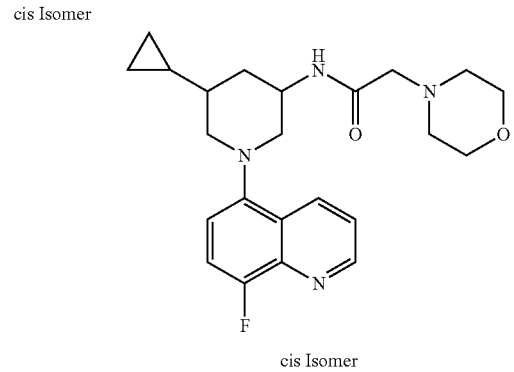

cis Isomer

Cis-N-[5-cyclopropyl-1-(8-fluoroquinolin-5-yl)piperidin-3-yl]-2-(morpholin-4-yl)acetamide: cis-N-[5-cyclopropyl-1-(8-fluoroquinolin-5-yl)piperidin-3-yl]-2-(morpholin-4-yl) acetamide was prepared from cis-5-cyclopropyl-1-(8-fluoroquinolin-5-yl)piperidin-3-amine and 2-(morpholin-4-yl)acetic acid using Method J. The crude product was purified by prep-HPLC under the following conditions: column, XBridge Prep C18 OBD Column, 5 um, 19 mm×150 mm; mobile phase, acetonitrile in water (with 10 mmol/L NH$_4$HCO$_3$ and 0.1% NH$_3$.H$_2$O), 36% to 47% gradient in 7 min; detector, UV 254 nm. Cis-N-[5-cyclopropyl-1-(8-fluoroquinolin-5-yl)piperidin-3-yl]-2-(morpholin-4-yl)acetamide was obtained as yellow solid (50 mg, 62%).

Compound 367: HPLC: 99.9% purity, RT=1.09 min. MS: m/z=413.4 [M+H]$^+$. $^1$H NMR (400 MHz, CD$_3$OD, ppm) δ 8.86 (dd, J=4.3, 1.6 Hz, 1H), 8.65 (dt, J=8.7, 1.6 Hz, 1H), 7.63 (dd, J=8.6, 4.3 Hz, 1H), 7.42 (dd, J=10.7, 8.4 Hz, 1H), 7.22 (dd, J=8.4, 4.2 Hz, 1H), 4.19-4.12 (m, 1H), 3.74-3.67 (m, 4H), 3.45-3.26 (m, 2H), 3.02 (s, 2H), 2.70-2.47 (m, 6H), 2.26-2.14 (m, 1H), 1.43-1.20 (m, 2H), 0.63-0.45 (m, 3H), 0.29-0.12 (m, 2H).

Example 103: Synthesis of Compound 368 (cis-N-[5-cyclopropyl-1-(8-fluoroquinolin-5-yl)piperidin-3-yl]-N-methyl-2-(morpholin-4-yl)acetamide

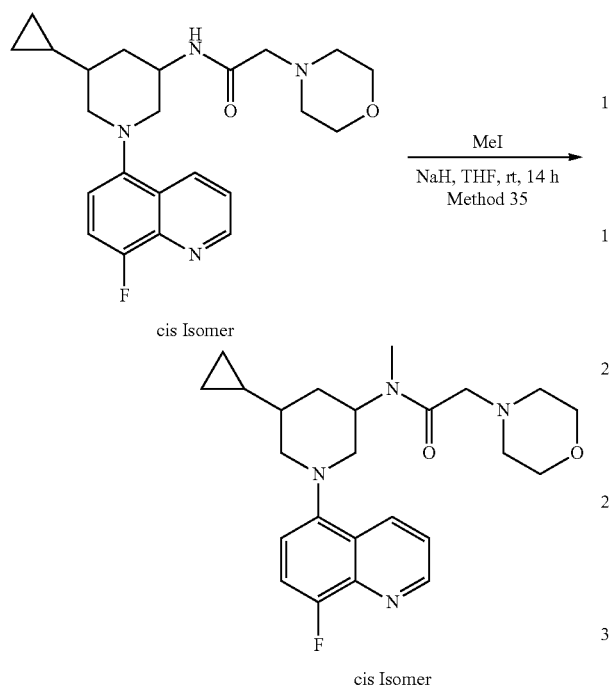

Example 104: Synthesis of Compound 369 and compound 370 ((2R)-2-(3-aminoazetidin-1-yl)-N-[(3R,5S)-5-methyl-1-[8-(trifluoromethyl)quinoxalin-5-yl]piperidin-3-yl]propanamide and (2S)-2-(3-aminoazetidin-1-yl)-N-[(3R,5S)-5-methyl-1-[8-(trifluoromethyl)quinoxalin-5-yl]piperidin-3-yl]propanamide)

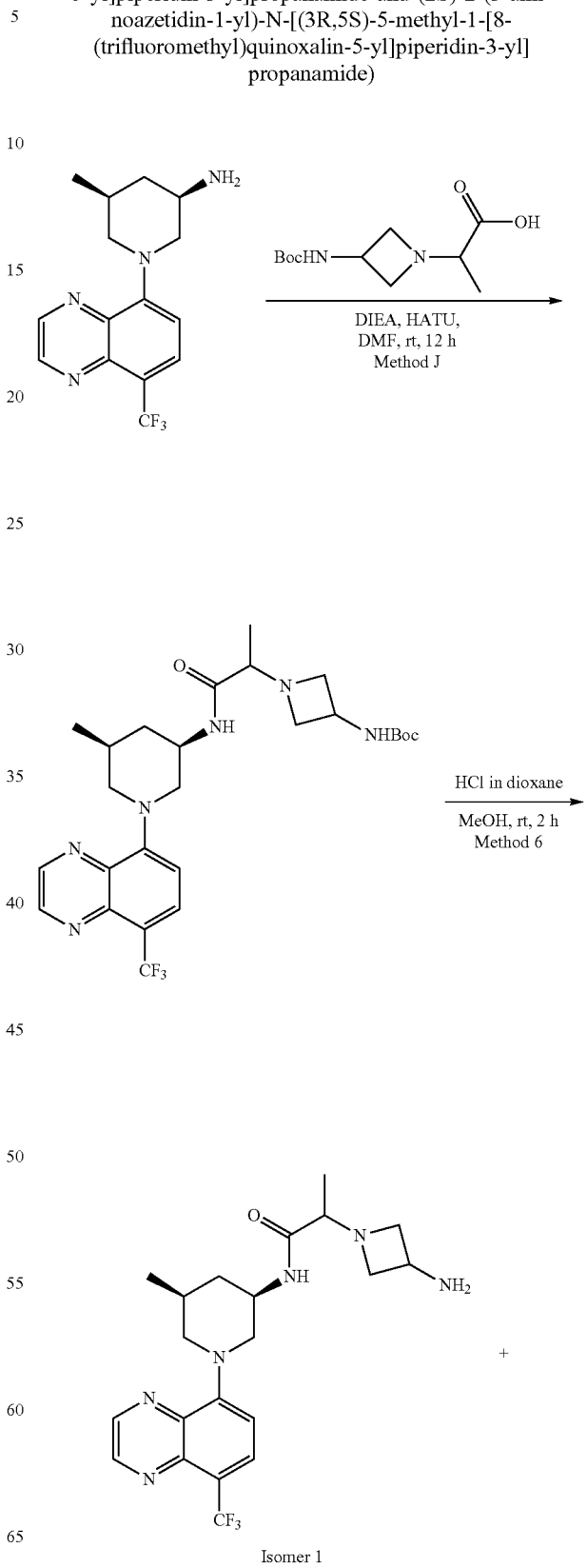

Method 35

Cis-N-[5-cyclopropyl-1-(8-fluoroquinolin-5-yl)piperidin-3-yl]-N-methyl-2-(morpholin-4-yl)acetamide: To a solution of cis-N-[5-cyclopropyl-1-(8-fluoroquinolin-5-yl)piperidin-3-yl]-2-(morpholin-4-yl)acetamide (100 mg, 0.24 mmol) in tetrahydrofuran (15 mL) was added sodium hydride (17 mg, 0.73 mmol) at room temperature. The mixture was stirred for 10 min at room temperature, and then was added by MeI (294 mg, 2.07 mmol). The resulting mixture was stirred for another 14 h at room temperature. When the reaction was done, it was quenched by the addition of water (20 mL). The resulting mixture was extracted with DCM (50 mL×3). The organic phases were combined, washed with brine and dried over $Na_2SO_4$. The solvent was removed under reduced pressure and the residue was purified by prep-HPLC under the following conditions: column, XBridge Prep C18 OBD Column, 5 um, 19 mm×150 mm; mobile phase, acetonitrile in water (with 0.05% $NH_3.H_2O$), 32% to 40% gradient in 8 min; detector, UV 254 nm. Cis-N-[5-cyclopropyl-1-(8-fluoroquinolin-5-yl)piperidin-3-yl]-N-methyl-2-(morpholin-4-yl)acetamide was obtained as light brown solid (10 mg, 9%).

Compound 368: HPLC: 95.5% purity, RT=0.91 min. MS: n/z=427.3 [M+H]$^+$. $^1$H NMR (400 MHz, $CD_3OD$, ppm) δ 8.87 (dd, J=4.2, 1.6 Hz, 1H), 8.64 (dt, J=8.7, 1.8 Hz, 1H), 7.63 (dd, J=8.7, 4.3 Hz, 1H), 7.43 (dd, J=10.6, 8.4 Hz, 1H), 7.23 (dd, J=8.4, 4.2 Hz, 1H), 4.27-4.14 (m, 3H), 4.03-3.98 (m, 4H), 3.75-3.66 (m, 4H), 3.48-3.47 (m, 1H), 3.42 (s, 3H), 2.71-2.51 (m, 2H), 2.27-2.21 (m, 1H), 1.36-1.25 (m, 3H), 0.63-0.59 (m, 1H), 0.53-0.43 (m, 2H), 0.21-0.18 (m, 2H).

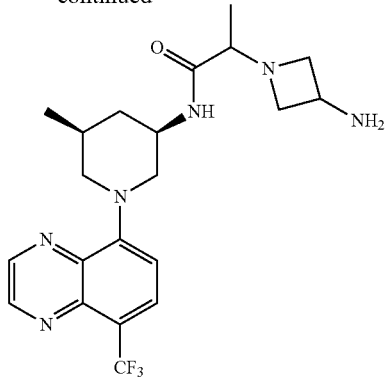

Isomer 2

(2R)-2-(3-aminoazetidin-1-yl)-N-[(3R,5S)-5-methyl-1-[8-(trifluoromethyl)quinoxalin-5-yl]piperidin-3-yl]propanamide and (2S)-2-(3-aminoazetidin-1-yl)-N-[(3R,5S)-5-methyl-1-[8-(trifluoromethyl)quinoxalin-5-yl]piperidin-3-yl]propanamide: 2-(3-aminoazetidin-1-yl)-N-[(3R,5S)-5-methyl-1-[8-(trifluoromethyl)quinoxalin-5-yl]piperidin-3-yl]propanamide was prepared from (3R,5S)-5-methyl-1-(8-(trifluoromethyl)quinoxalin-5-yl)piperidin-3-amine and 2-(3-(tert-butoxycarbonylamino)azetidin-1-yl)propanoic acid using Method J and 6. The crude product was first purified by prep-HPLC under the following conditions: column, XBridge Prep C18 OBD Column, 5 um, 19 mm×150 mm; mobile phase, acetonitrile in water (with 10 mmol/L $NH_4HCO_3$ and 0.1% $NH_3.H_2O$), 30% to 50% gradient in 7 min; detector, UV 254 nm. Then the two enantiomeric isomers were obtained by separation on chiral prep-HPLC under the following conditions: column, CHIRALPAK IC, 2×25 cm, 5 um; mobile phase, EtOH in Hexane (0.1% DEA), 30% isocratic in 18 min; detector, UV 254/220 nm.

Isomer 1: (18 mg, 26%, yellow solid) HPLC: 98.1% purity, RT=1.31 min. MS: n/z=437.5 [M+Na]$^+$. $^1$H NMR (300 MHz, DMSO-$d_6$, ppm) δ 9.06-8.94 (m, 2H), 8.06 (d, J=8.4 Hz, 1H), 7.57 (d, J=8.0 Hz, 1H), 7.25 (d, J=8.3 Hz, 1H), 4.20-3.85 (m, 3H), 3.54-3.35 (m, 3H), 2.86-2.51 (m, 6H), 2.02-1.85 (m, 2H), 1.35-0.85 (m, 8H).

Isomer 2: (28 mg, 26%, yellow solid) HPLC: 91.6% purity, RT=1.28 min. MS: m/z=437.4 [M+Na]$^+$. $^1$H NMR (300 MHz, DMSO-$d_6$, ppm) δ 9.06-8.94 (m, 2H), 8.07 (d, J=8.4 Hz, 1H), 7.53 (d, J=8.0 Hz, 1H), 7.27 (d, J=8.4 Hz, 1H), 4.14-3.97 (m, 3H), 3.49-3.32 (m, 3H), 2.87-2.52 (m, 4H), 2.20-1.85 (m, 4H), 1.31-0.89 (m, 8H).

The following compounds were synthesized in an analogous manner:

Compound 371 and compound 372 ((2R)-2-(4-hydroxypiperidin-1-yl)-N-[(3R,5S)-5-methyl-1-[8-(trifluoromethyl)quinoxalin-5-yl]piperidin-3-yl]propanamide and (2s)-2-(4-hydroxypiperidin-1-yl)-N-[(3R,5S)-5-methyl-1-[8-(trifluoromethyl)quinoxalin-5-yl]piperidin-3-yl]propanamide): From (3R,5S)-5-methyl-1-[8-(trifluoromethyl)quinoxalin-5-yl]piperidin-3-amine and 2-(4-hydroxypiperidin-1-yl)propanoic acid. Isomer 1: HPLC: 91.9% purity, RT=1.44 min. MS: m/z=466.5 [M+Na]$^+$. $^1$H NMR (300 MHz, DMSO-$d_6$, ppm) δ 9.06-8.94 (m, 2H), 8.07 (d, J=8.4 Hz, 1H), 7.72 (d, J=7.8 Hz, 1H), 7.27 (d, J=8.4 Hz, 1H), 4.62-4.46 (m, 1H), 4.20-3.90 (m, 3H), 3.50-3.34 (m, 1H), 3.14-3.00 (m, 1H), 2.85-2.50 (m, 4H), 2.30-2.05 (m, 2H), 2.03-1.87 (m, 2H), 1.79-1.63 (m, 2H), 1.46-1.17 (m, 3H), 1.07 (d, J=6.8 Hz, 3H), 0.93 (d, J=6.2 Hz, 3H). Isomer 2: HPLC: 97.0% purity, RT=5.48 min. MS: m/z=466.5 [M+Na]*. $^1$H NMR (300 MHz, DMSO-$d_6$, ppm) δ 9.09-8.95 (m, 2H), 8.08 (d, J=8.4 Hz, 1H), 7.77-7.63 (m, 1H), 7.28 (d, J=8.4 Hz, 1H), 4.62-4.48 (m, 1H), 4.24-3.90 (m, 3H), 3.49-3.30 (m, 1H), 3.03-3.01 (m, 1H), 2.83-2.53 (m, 4H), 2.21-2.12 (m, 2H), 1.95-1.92 (m, 2H), 1.79-1.68 (m, 2H), 1.42-1.38 (m, 2H), 1.24-1.20 (m, 1H), 1.09 (d, J=6.8 Hz, 3H), 0.94 (d, J=6.2 Hz, 3H).

Example 105: Synthesis of Compound 373 (1-Pyrido[2,3-b]pyrazin-8-yl-piperidine-4-carboxylic acid (2-piperidin-1-yl-ethyl)-amide)

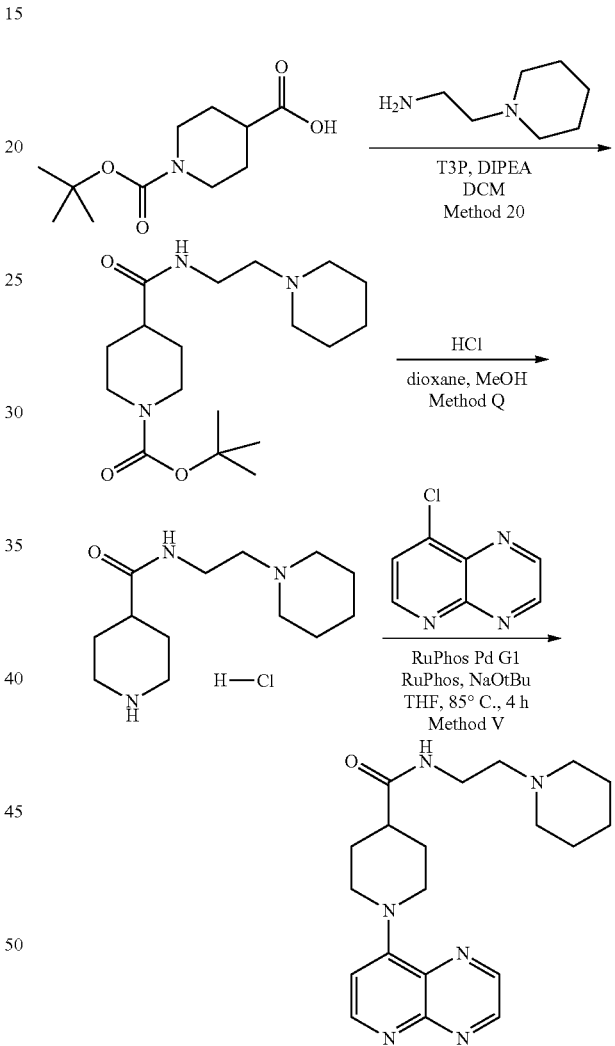

1-Pyrido[2,3-b]pyrazin-8-yl-piperidine-4-carboxylic acid (2-piperidin-1-yl-ethyl)-amide: 1-Pyrido[2,3-b]pyrazin-8-yl-piperidine-4-carboxylic acid (2-piperidin-1-yl-ethyl)-amide was obtained from 8-Chloro-pyrido[2,3-b]pyrazine, 1-(2-aminoethyl)piperidine and 1-tert-butoxycarbonylpiperidine-4-carboxylic acid in 11% yield over 3 steps, using method 20, Q and V.

Compound 373: HPLC: 97.0% purity, RT=1.13 min. MS: m/z=369 [M+H]$^+$. $^1$H NMR (400 MHz, Chloroform-d, ppm) δ 8.97 (d, J=1.7 Hz, 1H), 8.83 (d, J=5.4 Hz, 1H), 8.75 (d, J=1.7 Hz, 1H), 6.91 (d, J=5.4 Hz, 1H), 6.36 (s, 1H), 4.47 (dt, J=12.7, 2.9 Hz, 2H), 3.38 (q, J=5.7 Hz, 2H), 3.30-3.12 (m, 2H), 2.51-2.38 (m, 6H), 2.10-2.01 (m, 4H), 2.00-1.84 (m, 1H), 1.60 (p, J=5.6 Hz, 4H), 1.53-1.39 (m, 2H).

The following compounds were synthesized in an analogous manner:

Compound 379 (1-Pyrido[2,3-b]pyrazin-8-yl-piperidine-4-carboxylic acid (2-piperidin-1-yl-ethyl)-amide): From 8-Chloro-pyrido[2,3-b]pyrazine, N,N-diethylethylenediamine and 1-tert-butoxycarbonylpiperidine-4-carboxylic acid. HPLC: 93.2% purity, RT=1.06 min. MS: m/z=357 [M+H]$^+$. $^1$H NMR (400 MHz, Chloroform-d, ppm) δ 8.96 (d, J=1.7 Hz, 1H), 8.81 (d, J=5.3 Hz, 1H), 8.74 (d, J=1.7 Hz, 1H), 6.89 (d, J=5.4 Hz, 1H), 6.26 (s, 1H), 4.45 (dt, J=11.4, 2.9 Hz, 2H), 3.32 (q, J=5.5 Hz, 2H), 3.17 (ddd, J=12.7, 8.3, 6.1 Hz, 2H), 2.70-2.49 (m, 6H), 2.51-2.38 (m, 1H), 2.17-1.95 (m, 4H), 1.03 (t, J=7.1 Hz, 6H).

Compound 380 (4-[(2-Diethylamino-acetylamino)-methyl]-piperidine-1-carboxylic acid tert-butyl ester): From 8-Chloro-pyrido[2,3-b]pyrazine, 2-(diethylamino)acetic acid hydrochloride and 1-boc-4-(aminomethyl)piperidine. HPLC: >99% purity, RT=1.11 min. MS: n/z=357 [M+H]$^+$. $^1$H NMR (400 MHz, Chloroform-d, ppm) δ 8.92 (s, 1H), 8.77 (dd, J=5.8, 2.5 Hz, 1H), 8.70 (s, 1H), 7.57 (t, J=6.3 Hz, 1H), 6.85 (dd, J=5.8, 2.5 Hz, 1H), 4.43 (d, J=12.2 Hz, 3H), 3.23 (d, J=6.6 Hz, 4H), 3.14-2.96 (m, 5H), 2.54 (q, J=6.5 Hz, 7H), 1.85 (d, J=11.3 Hz, 5H), 1.55 (q, J=12.2 Hz, 4H), 1.01 (t, J=6.9 Hz, 10H).

Compound 432 (1-(8-Cyano-quinoxalin-5-yl)-piperidine-4-carboxylic acid (2-diethylamino-ethyl)-amide): From 8-Bromo-quinoxaline-5-carbonitrile, 1-tert-butoxycarbonylpiperidine-4-carboxylic acid and N,N-diethylethylenediamine. HPLC: 91.4% purity, RT=1.95 min. MS: m/z=381 [M+H]$^+$. $^1$H NMR (400 MHz, Chloroform-d, ppm) δ 8.95 (d, J=1.8 Hz, 1H), 8.83 (d, J=1.8 Hz, 1H), 8.00 (d, J=8.3 Hz, 1H), 7.06 (d, J=8.4 Hz, 1H), 4.24 (dt, J=12.3, 2.6 Hz, 2H), 3.44-3.29 (m, 2H), 3.19-3.07 (m, 2H), 2.58 (s, 5H), 2.44 (s, 2H), 2.21-1.95 (m, 4H), 1.20-0.83 (m, 6H).

Example 106: Synthesis of Compound 374 (N,N-diethyl-N'-[1-(6-fluoro-2-methyl-quinolin-4-yl)-piperidin-4-ylmethyl]-ethane-1,2-diamine)

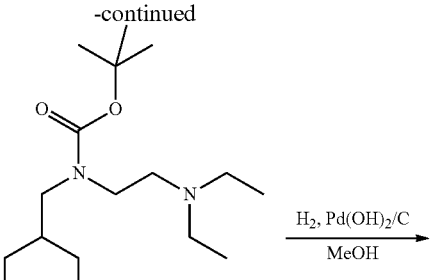

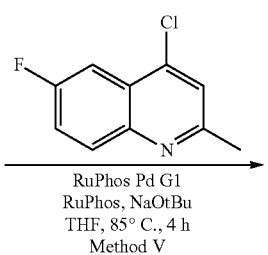

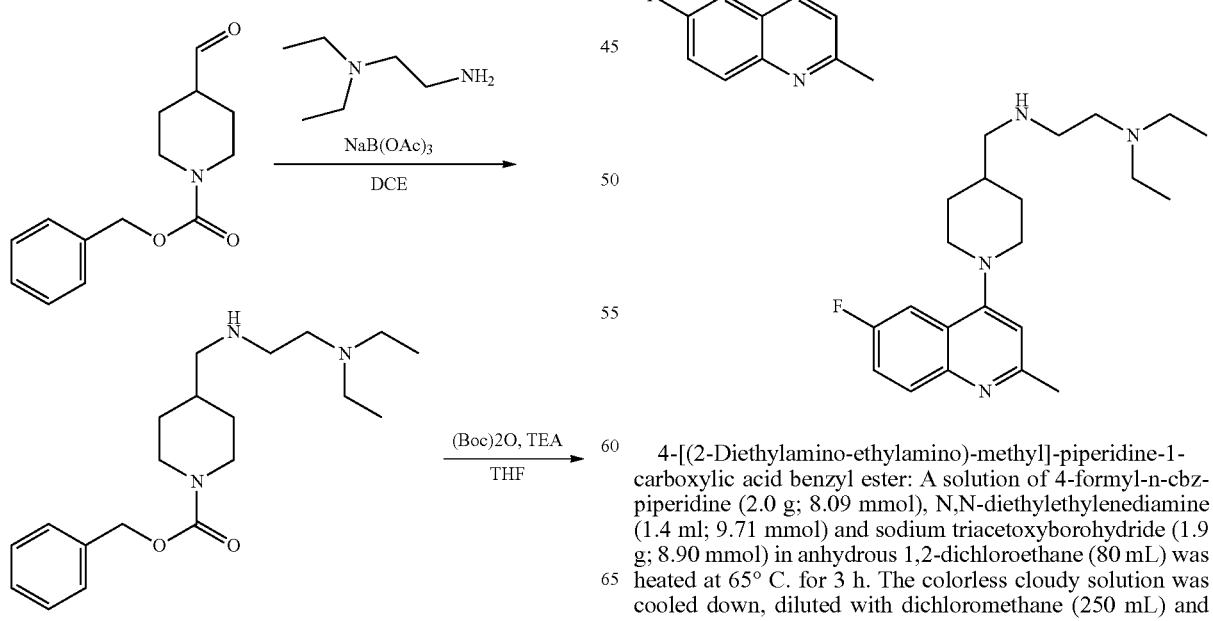

4-[(2-Diethylamino-ethylamino)-methyl]-piperidine-1-carboxylic acid benzyl ester: A solution of 4-formyl-n-cbz-piperidine (2.0 g; 8.09 mmol), N,N-diethylethylenediamine (1.4 ml; 9.71 mmol) and sodium triacetoxyborohydride (1.9 g; 8.90 mmol) in anhydrous 1,2-dichloroethane (80 mL) was heated at 65° C. for 3 h. The colorless cloudy solution was cooled down, diluted with dichloromethane (250 mL) and washed with saturated aqueous sodium carbonate (2×250 mL). The organic phase was dried over sodium sulfate, filtered and concentrated under reduced pressure. The residue was dissolved in DCM and purified by chromatography on a PuriFlash 40 g 30 m, eluting with a gradient of methanol in DCM to afford 4-[(2-Diethylamino-ethyl-amino)-methyl]-piperidine-1-carboxylic acid benzyl ester (1.5 g, 43%). MS: m/z=348 [M+H]$^+$. $^1$H NMR (400 MHz, DMSO-d$_6$, ppm) δ 7.52-7.17 (m, 5H), 5.06 (s, 2H), 3.99 (d, J=13.2 Hz, 2H), 2.77 (s, 2H), 2.48-2.34 (m, 1OH), 1.68 (d, J=12.6 Hz, 2H), 1.62-1.47 (m, 1H), 1.01 (td, J=12.2, 4.2 Hz, 2H), 0.93 (t, J=7.1 Hz, 6H).

4-{[tert-Butoxycarbonyl-(2-diethylamino-ethyl)-amino]-methyl}-piperidine-1-carboxylic acid benzyl ester: A solution of 4-[(2-Diethylamino-ethylamino)-methyl]-piperidine-1-carboxylic acid benzyl ester (1.5 g; 4.32 mmol), triethylamine (1.2 mL; 8.63 mmol) and di-tert-butyl dicarbonate (1.2 ml; 5.18 mmol) in anhydrous THF (15 mL) was stirred overnight at room temperature. The colorless solution was concentrated under reduced pressure, the residue was dissolved in DCM and purified by chromatography on a PuriFlash 40 g 15 m column, eluting with a gradient of methanol in DCM to afford 4-{[tert-butoxycarbonyl-(2-diethylamino-ethyl)-amino]-methyl}-piperidine-1-carboxylic acid benzyl ester (1.57 g; 68%). MS: m/z=448 [M+H]$^+$. $^1$H NMR (400 MHz, DMSO-d$_6$, ppm) δ 7.46-7.21 (m, 5H), 5.06 (s, 2H), 3.99 (d, J=13.1 Hz, 2H), 3.17 (d, J=4.7 Hz, 2H), 3.05 (d, J=7.2 Hz, 2H), 2.77 (s, 2H), 2.45 (q, J=7.0 Hz, 4H), 1.86-1.69 (m, 1H), 1.56 (d, J=13.3 Hz, 2H), 1.38 (s, 9H), 1.03 (td, J=12.3, 4.0 Hz, 2H), 0.94 (t, J=7.2 Hz, 6H).

4-[(2-Diethylamino-ethylamino)-methyl]-piperidine-1-carboxylic acid benzyl ester: A solution of -{[tert-Butoxycarbonyl-(2-diethylamino-ethyl)-amino]-methyl}-piperidine-1-carboxylic acid benzyl ester (1.6 g; 3.46 mmol) in methanol (70 mL) was pumped through a H-Cube flow hydrogenator fitted with a 20 mol % Pd(OH)$_2$/C catalyst cartridge and heated to 50° C. (full hydrogen option, flow rate 1 mL/min). The resulting colorless solution was concentrated under reduced pressure and the colorless oil was dried under vacuo to obtain (2-Diethylamino-ethyl)-piperidin-4-ylmethyl-carbamic acid tert-butyl ester (1.06 g; 98%). MS: m/z=314 [M+H]$^+$. $^1$H NMR (400 MHz, DMSO-d$_6$, ppm) δ 3.34 (s, 1H), 3.12 (t, J=7.4 Hz, 2H), 3.02 (d, J=7.2 Hz, 2H), 2.92 (d, J=12.1 Hz, 2H), 2.48-2.35 (m, 8H), 1.69-1.55 (m, 1H), 1.48 (d, J=12.4 Hz, 2H), 1.38 (s, 9H), 1.01 (td, J=12.0, 3.7 Hz, 2H), 0.94 (t, J=7.1 Hz, 6H).

N,N-diethyl-N'-[1-(6-fluoro-2-methyl-quinolin-4-yl)-piperidin-4-ylmethyl]-ethane-1,2-diamine: N,N-diethyl-N'-[1-(6-fluoro-2-methyl-quinolin-4-yl)-piperidin-4-ylmethyl]-ethane-1,2-diamine was obtained in 43% yield over 2 steps from 4-chloro-6-fluoro-2-methylquinoline and (2-diethylamino-ethyl)-piperidin-4-ylmethyl-carbamic acid tert-butyl ester, using Methods V and Q.

Compound 374: HPLC: >99% purity, RT=1.33 min. MS: m/z=373 [M+H]$^+$. $^1$H NMR (400 MHz, Chloroform-d, ppm) δ 7.96 (dt, J=8.3, 3.2 Hz, 1H), 7.56 (d, J=10.4 Hz, 1H), 7.38 (t, J=8.8 Hz, 1H), 6.77 (s, 1H), 3.57 (d, J=11.8 Hz, 2H), 2.80 (t, J=11.7 Hz, 2H), 2.76-2.69 (m, 2H), 2.70-2.63 (m, 4H), 2.64-2.51 (m, 5H), 1.96 (d, J=12.8 Hz, 2H), 1.80-1.69 (m, 1H), 1.59 (q, J=11.9 Hz, 2H), 1.05 (t, J=6.8 Hz, 5H).

The following compounds were synthesized in an analogous manner:

Compound 375 (N,N-Diethyl-N'-[1-(6-fluoro-quinolin-4-yl)-piperidin-4-ylmethyl]-ethane-1,2-diamine): From 4-chloro-6-fluoroquinoline, 4-formyl-n-cbz-piperidine and N,N-diethylethylenediamine. HPLC: >99% purity, RT=1.23 min. MS: m/z=359 [M+H]$^+$. $^1$H NMR (400 MHz, Chloroform-d, ppm) δ 8.69 (t, J=3.8 Hz, 1H), 8.12-7.98 (m, 1H), 7.61 (dd, J=10.0, 3.3 Hz, 1H), 7.42 (td, J=8.0, 6.8, 3.9 Hz, 1H), 6.87 (t, J=3.8 Hz, 1H), 3.59 (d, J=11.7 Hz, 2H), 2.83 (t, J=12.0 Hz, 2H), 2.72 (q, J=6.2, 5.7 Hz, 2H), 2.65 (d, J=6.1 Hz, 2H), 2.64-2.47 (m, 6H), 1.96 (d, J=12.8 Hz, 2H), 1.79-1.68 (m, 3H), 1.60 (q, J=12.2 Hz, 2H), 1.05 (t, J=7.0 Hz, 6H).

Compound 376 (N,N-Diethyl-N'-[1-(7-trifluoromethyl-quinolin-4-yl)-piperidin-4-ylmethyl]-ethane-1,2-diamine): From 4-chloro-7-(trifluoromethyl)quinolone, 4-formyl-n-cbz-piperidine and N,N-diethylethylenediamine. HPLC: >99% purity, RT=1.65 min. MS: m/z=409 [M+H]$^+$. $^1$H NMR (400 MHz, Chloroform-d, ppm) δ 8.79 (d, J=5.0 Hz, 1H), 8.35 (s, 1H), 8.12 (d, J=8.8 Hz, 1H), 7.64 (dd, J=8.8, 1.9 Hz, 1H), 6.93 (d, J=5.0 Hz, 1H), 3.64 (d, J=12.1 Hz, 2H), 2.88 (td, J=12.1, 2.3 Hz, 2H), 2.73 (t, J=6.2 Hz, 2H), 2.66 (d, J=6.6 Hz, 2H), 2.63-2.40 (m, 6H), 2.05-1.92 (m, 2H), 1.77 (ddt, J=13.9, 6.6, 3.7 Hz, 1H), 1.61 (qd, J=12.1, 3.8 Hz, 2H), 1.05 (t, J=7.1 Hz, 6H).

Compound 377 (N,N-Diethyl-N'-[1-(6-trifluoromethyl-quinolin-4-yl)-piperidin-4-ylmethyl]-ethane-1,2-diamine): From 4-chloro-6-(trifluoromethyl)quinolone, 4-formyl-n-cbz-piperidine and N,N-diethylethylenediamine. HPLC: >99% purity, RT=1.59 min. MS: m/z=409 [M+H]$^+$. $^1$H NMR (400 MHz, Chloroform-d, ppm) δ 8.80 (d, J=5.1 Hz, 1H), 8.32 (s, 1H), 8.14 (d, J=8.8 Hz, 1H), 7.82 (dd, J=8.9, 2.1 Hz, 1H), 6.92 (d, J=5.1 Hz, 1H), 3.64 (d, J=12.3 Hz, 2H), 2.90 (td, J=11.9, 2.0 Hz, 2H), 2.73 (t, J=6.2 Hz, 2H), 2.67 (d, J=6.6 Hz, 2H), 2.60 (t, J=6.0 Hz, 2H), 2.56 (q, J=7.1 Hz, 4H), 1.99 (d, J=10.6 Hz, 2H), 1.77 (ddd, J=12.9, 8.9, 5.3 Hz, 1H), 1.64 (td, J=12.7, 4.0 Hz, 2H), 1.28 (s, 2H), 1.05 (t, J=7.1 Hz, 6H).

Compound 378 ([1-(6-Fluoro-quinolin-4-yl)-piperidin-4-ylmethyl]-(2-piperidin-1-yl-ethyl)-amine): From 4-chloro-6-fluoroquinoline, 4-formyl-n-cbz-piperidine and 1-(2-aminoethyl)piperidine. HPLC: >99% purity, RT=1.59 min. MS: m/z=409 [M+H]$^+$. $^1$H NMR (400 MHz, Chloroform-d, ppm) δ 8.69 (d, J=5.0 Hz, 1H), 8.05 (dd, J=9.2, 5.6 Hz, 1H), 7.61 (dd, J=10.2, 2.9 Hz, 1H), 7.43 (ddd, J=9.2, 8.0, 2.9 Hz, 1H), 6.88 (d, J=4.9 Hz, 1H), 3.59 (d, J=12.4 Hz, 1H), 2.83 (td, J=12.0, 2.3 Hz, 2H), 2.78 (t, J=6.3 Hz, 2H), 2.66 (d, J=6.6 Hz, 2H), 2.51 (t, J=6.3 Hz, 2H), 2.44 (t, J=5.3 Hz, 4H), 2.05 (s, 0H), 1.97 (dd, J=12.3, 2.8 Hz, 2H), 1.77 (ddtd, J=14.1, 10.3, 6.8, 3.6 Hz, 1H), 1.70-1.52 (m, 6H), 1.47 (p, J=5.6, 5.1 Hz, 2H).

Compound 381 ([1-(6-Fluoro-2-methyl-quinolin-4-yl)-piperidin-4-ylmethyl]-(2-piperidin-1-yl-ethyl)-amine): From 4-chloro-6-fluoro-2-methylquinoline, 4-formyl-n-cbz-piperidine and 1-(2-aminoethyl)piperidine. HPLC: >99% purity, RT=1.34 min. MS: m/z=385 [M+H]$^+$. $^1$H NMR (400 MHz, Chloroform-d, ppm) δ 7.94 (dd, J=9.2, 5.5 Hz, 1H), 7.54 (dd, J=10.2, 2.9 Hz, 1H), 7.36 (ddd, J=9.2, 8.0, 2.9 Hz, 1H), 6.75 (s, 1H), 3.55 (d, J=12.3 Hz, 2H), 2.80 (dd, J=12.0, 2.4 Hz, 2H), 2.74 (t, J=6.3 Hz, 2H), 2.65 (s, 3H), 2.63 (d, J=6.7 Hz, 2H), 2.47 (t, J=6.3 Hz, 2H), 2.40 (s, 4H), 1.94 (dd, J=13.2, 3.5 Hz, 2H), 1.79-1.67 (m, 1H), 1.64-1.49 (m, 6H), 1.49-1.34 (m, 2H).

Compound 382 (N,N-Diethyl-N'-[1-(6-methoxy-quinolin-4-yl)-piperidin-4-ylmethyl]-ethane-1,2-diamine): From 4-chloro-6-methoxyquinolined, 4-formyl-n-cbz-piperidine and N,N-diethylethylenediamine. HPLC: >99% purity, RT=1.31 min. MS: n/z=371 [M+H]$^+$. $^1$H NMR (400 MHz, Chloroform-d, ppm) δ 8.60 (d, J=4.9 Hz, 1H), 7.95 (d, J=9.1 Hz, 1H), 7.31 (dd, J=9.1, 2.9 Hz, 1H), 7.27 (d, J=2.8 Hz, 1H), 6.83 (d, J=5.0 Hz, 1H), 3.94 (s, 3H), 3.58 (d, J=11.7 Hz, 2H), 3.29 (s, 2H), 3.25 (d, J=6.8 Hz, 2H), 2.77 (t, J=11.8 Hz, 2H), 2.57 (q, J=7.1 Hz, 6H), 1.86 (d, J=10.9 Hz, 3H), 1.68-1.53 (m, 2H), 1.48 (s, 9H), 1.06 (t, J=7.1 Hz, 6H).

Compound 383 (N,N-Diethyl-N'-[1-(7-fluoro-quinolin-4-yl)-piperidin-4-ylmethyl]-ethane-1,2-diamine: From 4-chloro-7-fluoroquinoline, 4-formyl-n-cbz-piperidine and N,N-diethylethylenediamine. HPLC: 98.7% purity, RT=1.20 min. MS: m/z=359 [M+H]⁺. ¹H NMR (400 MHz, Chloroform-d, ppm) δ 8.68 (d, J=5.0 Hz, 1H), 7.99 (dd, J=9.3, 6.2 Hz, 1H), 7.64 (dd, J=10.2, 2.6 Hz, 1H), 7.23 (ddd, J=9.3, 8.0, 2.6 Hz, 1H), 6.80 (d, J=5.1 Hz, 1H), 3.59 (d, J=12.4 Hz, 2H), 2.84 (td, J=12.1, 2.1 Hz, 2H), 2.70 (t, J=6.1 Hz, 2H), 2.63 (d, J=6.6 Hz, 2H), 2.58 (t, J=6.1 Hz, 2H), 2.54 (q, J=7.1 Hz, 4H), 1.94 (dd, J=12.4, 3.2 Hz, 2H), 1.73 (dtt, J=14.1, 6.8, 3.9 Hz, 1H), 1.57 (qd, J=12.2, 3.8 Hz, 2H), 1.03 (t, J=7.1 Hz, 6H).

Compound 384 (N,N-Diethyl-N'-[1-(6-methyl-quinolin-4-yl)-piperidin-4-ylmethyl]-ethane-1,2-diamine): From 4-chloro-6-methylquinoline, 4-formyl-n-cbz-piperidine and N,N-diethylethylenediamine. HPLC: >99% purity, RT=1.36 min. MS: m/z=355 [M+H]⁺. ¹H NMR (400 MHz, Chloroform-d, ppm) δ 8.64 (d, J=4.9 Hz, 1H), 7.92 (d, J=8.6 Hz, 1H), 7.75 (s, 1H), 7.46 (dd, J=8.6, 2.0 Hz, 1H), 6.80 (d, J=5.0 Hz, 1H), 3.61 (d, J=12.3 Hz, 2H), 2.80 (td, J=12.0, 2.3 Hz, 2H), 2.71 (t, J=6.1 Hz, 2H), 2.64 (d, J=6.6 Hz, 2H), 2.58 (t, J=5.8 Hz, 2H), 2.57-2.49 (m, 7H), 1.94 (dd, J=12.6, 3.3 Hz, 2H), 1.73 (ddp, J=9.8, 6.4, 3.8, 3.3 Hz, 1H), 1.60 (qd, J=12.0, 3.8 Hz, 2H), 1.03 (t, J=7.1 Hz, 6H).

Compound 385 (N,N-Diethyl-N'-[1-(6-fluoro-2,3-dimethyl-quinolin-4-yl)-piperidin-4-ylmethyl]-ethane-1,2-diamine): From 4-chloro-6-fluoro-2,3-dimethylquinoline, 4-formyl-n-cbz-piperidine and N,N-diethylethylenediamine. HPLC: 97.2% purity, RT=1.33 min. MS: n/z=387 [M+H]⁺. ¹H NMR (400 MHz, Chloroform-d, ppm) δ 7.93 (dd, J=9.1, 5.5 Hz, 1H), 7.74 (s, 1H), 7.33 (ddd, J=9.1, 8.0, 2.9 Hz, 1H), 3.33 (s, 2H), 3.17 (d, J=11.8 Hz, 2H), 2.72 (t, J=6.2 Hz, 2H), 2.68-2.61 (m, 5H), 2.60 (d, J=5.8 Hz, 2H), 2.55 (q, J=7.1 Hz, 4H), 2.37 (s, 3H), 1.86 (d, J=12.1 Hz, 2H), 1.73 (s, 1H), 1.51 (q, J=11.7 Hz, 2H), 1.03 (t, J=7.1 Hz, 6H).

Compound 386 (N,N-Diethyl-N'-[1-(7-fluoro-2-methyl-quinolin-4-yl)-piperidin-4-ylmethyl]-ethane-1,2-diamine): From 4-chloro-7-fluoro-2-methylquinoline, 4-formyl-n-cbz-piperidine and N,N-diethylethylenediamine. HPLC: >99% purity, RT=1.13 min. MS: m/z=373 [M+H]⁺. ¹H NMR (400 MHz, Chloroform-d, ppm) δ 7.92 (dd, J=9.2, 6.2 Hz, 1H), 7.56 (dd, J=10.4, 2.6 Hz, 1H), 7.17 (ddd, J=9.2, 8.0, 2.6 Hz, 1H), 6.69 (s, 1H), 3.57 (d, J=12.3 Hz, 2H), 2.81 (td, J=12.1, 2.3 Hz, 2H), 2.70 (t, J=6.1 Hz, 2H), 2.64 (s, 3H), 2.63 (d, J=6.6 Hz, 2H), 2.58 (t, J=6.0 Hz, 2H), 2.53 (q, J=7.1 Hz, 4H), 1.93 (dd, J=12.6, 2.4 Hz, 2H), 1.73 (dtd, J=13.9, 7.5, 6.7, 3.6 Hz, 1H), 1.56 (qd, J=12.1, 3.8 Hz, 2H), 1.03 (t, J=7.1 Hz, 6H).

Compound 387 ((2-Piperidin-1-yl-ethyl)-[1-(6-trifluoromethyl-quinolin-4-yl)-piperidin-4-ylmethyl]-amine): From 4-chloro-6-(trifluoromethyl)quinolone, 4-formyl-n-cbz-piperidine and 1-(2-aminoethyl)piperidine. HPLC: 89.3% purity, RT=1.57 min. MS: m/z=421 [M+H]⁺. ¹H NMR (400 MHz, Chloroform-d, ppm) δ 8.78 (d, J=5.1 Hz, 1H), 8.29 (s, 1H), 8.12 (d, J=8.8 Hz, 1H), 7.80 (dd, J=8.8, 2.1 Hz, 1H), 6.90 (d, J=5.1 Hz, 1H), 3.62 (d, J=12.6 Hz, 2H), 2.88 (td, J=12.2, 2.4 Hz, 2H), 2.74 (t, J=6.3 Hz, 2H), 2.65 (d, J=6.7 Hz, 2H), 2.47 (t, J=6.3 Hz, 2H), 2.39 (s, 4H), 1.97 (dd, J=12.7, 3.2 Hz, 2H), 1.76 (dt, J=11.4, 3.0 Hz, 1H), 1.67-1.50 (m, 6H), 1.44 (td, J=6.2, 3.3 Hz, 2H).

Compound 389 (N,N-Diethyl-N'-[1-(7-methyl-quinolin-4-yl)-piperidin-4-ylmethyl]-ethane-1,2-diamine): From 4-chloro-7-methylquinoline, 4-formyl-n-cbz-piperidine and N,N-diethylethylenediamine. HPLC: 96.5% purity, RT=1.29 min. MS: m/z=355 [M+H]⁺. ¹H NMR (400 MHz, Chloroform-d, ppm) δ 8.65 (d, J=5.0 Hz, 1H), 7.88 (d, J=8.5 Hz, 1H), 7.80 (s, 1H), 7.29 (dd, J=8.6, 1.8 Hz, 1H), 6.77 (d, J=5.0 Hz, 1H), 3.62 (d, J=12.4 Hz, 2H), 2.81 (td, J=12.1, 2.3 Hz, 2H), 2.70 (t, J=6.1 Hz, 2H), 2.63 (d, J=6.6 Hz, 2H), 2.62-2.44 (m, 9H), 1.93 (dd, J=12.6, 2.3 Hz, 2H), 1.73 (ddq, J=13.9, 6.7, 3.6 Hz, 1H), 1.58 (qd, J=12.0, 3.8 Hz, 2H), 1.03 (t, J=7.1 Hz, 6H).

Compound 401 (5-{4-[(2-Diethylamino-ethylamino)-methyl]-piperidin-1-yl}-quinoline-8-carbonitrile): From 5-bromo-quinoline-8-carbonitrile, 4-formyl-n-cbz-piperidine and N,N-diethylethylenediamine. HPLC: >99% purity, RT=1.67 min. MS: m/z=366 [M+H]⁺. ¹H NMR (400 MHz, Chloroform-d, ppm) δ 9.04 (dd, J=4.2, 1.7 Hz, 1H), 8.43 (dd, J=8.6, 1.7 Hz, 1H), 8.00 (d, J=8.0 Hz, 1H), 7.47 (dd, J=8.6, 4.2 Hz, 1H), 7.05 (d, J=8.0 Hz, 1H), 3.50 (d, J=11.9 Hz, 2H), 2.87 (td, J=12.0, 2.3 Hz, 2H), 2.71 (t, J=6.1 Hz, 2H), 2.64 (d, J=6.6 Hz, 2H), 2.62-2.46 (m, 6H), 1.96 (tt, J=12.4, 2.1 Hz, 3H), 1.73 (dtt, J=14.0, 6.7, 3.7 Hz, 1H), 1.58 (qd, J=12.0, 3.8 Hz, 2H), 1.03 (t, J=7.1 Hz, 5H).

Example 107: Synthesis of Compound 393 (cis-5-(2,6-Dimethyl-morpholin-4-yl)-quinazoline-8-carbonitrile)

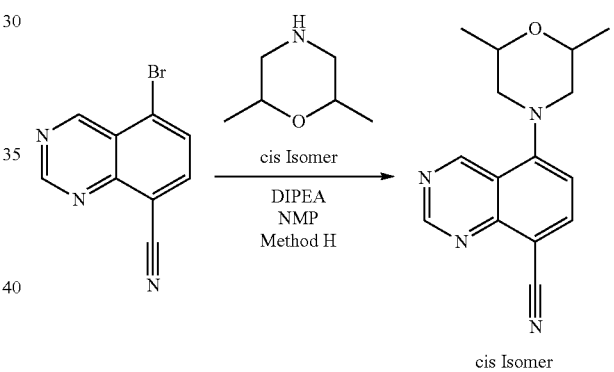

cis Isomer

Cis-5-(2,6-Dimethyl-morpholin-4-yl)-quinazoline-8-carbonitrile: cis-5-(2,6-Dimethyl-morpholin-4-yl)-quinazoline-8-carbonitrile was obtained from 5-Bromo-quinazoline-8-carbonitrile and cis-2,6-dimethylmorpholine in 79% yield, using method H.

Compound 393: HPLC: >99% purity, RT=2.70 min. MS: m/z=269 [M+H]⁺. ¹H NMR (400 MHz, Chloroform-d, ppm) δ 9.61 (s, 1H), 9.43 (s, 1H), 8.16 (d, J=8.2 Hz, 1H), 7.07 (d, J=8.2 Hz, 1H), 4.03 (dqd, J=10.2, 6.3, 2.1 Hz, 2H), 3.41 (dt, J=11.8, 1.8 Hz, 2H), 2.77 (dd, J=12.2, 10.3 Hz, 2H), 1.28 (d, J=6.3 Hz, 6H).

The following compounds were synthesized in an analogous manner:

Compound 455 (cis-5-(2,6-Dimethyl-morpholin-4-yl)-8-fluoro-pyrido[3,4-b]pyrazine): From 5-chloro-8-fluoro-pyrido[3,4-b]pyrazine and cis-2,6-dimethylmorpholine. HPLC: >99% purity, RT=2.38 min. MS: m/z=263 [M+H]⁺. ¹H NMR (400 MHz, Chloroform-d, ppm) δ 8.96 (d, J=1.9 Hz, 1H), 8.80 (d, J=1.8 Hz, 1H), 8.23 (d, J=1.3 Hz, 1H), 4.72-4.56 (m, 2H), 3.91 (dqd, J=10.4, 6.2, 2.2 Hz, 2H), 2.81 (dd, J=12.9, 10.4 Hz, 2H), 1.27 (d, J=6.3 Hz, 6H).

Example 108: Synthesis of Compound 395 (N-[1-(8-Cyano-quinazolin-5-yl)-piperidin-4-ylmethyl]-2-diethylamino-acetamide)

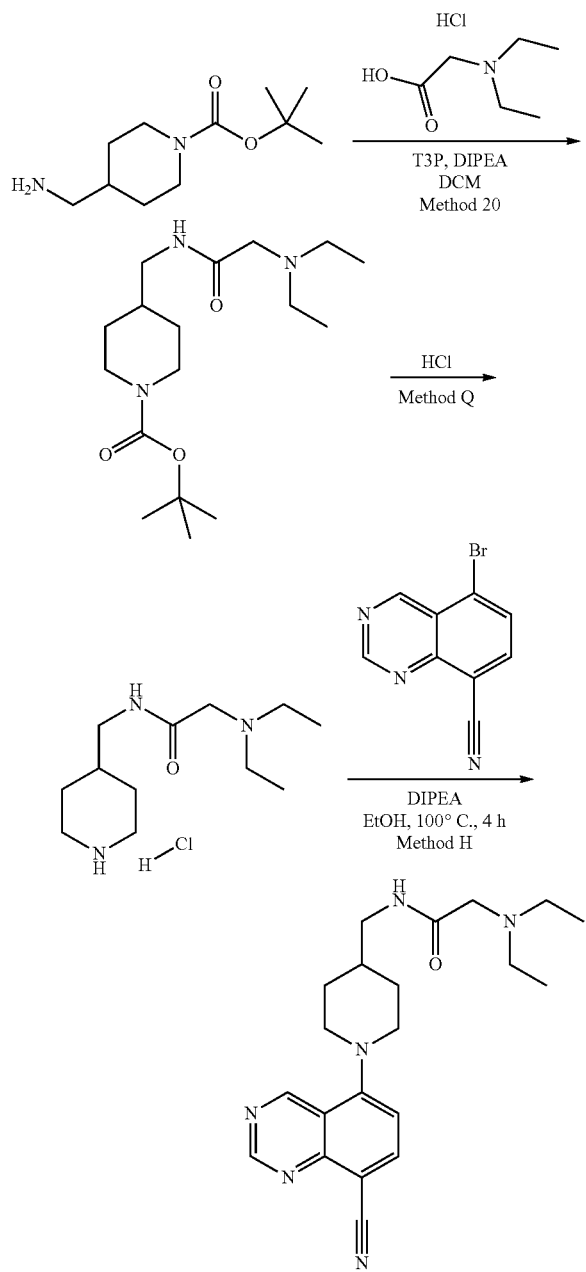

N-[1-(8-Cyano-quinazolin-5-yl)-piperidin-4-ylmethyl]-2-diethylamino-acetamide): N-[1-(8-Cyano-quinazolin-5-yl)-piperidin-4-ylmethyl]-2-diethylamino-acetamide) was obtained from 5-Bromo-quinazoline-8-carbonitrile, 2-(diethylamino)acetic acid hydrochloride and 1-boc-4-(aminomethyl)piperidine in 40% yield over 3 steps, using method 20, Q and H.

Compound 395: HPLC: >99% purity, RT=1.88 min. MS: n/z=381 [M+H]+. 1H NMR (400 MHz, Chloroform-d, ppm) δ 9.54 (s, 1H), 9.39 (s, 1H), 8.12 (d, J=8.2 Hz, 1H), 7.62 (t, J=5.9 Hz, 1H), 7.05 (d, J=8.2 Hz, 1H), 3.65 (dt, J=13.0, 2.8 Hz, 2H), 3.31 (t, J=6.5 Hz, 2H), 3.06 (s, 2H), 3.01 (td, J=12.2, 2.4 Hz, 2H), 2.58 (q, J=7.1 Hz, 4H), 1.93 (dd, J=13.3, 3.1 Hz, 2H), 1.84 (dtt, J=14.4, 6.9, 4.0 Hz, 1H), 1.62 (qd, J=12.4, 3.9 Hz, 2H), 1.05 (t, J=7.1 Hz, 6H).

The following compounds were synthesized in an analogous manner:

Compound 397 (1-(8-Cyano-quinazolin-5-yl)-piperidine-4-carboxylic acid (2-diethylamino-ethyl)-amide): From 5-Bromo-quinazoline-8-carbonitrile, 1-tert-butoxycarbonylpiperidine-4-carboxylic acid and N,N-diethylethylenediamine. HPLC: >99% purity, RT=1.75 min. MS: m/z=381 [M+H]+. 1H NMR (400 MHz, Chloroform-d, ppm) δ 9.58 (s, 1H), 9.41 (s, 1H), 8.13 (d, J=8.2 Hz, 1H), 7.06 (d, J=8.2 Hz, 1H), 6.28 (s, 1H), 3.69 (dt, J=12.1, 2.4 Hz, 2H), 3.34 (q, J=5.1 Hz, 2H), 3.06 (ddd, J=12.3, 10.3, 3.8 Hz, 2H), 2.63-2.47 (m, 6H), 2.39 (tt, J=10.2, 5.1 Hz, 1H), 2.19-2.03 (m, 4H), 1.03 (t, J=7.1 Hz, 6H).

Compound 398 (N-[1-(8-Cyano-quinolin-5-yl)-piperidin-4-ylmethyl]-2-diethylamino-acetamide): From 5-bromo-quinoline-8-carbonitrile, 2-(diethylamino)acetic acid hydrochloride and 2-(diethylamino)acetic acid hydrochloride. HPLC: 98.8% purity, RT=2.13 min. MS: m/z=380 [M+H]+. 1H NMR (400 MHz, Chloroform-d, ppm) δ 9.05 (dd, J=4.2, 1.7 Hz, 1H), 8.41 (dd, J=8.5, 1.7 Hz, 1H), 8.01 (d, J=8.0 Hz, 1H), 7.60 (s, 1H), 7.47 (dd, J=8.5, 4.2 Hz, 1H), 7.04 (d, J=8.0 Hz, 1H), 3.50 (d, J=11.9 Hz, 2H), 3.32 (t, J=6.5 Hz, 2H), 3.07 (s, 2H), 2.86 (td, J=12.0, 2.2 Hz, 2H), 2.59 (q, J=7.1 Hz, 4H), 1.90 (d, J=12.6 Hz, 2H), 1.78 (dtt, J=14.4, 6.8, 3.6 Hz, 1H), 1.62 (qd, J=12.1, 3.8 Hz, 2H), 1.06 (t, J=7.1 Hz, 6H).

Compound 403 (1-(8-Cyano-quinolin-5-yl)-piperidine-4-carboxylic acid (2-piperidin-1-yl-ethyl)-amide): From 5-bromo-quinoline-8-carbonitrile, 1-tert-butoxycarbonylpiperidine-4-carboxylic acid and 1-(2-aminoethyl)piperidine. HPLC: 96.7% purity, RT=2.07 min. MS: m/z=392 [M+H]+. 1H NMR (400 MHz, Chloroform-d, ppm) δ 9.06 (dd, J=4.2, 1.7 Hz, 1H), 8.45 (dd, J=8.6, 1.7 Hz, 1H), 8.02 (d, J=8.0 Hz, 1H), 7.49 (dd, J=8.5, 4.2 Hz, 1H), 7.06 (d, J=8.0 Hz, 1H), 6.22 (s, 1H), 3.54 (d, J=12.3 Hz, 2H), 3.37 (q, J=5.6 Hz, 2H), 2.91 (td, J=11.9, 2.8 Hz, 2H), 2.76-2.23 (m, 7H), 2.13 (qd, J=12.2, 11.3, 3.8 Hz, 2H), 2.08-1.94 (m, 2H), 1.73-1.52 (m, 4H), 1.53-1.36 (m, 2H).

Compound 407 (1-(8-Cyano-quinolin-5-yl)-piperidine-4-carboxylic acid (2-diethylamino-ethyl)-amide: From 5-bromo-quinoline-8-carbonitrile, 1-tert-butoxycarbonylpiperidine-4-carboxylic acid and N,N-diethylethylenediamine. HPLC: 98.2% purity, RT=2.01 min. MS: m/z=380 [M+H]+. 1H NMR (400 MHz, Chloroform-d, ppm) δ 9.05 (dd, J=4.2, 1.7 Hz, 1H), 8.44 (dd, J=8.5, 1.7 Hz, 1H), 8.01 (d, J=8.0 Hz, 1H), 7.49 (dd, J=8.6, 4.2 Hz, 1H), 7.05 (d, J=8.0 Hz, 1H), 6.25 (s, 1H), 3.53 (d, J=12.6 Hz, 2H), 3.34 (q, J=5.5 Hz, 2H), 2.90 (td, J=11.8, 2.8 Hz, 2H), 2.69-2.44 (m, 6H), 2.35 (tt, J=11.1, 4.3 Hz, 1H), 2.22-1.92 (m, 4H), 1.03 (t, J=7.1 Hz, 6H).

Example 109: Synthesis of Compound 404 (2-(3-Methoxy-phenylamino)-N-(1-pyrido[2,3-b]pyrazin-8-yl-piperidin-4-ylmethyl)-acetamide)

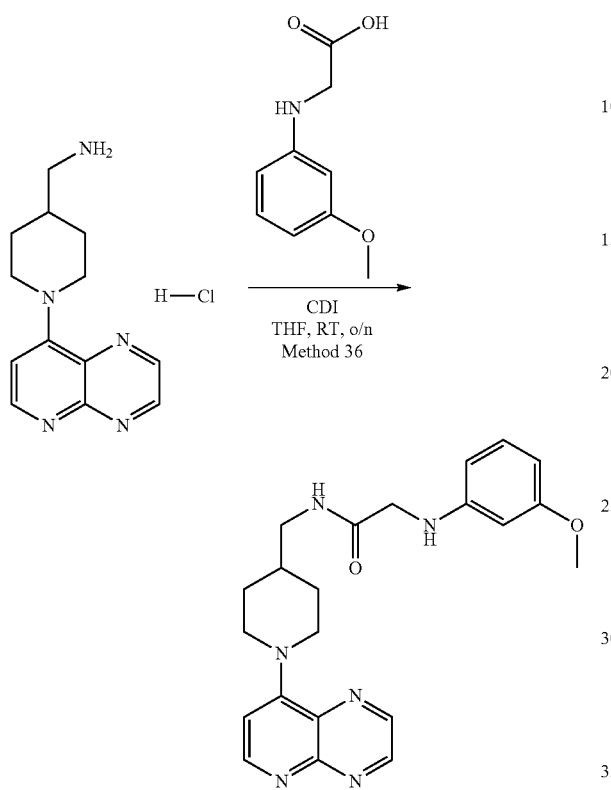

Method 36

2-(3-Methoxy-phenylamino)-N-(1-pyrido[2,3-b]pyrazin-8-yl-piperidin-4-ylmethyl)-acetamide: A solution of 2-[(3-methoxyphenyl)amino] acetic acid (77.7 mg; 0.429 mmol) and 1,1'-carbonyldiimidazole (69.6 mg; 0.429 mmol) in anhydrous THF (2.0 ml) was stirred at room temperature for 15 min before C-(1-Pyrido[2,3-b]pyrazin-8-yl-piperidin-4-yl)-methylamine hydrochloride (80.0 mg; 0.286 mmol) was added. The reaction mixture was stirred at room temperature overnight, then concentrated under reduced pressure. The residue was dissolved in DCM and purified by chromatography on a PuriFlash $NH_2$ 35 g 30 m column, eluting with a gradient of methanol in DCM to afford 2-(3-Methoxy-phenylamino)-N-(1-pyrido[2,3-b]pyrazin-8-yl-piperidin-4-ylmethyl)-acetamide (63 mg; 54.2%).

(Note: In Method 36, the solvent may also be DMF instead of THF)

Compound 404: HPLC: >99% purity, RT=1.93 min. MS: n/z=407 [M+H]$^+$. $^1$H NMR (400 MHz, Chloroform-d, ppm) δ 8.95 (d, J=1.7 Hz, 1H), 8.79 (d, J=5.4 Hz, 1H), 8.71 (d, J=1.7 Hz, 1H), 7.11 (t, J=8.1 Hz, 1H), 6.87 (s, 1H), 6.85 (d, J=5.5 Hz, 1H), 6.37 (ddd, J=8.2, 2.3, 0.8 Hz, 1H), 6.24 (ddd, J=8.1, 2.3, 0.9 Hz, 1H), 6.18 (t, J=2.3 Hz, 1H), 4.40 (d, J=12.4 Hz, 2H), 3.82 (s, 2H), 3.76 (s, 3H), 3.27 (t, J=6.4 Hz, 2H), 3.02 (td, J=12.4, 2.4 Hz, 2H), 1.95-1.73 (m, 3H), 1.51 (qd, J=12.0, 3.9 Hz, 2H).

The following compounds were synthesized in an analogous manner:

Compound 406 (2-tert-Butylamino-N-(1-pyrido[2,3-b]pyrazin-8-yl-piperidin-4-ylmethyl)-acetamide): From C-(1-Pyrido[2,3-b]pyrazin-8-yl-piperidin-4-yl)-methylamine hydrochloride and 2-(tert-butylamino)acetic acid hydrochloride. HPLC: 98.1% purity, RT=1.11 min. MS: m/z=357 [M+H]$^+$. $^1$H NMR (400 MHz, Chloroform-d, ppm) δ 8.95 (d, J=1.7 Hz, 1H), 8.79 (d, J=5.4 Hz, 1H), 8.72 (d, J=1.7 Hz, 1H), 7.67 (s, 1H), 6.87 (d, J=5.4 Hz, 1H), 4.44 (d, J=12.1 Hz, 2H), 3.33-3.19 (m, 4H), 3.07 (td, J=12.5, 2.3 Hz, 2H), 1.90-1.84 (m, 2H), 1.73-1.64 (m, 1H), 1.57 (qd, J=12.3, 11.8, 3.8 Hz, 2H), 1.09 (s, 8H).

Compound 413 (2-tert-Butylamino-N-[1-(8-cyano-quinolin-5-yl)-piperidin-4-ylmethyl]-acetamide): From 5-bromo-quinoline-8-carbonitrile, 4-(boc-aminomethyl)piperidine and 2-(tert-butylamino)acetic acid hydrochloride. HPLC: 97.7% purity, RT=2.19 min. MS: m/z=380 [M+H]$^+$. $^1$H NMR (400 MHz, Chloroform-d, ppm) δ 9.05 (dd, J=4.2, 1.7 Hz, 1H), 8.41 (dd, J=8.6, 1.7 Hz, 1H), 8.00 (d, J=8.0 Hz, 1H), 7.73 (s, 1H), 7.47 (dd, J=8.5, 4.2 Hz, 1H), 7.04 (d, J=8.0 Hz, 1H), 3.50 (d, J=12.3 Hz, 3H), 3.32 (t, J=6.5 Hz, 2H), 3.29 (s, 2H), 2.85 (td, J=12.0, 2.3 Hz, 2H), 1.91 (d, J=12.0 Hz, 2H), 1.78 (dddd, J=17.6, 10.3, 6.8, 3.1 Hz, 1H), 1.62 (qd, J=12.0, 3.8 Hz, 2H), 1.12 (s, 9H).

Example 110: Synthesis of Compound 425 (N-[1-(8-Cyano-quinolin-5-yl)-5,5-difluoro-piperidin-3-yl]-2-dimethylamino-acetamide)

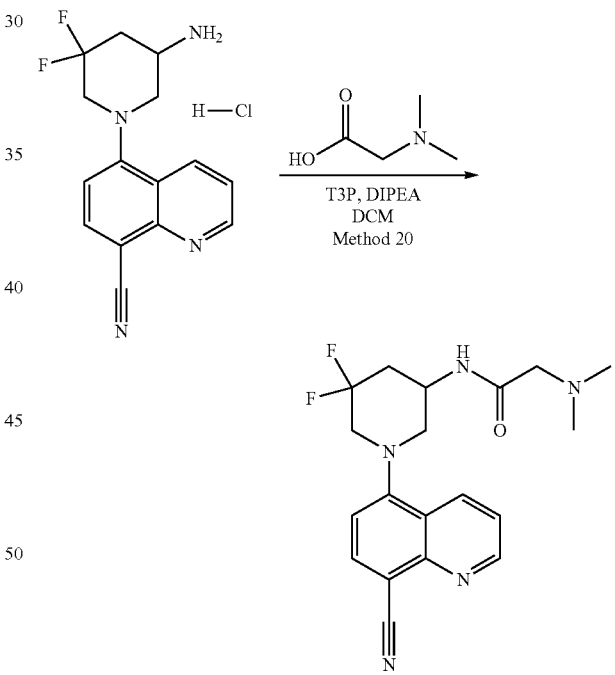

N-[1-(8-Cyano-quinolin-5-yl)-5,5-difluoro-piperidin-3-yl]-2-dimethylamino-acetamide: N-[1-(8-Cyano-quinolin-5-yl)-5,5-difluoro-piperidin-3-yl]-2-dimethylamino-acetamide was obtained from 5-(5-Amino-3,3-difluoro-piperidin-1-yl)-quinoline-8-carbonitrile hydrochloride and N,N-dimethylglycine in 39% yield, using method 20.

Compound 425: HPLC: 96.6% purity, RT=2.16 min. MS: m/z=374 [M+H]$^+$. $^1$H NMR (400 MHz, Chloroform-d, ppm) δ 9.11 (dd, J=4.2, 1.7 Hz, 1H), 8.65 (dd, J=8.6, 1.7 Hz, 1H), 8.06 (d, J=7.9 Hz, 1H), 7.87 (s, 1H), 7.57 (dd, J=8.6, 4.2 Hz, 1H), 7.14 (d, J=8.0 Hz, 1H), 4.63 (s, 1H), 3.51 (q, J=10.7, 10.3 Hz, 1H), 3.41 (q, J=12.4 Hz, 1H), 3.37-3.16 (m, 2H), 3.06-2.84 (m, 2H), 2.45-2.31 (m, 1H), 2.28 (s, 6H), 1.56 (s, 1H).

Example 111: Synthesis of Compound 436 (1-(8-Trifluoromethyl-quinolin-5-yl)-piperidine-4-carboxylicacid[2-(ethyl-methyl-amino)-ethyl]-amide)

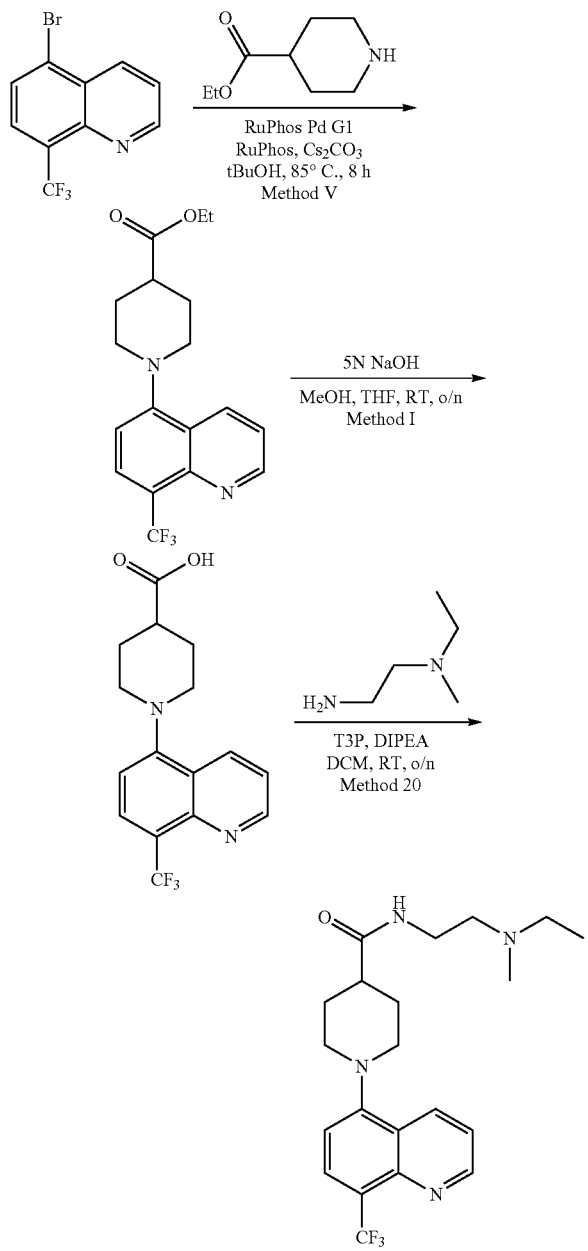

1-(8-Trifluoromethyl-quinolin-5-yl)-piperidine-4-carboxylic acid [2-(ethyl-methyl-amino)-ethyl]-amide: From 1-(8-Trifluoromethyl-quinolin-5-yl)-piperidine-4-carboxylic acid [2-(ethyl-methyl-amino)-ethyl]-amide was obtained from 5-bromo-8-(trifluoromethyl)quinolone, ethyl piperidine-4-carboxylate and (2-aminoethyl)(ethyl)methylamine in 48% yield over 3 steps, using method V, I and 20.

Compound 436: HPLC: 98.3% purity, RT=2.55 min. MS: m/z=409 [M+H]+. 1H NMR (400 MHz, Chloroform-d, ppm) δ 9.04 (dd, J=4.2, 1.8 Hz, 1H), 8.50 (dd, J=8.6, 1.8 Hz, 1H), 7.97 (d, J=8.0 Hz, 1H), 7.47 (dd, J=8.6, 4.2 Hz, 1H), 7.06 (d, J=8.0 Hz, 1H), 6.25 (s, 1H), 3.47 (dt, J=12.6, 3.5 Hz, 2H), 3.40 (d, J=6.2 Hz, 2H), 2.86 (td, J=11.9, 2.7 Hz, 2H), 2.53 (s, 4H), 2.42-2.20 (m, 4H), 2.13 (qd, J=12.1, 11.3, 3.8 Hz, 2H), 2.04 (dd, J=12.8, 3.6 Hz, 2H), 1.10 (t, J=5.9 Hz, 3H).

The following compounds were synthesized in an analogous manner:

Compound 441 (1-(8-Trifluoromethyl-quinolin-5-yl)-piperidine-4-carboxylic acid (2-piperidin-1-yl-ethyl)-amide): From 5-bromo-8-(trifluoromethyl)quinolone, ethyl piperidine-4-carboxylate and 1-(2-aminoethyl)piperidine. HPLC: 98.0% purity, RT=2.63 min. MS: m/z=435 [M+H]. 1H NMR (400 MHz, Chloroform-d, ppm) δ 9.03 (dd, J=4.2, 1.8 Hz, 1H), 8.50 (dd, J=8.6, 1.8 Hz, 1H), 7.96 (d, J=8.0 Hz, 1H), 7.47 (dd, J=8.6, 4.2 Hz, 1H), 7.06 (d, J=8.0 Hz, 1H), 6.24 (s, 1H), 3.47 (dt, J=11.9, 2.6 Hz, 2H), 3.37 (td, J=6.1, 4.8 Hz, 2H), 2.86 (td, J=11.8, 2.7 Hz, 2H), 2.47 (t, J=6.0 Hz, 2H), 2.44-2.27 (m, 5H), 2.13 (qd, J=12.1, 11.3, 3.8 Hz, 2H), 2.08-1.96 (m, 2H), 1.59 (p, J=5.6 Hz, 4H), 1.52-1.38 (m, 2H).

Compound 442 (1-(8-Trifluoromethyl-quinolin-5-yl)-piperidine-4-carboxylic acid (1-methyl-pyrrolidin-2-ylmethyl)-amide): From 5-bromo-8-(trifluoromethyl)quinolone, ethyl piperidine-4-carboxylate and (1-methylpyrrolidin-2-yl)methanamine. HPLC: 98.7% purity, RT=2.55 min. MS: m/z=421 [M+H]+. 1H NMR (400 MHz, Chloroform-d, ppm) δ 9.04 (dd, J=4.2, 1.8 Hz, 1H), 8.50 (dd, J=8.6, 1.8 Hz, 1H), 7.97 (d, J=8.0 Hz, 1H), 7.47 (dd, J=8.6, 4.2 Hz, 1H), 7.06 (d, J=7.9 Hz, 1H), 6.12 (d, J=7.8 Hz, 1H), 3.66 (ddd, J=13.7, 7.9, 2.5 Hz, 1H), 3.47 (dt, J=12.1, 3.3 Hz, 2H), 3.13 (ddd, J=13.7, 4.1, 2.4 Hz, 1H), 3.07 (ddd, J=9.3, 6.8, 2.5 Hz, 1H), 2.86 (tt, J=11.8, 3.2 Hz, 2H), 2.46-2.38 (m, 1H), 2.33 (s, 3H), 2.24 (td, J=9.4, 7.5 Hz, 1H), 2.14 (qt, J=11.3, 3.3 Hz, 2H), 2.03 (dd, J=13.5, 3.6 Hz, 2H), 1.96-1.83 (m, 1H), 1.80-1.65 (m, 2H), 1.60-1.47 (m, 2H).

Compound 446 (1-(8-Trifluoromethyl-quinolin-5-yl)-piperidine-4-carboxylic acid (2-diethylamino-ethyl)-amide): From 5-bromo-8-(trifluoromethyl)quinolone, ethyl piperidine-4-carboxylate and n,n-diethylethylenediamine. HPLC: >99% purity, RT=2.63 min. MS: m/z=423 [M+H]+. 1H NMR (400 MHz, Chloroform-d, ppm) δ 9.04 (dd, J=4.2, 1.8 Hz, 1H), 8.49 (dd, J=8.6, 1.8 Hz, 1H), 7.97 (d, J=8.1 Hz, 1H), 7.47 (dd, J=8.6, 4.2 Hz, 1H), 7.06 (d, J=8.0 Hz, 1H), 6.25 (s, 1H), 3.47 (dt, J=11.8, 2.8 Hz, 2H), 3.34 (q, J=5.3 Hz, 2H), 2.86 (td, J=11.8, 2.8 Hz, 2H), 2.63-2.49 (m, 6H), 2.34 (tt, J=11.2, 4.3 Hz, 1H), 2.12 (qd, J=12.2, 11.2, 3.8 Hz, 2H), 2.07-1.97 (m, 2H), 1.04 (t, J=7.1 Hz, 6H).

Example 112: Synthesis of Compound 443 (2-Diethylamino-N-[1-(8-trifluoromethyl-quinolin-5-yl)-piperidin-4-ylmethyl]-acetamide)

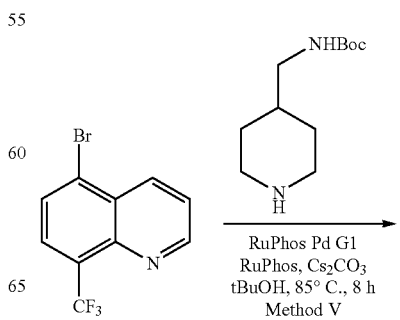

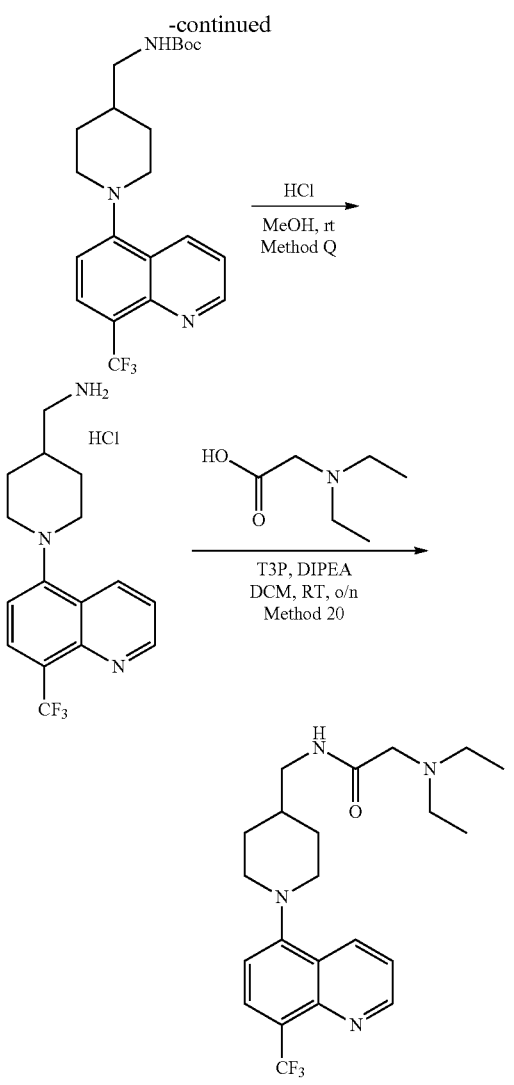

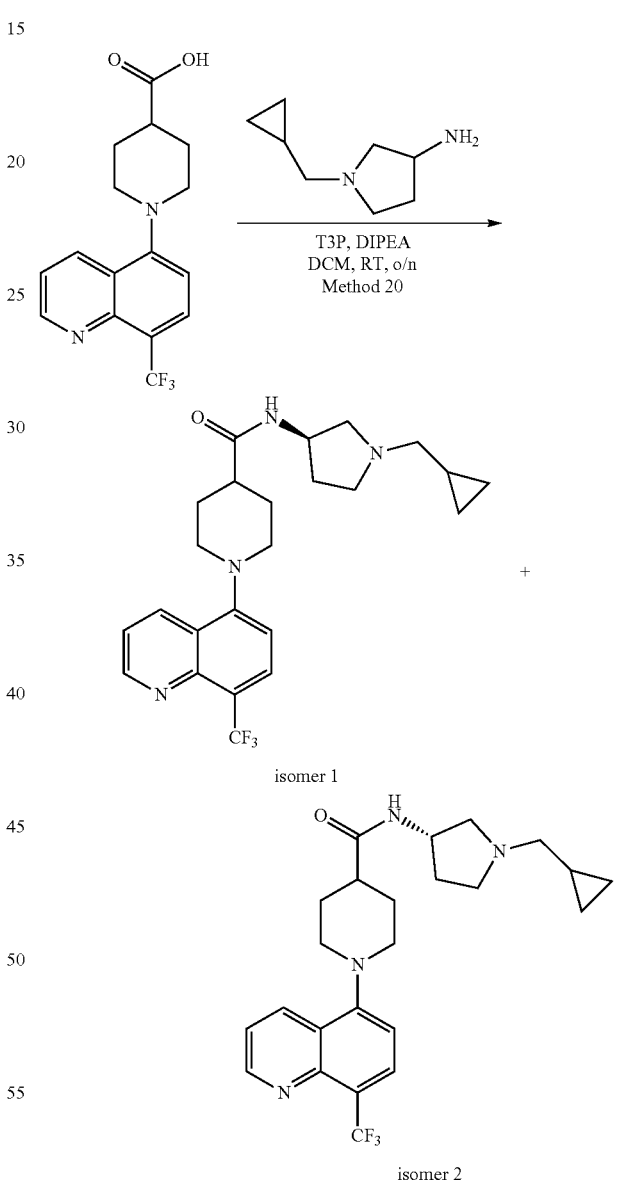

isomer 1 isomer 2

1H), 7.45 (dd, J=8.6, 4.2 Hz, 2H), 7.05 (d, J=8.0 Hz, 1H), 3.44 (dt, J=11.7, 2.4 Hz, 2H), 3.33 (t, J=6.5 Hz, 2H), 2.99 (s, 2H), 2.82 (td, J=11.9, 2.3 Hz, 2H), 2.49 (t, J=5.3 Hz, 4H), 1.89 (dd, J=12.3, 2.6 Hz, 2H), 1.77 (tdd, J=10.0, 8.6, 5.0 Hz, 1H), 1.70-1.54 (m, 6H), 1.54-1.42 (m, 2H).

Example 113: Synthesis of Compound 444 and compound 445 (1-(8-Trifluoromethyl-quinolin-5-yl)-piperidine-4-carboxylic acid ((R)-1-cyclopropyl-methyl-pyrrolidin-3-yl)-amide and 1-(8-Trifluoromethyl-quinolin-5-yl)-piperidine-4-carboxylic acid ((S)-1-cyclopropylmethyl-pyrrolidin-3-yl)-amide)

2-Diethylamino-N-[1-(8-trifluoromethyl-quinolin-5-yl)-piperidin-4-ylmethyl]-acetamide: 2-Diethylamino-N-[1-(8-trifluoromethyl-quinolin-5-yl)-piperidin-4-ylmethyl]-acetamide was obtained from 5-Bromo-8-trifluoromethyl-quinoline, 4-(boc-aminomethyl)piperidine and 2-(diethylamino)acetic acid hydrochloride in 55% yield over 3 steps, using method V, Q and 20.

Compound 443: HPLC: >99% purity, RT=2.76 min. MS: m/z=423 [M+H]+. 1H NMR (400 MHz, Chloroform-d, ppm) δ 9.02 (dd, J=4.2, 1.8 Hz, 1H), 8.45 (dd, J=8.6, 1.8 Hz, 1H), 7.95 (d, J=8.1 Hz, 1H), 7.60 (s, 1H), 7.44 (dd, J=8.6, 4.2 Hz, 1H), 7.04 (d, J=8.0 Hz, 1H), 3.43 (dt, J=12.7, 2.9 Hz, 2H), 3.32 (t, J=6.5 Hz, 2H), 3.06 (s, 2H), 2.81 (td, J=11.9, 2.3 Hz, 2H), 2.58 (q, J=7.2 Hz, 4H), 1.89 (dd, J=12.8, 3.0 Hz, 2H), 1.77 (ddtd, J=13.6, 10.0, 6.6, 3.6 Hz, 1H), 1.62 (qd, J=11.9, 3.8 Hz, 2H), 1.05 (t, J=7.2 Hz, 6H).

The following compounds were synthesized in an analogous manner:

Compound 448 (2-Piperidin-1-yl-N-[1-(8-trifluoromethyl-quinolin-5-yl)-piperidin-4-ylmethyl]-acetamide): From 5-Bromo-8-trifluoromethyl-quinoline, 4-(boc-aminomethyl)piperidine and piperidin-1-yl-acetic acid. HPLC: 97.6% purity, RT=2.79 min. MS: m/z=435 [M+H]+. 1H NMR (400 MHz, Chloroform-d, ppm) δ 9.03 (dd, J=4.2, 1.8 Hz, 1H), 8.46 (dd, J=8.6, 1.8 Hz, 1H), 7.96 (d, J=8.0 Hz, 1-(8-Trifluoromethyl-quinolin-5-yl)-piperidine-4-carboxylic acid ((R)-1-cyclopropylmethyl-pyrrolidin-3-yl)-amide and 1-(8-Trifluoromethyl-quinolin-5-yl)-piperidine-4-carboxylic acid ((S)-1-cyclopropylmethyl-pyrrolidin-3-yl)-amide: 1-(8-Trifluoromethyl-quinolin-5-yl)-piperidine-4-carboxylic acid ((R)-1-cyclopropylmethyl-pyrrolidin-3-yl)-amide and 1-(8-Trifluoromethyl-quinolin-5-yl)-piperidine- 4-carboxylic acid ((S)-1-cyclopropylmethyl-pyrrolidin-3-yl)-amide were prepared from 1-(8-Trifluoromethyl-quinolin-5-yl)-piperidine-4-carboxylic acid and 1-(cyclopropylmethyl)pyrrolidin-3-amine in 62% yield using method 20. The enantiomers were isolated via chiral SFC chromatography. (Column: 1.0×25.0 cm Lux Amylose-1); CO2 Co-solvent (Solvent B): ethanol with 0.5% dimethylamine; Isocratic Method: 55% Co-solvent at 10 mL/min; System Pressure: 100 bar; Column Temperature: 40° C.).

Isomer 1: HPLC: 98.6% purity, RT=2.84 min. MS: m/z=447 [M+H]+. 1H NMR (400 MHz, Chloroform-d, ppm) δ 9.04 (dd, J=4.2, 1.8 Hz, 1H), 8.49 (dd, J=8.6, 1.8 Hz, 1H), 7.96 (d, J=8.0 Hz, 1H), 7.47 (dd, J=8.6, 4.2 Hz, 1H), 7.06 (d, J=7.9 Hz, 1H), 5.95 (s, 1H), 4.50 (dddd, J=10.6, 8.5, 4.5, 2.8 Hz, 1H), 3.47 (d, J=12.5 Hz, 2H), 3.02 (td, J=8.7, 3.5 Hz, 1H), 2.84 (td, J=11.8, 2.6 Hz, 2H), 2.77 (dd, J=10.1, 2.4 Hz, 1H), 2.53 (dd, J=10.0, 6.5 Hz, 1H), 2.41-2.19 (m, 5H), 2.12 (qd, J=12.0, 11.5, 3.7 Hz, 2H), 2.06-1.96 (m, 2H), 1.63 (dtd, J=11.9, 7.9, 3.7 Hz, 1H), 0.89 (dddd, J=11.5, 8.1, 4.8, 2.4 Hz, 1H), 0.58-0.45 (m, 2H), 0.13 (ddd, J=6.7, 4.9, 3.7 Hz, 2H).

Isomer 2: HPLC: >99% purity, RT=2.84 min. MS: n/z=447 [M+H]+. 1H NMR (400 MHz, Chloroform-d, ppm) δ 9.04 (dd, J=4.2, 1.8 Hz, 1H), 8.49 (dd, J=8.6, 1.8 Hz, 1H), 7.96 (d, J=8.0 Hz, 1H), 7.47 (dd, J=8.6, 4.2 Hz, 1H), 7.06 (d, J=8.0 Hz, 1H), 5.96 (s, 1H), 4.52 (s, 1H), 3.47 (d, J=11.9 Hz, 2H), 3.04 (s, 1H), 2.84 (td, J=11.9, 2.7 Hz, 2H), 2.78 (d, J=8.2 Hz, 1H), 2.54 (dd, J=10.1, 6.5 Hz, 1H), 2.47-2.19 (m, 4H), 2.12 (qd, J=11.9, 11.4, 3.7 Hz, 2H), 2.02 (d, J=12.8 Hz, 2H), 1.62 (s, 2H), 0.98-0.82 (m, 1H), 0.65-0.41 (m, 2H), 0.14 (q, J=5.0 Hz, 2H).

Example 114: Synthesis of Compound 447 (N-[(3R,5S)-1-(8-Cyano-quinazolin-5-yl)-5-methyl-piperidin-3-yl]-2-dimethylamino-acetamide)

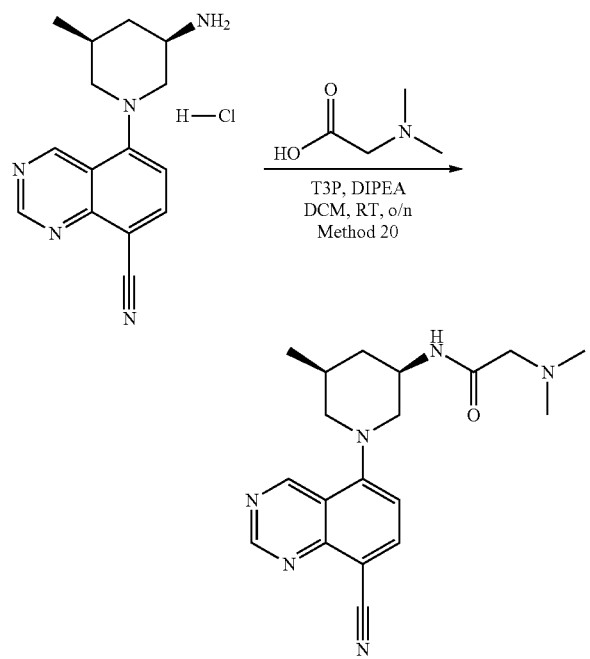

N-[(3R,5S)-1-(8-Cyano-quinazolin-5-yl)-5-methyl-piperidin-3-yl]-2-dimethylamino-acetamide: N-[(3R,5S)-1-(8-Cyano-quinazolin-5-yl)-5-methyl-piperidin-3-yl]-2-dimethylamino-acetamide was prepared from 5-[(3R,5S)-3-amino-5-methyl-1-piperidyl]quinazoline-8-carbonitrile hydrochloride and N,N-dimethylglycine in 77% yield, using method 20.

Compound 447: HPLC: 97.2% purity, RT=2.01 min. MS: m/z=353 [M+H]+. 1H NMR (400 MHz, Chloroform-d, pppm) δ 9.61 (s, 1H), 9.41 (s, 1H), 8.11 (d, J=8.2 Hz, 1H), 7.14 (d, J=8.9 Hz, 1H), 7.11 (d, J=8.2 Hz, 1H), 4.34-4.20 (m, 1H), 3.92 (ddt, J=11.7, 4.0, 1.9 Hz, 1H), 3.61 (ddd, J=12.3, 4.0, 2.0 Hz, 1H), 2.96 (s, 2H), 2.76-2.59 (m, 2H), 2.30 (s, 6H), 2.26-2.05 (m, 2H), 1.18 (q, J=11.9 Hz, 1H), 1.01 (d, J=6.5 Hz, 3H).

The following compounds were synthesized in an analogous manner:

Compound 460 (2-Dimethylamino-N-[(3R,5S)-1-(8-fluoro-pyrido[3,4-b]pyrazin-5-yl)-5-methyl-piperidin-3-yl]-acetamide): From (3R,5S)-1-(8-Fluoro-pyrido[3,4-b]pyrazin-5-yl)-5-methyl-piperidin-3-ylamine hydrochloride and N,N-dimethylglycine. HPLC: >99% purity, RT=1.65 min. MS: m/z=347 [M+H]+. 1H NMR (400 MHz, Chloroform-d, ppm) δ 8.94 (d, J=1.8 Hz, 1H), 8.82 (d, J=1.8 Hz, 1H), 8.21 (d, J=1.4 Hz, 1H), 7.12 (d, J=8.5 Hz, 1H), 4.90 (ddt, J=12.3, 4.1, 1.8 Hz, 1H), 4.66 (ddt, J=12.7, 3.8, 1.8 Hz, 1H), 4.25-4.13 (m, 1H), 3.01-2.89 (m, 2H), 2.79 (dd, J=12.3, 10.7 Hz, 1H), 2.61 (dd, J=12.7, 11.0 Hz, 1H), 2.30 (s, 6H), 2.22-2.14 (m, 1H), 2.08 (dddt, J=14.9, 10.8, 7.8, 3.6 Hz, 1H), 1.13 (q, J=11.8 Hz, 1H), 1.00 (d, J=6.7 Hz, 3H).

Compound 466 (N-[(3R,5S)-5-Methyl-1-(8-methyl-quinolin-5-yl)-piperidin-3-yl]-2-morpholin-4-yl-acetamide): From (3R,5S)-5-Methyl-1-(8-methyl-quinolin-5-yl)-piperidin-3-ylamine hydrochloride and 2-morpholinoacetic acid hydrochloride. HPLC: >99% purity, RT=1.62 min. MS: m/z=383 [M+H]+. 1H NMR (400 MHz, Chloroform-d, ppm) δ 8.93 (dd, J=4.2, 1.8 Hz, 1H), 8.54 (dd, J=8.5, 1.8 Hz, 1H), 7.48-7.38 (m, 2H), 7.02 (d, J=7.6 Hz, 1H), 6.98 (s, 1H), 4.42-4.26 (m, 1H), 3.71 (t, J=4.6 Hz, 4H), 3.52 (ddt, J=10.8, 4.1, 1.7 Hz, 1H), 3.22 (ddt, J=11.4, 3.7, 1.7 Hz, 1H), 3.08-2.93 (m, 2H), 2.74 (d, J=0.9 Hz, 3H), 2.60-2.44 (m, 4H), 2.39 (td, J=10.8, 2.1 Hz, 2H), 2.24-2.07 (m, 2H), 1.11-0.93 (m, 4H).

Compound 469 (2-Dimethylamino-N-[(3R,5S)-1-(8-fluoro-quinolin-5-yl)-5-methyl-piperidin-3-yl]-acetamide): From (3R,5S)-1-(8-Fluoro-quinolin-5-yl)-5-methyl-piperidin-3-ylamine hydrochloride and N,N-dimethylglycine. HPLC: 94.0% purity, RT=1.70 min. MS: m/z=345 [M+H]+. 1H NMR (400 MHz, Chloroform-d, ppm) δ 8.95 (dd, J=4.2, 1.7 Hz, 1H), 8.55 (dt, J=8.6, 1.7 Hz, 1H), 7.50 (dd, J=8.6, 4.2 Hz, 1H), 7.29 (dd, J=10.4, 8.3 Hz, 1H), 7.07 (d, J=8.5 Hz, 1H), 7.02 (dd, J=8.3, 4.2 Hz, 1H), 4.32 (dddd, J=14.6, 10.5, 8.4, 4.1 Hz, 1H), 3.52 (ddt, J=10.9, 4.1, 1.8 Hz, 1H), 3.20 (ddt, J=11.3, 3.7, 1.8 Hz, 1H), 2.93 (d, J=2.2 Hz, 2H), 2.39 (q, J=10.9 Hz, 2H), 2.28 (s, 6H), 2.21-2.04 (m, 2H), 1.11-0.92 (m, 4H).

Compound 470 (N-[(3R,5S)-1-(8-Fluoro-quinolin-5-yl)-5-methyl-piperidin-3-yl]-2-morpholin-4-yl-acetamide): From (3R,5S)-1-(8-Fluoro-quinolin-5-yl)-5-methyl-piperidin-3-ylamine hydrochloride and 2-morpholinoacetic acid hydrochloride. HPLC: >99% purity, RT=1.73 min. MS: m/z=387 [M+H]+. 1H NMR (400 MHz, Chloroform-d, ppm) δ 8.95 (dd, J=4.1, 1.7 Hz, 1H), 8.55 (dt, J=8.6, 1.7 Hz, 1H), 7.50 (dd, J=8.6, 4.2 Hz, 1H), 7.29 (dd, J=10.4, 8.3 Hz, 1H), 7.03 (dd, J=8.3, 4.2 Hz, 1H), 6.99 (s, 1H), 4.41-4.23 (m, 1H), 3.71 (s, 4H), 3.55-3.46 (m, 1H), 3.25-3.16 (m, 1H), 3.00 (s, 2H), 2.51 (s, 4H), 2.44-2.27 (m, 2H), 2.22-2.05 (m, 2H), 1.11-0.90 (m, 4H).

Compound 471 (N-[(3R,5S)-1-(8-Fluoro-quinolin-5-yl)-5-methyl-piperidin-3-yl]-2-(1-methyl-piperidin-4-yl)-acetamide): From (3R,5S)-1-(8-Fluoro-quinolin-5-yl)-5-methyl-piperidin-3-ylamine hydrochloride and 1-methyl-4-piperidineacetic acid. HPLC: >99% purity, RT=1.84 min. MS: m/z=399 [M+H]⁺. ¹H NMR (400 MHz, Chloroform-d, ppm) δ 8.95 (dd, J=4.2, 1.7 Hz, 1H), 8.55 (dt, J=8.6, 1.7 Hz, 1H), 7.51 (dd, J=8.6, 4.2 Hz, 1H), 7.29 (dd, J=10.4, 8.3 Hz, 1H), 7.01 (dd, J=8.3, 4.2 Hz, 1H), 5.25 (d, J=8.0 Hz, 1H), 4.31 (ddq, J=16.1, 8.3, 4.1 Hz, 1H), 3.63-3.48 (m, 1H), 3.26-3.08 (m, 1H), 2.81 (t, J=10.3 Hz, 2H), 2.35 (dt, J=17.8, 10.8 Hz, 2H), 2.25 (s, 3H), 2.21-2.07 (m, 2H), 1.93 (tdd, J=11.7, 5.4, 2.6 Hz, 2H), 1.80 (dp, J=11.2, 3.5 Hz, 1H), 1.74-1.64 (m, 2H), 1.34-1.21 (m, 2H), 1.04-0.91 (m, 4H).

Example 115: Synthesis of Compound 449 and Compound 450 (N—[(R)-1-(8-Cyano-quinolin-5-yl)-5,5-difluoro-piperidin-3-yl]-2-dimethylamino-acetamide and N—[(S)-1-(8-Cyano-quinolin-5-yl)-5,5-difluoro-piperidin-3-yl]-2-dimethylamino-acetamide)

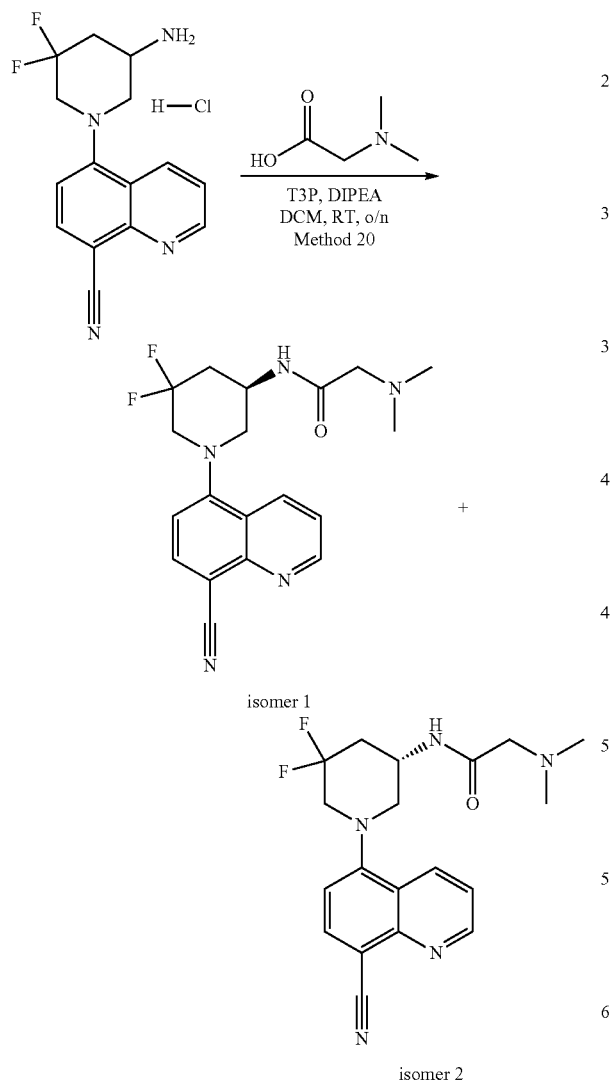

N—[(R)-1-(8-Cyano-quinolin-5-yl)-5,5-difluoro-piperidin-3-yl]-2-dimethylamino-acetamide and N—[(S)-1-(8-Cyano-quinolin-5-yl)-5,5-difluoro-piperidin-3-yl]-2-dim-ethylamino-acetamide: N—[(R)-1-(8-Cyano-quinolin-5-yl)-5,5-difluoro-piperidin-3-yl]-2-dimethylamino-acetamide and N—[(S)-1-(8-Cyano-quinolin-5-yl)-5,5-difluoro-piperidin-3-yl]-2-dimethylamino-acetamide were prepared from 5-(5-Amino-3,3-difluoro-piperidin-1-yl)-quinoline-8-carbonitrile hydrochloride and N,N-dimethylglycine in 25% yield, using method 20. The enantiomers were isolated via chiral SFC chromatography. (Column: 1.0×25.0 cm Chiralpak IA; CO2 Co-solvent (Solvent B): Methanol with 0.5% dimethylamine; Isocratic Method: 45% Co-solvent at 6 mL/min; System Pressure: 100 bar; Column Temperature: 30° C.).

Isomer 1: HPLC: >99% purity, RT=2.06 min. MS: m/z=374 [M+H]⁺. ¹H NMR (400 MHz, Chloroform-d, ppm) δ 9.11 (dd, J=4.2, 1.7 Hz, 1H), 8.65 (dd, J=8.6, 1.7 Hz, 1H), 8.06 (d, J=7.9 Hz, 1H), 7.87 (s, 1H), 7.57 (dd, J=8.6, 4.2 Hz, 1H), 7.14 (d, J=7.9 Hz, 1H), 4.63 (s, 1H), 3.51 (dd, J=21.5, 10.2 Hz, 1H), 3.43 (d, J=11.9 Hz, 1H), 3.35-3.18 (m, 2H), 3.04-2.90 (m, 2H), 2.46-2.30 (m, 2H), 2.28 (s, 6H).

Isomer 2: HPLC: >99% purity, RT=2.08 min. MS: m/z=374 [M+H]⁺. ¹H NMR (400 MHz, Chloroform-d, ppm) δ 9.11 (dd, J=4.2, 1.7 Hz, 1H), 8.65 (dd, J=8.6, 1.7 Hz, 1H), 8.06 (d, J=7.9 Hz, 1H), 7.86 (s, 1H), 7.57 (dd, J=8.6, 4.2 Hz, 1H), 7.14 (d, J=7.9 Hz, 1H), 4.63 (s, 1H), 3.51 (q, J=10.4 Hz, 1H), 3.43 (d, J=11.9 Hz, 1H), 3.37-3.17 (m, 2H), 3.04-2.90 (m, 2H), 2.46-2.29 (m, 2H), 2.28 (s, 6H).

Example 116: Synthesis of Compound 451 (Methyl-[(3R,5S)-5-methyl-1-(8-trifluoromethyl-quinolin-5-yl)-piperidin-3-yl]-amine hydrochloride)

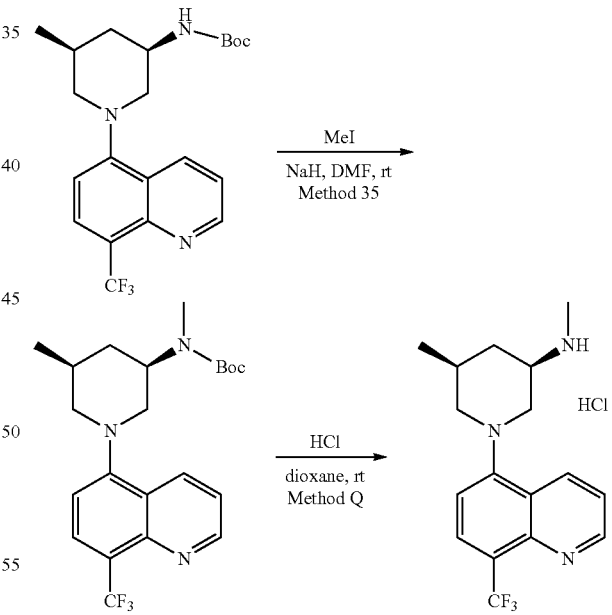

Methyl-[(3R,5S)-5-methyl-1-(8-trifluoromethyl-quinolin-5-yl)-piperidin-3-yl]-amine hydrochloride: Methyl-[(3R,5S)-5-methyl-1-(8-trifluoromethyl-quinolin-5-yl)-piperidin-3-yl]-amine hydrochloride was prepared from [(3R,5S)-5-Methyl-1-(8-trifluoromethyl-quinolin-5-yl)-piperidin-3-yl]-carbamic acid tert-butyl ester and iodomethane in 68% yield over 2 steps, using method 35 and Q.

Compound 451: HPLC: 98.8% purity, RT=2.74 min. MS: m/z=324 [M+H]⁺. ¹H NMR (400 MHz, Deuterium Oxide, ppm) δ 9.21 (dt, J=8.7, 1.3 Hz, 1H), 9.13 (dt, J=5.2, 1.4 Hz, 1H), 8.41 (d, J=8.3 Hz, 1H), 8.08 (ddd, J=8.5, 5.2, 1.1 Hz, 1H), 7.55 (d, J=8.3 Hz, 1H), 3.86 (d, J=11.2 Hz, 1H), 3.72 (tt, J=7.7, 3.8 Hz, 1H), 3.51 (d, J=12.1 Hz, 1H), 3.07 (t, J=11.0 Hz, 1H), 2.85 (s, 3H), 2.62 (t, J=11.8 Hz, 1H), 2.47 (d, J=12.5 Hz, 1H), 2.36-2.21 (m, 1H), 1.34 (q, J=12.0 Hz, 1H), 1.07 (d, J=6.6 Hz, 3H).

Example 117: Synthesis of Compound 452 (2-Dimethylamino-N-methyl-N-[(3R,5S)-5-methyl-1-(8-trifluoromethyl-quinolin-5-yl)-piperidin-3-yl]-acetamide)

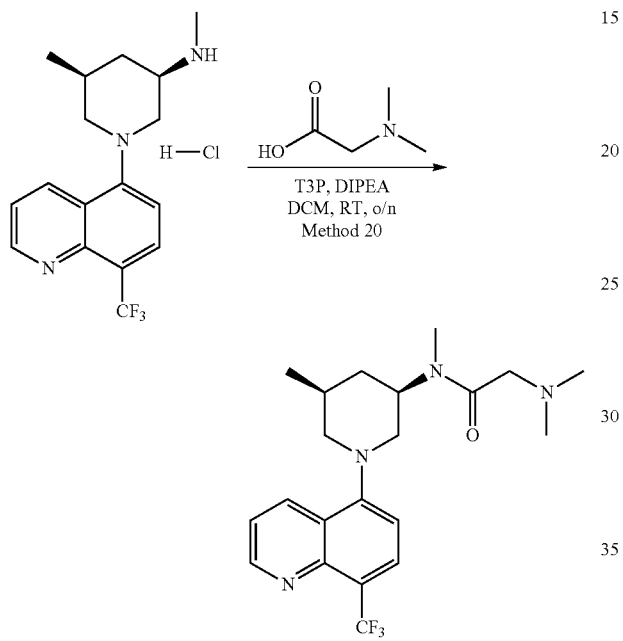

2-Dimethylamino-N-methyl-N-[(3R,5S)-5-methyl-1-(8-trifluoromethyl-quinolin-5-yl)-piperidin-3-yl]-acetamide: 2-Dimethylamino-N-methyl-N-[(3R,5S)-5-methyl-1-(8-trifluoromethyl-quinolin-5-yl)-piperidin-3-yl]-acetamide was prepared from Methyl-[(3R,5S)-5-methyl-1-(8-trifluoromethyl-quinolin-5-yl)-piperidin-3-yl]-amine hydrochloride and N,N-dimethylglycine in 56% yield, using method 20.

Compound 452: HPLC: 95.0% purity, RT=3.11 min. MS: m/z=409 [M+H]+.

Example 118: Synthesis of Compound 453 (4-(8-Cyano-quinoxalin-5-yl)-piperazine-1-carboxylic acid (2-diethylamino-ethyl)-amide)

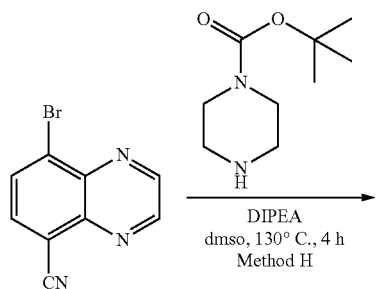

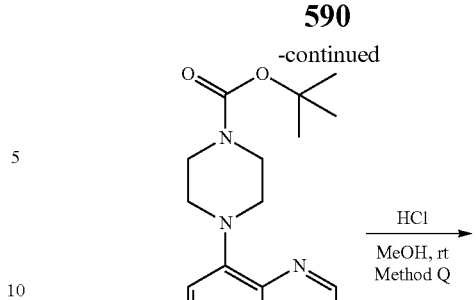

-continued

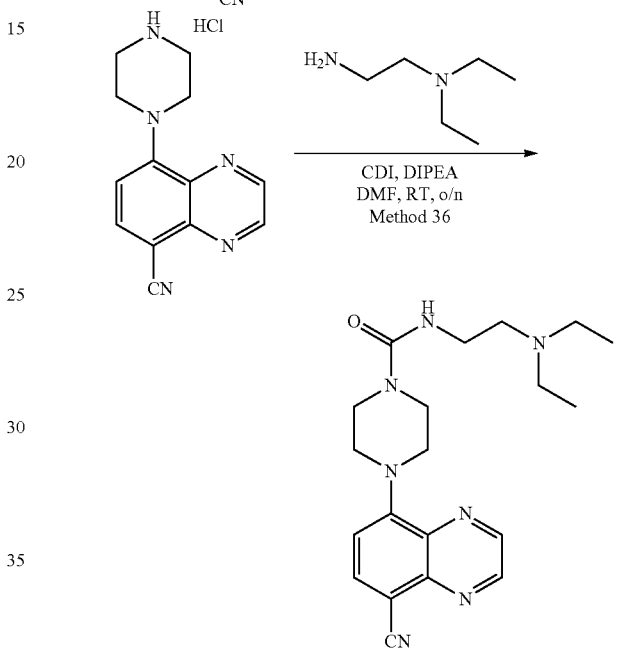

4-(8-Cyano-quinoxalin-5-yl)-piperazine-1-carboxylic acid (2-diethylamino-ethyl)-amide: 4-(8-Cyano-quinoxalin-5-yl)-piperazine-1-carboxylic acid (2-diethylamino-ethyl)-amide was prepared from 8-Bromo-quinoxaline-5-carbonitrile, 1-boc-piperazine and N,N-diethylethylenediamine in 11% yield over 3 steps, using method H, Q and 36.

Compound 453: HPLC: 96.4% purity, RT=1.85 min. MS: m/z=382 [M+H]+. 1H NMR (400 MHz, Chloroform-d, ppm) δ 8.98 (d, J=1.8 Hz, 1H), 8.84 (d, J=1.8 Hz, 1H), 8.03 (d, J=8.3 Hz, 1H), 7.05 (d, J=8.3 Hz, 1H), 5.36 (s, 1H), 3.77-3.59 (m, 8H), 3.37-3.25 (m, 2H), 2.56 (s, 6H), 1.03 (s, 6H).

The following compound was synthesized in an analogous manner:

Compound 463 (4-(8-Cyano-quinoxalin-5-yl)-piperazine-1-carboxylic acid (2-dimethylamino-ethyl)-amide): HPLC: >99% purity, RT=1.62 min. MS: m/z=354 [M+H]+. 1H NMR (400 MHz, Chloroform-d, ppm) δ 8.98 (d, J=1.8 Hz, 1H), 8.83 (d, J=1.8 Hz, 1H), 8.03 (d, J=8.3 Hz, 1H), 7.05 (d, J=8.3 Hz, 1H), 5.28 (s, 1H), 3.79-3.67 (m, 4H), 3.67-3.57 (m, 4H), 3.35 (dt, J=5.9, 4.8 Hz, 2H), 2.47 (t, J=5.8 Hz, 2H), 2.26 (s, 6H).

Example 119: Synthesis of Compound 458 (5-((3R, 5S)-3-Amino-5-methyl-piperidin-1-yl)-pyrido[4,3-d]pyrimidine-8-carbonitrile hydrochloride)

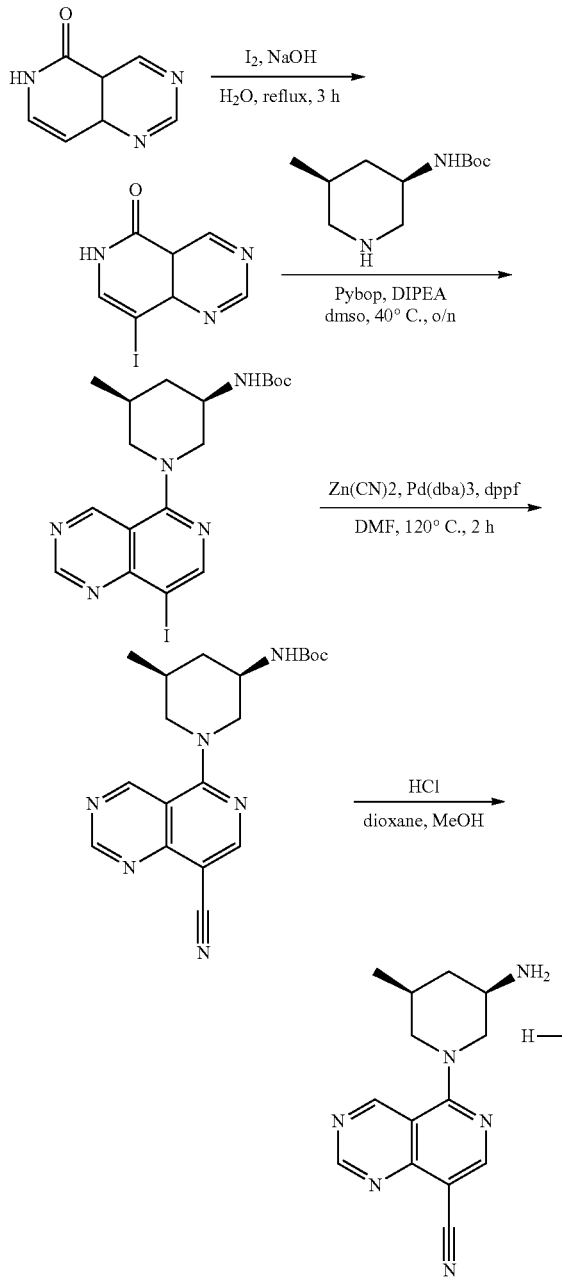

8-Iodo-6H-pyrido[4,3-d]pyrimidin-5-one: A mixture of 5H,6H-pyrido[4,3-d]pyrimidin-5-one (500 mg; 3.40 mmol) and iodine (863 mg; 3.40 mmol) in a 0.4 N solution of sodium hydroxide (15 mL) was heated to reflux for 3 h. The light yellow suspension was cooled to room temperature, water (30 mL) was added and the suspension was stirred at room temperature for 15 min. The suspension was filtered, the solid was rinsed with water and dried under vacuo to afford 8-Iodo-6H-pyrido[4,3-d]pyrimidin-5-one (727 mg; 76%), as a light yellow solid. MS: m/z=274 [M+H]$^+$. $^1$H NMR (400 MHz, DMSO-d$_6$, ppm) δ 12.15 (s, 1H), 9.42 (s, 1H), 9.33 (s, 1H), 8.13 (s, 1H).

[(3R,5S)-1-(8-Iodo-pyrido[4,3-d]pyrimidin-5-yl)-5-methyl-piperidin-3-yl]-carbamic acid tert-butyl ester: A solution of 8-Iodo-6H-pyrido[4,3-d]pyrimidin-5-one (300 mg; 1.10 mmol), tert-butyl N-[(3R,5S)-5-methylpiperidin-3-yl]carbamate (283 mg; 1.32 mmol), pybop (858 mg; 1.65 mmol) and DIPEA (574 µl; 3.30 mmol) in anhydrous DMSO (9 mL) was placed in a sealed tube and heated at 40° C. overnight. The light yellow solution was cooled to room temperature, poured over a saturated solution of ammonium chloride (100 mL) and extracted with ethyl acetate (3×50 mL). The combined organic phase was washed with brine (100 mL), dried over anhydrous sodium sulfate, filtered and concentrated under reduced pressure. The residue was purified by chromatography on a PuriFlash column (25 g 30 m), eluting with hexanes and ethyl acetate to afford [(3R,5S)-1-(8-Iodo-pyrido[4,3-d]pyrimidin-5-yl)-5-methyl-piperidin-3-yl]-carbamic acid tert-butyl ester (212 mg; 41%) as a yellow solid. MS: m/z=470 [M+H]$^+$. $^1$H NMR (400 MHz, Chloroform-d, ppm) δ 9.41 (s, 1H), 9.38 (s, 1H), 8.77 (s, 1H), 4.45 (s, 1H), 4.33 (ddt, J=12.4, 4.2, 1.9 Hz, 1H), 4.02 (ddt, J=12.9, 4.0, 1.8 Hz, 1H), 3.87 (s, 1H), 2.74 (dd, J=12.3, 10.8 Hz, 1H), 2.66 (t, J=12.1 Hz, 1H), 2.19 (d, J=12.6 Hz, 1H), 2.06 (s, 1H), 1.45 (s, 9H), 1.13-0.95 (m, 4H).

[(3R,5S)-1-(8-Cyano-pyrido[4,3-d]pyrimidin-5-yl)-5-methyl-piperidin-3-yl]-carbamic acid tert-butyl ester: A mixture of [(3R,5S)-1-(8-Iodo-pyrido[4,3-d]pyrimidin-5-yl)-5-methyl-piperidin-3-yl]-carbamic acid tert-butyl ester (100 mg; 0.213 mmol), zinc cyanide (62.6 mg; 0.533 mmol), tris(dibenzylideneacetone)dipalladium(0) (19.5 mg; 0.021 mmol) and 1,1'-bis(diphenylphosphino)ferrocene (5.9 mg; 0.011 mmol) in anhydrous DMF (3 mL) was microwaved at 120° C. for 2 h. The black suspension was filtered on celite, washed with ethyl acetate and concentrated under reduced pressure. The residue purified by chromatography on a PuriFlash column (12 g 30 µm), eluting with hexanes and ethyl acetate to afford [(3R,5S)-1-(8-Cyano-pyrido[4,3-d]pyrimidin-5-yl)-5-methyl-piperidin-3-yl]-carbamic acid tert-butyl ester (50 mg; 64%) as a yellow solid. MS: m/z=369 [M+H]$^+$. $^1$H NMR (400 MHz, Chloroform-d, ppm) δ 9.54 (s, 1H), 9.40 (s, 1H), 8.66 (s, 1H), 4.70 (d, J=12.7 Hz, 1H), 4.48 (d, J=12.0 Hz, 2H), 3.81 (s, 1H), 2.89 (dd, J=12.6, 11.0 Hz, 1H), 2.75 (t, J=12.4 Hz, 1H), 2.21 (d, J=12.5 Hz, 1H), 1.99 (s, 1H), 1.45 (s, 9H), 1.15 (q, J=12.0 Hz, 1H), 1.05 (d, J=6.6 Hz, 3H).

5-((3R,5S)-3-Amino-5-methyl-piperidin-1-yl)-pyrido[4,3-d]pyrimidine-8-carbonitrile hydrochloride: A solution of hydrochloric acid (692 µl; 2.77 mmol) 4M in dioxane was added to a solution of [(3R,5S)-1-(8-Cyano-pyrido[4,3-d]pyrimidin-5-yl)-5-methyl-piperidin-3-yl]-carbamic acid tert-butyl ester (34.0 mg; 0.092 mmol) in methanol (2 mL) and the reaction mixture was stirred at room temperature overnight. The yellow solution was concentrated under reduced pressure, the residue was dissolved in methanol (1 mL) and ethyl acetate was added (10 mL). The yellow suspension was filtered, the yellow solid was washed with ethyl acetate and dried under vacuo to afford 5-((3R,5S)-3-Amino-5-methyl-piperidin-1-yl)-pyrido[4,3-d]pyrimidine-8-carbonitrile hydrochloride (18 mg; 64%) as a yellow solid.

Compound 453: HPLC: >99% purity, RT=1.42 min. MS: n/z=269 [M+H]$^+$. $^1$H NMR (400 MHz, Deuterium Oxide, ppm) δ 9.58 (s, 1H), 9.32 (s, 1H), 8.79 (s, 1H), 4.85 (d, J=12.5 Hz, 1H), 4.38 (d, J=13.7 Hz, 1H), 3.73-3.62 (m, 1H), 3.42-3.33 (m, 1H), 3.22 (t, J=12.5 Hz, 1H), 2.37 (d, J=12.8 Hz, 1H), 2.08 (s, 1H), 1.51 (q, J=12.2 Hz, 1H), 1.06 (d, J=6.7 Hz, 3H).

Example 119: Synthesis of Compound 461 (cis-5-Methyl-1-(8-trifluoromethyl-quinolin-5-yl)-piperidin-3-ol)

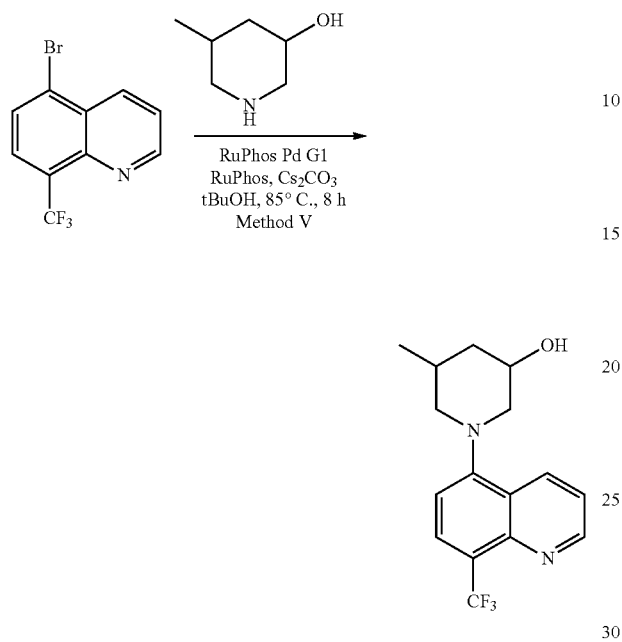

cis-5-Methyl-1-(8-trifluoromethyl-quinolin-5-yl)-piperidin-3-ol: cis-5-Methyl-1-(8-trifluoromethyl-quinolin-5-yl)-piperidin-3-ol was obtained from 5-bromo-8-(trifluoromethyl)quinolone and cis-5-Methyl-piperidin-3-ol in 7% yield, using method V.

Compound 461: HPLC: 95.7% purity, RT=3.67 min. MS: m/z=311 [M+H]$^+$. $^1$H NMR (400 MHz, Chloroform-d, ppm) δ 9.04 (dd, J=4.2, 1.8 Hz, 1H), 8.44 (dd, J=8.6, 1.8 Hz, 1H), 7.98 (dd, J=8.0, 0.9 Hz, 1H), 7.47 (dd, J=8.5, 4.2 Hz, 1H), 7.08 (d, J=8.0 Hz, 1H), 4.18-4.03 (m, 1H), 3.57 (ddt, J=11.0, 4.4, 1.9 Hz, 1H), 3.30 (ddt, J=11.7, 3.7, 1.7 Hz, 1H), 2.59 (dd, J=11.0, 10.0 Hz, 1H), 2.38 (t, J=11.3 Hz, 1H), 2.26 (dtd, J=11.8, 3.9, 1.8 Hz, 1H), 2.10 (dddt, J=11.9, 10.6, 6.6, 4.0 Hz, 1H), 1.12 (td, J=12.1, 10.8 Hz, 1H), 1.02 (d, J=6.7 Hz, 3H).

Example 120: Synthesis of Compound 464 (1-(8-Trifluoromethyl-quinolin-5-yl)-piperidine-4-carboxylic acid ((3R,4S)-4-fluoro-pyrrolidin-3-yl)-amide hydrochloride)

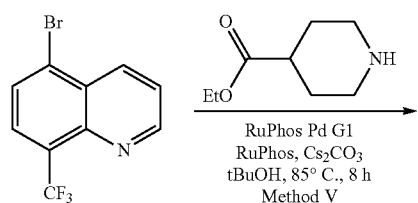

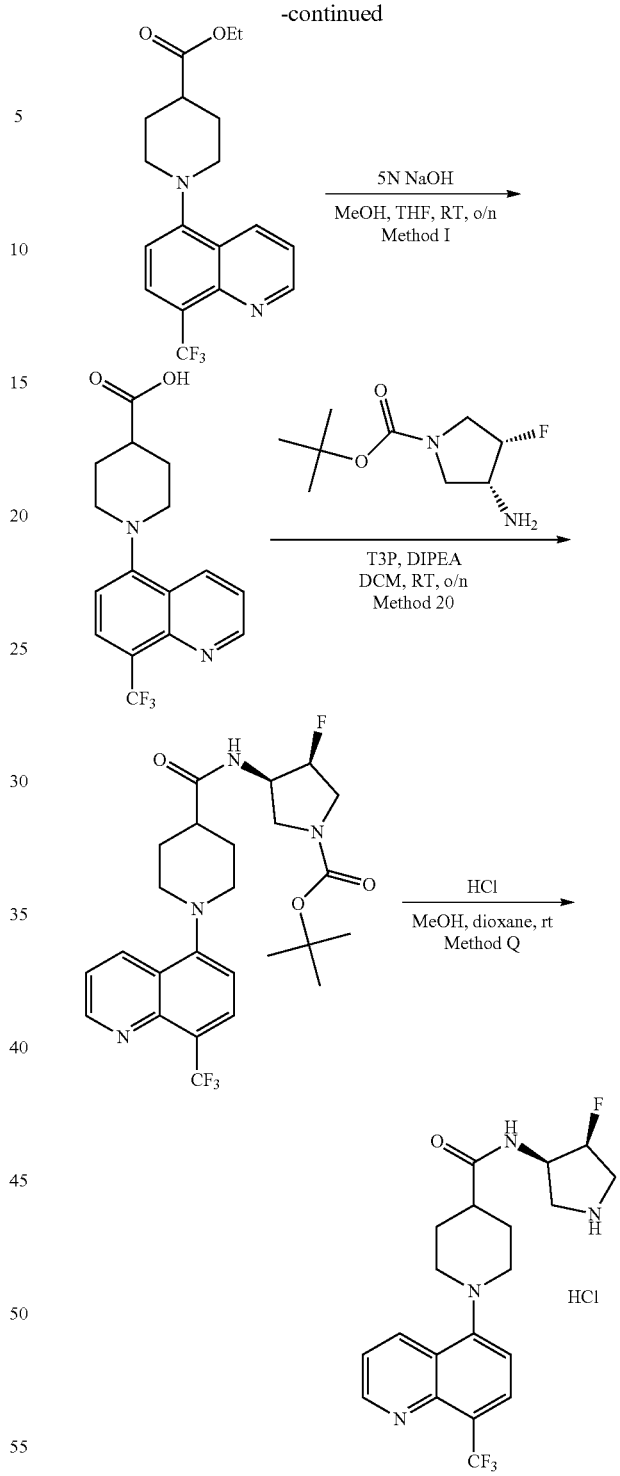

1-(8-Trifluoromethyl-quinolin-5-yl)-piperidine-4-carboxylic acid ((3R,4S)-4-fluoro-pyrrolidin-3-yl)-amide hydrochloride: 1-(8-Trifluoromethyl-quinolin-5-yl)-piperidine-4-carboxylic acid ((3R,4S)-4-fluoro-pyrrolidin-3-yl)-amide hydrochloride was prepared from 5-bromo-8-(trifluoromethyl)quinolone, ethyl piperidine-4-carboxylate and (3R,4S)-3-Amino-4-fluoro-pyrrolidine-1-carboxylic acid tert-butyl ester in 45% yield over 4 steps, using method V, I, 20 and Q.

Compound 464: HPLC: >99% purity, RT=2.45 min. MS: m/z=411 [M+H]+. 1H NMR (400 MHz, Deuterium Oxide, ppm) δ 8.97 (dd, J=4.7, 1.6 Hz, 1H), 8.79 (dd, J=8.6, 1.7 Hz, 1H), 8.19 (d, J=8.2 Hz, 1H), 7.79 (dd, J=8.6, 4.7 Hz, 1H), 7.32 (d, J=8.2 Hz, 1H), 5.42 (dt, J=52.4, 3.3 Hz, 1H), 4.92-4.81 (m, 1H), 3.95-3.76 (m, 3H), 3.52 (d, J=12.2 Hz, 2H), 3.35 (t, J=11.4 Hz, 1H), 3.02-2.87 (m, 2H), 2.73-2.59 (m, 1H), 2.17-1.92 (m, 4H).

Example 121: Synthesis of Compound 465 (3-Amino-3,N-dimethyl-N-[(3R,5S)-5-methyl-1-(8-trifluoromethyl-quinolin-5-yl)-piperidin-3-yl]-butyramide)

Example 121: Synthesis of Compound 477 (1-(2-Dimethylamino-ethyl)-3-[(3R,5S)-5-methyl-1-(8-trifluoromethyl-quinolin-5-yl)-piperidin-3-yl]-urea)

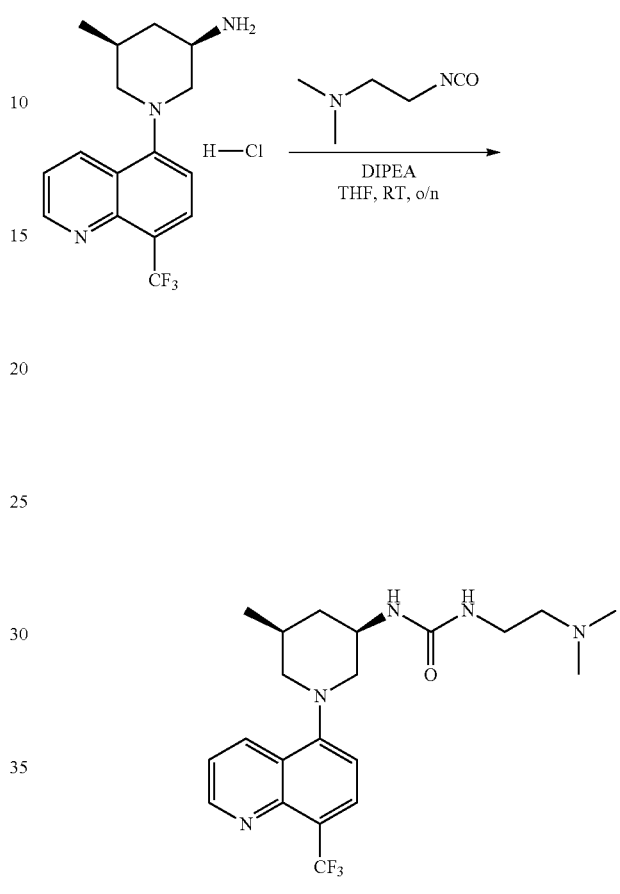

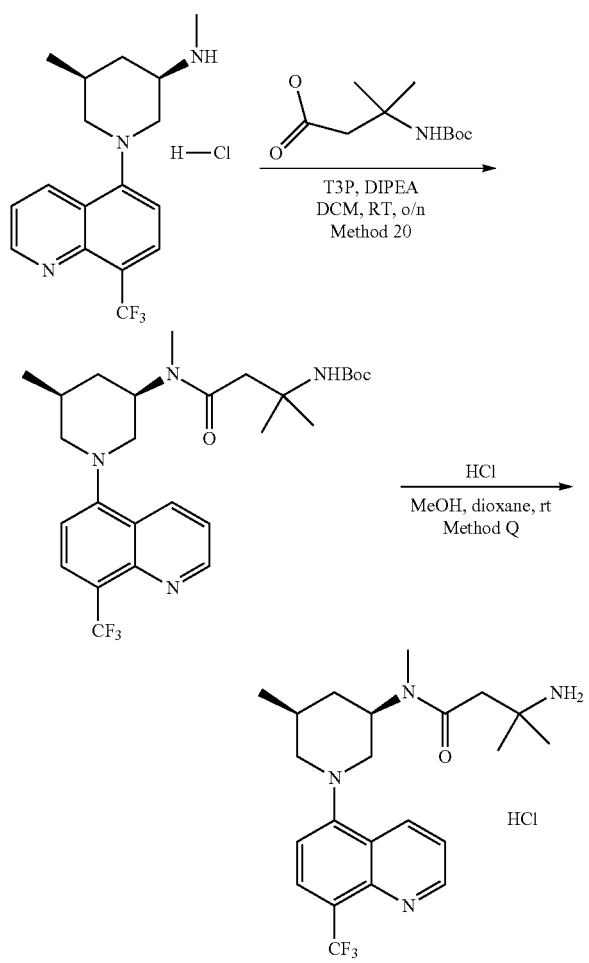

3-Amino-3,N-dimethyl-N-[(3R,5S)-5-methyl-1-(8-trifluoromethyl-quinolin-5-yl)-piperidin-3-yl]-butyramide: 3-Amino-3,N-dimethyl-N-[(3R,5S)-5-methyl-1-(8-trifluoromethyl-quinolin-5-yl)-piperidin-3-yl]-butyramide was prepared from Methyl-[(3R,5S)-5-methyl-1-(8-trifluoromethyl-quinolin-5-yl)-piperidin-3-yl]-amine hydrochloride and 3-(tert-butoxycarbonylamino)-3-methylbutanoic acid in 13% yield over 2 steps, using method 20 and Q.

Compound 465: HPLC: 93.2% purity, RT=3.29 min. MS: m/z=423 [M+H]+.

1-(2-Dimethylamino-ethyl)-3-[(3R,5S)-5-methyl-1-(8-trifluoromethyl-quinolin-5-yl)-piperidin-3-yl]-urea: To a solution (3R,5S)-1-[8-(trifluoromethyl)quinolin-5-yl]-5-methylpiperidin-3-amine (1.0 eq.) in THF was added DIEA (5.0 eq.). The solution was stirred at room temperature for 10 minutes then the flask was charged with (2-isocyanatoethyl)dimethylamine. The reaction was stirred for 16 hours. The reaction mixture was filtered and concentrated. The crude product was purified by prep-HPLC under the following conditions: column, XBridge Prep C18 OBD Column, 5 um, 19 mm×150 mm; mobile phase, acetonitrile in water (with 0.05% NH3.H2), 30% to 65% gradient in 7 min; detector, UV 254 nm.

Compound 477: HPLC: >99% purity, RT=2.86 min. MS: m/z=424.2 [M+H]+. 1H NMR (400 MHz, DMSO-d6, ppm) δ 9.00 (dd, J=4.2, 1.7 Hz, 1H), 8.52 (dd, J=8.6, 1.8 Hz, 1H), 8.03 (d, J=8.1 Hz, 1H), 7.65 (dd, J=8.6, 4.2 Hz, 1H), 7.19 (d, J=8.1 Hz, 1H), 6.09 (d, J=7.4 Hz, 1H), 5.71 (t, J=5.4 Hz, 1H), 3.56 (d, J=9.2 Hz, 1H), 3.14-2.98 (m, 2H), 2.46-2.33 (m, 2H), 2.23 (t, J=6.3 Hz, 2H), 2.12 (s, 6H), 1.98 (d, J=20.5 Hz, 2H), 1.03-0.88 (m, 4H).

Example 122: Synthesis of Compound 478 (cis-N-[1-(8-Cyano-quinolin-5-yl)-5-trifluoromethyl-piperidin-3-yl]-2-(1-methyl-piperidin-4-yl)-acetamide)

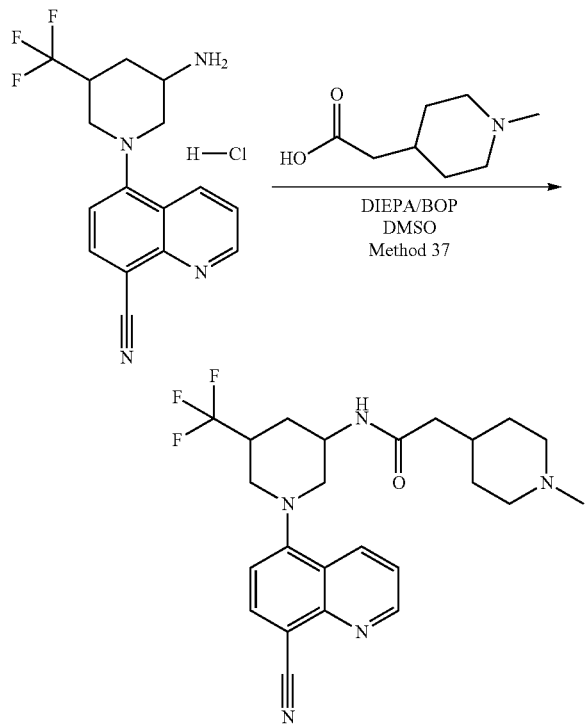

Method 37 cis-N-[1-(8-Cyano-quinolin-5-yl)-5-trifluoromethyl-piperidin-3-yl]-2-(1-methyl-piperidin-4-yl)-acetamide: A solution of cis-5-(3-Amino-5-trifluoromethyl-piperidin-1-yl)-quinoline-8-carbonitrile hydrochloride (100 mg; 0.28 mmol), (1-Methyl-piperidin-4-yl)-acetic acid (53 mg; 0.34 mmol) and DIPEA (0.2 mL; 0.84 mmol) in DMSO (2 mL) was stirred at room temperature for 5 min, and then added bop (149 mg; 0.34 mmol). The mixture was stirred at room temperature for 1 hr and concentrated under reduced pressure. The residue was purified by reverse phase chromatography (XBridge column), eluting with acetonitrile in water (0.1% NH$_3$H$_2$O), 30% to 70% gradient to afford [00984] cis-N-[1-(8-Cyano-quinolin-5-yl)-5-trifluoromethyl-piperidin-3-yl]-2-(1-methyl-piperidin-4-yl)-acetamide as white solid (70 mg, 54%).

Compound 478: $^1$H NMR (400 MHz, Methanol-d$_4$, ppm) δ 9.01 (dd, J=4.3, 1.6 Hz, 1H), 8.67 (dd, J=8.6, 1.7 Hz, 1H), 8.16 (d, J=8.0 Hz, 1H), 7.70 (dd, J=8.6, 4.3 Hz, 1H), 7.32 (d, J=8.0 Hz, 1H), 4.32 (tt, J=11.3, 4.3 Hz, 1H), 3.76-3.62 (m, 2H), 3.16-2.94 (m, 2H), 2.87 (t, J=10.8 Hz, 2H), 2.60 (t, J=11.2 Hz, 1H), 2.35 (d, J=12.5 Hz, 1H), 2.27 (s, 3H), 2.21-2.11 (m, 2H), 2.02 (ddt, J=14.5, 9.0, 2.9 Hz, 2H), 1.90-1.46 (m, 4H), 1.32 (dt, J=11.9, 5.4 Hz, 2H). MS: m/z=460 [M+H]$^+$.

The following compounds were synthesized in an analogous manner:

Compound 481 (cis-N-1-(8-Cyano-quinolin-5-yl)-5-trifluoromethyl-piperidin-3-yl]-3-hydroxy-3-methyl-butyramide): From cis-5-(3-Amino-5-trifluoromethyl-piperidin-1-yl)-quinoline-8-carbonitrile hydrochloride and 3-Hydroxy-3-methyl-butyric acid. $^1$H NMR (400 MHz, DMSO-d$_6$, ppm) δ 9.07 (dd, J=4.2, 1.6 Hz, 1H), 8.59 (dd, J=8.6, 1.7 Hz, 1H), 8.26 (d, J=8.0 Hz, 1H), 8.02 (d, J=7.5 Hz, 1H), 7.73 (dd, J=8.6, 4.2 Hz, 1H), 7.33 (d, J=8.1 Hz, 1H), 4.70 (s, 1H), 4.19 (s, 1H), 3.57 (d, J=9.3 Hz, 2H), 3.21 (s, 1H), 2.95 (t, J=11.6 Hz, 1H), 2.65 (t, J=11.3 Hz, 1H), 2.22 (s, 2H), 1.53 (q, J=12.2 Hz, 1H), 1.16 (s, 6H). MS: m/z=421 [M+H]$^+$.

Compound 484 (2-(1-Hydroxy-cyclohexyl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine hydrochloride and (1-tButoxycarbonylamino-cyclohexyl)-acetic acid. $^1$H NMR (400 MHz, Methanol-d$_4$, ppm) δ 8.95 (d, J=4.2 Hz, 1H), 8.66 (d, J=8.6 Hz, 1H), 8.04 (d, J=8.0 Hz, 1H), 7.63 (dd, J=8.7, 4.1 Hz, 1H), 7.23 (d, J=8.0 Hz, 1H), 4.25 (s, 1H), 3.63 (d, J=11.4 Hz, 1H), 3.40 (d, J=11.6 Hz, 1H), 2.50 (q, J=11.4 Hz, 2H), 2.31 (s, 2H), 2.14 (d, J=12.6 Hz, 2H), 1.67-1.35 (m, 11H), 1.16 (q, J=12.4 Hz, 1H), 1.05 (d, J=6.2 Hz, 3H). MS: m/z=449 [M+H]$^+$.

Compound 485 (2-(1-Hydroxy-cyclohexyl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine hydrochloride and 3-Hydroxy-3-methyl-butyric. $^1$H NMR (400 MHz, Methanol-d$_4$, ppm) δ 8.94 (dd, J=4.2, 1.7 Hz, 1H), 8.67 (dd, J=8.6, 1.8 Hz, 1H), 8.04 (d, J=8.1 Hz, 1H), 7.63 (dd, J=8.6, 4.2 Hz, 1H), 7.23 (d, J=8.0 Hz, 1H), 4.26 (ddt, J=17.3, 13.6, 6.9 Hz, 1H), 3.68-3.59 (m, 1H), 3.47-3.36 (m, 2H), 2.55-2.37 (m, 2H), 2.36 (s, 2H), 2.17 (s, 2H), 1.27 (d, J=0.9 Hz, 6H), 1.17 (q, J=12.6 Hz, 1H), 1.05 (d, J=6.4 Hz, 3H). MS: m/z=410 [M+H]$^+$.

Compound 490 (cis-N-[(1-(8-Cyano-quinolin-5-yl)-5-trifluoromethyl-piperidin-3-yl]-2-(1-methyl-azetidin-3-yl)-acetamide): From cis-5-(3-Amino-5-trifluoromethyl-piperidin-1-yl)-quinoline-8-carbonitrile hydrochloride and (1-Methyl-azetidin-3-yl)-acetic acid hydrochloride. $^1$H NMR (400 MHz, DMSO-d$_6$) δ 9.06 (dd, J=4.2, 1.6 Hz, 1H), 8.57 (dd, J=8.6, 1.7 Hz, 1H), 8.25 (d, J=8.0 Hz, 1H), 8.02 (d, J=7.4 Hz, 1H), 7.72 (dd, J=8.6, 4.2 Hz, 1H), 7.32 (d, J=8.1 Hz, 1H), 4.12 (s, 2H), 3.56 (t, J=8.9 Hz, 2H), 3.24 (tdd, J=7.2, 4.0, 2.1 Hz, 2H), 2.93 (t, J=11.6 Hz, 1H), 2.82-2.68 (m, 2H), 2.64-2.53 (m, 2H), 2.43-2.28 (m, 2H), 2.15 (s, 3H), 1.50 (q, J=12.3 Hz, 1H). MS: m/z=432 [M+H]$^+$.

Compound 491 (cis-N-[1-(8-Cyano-quinolin-5-yl)-5-trifluoromethyl-piperidin-3-yl]-2-(1-methyl-azetidin-3-yl)-acetamide): From cis-5-(3-Amino-5-trifluoromethyl-piperidin-1-yl)-quinoline-8-carbonitrile hydrochloride and (1-Hydroxy-cyclohexyl)-acetic acid. $^1$H NMR (400 MHz, DMSO-d$_6$) δ 9.07 (dd, J=4.2, 1.6 Hz, 1H), 8.59 (dd, J=8.6, 1.7 Hz, 1H), 8.26 (d, J=8.0 Hz, 1H), 8.06 (d, J=7.4 Hz, 1H), 7.73 (dd, J=8.6, 4.2 Hz, 1H), 7.32 (d, J=8.1 Hz, 1H), 4.25 (m, 1H), 4.57 (s, 1H), 3.70-3.48 (m, 2H), 3.21 (d, J=11.2 Hz, 1H), 2.95 (t, J=11.6 Hz, 1H), 2.64 (t, J=11.2 Hz, 1H), 2.21 (s, 3H), 1.65-1.28 (m, 9H), 1.19 (q, J=10.7, 10.1 Hz, 1H). MS: m/z=461 [M+H]$^+$.

Compound 496 (cis-N-[-1-(8-Cyano-quinolin-5-yl)-5-trifluoromethyl-piperidin-3-yl]-4-(4-methyl-piperazin-1-yl)-4-oxo-butyramide): From cis-N-[1-(8-Cyano-quinolin-5-yl)-5-trifluoromethyl-piperidin-3-yl]-succinamic acid methyl ester and 1-Methyl-piperazine. $^1$H NMR (400 MHz, DMSO-d$_6$) 9.06 (dd, J=4.2, 1.6 Hz, 1H), 8.58 (dd, J=8.6, 1.7 Hz, 1H), 8.25 (d, J=8.0 Hz, 1H), 8.02 (d, J=7.3 Hz, 1H), 7.72 (dd, J=8.6, 4.2 Hz, 1H), 7.32 (d, J=8.1 Hz, 1H), 4.13 (d, J=8.2 Hz, 1H), 3.57 (d, J=11.7 Hz, 1H), 3.41 (d, J=5.0 Hz, 3H), 3.19 (s, 1H), 2.95 (t, J=11.6 Hz, 1H), 2.70-2.54 (m, 2H), 2.41-2.24 (m, 3H), 2.15 (s, 3H), 1.51 (q, J=12.3 Hz, 1H). MS: m/z=503 [M+H]$^+$.

Compound 554 (N-[(3R,5S)-5-Methyl-1-(8-methyl-[1,7] naphthyridin-5-yl)-piperidin-3-yl]-2-(1-methyl-piperidin-4-yl)-acetamide): From 3R,5S)-5-Methyl-1-(8-methyl-[1,7] naphthyridin-5-yl)-piperidin-3-ylamine dihydrochloride and 1-methyl-4-piperidineacetic acid. MS: m/z=396 [M+H]+. 1H NMR (400 MHz, DMSO-d6) 9.03 (dd, J=4.1, 1.7 Hz, 1H), 8.44 (dd, J=8.5, 1.7 Hz, 1H), 8.10 (s, 1H), 7.87-7.76 (m, 2H), 4.06-3.97 (m, 1H), 3.45-3.36 (m, 1H), 3.26-3.19 (m, 1H), 2.88 (s, 3H), 2.74-2.63 (m, 2H), 2.42 (q, J=11.0 Hz, 2H), 2.11 (s, 3H), 2.08-1.91 (m, 4H), 1.85-1.72 (m, 2H), 1.65-1.48 (m, 3H), 1.22-1.06 (m, 2H), 1.05 (q, J=11.8 Hz, 1H), 0.95 (d, J=6.5 Hz, 3H).

Compound 555 (3-Hydroxy-3-methyl-N-[(3R,5S)-5-methyl-1-(8-methyl-[1,7]naphthyridin-5-yl)-piperidin-3-yl]-butyramide): From (3R,5S)-5-Methyl-1-(8-methyl-[1,7] naphthyridin-5-yl)-piperidin-3-ylamine dihydrochloride and beta-hydroxyisovaleric acid. MS: m/z=357 [M+H]+. 1H NMR (400 MHz, DMSO-d6, ppm) δ 9.03 (dd, J=4.1, 1.7 Hz, 1H), 8.45 (dd, J=8.5, 1.7 Hz, 1H), 8.11 (s, 1H), 7.88 (d, J=7.6 Hz, 1H), 7.80 (dd, J=8.5, 4.1 Hz, 1H), 4.77 (s, 1H), 4.13-3.95 (m, 1H), 3.47-3.37 (m, 1H), 3.28-3.18 (m, 1H), 2.88 (s, 3H), 2.43 (dd, J=23.0, 11.1 Hz, 2H), 2.21 (s, 2H), 2.12-1.91 (m, 2H), 1.14 (s, 3H), 1.13 (s, 3H), 1.12-1.00 (m, 1H), 0.95 (d, J=6.4 Hz, 3H).

Compound 556 (2-(1-Methyl-azetidin-3-yl)-N-[(3R,5S)-5-methyl-1-(8-methyl-[1,7]naphthyridin-5-yl)-piperidin-3-yl]-acetamide): From (3R,5S)-5-Methyl-1-(8-methyl-[1,7] naphthyridin-5-yl)-piperidin-3-ylamine dihydrochloride and (1-Methyl-azetidin-3-yl)-acetic acid hydrochloride. MS: m/z=357 [M+H]+. 1H NMR (400 MHz, DMSO-d6, ppm) δ 9.02 (dd, J=4.1, 1.7 Hz, 1H), 8.43 (dd, J=8.5, 1.7 Hz, 1H), 8.10 (s, 1H), 7.85 (d, J=7.6 Hz, 1H), 7.79 (dd, J=8.5, 4.1 Hz, 1H), 4.03-3.95 (m, 1H), 3.44-3.35 (m, 1H), 3.23 (ddt, J=8.4, 4.6, 2.4 Hz, 3H), 2.88 (s, 3H), 2.73 (td, J=6.3, 2.2 Hz, 2H), 2.61-2.52 (m, 1H), 2.41 (dt, J=15.1, 11.0 Hz, 2H), 2.32 (dd, J=7.7, 1.6 Hz, 2H), 2.14 (s, 3H), 2.05-1.93 (m, 2H), 1.05 (q, J=12.0 Hz, 1H), 0.94 (d, J=6.5 Hz, 3H).

Compound 557 (3-{[[(3R,5S)-5-Methyl-1-(8-methyl-[1,7] naphthyridin-5-yl)-piperidin-3-ylcarbamoyl]-methyl}-azetidine-1-carboxylic acid tert-butyl ester): From (3R,5S)-5-Methyl-1-(8-methyl-[1,7]naphthyridin-5-yl)-piperidin-3-ylamine dihydrochloride and 3-carboxymethyl-azetidine-1-carboxylic acid tert-butyl ester. MS: m/z=454 [M+H]+. 1H NMR (400 MHz, Methanol-d4, ppm) δ 9.02 (dd, J=4.2, 1.7 Hz, 1H), 8.60 (dd, J=8.6, 1.7 Hz, 1H), 8.05 (s, 1H), 7.79 (dd, J=8.6, 4.2 Hz, 1H), 4.25-4.13 (m, 1H), 4.05 (q, J=8.0 Hz, 2H), 3.69-3.58 (m, 2H), 3.56-3.52 (m, 1H), 2.96 (s, 3H), 2.96-2.82 (m, 1H), 2.55-2.43 (m, 4H), 2.18-2.07 (m, 2H), 1.42 (s, 9H), 1.41-1.35 (m, 1H), 1.14 (q, J=12.6 Hz, 1H), 1.04 (d, J=6.4 Hz, 3H).

Compound 558 ((R)-2-Cyclopropyl-2-hydroxy-N-[(3R, 5S)-5-methyl-1-(8-methyl-[1,7]naphthyridin-5-yl)-piperidin-3-yl]-acetamide): From (3R,5S)-5-Methyl-1-(8-methyl-[1,7]naphthyridin-5-yl)-piperidin-3-ylamine dihydrochloride and cyclopropyl-hydroxy-acetic acid. MS: m/z=355 [M+H]+. 1H NMR (400 MHz, DMSO-d6, ppm) δ 9.03 (dd, J=4.1, 1.7 Hz, 1H), 8.46 (dd, J=8.5, 1.7 Hz, 1H), 8.11 (s, 1H), 7.80 (dd, J=8.5, 4.1 Hz, 1H), 7.58 (d, J=8.0 Hz, 1H), 5.28 (s, 1H), 4.13-4.00 (m, 1H), 3.51 (d, J=6.2 Hz, 1H), 3.37-3.33 (m, 1H), 3.26-3.22 (m, 1H), 2.88 (s, 3H), 2.57 (t, J=10.8 Hz, 1H), 2.41 (t, J=11.2 Hz, 1H), 2.09-2.01 (m, 1H), 1.99-1.90 (m, 1H), 1.19 (q, J=12.1 Hz, 1H), 1.09-0.98 (m, 1H), 0.95 (d, J=6.6 Hz, 3H), 0.42-0.23 (m, 4H).

Compound 559 ((S)-2-Cyclopropyl-2-hydroxy-N-[(3R, 5S)-5-methyl-1-(8-methyl-[1,7]naphthyridin-5-yl)-piperidin-3-yl]-acetamide): From (3R,5S)-5-Methyl-1-(8-methyl-[1,7]naphthyridin-5-yl)-piperidin-3-ylamine dihydrochloride and cyclopropyl-hydroxy-acetic acid. MS: m/z=355 [M+H]+. 1H NMR (400 MHz, DMSO-d6, ppm) δ 9.03 (dd, J=4.1, 1.7 Hz, 1H), 8.45 (dd, J=8.5, 1.8 Hz, 1H), 8.10 (s, 1H), 7.80 (dd, J=8.5, 4.1 Hz, 1H), 7.56 (d, J=8.0 Hz, 1H), 5.32 (s, 1H), 4.11-4.03 (m, 1H), 3.53 (d, J=6.0 Hz, 1H), 3.40-3.34 (m, 1H), 3.27-3.20 (m, 1H), 2.88 (s, 3H), 2.57 (t, J=10.8 Hz, 1H), 2.41 (t, J=11.2 Hz, 1H), 2.08-2.03 (m, 1H), 1.99-1.94 (m, 1H), 1.20 (q, J=12.0 Hz, 1H), 1.10-0.98 (m, 1H), 0.95 (d, J=6.5 Hz, 3H), 0.42-0.25 (m, 4H).

Compound 560 (N-[(3R,5S)-5-Methyl-1-(8-methyl-[1,7] naphthyridin-5-yl)-piperidin-3-yl]-2-(1-methyl-pyrrolidin-3-yl)-acetamide): From (3R,5S)-5-Methyl-1-(8-methyl-[1, 7]naphthyridin-5-yl)-piperidin-3-ylamine dihydrochloride and (1-methyl-pyrrolidin-3-yl)-acetic acid hydrochloride. MS: m/z=382 [M+H]+. 1H NMR (400 MHz, Methanol-d4, ppm) δ 9.02 (dd, J=4.2, 1.7 Hz, 1H), 8.60 (dd, J=8.6, 1.7 Hz, 1H), 8.05 (s, 1H), 7.79 (dd, J=8.5, 4.2 Hz, 1H), 4.24-4.17 (m, 1H), 3.60-3.50 (m, 1H), 2.96 (s, 3H), 2.85 (dt, J=9.8, 7.4 Hz, 1H), 2.75-2.56 (m, 3H), 2.49 (td, J=10.9, 6.8 Hz, 2H), 2.40 (d, J=4.0 Hz, 3H), 2.35-2.25 (m, 3H), 2.22-1.99 (m, J=5.1 Hz, 4H), 1.53 (dp, J=14.3, 7.0 Hz, 1H), 1.14 (q, J=12.5 Hz, 1H), 1.04 (d, J=6.4 Hz, 3H).

Example 123: Synthesis of Compound 479 (cis-5-(3-Amino-5-trifluoromethyl-piperidin-1-yl)-quinoline-8-carbonitrile hydrochloride)

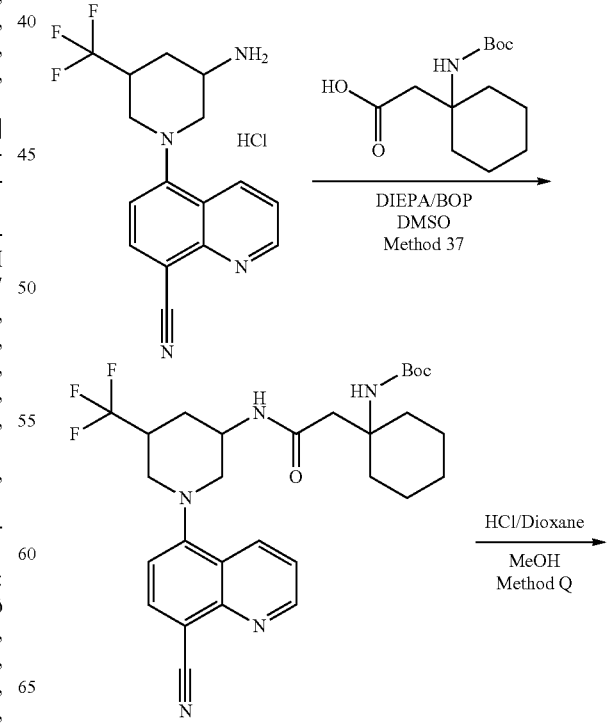

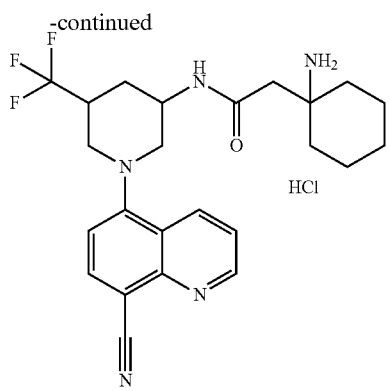

Cis-5-(3-Amino-5-trifluoromethyl-piperidin-1-yl)-quinoline-8-carbonitrile hydrochloride: Cis-5-(3-Amino-5-trifluoromethyl-piperidin-1-yl)-quinoline-8-carbonitrile hydrochloride was prepared from cis-5-(3-Amino-5-trifluoromethyl-piperidin-1-yl)-quinoline-8-carbonitrile hydrochloride and (1-tert-Butoxycarbonylamino-cyclohexyl)-acetic acid, using method 37 and Q.

Compound 479: $^1$H NMR (400 MHz, Methanol-$d_4$, ppm) δ 9.01 (dd, J=4.3, 1.6 Hz, 1H), 8.68 (dd, J=8.6, 1.7 Hz, 1H), 8.17 (d, J=8.0 Hz, 1H), 7.70 (dd, J=8.6, 4.3 Hz, 1H), 7.32 (d, J=8.0 Hz, 1H), 4.42-4.22 (m, 1H), 3.78-3.57 (m, 2H), 3.15-2.86 (m, 2H), 2.62 (t, J=11.2 Hz, 1H), 2.42-2.24 (m, 3H), 1.70-1.21 (m, 11H). MS: m/z=460 [M+H]$^+$.

The following compounds were synthesized in an analogous manner:

Compound 483 (2-(1-Amino-cyclohexyl)-N-[(3R,5S)-5-methyl-1-(8-trifluoromethyl-quinolin-5-yl)-piperidin-3-yl]-acetamide): From (3R,5S)-5-Methyl-1-(8-trifluoromethyl-quinolin-5-yl)-piperidin-3-ylamine hydrochloride and 2-(1-{[(tert-butoxy)carbonyl]amino}cyclohexyl)acetic acid. $^1$H NMR (400 MHz, Methanol-$d_4$, ppm) δ 8.95 (d, J=4.2 Hz, 1H), 8.66 (d, J=8.6 Hz, 1H), 8.04 (d, J=8.0 Hz, 1H), 7.63 (dd, J=8.7, 4.1 Hz, 1H), 7.23 (d, J=8.0 Hz, 1H), 4.25 (s, 1H), 3.63 (d, J=11.4 Hz, 1H), 3.40 (d, J=11.6 Hz, 1H), 2.50 (q, J=11.4 Hz, 2H), 2.31 (s, 2H), 2.14 (d, J=12.6 Hz, 2H), 1.67-1.35 (m, 11H), 1.16 (q, J=12.4 Hz, 1H), 1.05 (d, J=6.2 Hz, 3H). MS: m/z=449 [M+H]$^+$.

Compound 486 and compound 487 (rac-(R)-2-Amino-N-[(3R,5S)-1-(8-cyano-quinolin-5-yl)-5-trifluoromethyl-piperidin-3-yl]-2-cyclopropyl-acetamide and rac-(S)-2-Amino-N-[(3R,5S)-1-(8-cyano-quinolin-5-yl)-5-trifluoromethyl-piperidin-3-yl]-2-cyclopropyl-acetamide): From cis-5-((3-Amino-5-trifluoromethyl-piperidin-1-yl)-quinoline-8-carbonitrile hydrochloride and tert-Butoxycarbonylamino-cyclopropyl-acetic acid. Isomer 1: $^1$H NMR (400 MHz, Methanol-d4, ppm) δ 9.02 (dd, J=4.2, 1.6 Hz, 1H), 8.69 (dd, J=8.6, 1.7 Hz, 1H), 8.18 (d, J=8.0 Hz, 1H), 7.71 (dd, J=8.6, 4.3 Hz, 1H), 7.34 (d, J=8.0 Hz, 1H), 4.34 (dq, J=11.3, 5.2, 4.3 Hz, 1H), 3.68 (d, J=10.5 Hz, 2H), 3.12-2.84 (m, 2H), 2.73-2.50 (m, 2H), 1.65 (q, J=12.2 Hz, 1H), 0.99 (dtd, J=13.2, 8.3, 4.9 Hz, 1H), 0.68-0.23 (m, 3H). MS: m/z=418 [M+H]$^+$. Isomer 2: $^1$H NMR (400 MHz, Methanol-d4, ppm) δ 9.01 (dd, J=4.3, 1.6 Hz, 1H), 8.69 (dd, J=8.6, 1.7 Hz, 1H), 8.17 (d, J=8.0 Hz, 1H), 7.70 (dd, J=8.6, 4.3 Hz, 1H), 7.33 (d, J=8.0 Hz, 1H), 4.34 (ddd, J=15.4, 11.1, 4.2 Hz, 1H), 3.82-3.60 (m, 2H), 3.18-2.87 (m, 2H), 2.69-2.52 (m, 2H), 2.38 (d, J=12.5 Hz, 1H), 1.63 (q, J=12.2 Hz, 1H), 1.03 (qt, J=8.3, 4.9 Hz, 1H), 0.72-0.51 (m, 2H), 0.41 (ddq, J=45.4, 9.3, 5.0 Hz, 2H). MS: m/z=418 [M+H]$^+$.

Compound 493 (2-(4-Amino-tetrahydro-pyran-4-yl)-N-[1-(8-cyano-quinolin-5-yl)-5-trifluoromethyl-piperidin-3-yl]-acetamide hydrochloride): From cis-5-(3-Amino-5-trifluoromethyl-piperidin-1-yl)-quinoline-8-carbonitrile hydrochloride and (4-tert-Butoxycarbonylamino-tetrahydro-pyran-4-yl)-acetic acid. $^1$H NMR (400 MHz, DMSO-$d_6$) δ 9.08 (dd, J=4.2, 1.6 Hz, 1H), 8.78 (d, J=7.1 Hz, 1H), 8.59 (dd, J=8.6, 1.7 Hz, 1H), 8.28 (d, J=8.0 Hz, 1H), 8.16 (s, 3H), 7.72 (dd, J=8.6, 4.2 Hz, 1H), 7.35 (d, J=8.1 Hz, 1H), 3.91-3.66 (m, 3H), 3.67-3.42 (m, 4H), 3.33-3.11 (m, 1H), 2.98 (t, J=11.5 Hz, 1H), 2.78-2.56 (m, 3H), 2.25 (d, J=12.3 Hz, 1H), 1.88-1.41 (m, 5H). MS: m/z=462 [M+H]$^+$.

Compound 561 ((R)-2-Amino-2-cyclopropyl-N-[(3R,5S)-5-methyl-1-(8-methyl-[1,7]naphthyridin-5-yl)-piperidin-3-yl]-acetamide): From (3R,5S)-5-Methyl-1-(8-methyl-[1,7]naphthyridin-5-yl)-piperidin-3-ylamine dihydrochloride and tert-Butoxycarbonylamino-cyclopropyl-acetic acid. MS: m/z=354 [M+H]$^+$. $^1$H NMR (400 MHz, Chloroform-d, ppm) δ 9.02 (dd, J=4.1, 1.7 Hz, 1H), 8.51 (dd, J=8.5, 1.8 Hz, 1H), 8.30 (s, 1H), 8.14 (s, 1H), 7.67 (dd, J=8.5, 4.1 Hz, 1H), 7.14 (d, J=8.1 Hz, 1H), 4.35-4.27 (m, 1H), 3.66-3.61 (m, 2H), 3.35-3.23 (m, 1H), 3.04 (s, 3H), 2.88 (d, J=8.9 Hz, 1H), 2.50 (td, J=10.9, 6.6 Hz, 2H), 2.20-2.09 (m, 2H), 1.16-1.06 (m, 1H), 1.03 (d, J=6.5 Hz, 3H), 0.72-0.53 (m, 3H), 0.37-0.33 (m, 1H).

Compound 562 ((S)-2-Amino-2-cyclopropyl-N-[(3R,5S)-5-methyl-1-(8-methyl-[1,7]naphthyridin-5-yl)-piperidin-3-yl]-acetamide): From (3R,5S)-5-Methyl-1-(8-methyl-[1,7]naphthyridin-5-yl)-piperidin-3-ylamine dihydrochloride and tert-Butoxycarbonylamino-cyclopropyl-acetic acid. MS: m/z=354 [M+H]$^+$. $^1$H NMR (400 MHz, Chloroform-d, ppm) δ 8.99 (dd, J=4.2, 1.7 Hz, 1H), 8.41 (dd, J=8.5, 1.8 Hz, 1H), 8.10 (s, 1H), 7.68-7.48 (m, 2H), 4.96 (bs, 3H), 4.25 (bs, 1H), 3.62-3.45 (m, 1H), 3.28-3.22 (m, 1H), 3.01 (s, 3H), 2.61-2.43 (m, 1H), 2.39 (t, J=11.1 Hz, 1H), 2.19-2.04 (m, 2H), 1.18-1.05 (m, 2H), 0.99 (d, J=6.3 Hz, 3H), 0.57 (bs, 3H), 0.38 (bs, 1H).

Compound 563 (2-(1-Amino-cyclohexyl)-N-[(3R,5S)-5-methyl-1-(8-methyl-[1,7]naphthyridin-5-yl)-piperidin-3-yl]-acetamide): From (3R,5S)-5-Methyl-1-(8-methyl-[1,7]naphthyridin-5-yl)-piperidin-3-ylamine dihydrochloride and (1-tert-Butoxycarbonylamino-cyclohexyl)-acetic acid, followed by de-Boc using Method Q. MS: m/z=396 [M+H]$^+$. $^1$H NMR (400 MHz, Methanol-d4, ppm) δ 9.02 (dd, J=4.1, 1.7 Hz, 1H), 8.59 (dd, J=8.5, 1.8 Hz, 1H), 8.55 (bs, 1H), 8.06 (s, 1H), 7.78 (dd, J=8.6, 4.2 Hz, 1H), 4.28-4.21 (m, 1H), 3.61-3.53 (m, 1H), 3.37-3.35 (m, 1H), 2.97 (s, 3H), 2.70-2.41 (m, 4H), 2.20-2.08 (m, 2H), 1.88-1.47 (m, 9H), 1.45-1.35 (m, 1H), 1.16 (q, J=12.6 Hz, 1H), 1.04 (d, J=6.4 Hz, 3H).

Example 124: Synthesis of Compound 480 (cis-N-[1-(8-Cyano-quinolin-5-yl)-5-trifluoromethyl-piperidin-3-yl]-succinamide)

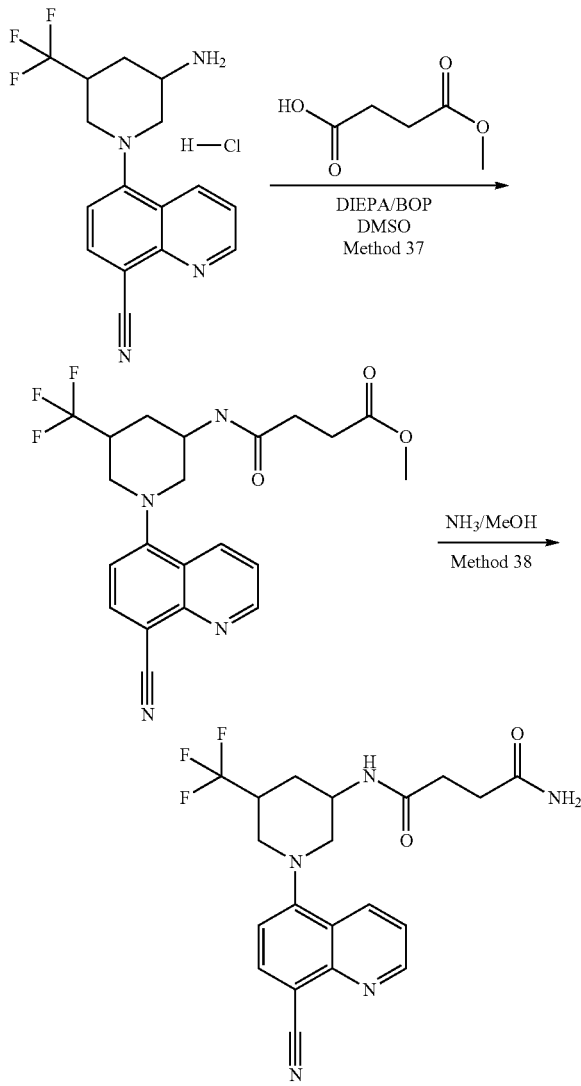

Cis-N-[1-(8-Cyano-quinolin-5-yl)-5-trifluoromethyl-piperidin-3-yl]-succinamic acid methyl ester: Cis-N-[(3R,5S)-1-(8-Cyano-quinolin-5-yl)-5-trifluoromethyl-piperidin-3-yl]-succinamic acid methyl ester was prepared from 5-((3R,5S)-3-Amino-5-trifluoromethyl-piperidin-1-yl)-quinoline-8-carbonitrile hydrochloride and Succinic acid monomethyl ester using method 37.

Method 38 cis-N-[1-(8-Cyano-quinolin-5-yl)-5-trifluoromethyl-piperidin-3-yl]-succinamide: A solution of cis-N-[1-(8-Cyano-quinolin-5-yl)-5-trifluoromethyl-piperidin-3-yl]-succinamic acid methyl ester (55 mg; 0.13 mmol) in ammonia 7.0M in methanol (2.00 mL; 14.00 mmol) was stirred at 60° C. for 1 hr, The reaction mixture was concentrated under reduced pressure and the residue was purified by reverse phase chromatography (XBridge column), eluting with acetonitrile in water (0.1% $NH_3.H_2O$), 20% to 70% gradient, to afford cis-N-[(3R,5S)-1-(8-Cyano-quinolin-5-yl)-5-trifluoromethyl-piperidin-3-yl]-succinamide (5 mg, 9%).

Compound 480: $^1$H NMR (400 MHz, DMSO-$d_6$) δ 9.06 (dd, J=4.2, 1.6 Hz, 1H), 8.58 (dd, J=8.6, 1.7 Hz, 1H), 8.25 (d, J=8.0 Hz, 1H), 8.02 (d, J=7.3 Hz, 1H), 7.72 (dd, J=8.6, 4.2 Hz, 1H), 7.32 (d, J=8.1 Hz, 1H), 7.25 (s, 1H), 6.70 (s, 1H), 4.23 (d, J=10.5 Hz, 1H), 3.57 (d, J=11.5 Hz, 2H), 2.94 (t, J=11.6 Hz, 1H), 2.60 (t, J=11.2 Hz, 1H), 2.35-2.25 (m, 3H), 2.18 (d, J=12.3 Hz, 1H), 1.50 (q, J=12.3 Hz, 1H). MS: m/z=420 [M+H]$^+$.

The following compounds were synthesized in an analogous manner:

Compound 482 (cis-4-Azetidin-1-yl-N-[(1-(8-cyano-quinolin-5-yl)-5-trifluoromethyl-piperidin-3-yl]-4-oxo-butyramide): From cis-N-[1-(8-Cyano-quinolin-5-yl)-5-trifluoromethyl-piperidin-3-yl]-succinamic acid methyl ester and Azetidine. $^1$H NMR (400 MHz, DMSO-$d_6$) δ 9.06 (dd, J=4.2, 1.6 Hz, 1H), 8.58 (dd, J=8.6, 1.7 Hz, 1H), 8.25 (d, J=8.0 Hz, 1H), 8.04 (d, J=7.3 Hz, 1H), 7.72 (dd, J=8.6, 4.2 Hz, 1H), 7.32 (d, J=8.1 Hz, 1H), 4.10 (t, J=7.6 Hz, 3H), 3.79 (td, J=7.8, 2.8 Hz, 2H), 3.56 (d, J=11.7 Hz, 2H), 3.20 (d, J=10.9 Hz, 1H), 2.95 (t, J=11.6 Hz, 1H), 2.60 (t, J=11.2 Hz, 1H), 2.38-1.99 (m, 7H), 1.50 (q, J=12.3 Hz, 1H). MS: m/z=460 [M+H]$^+$.

Compound 492 cis-(N-1-(8-Cyano-quinolin-5-yl)-5-trifluoromethyl-piperidin-3-yl]-N'-methyl-succinamide): From cis-N-[1-(8-Cyano-quinolin-5-yl)-5-trifluoromethyl-piperidin-3-yl]-succinamic acid methyl ester and Methylamine. $^1$H NMR (400 MHz, DMSO-$d_6$) δ 9.06 (dd, J=4.2, 1.6 Hz, 1H), 8.58 (dd, J=8.6, 1.7 Hz, 1H), 8.25 (d, J=8.0 Hz, 1H), 8.03 (d, J=7.3 Hz, 1H), 7.72 (dd, J=8.6, 4.2 Hz, 2H), 7.32 (d, J=8.1 Hz, 1H), 4.15 (m, 1H), 3.68-3.50 (m, 2H), 3.20 (d, J=10.0 Hz, 1H), 2.94 (t, J=11.6 Hz, 1H), 2.54 (d, J=4.6 Hz, 3H), 2.30 (qd, J=6.7, 6.0, 4.2 Hz, 4H), 2.18 (d, J=12.1 Hz, 1H), 1.50 (q, J=12.3 Hz, 1H). MS: m/z=434 [M+H]$^+$.

Compound 564 (N-[(3R,5S)-5-Methyl-1-(8-methyl-[1,7]naphthyridin-5-yl)-piperidin-3-yl]-succinamide): From (3R,5S)-5-Methyl-1-(8-methyl-[1,7]naphthyridin-5-yl)-piperidin-3-ylamine dihydrochloride and mono-methyl succinate, followed by reacting with ammonia in methanol at 50° C. overnight. MS: m/z=356 [M+H]$^+$. $^1$H NMR (400 MHz, DMSO-$d_6$, ppm) δ 9.02 (dd, J=4.1, 1.7 Hz, 1H), 8.44 (dd, J=8.5, 1.7 Hz, 1H), 8.10 (s, 1H), 7.84 (d, J=7.5 Hz, 1H), 7.79 (dd, J=8.5, 4.1 Hz, 1H), 7.24 (s, 1H), 6.69 (s, 1H), 4.05-3.95 (m, 1H), 3.48-3.36 (m, 1H), 3.24 (d, J=10.5 Hz, 1H), 2.88 (s, 3H), 2.41 (q, J=11.3 Hz, 2H), 2.36-2.21 (m, 4H), 2.10-1.92 (m, 2H), 1.05 (q, J=12.0 Hz, 1H), 0.95 (d, J=6.5 Hz, 3H).

Compound 565 (N-Methyl-N'-[(3R,5S)-5-methyl-1-(8-methyl-[1,7]naphthyridin-5-yl)-piperidin-3-yl]-succinamide): From (3R,5S)-5-Methyl-1-(8-methyl-[1,7]naphthyridin-5-yl)-piperidin-3-ylamine dihydrochloride and mono-methyl succinate, followed by reacting with methylamine in ethanol at rt overnight. MS: m/z=370 [M+H]$^+$. $^1$H NMR (400 MHz, DMSO-$d_6$, ppm) δ 9.02 (dd, J=4.1, 1.7 Hz, 1H), 8.44 (dd, J=8.5, 1.7 Hz, 1H), 8.10 (s, 1H), 7.86 (d, J=7.5 Hz, 1H), 7.79 (dd, J=8.5, 4.1 Hz, 1H), 7.71 (d, J=5.4 Hz, 1H), 4.05-3.94 (m, 1H), 3.43-3.37 (m, 1H), 3.24 (d, J=10.1 Hz, 1H), 2.88 (s, 3H), 2.54 (d, J=4.6 Hz, 3H), 2.41 (q, J=11.2 Hz, 2H), 2.35-2.24 (m, 4H), 2.07-1.93 (m, 2H), 1.05 (q, J=12.0 Hz, 1H), 0.95 (d, J=6.4 Hz, 3H).

Compound 566 (4-Azetidin-1-yl-N-[(3R,5S)-5-methyl-1-(8-methyl-[1,7]naphthyridin-5-yl)-piperidin-3-yl]-4-oxo-butyramide): From (3R,5S)-5-Methyl-1-(8-methyl-[1,7]naphthyridin-5-yl)-piperidin-3-ylamine dihydrochloride and mono-methyl succinate, followed by reacting with azetidine in ethanol at rt overnight. MS: m/z=396 [M+H]$^+$. $^1$H NMR (400 MHz, DMSO-$d_6$, ppm) δ 9.03 (dd, J=4.1, 1.7 Hz, 1H), 8.44 (dd, J=8.5, 1.7 Hz, 1H), 8.41 (s, 1H), 8.10 (s, 1H), 7.88 (d, J=7.4 Hz, 1H), 7.80 (dd, J=8.5, 4.1 Hz, 1H), 4.09 (t, J=7.7

Hz, 2H), 4.04-3.96 (m, 1H), 3.78 (td, J=7.8, 2.2 Hz, 2H), 3.42-3.38 (m, 1H), 3.25-3.22 (m, 1H), 2.88 (s, 3H), 2.41 (td, J=10.9, 7.6 Hz, 2H), 2.35-2.26 (m, 2H), 2.26-2.18 (m, 2H), 2.18-2.08 (m, 2H), 2.08-1.90 (m, 2H), 1.05 (q, J=12.0 Hz, 1H), 0.95 (d, J=6.5 Hz, 3H).

Example 125: Synthesis of Compound 488 ((3R, 5S)-1-(7-Fluoro-8-methyl-quinolin-5-yl)-5-methyl-piperidin-3-ylamine hydrochloride)

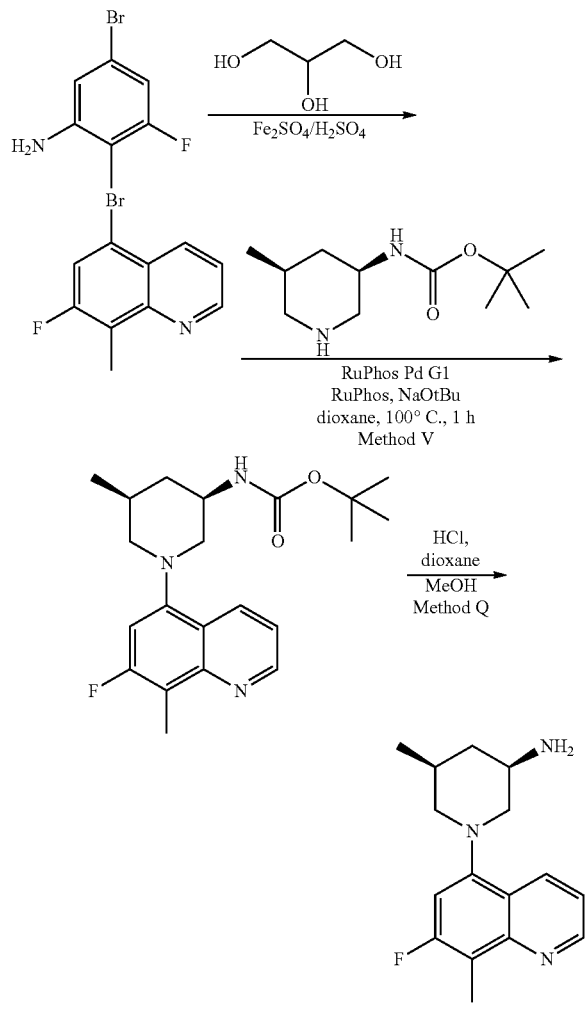

5-Bromo-7-fluoro-8-methyl-quinoline: A mixture of 5-bromo-3-fluoro-2-methyl-phenylamine (2.91 g; 14.3 mmol), glycerol (4.20 mL; 57.1 mmol), iron (II) sulfate heptahydrate (793 mg; 2.85 mmol) and sulfuric acid (4.66 mL; 85.6 mmol) was stirred at 120° C. for 2 hours. After the reaction mixture was cooled to room temperature, ice (50 g) and solid sodium hydroxide (4.5 g) were added, the mixture was stirred for 30 min and extracted with dichloromethane (70 mL×3). The combined organic layer was washed with brine (10 mL), dried over anhydrous magnesium sulfate and concentrated under reduced pressure. The residue was purified by chromatography on a silica gel column, eluting ethyl acetate and hexanes, to afford 5-bromo-7-fluoro-8-methyl-quinoline (1.10 g, 32%). $^1$H NMR (400 MHz, Chloroform-d, ppm) δ 8.99 (dd, J=4.2, 1.7 Hz, 1H), 8.53 (dd, J=8.5, 1.7 Hz, 1H), 7.68 (d, J=8.8 Hz, 1H), 7.50 (dd, J=8.5, 4.2 Hz, 1H), 2.70 (d, J=2.5 Hz, 3H). MS: m/z=239 [M+H]$^+$.

[(3R,5S)-1-(7-Fluoro-8-methyl-quinolin-5-yl)-5-methyl-piperidin-3-yl]-carbamic acid tert-butyl ester: [(3R,5S)-1-(7-Fluoro-8-methyl-quinolin-5-yl)-5-methyl-piperidin-3-yl]-carbamic acid tert-butyl ester was prepared from 5-bromo-7-fluoro-8-methyl-quinoline and ((3R,5S)-5-Methyl-piperidin-3-yl)-carbamic acid tert-butyl ester in 56% yield using method V. $^1$H NMR (400 MHz, DMSO-d, ppm) δ 8.94 (dd, J=4.2, 1.7 Hz, 1H), 8.43 (dd, J=8.5, 1.7 Hz, 1H), 7.53 (s, 1H), 7.04 (d, J=11.5 Hz, 1H), 6.93 (d, J=7.6 Hz, 1H), 3.73 (s, 1H), 3.36 (s, 1H), 3.18 (d, J=11.5 Hz, 1H), 2.54 (d, J=2.3 Hz, 3H), 2.34 (dt, J=27.7, 10.9 Hz, 2H), 2.08-1.80 (m, 2H), 1.39 (s, 8H), 1.03 (q, J=12.2 Hz, 1H), 0.93 (d, J=6.4 Hz, 3H). MS: n/z=374 [M+H]$^+$.

(3R,5S)-1-(7-Fluoro-8-methyl-quinolin-5-yl)-5-methyl-piperidin-3-ylamine hydrochloride: (3R,5S)-1-(7-Fluoro-8-methyl-quinolin-5-yl)-5-methyl-piperidin-3-ylamine hydrochloride was prepared from [(3R,5S)-1-(7-Fluoro-8-methyl-quinolin-5-yl)-5-methyl-piperidin-3-yl]-carbamic acid tert-butyl ester in 88% yield, using method Q.

Compound 388: $^1$H NMR (400 MHz, DMSO-d$_6$) δ 9.01 (dd, J=4.4, 1.7 Hz, 1H), 8.56 (d, J=8.3 Hz, 1H), 8.29 (s, 3H), 7.61 (dd, J=8.5, 4.4 Hz, 1H), 0.16 (d, J=11.4 Hz, 1H), 3.27-3.11 (m, 1H), 2.71-2.59 (m, 1H), 2.57 (d, J=2.3 Hz, 3H), 2.43 (t, J=11.3 Hz, 1H), 2.18 (d, J=12.4 Hz, 1H), 2.06 (s, 1H), 1.18 (q, J=11.9 Hz, 1H), 0.98 (d, J=6.6 Hz, 3H). MS: m/z=274 [M+H]$^+$.

The following compounds were synthesized in an analogous manner:

Compound 389 ((3R,5S)-1-(6-Fluoro-8-methyl-quinolin-5-yl)-5-methyl-piperidin-3-ylamine): From 5-Bromo-6-fluoro-8-methyl-quinoline and ((3R,5S)-5-Methyl-piperidin-3-yl)-carbamic acid tert-butyl ester. $^1$H NMR (400 MHz, DMSO-d$_6$) 8.89 (dd, J=4.1, 1.8 Hz, 1H), 8.58 (dd, J=8.5, 1.8 Hz, 1H), 7.65-7.54 (m, 1H), 7.51 (dd, J=13.1, 1.2 Hz, 1H), 3.06 (d, J=11.1 Hz, 1H), 2.95 (d, J=11.3 Hz, 2H), 2.78-2.58 (m, 5H), 2.02-1.83 (m, 2H), 1.60 (s, 2H), 0.97-0.84 (m, 3H). MS: n/z=274 [M+H]$^+$.

Example 126: Separation of Compound 494 and Compound 495 (4-Azetidin-1-yl-N-[(3R,5S)-1-(8-cyano-quinolin-5-yl)-5-trifluoromethyl-piperidin-3-yl]-4-oxo-butyramide and 4-Azetidin-1-yl-N-[(3S, 5R)-1-(8-cyano-quinolin-5-yl)-5-trifluoromethyl-piperidin-3-yl]-4-oxo-butyramide)

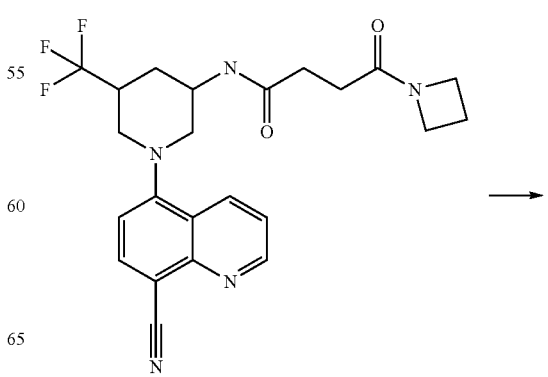

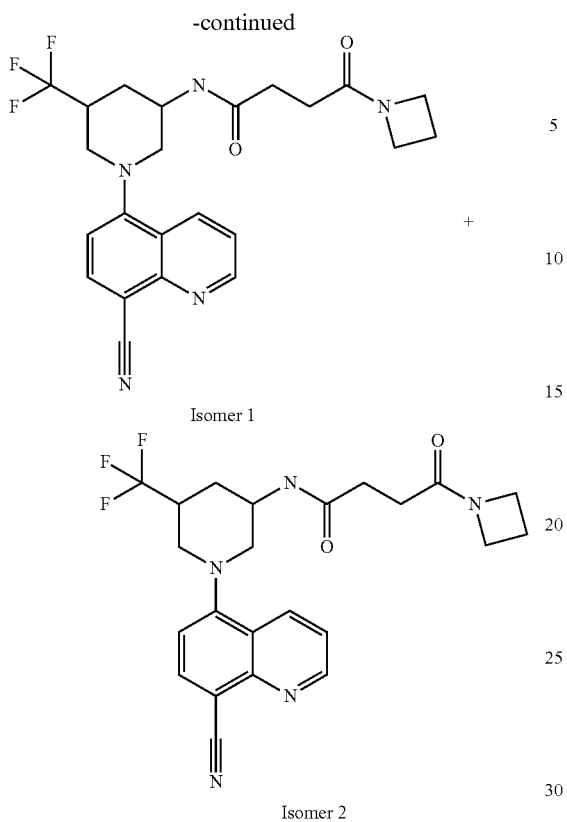

Isomer 1

Isomer 2

The title compounds were isolated via chiral SFC chromatography of compound 482. (Column: Phenomenex 250× 21.20 mm Lux Cellulose-2; CO₂ Co-solvent (Solvent B): Methanol; Isocratic Method: 40% Co-solvent at 70 mL/min; System Pressure: 100 bar; Column Temperature: 40° C.).

Isomer 1: MS: m/z=460 [M+H]⁺.
Isomer 2: MS: m/z=460 [M+H]⁺.

The following compounds were synthesized in an analogous manner:

Compound 497 and compound 498 (2-(1-Amino-cyclohexyl)-N-[(3R,5S)-1-(8-cyano-quinolin-5-yl)-5-trifluoromethyl-piperidin-3-yl]-acetamide and 2-(1-Amino-cyclohexyl)-N-[(3S,5R)-1-(8-cyano-quinolin-5-yl)-5-trifluoromethyl-piperidin-3-yl]-acetamide): From compound 479 (Column: CHIRALPAK 10×250 mm IC; CO₂ Co-solvent (Solvent B): Ethanol with 0.5% dimethylethylamine; Isocratic Method: 55% Co-solvent at 9 mL/min; System Pressure: 100 bar; Column Temperature: 30° C.). Isomer 1: MS: m/z=460 [M+H]⁺. Isomer 2: MS: m/z=460 [M+H]⁺.

Compound 520 and compound 521 ((R)-2-Cyclopropyl-2-hydroxy-N-[(3R,5S)-5-methyl-1-(8-trifluoromethyl-quinolin-5-yl)-piperidin-3-yl]-acetamide and S)-2-Cyclopropyl-2-hydroxy-N-[(3R,5S)-5-methyl-1-(8-trifluoromethyl-quinolin-5-yl)-piperidin-3-yl]-acetamide): From compound 515 (Column: CHIRALPAK 10×250 mm ADH; CO2 Co-solvent (Solvent B): Methanol with 0.5% dimethylethylamine; Isocratic Method: 40% Co-solvent at 8 mL/min; System Pressure: 100 bar; Column Temperature: 35° C.). Isomer 1: MS: m/z=408 [M+H]⁺. Isomer 2: MS: m/z=408 [M+H]⁺.

Compound 522 and compound 523 (N—[(S)-1-(8-Cyano-quinoxalin-5-yl)-5,5-difluoro-piperidin-3-yl]-2-(1-methyl-piperidin-4-yl)-acetamide and N—[(R)-1-(8-Cyano-quinoxalin-5-yl)-5,5-difluoro-piperidin-3-yl]-2-(1-methyl-piperidin-4-yl)-acetamide): From compound 504 (Column: CHIRALPAK 10×250 mm IF; CO2 Co-solvent (Solvent B): Ethanol with 0.5% dimethylethylamine; Isocratic Method: 55% Co-solvent at 8 mL/min; System Pressure: 100 bar; Column Temperature: 35° C.). Isomer 1: MS: m/z=429 [M+H]⁺. Isomer 2: MS: m/z=429 [M+H]⁺.

Compound 527 and compound 528 ((S)-5,5-Difluoro-1-(8-trifluoromethyl-quinolin-5-yl)-piperidin-3-ylamine and (R)-5,5-Difluoro-1-(8-trifluoromethyl-quinolin-5-yl)-piperidin-3-ylamine): From compound 510 (Column: CHIRALPAK 10×250 mm IF; CO₂ Co-solvent (Solvent B): Ethanol with 0.5% dimethylethylamine; Isocratic Method: 55% Co-solvent at 4 mL/min; System Pressure: 100 bar; Column Temperature: 40° C.). Isomer 1: MS: m/z=332 [M+H]⁺. Isomer 2: MS: m/z=332 [M+H]⁺.

Example 127: Synthesis of Compound 499 (8-((3R, 5S)-3-Amino-5-fluoro-piperidin-1-yl)-quinoxaline-5-carbonitrile hydrochloride)

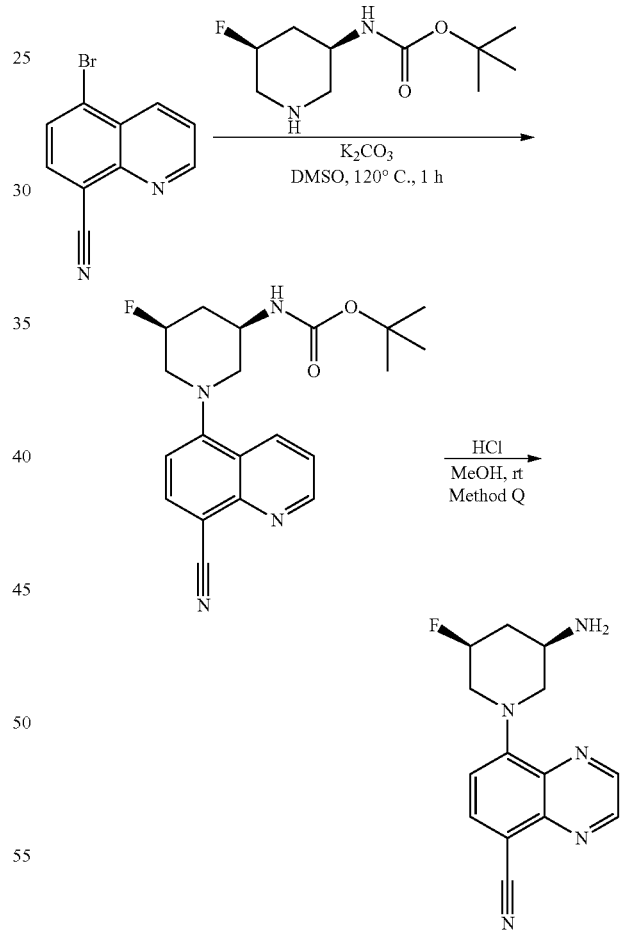

[(3R,5S)-1-(8-Cyano-quinoxalin-5-yl)-5-fluoro-piperidin-3-yl]-carbamic acid tert-butyl ester: A mixture of 8-Bromo-quinoxaline-5-carbonitrile (84 mg; 0.36 mmol), ((S)-5-Fluoro-piperidin-3-yl)-carbamic acid tert-butyl ester (94 mg; 0.43 mmol) dipotassium carbonate (64 mg; 0.47 mmol) and DMSO (2 mL) was microwaved at 120° C. for 1 hour. The reaction mixture was purified by reverse phase chromatography (XBridge column), eluting with acetonitrile in water (0.1% NH₃.H₂O), to afford [(3R,5S)-1-(8-Cyano-quinoxalin-5-yl)-5-fluoro-piperidin-3-yl]-carbamic acid tert-butyl ester. ¹H NMR (400 MHz, DMSO-d₆) δ 9.07 (d, J=1.8 Hz, 1H), 8.99 (d, J=1.8 Hz, 1H), 8.25 (d, J=8.4 Hz, 1H), 7.33 (d, J=8.4 Hz, 1H), 7.02 (d, J=7.6 Hz, 1H), 4.85 (dt, J=9.2, 4.7 Hz, 1H), 4.49 (s, 1H), 3.93 (d, J=12.1 Hz, 1H), 3.73 (s, 1H), 3.17 (ddd, J=13.2, 9.1, 4.9 Hz, 1H), 3.04 (t, J=10.9 Hz, 1H), 1.76 (q, J=11.1 Hz, 1H), 1.40 (s, 9H). MS: m/z=373 [M+H]⁺.

8-((3R,5S)-3-Amino-5-fluoro-piperidin-1-yl)-quinoxaline-5-carbonitrile hydrochloride: 8-((3R,5S)-3-Amino-5-fluoro-piperidin-1-yl)-quinoxaline-5-carbonitrile hydrochloride was prepared from [(3R,5S)-1-(8-Cyano-quinoxalin-5-yl)-5-fluoro-piperidin-3-yl]-carbamic acid tert-butyl ester using method Q.

Compound 499: ¹H NMR (400 MHz, DMSO-d₆) δ 9.20-9.07 (m, 1H), 9.03 (d, J=1.8 Hz, 1H), 8.42-8.12 (m, 4H), 7.38 (d, J=8.4 Hz, 1H), 5.19-4.93 (m, 1H), 3.93 (ddd, J=33.2, 13.0, 8.3 Hz, 2H), 3.78 (dd, J=12.6, 3.0 Hz, 1H), 2.46-2.29 (m, 1H), 2.22-2.07 (m, 1H). MS: m/z=273 [M+H]⁺.

The following compounds were synthesized in an analogous manner:

Compound 500 ([(3R,5S)-1-(8-Cyano-quinolin-5-yl)-5-fluoro-piperidin-3-yl]-carbamic acid tert-butyl ester): From 5-Bromo-quinoline-8-carbonitrile and ((3R,5S)-5-Fluoro-piperidin-3-yl)-carbamic acid tert-butyl ester. ¹H NMR (400 MHz, DMSO-d₆) δ 9.06 (dd, J=4.2, 1.6 Hz, 1H), 8.55 (d, J=8.6 Hz, 1H), 8.25 (d, J=8.1 Hz, 1H), 7.71 (dd, J=8.7, 4.2 Hz, 1H), 7.30 (d, J=8.1 Hz, 1H), 6.97 (d, J=7.4 Hz, 1H), 4.99 (s, 1H), 3.85 (s, 1H), 3.63 (s, 1H), 3.44 (d, J=11.8 Hz, 1H), 3.00 (s, 1H), 2.71 (t, J=10.9 Hz, 1H), 2.37 (t, J=11.9 Hz, 1H), 1.70 (t, J=11.1 Hz, 1H), 1.39 (s, 5H). MS: m/z=372 [M+H]⁺.

Compound 501 (8-((3S,5R)-3-Amino-5-fluoro-piperidin-1-yl)-quinoxaline-5-carbonitrile hydrochloride): From [(3S,5R)-1-(8-Cyano-quinoxalin-5-yl)-5-fluoro-piperidin-3-yl]-carbamic acid tert-butyl ester. ¹H NMR (400 MHz, Methanol-d₄) δ 9.06 (d, J=1.8 Hz, 1H), 8.99 (d, J=1.8 Hz, 1H), 8.23 (d, J=8.2 Hz, 1H), 7.41 (d, J=8.2 Hz, 1H), 5.16 (dt, J=46.0, 2.7 Hz, 1H), 4.55-4.38 (m, 1H), 4.05-3.89 (m, 1H), 3.81 (s, 1H), 3.59 (ddd, J=36.7, 13.4, 1.8 Hz, 1H), 3.38 (dd, J=13.5, 1.9 Hz, 1H), 2.58-2.43 (m, 1H), 2.39 (ddd, J=15.8, 4.4, 3.1 Hz, 1H), 2.28 (ddd, J=15.8, 4.5, 3.1 Hz, 1H). MS: m/z=273 [M+H]⁺.

Example 128: Synthesis of Compound 502 (N-[(3R,5S)-1-(8-Cyano-quinoxalin-5-yl)-5-fluoro-piperidin-3-yl]-2-(4-methyl-piperazin-1-yl)-acetamide)

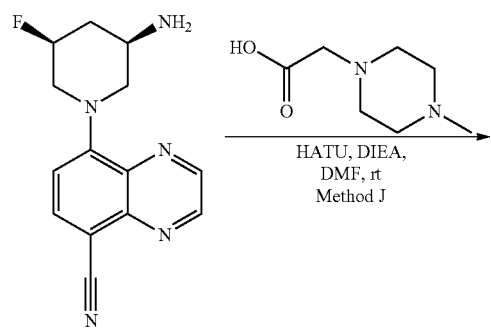

-continued

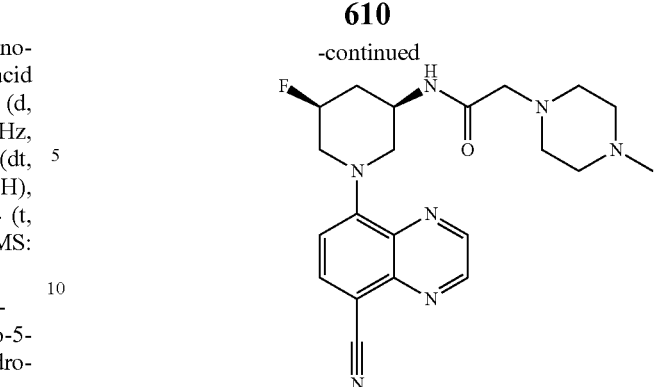

N-[(3R,5S)-1-(8-Cyano-quinoxalin-5-yl)-5-fluoro-piperidin-3-yl]-2-(4-methyl-piperazin-1-yl)-acetamide: N-[(3R,5S)-1-(8-Cyano-quinoxalin-5-yl)-5-fluoro-piperidin-3-yl]-2-(4-methyl-piperazin-1-yl)-acetamide was prepared from (4-methyl-piperazin-1-yl)-acetic and 8-((3R,5S)-3-Amino-5-fluoro-piperidin-1-yl)-quinoxaline-5-carbonitrile hydrochloride using method J. ¹H NMR (400 MHz, DMSO-d₆) δ 9.07 (d, J=1.8 Hz, 1H), 8.96 (d, J=1.8 Hz, 1H), 8.24 (d, J=8.4 Hz, 1H), 8.12 (d, J=7.4 Hz, 1H), 7.31 (d, J=8.4 Hz, 1H), 5.00 (s, 1H), 4.20-4.01 (m, 2H), 3.98 (d, J=14.5 Hz, 1H), 3.82 (dd, J=29.6, 12.7 Hz, 1H), 3.52 (d, J=11.8 Hz, 1H), 2.97-2.75 (m, 2H), 2.33 (d, J=24.5 Hz, 4H), 2.11 (d, J=4.5 Hz, 3H), 2.01 (s, 3H). MS: m/z=412 [M+H]⁺.

Example 129: Synthesis of Compound 503 (N-[1-(8-Cyano-quinoxalin-5-yl)-5,5-difluoro-piperidin-3-yl]-2-(4-methyl-piperazin-1-yl)-acetamide)

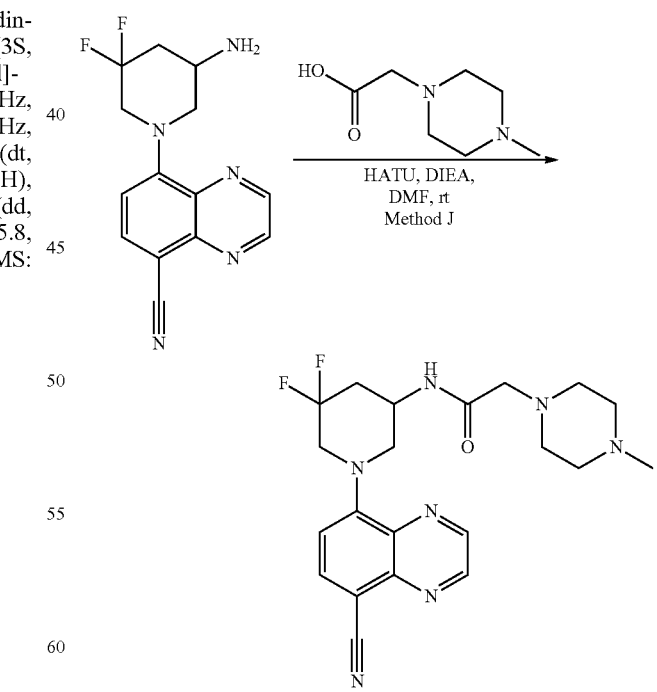

N-[1-(8-Cyano-quinoxalin-5-yl)-5,5-difluoro-piperidin-3-yl]-2-(4-methyl-piperazin-1-yl)-acetamide: N-[1-(8-Cyano-quinoxalin-5-yl)-5,5-difluoro-piperidin-3-yl]-2-(4-methyl-piperazin-1-yl)-acetamide was prepared from (4-methyl-piperazin-1-yl)-acetic acid and 8-(5-Amino-3,3-difluoro-piperidin-1-yl)-quinoxaline-5-carbonitrile hydrochloride using method J.

Compound 503: ¹H NMR (400 MHz, DMSO-d$_6$) δ 9.11 (d, J=1.8 Hz, 1H), 9.01 (d, J=1.8 Hz, 1H), 8.30 (d, J=8.4 Hz, 1H), 8.21 (d, J=7.6 Hz, 1H), 7.41 (d, J=8.4 Hz, 1H), 4.32-4.11 (m, 2H), 3.98 (s, 1H), 3.87-3.62 (m, 2H), 2.39 (d, J=13.8 Hz, 5H), 2.14 (s, 3H), 2.02 (s, 3H). MS: m/z=430 [M+H]⁺.

The following compounds were synthesized in an analogous manner:

Compound 504 (N-[1-(8-Cyano-quinoxalin-5-yl)-5,5-difluoro-piperidin-3-yl]-2-(1-methyl-piperidin-4-yl)-acetamide (racemic)): From (1-Methyl-piperidin-4-yl)-acetic acid and 8-(5-Amino-3,3-difluoro-piperidin-1-yl)-quinoxaline-5-carbonitrile hydrochloride. ¹H NMR (400 MHz, DMSO-d$_6$) δ 9.09 (d, J=1.8 Hz, 1H), 8.99 (d, J=1.8 Hz, 1H), 8.30 (d, J=8.4 Hz, 1H), 8.12 (d, J=6.9 Hz, 1H), 7.45 (d, J=8.4 Hz, 1H), 4.80 (s, 1H), 4.20 (s, 1H), 4.07 (d, J=13.4 Hz, 1H), 3.79 (dd, J=29.1, 13.5 Hz, 2H), 3.16 (dd, J=13.0, 10.2 Hz, 2H), 2.71 (d, J=11.4 Hz, 2H), 2.41 (m, 2H), 2.13 (s, 3H), 2.06 (d, J=6.8 Hz, 1H), 1.82 (t, J=11.2 Hz, 2H), 1.60 (d, J=12.9 Hz, 2H), 1.18 (q, J=11.9, 11.3 Hz, 2H). MS: n/z=429 [M+H]⁺.

Compound 506 (2-Chloro-N-[1-(8-cyano-quinoxalin-5-yl)-5,5-difluoro-piperidin-3-yl]-propionamide): From 2-Chloro-propionic acid and 8-(5-Amino-3,3-difluoro-piperidin-1-yl)-quinoxaline-5-carbonitrile hydrochloride. ¹H NMR (400 MHz, DMSO-d$_6$) δ 9.10 (d, J=1.8 Hz, 1H), 9.00 (d, J=1.8 Hz, 1H), 8.56 (d, J=6.9 Hz, 1H), 8.31 (d, J=8.3 Hz, 1H), 7.44 (dd, J=8.4, 3.6 Hz, 1H), 4.75-4.45 (m, 2H), 4.21 (s, 1H), 3.97 (t, J=11.3 Hz, 1H), 3.82 (dd, J=25.6, 13.4 Hz, 1H), 3.41-3.32 (m, 1H), 2.44 (d, J=13.2 Hz, 1H), 2.26 (s, 1H), 1.59 (dd, J=6.8, 2.4 Hz, 3H). MS: m/z=380 [M+H]⁺.

Example 130: Synthesis of Compound 505 (3-Amino-N-[1-(8-cyano-quinoxalin-5-yl)-5,5-difluoro-piperidin-3-yl]-3-methyl-butyramide hydrochloride)

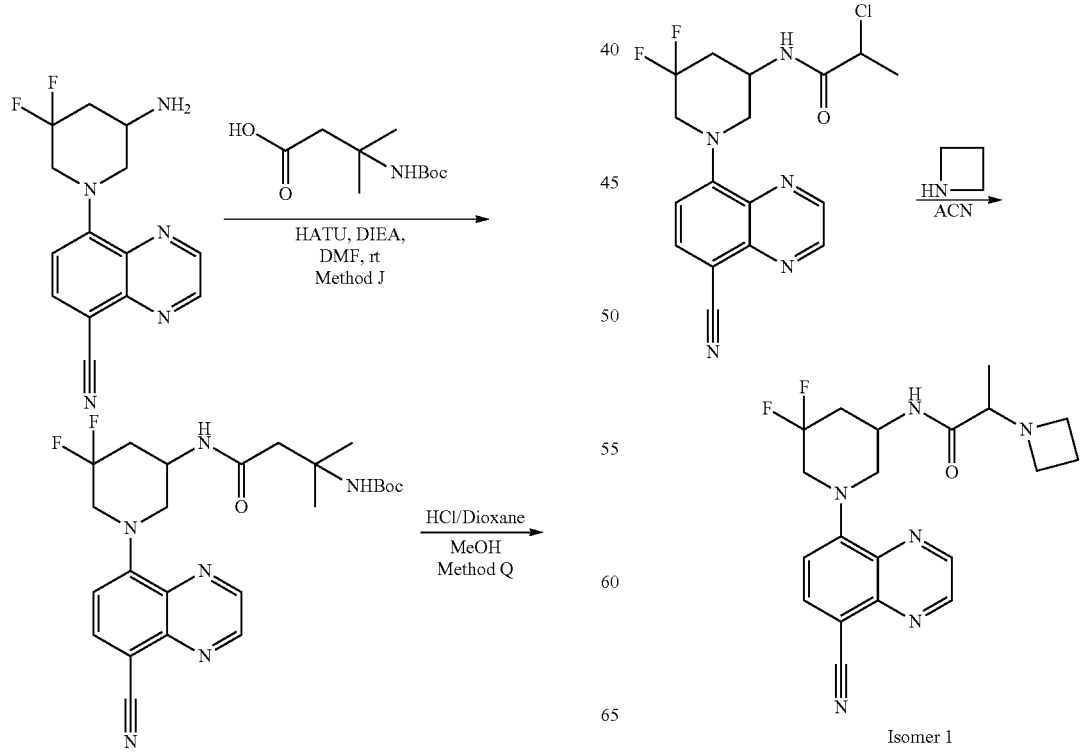

-continued

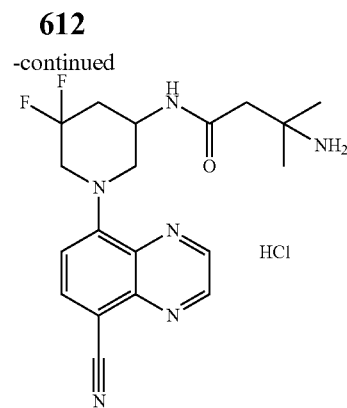

3-Amino-N-[1-(8-cyano-quinoxalin-5-yl)-5,5-difluoro-piperidin-3-yl]-3-methyl-butyramide hydrochloride: 3-Amino-N-[1-(8-cyano-quinoxalin-5-yl)-5,5-difluoro-piperidin-3-yl]-3-methyl-butyramide hydrochloride was prepared from 3-tert-Butoxycarbonylamino-3-methyl-butyric acid and 8-(5-Amino-3,3-difluoro-piperidin-1-yl)-quinoxaline-5-carbonitrile hydrochloride using method J and Q.

Compound 505: ¹H NMR (400 MHz, DMSO-d$_6$) δ 9.10 (d, J=1.8 Hz, 1H), 9.01 (d, J=1.8 Hz, 1H), 8.64 (d, J=7.0 Hz, 1H), 8.29 (d, J=8.4 Hz, 1H), 8.00 (s, 2H), 7.42 (d, J=8.5 Hz, 1H), 4.72 (s, 1H), 4.26 (s, 1H), 4.11 (d, J=12.9 Hz, 1H), 3.81 (dd, J=28.3, 13.6 Hz, 2H), 3.25 (dd, J=12.9, 10.0 Hz, 2H), 2.50 (s, 2H), 2.19 (dtd, J=30.2, 12.3, 6.4 Hz, 1H), 1.31 (s, 6H). MS: m/z=389 [M+H]⁺.

Example 131: Synthesis of Compound 507 and Compound 508 (2-Azetidin-1-yl-N—[(R)-1-(8-cyano-quinoxalin-5-yl)-5,5-difluoro-piperidin-3-yl]-propionamide and 2-Azetidin-1-yl-N—[(R)-1-(8-cyano-quinoxalin-5-yl)-5,5-difluoro-piperidin-3-yl]-propionamide)

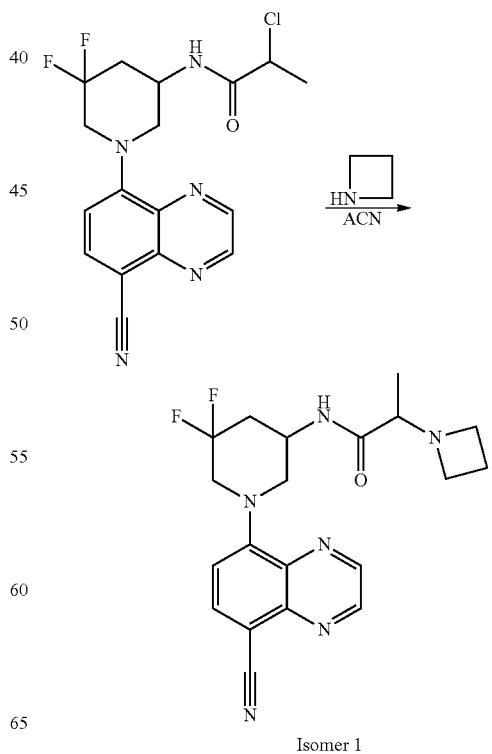

Isomer 1

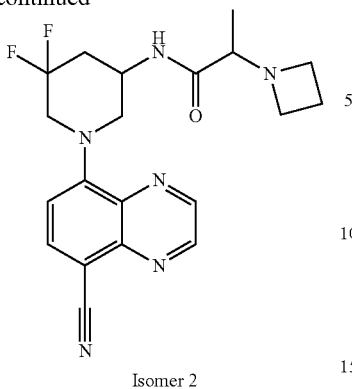

Isomer 2

Cis-2-Azetidin-1-yl-N-[1-(8-cyano-quinoxalin-5-yl)-5,5-difluoro-piperidin-3-yl]-propionamide and trans-2-Azetidin-1-yl-N-[1-(8-cyano-quinoxalin-5-yl)-5,5-difluoro-piperidin-3-yl]-propionamide: A mixture of 2-Chloro-N-[1-(8-cyano-quinoxalin-5-yl)-5,5-difluoro-piperidin-3-yl]-propionamide (30 mg; 0.08 mmol) and Azetidine (45 mg; 0.79 mmol) in acetonitrile was stirred at 100° C. for 2 hours. The reaction mixture was purified by reverse phase chromatography (XBridge column), eluting with acetonitrile in water (0.1% $NH_3.H_2O$), to afford cis-2-Azetidin-1-yl-N-[1-(8-cyano-quinoxalin-5-yl)-5,5-difluoro-piperidin-3-yl]-propionamide and trand-2-Azetidin-1-yl-N-[1-(8-cyano-quinoxalin-5-yl)-5,5-difluoro-piperidin-3-yl]-propionamide.

Isomer 1: $^1$H NMR (400 MHz, DMSO-$d_6$) δ 9.12 (d, J=1.8 Hz, 1H), 9.02 (d, J=1.8 Hz, 1H), 8.31 (d, J=8.3 Hz, 1H), 7.96 (d, J=7.5 Hz, 1H), 7.42 (d, J=8.4 Hz, 1H), 4.50-4.32 (m, 1H), 4.21 (s, 1H), 3.89-3.68 (m, 2H), 3.62 (dd, J=12.9, 7.7 Hz, 1H), 3.21 (q, J=6.8 Hz, 2H), 3.09 (q, J=6.8 Hz, 2H), 2.79 (q, J=6.8 Hz, 1H), 2.33 (s, 2H), 1.96 (p, J=6.9 Hz, 2H), 1.02 (d, J=6.8 Hz, 3H). MS: m/z=401 [M+H]$^+$.

Isomer 2: $^1$H NMR (400 MHz, DMSO-$d_6$) 9.13 (d, J=1.8 Hz, 1H), 9.04 (d, J=1.8 Hz, 1H), 8.31 (dd, J=7.7, 4.0 Hz, 2H), 7.42 (d, J=8.3 Hz, 1H), 4.31 (td, J=15.0, 14.5, 6.6 Hz, 1H), 4.19 (d, J=7.2 Hz, 1H), 3.81 (s, 1H), 3.65 (d, J=5.0 Hz, 1H), 3.28-3.19 (m, 1H), 3.18 (q, J=6.9 Hz, 2H), 3.09 (q, J=6.8 Hz, 2H), 2.77 (q, J=6.8 Hz, 1H), 2.39-2.16 (m, 2H), 1.83 (p, J=6.9 Hz, 2H), 1.07 (d, J=6.8 Hz, 3H). MS: m/z=401 [M+H]$^+$.

The following compounds were synthesized in an analogous manner:

Compound 509 (N-[1-(8-Cyano-quinoxalin-5-yl)-5,5-difluoro-piperidin-3-yl]-2-morpholin-4-yl-propionamide): From 2-Chloro-N-[1-(8-cyano-quinoxalin-5-yl)-5,5-difluoro-piperidin-3-yl]-propionamide and morphine. $^1$H NMR (400 MHz, DMSO-$d_6$) δ 9.11 (t, J=1.9 Hz, 1H), 9.01 (dd, J=8.7, 1.8 Hz, 1H), 8.37-8.16 (m, 2H), 7.43 (dd, J=8.4, 3.9 Hz, 1H), 4.44-4.14 (m, 2H), 4.01-3.85 (m, 1H), 3.82-3.71 (m, 1H), 3.65 (dt, J=13.2, 6.8 Hz, 1H), 3.46 (q, J=4.3 Hz, 4H), 2.97 (q, J=6.9 Hz, 1H), 2.51-2.23 (m, 6H), 1.14 (dd, J=10.9, 7.0 Hz, 3H). MS: m/z=431 [M+H]$^+$.

Example 132: Synthesis of Compound 518 (1-Cyclopropyl-3-[(3R,5S)-5-methyl-1-(8-trifluoromethyl-quinolin-5-yl)-piperidin-3-yl]-urea)

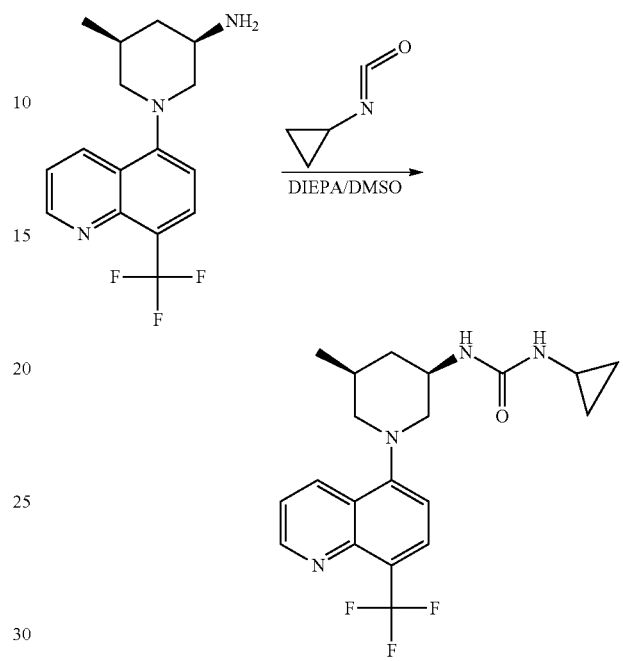

1-Cyclopropyl-3-[(3R,5S)-5-methyl-1-(8-trifluoromethyl-quinolin-5-yl)-piperidin-3-yl]-urea: A mixture of (3R,5S)-5-Methyl-1-(8-trifluoromethyl-quinolin-5-yl)-piperidin-3-ylamine hydrochloride (60 mg; 0.17 mmol), Ethyl-diisopropyl-amine (0.04 mL; 0.21 mmol) and isocyanatocyclopropane (28 mg; 0.35 mmol) in DMSO (1 mL) was stirred at room temperature overnight. The mixture was purified by reverse phase chromatography (XBridge column), eluting with acetonitrile in water (0.1% $NH_3.H_2O$), to afford 1-Cyclopropyl-3-[(3R,5S)-5-methyl-1-(8-trifluoromethyl-quinolin-5-yl)-piperidin-3-yl]-urea as white solid.

Compound 518: $^1$H NMR (400 MHz, DMSO-$d_6$) δ 9.02 (dd, J=4.2, 1.7 Hz, 1H), 8.54 (dd, J=8.6, 1.8 Hz, 1H), 8.05 (d, J=8.1 Hz, 1H), 7.67 (dd, J=8.6, 4.2 Hz, 1H), 7.21 (d, J=8.1 Hz, 1H), 6.09 (d, J=2.7 Hz, 1H), 5.80 (d, J=7.5 Hz, 1H), 3.56 (d, J=8.9 Hz, 1H), 2.48-2.35 (m, 3H), 2.14-1.82 (m, 2H), 1.06 (q, J=11.9 Hz, 1H), 0.95 (d, J=6.4 Hz, 3H), 0.56 (dd, J=7.0, 2.1 Hz, 2H), 0.32 (dd, J=3.7, 2.3 Hz, 2H). MS: m/z=293 [M+H]$^+$.

Example 133: Synthesis of Compound 525 (8-((3R,5S)-3-Amino-5-methyl-piperidin-1-yl)-3-methyl-quinoxaline-5-carbonitrile)

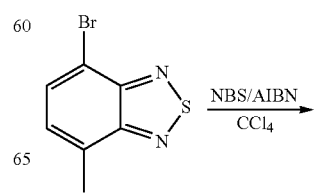

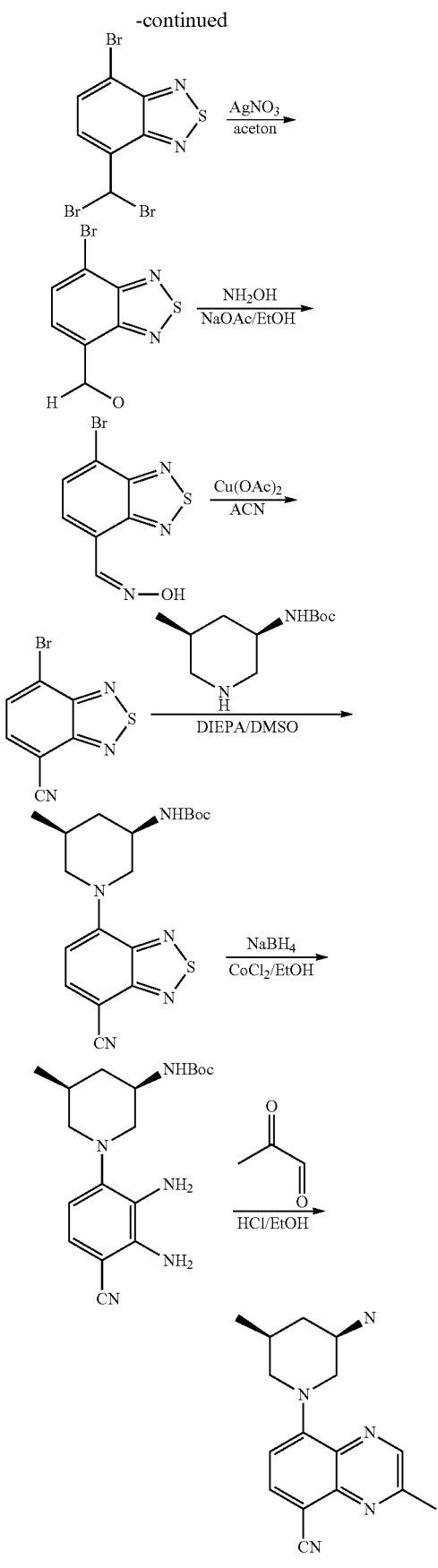

4-Bromo-7-dibromomethyl-benzo [1,2,5] thiadiazole: A mixture of 4-Bromo-7-methyl-benzo[1,2,5]thiadiazole (5.00 g; 21.8 mmol), N-bromosuccinimide (8.24 g; 45.8 mmol) and 2,2'-azobis(2-methylpropionitrile) (0.54 g; 3.27 mmol) in tetrachlorocarbon (150 mL) was stirred at 80° C. overnight. The suspension was filtered, the filtrate diluted with ethyl acetate and washed with brine. The organic phase was dried over anhydrous magnesium sulfate, filtered and concentrated under reduced pressure to afford 4-Bromo-7-dibromomethyl-benzo[1,2,5]thiadiazole (8.36 g quantitative yield) as yellow solid. MS: m/z=386 [M+H]$^+$.

7-Bromo-benzo [1,2,5] thiadiazole-4-carbaldehyde: A solution of 4-Bromo-7-dibromomethyl-benzo[1,2,5]thiadiazole (8.36 g; 21.61 mmol) and silver nitrate (9.18 g; 54.02 mmol) in acetone (100 mL) and water (20 mL) was stirred at room temperature for 1 hour. The reaction mixture was concentrated under reduced pressure, the resulting solid was washed with water and dried to afford 7-Bromo-benzo [1,2,5] thiadiazole-4-carbaldehyde. MS: m/z=242 [M+H]$^+$.

7-Bromo-benzo [1,2,5] thiadiazole-4-carbaldehyde oxime: A mixture of 7-Bromo-benzo [1,2,5] thiadiazole-4-carbaldehyde (5.25 g; 21.6 mmol) and sodium acetate (1.95 g; 23.77 mmol) in ethanol (200 mL) and a solution of ammonium chloride (1.58. mg; 22.7 mmol) was stirred at 70° C. for 1 hour. The reaction mixture was cooled, filtered and the solid was washed with ethanol. The filtrate was concentrated under reduced pressure to afford 7-Bromo-benzo [1,2,5] thiadiazole-4-carbaldehyde oxime (4.30 g, 78%) as yellow solid. MS: m/z=257 [M+H]$^+$.

7-Bromo-benzo [1,2,5] thiadiazole-4-carbonitrile: A mixture of 7-Bromo-benzo[1,2,5]thiadiazole-4-carbaldehyde oxime (4.30 g; 16.7 mmol), copper (II) acetate (302 mg; 1.67 mmol) and acetic acid (2.00 mL; 35.0 mmol) in acetonitrile (20 mL) was refluxed over the weekend. The reaction mixture was cooled, added water (20 mL) and slowly a solution of 2M sodium hydroxide (17.5 mL). The mixture was concentrated to ⅓ under reduced pressure, diluted with water (20 mL) and filtered. The solid was washed with water and dried to afford 7-Bromo-benzo[1,2,5] thiadiazole-4-carbonitrile (3.0 g, 75%) as light green solid. MS: m/z=239 [M+H]$^+$.

[(3R,5S)-1-(7-Cyano-benzo[1,2,5]thiadiazol-4-yl)-5-methyl-piperidin-3-yl]-carbamic acid tert-butyl ester: A mixture of 7-Bromo-benzo[1,2,5]thiadiazole-4-carbonitrile (1.80 g; 7.50 mmol), tert-butyl N-[(3R,5S)-5-methylpiperidin-3-yl]carbamate (1.80 g; 8.25 mmol) and Ethyl-diisopropyl-amine (1.61 mL; 9.00 mmol) in DMSO (2 mL) was microwaved at 120° C. for 60 min. The reaction mixture was diluted with methanol (10 mL). A brown solid precipitated and was filtered to afford [(3R,5S)-1-(7-Cyano-benzo[1,2,5]thiadiazol-4-yl)-5-methyl-piperidin-3-yl]-carbamic acid tert-butyl ester (2.16 mg, 77%). MS: m/z=374 [M+H]$^+$.

[(3R,5S)-1-(2,3-Diamino-4-cyano-phenyl)-5-methyl-piperidin-3-yl]-carbamic acid tert-butyl ester: A mixture of [(3R,5S)-1-(7-Cyano-benzo[1,2,5]thiadiazol-4-yl)-5-methyl-piperidin-3-yl]-carbamic acid tert-butyl ester (2.16 g; 5.78 mmol) and sodium borohydride (0.24 g; 6.36 mmol) in ethanol (130 mL) was refluxed over 2 days. Additional sodium borohydride was added during the course of the reaction until completion. The reaction mixture was cooled and filtered. The filtrated was concentrated under reduced pressure, diluted with ether and washed with brine. The organic phase was dried over anhydrous magnesium sulfate and concentrated under reduced pressure to afford [(3R,5S)-1-(2,3-Diamino-4-cyano-phenyl)-5-methyl-piperidin-3-yl]-carbamic acid tert-butyl ester (1.6 g, 80%) as brown solid. MS: m/z=346 [M+H]$^+$.

8-((3R,5S)-3-Amino-5-methyl-piperidin-1-yl)-3-methyl-quinoxaline-5-carbonitrile: To a solution of [(3R,5S)-1-(2,3-Diamino-4-cyano-phenyl)-5-methyl-piperidin-3-yl]-carbamic acid tert-butyl ester (70.0 mg; 0.20 mmol) in ethanol (2 mL) was added hydrogen chloride (0.10 mL; 0.41 mmol) and 2-Oxo-propionaldehyde (0.03 mL; 0.20 mmol). The mixture was stirred at 70° C. for 3 hour. The reaction mixture was concentrated under reduced pressure and the residue was purified by reverse phase chromatography (XBridge column), eluting with acetonitrile in water (0.1% NH$_3$.H$_2$O) to afford 8-((3R,5S)-3-Amino-5-methyl-piperidin-1-yl)-3-methyl-quinoxaline-5-carbonitrile as white solid.

Compound 525: $^1$H NMR (400 MHz, DMSO-d$_6$) δ 8.83 (s, 1H), 8.08 (dd, J=9.7, 8.4 Hz, 1H), 7.13 (t, J=8.7 Hz, 1H), 4.21 (s, 2H), 3.01-2.79 (m, 1H), 2.73 (d, J=2.8 Hz, 3H), 2.57 (dt, J=11.3, 5.5 Hz, 1H), 2.02-1.47 (m, 4H), 0.99-0.75 (m, 3H). MS: m/z=282 [M+H]$^+$.

Example 134: Synthesis of Compound 529 (1-(8-Cyano-quinoxalin-5-yl)-5,5-difluoro-piperidine-3-carboxylic acid (1-methyl-piperidin-4-yl)-amide)

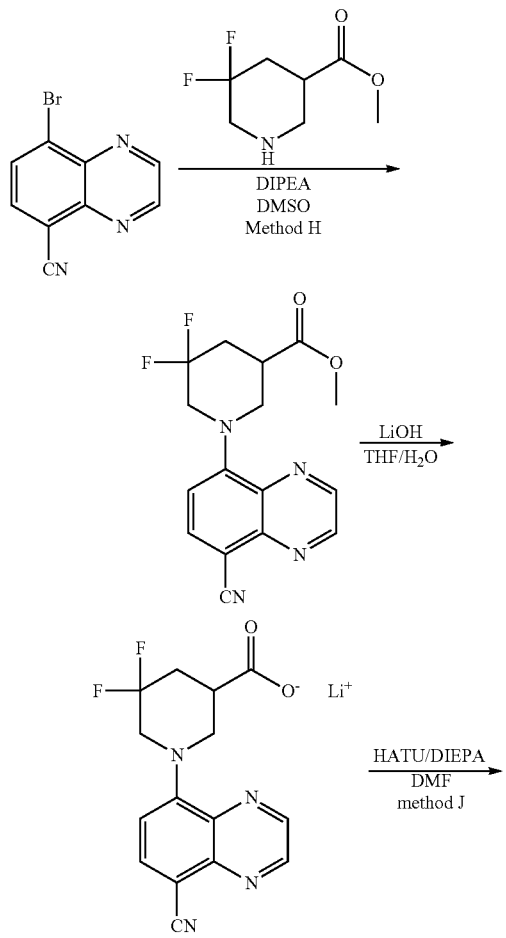

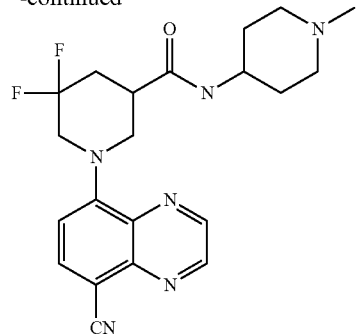

1-(8-Cyano-quinoxalin-5-yl)-5,5-difluoro-piperidine-3-carboxylic acid methyl ester: 1-(8-Cyano-quinoxalin-5-yl)-5,5-difluoro-piperidine-3-carboxylic acid methyl ester was prepared from 8-Bromo-quinoxaline-5-carbonitrile and 5,5-Difluoro-piperidine-3-carboxylic acid methyl ester hydrochloride using method H. $^1$H NMR (400 MHz, DMSO-d$_6$) δ 9.09 (d, J=1.8 Hz, 1H), 9.01 (d, J=1.8 Hz, 1H), 8.27 (d, J=8.4 Hz, 1H), 7.36 (d, J=8.4 Hz, 1H), 4.39 (d, J=12.5 Hz, 1H), 3.83-3.72 (m, 1H), 3.69 (s, 3H), 3.49-3.33 (m, 1H), 3.20 (s, 1H), 2.31 (dtd, J=31.9, 12.8, 6.4 Hz, 1H). MS: m/z=333 [M+H]$^+$.

1-(8-Cyano-quinoxalin-5-yl)-5,5-difluoro-piperidine-3-carboxylic acid lithium: A mixture of 1-(8-Cyano-quinoxalin-5-yl)-5,5-difluoro-piperidine-3-carboxylic acid methyl ester (25 mg; 0.08 mmol) and lithium hydroxide (7 mg; 0.30 mmol) in THF (1.0 mL) and water (1.0 mL) was stirred at room temperature for 2 hour. The reaction mixture was concentrated under reduced pressure and the resulting solid was dried to afford 1-(8-Cyano-quinoxalin-5-yl)-5,5-difluoro-piperidine-3-carboxylic acid lithium as yellow solid. MS: m/z=319 [M+H]$^+$.

1-(8-Cyano-quinoxalin-5-yl)-5,5-difluoro-piperidine-3-carboxylic acid (1-methyl-piperidin-4-yl)-amide: 1-(8-Cyano-quinoxalin-5-yl)-5,5-difluoro-piperidine-3-carboxylic acid (1-methyl-piperidin-4-yl)-amide was prepared from 1-(8-Cyano-quinoxalin-5-yl)-5,5-difluoro-piperidine-3-carboxylic acid lithium and 4-amino-1-methylpiperidine as a white solid, using Method J.

Compound 529: $^1$H NMR (400 MHz, DMSO-d$_6$) δ 9.08 (d, J=1.8 Hz, 1H), 8.99 (d, J=1.8 Hz, 1H), 8.26 (d, J=8.4 Hz, 1H), 8.12 (d, J=7.6 Hz, 1H), 7.38 (d, J=8.5 Hz, 1H), 4.73 (s, 2H), 4.16 (d, J=13.3 Hz, 1H), 3.77-3.40 (m, 4H), 3.01 (s, 2H), 2.71 (s, 2H), 2.33 (s, 1H), 2.15 (s, 3H), 1.93 (t, J=11.1 Hz, 2H), 1.73 (d, J=12.3 Hz, 2H), 1.53-1.32 (m, 2H). MS: m/z=415 [M+H]$^+$.

The following compounds were synthesized in an analogous manner:

Compound 530 (1-(8-Cyano-quinolin-5-yl)-5,5-difluoro-piperidine-3-carboxylic acid (1-methyl-piperidin-4-yl)-amide): From 5-Bromo-quinoline-8-carbonitrile, 5,5-Difluoro-piperidine-3-carboxylic acid methyl ester hydrochloride and 4-amino-1-methylpiperidine. $^1$H NMR (400 MHz, DMSO-d$_6$) δ 9.08 (dd, J=4.2, 1.6 Hz, 1H), 8.56 (dd, J=8.6, 1.7 Hz, 1H), 8.28 (d, J=8.0 Hz, 1H), 8.04 (d, J=7.6 Hz, 1H), 7.75 (dd, J=8.6, 4.2 Hz, 1H), 7.36 (d, J=8.1 Hz, 1H), 3.67 (s, 1H), 3.55-3.34 (m, 3H), 3.18-2.93 (m, 2H), 2.77-2.58 (m, 2H), 2.37 (d, J=12.3 Hz, 1H), 2.30 (s, 1H), 2.13 (s, 3H), 1.92 (tdd, J=10.9, 5.3, 2.2 Hz, 2H), 1.78-1.60 (m, 2H), 1.47-1.26 (m, 2H). MS: m/z=414 [M+H]$^+$.

Compound 531 (1-(8-Cyano-quinolin-5-yl)-5,5-difluoro-piperidine-3-carboxylic acid (1-methyl-piperidin-4-ylmethyl)-amide): From 5-Bromo-quinoline-8-carbonitrile, 5,5-

Difluoro-piperidine-3-carboxylic acid methyl ester hydrochloride and C-(1-Methyl-piperidin-4-yl)-methylamine. $^1$H NMR (400 MHz, Methanol-$d_4$) δ 9.02 (dd, J=4.2, 1.7 Hz, 1H), 8.69 (dd, J=8.6, 1.7 Hz, 1H), 8.18 (d, J=8.0 Hz, 1H), 7.69 (dd, J=8.6, 4.3 Hz, 1H), 7.37 (d, J=8.0 Hz, 1H), 3.79-3.52 (m, 2H), 3.26-3.07 (m, 4H), 2.88 (d, J=11.8 Hz, 2H), 2.46 (s, 1H), 2.33 (dd, J=13.6, 6.1 Hz, 1H), 2.27 (s, 3H), 2.07-1.91 (m, 2H), 1.71 (dd, J=13.3, 3.2 Hz, 2H), 1.52 (dtd, J=14.3, 7.6, 6.5, 4.1 Hz, 1H), 1.29 (qd, J=12.1, 3.9 Hz, 2H). MS: m/z=428 [M+H]$^+$.

Compound 532 (1-(8-Cyano-quinolin-5-yl)-5,5-difluoro-piperidine-3-carboxylic acid (1-ethyl-piperidin-4-yl)-amide): From 5-Bromo-quinoline-8-carbonitrile, 5,5-Difluoro-piperidine-3-carboxylic acid methyl ester hydrochloride and 1-Ethyl-piperidin-4-ylamine. $^1$H NMR (400 MHz, Methanol-$d_4$) δ 9.02 (dd, J=4.3, 1.7 Hz, 1H), 8.69 (dd, J=8.6, 1.7 Hz, 1H), 8.18 (d, J=8.0 Hz, 1H), 7.69 (dd, J=8.6, 4.3 Hz, 1H), 7.38 (d, J=8.0 Hz, 1H), 3.77-3.64 (m, 2H), 3.60 (d, J=10.2 Hz, 1H), 3.26-3.09 (m, 3H), 2.98 (d, J=25.7 Hz, 3H), 2.45 (q, J=7.2 Hz, 3H), 2.39-2.17 (m, 1H), 2.10 (dp, J=7.0, 3.5, 3.0 Hz, 2H), 1.90 (t, J=13.7 Hz, 2H), 1.57 (dd, J=12.4, 8.9 Hz, 2H), 1.12 (t, J=7.2 Hz, 3H). MS: m/z=428 [M+H]$^+$.

Compound 537 and compound 538 (cis-1-(8-Cyano-quinoxalin-5-yl)-5-methyl-piperidine-3-carboxylic acid [2-(4-methyl-piperazin-1-yl)-ethyl]-amide and trans-1-(8-Cyano-quinoxalin-5-yl)-5-methyl-piperidine-3-carboxylic acid [2-(4-methyl-piperazin-1-yl)-ethyl]-amide): From 8-Bromo-quinoxaline-5-carbonitrile, 5-Methyl-piperidine-3-carboxylic acid methyl ester hydrochloride and 2-(1-Methyl-piperidin-4-yl)-ethylamine. Isomer 1: $^1$H NMR (400 MHz, Methanol-d4) δ 8.92 (dd, J=19.8, 1.8 Hz, 2H), 8.10 (d, J=8.4 Hz, 1H), 7.24 (d, J=8.4 Hz, 1H), 4.41 (ddt, J=12.3, 3.6, 1.7 Hz, 1H), 4.17 (ddd, J=10.4, 4.5, 2.5 Hz, 1H), 3.37 (d, J=6.8 Hz, 2H), 3.09 (dd, J=12.3, 11.3 Hz, 1H), 2.90-2.75 (m, 1H), 2.67 (dd, J=12.5, 10.9 Hz, 2H), 2.54 (q, J=10.2, 6.8 Hz, 8H), 2.29 (s, 3H), 2.13-1.98 (m, 2H), 1.45 (q, J=13.1, 12.7 Hz, 1H), 1.03 (d, J=6.4 Hz, 3H). MS: m/z=422 [M+H]$^+$. Isomer 2: $^1$H NMR (400 MHz, Methanol-d4) δ 9.03 (dd, J=24.4, 1.8 Hz, 2H), 8.22 (d, J=8.3 Hz, 1H), 7.40 (d, J=8.3 Hz, 1H), 4.60-4.48 (m, 1H), 3.67-3.46 (m, 2H), 3.46-3.34 (m, 3H), 3.14 (dd, J=13.2, 3.3 Hz, 1H), 2.96-2.83 (m, 1H), 2.75 (s, 1H), 2.49 (td, J=6.5, 1.3 Hz, 3H), 2.43-2.27 (m, 4H), 2.10 (s, 5H), 1.50 (ddd, J=13.2, 11.3, 5.1 Hz, 1H), 1.06 (dd, J=10.1, 6.7 Hz, 3H).

Compound 539 (1-(8-Cyano-quinoxalin-5-yl)-5-methyl-piperidine-3-carboxylic acid (1-methyl-piperidin-4-ylmethyl)-amide): From 8-Bromo-quinoxaline-5-carbonitrile, 5-Methyl-piperidine-3-carboxylic acid methyl ester hydrochloride and C-(1-Methyl-piperidin-4-yl)-methylamine. $^1$H NMR (400 MHz, Methanol-$d_4$) δ 9.06 (d, J=1.8 Hz, 1H), 8.98 (d, J=1.9 Hz, 1H), 8.20 (d, J=8.3 Hz, 1H), 7.39 (d, J=8.3 Hz, 1H), 4.39 (dd, J=13.3, 3.5 Hz, 1H), 3.62-3.38 (m, 2H), 3.17-3.05 (m, 2H), 2.97-2.85 (m, 2H), 2.85-2.71 (m, 2H), 2.24 (s, 3H). 2.14-1.84 (m, 4H), 1.71 (t, J=16.2 Hz, 2H), 1.56-1.43 (m, 2H), 1.37-1.18 (m, 2H), 1.08 (d, J=6.6 Hz, 3H). MS: n/z=407 [M+H]$^+$.

Compound 540 (1-(8-Cyano-quinoxalin-5-yl)-5-methyl-piperidine-3-carboxylic acid (1-ethyl-piperidin-4-yl)-amide): From 8-Bromo-quinoxaline-5-carbonitrile, 5-Methyl-piperidine-3-carboxylic acid methyl ester hydrochloride and 1-Ethyl-piperidin-4-ylamine. $^1$H NMR (400 MHz, Methanol-$d_4$) δ 9.07 (s, 2H), 8.20 (d, J=8.3 Hz, 1H), 7.39 (d, J=8.4 Hz, 1H), 4.45 (d, J=12.4 Hz, 1H), 3.85 (ddd, J=15.5, 11.4, 4.3 Hz, 1H), 3.59-3.46 (m, 1H), 3.13 (dd, J=13.1, 3.2 Hz, 1H), 3.01 (t, J=10.2 Hz, 1H), 2.91 (dd, J=11.4, 9.8 Hz, 2H), 2.75 (t, J=4.3 Hz, 1H), 2.44 (q, J=7.2 Hz, 2H), 2.18-1.91 (m, 4H), 1.82 (d, J=13.0 Hz, 1H), 1.65 (qd, J=12.0, 3.9 Hz, 1H), 1.57-1.39 (m, 2H), 1.18-1.00 (m, 5H). MS: n/z=407 [M+H]$^+$.

Compound 541 and compound 542 (cis-1-(8-Cyano-quinoxalin-5-yl)-5-methyl-piperidine-3-carboxylic acid methylamide and trans-1-(8-Cyano-quinoxalin-5-yl)-5-methyl-piperidine-3-carboxylic acid methylamide): From 8-Bromo-quinoxaline-5-carbonitrile, 5-Methyl-piperidine-3-carboxylic acid methyl ester hydrochloride and methylamine hydrochloride. Isomer 1: $^1$H NMR (400 MHz, DMSO-$d_6$) δ 9.03 (d, J=1.8 Hz, 1H), 8.96 (d, J=1.8 Hz, 1H), 8.18 (d, J=8.4 Hz, 1H), 7.84 (d, J=5.1 Hz, 1H), 7.24 (d, J=8.5 Hz, 1H), 4.34 (d, J=12.8 Hz, 1H), 4.18 (d, J=12.2 Hz, 1H), 3.05 (t, J=12.0 Hz, 1H), 2.76-2.63 (m, 2H), 2.58 (d, J=4.6 Hz, 3H), 1.91 (t, J=15.5 Hz, 2H), 1.35 (q, J=12.1 Hz, 1H), 1.04-0.86 (m, 3H). MS: m/z=310 [M+H]$^+$. Isomer 2: $^1$H NMR (400 MHz, DMSO-$d_6$) δ 9.12-9.03 (m, 1H), 8.99 (d, J=1.8 Hz, 1H), 8.43 (d, J=5.2 Hz, 1H), 8.23 (d, J=8.4 Hz, 1H), 7.27 (d, J=8.4 Hz, 1H), 3.92 (dd, J=12.9, 6.4 Hz, 1H), 3.48 (ddd, J=20.3, 12.5, 3.6 Hz, 2H), 2.82-2.68 (m, 1H), 2.64 (d, J=4.4 Hz, 3H), 2.20-1.91 (m, 2H), 1.48 (ddd, J=12.5, 7.7, 4.7 Hz, 1H), 1.00 (d, J=6.7 Hz, 3H). MS: m/z=310 [M+H]$^+$.

Compound 543 and compound 544 (cis-1-(8-cyanoquinoxalin-5-yl)-5-methyl-N-(1-methyl-3-piperidyl) piperidine-3-carboxamide and trans-1-(8-cyanoquinoxalin-5-yl)-5-methyl-N-(1-methyl-3-piperidyl) piperidine-3-carboxamide): From 8-Bromo-quinoxaline-5-carbonitrile, 5-Methyl-piperidine-3-carboxylic acid methyl ester hydrochloride and 1-Methyl-piperidin-3-ylamine. Isomer 1: $^1$H NMR (400 MHz, DMSO-$d_6$) δ 9.04 (dd, J=1.8, 0.7 Hz, 1H), 8.95 (t, J=1.8 Hz, 1H), 8.18 (dd, J=8.5, 1.3 Hz, 1H), 7.74 (d, J=8.0 Hz, 1H), 7.24 (d, J=8.5 Hz, 2H), 4.30 (s, 1H), 4.19 (d, J=12.3 Hz, 1H), 3.69 (s, 1H), 3.07 (t, J=12.0 Hz, 1H), 2.75-2.59 (m, 3H), 2.55 (s, 2H), 2.14 (d, J=1.5 Hz, 2H), 1.89 (s, 3H), 1.64 (s, 3H), 1.43 (d, J=31.3 Hz, 1H), 1.13 (d, J=11.1 Hz, 2H), 0.94 (d, J=6.0 Hz, 3H). MS: m/z=393 [M+H]$^+$. Isomer 2: $^1$H NMR (400 MHz, DMSO-$d_6$) δ 9.08 (d, J=1.8 Hz, 1H), 8.97 (d, J=1.8 Hz, 1H), 8.22 (d, J=8.4 Hz, 1H), 8.08 (d, J=8.0 Hz, 1H), 7.26 (d, J=8.5 Hz, 1H), 4.11-3.99 (m, 1H), 3.71 (d, J=9.5 Hz, 2H), 3.57-3.44 (m, 2H), 2.73 (s, 2H), 2.60 (s, 1H), 2.08 (s, 4H), 1.93-1.62 (m, 3H), 1.45 (d, J=47.0 Hz, 4H), 1.01 (d, J=6.6 Hz, 3H). MS: m/z=393 [M+H]$^+$.

Compound 547 and compound 548 (cis-5-Methyl-1-(8-trifluoromethyl-quinolin-5-yl)-piperidine-3-carboxylic acid (1-methyl-piperidin-4-ylmethyl)-amide and trans-S-Methyl-1(8-trifluoromethyl-quinolin-5-yl)-piperidine-3-carboxylic acid (1-methyl-piperidin-4-ylmethyl)-amide): From 5-Bromo-8-trifluoromethyl-quinoline, 5,5-Difluoro-piperidine-3-carboxylic acid methyl ester hydrochloride and C-(1-Methyl-piperidin-4-yl)-methylamine. Isomer 1:: $^1$H NMR (400 MHz, DMSO-$d_6$) δ 9.02 (dd, J=4.2, 1.7 Hz, 1H), 8.65 (dd, J=8.6, 1.8 Hz, 1H), 8.07 (d, J=8.1 Hz, 1H), 7.85 (t, J=5.9 Hz, 1H), 7.66 (dd, J=8.5, 4.2 Hz, 1H), 7.22 (d, J=8.0 Hz, 1H), 3.21-3.05 (m, 2H), 2.98 (hept, J=6.4 Hz, 2H), 2.79 (s, 2H), 2.66-2.56 (m, 2H), 2.26 (s, 3H), 2.05-1.96 (m, 1H), 1.64 (dt, J=22.8, 11.5 Hz, 2H), 1.51 (t, J=13.0 Hz, 1H), 1.29 (dt, J=7.7, 4.1 Hz, 1H), 1.12 (d, J=6.9 Hz, 1H), 1.10-0.98 (m, 1H). Isomer 2: $^1$H NMR (400 MHz, DMSO-$d_6$) δ 9.02 (dd, J=4.2, 1.7 Hz, 1H), 8.52 (dd, J=8.6, 1.8 Hz, 1H), 8.06 (d, J=8.1 Hz, 1H), 7.90 (t, J=5.8 Hz, 1H), 7.66 (dd, J=8.6, 4.1 Hz, 1H), 7.24 (d, J=8.0 Hz, 1H), 3.45-3.32 (m, 2H), 3.06-2.86 (m, 2H), 2.82 (t, J=11.7 Hz, 2H), 2.71 (d, J=11.3 Hz, 2H), 2.41 (t, J=11.3 Hz, 1H), 2.12 (s, 3H), 1.99 (t, J=14.9 Hz, 2H), 1.76 (td, J=11.6, 2.5 Hz, 2H), 1.57 (d, J=12.9 Hz, 2H), 1.30 (dd, J=16.6, 8.1 Hz, 2H), 1.12 (tt, J=13.0, 6.5 Hz, 2H), 0.95 (dd, J=6.5, 3.9 Hz, 3H). MS: m/z=449 [M+H]$^+$.

Compound 549 (4-Methyl-piperazin-1-yl)-[5-methyl-1-(8-trifluoromethyl-quinolin-5-yl)-piperidin-3-yl]-methanone): From 5-Bromo-8-trifluoromethyl-quinoline, 5-Methyl-piperidine-3-carboxylic acid methyl ester hydrochloride and 1-Methyl-piperazine. $^1$H NMR (400 MHz, DMSO-d$_6$) δ 9.02 (dd, J=4.2, 1.7 Hz, 1H), 8.62 (ddd, J=48.2, 8.6, 1.8 Hz, 1H), 8.07 (d, J=8.1 Hz, 1H), 7.67 (ddd, J=8.6, 4.1, 1.7 Hz, 1H), 7.23 (d, J=8.0 Hz, 1H), 3.68-3.40 (m, 4H), 3.12-3.01 (m, 1H), 2.85 (t, J=11.3 Hz, 1H), 2.44 (t, J=11.5 Hz, 1H), 2.32 (d, J=5.3 Hz, 4H), 2.18 (d, J=1.7 Hz, 3H), 2.10 (s, 1H), 1.93 (d, J=13.3 Hz, 1H), 1.56 (d, J=13.5 Hz, 1H), 1.23 (d, J=7.2 Hz, 2H), 0.95 (d, J=6.6 Hz, 3H). MS: m/z=421 [M+H]$^+$.

Example 135: Synthesis of Compound 533 and compound 534 (cis-5-[3-Methyl-5-(4-methyl-piperazin-1-ylmethyl)-piperidin-1-yl]-8-trifluoromethyl-quinoline and trans-5-[3-Methyl-5-(4-methyl-piperazin-1-ylmethyl)-piperidin-1-yl]-8-trifluoromethyl-quinoline)

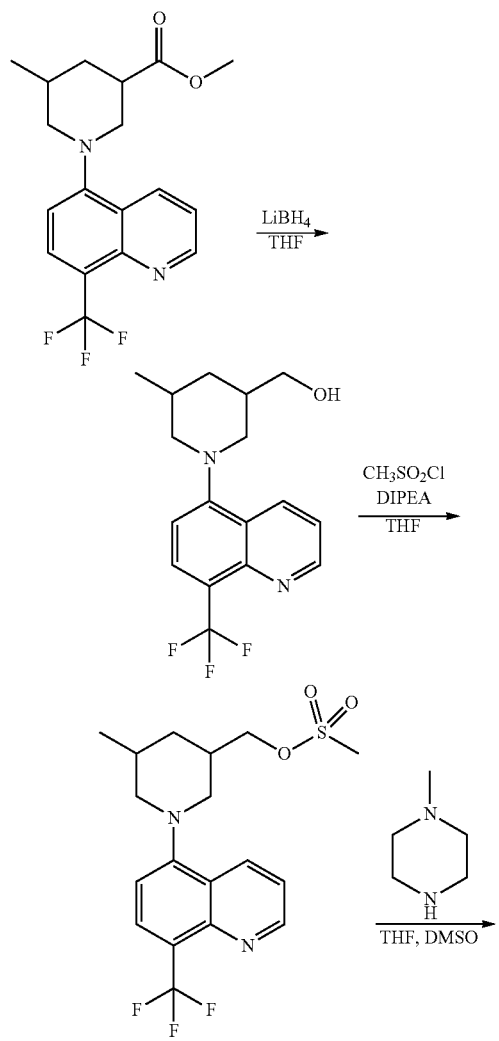

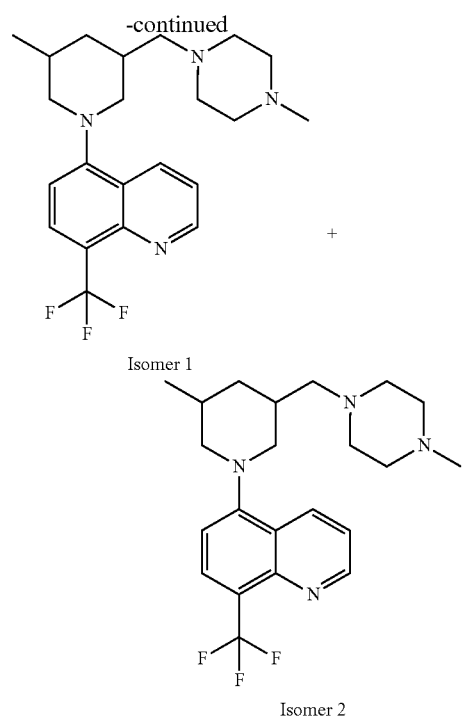

Isomer 1

Isomer 2

[5-Methyl-1-(8-trifluoromethyl-quinolin-5-yl)-piperidin-3-yl]-methanol: To a solution of 5-Methyl-1-(8-trifluoromethyl-quinolin-5-yl)-piperidine-3-carboxylic acid methyl ester (200 mg; 0.57 mmol) in anhydrous THF (2 mL) was added a 2N solution of sodium borohydride (1.14 mL; 2.27 mmol) in THF and the reaction mixture was stirred at room temperature for 48 hours. A 10% solution of citric acid (3 mL) was added, the resulting mixture was brought to pH>8 and extracted with dichloromethane. The combined organic phase was washed with brine, dried over anhydrous magnesium sulfate and concentrated under reduced pressure to afford [5-Methyl-1-(8-trifluoromethyl-quinolin-5-yl)-piperidin-3-yl]-methanol as a light yellow solid. $^1$H NMR (400 MHz, Chloroform-d) 9.06 (dd, J=4.2, 1.8 Hz, 1H), 8.50 (dd, J=8.6, 1.8 Hz, 1H), 7.99 (ddd, J=8.0, 4.1, 0.9 Hz, 1H), 7.49 (ddd, J=8.5, 4.2, 1.0 Hz, 1H), 7.11 (t, J=7.4 Hz, 1H), 4.07-3.80 (m, 1H), 3.73-3.61 (m, 1H), 3.58 (ddd, J=8.4, 7.2, 3.2 Hz, 1H), 3.39 (ddt, J=11.7, 3.9, 1.8 Hz, 1H), 3.28-3.05 (m, 1H), 2.27-2.16 (m, 1H), 2.16-2.05 (m, 1H), 2.06-1.93 (m, 1H), 1.38 (s, 1H), 1.11 (d, J=6.7 Hz, 1H), 1.01 (d, J=6.6 Hz, 2H), 0.88 (q, J=12.2 Hz, 1H). MS: m/z=325 [M+H]$^+$.

Methane sulfonic acid 5-methyl-1-(8-trifluoromethyl-quinolin-5-yl)-piperidin-3-ylmethyl ester: A mixture of [5-Methyl-1-(8-trifluoromethyl-quinolin-5-yl)-piperidin-3-yl]-methanol (175 mg; 0.54 mmol), methane sulfonyl chloride (0.05 mL; 0.70 mmol) and Ethyl-diisopropyl-amine (0.15 mL; 0.81 mmol) in THF (2 mL) was stirred at room temperature for 1 hour. The reaction mixture was directly carried on to the next step without any further purification. MS: m/z=403 [M+H]$^+$.

Cis-5-[3-Methyl-5-(4-methyl-piperazin-1-ylmethyl)-piperidin-1-yl]-8-trifluoromethyl-quinoline and trans-5-[3-

Methyl-5-(4-methyl-piperazin-1-ylmethyl)-piperidin-1-yl]-8-trifluoromethyl-quinoline: A mixture of methanesulfonic acid 5-methyl-1-(8-trifluoromethyl-quinolin-5-yl)-piperidin-3-ylmethyl ester (100 mg; 0.25 mmol) and 1-methyl-piperazine (0.31 mL; 2.48 mmol) in THF (1 mL) and DMSO (1 mL) was heated at 80° C. overnight. The reaction mixture was purified vis reverse phase chromatography (XBridge column), eluting with acetonitrile in water (0.1% $NH_3.H_2O$), to afford cis-5-[3-Methyl-5-(4-methyl-piperazin-1-ylmethyl)-piperidin-1-yl]-8-trifluoromethyl-quinoline and trans-5-[3-Methyl-5-(4-methyl-piperazin-1-ylmethyl)-piperidin-1-yl]-8-trifluoromethyl-quinoline as a mixture of 2 enantiomers.

Isomer 1: Isomer1 $^1$H NMR (400 MHz, DMSO-$d_6$) δ 9.02 (dd, J=4.2, 1.6 Hz, 1H), 8.48 (dd, J=8.6, 1.8 Hz, 1H), 8.06 (d, J=8.0 Hz, 1H), 7.64 (dd, J=8.6, 4.1 Hz, 1H), 7.18 (d, J=8.1 Hz, 1H), 3.60-3.45 (m, 1H), 2.49-2.33 (m, 3H), 2.28 (q, J=16.3, 13.4 Hz, 5H), 2.21-2.15 (m, 2H), 2.12 (s, 3H), 2.01 (d, J=12.3 Hz, 1H), 1.88 (d, J=12.8 Hz, 1H), 0.94 (dd, J=6.6, 1.9 Hz, 3H), 0.74 (q, J=11.8, 11.3 Hz, 1H). MS: n/z=407 $[M+H]^+$.

Isomer 2: $^1$H NMR (400 MHz, DMSO-$d_6$) δ 9.02 (dd, J=4.1, 1.7 Hz, 1H), 8.73 (dd, J=8.6, 1.8 Hz, 1H), 8.05 (d, J=8.1 Hz, 1H), 7.63 (dd, J=8.6, 4.1 Hz, 1H), 7.20 (d, J=8.1 Hz, 1H), 3.18 (d, J=9.0 Hz, 1H), 2.95 (d, J=11.5 Hz, 1H), 2.73 (s, 2H), 2.42-2.17 (m, 6H), 2.15 (s, 3H), 1.60 (d, J=13.0 Hz, 1H), 1.40 (s, 1H), 1.04 (d, J=6.6 Hz, 3H). MS: m/z=407 $[M+H]^+$.

The following compounds were synthesized in an analogous manner:

Compound 535 and compound 536 (cis-5-[3-Methyl-5-(4-morpholin-4-yl-piperidin-1-ylmethyl)-piperidin-1-yl]-8-trifluoromethyl-quinoline and trans-5-[3-Methyl-5-(4-morpholin-4-yl-piperidin-1-ylmethyl)-piperidin-1-yl]-8-trifluoromethyl-quinoline): From 5-Bromo-8-trifluoromethyl-quinoline, 5-Methyl-piperidine-3-carboxylic acid methyl ester hydrochloride and 4-Piperidin-4-yl-morpholine. Isomer 1: $^1$H NMR (400 MHz, Methanol-$d_4$) δ 8.93 (dd, J=4.2, 1.7 Hz, 1H), 8.60 (dd, J=8.6, 1.8 Hz, 1H), 8.04 (d, J=8.1 Hz, 1H), 7.60 (dd, J=8.6, 4.2 Hz, 1H), 7.21 (d, J=8.0 Hz, 1H), 3.70 (t, J=4.7 Hz, 4H), 3.62 (d, J=11.5 Hz, 1H), 3.41 (d, J=11.5 Hz, 1H), 3.14 (d, J=11.7 Hz, 1H), 2.94 (d, J=11.7 Hz, 1H), 2.57 (t, J=4.7 Hz, 4H), 2.40 (dt, J=16.9, 11.1 Hz, 2H), 2.33-2.15 (m, 4H), 2.15-1.79 (m, 6H), 1.60-1.40 (m, 2H), 1.01 (d, J=6.6 Hz, 3H), 0.82 (q, J=11.7 Hz, 1H). MS: m/z=477 $[M+H]^+$. Isomer 2: $^1$H NMR (400 MHz, Methanol-$d_4$) δ 8.93 (dd, J=4.2, 1.7 Hz, 1H), 8.79 (dd, J=8.6, 1.8 Hz, 1H), 8.03 (d, J=8.1 Hz, 1H), 7.61 (dd, J=8.6, 4.2 Hz, 1H), 7.23 (d, J=8.0 Hz, 1H), 3.79-3.63 (m, 3H), 3.26 (d, J=12.9 Hz, 1H), 3.10 (s, 2H), 2.96 (d, J=11.7 Hz, 1H), 2.75 (s, 2H), 2.58 (t, J=4.7 Hz, 3H), 2.41-2.11 (m, 4H), 2.07 (t, J=11.5 Hz, 1H), 1.92 (d, J=10.7 Hz, 2H), 1.72 (d, J=12.8 Hz, 1H), 1.60-1.40 (m, 3H), 1.11 (d, J=6.6 Hz, 3H). MS: m/z=477 $[M+H]^+$.

Example 136: Separation of Compound 545 and Compound 546 ((R)-1-(8-Cyano-quinolin-5-yl)-5,5-difluoro-piperidine-3-carboxylic acid (1-methyl-piperidin-4-ylmethyl)-amide and (S)-1-(8-Cyano-quinolin-5-yl)-5,5-difluoro-piperidine-3-carboxylic acid (1-methyl-piperidin-4-ylmethyl)-amide)

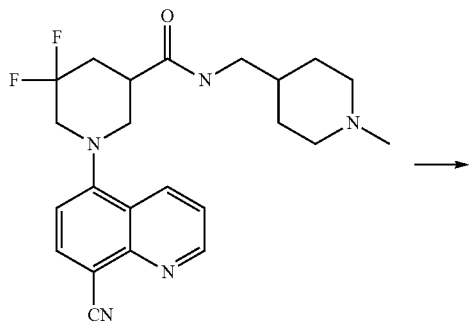

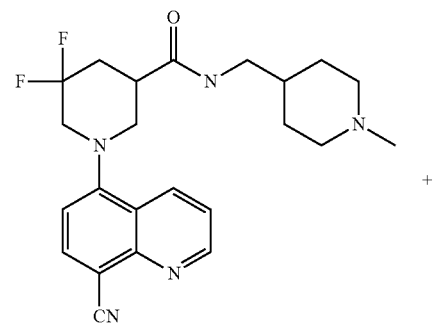

Isomer 1

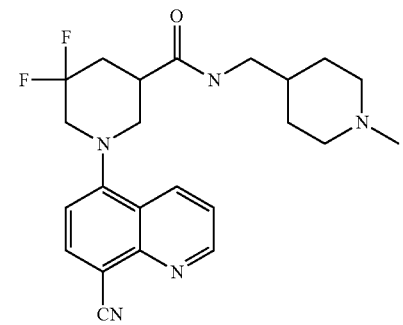

Isomer 2

The title compounds were isolated via chiral SFC chromatography of compound 531. (Column: CHIRALPAK 10×250 mm ADH; CO2 Co-solvent (Solvent B): Methanol with 0.5% dimethylethylamine; Isocratic Method: 45% Co-solvent at 5 mL/min; System Pressure: 100 bar; Column Temperature: 35° C.).

Isomer 1: MS: m/z=428 $[M+H]^+$.
Isomer 2: MS: m/z=428 $[M+H]^+$.

Example 137: Synthesis of Compound 552 (7-((3R, 5S)-3-Amino-5-methyl-piperidin-1-yl)-benzo [1,2,5] thiadiazole-4-carbonitrile hydrochloride)

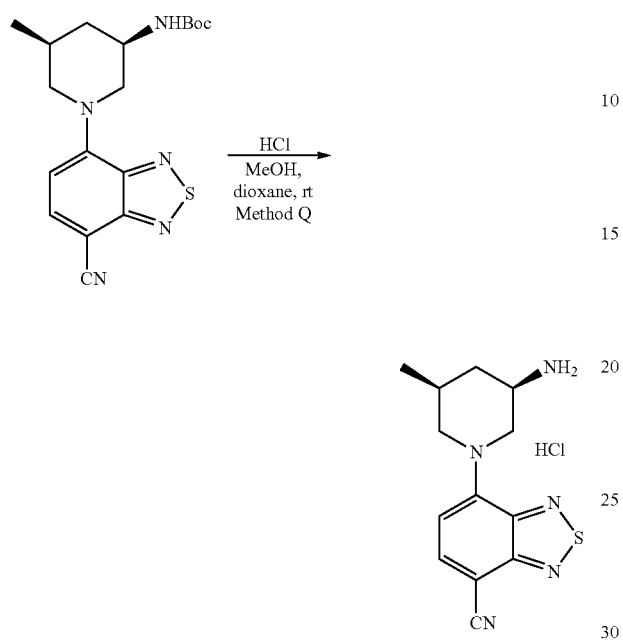

7-((3R,5S)-3-Amino-5-methyl-piperidin-1-yl)-benzo[1,2,5]thiadiazole-4-carbonitrile hydrochloride: 7-((3R,5S)-3-Amino-5-methyl-piperidin-1-yl)-benzo[1,2,5]thiadiazole-4-carbonitrile hydrochloride was prepared from [(3R,5S)-1-(7-Cyano-benzo[1,2,5] thiadiazol-4-yl)-5-methyl-piperidin-3-yl]-carbamic acid tert-butyl ester using method Q.

Compound 552: $^1$H NMR (400 MHz, DMSO-$d_6$) δ 8.32 (s, 2H), 8.16 (dd, J=8.3, 1.2 Hz, 1H), 6.95 (d, J=8.3 Hz, 1H), 4.94 (d, J=12.1 Hz, 1H), 4.65 (d, J=11.9 Hz, 1H), 3.13 (q, J=12.6, 11.8 Hz, 1H), 2.75 (t, J=12.3 Hz, 1H), 2.16 (d, J=12.3 Hz, 1H), 1.88 (s, 1H), 1.33 (q, J=12.0 Hz, 1H), 0.99 (d, J=6.5 Hz, 3H). MS: m/z=354 [M+H]$^+$.

Example 138: Synthesis of Compound 567 (N-[(3R,5S)-5-Methyl-1-(8-methyl-[1,7]naphthyridin-5-yl)-piperidin-3-yl]-succinamic acid)

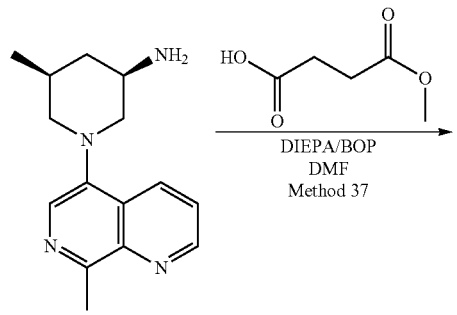

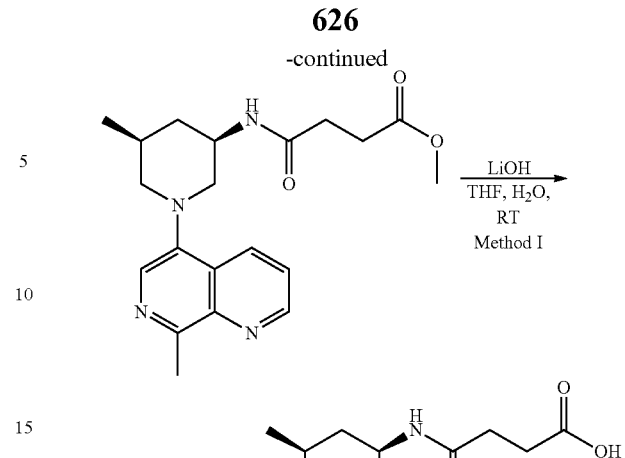

N-[(3R,5S)-5-Methyl-1-(8-methyl-[1,7]naphthyridin-5-yl)-piperidin-3-yl]-succinamic acid: N-[(3R,5S)-5-Methyl-1-(8-methyl-[1,7]naphthyridin-5-yl)-piperidin-3-yl]-succinamic acid was prepared from (3R,5S)-5-Methyl-1-(8-methyl-[1,7]naphthyridin-5-yl)-piperidin-3-ylamine dihydrochloride and mono-methyl succinate using Method 37, followed by saponification of ester to carboxylic acid using Method I to afford N-[(3R,5S)-5-Methyl-1-(8-methyl-[1,7]naphthyridin-5-yl)-piperidin-3-yl]-succinamic acid in 71% yield over 2 steps.

Compound 567: MS: m/z=357 [M+H]$^+$. $^1$H NMR (400 MHz, DMSO-$d_6$, ppm) δ 9.02 (dd, J=4.1, 1.7 Hz, 1H), 8.44 (dd, J=8.5, 1.8 Hz, 1H), 8.10 (s, 1H), 7.90 (d, J=7.5 Hz, 1H), 7.80 (dd, J=8.5, 4.1 Hz, 1H), 4.04-3.97 (m, 1H), 3.42-3.37 (m, 1H), 3.27-3.20 (m, 1H), 2.88 (s, 3H), 2.47-2.35 (m, 4H), 2.35-2.25 (m, 2H), 2.09-1.91 (m, 2H), 1.06 (q, J=12.1 Hz, 1H), 0.95 (d, J=6.4 Hz, 3H).

Example 139: Synthesis of Compound 568 (1-Azetidin-1-yl-2-[(3R,5S)-5-methyl-1-(8-trifluoromethyl-quinolin-5-yl)-piperidin-3-ylamino]-ethanone)

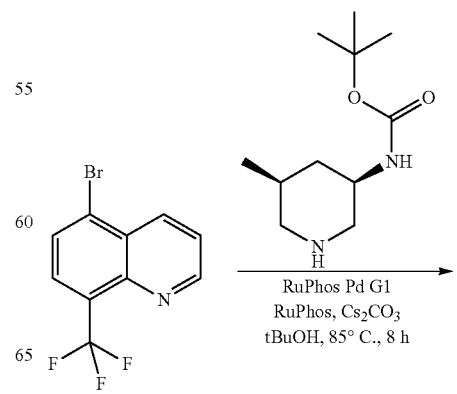

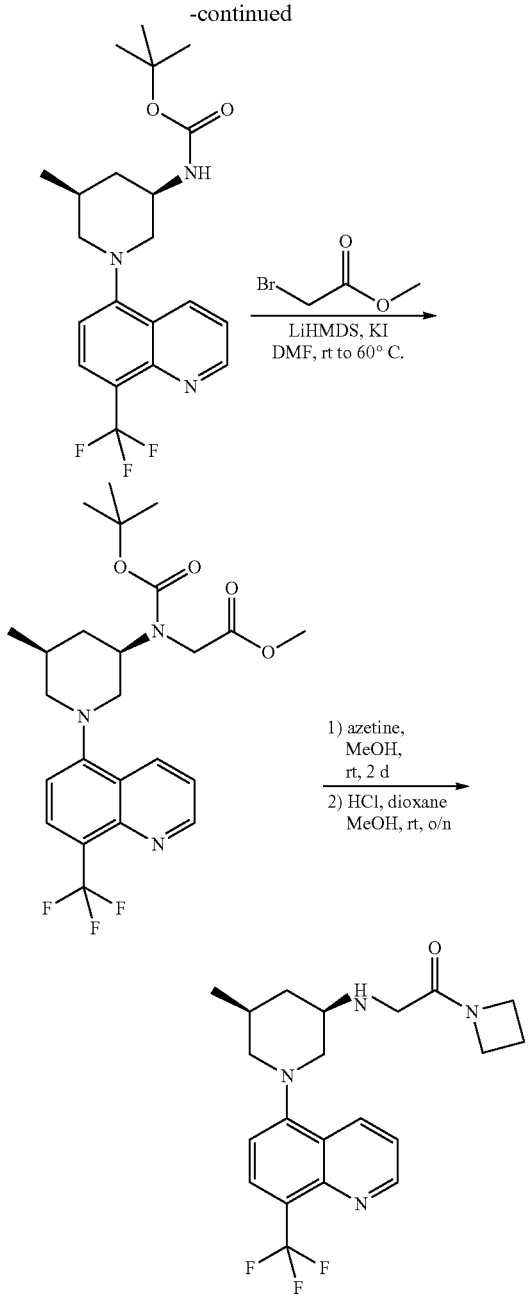

[(3R,5S)-5-Methyl-1-(8-trifluoromethyl-quinolin-5-yl)-piperidin-3-yl]-carbamic acid tert-butyl ester: A mixture of 5-bromo-8-trifluoromethyl-quinoline (600 mg; 2.0 mmol), tert-butyl N-[(3R,5S)-5-methylpiperidin-3-yl]carbamate (486 mg; 2.27 mmol), cesium carbonate (1345 mg; 4.1 mmol), 2-dicyclohexylphosphino-2',6'-di-1-propoxy-1,1'-biphenyl (48 mg; 0.1 mmol), chloro(2-dicyclohexylphosphino-2',6'-di-1-propoxy-1,1'-biphenyl)[2-(2-aminoethylphenyl)]palladium(II), methyl-t-butylether adduct (84 mg; 0.1 mmol) and tBuOH (15 mL) in 20 ml microwave tube was degassed and placed in microwave at 85° C. for 8 h. The reaction mixture was filtered. The filtrate was concentrated. The crude was purified by chromatography on silica gel, eluting with ethyl acetate and hexanes, to afford [(3R5S)-5-methyl-1-(8-trifluoromethyl-quinolin-5-yl)-piperidin-3-yl]-carbamic acid tert-butyl ester (764 mg; 90%). MS: n/z=410 [M+H]$^+$.

{tert-Butoxycarbonyl-[(3R,5S)-5-methyl-1-(8-trifluoromethyl-quinolin-5-yl)-piperidin-3-yl]-amino}-acetic acid methyl ester: Lithium bis(trimethylsilyl)amide (2.3 mL; 2.38 mmol) was added to the solution of [(3R,5S)-5-methyl-1-(8-trifluoromethyl-quinolin-5-yl)-piperidin-3-yl]-carbamic acid tert-butyl ester (750 mg; 1.8 mmol) and potassium iodide (30 mg; 0.18 mmol) in THF (2 mL) and the reaction mixture was stirred at room temperature for 30 min. Methyl bromoacetate (0.8 ml; 9.1 mmol) was added to the reaction mixture. The resulting mixture was stirred at 60° C. for 2 days. After cooling to room temperature, the reaction mixture was quenched with a saturated ammonium chloride solution and extracted with ethyl acetate. The separated organic layer was washed with brine, dried and concentrated. The crude was purified by prep-HPLC (XBridge Prep C18, 10 M, OBD 30×250 mm column, 50-95% ACN in water with 0.1% NH$_4$OH) to afford {tert-Butoxycarbonyl-[(3R,5S)-5-methyl-1-(8-trifluoromethyl-quinolin-5-yl)-piperidin-3-yl]-amino}-acetic acid methyl ester (160 mg; 19%). MS: m/z=482 [M+H]$^+$.

(2-Azetidin-1-yl-2-oxo-ethyl)-[(3R,5S)-5-methyl-1-(8-trifluoromethyl-quinolin-5-yl)-piperidin-3-yl]-carbamic acid tert-butyl ester: A mixture of {tert-butoxycarbonyl-[(3R,5S)-5-methyl-1-(8-trifluoromethyl-quinolin-5-yl)-piperidin-3-yl]-amino}-acetic acid methyl ester (25 mg; 0.05 mmol) and azetidine (0.14 mL; 2.0 mmol) in methanol (1 mL) was stirred at room temperature for 2 days. The reaction mixture was concentrated to dryness to afford the crude (2-azetidin-1-yl-2-oxo-ethyl)-[(3R,5S)-5-methyl-1-(8-trifluoromethyl-quinolin-5-yl)-piperidin-3-yl]-carbamic acid tert-butyl ester (25 mg), which was used directly for the next reaction. MS: m/z=507 [M+H]$^+$.

1-Azetidin-1-yl-2-[(3R,5S)-5-methyl-1-(8-trifluoromethyl-quinolin-5-yl)-piperidin-3-ylamino]-ethanone: 1-Azetidin-1-yl-2-[(3R,5S)-5-methyl-1-(8-trifluoromethyl-quinolin-5-yl)-piperidin-3-ylamino]-ethanone was prepared from (2-azetidin-1-yl-2-oxo-ethyl)-[(3R,5S)-5-methyl-1-(8-trifluoromethyl-quinolin-5-yl)-piperidin-3-yl]-carbamic acid tert-butyl ester using Method Q. The crude was purified by prep-HPLC (XBridge Prep C18, 10 µM, OBD 30×250 mm column, 10-60% ACN in water with 0.1% NH$_4$OH) to afford 1-Azetidin-1-yl-2-[(3R,5S)-5-methyl-1-(8-trifluoromethyl-quinolin-5-yl)-piperidin-3-ylamino]-ethanone (18 mg; 90%).

Compound 568: MS: m/z=407 [M+H]$^+$. $^1$H NMR (400 MHz, Methanol-d4, ppm) δ 8.96 (dd, J=4.2, 1.8 Hz, 1H), 8.59 (dd, J=8.6, 1.8 Hz, 1H), 8.49 (s, 1H), 8.06 (d, J=8.0 Hz, 1H), 7.63 (dd, J=8.6, 4.2 Hz, 1H), 7.28 (d, J=8.0 Hz, 1H), 4.24 (t, J=7.7 Hz, 2H), 4.08 (t, J=7.8 Hz, 2H), 3.74-3.65 (m, 1H), 3.62 (s, 2H), 3.45-3.35 (m, 2H), 2.69 (t, J=10.9 Hz, 1H), 2.47 (t, J=11.4 Hz, 1H), 2.38 (q, J=7.8 Hz, 2H), 2.34-2.26 (m, 1H), 2.23-2.06 (m, 1H), 1.15 (q, J=11.9 Hz, 1H), 1.06 (d, J=6.6 Hz, 3H).

The following compounds were synthesized in an analogous manner:

Compound 569 (1-Azetidin-1-yl-2-[(3R,5S)-5-methyl-1-(8-trifluoromethyl-quinolin-5-yl)-piperidin-3-ylamino]-ethanone): From {tert-butoxycarbonyl-[(3R,5S)-5-methyl-1-(8-trifluoromethyl-quinolin-5-yl)-piperidin-3-yl]-amino}-acetic acid methyl ester and methylamine. MS: m/z=381 [M+H]$^+$. $^1$H NMR (400 MHz, Methanol-d4, ppm) δ 8.95 (dd, J=4.3, 1.7 Hz, 1H), 8.58 (dd, J=8.6, 1.8 Hz, 1H), 8.46 (s, 1H), 8.06 (d, J=8.0 Hz, 1H), 7.62 (dd, J=8.6, 4.2 Hz, 1H), 7.26 (d, J=8.0 Hz, 1H), 3.72-3.63 (m, 1H), 3.59 (bs, 2H), 3.43-3.35 (m, 1H), 3.32-3.27 (m, 1H), 2.80 (s, 3H), 2.67 (t, J=10.9 Hz, 1H), 2.46 (t, J=11.4 Hz, 1H), 2.28 (d, J=12.4 Hz, 1H), 2.22-2.07 (m, 1H), 1.13 (q, J=11.8 Hz, 1H), 1.05 (d, J=6.6 Hz, 3H).

Compound 570 (1-Azetidin-1-yl-2-[(3R,5S)-5-methyl-1-(8-trifluoromethyl-quinolin-5-yl)-piperidin-3-ylamino]-ethanone): From {tert-butoxycarbonyl-[(3R,5S)-5-methyl-1-(8-trifluoromethyl-quinolin-5-yl)-piperidin-3-yl]-amino}-acetic acid methyl ester and ammonia. MS: m/z=367 [M+H]$^+$. $^1$H NMR (400 MHz, Methanol-d4, ppm) δδ 8.96 (dd, J=4.2, 1.7 Hz, 1H), 8.59 (dd, J=8.6, 1.8 Hz, 1H), 8.46 (s, 2H), 8.06 (d, J=8.0 Hz, 1H), 7.63 (dd, J=8.6, 4.2 Hz, 1H), 7.27 (d, J=8.0 Hz, 1H), 3.78-3.56 (m, 3H), 3.39 (dd, J=11.9, 4.0 Hz, 2H), 2.69 (t, J=10.8 Hz, 1H), 2.47 (t, J=11.4 Hz, 1H), 2.30 (d, J=12.3 Hz, 1H), 2.22-2.10 (m, 1H), 1.15 (q, J=11.9 Hz, 1H), 1.06 (d, J=6.6 Hz, 3H).

Example 140: Synthesis of Compound 571 ([(3R, 5S)-5-Methyl-1-(8-trifluoromethyl-quinolin-5-yl)-piperidin-3-ylamino]-acetic acid)

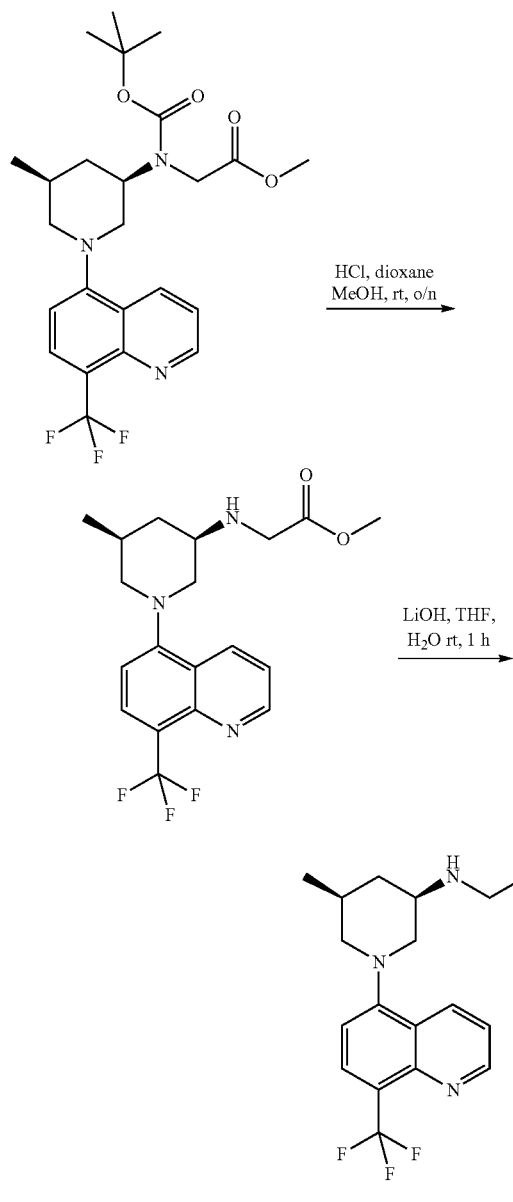

[(3R,5S)-5-Methyl-1-(8-trifluoromethyl-quinolin-5-yl)-piperidin-3-ylamino]-acetic acid methyl ester dihydrochloride: A solution of {tert-Butoxycarbonyl-[(3R,5S)-5-methyl-1-(8-trifluoromethyl-quinolin-5-yl)-piperidin-3-yl]-amino}-acetic acid methyl ester (18 mg; 0.04 mmol) and 4.0M HCl in Dioxane (186 μL; 0.75 mmol) in methanol (1 mL) was stirred at room temperature overnight. The reaction mixture was concentrated to dryness to afford the crude [(3R,5S)-5-methyl-1-(8-trifluoromethyl-quinolin-5-yl)-piperidin-3-ylamino]-acetic acid methyl ester dihydrochloride (17 mg; >99%), which was used for the next reaction directly. MS: m/z=382 [M+H]$^+$.

[(3R,5S)-5-Methyl-1-(8-trifluoromethyl-quinolin-5-yl)-piperidin-3-ylamino]-acetic acid: A solution of [(3R,5S)-5-methyl-1-(8-trifluoromethyl-quinolin-5-yl)-piperidin-3-ylamino]-acetic acid methyl ester dihydrochloride (17 mg; 0.04 mmol) and lithium hydroxide monohydrate (9.4 mg; 0.2 mmol) in THF (1 mL) and water (1 mL) was stirred at room temperature for 1 h. The reaction mixture was concentrated and then purified by prep-HPLC (XBridge Prep C18, 10 M, OBD 30×250 mm column, 5-60% ACN in water with 0.1% formic acid) to afford [(3R,5S)-5-Methyl-1-(8-trifluoromethyl-quinolin-5-yl)-piperidin-3-ylamino]-acetic acid (11 mg; 80%).

Compound 571: MS: m/z=368 [M+H]. $^1$H NMR (400 MHz, DMSO-d$_6$, ppm) δ 9.03 (dd, J=4.2, 1.7 Hz, 1H), 8.49 (dd, J=8.6, 1.8 Hz, 1H), 8.07 (d, J=8.0 Hz, 1H), 7.67 (dd, J=8.6, 4.1 Hz, 1H), 7.23 (d, J=8.0 Hz, 1H), 3.73-3.64 (m, 1H), 3.48-3.41 (m, 1H), 3.34-3.30 (m, 1H), 3.28 (d, J=4.6 Hz, 2H), 2.62 (t, J=11.0 Hz, 1H), 2.41 (t, J=11.4 Hz, 1H), 2.20 (d, J=12.3 Hz, 1H), 2.07-1.95 (m, 1H), 1.09 (q, J=12.0 Hz, 1H), 0.96 (d, J=6.6 Hz, 3H).

Example 141: Synthesis of Compound 580 (1-[(3R, 5S)-1-(8-Cyano-quinolin-5-yl)-5-trifluoromethyl-piperidin-3-yl]-3-(3,3-difluoro-cyclobutylmethyl)-urea)

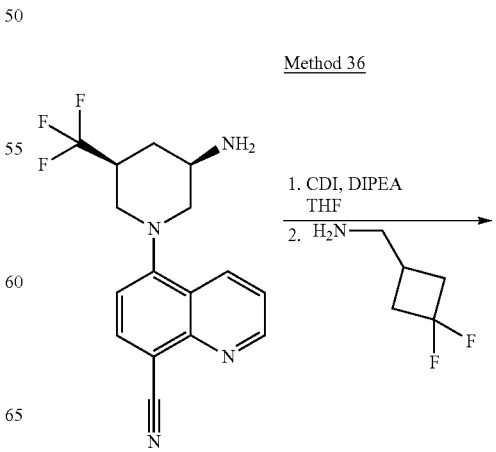

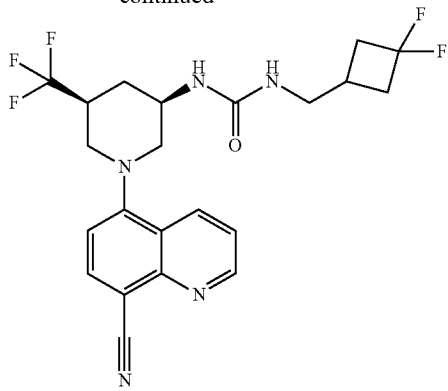

1-[(3R,5S)-1-(8-Cyano-quinolin-5-yl)-5-trifluoromethyl-piperidin-3-yl]-3-(3,3-difluoro-cyclobutylmethyl)-urea: A solution of 5-((3R,5S)-3-Amino-5-trifluoromethyl-piperidin-1-yl)-quinoline-8-carbonitrile hydrochloride (60 mg; 0.17 mmol) and 1,1'-carbonyldiimidazole (30 mg; 0.18 mmol) in DMF (1 mL) was stirred for 1 hour and then added C-(3,3-Difluoro-cyclobutyl)-methylamine hydrochloride (32 mg; 0.20 mmol) and the reaction mixture was stirred overnight. The solvent was removed under reduced pressure and the residue was purified by prep-HPLC under the following conditions: Column, XBridge C18 OBD Prep Column, 5 um, 19 mm×250 mm; Mobile phase, acetonitrile in water (with 10 mmol/L NH$_4$OH), 10% to 80% gradient over 25 min; Detector, UV 254 nm, to afford 1-[(3R,5S)-1-(8-Cyano-quinolin-5-yl)-5-trifluoromethyl-piperidin-3-yl]-3-(3,3-difluoro-cyclobutylmethyl)-urea (6.8 mg, 9%) as a white solid.

Compound 580: HPLC: <99% purity, RT=4.03 min. MS: m/z=468.3 [M+H]$^+$. $^1$H NMR (400 MHz, DMSO-d$_6$, ppm) δ 9.06 (dd, J=4.2, 1.6 Hz, 1H), 8.58 (dd, J=8.6, 1.7 Hz, 1H), 8.25 (d, J=8.0 Hz, 1H), 7.71 (dd, J=8.6, 4.2 Hz, 1H), 7.32 (d, J=8.1 Hz, 1H), 6.13 (d, J=7.7 Hz, 2H), 3.99 (s, 1H), 3.58 (t, J=10.3 Hz, 2H), 3.12 (qt, J=13.2, 6.0 Hz, 3H), 2.93 (t, J=11.5 Hz, 1H), 2.64-2.54 (m, 2H), 2.35-2.16 (m, 4H), 1.46 (q, J=12.2 Hz, 1H).

The following compounds were synthesized in an analogous manner: Compound 581 ((3R,4S)-3,4-Difluoro-pyrrolidine-1-carboxylic acid [(3R,5S)-1-(8-cyano-quinolin-5-yl)-5-trifluoromethyl-piperidin-3-yl]-amide): From 5-((3R,5S)-3-Amino-5-trifluoromethyl-piperidin-1-yl)-quinoline-8-carbonitrile hydrochloride and (3R,4S)-3,4-Difluoro-pyrrolidine hydrochloride. HPLC: <99% purity, RT=3.73 min. MS: m/z=454.5 [M+H]$^+$. $^1$H NMR (400 MHz, DMSO-d$_6$) δ 9.06 (dd, J=4.2, 1.6 Hz, 1H), 8.59 (dd, J=8.6, 1.7 Hz, 1H), 8.25 (d, J=8.0 Hz, 1H), 7.72 (dd, J=8.6, 4.2 Hz, 1H), 7.33 (d, J=8.1 Hz, 1H), 6.39 (d, J=7.4 Hz, 1H), 5.40-5.18 (m, 3H), 4.06 (s, 2H), 3.68 (dd, J=12.6, 5.9 Hz, 2H), 3.64-3.55 (m, 3H), 3.47-3.35 (m, 3H), 2.92 (t, J=11.6 Hz, 2H), 2.64 (t, J=11.3 Hz, 1H), 2.20 (d, J=12.0 Hz, 1H), 1.63 (q, J=12.4 Hz, 2H).

Compound 582 (1-(3,3-Difluoro-cyclobutylmethyl)-3-[(3R,5S)-5-methyl-1-(8-trifluoromethyl-quinolin-5-yl)-piperidin-3-yl]-urea): From (3R,5S)-5-Methyl-1-(8-trifluoromethyl-quinolin-5-yl)-piperidin-3-ylamine hydrochloride and C-(3,3-Difluoro-cyclobutyl)-methylamine hydrochloride. HPLC: <99% purity, RT=4.39 min. MS: m/z=457.4 [M+H]$^+$. $^1$H NMR (400 MHz, DMSO-d$_6$, ppm) δ 9.01 (dd, J=4.2, 1.7 Hz, 1H), 8.53 (dd, J=8.6, 1.8 Hz, 1H), 8.05 (d, J=8.1 Hz, 1H), 7.66 (dd, J=8.6, 4.2 Hz, 1H), 7.20 (d, J=8.1 Hz, 1H), 6.02 (t, J=5.9 Hz, 1H), 5.93 (d, J=7.5 Hz, 1H), 3.61-3.51 (m, 1H), 3.35 (s, 1H), 3.11 (qt, J=13.3, 6.1 Hz, 2H), 2.62-2.52 (m, 2H), 2.41 (t, J=11.0 Hz, 2H), 2.32-2.16 (m, 3H), 2.02 (s, 2H), 1.02 (q, J=11.9 Hz, 1H), 0.95 (d, J=6.4 Hz, 3H).

Compound 583 ((3R,4S)-3,4-Difluoro-pyrrolidine-1-carboxylic acid [(3R,5S)-5-methyl-1-(8-trifluoromethyl-quinolin-5-yl)-piperidin-3-yl]-amide): From (3R,5S)-5-Methyl-1-(8-trifluoromethyl-quinolin-5-yl)-piperidin-3-ylamine hydrochloride and (3R,4S)-3,4-Difluoro-pyrrolidine hydrochloride. HPLC: <99% purity, RT=4.08 min. MS: m/z=44.3.4 [M+H]$^+$. $^1$H NMR (400 MHz, DMSO-d$_6$, ppm) δ 9.01 (dd, J=4.2, 1.7 Hz, 1H), 8.53 (dd, J=8.6, 1.8 Hz, 1H), 8.05 (d, J=8.1 Hz, 1H), 7.67 (dd, J=8.6, 4.2 Hz, 1H), 7.21 (d, J=8.1 Hz, 1H), 6.23 (d, J=7.5 Hz, 1H), 5.21 (dd, J=9.6, 5.5 Hz, 2H), 3.94 (s, 1H), 3.73-3.49 (m, 3H), 3.49-3.32 (m, 4H), 2.48 (s, 3H), 2.40 (t, J=11.3 Hz, 1H), 2.12-1.96 (m, 2H), 1.20 (q, J=12.1 Hz, 1H), 0.96 (d, J=6.4 Hz, 3H).

Example 142: HEK Cell Assay

Into 384 CulturePlates (Corning 3707) was placed 5000 c/w of TLR7/NFKb HEK cells in 30 uL DMEM without Phenil red (gibco #31053) and 10% i.a. FCS and 2 mM L-ZGLutamin. The cells were incubated for 24 h at 37° C., 10% carbon dioxide and 90% relative humidity. 3 uL of controls, standards, and compounds were dispensed into wells, incubated for 30 min then 3 uL of R*48 agonist in 20 mM Hepes was added. After incubation for 5 hours, they were allowed to stand at room temperature for 15 min. To this was added 10 uL of Steady-Glo substrate reagent and shake assay plate for 5 min at 1500 rpm. The assay plate was allowed to sit for 30 min at room temperature and then the plate was read on EnVision.

Results are given in the following table.
A: $IC_{50}$<1 uM
B: $IC_{50}$: 1 UM-10 UM
C: $IC_{50}$>10 UM

TABLE 1

| Example | Compound | Potency |
|---------|----------|---------|
| 1 | 1 | C |
| 1 | 2 | B |
| 2 | 3 | B |
| 3 | 4 | B |
| 4 | 5 | B |
| 5 | 6 | B |
| 6 | 7 | C |
| 7 | 8 | B |
| 8 | 9 | C |
| 9 | 10 | A |
| 9 | 11 | B |
| 9 | 12 | A |
| 10 | 13 | C |
| 10 | 14 | C |
| 10 | 15 | C |
| 11 | 16 | A |
| 11 | 17 | C |
| 12 | 18 | C |
| 12 | 19 | A |
| 10 | 20 | A |
| 10 | 21 | A |
| 10 | 22 | B |
| 10 | 23 | C |
| 13 | 24 | A |
| 13 | 25 | A |
| 13 | 26 | B |
| 13 | 27 | B |
| 13 | 28 | A |
| 13 | 29 | C |
| 13 | 30 | C |

TABLE 1-continued

| Example | Compound | Potency |
|---------|----------|---------|
| 13 | 31 | B |
| 10 | 32 | A |
| 10 | 33 | B |
| 13 | 34 | C |
| 13 | 35 | A |
| 10 | 36 | B |
| 10 | 37 | C |
| 12 | 38 | A |
| 12 | 39 | B |
| 10 | 40 | A |
| 10 | 41 | B |
| 14 | 42 | C |
| 15 | 43 | C |
| 16 | 44 | A |
| 16 | 45 | C |
| 17 | 46 | C |
| 18 | 47 | B |
| 19 | 48 | B |
| 20 | 49 | C |
| 21 | 50 | A |
| 22 | 51 | C |
| 22 | 52 | A |
| 22 | 53 | A |
| 22 | 54 | A |
| 22 | 55 | A |
| 22 | 56 | B |
| 22 | 57 | A |
| 22 | 58 | A |
| 22 | 59 | A |
| 22 | 60 | B |
| 23 | 61 | B |
| 24 | 62 | B |
| 25 | 63 | C |
| 25 | 64 | B |
| 25 | 65 | A |
| 26 | 66 | A |
| 27 | 67 | A |
| 28 | 68 | A |
| 29 | 69 | B |
| 29 | 70 | A |
| 30 | 71 | A |
| 31 | 72 | A |
| 31 | 73 | A |
| 32 | 74 | A |
| 33 | 75 | A |
| 33 | 76 | B |
| 34 | 77 | A |
| 35 | 78 | A |
| 36 | 79 | B |
| 37 | 80 | B |
| 38 | 81 | A |
| 39 | 82 | A |
| 39 | 83 | A |
| 39 | 84 | B |
| 40 | 85 | A |
| 40 | 86 | C |
| 41 | 87 | A |
| 41 | 88 | A |
| 41 | 89 | C |
| 41 | 90 | C |
| 42 | 91 | A |
| 42 | 92 | B |
| 42 | 93 | C |
| 42 | 94 | C |
| 42 | 95 | B |
| 42 | 96 | C |
| 10 | 97 | A |
| 43 | 98 | A |
| 43 | 99 | A |
| 43 | 100 | B |
| 43 | 101 | B |
| 13 | 102 | A |
| 13 | 103 | A |
| 13 | 104 | C |
| 13 | 105 | A |
| 13 | 106 | A |
| 13 | 107 | C |
| 10 | 108 | A |
| 10 | 109 | A |
| 10 | 110 | C |
| 10 | 111 | A |
| 44 | 112 | B |
| 44 | 113 | A |
| 44 | 114 | C |
| 44 | 115 | C |
| 13 | 116 | A |
| 13 | 117 | A |
| 13 | 118 | B |
| 13 | 119 | A |
| 10 | 120 | C |
| 12 | 121 | C |
| 12 | 122 | A |
| 45 | 123 | A |
| 46 | 124 | A |
| 46 | 125 | A |
| 12 | 126 | C |
| 45 | 127 | C |
| 13 | 128 | C |
| 13 | 129 | B |
| 10 | 130 | A |
| 10 | 131 | C |
| 10 | 132 | A |
| 10 | 133 | C |
| 10 | 134 | B |
| 42 | 135 | A |
| 42 | 136 | A |
| 42 | 137 | A |
| 42 | 138 | A |
| 42 | 139 | C |
| 10 | 140 | A |
| 10 | 141 | C |
| 10 | 142 | A |
| 10 | 143 | C |
| 10 | 144 | A |
| 10 | 145 | C |
| 41 | 146 | A |
| 41 | 147 | A |
| 41 | 148 | C |
| 41 | 149 | C |
| 41 | 150 | A |
| 41 | 151 | A |
| 41 | 152 | B |
| 41 | 153 | B |
| 41 | 154 | A |
| 41 | 155 | B |
| 41 | 156 | C |
| 41 | 157 | C |
| 41 | 158 | B |
| 41 | 159 | B |
| 41 | 160 | C |
| 41 | 161 | C |
| 47 | 162 | B |
| 10 | 163 | A |
| 10 | 164 | C |
| 10 | 165 | A |
| 10 | 166 | A |
| 10 | 167 | A |
| 10 | 168 | C |
| 10 | 169 | A |
| 10 | 170 | C |
| 10 | 171 | A |
| 10 | 172 | B |
| 41 | 173 | B |
| 41 | 174 | C |
| 10 | 175 | B |
| 12 | 176 | B |
| 48 | 177 | B |
| 48 | 178 | B |
| 10 | 179 | B |
| 49 | 180 | A |
| 50 | 181 | C |
| 50 | 182 | B |
| 51 | 183 | C |
| 52 | 184 | C |
| 52 | 185 | C |
| 42 | 186 | C |

TABLE 1-continued

| Example | Compound | Potency |
|---|---|---|
| 53 | 187 | A |
| 54 | 188 | A |
| 54 | 189 | B |
| 55 | 190 | A |
| 56 | 191 | B |
| 56 | 192 | B |
| 54 | 193 | B |
| 57 | 194 | A |
| 57 | 195 | A |
| 58 | 196 | A |
| 59 | 197 | B |
| 59 | 198 | A |
| 57 | 199 | A |
| 60 | 200 | A |
| 27 | 201 | B |
| 27 | 202 | B |
| 27 | 203 | B |
| 61 | 204 | A |
| 61 | 205 | A |
| 62 | 206 | A |
| 63 | 207 | B |
| 63 | 208 | A |
| 61 | 209 | A |
| 64 | 210 | A |
| 65 | 211 | B |
| 65 | 212 | B |
| 66 | 213 | A |
| 66 | 214 | B |
| 66 | 215 | A |
| 67 | 216 | A |
| 66 | 217 | A |
| 66 | 218 | B |
| 67 | 219 | A |
| 66 | 220 | B |
| 68 | 221 | B |
| 40 | 222 | A |
| 40 | 223 | B |
| 69 | 224 | B |
| 69 | 225 | B |
| 69 | 226 | A |
| 69 | 227 | B |
| 40 | 228 | B |
| 40 | 229 | A |
| 10 | 230 | A |
| 70 | 231 | A |
| 10 | 232 | A |
| 10 | 233 | A |
| 10 | 234 | A |
| 10 | 235 | A |
| 10 | 236 | A |
| 69 | 237 | A |
| 69 | 238 | A |
| 57 | 239 | A |
| 57 | 240 | A |
| 57 | 241 | A |
| 70 | 242 | B |
| 57 | 243 | A |
| 57 | 244 | A |
| 57 | 245 | A |
| 57 | 246 | A |
| 57 | 247 | A |
| 57 | 248 | A |
| 71 | 249 | A |
| 71 | 250 | A |
| 71 | 251 | B |
| 70 | 252 | B |
| 71 | 253 | A |
| 71 | 254 | A |
| 71 | 255 | A |
| 71 | 256 | A |
| 71 | 257 | B |
| 71 | 258 | A |
| 71 | 259 | A |
| 72 | 260 | A |
| 72 | 261 | A |
| 73 | 262 | A |
| 73 | 263 | A |
| 73 | 264 | A |
| 10 | 265 | A |
| 10 | 266 | A |
| 74 | 267 | A |
| 13 | 268 | A |
| 10 | 269 | A |
| 75 | 270 | A |
| 75 | 271 | A |
| 76 | 272 | A |
| 75 | 273 | B |
| 77 | 274 | A |
| 75 | 275 | A |
| 78 | 276 | A |
| 13 | 277 | A |
| 57 | 278 | A |
| 57 | 279 | A |
| 79 | 280 | A |
| 80 | 281 | A |
| 80 | 282 | A |
| 57 | 283 | A |
| 75 | 284 | A |
| 75 | 285 | A |
| 76 | 286 | A |
| 57 | 287 | A |
| 80 | 288 | A |
| 57 | 289 | A |
| 78 | 290 | A |
| 80 | 291 | A |
| 71 | 292 | B |
| 71 | 293 | A |
| 81 | 294 | A |
| 71 | 295 | A |
| 75 | 296 | A |
| 75 | 297 | A |
| 76 | 298 | A |
| 71 | 299 | B |
| 81 | 300 | A |
| 81 | 301 | A |
| 61 | 302 | B |
| 61 | 303 | A |
| 82 | 304 | A |
| 83 | 305 | A |
| 83 | 306 | A |
| 61 | 307 | A |
| 75 | 308 | B |
| 75 | 309 | A |
| 76 | 310 | A |
| 61 | 311 | B |
| 83 | 312 | B |
| 61 | 313 | A |
| 78 | 314 | A |
| 83 | 315 | A |
| 61 | 316 | A |
| 61 | 317 | C |
| 61 | 318 | A |
| 61 | 319 | A |
| 75 | 320 | B |
| 75 | 321 | B |
| 76 | 322 | B |
| 61 | 323 | B |
| 83 | 324 | B |
| 61 | 325 | B |
| 78 | 326 | A |
| 83 | 327 | A |
| 61 | 328 | A |
| 61 | 329 | B |
| 84 | 330 | A |
| 84 | 331 | A |
| 85 | 332 | A |
| 84 | 333 | A |
| 84 | 334 | A |
| 86 | 335 | C |
| 86 | 336 | C |
| 87 | 337 | C |
| 86 | 338 | A |
| 88 | 339 | A |
| 88 | 340 | B |
| 89 | 341 | A |
| 90 | 342 | B |

TABLE 1-continued

| Example | Compound | Potency |
|---|---|---|
| 91 | 343 | B |
| 95 | 344 | B |
| 93 | 345 | C |
| 93 | 346 | C |
| 94 | 347 | B |
| 95 | 348 | A |
| 96 | 349 | A |
| 95 | 350 | A |
| 96 | 351 | A |
| 97 | 352 | A |
| 98 | 353 | A |
| 95 | 354 | B |
| 96 | 355 | A |
| 98 | 356 | A |
| 99 | 357 | A |
| 99 | 358 | A |
| 100 | 359 | A |
| 100 | 360 | A |
| 82 | 361 | A |
| 78 | 362 | A |
| 100 | 363 | A |
| 100 | 364 | A |
| 82 | 365 | B |
| 101 | 366 | B |
| 102 | 367 | C |
| 103 | 368 | C |
| 104 | 369 | A |
| 104 | 370 | A |
| 104 | 371 | A |
| 104 | 372 | A |
| 105 | 373 | B |
| 106 | 374 | B |
| 106 | 375 | B |
| 106 | 376 | B |
| 106 | 377 | B |
| 106 | 378 | B |
| 105 | 379 | B |
| 105 | 380 | B |
| 106 | 381 | B |
| 106 | 382 | B |
| 106 | 383 | B |
| 106 | 384 | B |
| 106 | 385 | B |
| 106 | 386 | B |
| 106 | 387 | B |
| 7 | 388 | B |
| 106 | 389 | B |
| 7 | 390 | B |
| 7 | 391 | C |
| 7 | 392 | C |
| 107 | 393 | B |
| 7 | 394 | B |
| 108 | 395 | B |
| 7 | 396 | C |
| 108 | 397 | B |
| 108 | 398 | A |
| 7 | 399 | C |
| 7 | 400 | C |
| 106 | 401 | B |
| 7 | 402 | B |
| 108 | 403 | A |
| 109 | 404 | C |
| 7 | 405 | B |
| 109 | 406 | B |
| 108 | 407 | A |
| 7 | 408 | B |
| 7 | 409 | A |
| 7 | 410 | A |
| 7 | 411 | B |
| 7 | 412 | C |
| 109 | 413 | A |
| 1 | 414 | A |
| 1 | 415 | A |
| 1 | 416 | A |
| 7 | 417 | A |
| 7 | 418 | A |
| 1 | 419 | B |
| 1 | 420 | A |
| 1 | 421 | A |
| 1 | 422 | A |
| 30 | 423 | A |
| 40 | 424 | B |
| 110 | 425 | A |
| 40 | 426 | A |
| 1 | 427 | B |
| 40 | 428 | A |
| 41 | 429 | C |
| 41 | 430 | A |
| 40 | 431 | A |
| 105 | 432 | A |
| 1 | 433 | A |
| 1 | 434 | A |
| 1 | 435 | A |
| 111 | 436 | A |
| 41 | 437 | B |
| 41 | 438 | B |
| 1 | 439 | A |
| 1 | 440 | A |
| 111 | 441 | A |
| 111 | 442 | A |
| 112 | 443 | A |
| 113 | 444 | A |
| 113 | 445 | A |
| 111 | 446 | A |
| 114 | 447 | A |
| 112 | 448 | B |
| 115 | 449 | A |
| 115 | 450 | B |
| 116 | 451 | A |
| 117 | 452 | A |
| 118 | 453 | A |
| 1 | 454 | B |
| 107 | 455 | C |
| 1 | 456 | C |
| 32 | 457 | A |
| 119 | 458 | C |
| 32 | 459 | B |
| 114 | 460 | C |
| 119 | 461 | A |
| 89 | 462 | A |
| 118 | 463 | A |
| 120 | 464 | A |
| 121 | 465 | A |
| 114 | 466 | B |
| 22 | 467 | A |
| 25 | 468 | A |
| 114 | 469 | B |
| 114 | 470 | B |
| 114 | 471 | A |
| 57 | 472 | A |
| 57 | 473 | A |
| 57 | 474 | B |
| 57 | 475 | |
| 80 | 476 | A |
| 121 | 477 | A |
| 122 | 478 | A |
| 123 | 479 | A |
| 124 | 480 | B |
| 122 | 481 | B |
| 124 | 482 | B |
| 123 | 483 | A |
| 122 | 484 | A |
| 122 | 485 | A |
| 123 | 486 | A |
| 123 | 487 | A |
| 125 | 488 | A |
| 125 | 489 | A |
| 122 | 490 | A |
| 122 | 491 | A |
| 124 | 492 | B |
| 123 | 493 | A |
| 126 | 494 | C |
| 126 | 495 | B |
| 122 | 496 | A |
| 126 | 497 | A |
| 126 | 498 | A |

TABLE 1-continued

| Example | Compound | Potency |
|---|---|---|
| 127 | 499 | B |
| 127 | 500 | B |
| 127 | 501 | C |
| 128 | 502 | B |
| 129 | 503 | A |
| 129 | 504 | A |
| 130 | 505 | B |
| 129 | 506 | B |
| 131 | 507 | A |
| 131 | 508 | B |
| 131 | 509 | C |
| 30 | 510 | A |
| 40 | 511 | A |
| 40 | 512 | B |
| 40 | 513 | B |
| 80 | 514 | A |
| 57 | 515 | A |
| 57 | 516 | A |
| 57 | 517 | A |
| 132 | 518 | A |
| 57 | 519 | A |
| 126 | 520 | A |
| 126 | 521 | A |
| 126 | 522 | A |
| 126 | 523 | A |
| 30 | 524 | B |
| 133 | 525 | A |
| 57 | 526 | A |
| 126 | 527 | A |
| 126 | 528 | B |
| 134 | 529 | A |
| 134 | 530 | A |
| 134 | 531 | A |
| 134 | 532 | A |
| 135 | 533 | A |
| 135 | 534 | B |
| 135 | 535 | A |
| 135 | 536 | B |
| 134 | 537 | A |
| 134 | 538 | A |
| 134 | 539 | A |
| 134 | 540 | A |
| 134 | 541 | B |
| 134 | 542 | B |
| 134 | 543 | A |
| 134 | 544 | A |
| 136 | 545 | B |
| 136 | 546 | A |
| 134 | 547 | A |
| 134 | 548 | A |
| 134 | 549 | B |
| 57 | 550 | |
| 57 | 551 | |
| 137 | 552 | A |
| 30 | 553 | A |
| 122 | 554 | A |
| 122 | 555 | B |
| 122 | 556 | B |
| 122 | 557 | B |
| 122 | 558 | B |
| 122 | 559 | B |
| 122 | 560 | A |
| 123 | 561 | A |
| 123 | 562 | A |
| 123 | 563 | A |
| 124 | 564 | C |
| 124 | 565 | B |
| 124 | 566 | B |
| 138 | 567 | C |
| 139 | 568 | A |
| 139 | 569 | A |
| 139 | 570 | A |
| 140 | 571 | B |
| 57 | 572 | A |
| 57 | 573 | A |
| 57 | 574 | A |
| 57 | 575 | B |
| 40 | 576 | A |
| 40 | 577 | A |
| 40 | 578 | A |
| 40 | 579 | B |
| 141 | 580 | B |
| 141 | 581 | B |
| 141 | 582 | B |
| 141 | 583 | B |
| 40 | 584 | A |
| 40 | 585 | A |
| 89 | 586 | A |

Example 77. Pharmaceutical Preparations (A) Injection vials: A solution of 100 g of an active ingredient according to the invention and 5 g of disodium hydrogen phosphate in 3 l of bidistilled water is adjusted to pH 6.5 using 2 N hydrochloric acid, sterile filtered, transferred into injection vials, is lyophilized under sterile conditions and is sealed under sterile conditions. Each injection vial contains 5 mg of active ingredient.

(B) Suppositories: A mixture of 20 g of an active ingredient according to the invention is melted with 100 g of soy lecithin and 1400 g of cocoa butter, is poured into moulds and is allowed to cool. Each suppository contains 20 mg of active ingredient.

(C) Solution: A solution is prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilized by irradiation. This solution could be used in the form of eye drops.

(D) Ointment: 500 mg of an active ingredient according to the invention is mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

(F) Coated tablets: Tablets are pressed analogously to Example E and subsequently are coated in a conventional manner with a coating of sucrose, potato starch, talc, tragacanth and dye.

(G) Capsules: 2 kg of an active ingredient according to the invention are introduced into hard gelatin capsules in a conventional manner in such a way that each capsule contains 20 mg of the active ingredient.

(H) Ampoules: A solution of 1 kg of an active ingredient according to the invention in 60 l of bidistilled water is sterile filtered, transferred into ampoules, is lyophilized under sterile conditions and is sealed under sterile conditions. Each ampoule contains 10 mg of active ingredient.

(I) Inhalation spray: 14 g of an active ingredient according to the invention are dissolved in 10 l of isotonic NaCl solution, and the solution is transferred into commercially available spray containers with a pump mechanism. The solution could be sprayed into the mouth or nose. One spray shot (about 0.1 ml) corresponds to a dose of about 0.14 mg.

While a number of embodiments of this invention are described herein, it is apparent that the basic examples may be altered to provide other embodiments that utilize the compounds and methods of this invention. Therefore, it will be appreciated that the scope of this invention is to be defined by the various embodiments described herein rather than by the specific embodiments that have been represented by way of example.

We claim:
1. A compound of formula I,

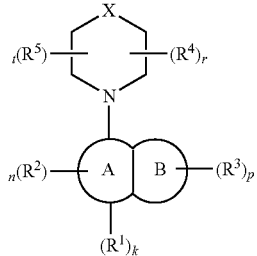

or a pharmaceutically acceptable salt thereof, wherein:
Ring A is pyridyl;
Ring B is pyridyl or pyrazinyl;
$R^1$ is —$CHF_2$, —$CH_3$, —F, —$CF_3$, —OMe, or —CN;
each $R^2$ is independently —H, —$C_{1-8}$ alkyl, $C_{1-6}$ aliphatic, $C_{3-10}$ aryl, a 3-8 membered saturated or partially unsaturated carbocyclic ring, halogen, -haloalkyl, —OR, —SR, —CN, —$NO_2$, —$SO_2R$, —SOR, —C(O)R, —$CO_2R$, —C(O)N(R)$_2$, —NRC(O)R, —NRC(O)N(R)$_2$, —$NRSO_2R$, or —N(R)$_2$;
each $R^3$ is independently —H, alkyl, -haloalkyl, and —CN;
X is $CH_2$ or O;
each $R^4$ is independently selected from the group consisting of

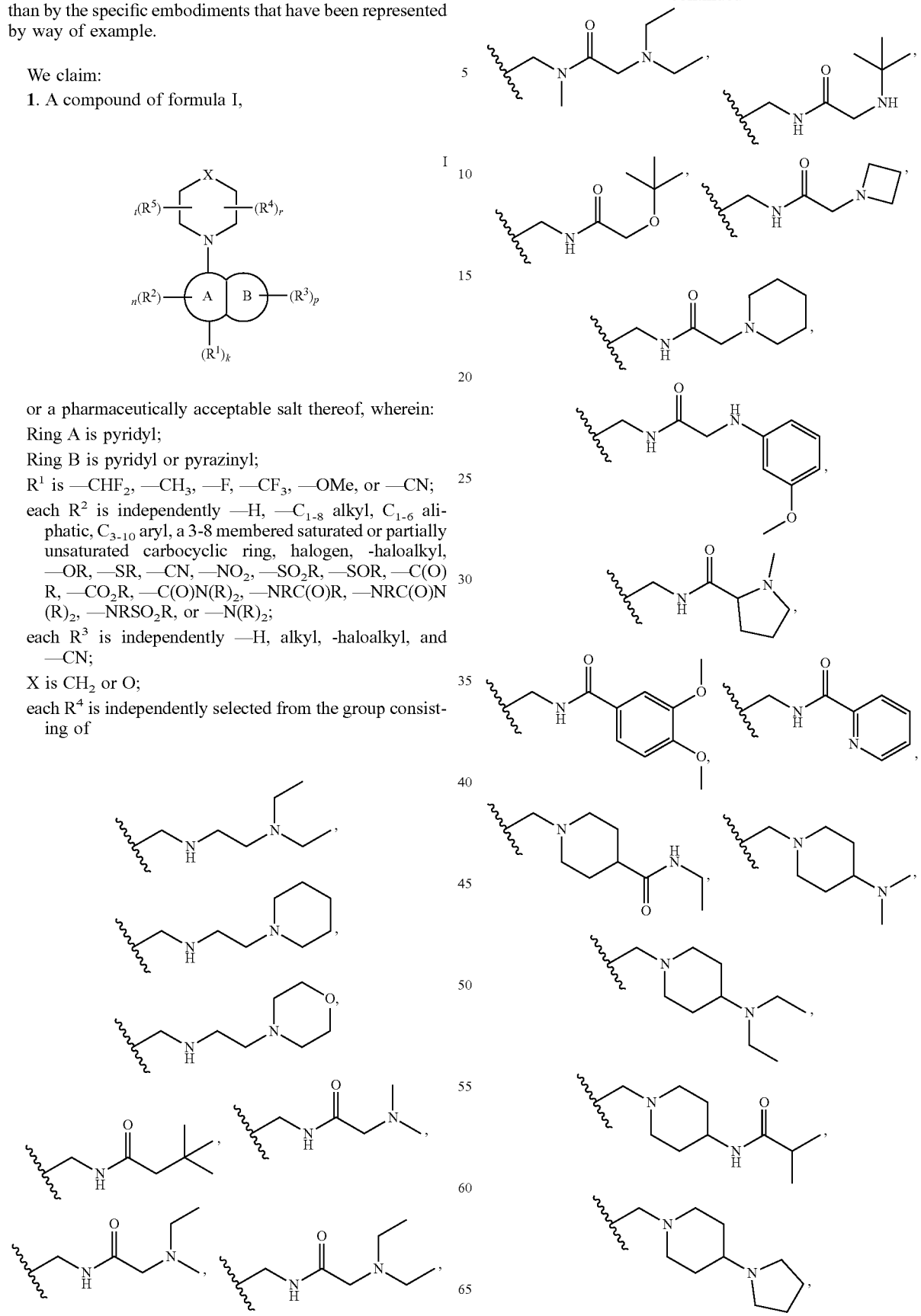

643
-continued
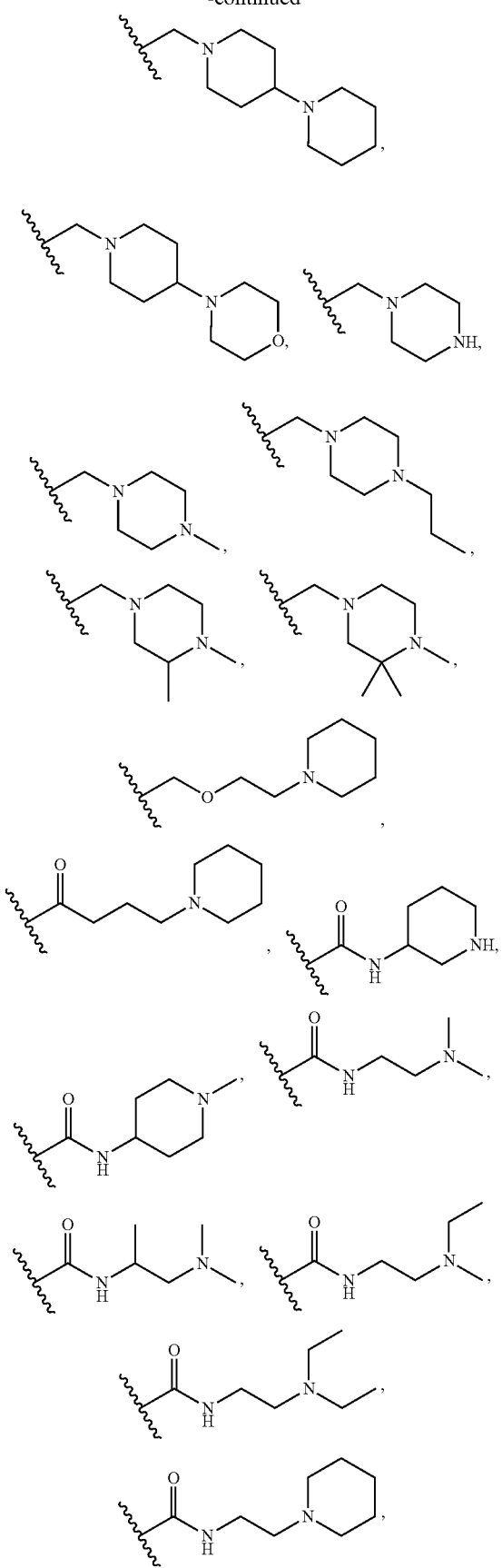
644
-continued
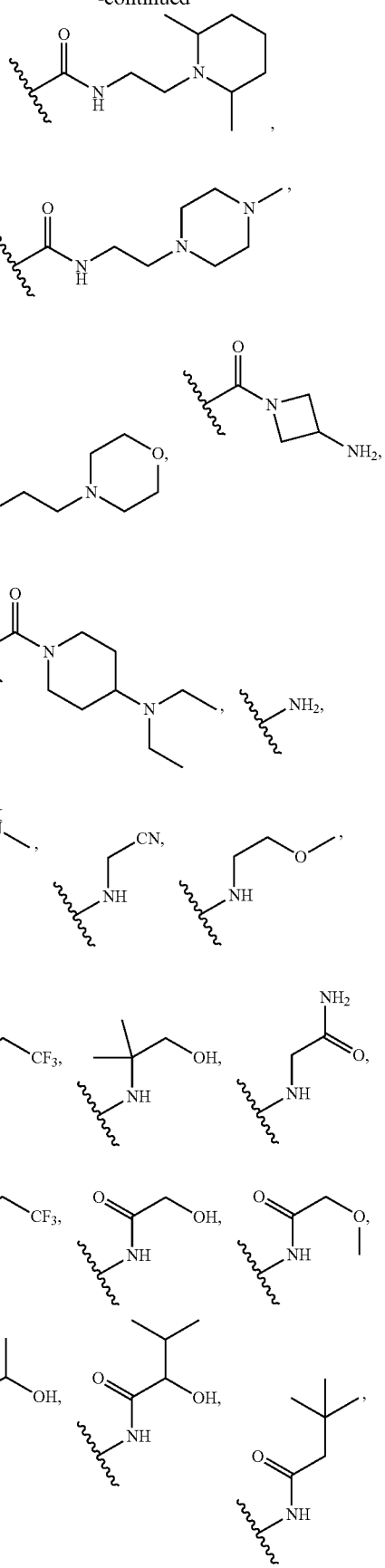

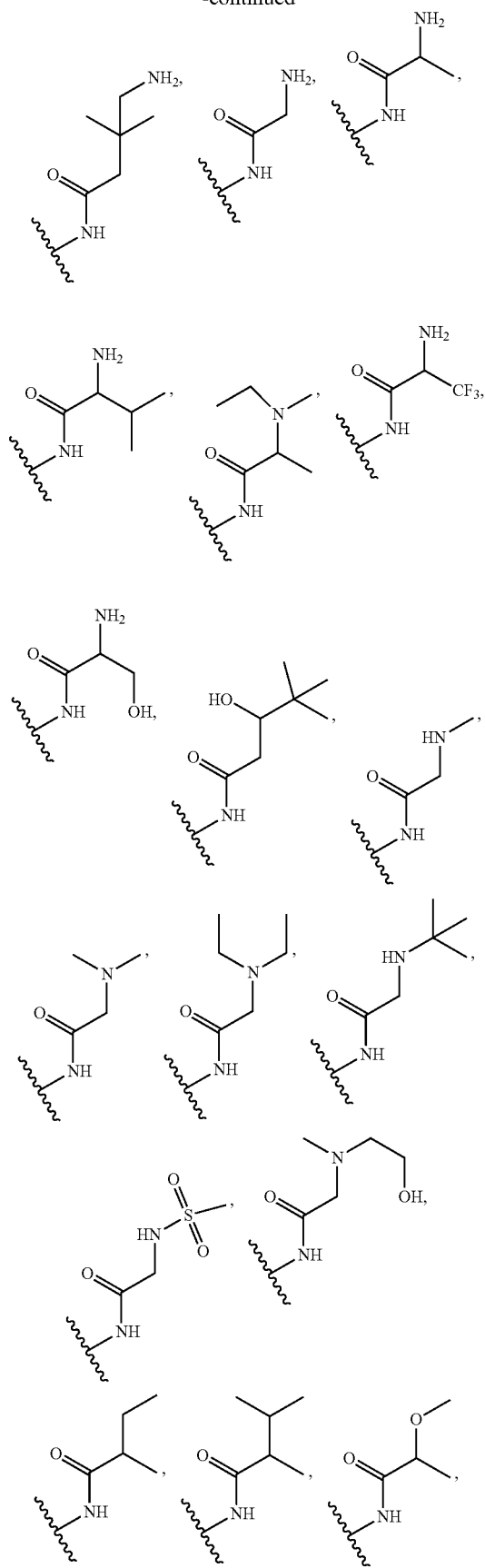
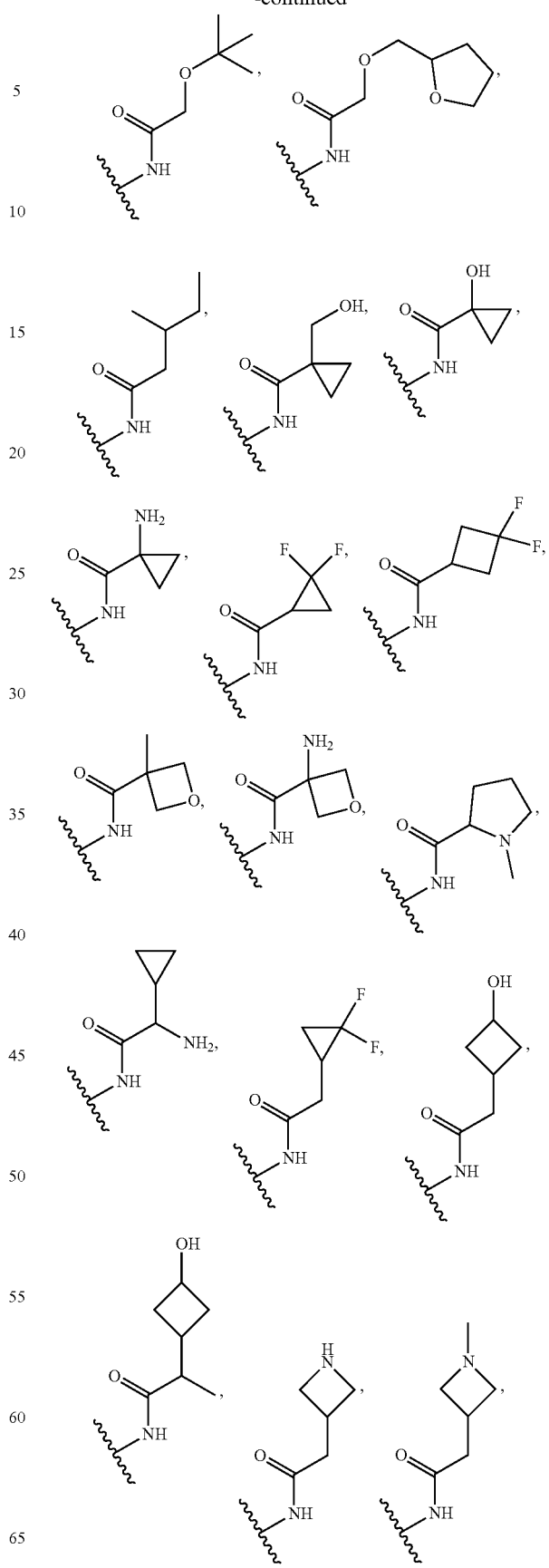

647
-continued
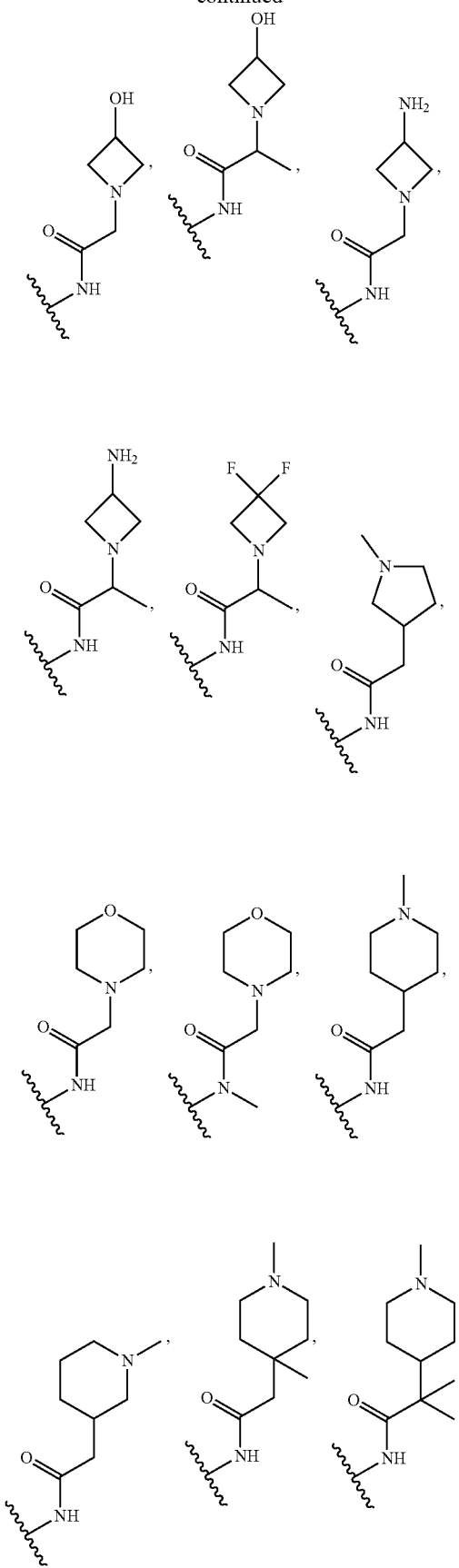
648
-continued
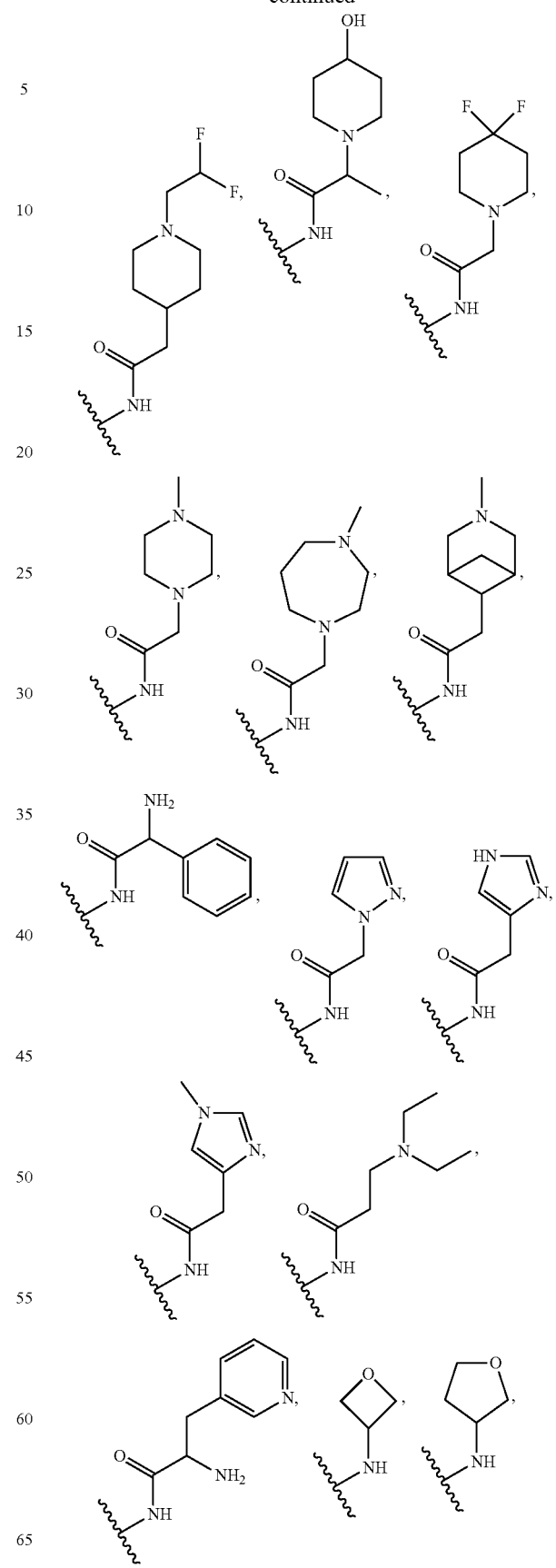

-continued

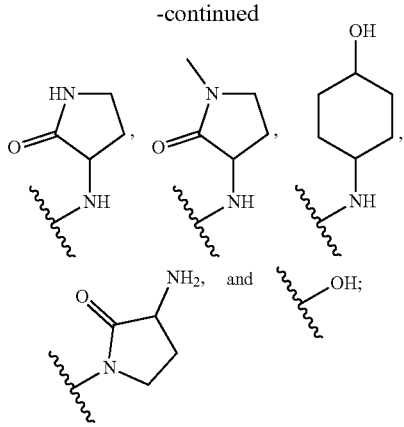

each R⁵ is independently alkyl or -haloalkyl;
each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted, with the exception of H; or
two R groups on the same atom are taken together with the atom to which they are attached to form a 3-7 membered heterocyclic ring having 1-4 heteroatoms independently selected from nitrogen, oxygen, or sulfur, or a 5-6 membered monocyclic heteroaryl ring having 1-4 heteroatoms independently selected from nitrogen, oxygen, or sulfur; each of which is optionally substituted;
k is 0 or 1;
n is 0, 1, or 2;
p is 0, 1, or 2;
r is 1 or 2; and
t is 1 or 2.

2. The compound of claim 1, wherein Ring A is

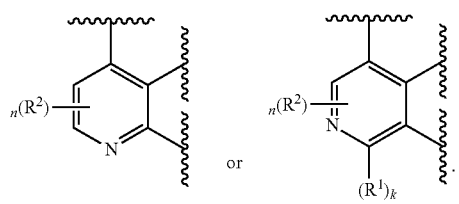

3. The compound of claim 1, wherein Ring A is

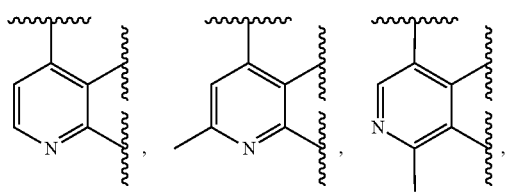

-continued

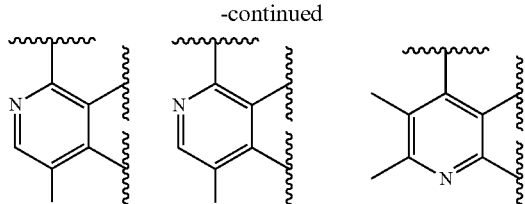

4. The compound of claim 1, wherein Ring B is

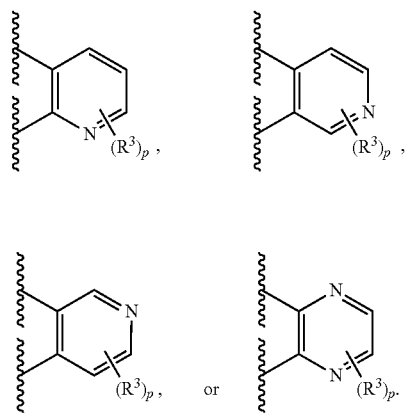

5. The compound of claim 1, wherein Ring B is

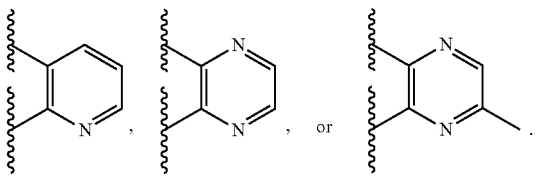

6. The compound of claim 1, wherein X is $CH_2$.
7. The compound of claim 1, wherein X is O.
8. The compound of claim 1, of formula I-j

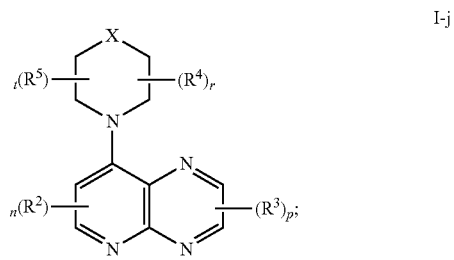

I-j or a pharmaceutically acceptable salt thereof.
9. The compound of claim 1, wherein R⁴ is —NH₂; R⁵ is methyl; r is 1; and t is 1, or a pharmaceutically acceptable salt thereof.
10. A compound selected from the group consisting of one of the compounds of the following Table, or a pharmaceutically acceptable salt thereof:

| Compound Number | Example Number | Chemical Structure |
|---|---|---|
| 10 | 9 | 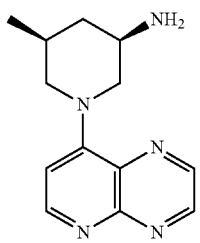 [SMILES: C[C@H]1C[C@@H](N)CN(c2ccnc3nccnc23)C1] |
| 15 | 10 | 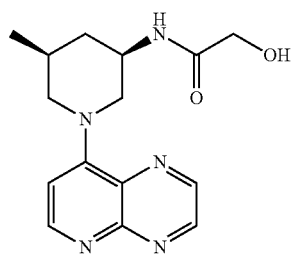 [SMILES: C[C@H]1C[C@@H](NC(=O)CO)CN(c2ccnc3nccnc23)C1] |
| 17 | 11 | 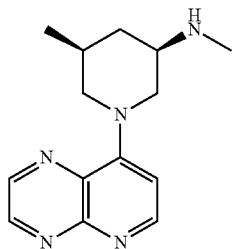 [SMILES: CN[C@@H]1C[C@H](C)CN(c2ccnc3nccnc23)C1] |
| 18 | 12 | 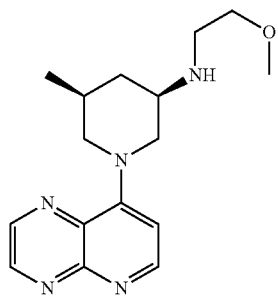 [SMILES: COCCN[C@@H]1C[C@H](C)CN(c2ccnc3nccnc23)C1] |
| 22 | 10 | 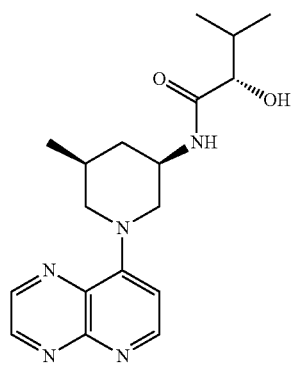 [SMILES: CC(C)[C@H](O)C(=O)N[C@@H]1C[C@H](C)CN(c2ccnc3nccnc23)C1] |

-continued
| Compound Number | Example Number | Chemical Structure |
|---|---|---|
| 23 | 10 | 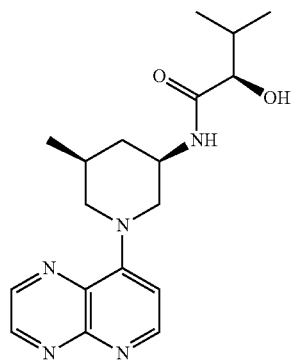 [SMILES: CC(C)[C@@H](O)C(=O)N[C@@H]1C[C@H](C)CN(c2ccnc3nccnc23)C1] |
| 26 | 13 | 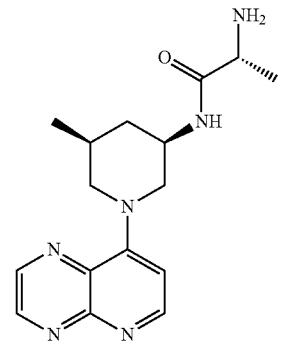 [SMILES: C[C@H]1C[C@@H](NC(=O)[C@@H](C)N)CN(c2ccnc3nccnc23)C1] |
| 27 | 13 | 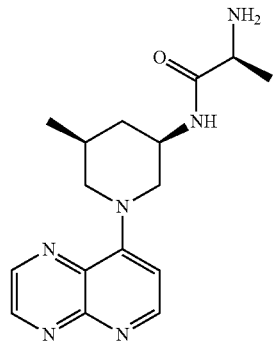 [SMILES: C[C@H]1C[C@@H](NC(=O)[C@H](C)N)CN(c2ccnc3nccnc23)C1] |
| 29 | 13 | 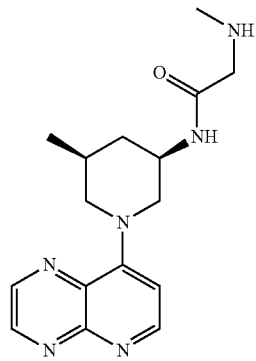 [SMILES: CNCC(=O)N[C@@H]1C[C@H](C)CN(c2ccnc3nccnc23)C1] |

-continued
| Compound Number | Example Number | Chemical Structure |
|---|---|---|
| 30 | 13 | 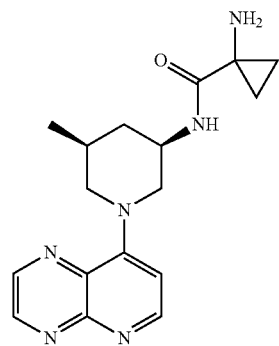 [SMILES: C[C@H]1C[C@@H](NC(=O)C2(N)CC2)CN(c2ccnc3nccnc23)C1] |
| 33 | 10 | 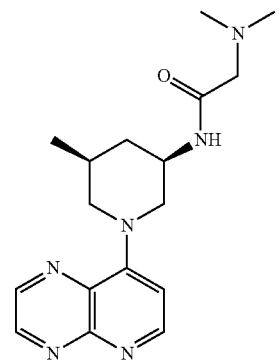 [SMILES: C[C@H]1C[C@@H](NC(=O)CN(C)C)CN(c2ccnc3nccnc23)C1] |
| 34 | 13 | 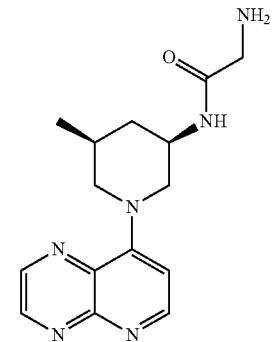 [SMILES: C[C@H]1C[C@@H](NC(=O)CN)CN(c2ccnc3nccnc23)C1] |
| 37 | 10 | 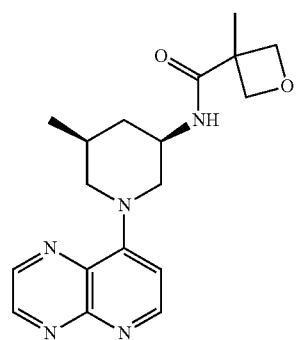 [SMILES: C[C@H]1C[C@@H](NC(=O)C2(C)COC2)CN(c2ccnc3nccnc23)C1] |

-continued
| Compound Number | Example Number | Chemical Structure |
|---|---|---|
| 39 | 12 | 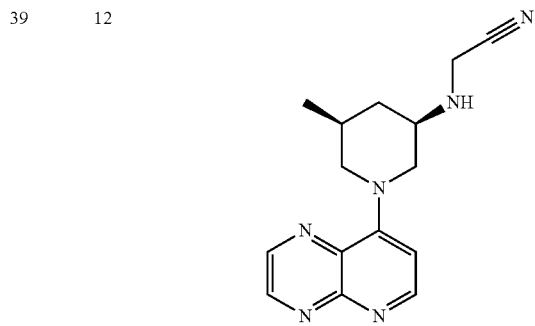 |
| 41 | 10 | 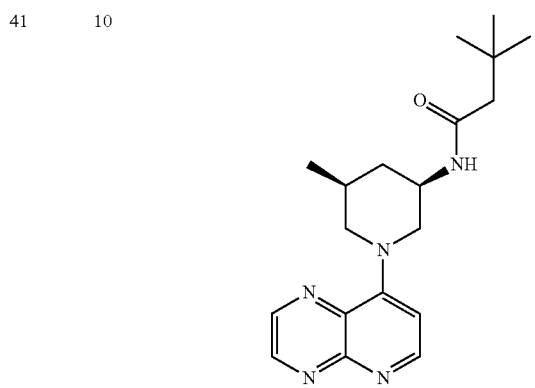 |
| 42 | 14 | 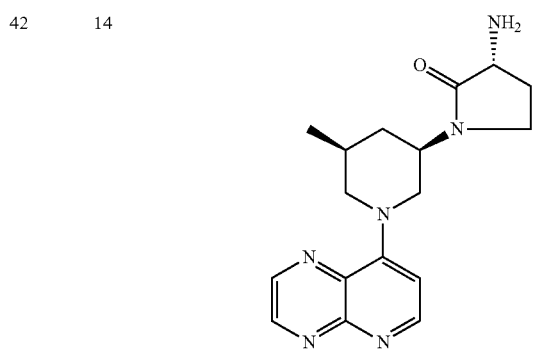 |
| 47 | 18 | 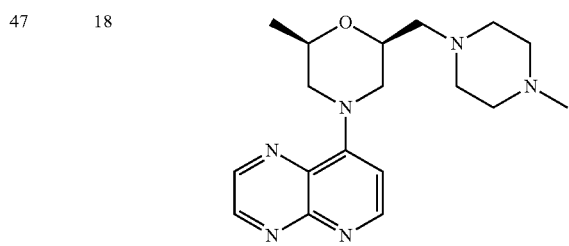 |
| 48 | 19 | 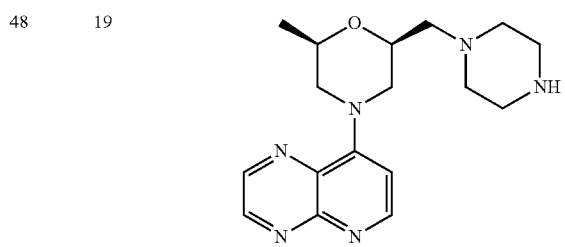 |

-continued
| Compound Number | Example Number | Chemical Structure |
|---|---|---|
| 52 | 22 | 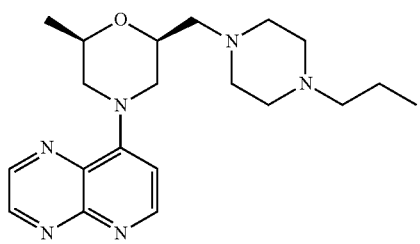 [SMILES: CCCN1CCN(C[C@H]2CN(c3ccnc4nccnc34)C[C@@H](C)O2)CC1] |
| 53 | 22 | 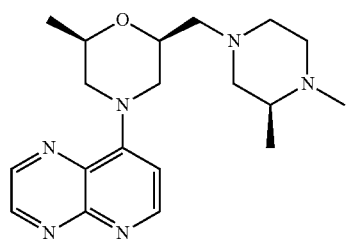 [SMILES: C[C@@H]1CN(c2ccnc3nccnc23)C[C@H](CN2CCN(C)[C@@H](C)C2)O1] |
| 54 | 22 | 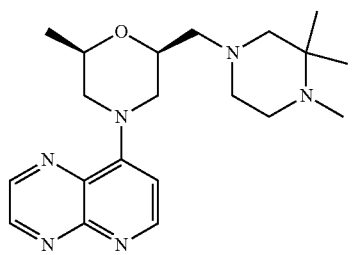 [SMILES: C[C@@H]1CN(c2ccnc3nccnc23)C[C@H](CN2CCN(C)C(C)(C)C2)O1] |
| 55 | 22 | 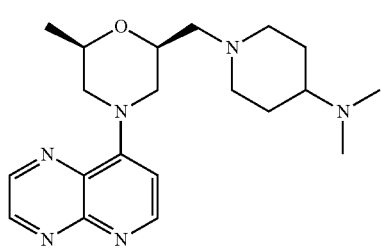 [SMILES: C[C@@H]1CN(c2ccnc3nccnc23)C[C@H](CN2CCC(N(C)C)CC2)O1] |
| 56 | 22 | 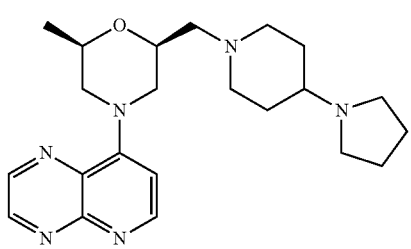 [SMILES: C[C@@H]1CN(c2ccnc3nccnc23)C[C@H](CN2CCC(N3CCCC3)CC2)O1] |
| 58 | 22 | 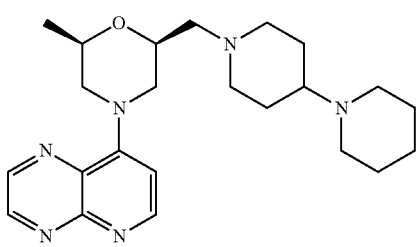 [SMILES: C[C@@H]1CN(c2ccnc3nccnc23)C[C@H](CN2CCC(N3CCCCC3)CC2)O1] |

-continued
| Compound Number | Example Number | Chemical Structure |
|---|---|---|
| 60 | 22 | 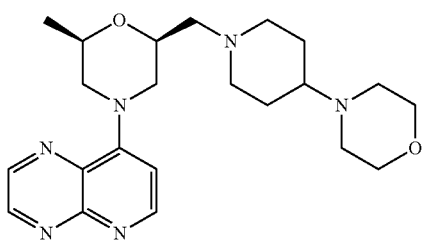 [SMILES: C[C@@H]1CN(c2ccnc3nccnc23)C[C@H](CN2CCC(N3CCOCC3)CC2)O1] |
| 61 | 23 | 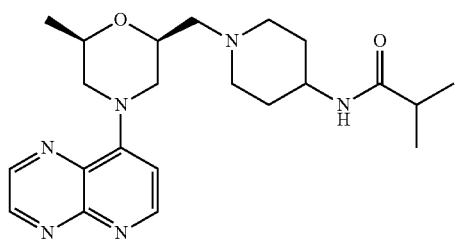 [SMILES: CC(C)C(=O)NC1CCN(C[C@H]2CN(c3ccnc4nccnc34)C[C@@H](C)O2)CC1] |
| 62 | 24 | 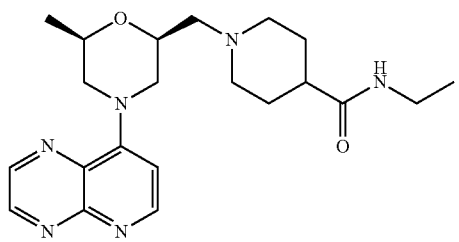 [SMILES: CCNC(=O)C1CCN(C[C@H]2CN(c3ccnc4nccnc34)C[C@@H](C)O2)CC1] |
| 63 | 25 | 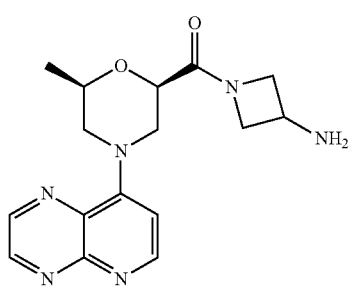 [SMILES: C[C@@H]1CN(c2ccnc3nccnc23)C[C@H](C(=O)N2CC(N)C2)O1] |
| 64 | 25 | 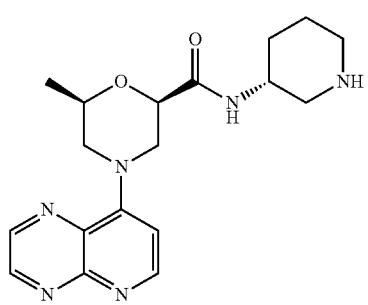 [SMILES: C[C@@H]1CN(c2ccnc3nccnc23)C[C@H](C(=O)N[C@@H]2CCCNC2)O1] |

-continued
| Compound Number | Example Number | Chemical Structure |
|---|---|---|
| 65 | 25 | 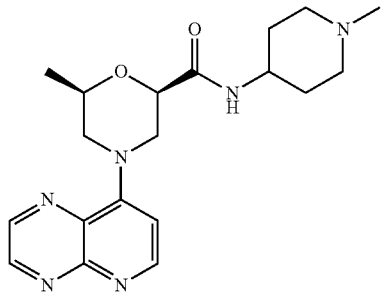 [SMILES: C[C@@H]1CN(c2ccnc3nccnc23)C[C@H](C(=O)NC2CCN(C)CC2)O1] |
| 80 | 37 | 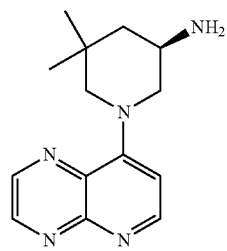 [SMILES: CC1(C)C[C@@H](N)CN(c2ccnc3nccnc23)C1] |
| 84 | 39 | 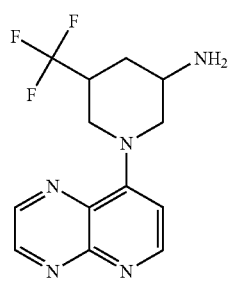<br>cis racemic |
| 86 | 40 | 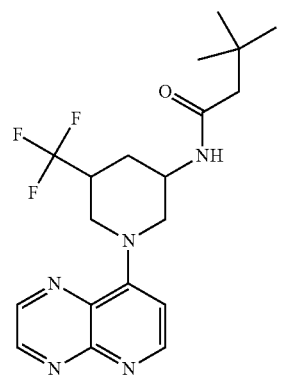<br>cis racemic |

-continued
| Compound Number | Example Number | Chemical Structure |
|---|---|---|
| 89 | 41 | 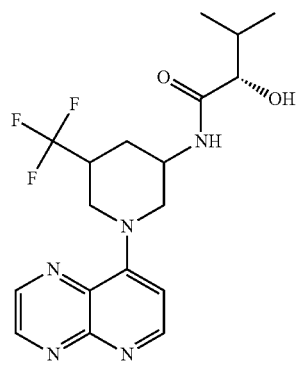
Isomer 1 |
| 90 | 41 | 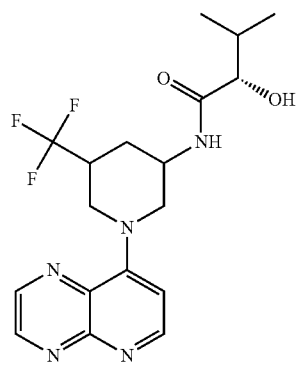
cis Isomer 2 |
| 93 | 42 | 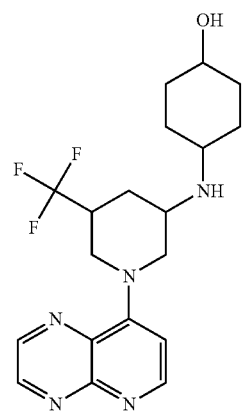
Isomer 1 |

-continued
| Compound Number | Example Number | Chemical Structure |
|---|---|---|
| 94 | 42 | 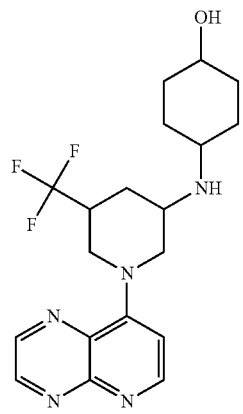<br>Isomer 2 |
| 96 | 42 | 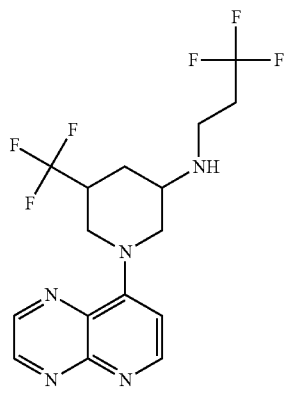<br>cis racemic |
| 100 | 43 | 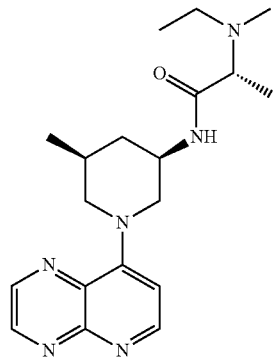 [SMILES: CCN(C)[C@H](C)C(=O)N[C@@H]1C[C@H](C)CN(c2ccnc3nccnc23)C1] |
| 101 | 43 | 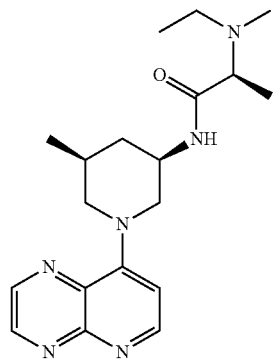 [SMILES: CCN(C)[C@@H](C)C(=O)N[C@@H]1C[C@H](C)CN(c2ccnc3nccnc23)C1] |

-continued
| Compound Number | Example Number | Chemical Structure |
|---|---|---|
| 104 | 13 | 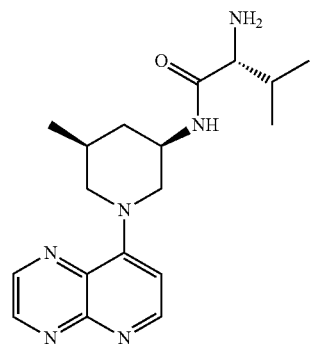 [SMILES: CC(C)[C@@H](N)C(=O)N[C@@H]1C[C@H](C)CN(c2ccnc3nccnc23)C1] |
| 105 | 13 | 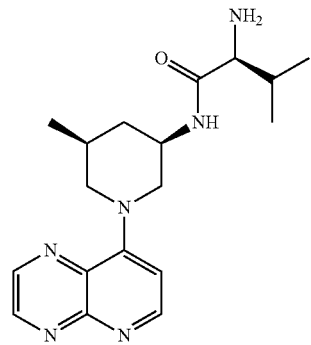 [SMILES: CC(C)[C@H](N)C(=O)N[C@@H]1C[C@H](C)CN(c2ccnc3nccnc23)C1] |
| 107 | 13 | 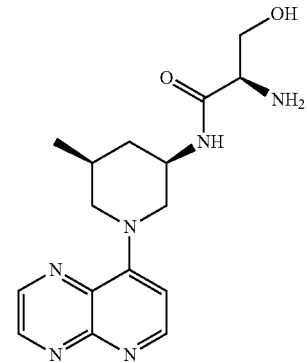 [SMILES: C[C@H]1C[C@@H](NC(=O)[C@H](N)CO)CN(c2ccnc3nccnc23)C1] |
| 110 | 10 | 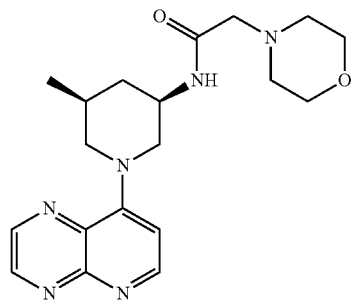 [SMILES: C[C@H]1C[C@@H](NC(=O)CN2CCOCC2)CN(c2ccnc3nccnc23)C1] |

-continued
| Compound Number | Example Number | Chemical Structure |
|---|---|---|
| 114 | 44 | 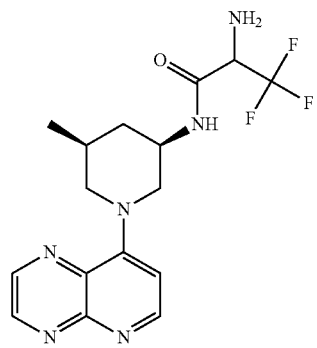<br>Isomer 1 |
| 115 | 44 | 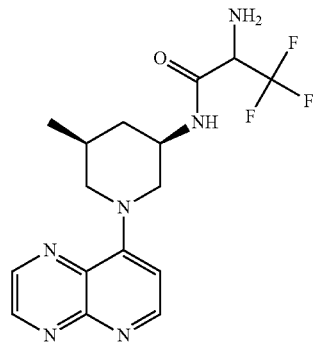<br>Isomer 2 |
| 118 | 13 | 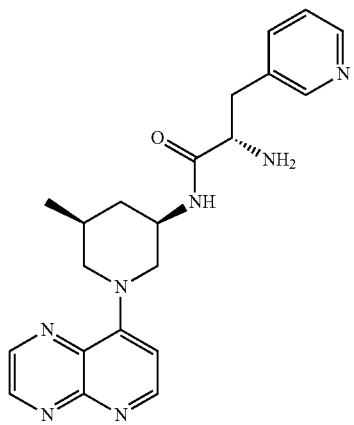 [SMILES: C[C@H]1C[C@@H](NC(=O)[C@@H](N)Cc2cccnc2)CN(c2ccnc3nccnc23)C1] |
| 120 | 10 | 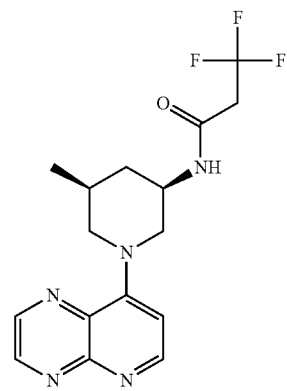 [SMILES: C[C@H]1C[C@@H](NC(=O)CC(F)(F)F)CN(c2ccnc3nccnc23)C1] |

-continued
| Compound Number | Example Number | Chemical Structure |
|---|---|---|
| 121 | 12 | 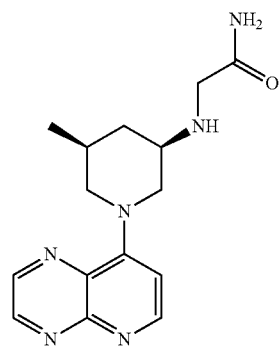 [SMILES: C[C@H]1C[C@@H](NCC(N)=O)CN(c2ccnc3nccnc23)C1] |
| 126 | 12 | 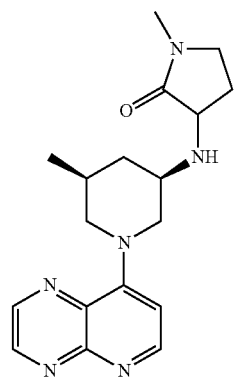 [SMILES: C[C@H]1C[C@@H](NC2CCN(C)C2=O)CN(c2ccnc3nccnc23)C1] |
| 127 | 45 | 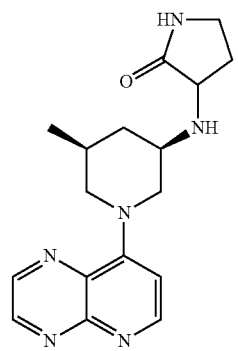 [SMILES: C[C@H]1C[C@@H](NC2CCNC2=O)CN(c2ccnc3nccnc23)C1] |
| 128 | 13 | 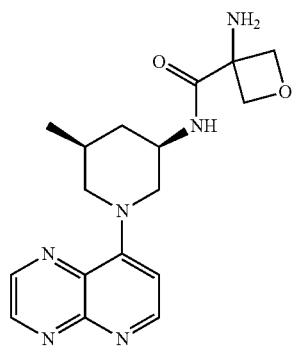 [SMILES: C[C@H]1C[C@@H](NC(=O)C2(N)COC2)CN(c2ccnc3nccnc23)C1] |

-continued
| Compound Number | Example Number | Chemical Structure |
|---|---|---|
| 131 | 10 | 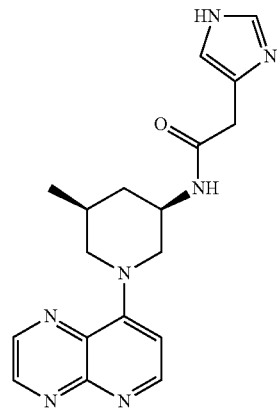 [SMILES: C[C@H]1C[C@@H](NC(=O)Cc2c[nH]cn2)CN(c2ccnc3nccnc23)C1] |
| 133 | 10 | 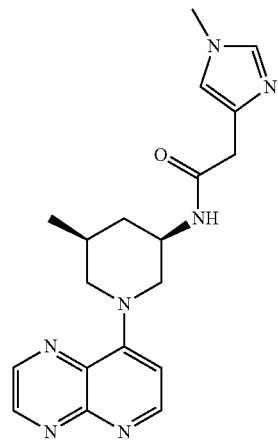 [SMILES: C[C@H]1C[C@@H](NC(=O)Cc2cn(C)cn2)CN(c2ccnc3nccnc23)C1] |
| 139 | 42 | 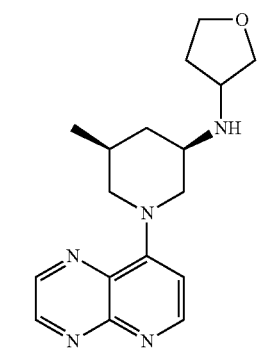 [SMILES: C[C@H]1C[C@@H](NC2CCOC2)CN(c2ccnc3nccnc23)C1] |
| 141 | 10 | 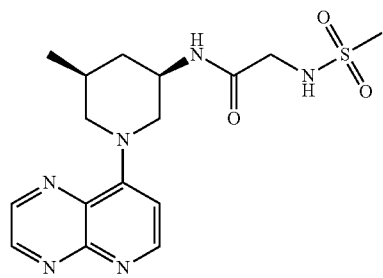 [SMILES: C[C@H]1C[C@@H](NC(=O)CNS(C)(=O)=O)CN(c2ccnc3nccnc23)C1] |

-continued
| Compound Number | Example Number | Chemical Structure |
|---|---|---|
| 143 | 10 | 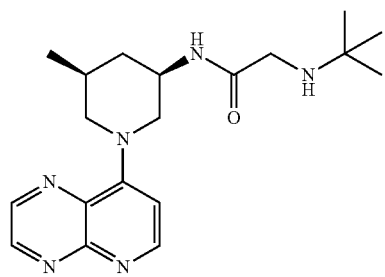 [SMILES: C[C@H]1C[C@@H](NC(=O)CNC(C)(C)C)CN(c2ccnc3nccnc23)C1] |
| 145 | 10 | 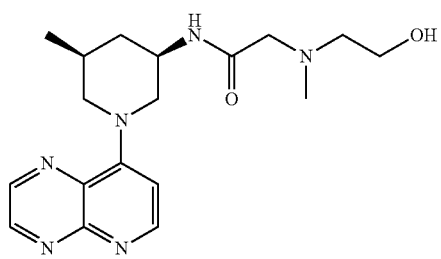 [SMILES: C[C@H]1C[C@@H](NC(=O)CN(C)CCO)CN(c2ccnc3nccnc23)C1] |
| 148 | 41 | 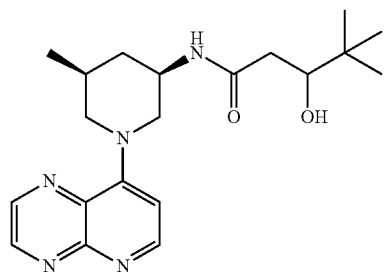  Isomer 1 |
| 149 | 41 | 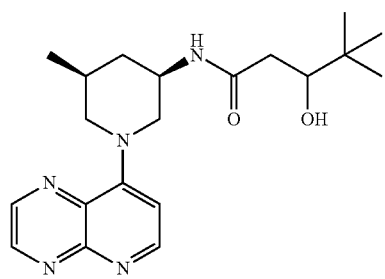  Isomer 2 |
| 152 | 41 | 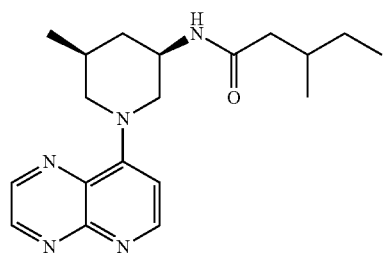  Isomer 1 |

-continued
| Compound Number | Example Number | Chemical Structure |
|---|---|---|
| 153 | 41 | 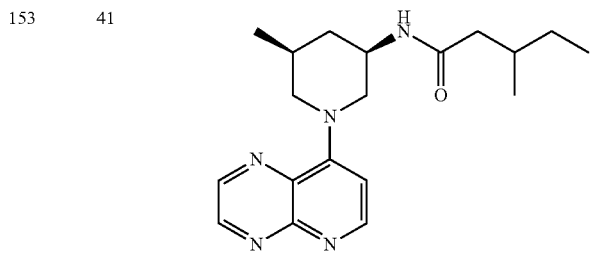<br>Isomer 2 |
| 156 | 41 | 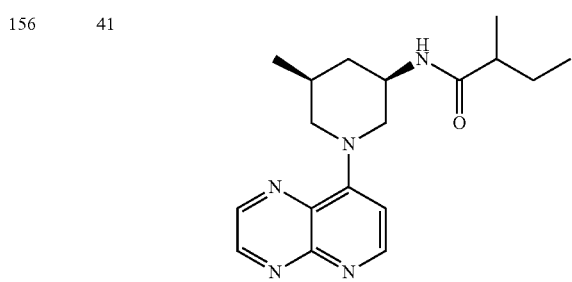<br>Isomer 1 |
| 157 | 41 | 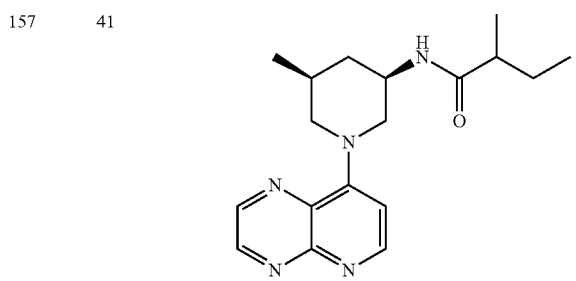<br>Isomer 2 |
| 160 | 41 | 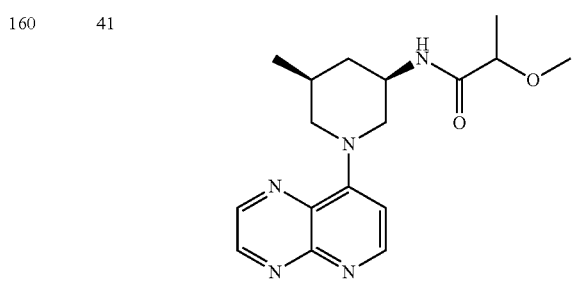<br>Isomer 1 |
| 161 | 41 | 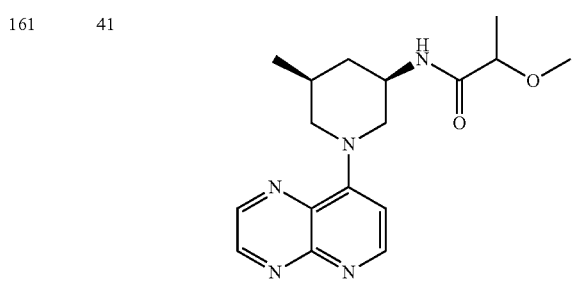<br>Isomer 2 |

-continued
| Compound Number | Example Number | Chemical Structure |
|---|---|---|
| 164 | 10 | 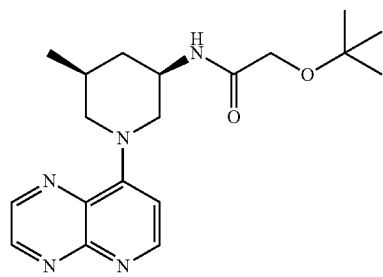 [SMILES: C[C@H]1C[C@@H](NC(=O)COC(C)(C)C)CN(c2ccnc3nccnc23)C1] |
| 168 | 10 | 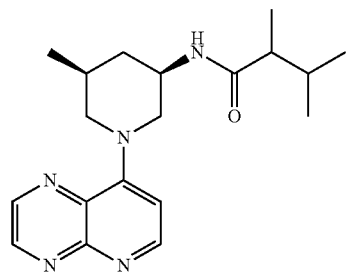 [SMILES: CC(C)C(C)C(=O)N[C@@H]1C[C@H](C)CN(c2ccnc3nccnc23)C1] |
| 170 | 10 | 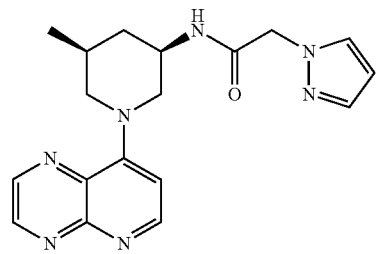 [SMILES: C[C@H]1C[C@@H](NC(=O)Cn2cccn2)CN(c2ccnc3nccnc23)C1] |
| 172 | 10 | 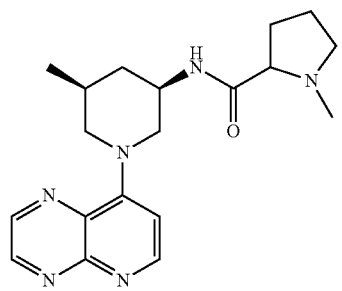 [SMILES: C[C@H]1C[C@@H](NC(=O)C2CCCN2C)CN(c2ccnc3nccnc23)C1] |
| 459 | 32 | 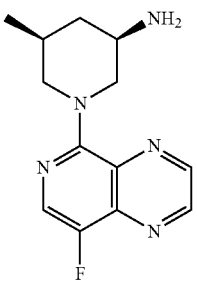 [SMILES: C[C@H]1C[C@@H](N)CN(c2ncc(F)c3nccnc23)C1] |

-continued
| Compound Number | Example Number | Chemical Structure |
|---|---|---|
| 460 | 114 | 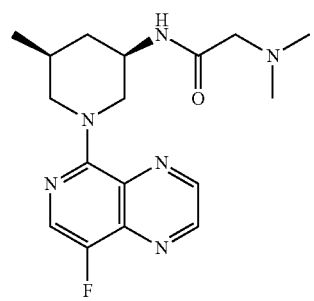 |
| 553 | 30 | 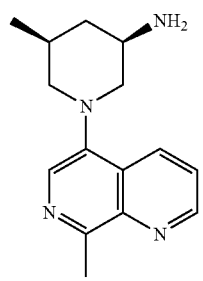 [SMILES: Cc1ncc(N2C[C@@H](C)C[C@@H](N)C2)c2cccnc12] |
| 554 | 122 | 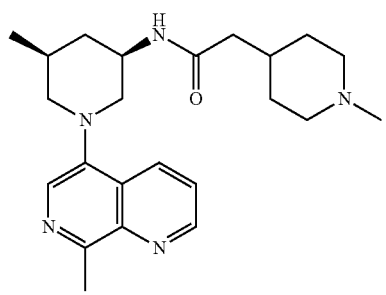 |
| 555 | 122 | 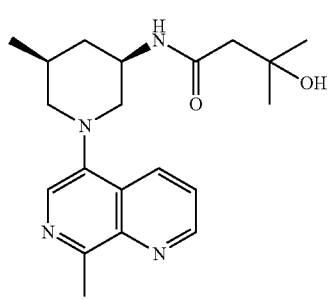 [SMILES: Cc1ncc(N2C[C@@H](C)C[C@@H](NC(=O)CC(C)(C)O)C2)c2cccnc12] |
| 556 | 122 | 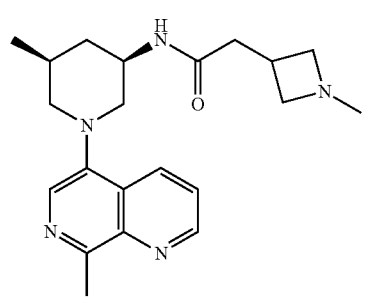 |

-continued
| Compound Number | Example Number | Chemical Structure |
|---|---|---|
| 557 | 122 | 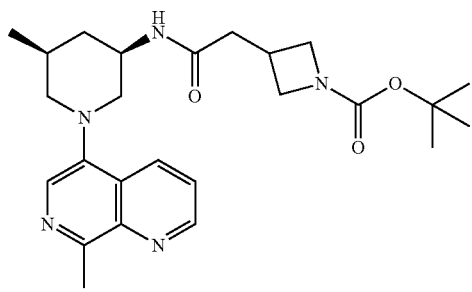 [SMILES: Cc1ncc(N2C[C@@H](C)C[C@@H](NC(=O)CC3CN(C(=O)OC(C)(C)C)C3)C2)c2cccnc12] |
| 558 | 122 | 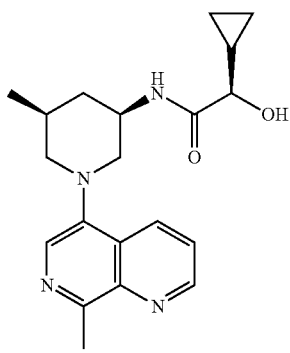 [SMILES: Cc1ncc(N2C[C@@H](C)C[C@@H](NC(=O)[C@H](O)C3CC3)C2)c2cccnc12] |
| 559 | 122 | 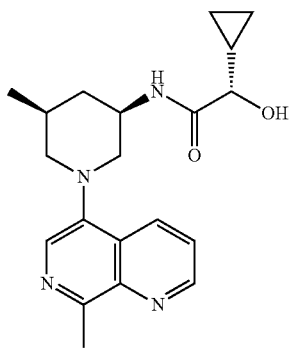 [SMILES: Cc1ncc(N2C[C@@H](C)C[C@@H](NC(=O)[C@@H](O)C3CC3)C2)c2cccnc12] |
| 560 | 122 | 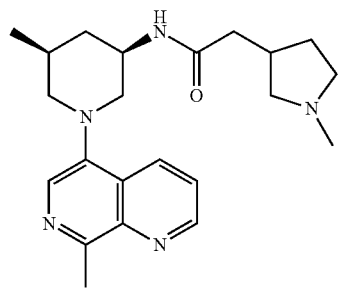 [SMILES: Cc1ncc(N2C[C@@H](C)C[C@@H](NC(=O)CC3CCN(C)C3)C2)c2cccnc12] |

-continued
| Compound Number | Example Number | Chemical Structure |
|---|---|---|
| 561 | 123 | 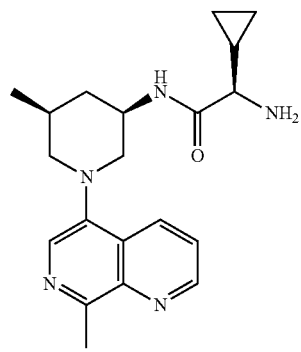 [SMILES: Cc1ncc(N2C[C@@H](C)C[C@@H](NC(=O)[C@H](N)C3CC3)C2)c2cccnc12] |
| 562 | 123 | 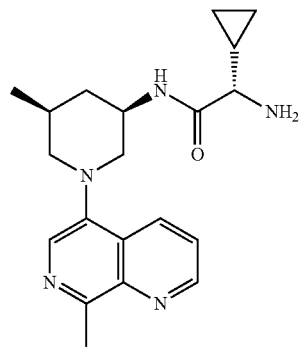 [SMILES: Cc1ncc(N2C[C@@H](C)C[C@@H](NC(=O)[C@@H](N)C3CC3)C2)c2cccnc12] |
| 563 | 123 | 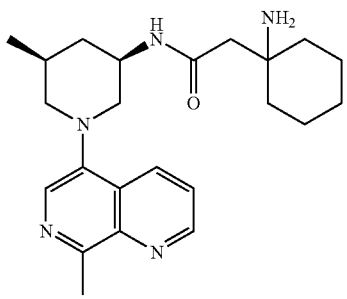 [SMILES: Cc1ncc(N2C[C@@H](C)C[C@@H](NC(=O)CC3(N)CCCCC3)C2)c2cccnc12] |
| 564 | 124 | 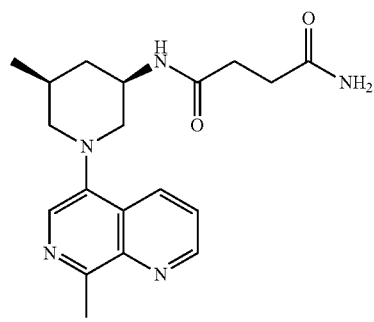 [SMILES: Cc1ncc(N2C[C@@H](C)C[C@@H](NC(=O)CCC(N)=O)C2)c2cccnc12] |

-continued

| Compound Number | Example Number | Chemical Structure |
|---|---|---|
| 565 | 124 | 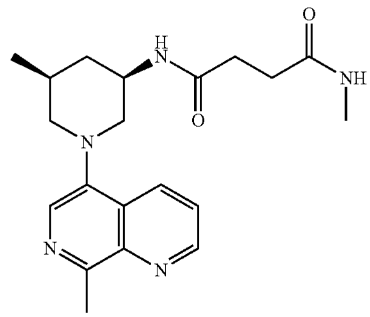 |
| 566 | 124 | , and |
| 567 | 138 | 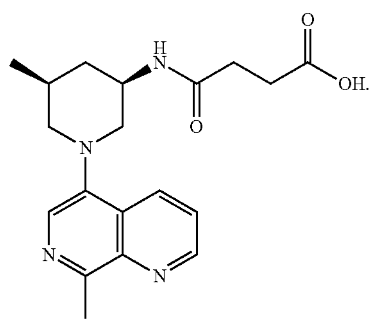 [SMILES: Cc1ncc(N2C[C@@H](C)C[C@@H](NC(=O)CCC(=O)O)C2)c2cccnc12] |

11. A pharmaceutical composition, comprising:
   a compound of claim 1, and
   a pharmaceutically acceptable adjuvant, carrier, or vehicle.

12. A method for inhibiting TLR7/8, or a mutant thereof, activity in a patient or in a biological sample, the method comprising:
   administering to said patient or contacting said biological sample with a compound of claim 1 or a physiologically acceptable salt thereof.

13. A method for treating a TLR7/8-mediated disorder in a patient in need thereof, the method comprising:
   administering to said patient a compound of claim 1 or a physiologically acceptable salt thereof.

14. The method of claim 13, wherein the disorder is selected from rheumatoid arthritis, psoriatic arthritis, osteoarthritis, systemic lupus erythematosus, lupus nephritis, ankylosing spondylitis, polymyositis, dermatomyositis, Sjogren's disease, osteoporosis, systemic sclerosis, multiple sclerosis, psoriasis, type I diabetes, type II diabetes, inflammatory bowel disease, Crohn's disease, ulcerative colitis, hyperimmunoglobulinemia D, periodic fever syndrome, cryopyrin-associated periodic syndromes, Schnitzler's syndrome, systemic juvenile idiopathic arthritis, adult onset Still's disease, gout, pseudogout, SAPHO syndrome, Castleman's disease, sepsis, stroke, atherosclerosis, celiac disease, DIRA (Deficiency of IL-1 Receptor Antagonist), Alzheimer's disease, Parkinson's disease, and cancer.

* * * * *